(12) United States Patent
La et al.

(10) Patent No.: US 9,728,731 B2
(45) Date of Patent: Aug. 8, 2017

(54) HETEROCYCLIC COMPOUND AND ORGANIC LIGHT EMITTING DEVICE USING SAME

(71) Applicant: HEESUNG MATERIAL LTD., Yongin, Gyeonggi-do (KR)

(72) Inventors: Hyun-Ju La, Hwaseong (KR); Young-Seok No, Osan (KR); Mi-Jin Kim, Ulsan (KR); Kee-Yong Kim, Suwon (KR); Jin-Seok Choi, Suwon (KR); Dae-Hyuk Choi, Yongin (KR); Sung-Jin Eum, Yongin (KR); Joo-Dong Lee, Seongnam (KR)

(73) Assignee: HEESUNG MATERIAL LTD., Yongin (KR)

( * ) Notice: Subject to any disclaimer, the term of this patent is extended or adjusted under 35 U.S.C. 154(b) by 0 days.

(21) Appl. No.: 14/898,342

(22) PCT Filed: Dec. 26, 2014

(86) PCT No.: PCT/KR2014/012936
§ 371 (c)(1),
(2) Date: Dec. 14, 2015

(87) PCT Pub. No.: WO2015/099508
PCT Pub. Date: Jul. 2, 2015

(65) Prior Publication Data
US 2016/0380208 A1    Dec. 29, 2016

(30) Foreign Application Priority Data

Dec. 27, 2013  (KR) .................... 10-2013-0164764
Sep. 24, 2014  (KR) .................... 10-2014-0127878

(51) Int. Cl.
*H01L 51/00* (2006.01)
*C07D 401/04* (2006.01)
(Continued)

(52) U.S. Cl.
CPC ........ *H01L 51/0072* (2013.01); *C07D 221/12* (2013.01); *C07D 221/18* (2013.01);
(Continued)

(58) Field of Classification Search
CPC combination set(s) only.
See application file for complete search history.

(56) References Cited

U.S. PATENT DOCUMENTS

| | | | | |
|---|---|---|---|---|
| 4,356,429 A * | 10/1982 | Tang | ................. | H05B 33/20 313/503 |
| 2008/0014464 A1* | 1/2008 | Kawamura | ............ | C09K 11/06 428/690 |

(Continued)

FOREIGN PATENT DOCUMENTS

| | | |
|---|---|---|
| CN | 104860883 A | 8/2015 |
| KR | 10-2010-0101315 A * | 9/2010 |
| KR | 10-2013-0135178 A * | 12/2013 |

OTHER PUBLICATIONS

Anger, et al, "Multifunctional and Reactive Enantiopure Organometallic Helicenes: Tunii Chiroptical Properties by Structural Variations of Mono- and Bis (platinahelicene) s" Chem. Rur. J., 2011, vol. 17, pp. 14178-14198.*

(Continued)

*Primary Examiner* — Mamadou Diallo
(74) *Attorney, Agent, or Firm* — Birch, Stewart, Kolasch & Birch, LLP

(57) ABSTRACT

Disclosed are a heterocyclic compound and an organic light emitting device including the same.

12 Claims, 30 Drawing Sheets

(51) Int. Cl.
| | |
|---|---|
| *C07D 401/14* | (2006.01) |
| *C07D 221/12* | (2006.01) |
| *C07D 401/10* | (2006.01) |
| *C07D 471/04* | (2006.01) |
| *C09K 11/06* | (2006.01) |
| *H01L 51/50* | (2006.01) |
| *C07D 221/18* | (2006.01) |
| *C07D 417/04* | (2006.01) |
| *C07D 417/10* | (2006.01) |
| *C07D 487/04* | (2006.01) |
| *C07F 9/576* | (2006.01) |
| *C07F 9/6506* | (2006.01) |
| *C07F 9/6521* | (2006.01) |
| *C09K 11/02* | (2006.01) |

(52) U.S. Cl.
CPC ......... *C07D 401/04* (2013.01); *C07D 401/10* (2013.01); *C07D 401/14* (2013.01); *C07D 417/04* (2013.01); *C07D 417/10* (2013.01); *C07D 471/04* (2013.01); *C07D 487/04* (2013.01); *C07F 9/5765* (2013.01); *C07F 9/65068* (2013.01); *C07F 9/65212* (2013.01); *C09K 11/025* (2013.01); *C09K 11/06* (2013.01); *H01L 51/0052* (2013.01); *H01L 51/0054* (2013.01); *H01L 51/0058* (2013.01); *H01L 51/0067* (2013.01); *H01L 51/0071* (2013.01); *H01L 51/50* (2013.01); *C09K 2211/1007* (2013.01); *C09K 2211/1011* (2013.01); *C09K 2211/1029* (2013.01); *C09K 2211/1037* (2013.01); *C09K 2211/1044* (2013.01); *C09K 2211/1059* (2013.01); *C09K 2211/1096* (2013.01); *H01L 51/5012* (2013.01); *H01L 51/5072* (2013.01); *H01L 51/5092* (2013.01)

(56) References Cited

U.S. PATENT DOCUMENTS

2013/0009118 A1* 1/2013 Stoessel ............ H01L 51/0085
  252/519.21
2015/0243908 A1    8/2015 Lee et al.
2016/0218301 A1* 7/2016 Kang ................ C07F 9/65846

OTHER PUBLICATIONS

International Search Report for Appl. No. PCT/KR2014/012936 dated Mar. 20, 2015 (w/English translation).*
Korean Office Action for Appl. No. 10-2014-0127878 dated Nov. 8, 2014 (w/English translation).*
Taiwanese Office Action for Appl. No. 103145903 dated Oct. 14, 2015 (w/English translation).*
Written Opinion of the international Searching Authority for Appl. No. PCT/KR2014/012936 dated Mar. 20, 2015 (w/English translation).*
Zheng, Y-H. et al, "Synthesis, Structures, and Optical Properties of Aza[4]Helicenes," Eur. J. Org. Chem., 2013, pp. 3059-3066.*
Demeter, A., et al, "Dual luminescence properties of differently benzo-fused N-phenylphenanthridinones," Photochem. Photobiol. Sci., 2003, vol. 2, pp. 273-281.
Chinese Office Action for Appl. No. 201480038480.9 dated Sep. 19, 2016 (w/ English translation).
Graule, S. et al, "Assembly of π-Conjugated Phosphole Azahelicene Derivatives into Chiral Coordination Complexes: An Experimental and Theoretical Study," Chem. Eur. J., 2010, vol. 16, pp. 5976-6005.

* cited by examiner

[Figure 1]
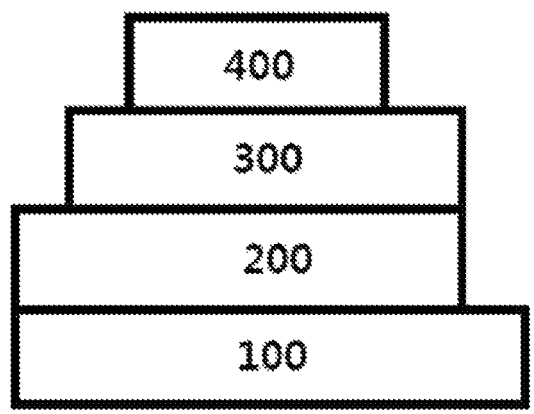
[Figure 2]
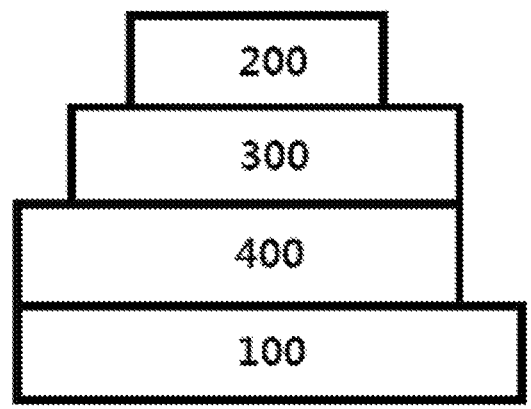

[Figure 3]
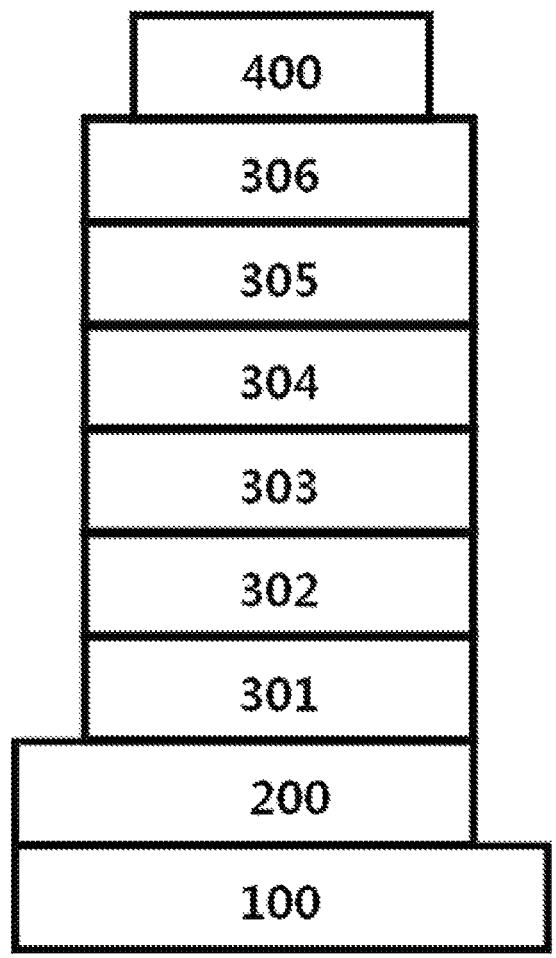

[Figure 4]
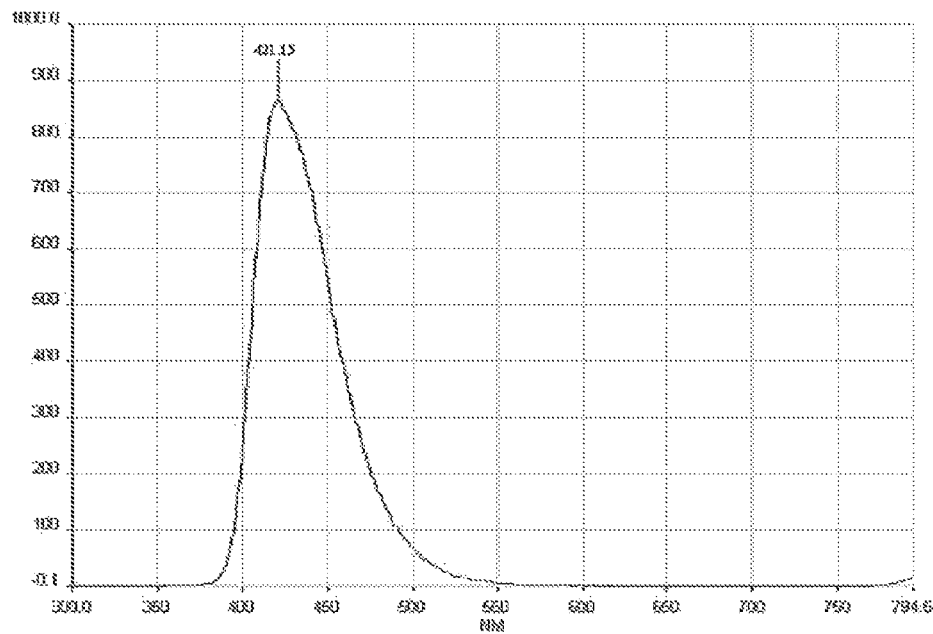
[Figure 5]
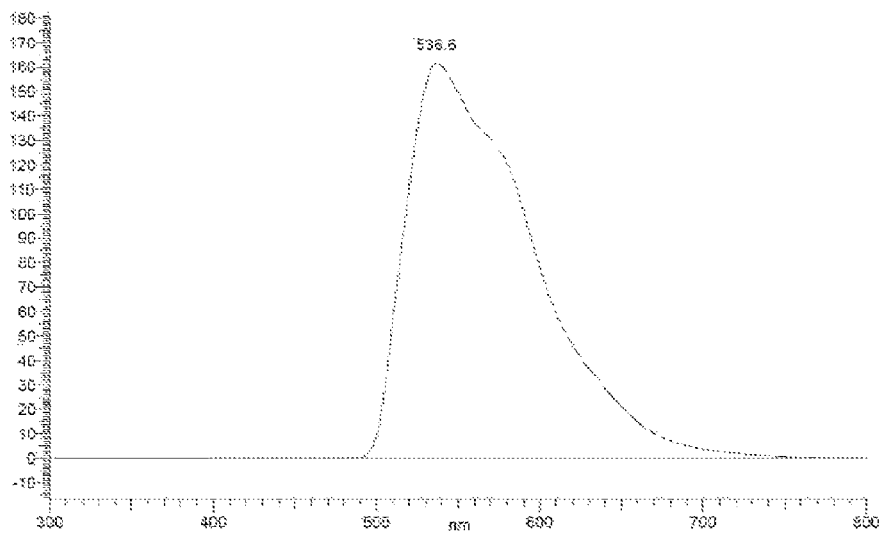

[Figure 6]
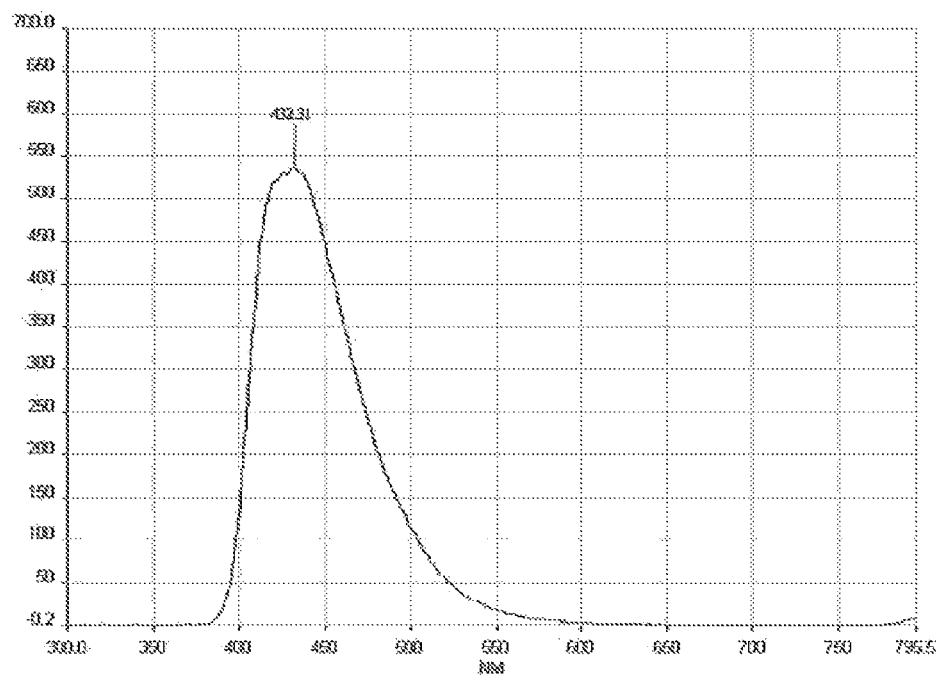
[Figure 7]
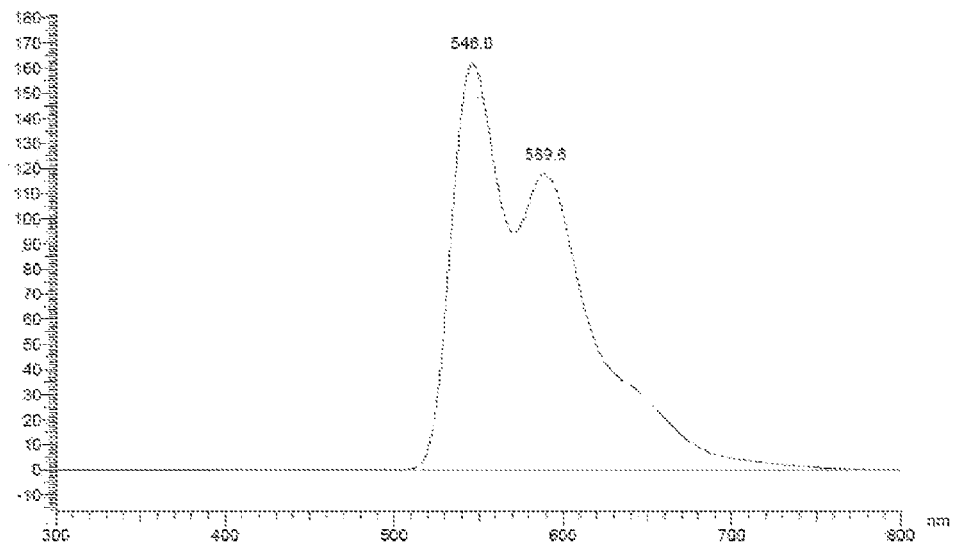

[Figure 8]
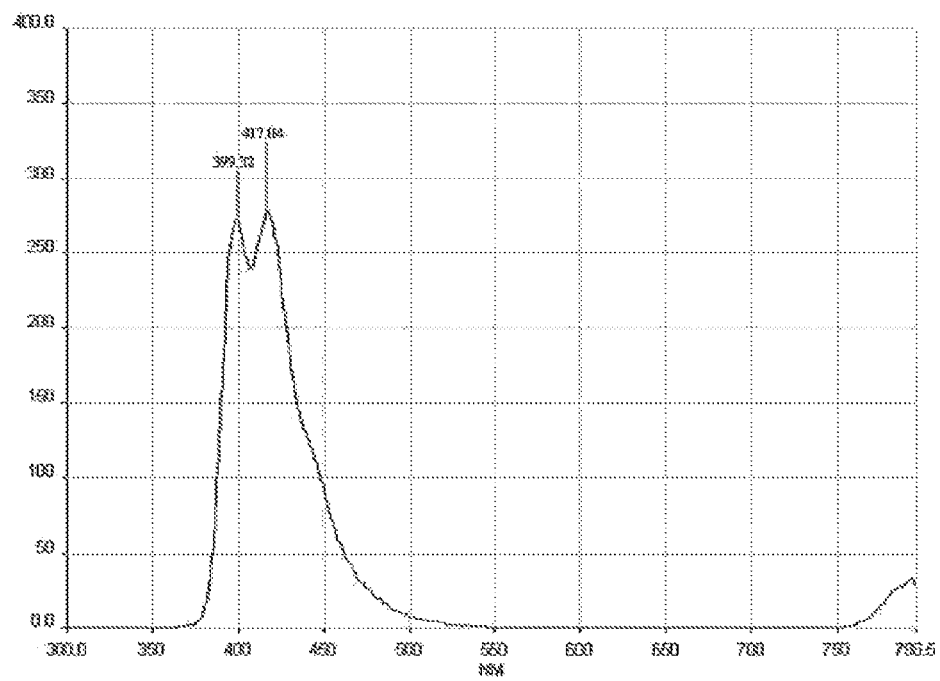
[Figure 9]
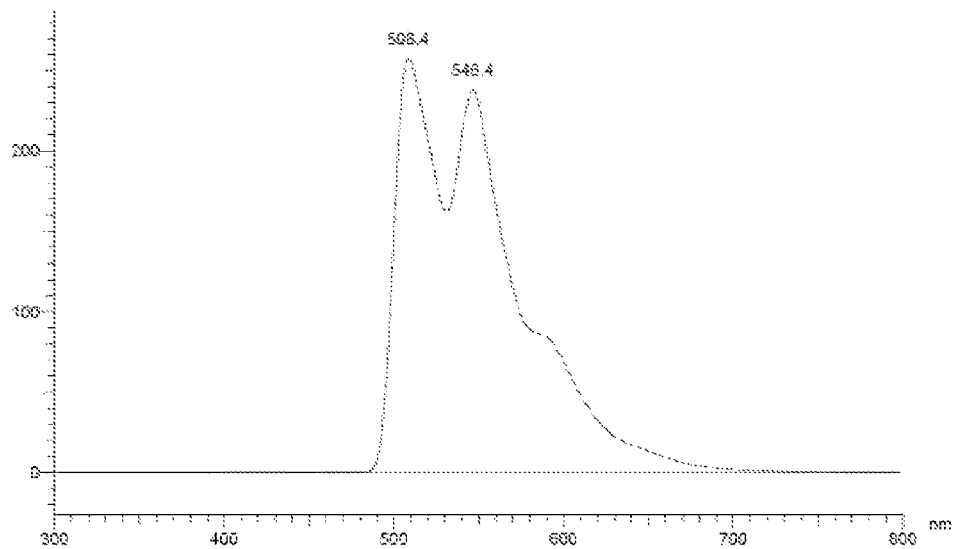

[Figure 10]
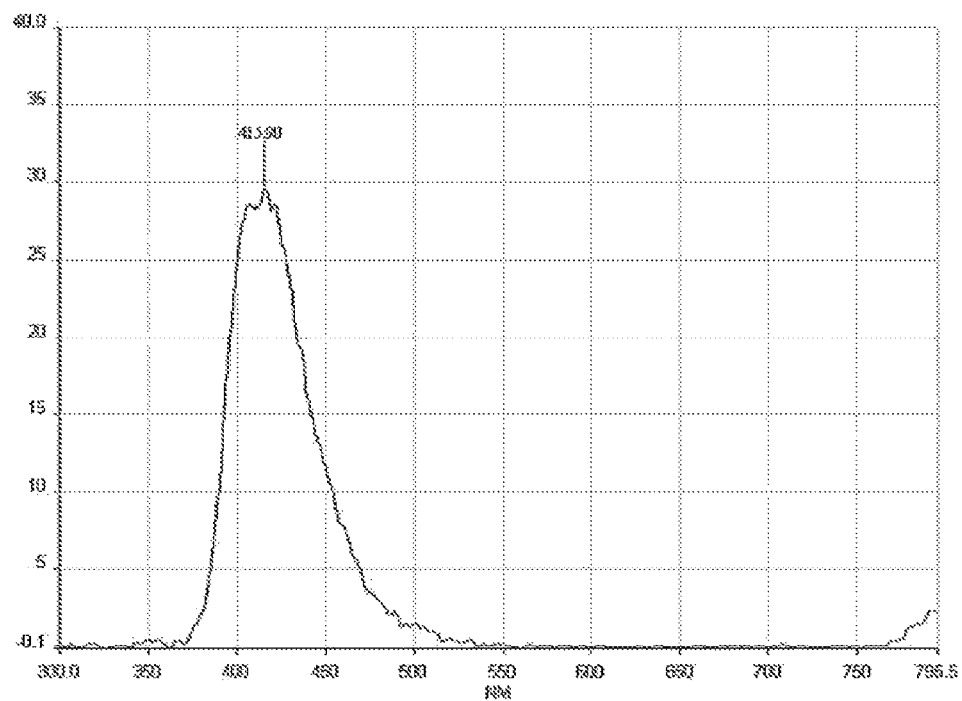
[Figure 11]
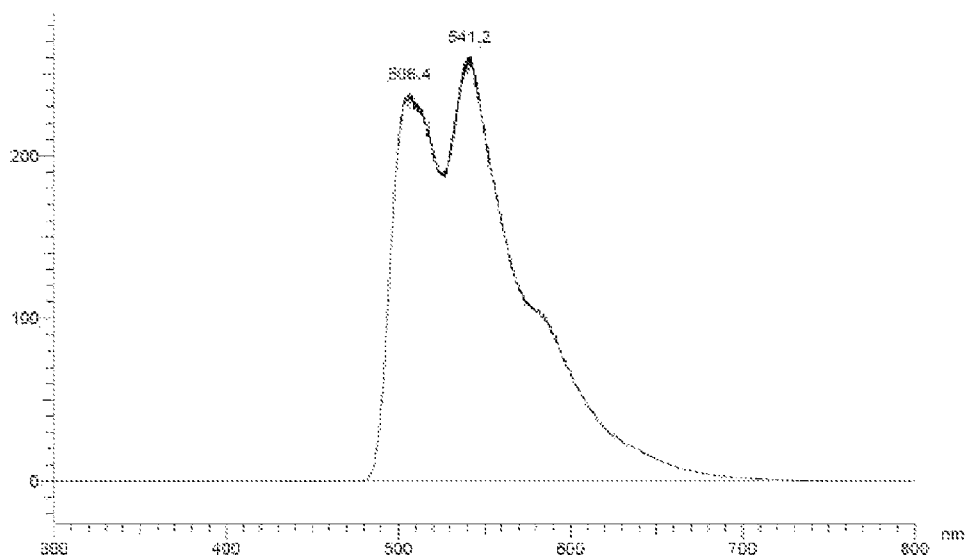

[Figure 12]
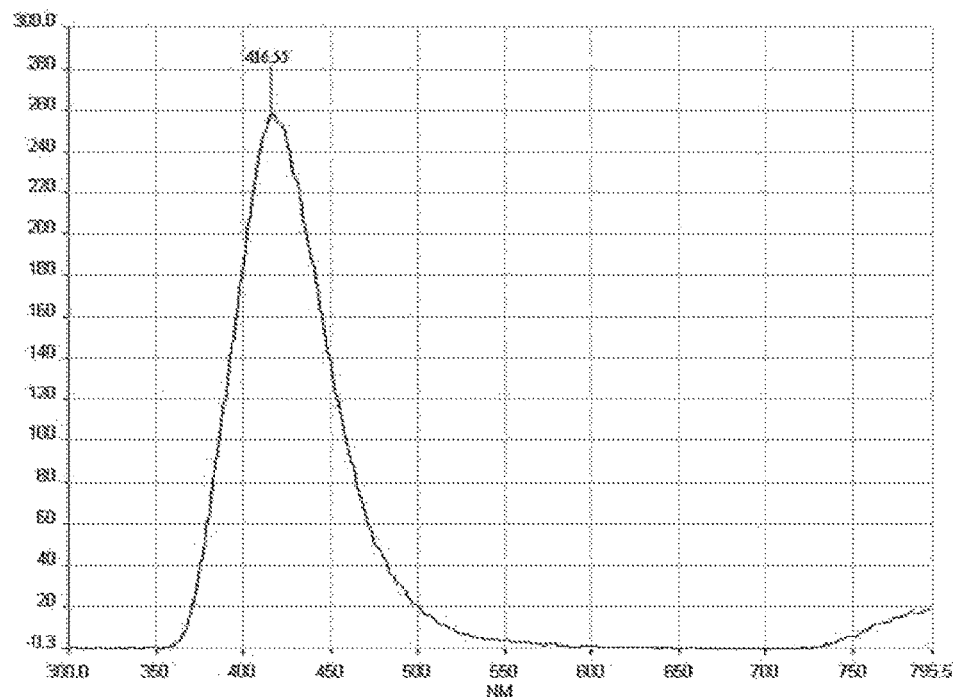
[Figure 13]
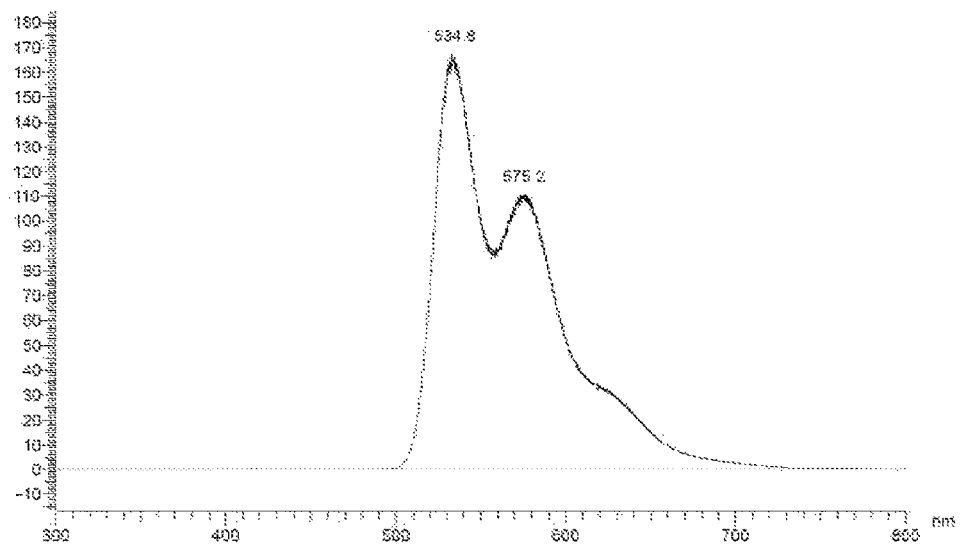

[Figure 14]
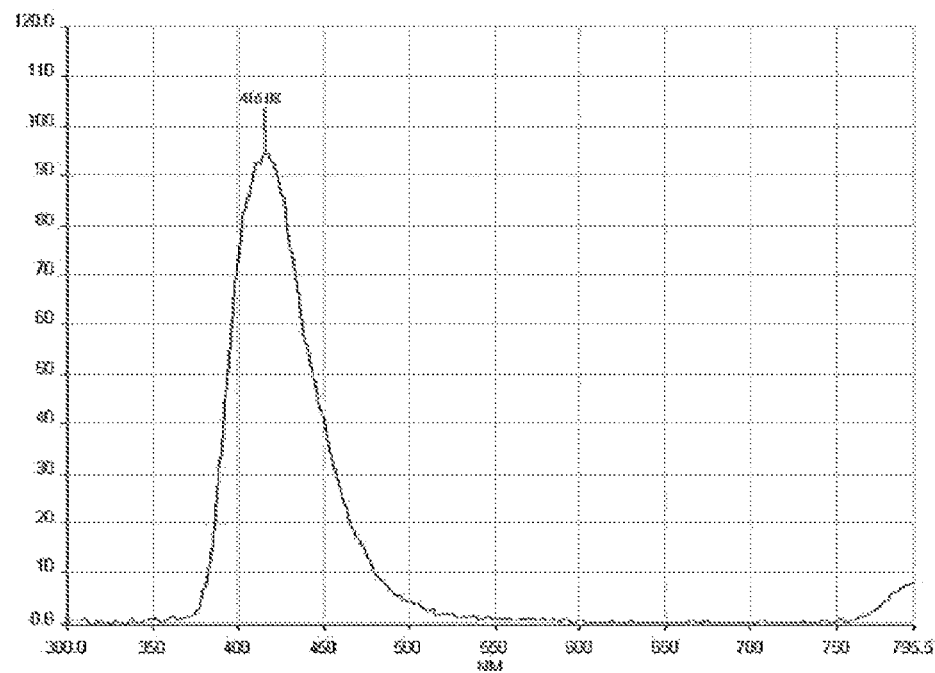
[Figure 15]
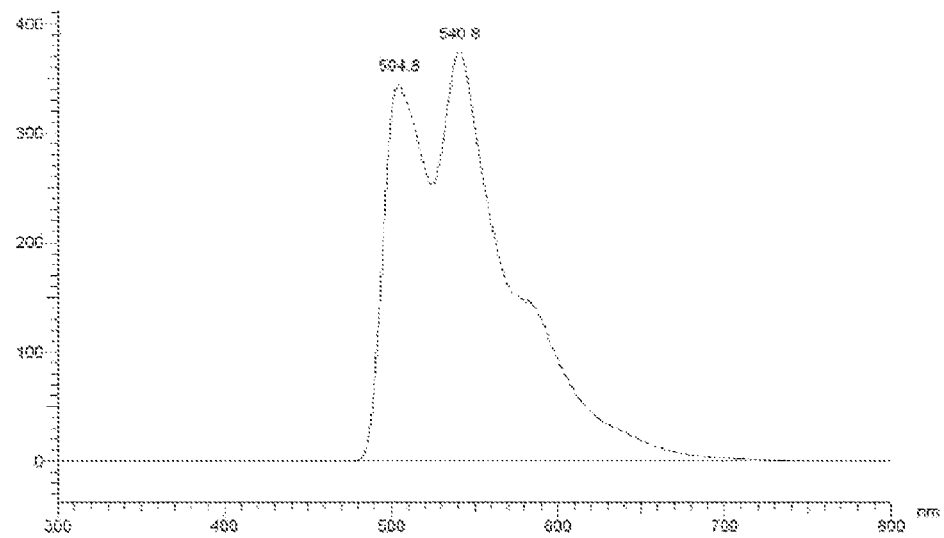

[Figure 16]
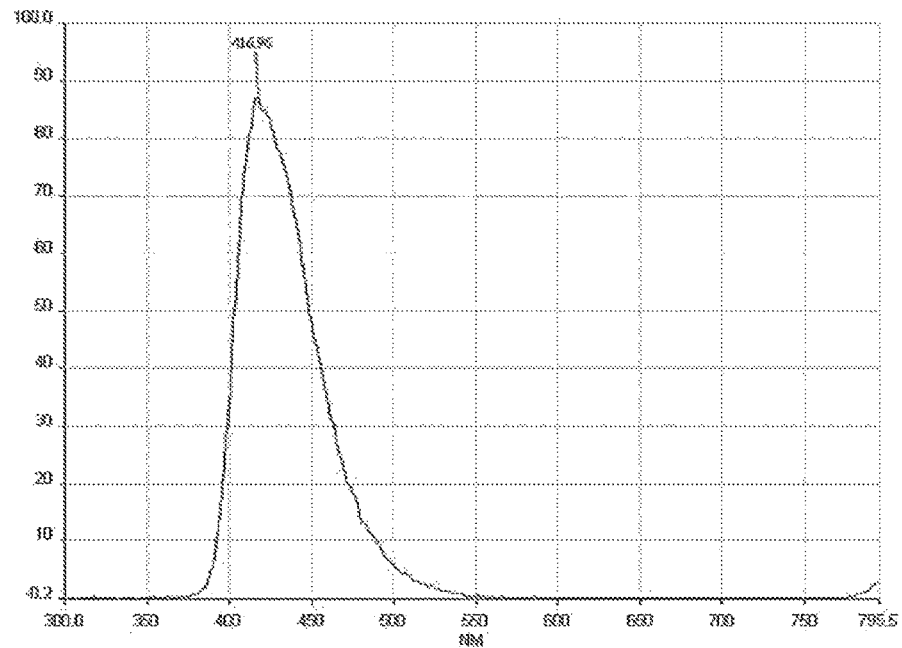
[Figure 17]
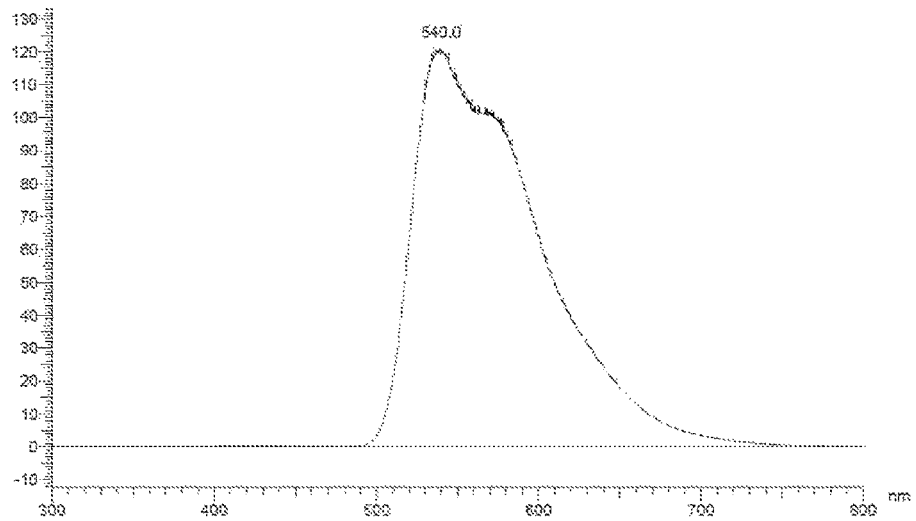

[Figure 18]
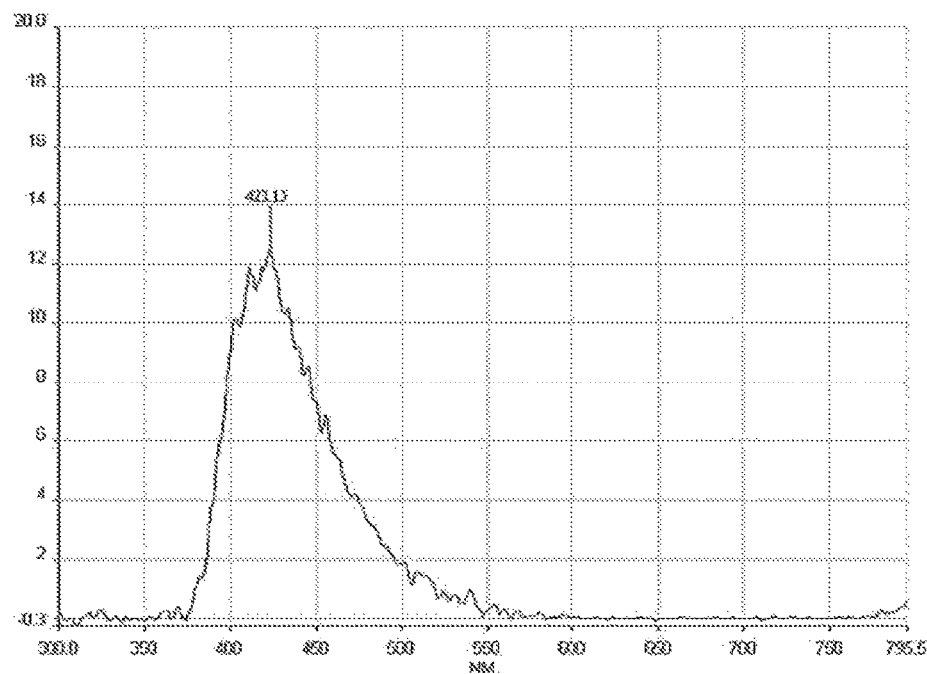
[Figure 19]
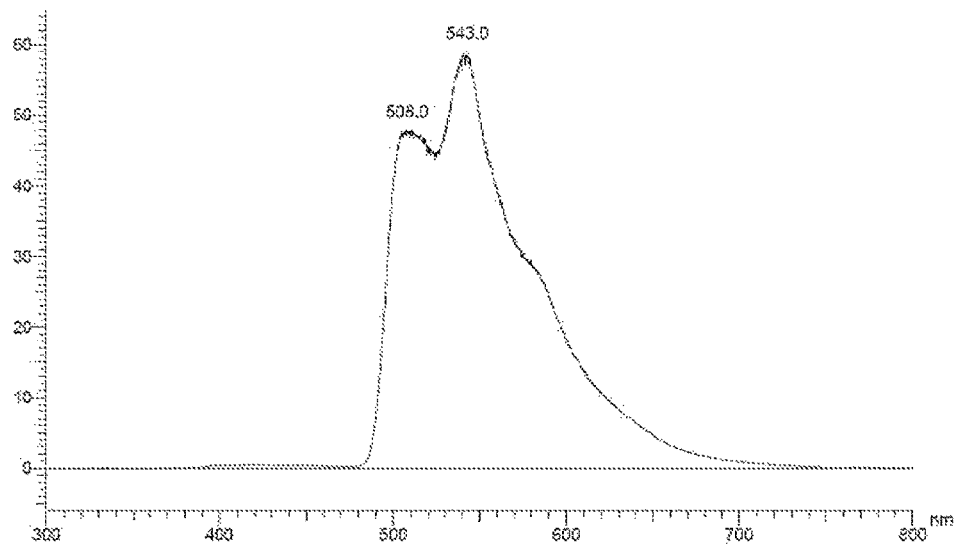

[Figure 20]
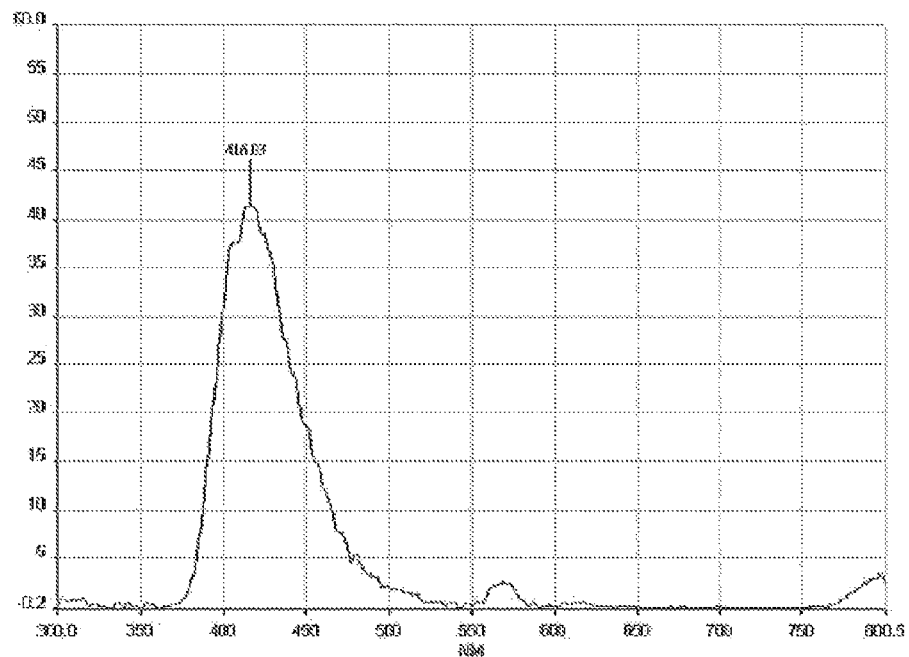
[Figure 21]
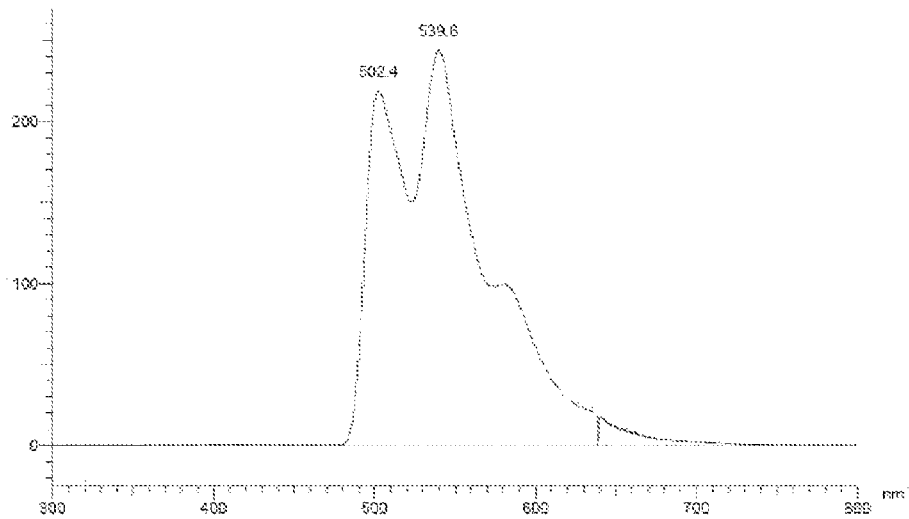

[Figure 22]
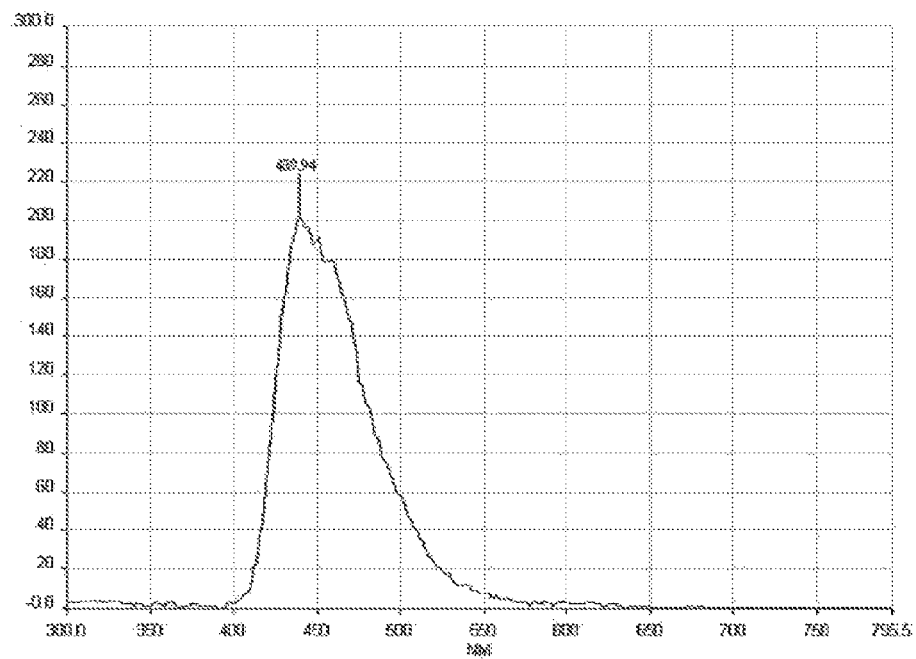
[Figure 23]
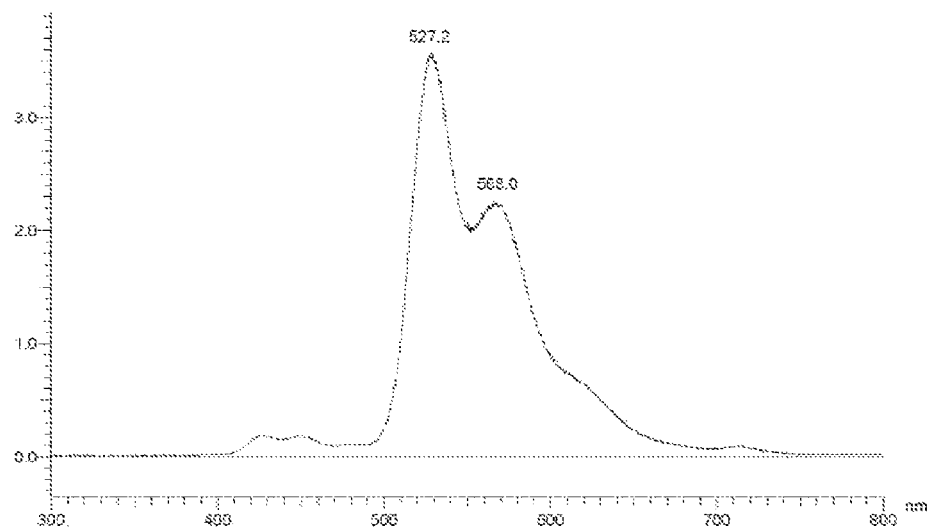

[Figure 24]
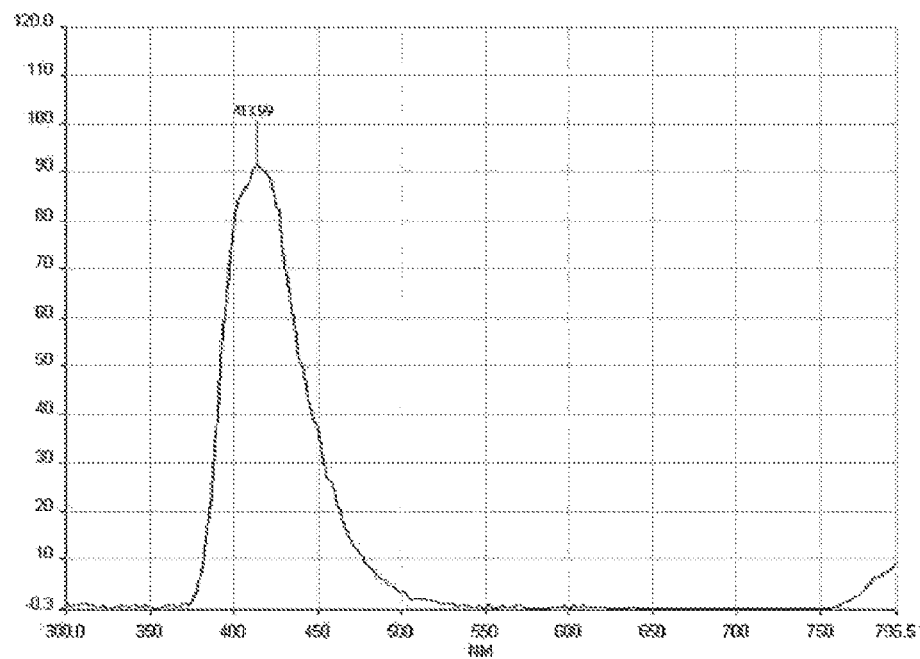
[Figure 25]
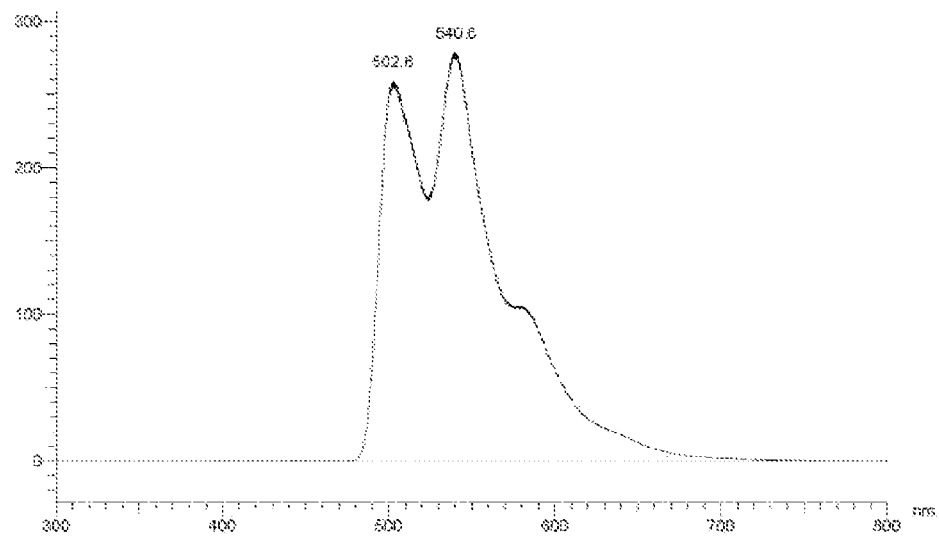

[Figure 26]
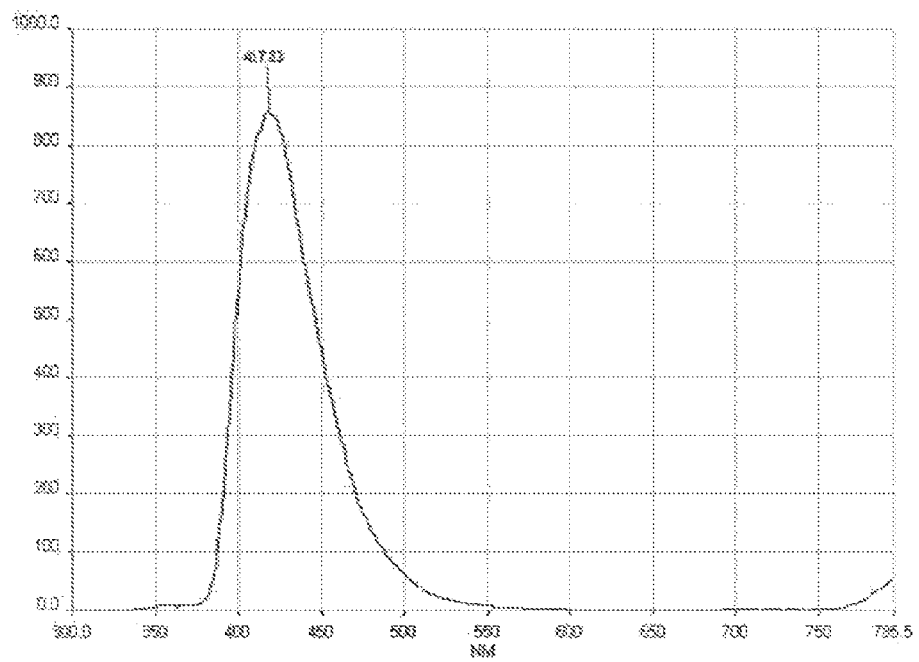
[Figure 27]
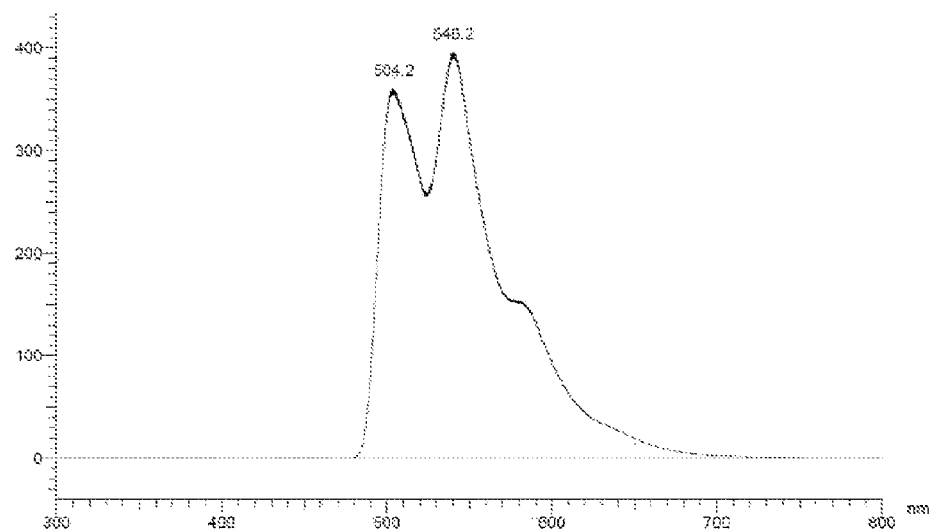

[Figure 28]
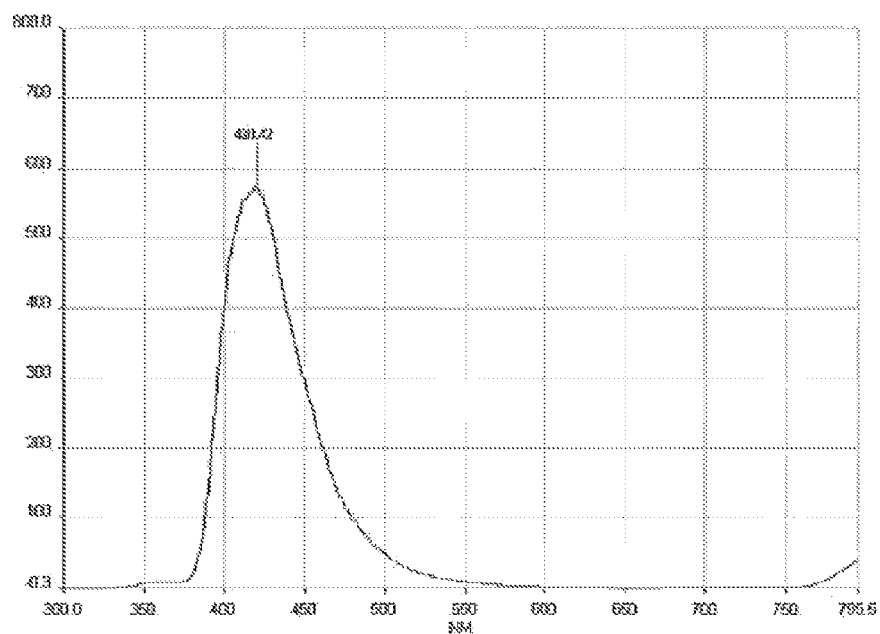
[Figure 29]
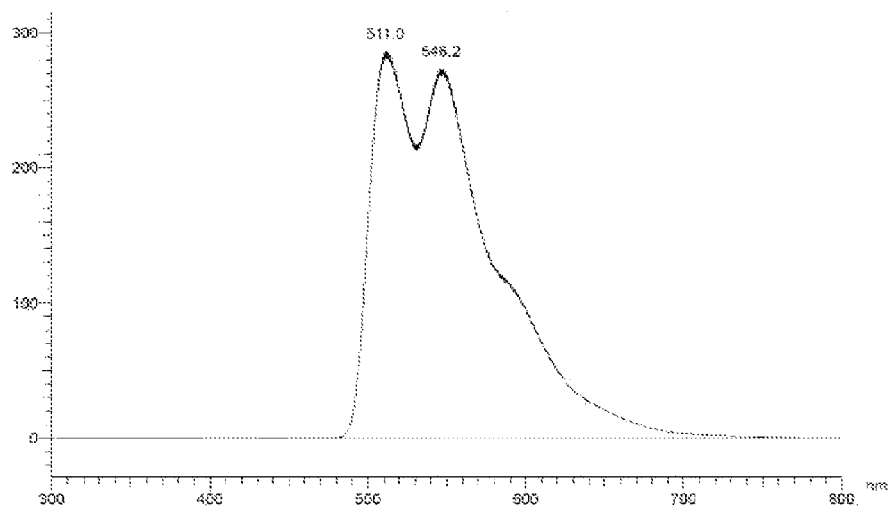

[Figure 30]
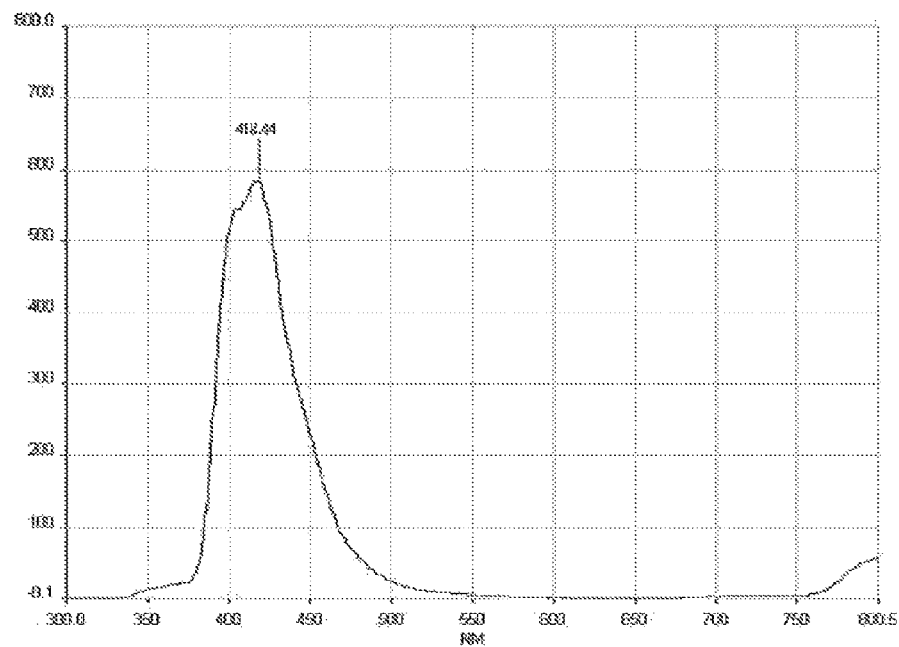
[Figure 31]
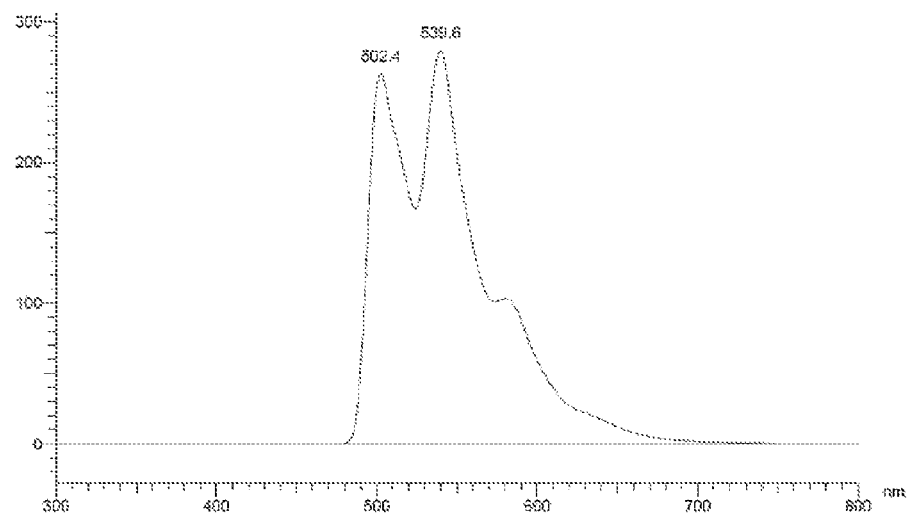

[Figure 32]
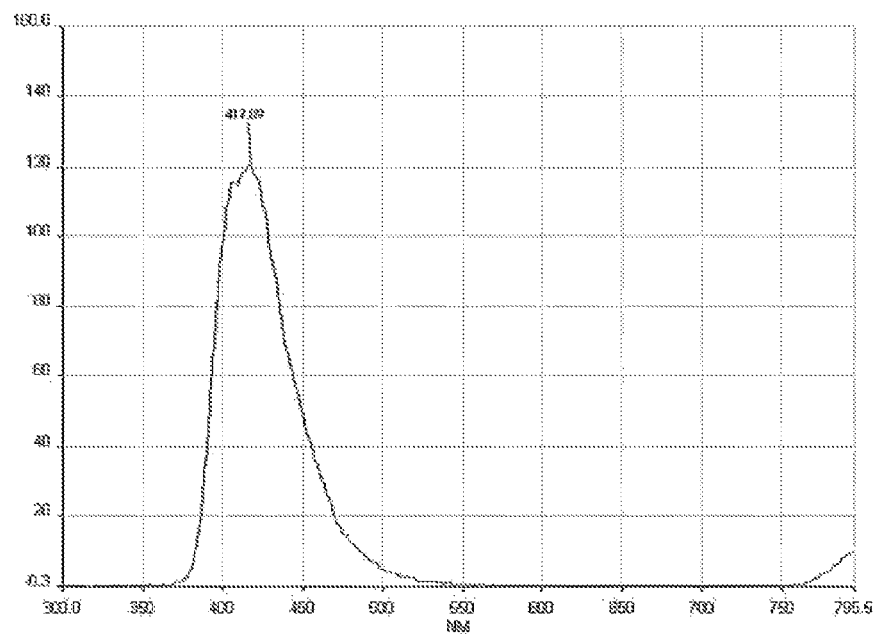
[Figure 33]
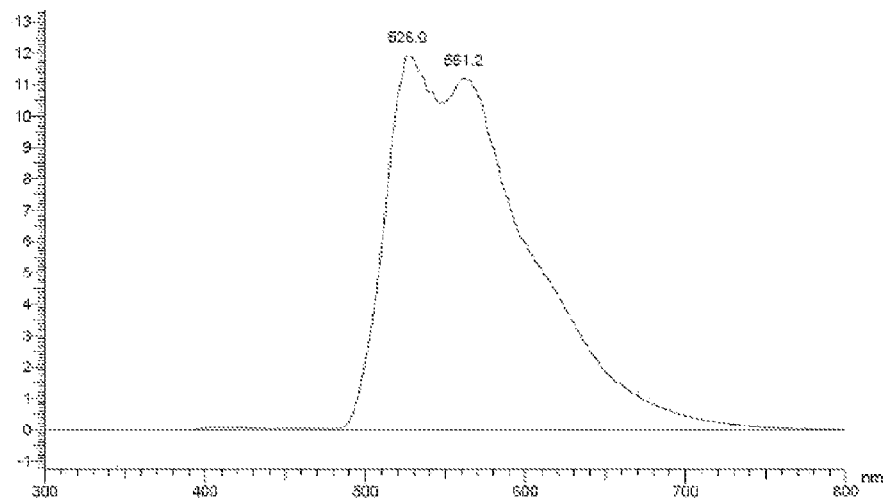

[Figure 34]
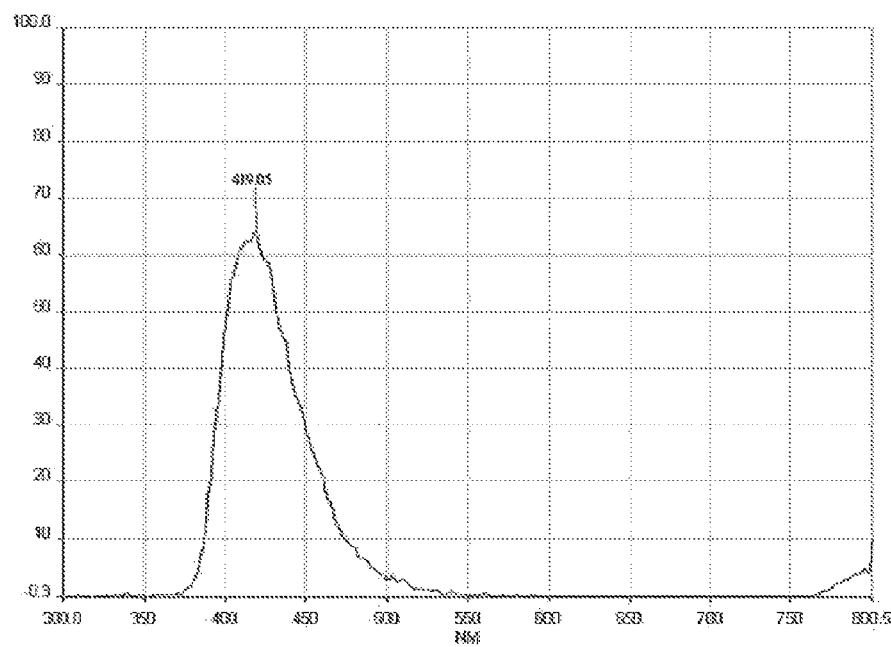
[Figure 35]
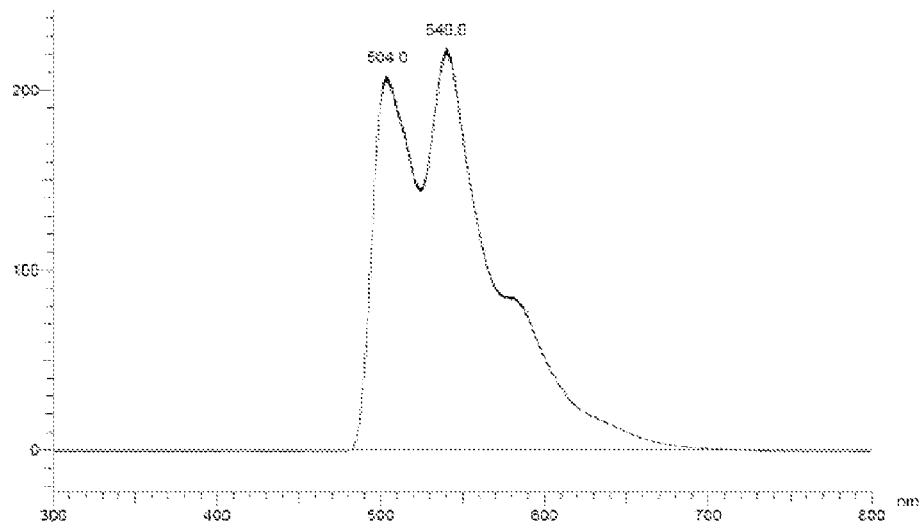

[Figure 36]
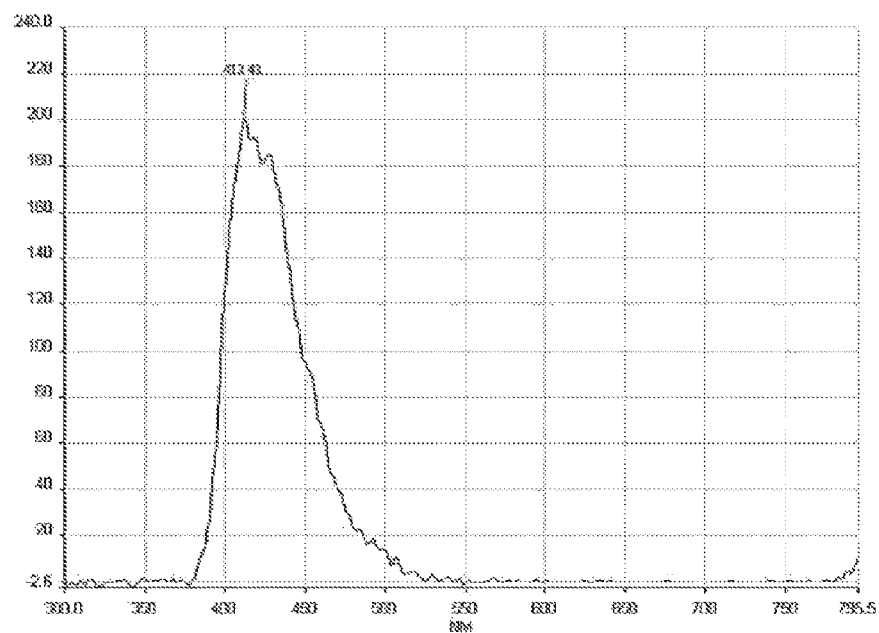
[Figure 37]
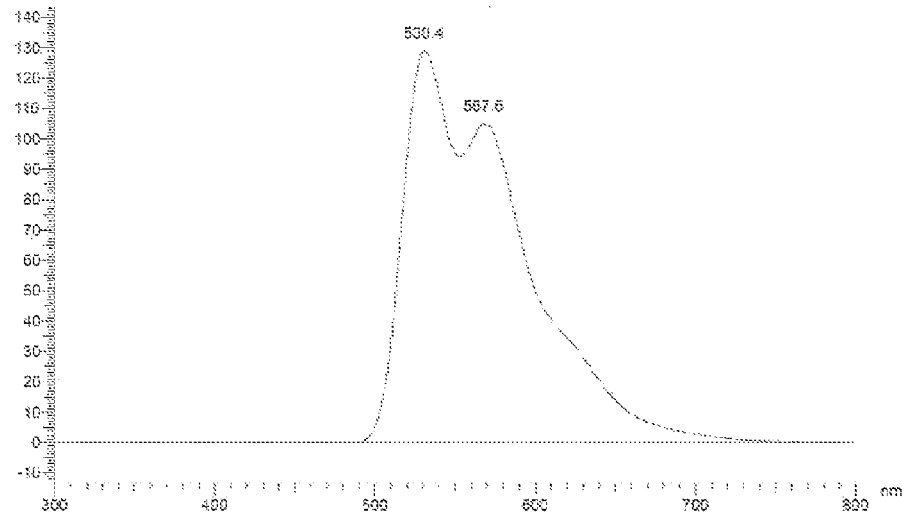

[Figure 38]
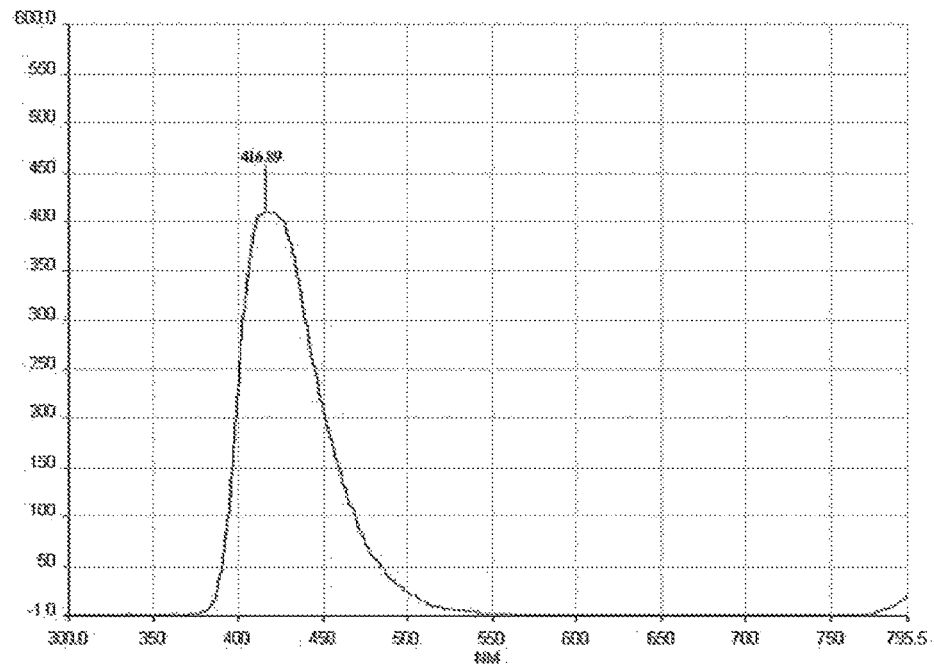
[Figure 39]
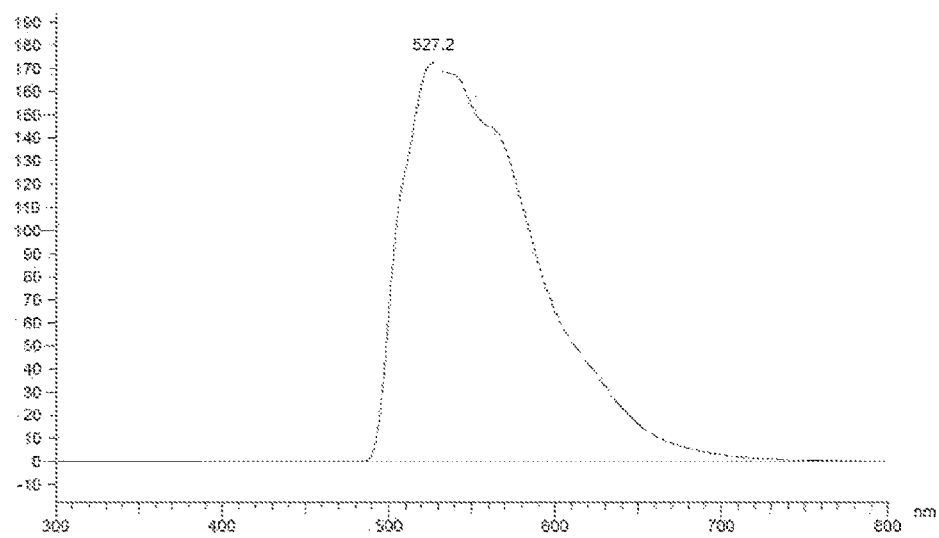

[Figure 40]
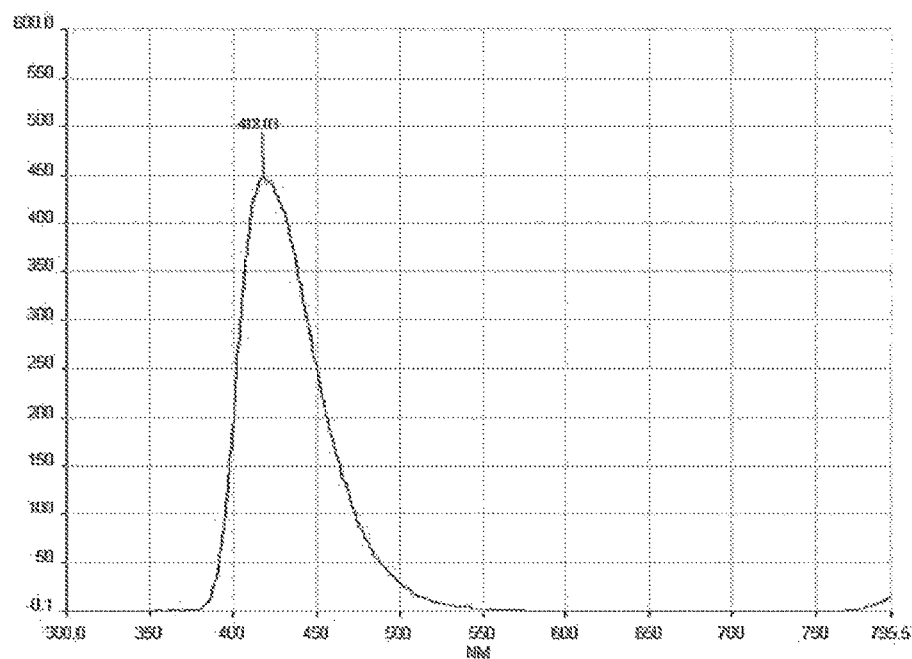
[Figure 41]
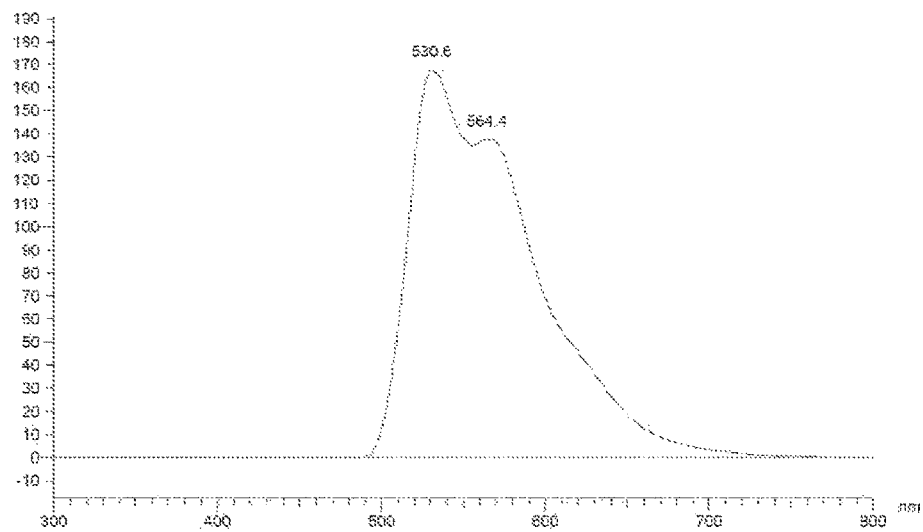

[Figure 42]
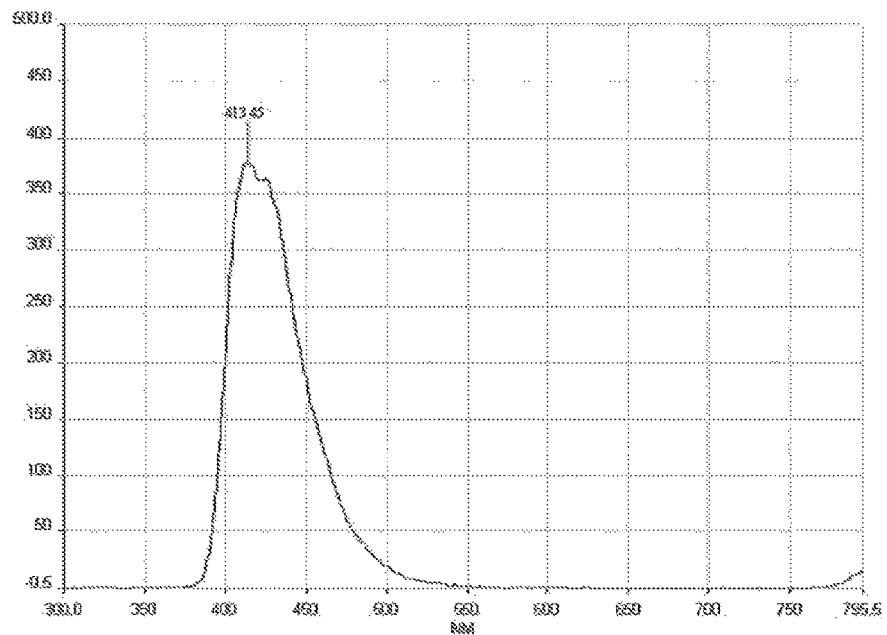
[Figure 43]
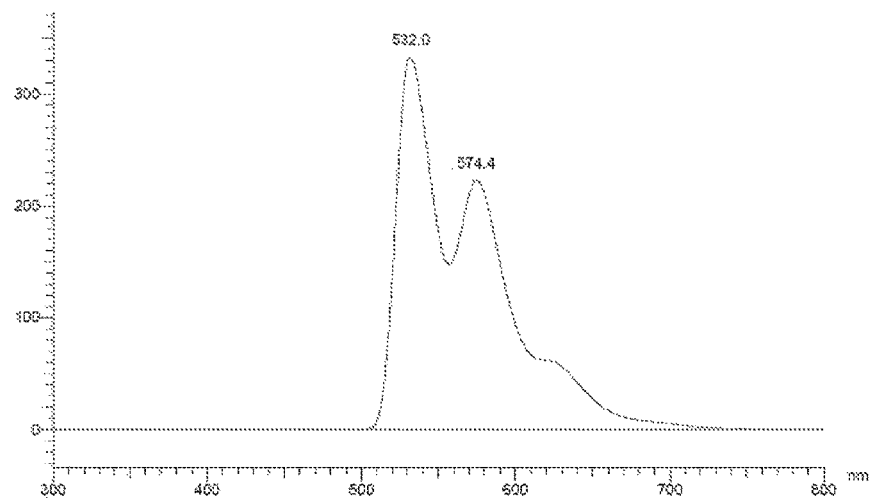

[Figure 44]
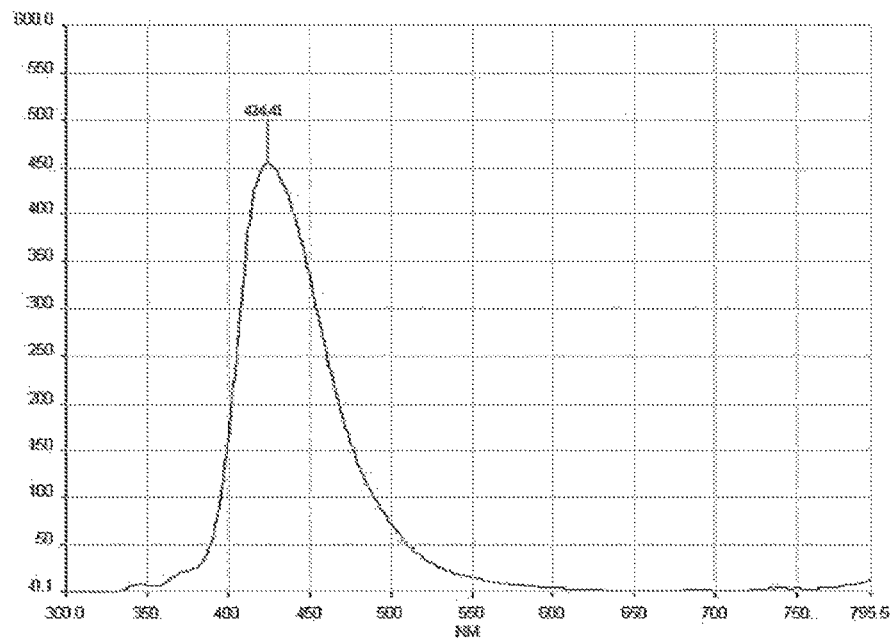
[Figure 45]
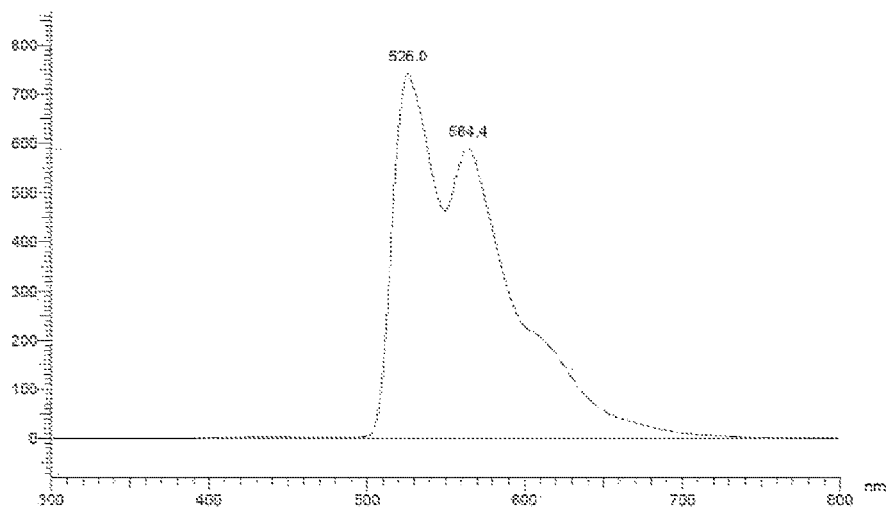

[Figure 46]
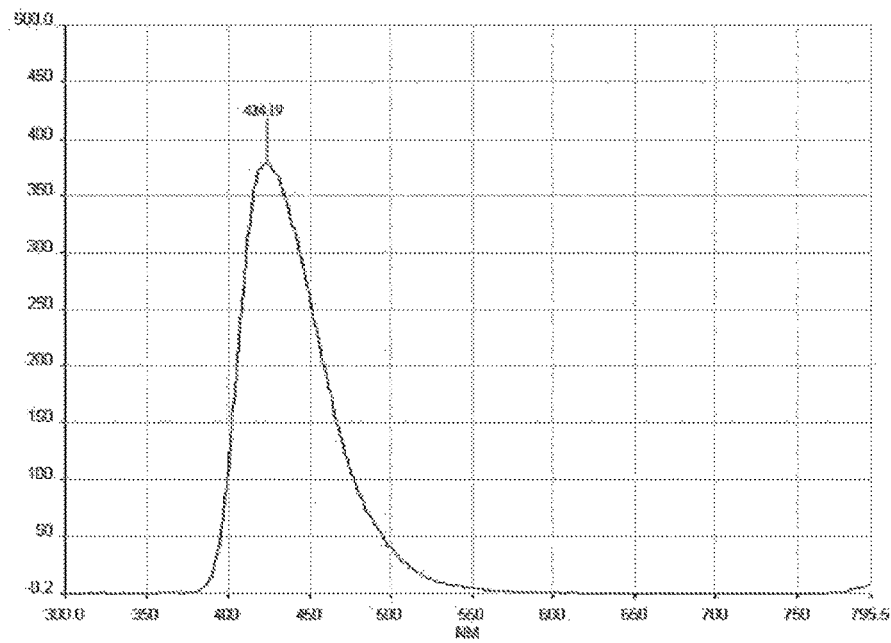
[Figure 47]
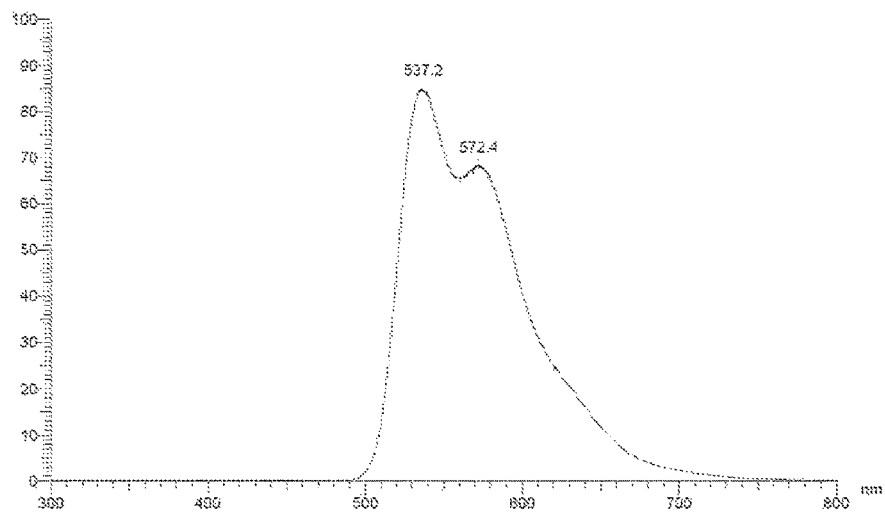

[Figure 48]
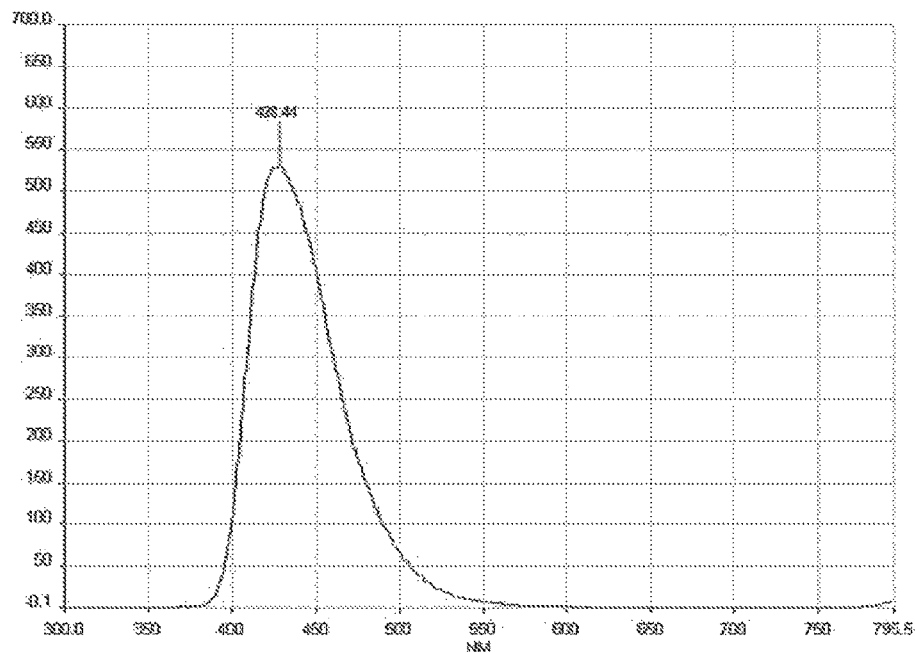
[Figure 49]
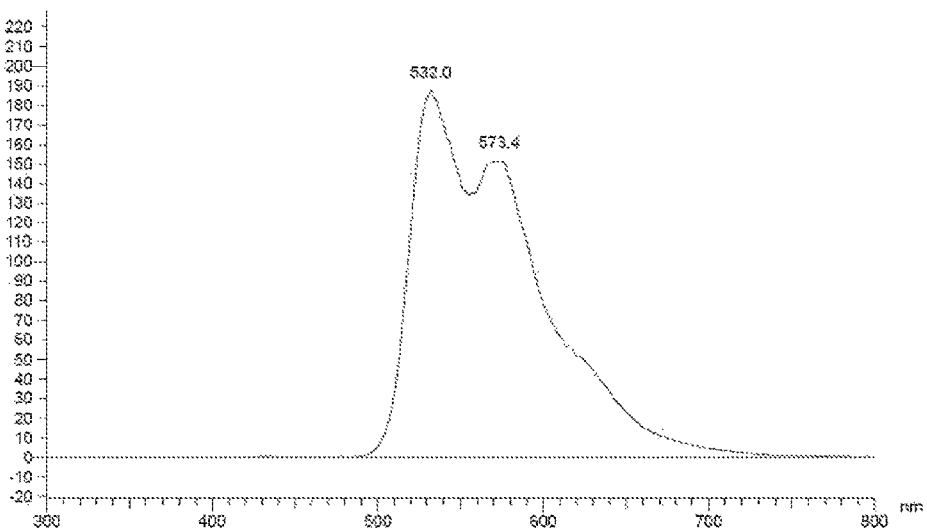

[Figure 50]
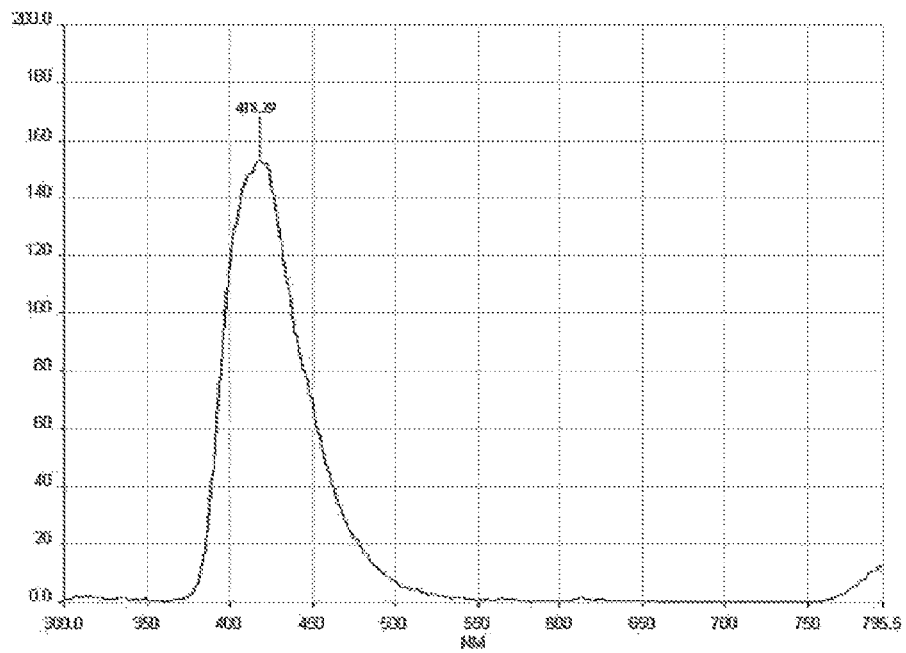
[Figure 51]
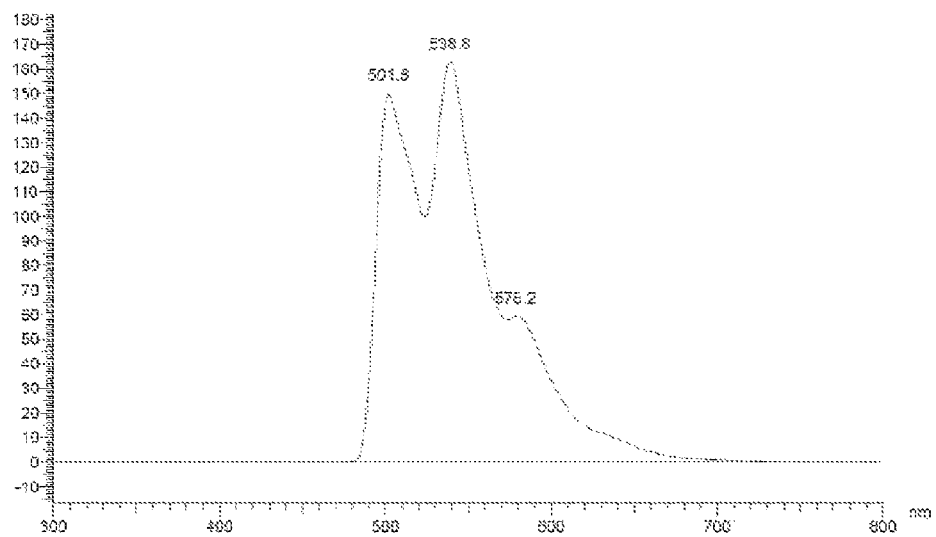

[Figure 52]
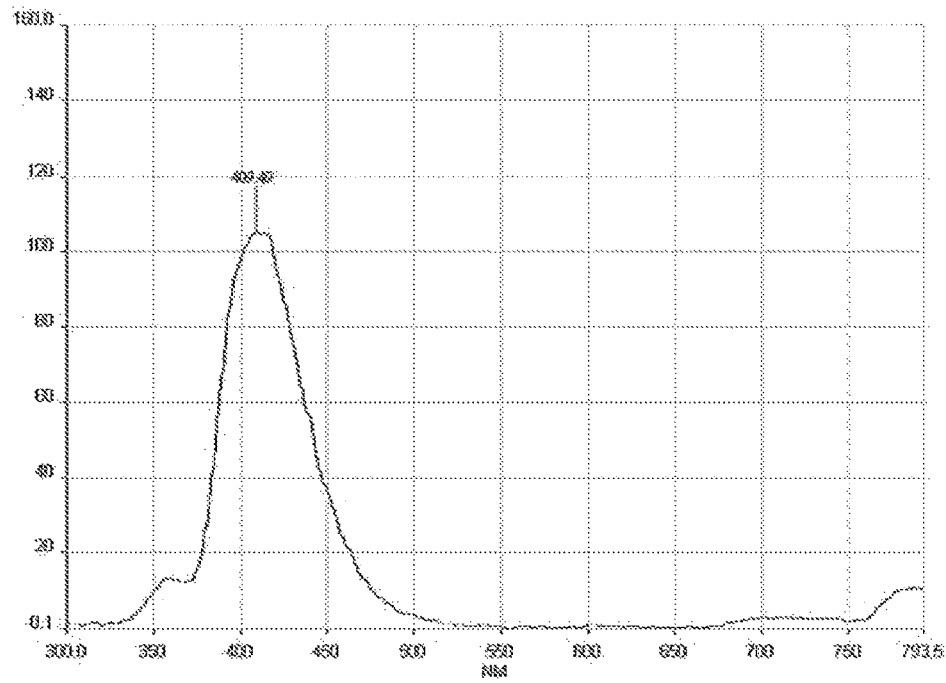
[Figure 53]
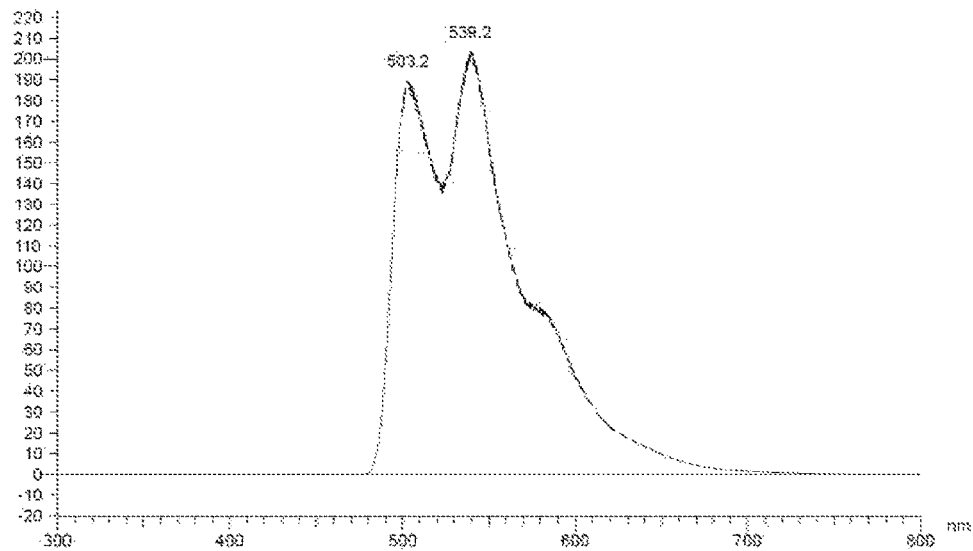

[Figure 54]
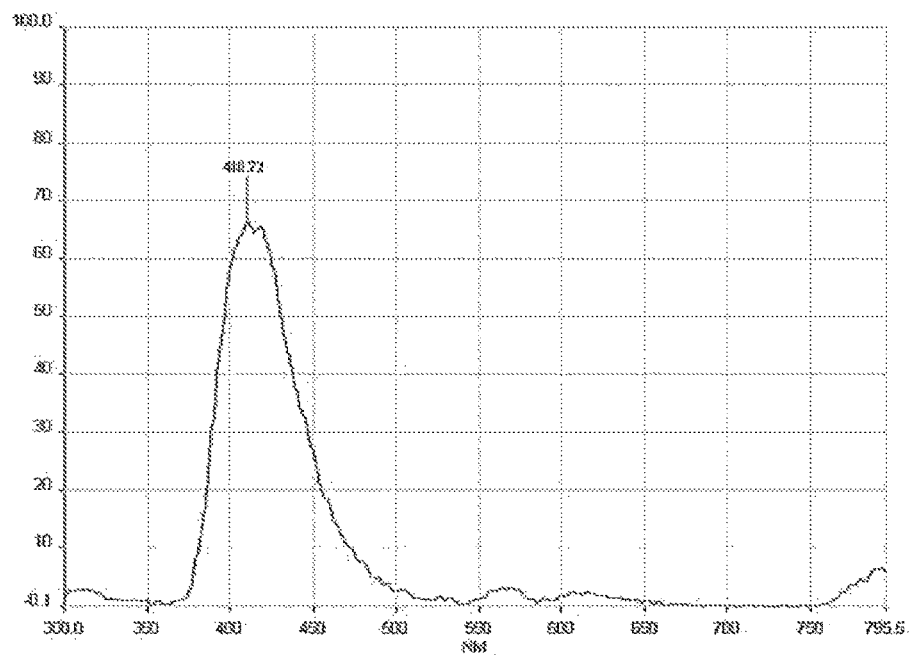
[Figure 55]
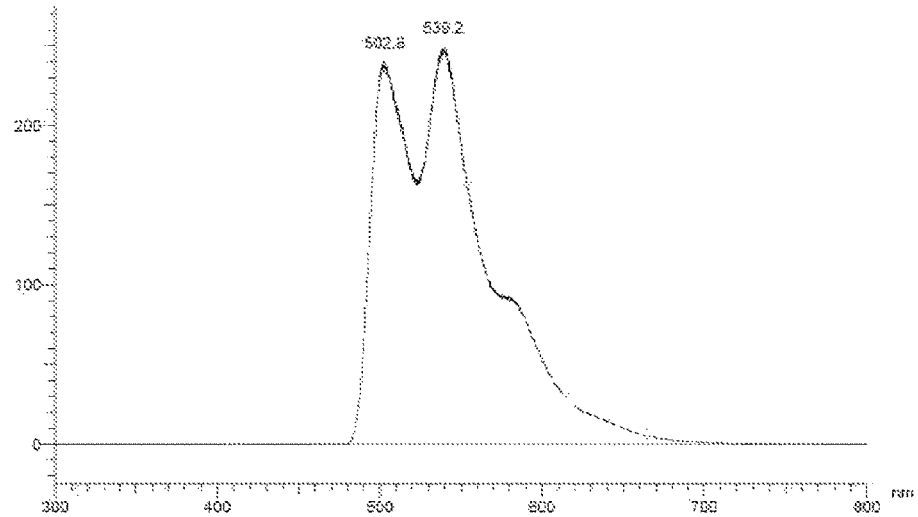

[Figure 56]
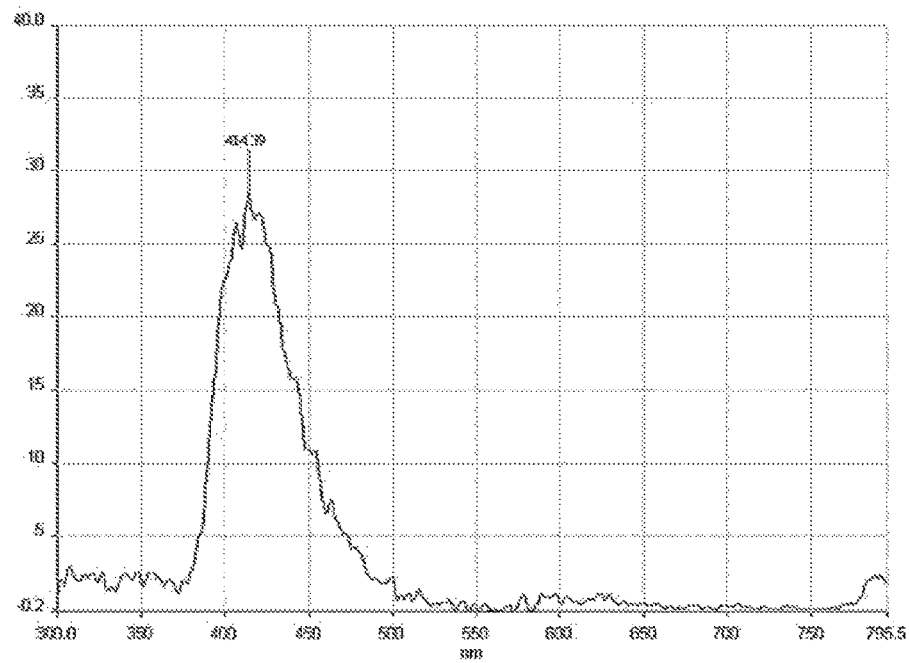
[Figure 57]
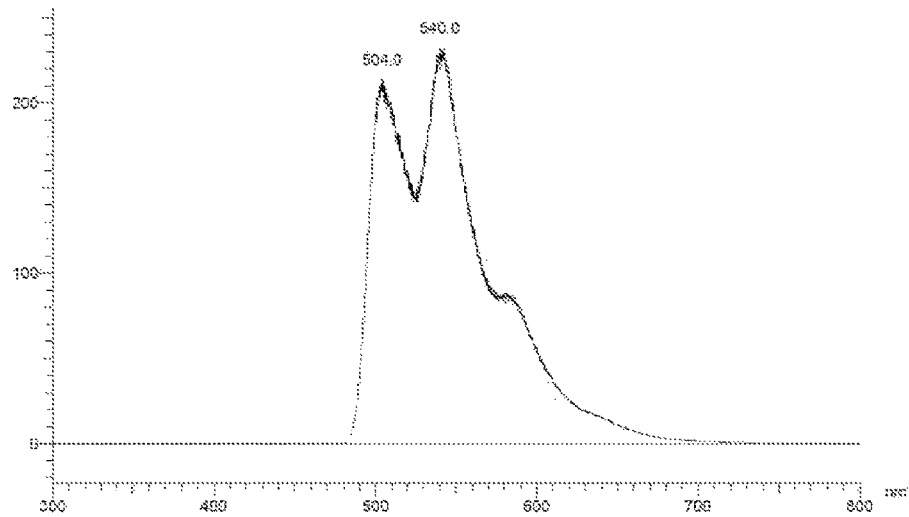

[Figure 58]
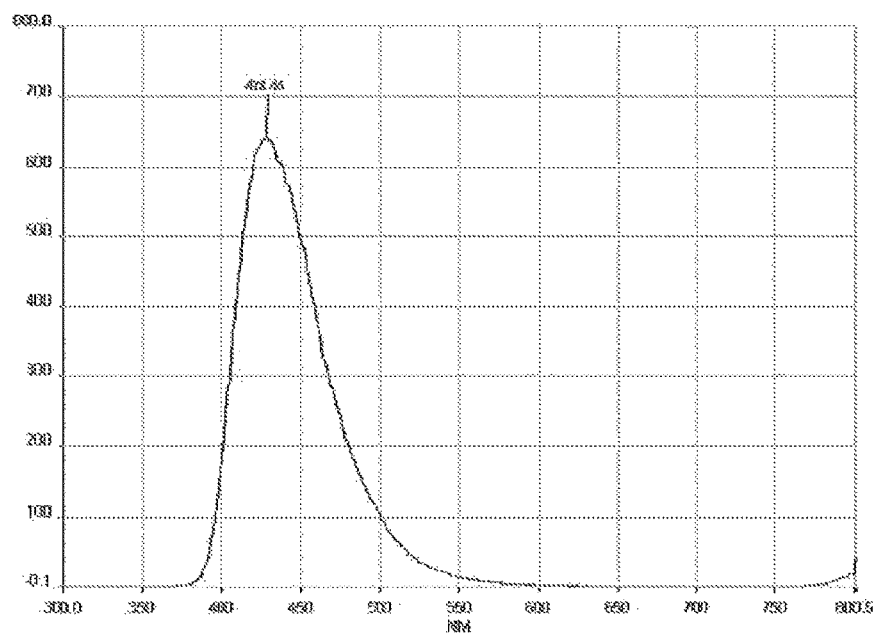
[Figure 59]
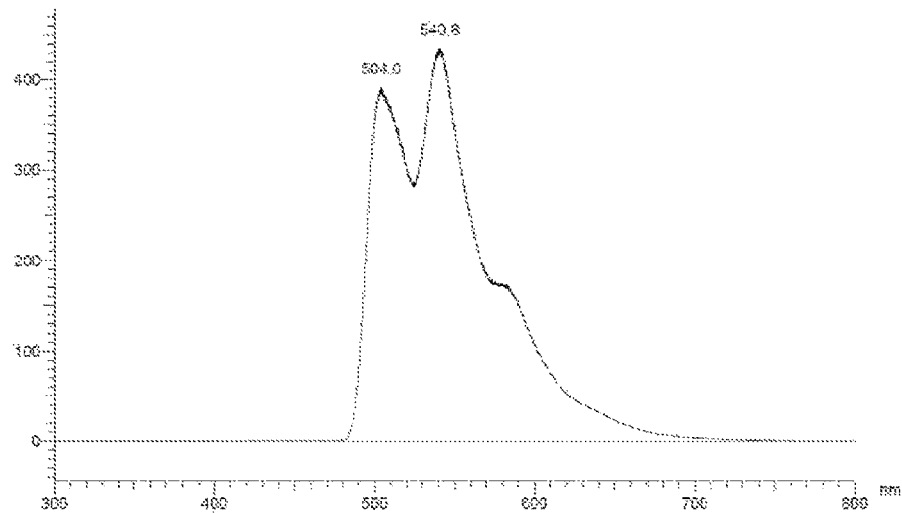

HETEROCYCLIC COMPOUND AND ORGANIC LIGHT EMITTING DEVICE USING SAME

CROSS-REFERENCE TO RELATED APPLICATIONS

This application claims priority to and the benefit of Korean Patent Application No. 10-2013-0164764 and 10-2014-0127878 filed in the Korean Intellectual Property Office on Dec. 27, 2013 and Sep. 24, 2014, the entire contents of which are incorporated herein by reference.

TECHNICAL FIELD

The present invention relates to a novel heterocyclic compound and an organic light emitting device including the same.

BACKGROUND ART

An electroluminescent device is a self-luminous display device, and has advantages in that the device has a wide viewing angle, an excellent contrast, and quick response time.

An organic light emitting device has a structure in which an organic thin film is arranged between two electrodes. When voltage is applied to an organic light emitting device having such a structure, light is emitted by electrons and holes injected from the two electrodes being dissipated after the electrons and holes are bonded and make a pair in the organic thin film. The organic thin film may be formed as monolayer or a multilayer as necessary.

Materials of the organic thin film may have a light emitting function as necessary. For example, as a material of the organic thin film, compounds capable of forming a light emitting layer alone may be used, or compounds capable of performing as a host or a dopant of a host-dopant-based light emitting layer may also be used. In addition to these, compounds capable of performing hole injection, hole transport, electron blocking, hole blocking, electron transport, electron injection, or the like, may also be used as a material of the organic thin film.

There have been continuous demands for the development of organic thin film materials in order to improve the performance, life span, or efficiency of an organic light emitting device.

SUMMARY OF THE INVENTION

The present invention has been made in an effort to provide a novel heterocyclic compound and an organic light emitting device including the same.

An exemplary embodiment of the present invention provides a compound of the following chemical formula 1:

[Chemical Formula 1]

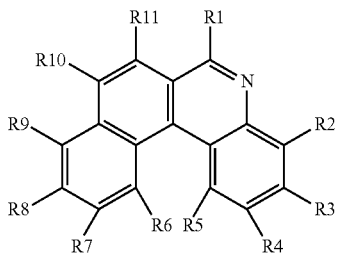

wherein in the chemical formula 1,

R1 is substituted or unsubstituted $C_6$ to $C_{60}$ monocyclic or polycyclic aryl; or substituted or unsubstituted $C_2$ to $C_{60}$ monocyclic or polycyclic heteroaryl;

R2 to R11 are the same as or different from each other, and are each independently one selected from the group consisting of hydrogen; deuterium; halogen; linear or branched substituted or unsubstituted $C_1$ to $C_{60}$ alkyl; linear or branched substituted or unsubstituted $C_2$ to $C_{60}$ alkenyl; linear or branched substituted or unsubstituted $C_2$ to $C_{60}$ alkynyl; linear or branched substituted or unsubstituted $C_1$ to $C_{60}$ alkoxy; linear or branched substituted or unsubstituted $C_6$ to $C_{60}$ aryloxy; substituted or unsubstituted $C_3$ to $C_{60}$ monocyclic or polycyclic cycloalkyl; substituted or unsubstituted $C_2$ to $C_{60}$ monocyclic or polycyclic heterocycloalkyl; substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R"; —P(=O)RR'; substituted or unsubstituted $C_1$ to $C_{20}$ alkylamine; substituted or unsubstituted $C_6$ to $C_{60}$ monocyclic or polycyclic arylamine; and substituted or unsubstituted $C_2$ to $C_{60}$ monocyclic or polycyclic heteroarylamine; and R, R', and R" are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

Another exemplary embodiment of the present invention provides an organic light emitting device including: an anode; a cathode; and one or more organic material layers provided between the anode and the cathode, wherein one or more of the organic material layers include the compound of the chemical formula 1.

According to the exemplary embodiments of the present invention, a compound described in the present specification may be used as a material of an organic material layer of an organic light emitting device. The compound may be used as a hole injection material, a hole transport material, a light emitting material, a hole blocking material, an electron transport material, an electron injection material, or the like, in an organic light emitting device. Further, the compound may be used as a host material of a phosphorescent light emitting layer in an organic light emitting device.

BRIEF DESCRIPTION OF THE DRAWINGS

FIGS. 1 to 3 illustrate examples of laminating order of electrodes and organic material layers of an organic light emitting device according to exemplary embodiments of the present invention.

FIG. 4 is a graph illustrating a PL spectrum of a compound 1 at a wavelength of 259 nm.

FIG. 5 is a graph illustrating an LTPL spectrum of the compound 1 at a wavelength of 388 nm.

FIG. 6 is a graph illustrating a PL spectrum of a compound 75 at a wavelength of 271 nm.

FIG. 7 is a graph illustrating an LTPL spectrum of the compound 75 at a wavelength of 356 nm.

FIG. 8 is a graph illustrating a PL spectrum of a compound 100 at a wavelength of 281 nm.

FIG. 9 is a graph illustrating an LTPL spectrum of the compound 100 at a wavelength of 381 nm.

FIG. 10 is a graph illustrating a PL spectrum of a compound 106 at a wavelength of 317 nm.

FIG. 11 is a graph illustrating an LTPL spectrum of the compound 106 at a wavelength of 381 nm.

FIG. 12 is a graph illustrating a PL spectrum of a compound 112 at a wavelength of 267 nm.

FIG. 13 is a graph illustrating an LTPL spectrum of the compound 112 at a wavelength of 323 nm.

FIG. 14 is a graph illustrating a PL spectrum of a compound 124 at a wavelength of 284 nm.

FIG. 15 is a graph illustrating an LTPL spectrum of the compound 124 at a wavelength of 382 nm.

FIG. 16 is a graph illustrating a PL spectrum of a compound 168 at a wavelength of 305 nm.

FIG. 17 is a graph illustrating an LTPL spectrum of the compound 168 at a wavelength of 387 nm.

FIG. 18 is a graph illustrating a PL spectrum of a compound 189 at a wavelength of 284 nm.

FIG. 19 is a graph illustrating an LTPL spectrum of the compound 189 at a wavelength of 284 nm.

FIG. 20 is a graph illustrating a PL spectrum of a compound 201 at a wavelength of 282 nm.

FIG. 21 is a graph illustrating an LTPL spectrum of the compound 201 at a wavelength of 282 nm.

FIG. 22 is a graph illustrating a AL spectrum of a compound 227 at a wavelength of 229 nm.

FIG. 23 is a graph illustrating an LTPL spectrum of the compound 227 at a wavelength of 323 nm.

FIG. 24 is a graph illustrating a PL spectrum of a compound 238 at a wavelength of 277 nm.

FIG. 25 is a graph illustrating an LTPL spectrum of the compound 238 at a wavelength of 382 nm.

FIG. 26 is a graph illustrating a PL spectrum of a compound 325 at a wavelength of 270 nm.

FIG. 27 is a graph illustrating an LTPL spectrum of the compound 325 at a wavelength of 381 nm.

FIG. 28 is a graph illustrating a PL spectrum of a compound 365 at a wavelength of 285 nm.

FIG. 29 is a graph illustrating an LTPL spectrum of the compound 365 at a wavelength of 381 nm.

FIG. 30 is a graph illustrating a PL spectrum of a compound 390 at a wavelength of 283 nm.

FIG. 31 is a graph illustrating an LTPL spectrum of the compound 390 at a wavelength of 381 nm.

FIG. 32 is a graph illustrating a PL spectrum of a compound 457 at a wavelength of 321 nm.

FIG. 33 is a graph illustrating an LTPL spectrum of the compound 457 at a wavelength of 321 nm.

FIG. 34 is a graph illustrating a PL spectrum of a compound 492 at a wavelength of 285 nm.

FIG. 35 is a graph illustrating an LTPL spectrum of the compound 492 at a wavelength of 381 nm.

FIG. 36 is a graph illustrating a PL spectrum of a compound 504 at a wavelength of 223 nm.

FIG. 37 is a graph illustrating an LTPL spectrum of the compound 504 at a wavelength of 387 nm.

FIG. 38 is a graph illustrating a PL spectrum of a compound 530 at a wavelength of 277 nm.

FIG. 39 is a graph illustrating an LTPL spectrum of the compound 530 at a wavelength of 387 nm.

FIG. 40 is a graph illustrating a PL spectrum of a compound 566 at a wavelength of 294 nm.

FIG. 41 is a graph illustrating an LTPL spectrum of the compound 566 at a wavelength of 387 nm.

FIG. 42 is a graph illustrating a PL spectrum of a compound 655 at a wavelength of 254 nm.

FIG. 43 is a graph illustrating an LTPL spectrum of the compound 655 at a wavelength of 370 nm.

FIG. 44 is a graph illustrating a PL spectrum of a compound 758 at a wavelength of 311 nm.

FIG. 45 is a graph illustrating an LTPL spectrum of the compound 758 at a wavelength of 282 nm.

FIG. 46 is a graph illustrating a PL spectrum of a compound 760 at a wavelength of 301 nm.

FIG. 47 is a graph illustrating an LTPL spectrum of the compound 760 at a wavelength of 388 nm.

FIG. 48 is a graph illustrating a PL spectrum of a compound 762 at a wavelength of 260 nm.

FIG. 49 is a graph illustrating an LTPL spectrum of the compound 762 at a wavelength of 290 nm.

FIG. 50 is a graph illustrating a PL spectrum of a compound 784 at a wavelength of 282 nm.

FIG. 51 is a graph illustrating an LTPL spectrum of the compound 784 at a wavelength of 382 nm.

FIG. 52 is a graph illustrating a PL spectrum of a compound 802 at a wavelength of 257 nm.

FIG. 53 is a graph illustrating an LTPL spectrum of the compound 802 at a wavelength of 381 nm.

FIG. 54 is a graph illustrating a PL spectrum of a compound 809 at a wavelength of 280 nm.

FIG. 55 is a graph illustrating an LTPL spectrum of the compound 809 at a wavelength of 381 nm.

FIG. 56 is a graph illustrating a PL spectrum of a compound 812 at a wavelength of 239 nm.

FIG. 57 is a graph illustrating an LTPL spectrum of the compound 812 at a wavelength of 382 nm.

FIG. 58 is a graph illustrating a PL spectrum of a compound 815 at a wavelength of 275 nm.

FIG. 59 is a graph illustrating an LTPL spectrum of the compound 815 at a wavelength of 362 nm.

EXPLANATION OF SYMBOLS

100 Substrate
200 Anode
300 Organic material layer
301 Hole injection layer
302 Hole transport layer
303 Light emitting layer
304 Hole blocking layer
305 Electron transport layer
306 Electron injection layer
400 Cathode

DETAILED DESCRIPTION

Hereinafter, the present invention will be described in detail.

A compound described in the present specification may be expressed by the chemical formula 1. To be specific, the compound of the chemical formula 1 may be used as a material of an organic material layer of an organic light emitting device due to the above-described structural properties of a core structure and a substituent.

In the present specification, the term "substituted or unsubstituted" refers to a group that may be substituted or may not be further substituted with one or more substituents selected from the group consisting of linear or branched $C_1$ to $C_{60}$ alkyl; linear or branched $C_2$ to $C_{60}$ alkenyl; linear or branched $C_2$ to $C_{60}$ alkynyl; $C_3$ to $C_{60}$ monocyclic or polycyclic cycloalkyl; $C_2$ to $C_{60}$ monocyclic or polycyclic heterocycloalkyl; $C_6$ to $C_{60}$ monocyclic or polycyclic aryl; $C_2$ to $C_{60}$ monocyclic or polycyclic heteroaryl; —SiRR'R"; —P(=O)RR'; $C_1$ to $C_{20}$ alkylamine; $C_6$ to $C_{60}$ monocyclic or polycyclic arylamine; and $C_2$ to $C_{60}$ monocyclic or polycyclic or polycyclic heteroarylamine, or a substituent bonded to two or more selected from the substituents. For example, "the substituent bonded to two or more substituents" may be a biphenyl group. That is, the biphenyl group may be an aryl group or can be construed as a substituent bonded to two phenyl groups. The R, R', and R" are the same as or different from each other, and are each independently one selected from the group consisting of hydrogen; deuterium; linear or branched $C_1$ to $C_{60}$ alkyl substituted or unsubstituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; $C_6$ to $C_{60}$ monocyclic or polycyclic aryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; and $C_2$ to $C_{60}$ monocyclic or polycyclic heteroaryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl.

According to an exemplary embodiment of the present invention, the term "substituted or unsubstituted" refers to a group that may be substituted or may not be further substituted with one or more substituents selected from the group consisting of linear or branched $C_1$ to $C_{60}$ alkyl; $C_6$ to $C_{60}$ monocyclic or polycyclic aryl; $C_2$ to $C_{60}$ monocyclic or polycyclic heteroaryl; —SiRR'R"; and —P(=O)RR', or a substituent bonded to two or more selected from the substituents, and R, R', and R" are the same as or different from each other, and are each independently one selected from the group consisting of hydrogen; deuterium; linear or branched $C_1$ to $C_{60}$ alkyl substituted or unsubstituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; $C_6$ to $C_{60}$ monocyclic or polycyclic aryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; and $C_2$ to $C_{60}$ monocyclic or polycyclic heteroaryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl. In the present specification, alkyl includes linear or branched alkyl having 1 to 60 carbon atoms, and may be further substituted with other substituents. The number of carbon atoms of the alkyl may be 1 to 60, specifically 1 to 40, and more specifically 1 to 20.

In the present specification, alkenyl includes linear or branched alkenyl having 2 to 60 carbon atoms, and may be further substituted with other substituents. The number of carbon atoms of the alkenyl may be 2 to 60, specifically 2 to 40, and more specifically 2 to 20.

In the present specification, alkynyl includes linear or branched alkynyl having 2 to 60 carbon atoms, and may be further substituted with other substituents. The number of carbon atoms of the alkynyl may be 2 to 60, specifically 2 to 40, and more specifically 2 to 20.

In the present specification, cycloalkyl includes monocyclic or polycyclic cycloalkyl having 3 to 60 carbon atoms, and may be further substituted with other substituents. Herein, the term "polycyclic" means a group in which cycloalkyl is directly bonded to or fused with other ring groups. Herein, the term "other ring groups" may be cycloalkyl, but may also be other types of ring groups, for example, heterocycloalkyl, aryl, heteroaryl, or the like. The number of carbon atoms of the cycloalkyl may be 3 to 60, specifically 3 to 40, and more specifically 5 to 20.

In the present specification, heterocycloalkyl includes S, Se, N, or Si as a heteroatom, includes monocyclic or polycyclic heterocycloalkyl having 2 to 60 carbon atoms, and may be further substituted with other substituents. Herein, the term "polycyclic" means a group in which heterocycloalkyl is directly bonded to or fused with other ring groups. Herein, the term "other ring groups" may be heterocycloalkyl, but may also be other types of ring groups, for example, cycloalkyl, aryl, heteroaryl, or the like. The number of carbon atoms of the heterocycloalkyl may be 2 to 60, specifically 2 to 40, and more specifically 3 to 20.

In the present specification, aryl includes monocyclic or polycyclic aryl having 6 to 60 carbon atoms, and may be further substituted with other substituents. Herein, the term "polyclic" means a group in which aryl is directly bonded to or fused with other ring groups. Herein, the term "other ring groups" may be aryl, but may also be other types of ring groups, for example, cycloalkyl, heterocycloalkyl, heteroaryl, or the like. The aryl includes a Spiro group. The number of carbon atoms of the aryl may be 6 to 60, specifically 6 to 40, and more specifically 6 to 25. Specific examples of the aryl include phenyl, biphenyl, triphenyl, naphthyl, anthracenyl, chrysenyl, benzo chrysenyl, phenanthrenyl, perylenyl, fluoranthenyl, triphenylenyl, phenalenyl, pyrenyl, tetracenyl, pentacenyl, indenyl, acenaphthylenyl, fluorenyl, spirobifluorenyl, or fused rings thereof, but are not limited thereto.

In the present specification, the spiro group is a group including a spiro structure, and may have 15 to 60 carbon atoms. For example, the Spiro group may include a structure in which a 2,3-dihydro-1H-indene group or a cyclohexane group is spiro-bonded to a fluorene group. To be specific, the spiro group includes a group of the following structural formulas.

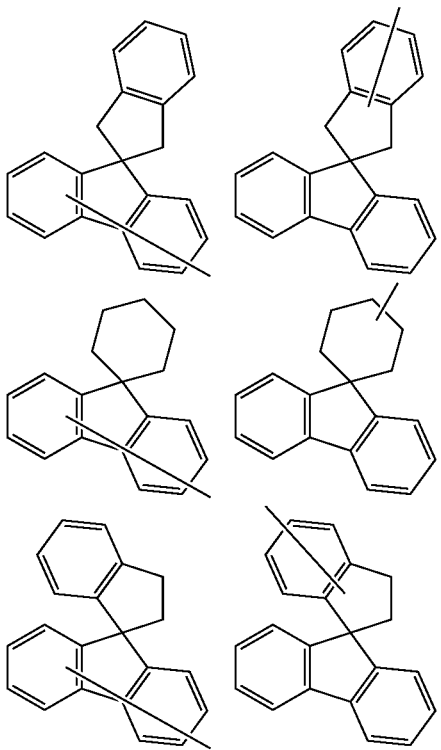

In the present specification, heteroaryl includes S, O, Se, N, or Si as a heteroatom, includes monocyclic or polycyclic heteroaryl having 2 to 60 carbon atoms, and may be further substituted with other substituents. Herein, the term "polycyclic" means a group in which heteroaryl is directly bonded to or fused with other ring groups. Herein, the term "other ring groups" may be heteroaryl, but may also be other types of ring groups, for example, cycloalkyl, heterocycloalkyl, aryl, or the like. The number of carbon atoms of the heteroaryl may be 2 to 60, specifically 2 to 40, and more specifically 3 to 25. Specific examples of the heteroaryl include pyridyl, imidazol pyridyl, pyrolyl, pyrimidyl, pyridazinyl, furanyl, a thiophene group, imidazolyl, benzimidazolyl, pyrazolyl, oxazolyl, isoxazolyl, thiazolyl, benzo thiazolyl, isothiazolyl, triazolyl, furazanyl, oxadiazolyl, thiadiazolyl, dithiazolyl, tetrazolyl, pyranyl, thiopyranyl, diazinyl, oxazinyl, thiazinyl, dioxynyl, triazinyl, tetrazinyl, quinolinyl, isoquinolinyl, quinazolinyl, isoquinazolinyl, pyrazoloquinazolinyl, imidazoquinazolinyl, naphtyridyl, acridinyl, dibenzo acridinyl, phenanthridinyl, phenanthrolinyl, imidazopyridinyl, diazanaphthalenyl, triazaindene, indolyl, indolizinyl, benzothiazolyl, benzoxazolyl, benzimidazolyl, a benzothiophene group, a benzofuran group, a dibenzothiophene group, a dibenzofuran group, carbazolyl, benzocarbazolyl, dibenzocarbazolyl, phenazinyl, benzoxylolyl, dibenzoxylolyl, spirobidibenzoxylolyl, or fused rings thereof, but are not limited thereto.

In the present specification, arylene and heteroarylene can be construed in the same manner as the above-described aryl and heteroaryl, respectively, except that arylene and heteroarylene are divalent groups.

According to an exemplary embodiment of the present invention, R1 is substituted or unsubstituted $C_6$ to $C_{60}$ monocyclic or polycyclic aryl; or substituted or unsubstituted $C_2$ to $C_{60}$ monocyclic or polycyclic heteroaryl.

According to an exemplary embodiment of the present invention, R1 is substituted or unsubstituted $C_6$ to $C_{20}$ monocyclic or polycyclic aryl; or substituted or unsubstituted $C_2$ to $C_{20}$ monocyclic or polycyclic heteroaryl.

According to an exemplary embodiment of the present invention, R1 is substituted or unsubstituted $C_6$ to $C_{20}$ monocyclic or polycyclic aryl.

According to an exemplary embodiment of the present invention, R1 is substituted or unsubstituted phenyl, substituted or unsubstituted naphthyl, substituted or unsubstituted biphenyl, or substituted or unsubstituted phenanthrenyl.

According to an exemplary embodiment of the present invention, R1 is phenyl, naphthyl, biphenyl, or phenanthrenyl, and may further include a substituent.

According to an exemplary embodiment of the present invention, R2 to R11 are hydrogen or deuterium.

According to an exemplary embodiment of the present invention, R2 to R11 are hydrogen.

According to an exemplary embodiment of the present invention, at least one of R2 to R11 is selected from the group consisting of linear or branched substituted or unsubstituted $C_1$ to $C_{60}$ alkyl; linear or branched substituted or unsubstituted $C_2$ to $C_{60}$ alkenyl; linear or branched substituted or unsubstituted $C_2$ to $C_{60}$ alkynyl; linear or branched substituted or unsubstituted $C_1$ to $C_{60}$ alkoxy; linear or branched substituted or unsubstituted $C_6$ to $C_{60}$ aryloxy; substituted or unsubstituted $C_3$ to $C_{60}$ monocyclic or polycyclic cycloalkyl; substituted or unsubstituted $C_2$ to $C_{60}$ monocyclic or polycyclic heterocycloalkyl; substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R"; —P(=O)RR'; substituted or unsubstituted $C_1$ to $C_{20}$ alkylamine; substituted or unsubstituted $C_6$ to $C_{60}$ monocyclic or polycyclic arylamine; and substituted or unsubstituted $C_2$ to $C_{60}$ monocyclic or polycyclic heteroarylamine, and R, R', and R" are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

According to an exemplary embodiment of the present invention, at least one of R2 to R11 is selected from the group consisting of substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R"; —P(=O)RR'; substituted or unsubstituted $C_1$ to $C_{20}$ alkylamine; substituted or unsubstituted $C_6$ to $C_{60}$ monocyclic or polycyclic arylamine; and substituted or unsubstituted $C_2$ to $C_{60}$ monocyclic or polycyclic heteroarylamine, and R, R', and R" are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

According to an exemplary embodiment of the present invention, at least one of R2 to R11 is substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R"; or —P(=O)RR', and R, R', and R" are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

According to an exemplary embodiment of the present invention, at least one of R2 to R11 is substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R"; or —P(=O)RR', and R, R', and R" are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl, and the other substituents are hydrogen or deuterium.

According to an exemplary embodiment of the present invention, one of R2 to R11 is substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R"; or —P(=O)RR', and R, R', and R" are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl, and the other substituents are hydrogen or deuterium.

According to an exemplary embodiment of the present invention, the R10 is a hydrogen; deuterium; substituted or unsubstituted $C_6$ to $C_{60}$ monocyclic or polycyclic aryl; substituted or unsubstituted $C_2$ to $C_{60}$ monocyclic or polycyclic heteroaryl; SiRR'R"; or —P(=O)RR', and the R, R', and R" are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

According to an exemplary embodiment of the present invention, at least one of the R1 to R11 is -(A)m-(B)n, A is selected from the group consisting of substituted or unsubstituted $C_6$ to $C_{60}$ monocyclic or polycyclic arylene; and substituted or unsubstituted $C_2$ to $C_{60}$ monocyclic or polycyclic heteroarylene, B is selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R''; and —P(=O)RR', and the R, R', and R'' are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl, m is an integer of 1 to 5, n is an integer of 1 to 3, and when m and n are independently integers of 2 or more, multiple A and B are the same as or different from each other.

According to an exemplary embodiment of the present invention, with respect to the A and B, the term "substituted or unsubstituted" refers to a group that may be substituted or may not be further substituted with a substituent selected from the group consisting of linear or branched $C_1$ to $C_{60}$ alkyl; $C_6$ to $C_{60}$ monocyclic or polycyclic aryl; $C_2$ to $C_{60}$ monocyclic or polycyclic heteroaryl.

According to an exemplary embodiment of the present invention, among the R1 to R11, the substituent which is not -(A)m-(B)n may be selected from the group consisting of hydrogen; deuterium; linear or branched $C_1$ to $C_{60}$ alkyl; $C_6$ to $C_{60}$ monocyclic or polycyclic aryl; $C_2$ to $C_{60}$ monocyclic or polycyclic heteroaryl; —SiRR'R''; or —P(=O)RR', and the R, R', and R'' are the same as or different from each other, and are each independently one selected from the group consisting of hydrogen; deuterium; linear or branched $C_1$ to $C_{60}$ alkyl; $C_6$ to $C_{60}$ monocyclic or polycyclic aryl; and $C_2$ to $C_{60}$ monocyclic or polycyclic heteroaryl.

According to an exemplary embodiment of the present invention, at least one of the R1 to R11 is -(A)m-(B)n, A is selected from the group consisting of $C_6$ to $C_{60}$ monocyclic or polycyclic arylene unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; and $C_2$ to $C_{60}$ monocyclic or polycyclic heteroarylene unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl, B is selected from the group consisting of hydrogen; deuterium; linear or branched $C_1$ to $C_{60}$ alkyl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; $C_6$ to $C_{60}$ monocyclic or polycyclic aryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; $C_2$ to $C_{60}$ monocyclic or polycyclic heteroaryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; —SiRR'R''; and —P(=O)RR', and the R, R', and R'' are the same as or different from each other, and are each independently one selected from the group consisting of hydrogen; deuterium; linear or branched $C_1$ to $C_{60}$ alkyl substituted or unsubstituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; $C_6$ to $C_{60}$ monocyclic or polycyclic aryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; and $C_2$ to $C_{60}$ monocyclic or polycyclic heteroaryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl, m is an integer of 1 to 5, n is an integer of 1 to 3, when m and n are independently integers of 2 or more, multiple A and B are the same as or different from each other, and the other substituent is selected from the group consisting of hydrogen; deuterium; linear or branched $C_1$ to $C_{60}$ alkyl; $C_6$ to $C_{60}$ monocyclic or polycyclic aryl; $C_2$ to $C_{60}$ monocyclic or polycyclic heteroaryl; —SiRR'R''; or —P(=O)RR', and the R, R', and R'' are the same as or different from each other, and are each independently one selected from the group consisting of hydrogen; deuterium; linear or branched $C_1$ to $C_{60}$ alkyl; $C_6$ to $C_{60}$ monocyclic or polycyclic aryl; and $C_2$ to $C_{60}$ monocyclic or polycyclic heteroaryl.

According to an exemplary embodiment of the present invention, A is selected from the group consisting of substituted or unsubstituted $C_6$ to $C_{30}$ monocyclic or polycyclic arylene; and substituted or unsubstituted $C_2$ to $C_{30}$ monocyclic or polycyclic heteroarylene.

According to an exemplary embodiment of the present invention, B is selected from the group consisting of hydrogen; deuterium; linear or branched substituted or unsubstituted $C_1$ to $C_{60}$ alkyl; substituted or unsubstituted $C_6$ to $C_{30}$ monocyclic or polycyclic aryl; substituted or unsubstituted $C_2$ to $C_{30}$ monocyclic or polycyclic heteroaryl; —SiRR'R''; and —P(=O)RR', and the R, R', and R'' are the same as or different from each other, and are each independently one selected from the group consisting of linear or branched substituted or unsubstituted $C_1$ to $C_{30}$ alkyl; substituted or unsubstituted $C_6$ to $C_{30}$ monocyclic or polycyclic aryl; and substituted or unsubstituted $C_2$ to $C_{30}$ monocyclic or polycyclic heteroaryl.

According to an exemplary embodiment of the present invention, A may be substituted or unsubstituted $C_6$ to $C_{30}$ monocyclic to pentacyclic arylene. For example, the arylene may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with $C_1$ to $C_{10}$ alkyl; $C_6$ to $C_{30}$ aryl; or $C_2$ to $C_{30}$ heteroaryl.

According to an exemplary embodiment of the present invention, A may be substituted or unsubstituted $C_2$ to $C_{30}$ monocyclic to pentacyclic heteroarylene. The heteroarylene may include at least one selected from the group consisting of N, S, Si, and O as a heteroatom. For example, the heteroarylene may be selected from the group consisting of pyridylene, imidazopyridylene, pyrimidylene, triazinylene, carbazolylene, benzimidazo lylene, benzocarbazolylene, dibenzocarbazolylene, quinolinylene, isoquinolinylene, quinazolinylene, pyrazoloquinazolinylene, imidazoquinazolinylene, thiazolylene, benzothiazolylene, phenanthrolinylene, phenanthridinylene, dibenzo acridinylene, xylolylene, benzoxylolylene, dibenzoxylolylene, and spirobidibenzoxylolylene, and may be further substituted with $C_1$ to $C_{10}$ alkyl; $C_6$ to $C_{30}$ aryl; or $C_2$ to $C_{30}$ heteroaryl.

According to an exemplary embodiment of the present invention, B may be substituted or unsubstituted $C_6$ to $C_{30}$ monocyclic to pentacyclic aryl. For example, the aryl may be selected from the group consisting of phenyl, biphenyl, naphthyl, anthracenyl, phenanthrenyl, triphenylenyl, chrysenyl, benzo chrysenyl, fluorenyl, and spirobifluorenyl, and may be further substituted with $C_1$ to $C_{10}$ alkyl; $C_6$ to $C_{30}$ aryl; or $C_2$ to $C_{30}$ heteroaryl.

According to an exemplary embodiment of the present invention, B may be substituted or unsubstituted $C_2$ to $C_{30}$ monocyclic to pentacyclic heteroaryl. The heteroaryl may include at least one selected from the group consisting of N, S, Si, and O as a heteroatom. For example, the heteroaryl may be selected from the group consisting of pyridyl, imidazopyridyl, pyrimidyl, triazinyl, carbazolyl, benzimidazolyl, benzocarbazolyl, dibenzocarbazolyl, quinolinyl, isoquinolinyl, quinazolinyl, pyrazoloquinazolinyl, imidazoquinazolinyl, thiazolyl, benzothiazolyl, phenanthrolinyl, phenanthridinyl, dibenzo acridinyl, xylolyl, benzoxylolyl, dibenzoxylolyl, and spirobidibenzoxylolyl, and may be further substituted with $C_1$ to $C_{10}$ alkyl; $C_6$ to $C_{30}$ aryl; or $C_2$ to $C_{30}$ heteroaryl.

According to an exemplary embodiment of the present invention, B may be —P(=O)RR', and the R and R' are the same as or different from each other, and may be each independently linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

According to an exemplary embodiment of the present invention, B may be —P(=O)RR', and the R and R' are the same as or different from each other, and may be each independently $C_6$ to $C_{30}$ monocyclic or polycyclic aryl; and $C_2$ to $C_{30}$ monocyclic or polycyclic heteroaryl, and may be further substituted with $C_1$ to $C_{10}$ alkyl; $C_6$ to $C_{30}$ aryl; or $C_2$ to $C_{30}$ heteroaryl.

According to an exemplary embodiment of the present invention, B may be —P(=O)RR', and the R and R' are the same as or different from each other, and may be each independently phenyl, biphenyl, naphthyl, or anthracenyl.

According to an exemplary embodiment of the present invention, B may be —SiRR'R", and the R, R', and R" are the same as or different from each other, and may be each independently linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

According to an exemplary embodiment of the present invention, B may be —SiRR'R", and the R, R', and R" are the same as or different from each other, and may be each independently $C_6$ to $C_{30}$ monocyclic or polycyclic aryl; and $C_2$ to $C_{30}$ monocyclic or polycyclic heteroaryl, and may be further substituted with $C_1$ to $C_{10}$ alkyl; $C_6$ to $C_{30}$ aryl; or $C_2$ to $C_{30}$ heteroaryl.

According to an exemplary embodiment of the present invention, B may be —SiRR'R", and the R, R', and R" are the same as or different from each other, and may be each independently phenyl, biphenyl, naphthyl, or anthracenyl.

According to an exemplary embodiment of the present invention, A may be selected from the group consisting of substituted or unsubstituted $C_6$ to $C_{60}$ monocyclic or polycyclic arylene; and substituted or unsubstituted $C_2$ to $C_{60}$ monocyclic or polycyclic heteroarylene, and B may be hydrogen or deuterium.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, pyridylene, imidazopyridylene, pyrimidylene, triazinylene, carbazolylene, benzimidazolylene, benzocarbazolylene, dibenzocarbazolylene, quinolinylene, isoquinolinylene, quinazolinylene, pyrazoloquinazolinylene, imidazoquinazolinylene, thiazolylene, benzothiazolylene, phenanthrolinylene, phenanthridinylene, dibenzo acridinylene, xylolylene, benzoxylolylene, dibenzoxylolylene, and spirobidibenzoxylolylene and may be further substituted with $C_1$ to $C_{10}$ alkyl; $C_6$ to $C_{30}$ aryl; or $C_2$ to $C_{30}$ heteroaryl, and B may be hydrogen or deuterium.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, pyridylene, imidazopyridylene, pyrimidylene, triazinylene, carbazolylene, benzimidazolylene, benzocarbazolylene, dibenzocarbazolylene, quinolinylene, isoquinolinylene, quinazolinylene, pyrazoloquinazolinylene, imidazoquinazolinylene, thiazolylene, benzothiazolylene, phenanthrolinylene, phenanthridinylene, dibenzo acridinylene, xylolylene, benzoxylolylene, dibenzoxylolylene, and spirobidibenzoxylolylene and may be further substituted with at least one substituent selected from the group consisting of methyl, ethyl, propyl, phenyl, biphenyl, naphthyl, anthracenyl, phenanthrenyl, pyridyl, and pyrimidyl, and B may be hydrogen or deuterium.

According to an exemplary embodiment of the present invention, A may be selected from the group consisting of substituted or unsubstituted $C_6$ to $C_{60}$ monocyclic or polycyclic arylene and substituted or unsubstituted $C_2$ to $C_{60}$ monocyclic or polycyclic heteroarylene, and B may be selected from the group consisting of substituted or unsubstituted $C_6$ to $C_{60}$ monocyclic or polycyclic aryl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, pyridylene, imidazopyridylene, pyrimidylene, triazinylene, carbazolylene, benzimidazolylene, benzocarbazolylene, dibenzocarbazolylene, quinolinylene, isoquinolinylene, quinazolinylene, pyrazoloquinazolinylene, imidazoquinazolinylene, thiazolylene, benzothiazolylene, phenanthrolinylene, phenanthridinylene, dibenzo acridinylene, xylolylene, benzoxylolylene, dibenzoxylolylene, and spirobidibenzoxylolylene and may be further substituted with $C_1$ to $C_{10}$ alkyl; $C_6$ to $C_{30}$ aryl; or $C_2$ to $C_{30}$ heteroaryl, and B may be selected from the group consisting of phenyl, biphenyl, naphthyl, anthracenyl, phenanthrenyl, triphenylenyl, chrysenyl, benzo chrysenyl, fluorenyl, and spirobifluorenyl and may be further substituted with $C_1$ to $C_{10}$ alkyl; $C_6$ to $C_{30}$ aryl; or $C_2$ to $C_{30}$ heteroaryl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, pyridylene, imidazopyridylene, pyrimidylene, triazinylene, carbazolylene, benzimidazolylene, benzocarbazolylene, dibenzocarbazolylene, quinolinylene, isoquinolinylene, quinazolinylene, pyrazoloquinazolinylene, imidazoquinazolinylene, thiazolylene, benzothiazolylene, phenanthrolinylene, phenanthridinylene, dibenzo acridinylene, xylolylene, benzoxylolylene, dibenzoxylolylene, and spirobidibenzoxylolylene and may be further substituted with at least one substituent selected from the group consisting of methyl, ethyl, propyl, phenyl, biphenyl, naphthyl, anthracenyl, phenanthrenyl, pyridyl, and pyrimidyl, and B may be selected from the group consisting of phenyl, biphenyl, naphthyl, anthracenyl, phenanthrenyl, triphenylenyl, chrysenyl, benzo chrysenyl, fluorenyl, and spirobifluorenyl and may be further substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of substituted or unsubstituted $C_6$ to $C_{60}$ monocyclic or polycyclic arylene and substituted or unsubstituted $C_2$ to $C_{60}$ monocyclic or polycyclic heteroarylene, and B may be selected from the group consisting of substituted or unsubstituted $C_2$ to $C_{60}$ monocyclic or polycyclic heteroaryl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, pyridylene, imidazopyridylene, pyrimidylene, triazinylene, carbazolylene, benzimidazolylene, benzocarbazolylene, dibenzocarbazolylene, quinolinylene, isoquinolinylene, quinazolinylene, pyrazoloquinazolinylene, imidazoquinazolinylene, thiazolylene, benzothiazolylene, phenanthrolinylene, phenanthridinylene, dibenzo acridinylene, xylolylene, benzoxylolylene, dibenzoxylolylene, and spirobidibenzoxylolylene and may be further substituted with $C_1$ to $C_{10}$ alkyl; $C_6$ to $C_{30}$ aryl; or $C_2$ to $C_{30}$ heteroaryl, and B may be selected from the group consisting of pyridyl, imidazopyridyl, pyrimidyl, triazinyl, carbazolyl, benzimidazolyl, benzocarbazolyl, dibenzocarbazolyl, quinolinyl, isoquinolinyl, quinazolinyl, pyrazoloquinazolinyl, imidazoquinazolinyl, thiazolyl, benzothiazolyl, phenanthrolinyl, phenanthridinyl, dibenzo acridinyl, xylolyl, benzoxylolyl, dibenzoxylolyl, and spirobidibenzoxylolyl, and may be further substituted with $C_1$ to $C_{10}$ alkyl; $C_6$ to $C_{30}$ aryl; or $C_2$ to $C_{30}$ heteroaryl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, pyridylene, imidazopyridylene, pyrimidylene, triazinylene, carbazolylene, benzimidazolylene, benzocarbazolylene, dibenzocarbazolylene, quinolinylene, isoquinolinylene, quinazolinylene, pyrazoloquinazolinylene, imidazoquinazolinylene, thiazolylene, benzothiazolylene, phenanthrolinylene, phenanthridinylene, dibenzo acridinylene, xylolylene, benzoxylolylene, dibenzoxylolylene, and spirobidibenzoxylolylene and may be further substituted with at least one substituent selected from the group consisting of methyl, ethyl, propyl, phenyl, biphenyl, naphthyl, anthracenyl, phenanthrenyl, pyridyl, and pyrimidyl, and B may be selected from the group consisting of pyridyl, imidazopyridyl, pyrimidyl, triazinyl, carbazolyl, benzimidazolyl, benzocarbazolyl, dibenzocarbazolyl, quinolinyl, isoquinolinyl, quinazolinyl, pyrazoloquinazolinyl, imidazoquinazolinyl, thiazolyl, benzothiazolyl, phenanthrolinyl, phenanthridinyl, dibenzo acridinyl, xylolyl, benzoxylolyl, dibenzoxylolyl, and spirobidibenzoxylolyl, and may be further substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be substituted or unsubstituted $C_6$ to $C_{60}$ monocyclic or polycyclic arylene, B may be —SiRR'R", and the R, R', and R" are the same as or different from each other, and may be each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with $C_1$ to $C_{10}$ alkyl; $C_6$ to $C_{30}$ aryl; or $C_2$ to $C_{30}$ heteroaryl, and B is —SiRR'R", and the R, R', and R" are the same as or different from each other, and may be each independently one selected from the group consisting of phenyl, biphenyl, naphthyl, and anthracenyl, and may be further substituted with $C_1$ to $C_{10}$ alkyl; $C_6$ to $C_{30}$ aryl; or $C_2$ to $C_{30}$ heteroaryl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, and B is —SiRR'R", and the R, R', and R" are the same as or different from each other, and may be each independently one selected from the group consisting of phenyl, biphenyl, naphthyl, and anthracenyl, and may be further substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be substituted or unsubstituted $C_6$ to $C_{60}$ monocyclic or polycyclic arylene, B may be —P(=O)RR', and the R and R' are the same as or different from each other, and may be each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with $C_1$ to $C_{10}$ alkyl; $C_6$ to $C_{30}$ aryl; or $C_2$ to $C_{30}$ heteroaryl, and B is —P(=O)RR', and the R and R' are the same as or different from each other, and may be each independently one selected from the group consisting of phenyl, biphenyl, naphthyl, and anthracenyl, and may be further substituted with $C_1$ to $C_{10}$ alkyl; $C_6$ to $C_{30}$ aryl; or $C_2$ to $C_{30}$ heteroaryl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, and B is —P(=O)RR', and the R and R' are the same as or different from each other, and may be each independently one selected from the group consisting of phenyl, biphenyl, naphthyl, and anthracenyl, and may be further substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A is substituted or unsubstituted $C_6$ to $C_{60}$ monocyclic or polycyclic arylene, and B is substituted or unsubstituted N-containing $C_2$ to $C_{60}$ monocyclic or polycyclic heteroaryl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be pyridyl substituted or unsubstituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with $C_1$ to $C_{10}$ alkyl; $C_6$ to $C_{30}$ aryl; or $C_2$ to $C_{30}$ heteroaryl, and B may be pyrimidyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be imidazopyridyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be triazinyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be carbazolyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be quinolinyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be quinazolinyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be pyrazoloquinazolinyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be phenanthrolinyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be benzimidazolyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be benzothiazolyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, A may be selected from the group consisting of phenylene, biphenylene, naphthylene, anthracenylene, phenanthrenylene, triphenylenylene, chrysenylene, benzo chrysenylene, fluorenylene, and spirobifluorenylene, and may be further substituted with at least one substituent selected from the group consisting of methyl, ethyl, propyl, phenyl, biphenyl, naphthyl, anthracenyl, phenanthrenyl, pyridyl, and pyrimidyl, B may be dibenzo acridinyl unsubstituted or substituted with at least one substituent selected from the group consisting of methyl, ethyl, propyl, phenyl, biphenyl, naphthyl, anthracenyl, phenanthrenyl, pyridyl, and pyrimidyl.

According to an exemplary embodiment of the present invention, the R1 is -(A)m-(B)n, and the A, B, m, and n are the same as described above.

According to an exemplary embodiment of the present invention, at least two of the R1 to R11 are -(A)m-(B)n, and the A, B, m, and n are the same as described above.

According to an exemplary embodiment of the present invention, when two or more of the R1 to R11 are -(A)m-(B)n, A, B, m, and n may be one of identical to or different from each other in the two or more -(A)m-(B)n.

According to an exemplary embodiment of the present invention, the R1 and at least one of the R2 to R11 are -(A)m-(B)n, and the A, B, m, and n are the same as described above.

According to an exemplary embodiment of the present invention, at least one of the R1 to R10 is -(A)m-(B)n, and the A, B, m, and n are the same as described above.

According to an exemplary embodiment of the present invention, the R1 to R10 are -(A)m-(B)n, and the A, B, m, and n are the same as described above.

According to an exemplary embodiment of the present invention, the other substituent than -(A)m-(B)n among the R1 to R11 is hydrogen may be hydrogen or deuterium.

According to an exemplary embodiment of the present invention, m is an integer of 1, 2, or 3.

According to an exemplary embodiment of the present invention, n is an integer of 1 or 2.

According to an exemplary embodiment of the present invention, the chemical formula 1 can be selected from the following chemical formulas:

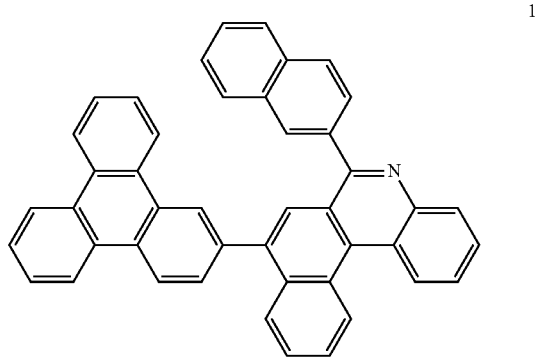

1

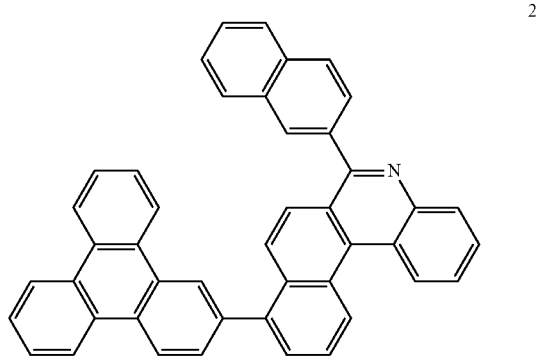

2

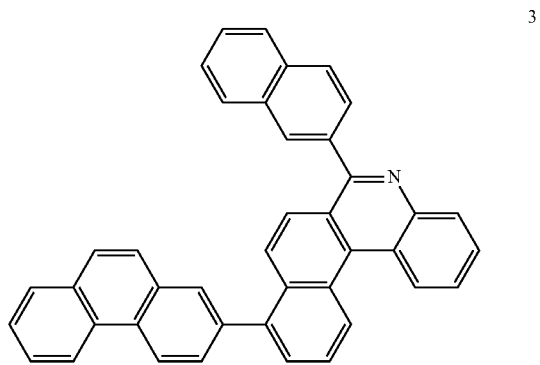

3

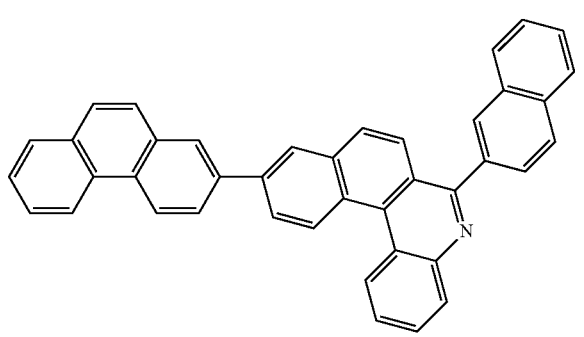

4

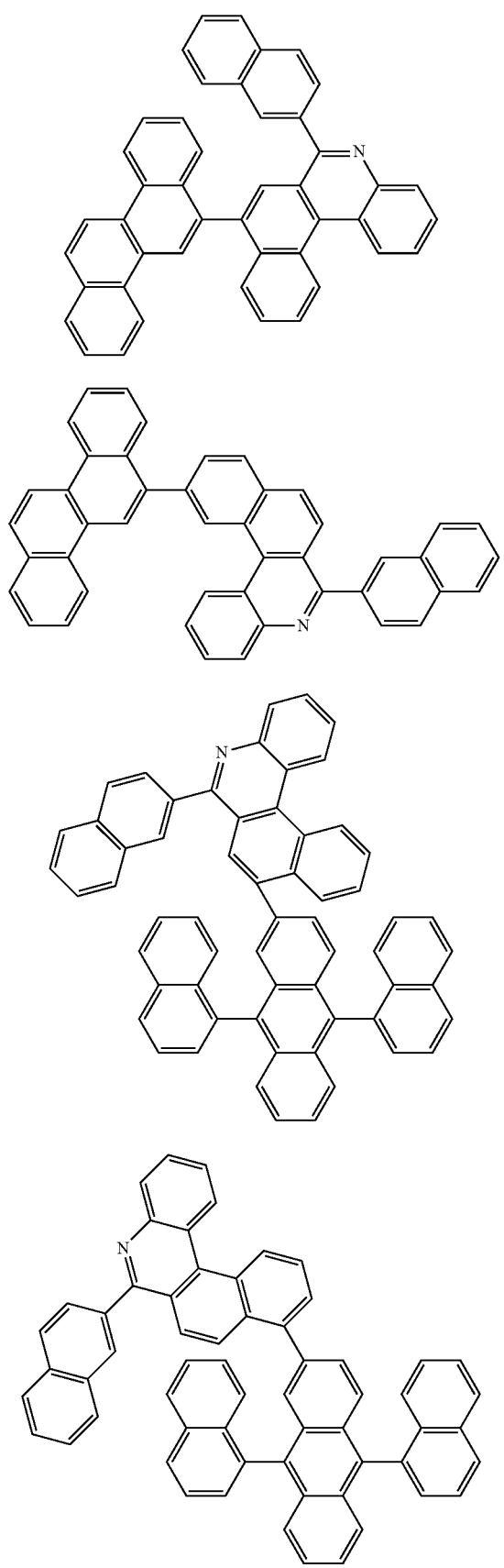
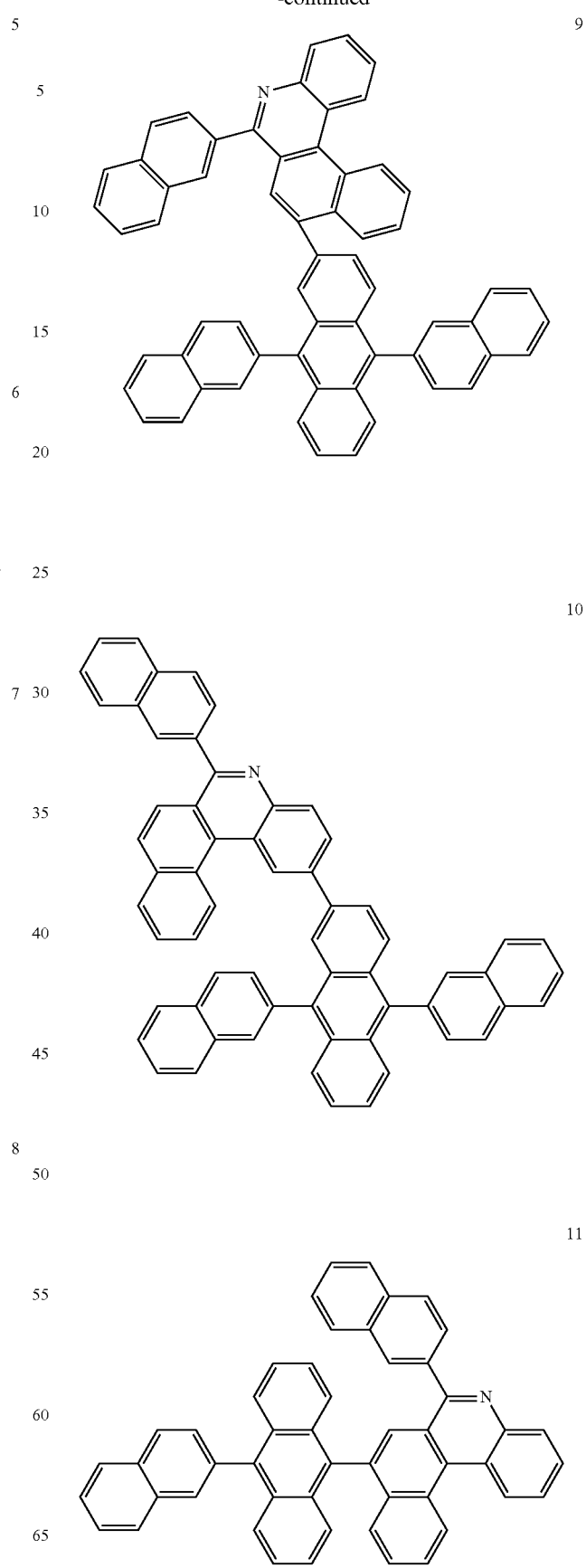

-continued
12
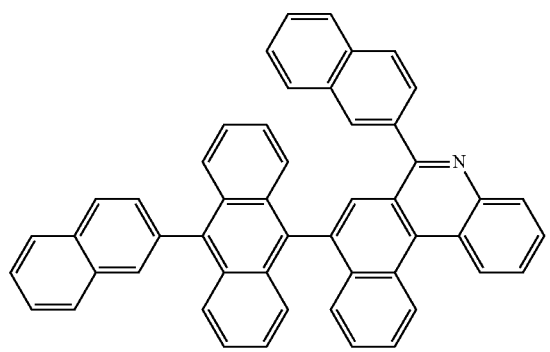
13
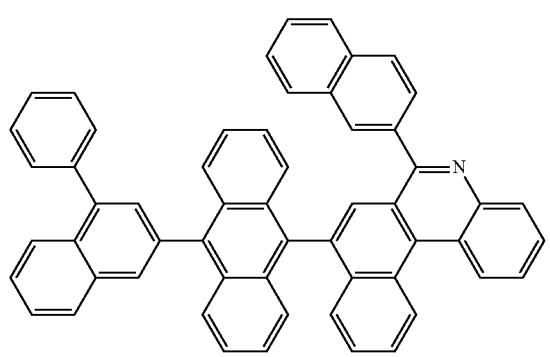
14
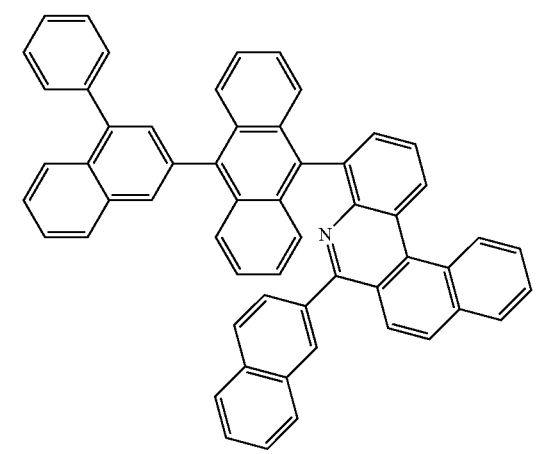
15
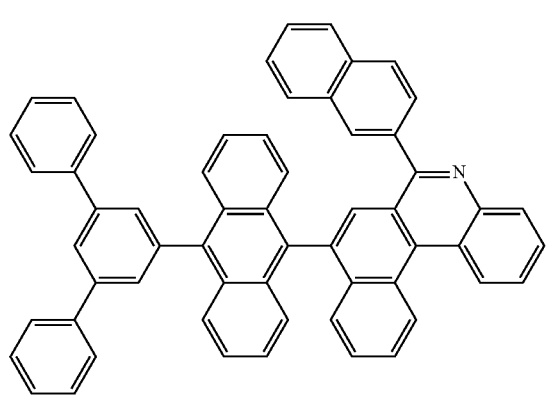
-continued
16
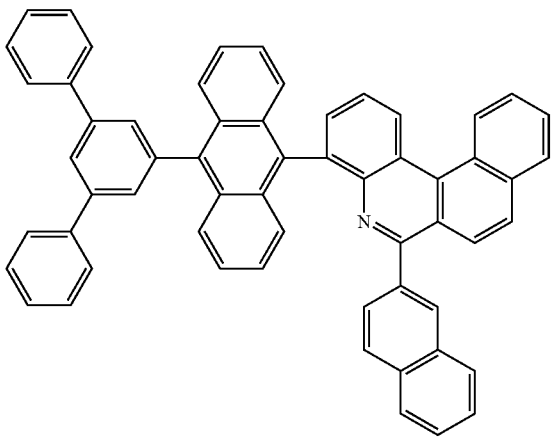
17
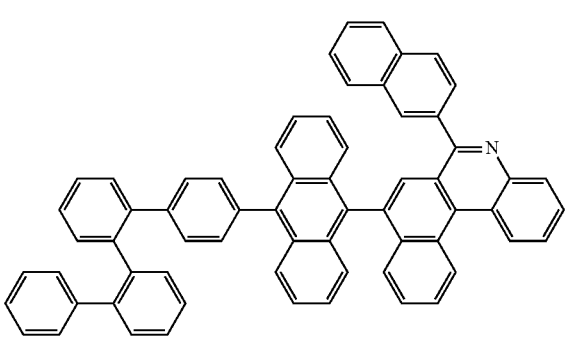
18
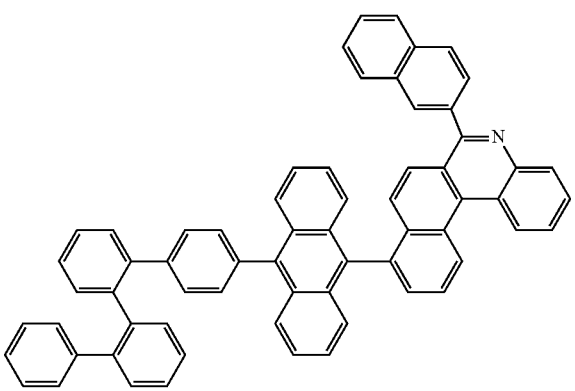
19
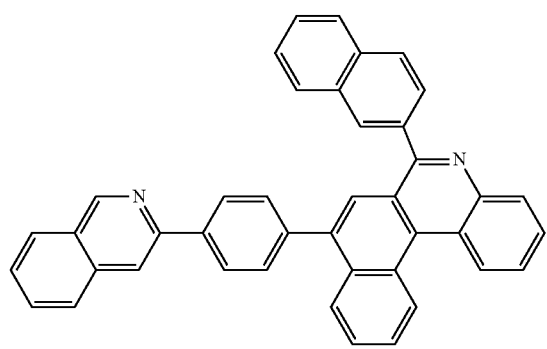

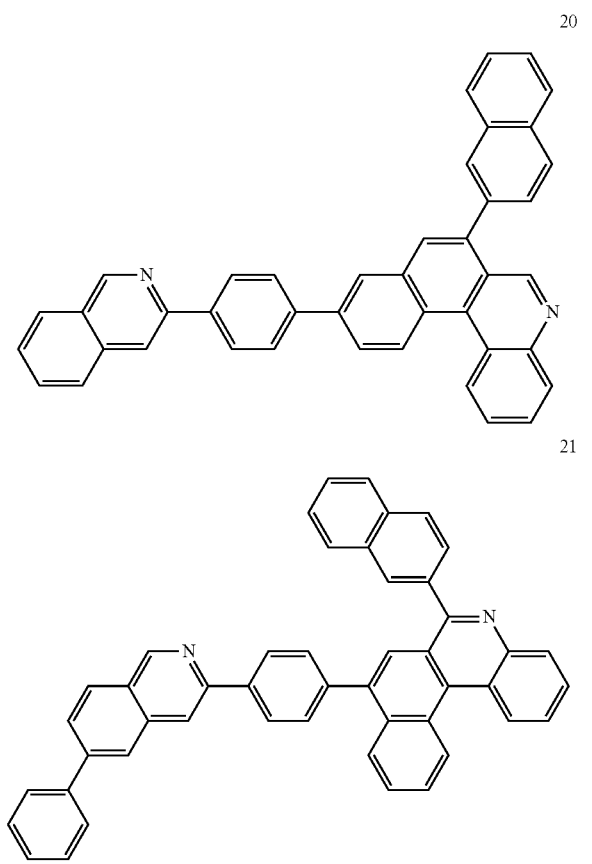
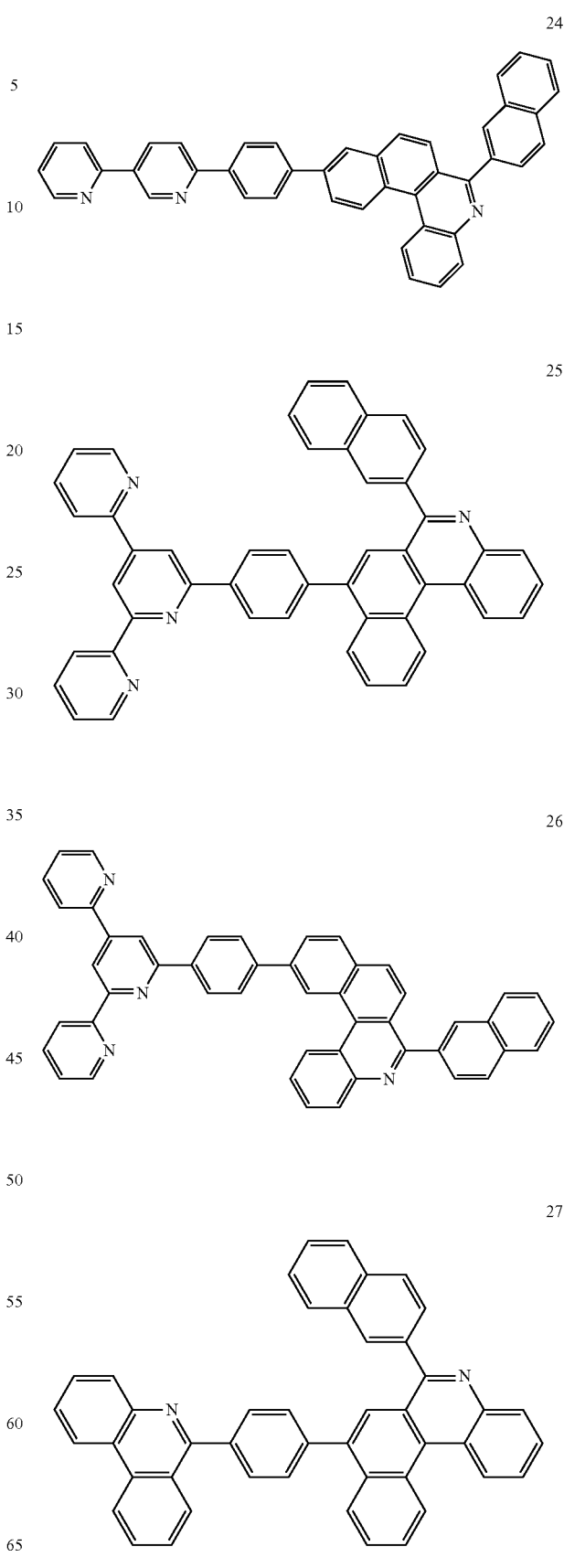

-continued
28
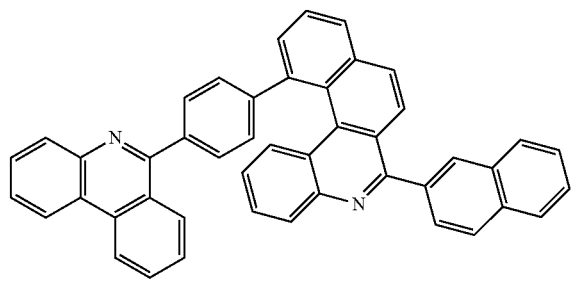
29
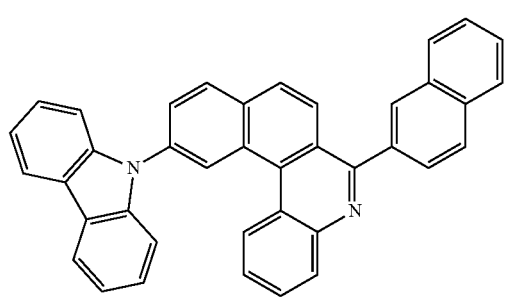
30
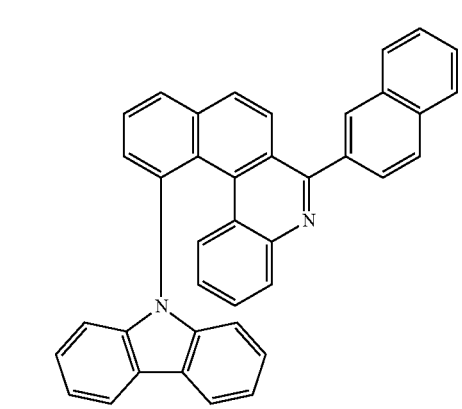
31
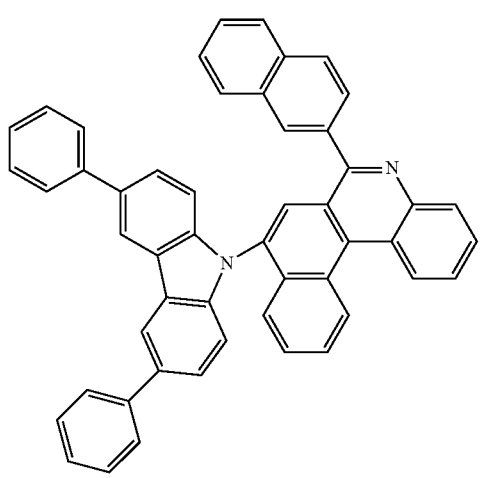
-continued
32
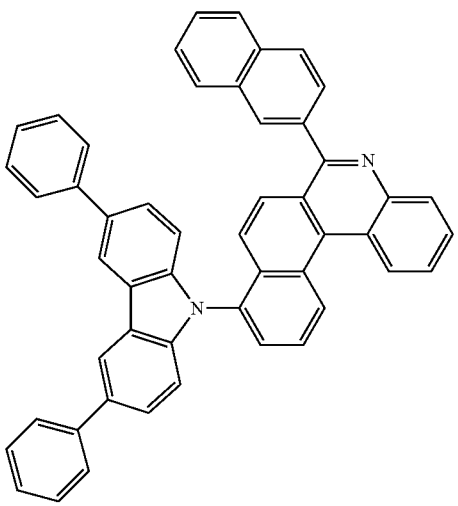
33
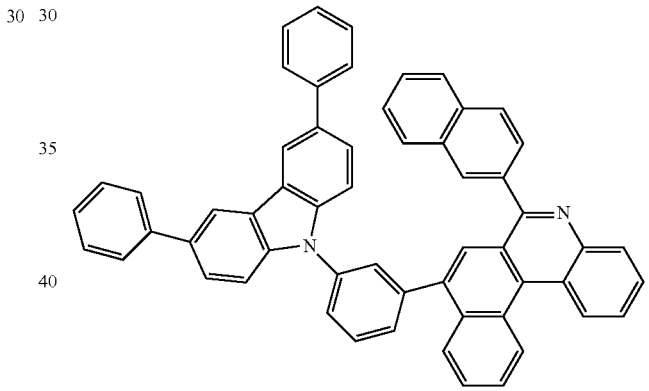
34
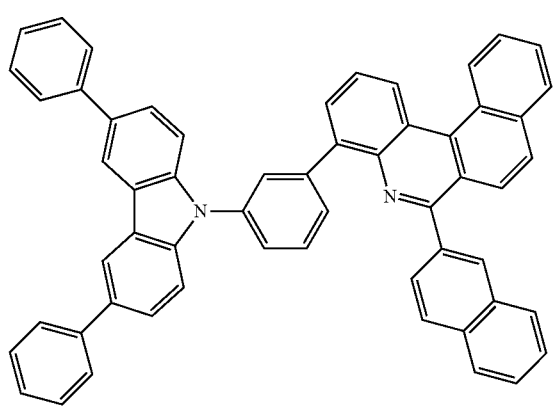

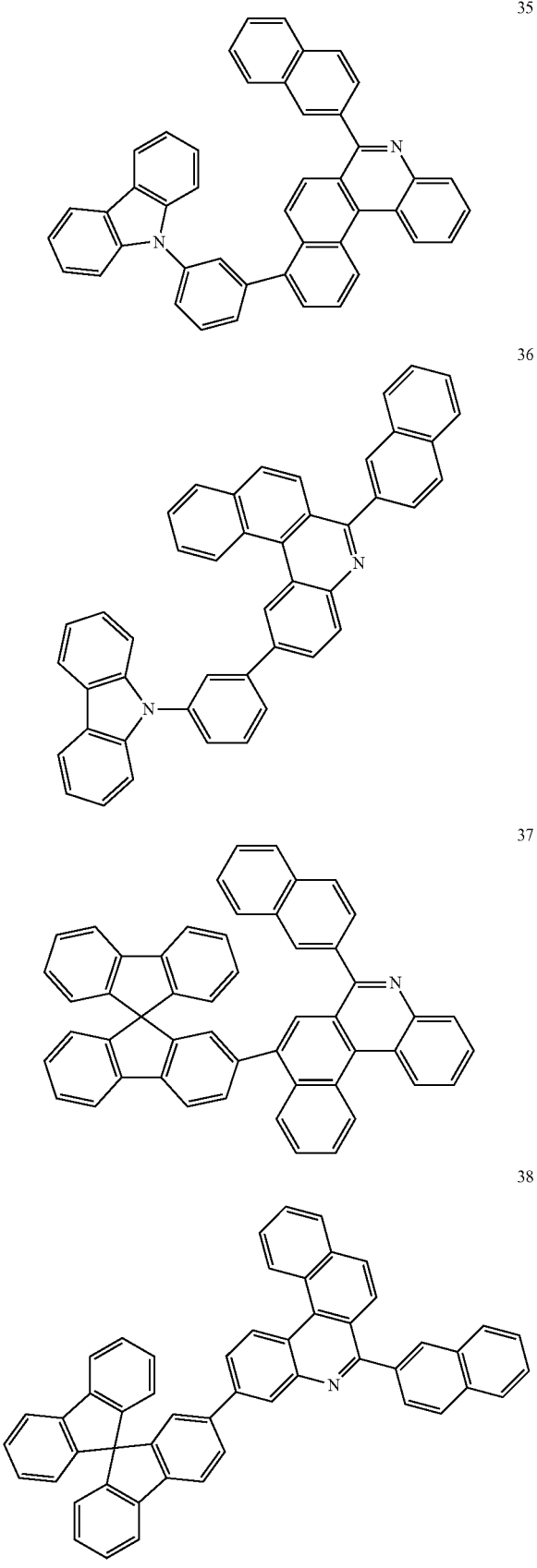
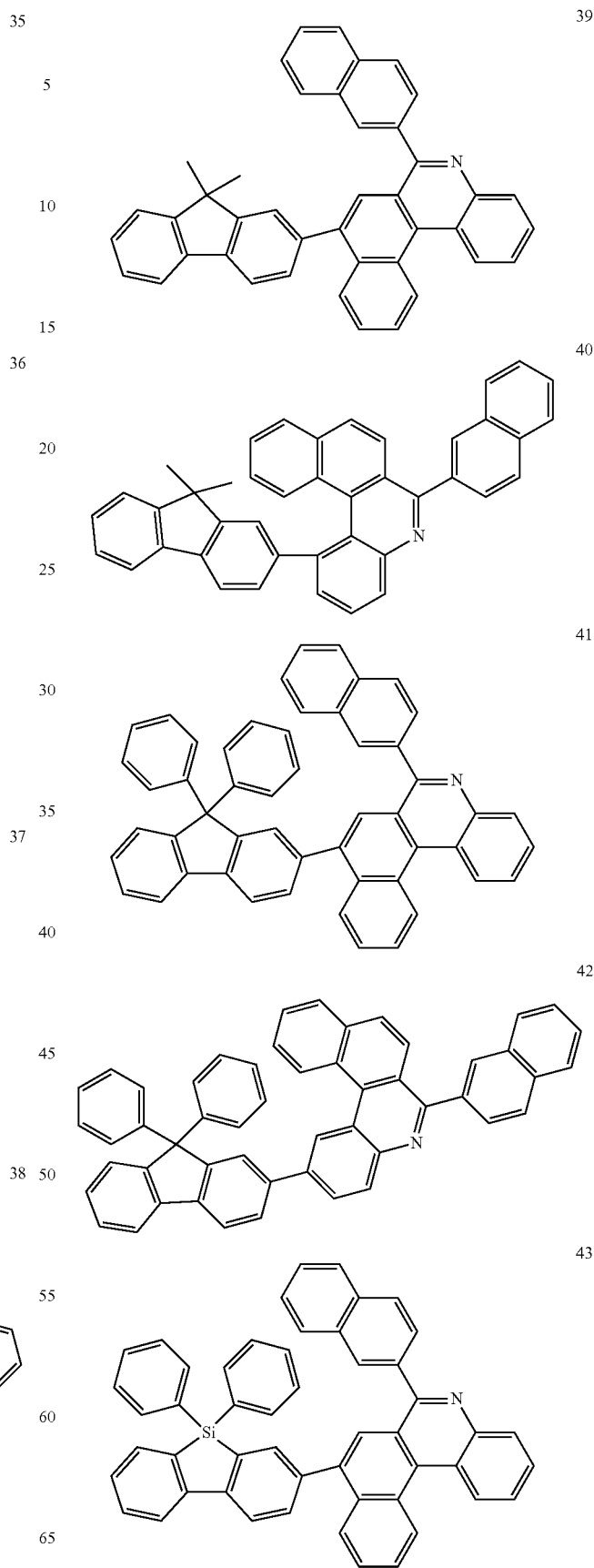

44
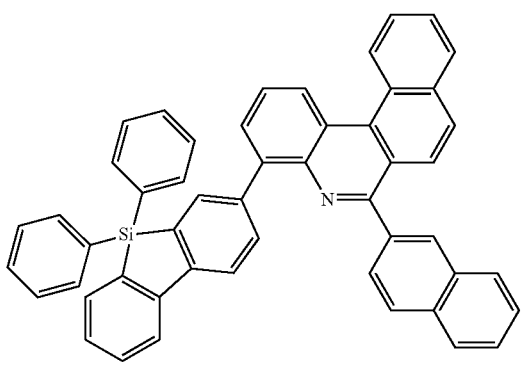
45
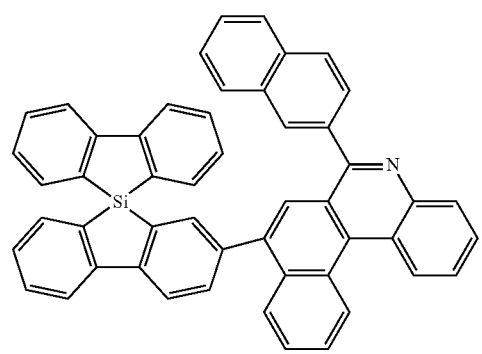
46
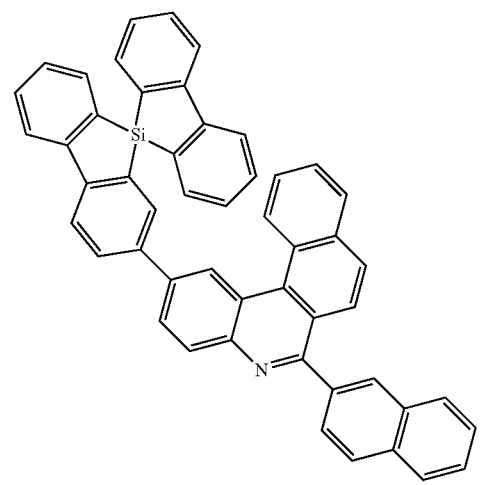
47
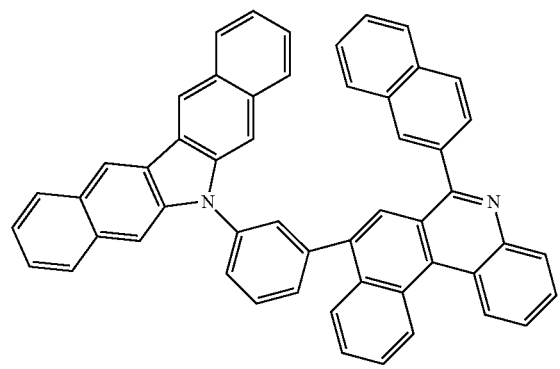
48
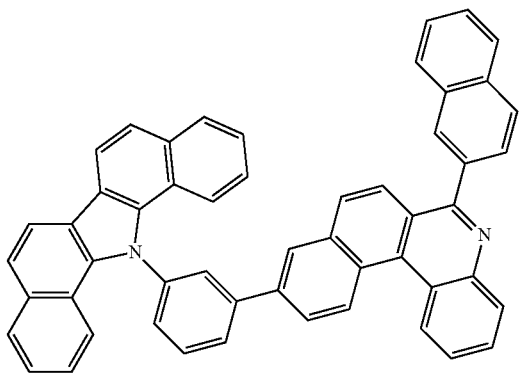
49
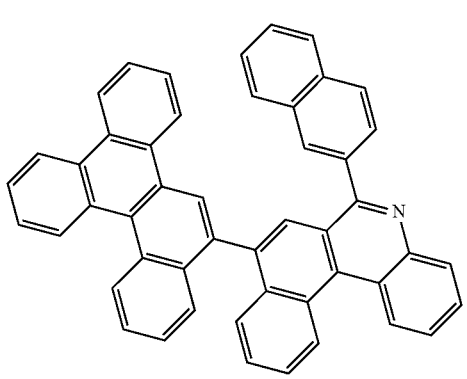
50
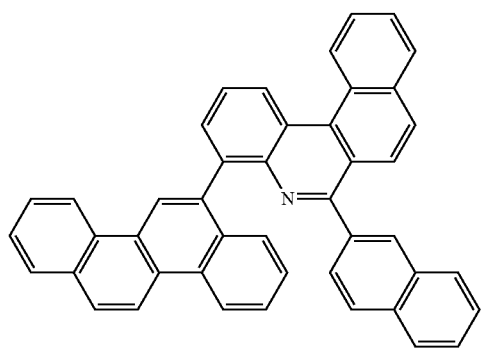
51
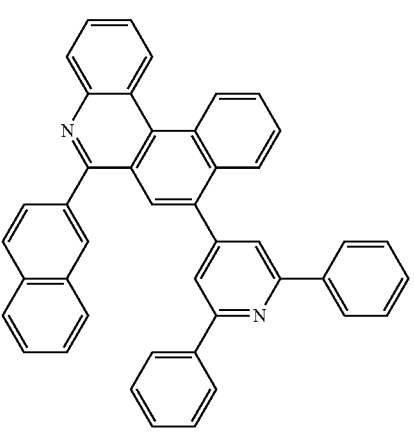

-continued
52
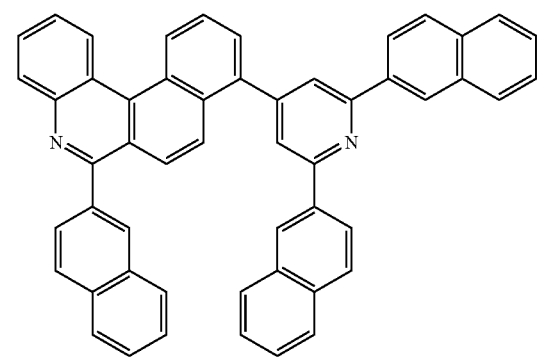
53
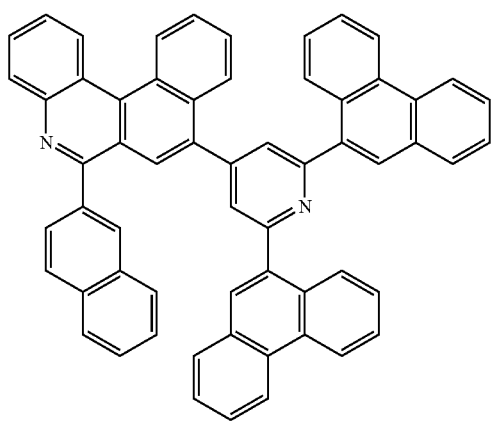
54
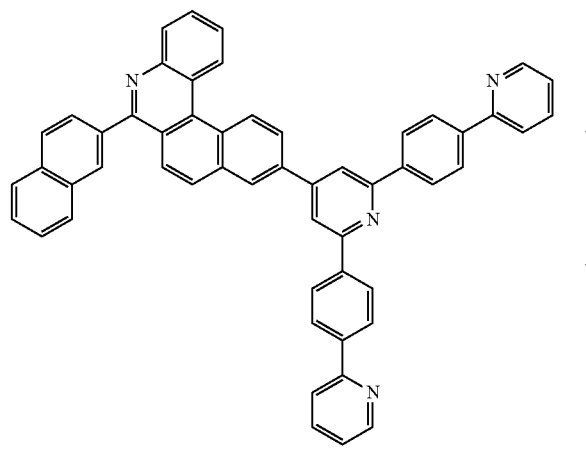
55
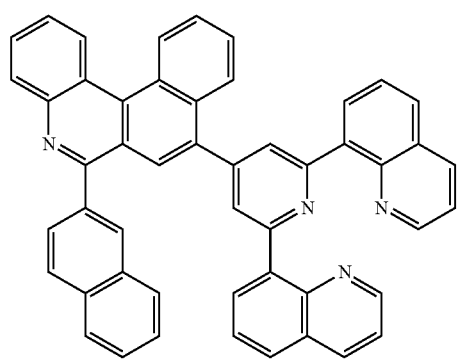
-continued
56
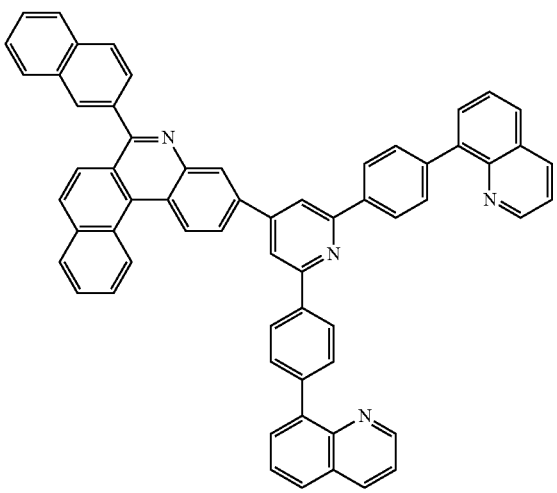
57
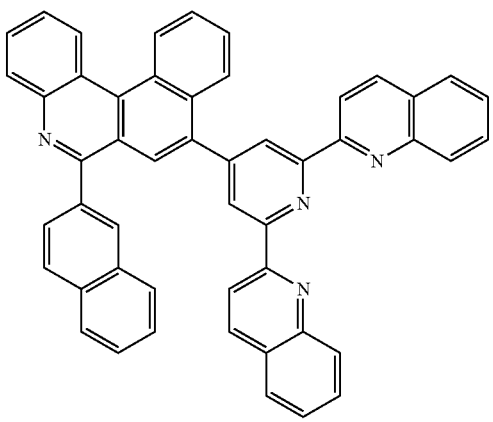
58
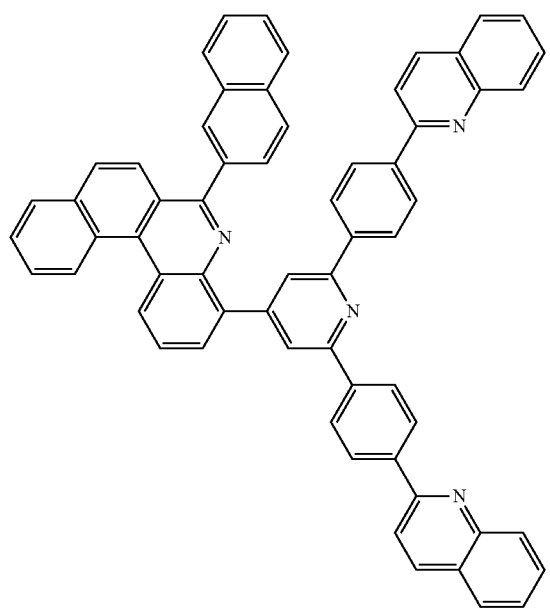

59
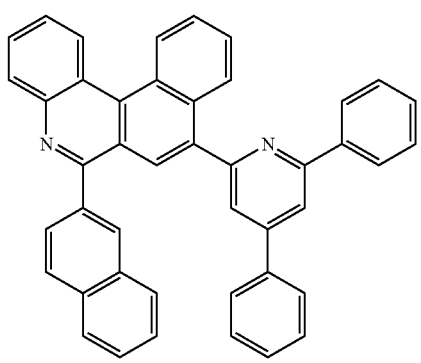
60
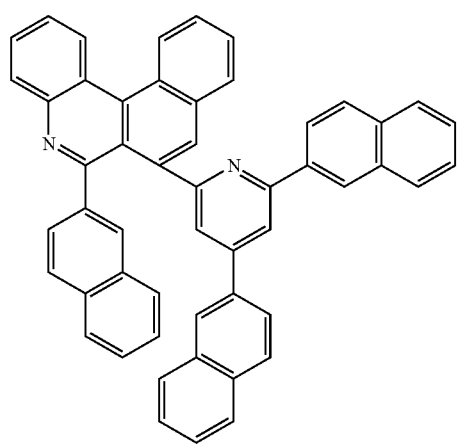
61
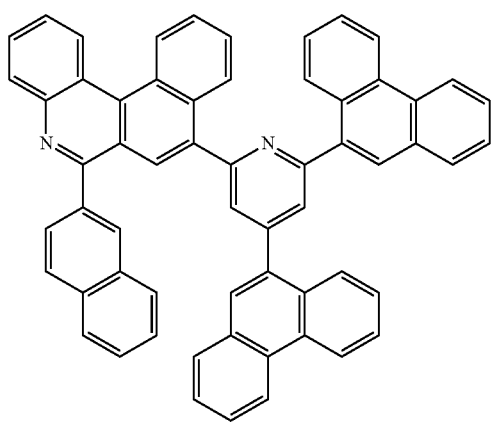
62
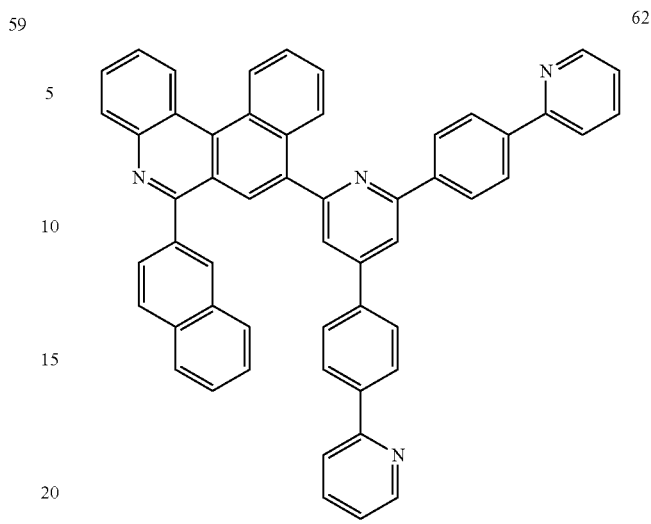
63
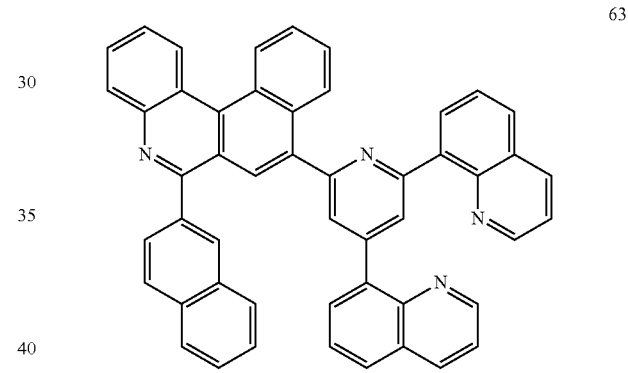
64
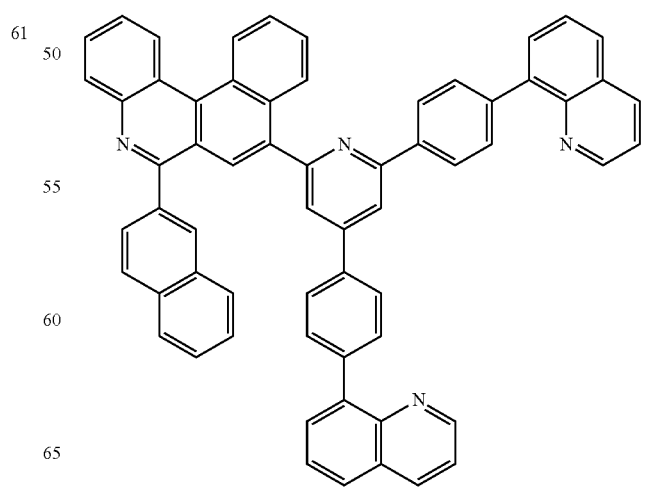

65
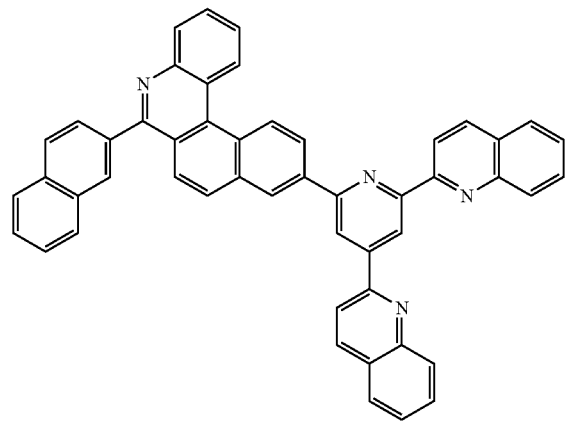
66
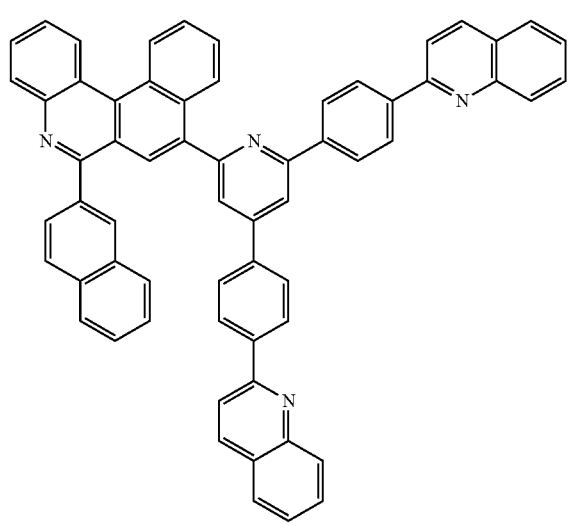
67
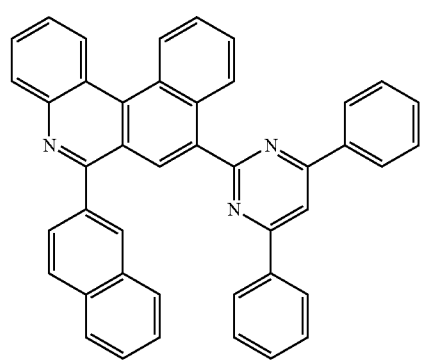
68
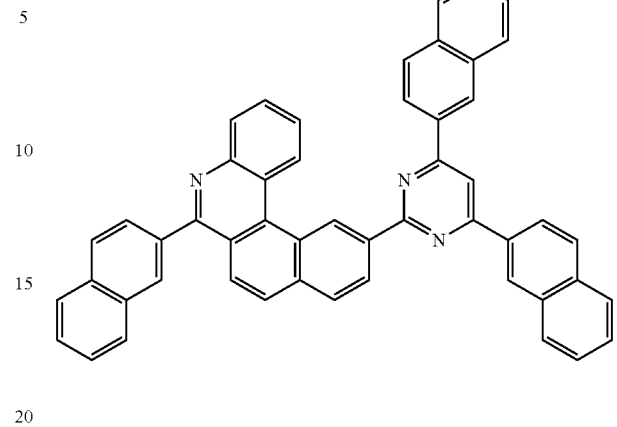
69
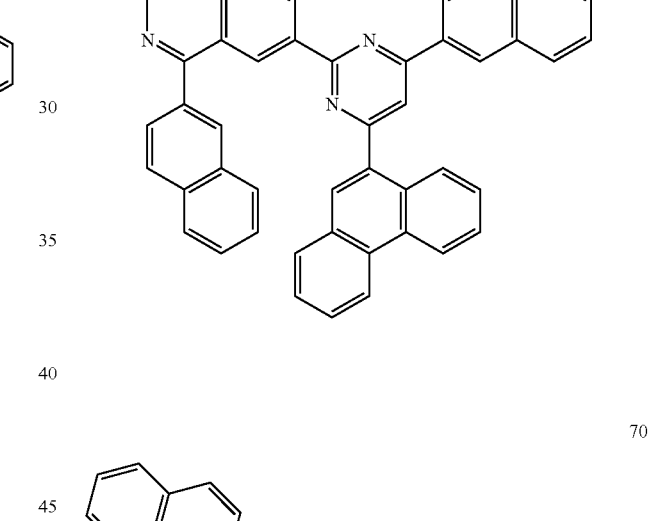
70
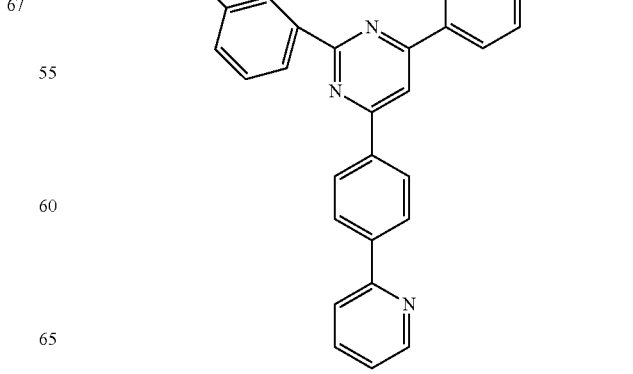

71
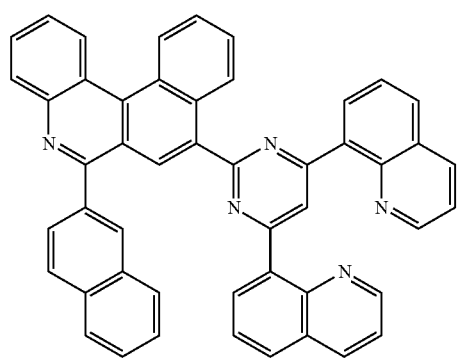
72
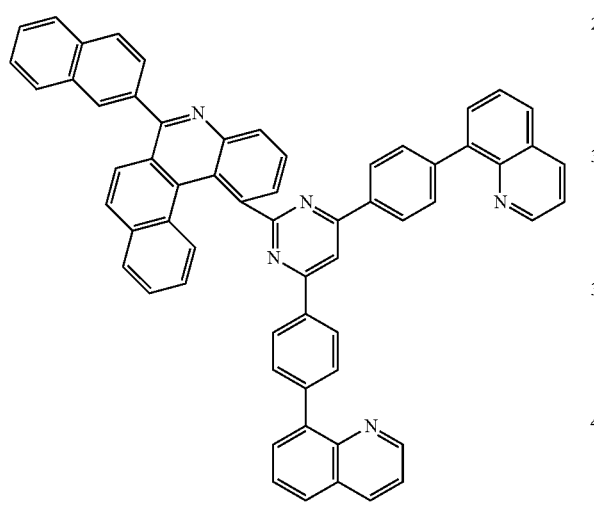
73
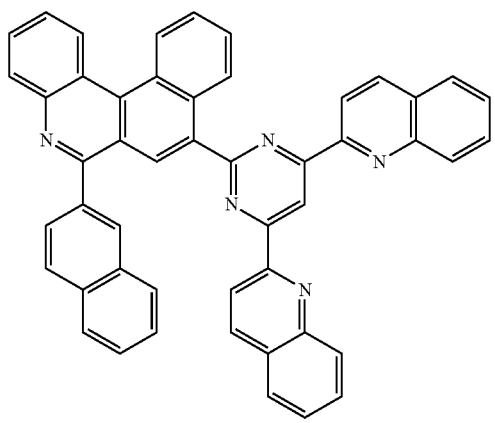
74
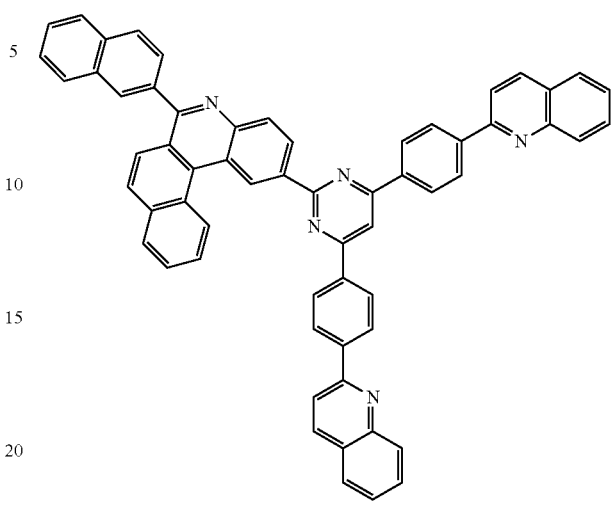
75
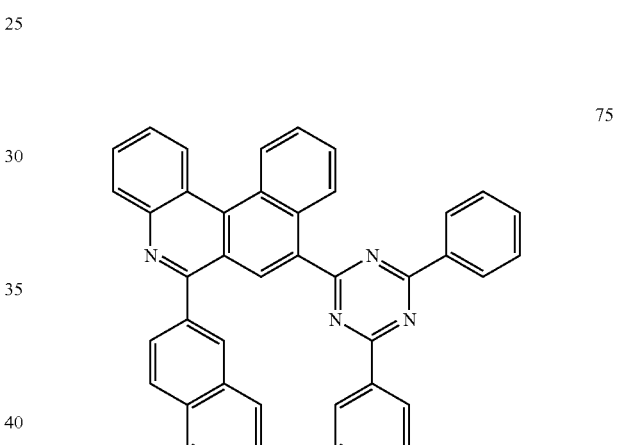
76
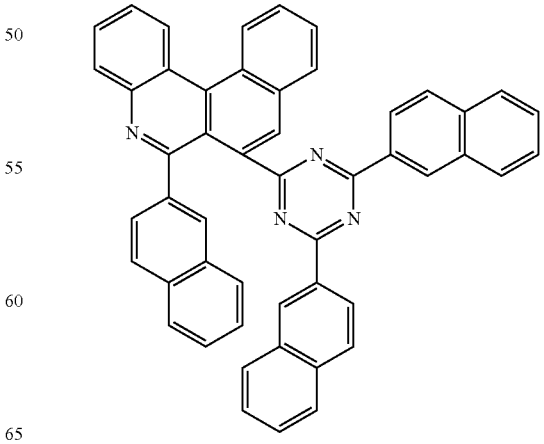

77
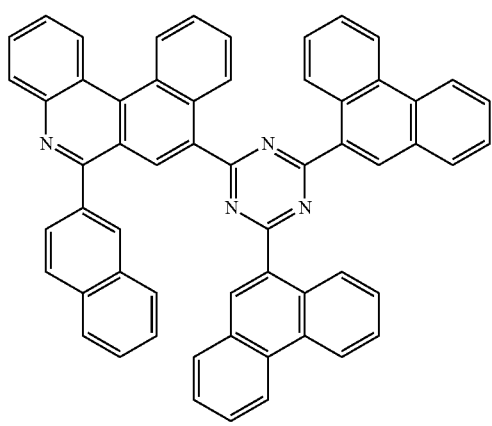
78
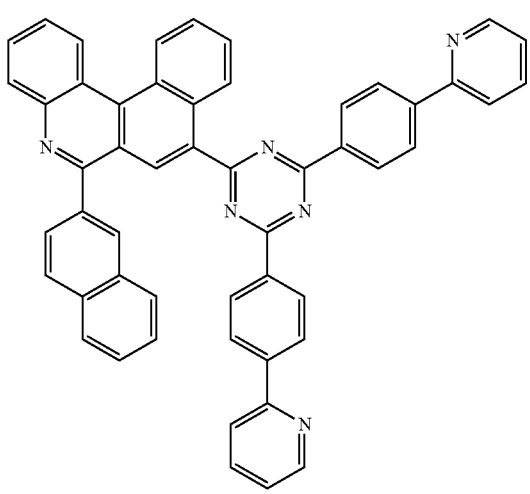
79
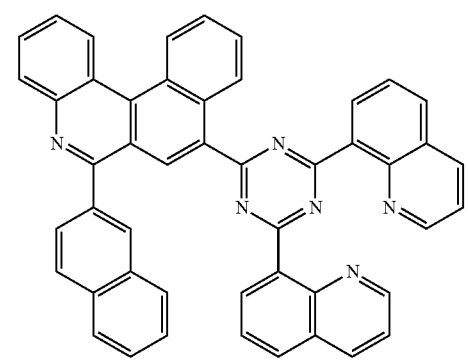
80
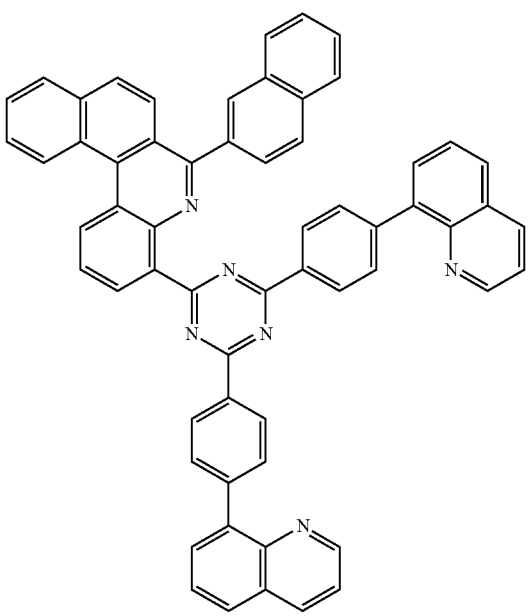
81
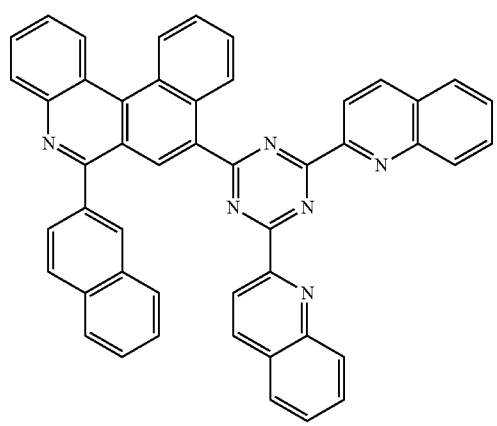
82
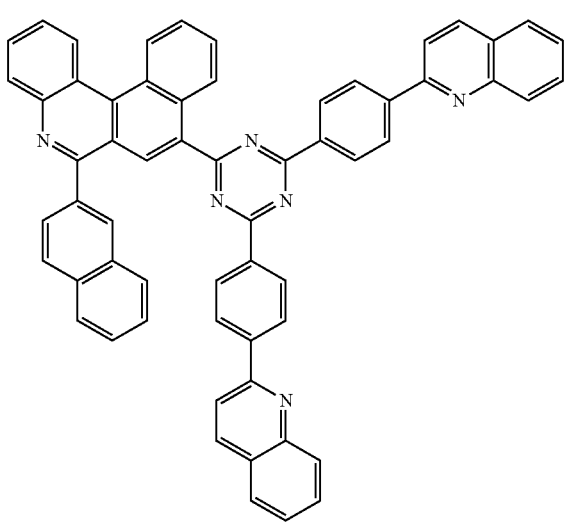

83
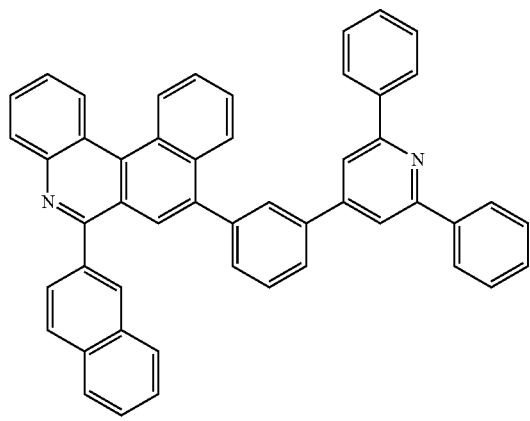
84
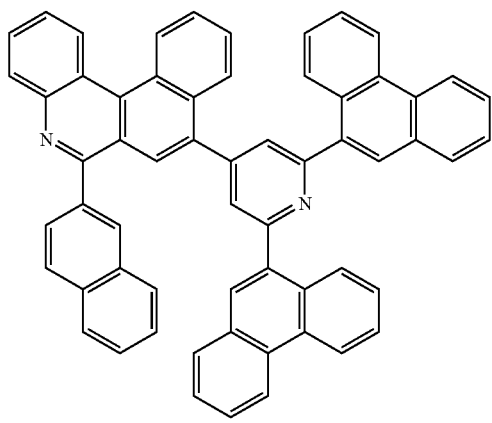
86
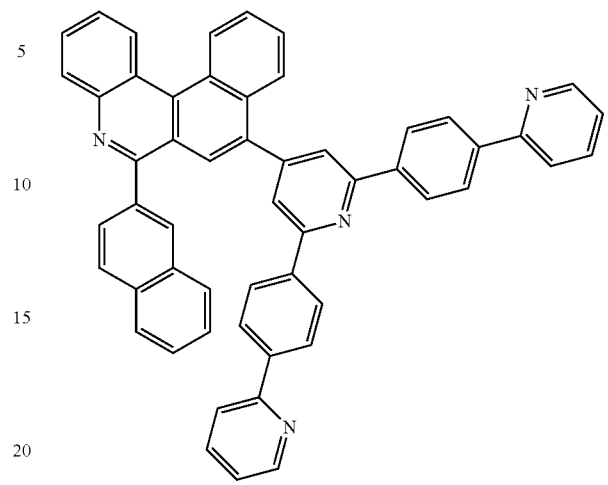
87
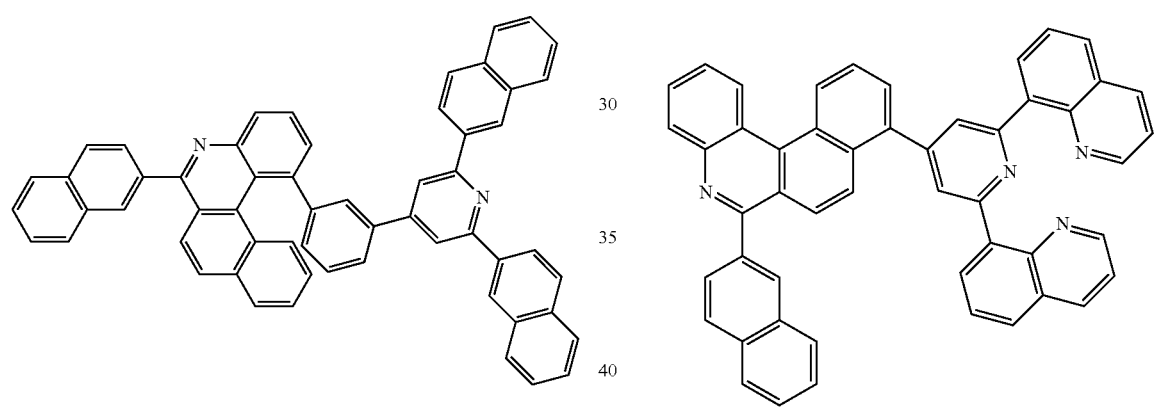
85
88
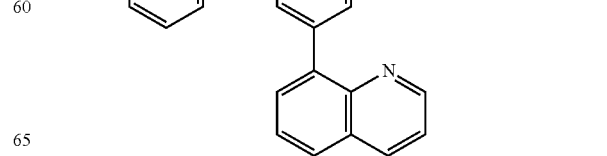

89
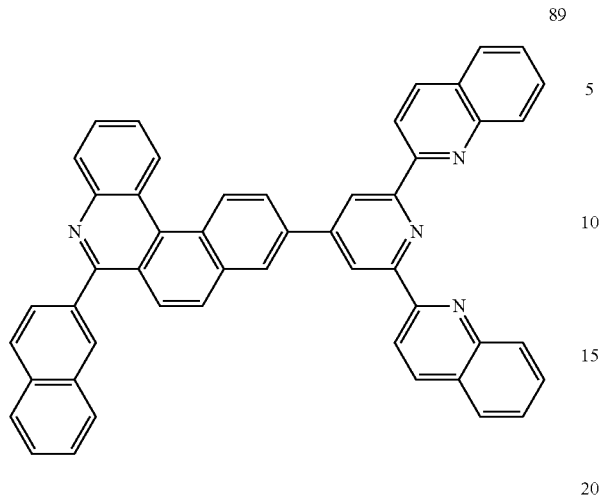
90
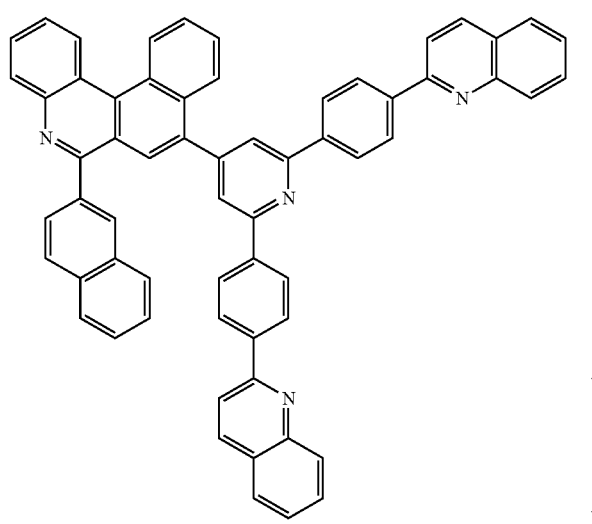
91
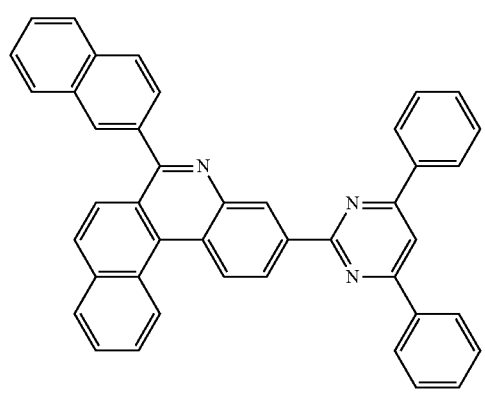
92
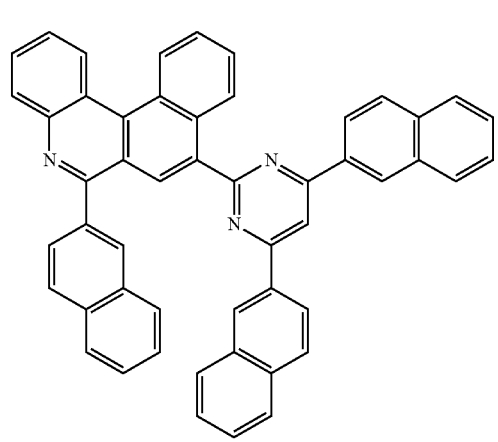
93
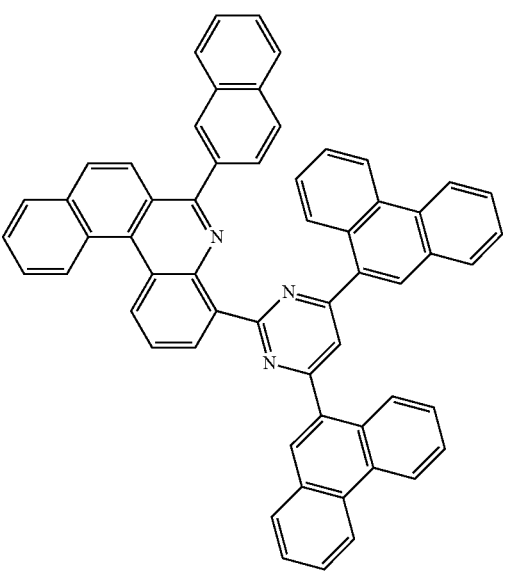
94
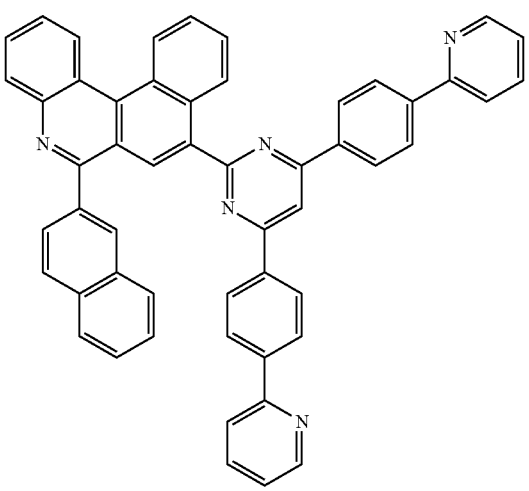

95
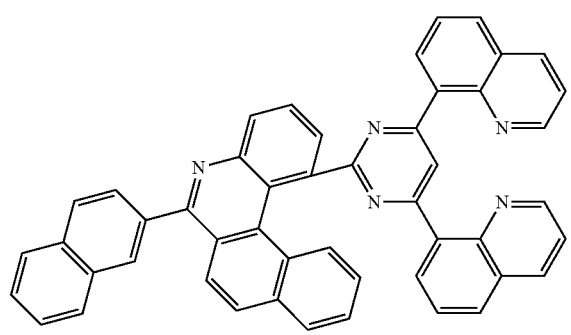
96
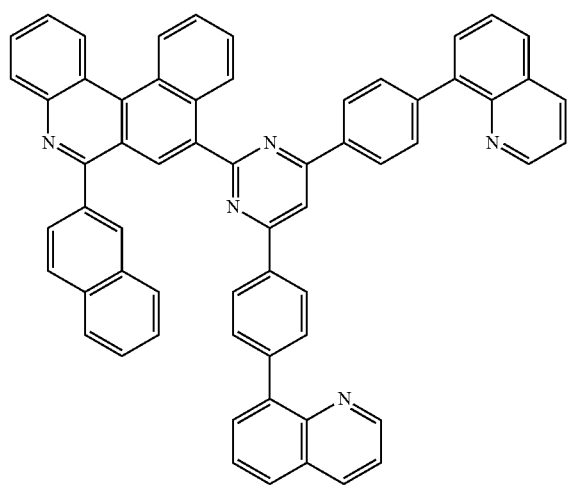
97
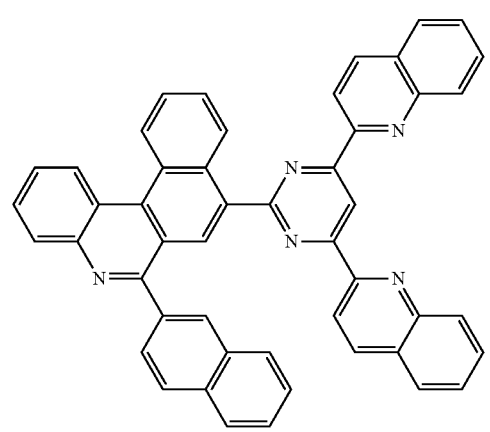
98
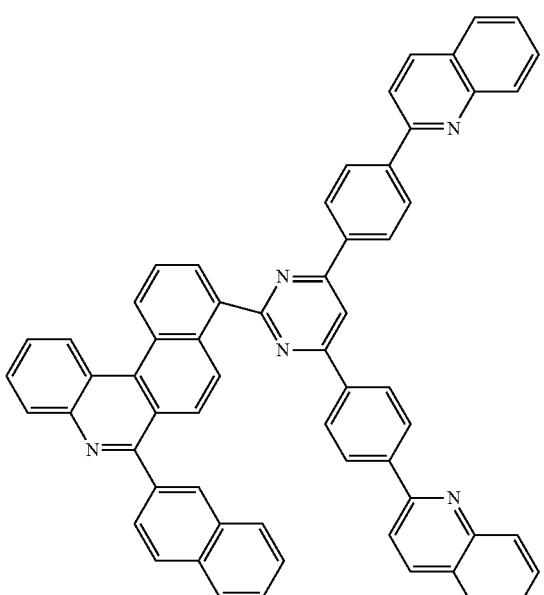
99
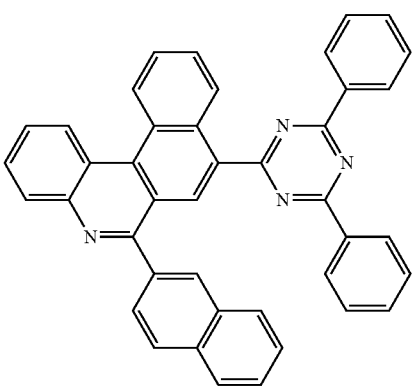
100
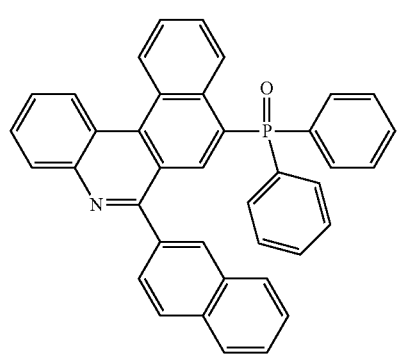

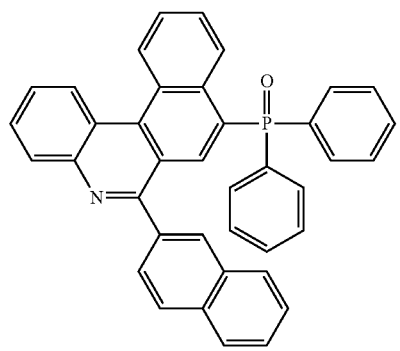
101
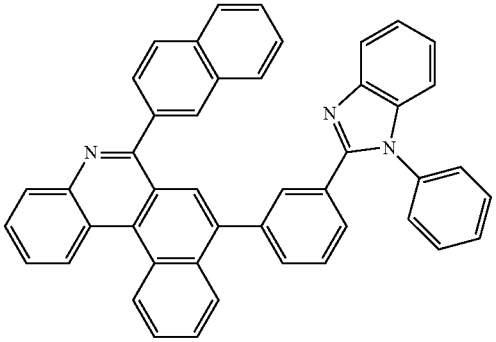
105
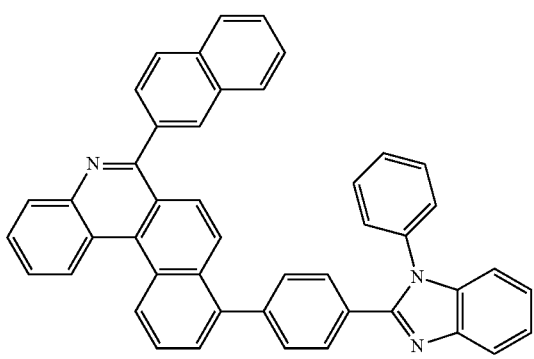
102
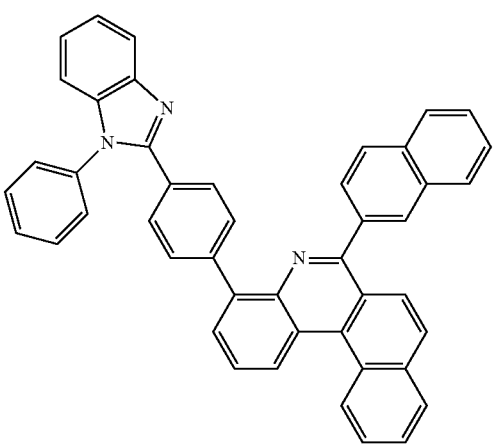
106
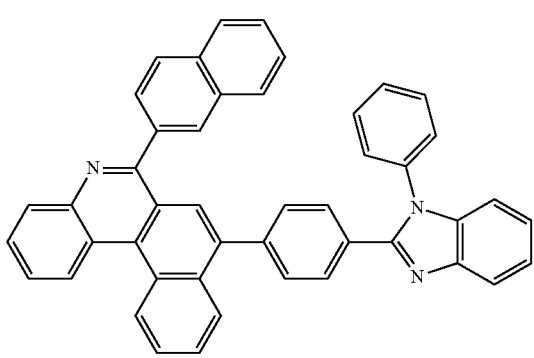
103
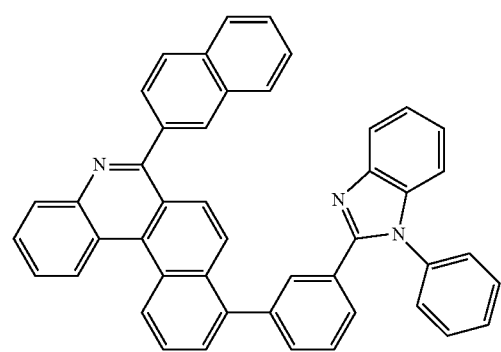
104

108
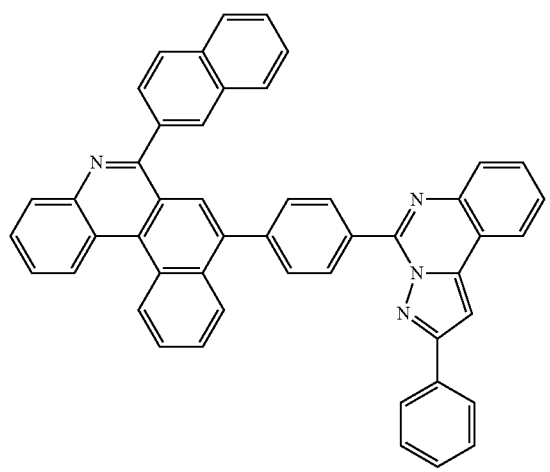
109
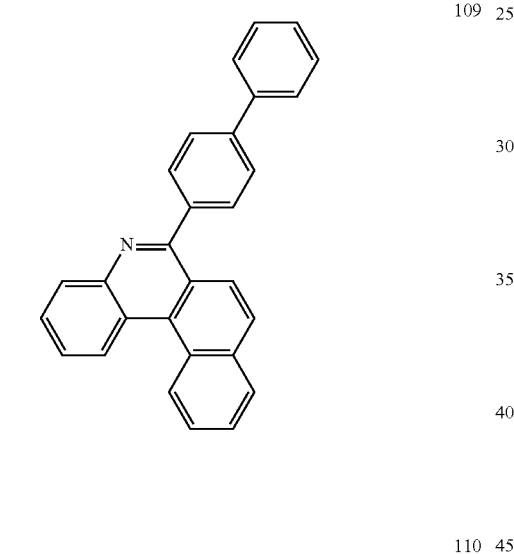
110
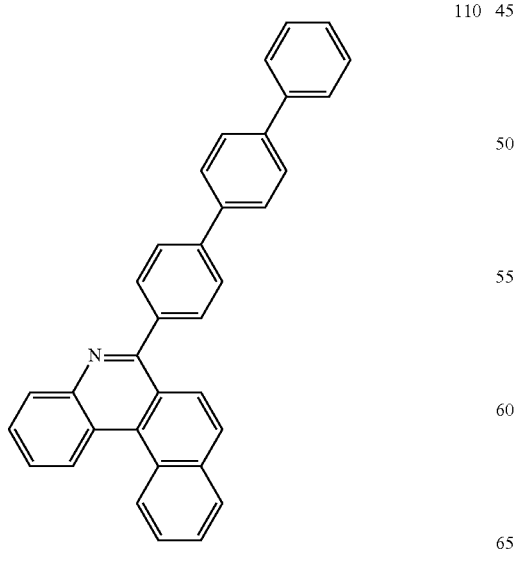
111
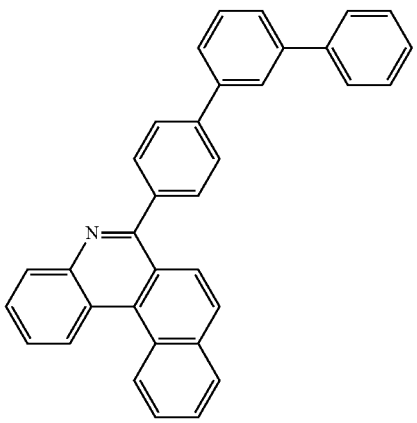
112
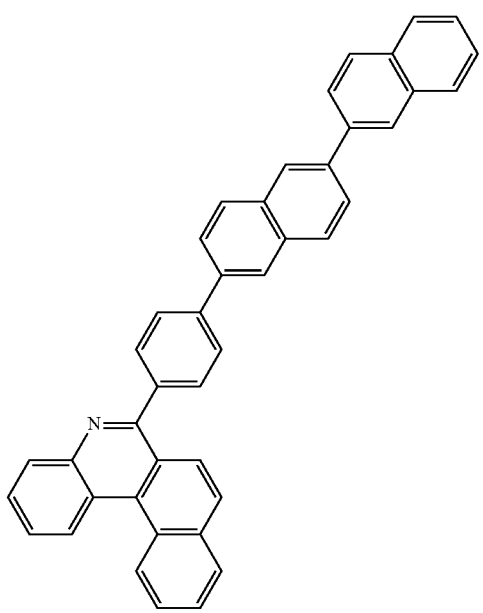
113

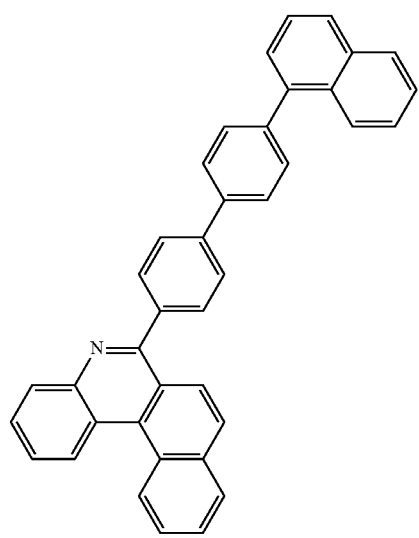
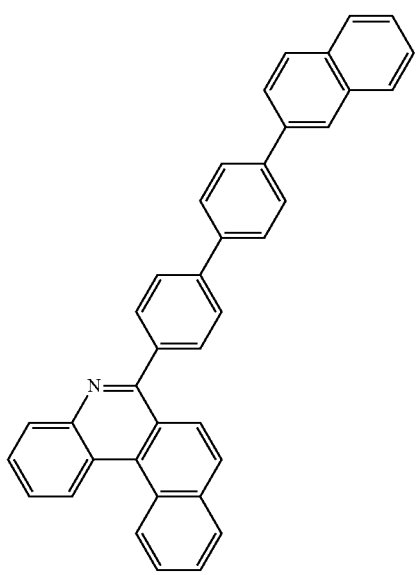
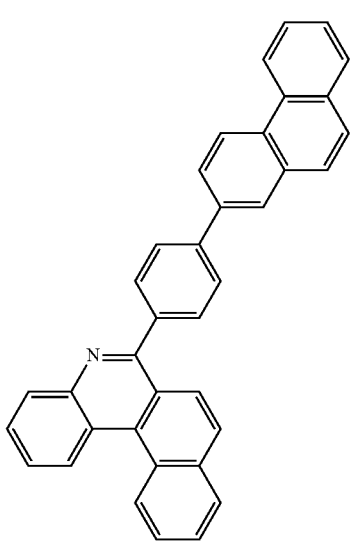

119
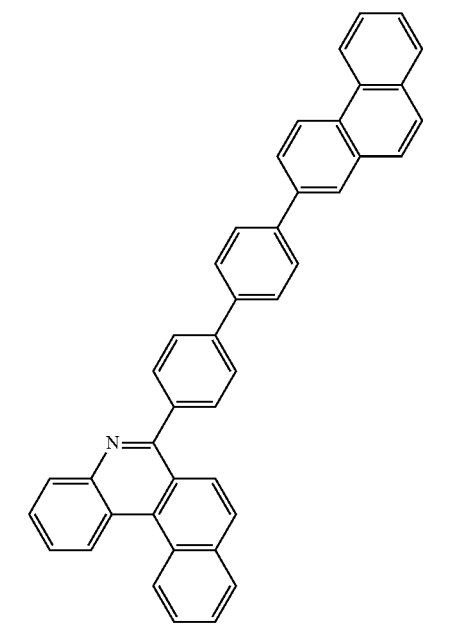
120
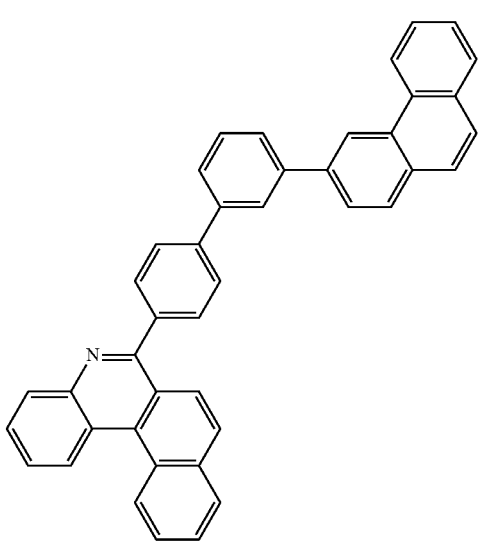
121
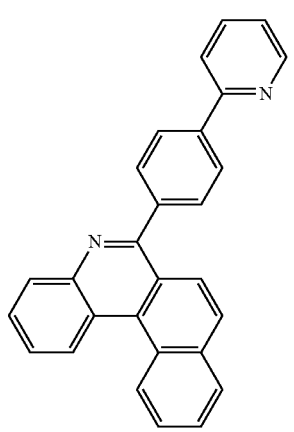
122
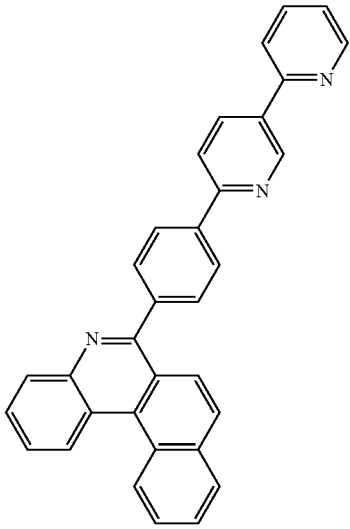
123
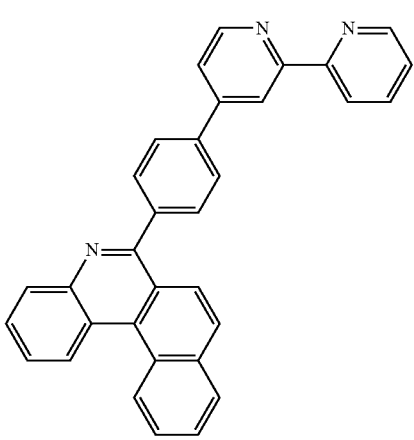
124
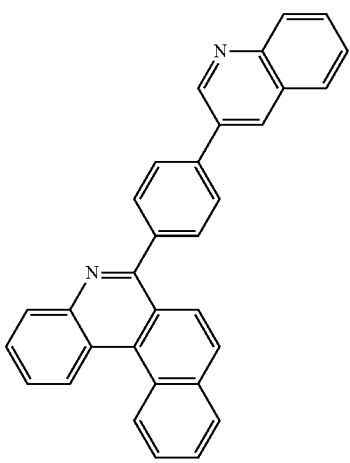

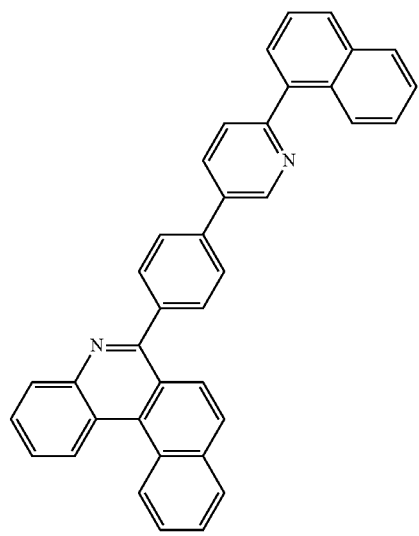
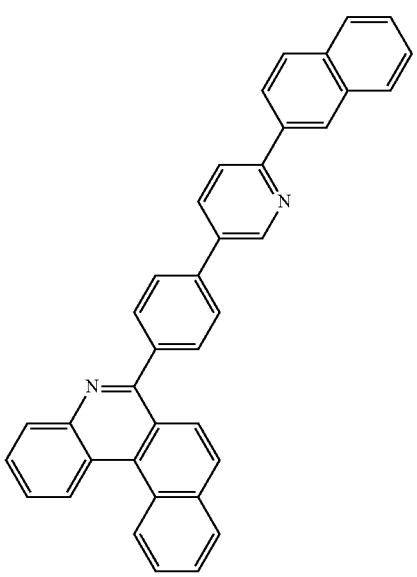

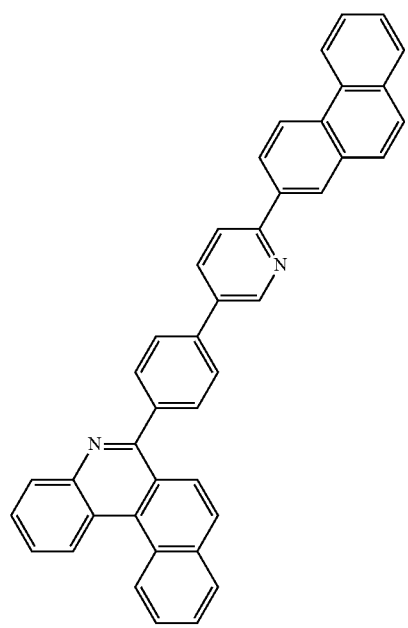
130
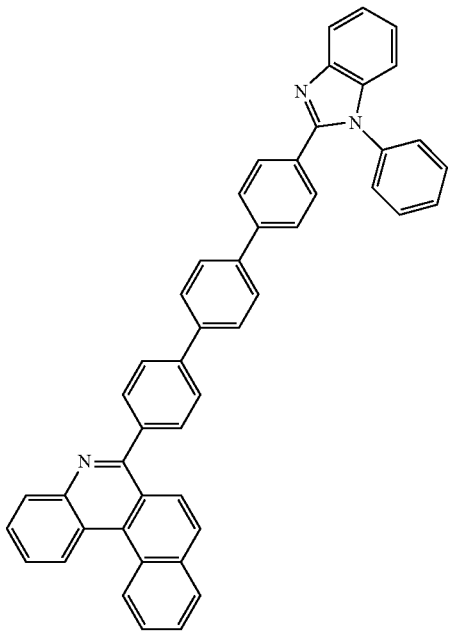
132
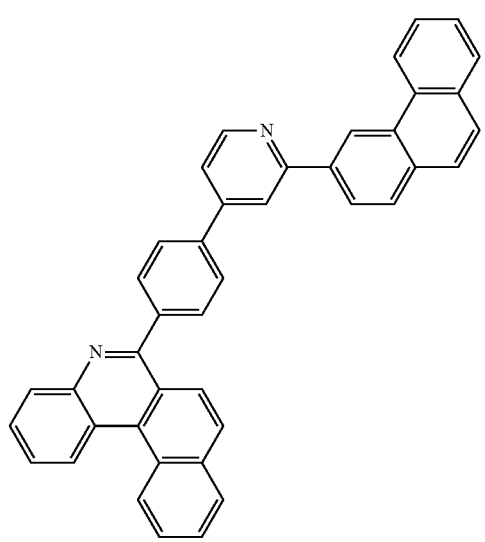
131
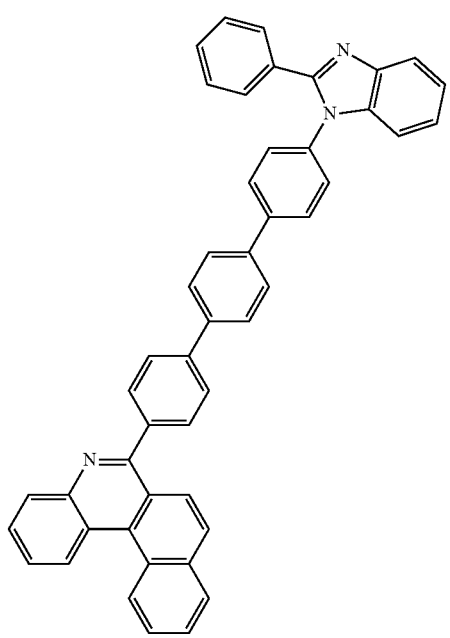
133

-continued
134
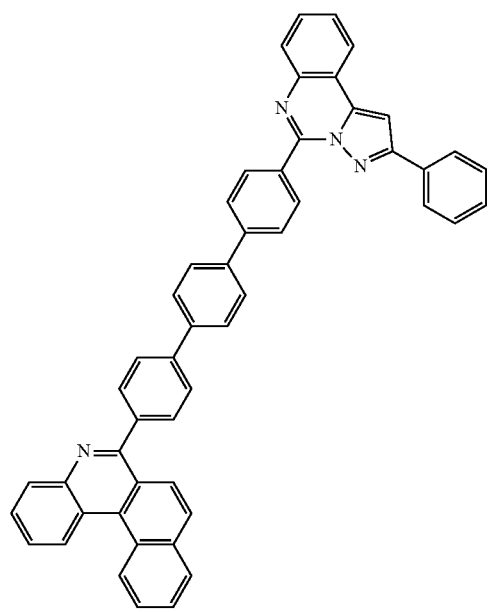
135
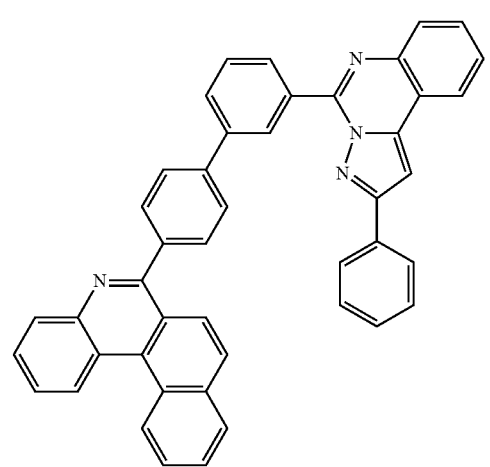
136
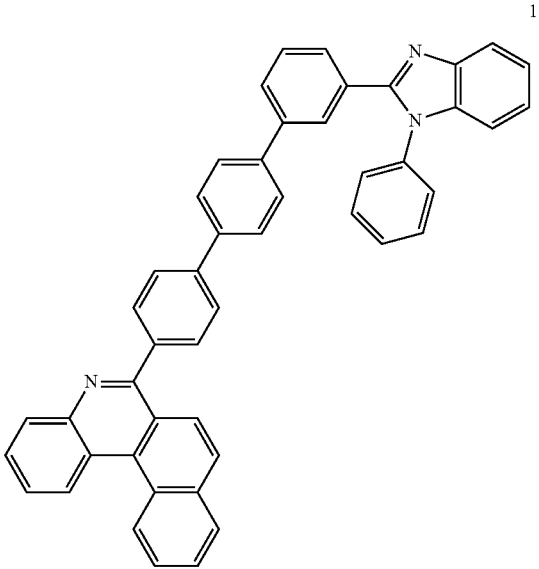
-continued
137
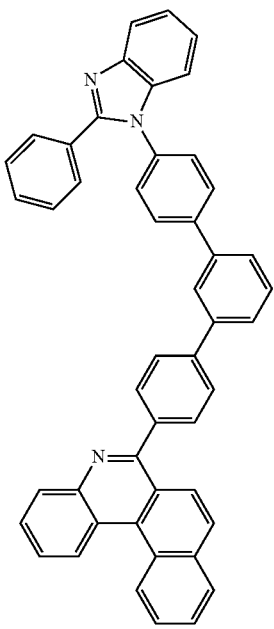
138
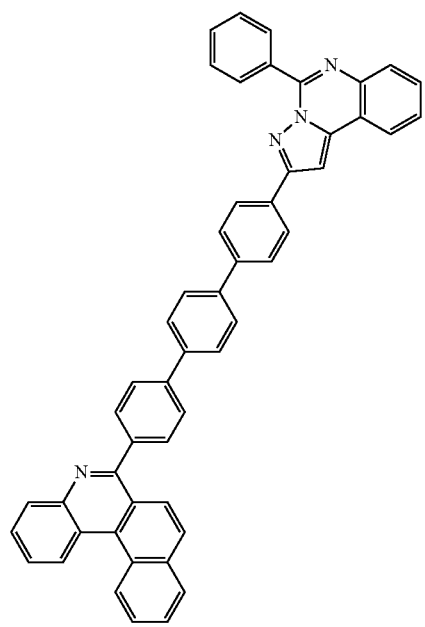

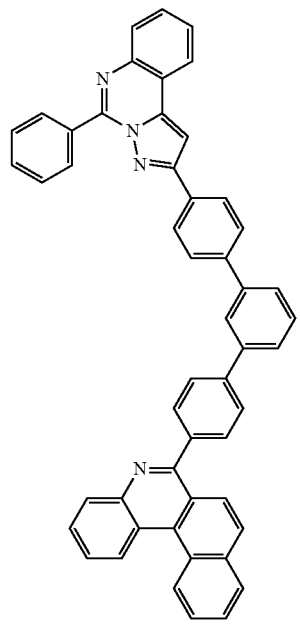
139
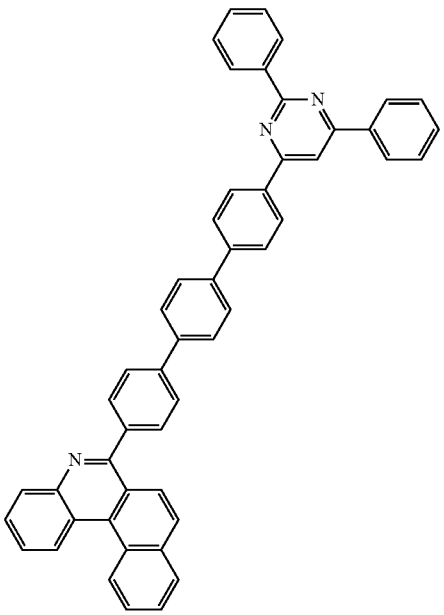
141
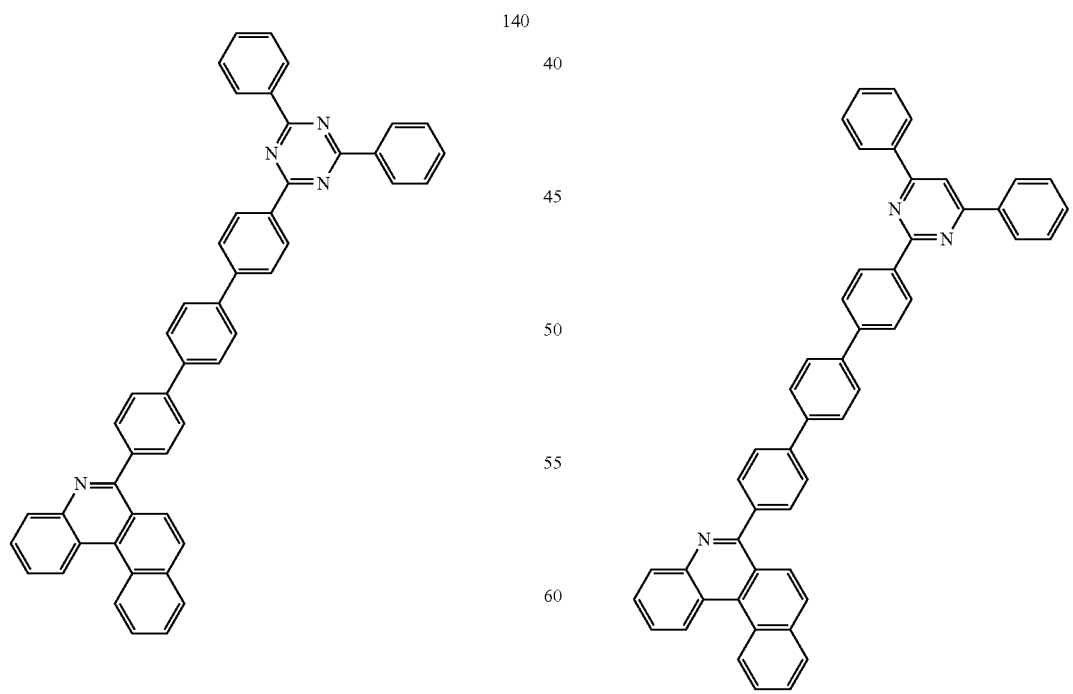

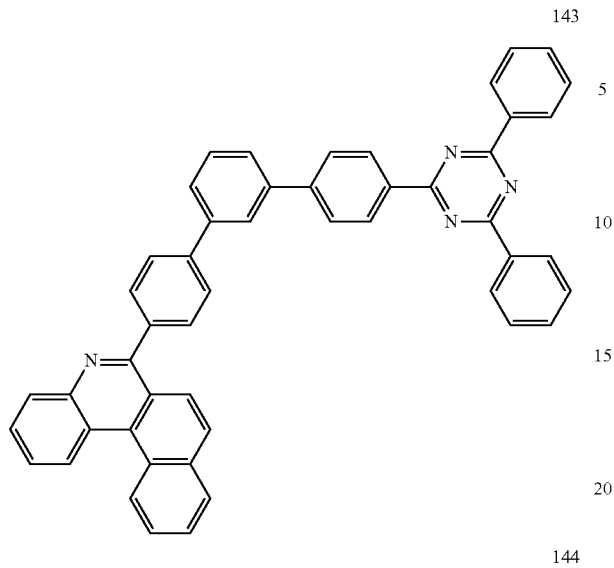
143
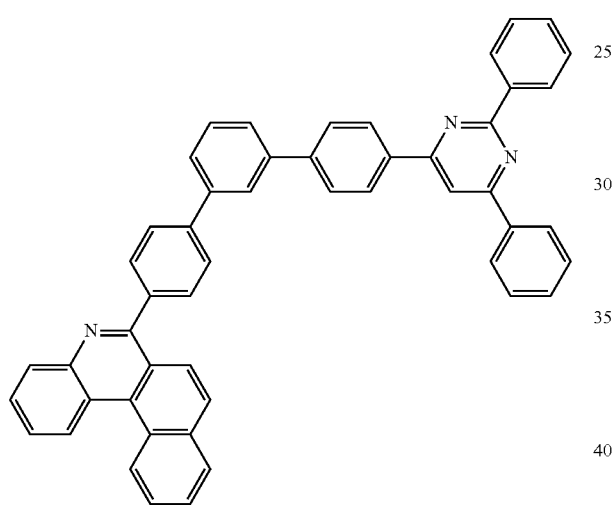
144
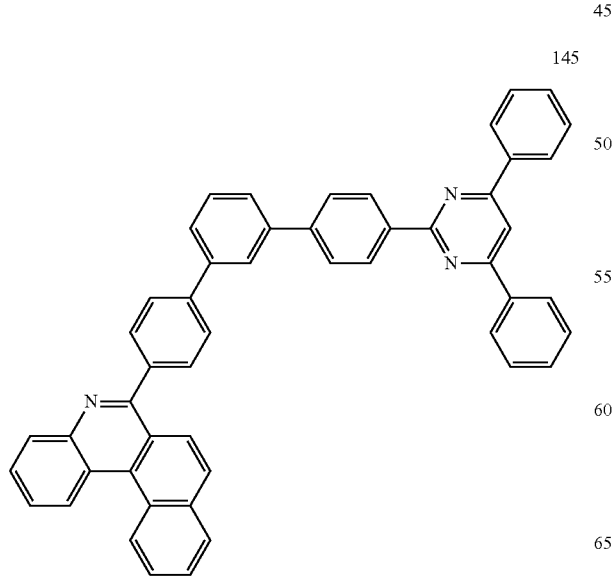
145
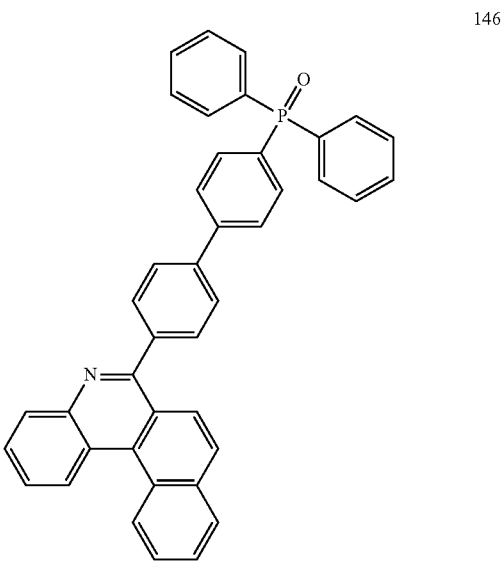
146
147

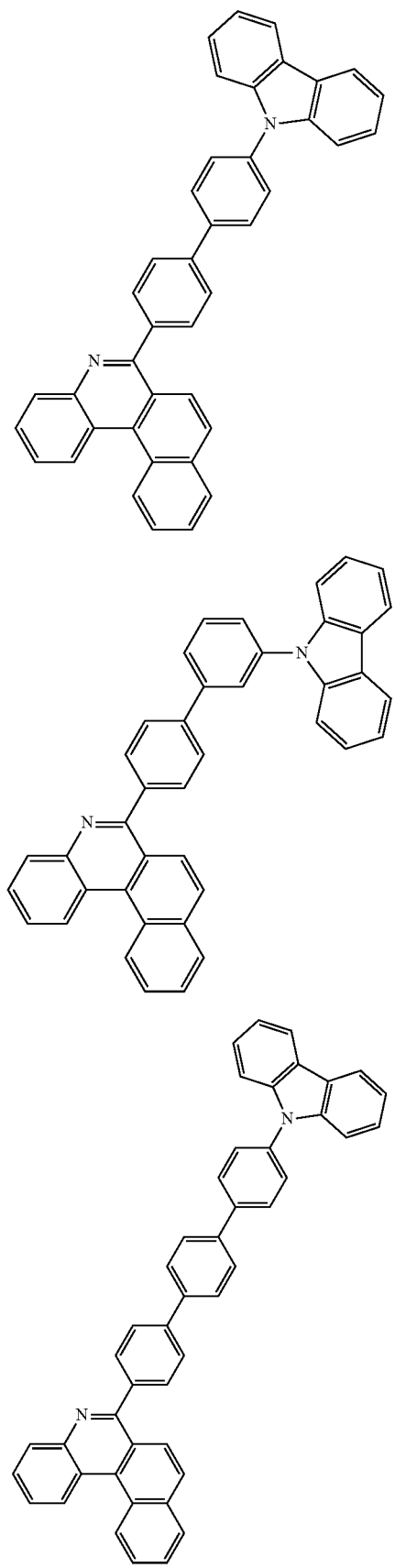
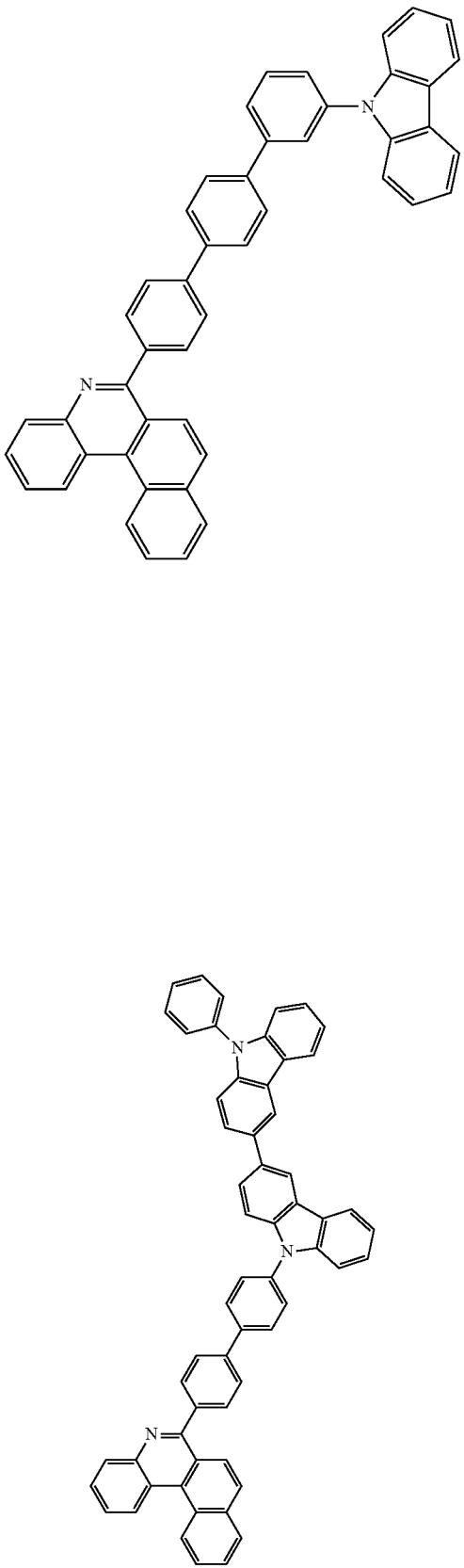

-continued
153
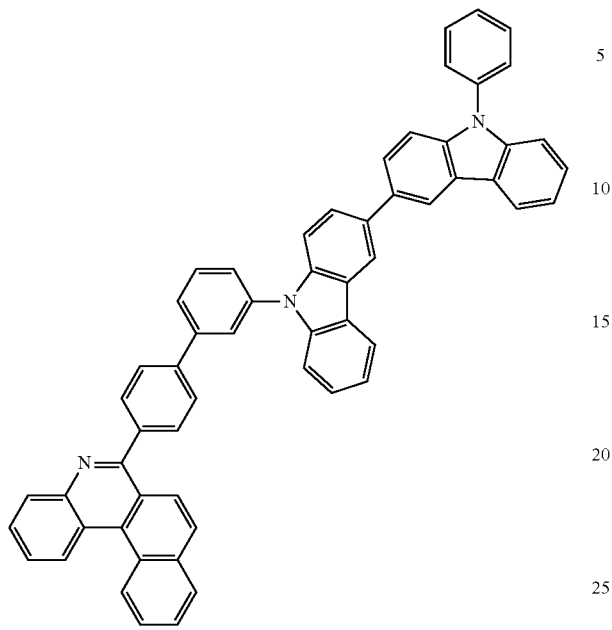
154
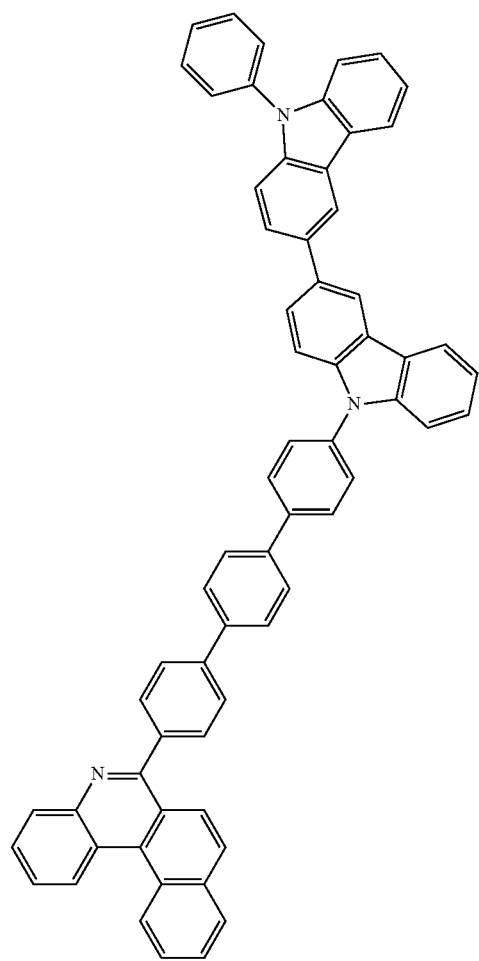
-continued
155
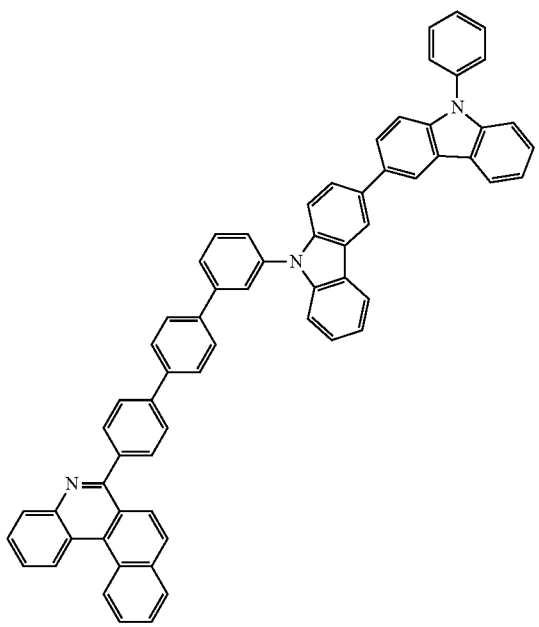
156
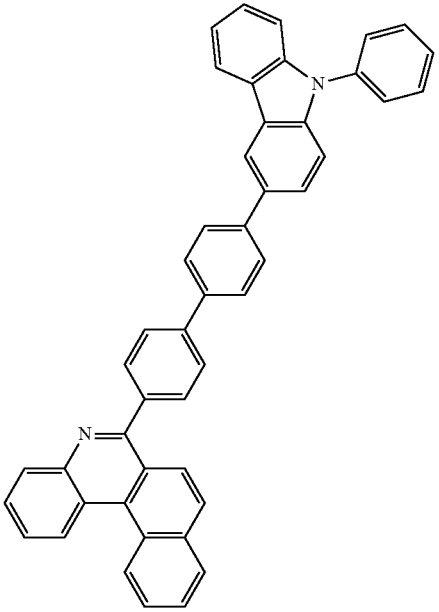

157
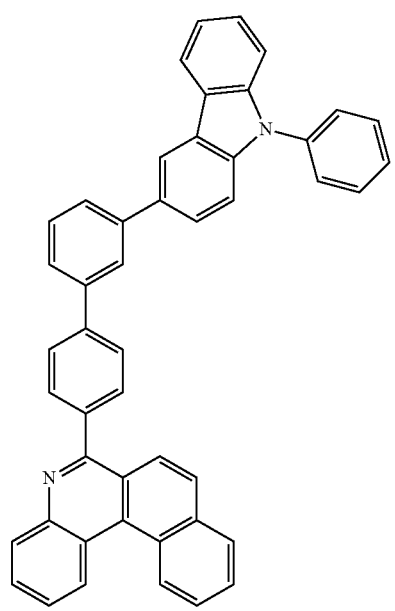
158
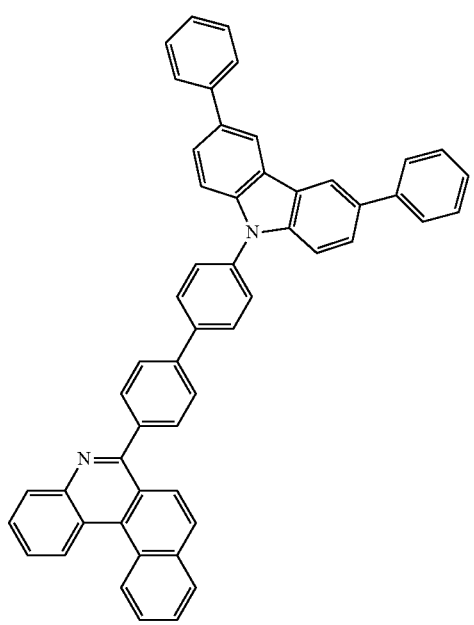
159
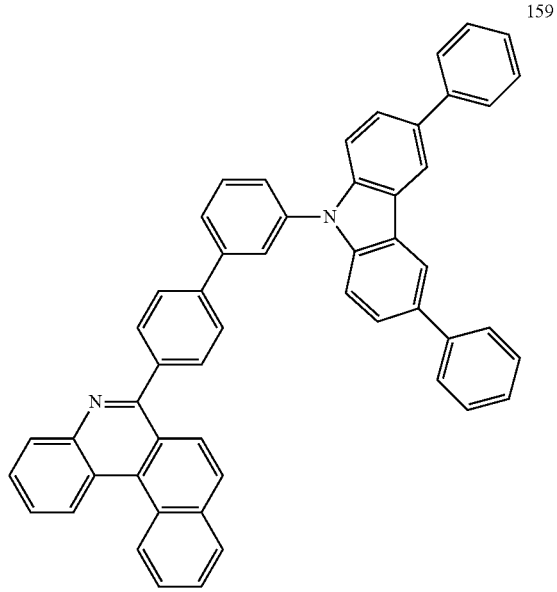
160
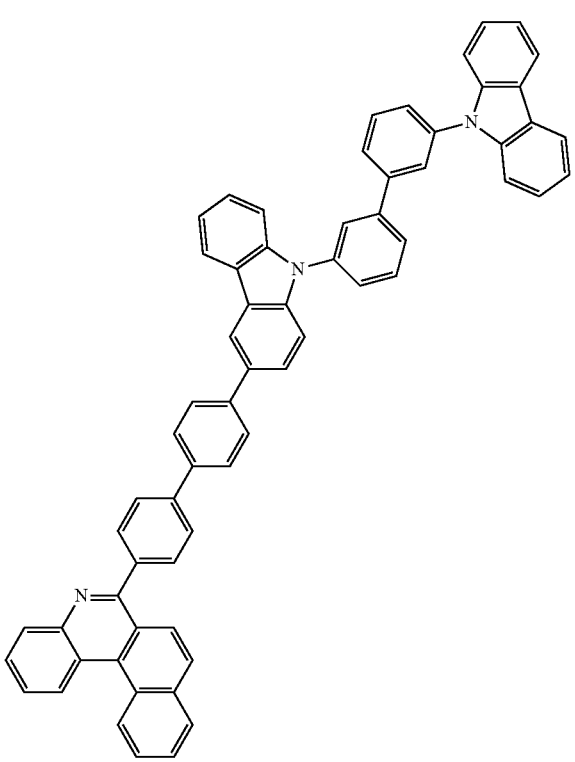

161
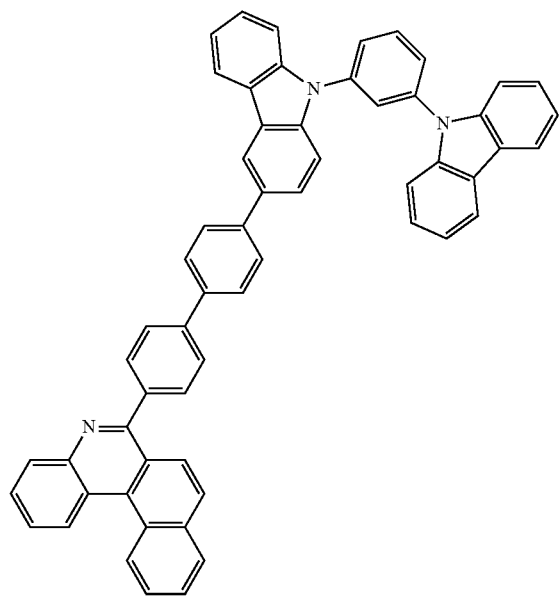
162
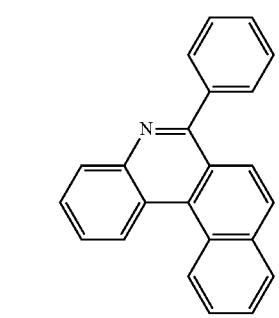
163
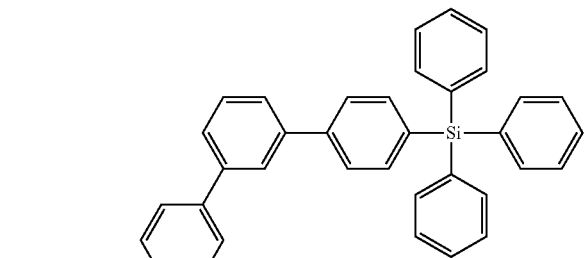
164
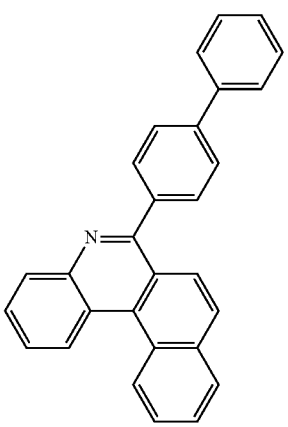
165
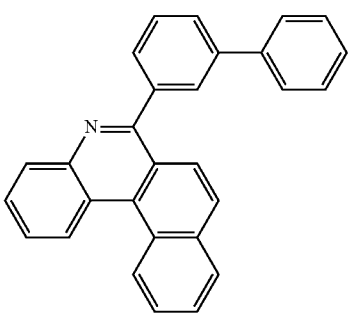
166

-continued
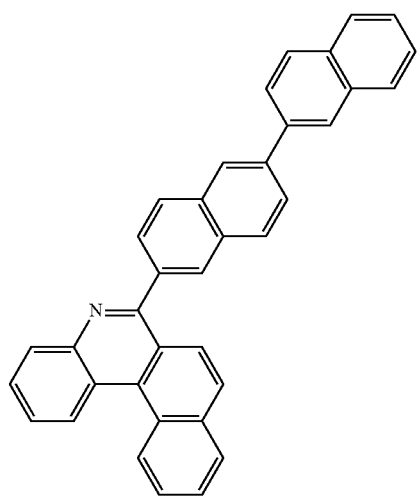
167
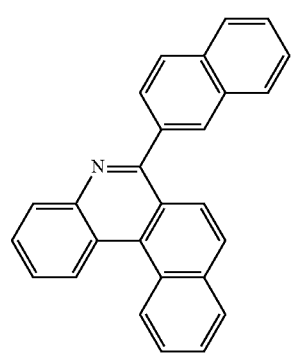
168
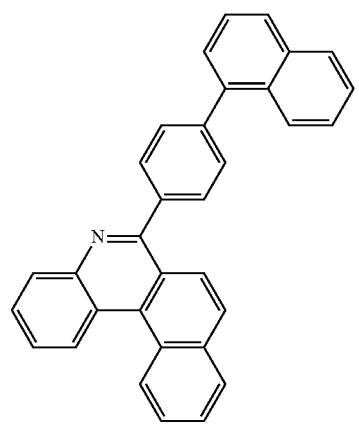
169
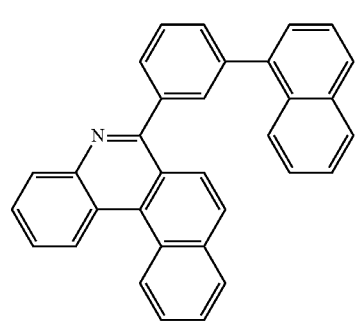
170
-continued
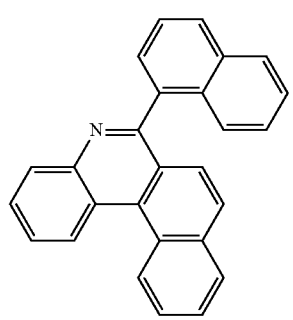
171
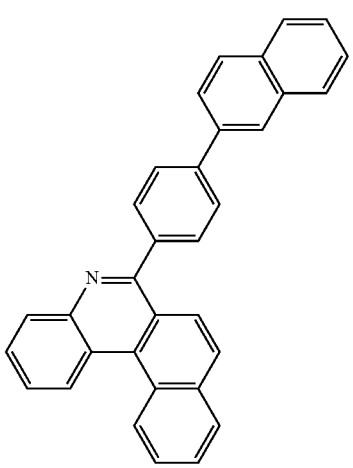
172
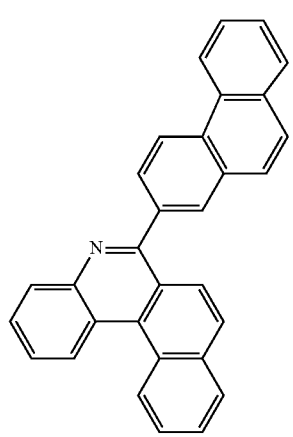
173

-continued
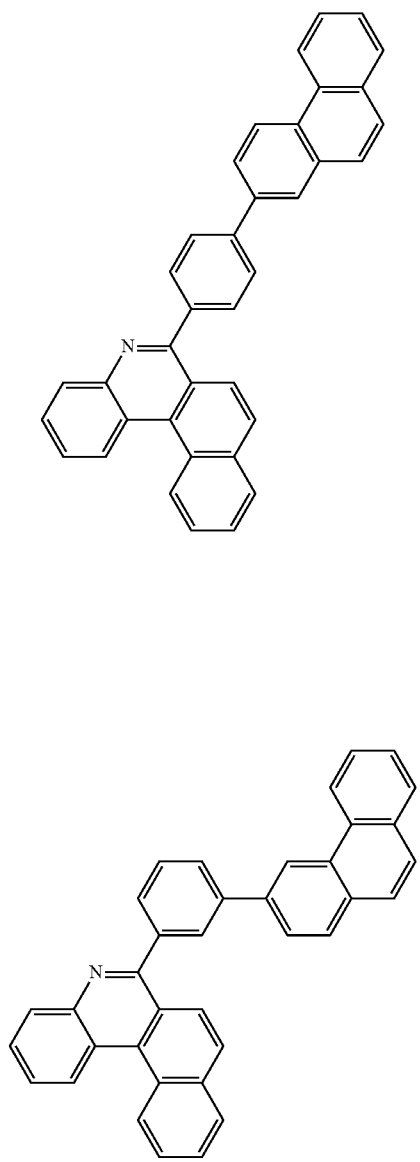
174
175
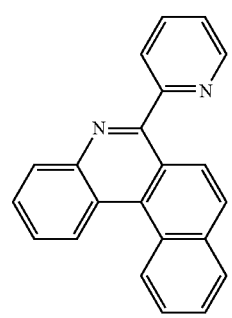
176
-continued
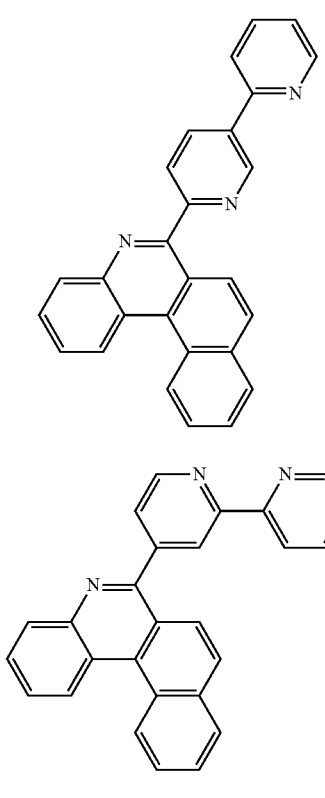
177
178
179
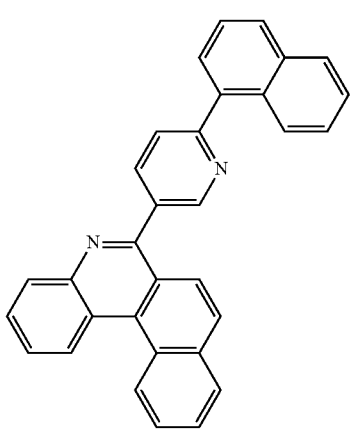
180

-continued
181
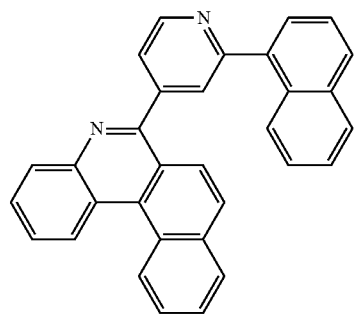
182
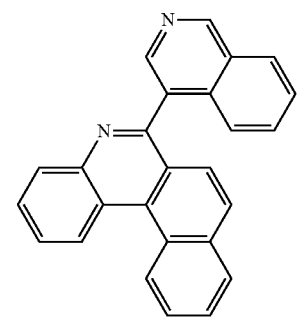
183
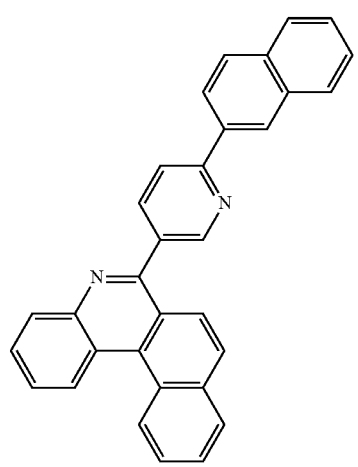
184
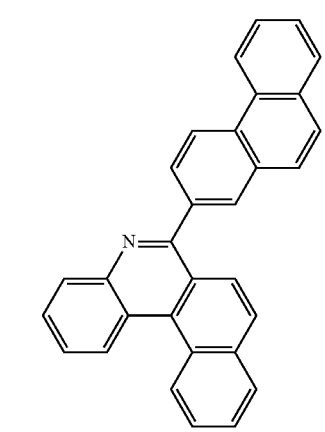
-continued
185
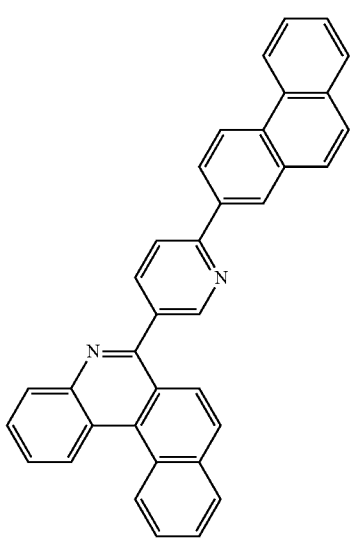
186
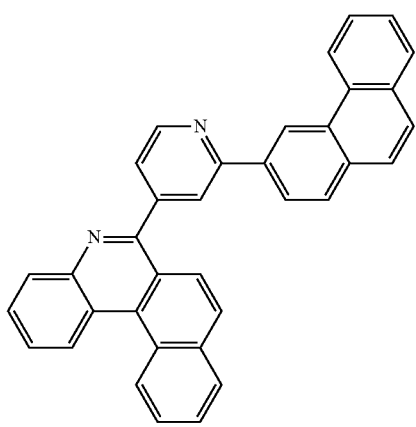
187
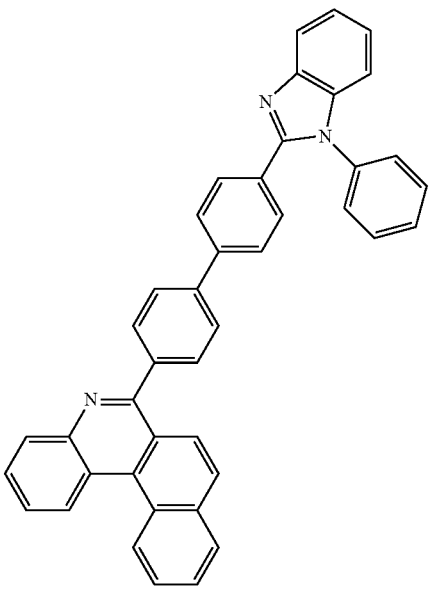

-continued
188
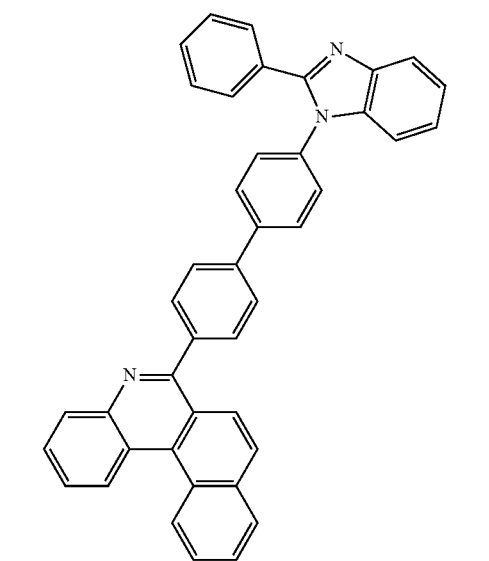
189
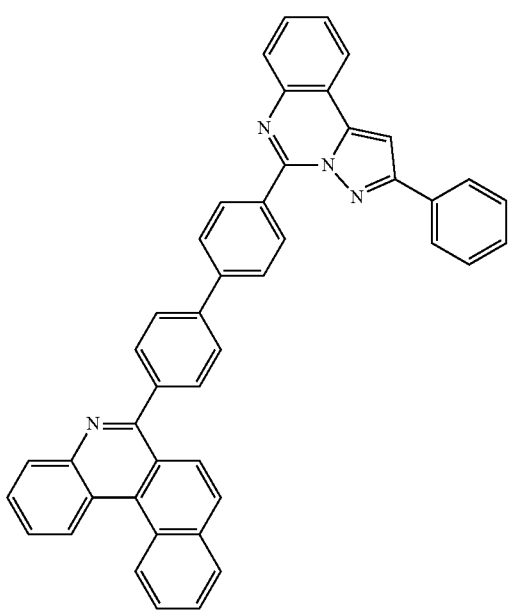
190
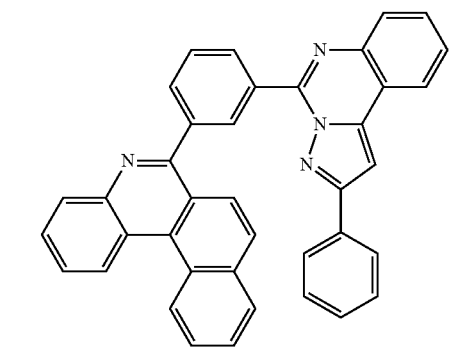
-continued
191
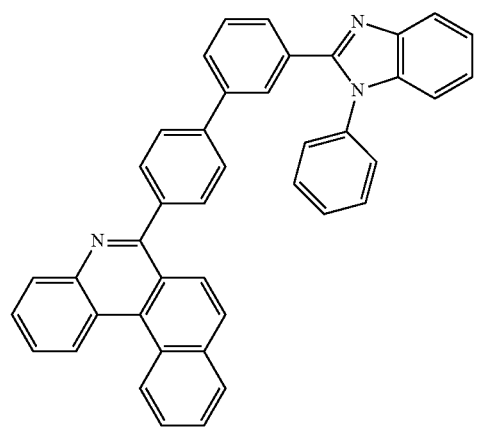
192
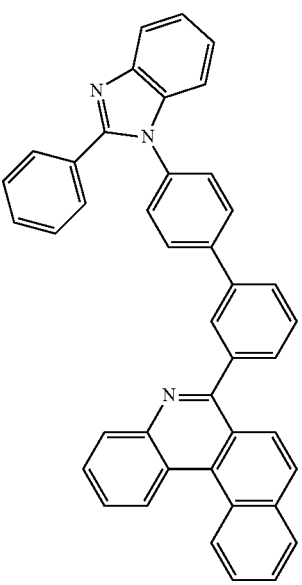
193
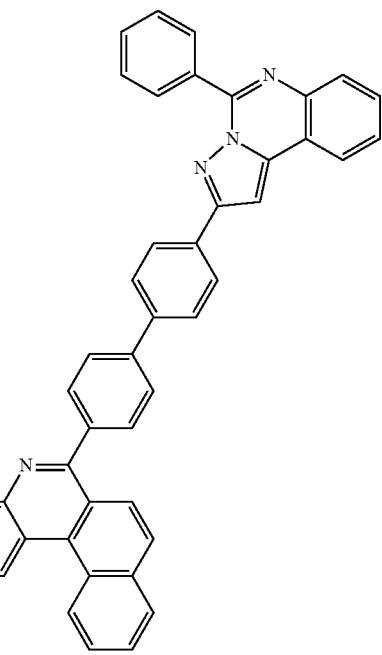

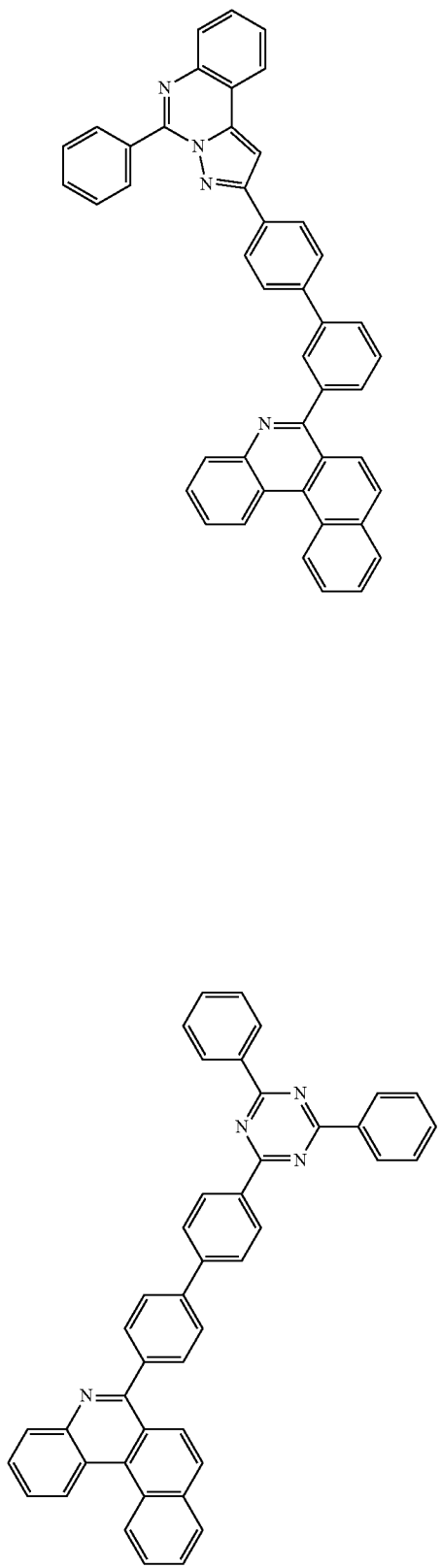
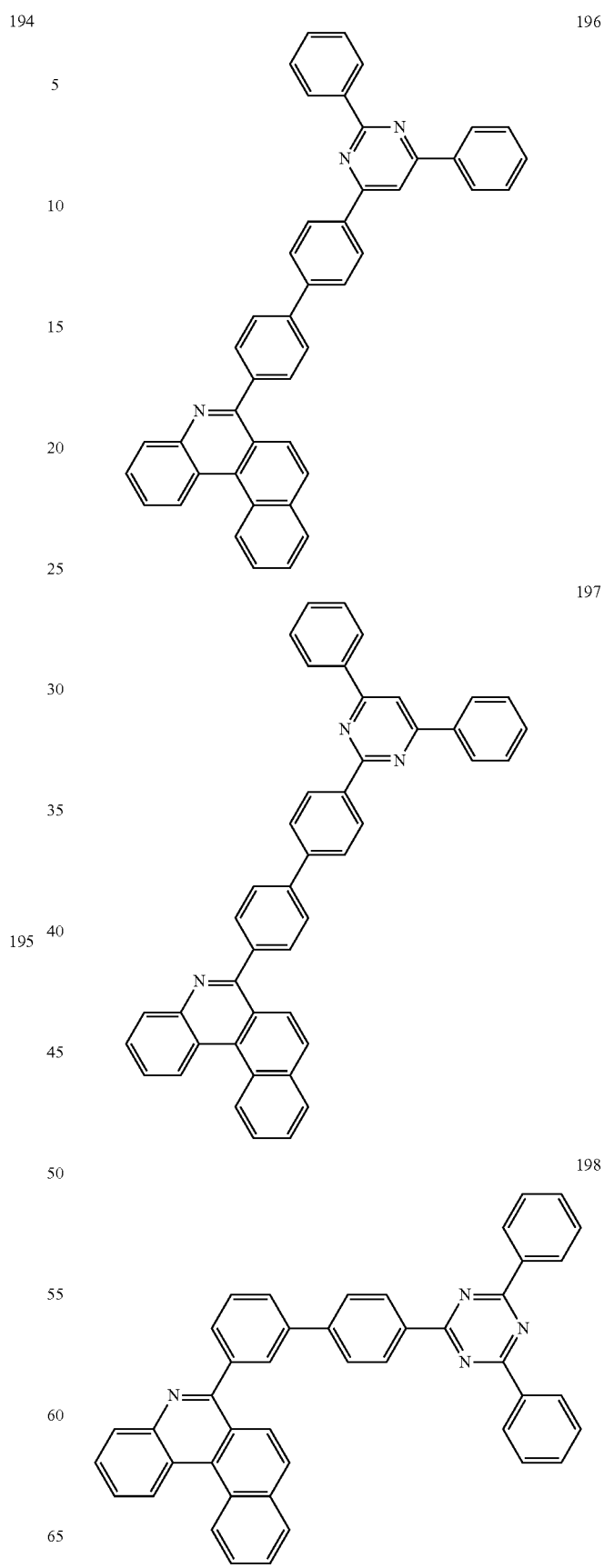

-continued
199
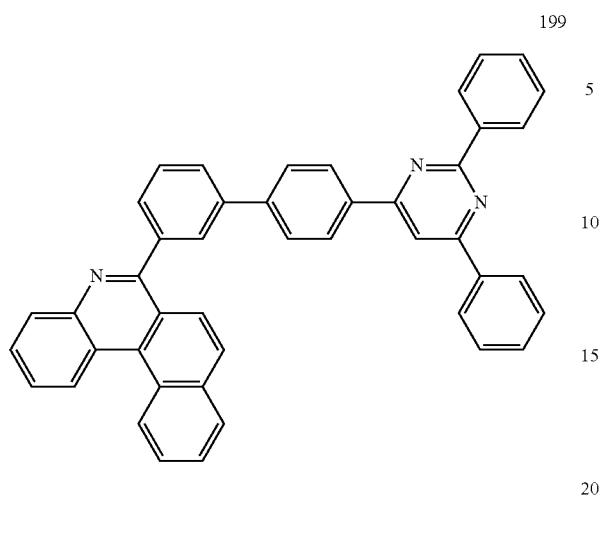
200
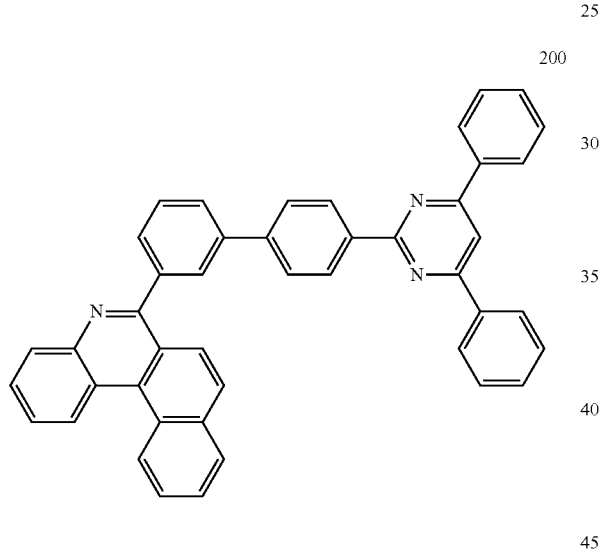
201
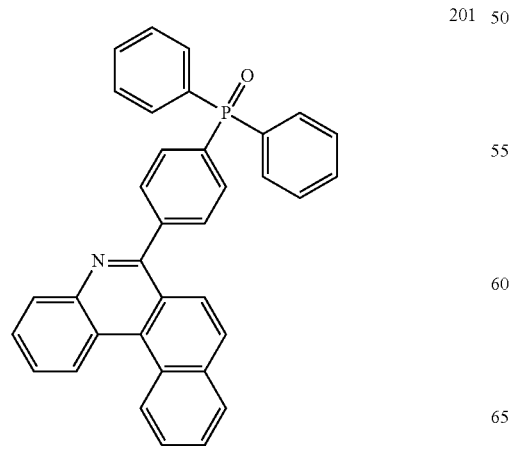
202
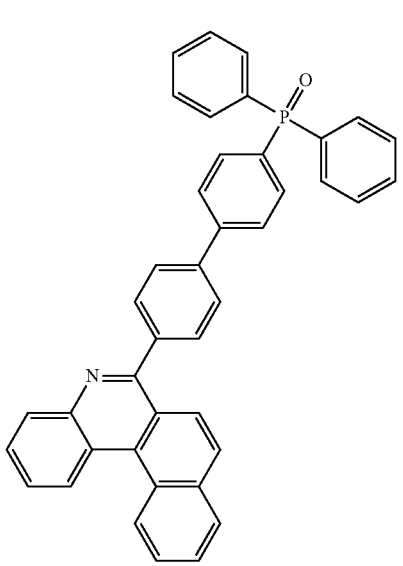
203
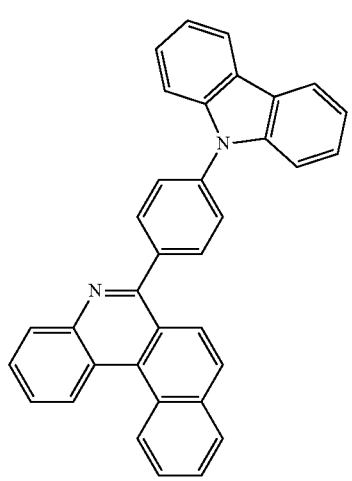
204
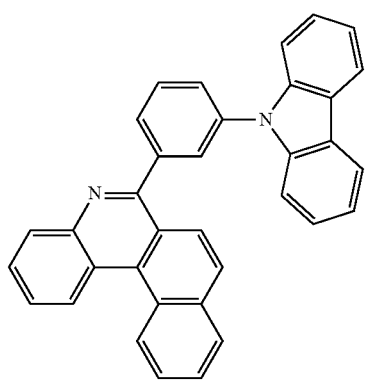

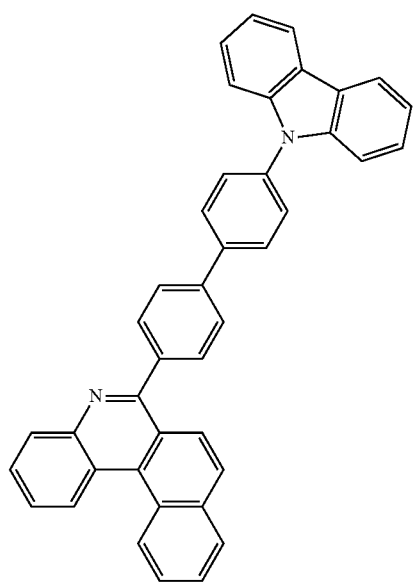
205
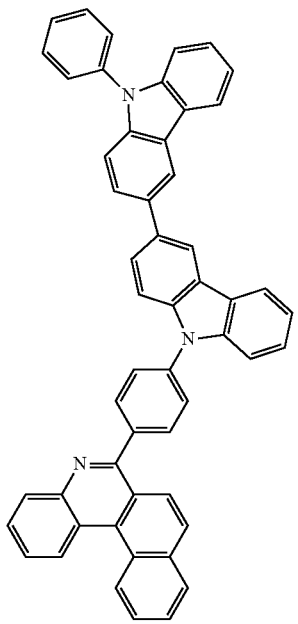
207
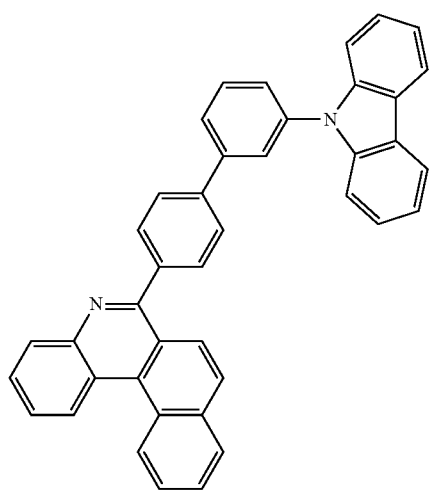
206
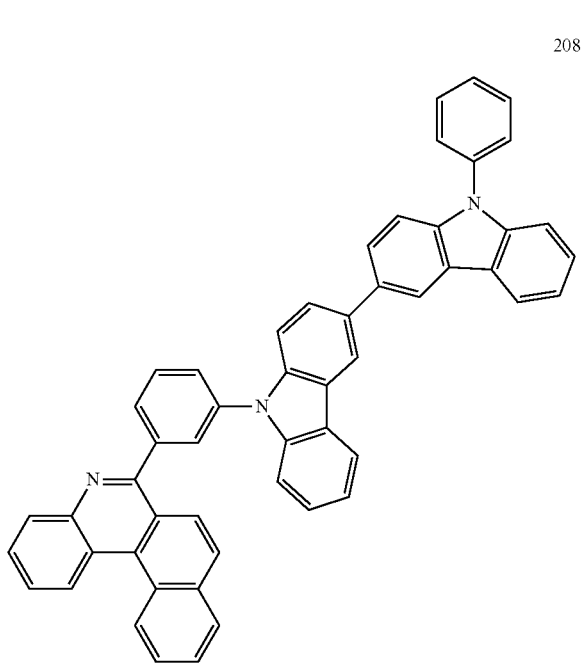
208

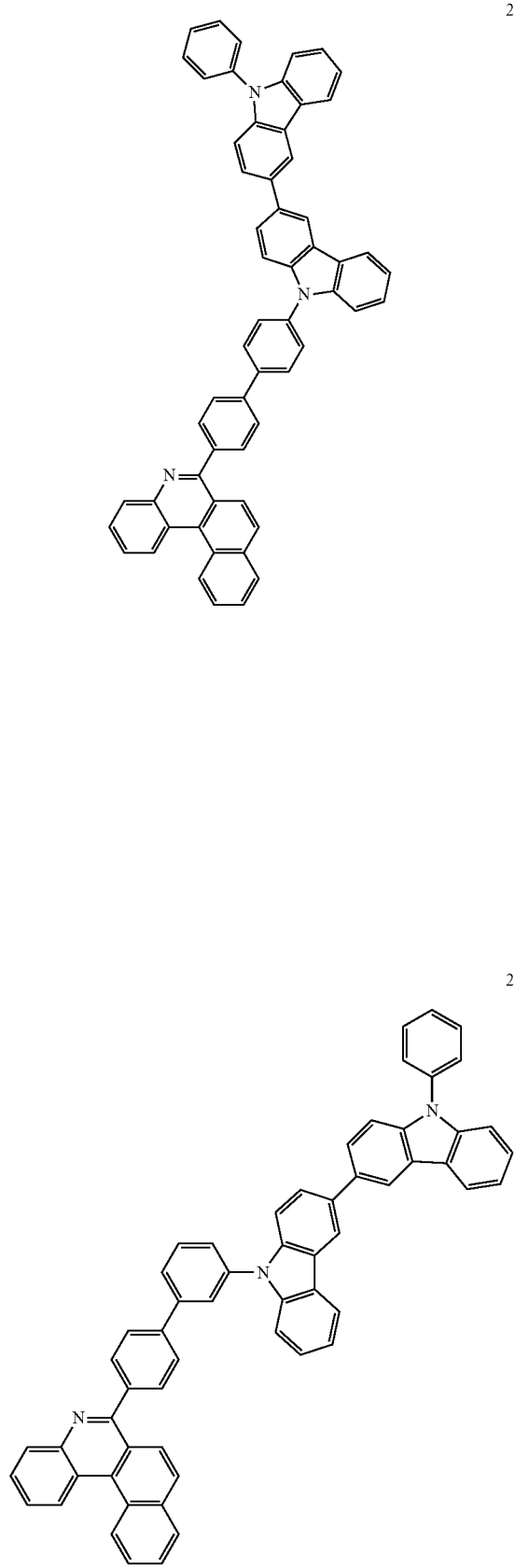
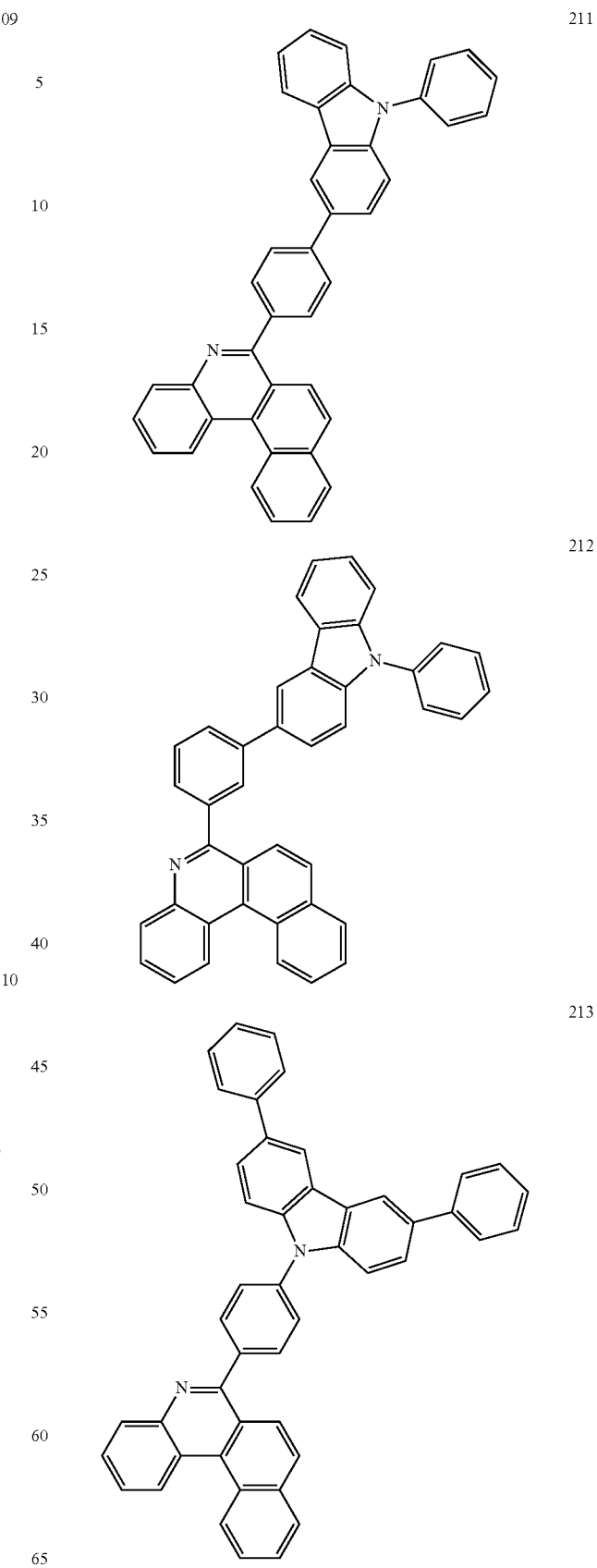

-continued
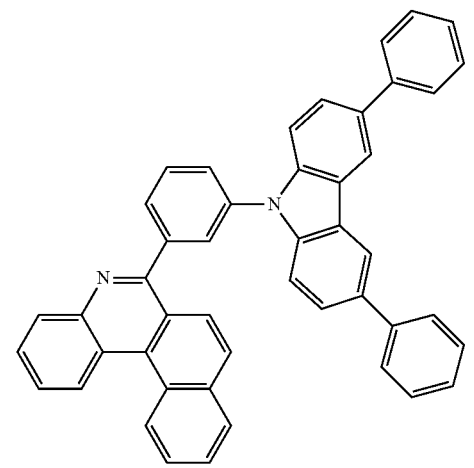
214
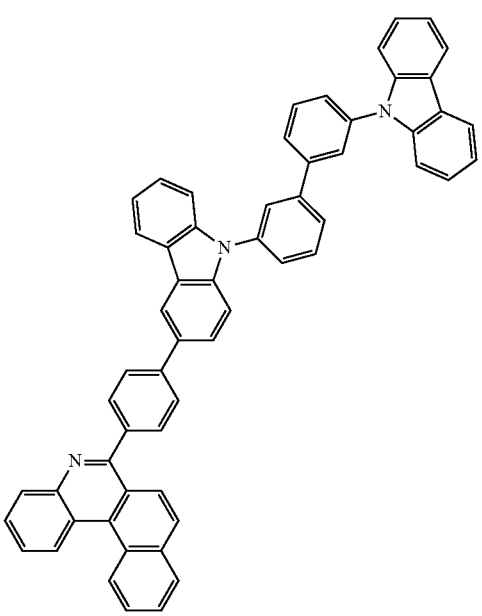
215
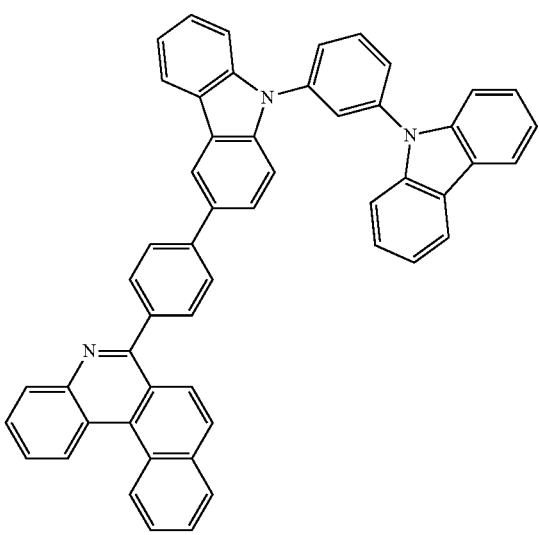
216
-continued
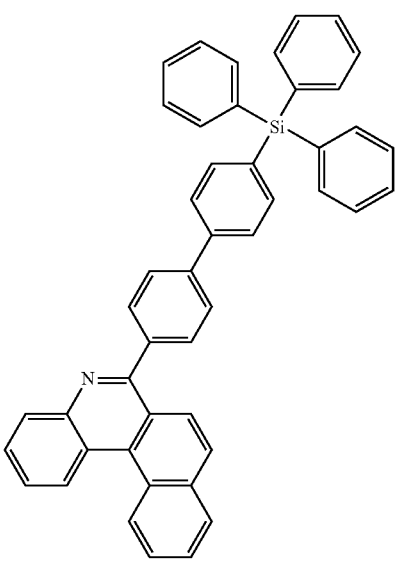
217
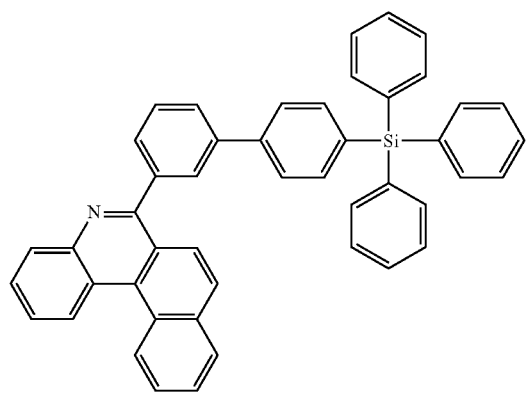
218
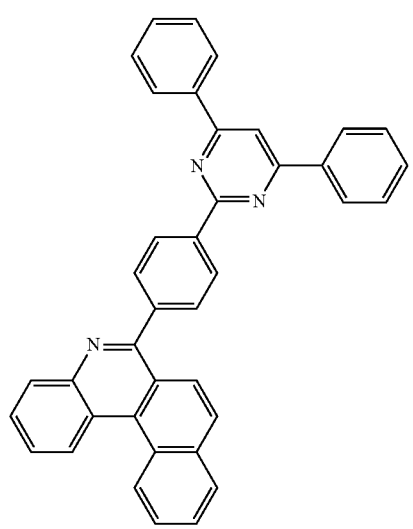
219

220
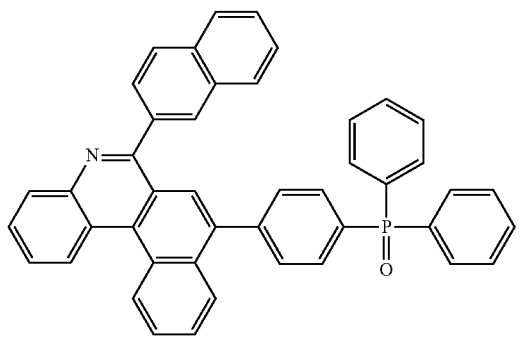
221
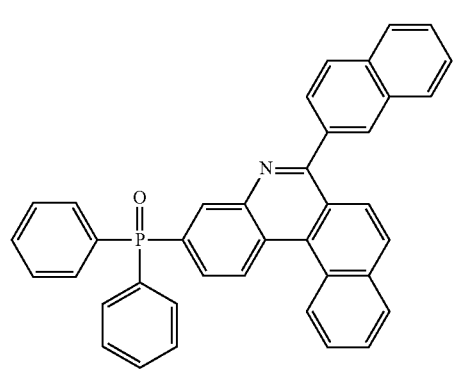
222
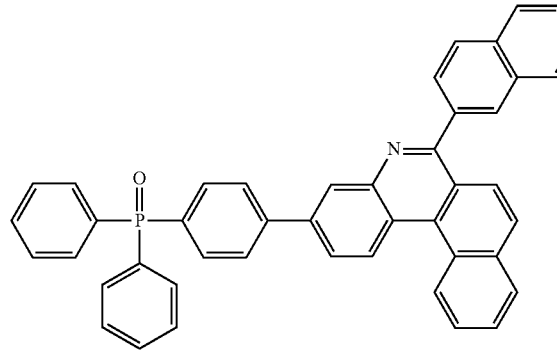
223
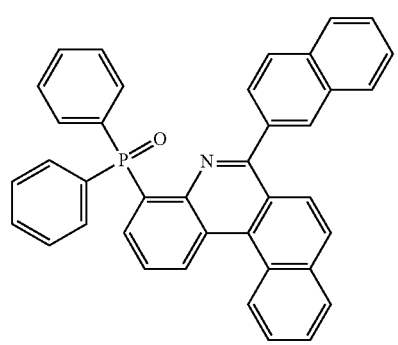
224
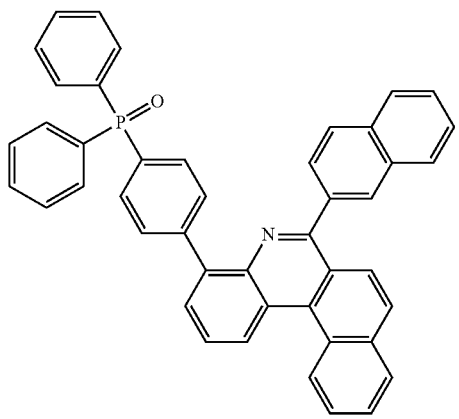
225
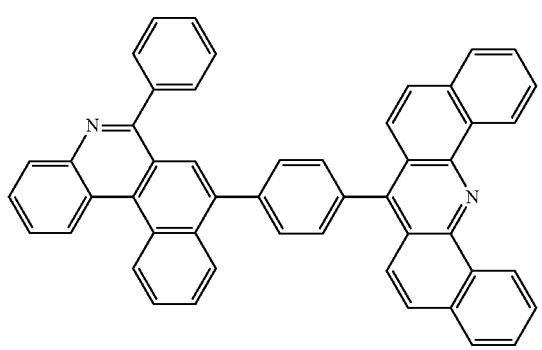
226
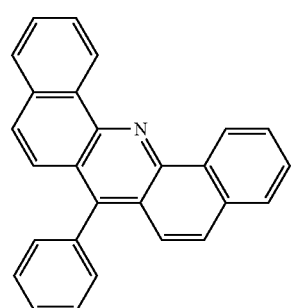
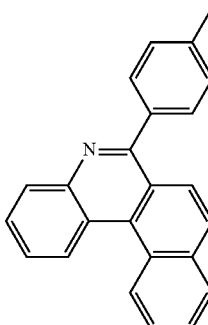

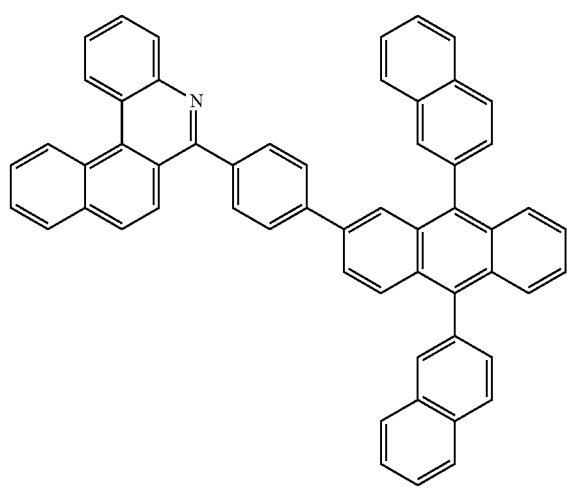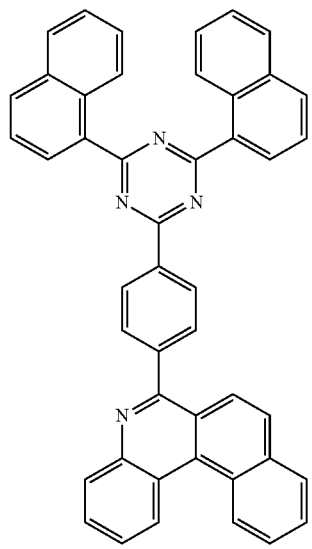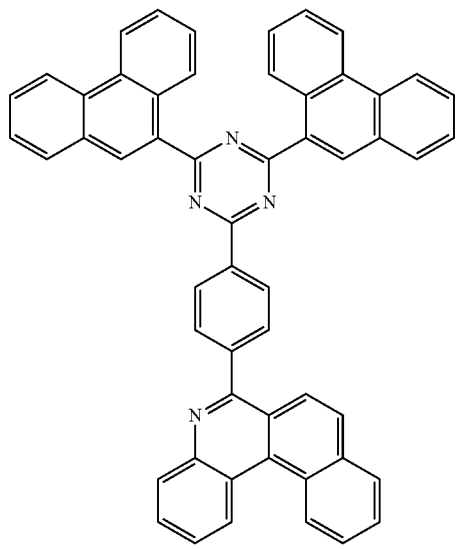

-continued
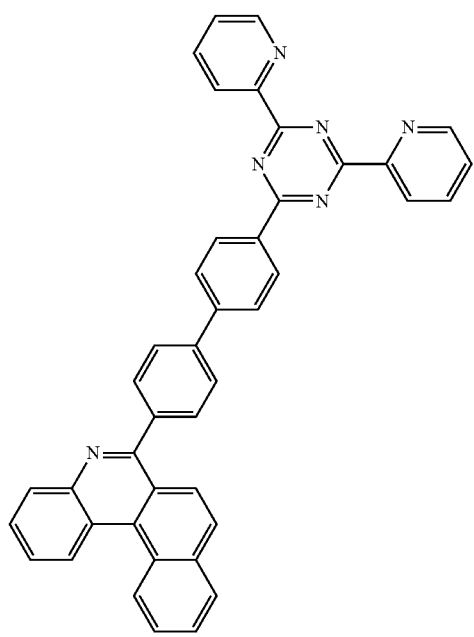
232
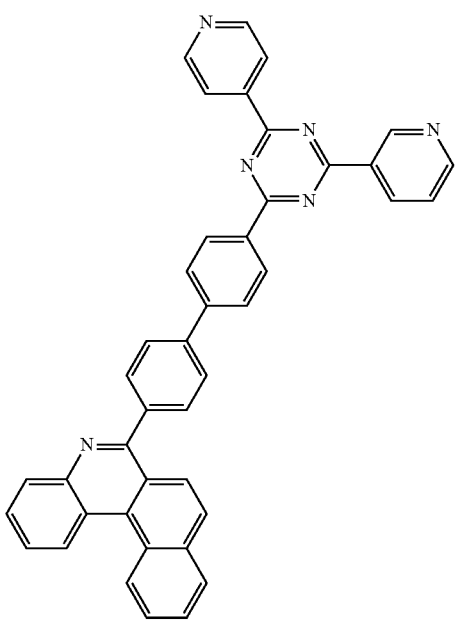
234
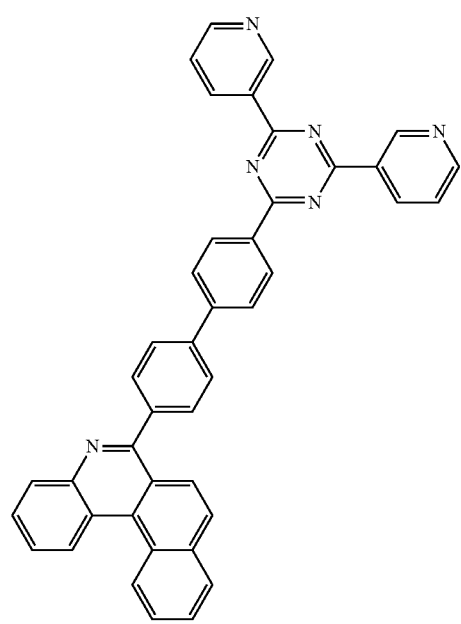
233
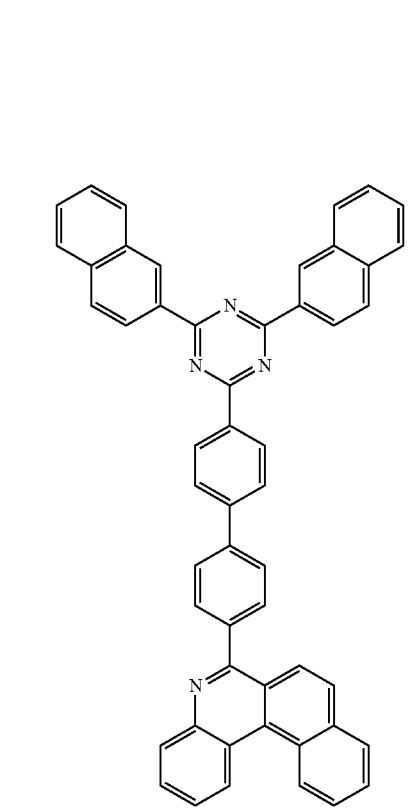
235

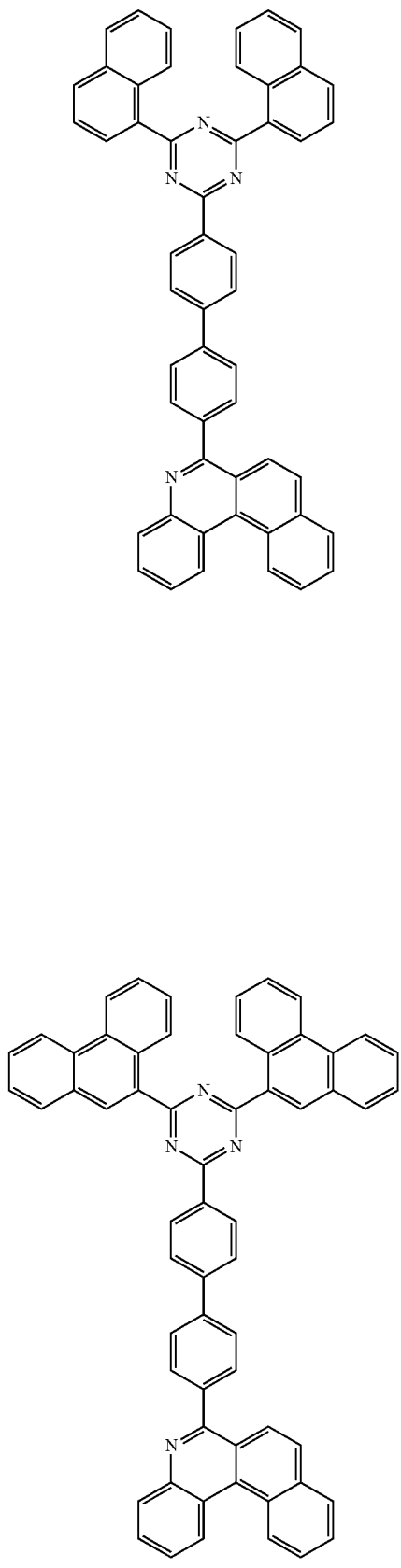
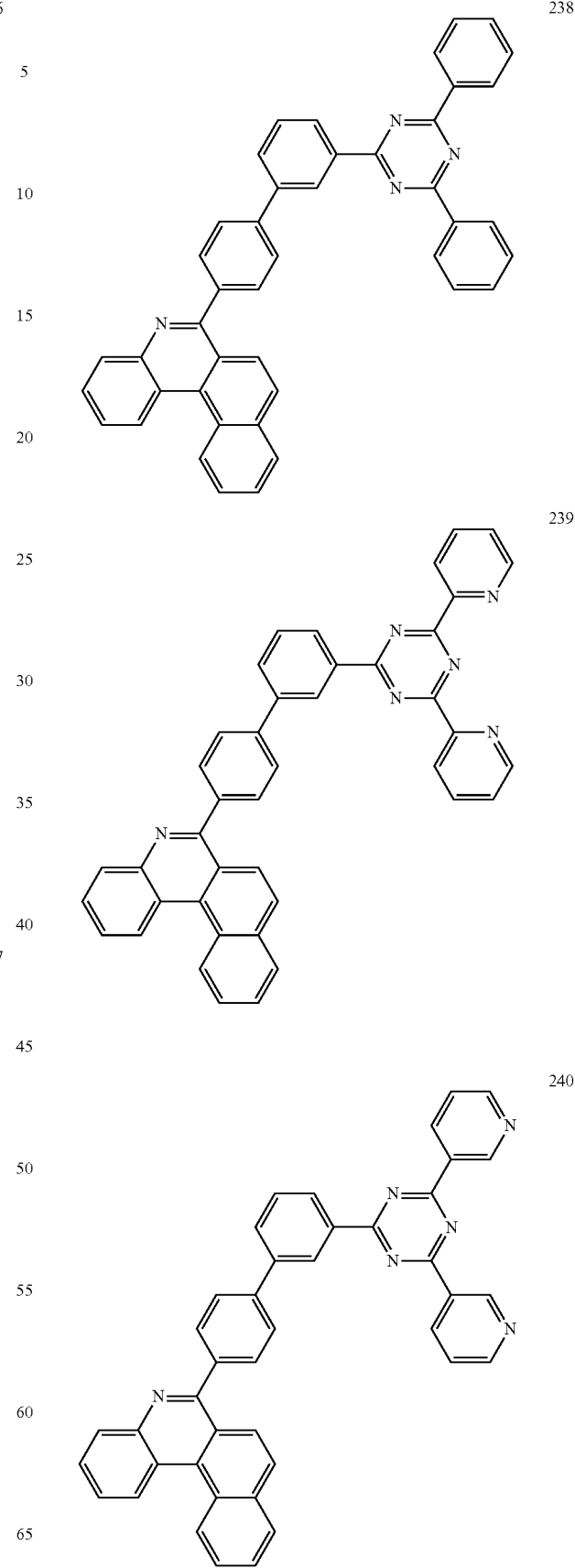

241
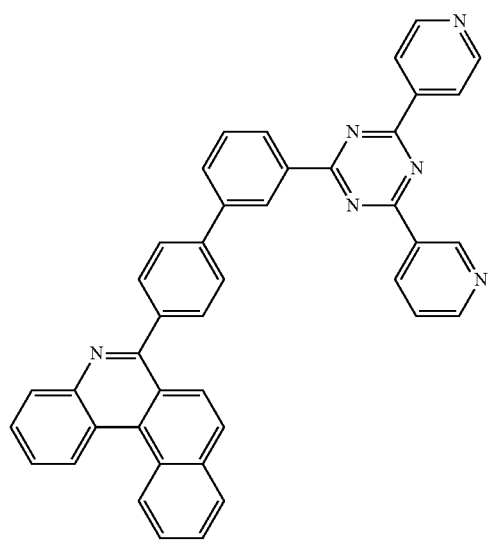
242
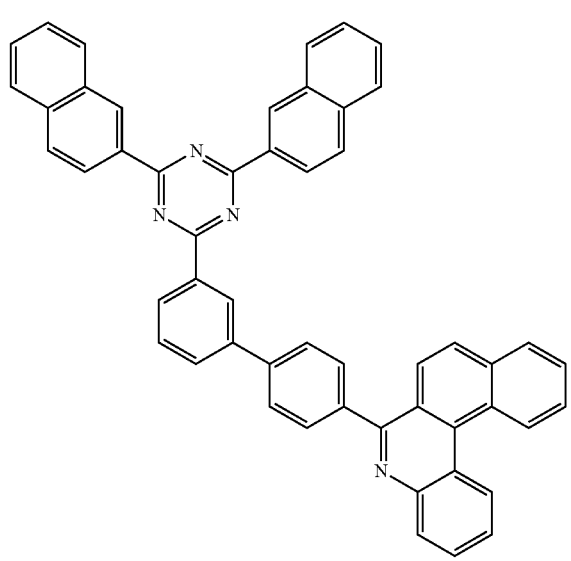
243
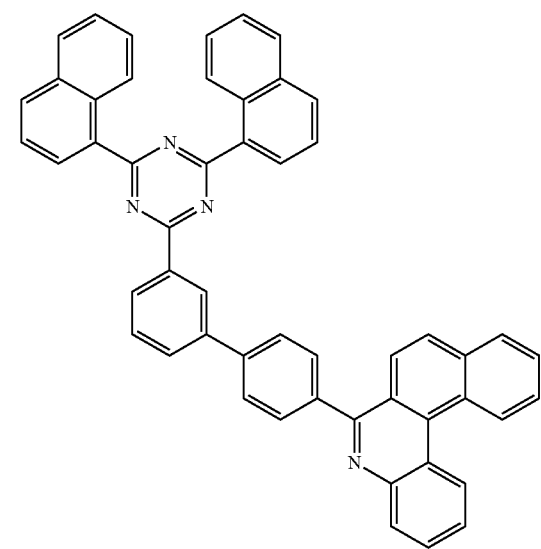
244
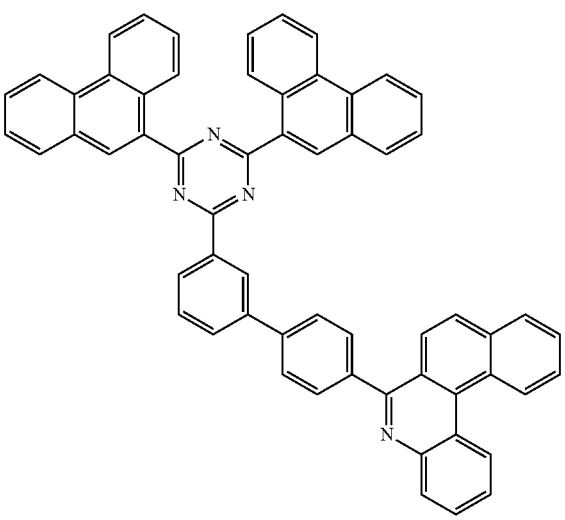
245
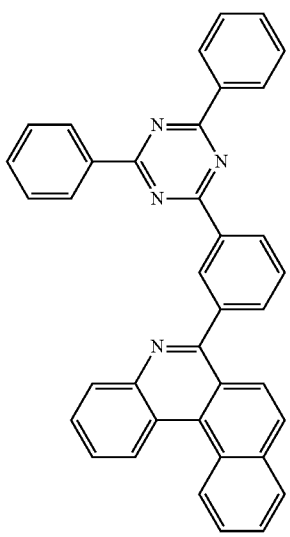
246
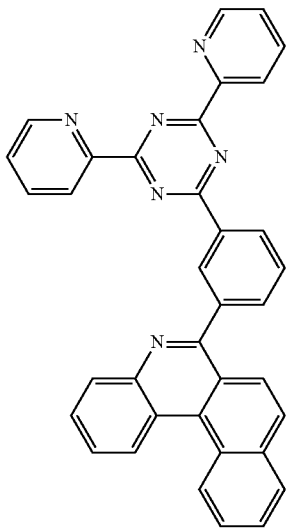

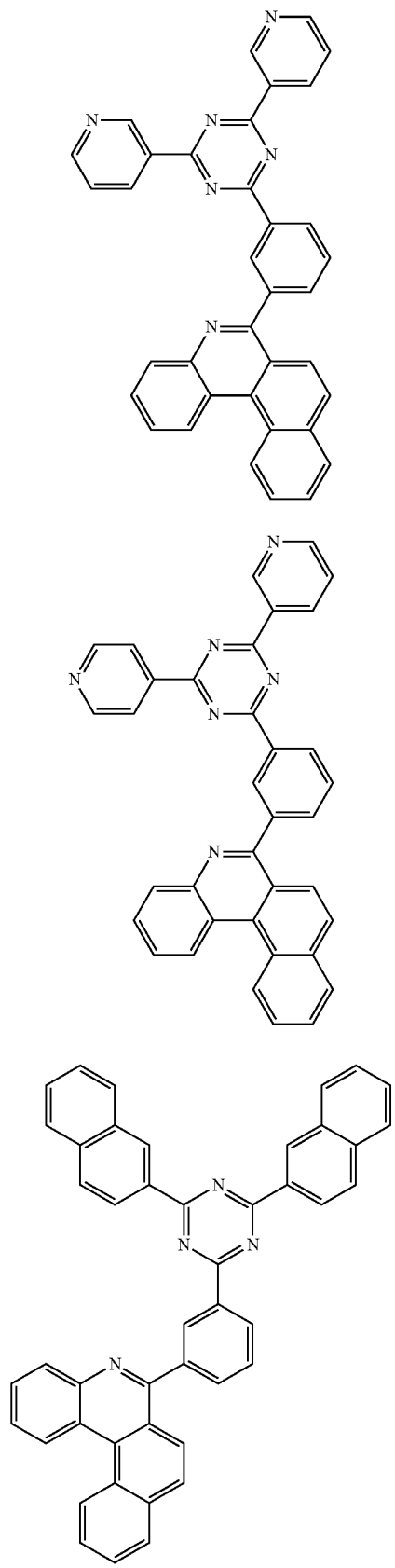

252
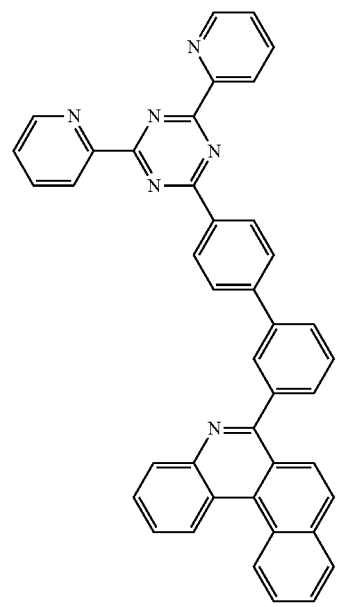
253
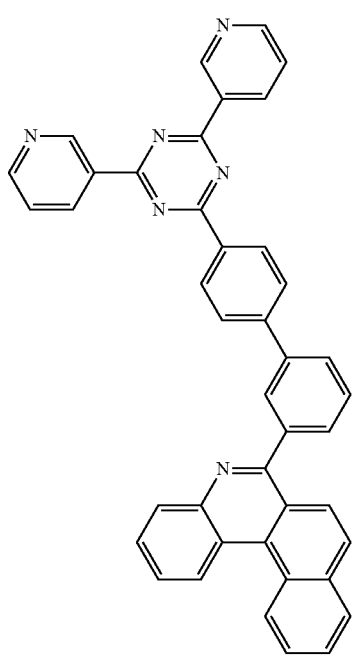
254
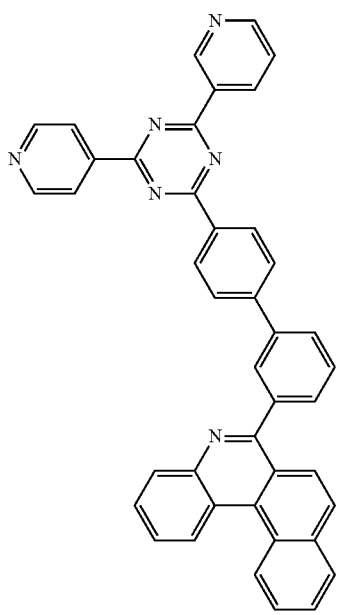
255
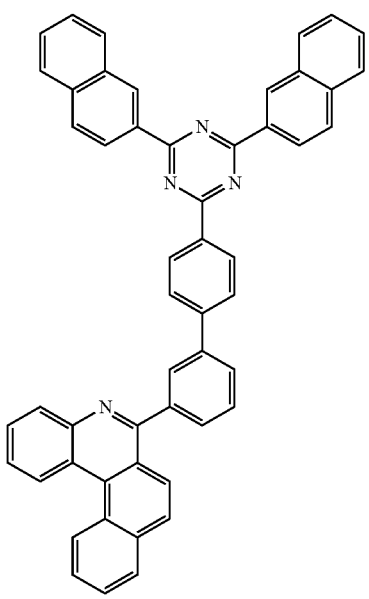

256
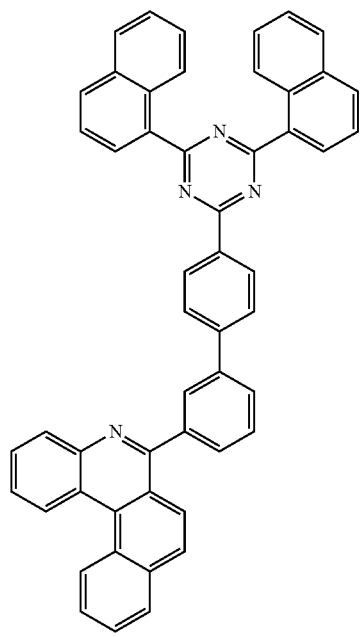
258
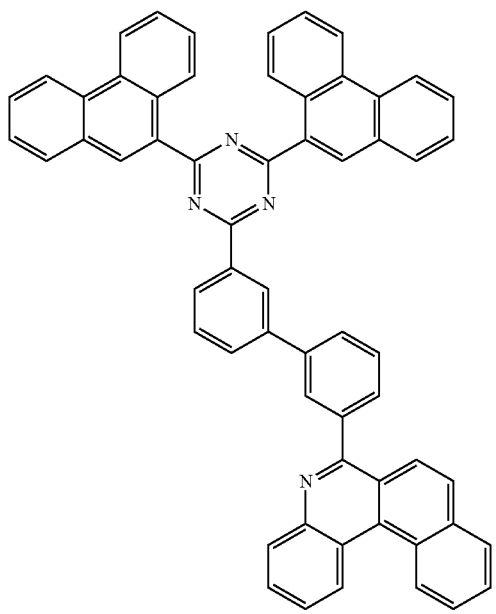
257
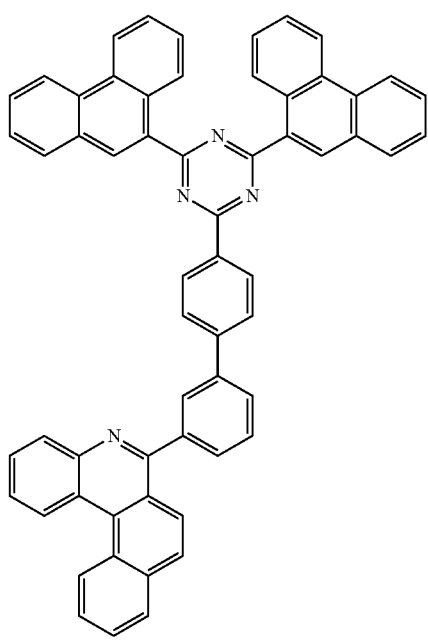
259
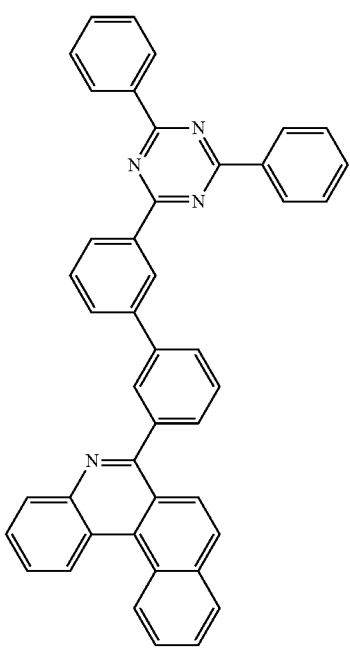

107
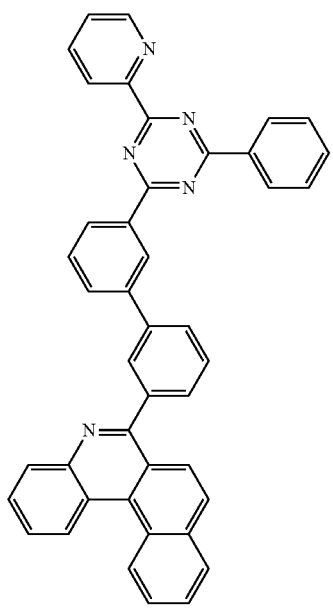
260
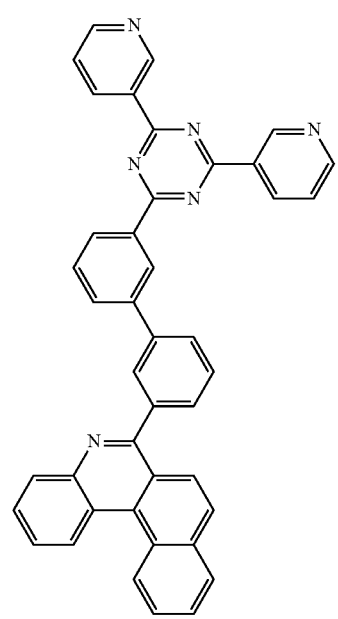
261
108
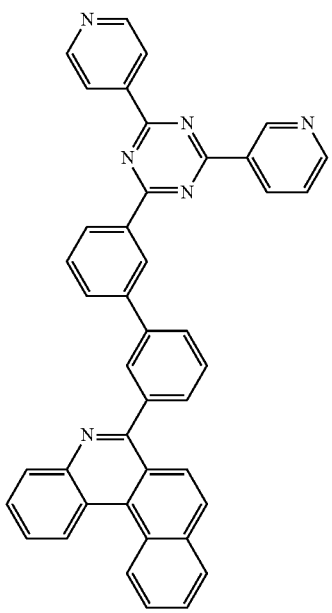
262
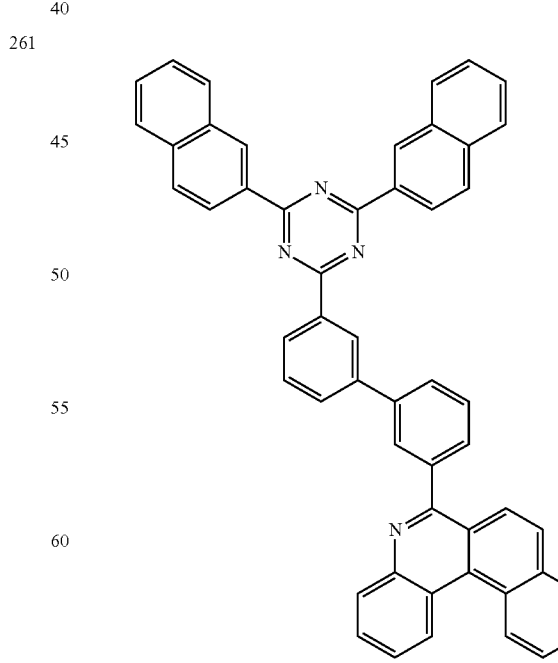
263

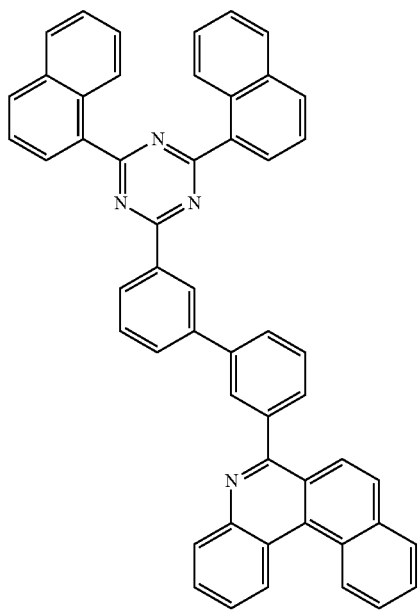
264
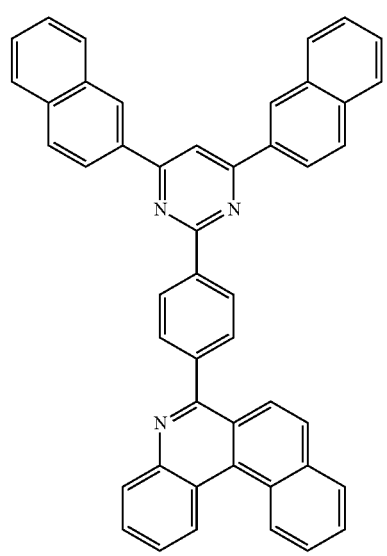
265
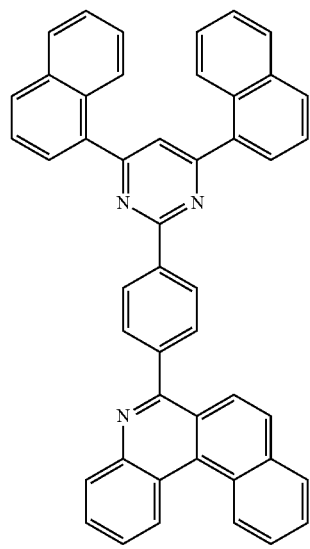
266
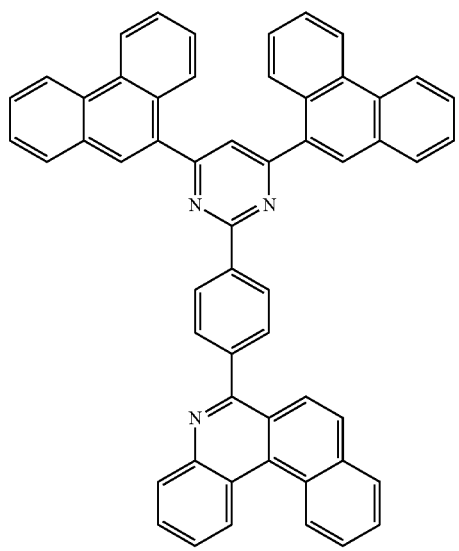
267
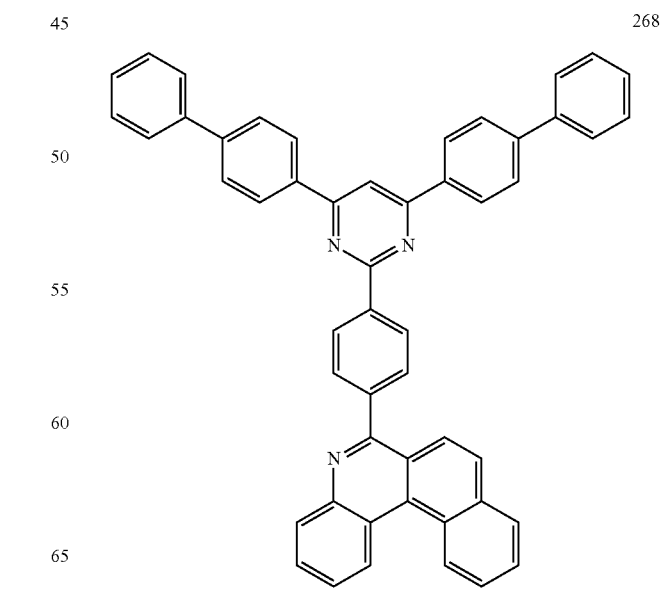
268

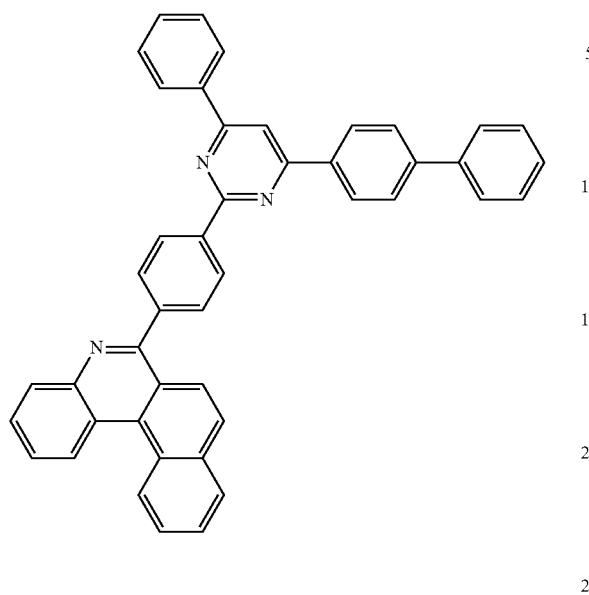
269
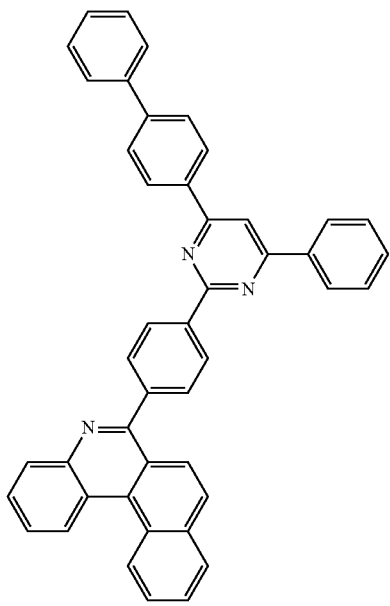
270
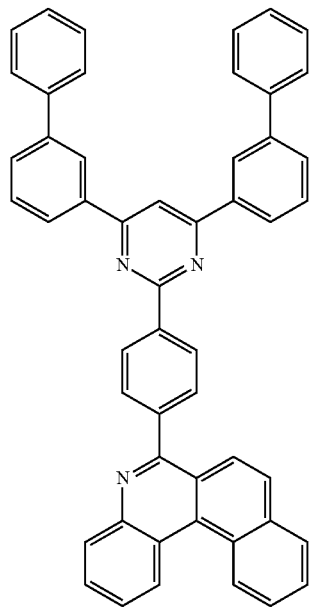
271
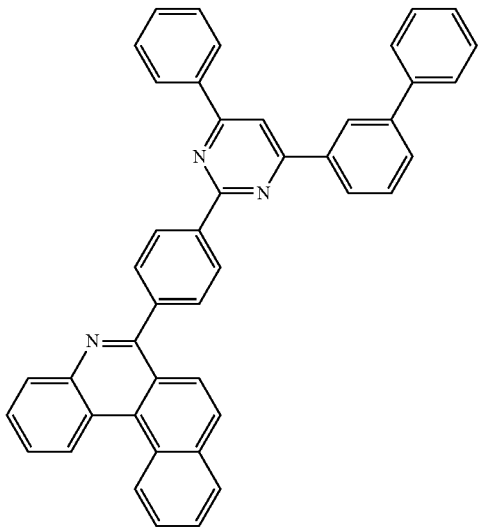
272

113
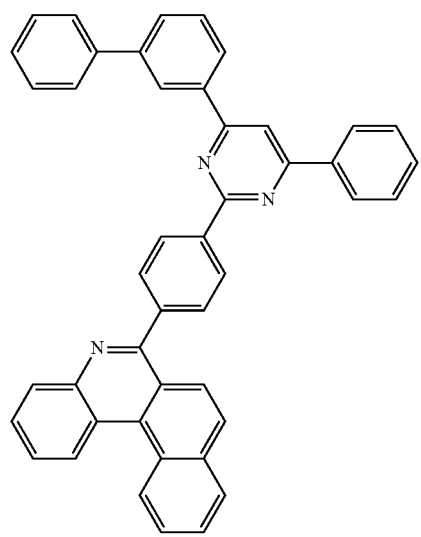
114
-continued
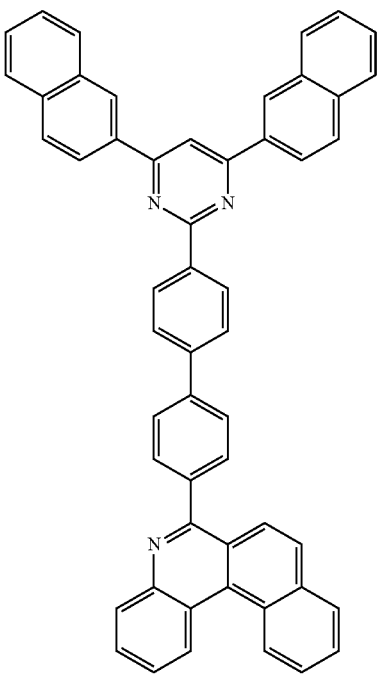
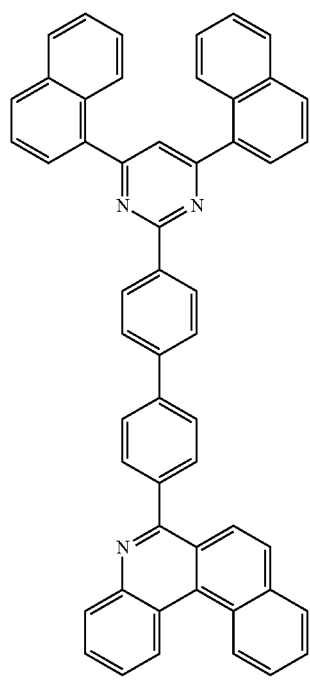
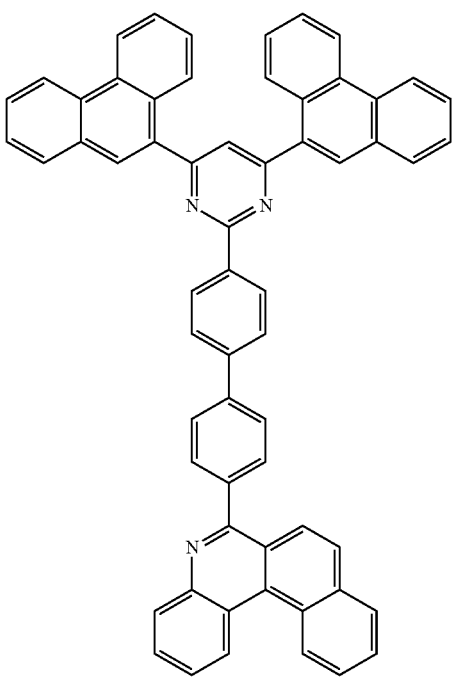

-continued
277
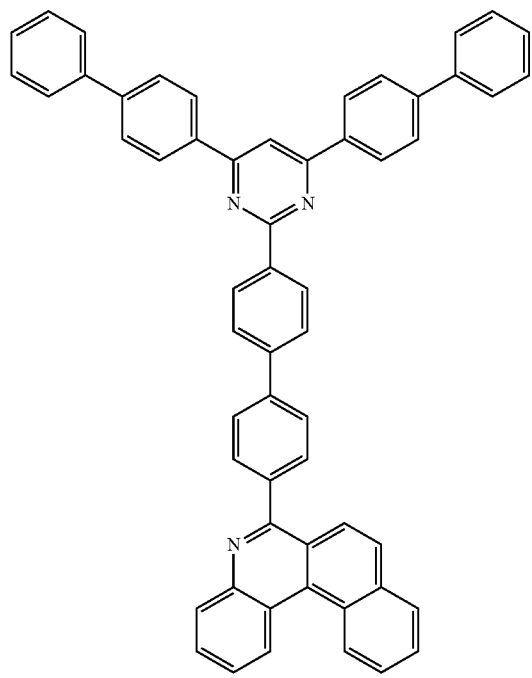
278
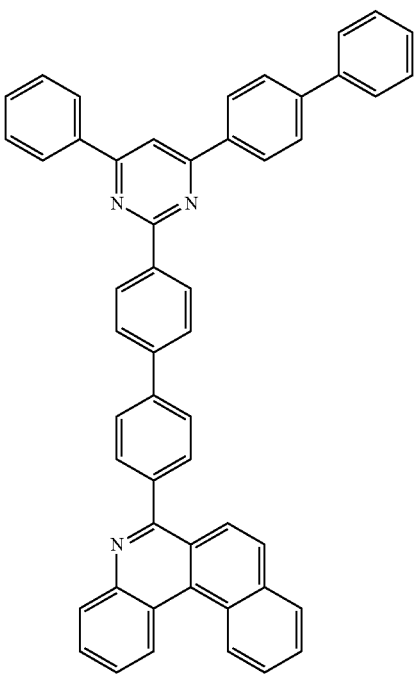
279
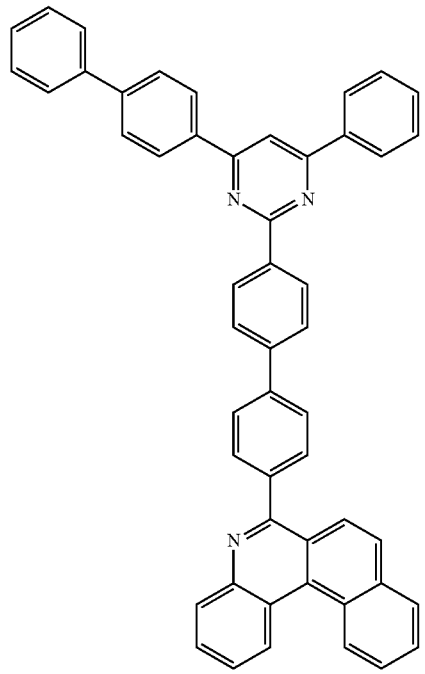
280
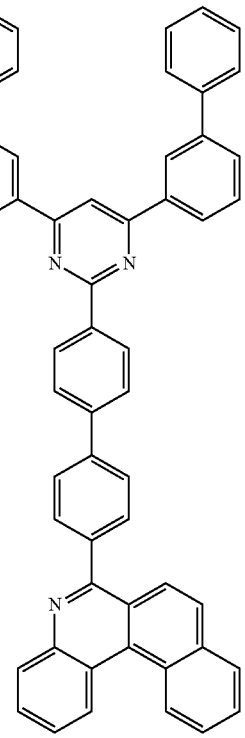

281
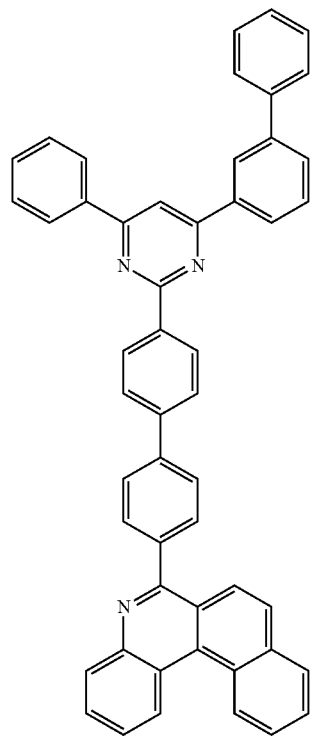
282
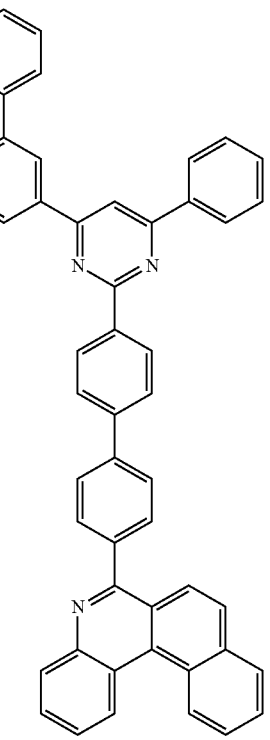
283
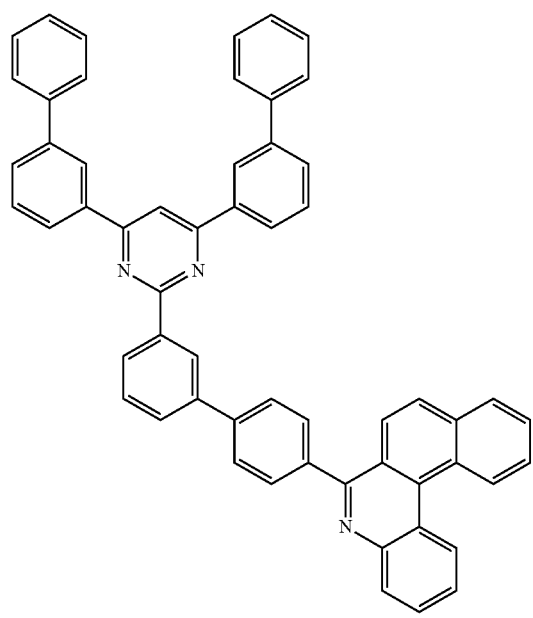
284
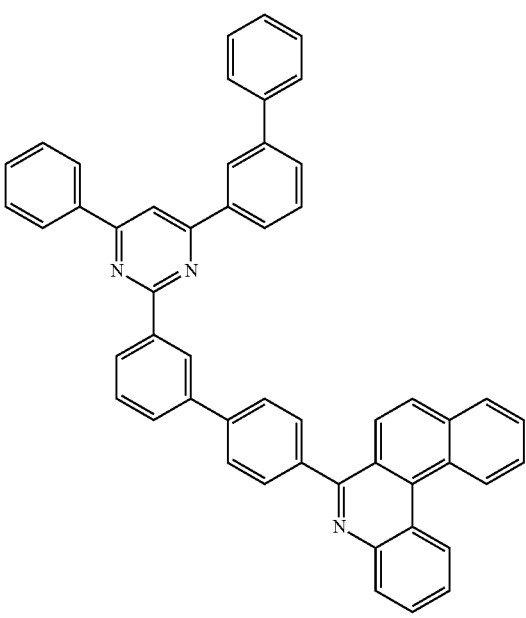

285
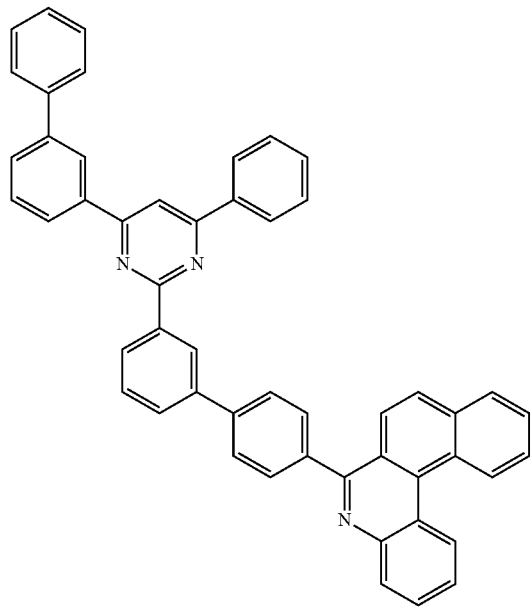
286
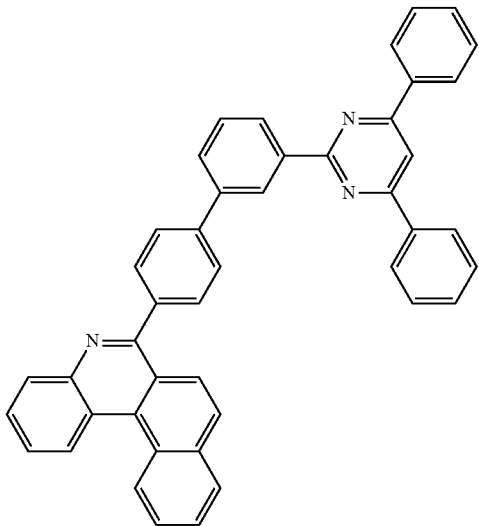
287
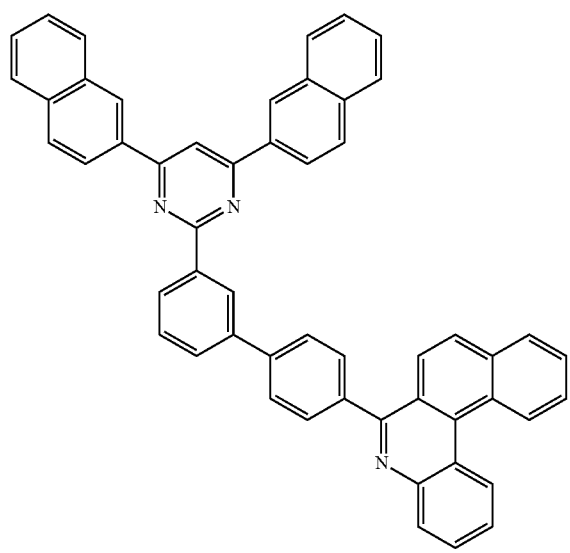
288
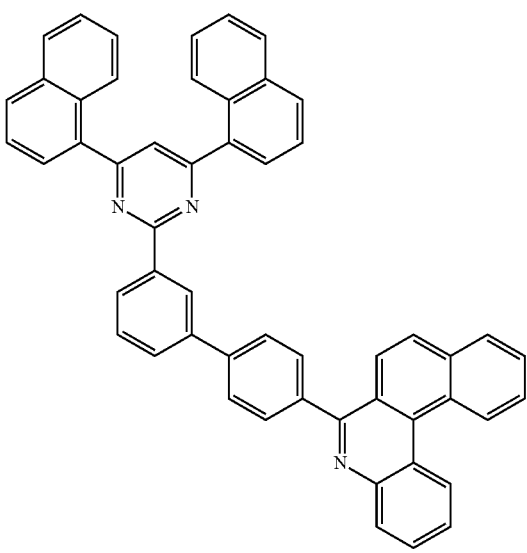

-continued
289
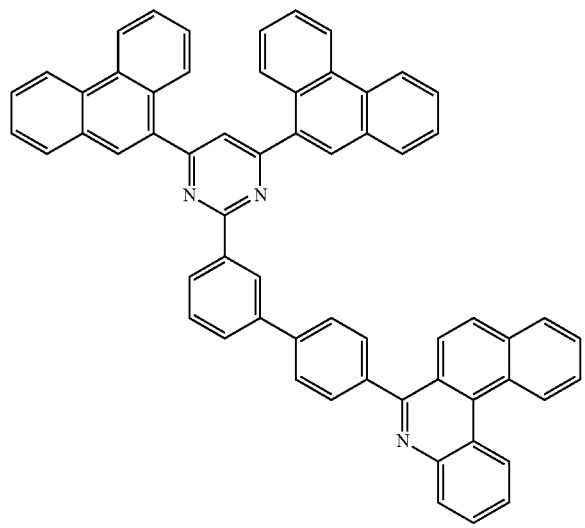
290
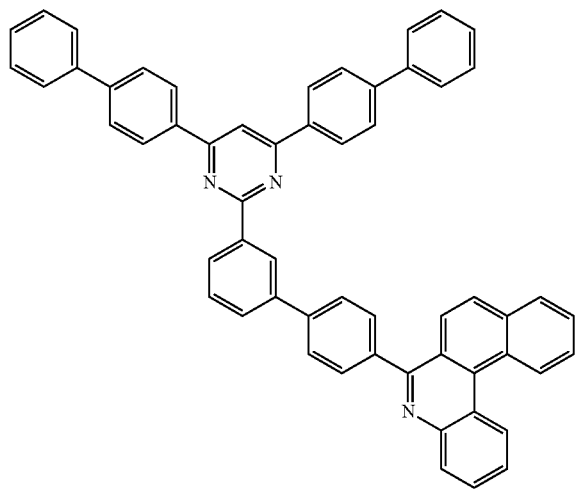
291
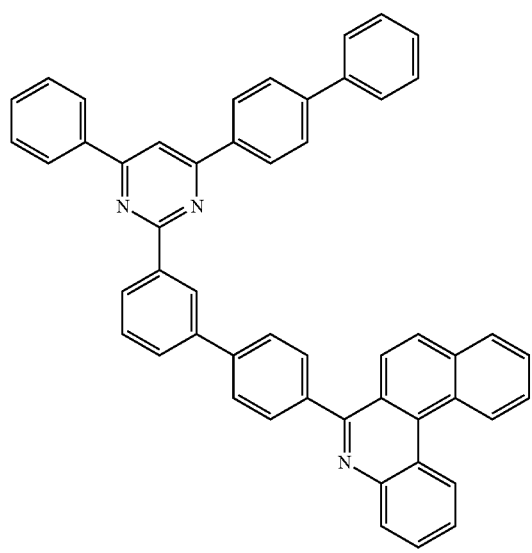
292
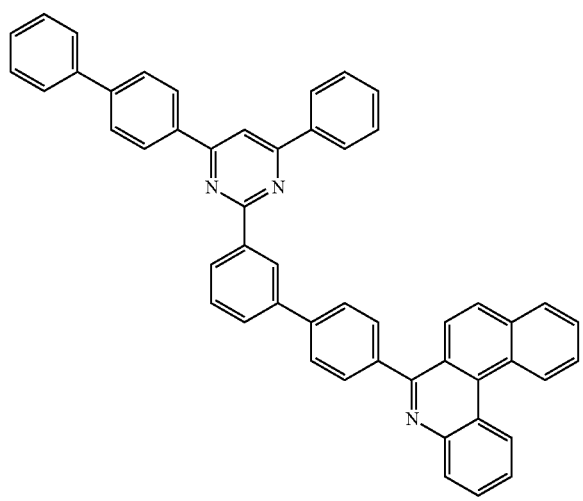
293
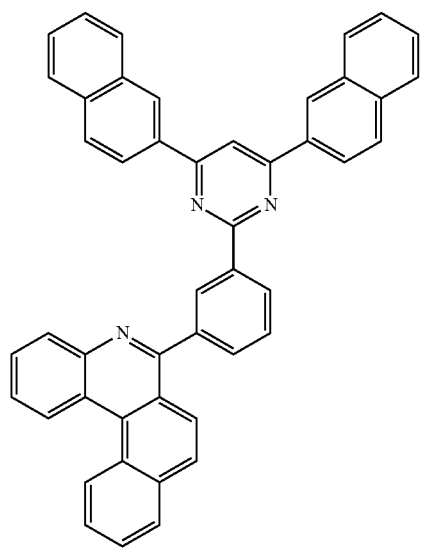
294
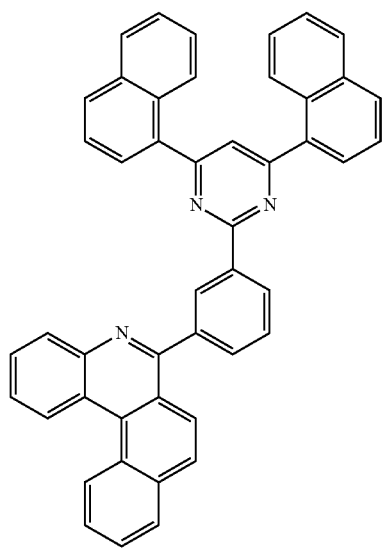

123
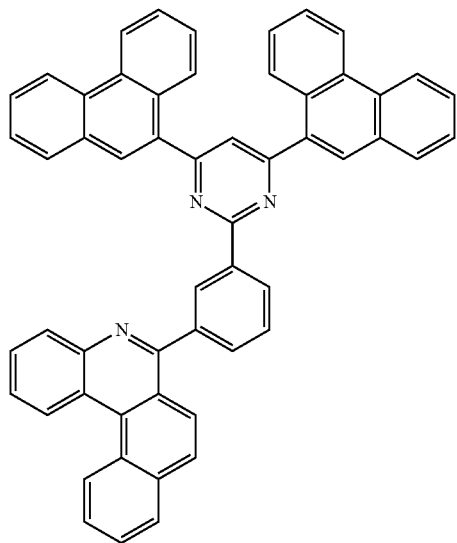
295
124
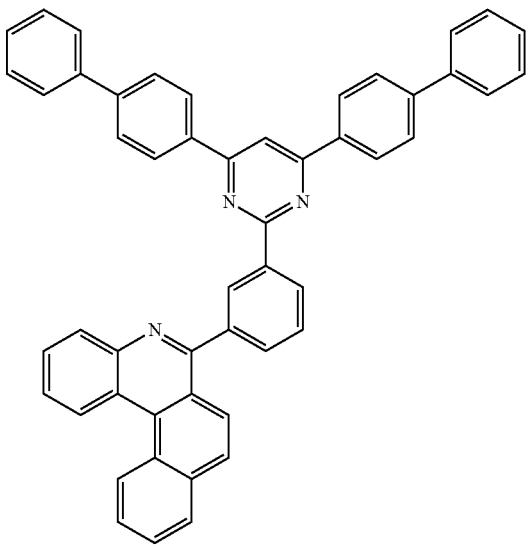
296
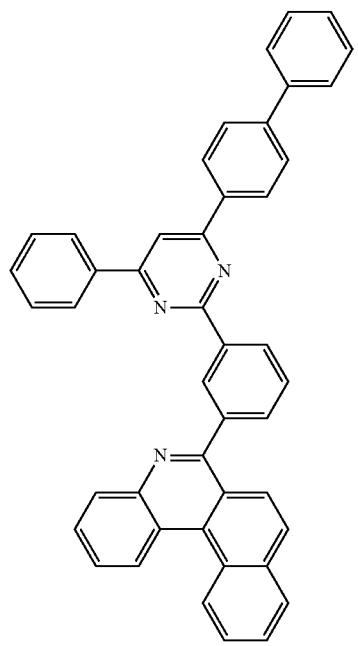
297
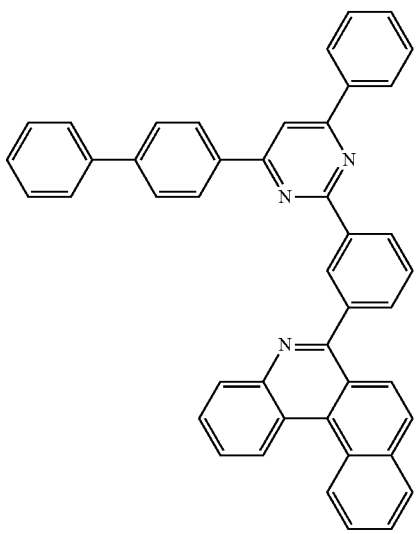
298

-continued
125
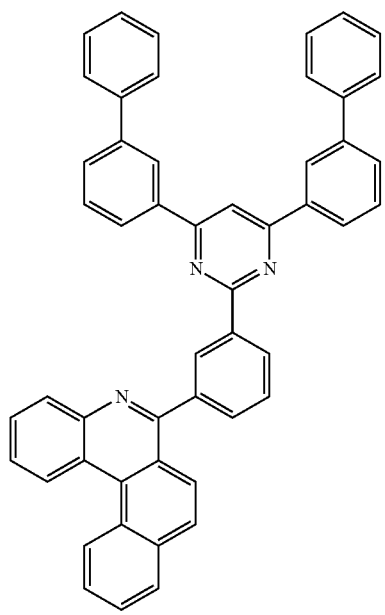
299
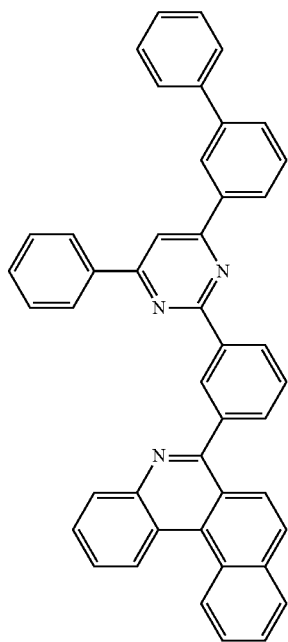
126
300
301
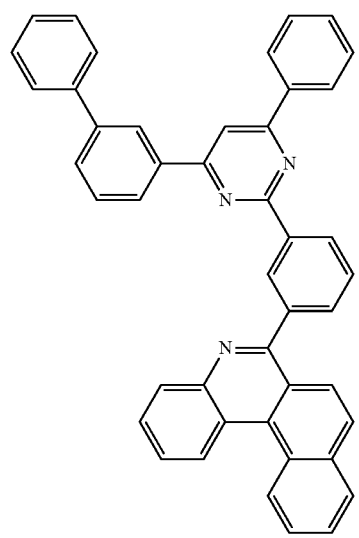
302
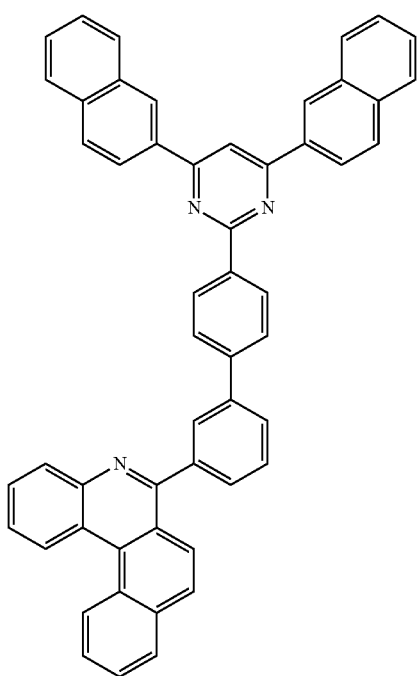

-continued
127
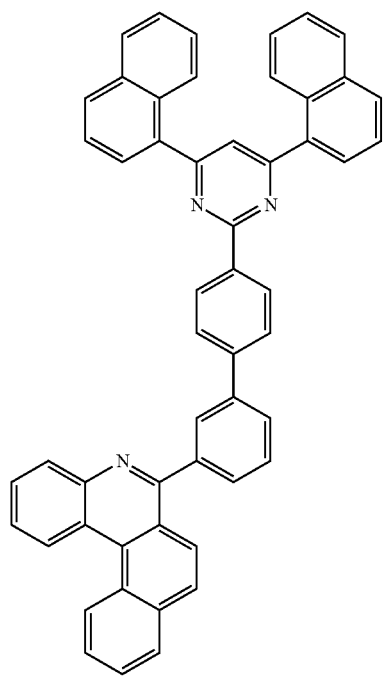
128
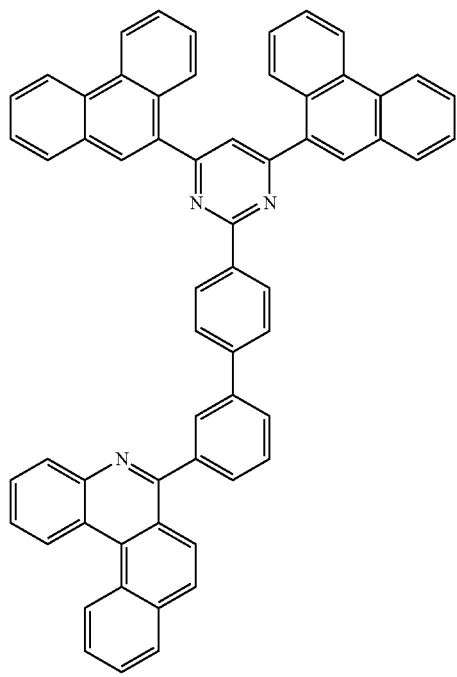
303
305
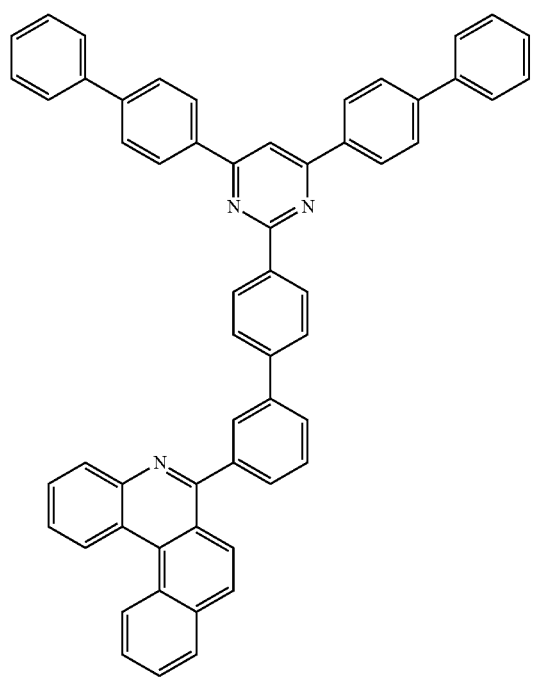
304
306
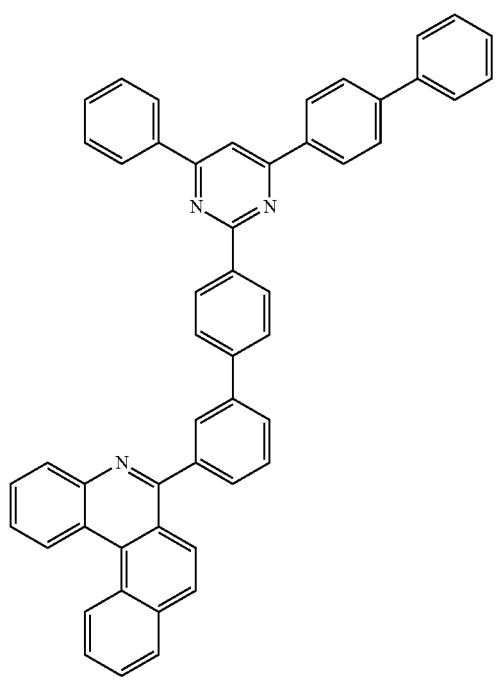

-continued
307
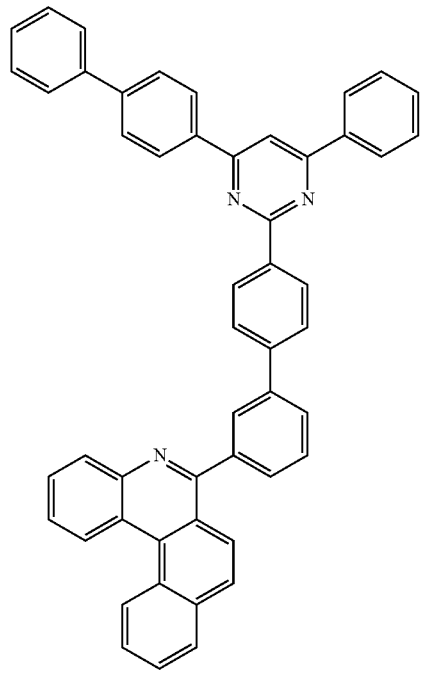
308
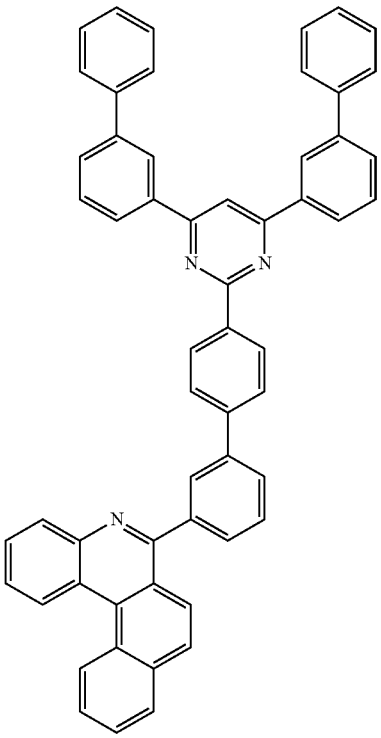
309
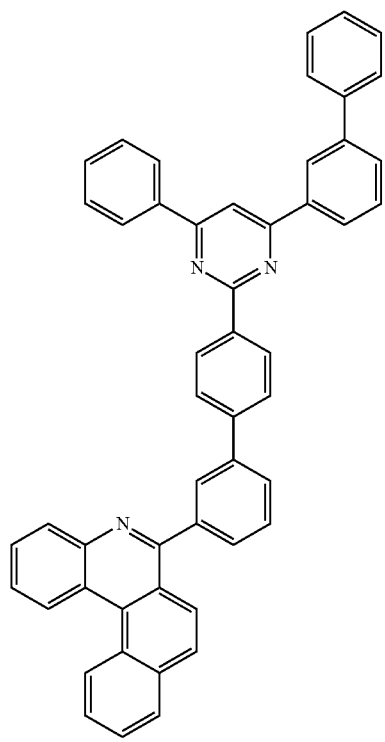
310
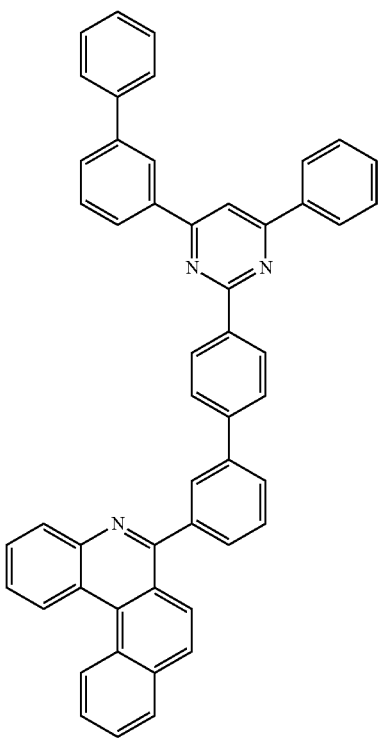

-continued
131
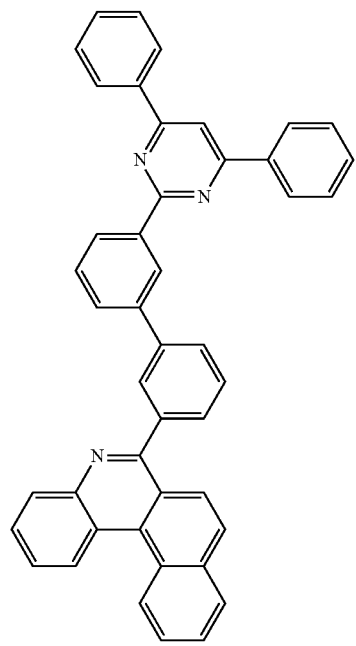
132
311
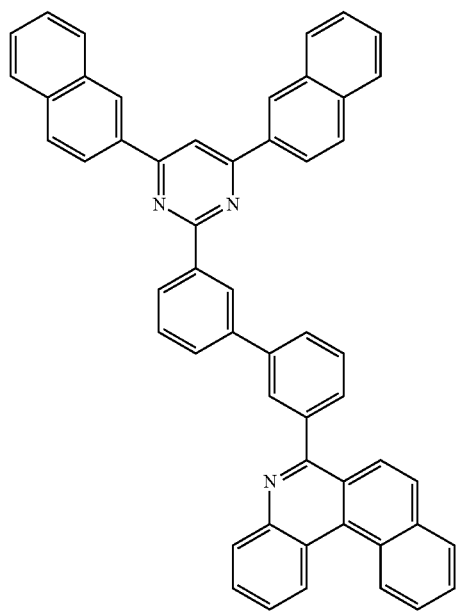
312
313
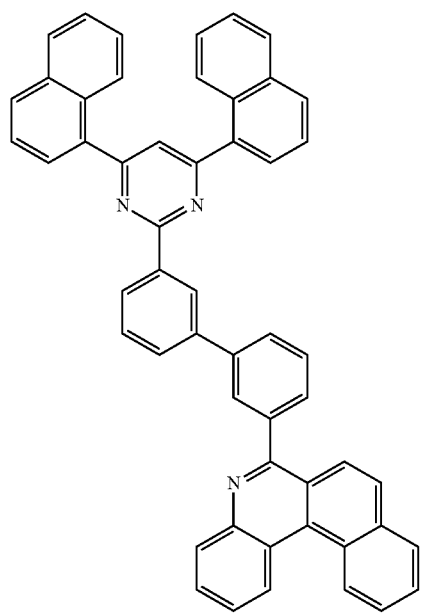
314
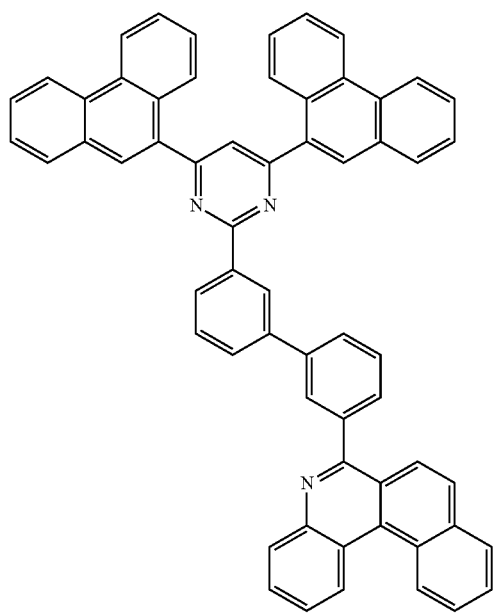

-continued
315
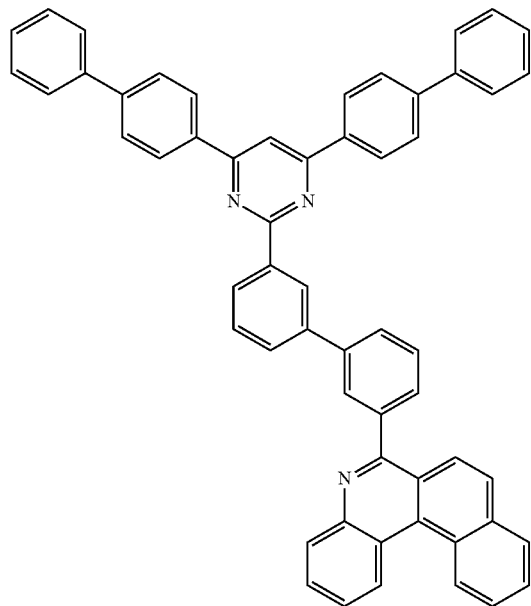
316
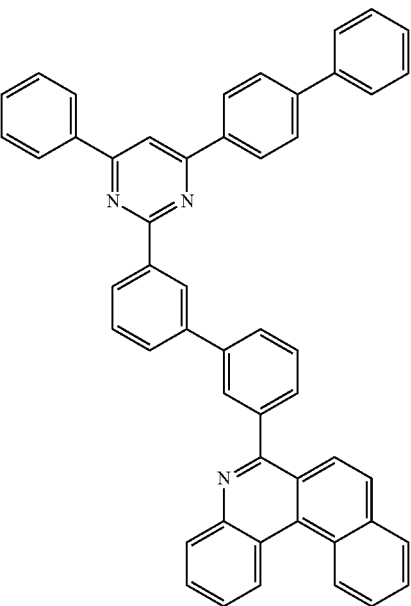
317
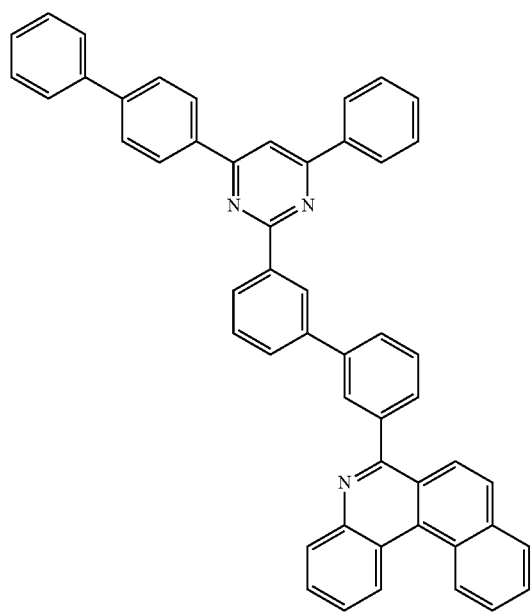
318
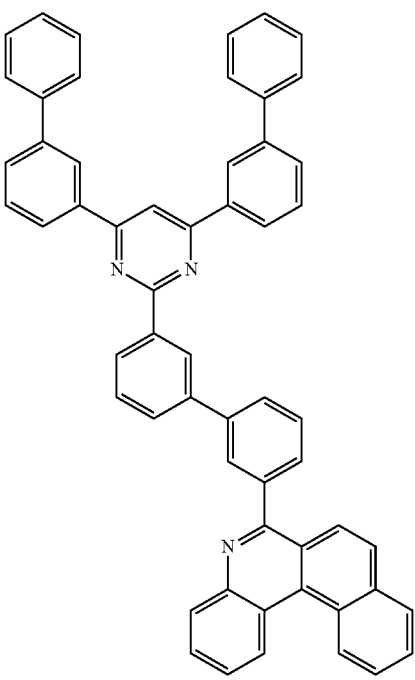

319
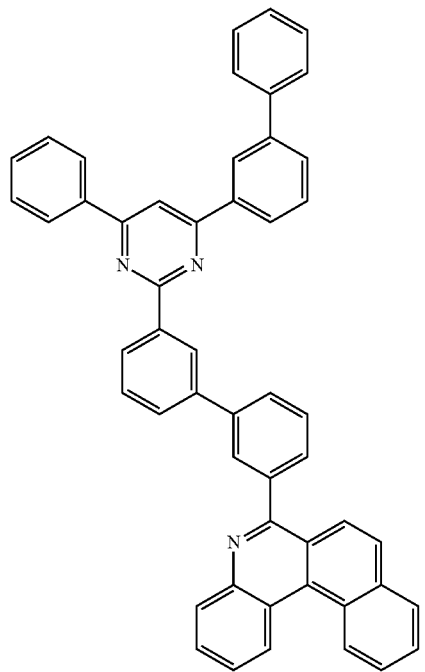
320
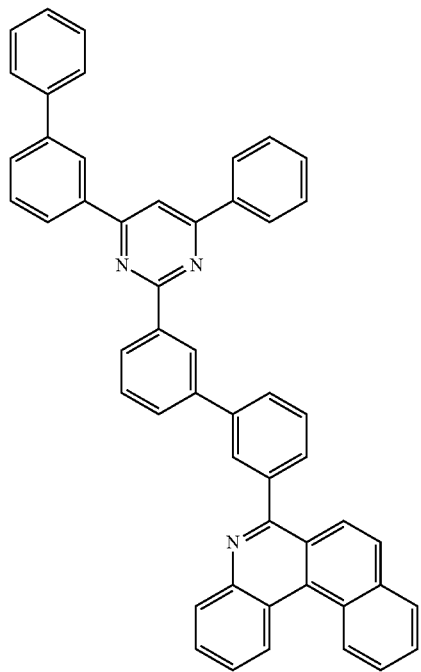
321
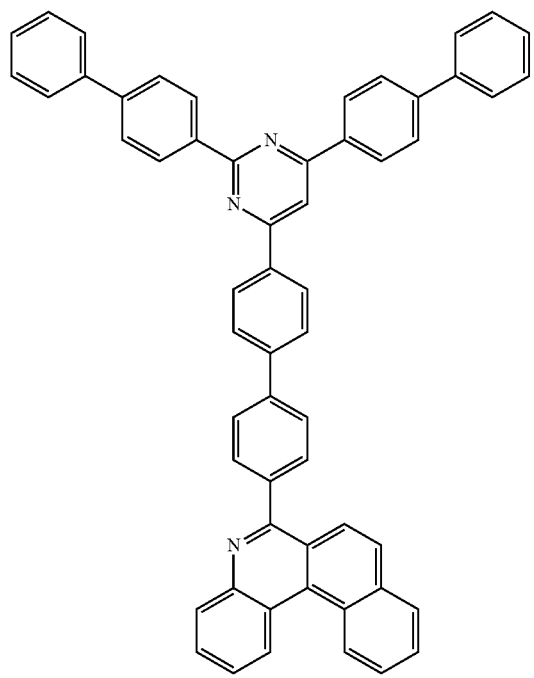
322
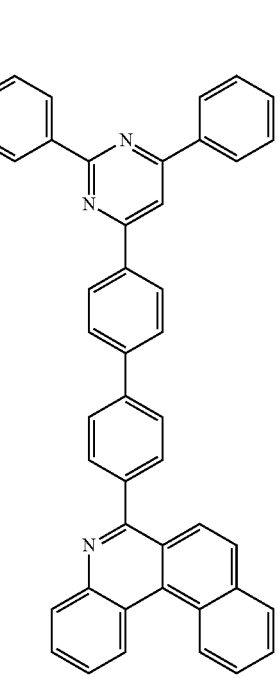

-continued
323
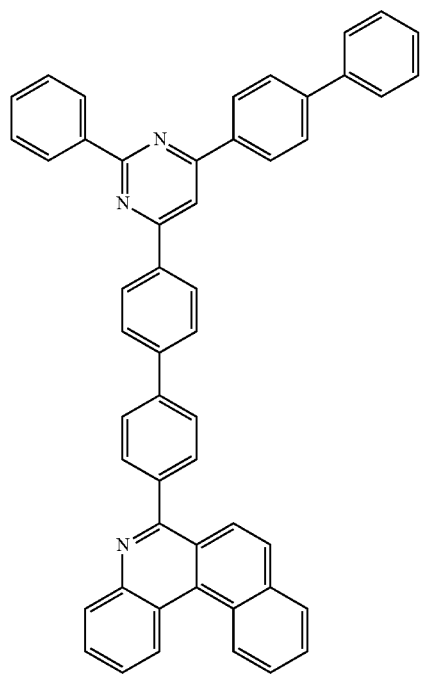
324
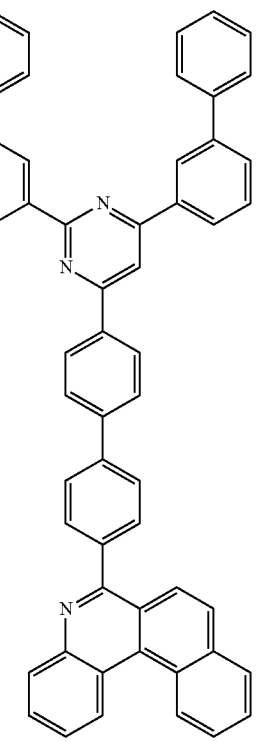
325
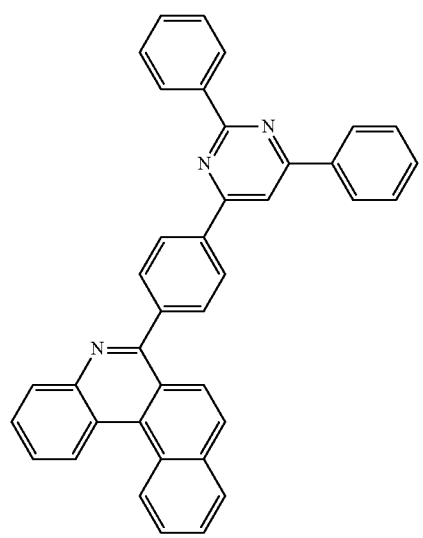
326
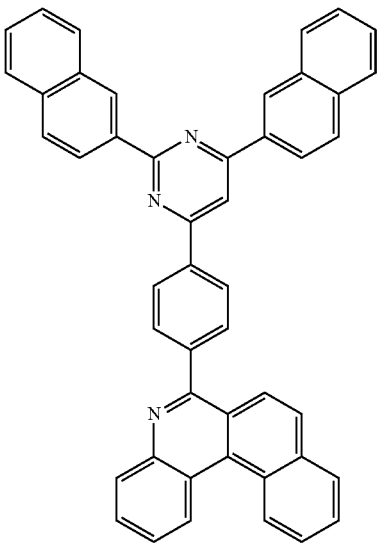

-continued
327
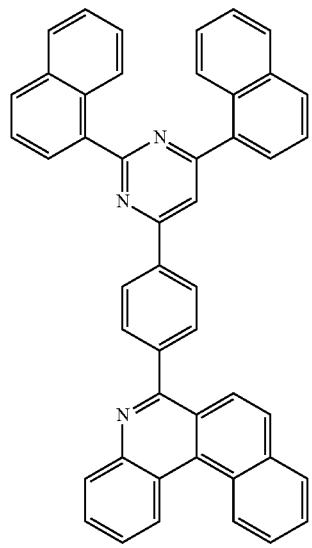
328
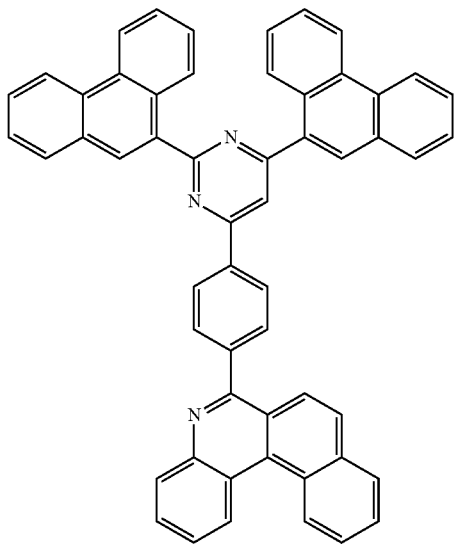
329
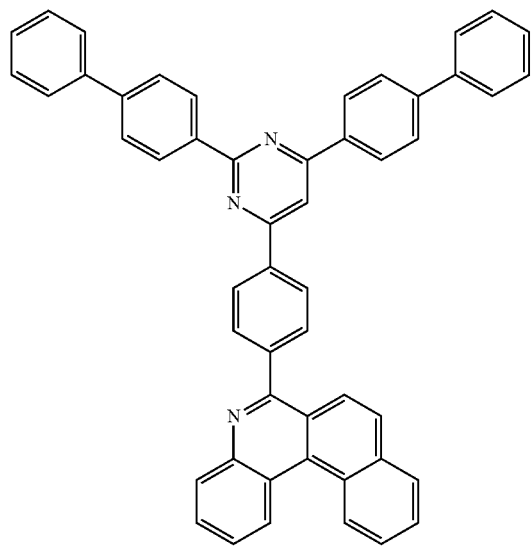
330
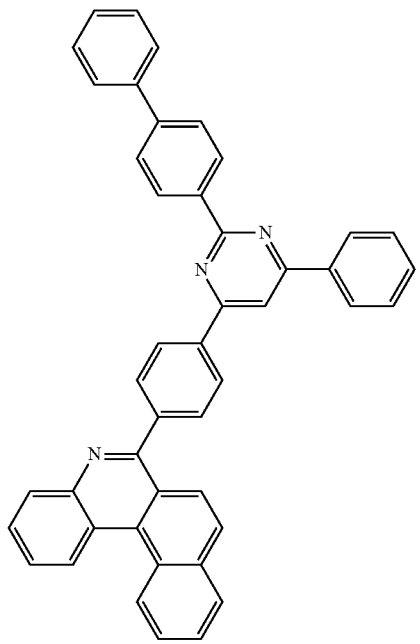

-continued
331 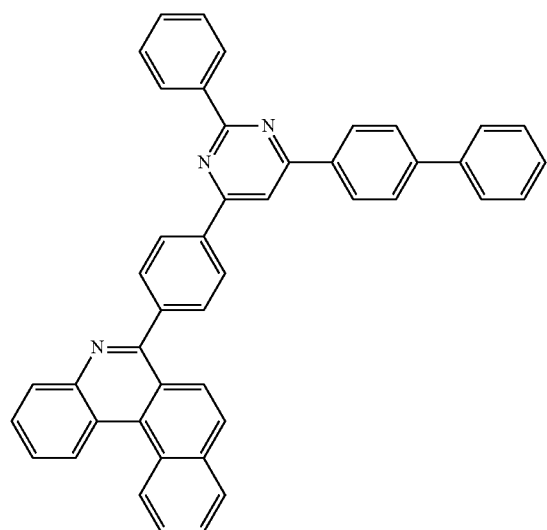
332 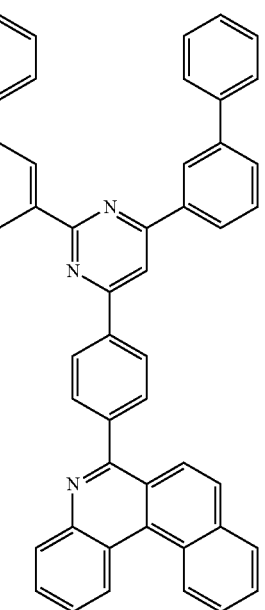
333 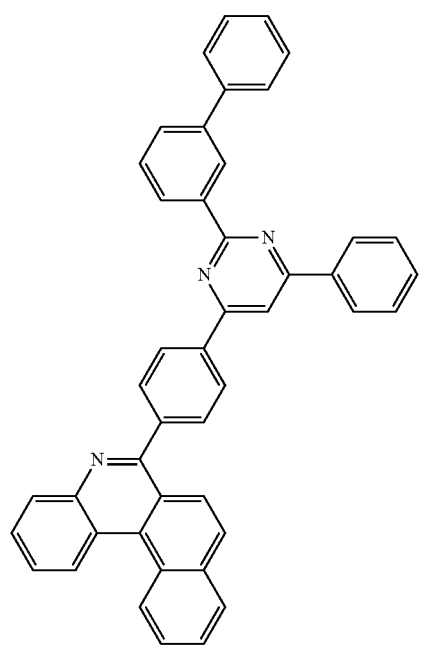
334 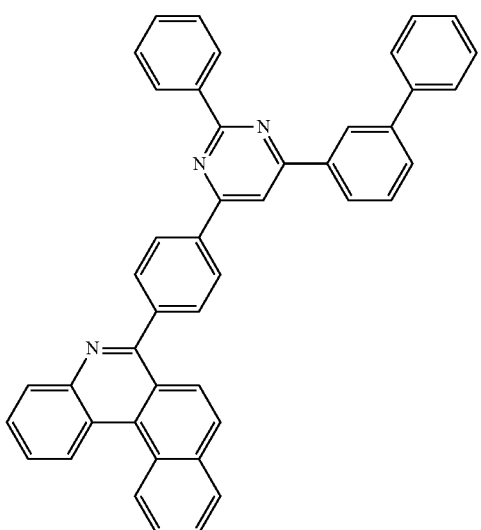

-continued
335
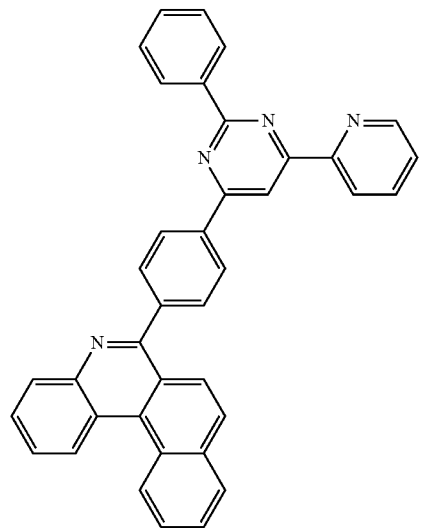
336
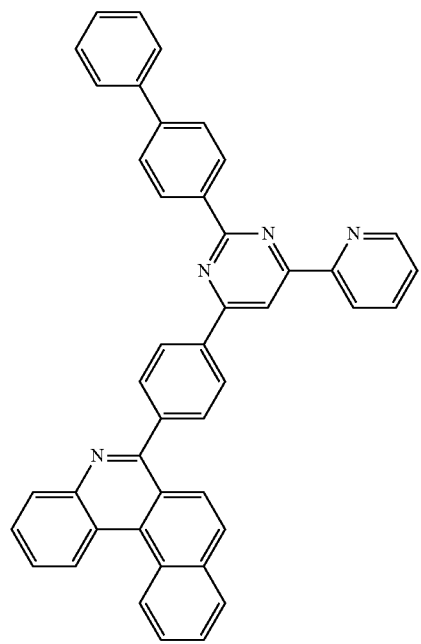
337
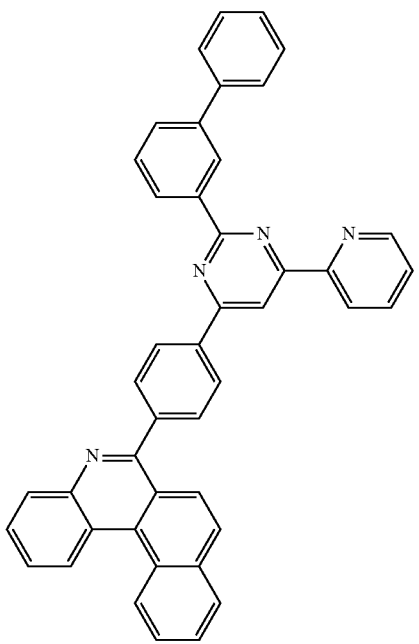

-continued
338
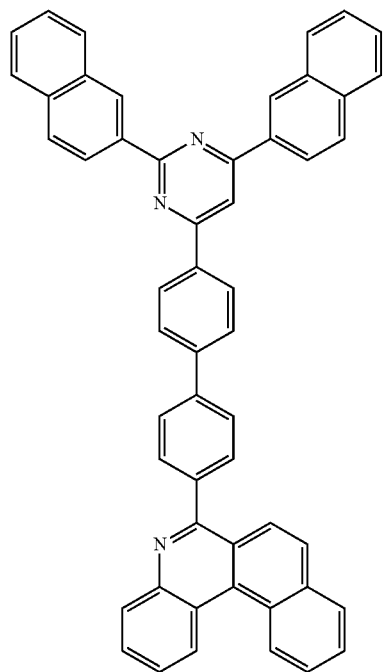
339
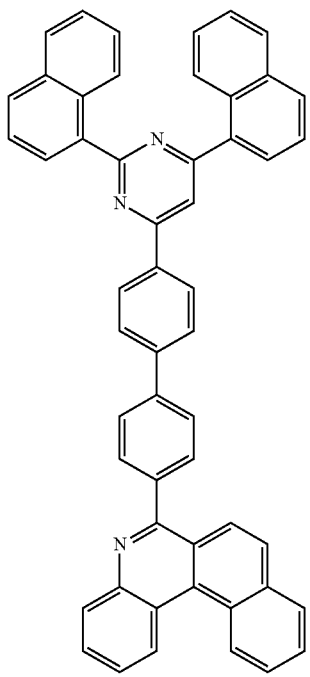
340
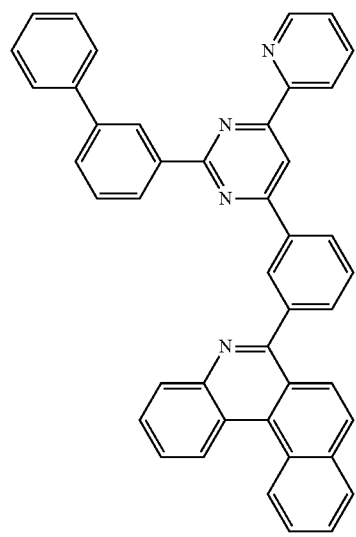
341
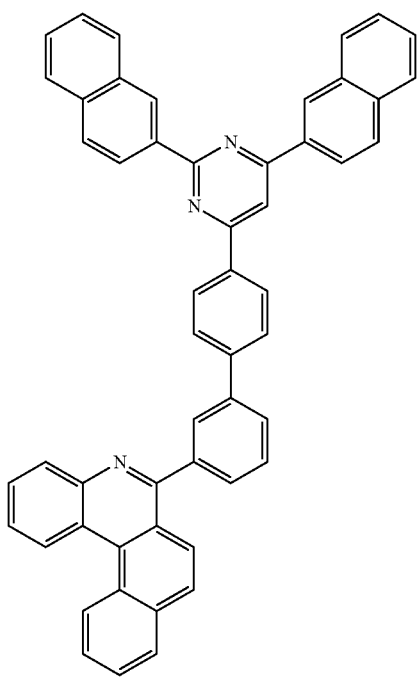

-continued
147
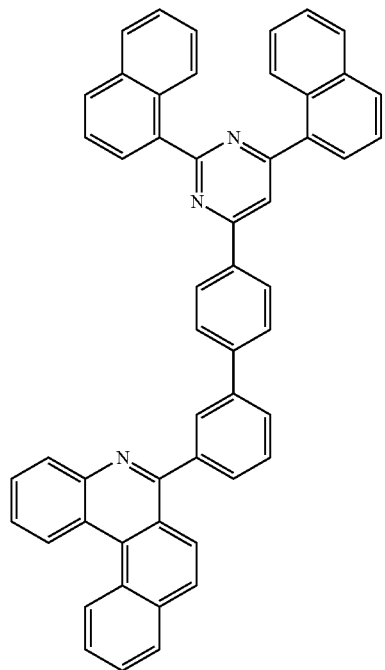
342
148
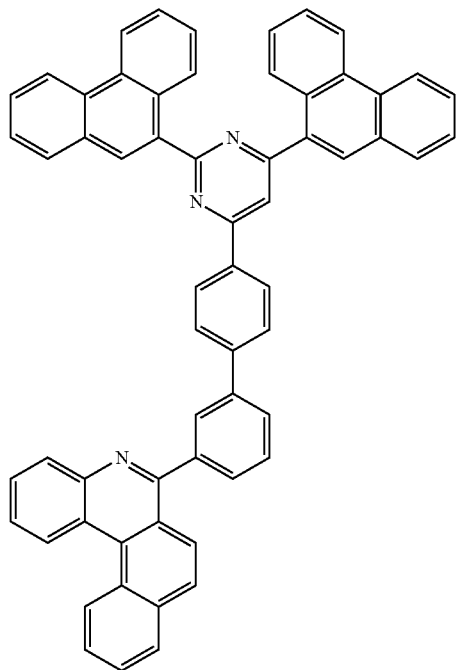
343
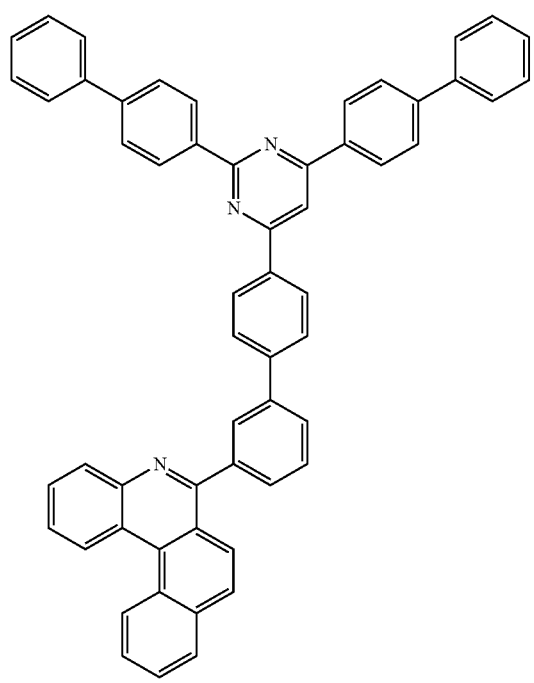
344
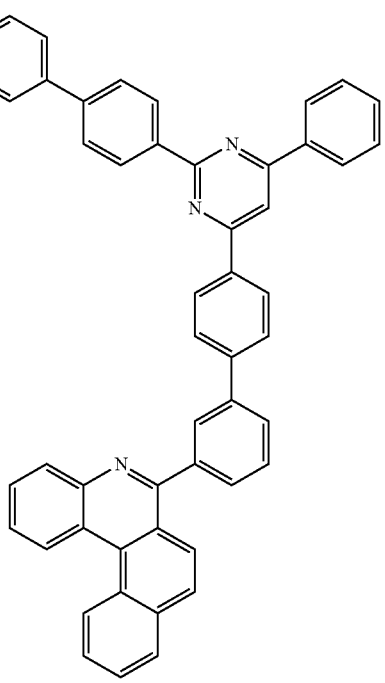
345

-continued
346
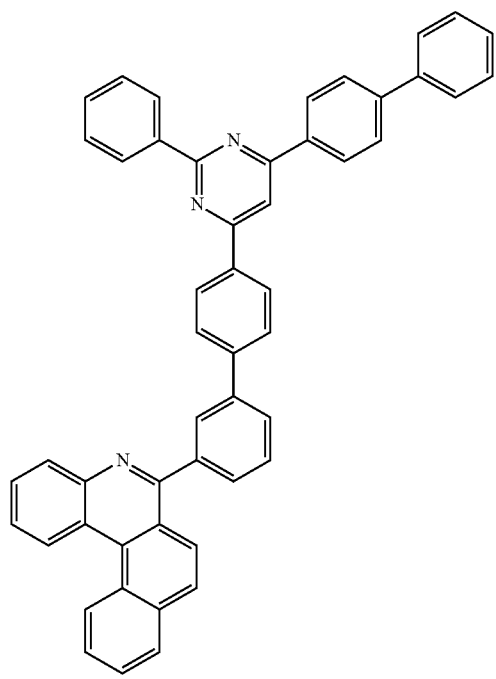
347
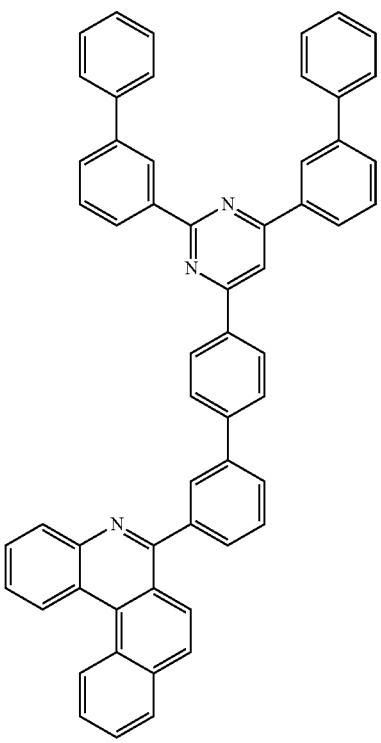
348
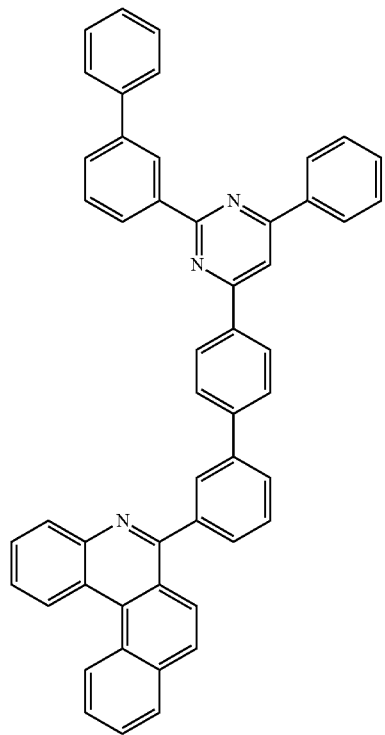
349
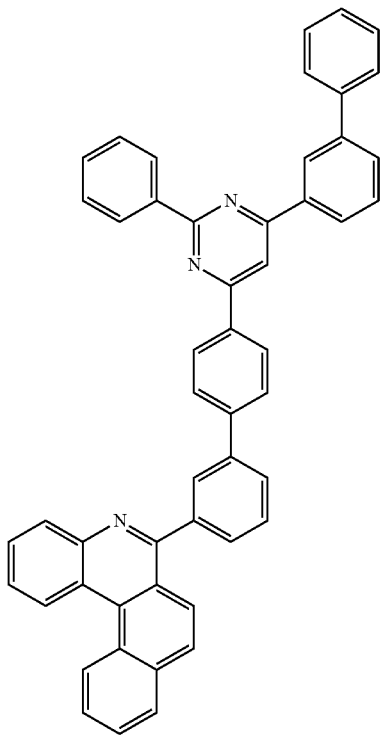

-continued
350 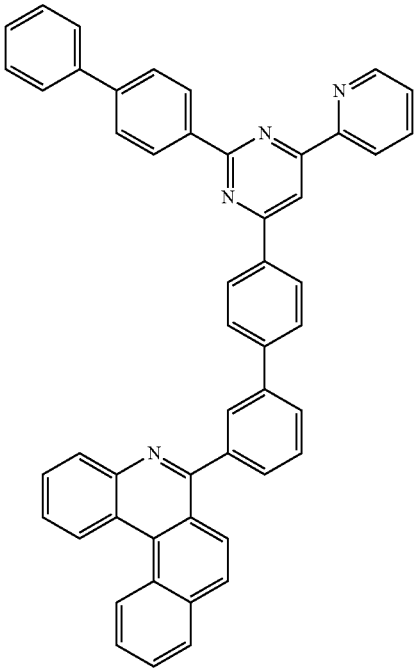
351
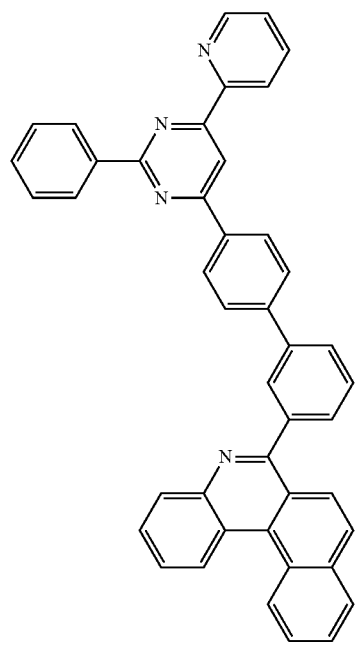
352 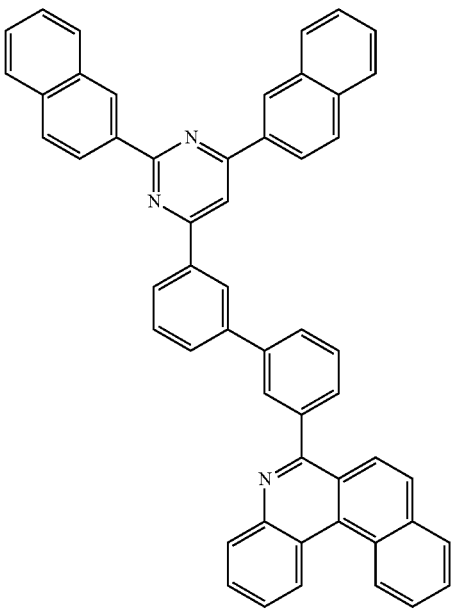
353
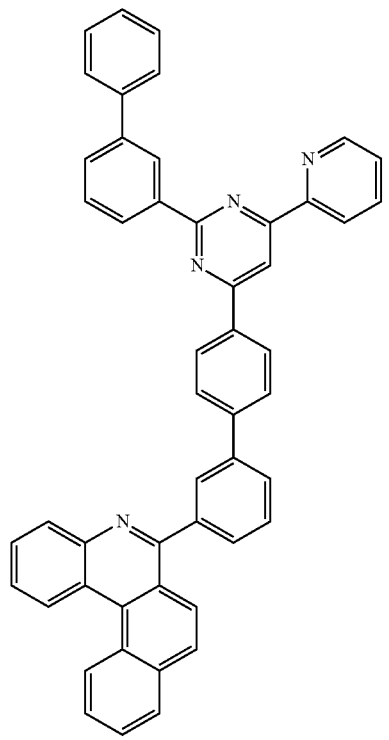

-continued
153
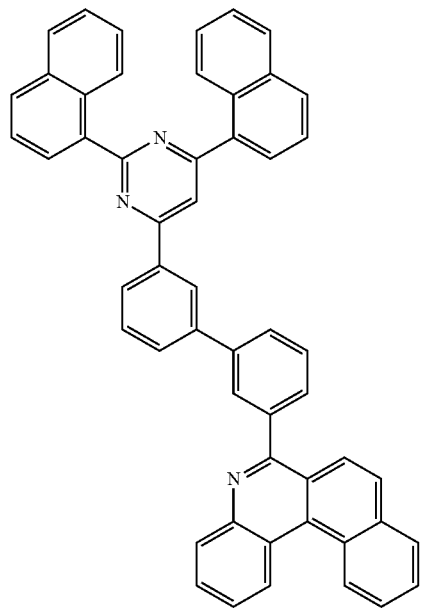
354
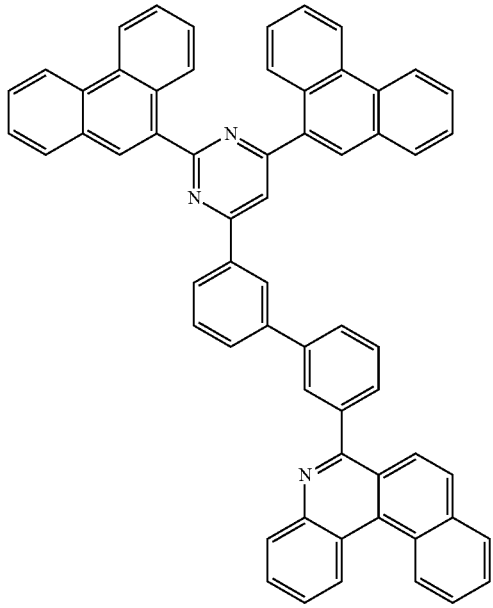
356
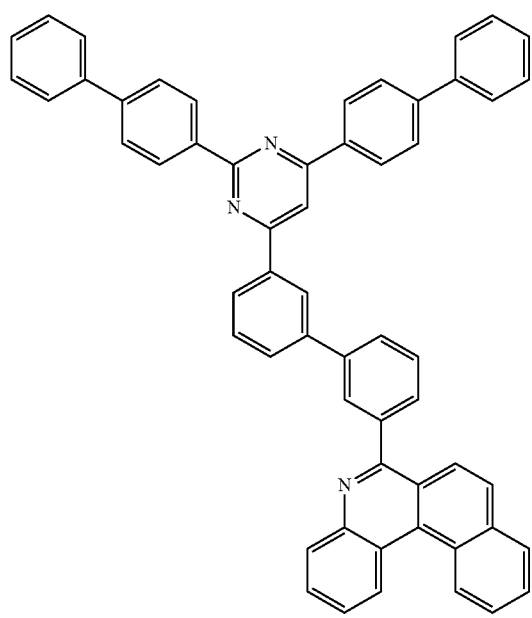
154
355
357
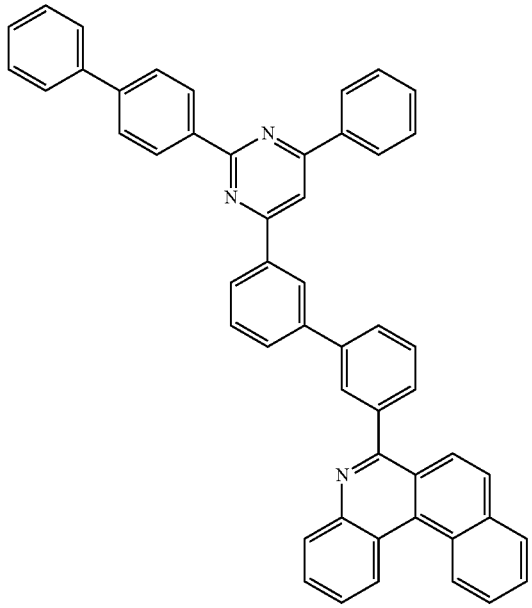

-continued
358
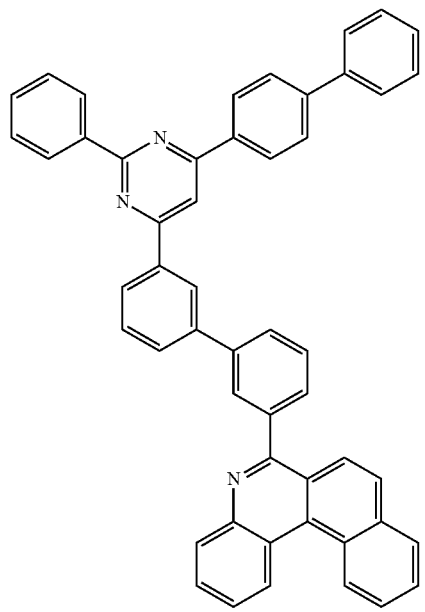
359
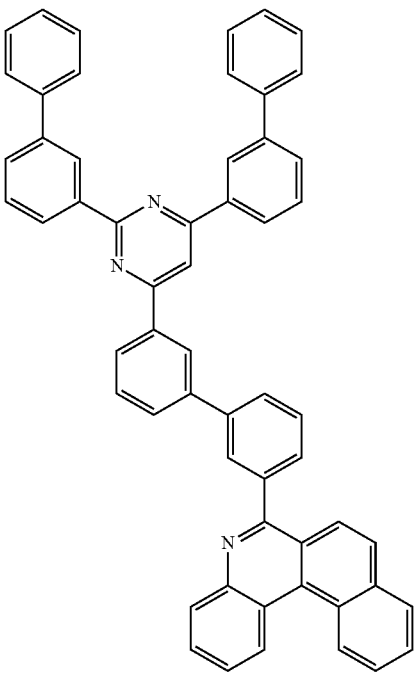
360
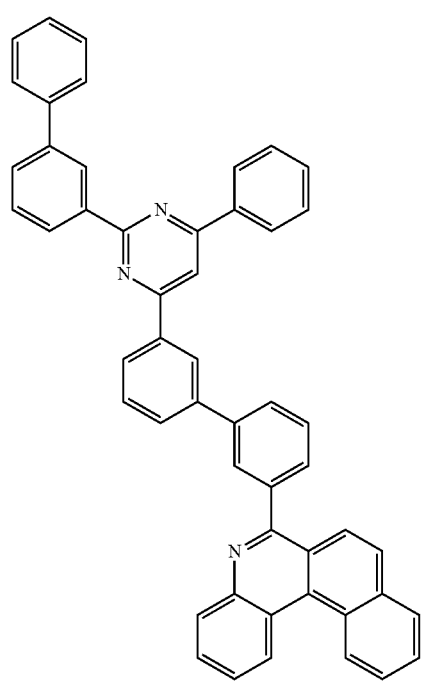
361
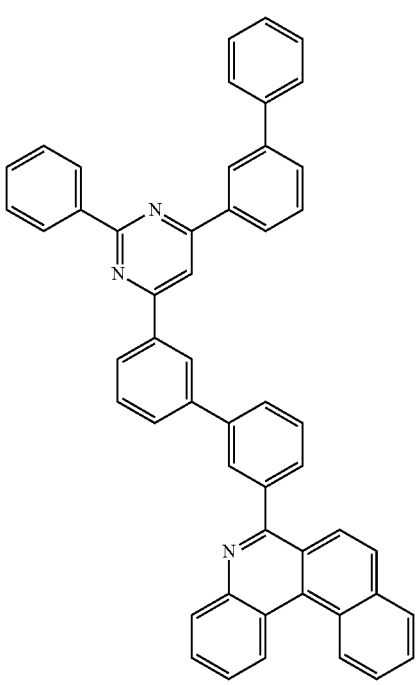

-continued
157
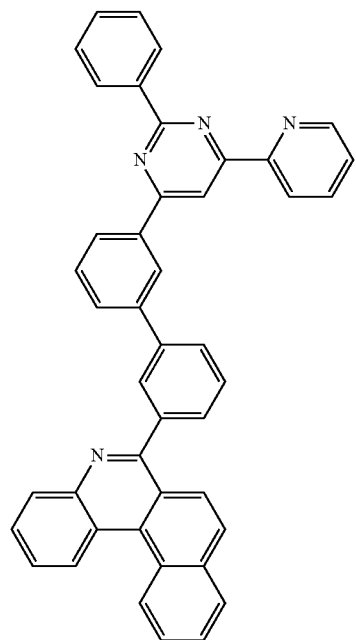
158
362
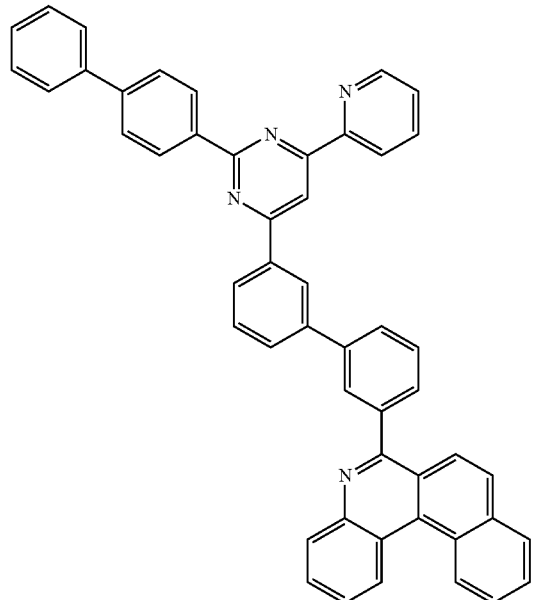
363
364
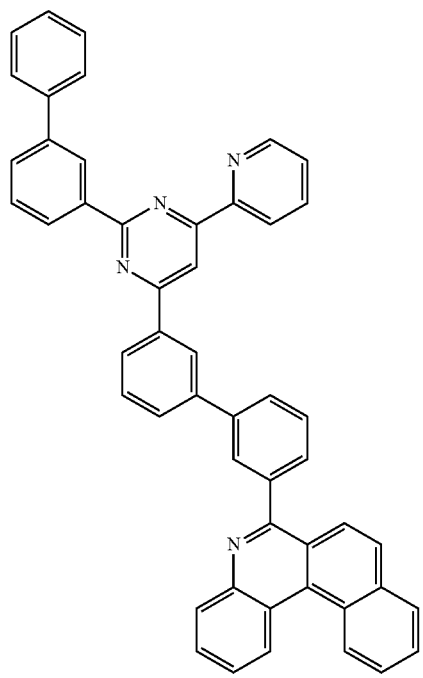
365
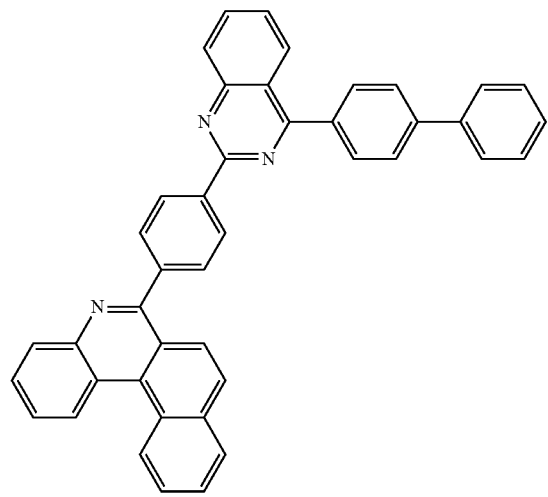

-continued
366
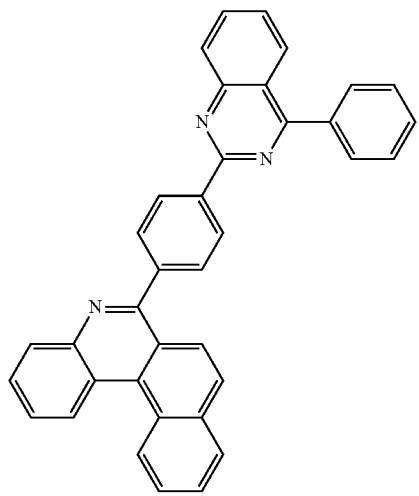
367
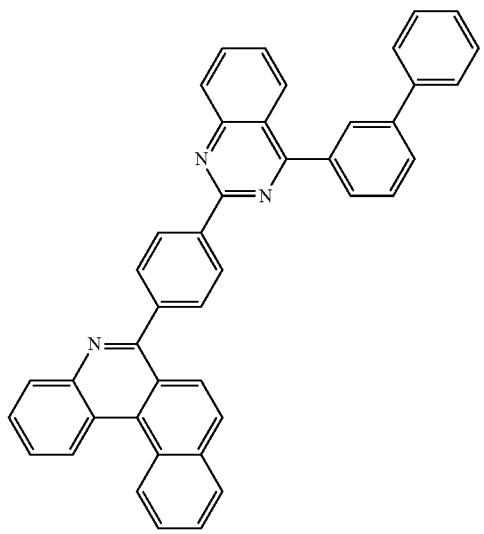
368
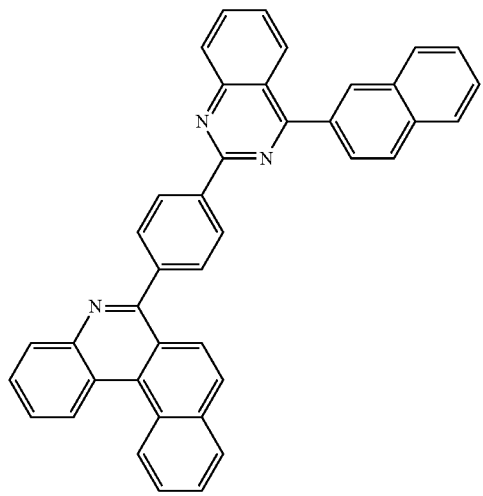
369
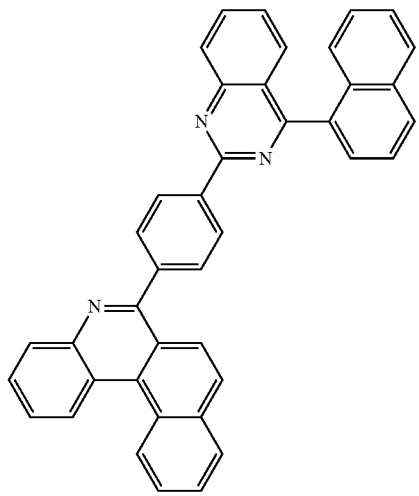

-continued
370
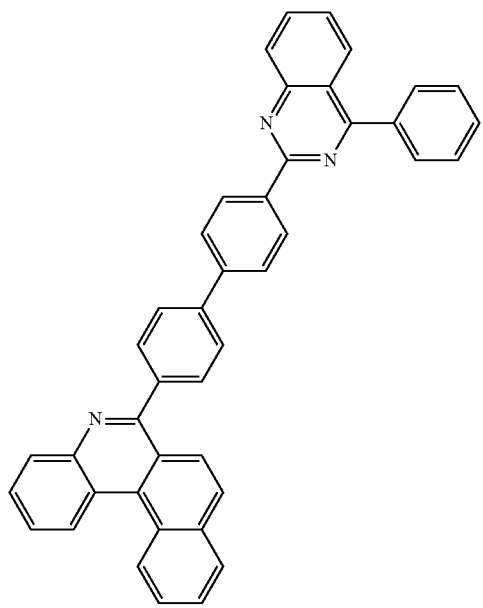
371
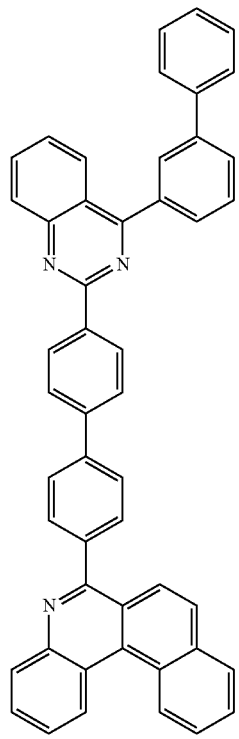
372
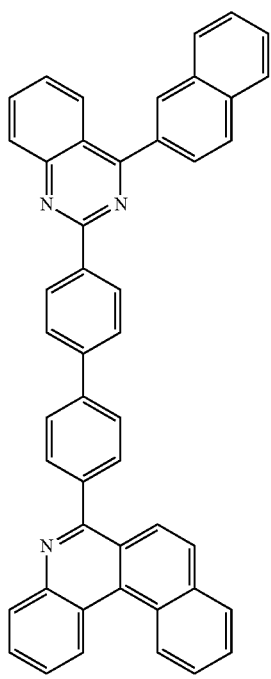
373
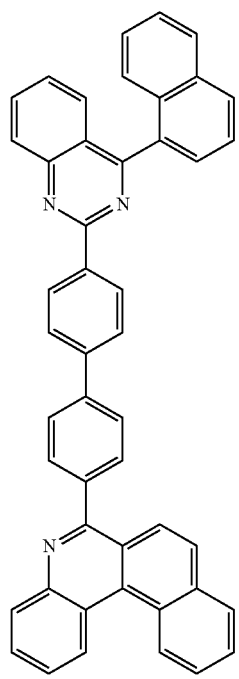

-continued
374
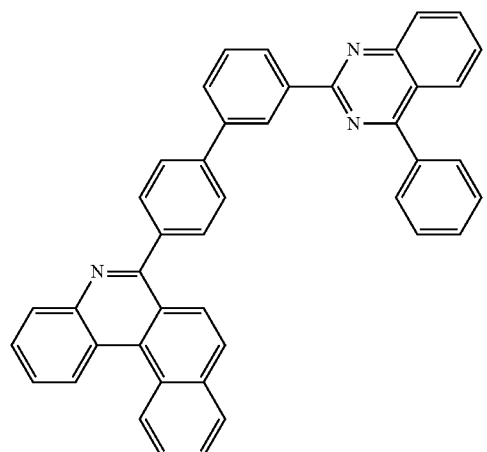
375
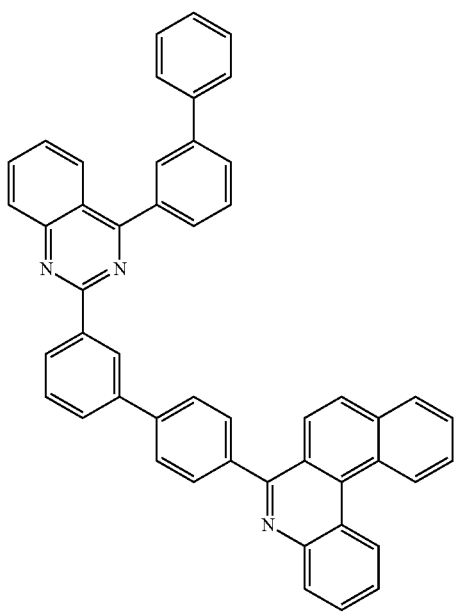
376
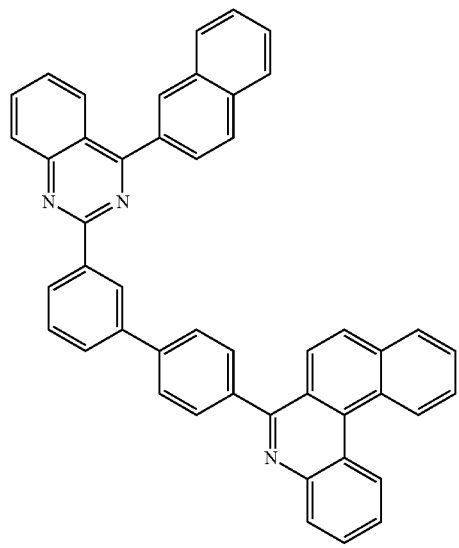
377
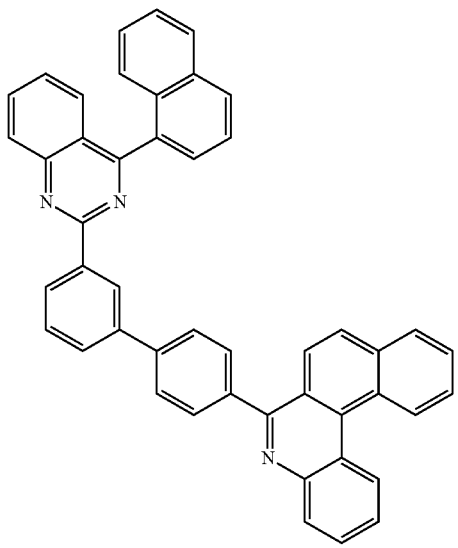

-continued
378 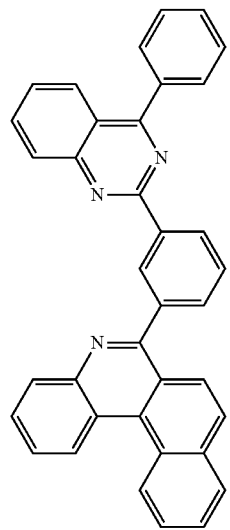 379 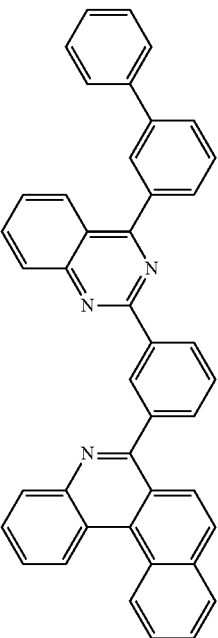
380 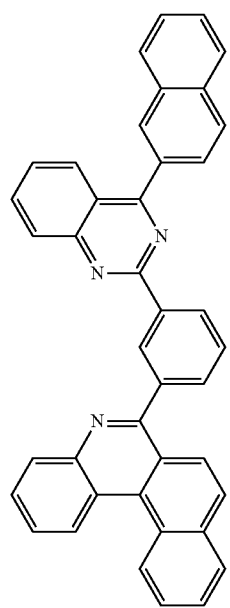 381 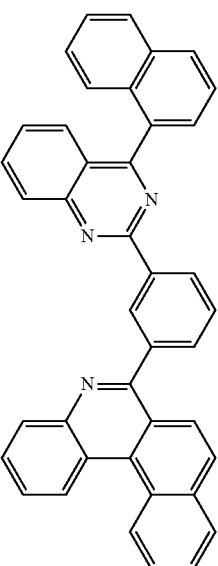

-continued
382
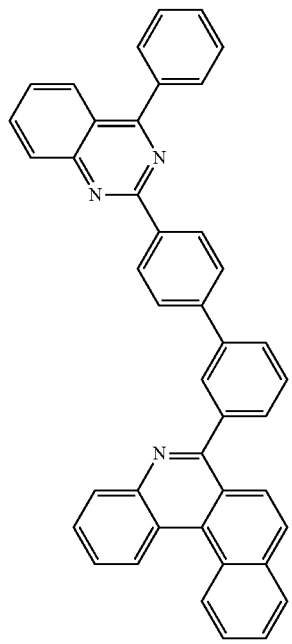
383
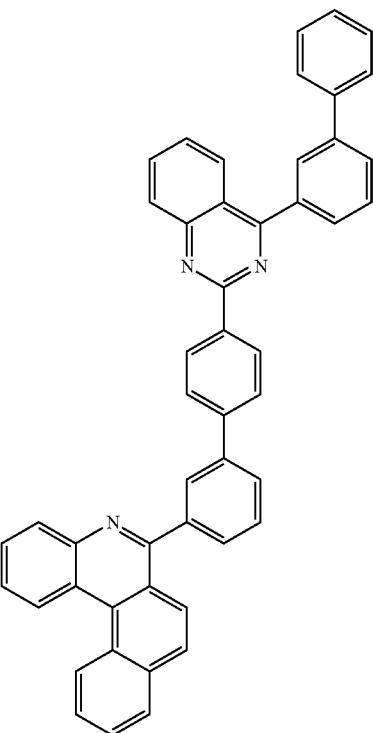
384
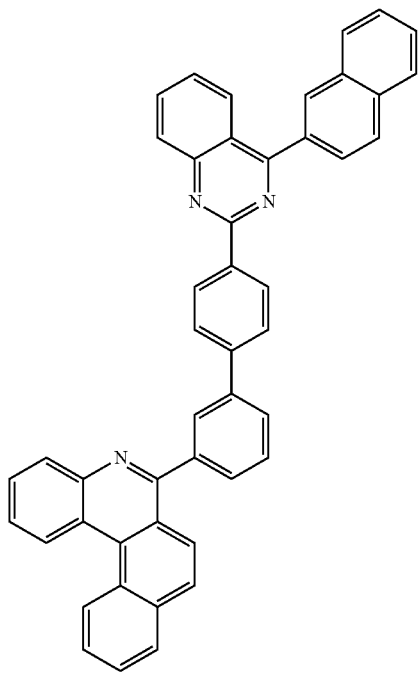
385
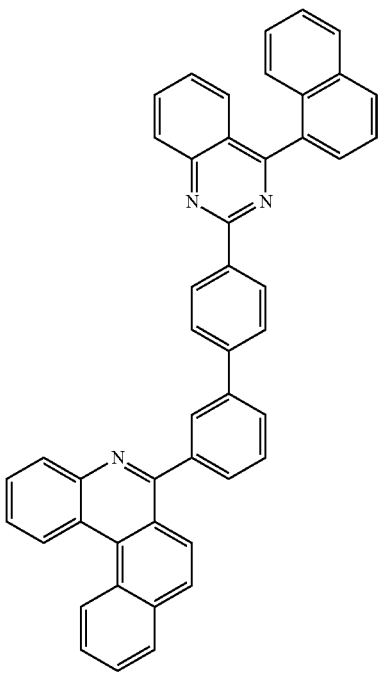

386
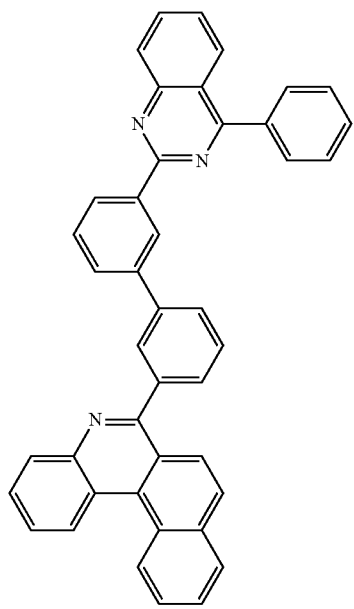
387
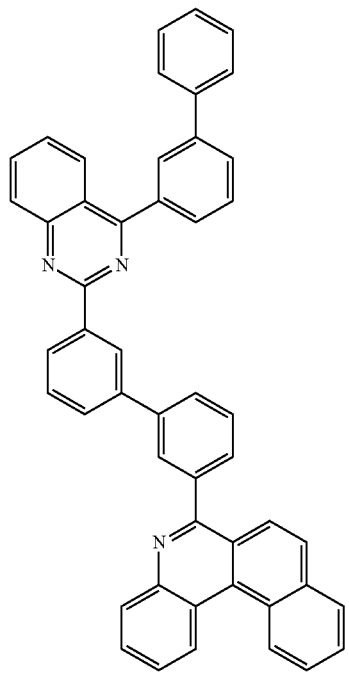
388
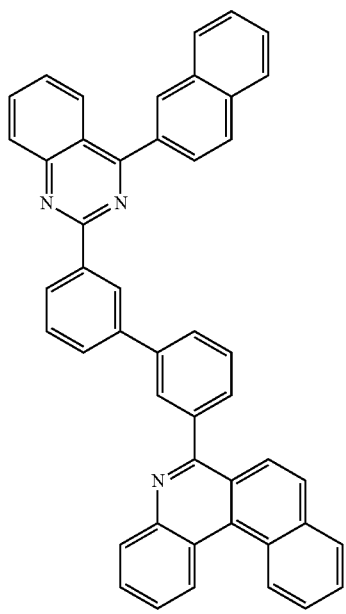
389
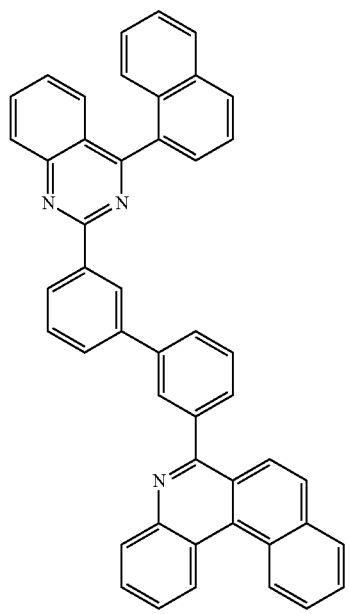

-continued
390 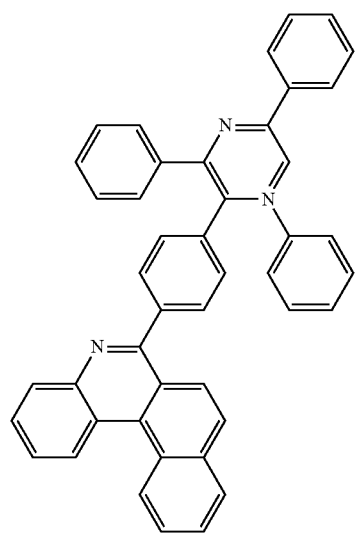 391 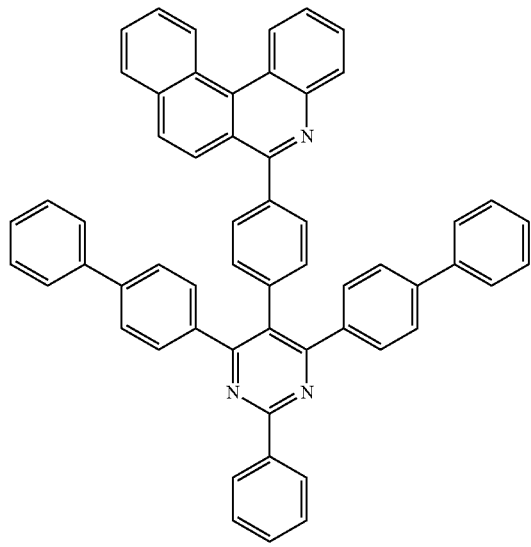
392 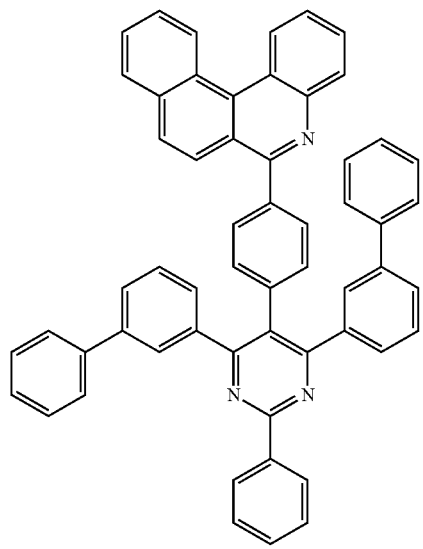 393 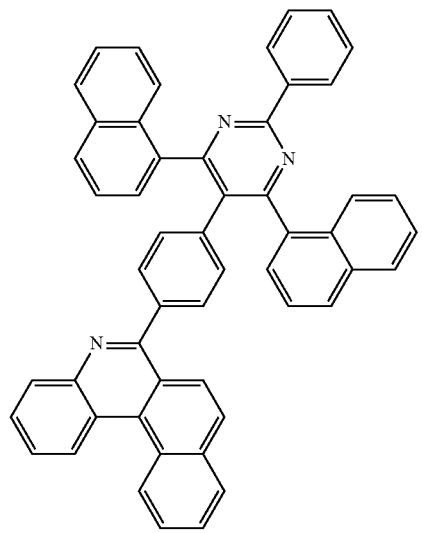

-continued
173
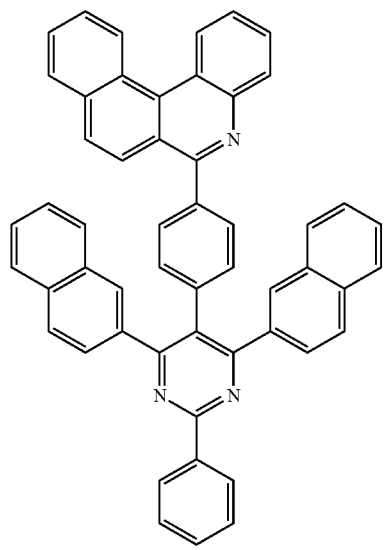
394
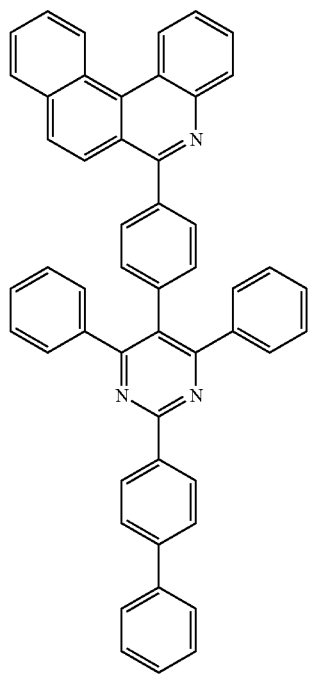
395
396
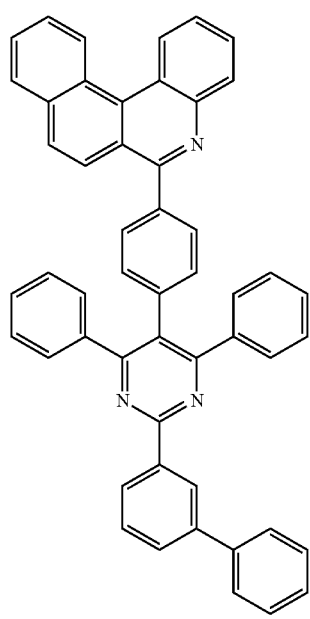
397
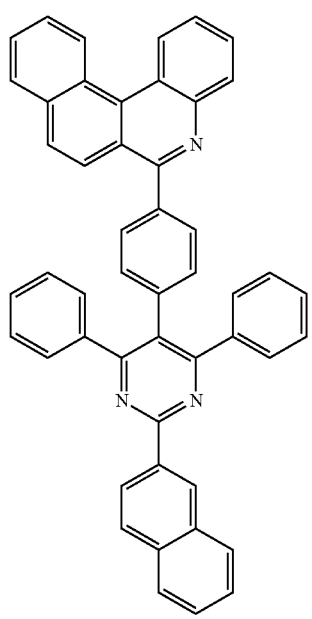

-continued
175
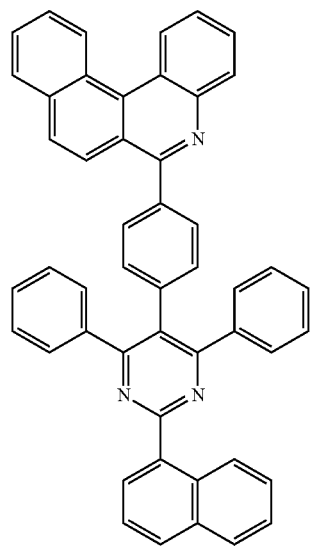
176
398
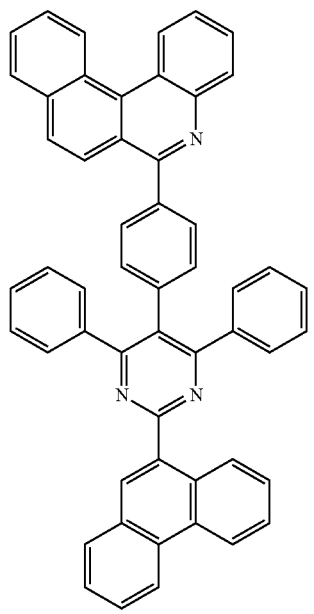
399
400
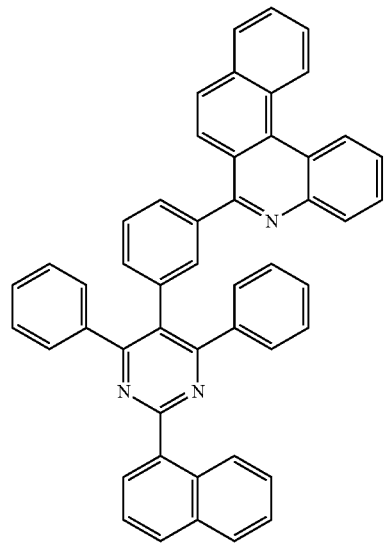
401
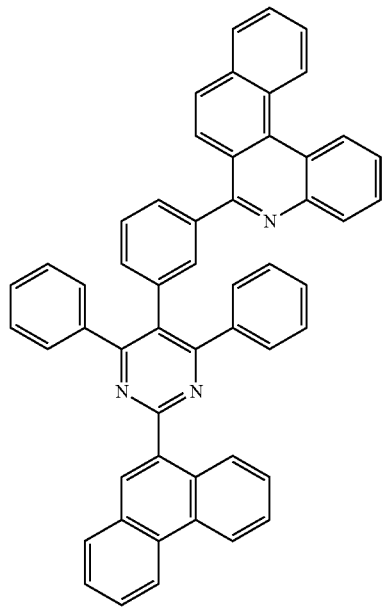

-continued
402 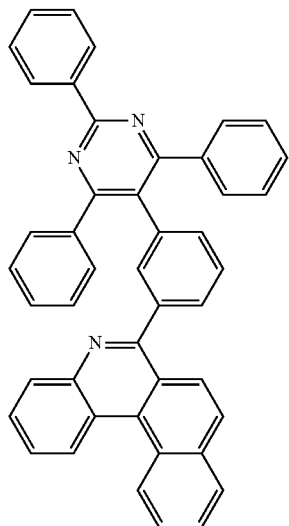
403 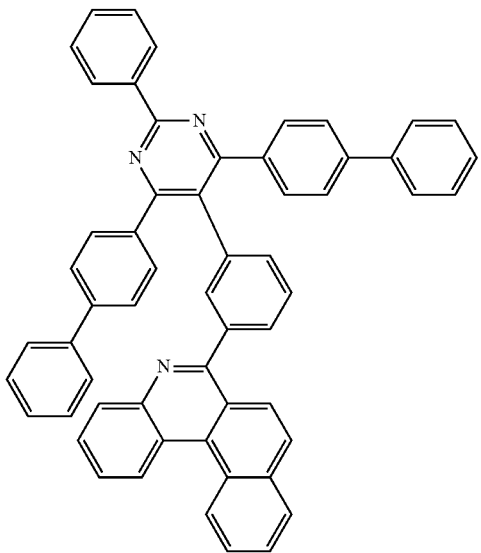
404 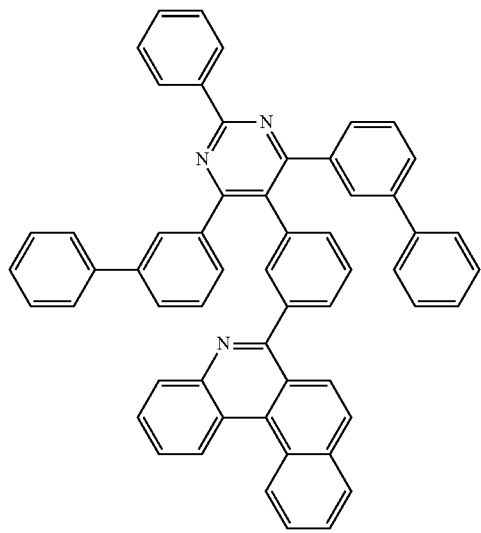
405 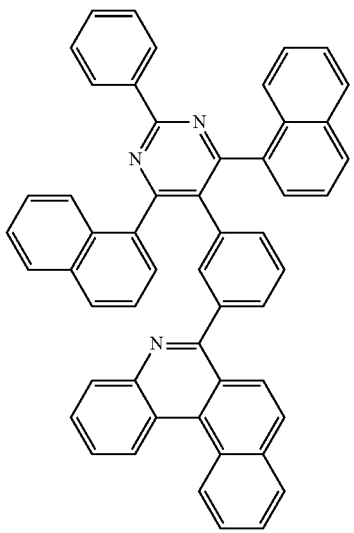

-continued
406
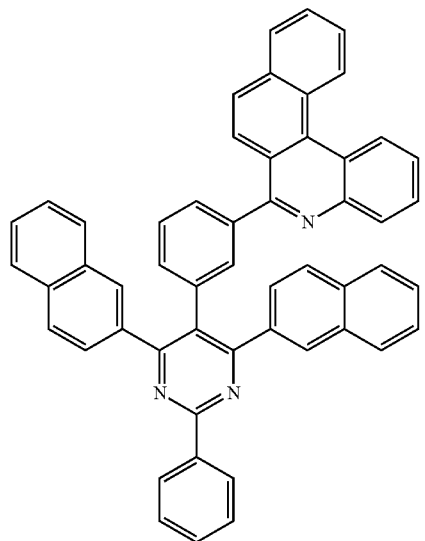
407
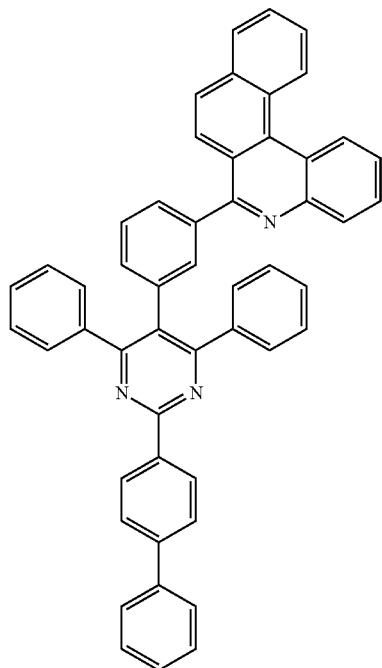
408
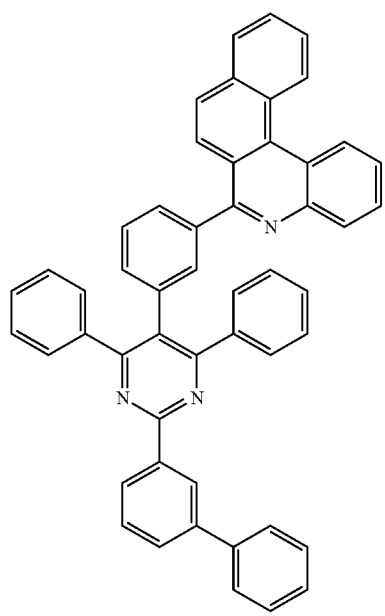
409
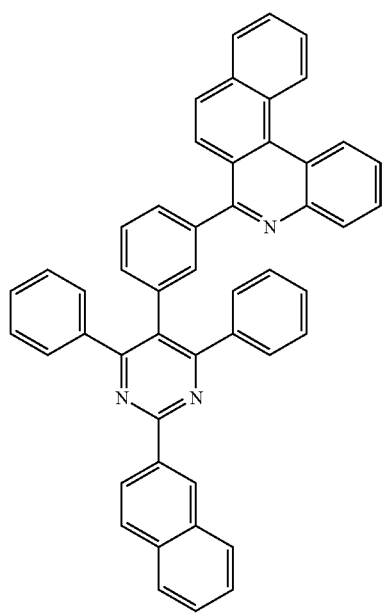

-continued
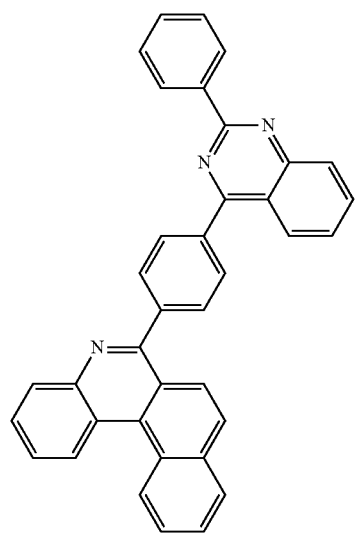
410
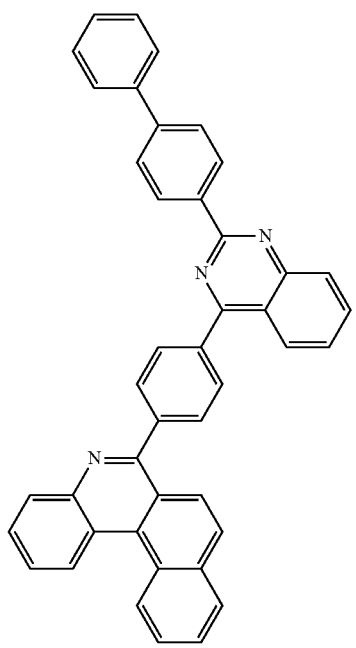
411
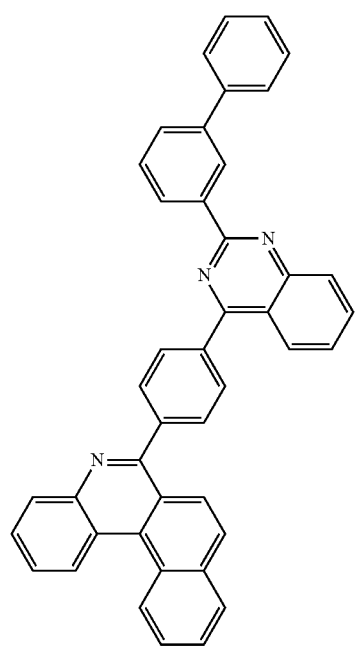
412
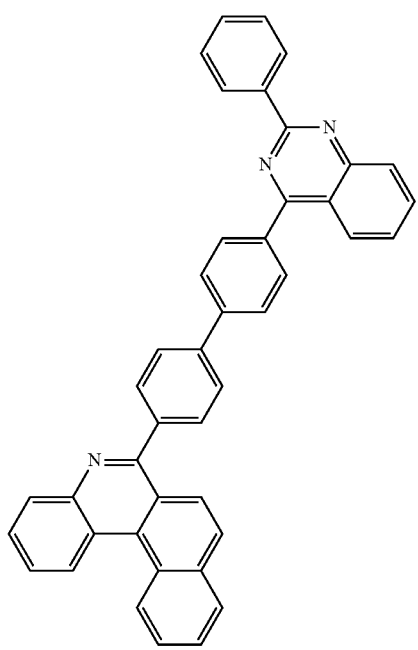
413

-continued
183
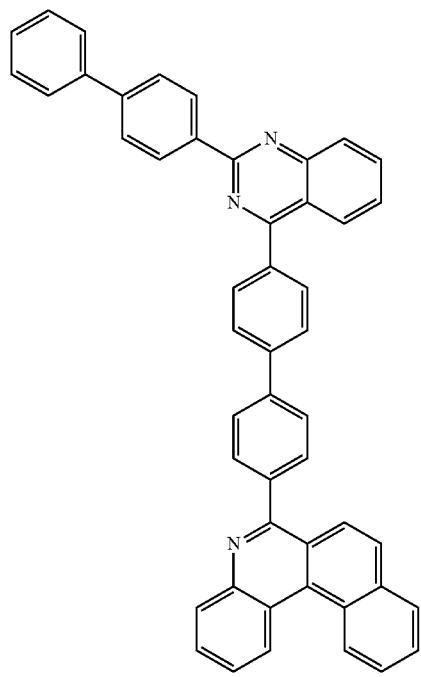
184
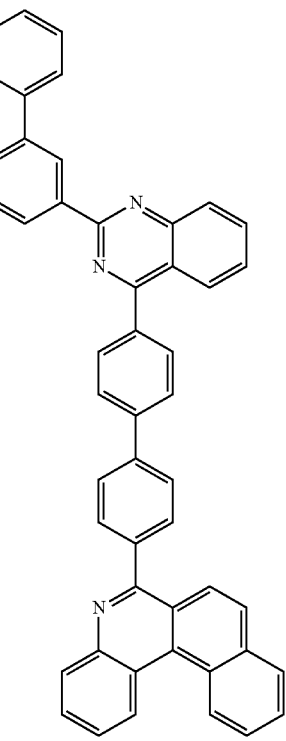
414
415
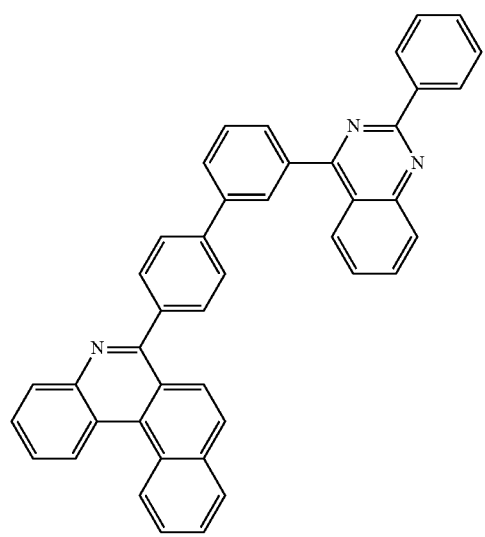
416
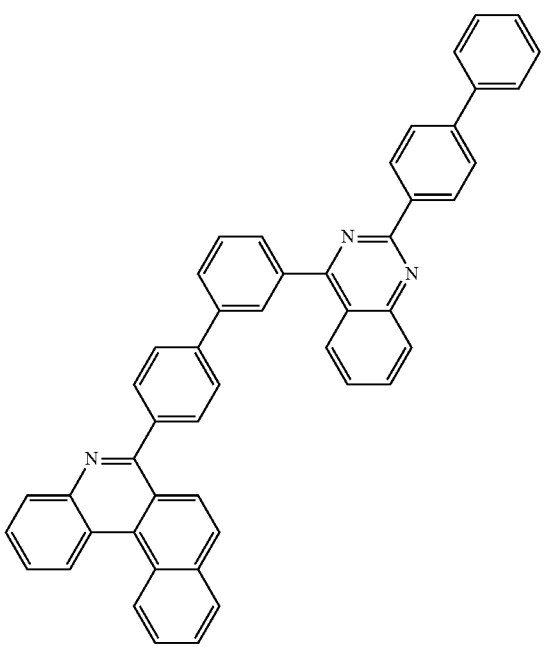
417

-continued
418 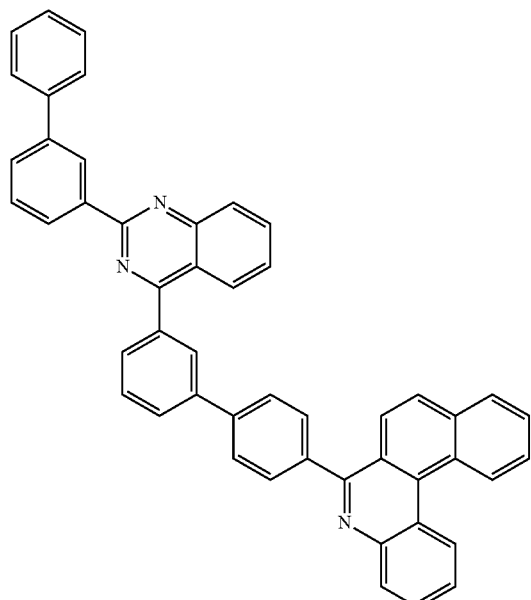
419 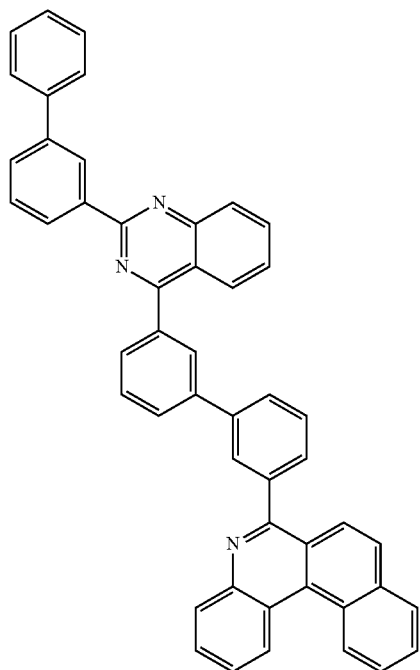
420 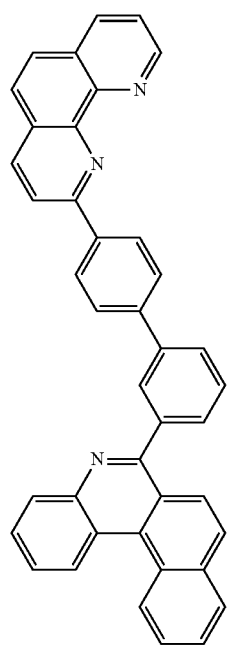
421 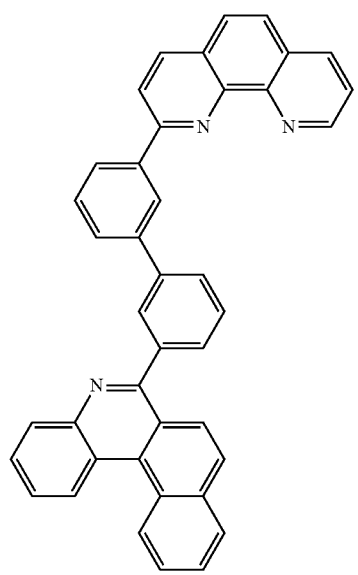

-continued
187 | 188
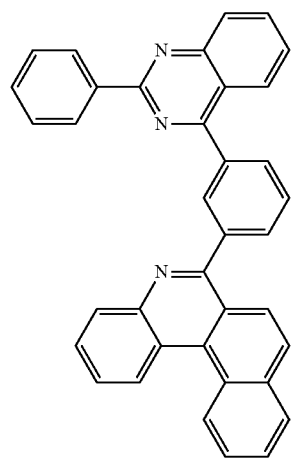
422
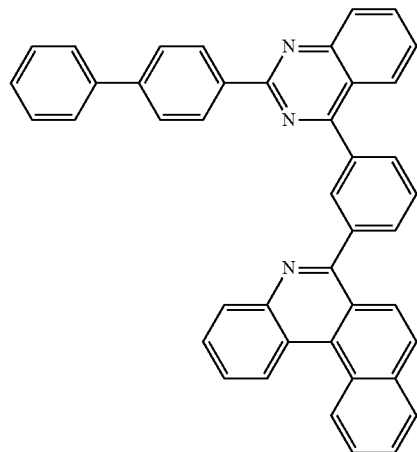
423
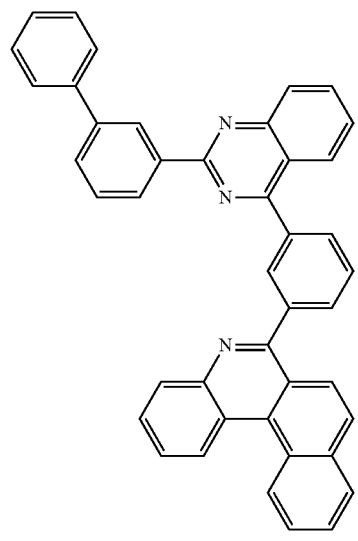
424
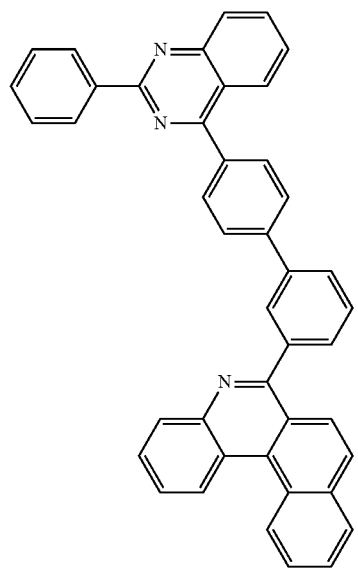
425

-continued
189 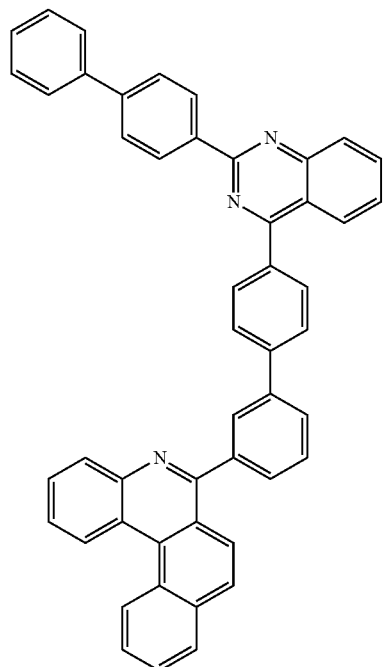
426 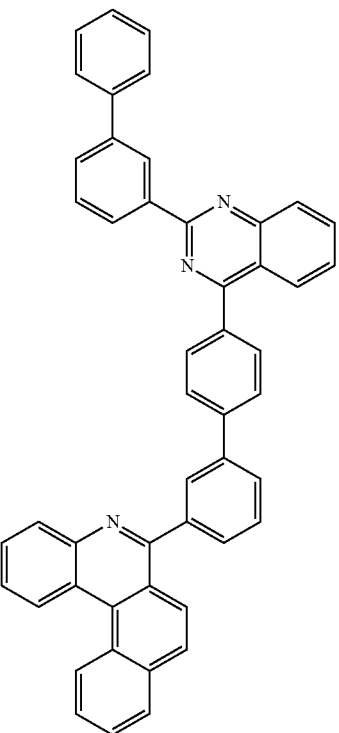 427
428 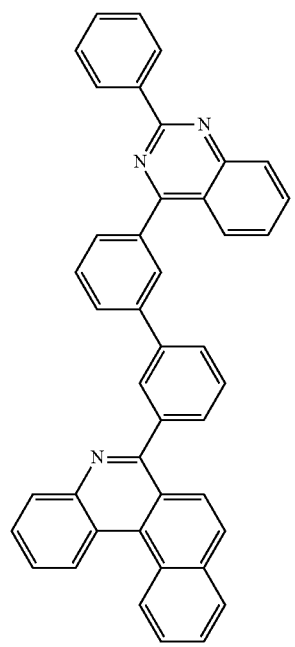 429 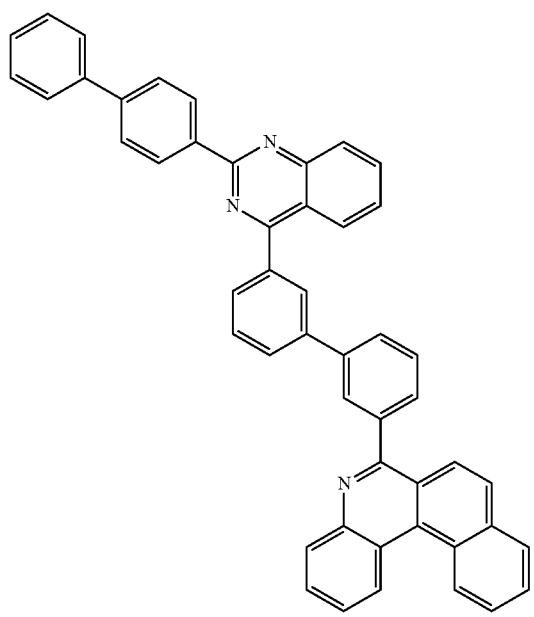

-continued
191   430
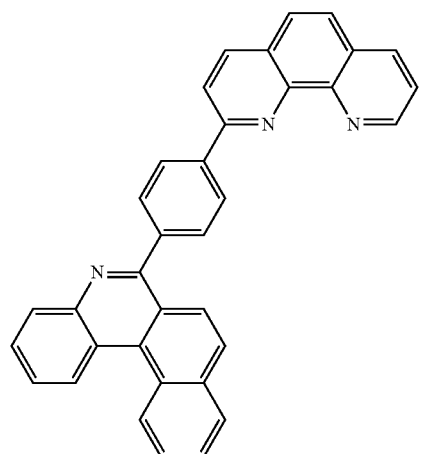
192   431
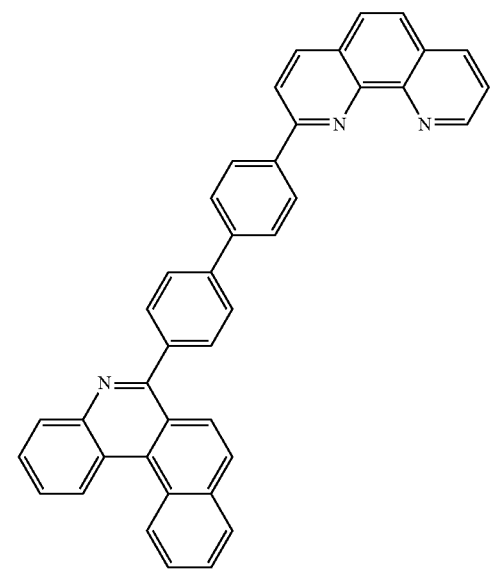
432
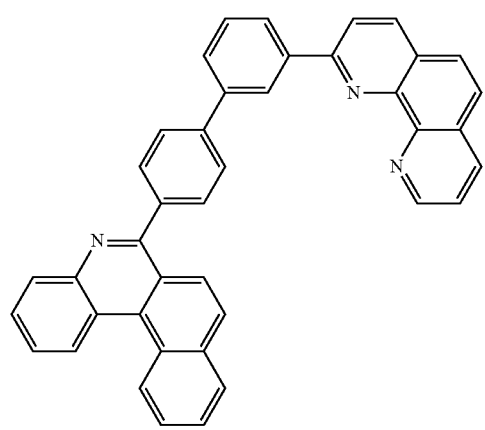
433
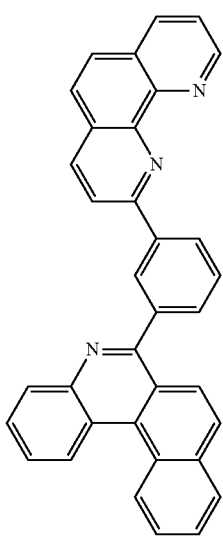

-continued
434
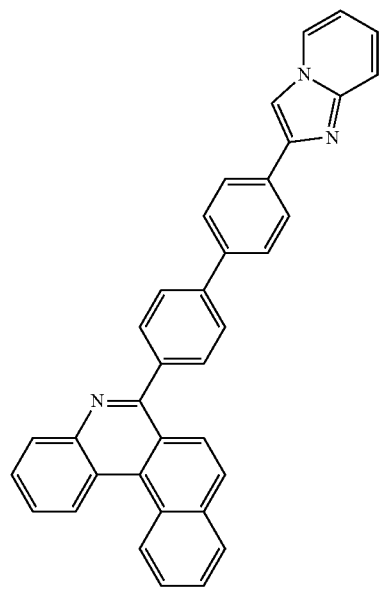
435
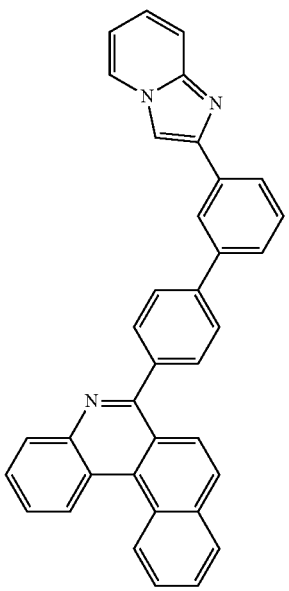
436
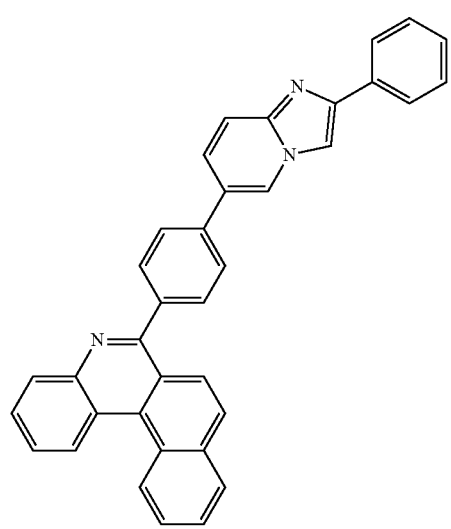
437
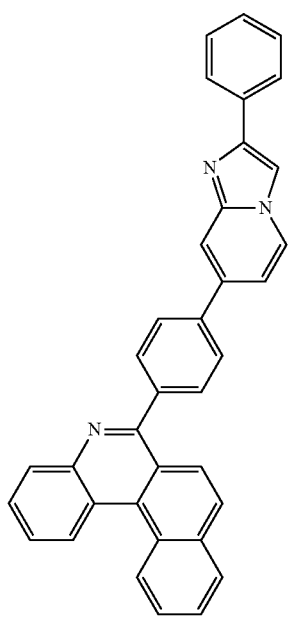

438
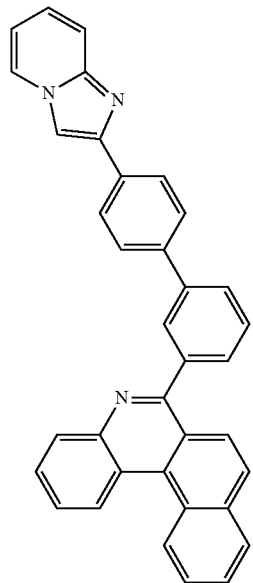
439
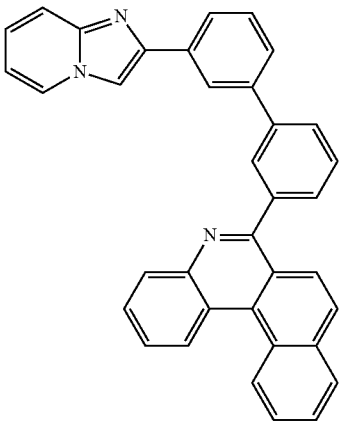
440
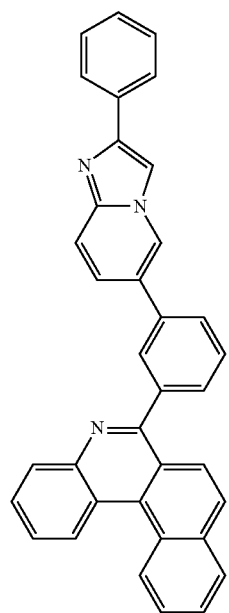
441
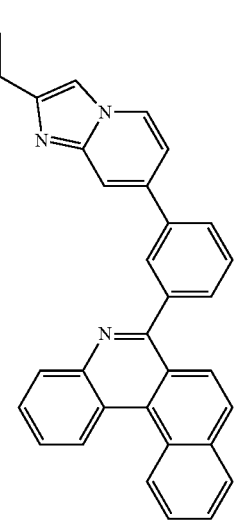

-continued
442
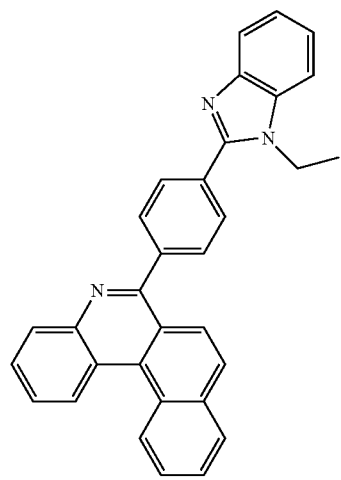
443
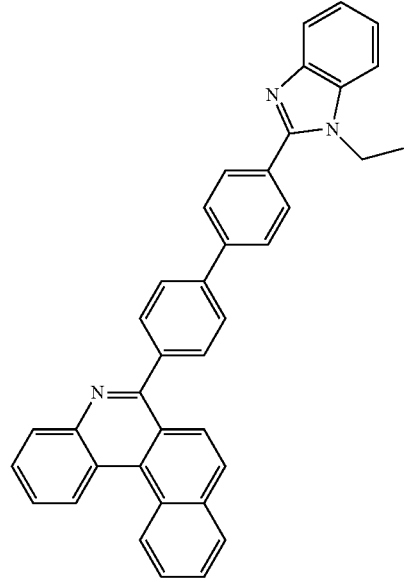
444
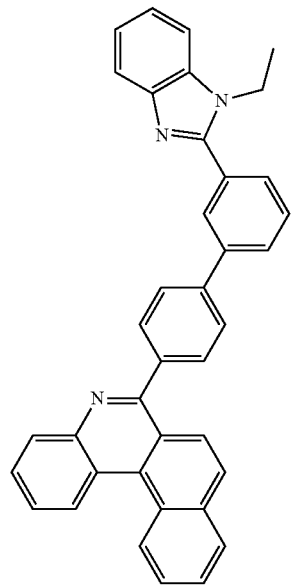
445
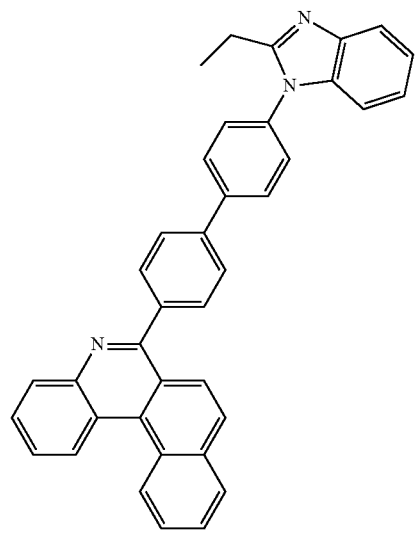
446
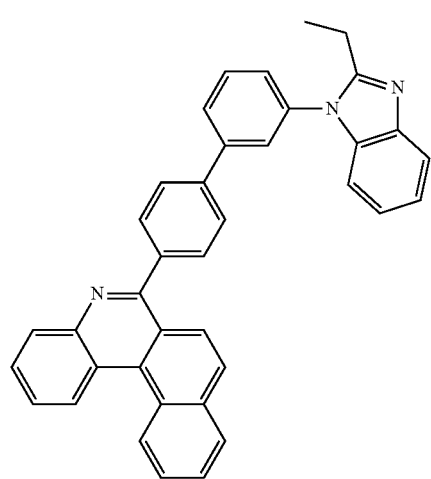
447
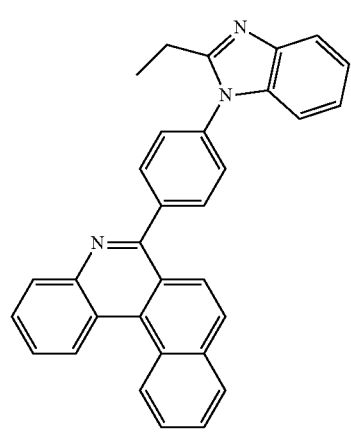

-continued
448 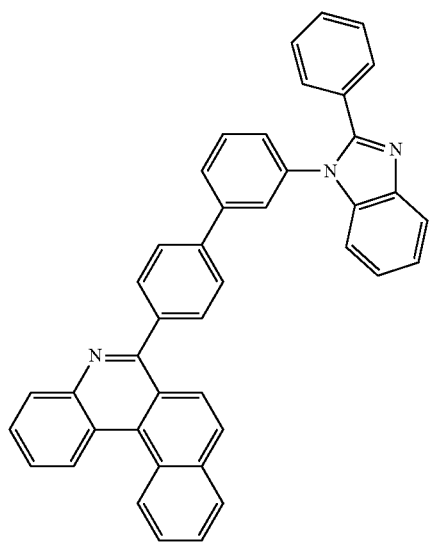
449 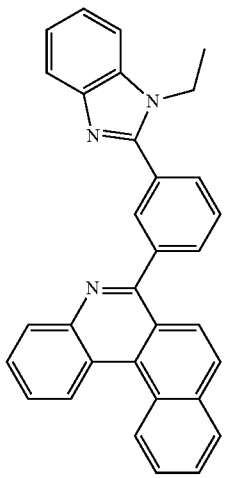
450 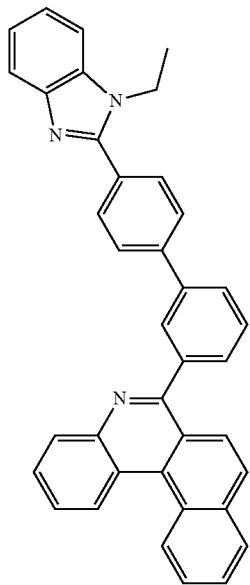
451 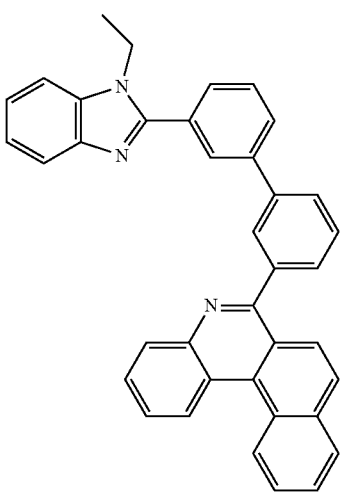

-continued
452 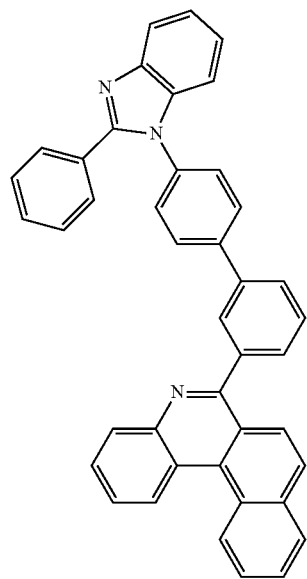 453 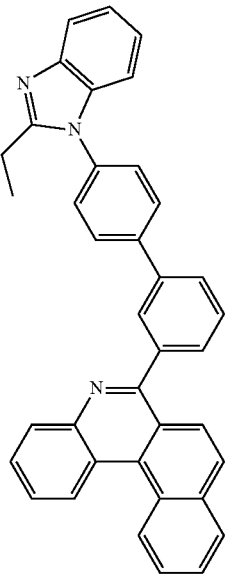
454 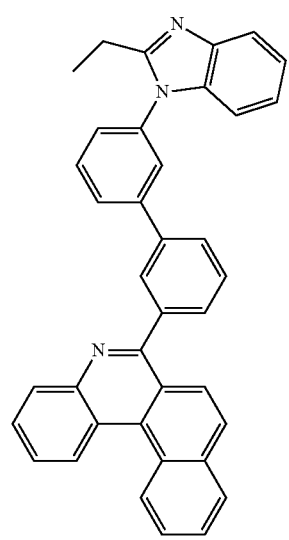 455 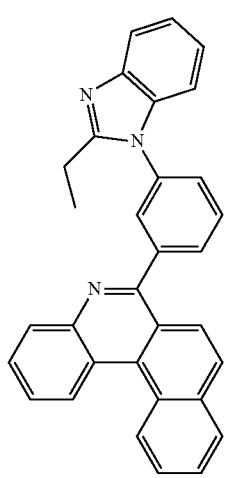

-continued
456
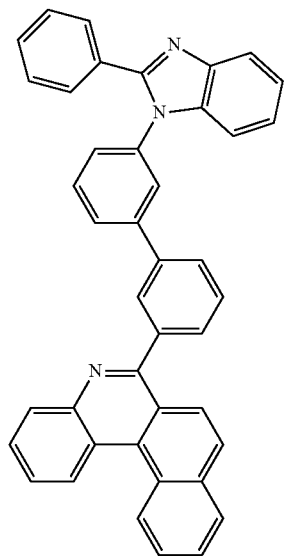
457
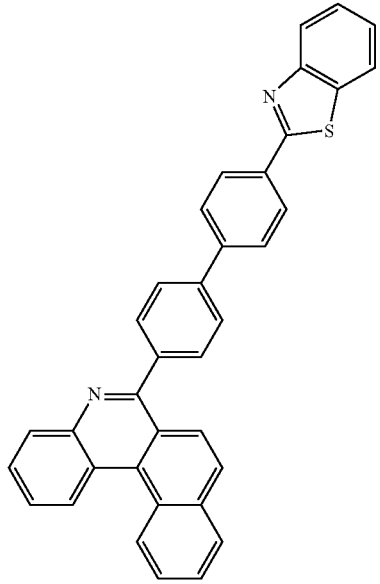
458
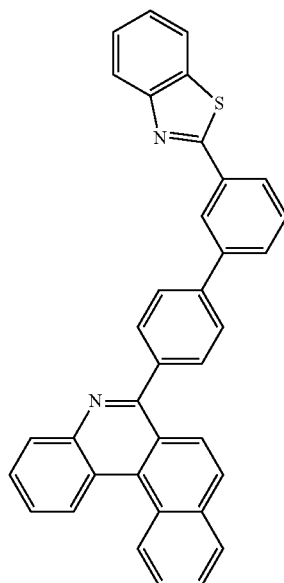
459
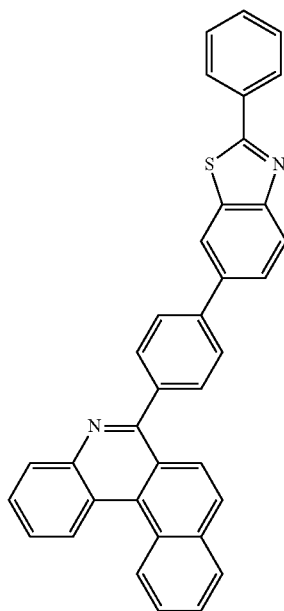

-continued
460
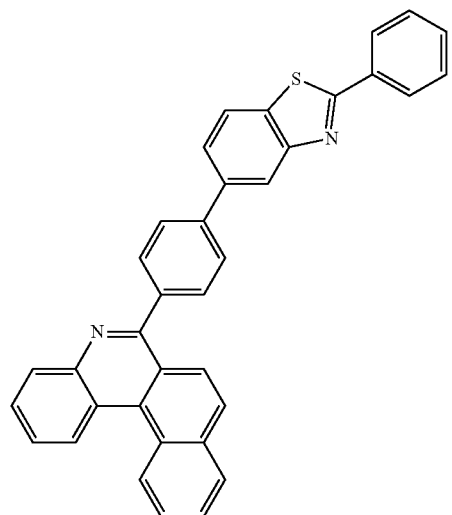
461
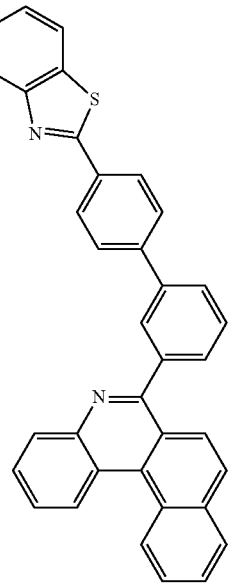
462
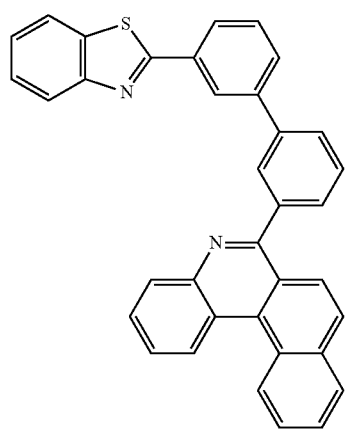
463
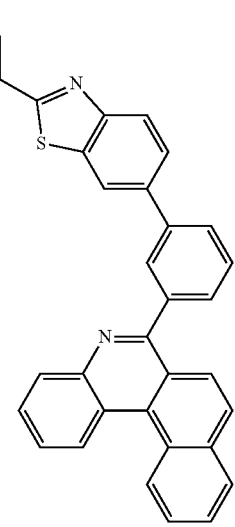

-continued
464
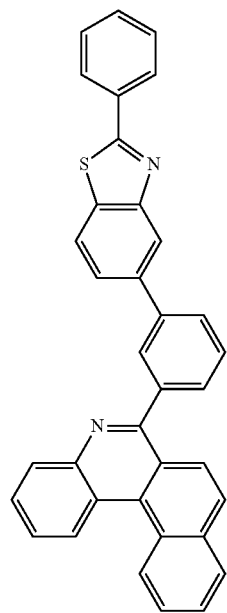
465
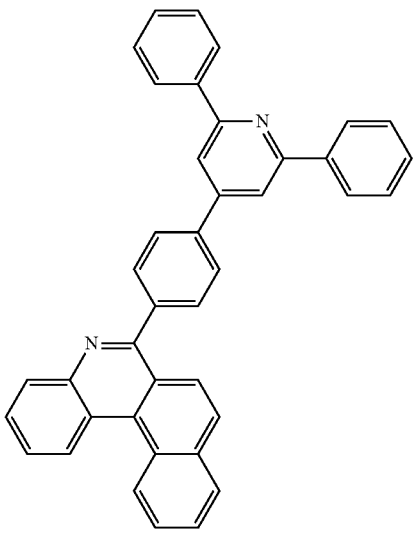
466
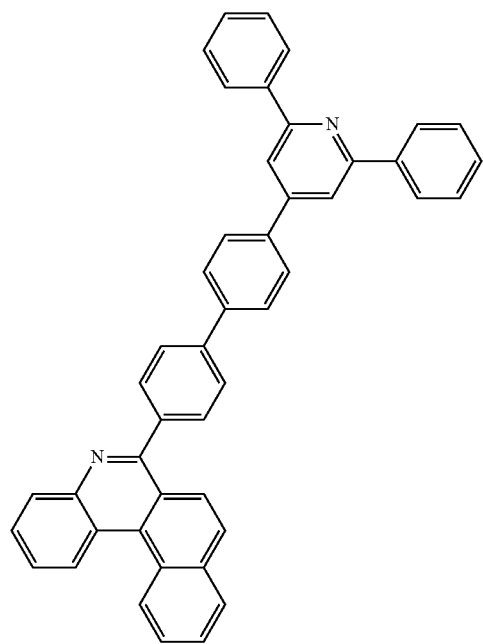
467
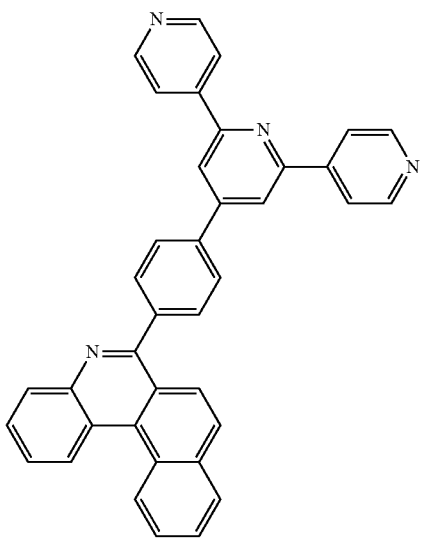

-continued
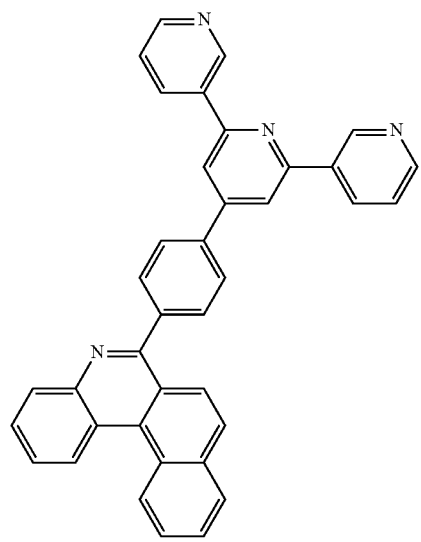
468
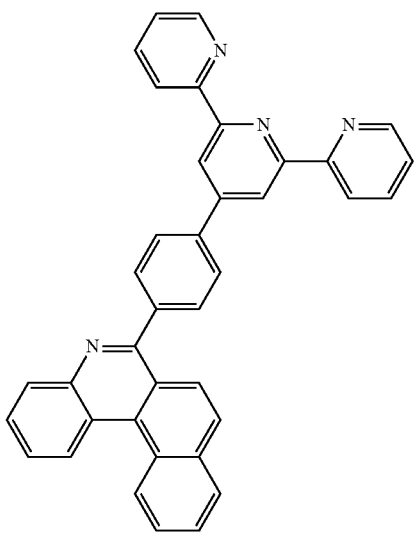
469
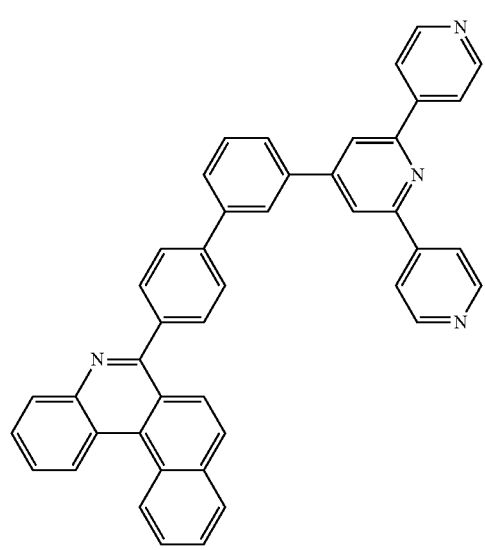
470
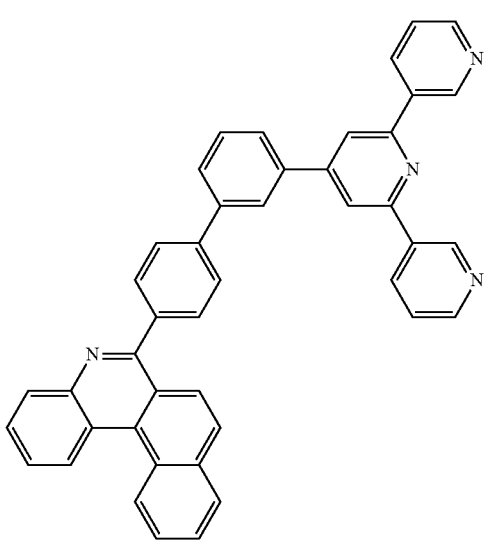
471
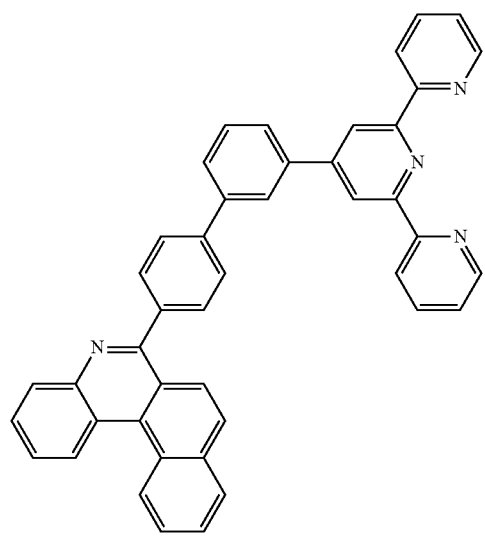
472
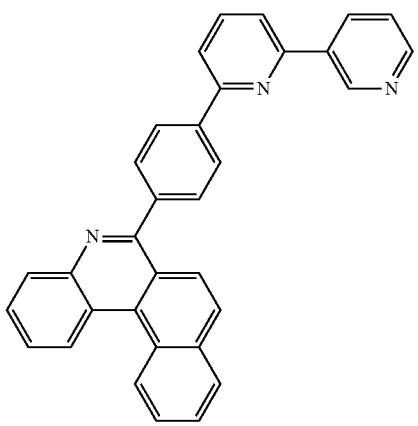
473

211 212
-continued
474 475
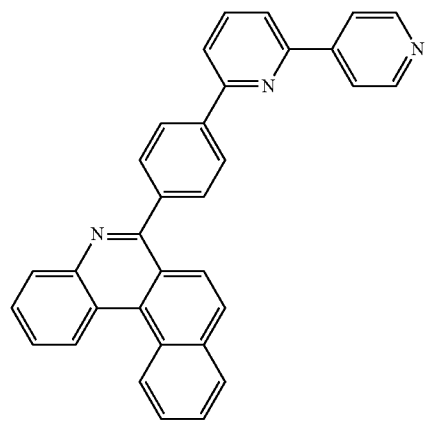 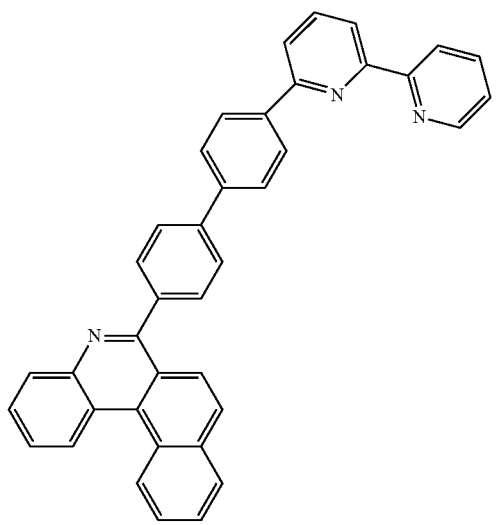
476 477
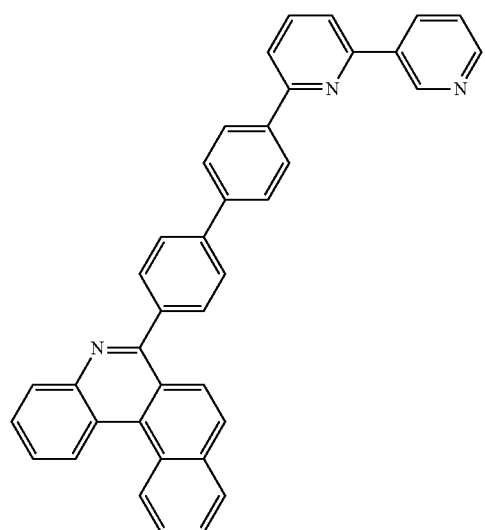 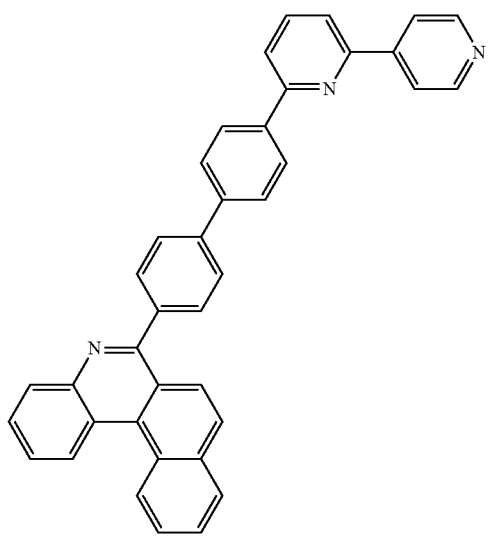

478
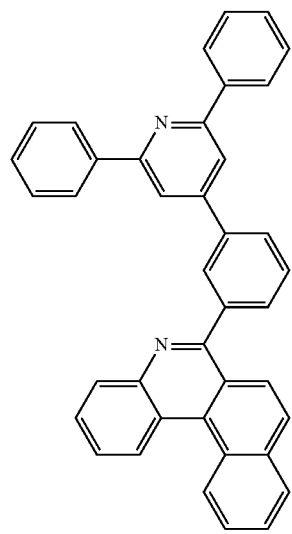
479
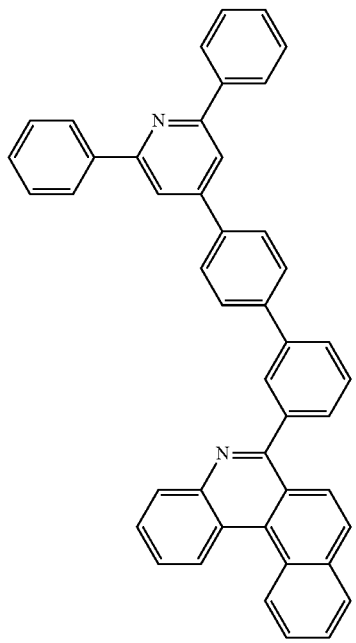
480
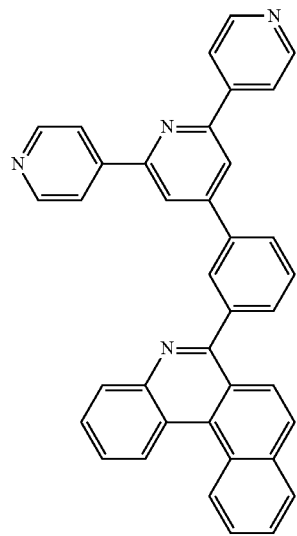
481
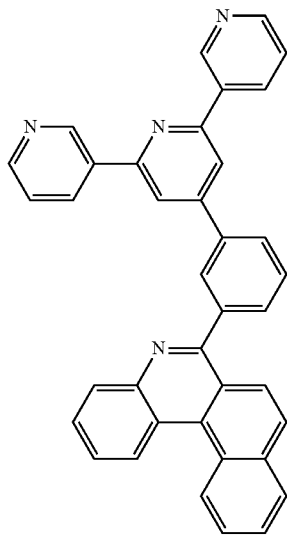

-continued
482 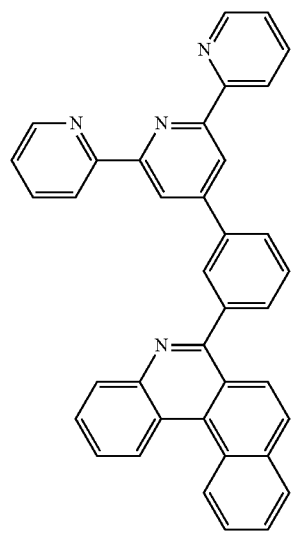 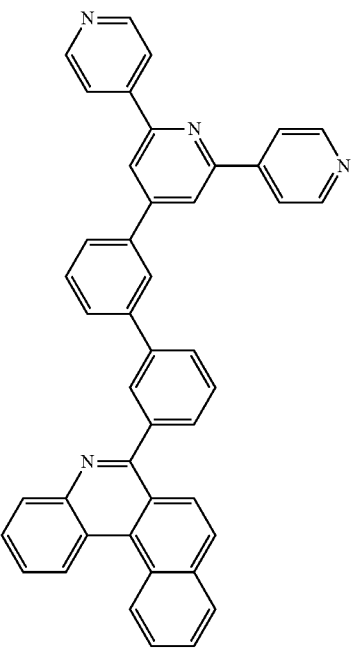 483
484 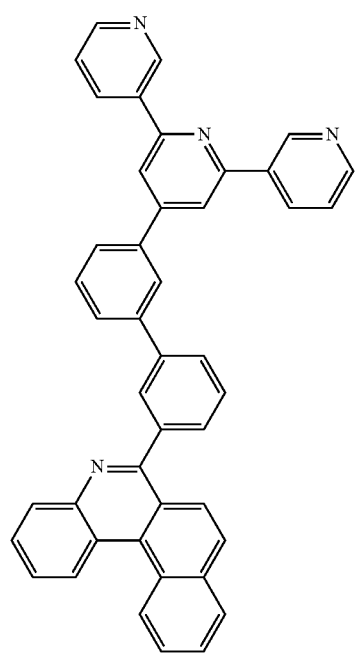 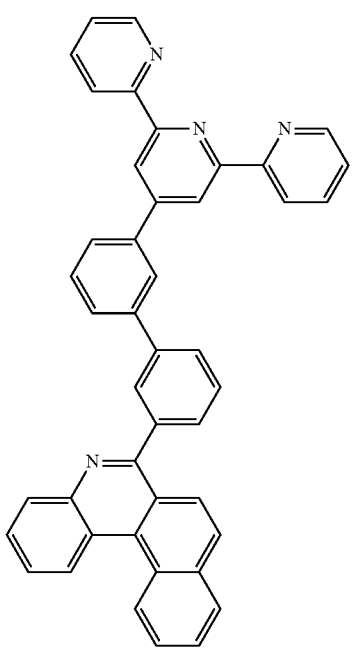 485

-continued
486 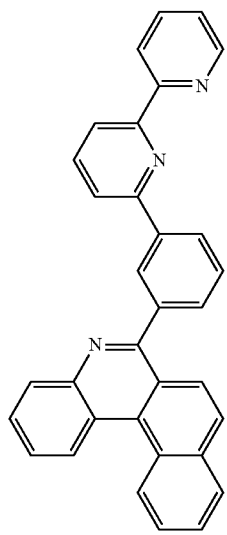
487 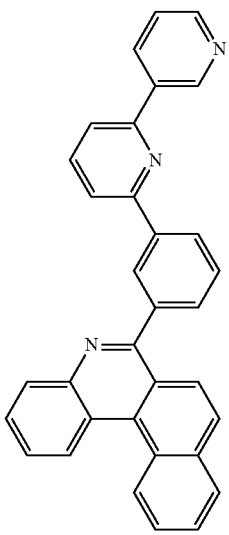
488 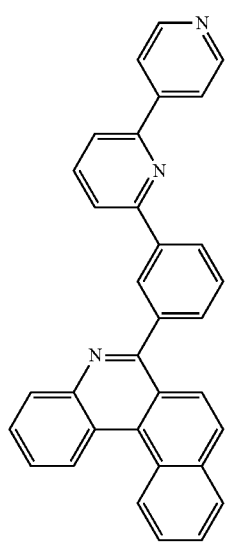
489 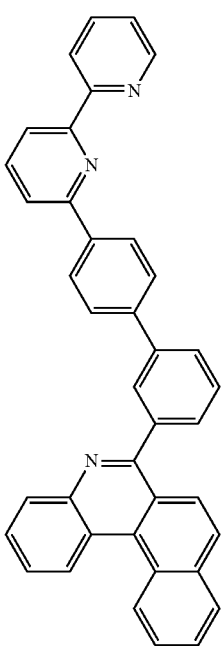

-continued
490
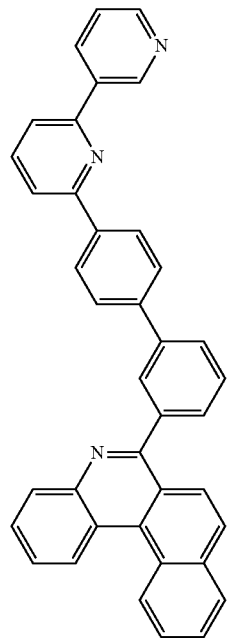
491
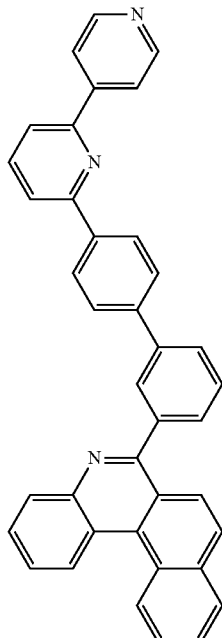
492
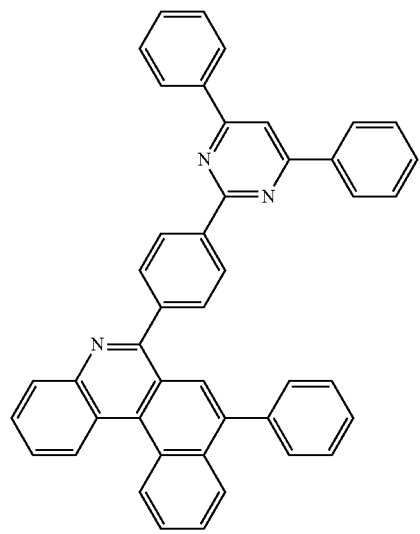
493
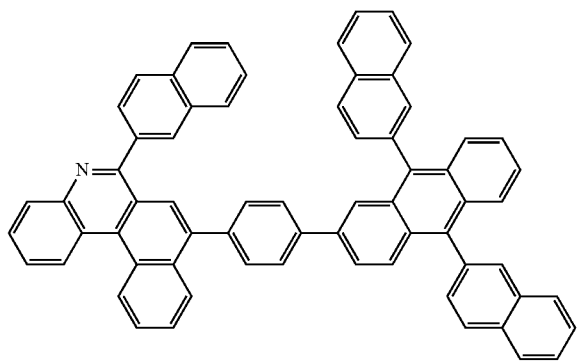
494
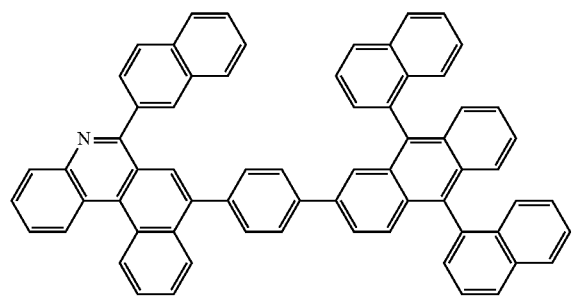
495
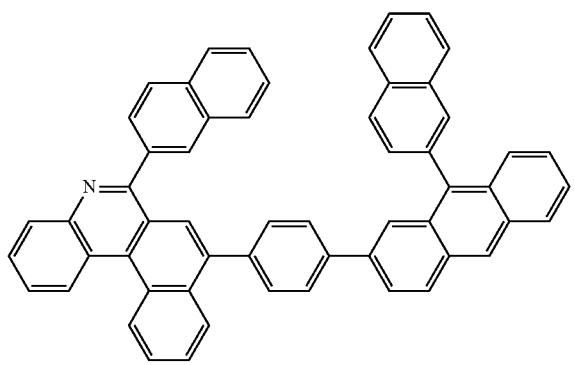

-continued
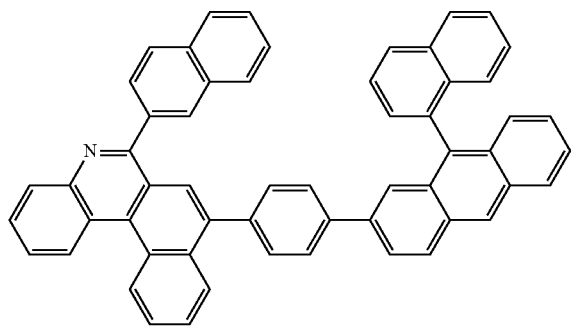
496
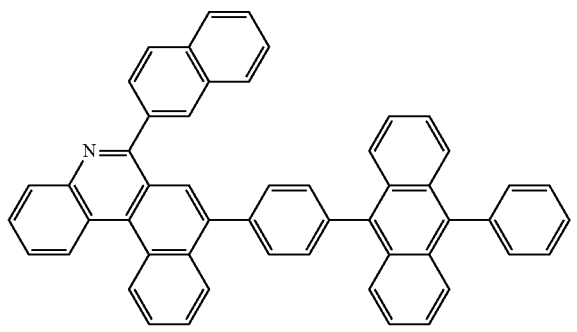
497
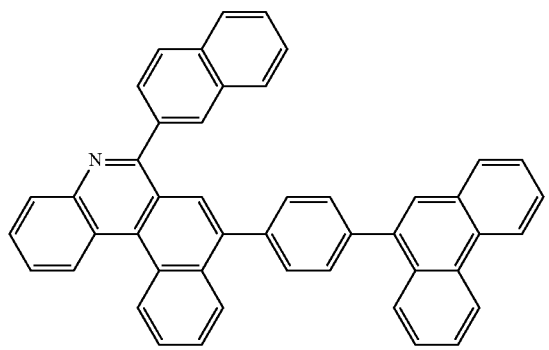
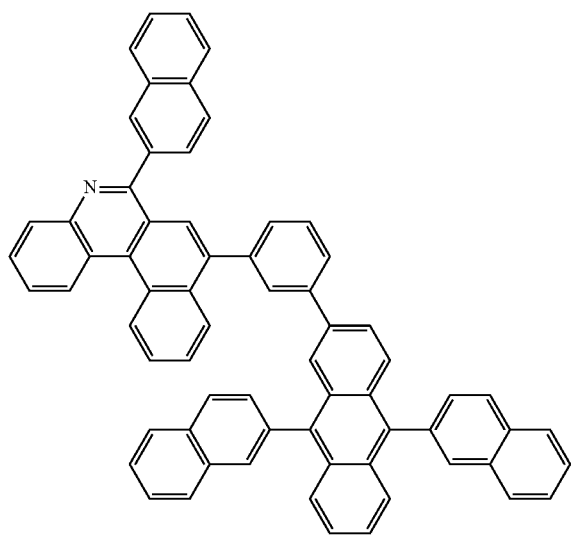
499
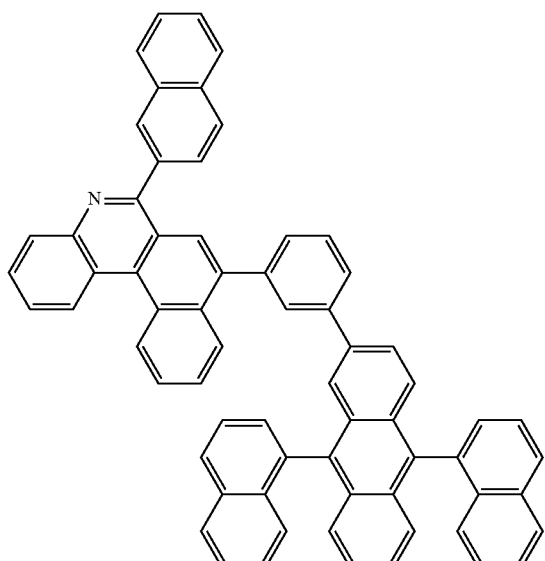
500

-continued
501
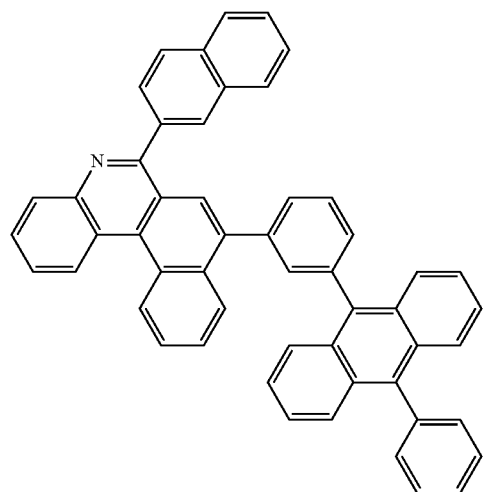
502
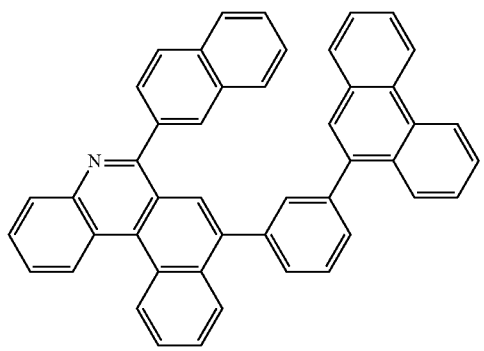
503
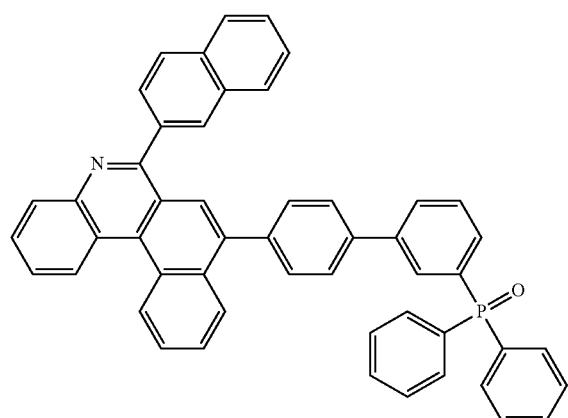
504
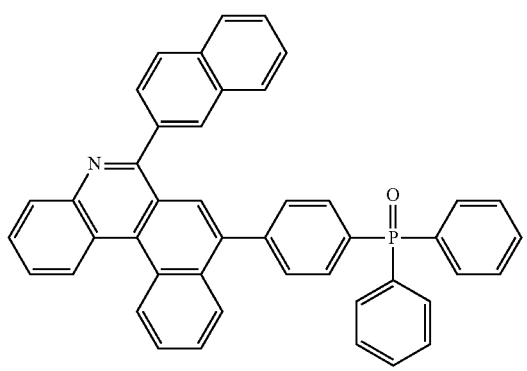
505
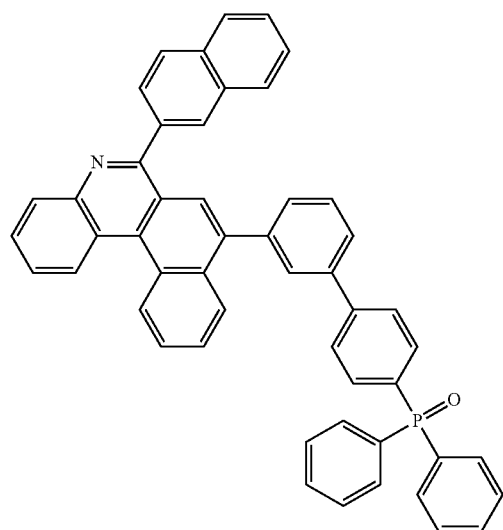
506
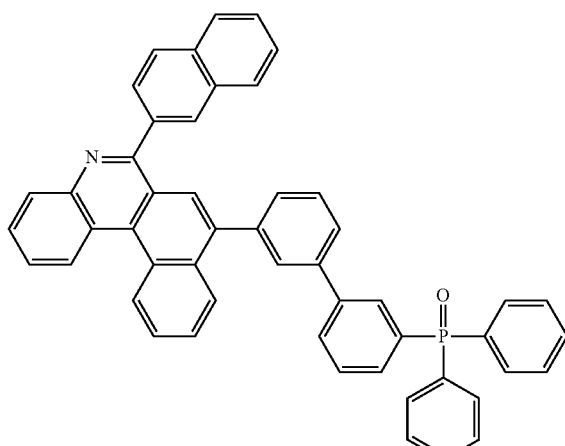

-continued
507
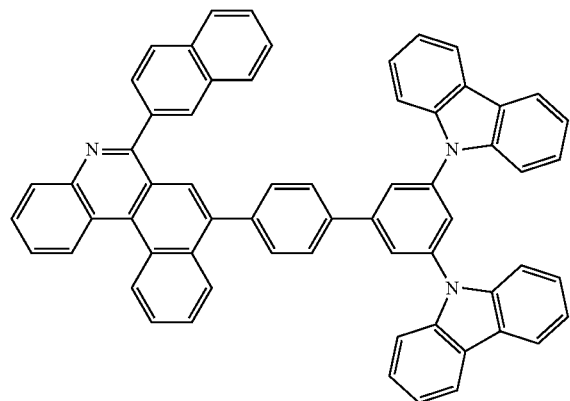
508
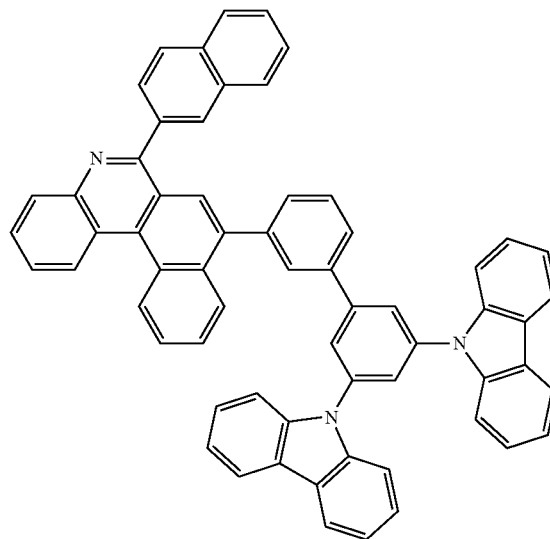
509
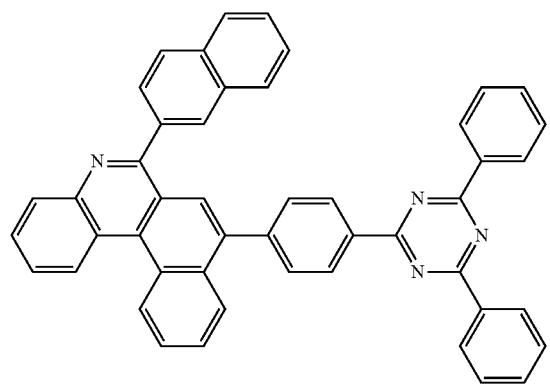
510
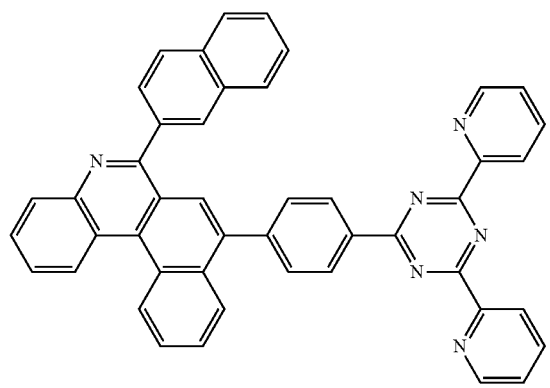
511
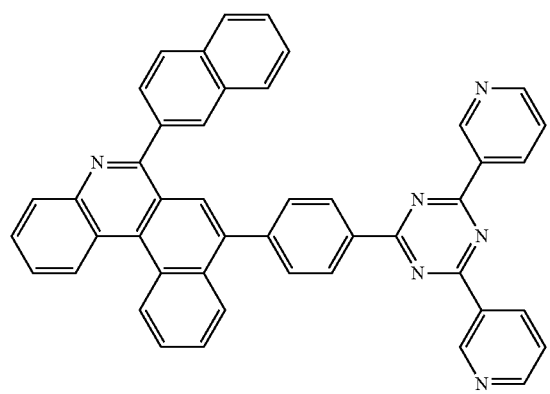
512
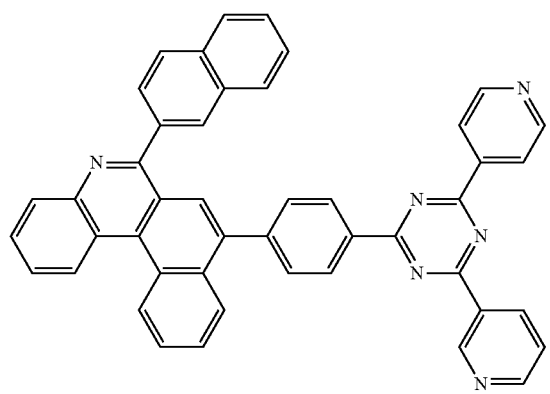

-continued
513
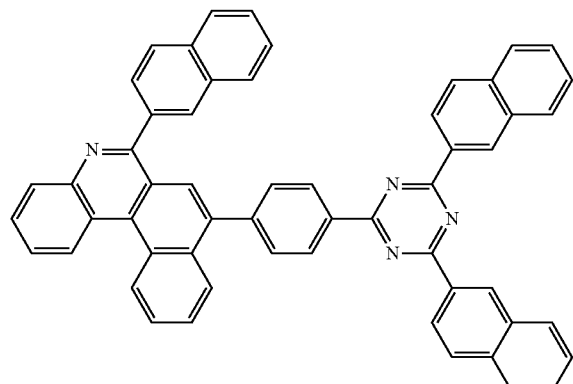
514
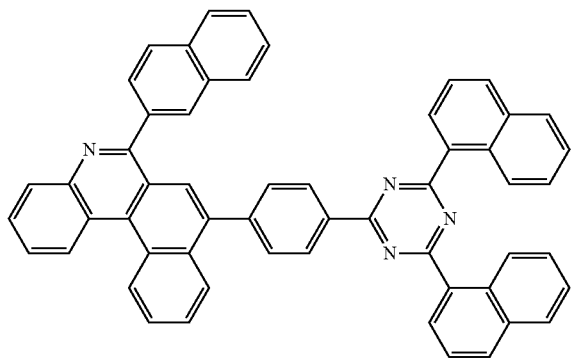
515
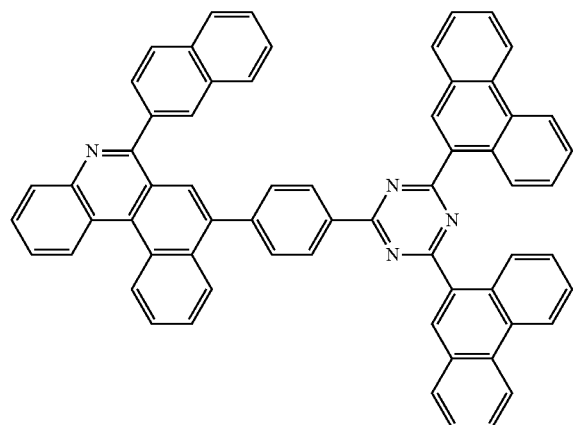
516
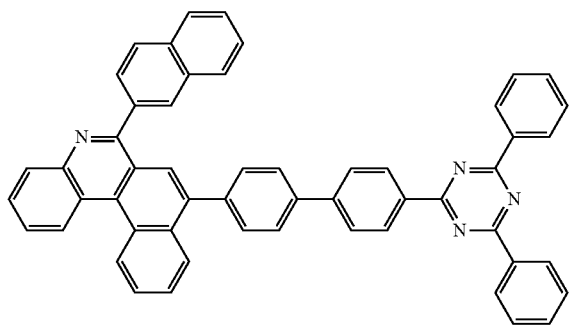
517
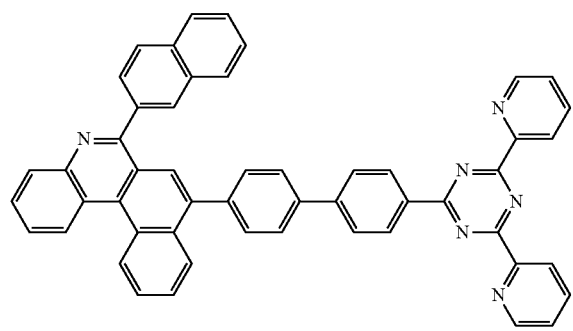
518
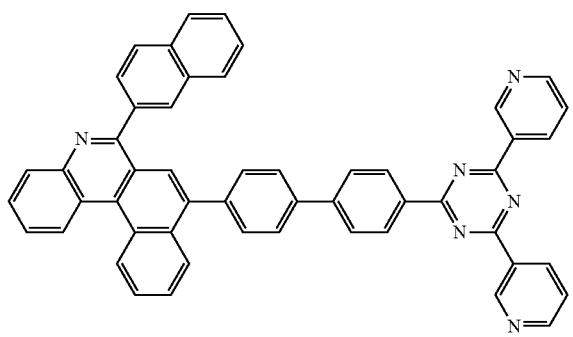
519
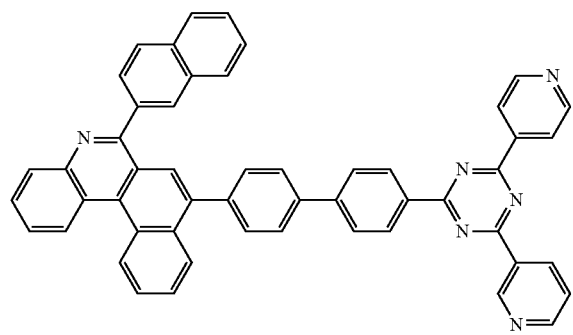
520
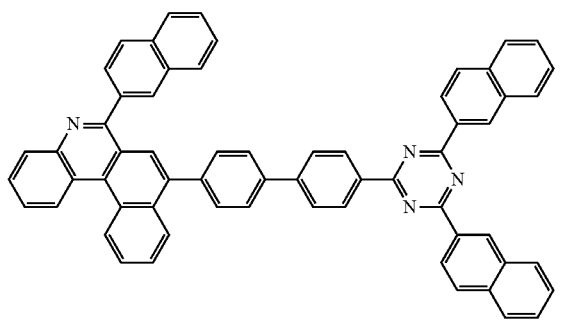

521
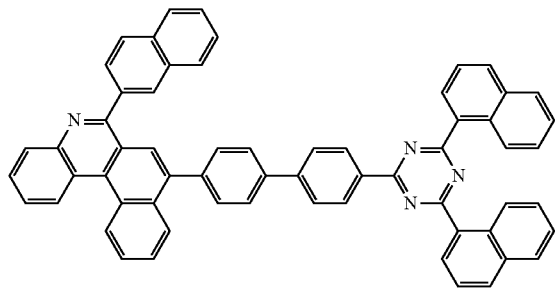
522
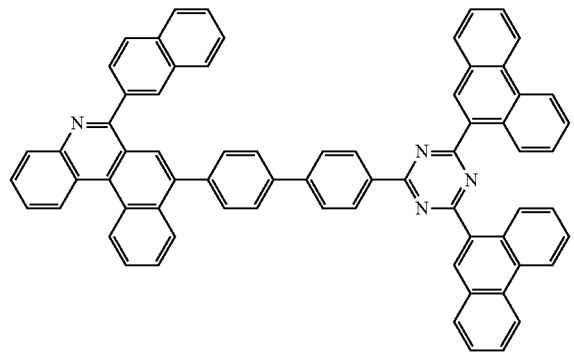
523
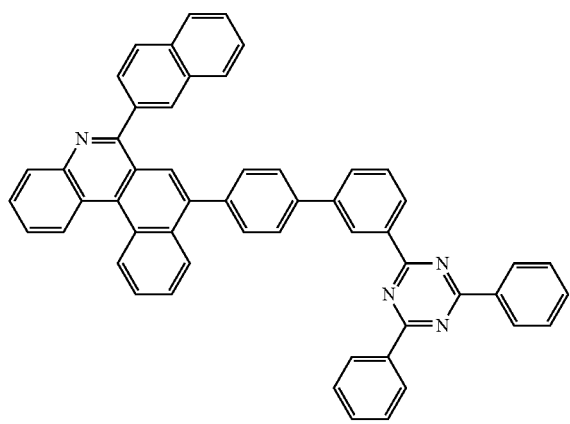
524
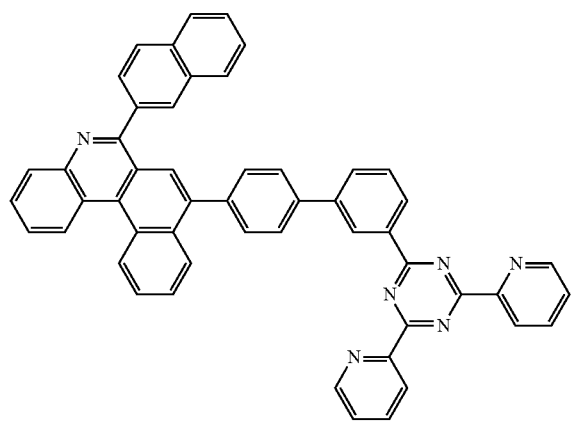
525
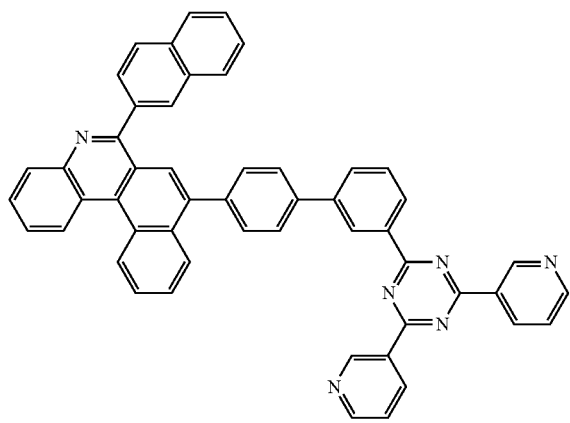
526
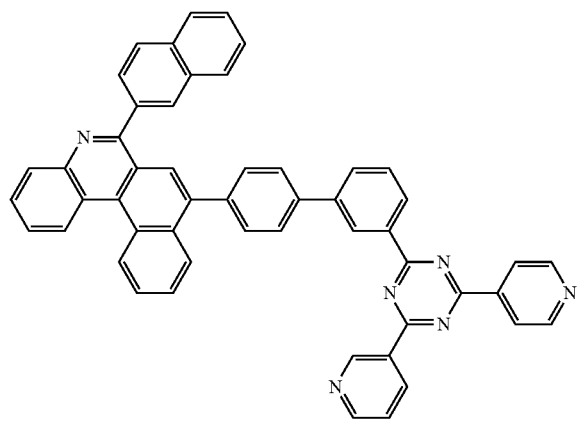

527
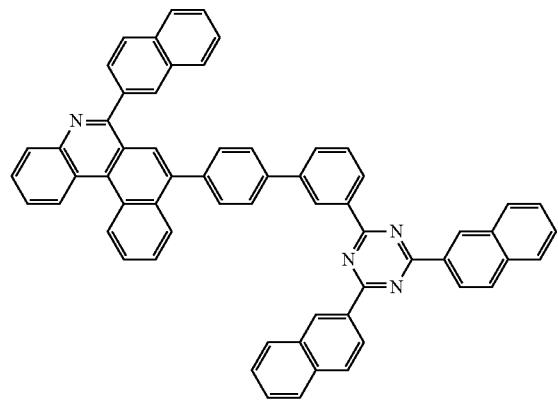
528
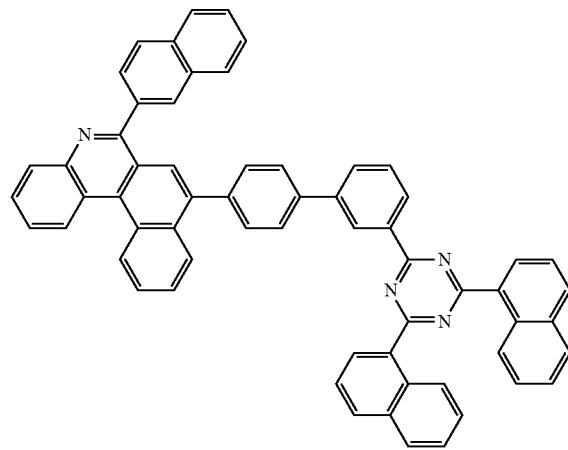
529
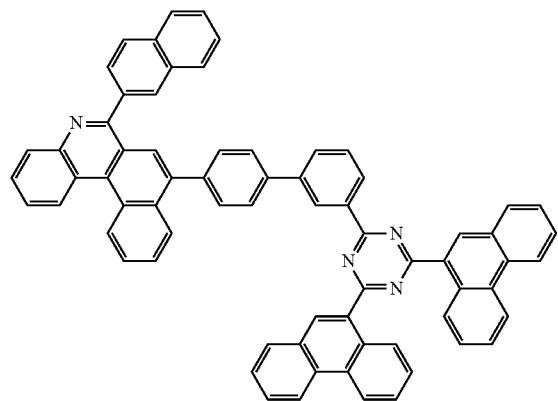
530
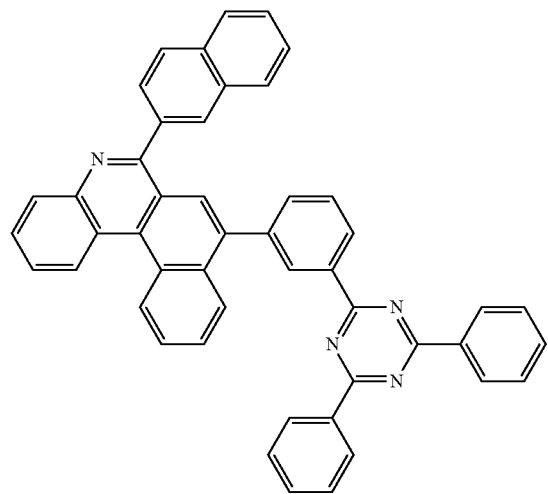
531
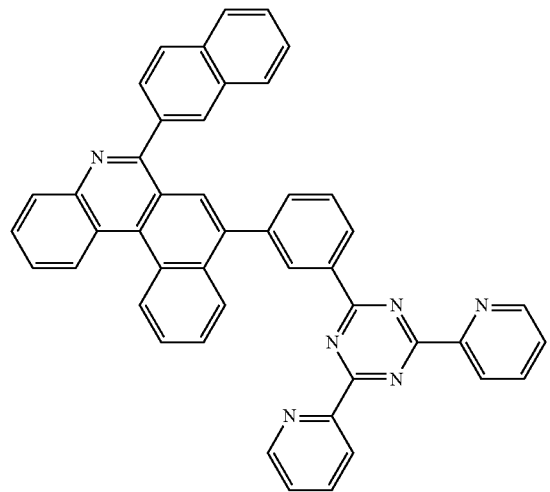
532
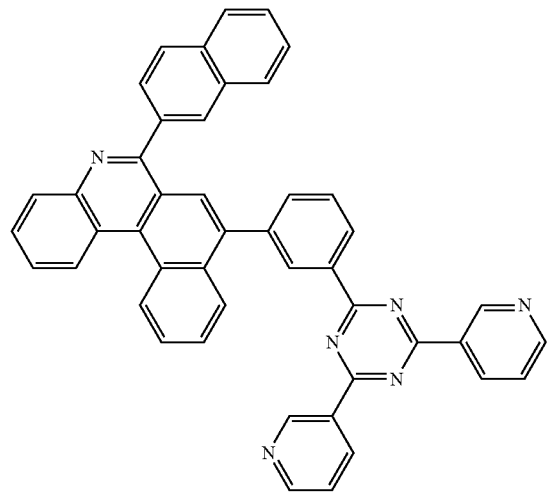

-continued
533
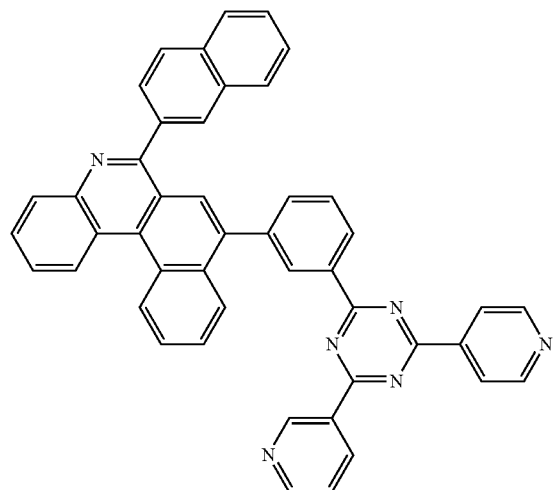
534
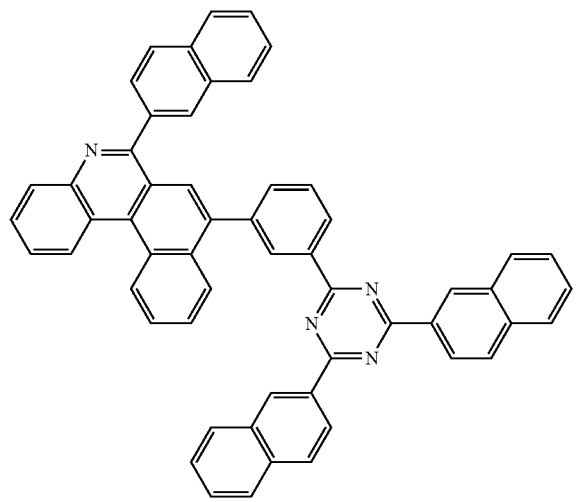
535
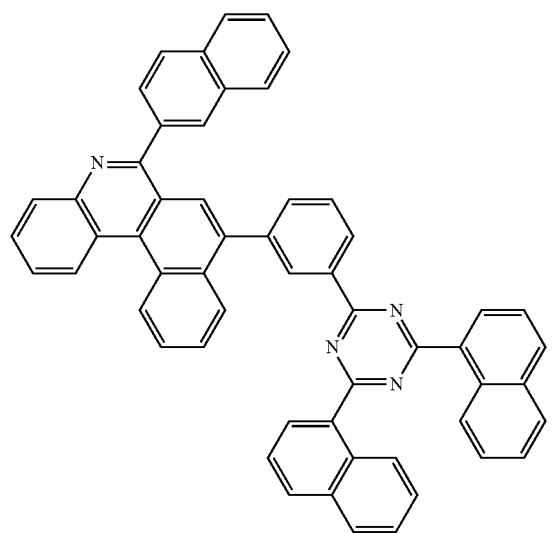
536
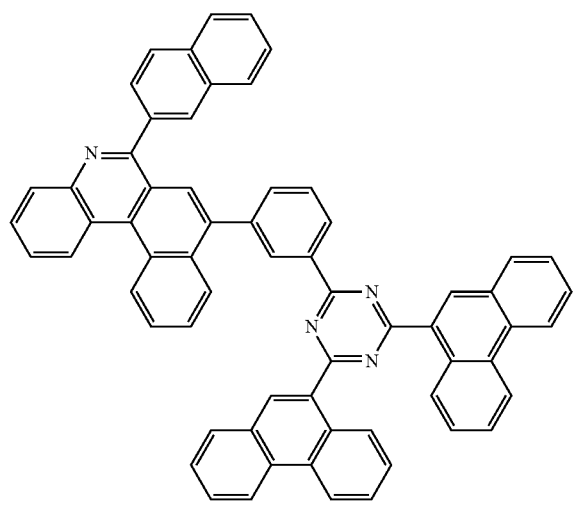
537
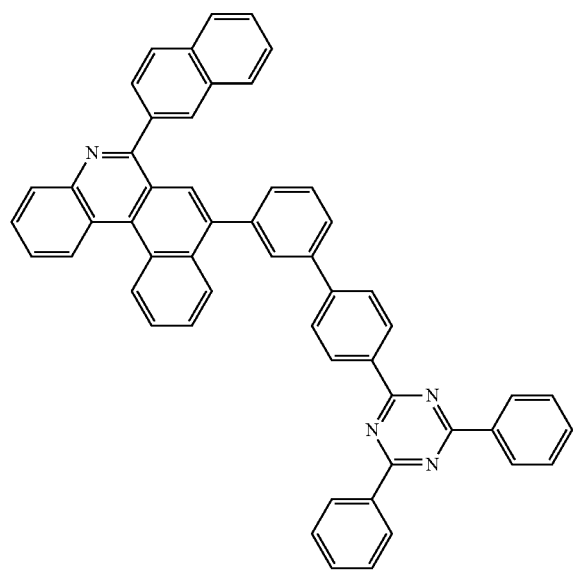
538
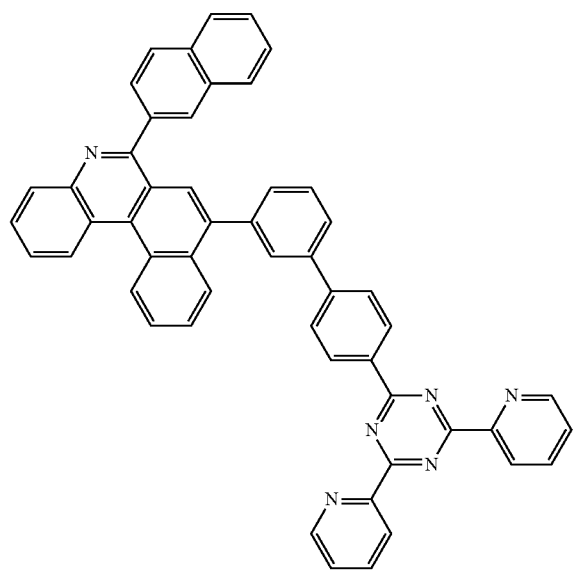

-continued
539
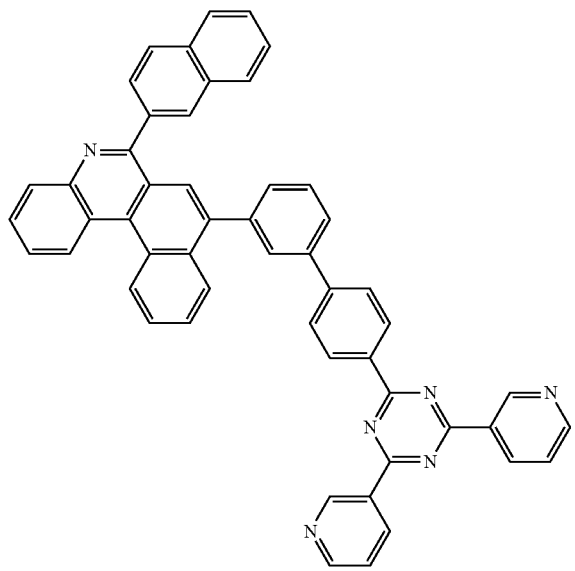
540
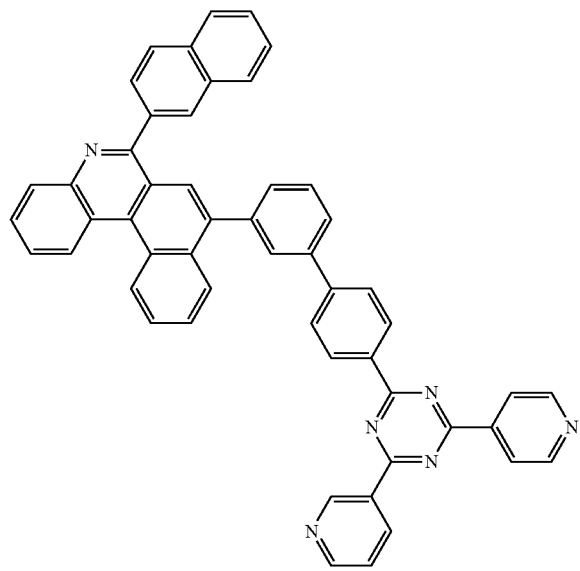
541
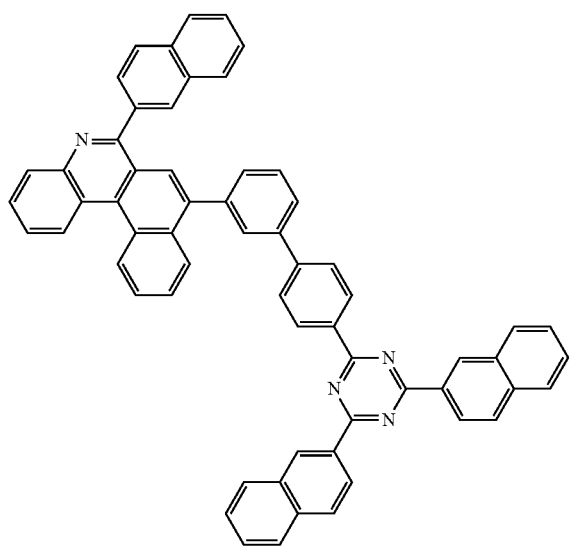
542
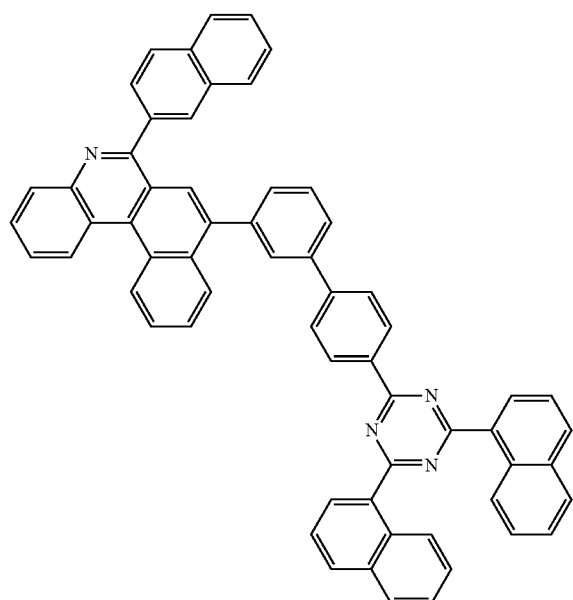

543
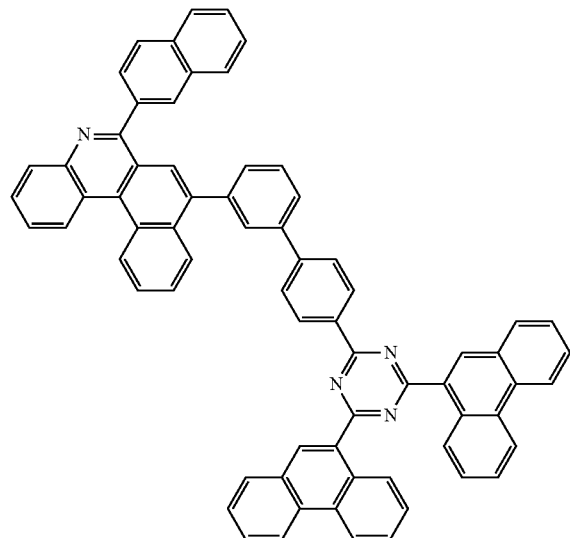
544
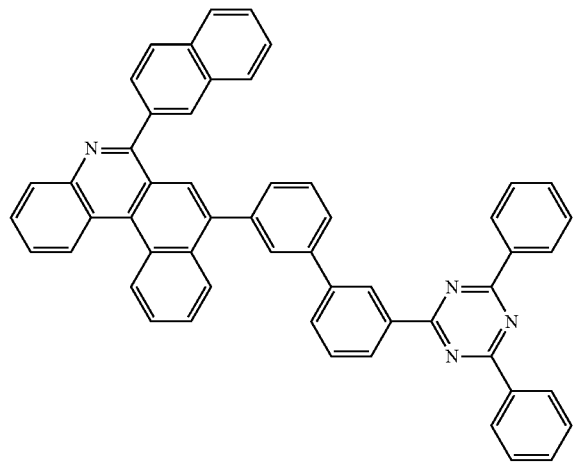
545
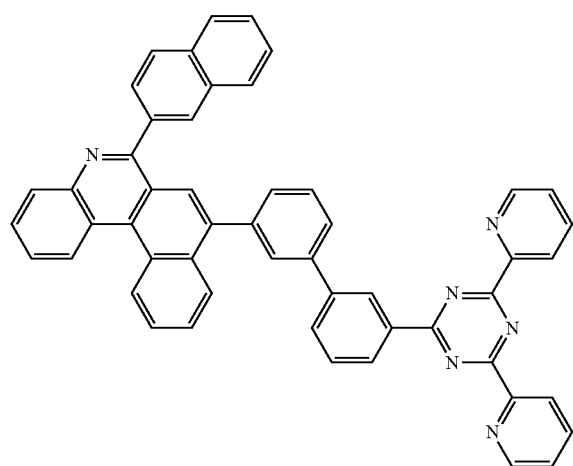
546
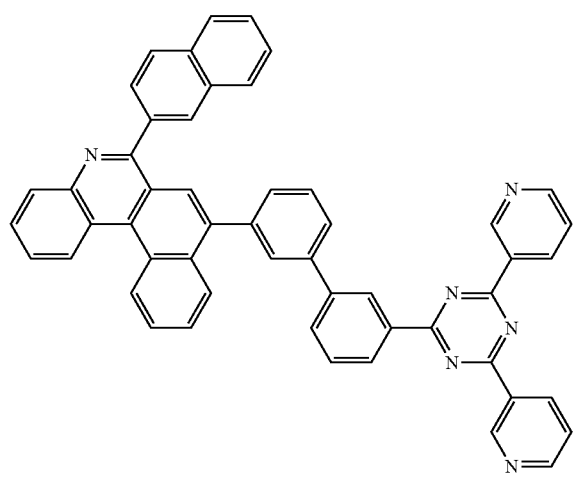
547
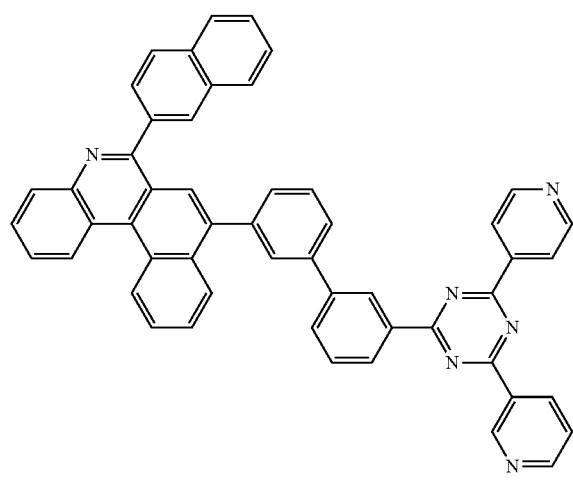
548
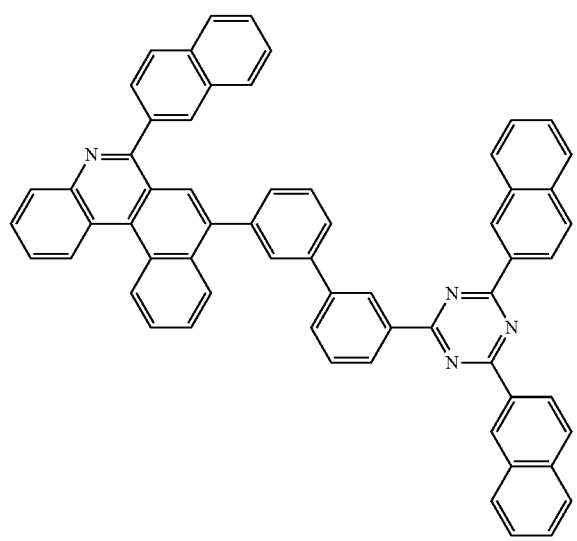

549
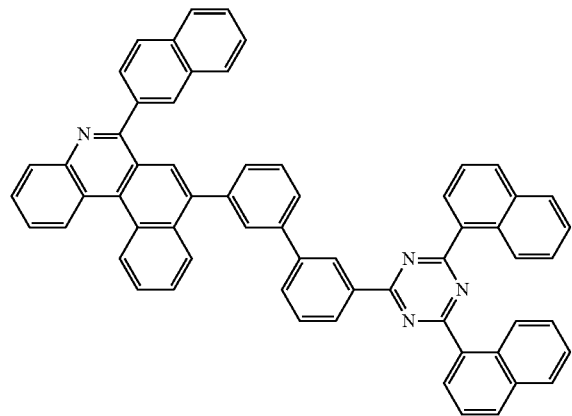
550
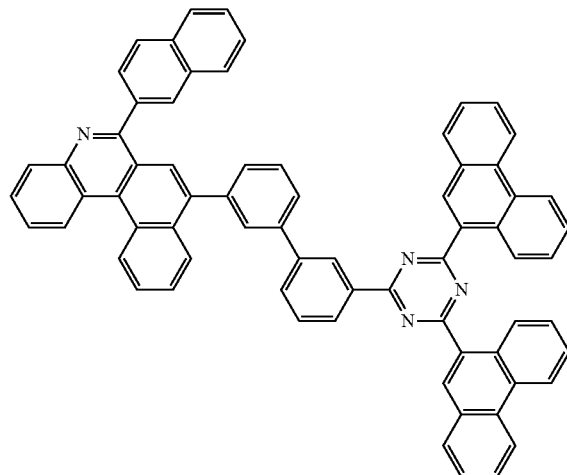
551
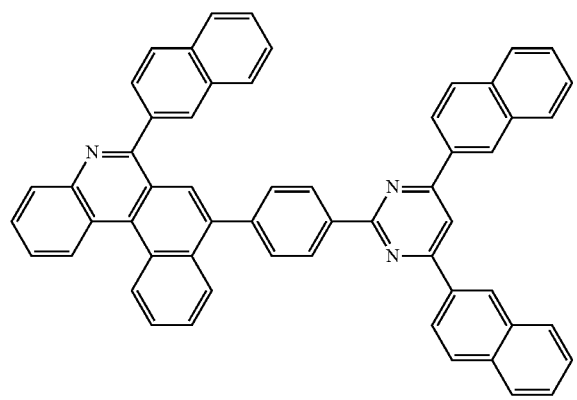
552
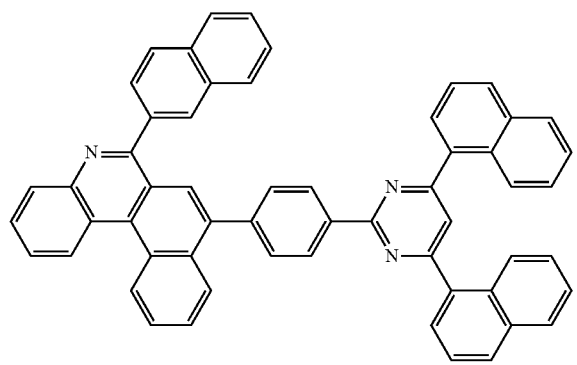
553
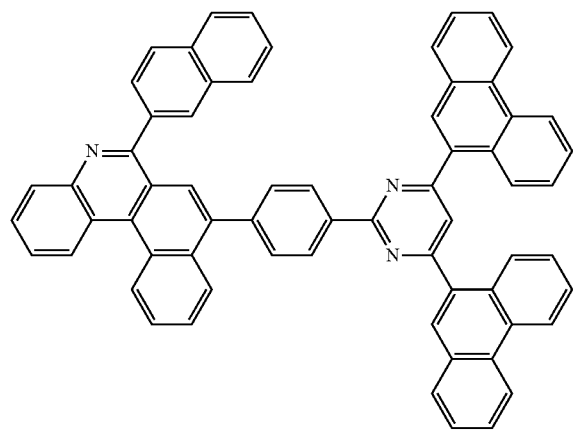
554
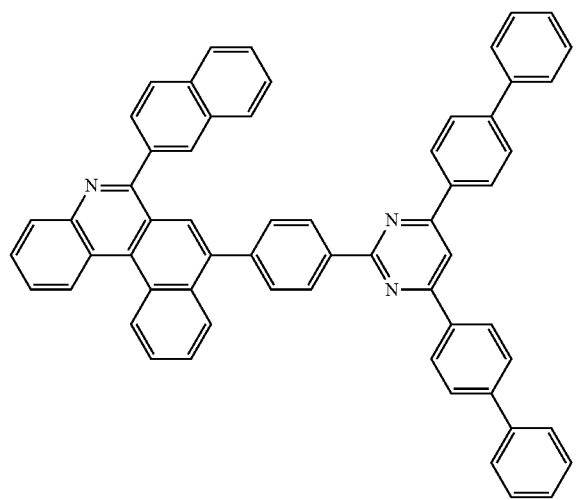

-continued
555
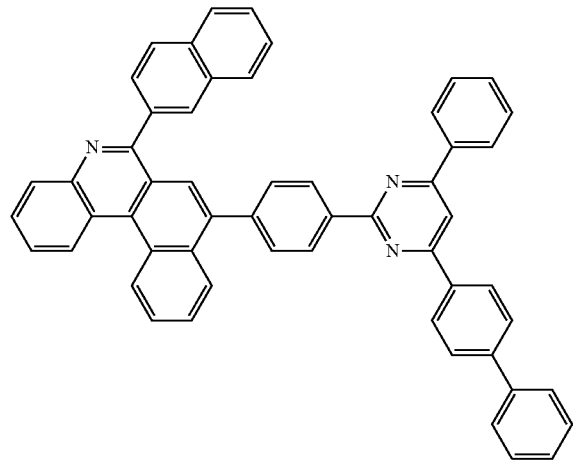
556
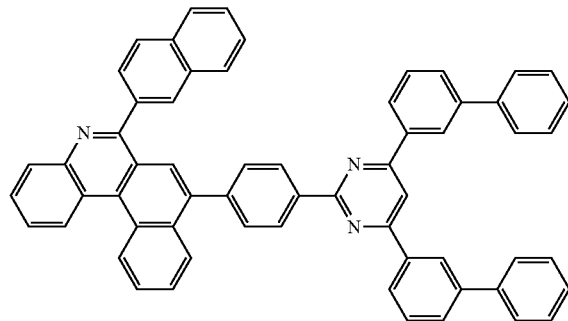
557
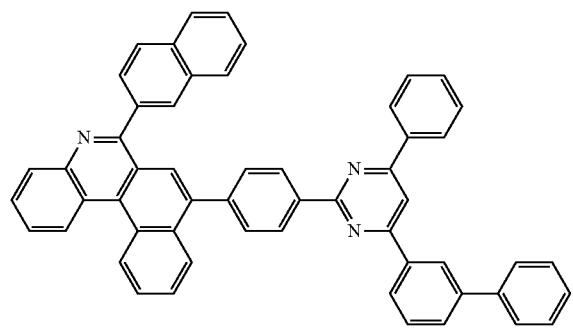
558
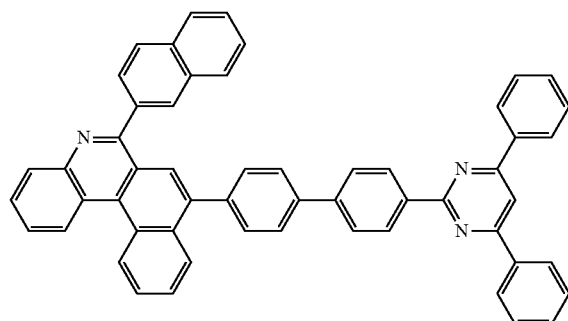
559
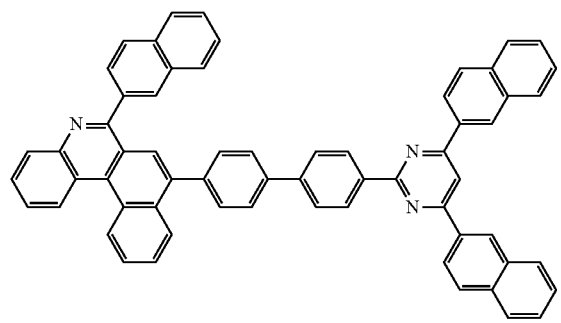
560
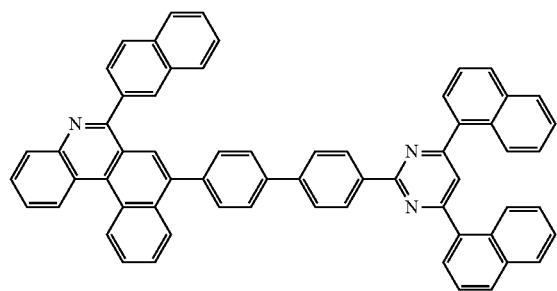
561
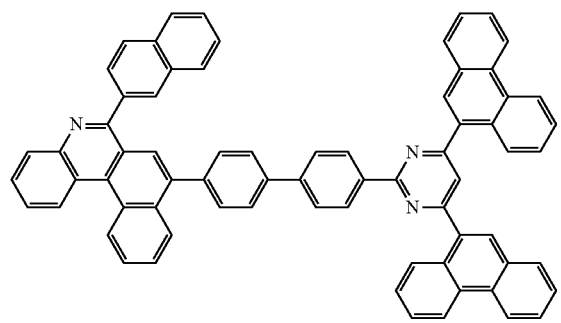
562
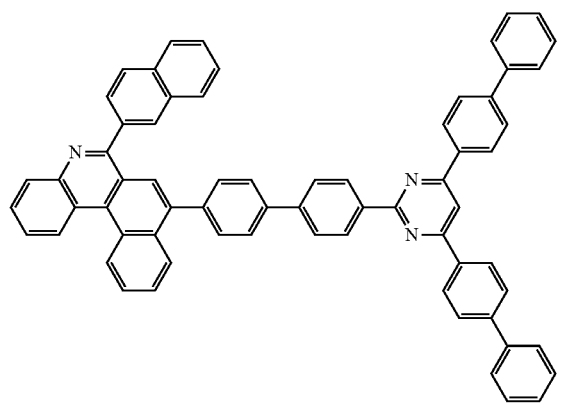

-continued
563
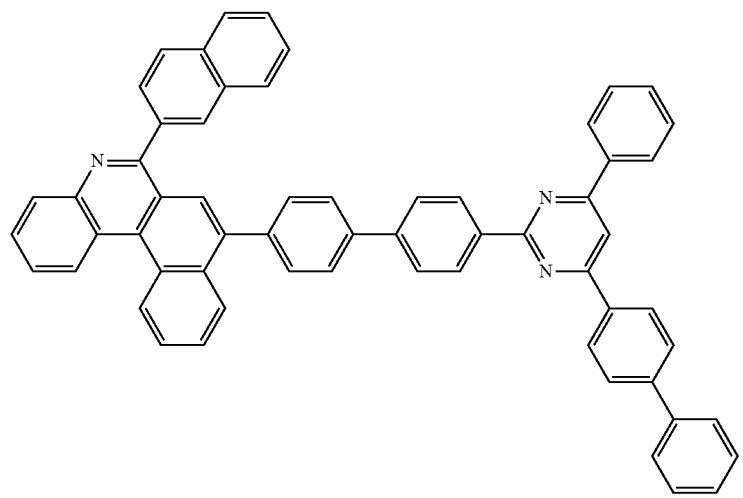
564
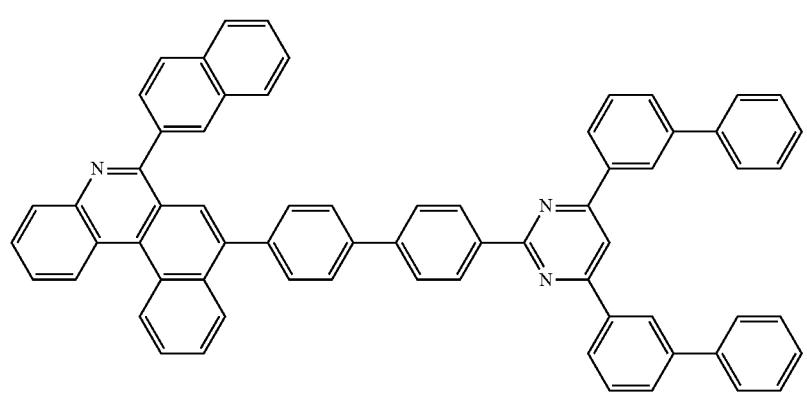
565
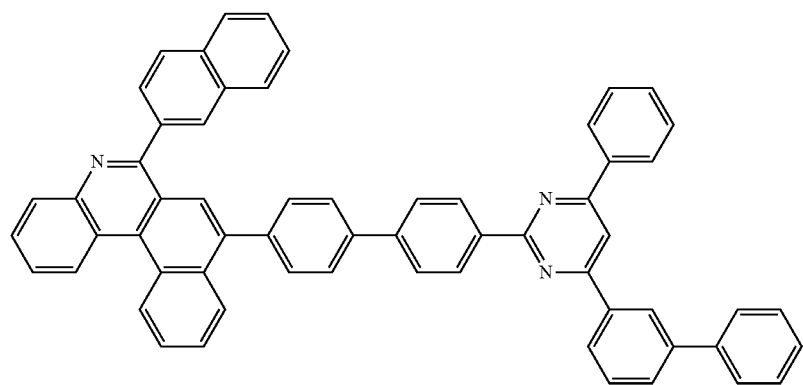
566
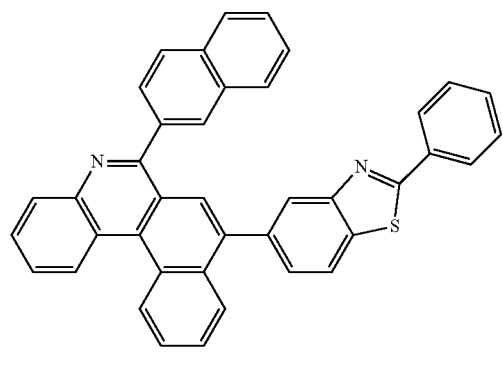
567
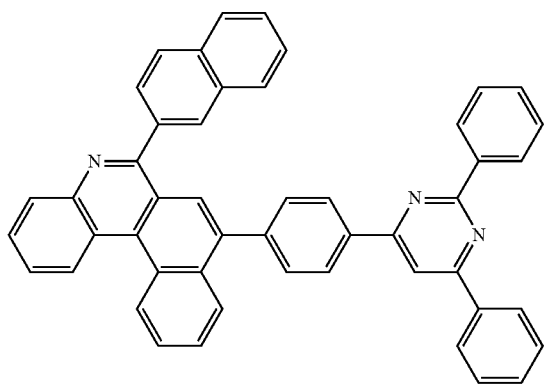

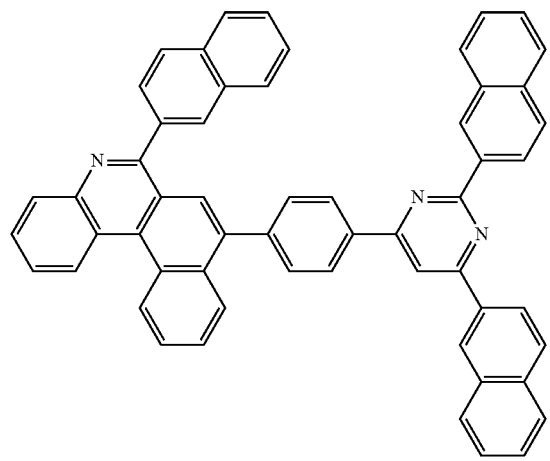
568
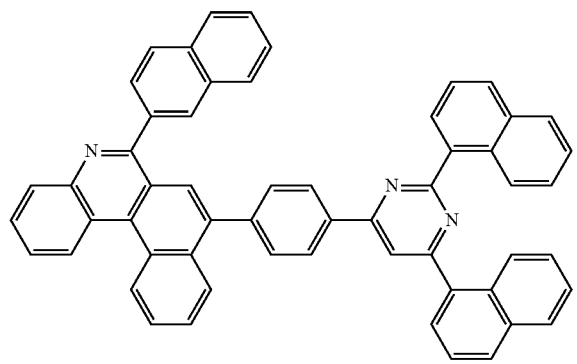
569
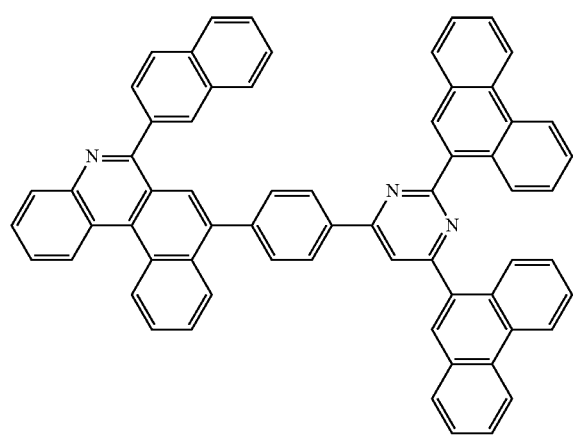
570
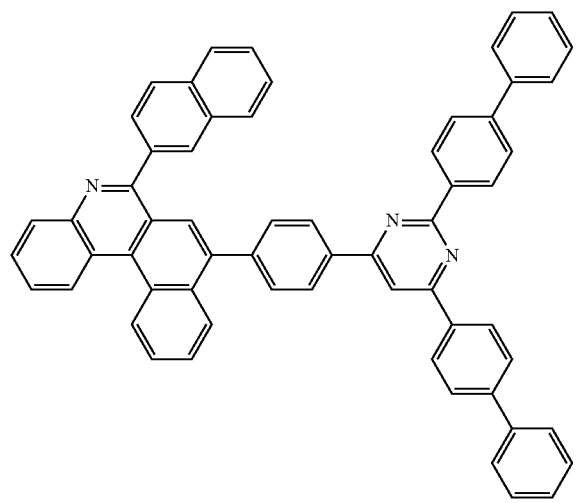
571
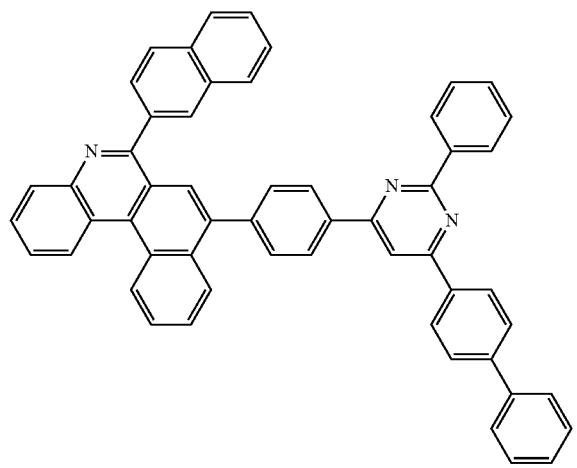
572

573
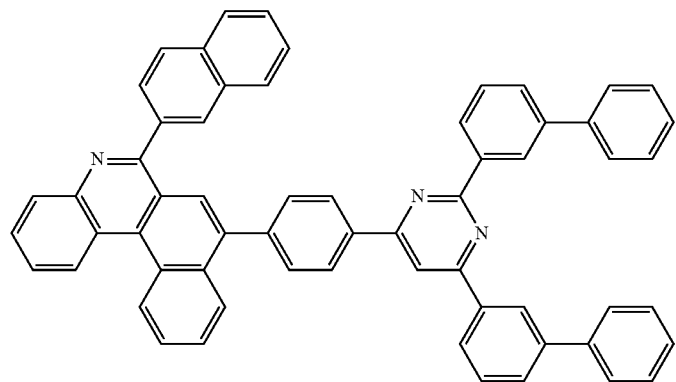
574 575
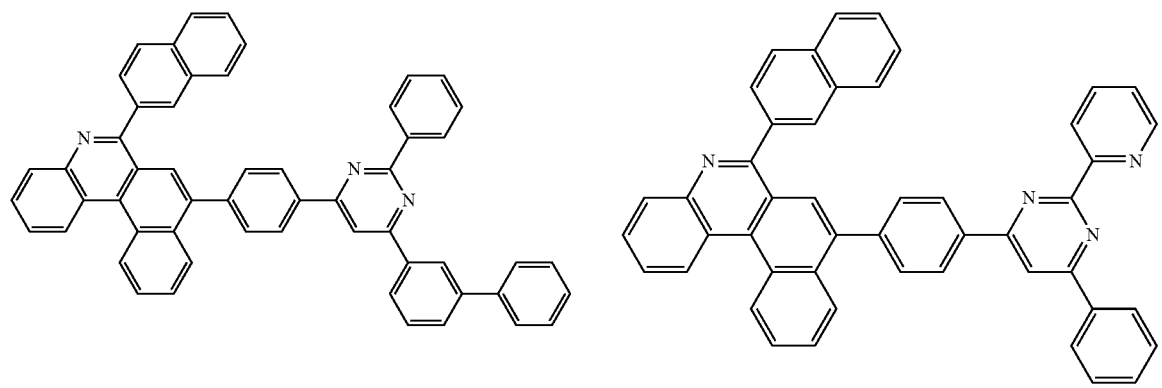
576 577
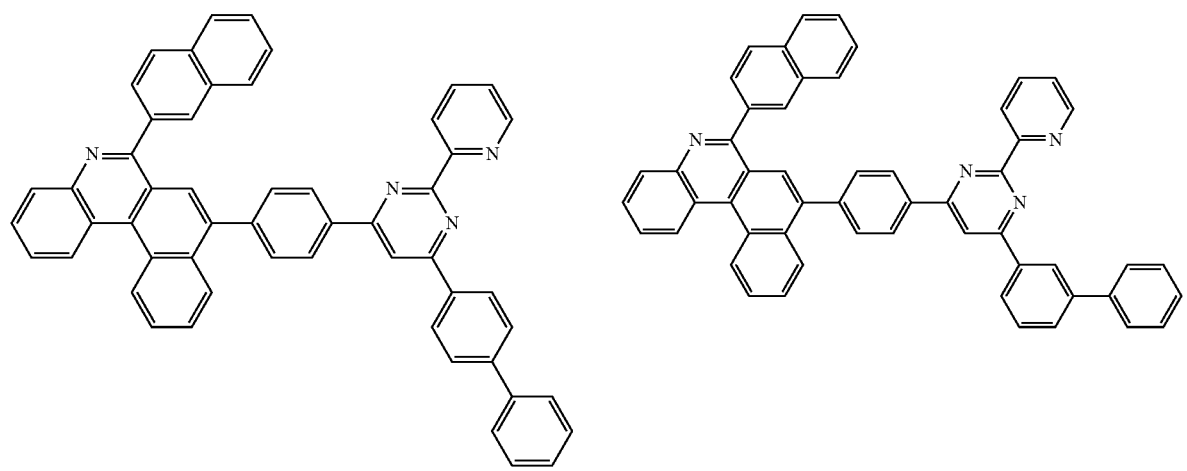

-continued
578
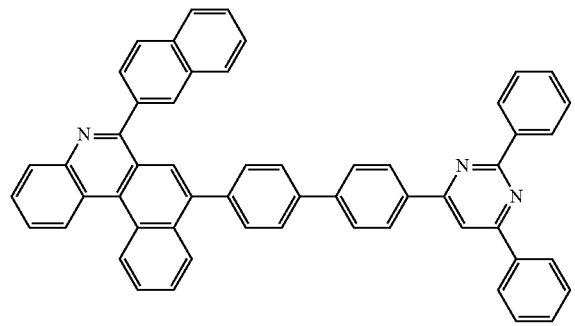
579
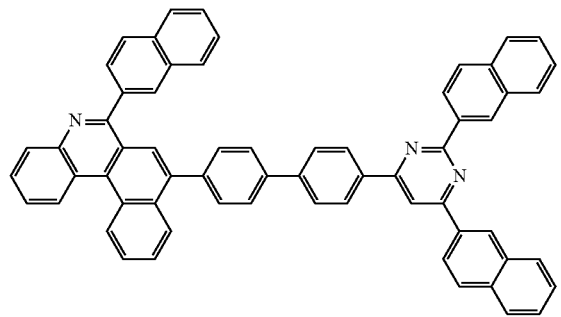
580
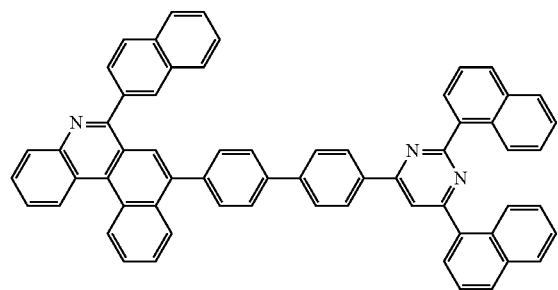
581
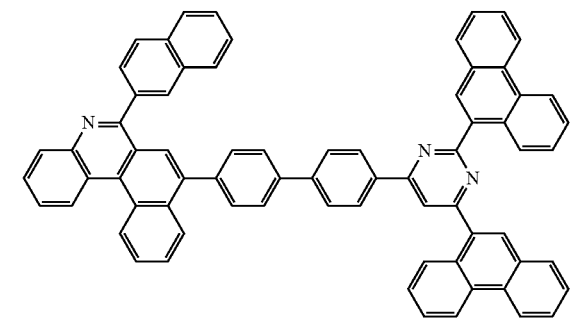
582
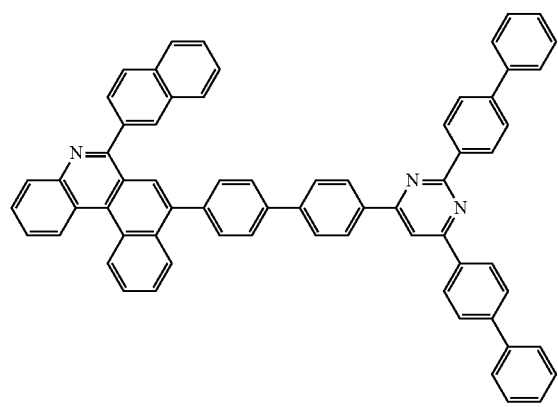
583
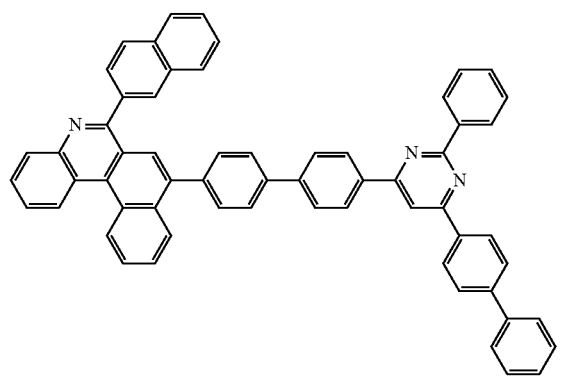
584
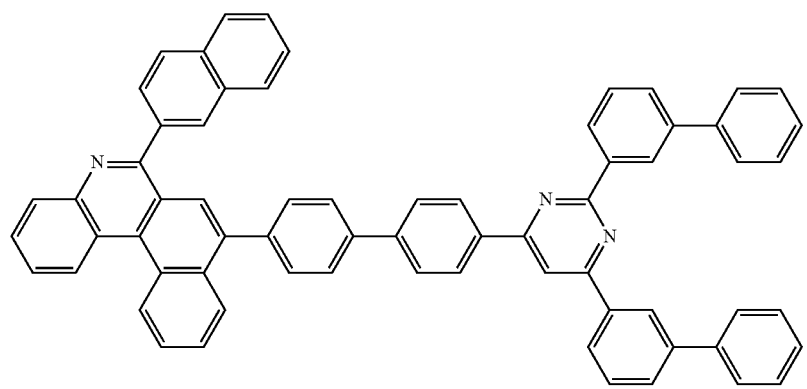

585
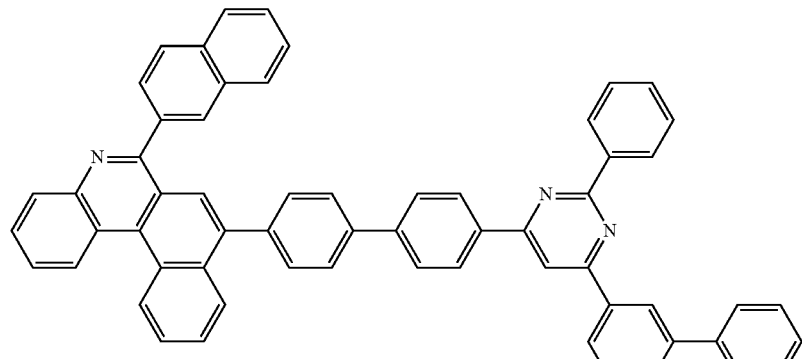
586 587
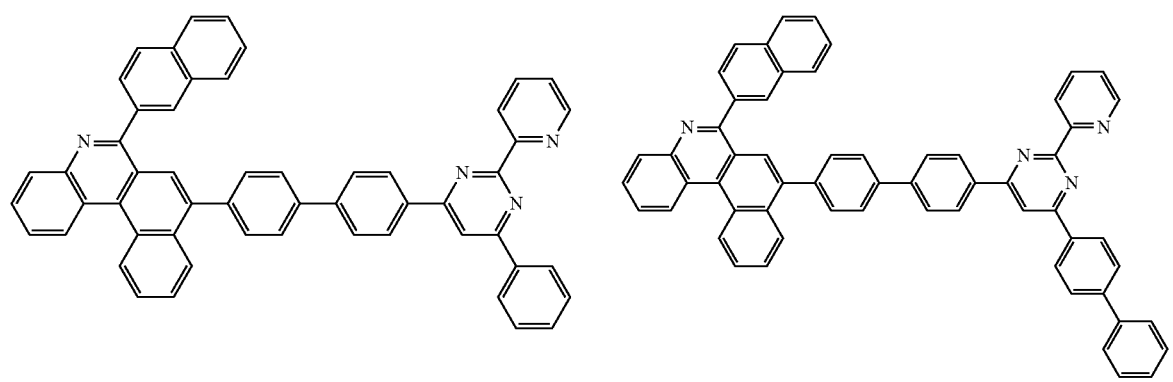
588
589 590
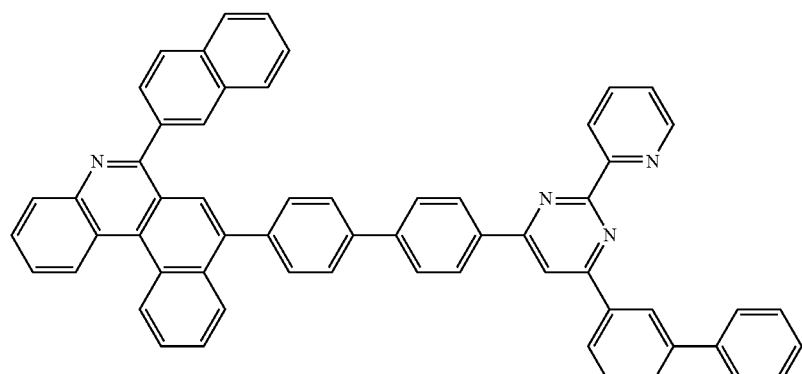
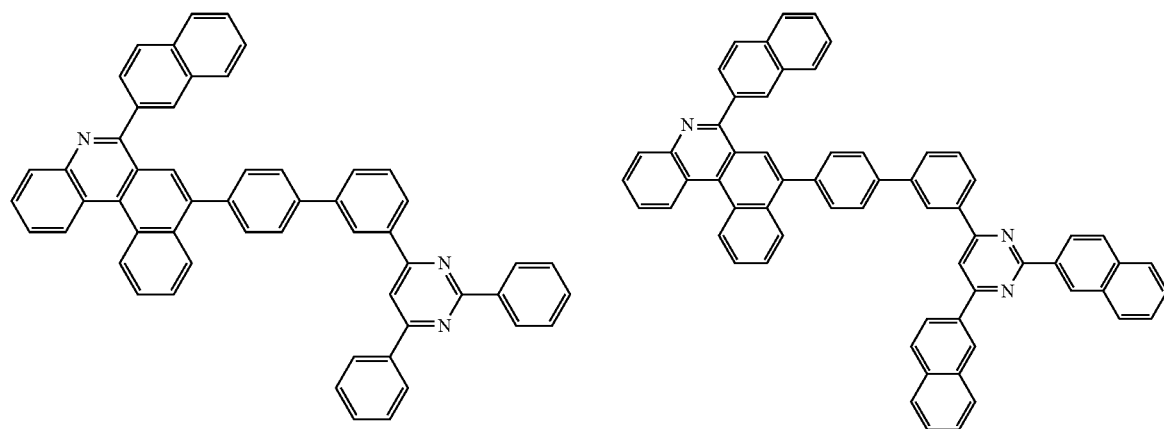

-continued
591
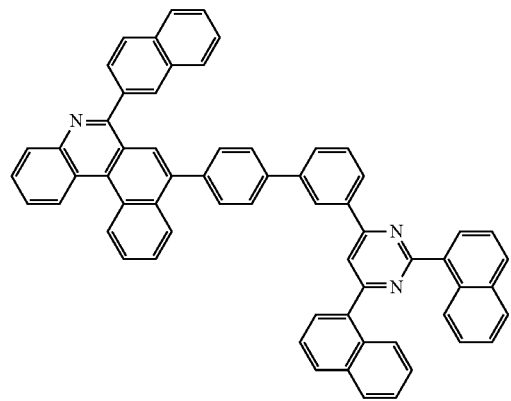
592
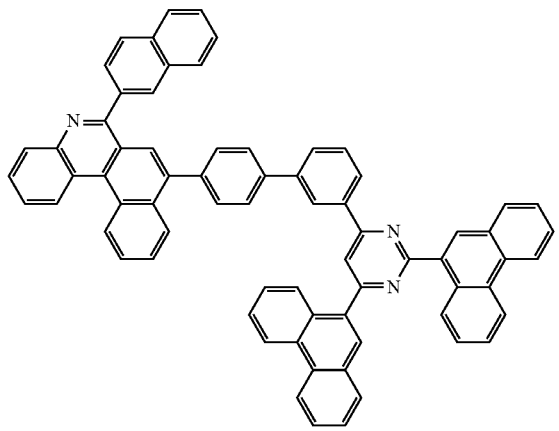
593
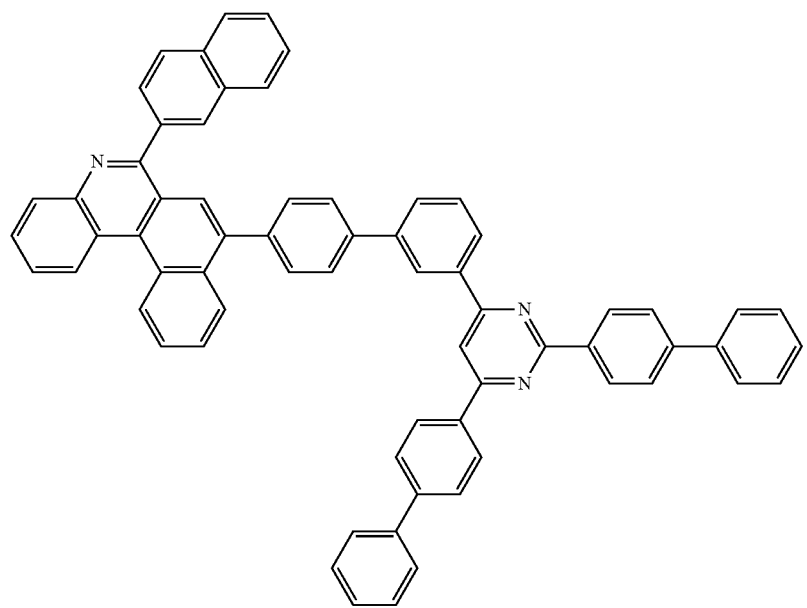
594
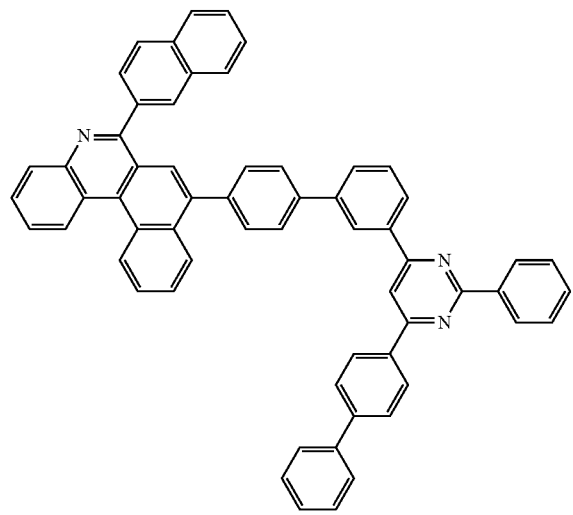
595
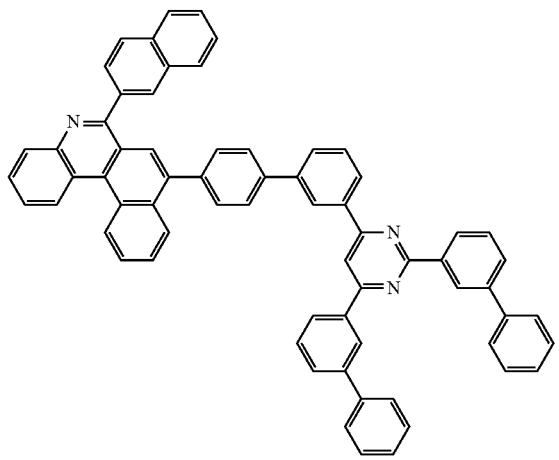

-continued
596
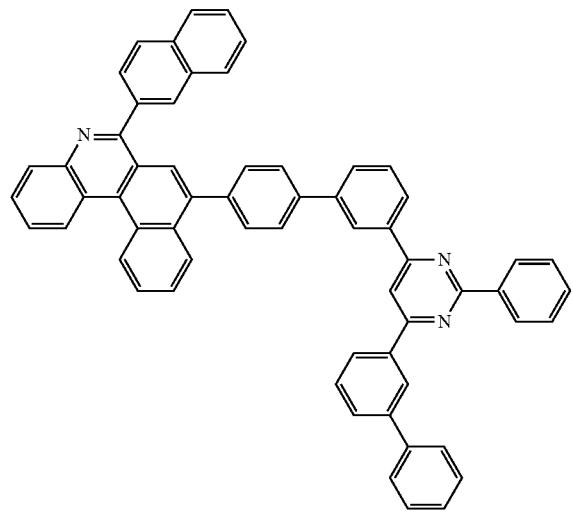
597
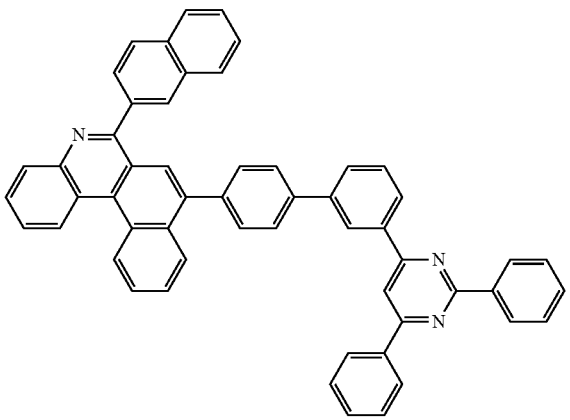
598
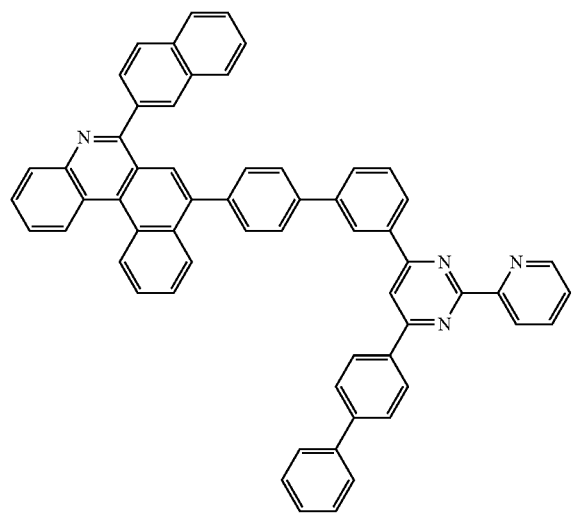
599
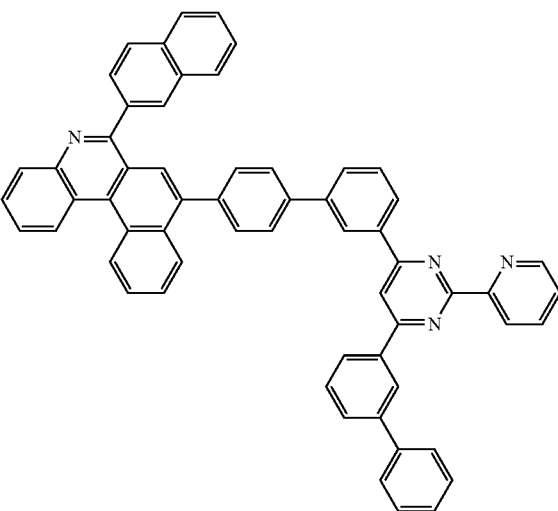
600
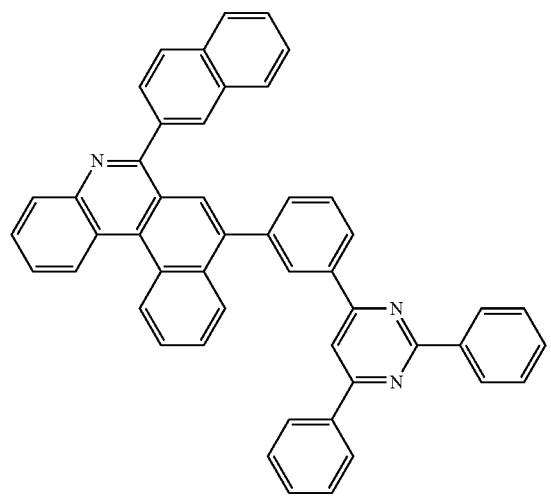
601
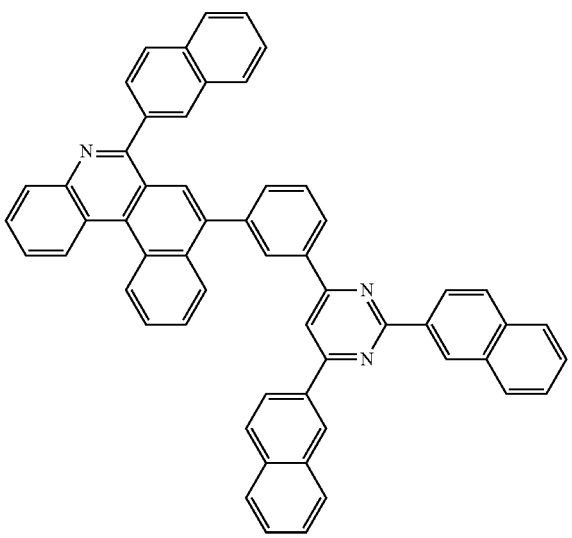

602
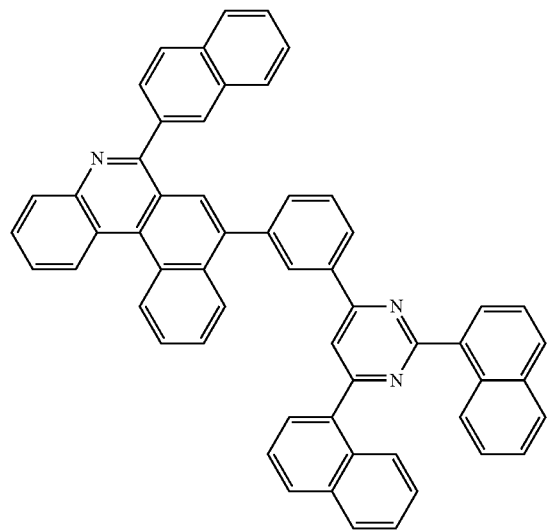
603
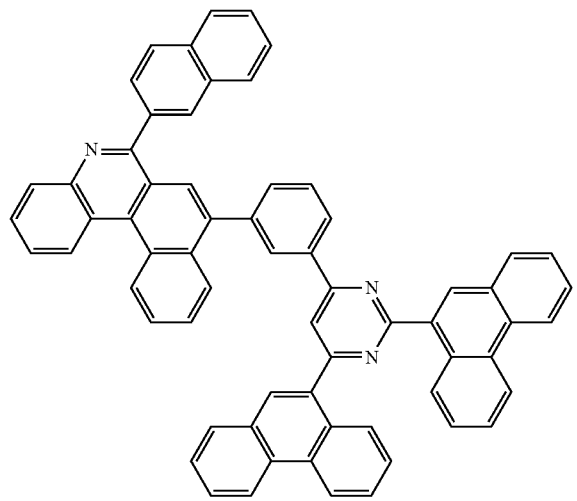
604
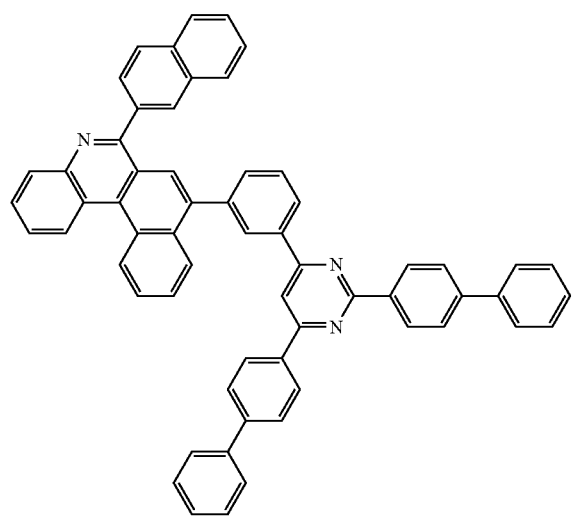
605
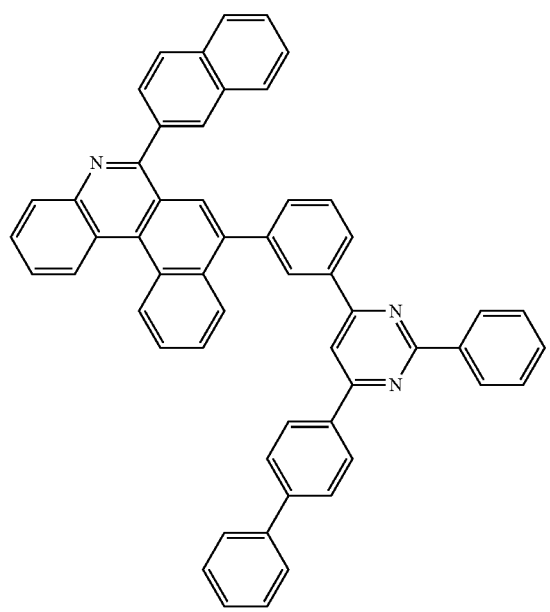

-continued
606
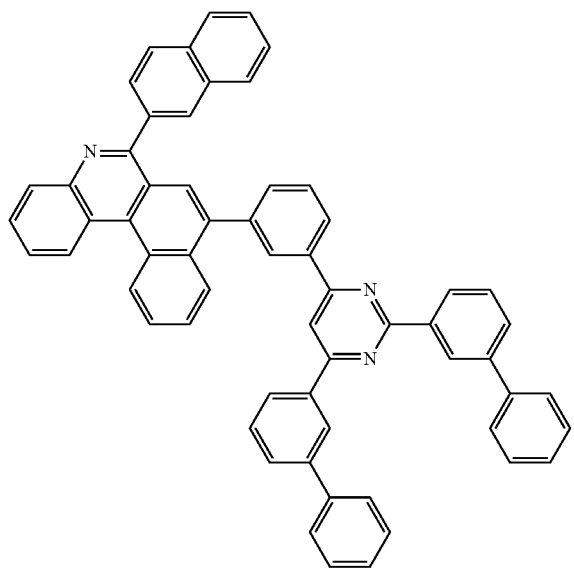
607
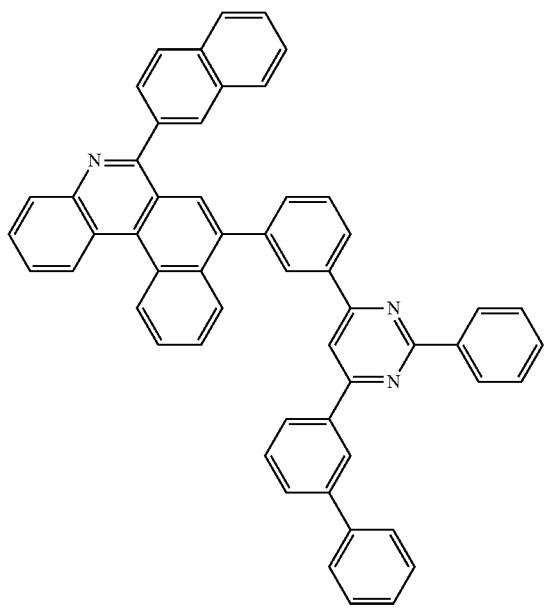
608
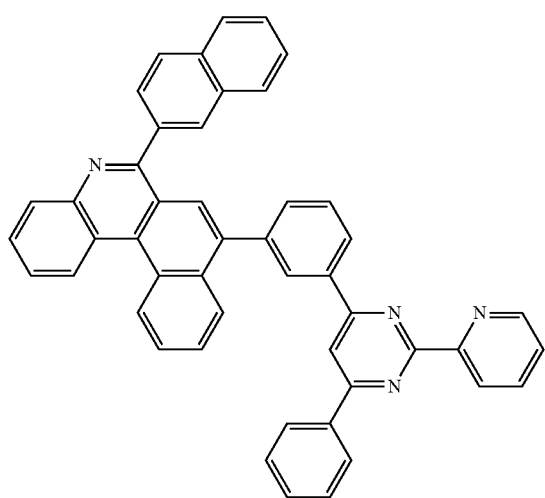

-continued
261
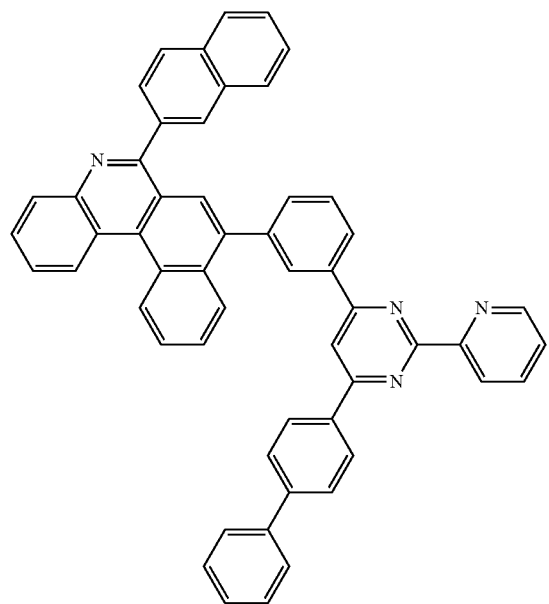
609
262
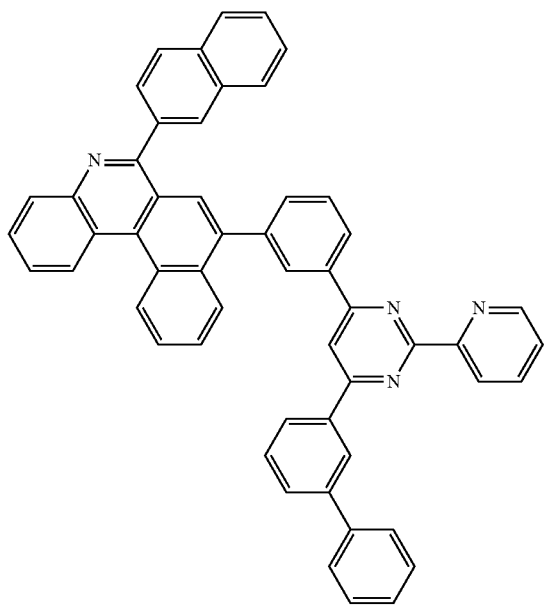
610
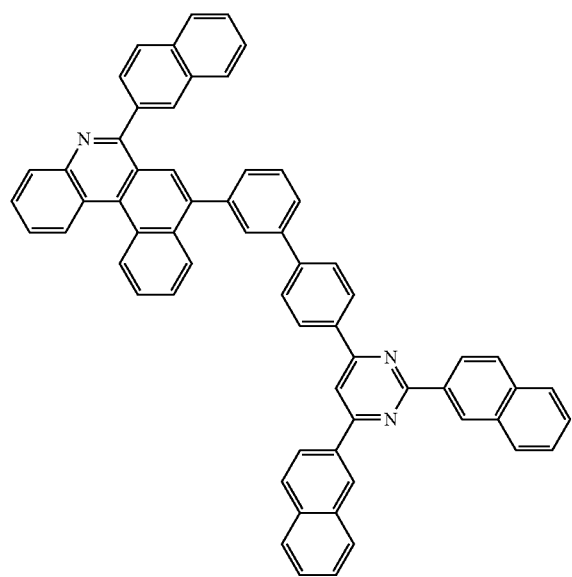
611
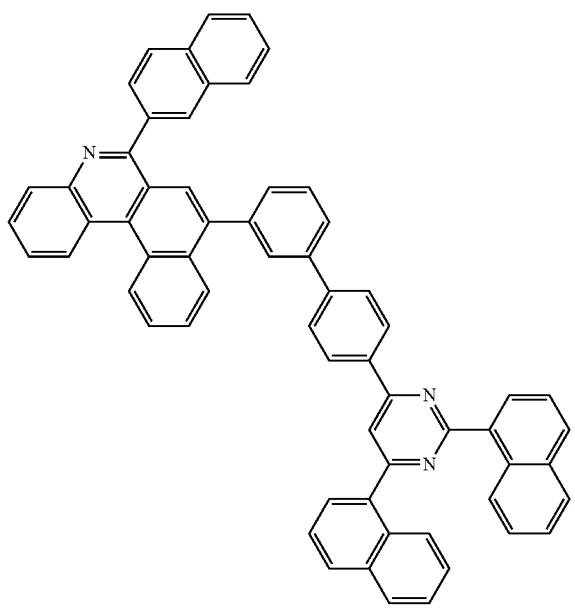
612

613
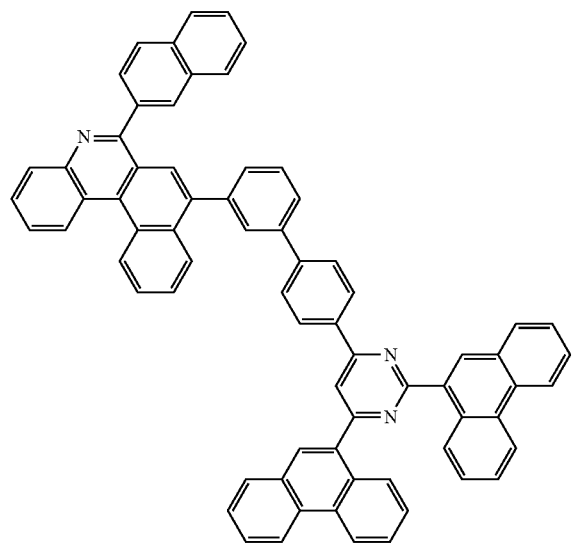
614
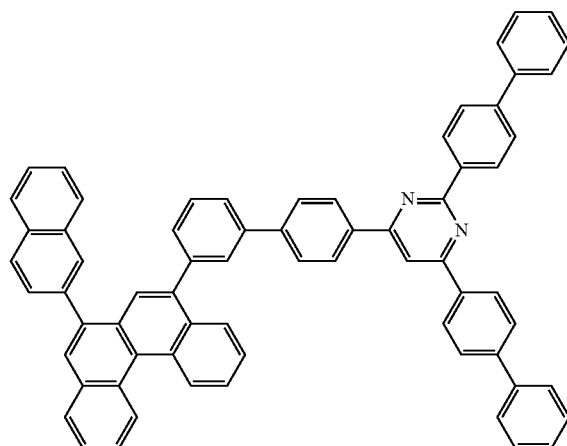
615
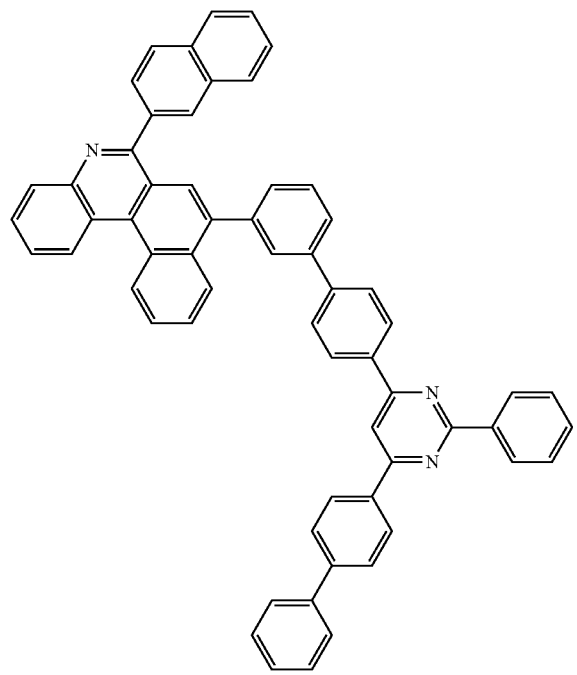
616
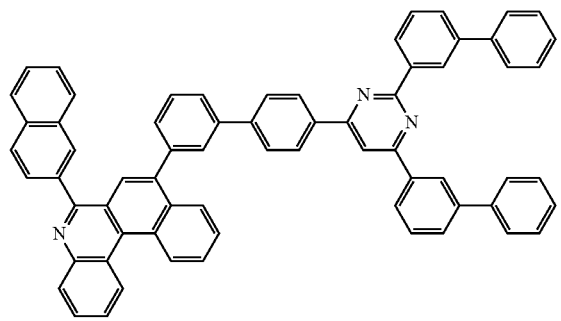

-continued
617
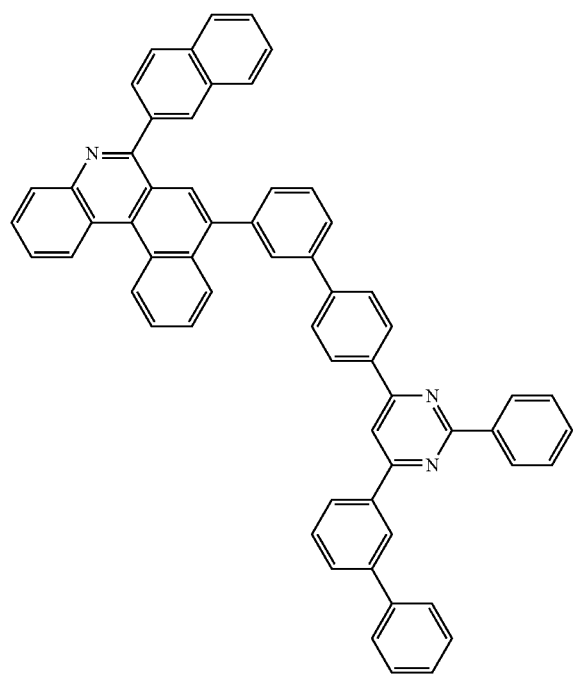
618
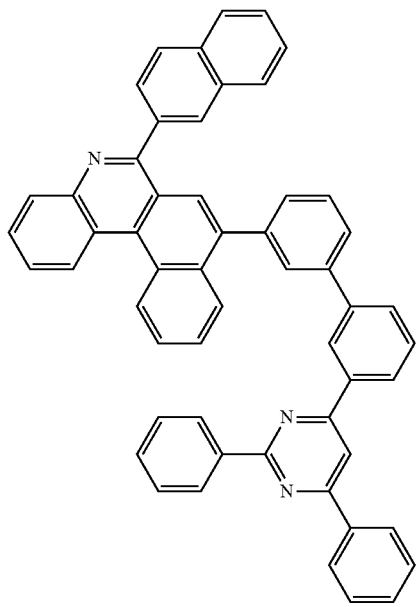
619
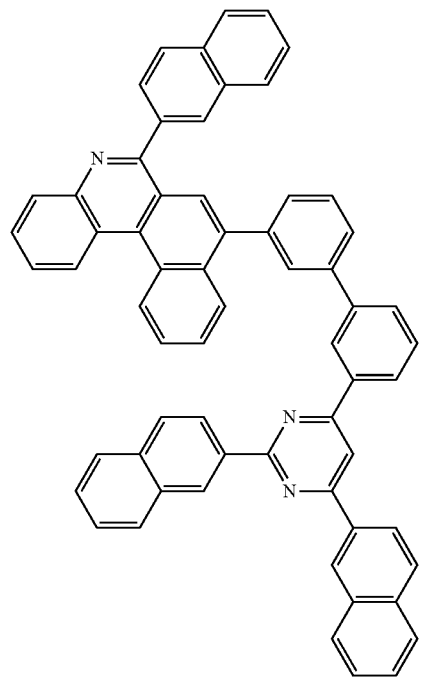
620
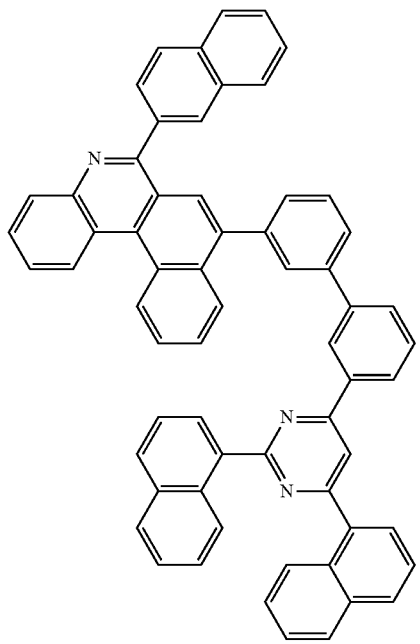

-continued
621
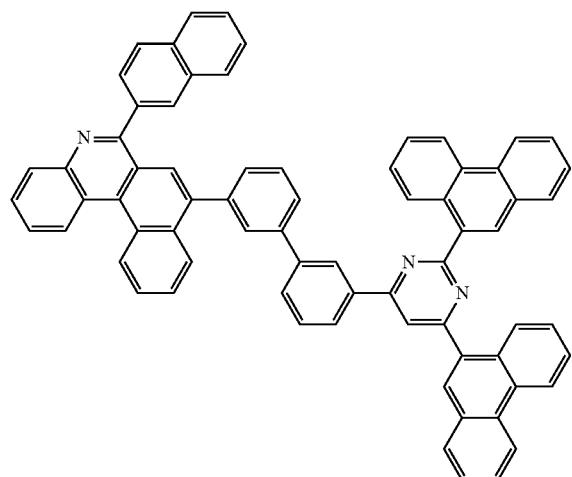
622
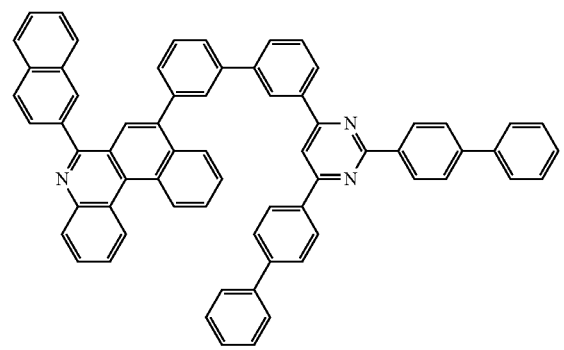
623
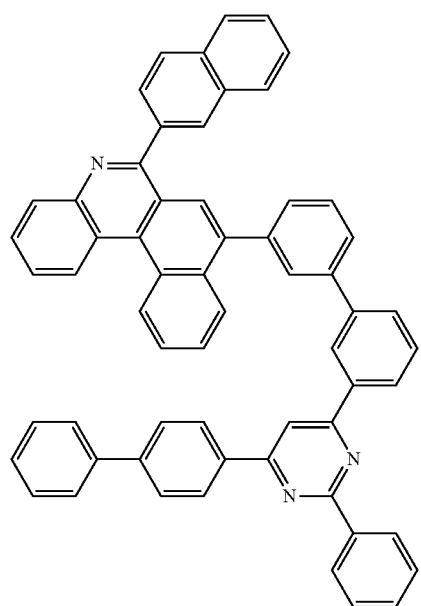
624
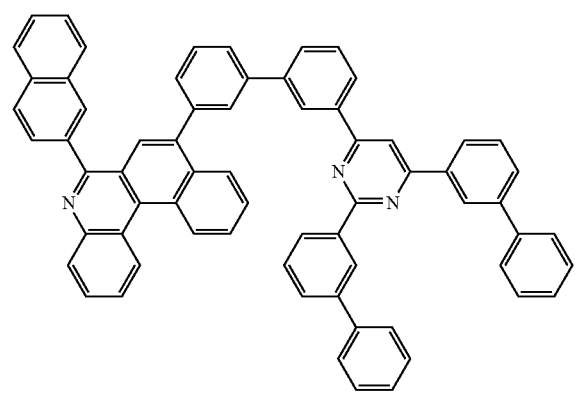

-continued
625
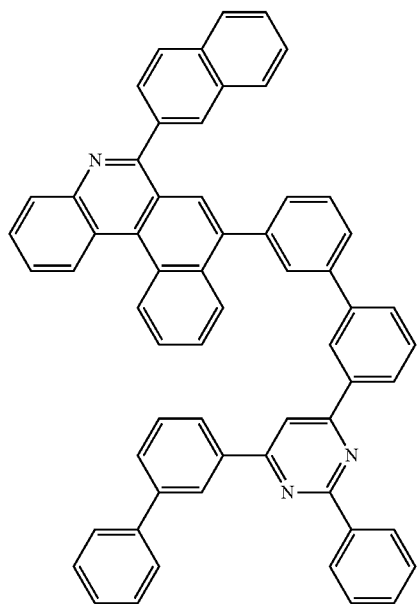
626
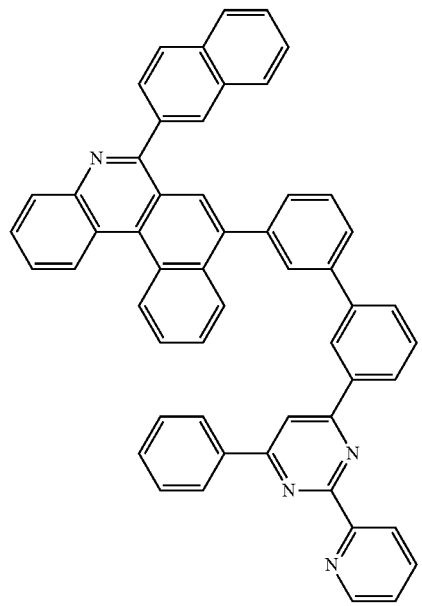
627
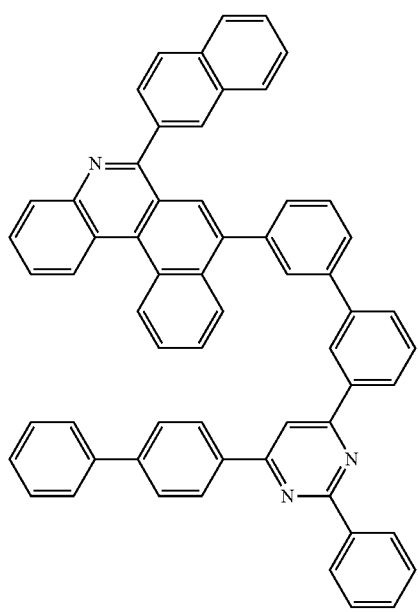
628
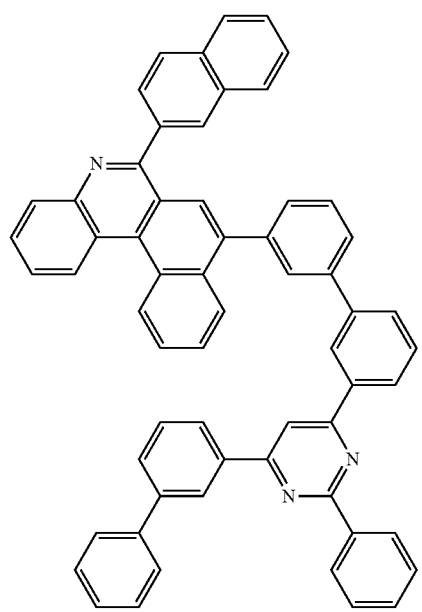
629
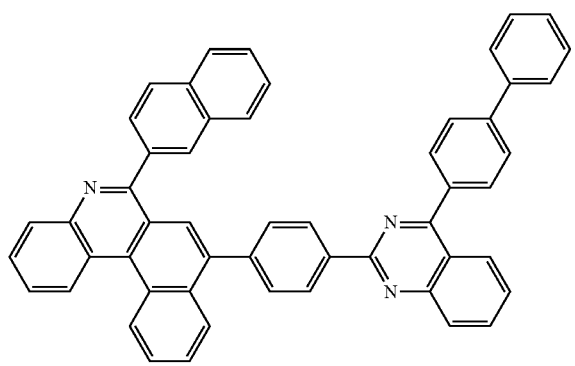
630
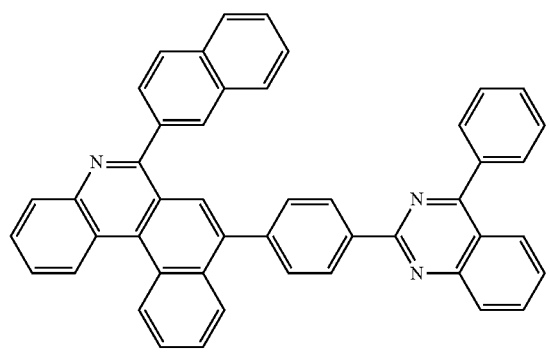

-continued
631
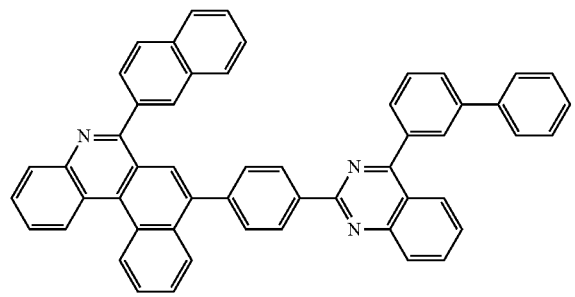
632
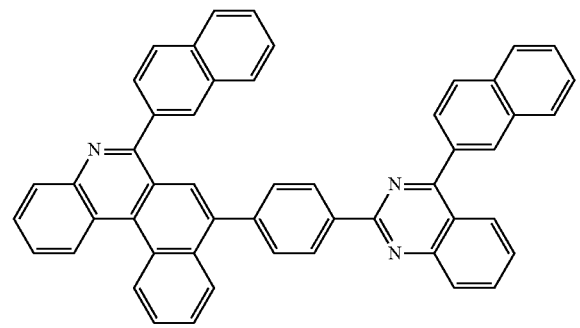
633
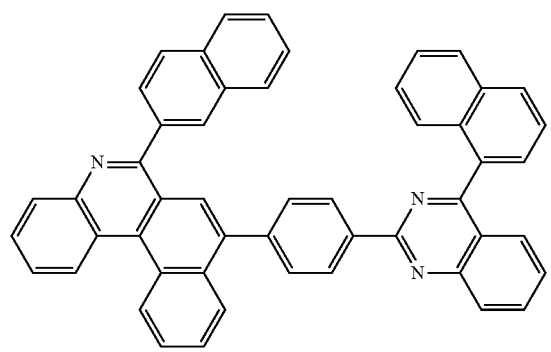
634
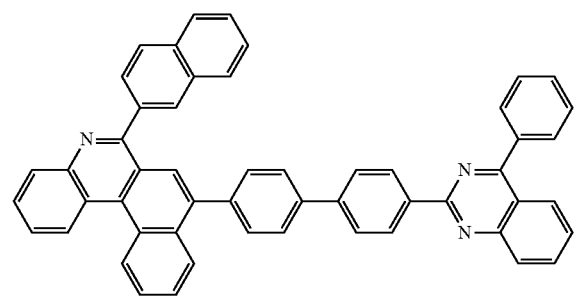
635
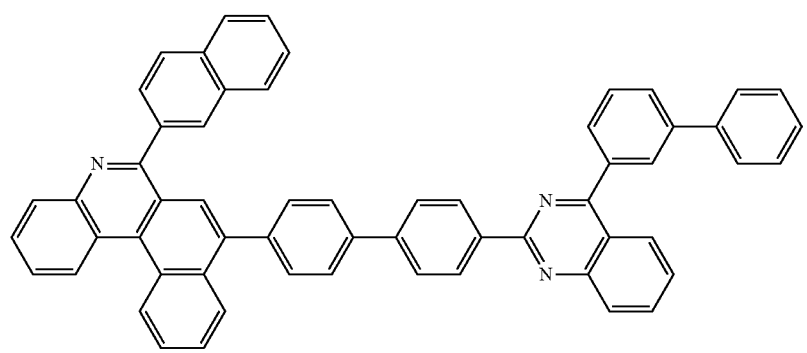
636
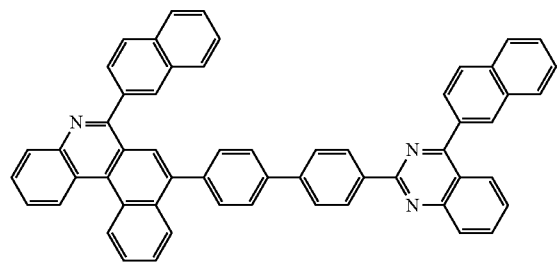
637
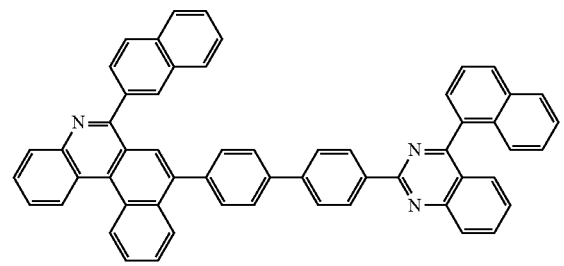

-continued
638
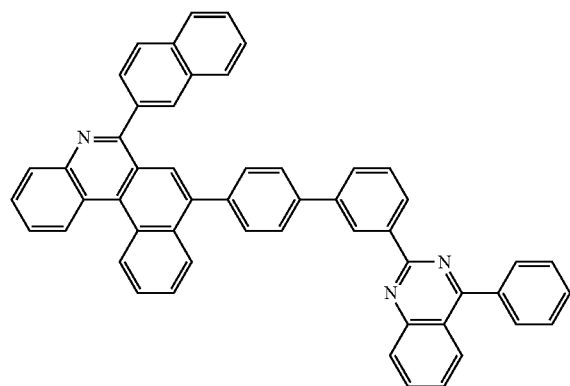
639
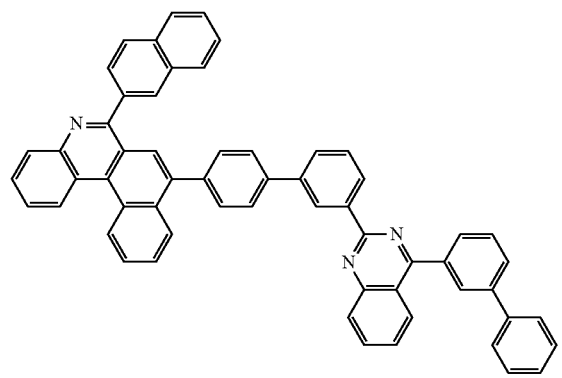
640
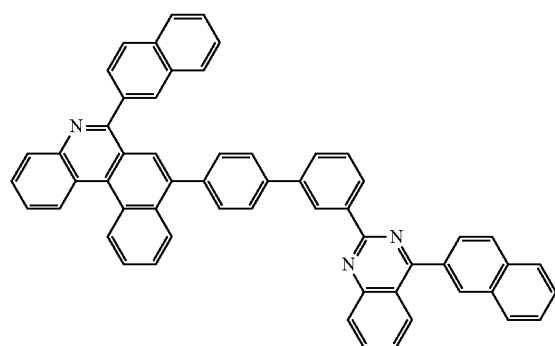
641
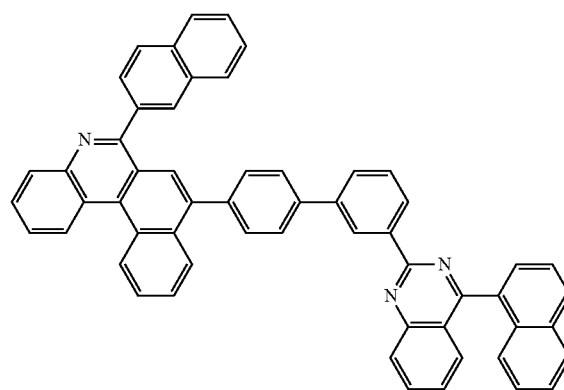
642
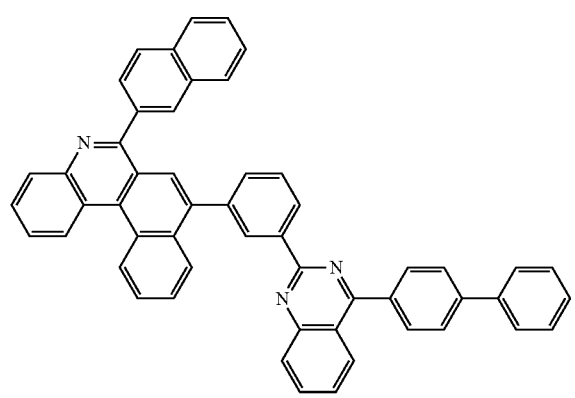
643
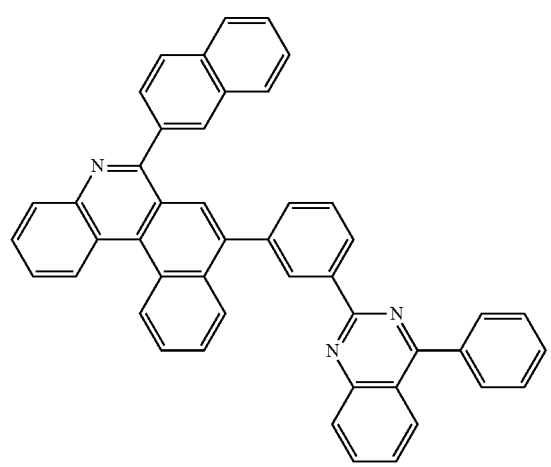

644
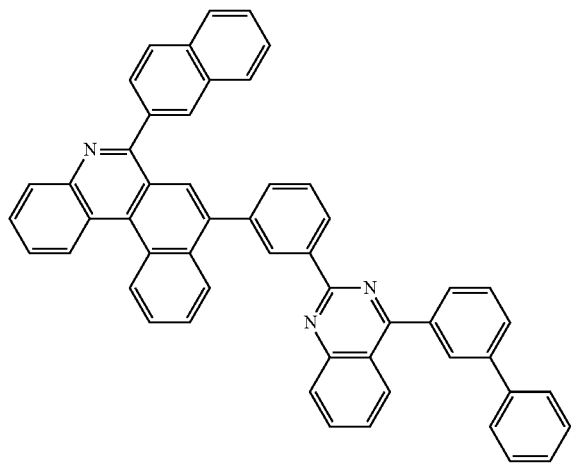
645
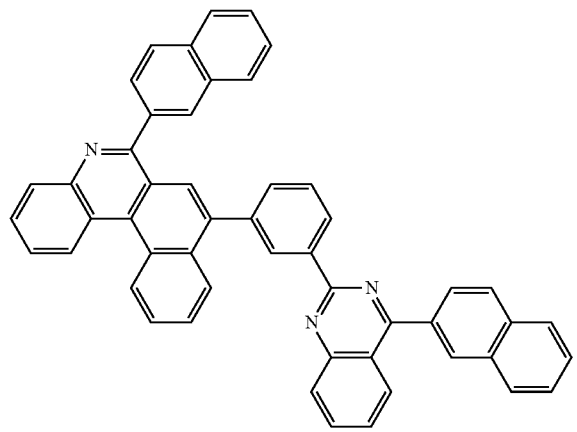
646
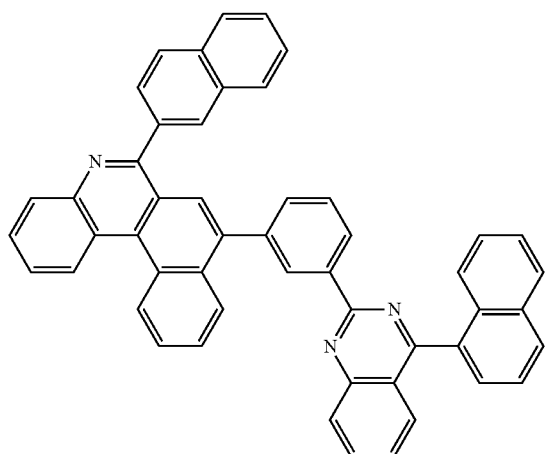
647
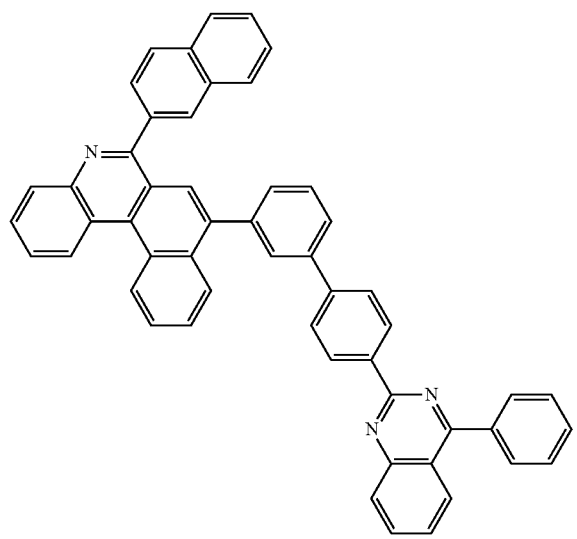
648
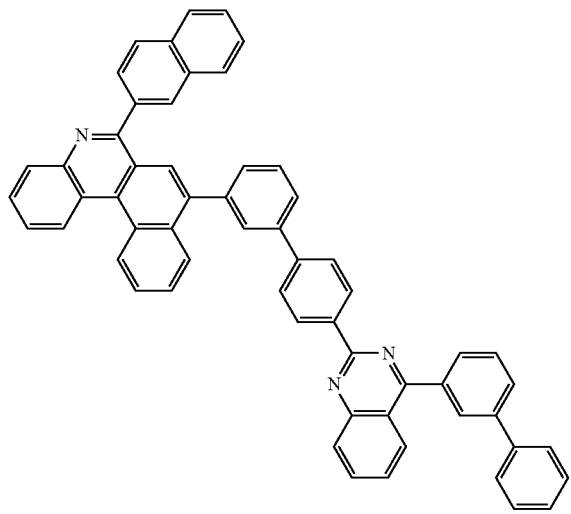
649
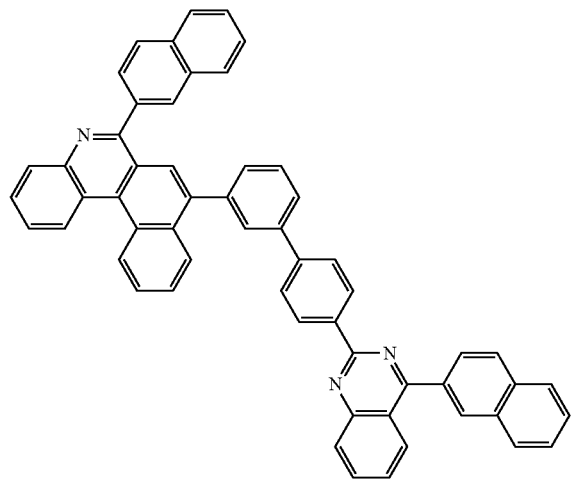

-continued
650
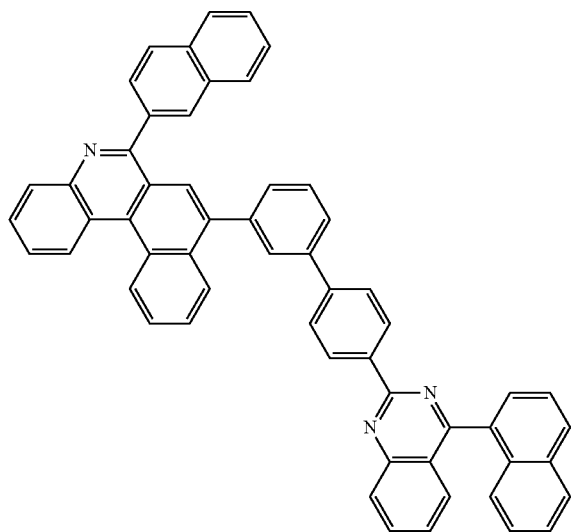
651
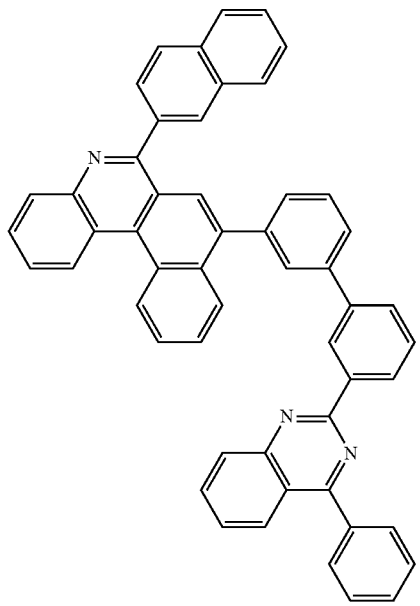
652
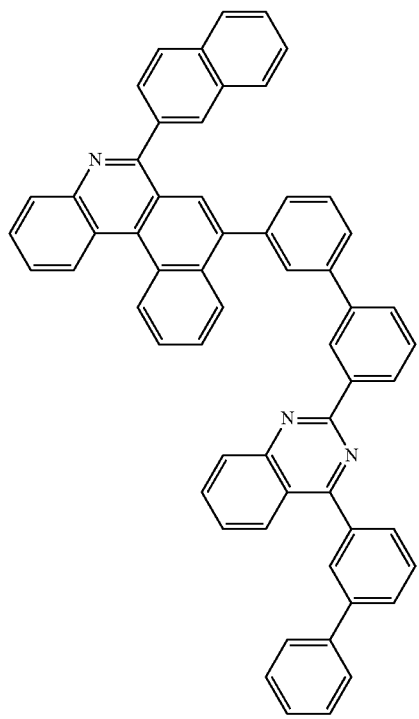
653
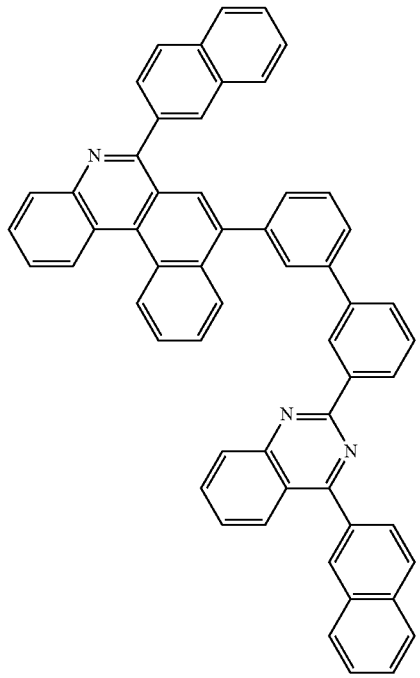

-continued
654
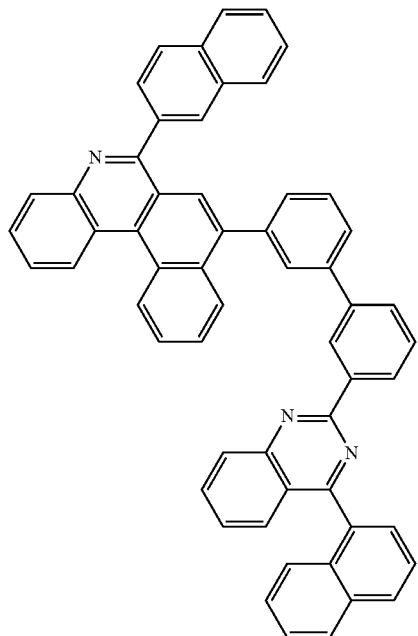
655
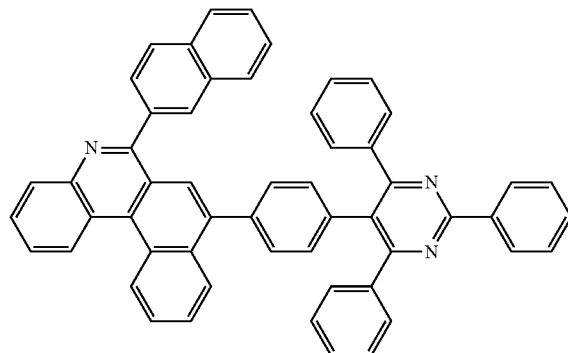
656
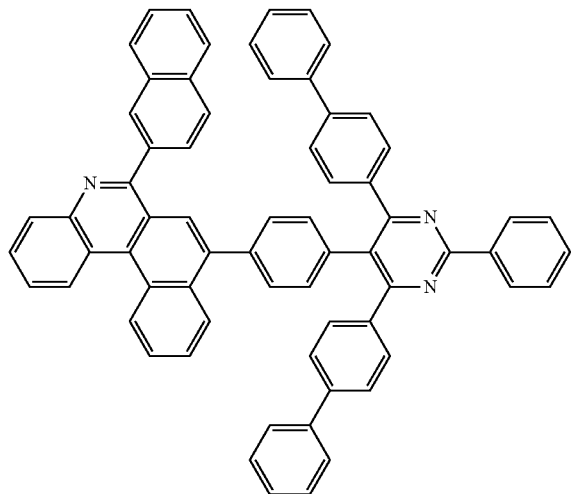
657
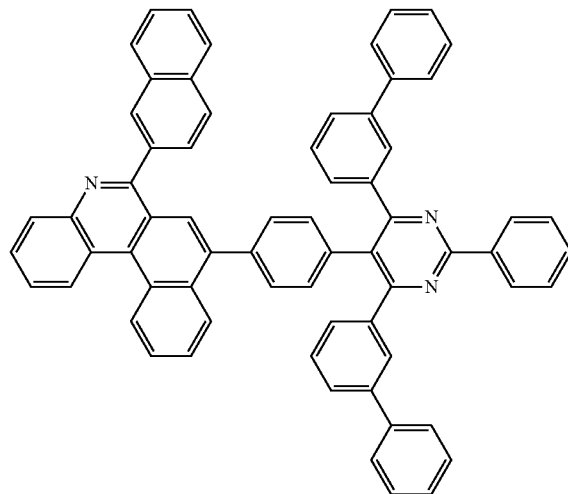
658
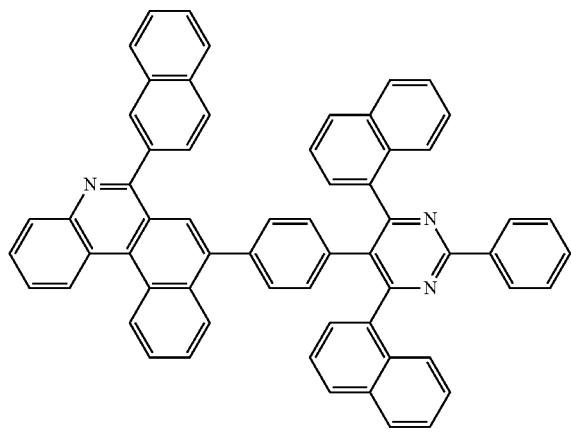
659
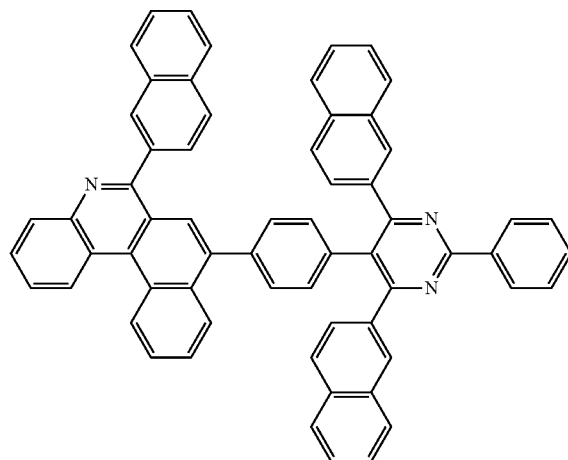

660
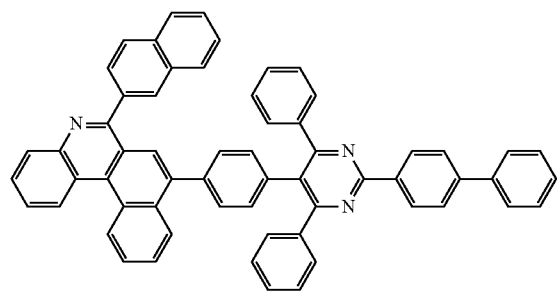
661
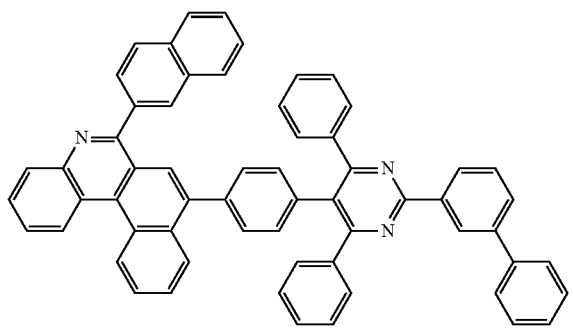
662
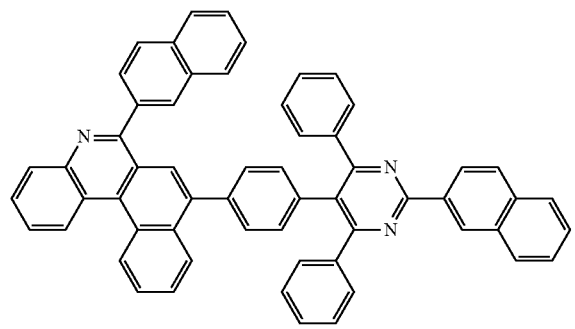
663
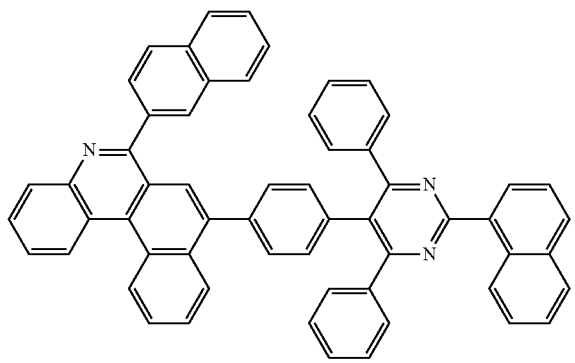
664
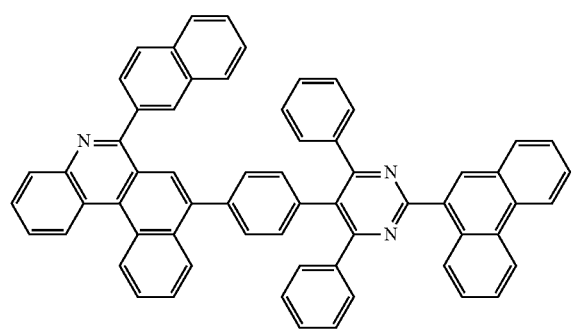
665
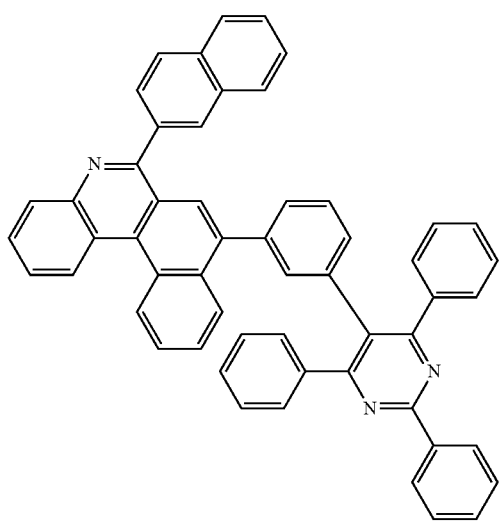

666
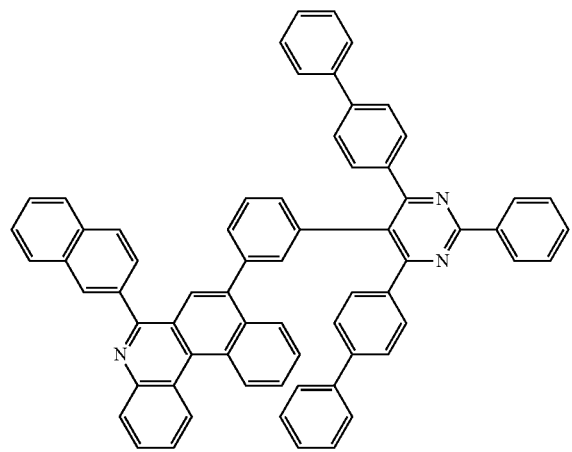
667
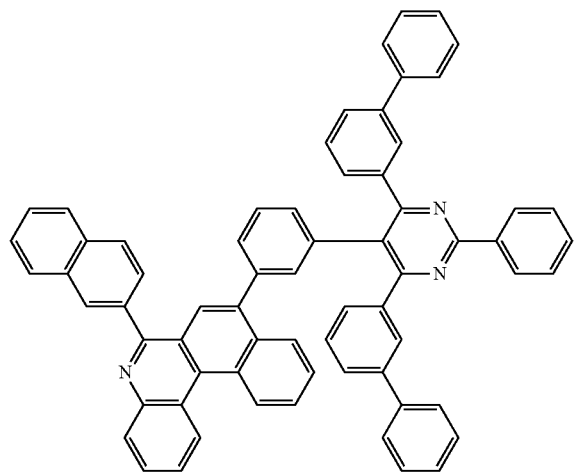
668
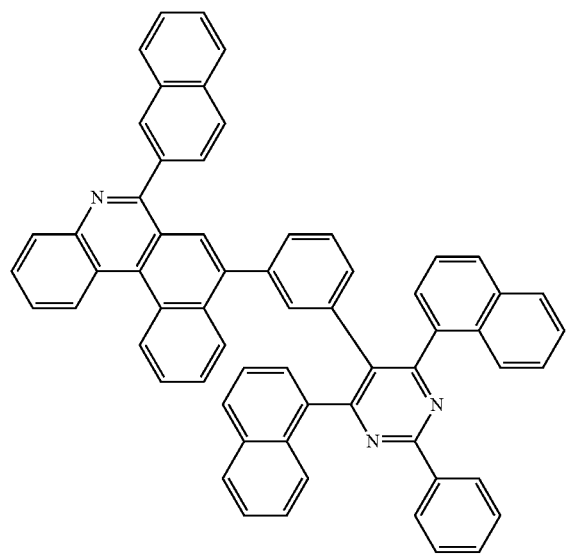
669
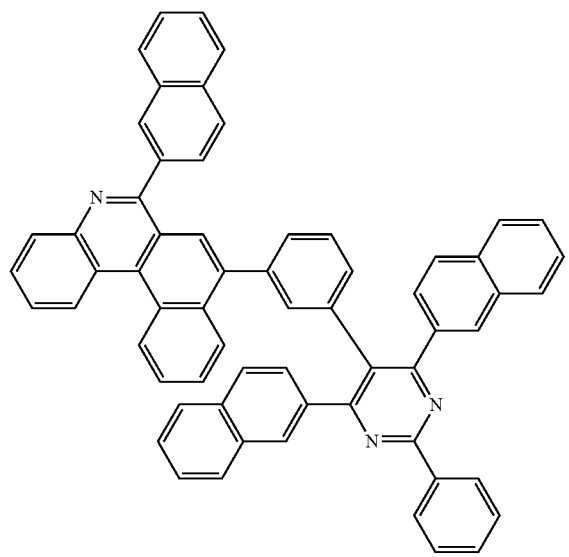

670
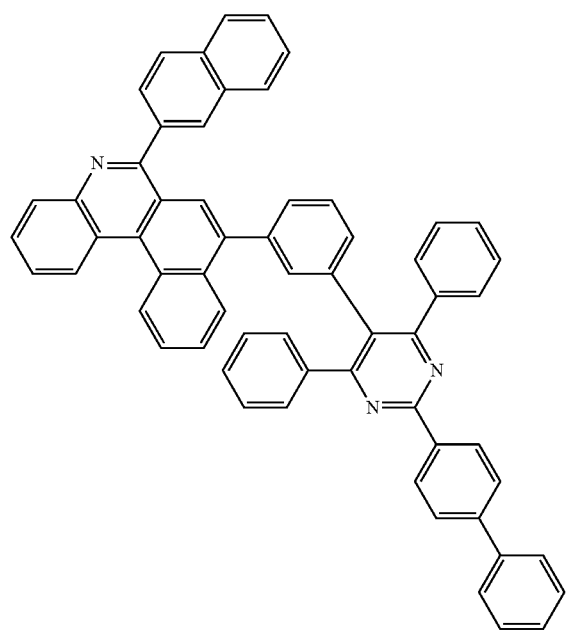
671
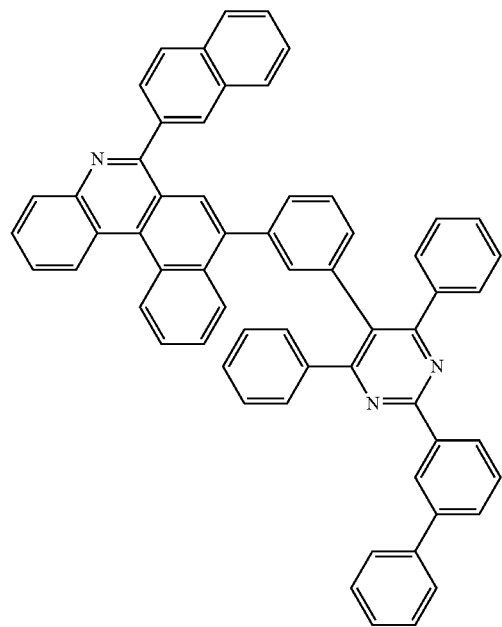
672
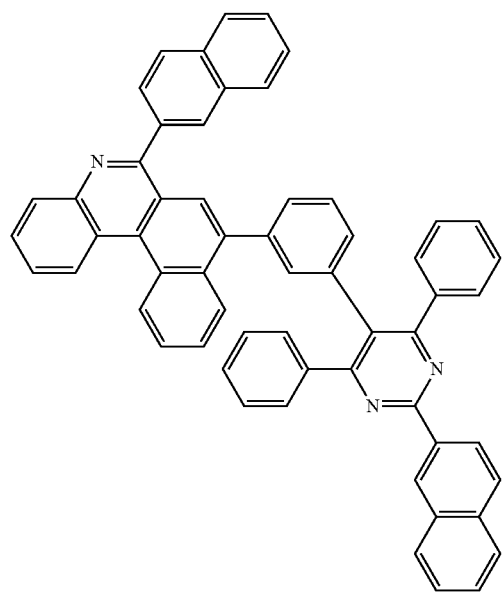
673
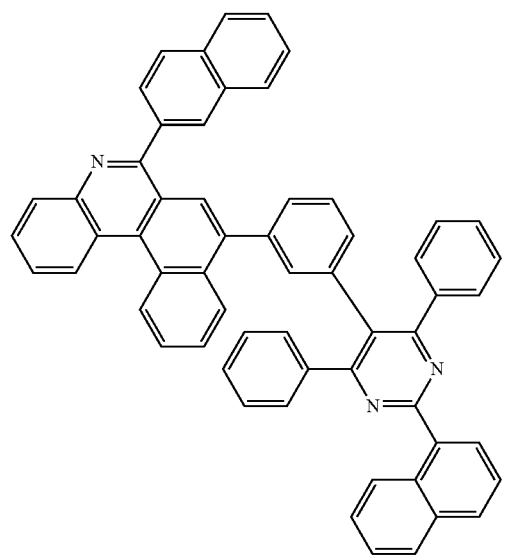

-continued
674
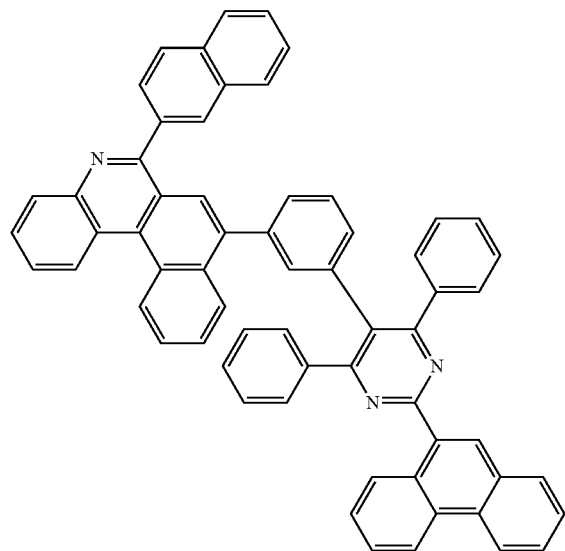
675
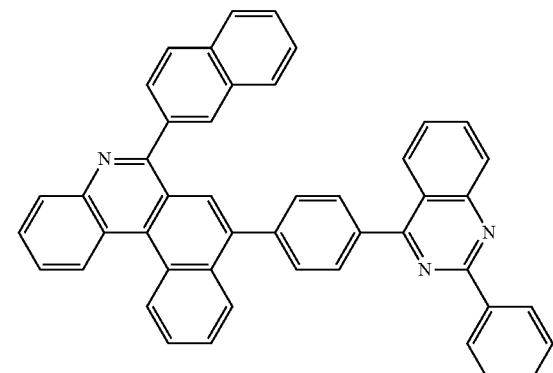
676
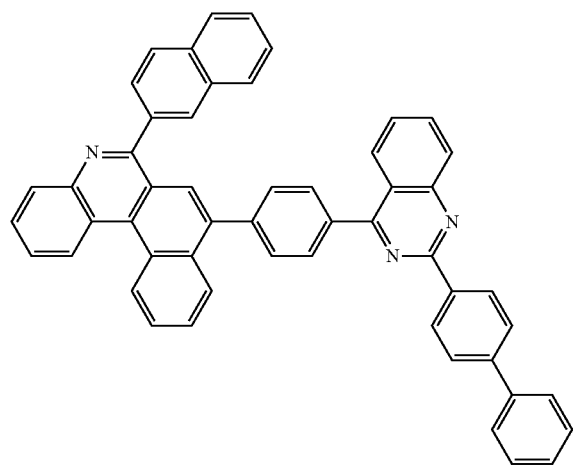
677
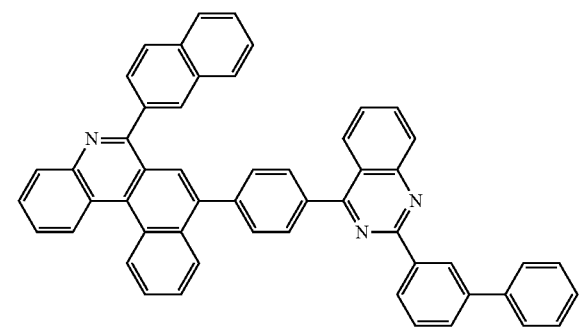
678
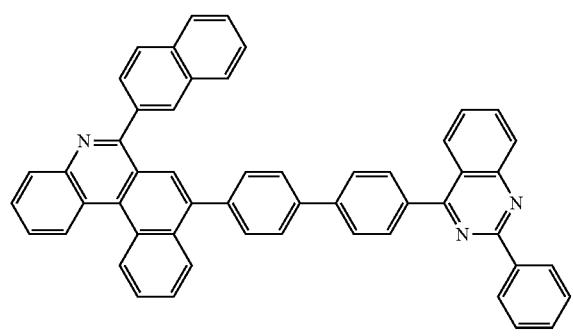
679
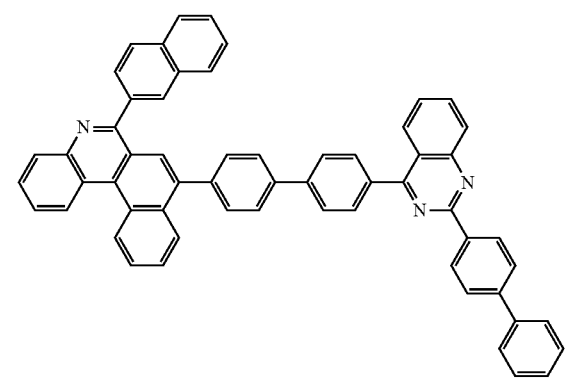

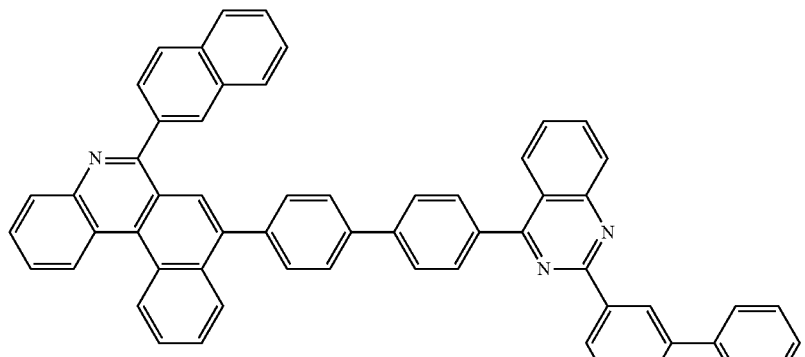
680
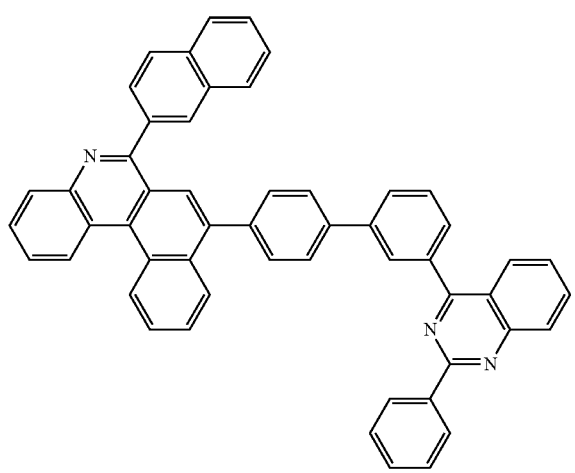
681
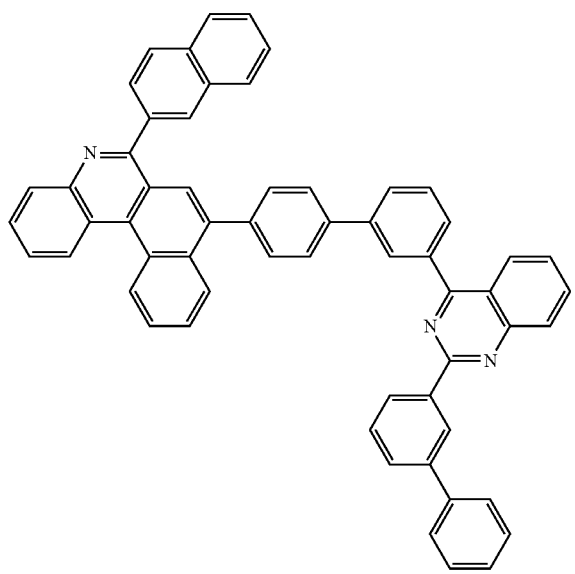
683
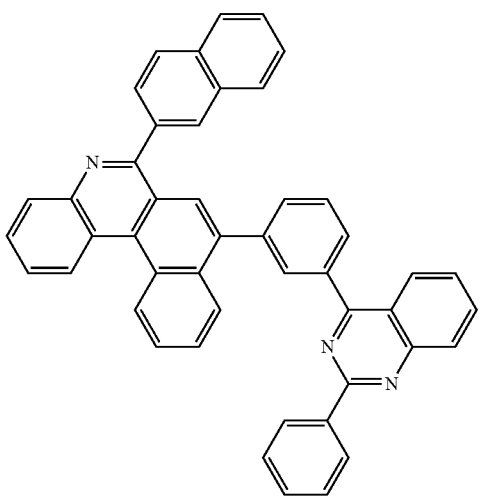

291 292
-continued
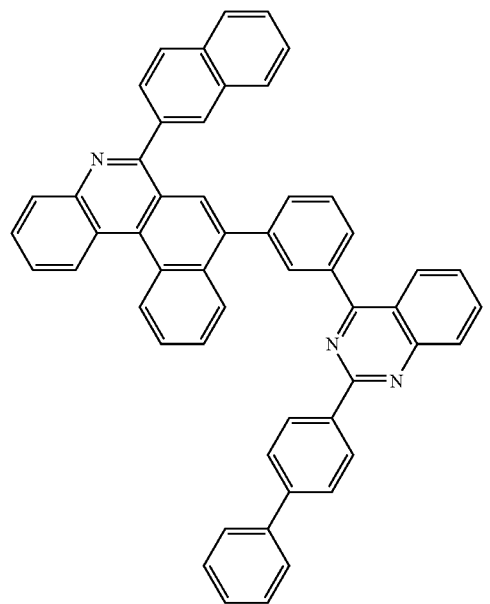
685
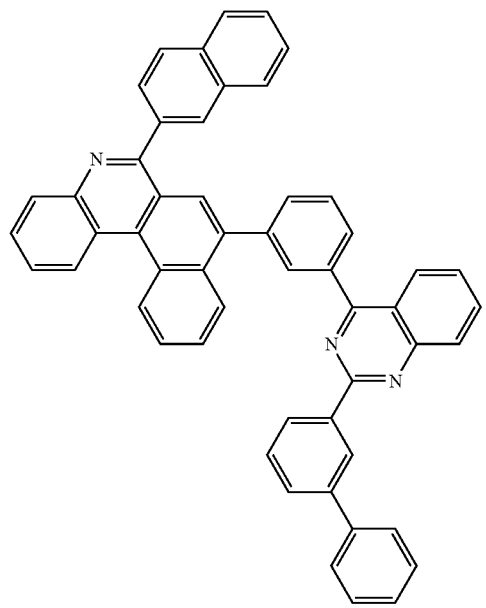
686
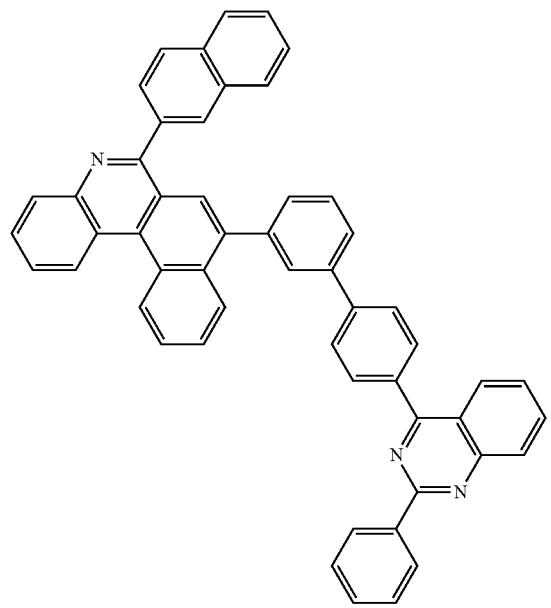
687
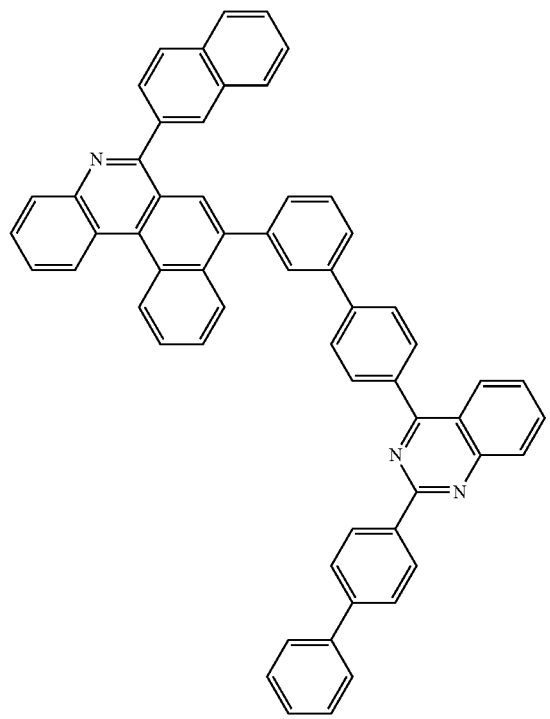
688

-continued
689
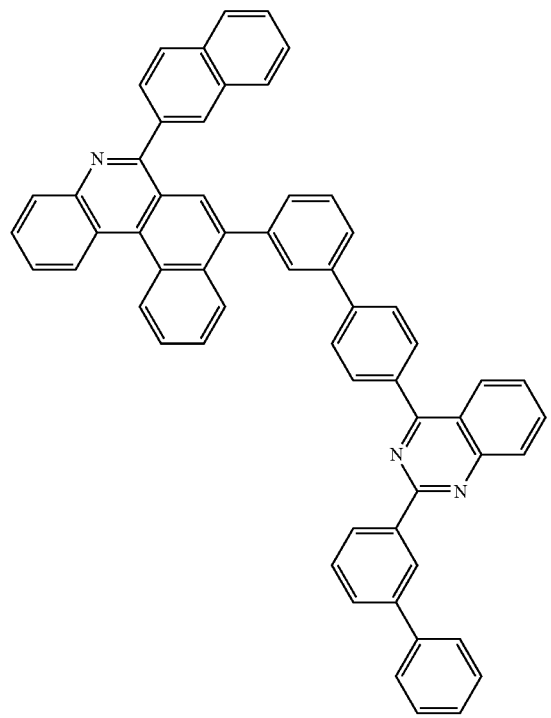
690
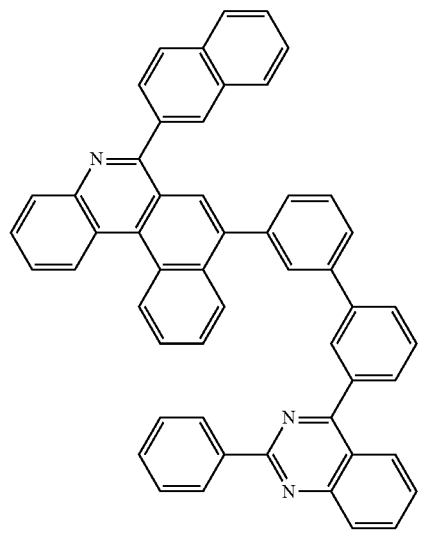
691
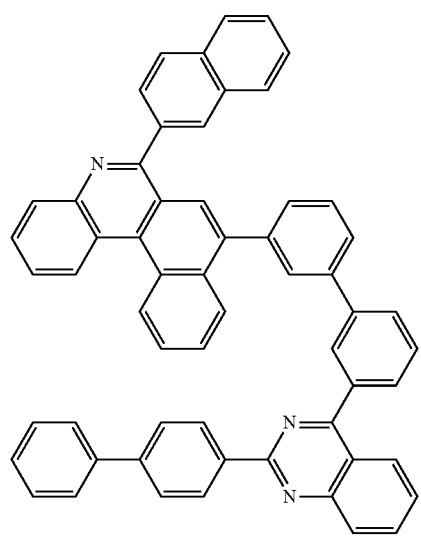
692
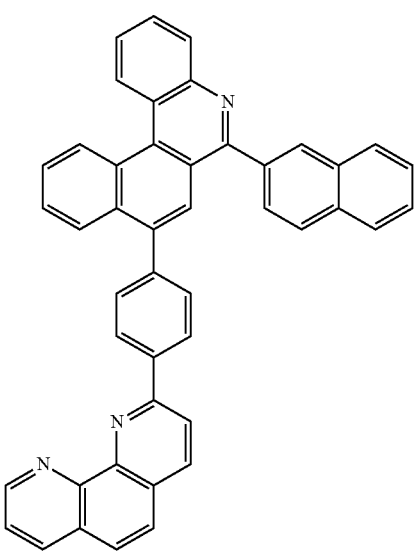

-continued
693
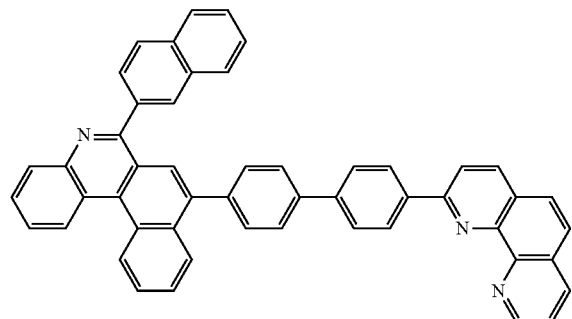
694
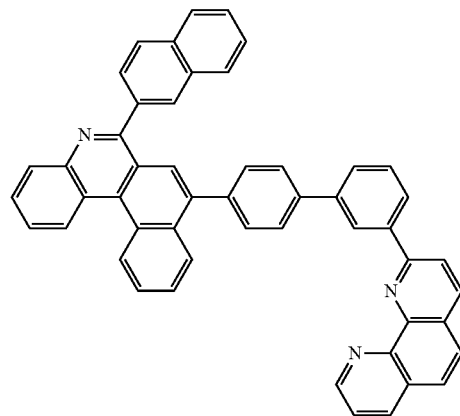
695
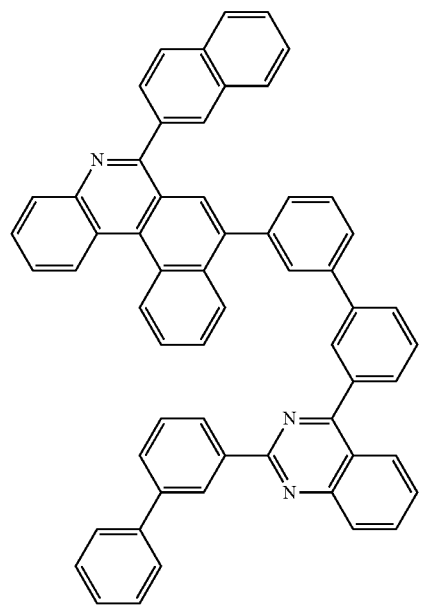
696
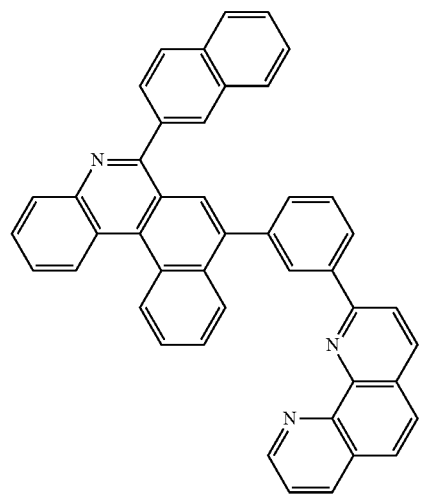
697
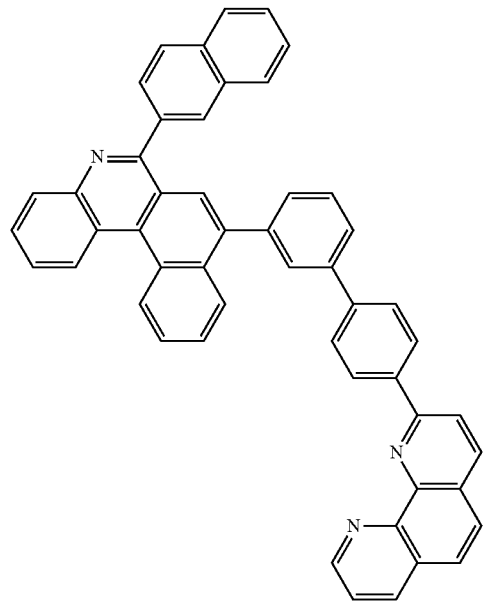
698
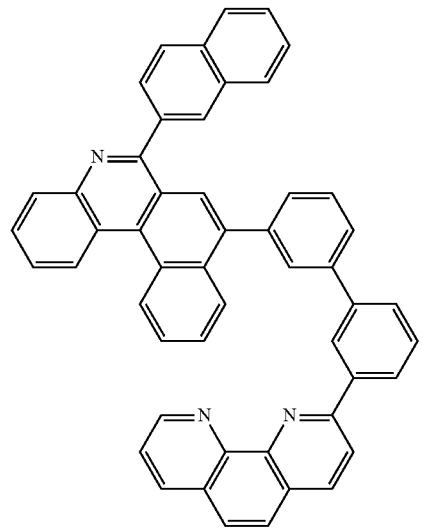

-continued
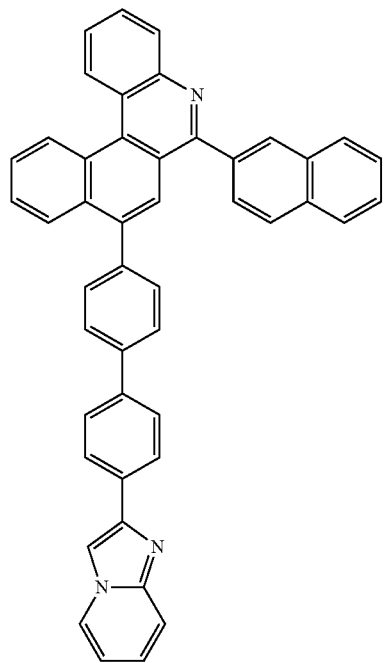
699
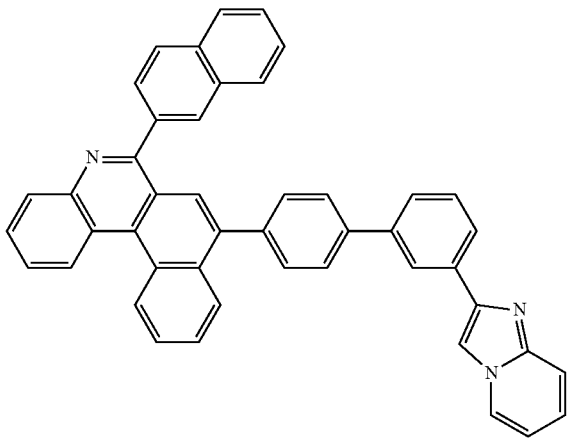
700
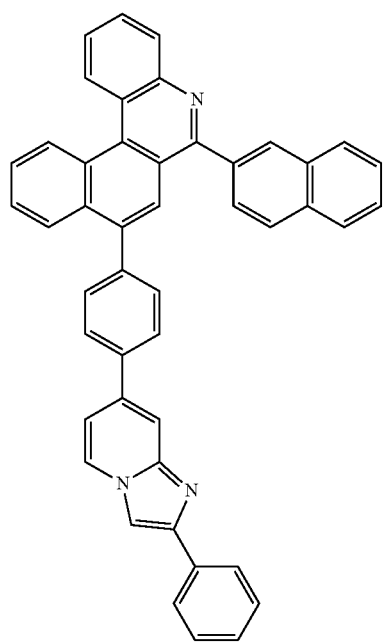
701
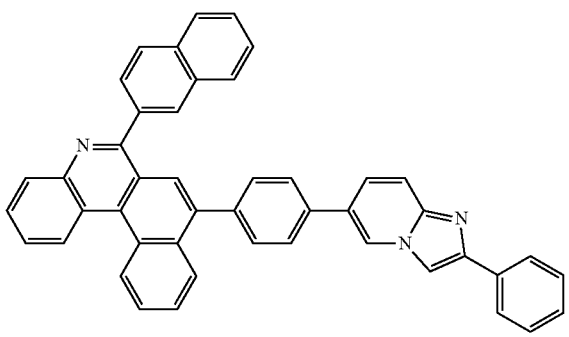
702

-continued
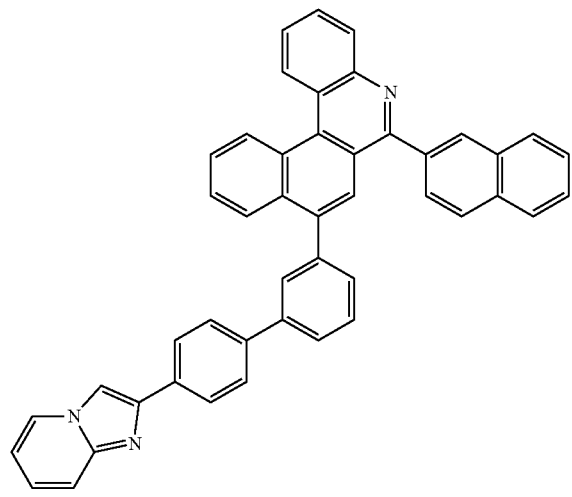
703
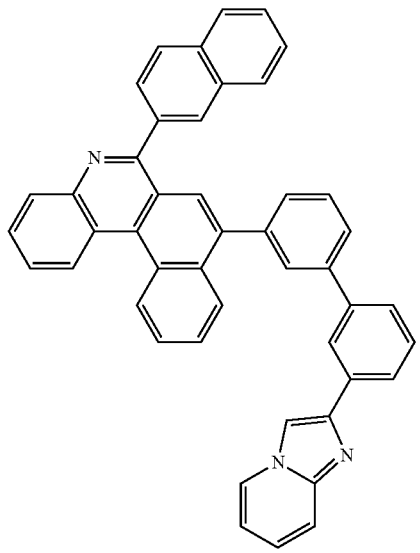
704
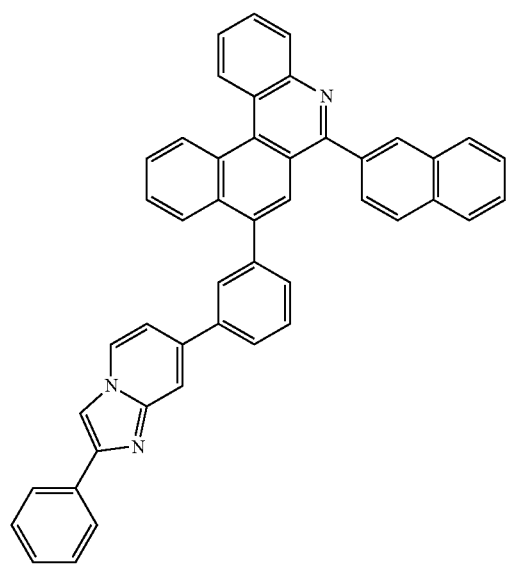
705
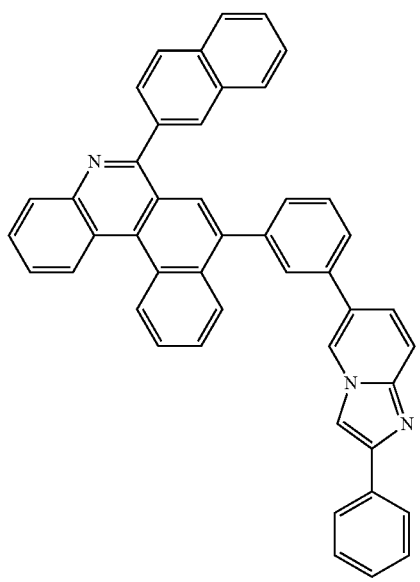
706
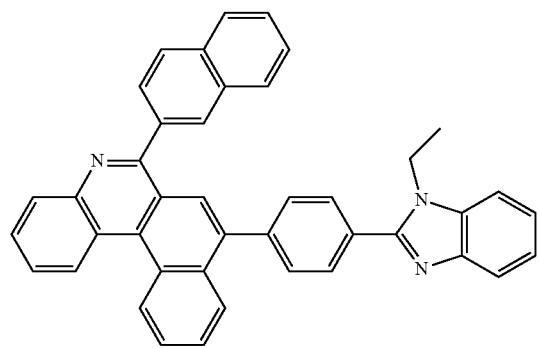
707
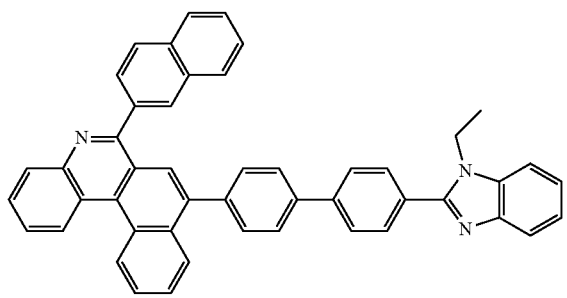
708

-continued
709
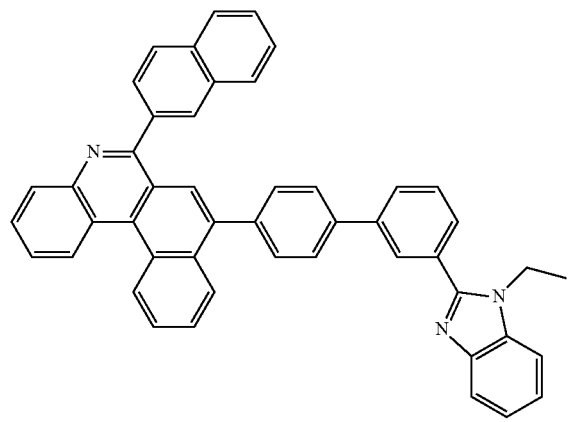
710
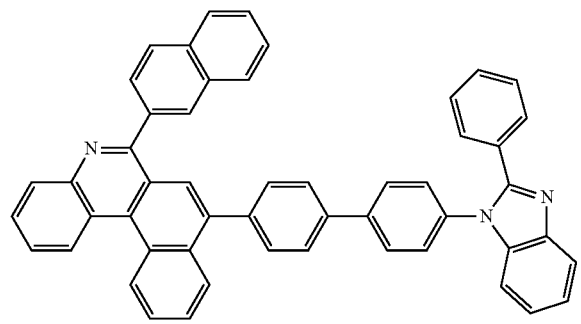
711
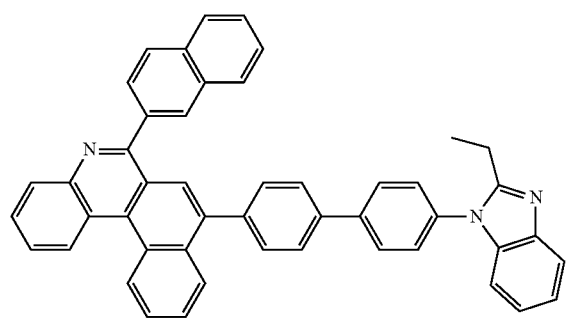
712
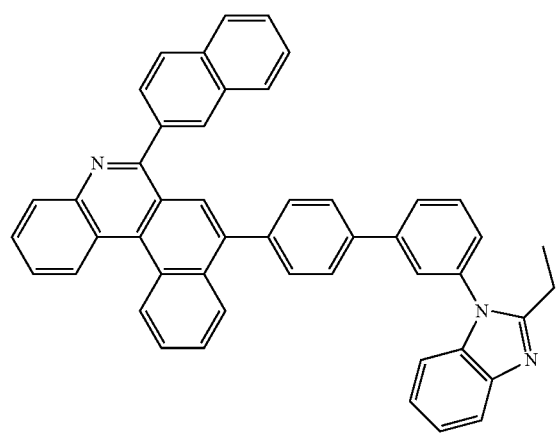
713
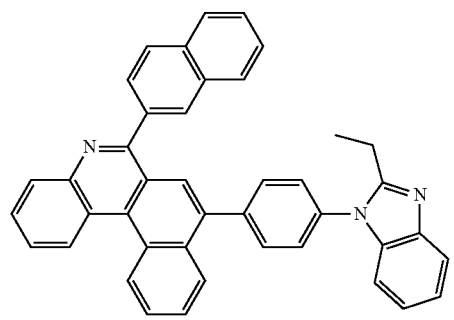
714
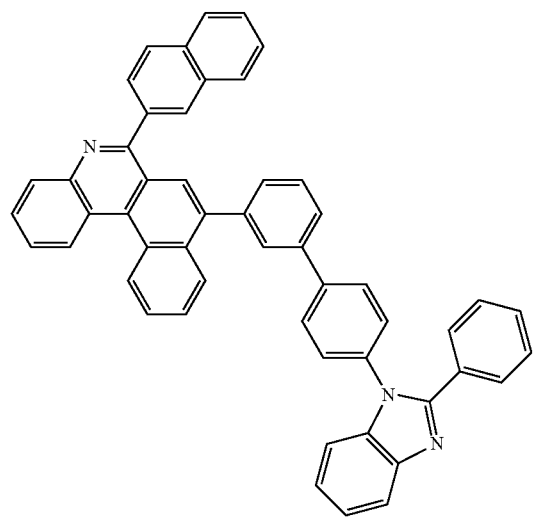

-continued
715
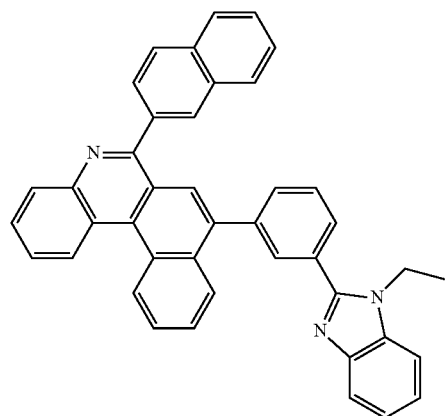
716
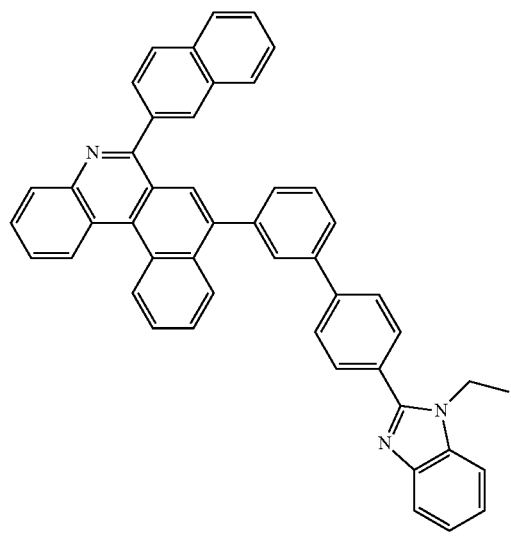
717
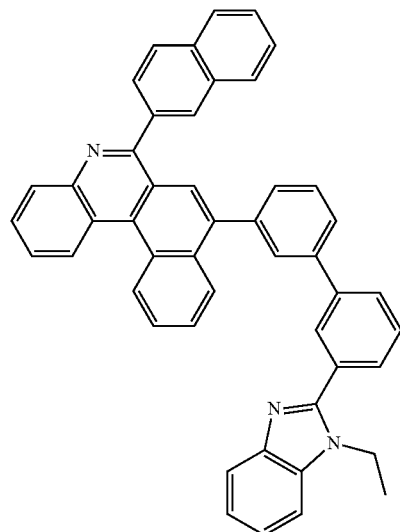
718
719
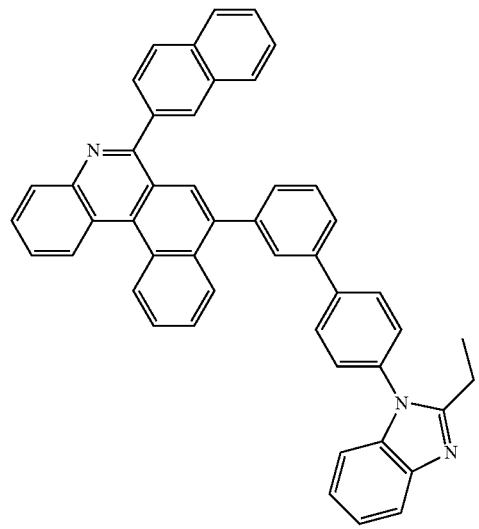
720
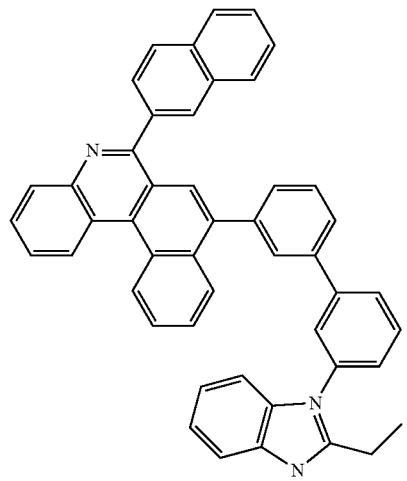

721
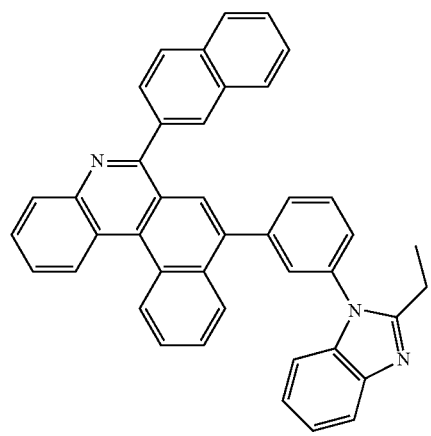
722
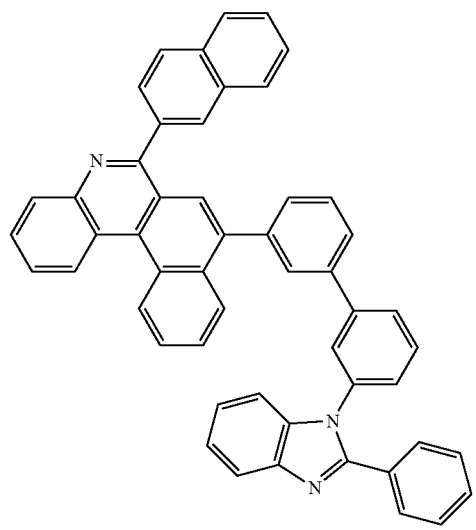
723
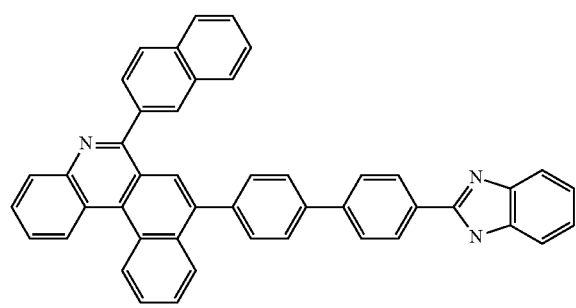
724
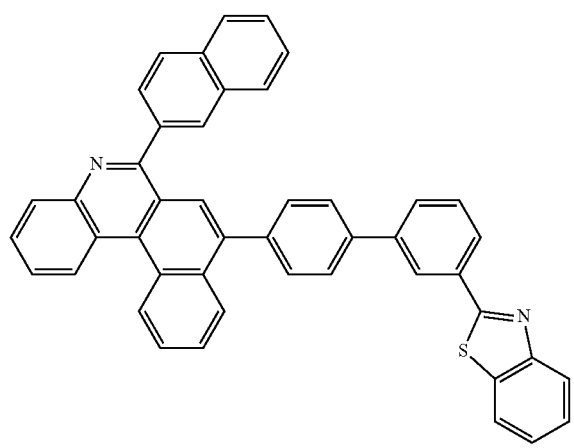
725
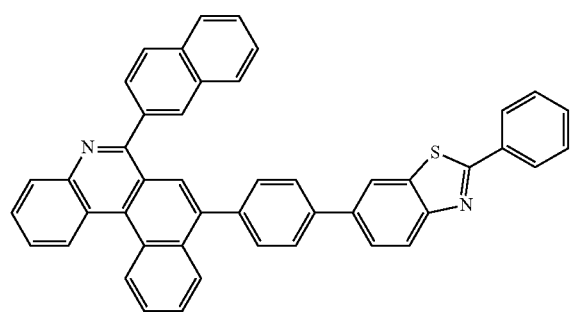
726
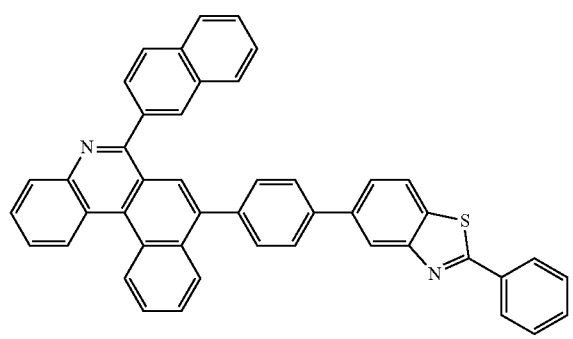

-continued
727
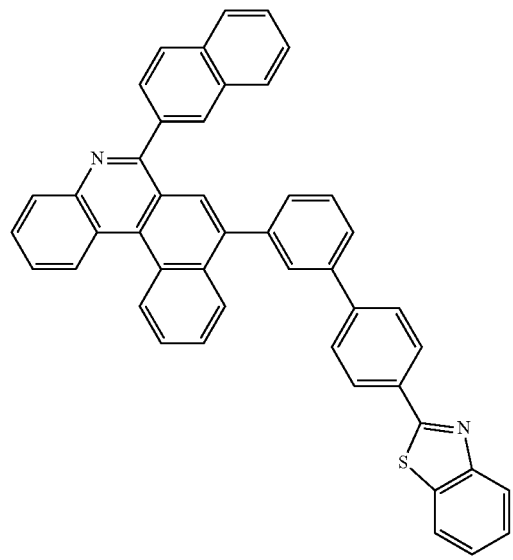
728
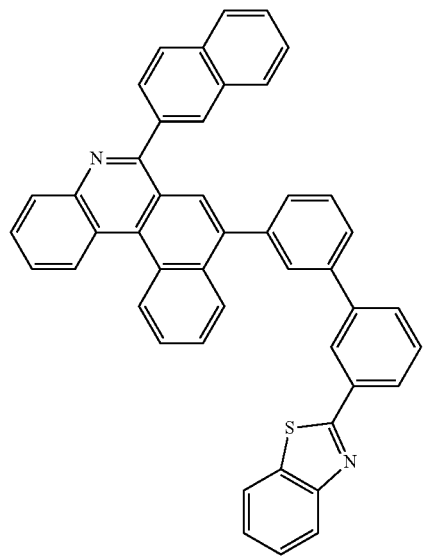
729
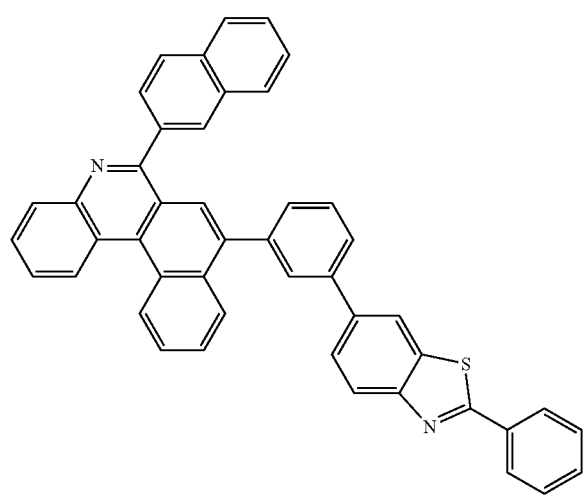
730
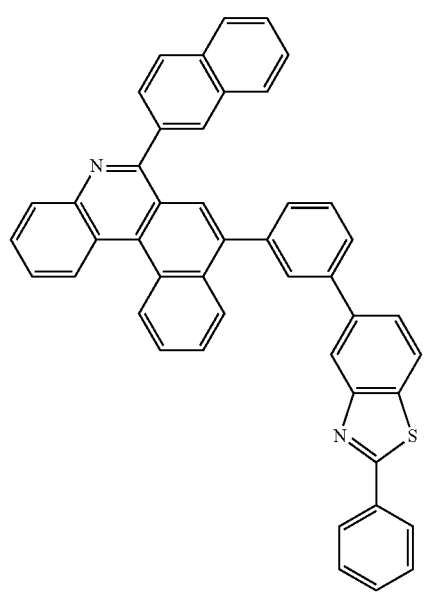
731
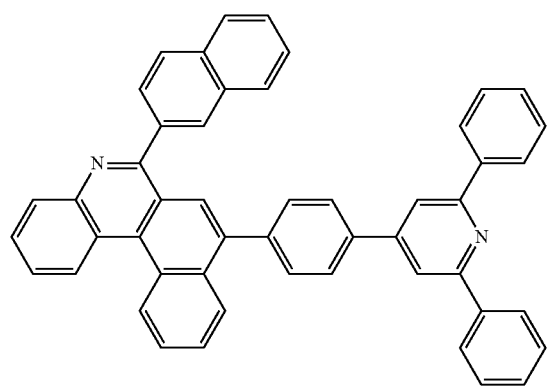
732
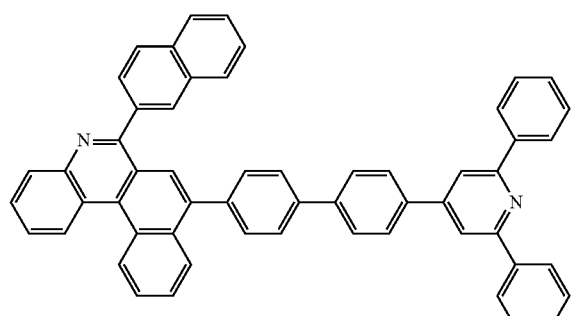

-continued
733
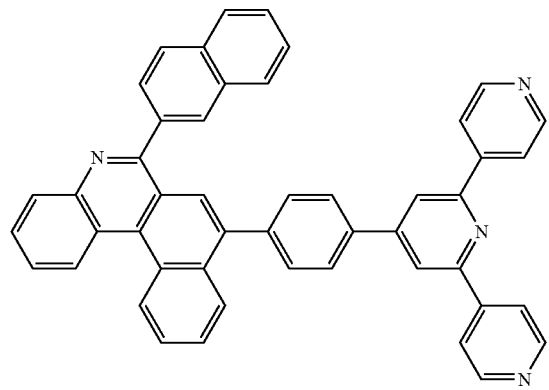
734
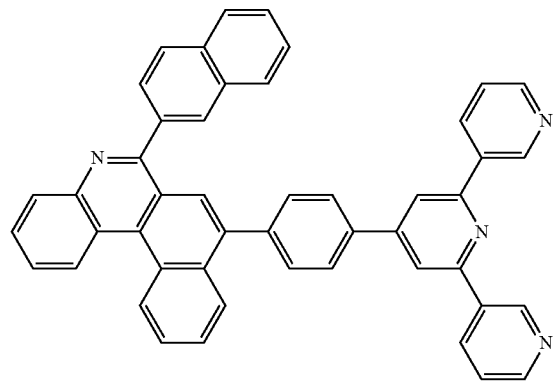
735
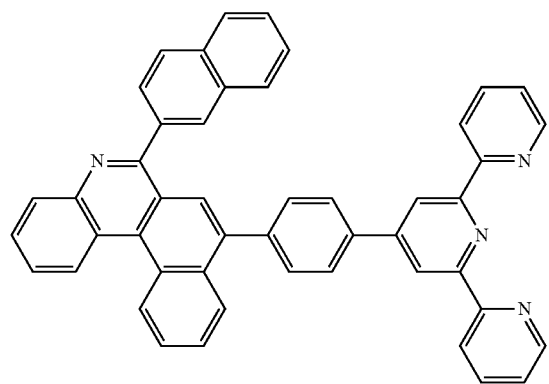
736
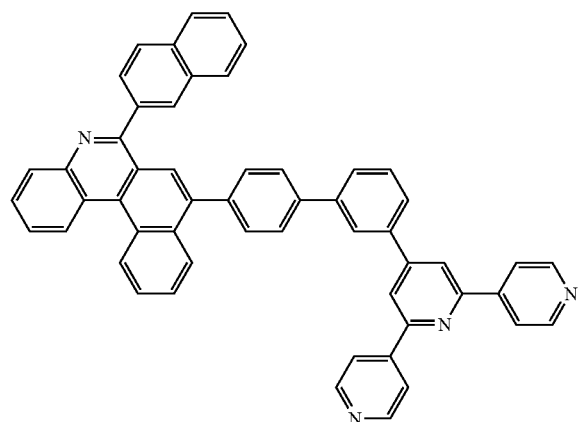
737
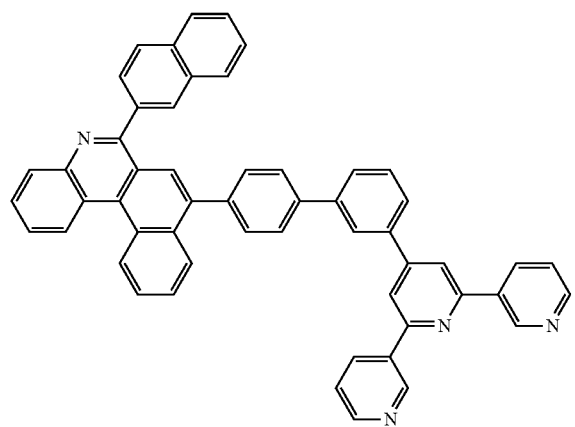
738
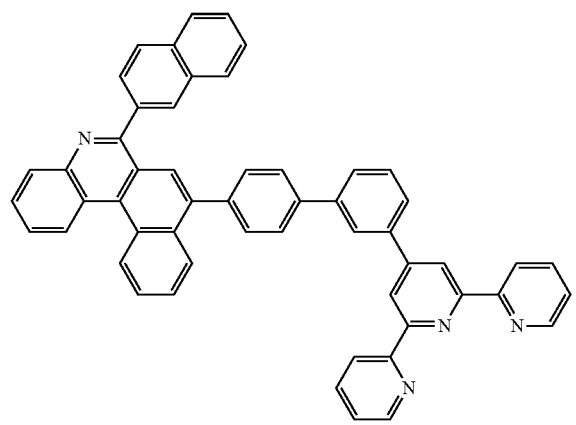

-continued
739
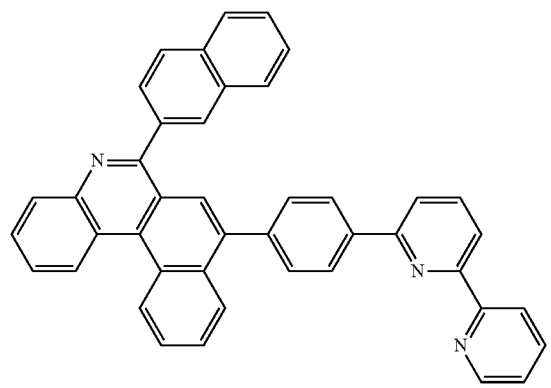
740
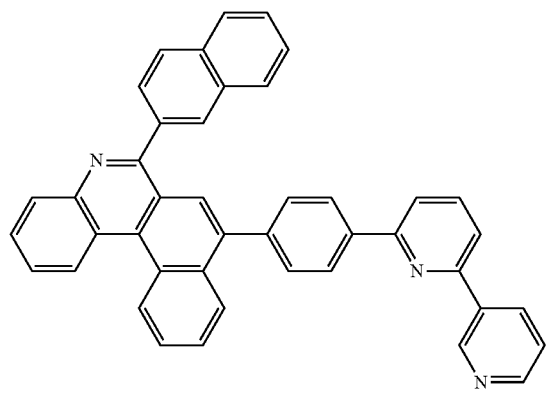
741
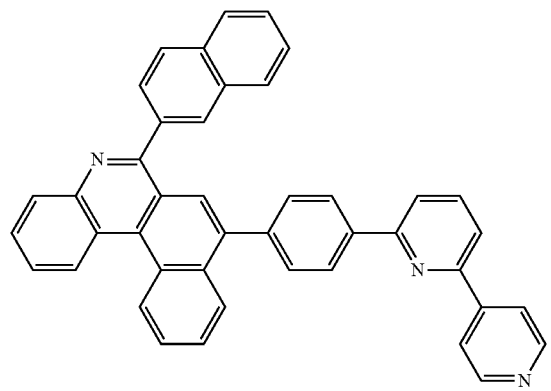
742
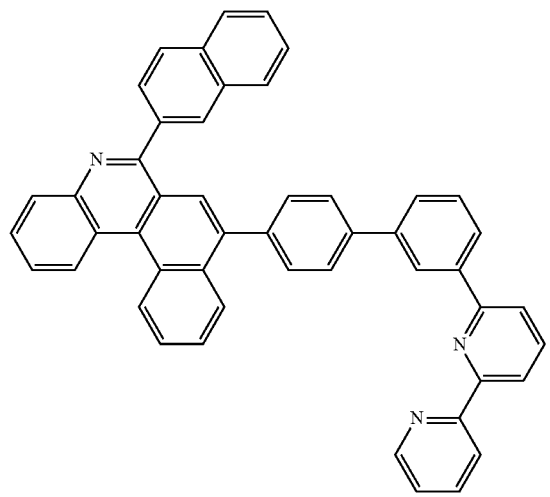
743
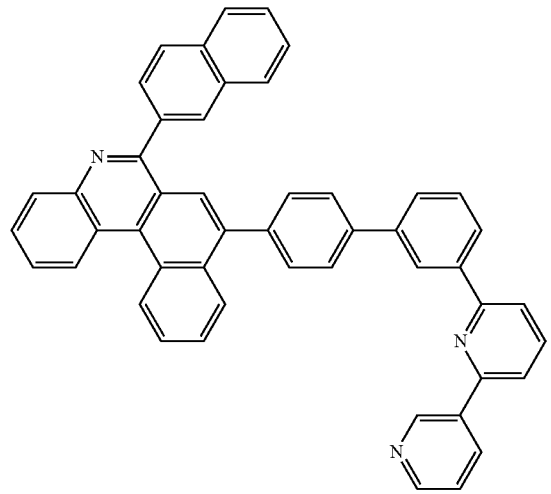
744
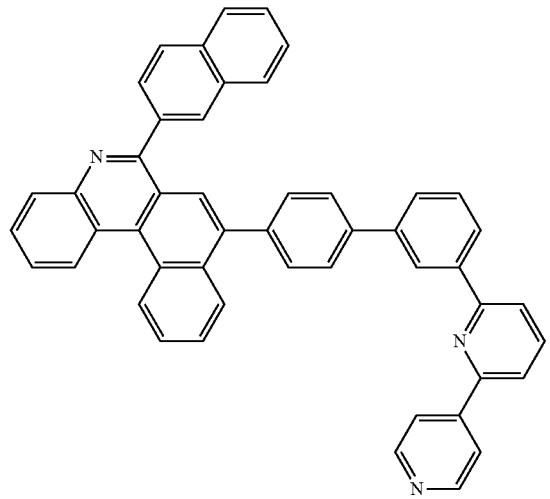

-continued
745
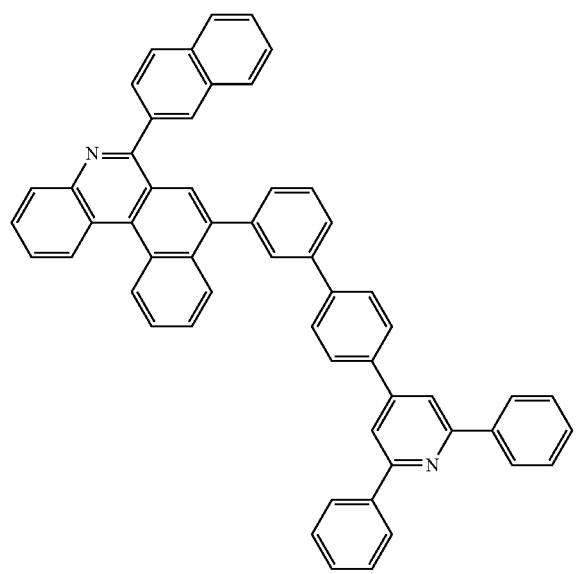
746
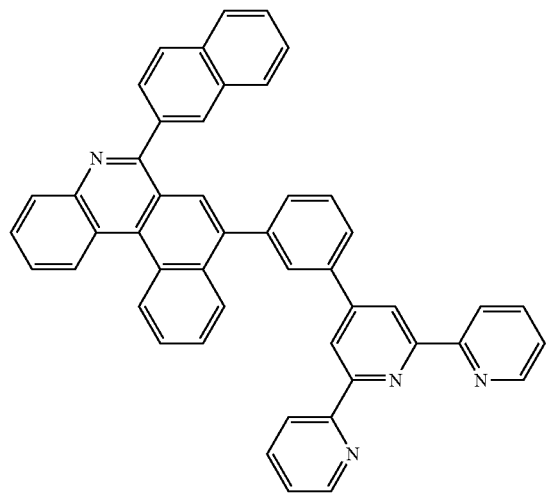
747
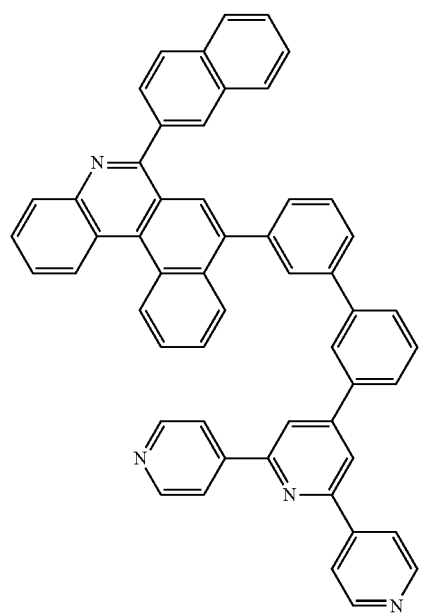
748
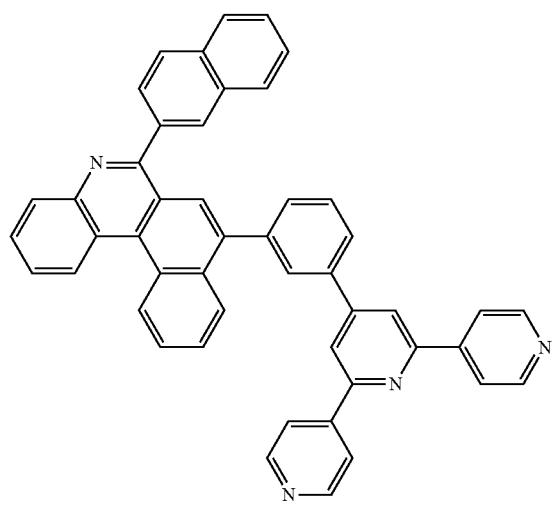

-continued
749
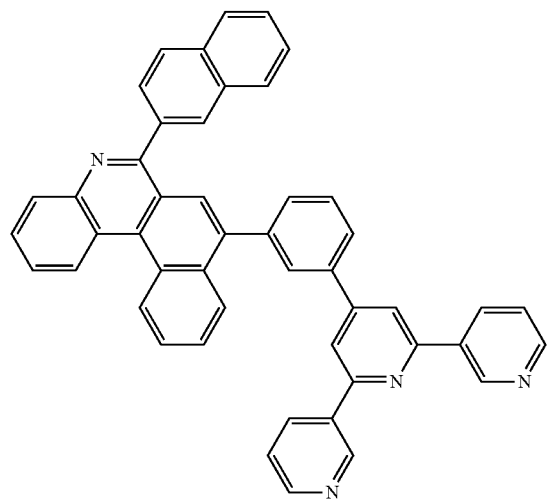
750
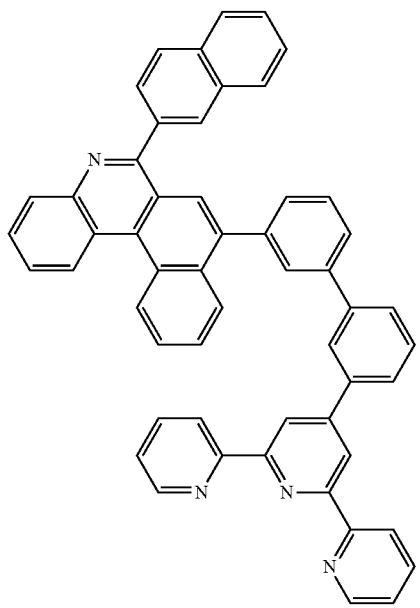
751
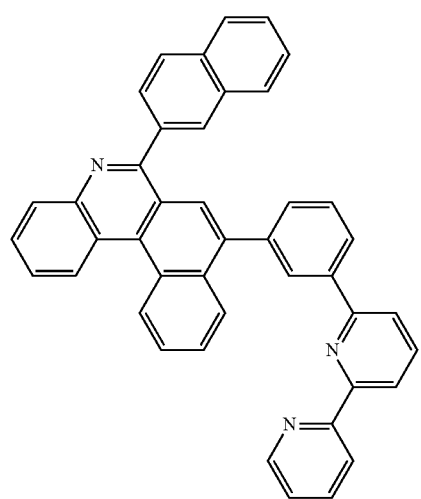
752
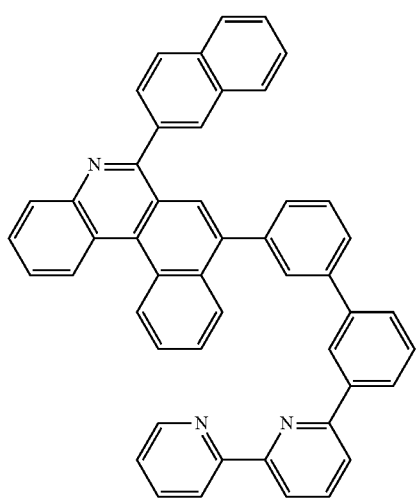
753
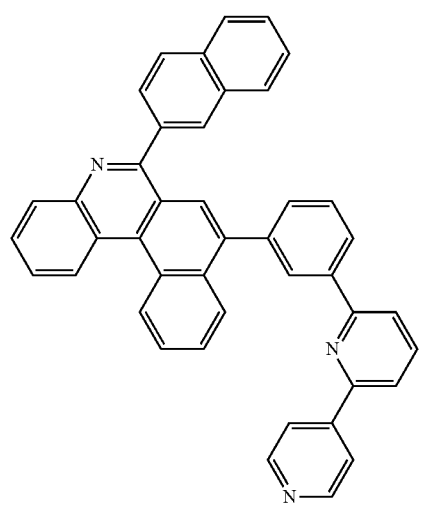
754

755
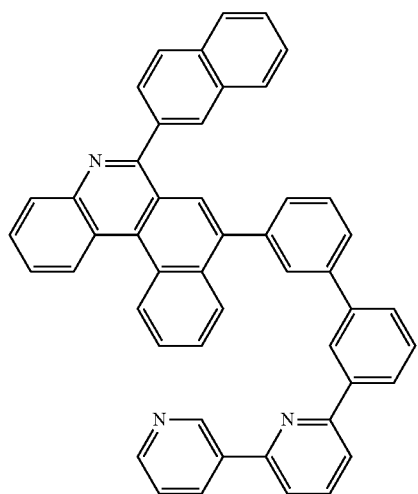
756
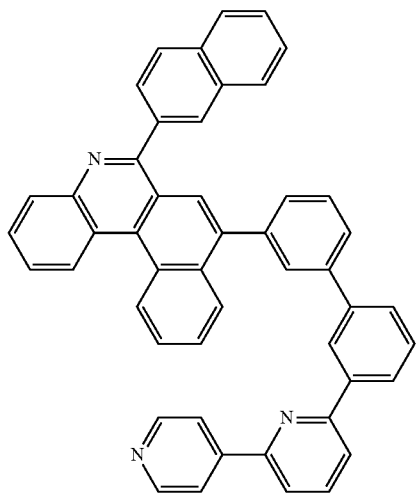
757
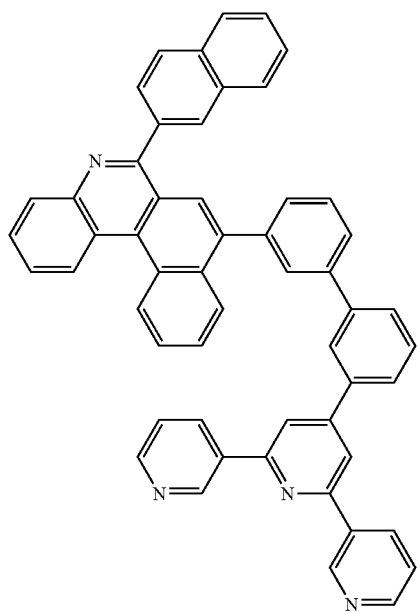
758
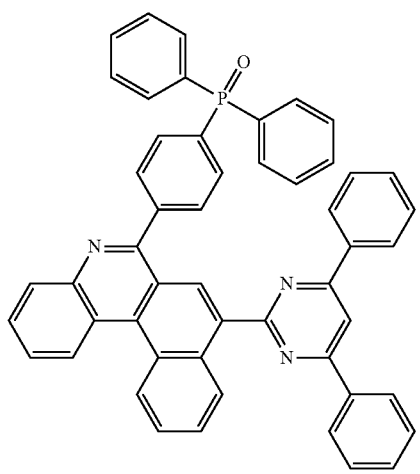
759
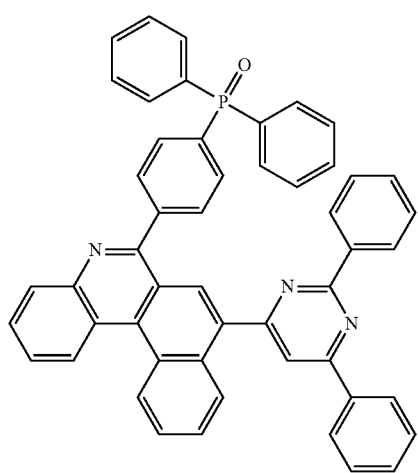
760
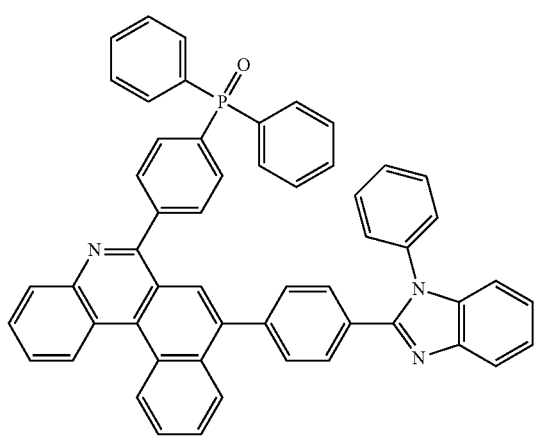

-continued
761
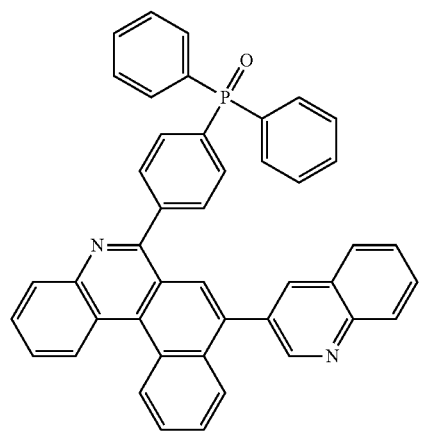
762
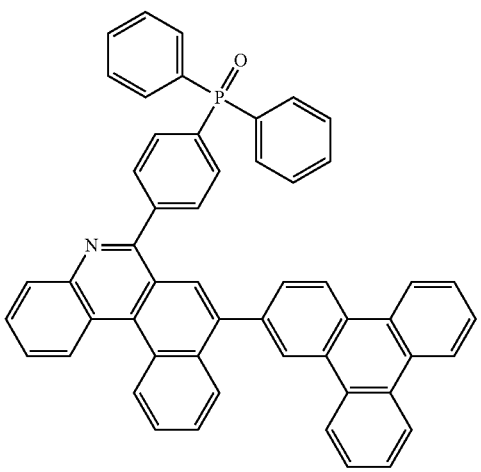
763
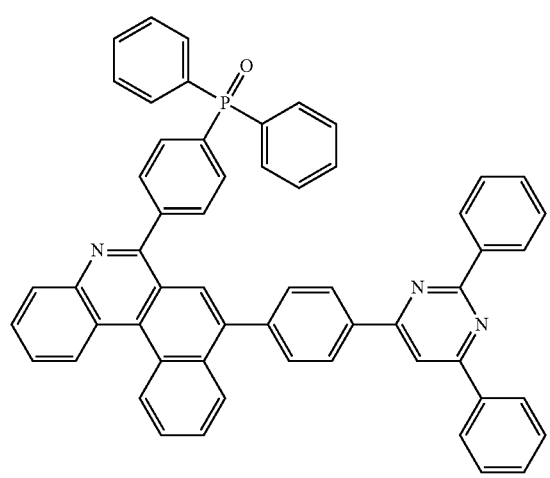
764
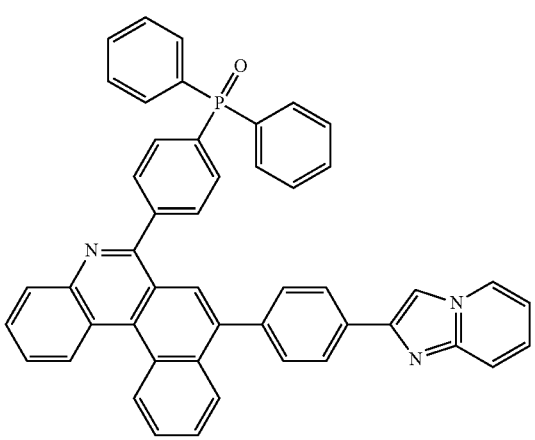
765
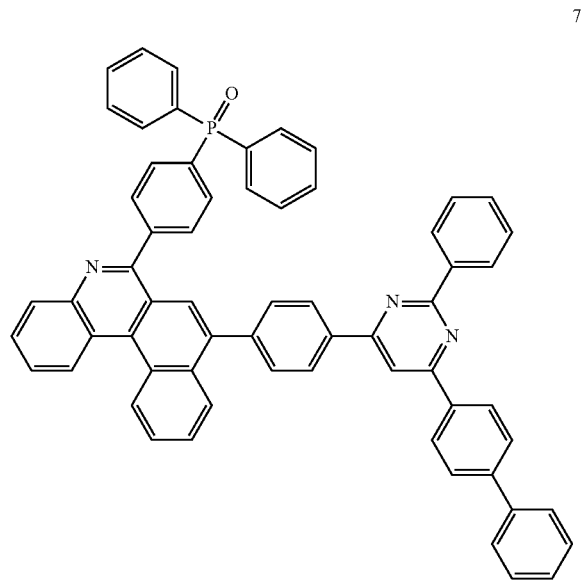
766
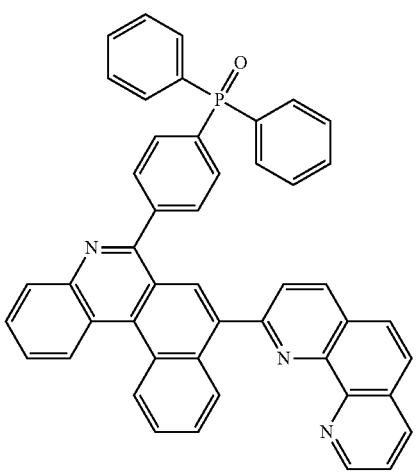

-continued
767
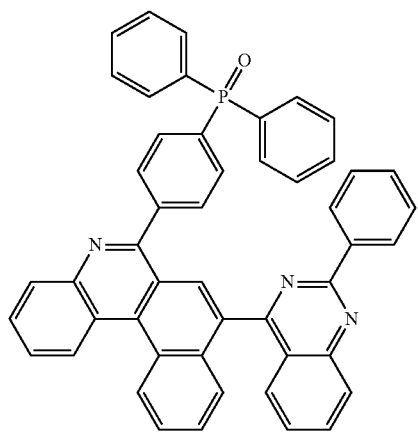
768
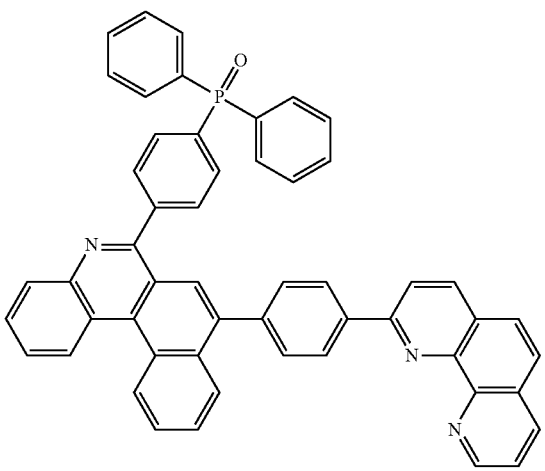
769
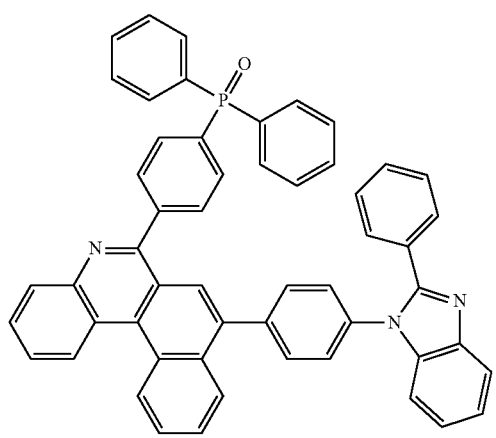
770
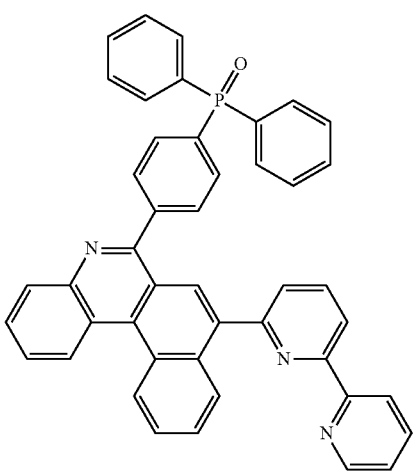
771
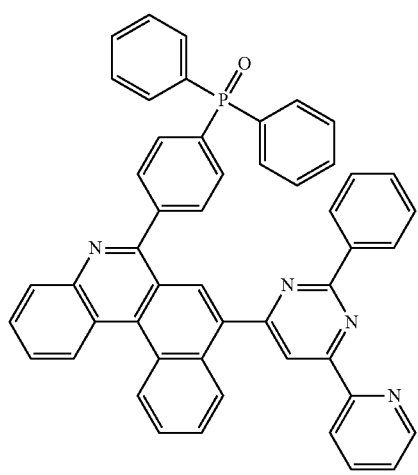
772
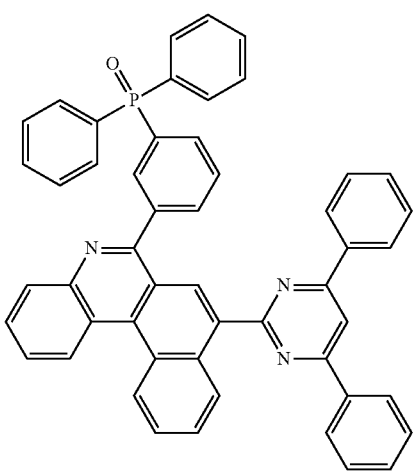

773
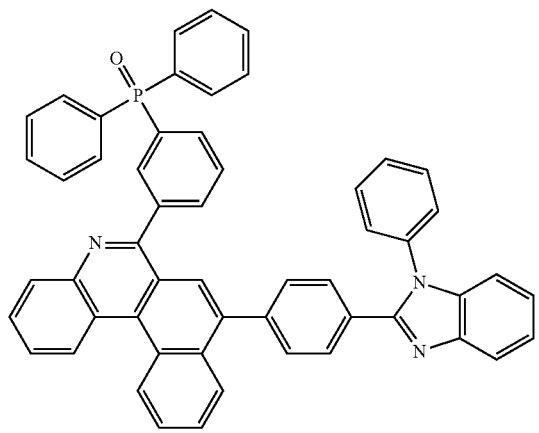
774
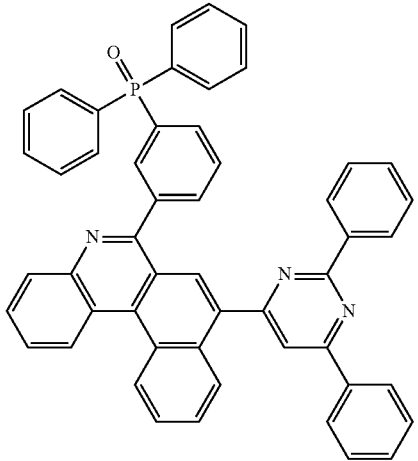
775
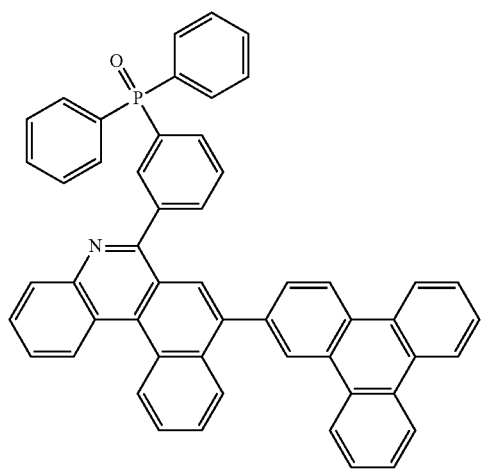
776
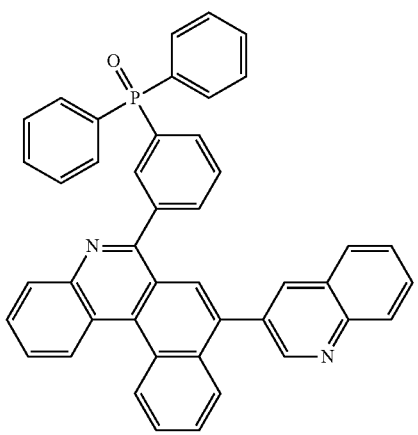
777
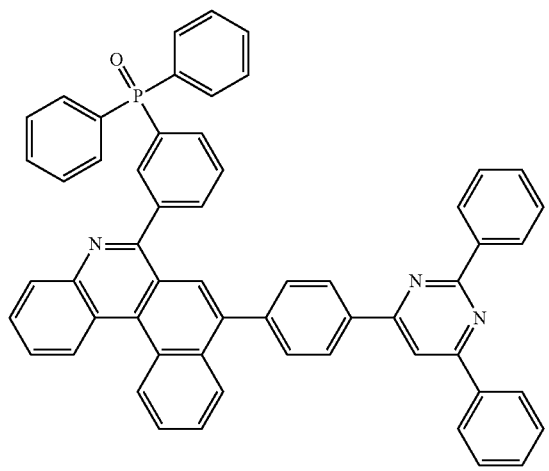
778
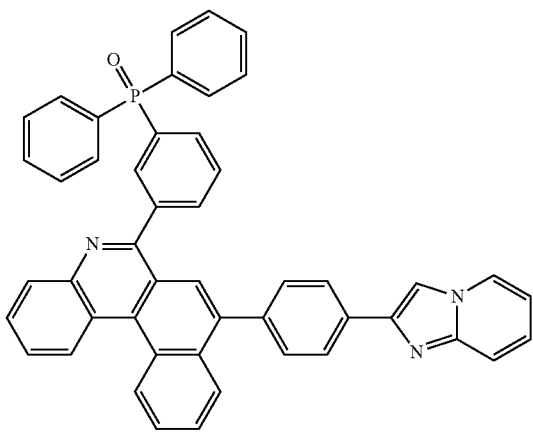

-continued
779
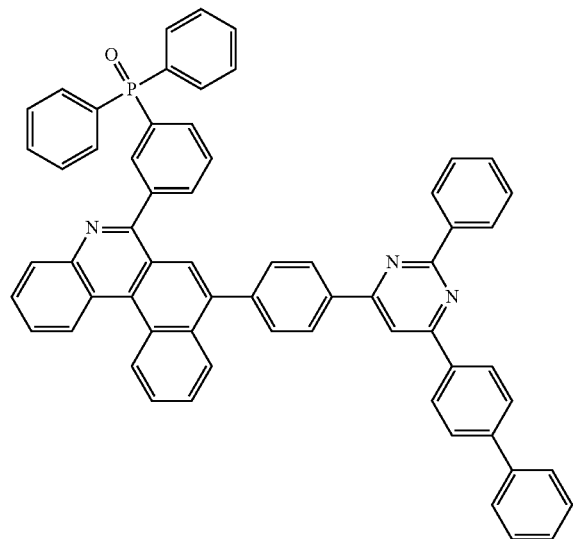
780
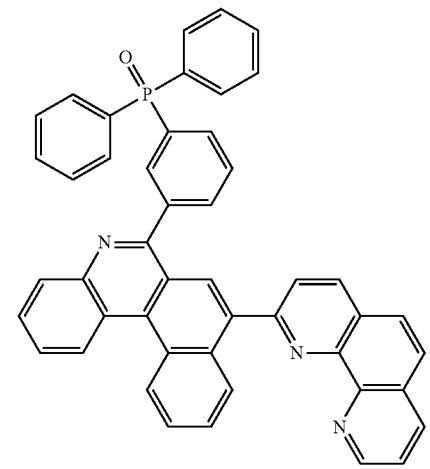
781
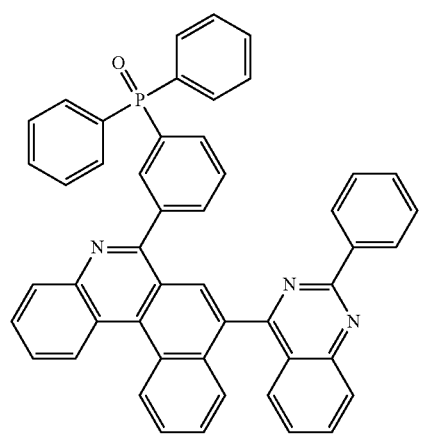
782
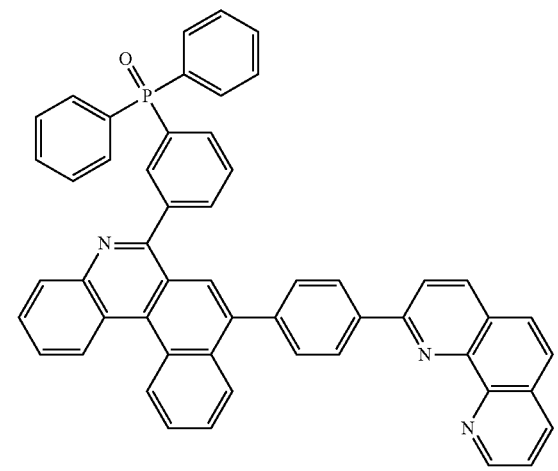
783
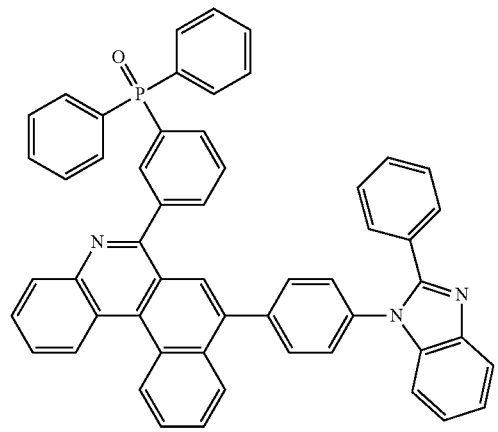
784
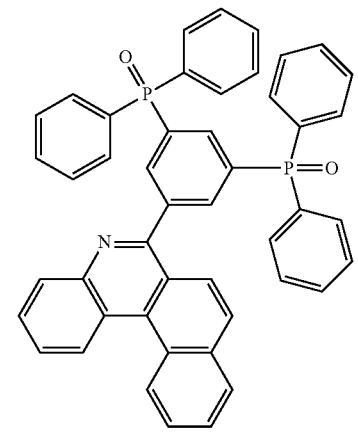

-continued
785
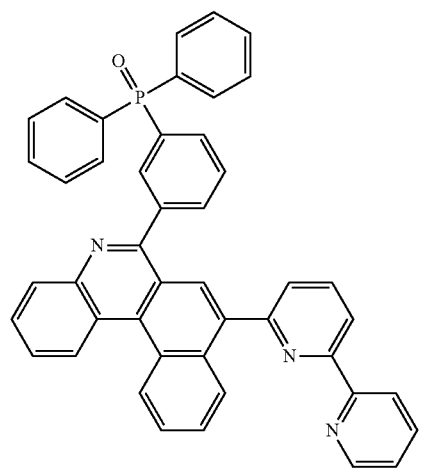
786
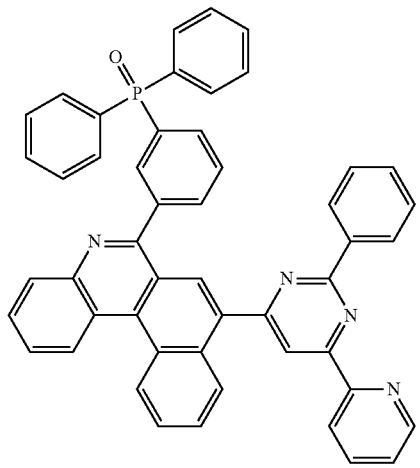
787
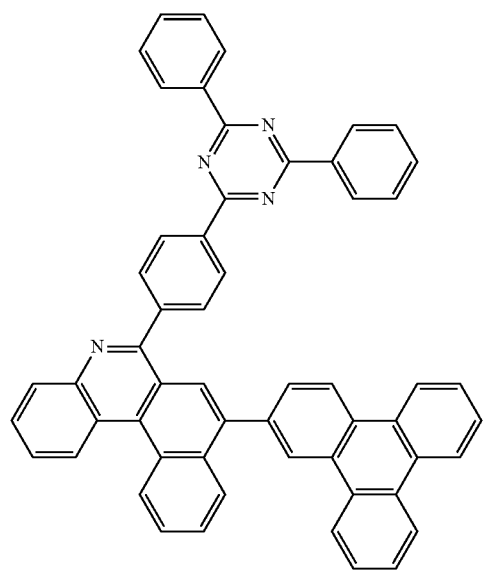
788
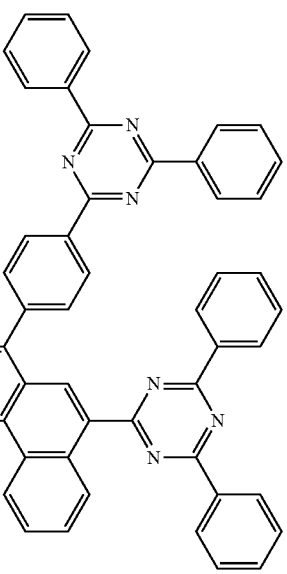
789
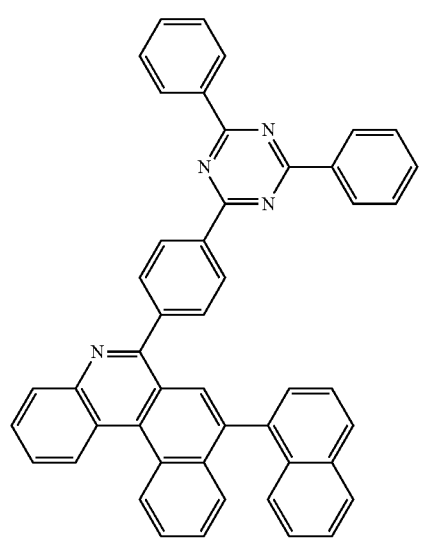
790
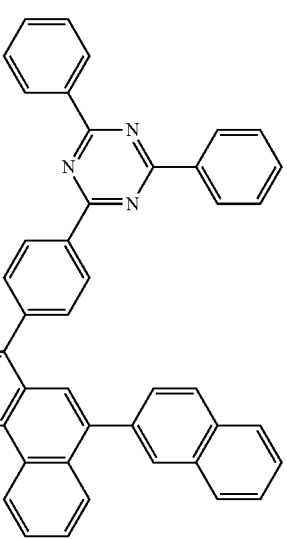

-continued
791
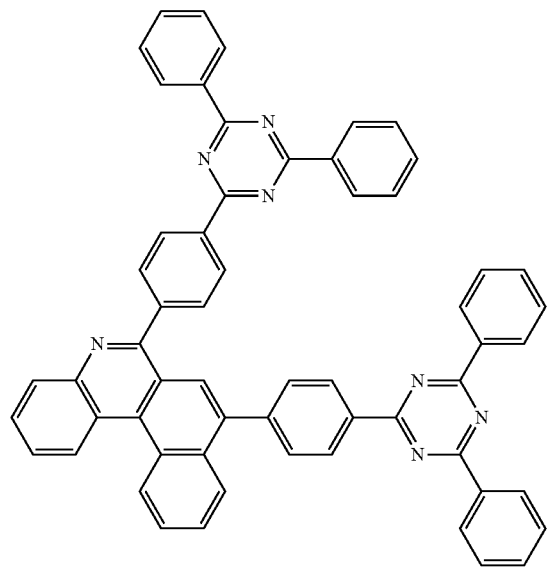
792
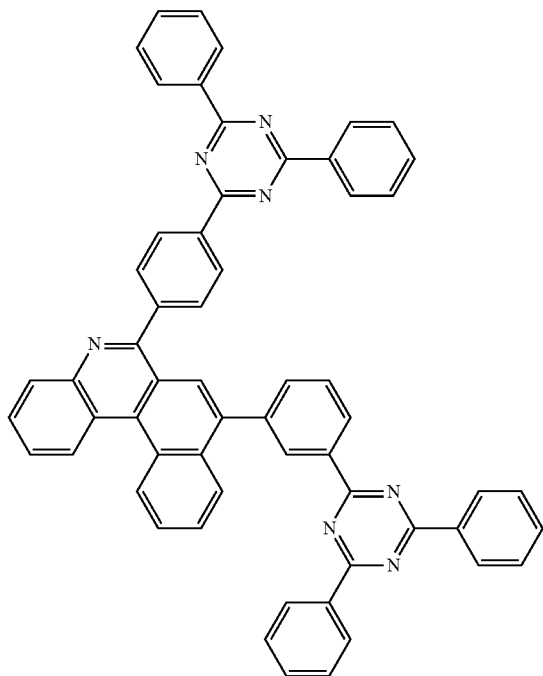
793
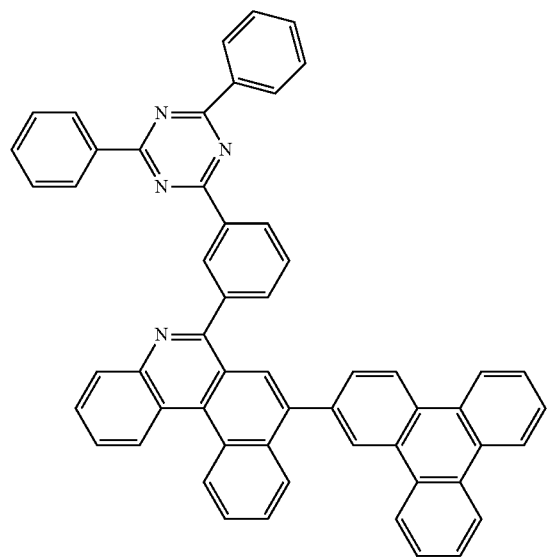
794
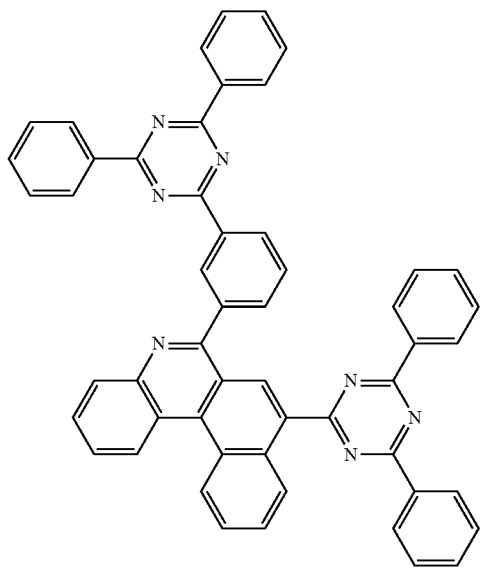

-continued
795
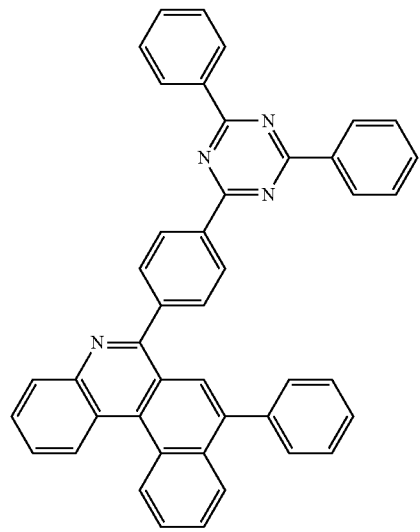
796
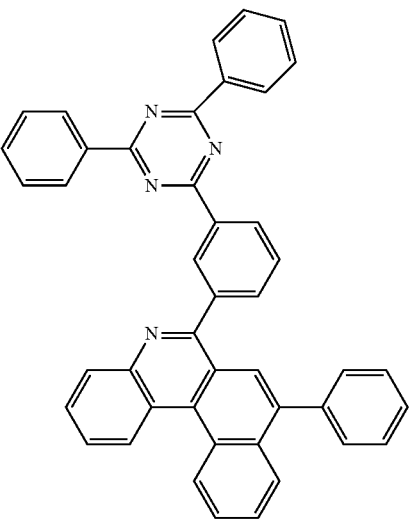
797
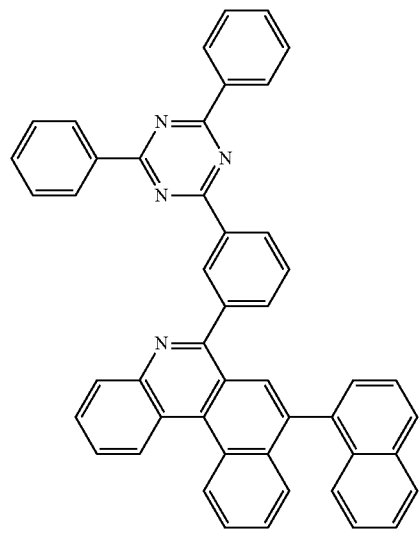
798
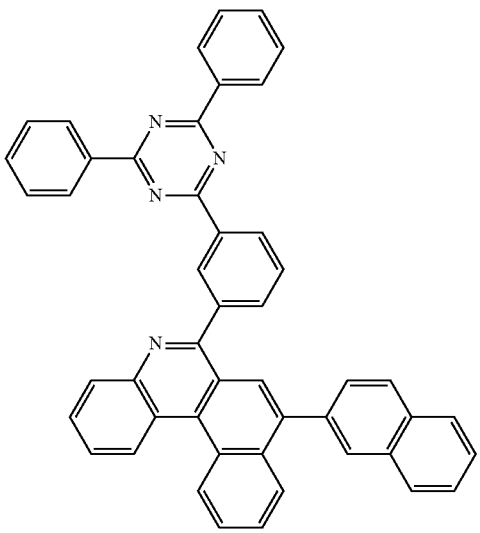
799
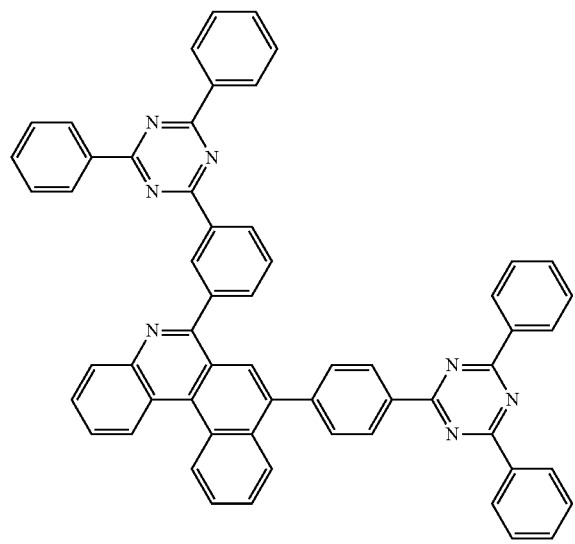
800
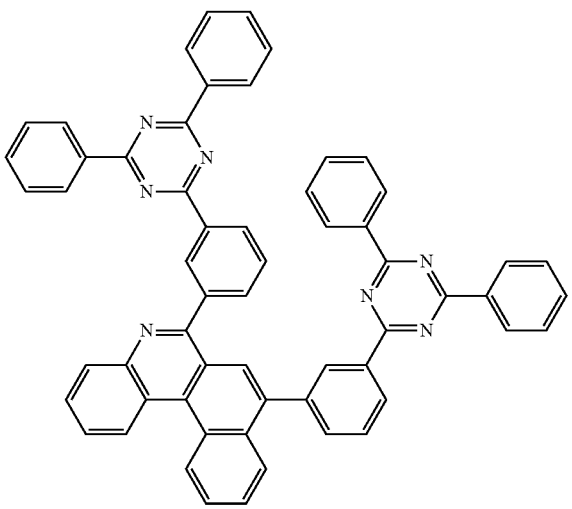

-continued
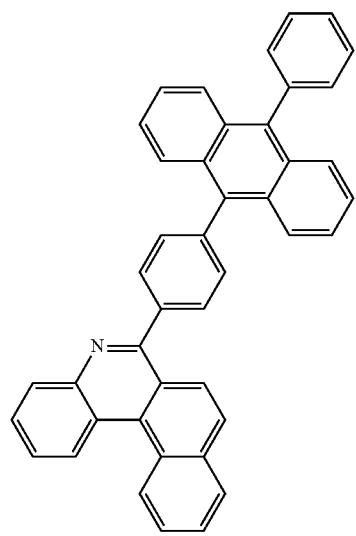
801
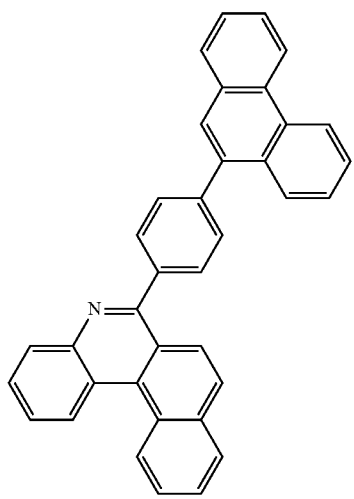
802
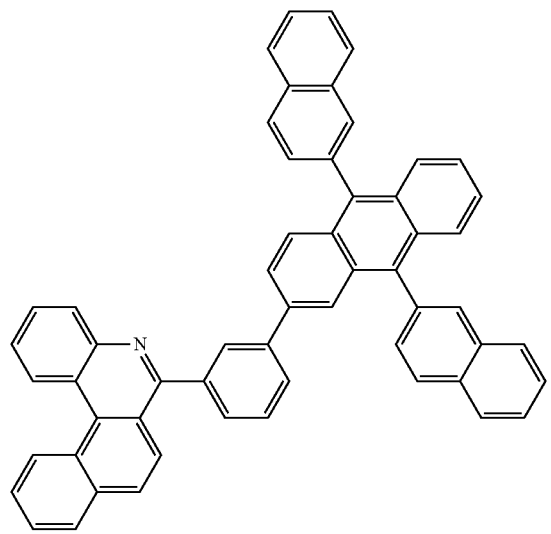
803
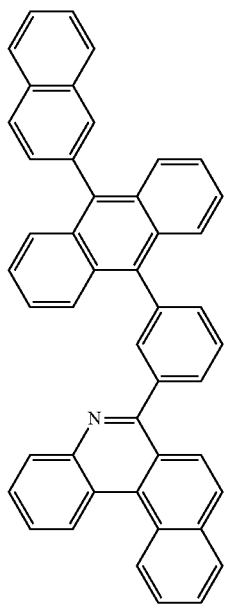
804

805 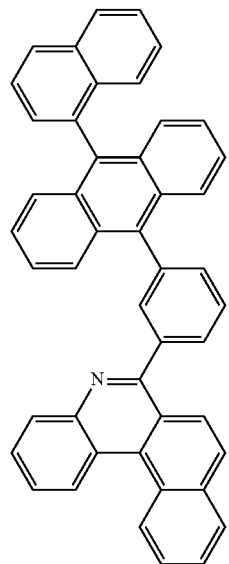
806 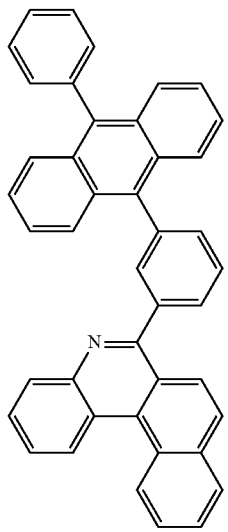
807 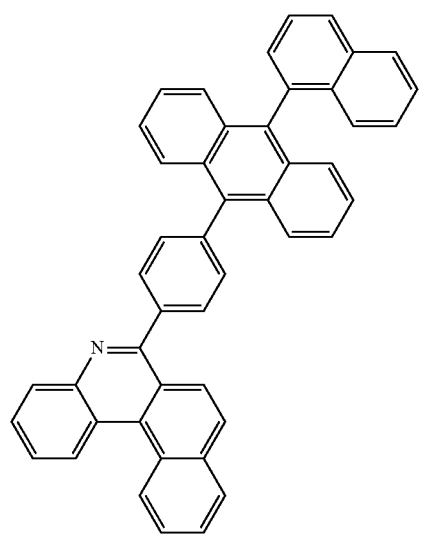
808 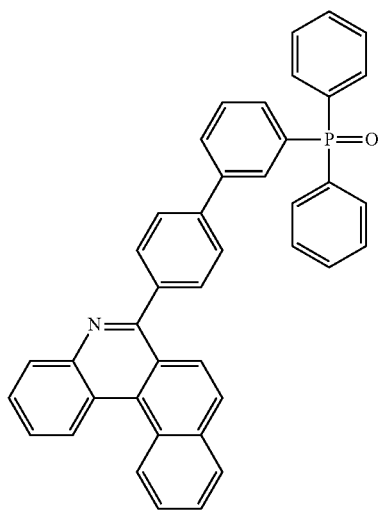
809 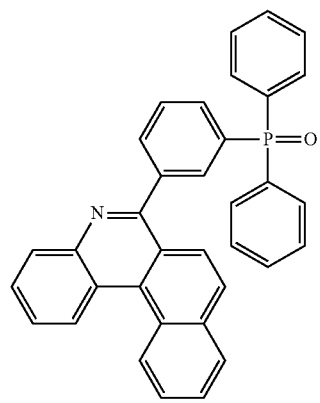
810 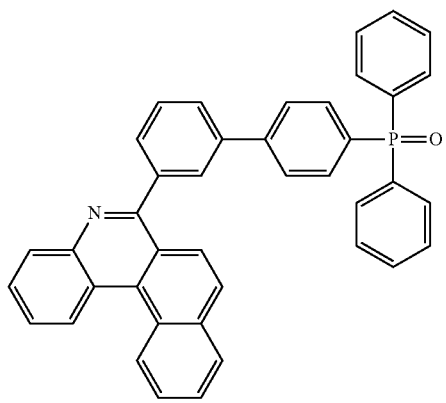

-continued
811 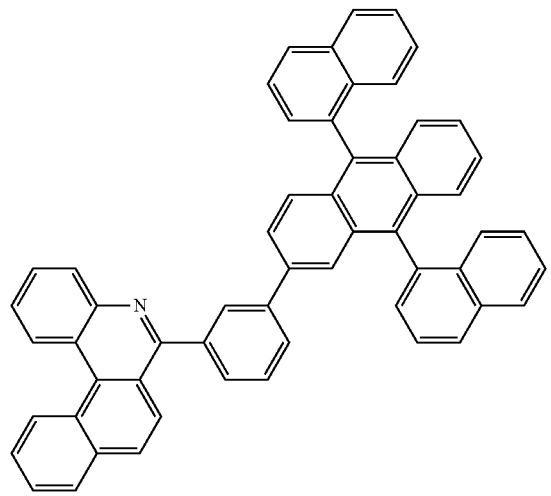
812 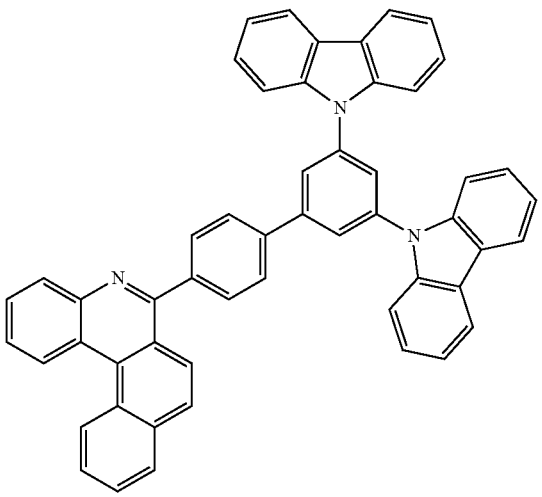
813 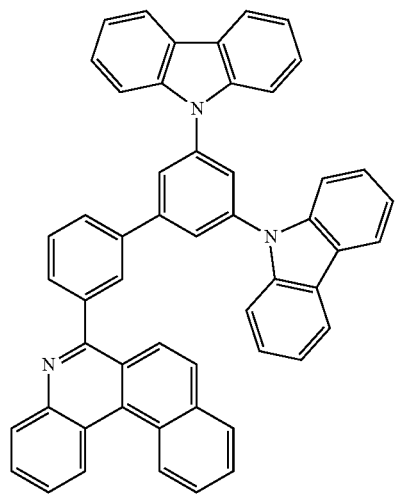
814 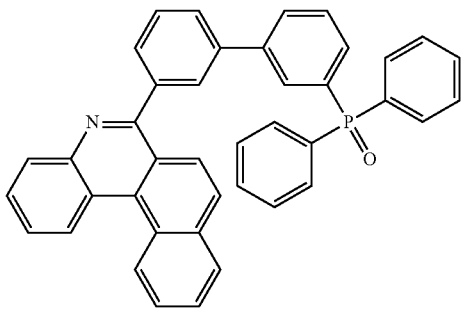
815 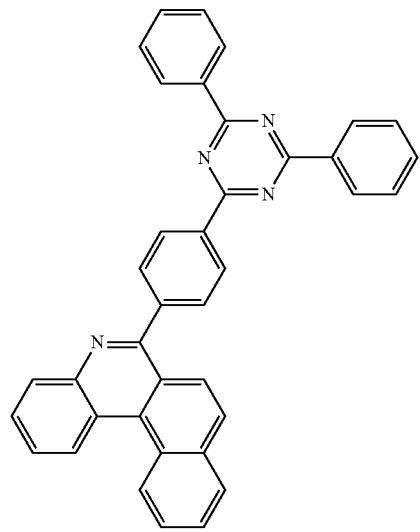
816 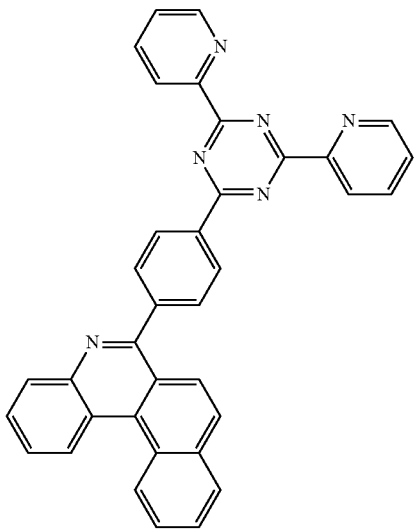

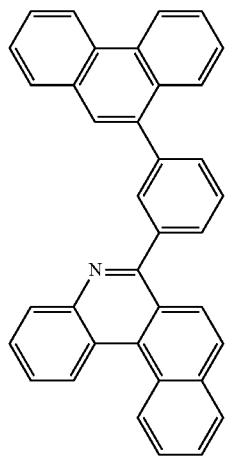
817
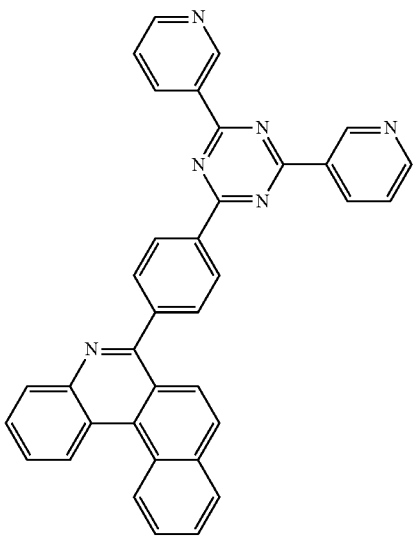
818
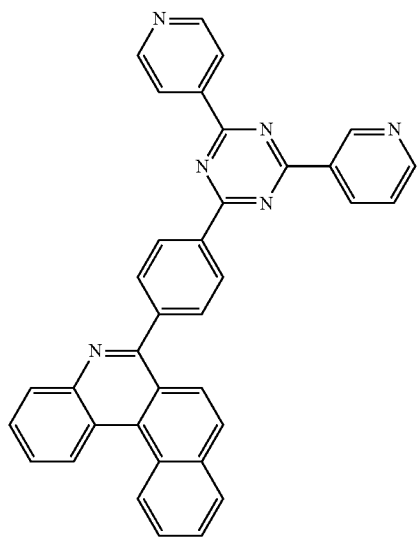
819
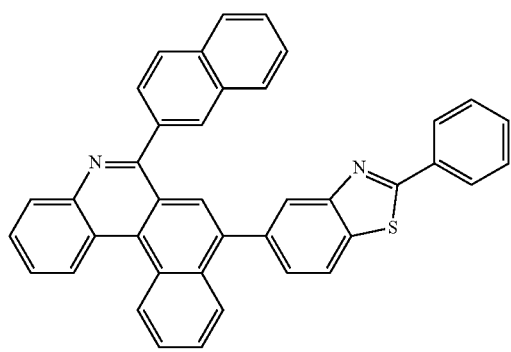
820
821
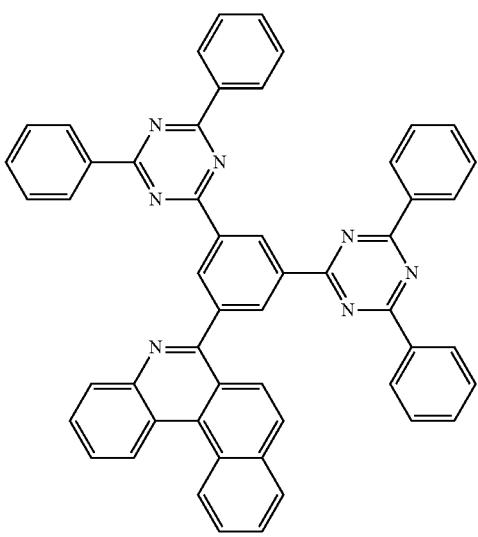
822

-continued
341
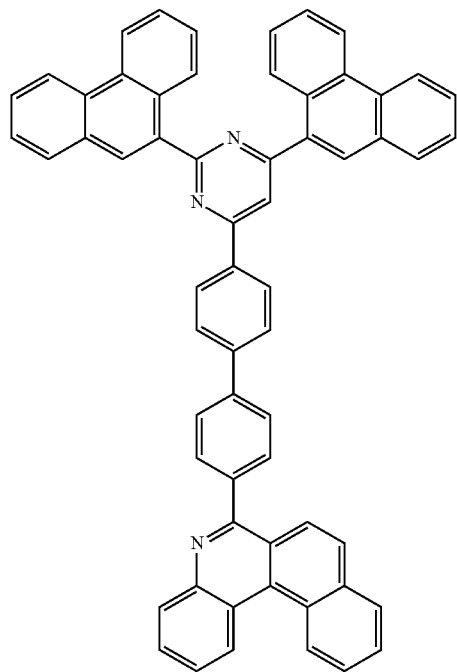
342
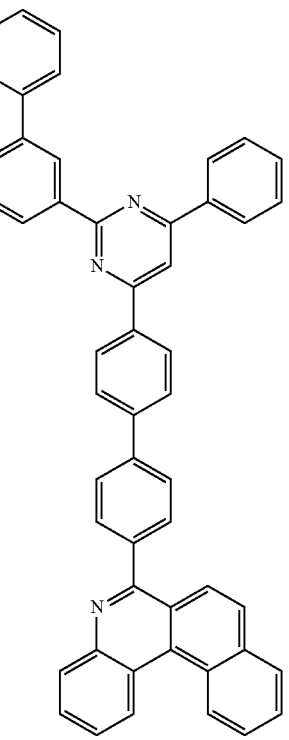
823
824
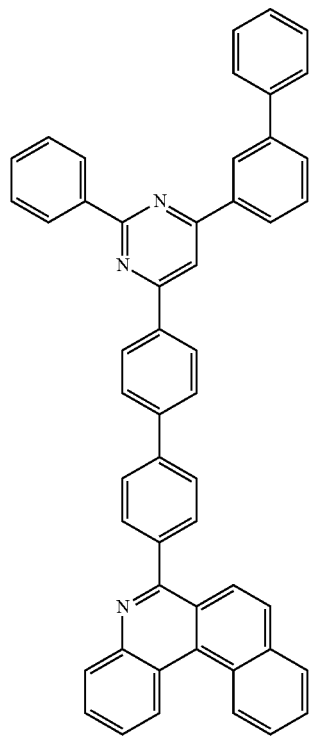
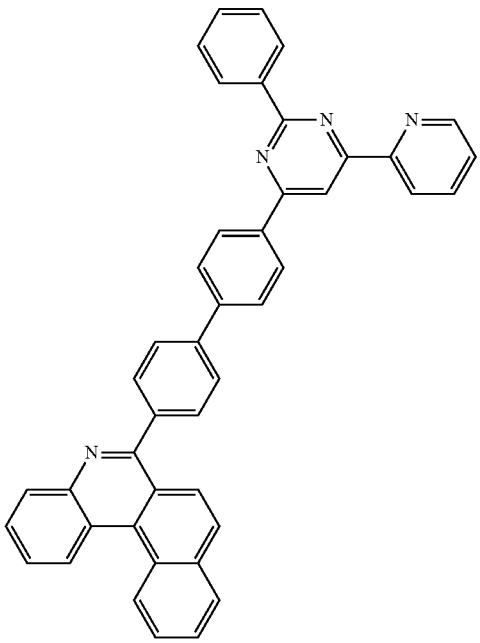
825
826

827
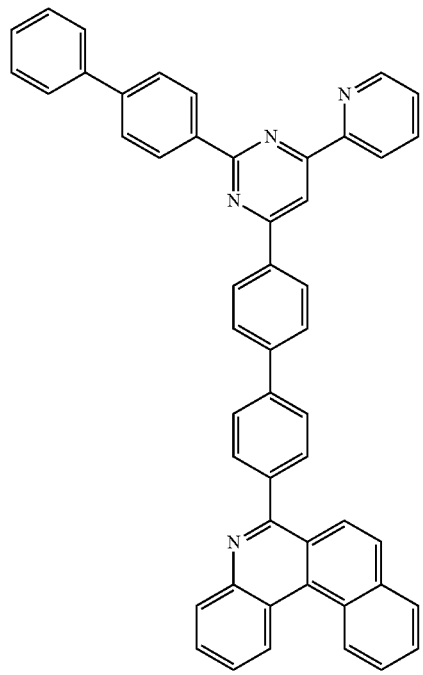
828
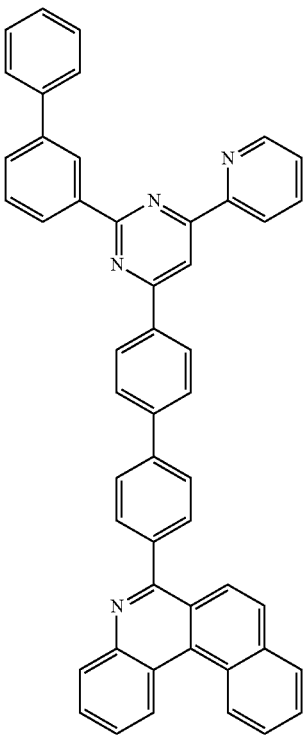
829
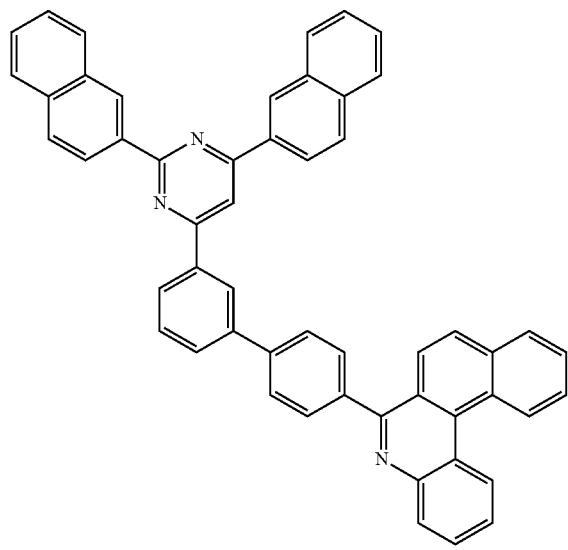
830
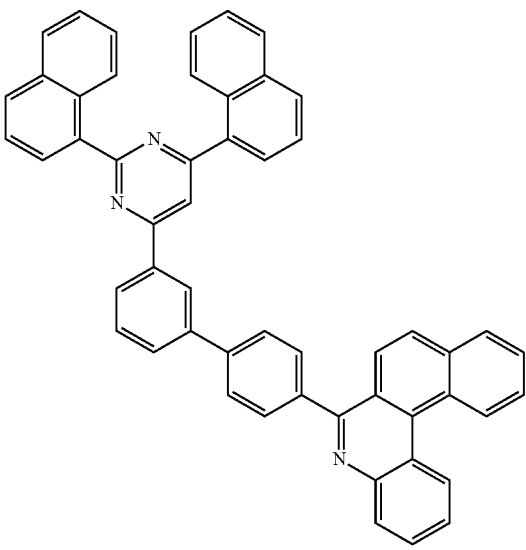

-continued
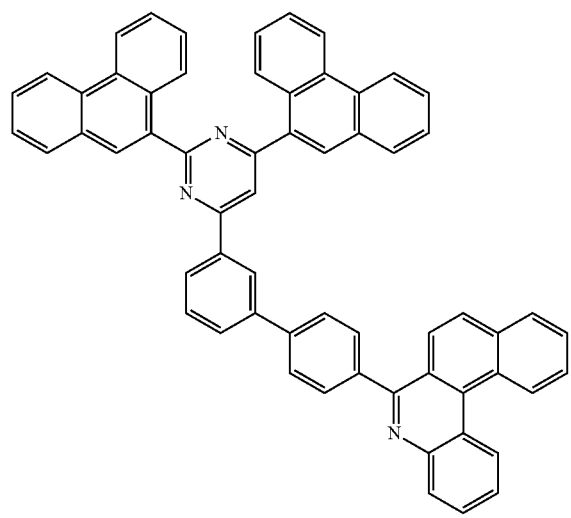
831
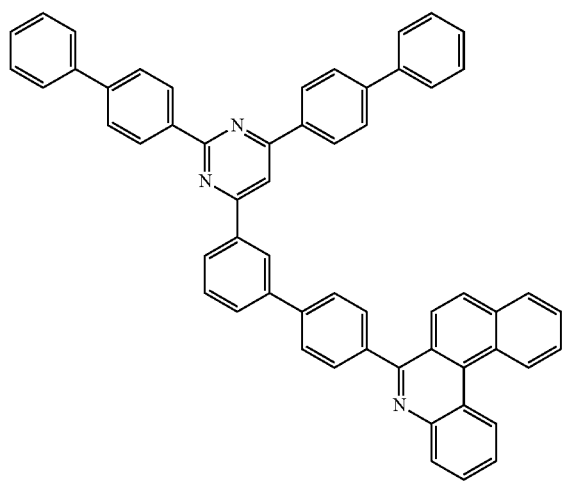
832
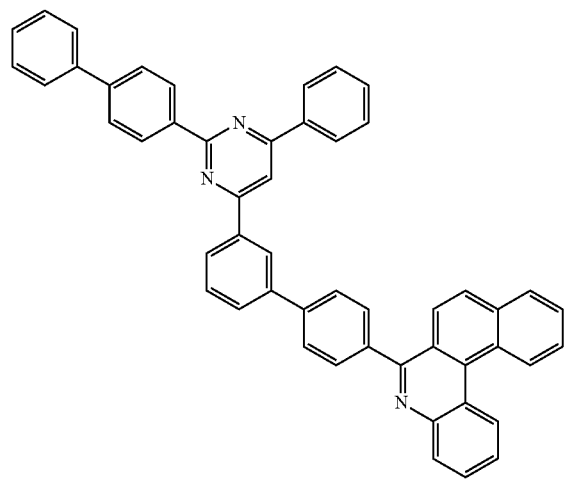
833
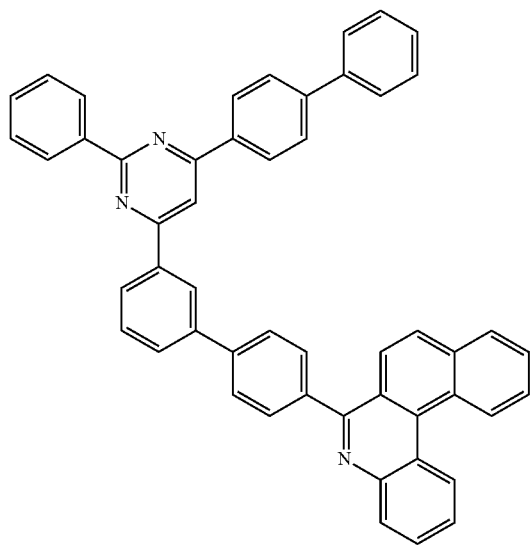
834

-continued
835 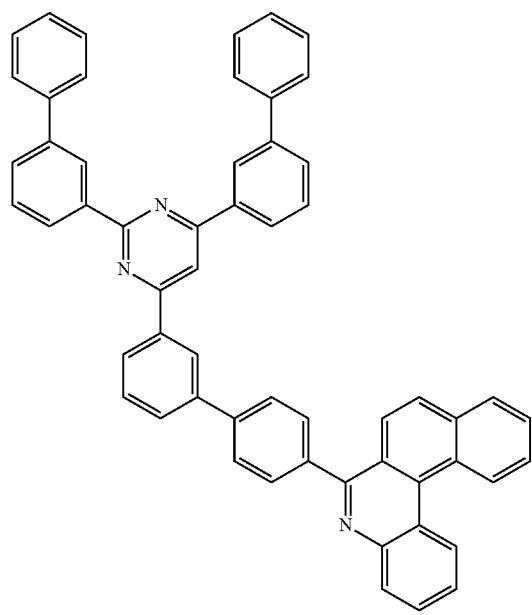
836 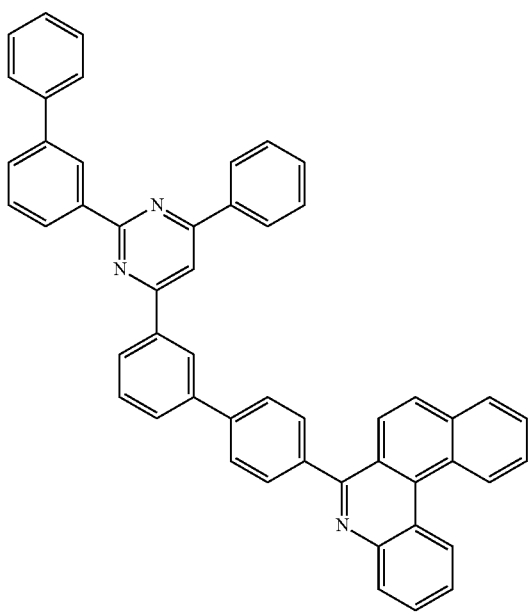
837 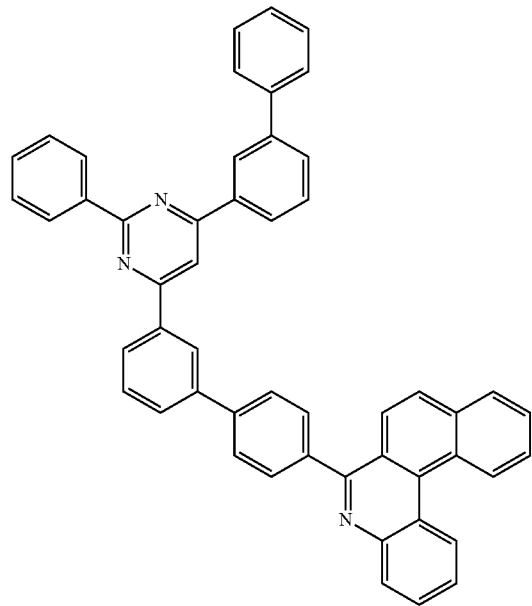
838 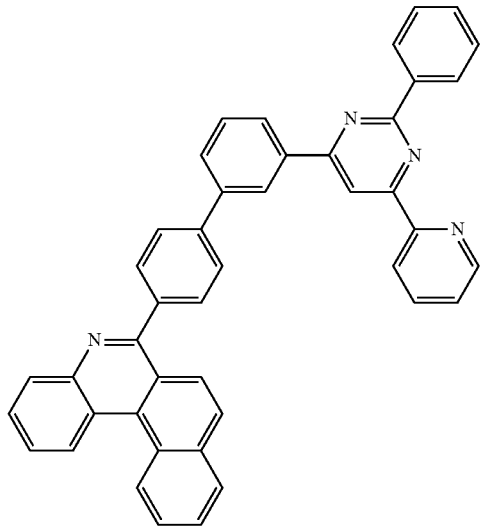

839
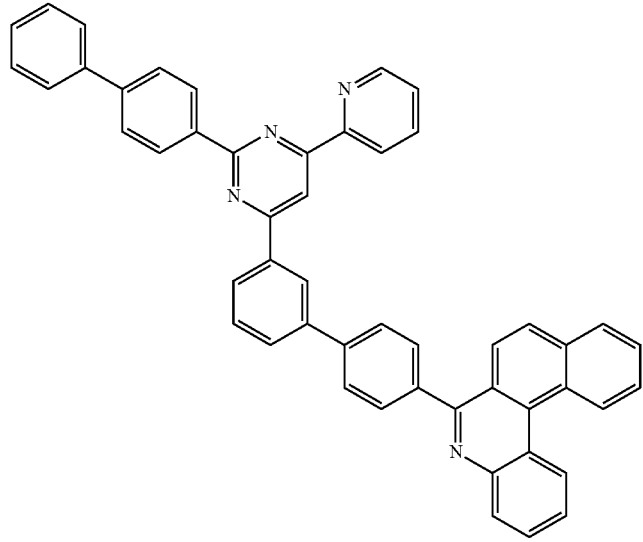
840
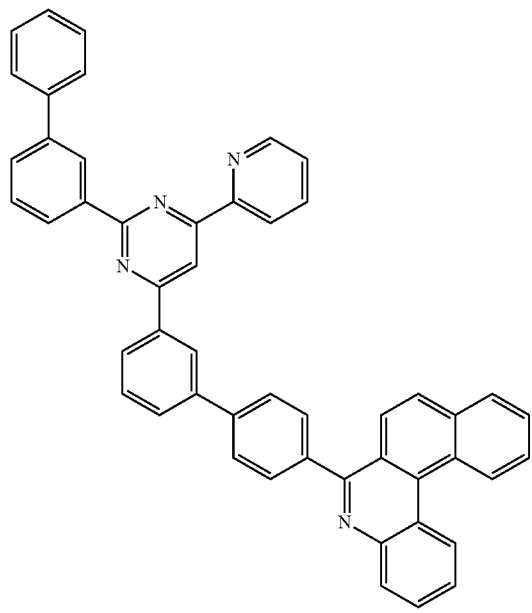
841
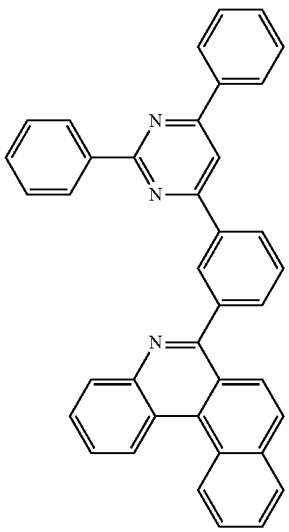

351
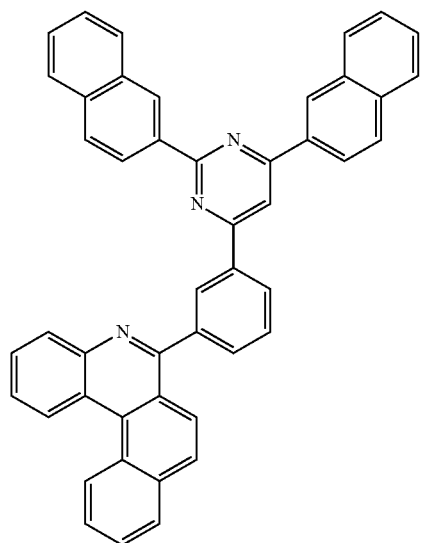
842
352
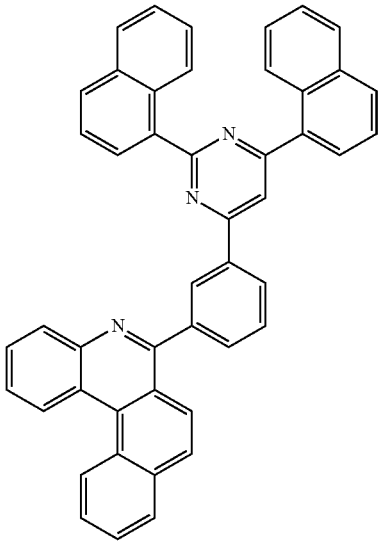
843
-continued
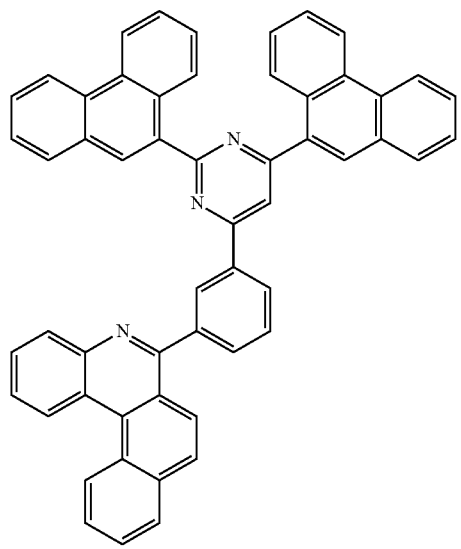
844
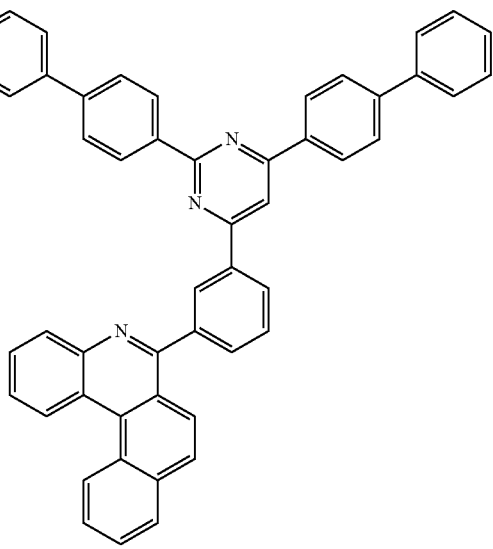
845

-continued
846
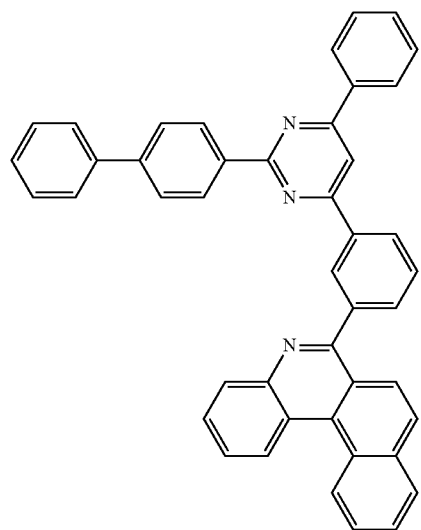
847
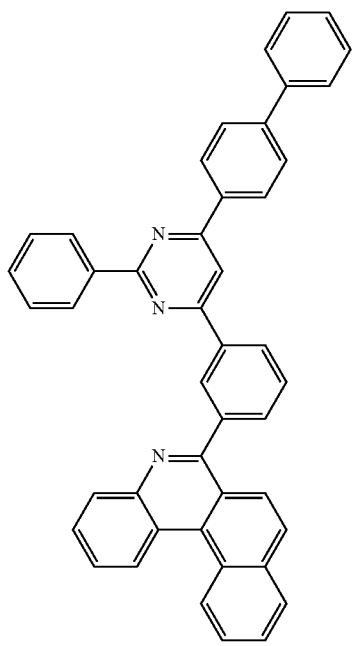
848
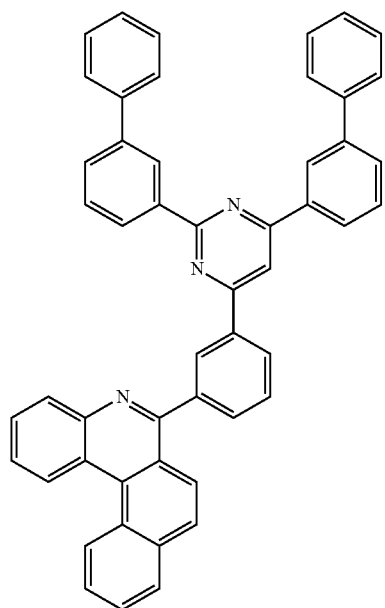
849
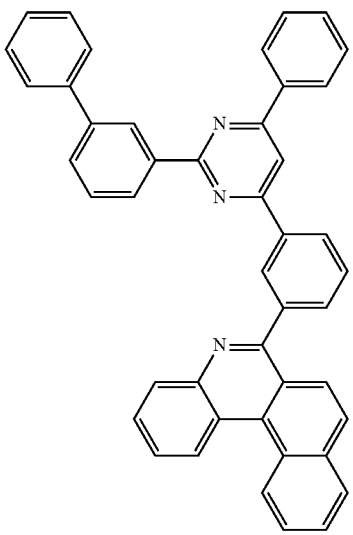

-continued
850
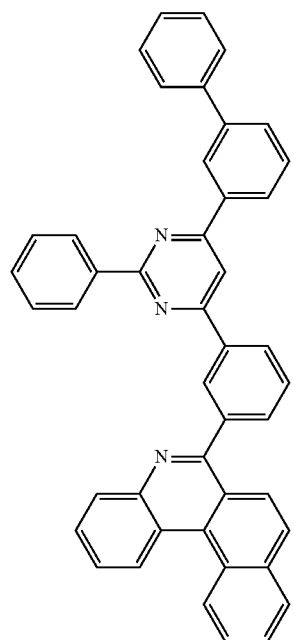
851
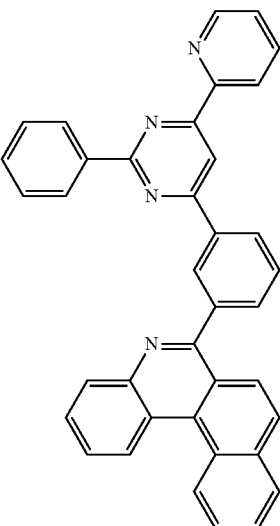
852
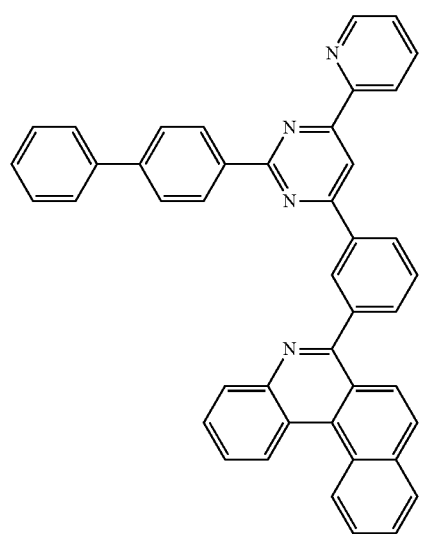

853
854
855
856
857
858
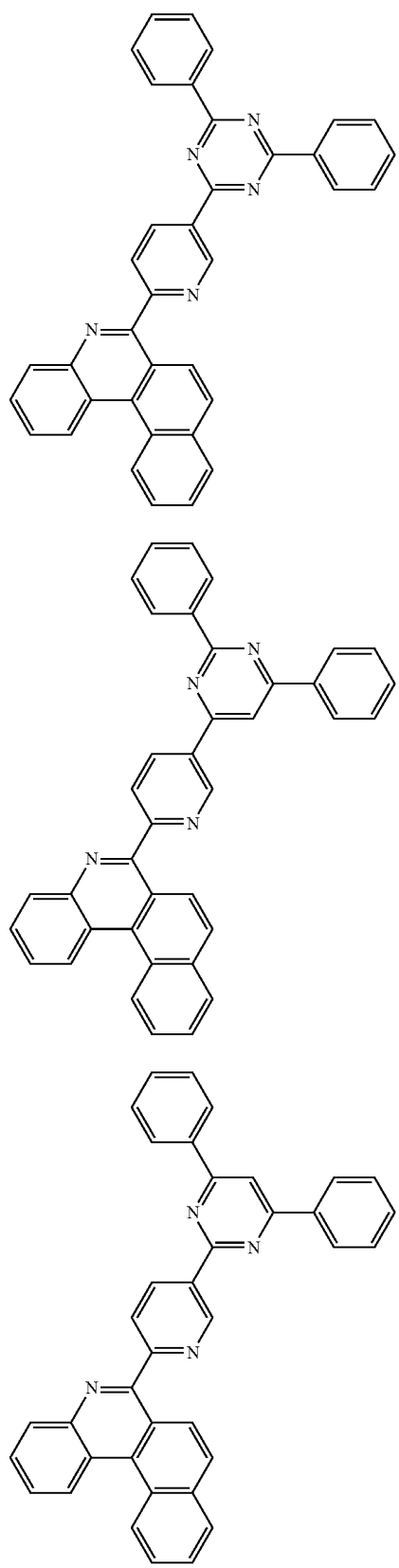
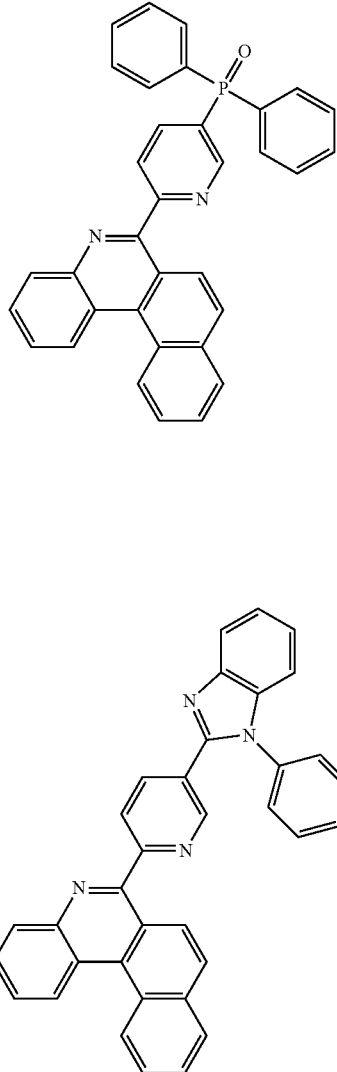
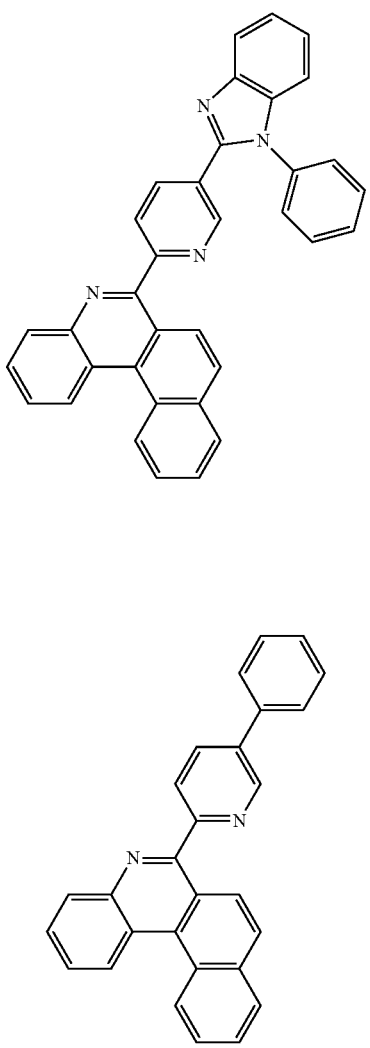

-continued
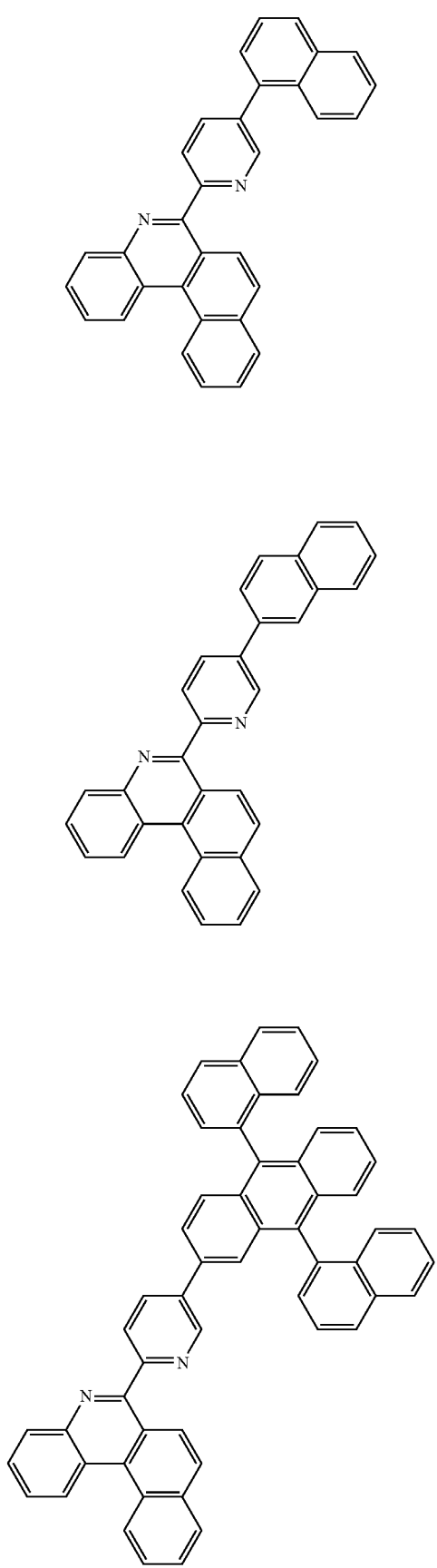
-continued
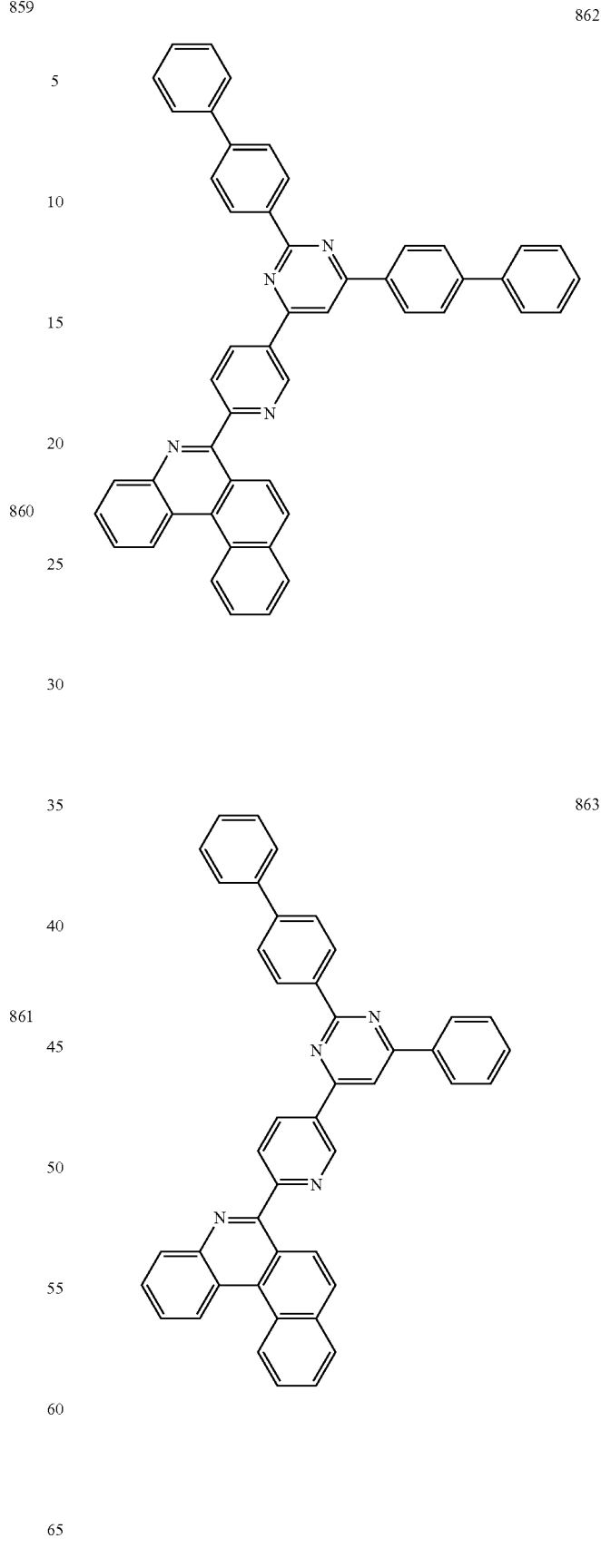

361
-continued
864
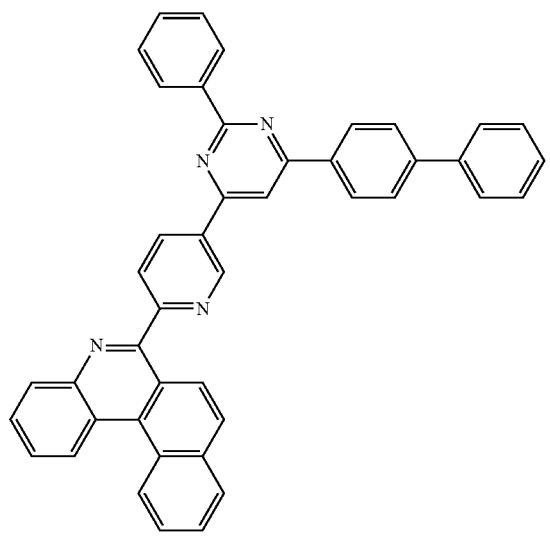
865
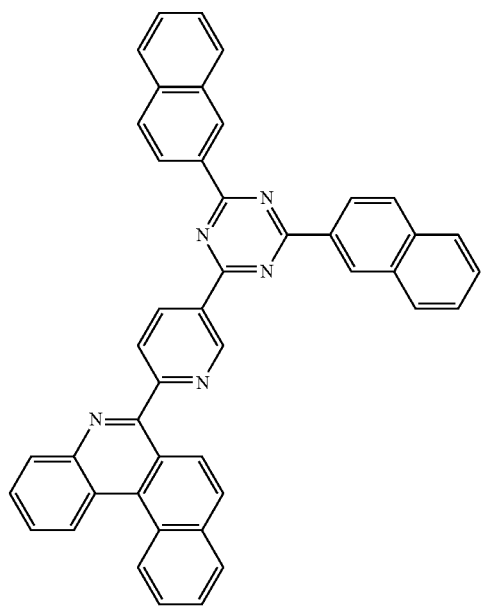
362
-continued
866
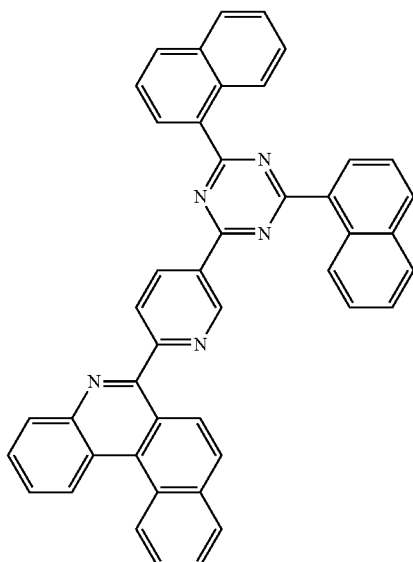
867
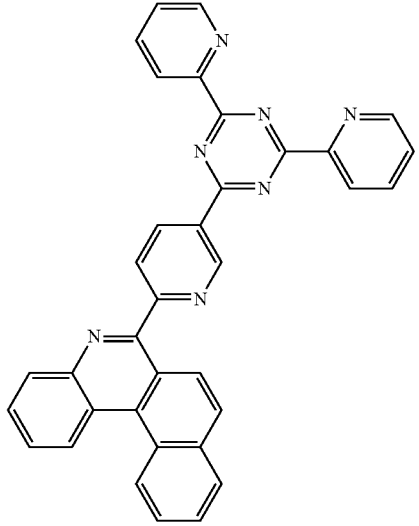
868
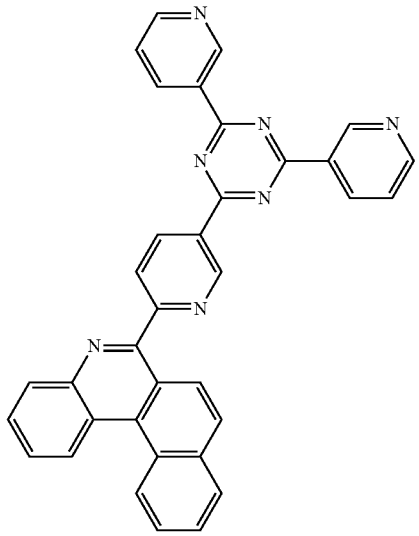

869
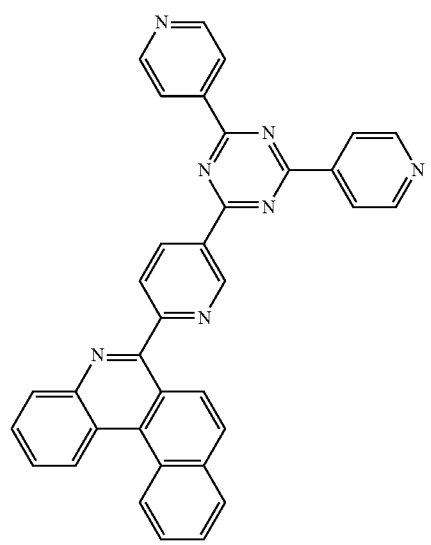
870
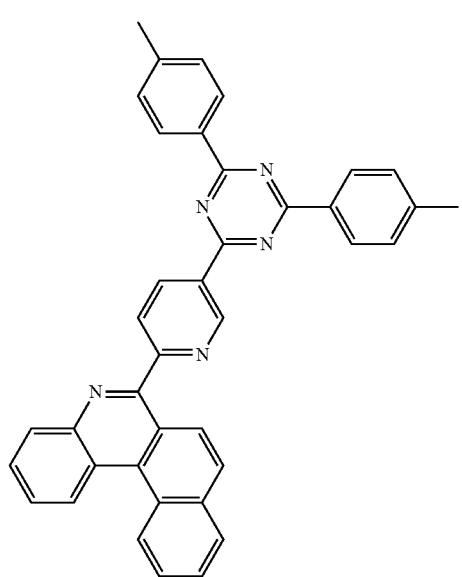
871
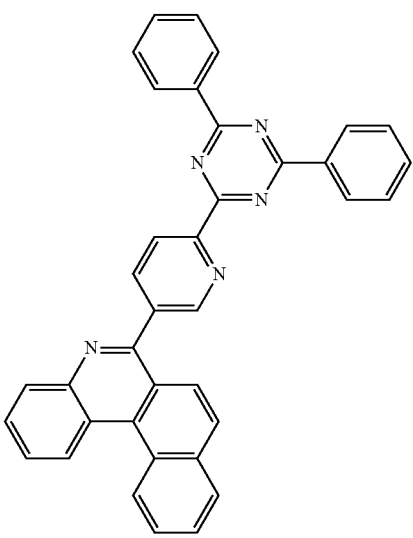
872
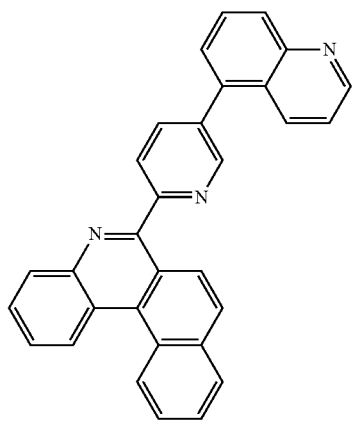
873
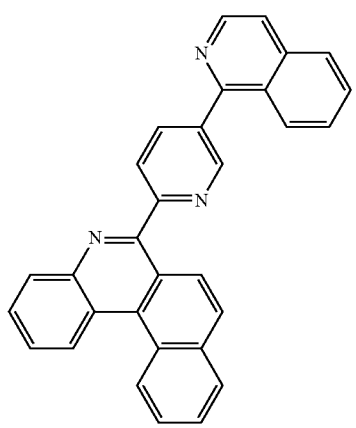
874
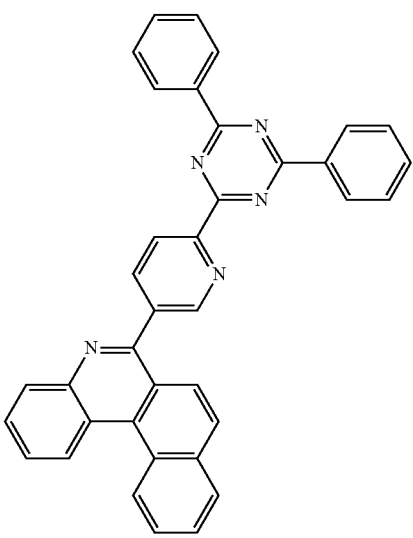

365
-continued
875
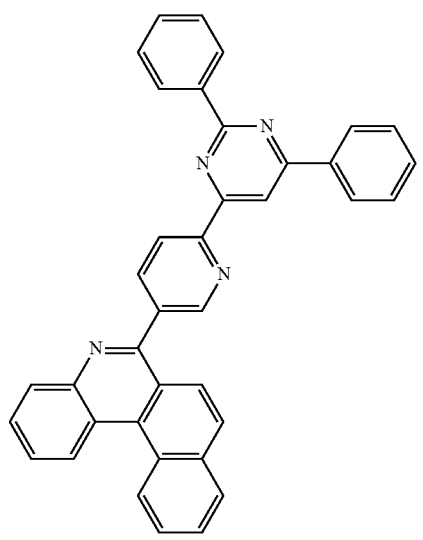
876
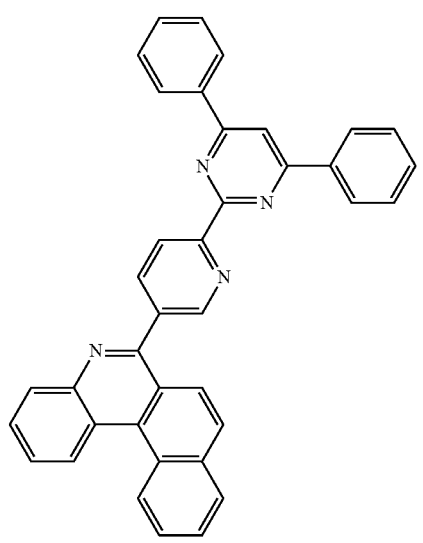
877
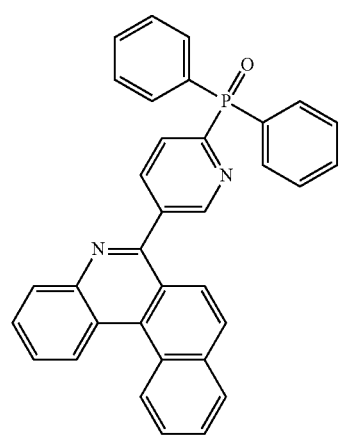
366
-continued
878
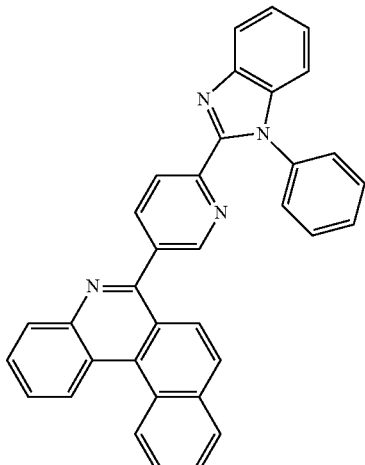
879
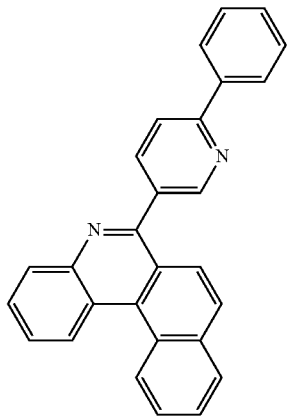
880
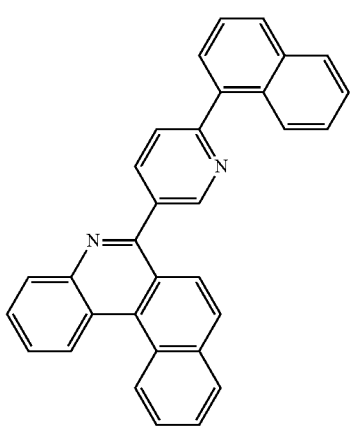

367
-continued
881
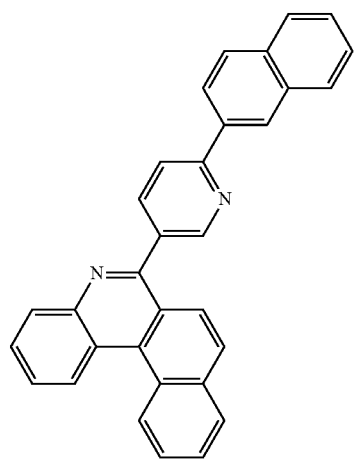
882
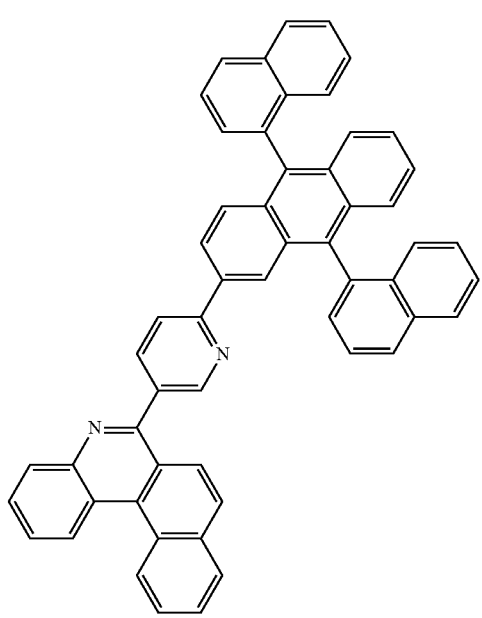
368
-continued
883
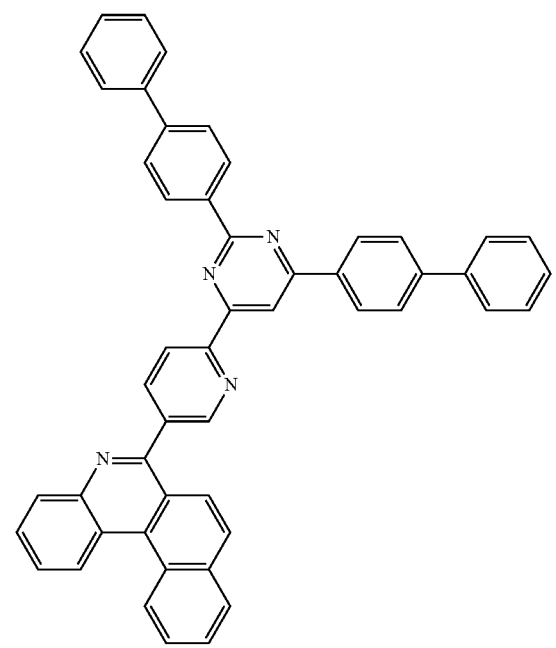
884
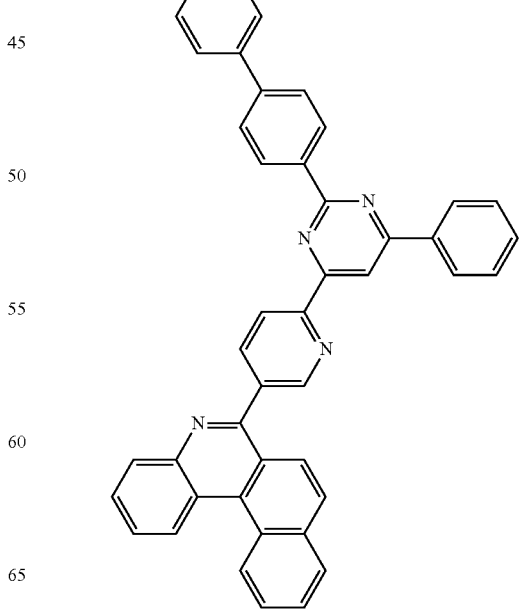

369
-continued
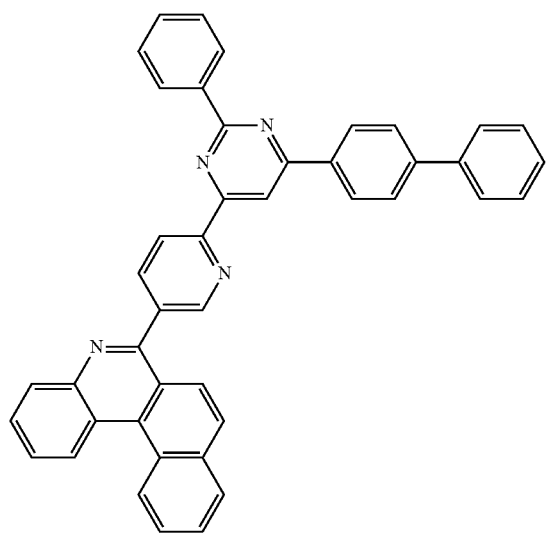
370
-continued
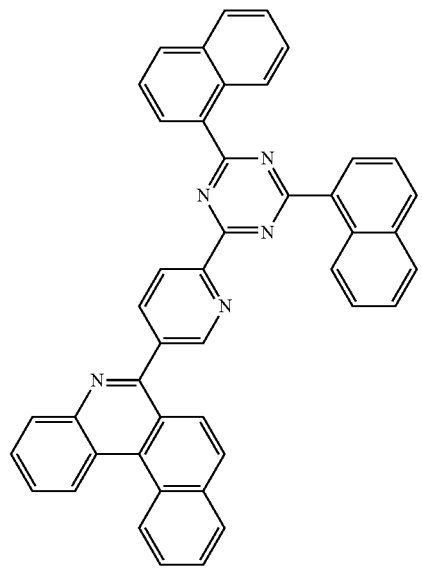
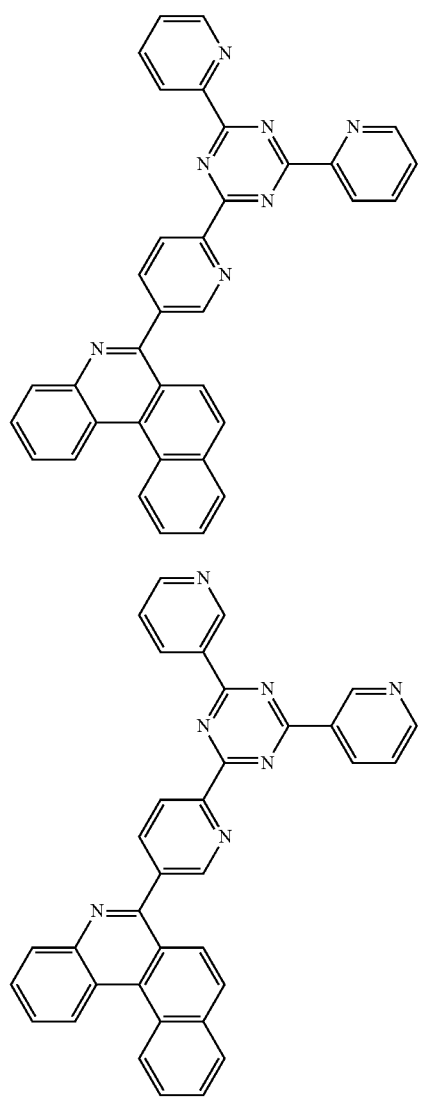

890
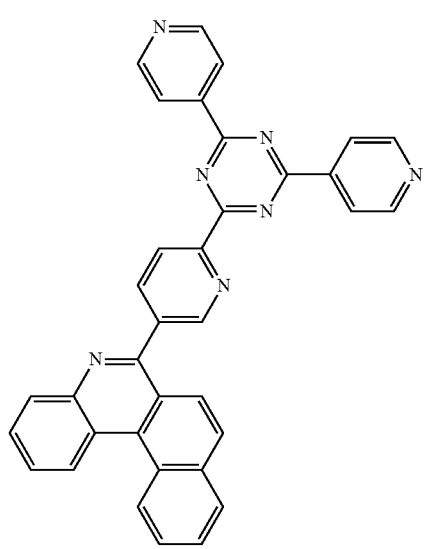
891
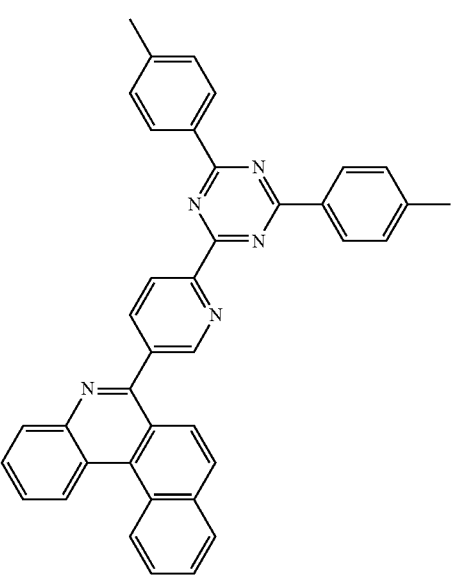
892
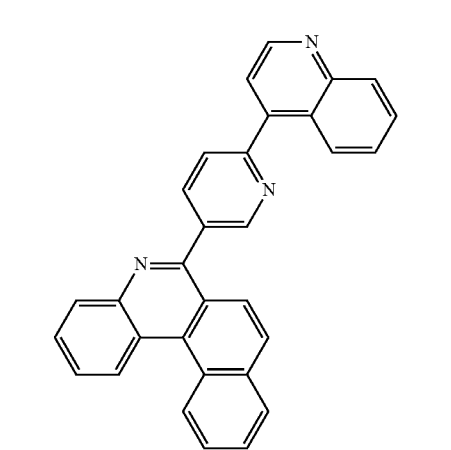
893
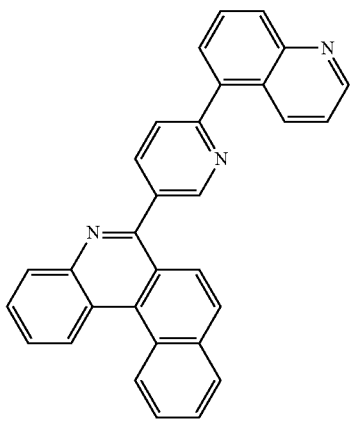
894
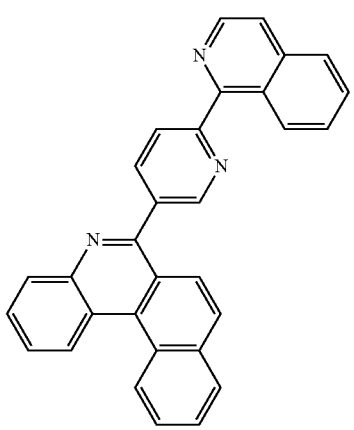
895
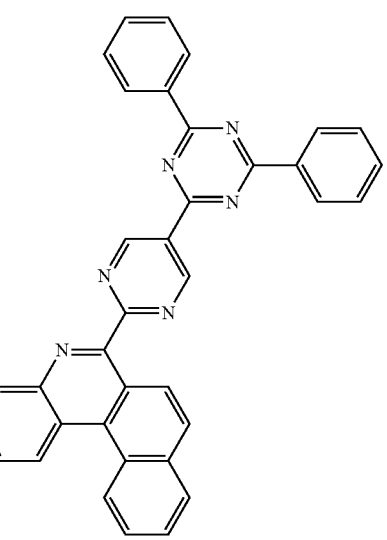

896 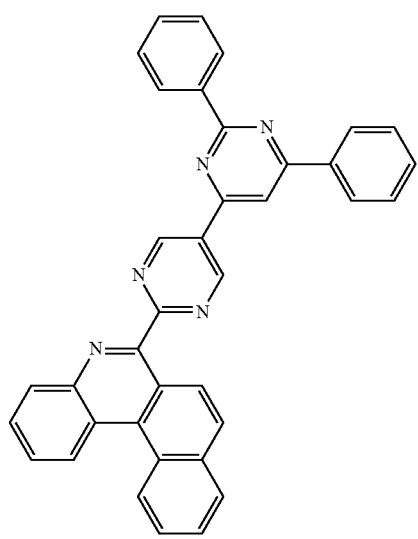
897 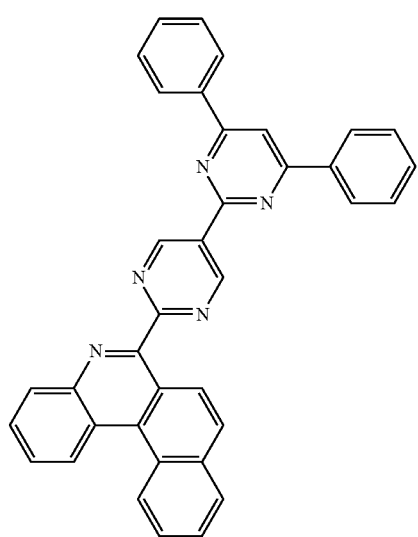
898 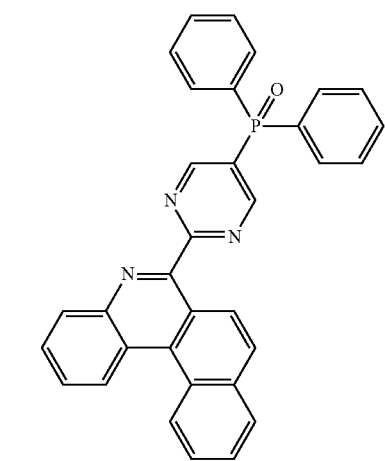
899 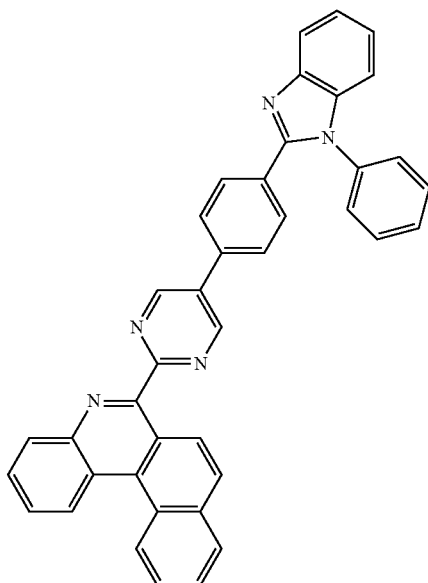
900 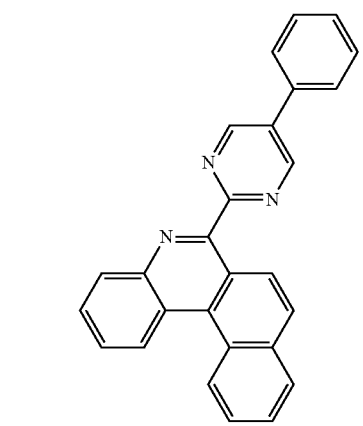
901 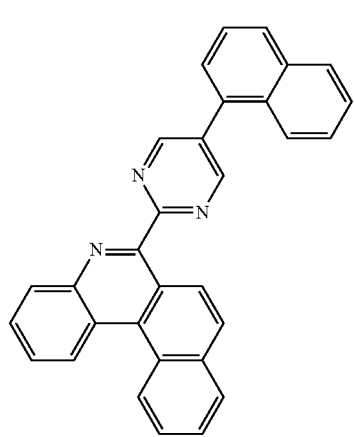

375
-continued
376
-continued
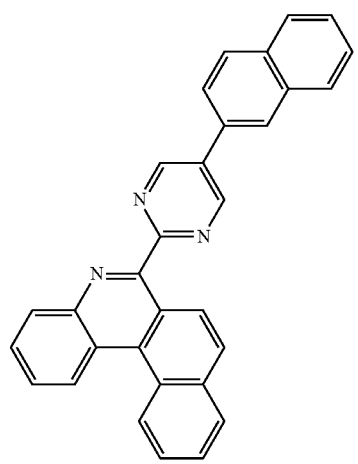
902
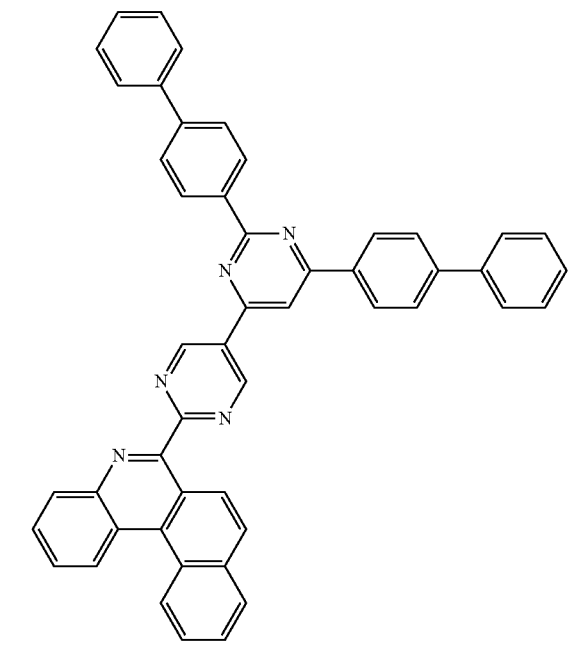
904
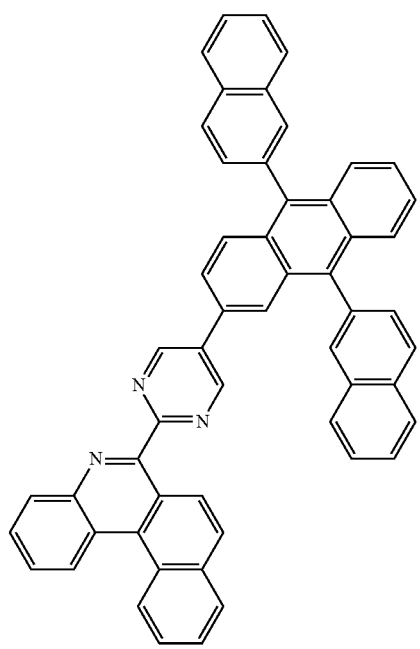
903
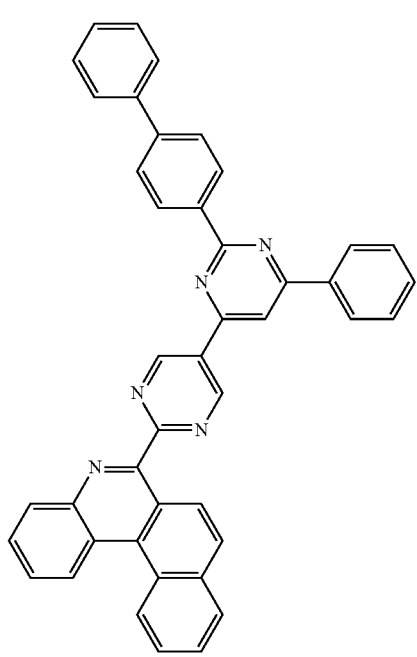
905

906
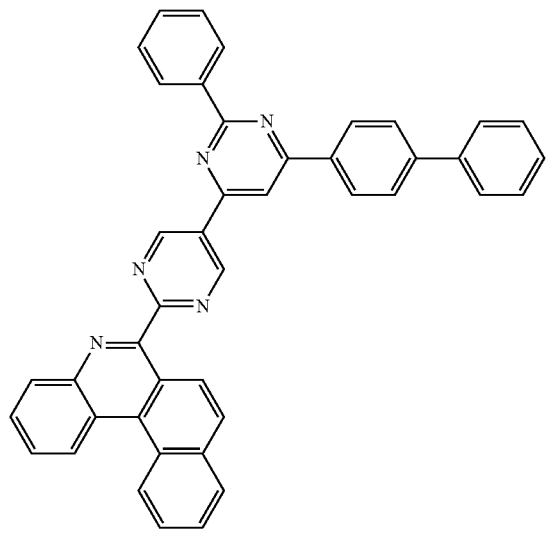
907
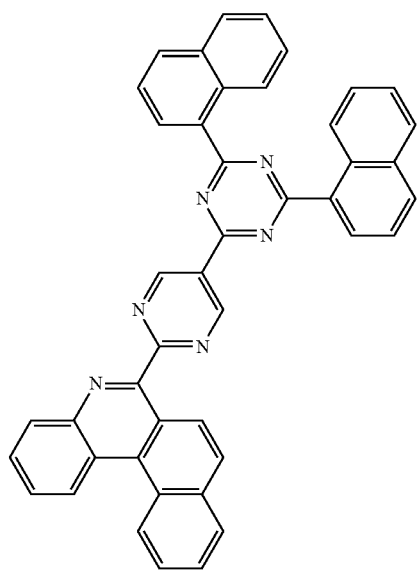
908
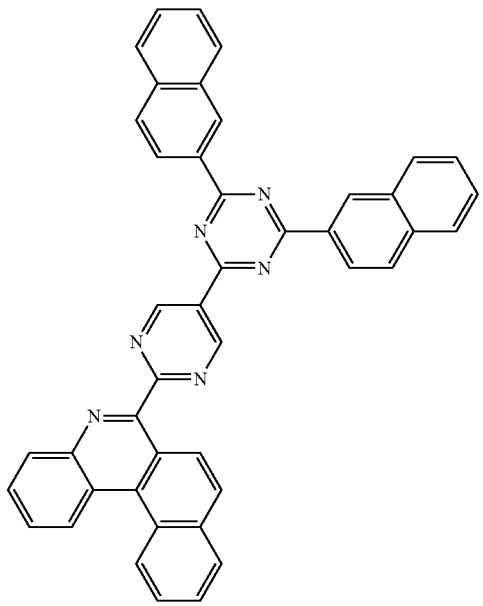
909
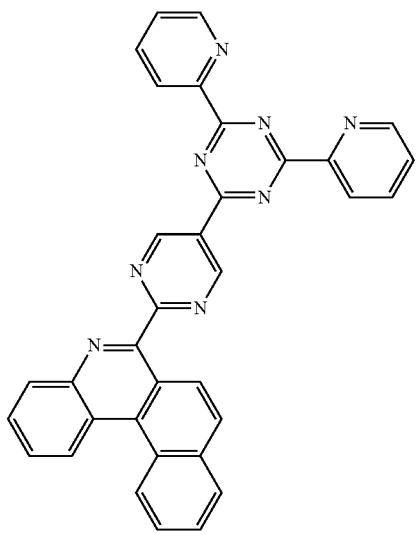

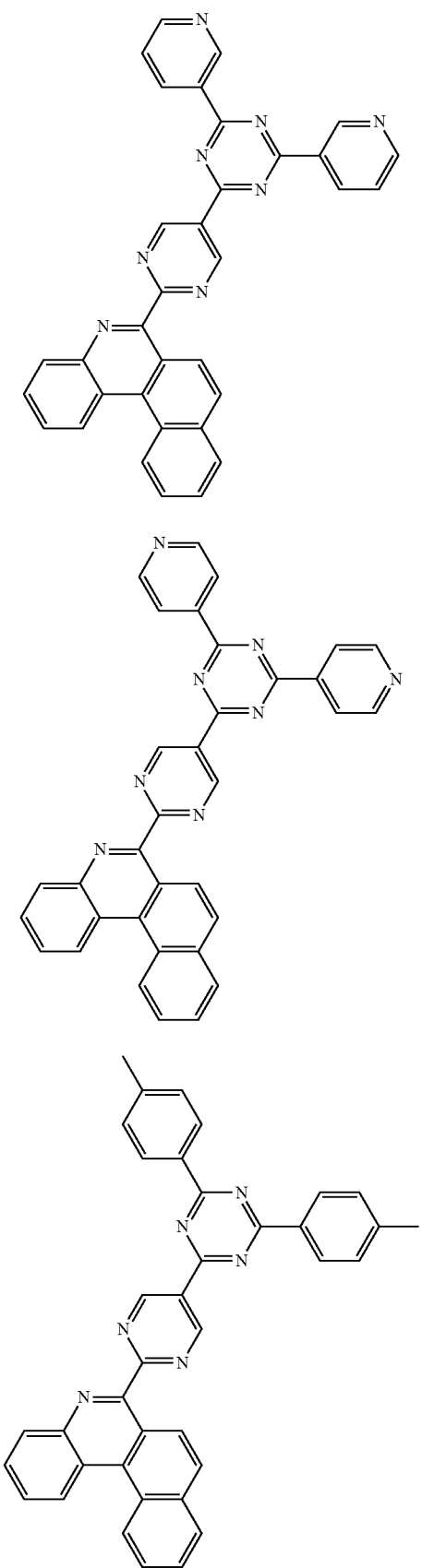
910
911
912
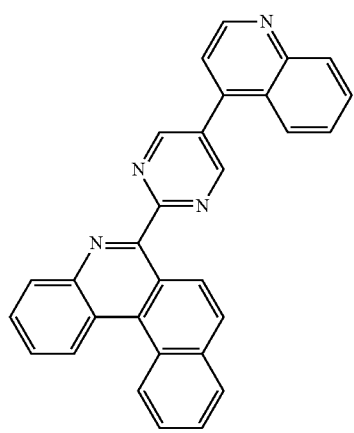
913
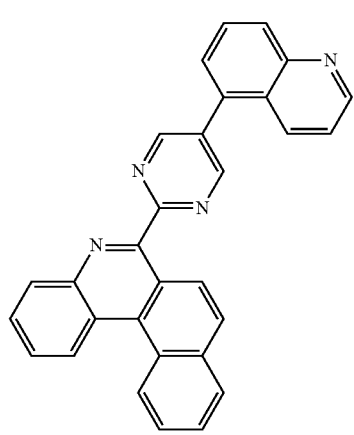
914
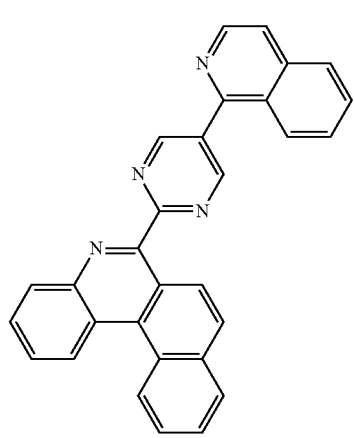
915

-continued
916
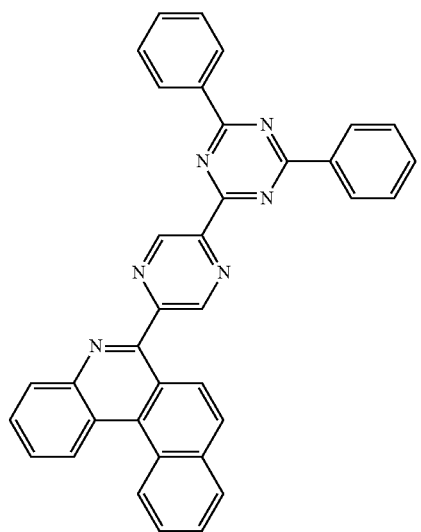
917
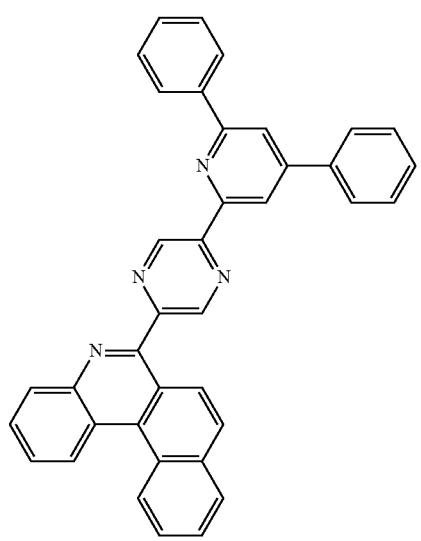
918
-continued
919
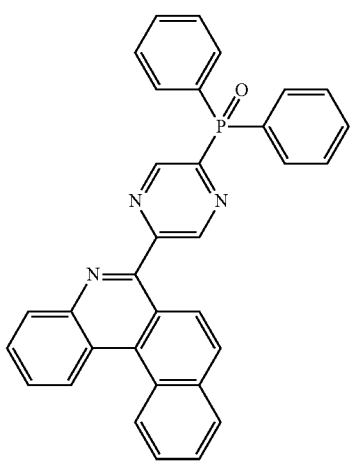
920
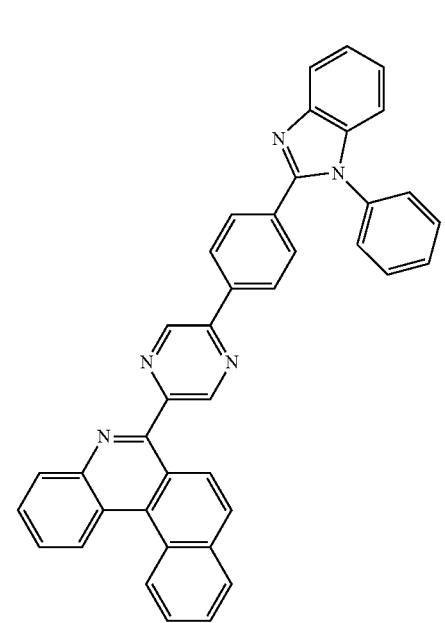
921
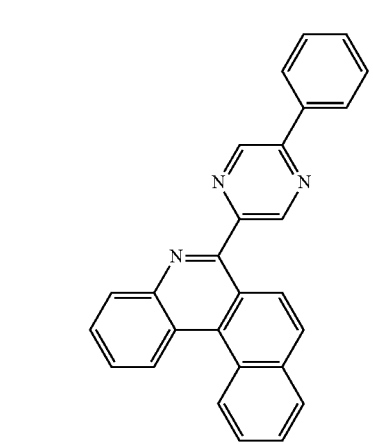

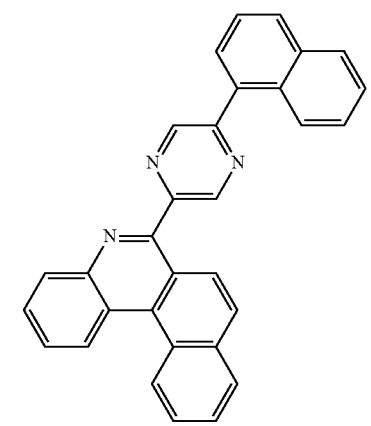
922
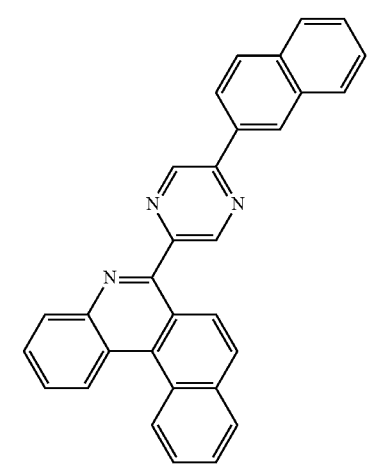
923
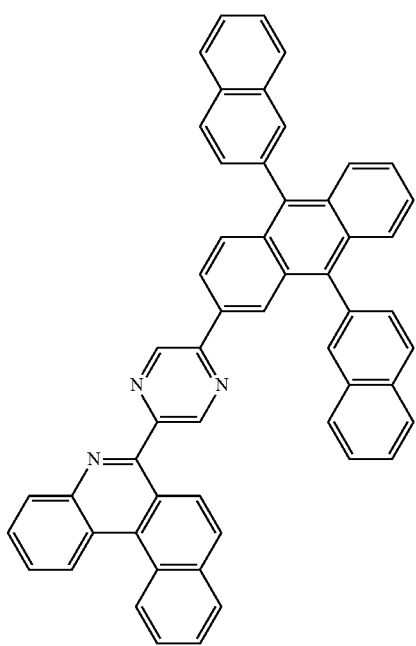
924
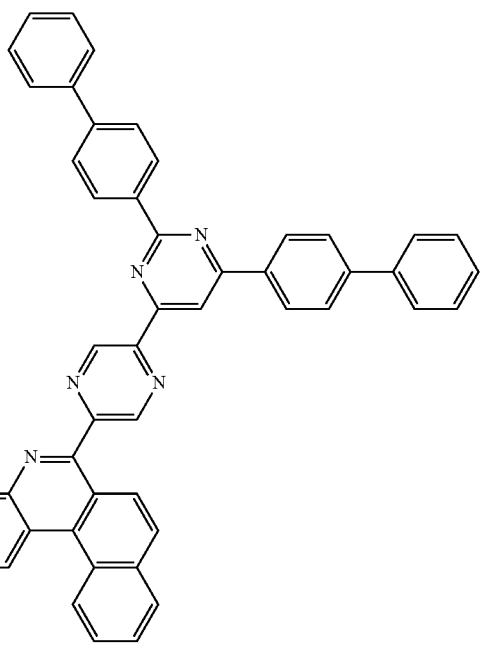
925
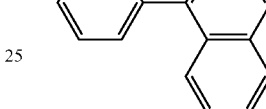
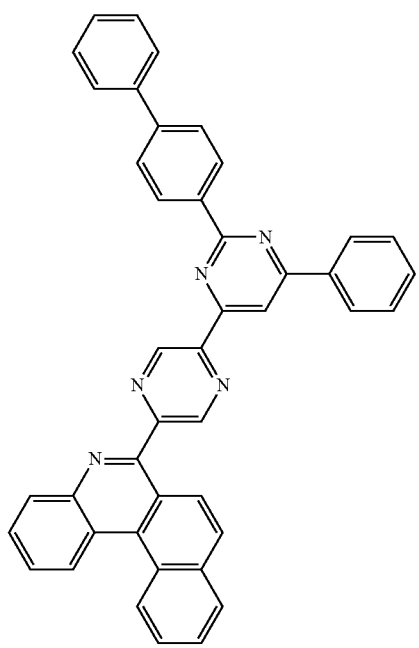
926

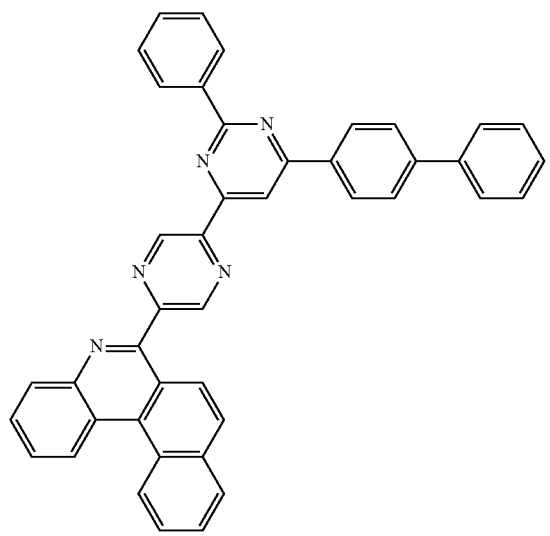
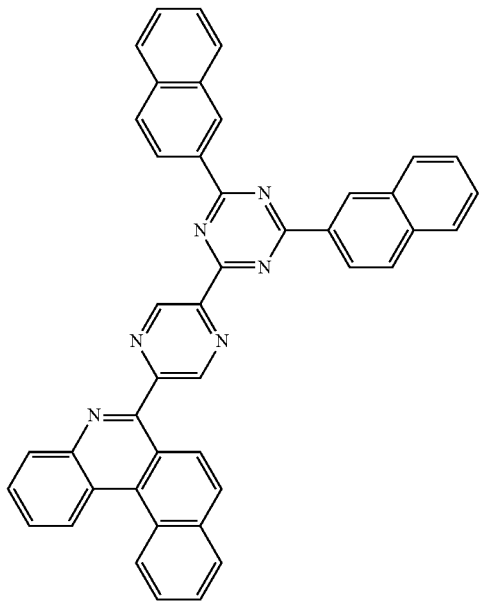
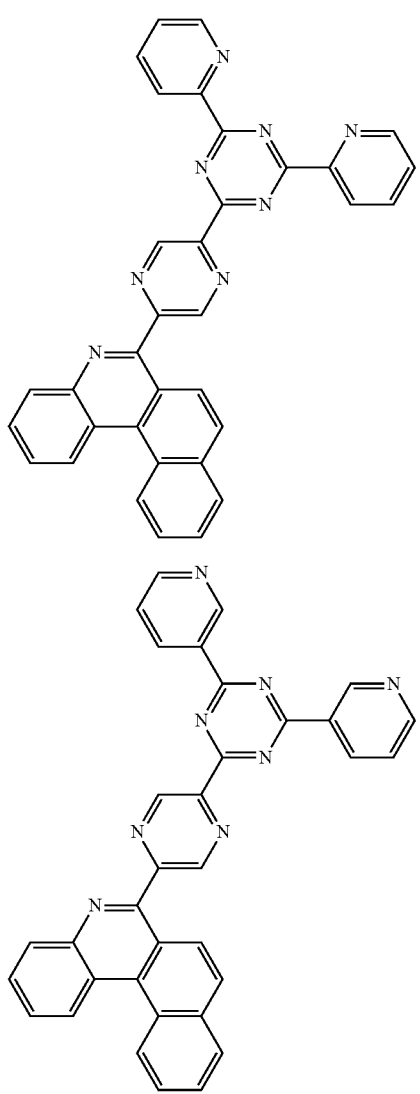

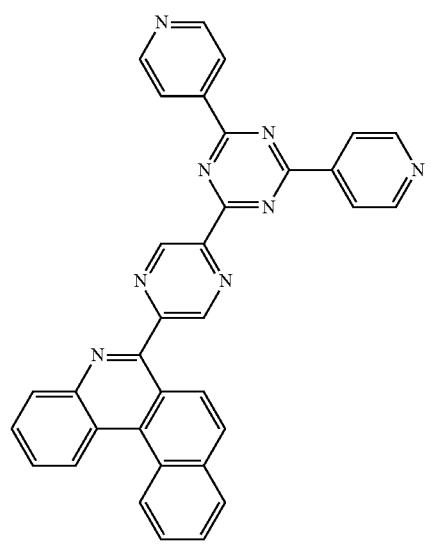
932
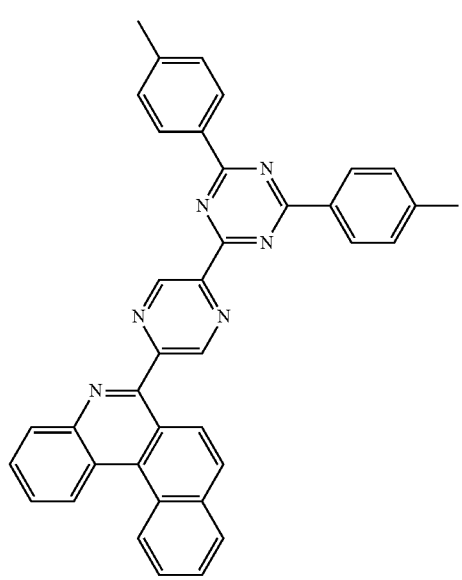
933
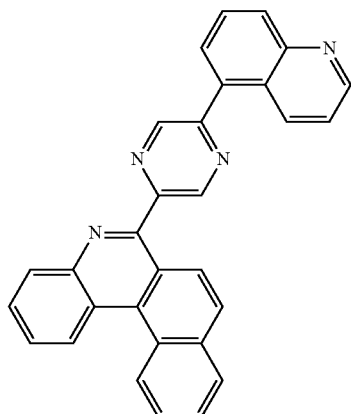
935
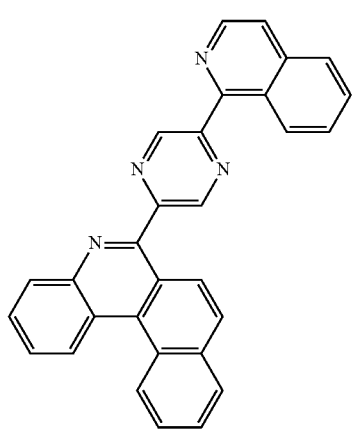
936
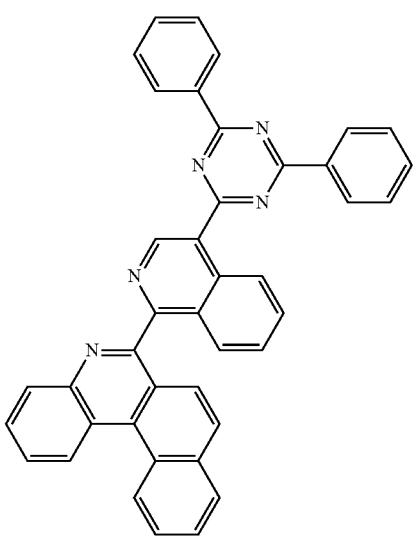
937

389
-continued
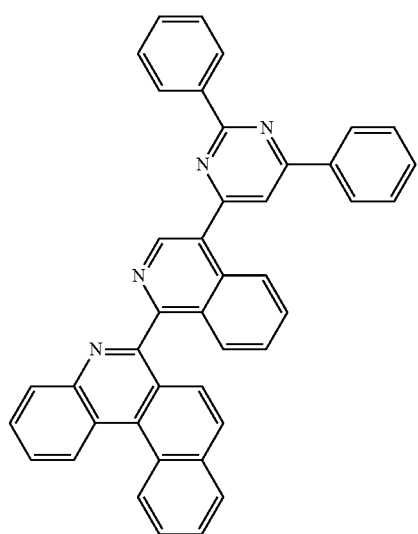
938
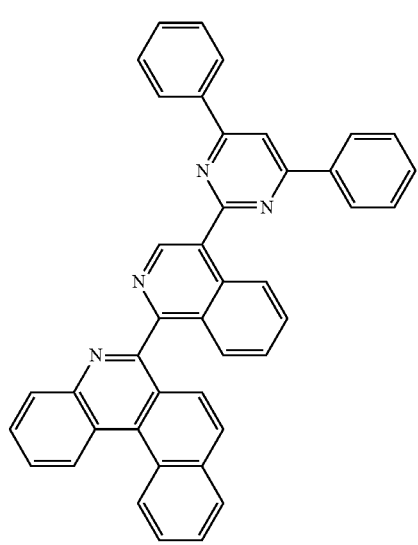
939
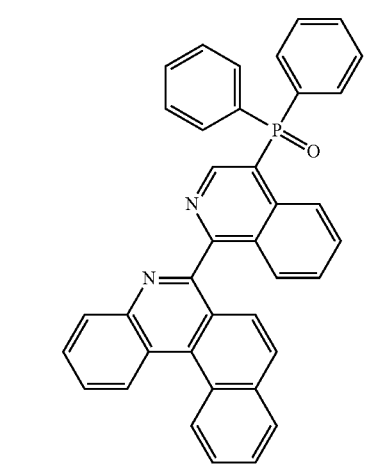
940
390
-continued
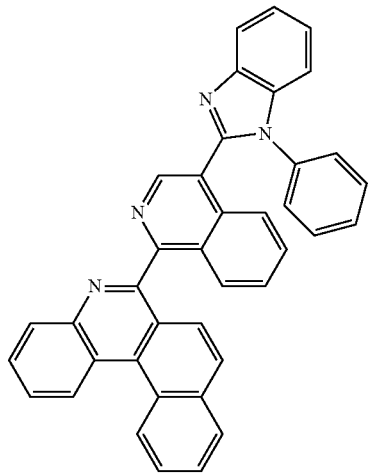
941
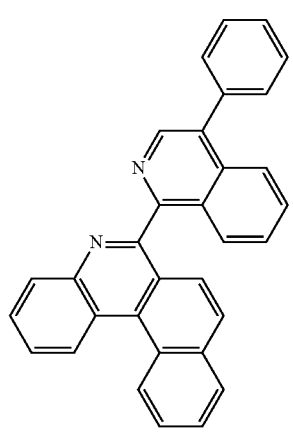
942
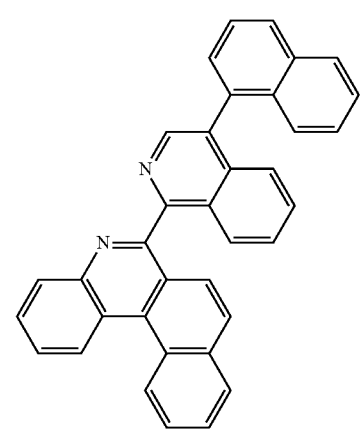
943

391
-continued
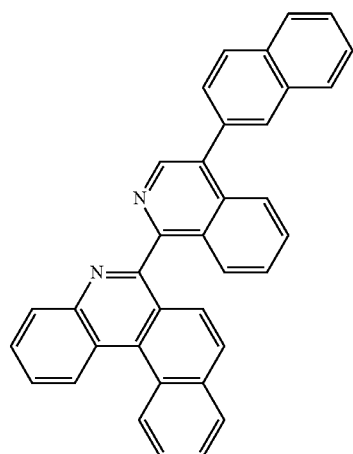
944
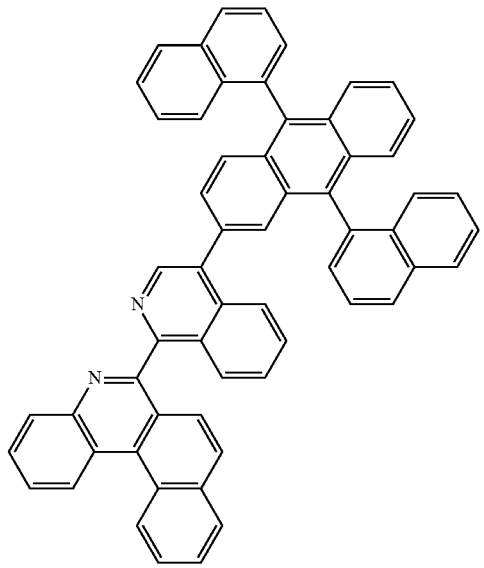
945
392
-continued
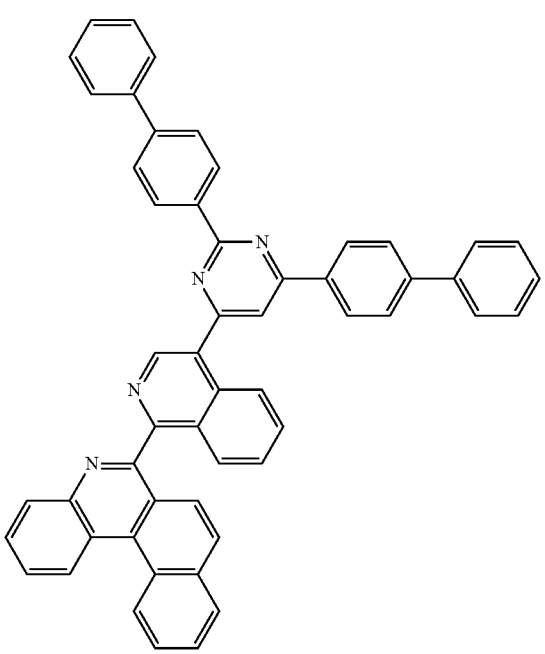
946
947

948
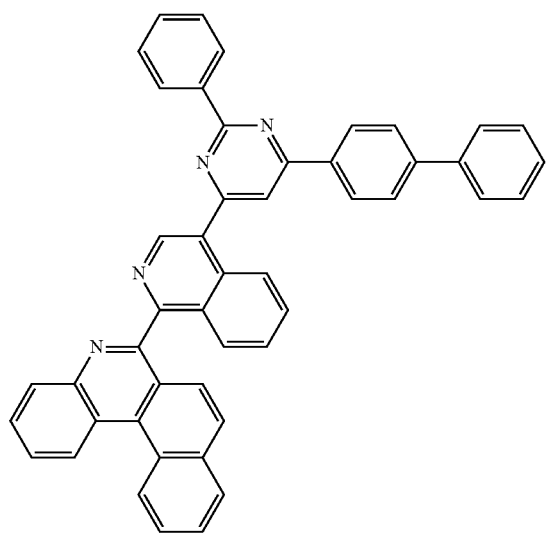
949
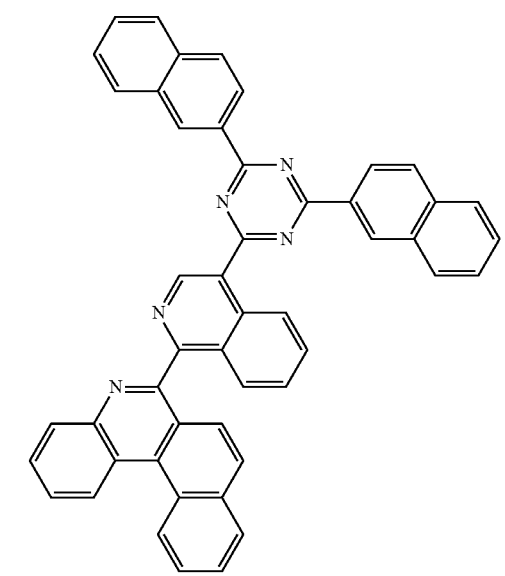
950
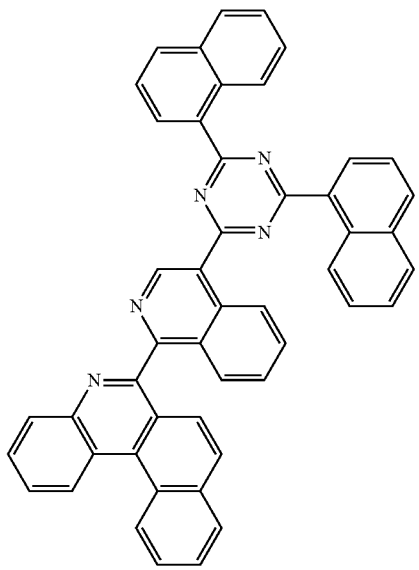
951
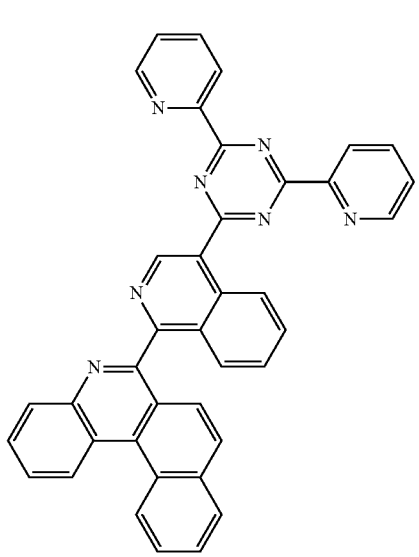
952
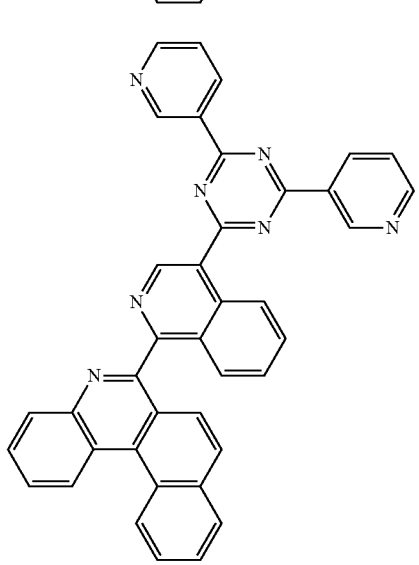

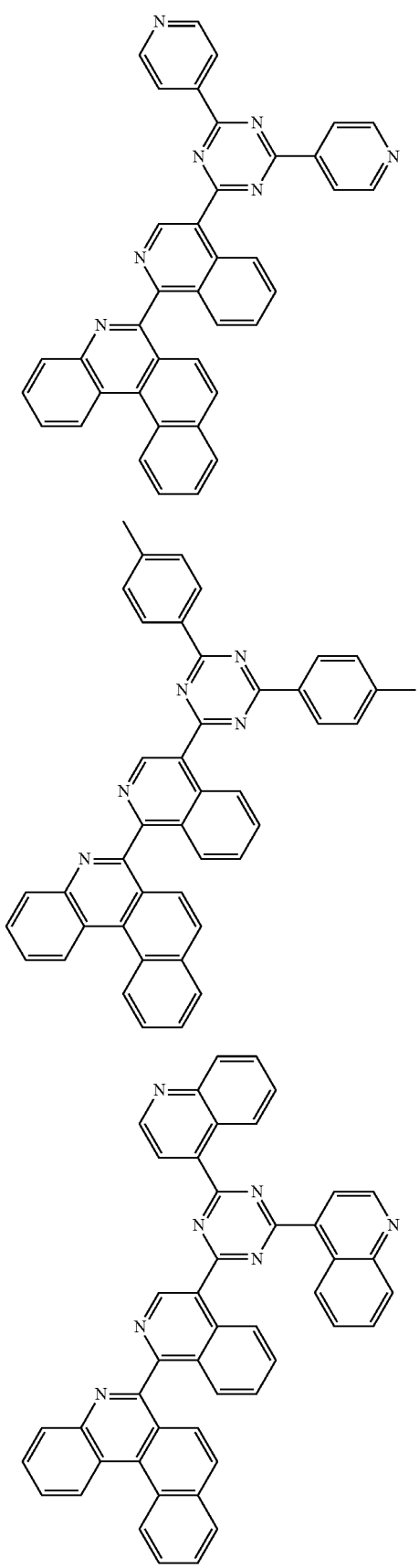
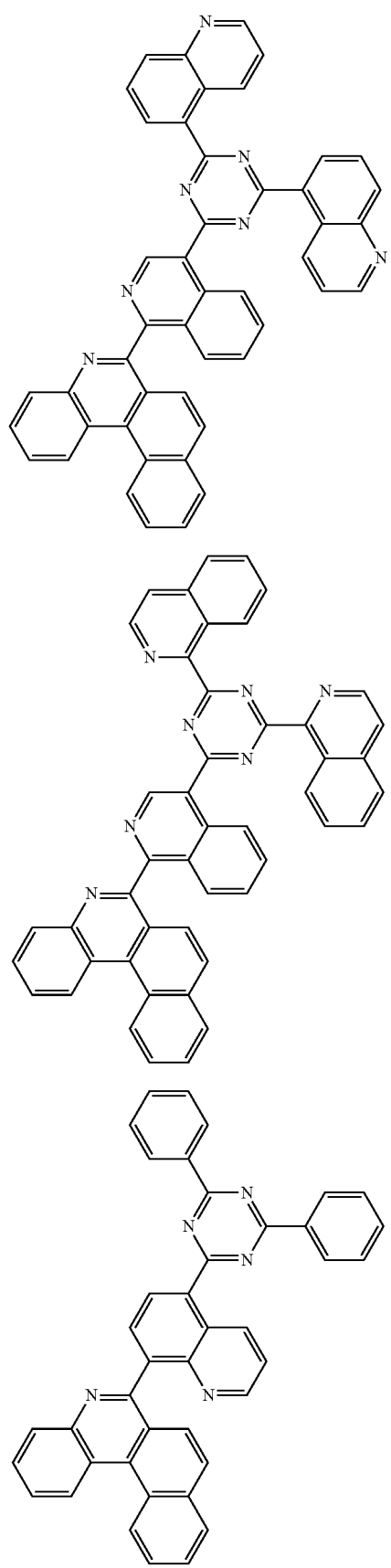

-continued
959
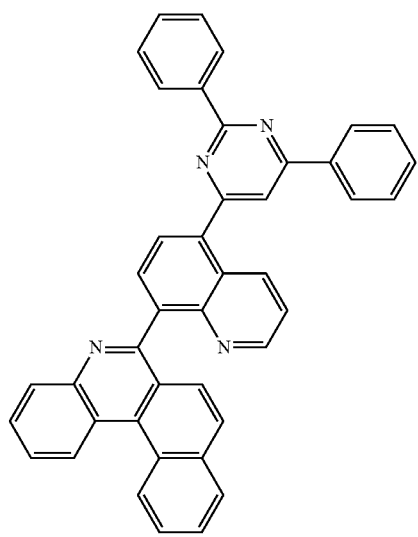
960
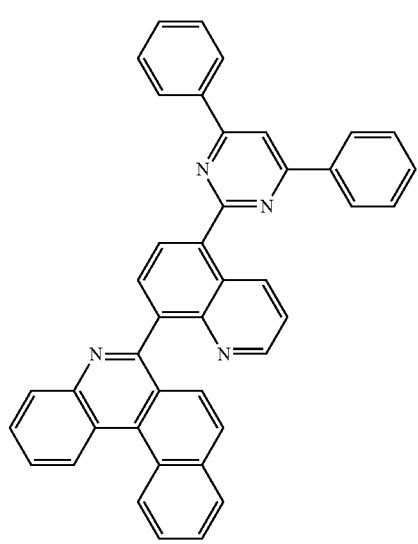
961
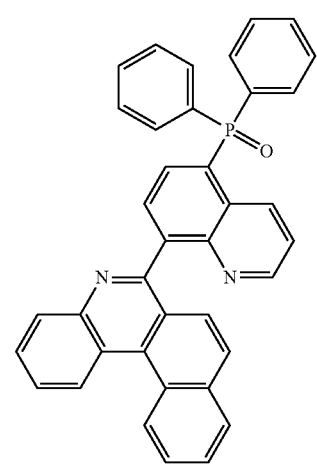
-continued
962
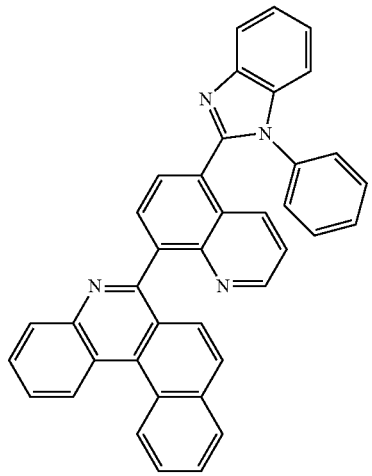
963
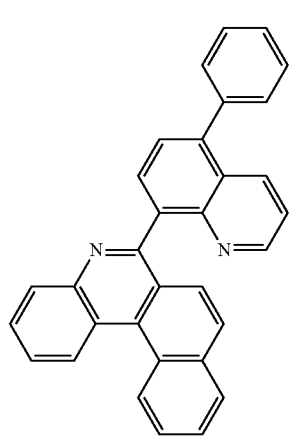
964
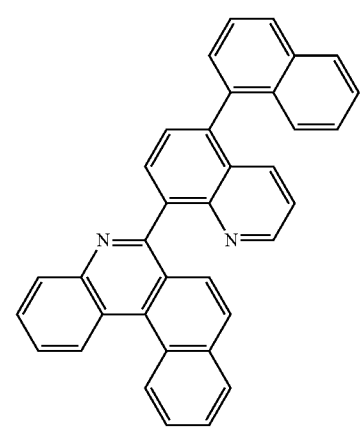

399
-continued
965
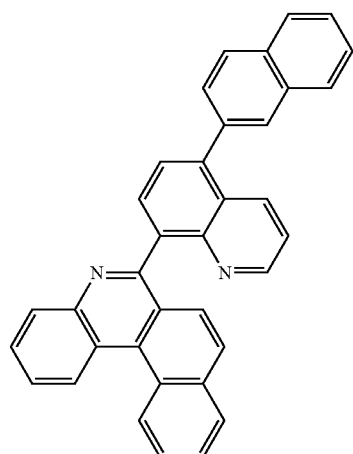
966
400
-continued
967
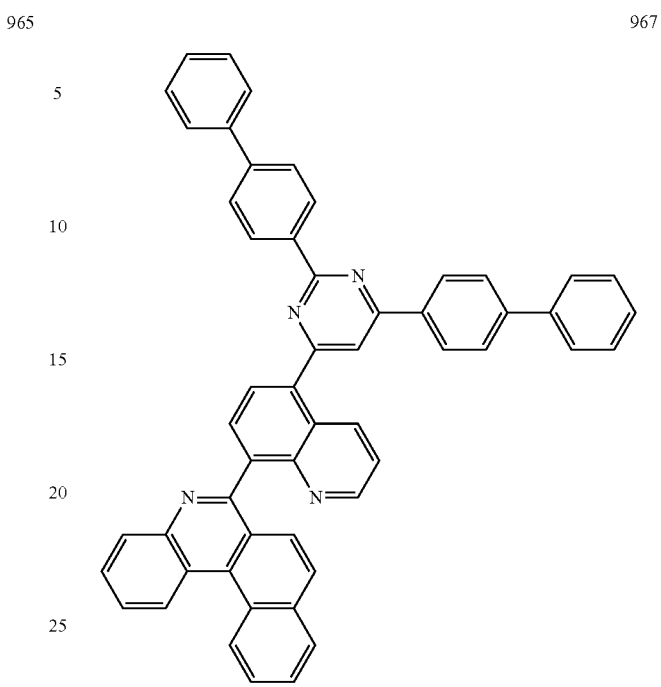
968
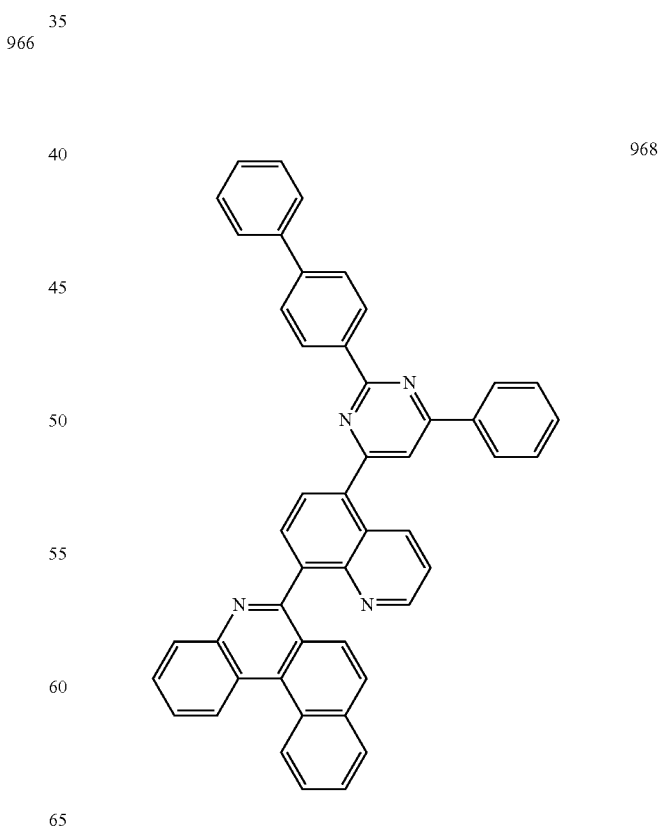

401
-continued
969
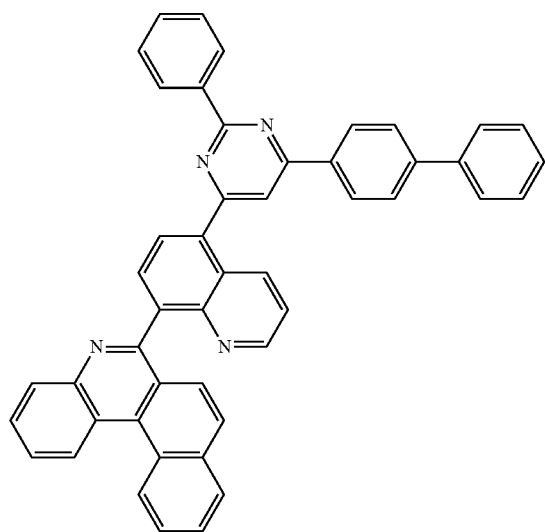
970
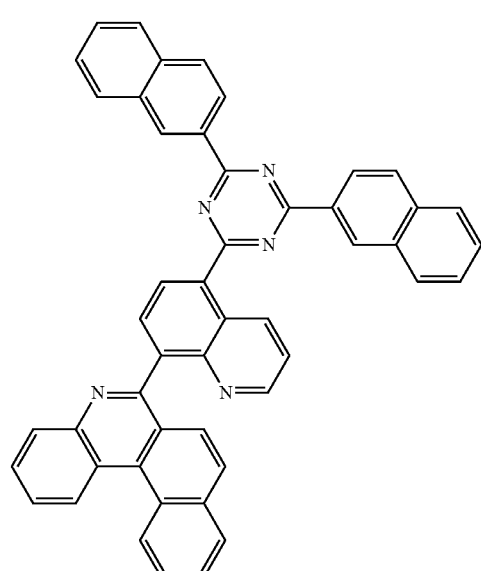
402
-continued
971
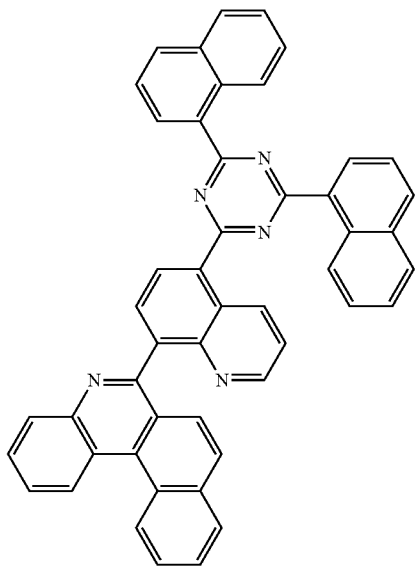
972
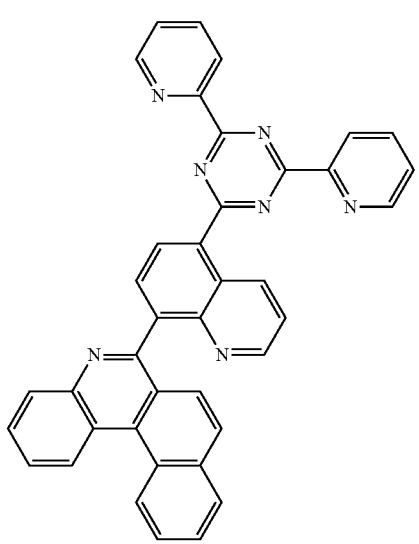
973
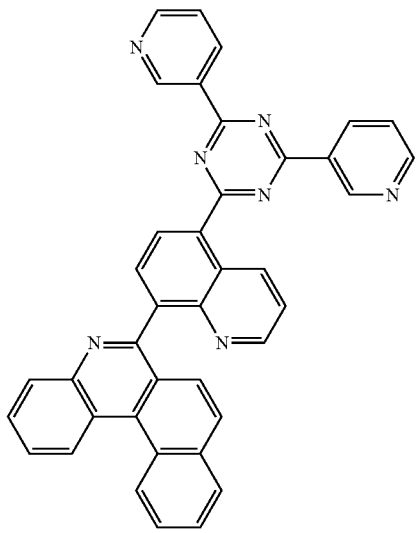

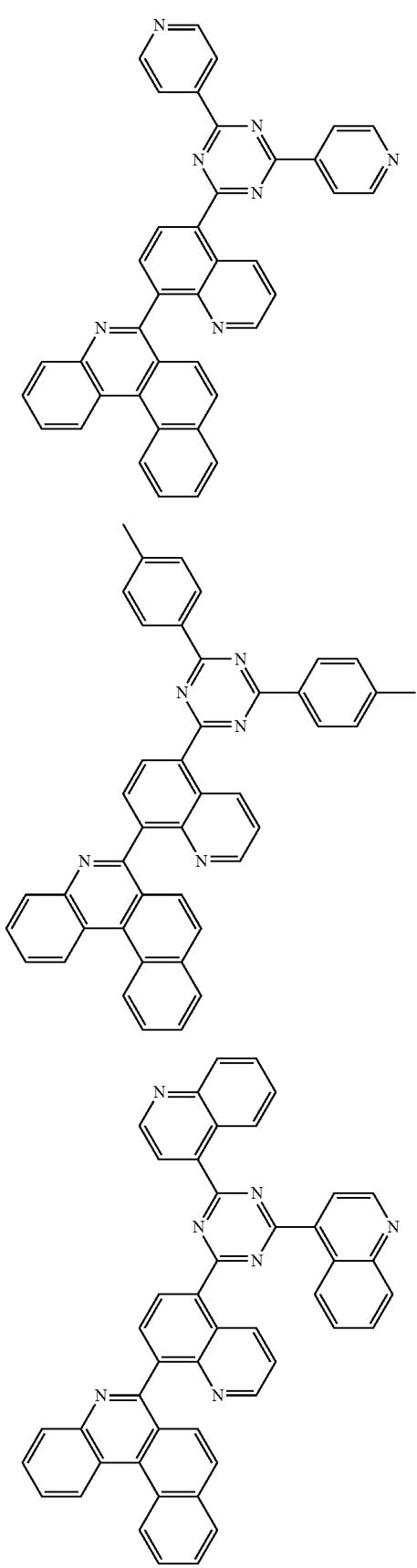
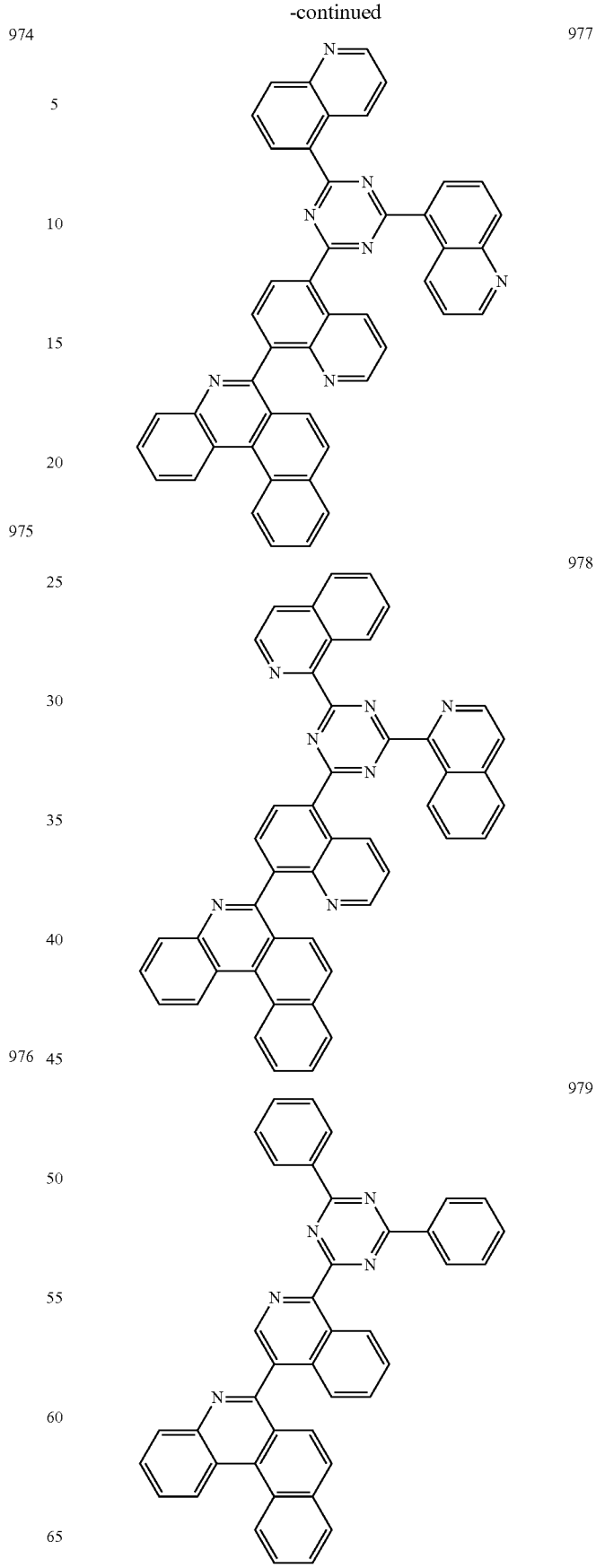

405
-continued
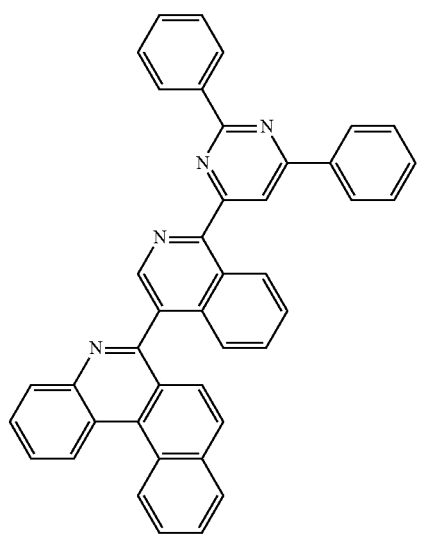
980
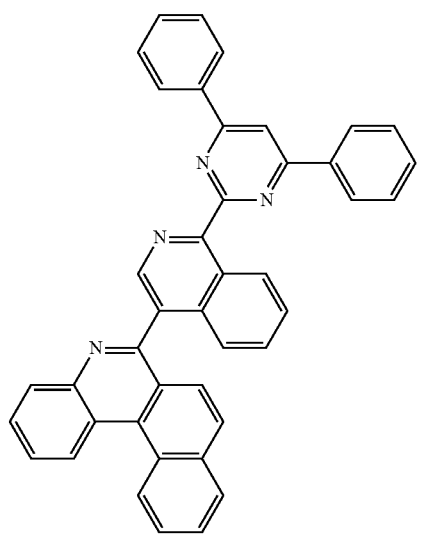
981
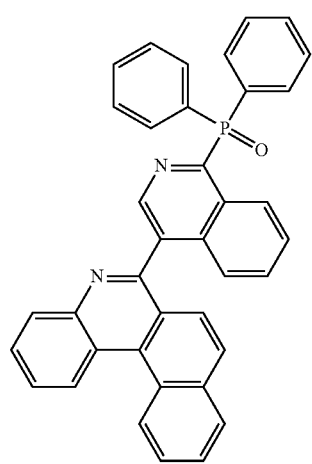
982
406
-continued
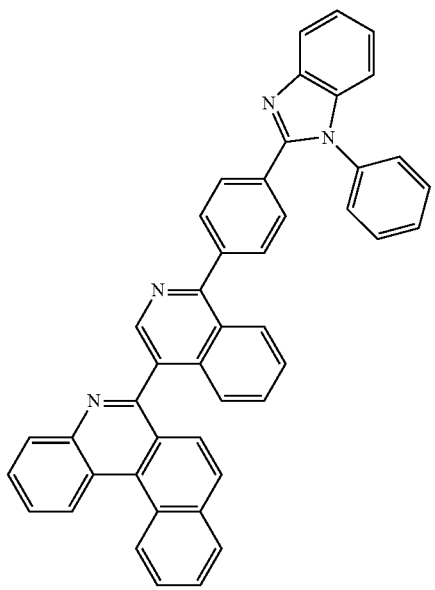
983
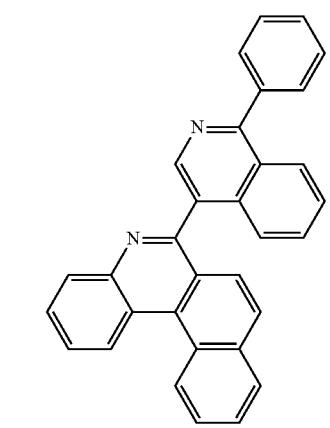
984
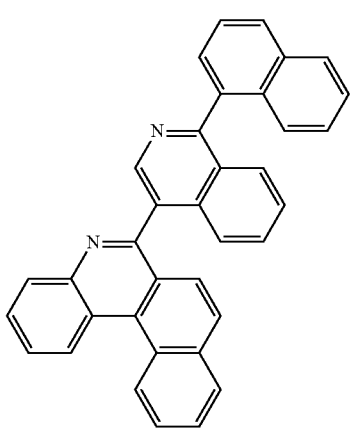
985

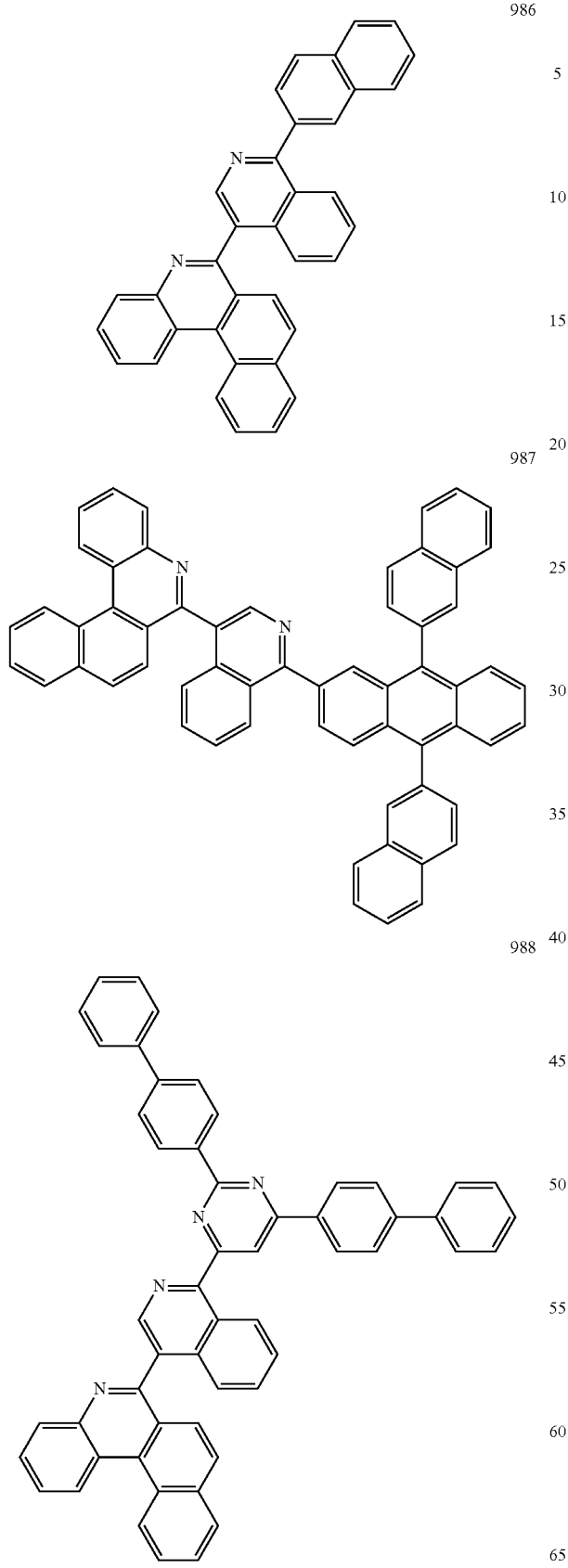
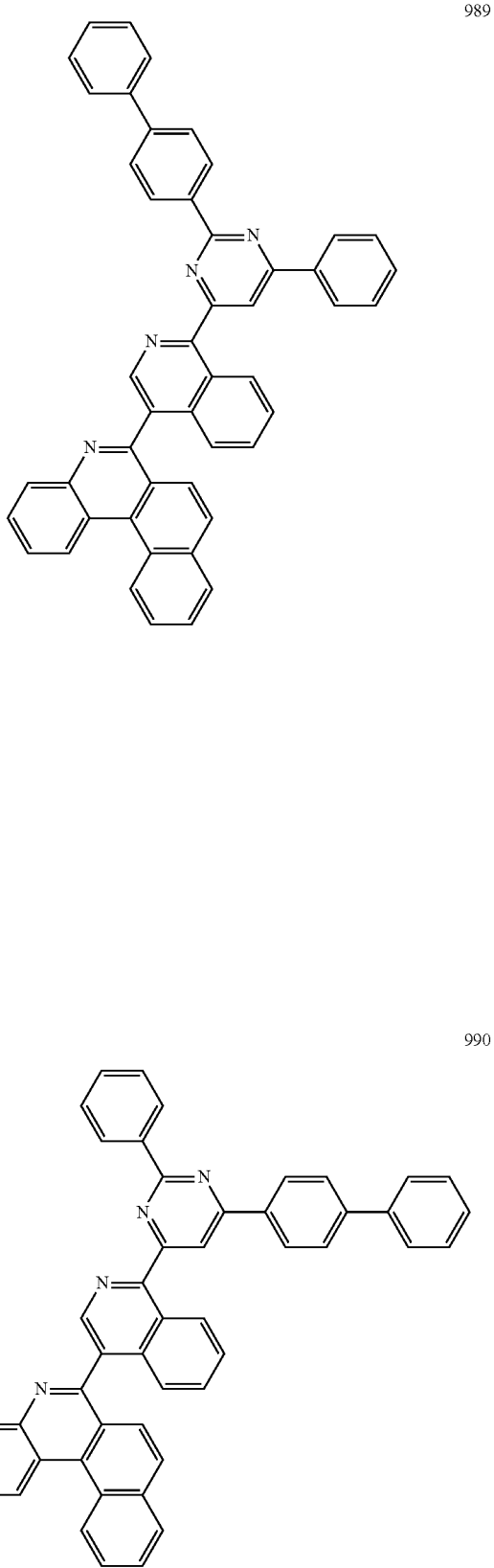

409
-continued
991
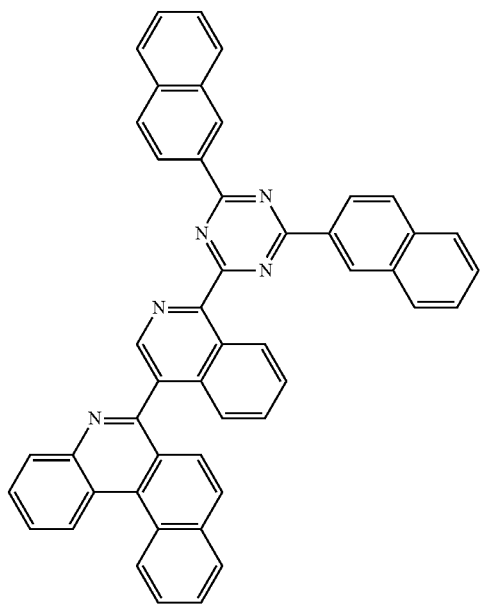
992
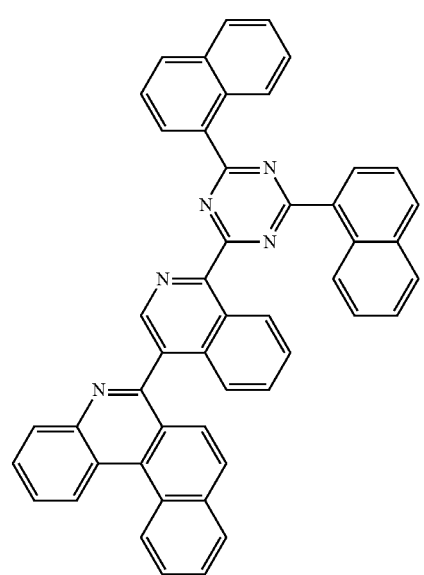
410
-continued
993
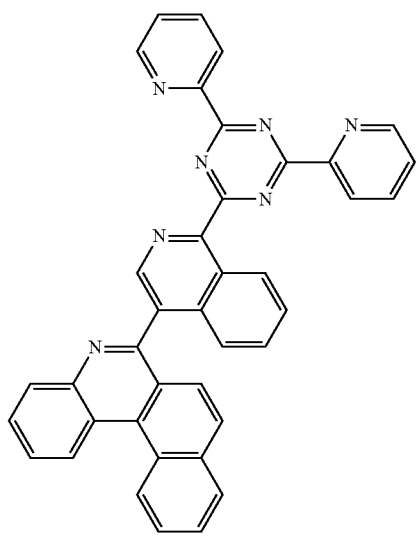
994
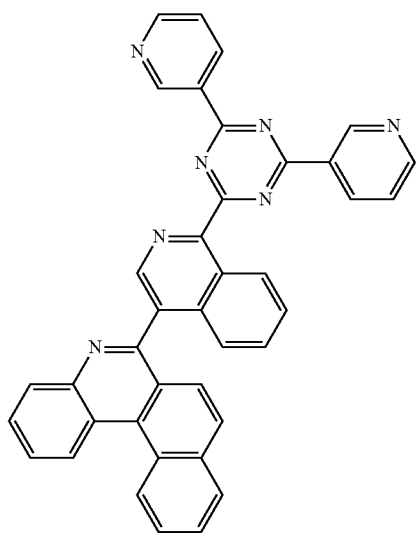
995
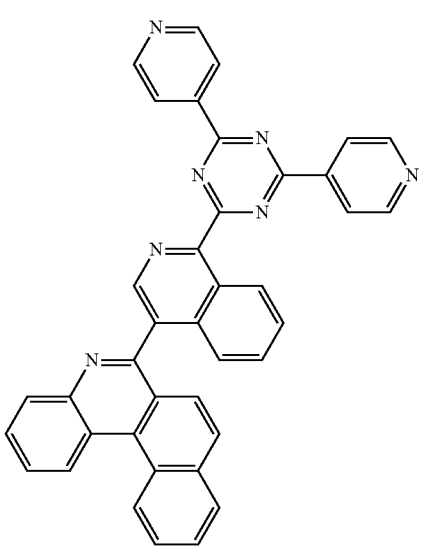

411
-continued
996
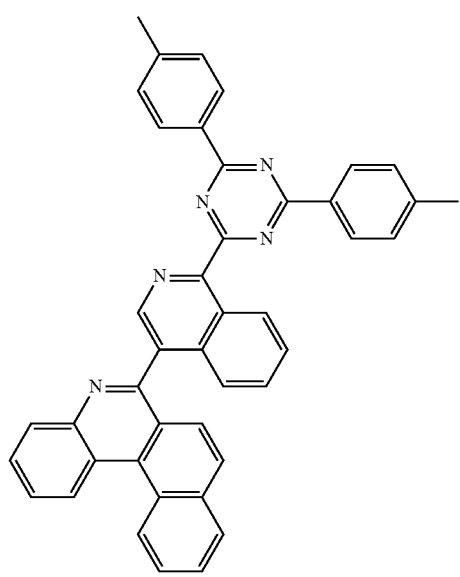
997
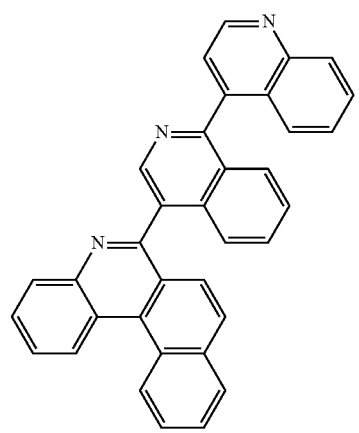
998
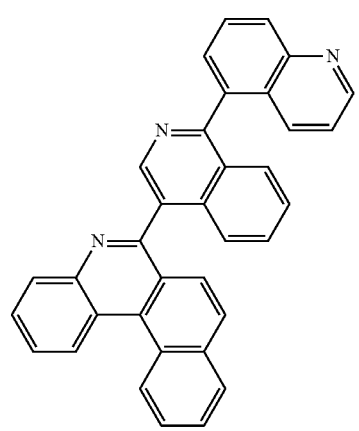
412
-continued
999
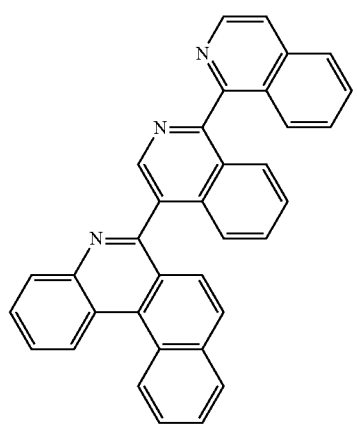
1000
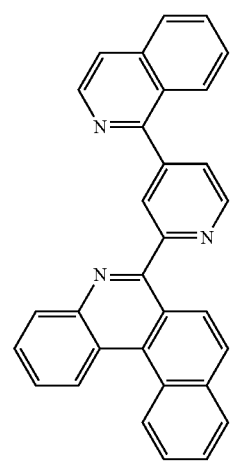
1001
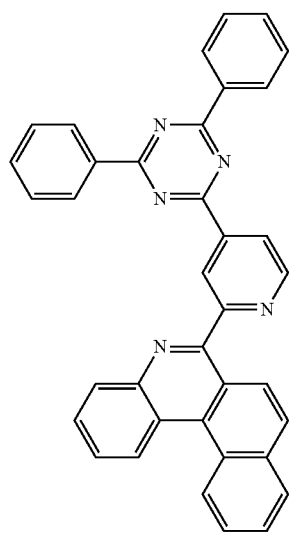

-continued
1002
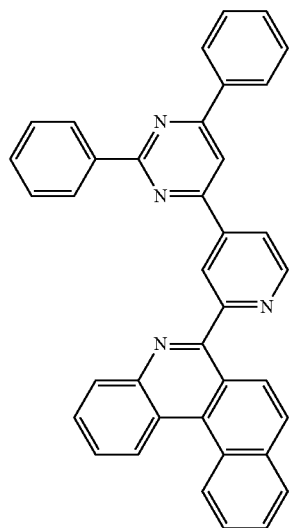
1003
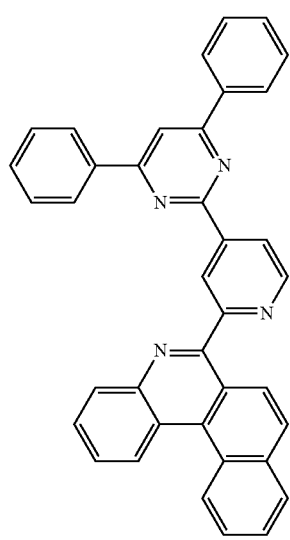
1004
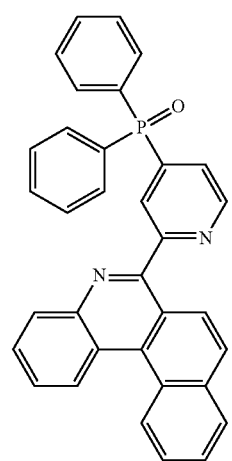
-continued
1005
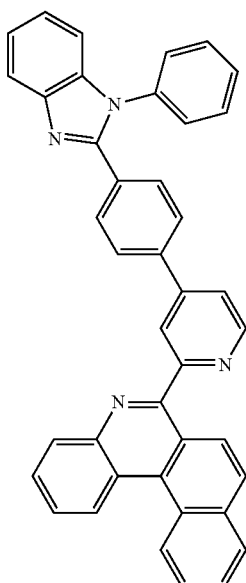
1006
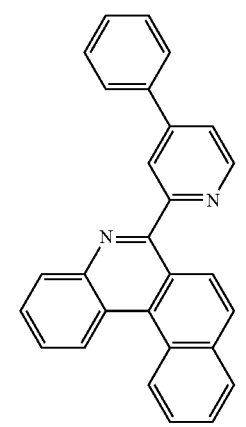
1007
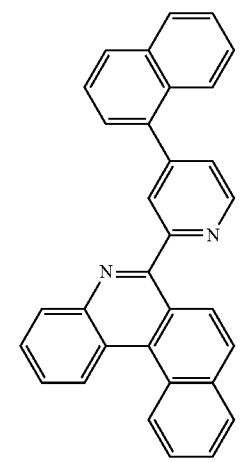

415
-continued
1008
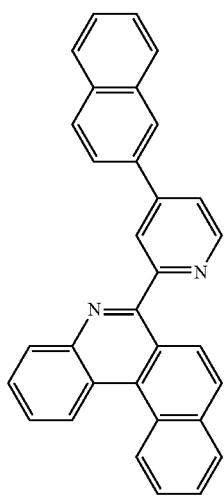
1009
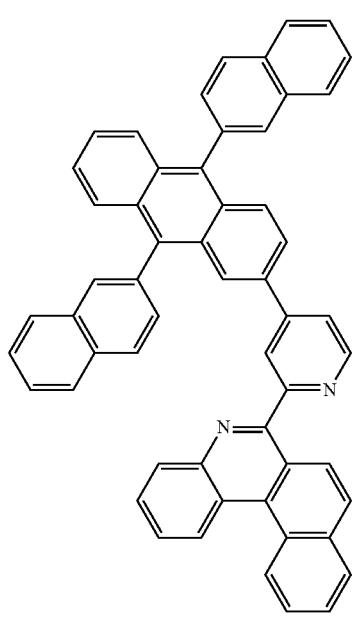
416
-continued
1010
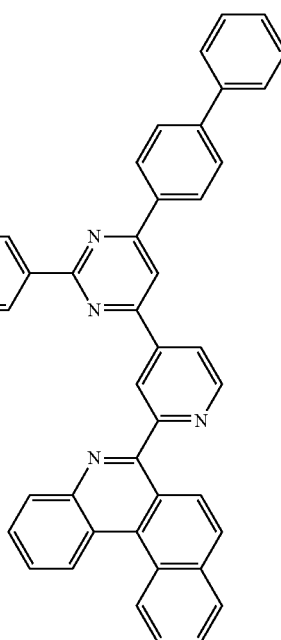
1011
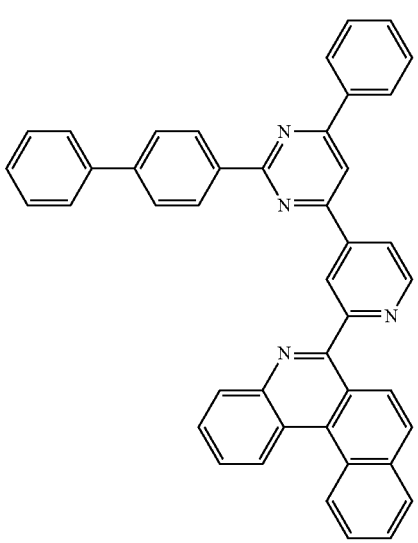

1012
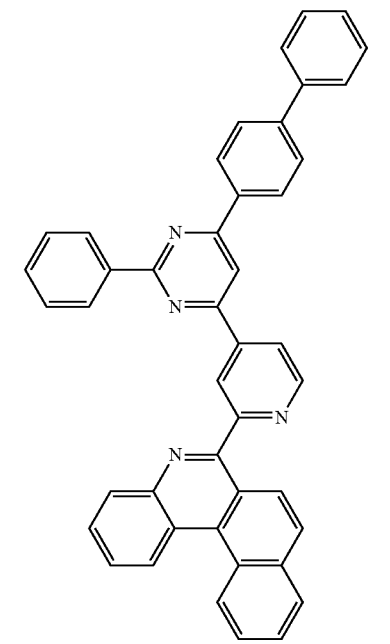
1013
1014
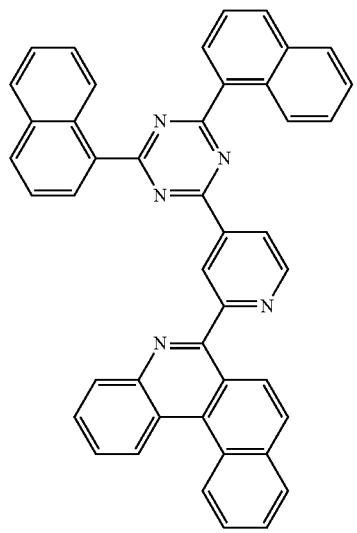
1015
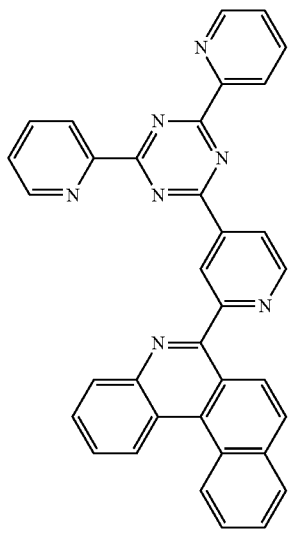
1016
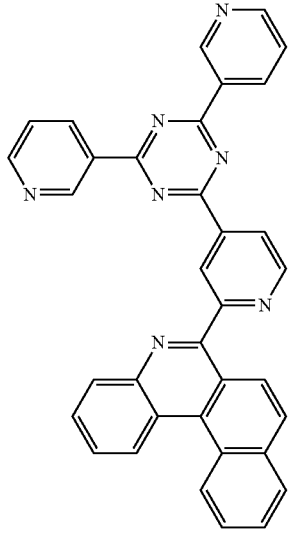

-continued
1017
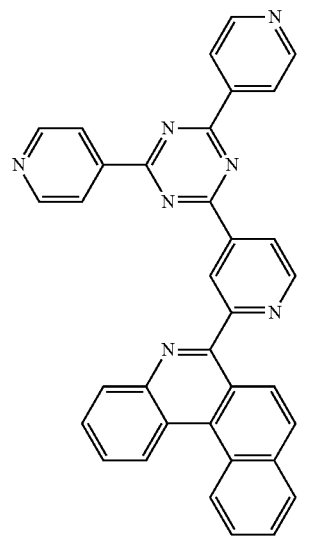
1018
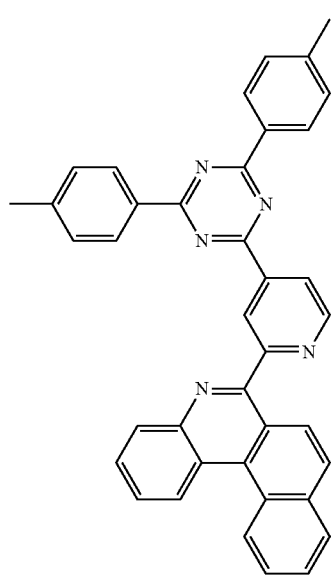
1019
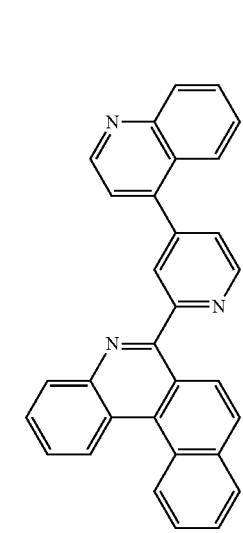
-continued
1020
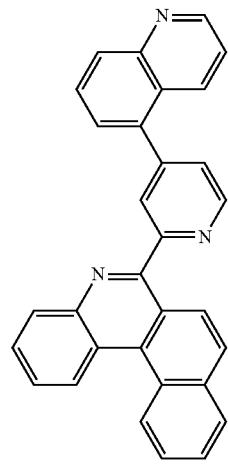
1021
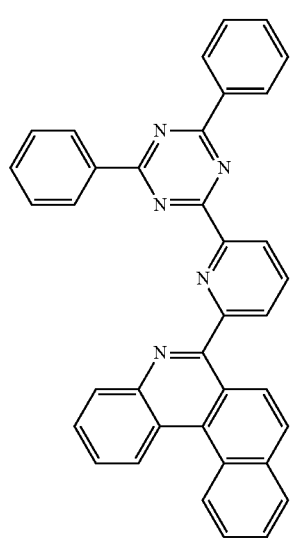
1022
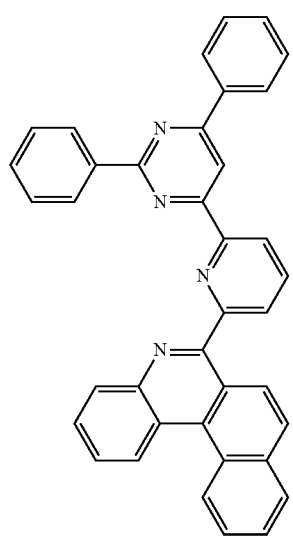

1023
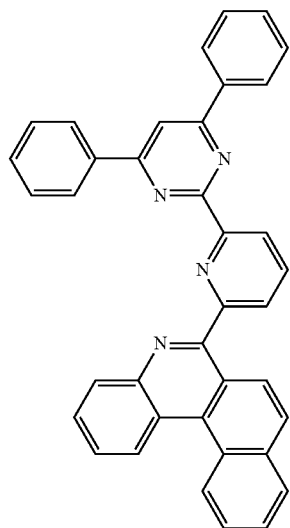
1024
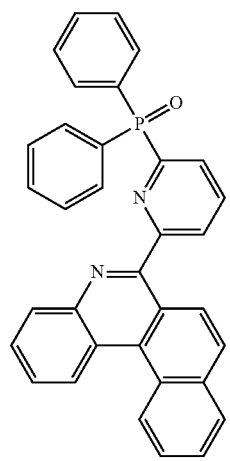
1025
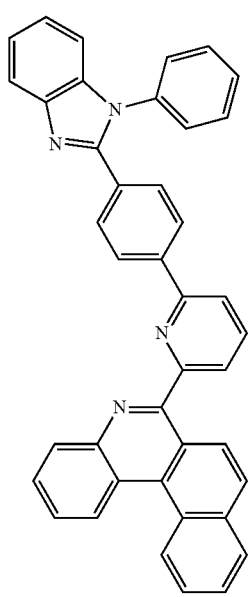
1026
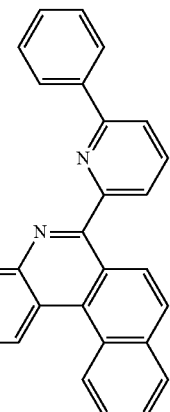
1027
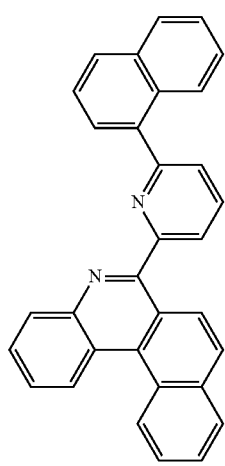
1028
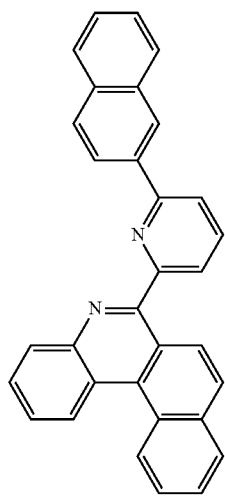

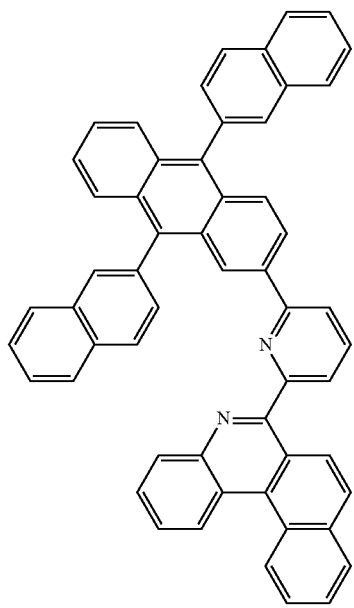
1029
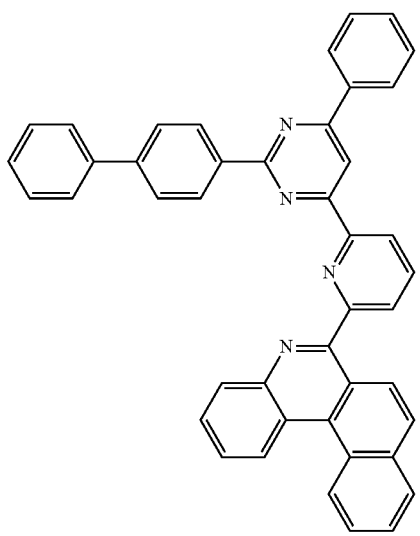
1031
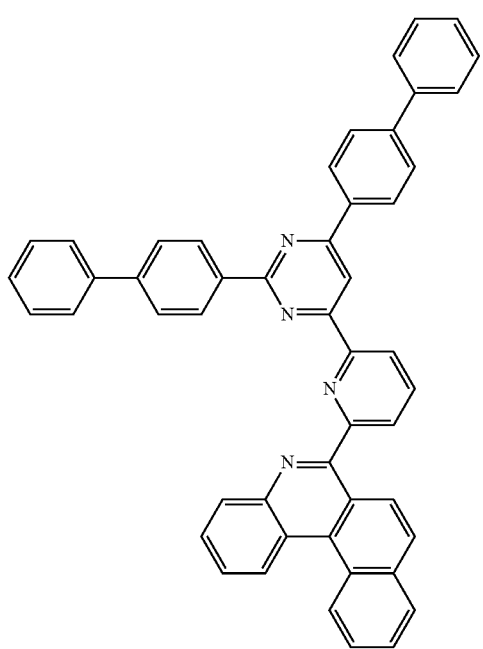
1030
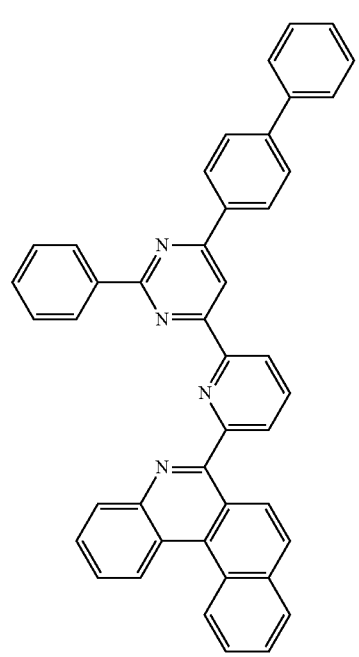
1032

1033
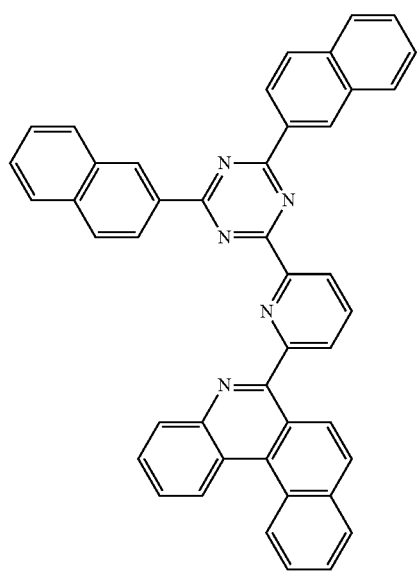
1034
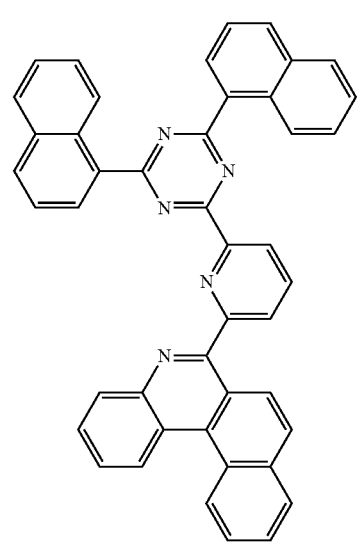
1035
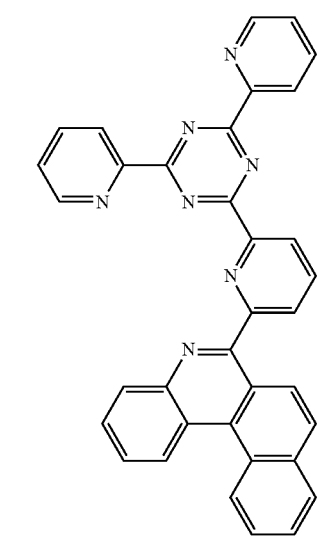
1036
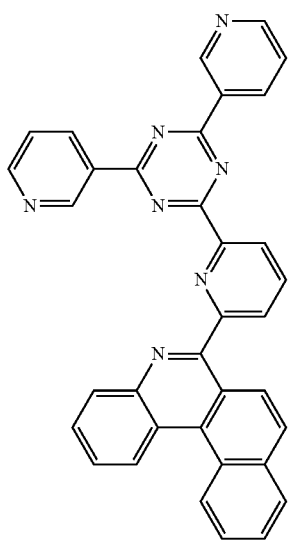
1037
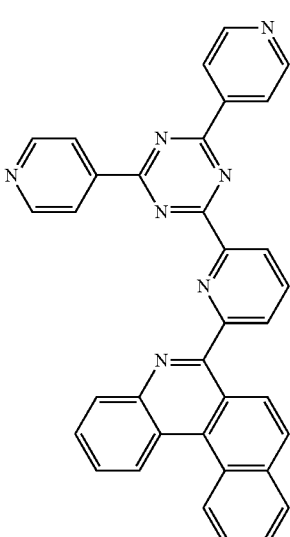
1038
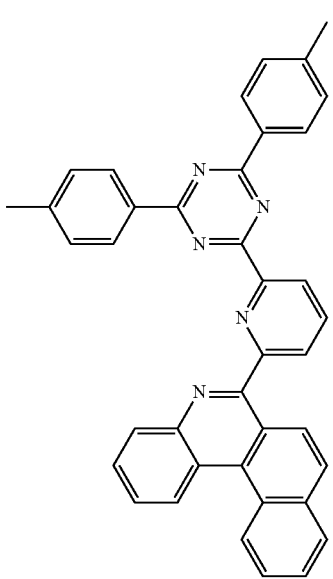

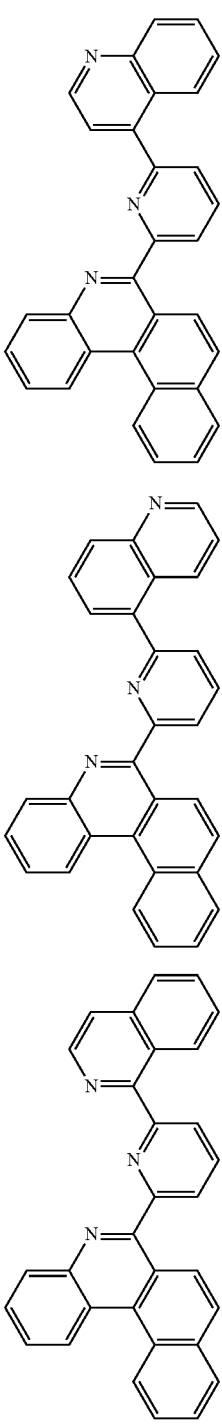

For example, in the chemical formula 1, if R1 is naphthyl, a compound having a substituent "—R" at any one of R2 to R11 may be prepared according to the following reaction equations 1 to 19. The R1 may be changed to other aryl groups or heteroaryl groups instead of naphthyl by using materials and methods known in the art.

[Reaction Equation 1]

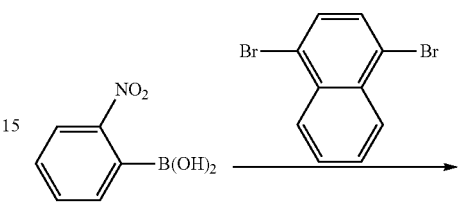

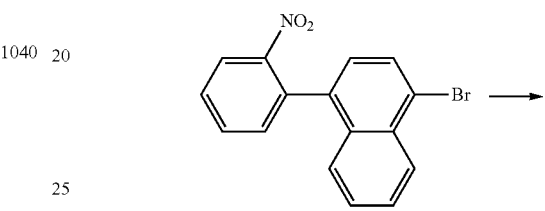

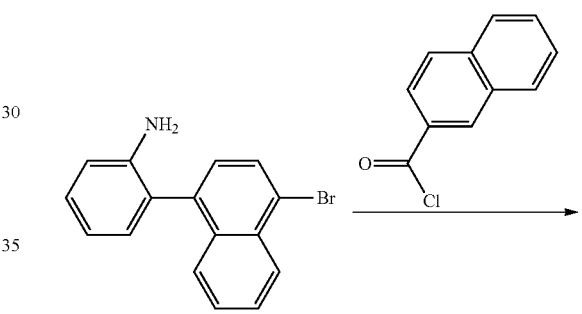

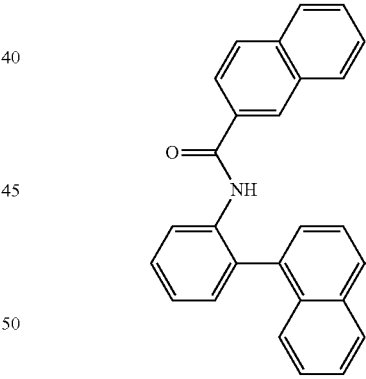

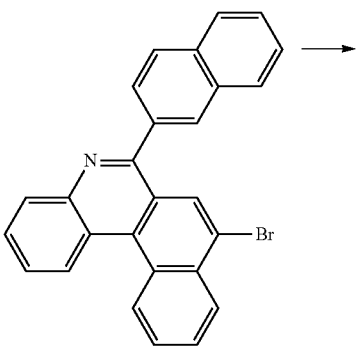

The compounds described above may be prepared based on the preparation examples described below. The following preparation examples are representative examples, but if necessary, substituents may be added or excluded and positions of substituents may be changed. Further, based on technologies known in the art, starting materials, reactants, reaction conditions, and the like may be changed. If necessary, kinds or positions of the substituents at the other positions may be modified by those skilled in the art using technologies known in the art.

429
-continued
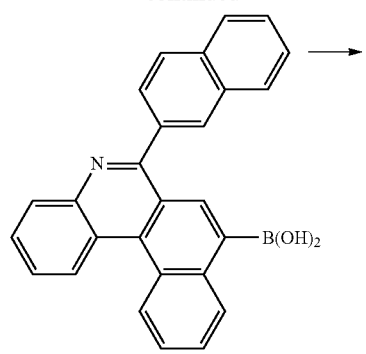
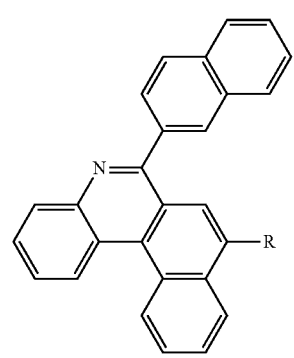
[Reaction Equation 2]
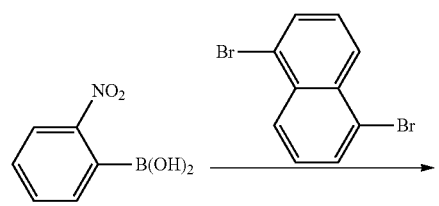
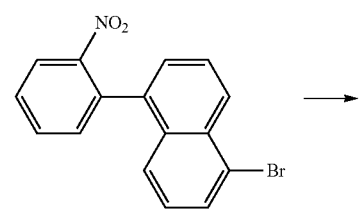
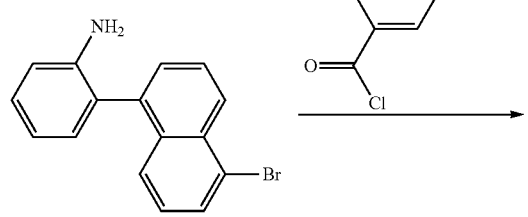
430
-continued
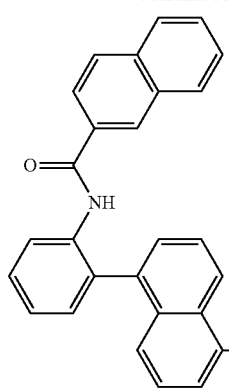
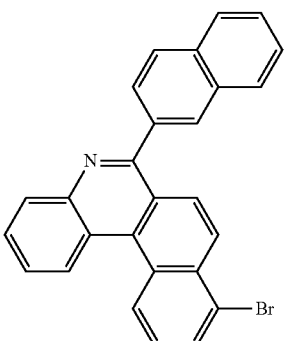
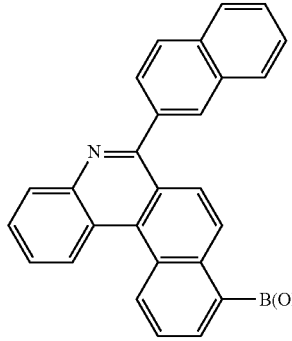
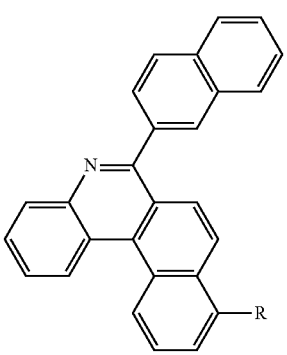
Reaction Equation 3]
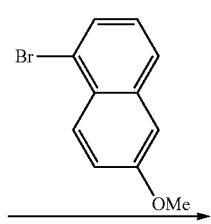

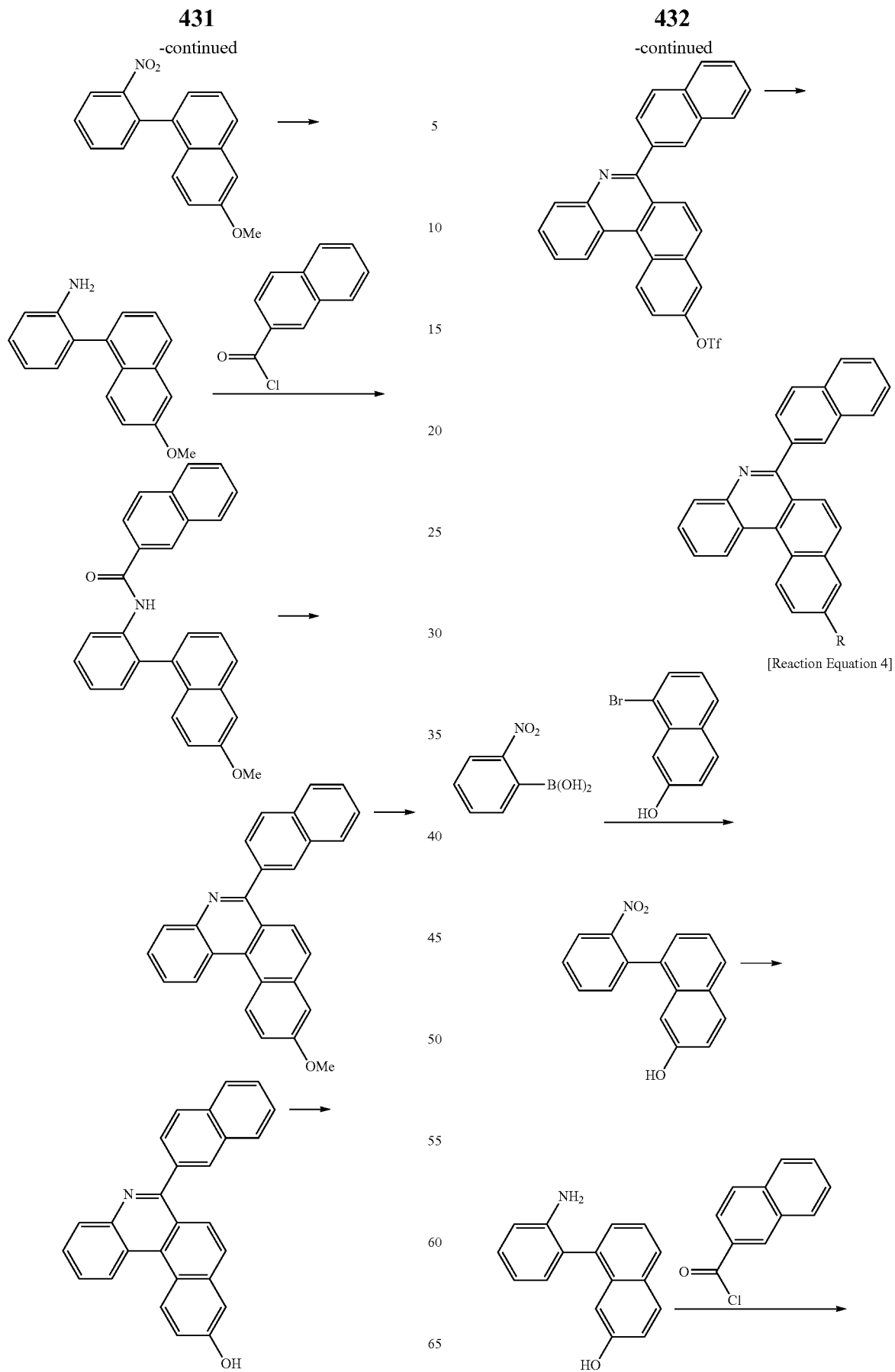
[Reaction Equation 4]

433
-continued
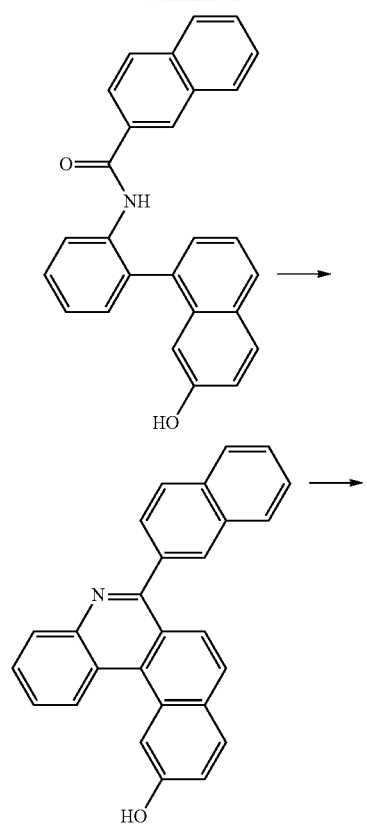
434
-continued
[Reaction Equation 5]
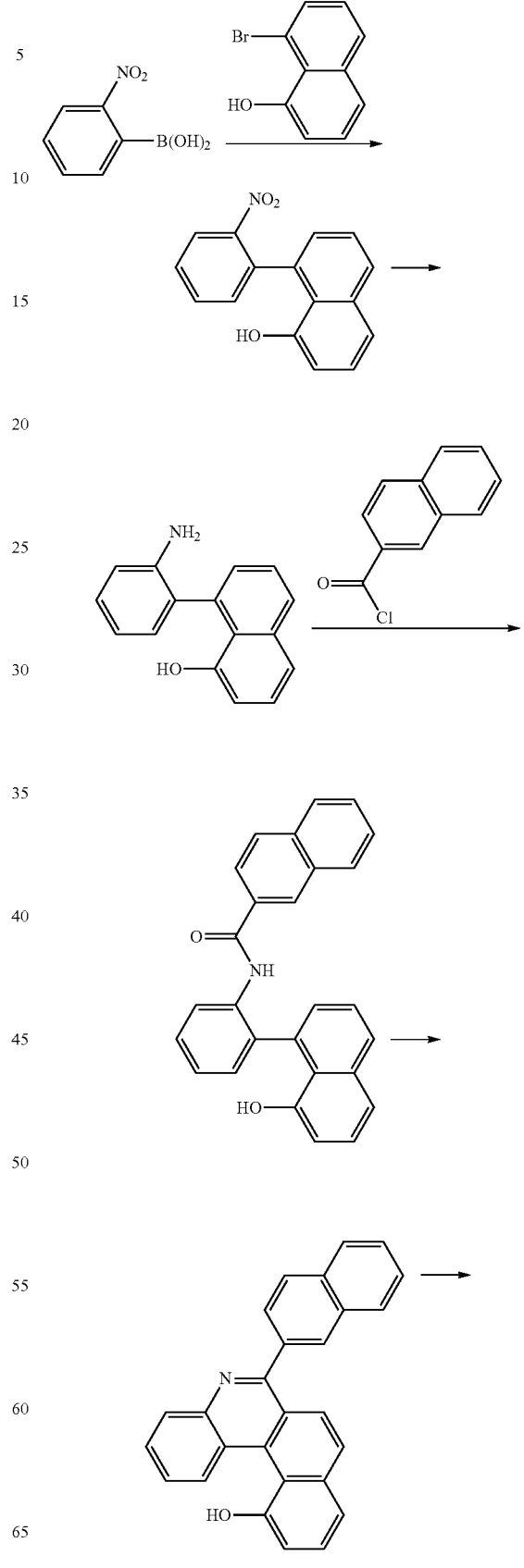

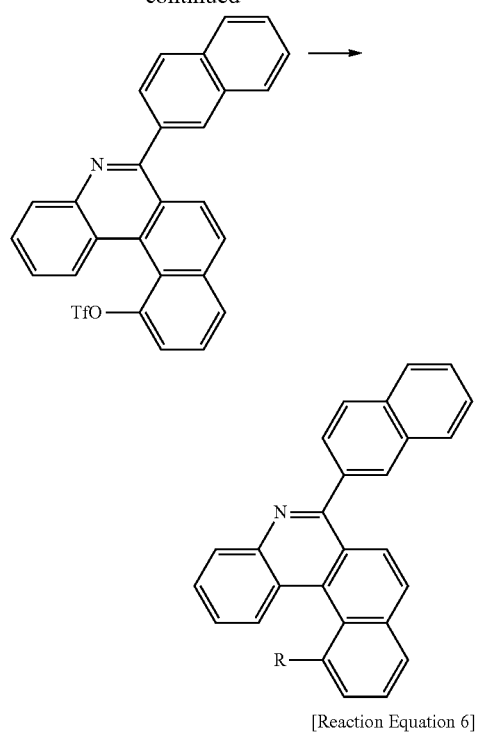
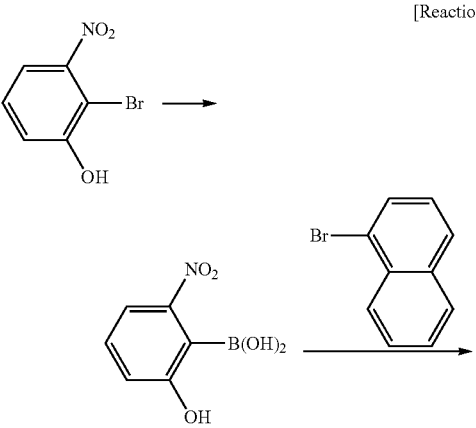
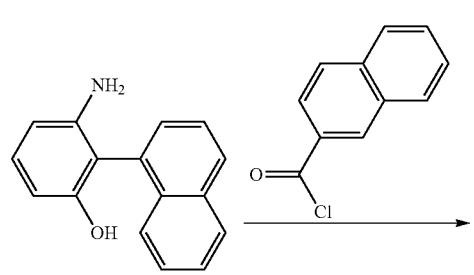
[Reaction Equation 6]
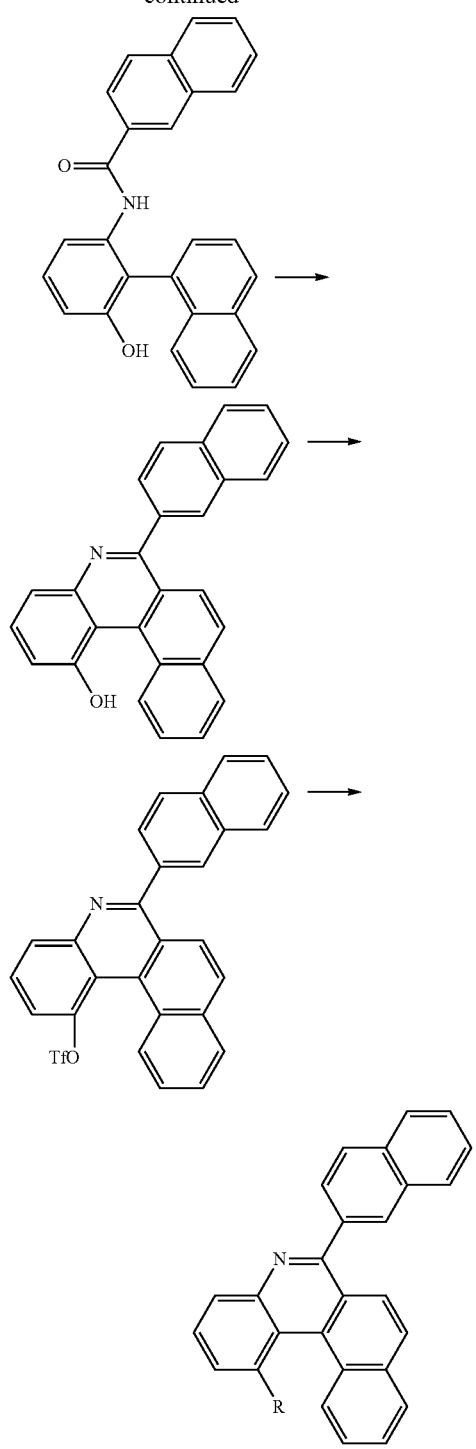
[Reaction Equation 7]

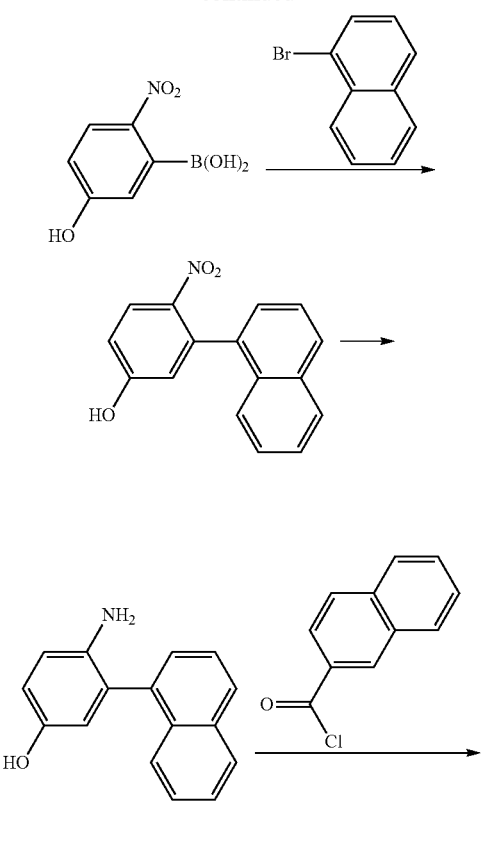
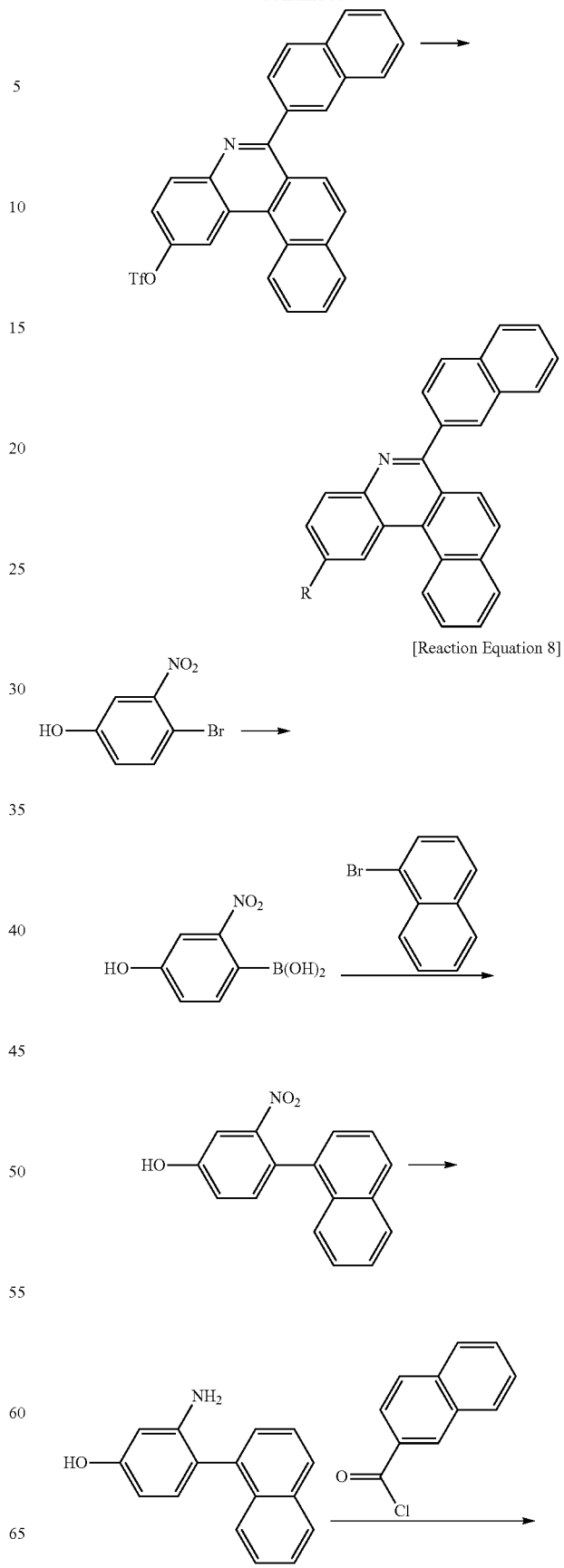
[Reaction Equation 8]

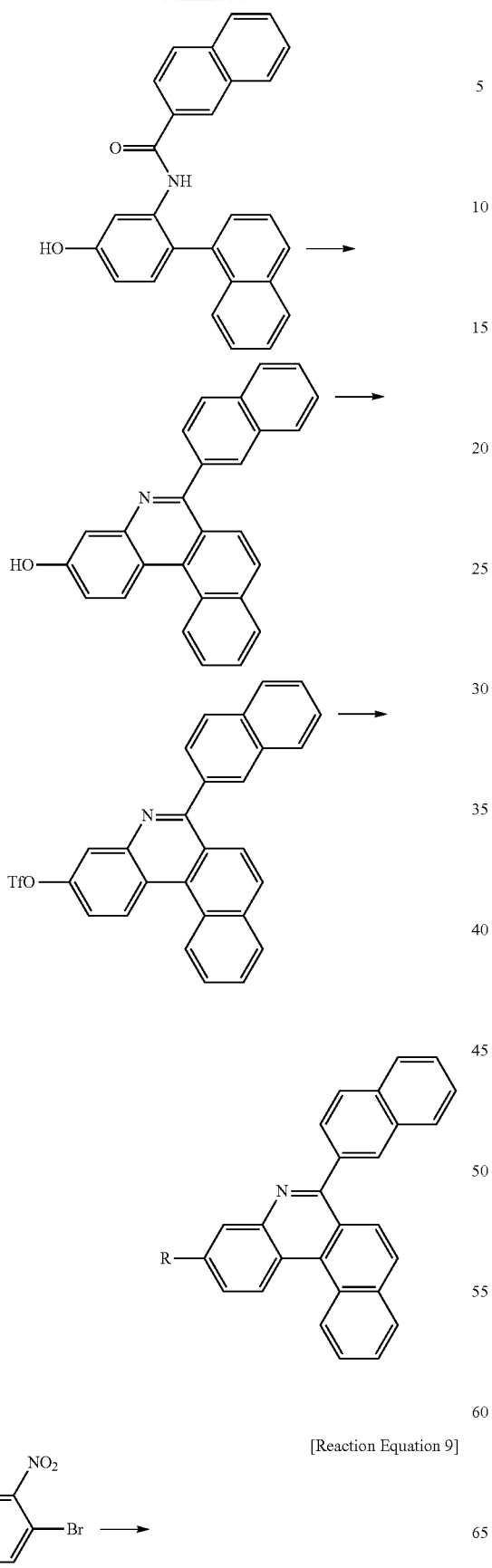
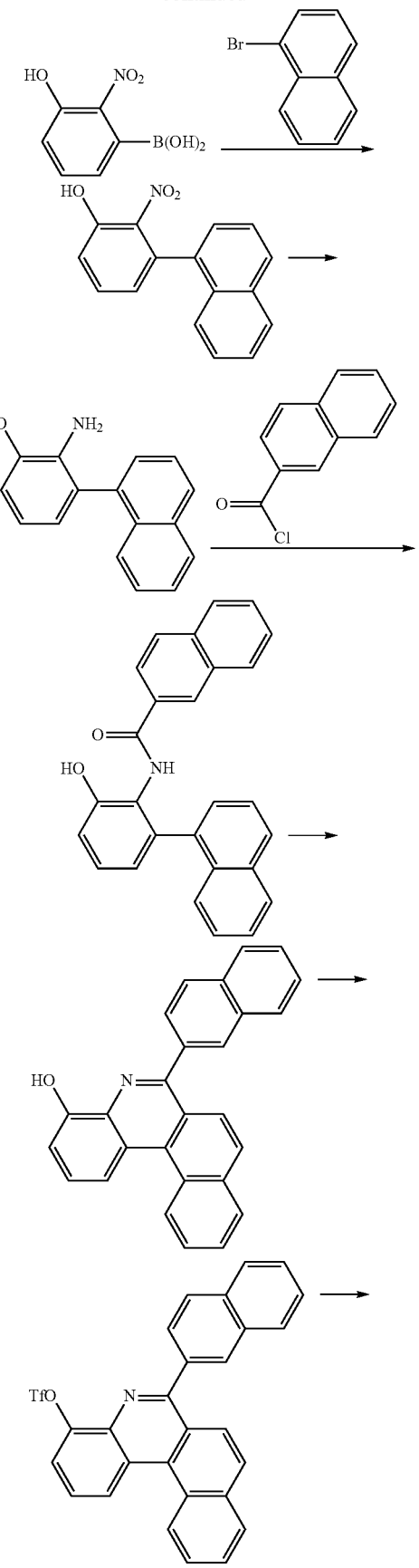
[Reaction Equation 9]

-continued

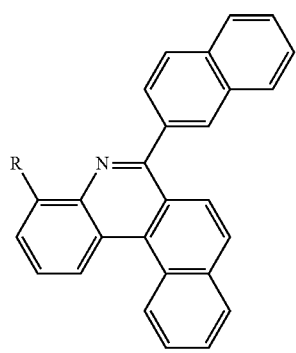

In the above reaction equations 1 to 9, R is the same as defined for R2 to R11.

For example, in the chemical formula 1, if R1 is "-phenylene-R", a compound may be prepared according to the following reaction equation 10. In the "-phenylene-R", phenylene may be changed to other arylene or heteroarylene instead of phenylene by using materials and methods known in the art.

[Reaction Equation 10]

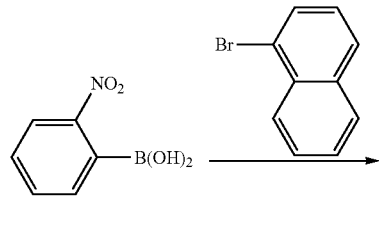

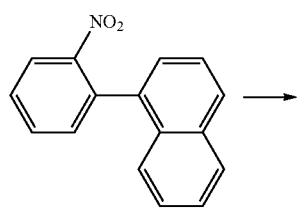

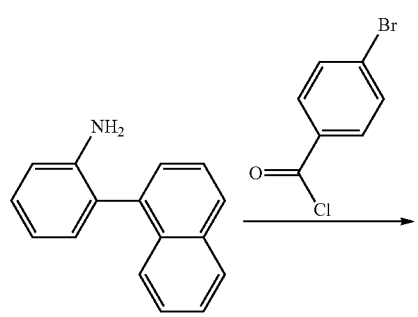

-continued

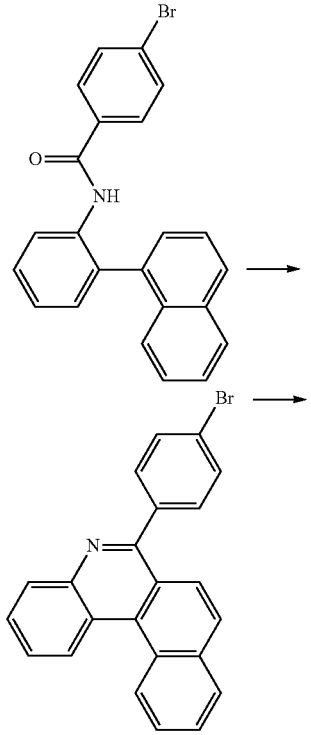

In the reaction equation 10, "-phenylene-R" is the same as defined for R1.

Further, when R1 in Formula 1 is "-heteroarylene-R", the compounds may be prepared by the following Reaction Formulae 11 to 19.

[Reaction Formula 11]

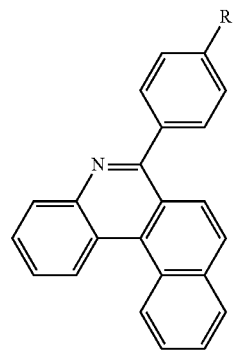

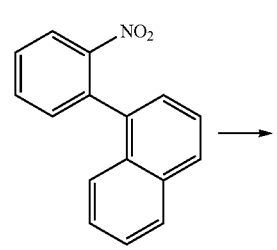

443
-continued
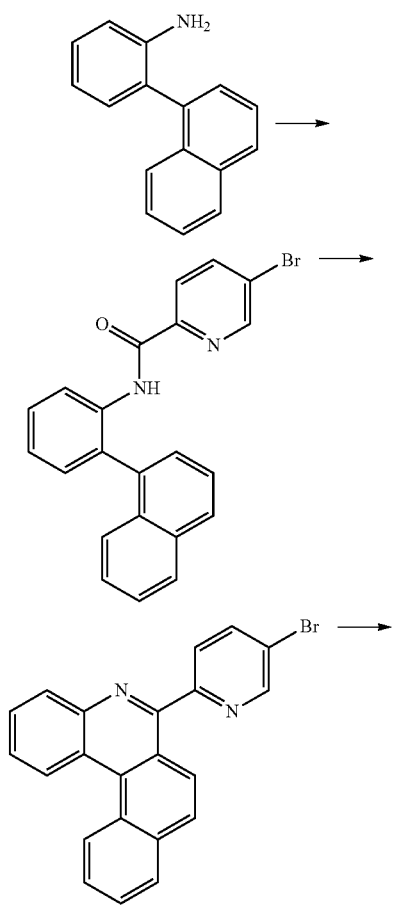
444
-continued
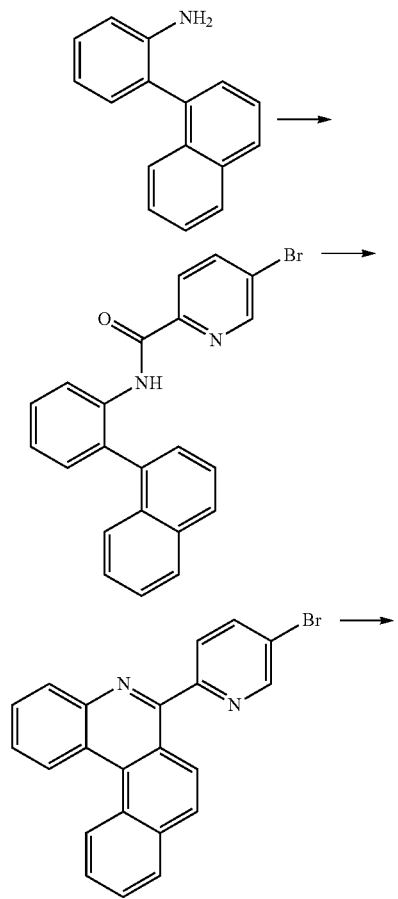
[Reaction Formula 12]
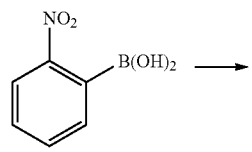
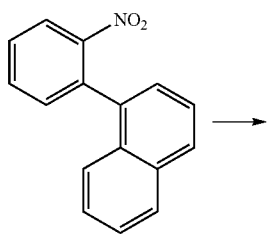
[Reaction Formula 13]
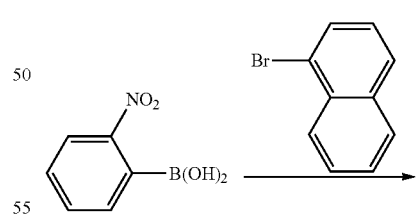
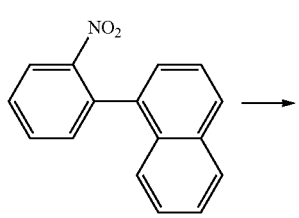

445
-continued
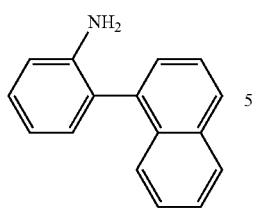
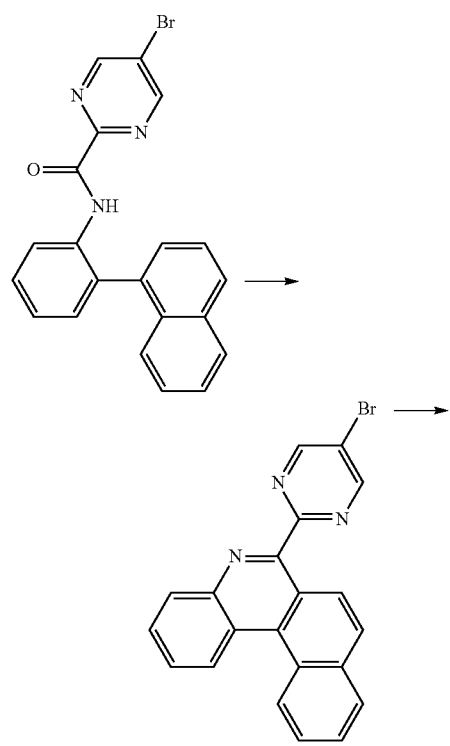
[Reaction Formula 14]
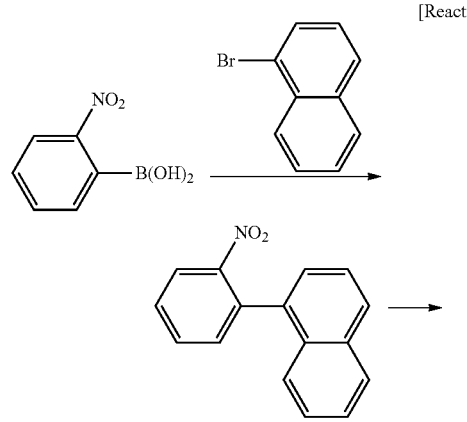
446
-continued
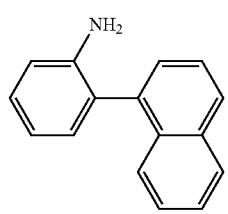
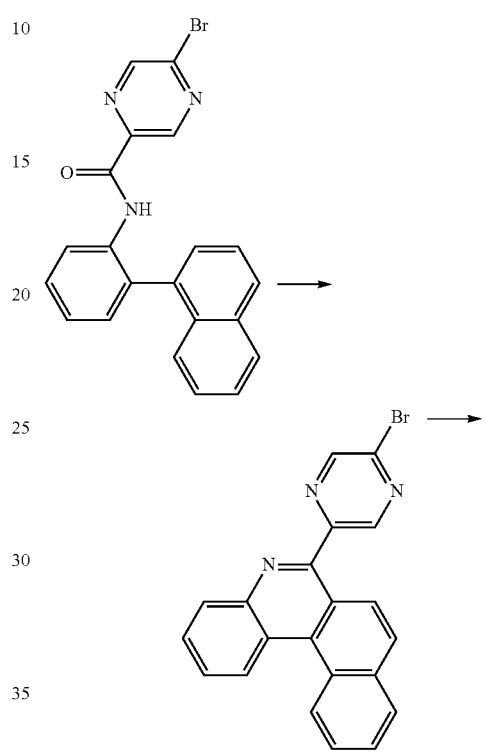
[Reaction Formula 15]
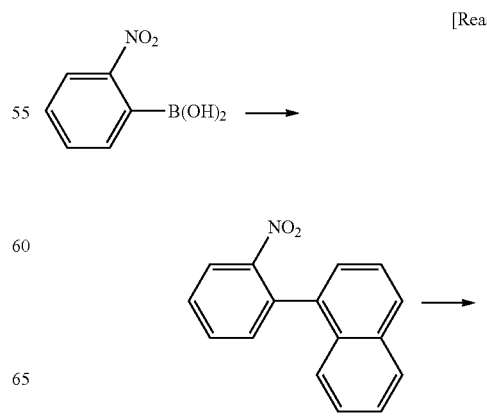

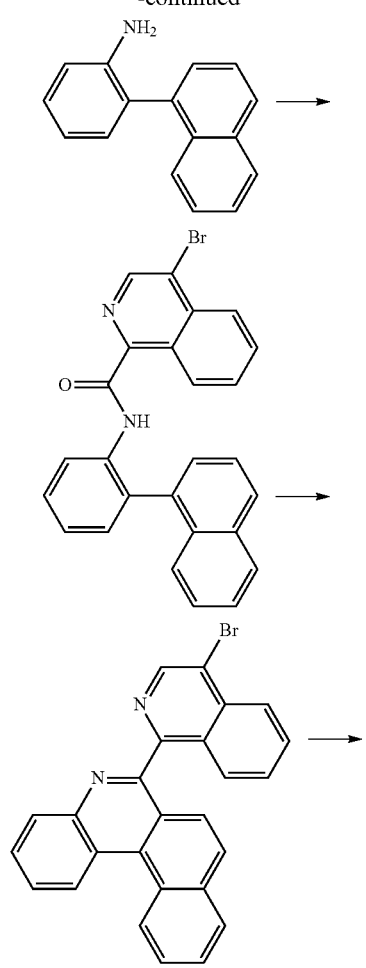
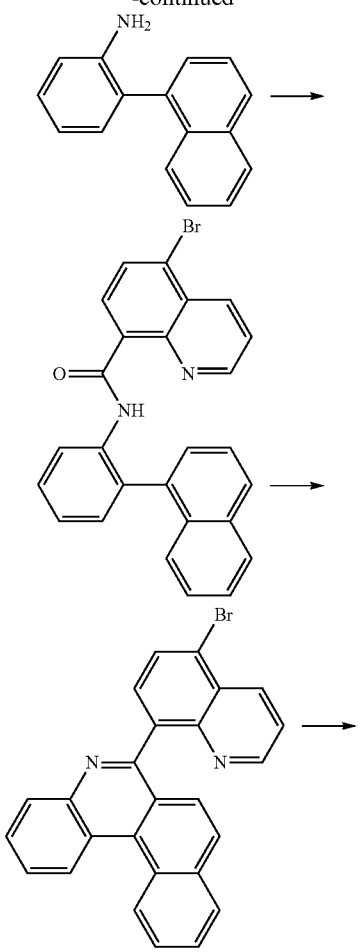
[Reaction Formula 16]
[Reaction Formula 17]
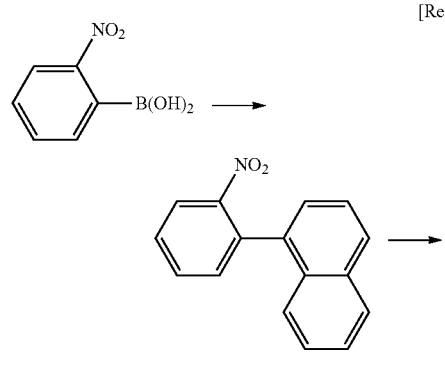

449
-continued

450
-continued

[Reaction Formula 18]

[Reaction Formula 19]

-continued

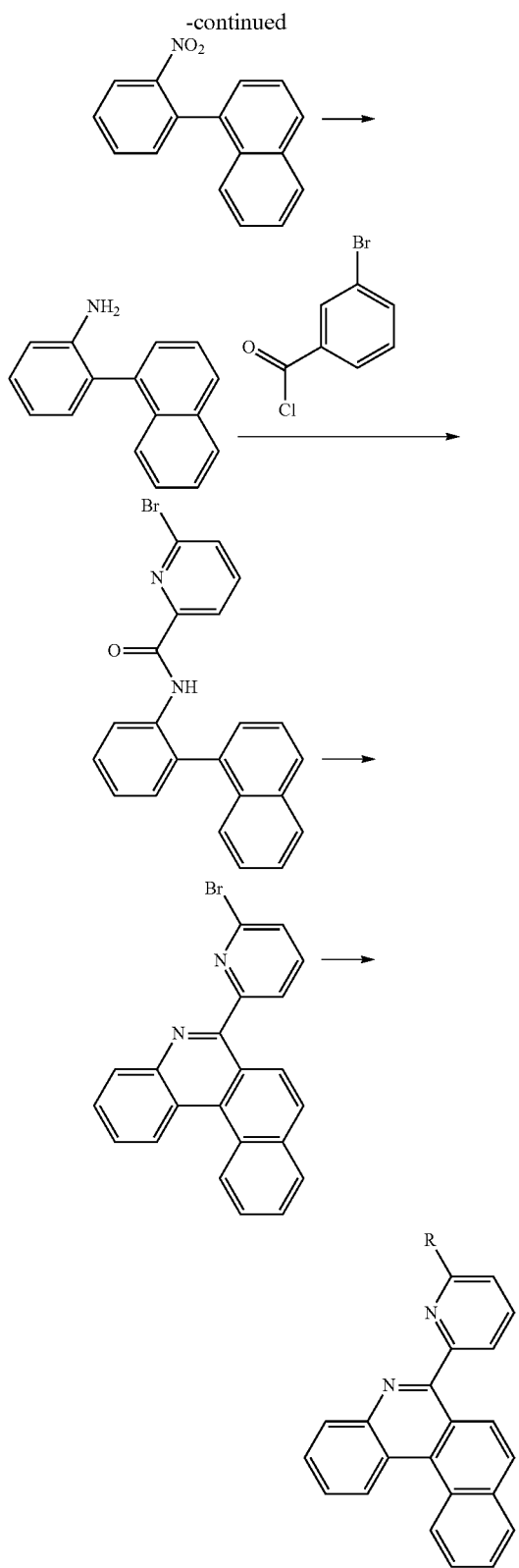

Another exemplary embodiment of the present invention provides an organic light emitting device including the compound of the chemical formula 1. To be specific, the organic light emitting device includes an anode, a cathode, and one or more organic material layers provided between the anode and the cathode, wherein one or more layers of the organic material layers include the compound of the chemical formula 1.

FIGS. 1 to 3 illustrate examples of laminating order of electrodes and organic material layers of an organic light emitting device according to exemplary embodiments of the present invention. However, these drawings are not provided for limiting the scope of the present invention, and the structure of the organic light emitting device known in the art can also be applied to the present invention.

Referring to FIG. 1, an organic light emitting device in which an anode 200, an organic material layer 300, and a cathode 400 are laminated in sequence on a substrate 100 is illustrated by the diagram. However, the structure of the organic light emitting device is not limited to this structure only, and as illustrated in FIG. 2, an organic light emitting device in which a cathode, an organic material layer, and an anode are laminated in sequence on a substrate may also be included.

FIG. 3 illustrates the case where the organic material layer is a multilayer. An organic light emitting device illustrated in FIG. 3 includes a hole injection layer 301, a hole transport layer 302, a light emitting layer 303, a hole blocking layer 304, an electron transport layer 305, and an electron injection layer 306. However, the scope of the present invention is not limited to this laminated structure, and when necessary, other layers except the light emitting layer may not be included, and other necessary layers having other functions may be added.

An organic light emitting device according to the present invention may be prepared using materials and methods known in the art except that the compound of the chemical formula 1 is included in one or more layers of the organic material layers.

The compound of the chemical formula 1 may form one or more layers of the organic material layers alone in an organic light emitting device. However, when necessary, the compound of the chemical formula 1 may be mixed with other materials to form the organic material layers.

The compound of the chemical formula 1 may be used as a hole injection material, a hole transport material, a light emitting material, a hole blocking material, an electron transport material, an electron injection material, or the like, in an organic light emitting device. In an example, the compound of the chemical formula 1 may be used as an electron injection and/or transport layer material in an organic light emitting device. Further, in another example, the compound of the chemical formula 1 may be used as an electron transport layer material in an organic light emitting device. Furthermore, in another example, the compound of the chemical formula 1 may be used as a light emitting layer material in an organic light emitting device. Moreover, in another example, the compound of the chemical formula 1 may be used as a host material of a phosphorescent light emitting layer in an organic light emitting device.

In the organic light emitting device according to the present invention, other materials than the compound of the chemical formula 1 are illustrated below, but they are for illustrative purposes only, and are not intended to limit the scope of the present invention, and can be substituted with materials known in the art.

As the anode material, materials having relatively large work function may be used, and transparent conductive oxides, metals, conductive polymers, or the like may be used.

As the cathode material, materials having relatively small work function may be used, and metals, metal oxides, conductive polymers, or the like may be used.

As the hole injection material, hole injection materials known in the art may be used, and for example, phthalocyanine compounds such as copper phthalocyanine disclosed in U.S. Pat. No. 4,356,429, or starbust-type amine derivatives disclosed in a literature [Advanced Material, 6, p. 677 (1994)], such as TCTA, m-MTDATA, m-MTDAPB, Pani/DBSA (polyaniline/dodecylbenzenesulfonic acid) or PEDOT/PSS (poly(3,4-ethylenedioxythiophene)/poly(4-styrenesulfonate)), Pani/CSA (polyaniline/camphor sulfonic acid) or PANI/PSS (polyaniline/poly(4-styrene-sulfonate), which is a conductive polymer having solubility, or the like, may be used.

As the hole transport material, a pyrazoline derivative, an arylamine-based derivative, a stilbene derivative, a triphenyldiamine derivative, or the like may be used, and a low molecular or high molecular material may also be used.

As the electron transport material, an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, 8-hydroxyquinoline and a metal complex of a derivative thereof, or the like, may be used, and a high molecular material as well as a low molecular material may also be used.

As the electron injection material, for example, LiF is typically used in the related industry. However, the present invention is not limited thereto.

As the light emitting material, a red, green, or blue light emitting material may be used, and when necessary, two or more light emitting materials may be mixed and used. Further, as the light emitting material, a fluorescent material may be used and a phosphorescent material may also be used. As the light emitting material, materials that emit light alone by bonding the holes and the electrons injected from an anode and a cathode, respectively, may be used. However, materials in which a host material and a dopant material are both involved in light emitting may also be used.

If the compound according to the present invention is used as a phosphorescent host material, a phosphorescent dopant material to be used together may employ those known in the art.

For example, phosphorescent dopant materials of LL'MX, LL'L"M, LMXX', L2MX, and L3M may be used, but the present invention is not limited thereto.

Herein, L, L', L", X, and X' are not equivalent, bidentate ligands, and M is a metal that forms octahedral complexes.

M may be iridium, platinum, osmium, or the like.

L is an anionic bidentate ligand which coordinates to M via an sp2 hybridized carbon and a heteroatom, and X functions to trap electrons or holes. Non-limiting examples of the L may include 2-(1-naphthyl) benzoxazole, (2-phenylbenzoxazole), (2-phenylbenzothiazole), (2-phenylbenzothiazole), (7,8-benzoquinoline), (thienylpyridine), phenylpyridine, benzothienylpyridine, 3-methoxy-2-phenylpyridine, thienylpyridine, and tolylpyridine. Non-limiting examples of the X may include acetylacetonate (acac), hexafluoroacetylacetonate, salicylidene, picolinate, and 8-hydroxyquinolinate.

More specific examples will be described below, but the present invention is not limited thereto.

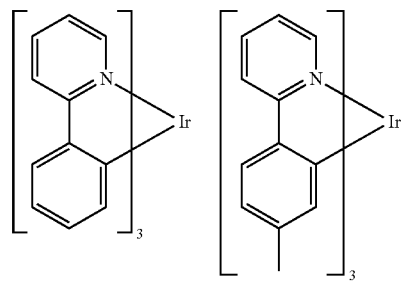

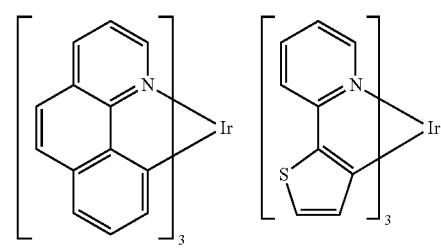

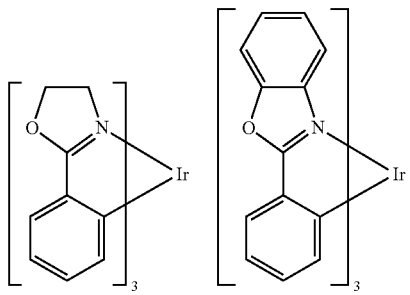

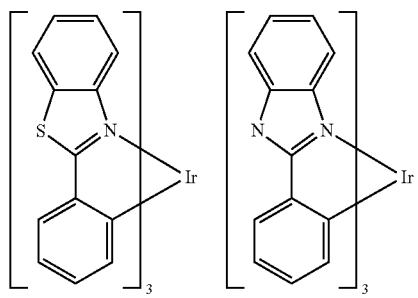

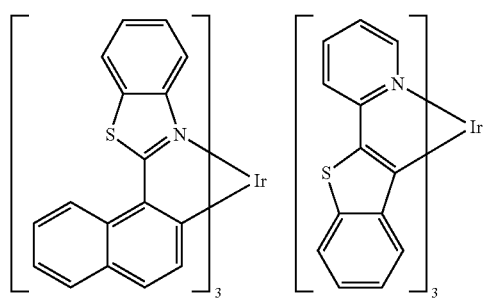

455
-continued
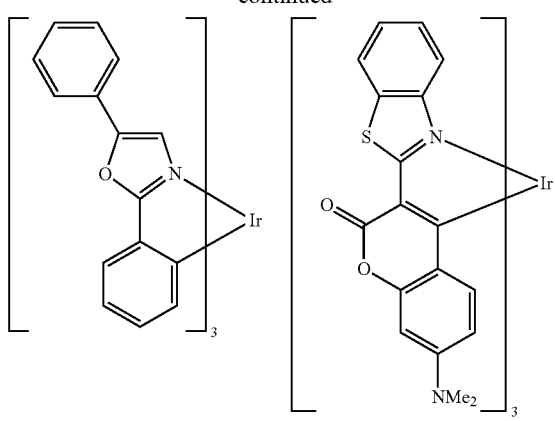
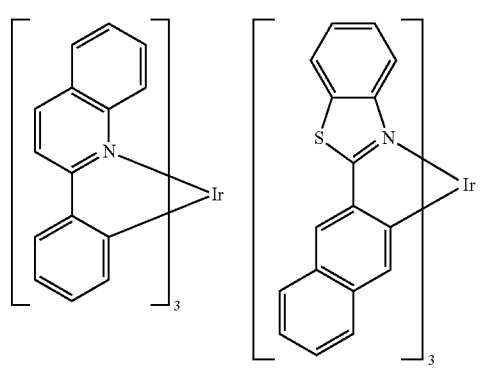
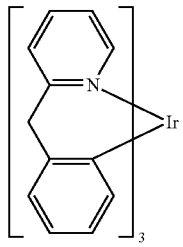
Hereinafter, the present invention will be described in more detail with reference to examples, however, it is to be understood that these are for illustrative purposes only, and are not intended to limit the scope of the present invention.
PREPARATION EXAMPLE 1
Preparation of Compound 103
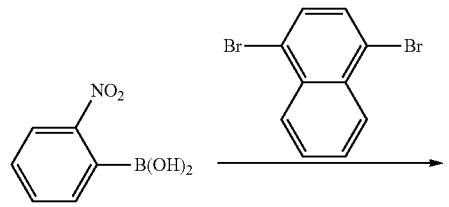
456
-continued
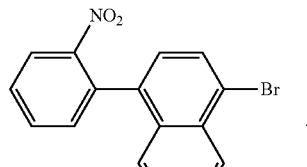
103-6
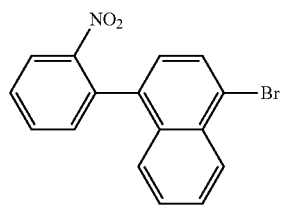
103-5
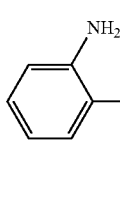
103-4
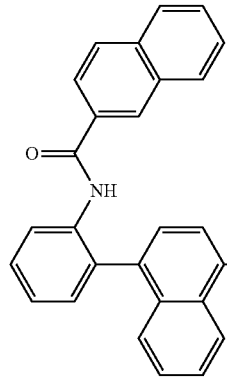
103-3
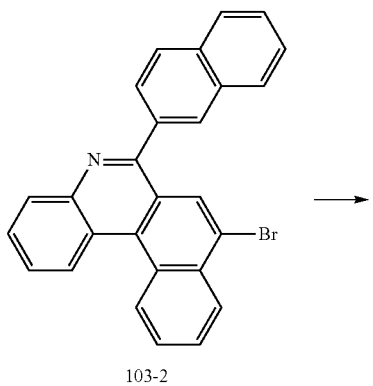
103-2

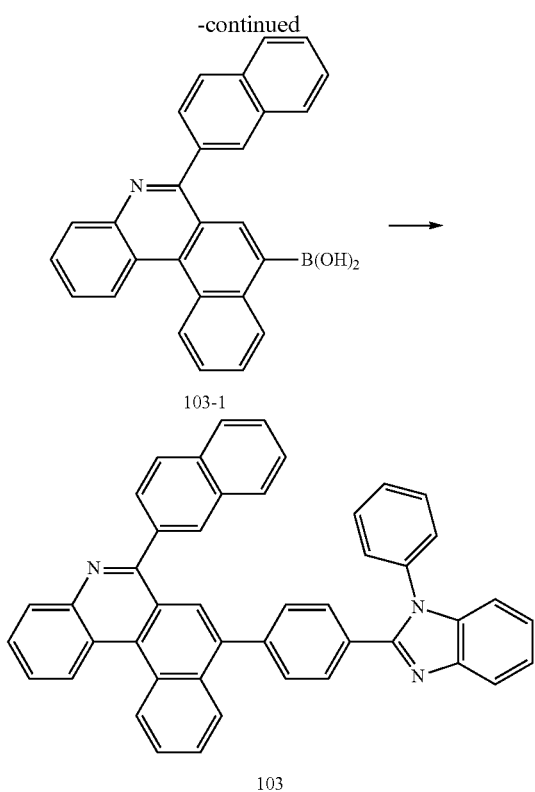

Preparation of Compound 103-6

A compound 1-bromo-2-nitrobenzene (15 g, 76.9 mmol), 1-naphthaleneboronic acid (14.5 g, 84.6 mmol), Pd(PPh$_3$)$_2$Cl$_2$ (2.7 g, 3.85 mmol), 2M K$_2$CO$_3$ aqueous solution (70 ml), toluene (200 ml), and ethanol (100 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and 14.1 g (75%) of the target compound 103-6 was obtained.

Preparation of Compound 103-5

After Compound 103-6 (14.1 g, 43.1 mmol) was dissolved in dichloromethane (300 ml), N-bromosuccinimide (7.6 g, 43.4 mmol) was added thereto, and the resultant reaction product was stirred at room temperature for 12 hours. After the reaction was completed, the resultant reaction product was extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 103-5 (11.4 g, 81%) was obtained.

Preparation of Compound 103-4

11.4 g (34.9 mmol) of Compound 103-5 was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 103-4 (10.2 g, 98%) was obtained.

Preparation of Compound 103-3

After Compound 103-4 (10.2 g, 34.2 mmol) was dissolved in THF, TEA (14 ml, 102.6 mmol) and 2-naphthoyl chloride (9.7 g, 51.3 mmol) were added thereto at 0° C. Then, a temperature was increased to room temperature and the resultant reaction product was stirred for 4 hours. After the reaction was completed, the resultant reaction product was extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 103-3 (13.3 g, 86%) was obtained.

Preparation of Compound 103-2

After Compound 103-3 (13.3 g, 29.4 mmol) was dissolved in nitrobenzene, POCl$_3$ (0.5 ml, 5.88 mmol) was added thereto at room temperature. Then, the resultant reaction product was stirred at 150° C. for 18 hours. After the reaction was completed, the resultant reaction product was neutralized with NaHCO$_3$ and extracted with EA. The organic layer was dried using anhydrous MgSO$_4$, and after the solvent was removed with a rotary evaporator, the resultant reaction product was purified by column chromatography using dichloromethane and methanol as a developing solvent, and the target compound 103-2 (9.7 g, 73%) was obtained.

Preparation of Compound 103-1

After Compound 103-2 (9.7 g, 21.4 mmol) was dissolved in THF, 2.5 M n-BuLi (10.2 ml, 25.6 mmol) was slowly added dropwise thereto at −78° C. Then, the resultant reaction product was stirred for 30 minutes. After trimethylborate was added thereto, a temperature was increased to room temperature and the resultant reaction product was stirred for 1 hour. After the reaction was completed, HCl was added thereto with stirring for 1 hour and the resultant reaction product was extracted with distilled water and EA. The organic layer was dried using anhydrous MgSO$_4$, and after the solvent was removed with a rotary evaporator, the resultant reaction product was purified by column chromatography using dichloromethane and methanol as a developing solvent, and the target compound 103-1 (3.6 g, 43%) was obtained.

Preparation of Compound 103

Compound 103-1 (3.6 g, 9.20 mmol), 1-phenyl-1H-benzo[d]imidazole-2-phenylboronic acid (5.4 g, 13.8 mmol), Pd(PPh$_3$)$_4$ (0.53 g, 0.46 mmol), 2M K$_2$CO$_3$ aqueous solution (70 ml), toluene (200 ml), and ethanol (100 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and 4.3 g (80%) of the target compound 103 was obtained.

PREPARATION EXAMPLE 2

Preparation of Compound 12

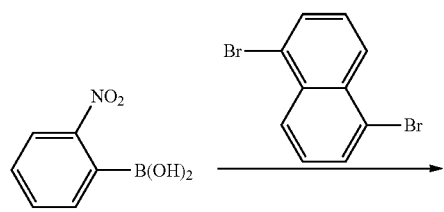

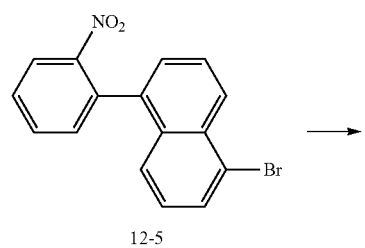

12-5

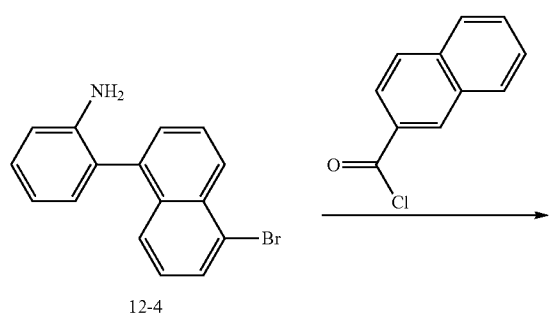

12-4

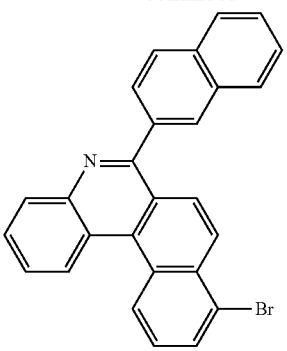

12-2

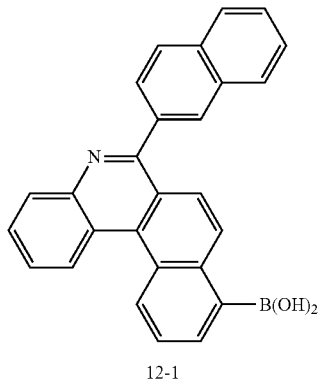

12-1

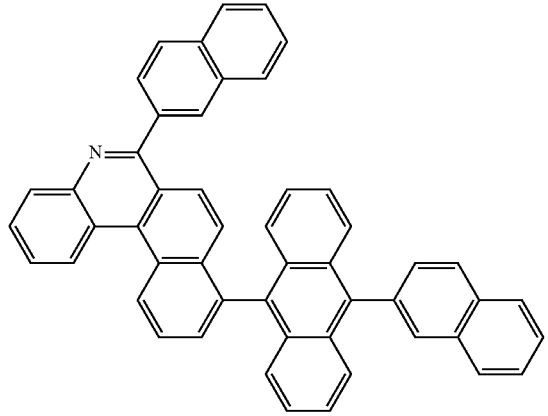

12

Preparation of Compound 12-5

A compound 2-nitrophenylboronic acid (10 g, 59.9 mmol), 1,5-dibromonaphthalene (51 g, 179 mmol), Pd(PPh$_3$)$_2$Cl$_2$ (2.1 g, 3.0 mmol), 2M K$_2$CO$_3$ aqueous solution (70 ml), toluene (200 ml), and ethanol (100 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and 12.8 g (65%) of the target compound 12-5 was obtained.

Preparation of Compound 12-4

Compound 12-5 (12.8 g, 38.9 mmol) was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 12-4 (11.2 g, 97%) was obtained.

Preparation of Compound 12-3

After Compound 12-4 (11.2 g, 37.7 mmol) was dissolved in THF, TEA (15.6 ml, 113.1 mmol) and 2-naphthoyl chloride (10.7 g, 56.5 mmol) were added thereto at 0° C. Then, a temperature was increased to room temperature and the resultant reaction product was stirred for 4 hours. After the reaction was completed, the resultant reaction product was extracted with distilled water and EA. The organic layer was dried using anhydrous MgSO₄, and after the solvent was removed with a rotary evaporator, the resultant reaction product was purified by column chromatography using dichloromethane and hexane as a developing solvent, and the target compound 12-3 (15.3 g, 90%) was obtained.

Preparation of Compound 12-2

After Compound 12-3 (15.3 g, 33.9 mmol) was dissolved in nitrobenzene, POCl₃ (0.63 ml, 6.78 mmol) was added thereto at room temperature. Then, the resultant reaction product was stirred at 150° C. for 18 hours. After the reaction was completed, the resultant reaction product was neutralized with NaHCO₃ and extracted with EA. The organic layer was dried using anhydrous MgSO₄, and after the solvent was removed with a rotary evaporator, the resultant reaction product was purified by column chromatography using dichloromethane and methanol as a developing solvent, and the target compound 12-2 (11.6 g, 79%) was obtained.

Preparation of Compound 12-1

After Compound 12-2 (11.6 g, 26.7 mmol) was dissolved in THF, 2.5 M n-BuLi (12.8 ml, 32.0 mmol) was slowly added dropwise thereto at −78° C. Then, the resultant reaction product was stirred for 30 minutes. After trimethylborate (8.9 ml, 80.1 mmol) was added thereto, a temperature was increased to room temperature and the resultant reaction product was stirred for 1 hour. After the reaction was completed, HCl was added thereto with stirring for 1 hour and the resultant reaction product was extracted with distilled water and EA. The organic layer was dried using anhydrous MgSO₄, and after the solvent was removed with a rotary evaporator, the resultant reaction product was purified by column chromatography using dichloromethane and methanol as a developing solvent, and the target compound 12-1 (5.9 g, 56%) was obtained.

Preparation of Compound 12

Compound 12-1 (5.9 g, 14.9 mmol), 9-bromo-10-(2-naphthyl)anthracene (6.2 g, 16.4 mmol), Pd(PPh₃)₄ (0.86 g, 0.74 mmol), 2M K₂CO₃ aqueous solution (30 ml), toluene (120 ml), and ethanol (30 ml) were added and then, refluxed for 12 hours. After the reaction was completed, the resultant reaction product was cooled to room temperature and then extracted with distilled water and EA. The organic layer was dried using anhydrous MgSO₄, and after the solvent was removed with a rotary evaporator, the resultant reaction product was purified by column chromatography using dichloromethane and hexane as a developing solvent, and 7.6 g (78%) of the target compound 12 was obtained.

PREPARATION EXAMPLE 3

Preparation of Compound 48

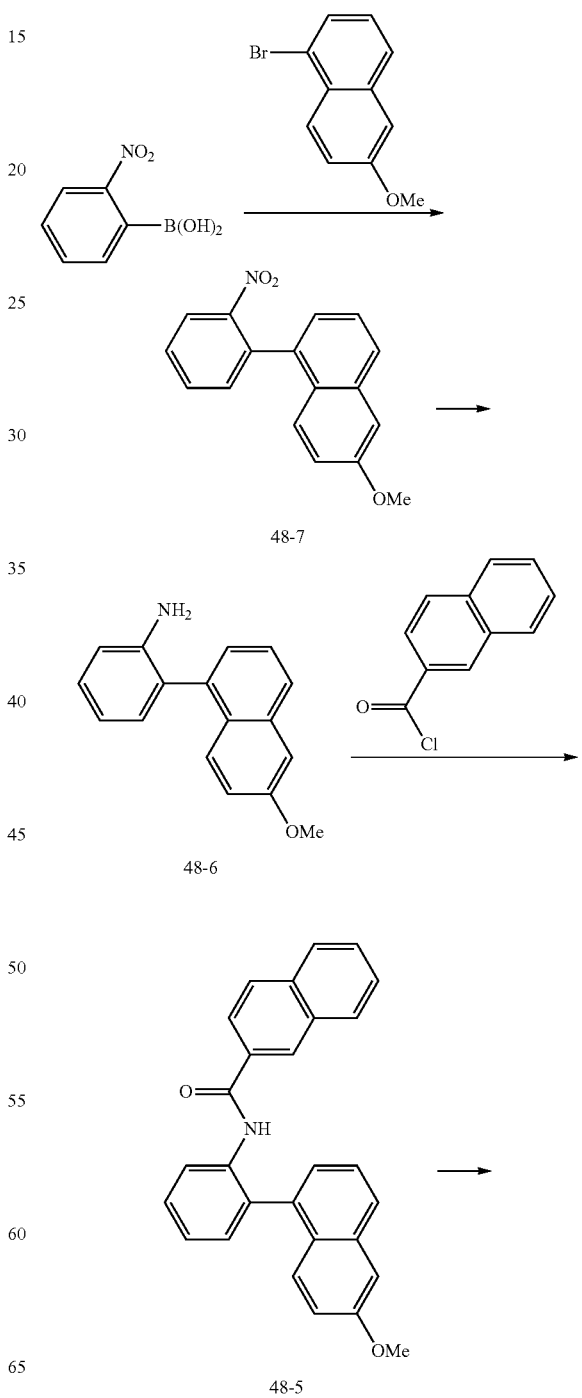

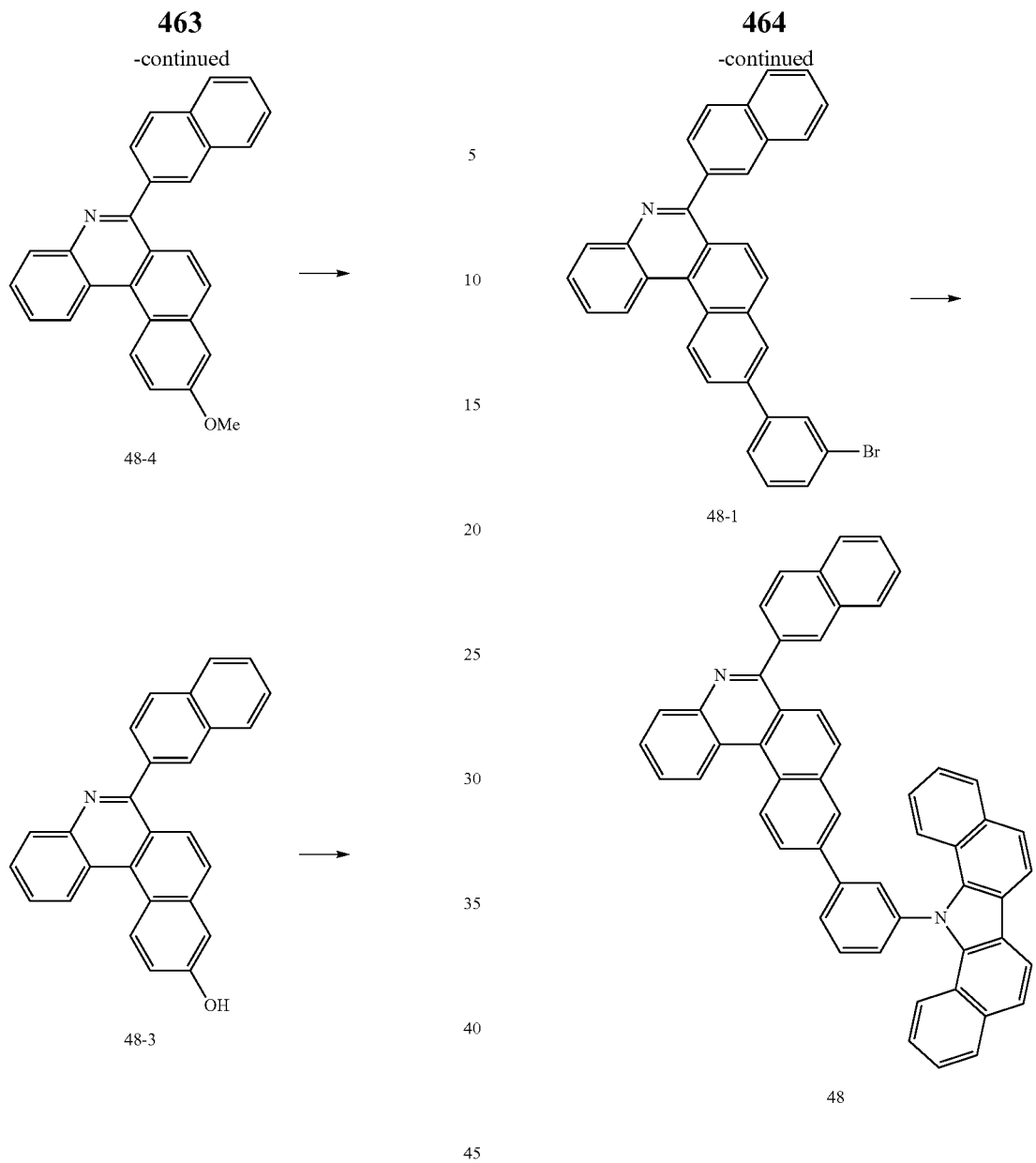

Preparation of Compound 48-7

A compound 2-nitrophenylboronic acid (10 g, 59.9 mmol), 1-bromo-6-methoxy-naphthalen (42.4 g, 179 mmol), Pd(PPh$_3$)$_2$Cl$_2$ (2.1 g, 3.0 mmol), 2M K$_2$CO$_3$ aqueous solution (70 ml), toluene (200 ml), and ethanol (100 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 48-7 (16.7 g, 83%) was obtained.

Preparation of Compound 48-6

Compound 48-7 (16.7 g, 59.8 mmol) was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 48-6 (14.6 g, 98%) was obtained.

Preparation of Compound 48-5

After Compound 48-6 (14.6 g, 58.5 mmol) was dissolved in THF, TEA (24.3 ml, 175.6 mmol) and 2-naphthoyl chloride (16.7 g, 87.7 mmol) were added thereto at 0° C. Then, a temperature was increased to room temperature and the resultant reaction product was stirred for 4 hours. After the reaction was completed, the resultant reaction product was extracted with distilled water and EA. The organic layer was dried using anhydrous $MgSO_4$, and after the solvent was removed with a rotary evaporator, the resultant reaction product was purified by column chromatography using dichloromethane and hexane as a developing solvent, and the target compound 48-5 (19.8 g, 84%) was obtained.

Preparation of Compound 48-4

After Compound 48-5 (19.8 g, 49.1 mmol) was dissolved in nitrobenzene, $POCl_3$ (0.92 ml, 9.82 mmol) was added thereto at room temperature. Then, the resultant reaction product was stirred at 150° C. for 18 hours. After the reaction was completed, the resultant reaction product was neutralized with $NaHCO_3$ and extracted with EA. The organic layer was dried using anhydrous $MgSO_4$, and after the solvent was removed with a rotary evaporator, the resultant reaction product was purified by column chromatography using dichloromethane and methanol as a developing solvent, and the target compound 48-4 (15.3 g, 81%) was obtained.

Preparation of Compound 48-3

After Compound 48-4 (15.3 g, 39.7 mmol) was dissolved in dichloromethane, boron tribromide (1 M in dichloromethane) (59.5 ml, 59.5 mmol) was added thereto at a time at 0° C. Then, the resultant reaction product was stirred at room temperature for 18 hours. After the reaction was completed, the resultant reaction product was neutralized with $NaHCO_3$ at 0° C. and extracted with distilled water and EA. The organic layer was dried using anhydrous $MgSO_4$, and after the solvent was removed with a rotary evaporator, the resultant reaction product was purified by column chromatography using dichloromethane and methanol as a developing solvent, and the target compound 48-3 (14.0 g, 95%) was obtained.

Preparation of Compound 48-2

After Compound 48-3 (14.0 g, 37.7 mmol) was dissolved in dichloromethane, pyridine (4.5 ml, 56.5 mmol) was added thereto and triflic anhydride was added dropwise thereto at 0° C. Then, the resultant reaction product was stirred at room temperature for 5 hours. After the reaction was completed, the reaction solution was allowed to pass through silica. The filtrate was removed with a rotary evaporator. Then, the resultant reaction product was purified by column chromatography using dichloromethane and methanol as a developing solvent, and the target compound 48-2 (18.2 g, 96%) was obtained.

Preparation of Compound 48-1

Compound 48-2 (18.2 g, 36.2 mmol) 1-bromo-3-iodinebenzene (12.2 g, 43.4 mmol), $Pd(PPh_3)_4$ (2.09 g, 1.81 mmol), 2M $K_2CO_3$ aqueous solution (80 ml), toluene (400 ml), and ethanol (80 ml) were added and then, refluxed for 12 hours. After the reaction was completed, the resultant reaction product was cooled to room temperature and extracted with distilled water and EA. The organic layer was dried using anhydrous $MgSO_4$, and after the solvent was removed with a rotary evaporator, the resultant reaction product was purified by column chromatography using dichloromethane and hexane as a developing solvent, and 14.4 g (78%) of the target compound 48-1 was obtained.

Preparation of Compound 48

Compound 48-1 (14.4 g, 28.2 mmol), 13H-dibenzo[a,i]carbazole (9.0 g, 33.8 mmol), $Pd(PPh_3)_4$ (1.6 g, 1.41 mmol), 2M $K_2CO_3$ aqueous solution (60 ml), toluene (300 ml), and ethanol (60 ml) were added and then, refluxed for 12 hours. After the reaction was completed, the resultant reaction product was cooled to room temperature and then extracted with distilled water and EA. The organic layer was dried using anhydrous $MgSO_4$, and after the solvent was removed with a rotary evaporator, the resultant reaction product was purified by column chromatography using dichloromethane and hexane as a developing solvent, and 12.7 g (65%) of the target compound 48 was obtained.

PREPARATION EXAMPLE 4

Preparation of Compound 29

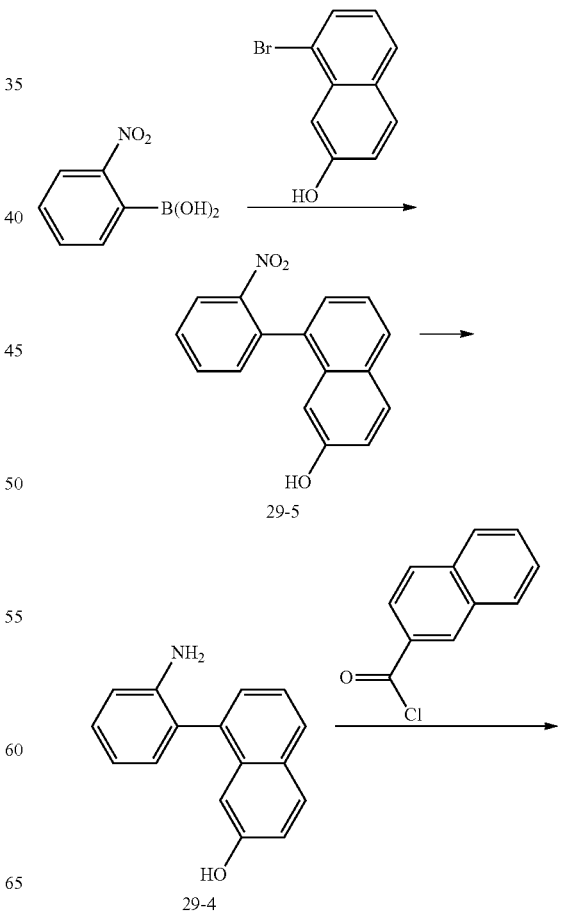

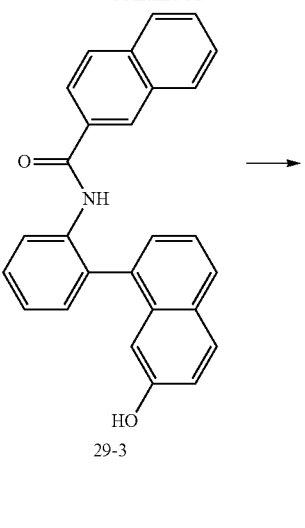

29-3

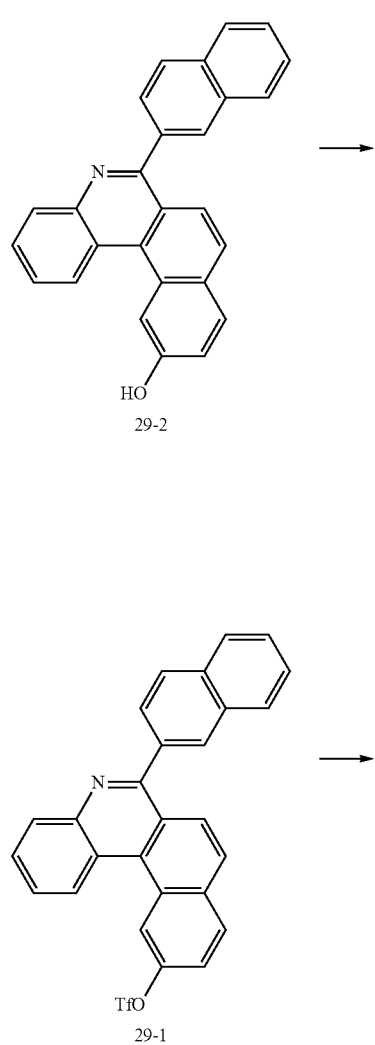

29-2

TfO
29-1

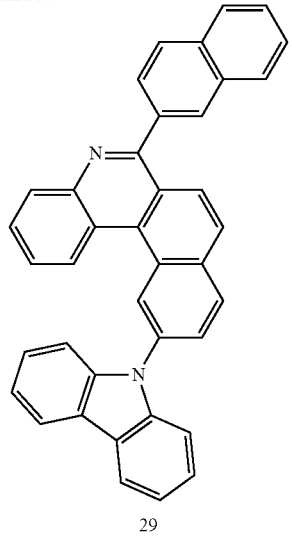

29

Preparation of Compound 29-5

A compound 2-nitrophenylboronic acid (10 g, 59.9 mmol), 8-bromo-2-naphthol (20.0 g, 89.8 mmol), Pd(PPh$_3$)$_2$Cl$_2$ (2.1 g, 3.0 mmol), 2M K$_2$CO$_3$ aqueous solution (70 ml), toluene (200 ml), and ethanol (100 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 29-5 (14.4 g, 91%) was obtained.

Preparation of Compound 29-4

Compound 29-5 (14.4 g, 54.5 mmol) was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 29-4 (12.5 g, 98%) was obtained.

Preparation of Compound 29-3

After Compound 29-4 (12.5 g, 53.4 mmol) was dissolved in THF, TEA (22.2 ml, 160.2 mmol) and 2-naphthoyl chloride (15.2 g, 80.1 mmol) were added thereto at 0° C. Then, a temperature was increased to room temperature and the resultant reaction product was stirred for 4 hours. After the reaction was completed, the resultant reaction product was extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 29-3 (17.8 g, 86%) was obtained.

Preparation of Compound 29-2

After Compound 29-3 (17.8 g, 45.9 mmol) was dissolved in nitrobenzene, POCl$_3$ (0.86 ml, 9.18 mmol) was added thereto at room temperature. Then, the resultant reaction product was stirred at 150° C. for 18 hours. After the reaction was completed, the resultant reaction product was neutralized with NaHCO₃ and extracted with EA. The organic layer was dried using anhydrous MgSO₄, and after the solvent was removed with a rotary evaporator, the resultant reaction product was purified by column chromatography using dichloromethane and methanol as a developing solvent, and the target compound 29-2 (14.1 g, 83%) was obtained.

Preparation of Compound 29-1

After Compound 29-2 (14.1 g, 38.0 mmol) was dissolved in dichloromethane, pyridine (4.6 ml, 57.1 mmol) was added thereto and triflic anhydride (9.6 ml, 57 mmol) was added dropwise thereto at 0° C. Then, the resultant reaction product was stirred at room temperature for 5 hours. After the reaction was completed, the reaction solution was allowed to pass through silica. The filtrate was removed with a rotary evaporator. Then, the resultant reaction product was purified by column chromatography using dichloromethane and methanol as a developing solvent, and the target compound 29-1 (17.6 g, 92%) was obtained.

Preparation of Compound 29

Compound 29-1 (17.6 g, 34.9 mmol), carbazole (7.00 g, 41.9 mmol), Pd(PPh₃)₄ (4.03 g, 3.49 mmol), 2M K₂CO₃ aqueous solution (80 ml), toluene (400 ml), and ethanol (80 ml) were added and then, refluxed for 12 hours. After the reaction was completed, the resultant reaction product was cooled to room temperature and then extracted with distilled water and EA. The organic layer was dried using anhydrous MgSO₄, and after the solvent was removed with a rotary evaporator, the resultant reaction product was purified by column chromatography using dichloromethane and hexane as a developing solvent, and 12.3 g (68%) of the target compound 29 was obtained.

PREPARATION EXAMPLE 5

Preparation of Compound 30

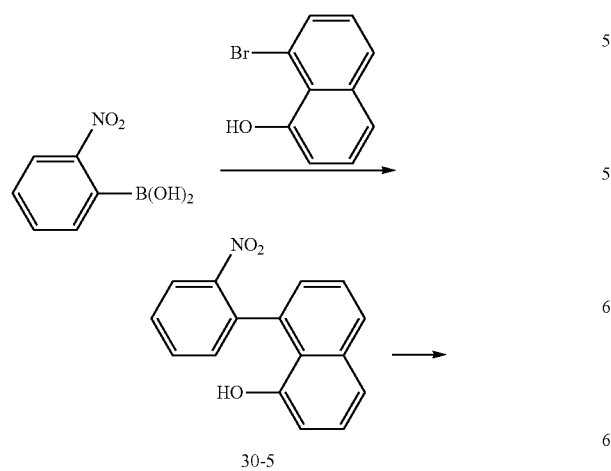

30-5

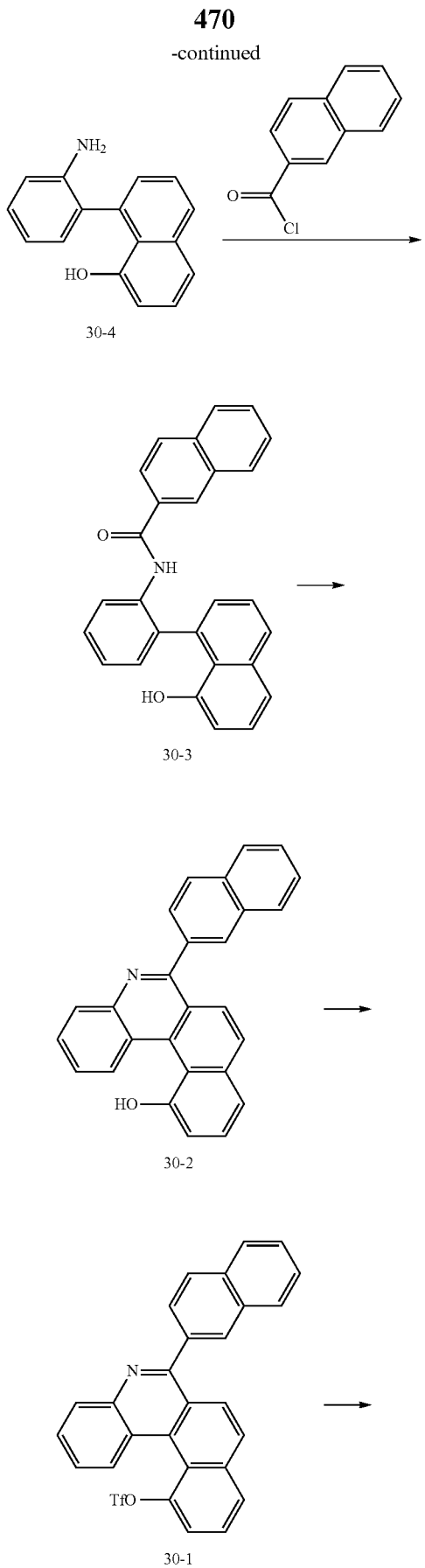

30-4

30-3

30-2

30-1

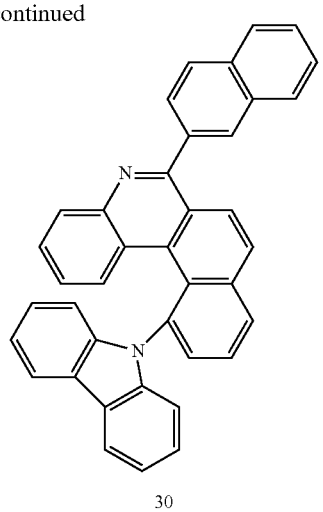

30

Preparation of Compound 30-5

A compound 2-nitrophenylboronic acid (10 g, 59.9 mmol), 1-hydroxy-8-bromonaphthalene (20.0 g, 89.8 mmol), Pd(PPh$_3$)$_2$Cl$_2$ (2.1 g, 3.0 mmol), 2M K$_2$CO$_3$ aqueous solution (70 ml), toluene (200 ml), and ethanol (100 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 30-5 (8.1 g, 51%) was obtained.

Preparation of Compound 30-4

Compound 30-5 (8.1 g, 30.5 mmol) was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 30-4 (12.5 g, 99%) was obtained.

Preparation of Compound 30-3

After Compound 30-4 (7.1 g, 30.1 mmol) was dissolved in THF, TEA (12.5 ml, 90.3 mmol) and 2-naphthoyl chloride (8.6 g, 45.1 mmol) were added thereto at 0° C. Then, a temperature was increased to room temperature and the resultant reaction product was stirred for 4 hours. After the reaction was completed, the resultant reaction product was extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 30-3 (9.6 g, 82%) was obtained.

Preparation of Compound 30-2

After Compound 30-3 (9.6 g, 24.6 mmol) was dissolved in nitrobenzene, POCl$_3$ (0.46 ml, 4.92 mmol) was added thereto at room temperature. Then, the resultant reaction product was stirred at 150° C. for 18 hours. After the reaction was completed, the resultant reaction product was neutralized with NaHCO$_3$ and extracted with EA. The organic layer was dried using anhydrous MgSO$_4$, and after the solvent was removed with a rotary evaporator, the resultant reaction product was purified by column chromatography using dichloromethane and methanol as a developing solvent, and the target compound 30-2 (7.31 g, 80%) was obtained.

Preparation of Compound 30-1

After Compound 30-2 (7.31 g, 19.7 mmol) was dissolved in dichloromethane, pyridine (2.3 ml, 29.5 mmol) was added thereto and triflic anhydride (4.98 ml, 29.5 mmol) was added dropwise thereto at 0° C. Then, the resultant reaction product was stirred at room temperature for 5 hours. After the reaction was completed, the reaction solution was allowed to pass through silica. The filtrate was removed with a rotary evaporator. Then, the resultant reaction product was purified by column chromatography using dichloromethane and methanol as a developing solvent, and the target compound 30-1 (8.03 g, 81%) was obtained.

Preparation of Compound 30

Compound 30-1 (8.03 g, 15.9 mmol), carbazole (3.98 g, 23.8 mmol), Pd(PPh$_3$)$_4$ (0.91 g, 0.795 mmol), 2M K$_2$CO$_3$ aqueous solution (70 ml), toluene (350 ml), and ethanol (70 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and 4.3 g (52%) of the target compound 30 was obtained.

PREPARATION EXAMPLE 6

Preparation of Compound 40

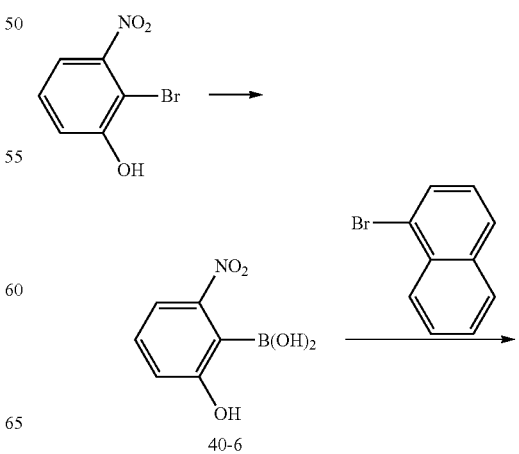

40-6

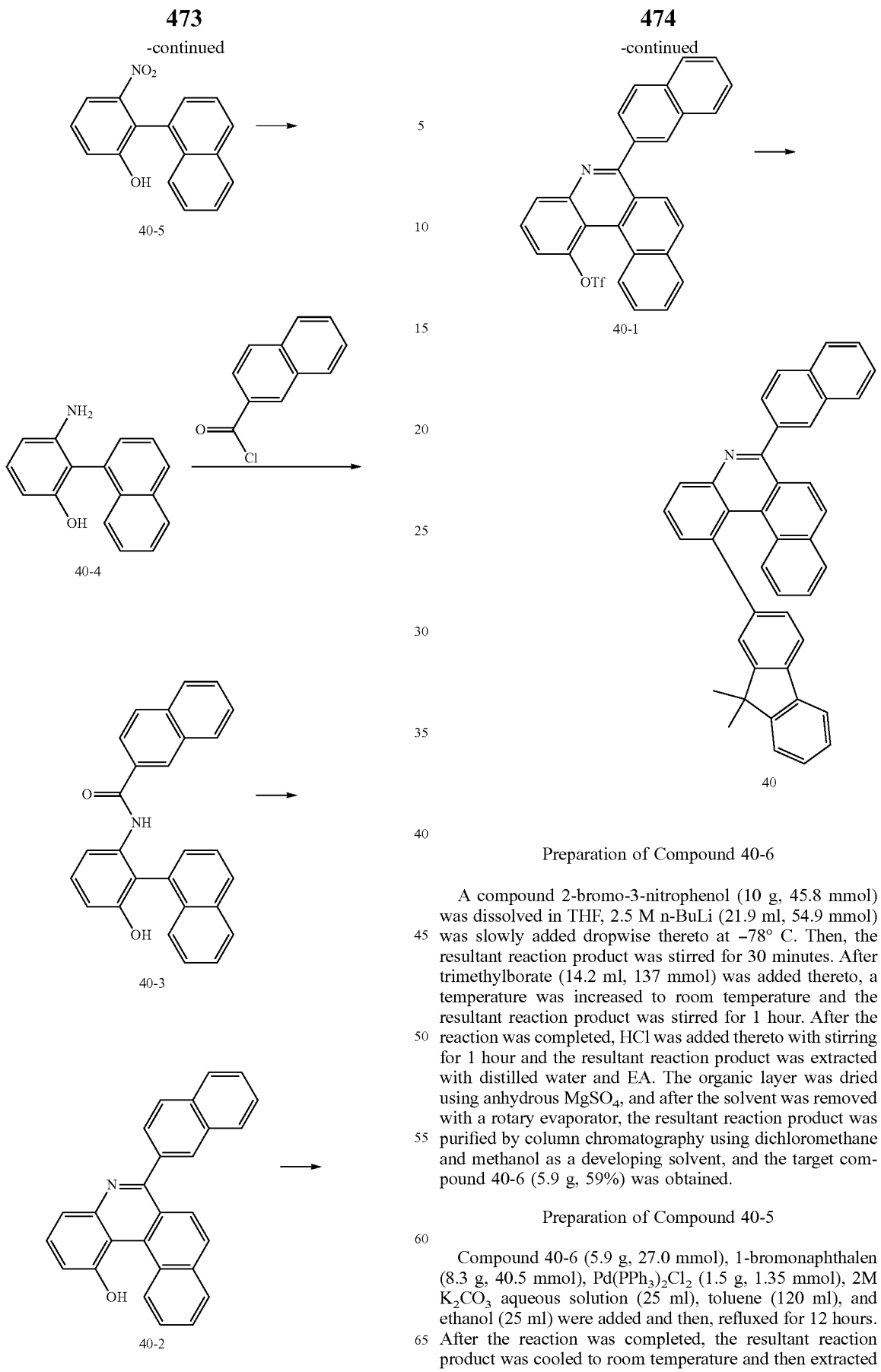

Preparation of Compound 40-6

A compound 2-bromo-3-nitrophenol (10 g, 45.8 mmol) was dissolved in THF, 2.5 M n-BuLi (21.9 ml, 54.9 mmol) was slowly added dropwise thereto at −78° C. Then, the resultant reaction product was stirred for 30 minutes. After trimethylborate (14.2 ml, 137 mmol) was added thereto, a temperature was increased to room temperature and the resultant reaction product was stirred for 1 hour. After the reaction was completed, HCl was added thereto with stirring for 1 hour and the resultant reaction product was extracted with distilled water and EA. The organic layer was dried using anhydrous $MgSO_4$, and after the solvent was removed with a rotary evaporator, the resultant reaction product was purified by column chromatography using dichloromethane and methanol as a developing solvent, and the target compound 40-6 (5.9 g, 59%) was obtained.

Preparation of Compound 40-5

Compound 40-6 (5.9 g, 27.0 mmol), 1-bromonaphthalen (8.3 g, 40.5 mmol), $Pd(PPh_3)_2Cl_2$ (1.5 g, 1.35 mmol), 2M $K_2CO_3$ aqueous solution (25 ml), toluene (120 ml), and ethanol (25 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 40-5 (4.9 g, 69%) was obtained.

Preparation of Compound 40-4

Compound 40-5 (4.9 g, 18.6 mmol) was dissolved in methanol and then substituted with nitrogen. After. Pd/C (10 wt %) was added thereto, the resultant reaction product was substituted with hydrogen and stirred at room temperature for 1 hour. After the reaction was completed, the resultant reaction product was allowed to pass through a Cellite, and the target compound 40-4 (4.3 g, 99%) was obtained.

Preparation of Compound 40-3

After Compound 40-4 (4.3 g, 18.4 mmol) was dissolved in THF, TEA (7.6 ml, 55.2 mmol) and 2-naphthoyl chloride (5.2 g, 27.6 mmol) were added thereto at 0° C. Then, a temperature was increased to room temperature and the resultant reaction product was stirred for 4 hours. After the reaction was completed, the resultant reaction product was extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 40-3 (6.3 g, 88%) was obtained.

Preparation of Compound 40-2

After Compound 40-3 (6.3 g, 16.2 mmol) was dissolved in nitrobenzene, POCl$_3$ (0.30 ml, 3.24 mmol) was added thereto at room temperature. Then, the resultant reaction product was stirred at 150° C. for 18 hours. After the reaction was completed, the resultant reaction product was neutralized with NaHCO$_3$ and extracted with EA. The organic layer was dried using anhydrous MgSO$_4$, and after the solvent was removed with a rotary evaporator, the resultant reaction product was purified by column chromatography using dichloromethane and methanol as a developing solvent, and the target compound 40-2 (5.17 g, 86%) was obtained.

Preparation of Compound 40-1

After Compound 40-2 (5.17 g, 13.9 mmol) was dissolved in dichloromethane, pyridine (1.6 ml, 20.8 mmol) was added thereto and triflic anhydride (5.27 ml, 20.8 mmol) was added dropwise thereto at 0° C. Then, the resultant reaction product was stirred at room temperature for 5 hours. After the reaction was completed, the reaction solution was allowed to pass through silica. The filtrate was removed with a rotary evaporator. Then, the resultant reaction product was purified by column chromatography using dichloromethane and methanol as a developing solvent, and the target compound 40-1 (5.94 g, 85%) was obtained.

Preparation of Compound 40

After Compound 40-1 (5.94 g, 11.8 mmol), 9,9-dimethylfluorene-2-boronic acid (4.83 g, 17.7 mmol), Pd(PPh$_3$)$_4$ (0.68 g, 0.590 mmol), 2M K$_2$CO$_3$ aqueous solution (45 ml), toluene (250 ml), and ethanol (45 ml) were added and then, refluxed for 12 hours. After the reaction was completed, the resultant reaction product was cooled to room temperature and extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and 3.3 g (51%) of the target compound 40 was obtained.

PREPARATION EXAMPLE 7

Preparation of Compound 10

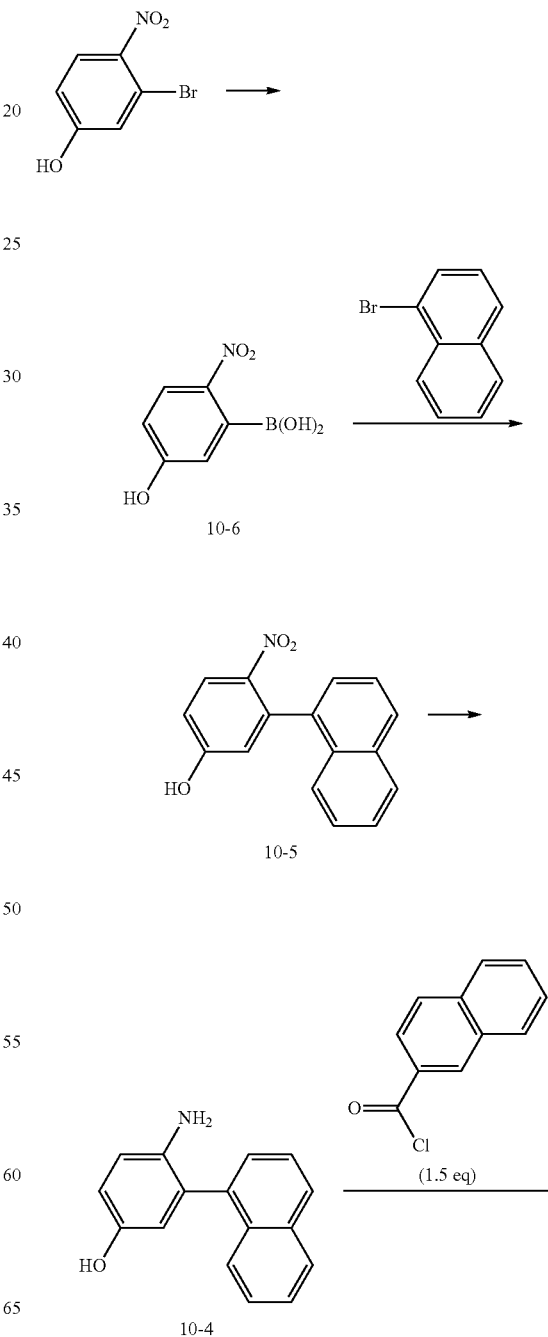

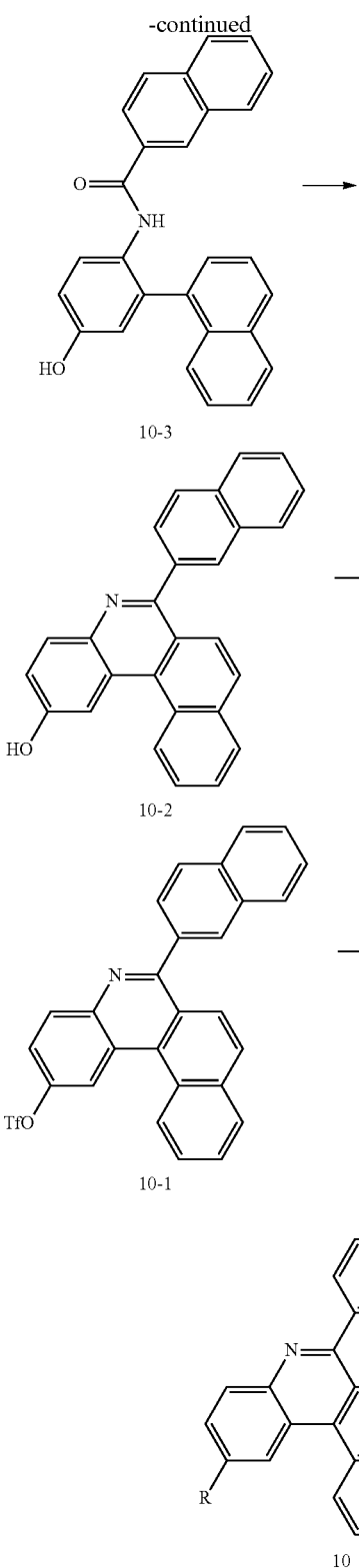

10-3

10-2

10-1

10

(herein, R is 9,10-bis(2-naphthyl)anthracenyl)

Preparation of Compound 10-6

After a compound 3-bromo-4-nitrophenol (10 g, 45.8 mmol) was dissolved in THF, 2.5 M n-BuLi (21.9 ml, 54.9 mmol) was slowly added dropwise thereto at −78° C. Then, the resultant reaction product was stirred for 30 minutes. After trimethylborate (14.2 ml, 137 mmol) was added thereto, a temperature was increased to room temperature and the resultant reaction product was stirred for 1 hour. After the reaction was completed, HCl was added thereto with stirring for 1 hour and the resultant reaction product was extracted with distilled water and EA. The organic layer was dried using anhydrous MgSO$_4$, and after the solvent was removed with a rotary evaporator, the resultant reaction product was purified by column chromatography using dichloromethane and methanol as a developing solvent, and the target compound 10-6 (5.7 g, 57%) was obtained.

Preparation of Compound 10-5

Compound 10-6 (5.7 g, 26.1 mmol), 1-bromonaphthalen (8.1 g, 39.1 mmol), Pd(PPh$_3$)$_2$Cl$_2$ (1.5 g, 1.30 mmol), 2M K$_2$CO$_3$ aqueous solution (25 ml), toluene (120 ml), and ethanol (25 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 10-5 (5.1 g, 74%) was obtained.

Preparation of Compound 10-4

Compound 10-5 (5.1 g, 19.3 mmol) was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 10-4 (4.45 g, 98%) was obtained.

Preparation of Compound 10-3

After Compound 10-4 (4.45 g, 18.9 mmol) was dissolved in THF, TEA (7.8 ml, 56.7 mmol) and 2-naphthoyl chloride (5.40 g, 28.3 mmol) were added thereto at 0° C. Then, a temperature was increased to room temperature and the resultant reaction product was stirred for 4 hours. After the reaction was completed, the resultant reaction product was extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 10-3 (6.70 g, 91%) was obtained.

Preparation of Compound 10-2

After Compound 10-3 (6.70 g, 17.2 mmol) was dissolved in nitrobenzene, POCl$_3$ (0.52 ml, 3.44 mmol) was added thereto at room temperature. Then, the resultant reaction product was stirred at 150° C. for 18 hours. After the reaction was completed, the resultant reaction product was neutralized with NaHCO$_3$ and extracted with EA. The organic layer was dried using anhydrous MgSO$_4$, and after the solvent was removed with a rotary evaporator, the resultant reaction product was purified by column chromatography using dichloromethane and methanol as a developing solvent, and the target compound 10-2 (5.62 g, 88%) was obtained.

Preparation of Compound 10-1

After Compound 10-2 (5.62 g, 15.1 mmol) was dissolved in dichloromethane, pyridine (1.8 ml, 22.6 mmol) was added thereto and triflic anhydride (3.82 ml, 22.6 mmol) was added dropwise thereto at 0° C. Then, the resultant reaction product was stirred at room temperature for 5 hours. After the reaction was completed, the reaction solution was allowed to pass through silica. The filtrate was removed with a rotary evaporator. Then, the resultant reaction product was purified by column chromatography using dichloromethane and methanol as a developing solvent, and the target compound 10-1 (6.23 g, 82%) was obtained.

Preparation of Compound 10

After Compound 10-1 (6.23 g, 12.3 mmol), 9,10-bis(2-naphthyl)anthracene-2-boronic acid (7.51 g, 14.7 mmol), Pd(PPh$_3$)$_4$ (0.71 g, 0.615 mmol), 2M K$_2$CO$_3$ aqueous solution (45 ml), toluene (250 ml), and ethanol (45 ml) were added and then, refluxed for 12 hours. After the reaction was completed, the resultant reaction product was cooled to room temperature and extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and 5.4 g (56%) of the target compound 10 was obtained.

PREPARATION EXAMPLE 8

Preparation of Compound 106

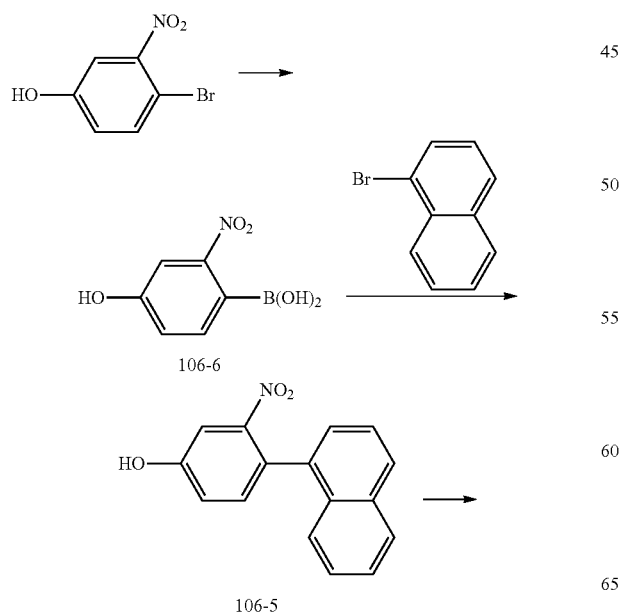

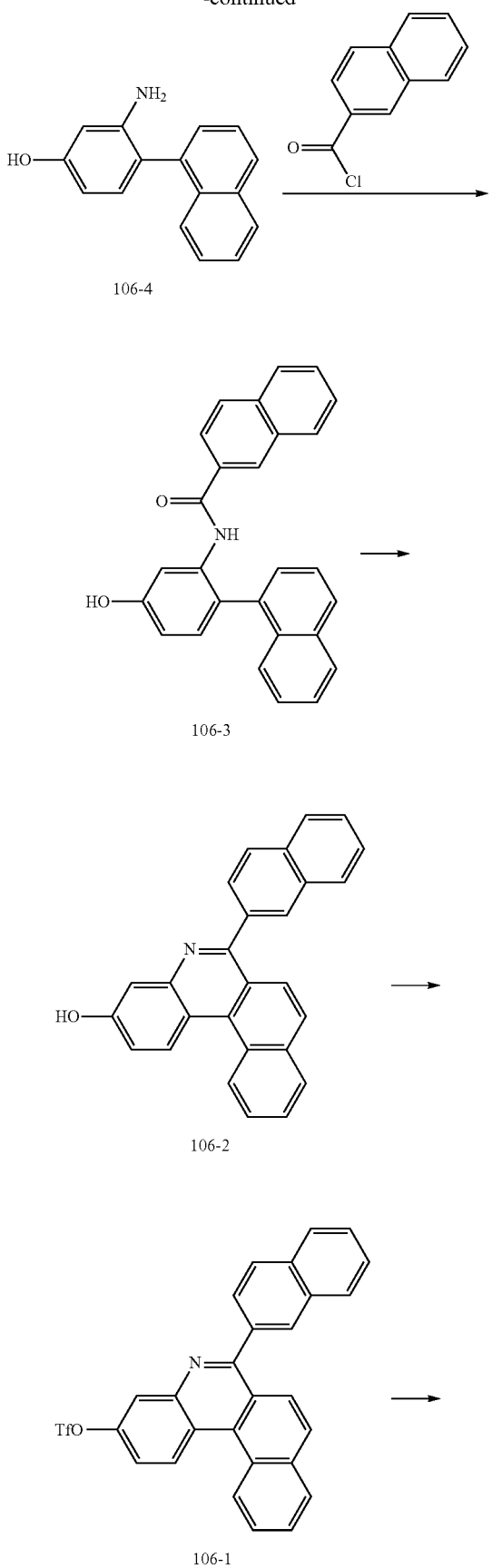

-continued

106

Preparation of Compound 106-6

After a compound 4-bromo-5-nitrophenol (10 g, 45.8 mmol) was dissolved in THF, 2.5 M n-BuLi (21.9 ml, 54.9 mmol) was slowly added dropwise thereto at −78° C. Then, the resultant reaction product was stirred for 30 minutes. After trimethylborate (14.2 ml, 137 mmol) was added thereto, a temperature was increased to room temperature and the resultant reaction product was stirred for 1 hour. After the reaction was completed, HCl was added thereto with stirring for 1 hour and the resultant reaction product was extracted with distilled water and EA. The organic layer was dried using anhydrous MgSO$_4$, and after the solvent was removed with a rotary evaporator, the resultant reaction product was purified by column chromatography using dichloromethane and methanol as a developing solvent, and the target compound 106-6 (4.44 g, 53%) was obtained.

Preparation of Compound 106-5

Compound 106-6 (4.44 g, 24.2 mmol), 1-bromonaphthalen (7.5 g, 36.3 mmol), Pd(PPh$_3$)$_2$Cl$_2$ (0.98 g, 1.21 mmol), 2M K$_2$CO$_3$ aqueous solution (25 ml), toluene (120 ml), and ethanol (25 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 106-5 (5.07 g, 79%) was obtained.

Preparation of Compound 106-4

Compound 106-5 (5.07 g, 19.1 mmol) was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 106-4 (4.44 g, 98%) was obtained.

Preparation of Compound 106-3

After Compound 106-4 (4.44 g, 18.9 mmol) was dissolved in THF, TEA (7.8 ml, 56.7 mmol) and 2-naphthoyl chloride (5.40 g, 28.3 mmol) were added thereto at 0° C. Then, a temperature was increased to room temperature and the resultant reaction product was stirred for 4 hours. After the reaction was completed, the resultant reaction product was extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 106-3 (6.55 g, 89%) was obtained.

Preparation of Compound 106-2

After Compound 106-3 (6.55 g, 16.8 mmol) was dissolved in nitrobenzene, POCl$_3$ (0.31 ml, 3.36 mmol) was added thereto at room temperature. Then, the resultant reaction product was stirred at 150° C. for 18 hours. After the reaction was completed, the resultant reaction product was neutralized with NaHCO$_3$ and extracted with EA. The organic layer was dried using anhydrous MgSO$_4$, and after the solvent was removed with a rotary evaporator, the resultant reaction product was purified by column chromatography using dichloromethane and methanol as a developing solvent, and the target compound 106-2 (5.74 g, 92%) was obtained.

Preparation of Compound 106-1

After Compound 106-2 (5.74 g, 15.4 mmol) was dissolved in dichloromethane, pyridine (1.8 ml, 22.6 mmol) was added thereto and triflic anhydride (3.82 ml, 22.6 mmol) was added dropwise thereto at 0° C. Then, the resultant reaction product was stirred at room temperature for 5 hours. After the reaction was completed, the reaction solution was allowed to pass through silica. The filtrate was removed with a rotary evaporator. Then, the resultant reaction product was purified by column chromatography using dichloromethane and methanol as a developing solvent, and the target compound 106-1 (6.59 g, 85%) was obtained.

Preparation of Compound 106

After Compound 106-1 (6.59 g, 13.1 mmol), 1-phenyl-1H-benzo[d]imidazole-2-phenylboronic acid (5.48 g, 15.7 mmol), Pd(PPh$_3$)$_4$ (0.75 g, 0.655 mmol), 2M K$_2$CO$_3$ aqueous solution (45 ml), toluene (250 ml), and ethanol (45 ml) were added and then, refluxed for 12 hours. After the reaction was completed, the resultant reaction product was cooled to room temperature and extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and 5.1 g (63%) of the target compound 106 was obtained.

PREPARATION EXAMPLE 9

Preparation of Compound 107

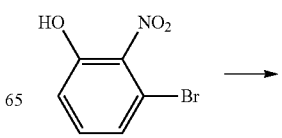

483
-continued

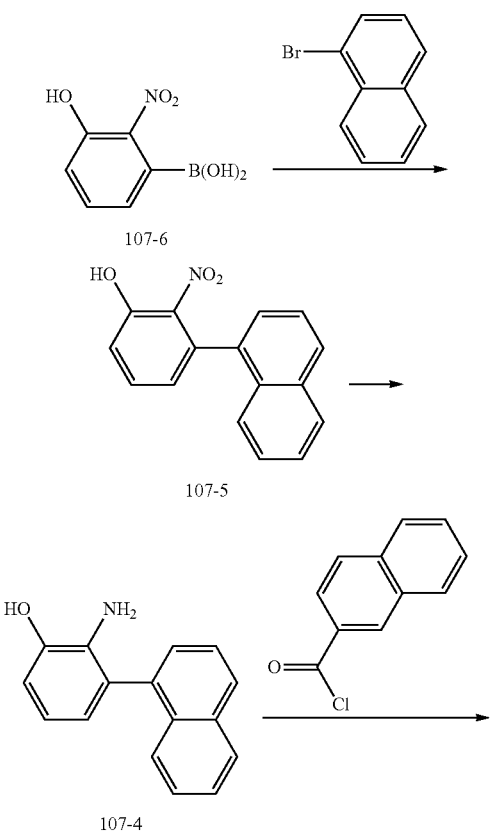

484
-continued

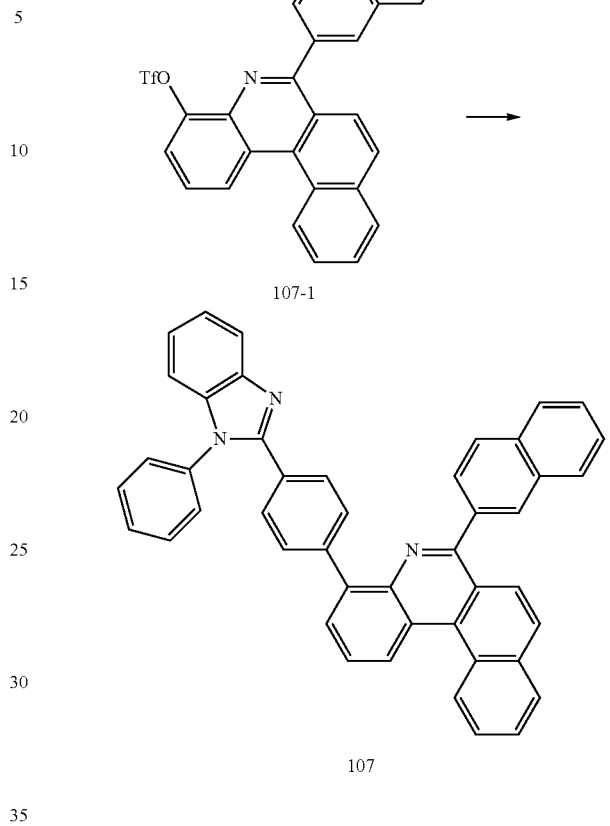

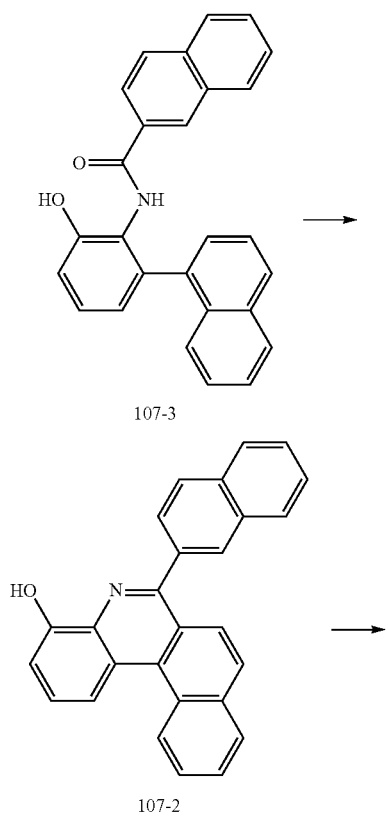

Preparation of Compound 107-6

After a compound 4-bromo-5-nitrophenol (10 g, 45.8 mmol) was dissolved in THF, 2.5 M n-BuLi (21.9 ml, 54.9 mmol) was slowly added dropwise thereto at −78° C. Then, the resultant reaction product was stirred for 30 minutes. After trimethylborate (14.2 ml, 137 mmol) was added thereto, a temperature was increased to room temperature and the resultant reaction product was stirred for 1 hour. After the reaction was completed, HCl was added thereto with stirring for 1 hour and the resultant reaction product was extracted with distilled water and EA. The organic layer was dried using anhydrous $MgSO_4$, and after the solvent was removed with a rotary evaporator, the resultant reaction product was purified by column chromatography using dichloromethane and methanol as a developing solvent, and the target compound 107-6 (4.60 g, 55%) was obtained.

Preparation of Compound 107-5

Compound 107-6 (4.60 g, 25.2 mmol), 1-bromonaphthalen (7.8 g, 37.7 mmol), $Pd(PPh_3)_2Cl_2$ (1.02 g, 1.26 mmol), 2M $K_2CO_3$ aqueous solution (20 ml), toluene (100 ml), and ethanol (20 ml) were added and then, refluxed for 12 hours. After the reaction was completed, the resultant reaction product was cooled to room temperature and then extracted with distilled water and EA. The organic layer was dried using anhydrous $MgSO_4$, and after the solvent was removed with a rotary evaporator, the resultant reaction product was purified by column chromatography using dichloromethane and hexane as a developing solvent, and the target compound 107-5 (5.48 g, 82%) was obtained.

Preparation of Compound 107-4

Compound 107-5 (5.48 g, 20.6 mmol) was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 107-4 (5.87 g, 99%) was obtained.

Preparation of Compound 107-3

After Compound 107-4 (5.84 g, 24.9 mmol) was dissolved in THF, TEA (10.3 ml, 74.7 mmol) and 2-naphthoyl chloride (7.12 g, 37.3 mmol) were added thereto at 0° C. Then, a temperature was increased to room temperature and the resultant reaction product was stirred for 4 hours. After the reaction was completed, the resultant reaction product was extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 107-3 (8.92 g, 92%) was obtained.

Preparation of Compound 107-2

After Compound 107-3 (8.92 g, 45.8 mmol) was dissolved in nitrobenzene, POCl$_3$ (0.43 ml, 45.8 mmol) was added thereto at room temperature. Then, the resultant reaction product was stirred at 150° C. for 18 hours. After the reaction was completed, the resultant reaction product was neutralized with NaHCO$_3$ and extracted with EA. The organic layer was dried using anhydrous MgSO$_4$, and after the solvent was removed with a rotary evaporator, the resultant reaction product was purified by column chromatography using dichloromethane and methanol as a developing solvent, and the target compound 107-2 (7.99 g, 94%) was obtained.

Preparation of Compound 107-1

After Compound 107-2 (7.99 g, 21.5 mmol) was dissolved in dichloromethane, pyridine (2.59 ml, 32.2 mmol) was added thereto and triflic anhydride (5.44 ml, 32.2 mmol) was added dropwise thereto at 0° C. Then, the resultant reaction product was stirred at room temperature for 5 hours. After the reaction was completed, the reaction solution was allowed to pass through silica. The filtrate was removed with a rotary evaporator. Then, the resultant reaction product was purified by column chromatography using dichloromethane and methanol as a developing solvent, and the target compound 107-1 (9.31 g, 86%) was obtained.

Preparation of Compound 107

After Compound 107-1 (9.31 g, 18.5 mmol), 1-phenyl-phenyl-1H-benzo[d]imidazole-2-phenylboronic acid (7.75 g, 22.2 mmol), Pd(PPh$_3$)$_4$ (1.06 g, 0.925 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and 7.6 g (66%) of the target compound 107 was obtained.

PREPARATION EXAMPLE 10

Preparation of Compound 187

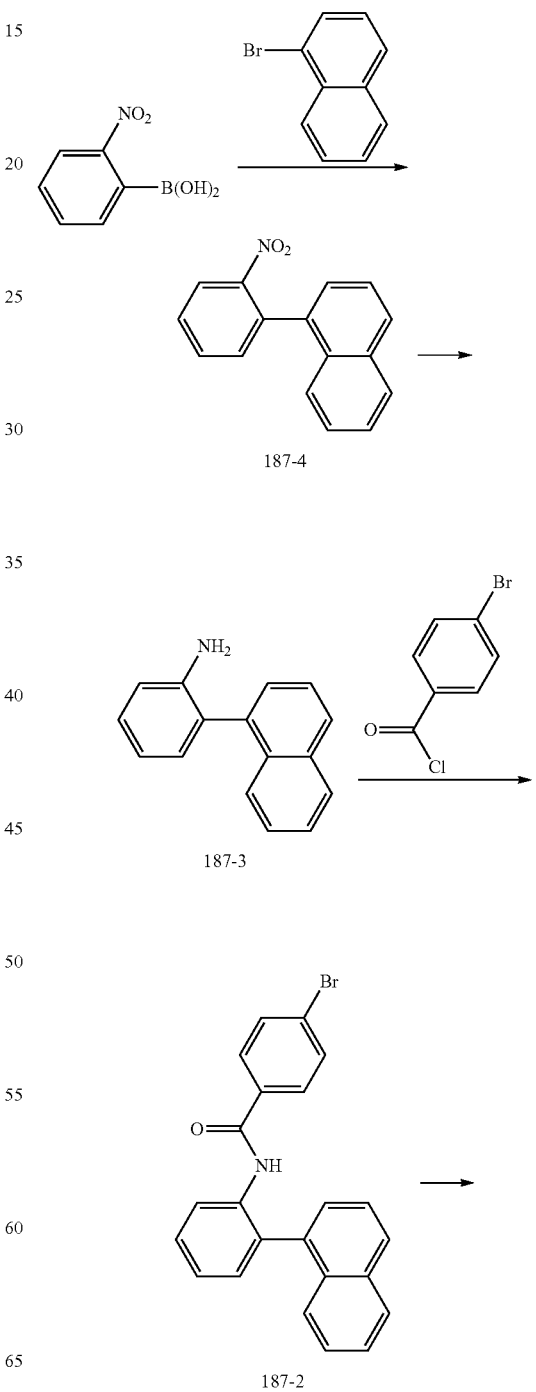

-continued

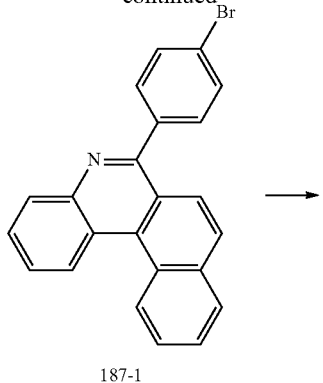
187-1

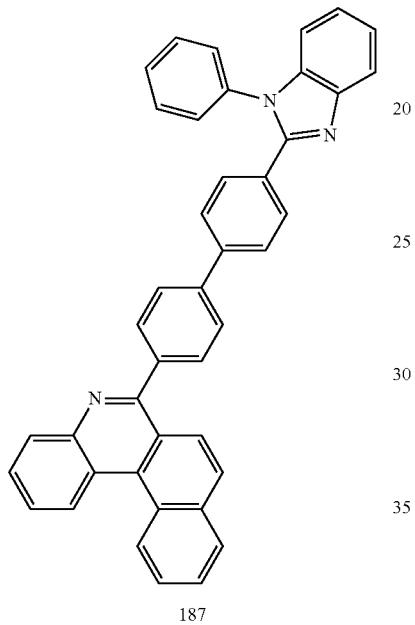
187

Preparation of Compound 187-4

A compound 1-bromo-2-nitrobenzene (10 g, 59.9 mmol), 1-naphthaleneboronic acid (15 g, 89.8 mmol), Pd(PPh₃)₄ (7.0 g, 5.99 mmol), 2M K₂CO₃ aqueous solution (40 ml), toluene (200 ml), and ethanol (40 ml) were added and then, refluxed for 3 hours. After the reaction was completed, the resultant reaction product was cooled to room temperature and then extracted with distilled water and EA. The organic layer was dried using anhydrous MgSO₄, and after the solvent was removed with a rotary evaporator, the resultant reaction product was purified by column chromatography using dichloromethane and hexane as a developing solvent, and the target compound 187-4 (5.48 g, 61%) was obtained.

Preparation of Compound 187-3

After Compound 187-4 (9.10 g, 36.5 mmol) was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 187-3 (7.92 g, 99%) was obtained.

Preparation of Compound 187-2

After Compound 187-3 (7.92 g, 36.1 mmol) was dissolved in THF, TEA (15.0 ml, 108 mmol) and 4-bromobenzoyl chloride (11.8 g, 54.1 mmol) were added thereto at 0° C. Then, a temperature was increased to room temperature and the resultant reaction product was stirred for 2 hours. After the reaction was completed, the resultant reaction product was extracted with distilled water and EA. The organic layer was dried using anhydrous MgSO₄, and after the solvent was removed with a rotary evaporator, the resultant reaction product was purified by column chromatography using dichloromethane and hexane as a developing solvent, and the target compound 187-2 (13.6 g, 94%) was obtained.

Preparation of Compound 187-1

After Compound 187-2 (13.6 g, 33.9 mmol) was dissolved in nitrobenzene, POCl₃ (1.58 ml, 16.9 mmol) was added thereto at room temperature. Then, the resultant reaction product was stirred at 150° C. for 18 hours. After the reaction was completed, the resultant reaction product was neutralized with NaHCO₃ and extracted with EA. The organic layer was dried using anhydrous MgSO₄, and after the solvent was removed with a rotary evaporator, the resultant reaction product was purified by column chromatography using dichloromethane and methanol as a developing solvent, and the target compound 187-1 (8.85 g, 68%) was obtained.

Preparation of Compound 187

Compound 187-1 (8.85 g, 23.0 mmol), 1-phenyl-1H-benzo[d]imidazole-2-phenylboronic acid (11.8 g, 29.9 mmol), Pd(PPh₃)₄ (1.32 g, 1.15 mmol), 2M K₂CO₃ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO₄, and after the solvent was removed with a rotary evaporator, the resultant reaction product was purified by column chromatography using dichloromethane and hexane as a developing solvent, and the target compound 187 (8.9 g, 68%) was obtained.

PREPARATION EXAMPLE 11

Preparation of Compound 201

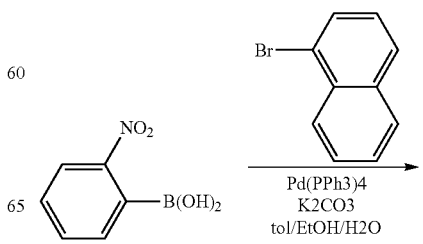

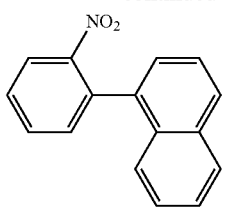

201-4

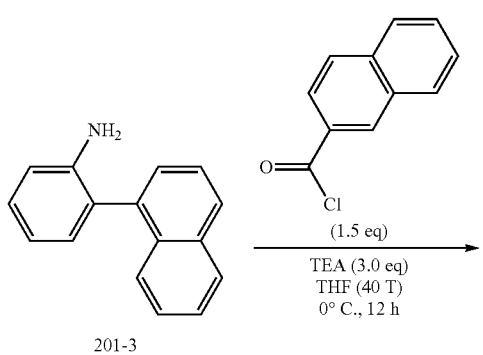

201-3

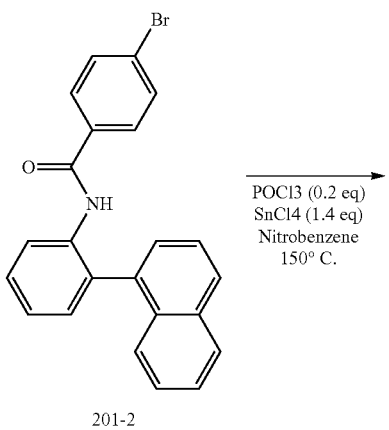

201-2

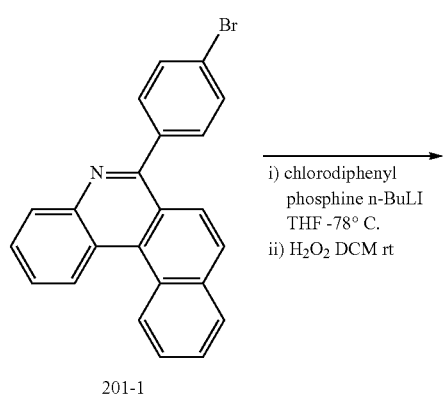

201-1

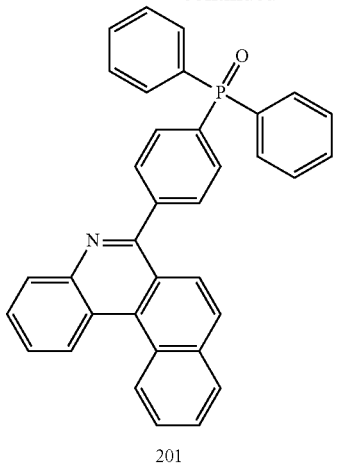 [SMILES: O=P(c1ccccc1)(c1ccccc1)c1ccc(-c2nc3ccccc3c3c2ccc2ccccc23)cc1]

201

Preparation of Compound 201-4

A compound 1-bromo-2-nitrobenzene (10 g, 59.9 mmol), 1-naphthaleneboronic acid (15 g, 89.8 mmol), Pd(PPh$_3$)$_4$ (7.0 g, 5.99 mmol), 2M K$_2$CO$_3$ aqueous solution (40 ml), toluene (200 ml), and ethanol (40 ml) were added and then, refluxed for 3 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 201-4 (5.48 g, 61%) was obtained.

Preparation of Compound 201-3

Compound 201-4 (9.10 g, 36.5 mmol) was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 201-3 (7.92 g, 99%) was obtained.

Preparation of Compound 201-2

After Compound 201-3 (7.92 g, 36.1 mmol) was dissolved in THF, TEA (15.0 ml, 108 mmol) and 4-bromobenzoyl chloride (11.8 g, 54.1 mmol) were added thereto at 0° C. Then, a temperature was increased to room temperature and the resultant reaction product was stirred for 2 hours. After the reaction was completed, the resultant reaction product was extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 201-2 (13.6 g, 94%) was obtained.

Preparation of Compound 201-1

After Compound 201-2 (13.6 g, 33.9 mmol) was dissolved in nitrobenzene, POCl$_3$ (1.58 ml, 16.9 mmol) was added thereto at room temperature. Then, the resultant reaction product was stirred at 150° C. for 18 hours. After the reaction was completed, the resultant reaction product was neutralized with NaHCO₃ and extracted with EA. The organic layer was dried using anhydrous MgSO₄, and after the solvent was removed with a rotary evaporator, the resultant reaction product was purified by column chromatography using dichloromethane and methanol as a developing solvent, and the target compound 201-1 (8.85 g, 68%) was obtained.

Preparation of Compound 201

After Compound 201-1 (8.85 g, 23.0 mmol) was dissolved in THF, 2.5 M n-BuLi (11.9 ml, 29.9 mmol) was slowly added dropwise thereto at −78° C. Then, the resultant reaction product was stirred for 30 minutes. After chlorodiphenylphosphine (14.2 ml, 29.9 mmol) was added thereto, the resultant reaction product was stirred for 1 hour. After the reaction was completed, methanol was added thereto with stirring for 1 hour and the resultant reaction product was extracted with distilled water and EA. After the organic layer was dried using anhydrous MgSO₄, the solvent was removed with a rotary evaporator. After dichloromethane (210 ml) was added to the concentrate and dissolved therein, H₂O₂ (7.0 ml) was added thereto with stirring at room temperature for 3 hours. After the reaction was completed, the resultant reaction product was extracted with distilled water and EA. The organic layer was dried using anhydrous MgSO₄, and after the solvent was removed with a rotary evaporator, toluene was added thereto and heated to be dissolved. Then, the resultant reaction product was recrystallized, and the target compound 201 (9.42 g, 81%) was obtained.

PREPARATION EXAMPLE 12

Preparation of Compound 112

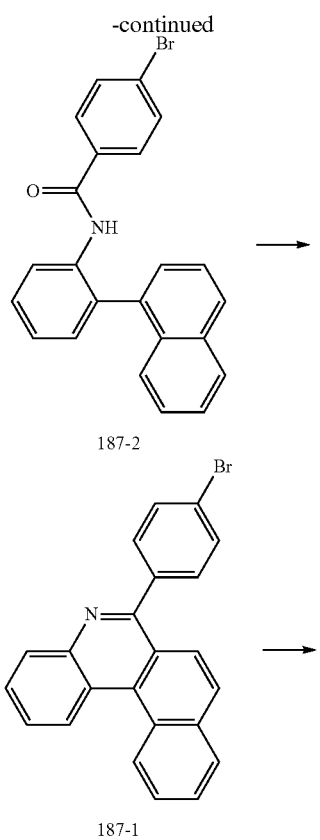

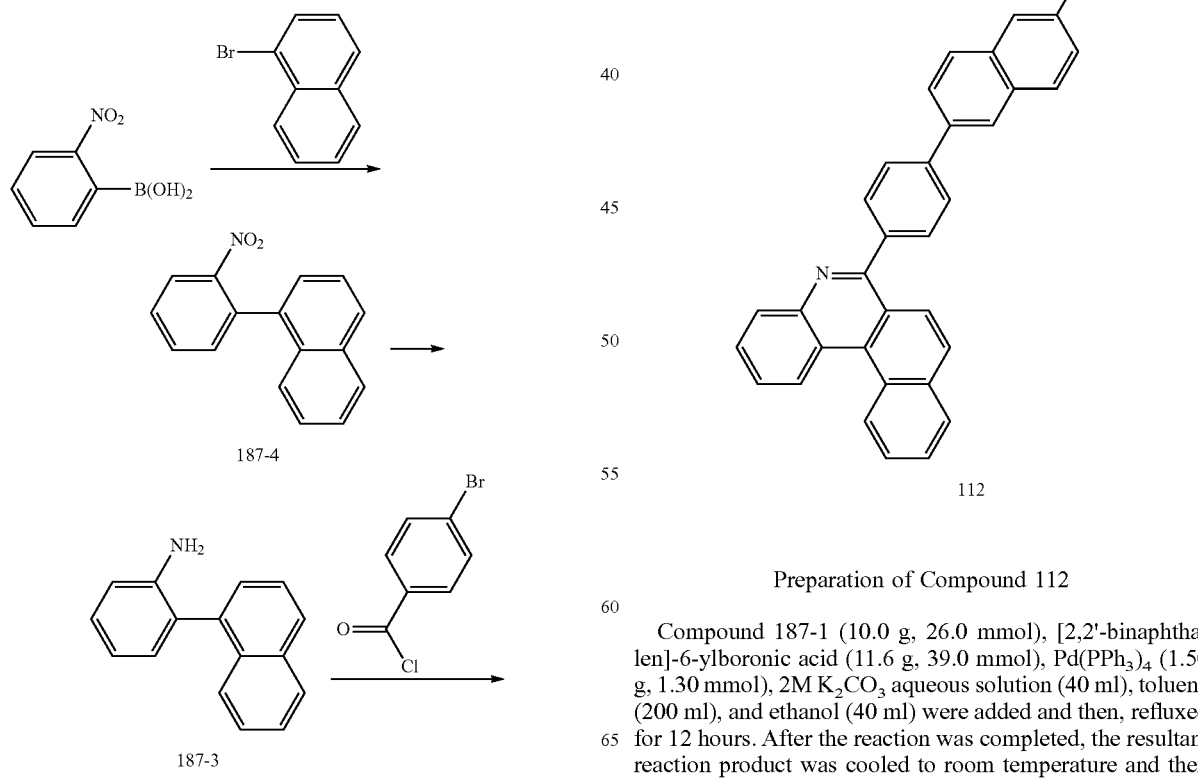

Preparation of Compound 112

Compound 187-1 (10.0 g, 26.0 mmol), [2,2'-binaphthalen]-6-ylboronic acid (11.6 g, 39.0 mmol), Pd(PPh₃)₄ (1.50 g, 1.30 mmol), 2M K₂CO₃ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 112 (10.4 g, 72%) was obtained.

PREPARATION EXAMPLE 13

Preparation of Compound 124

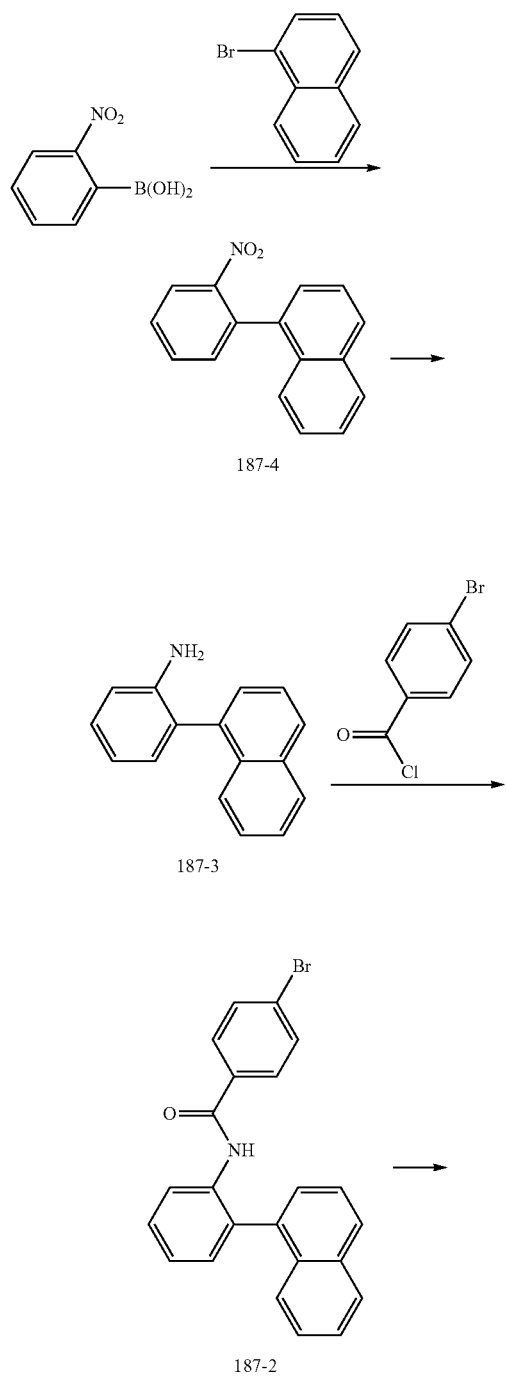

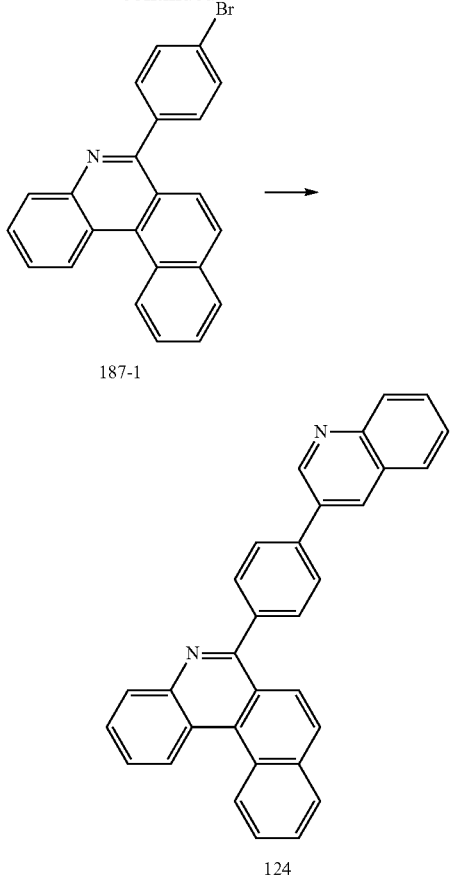

Preparation of Compound 124

Compound 187-1 (10.0 g, 26.0 mmol), quinolin-3-ylboronic acid (6.7 g, 39.0 mmol), Pd(PPh$_3$)$_4$ (1.50 g, 1.30 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 124 (10.4 g, 72%) was obtained.

PREPARATION EXAMPLE 14

Preparation of Compound 189

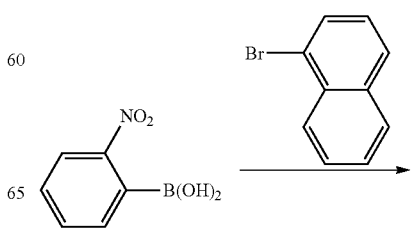

495
-continued

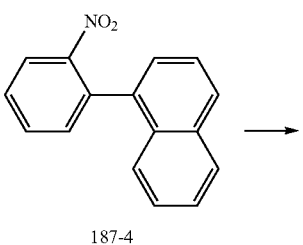
187-4

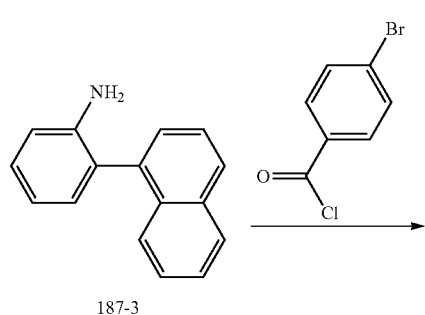
187-3

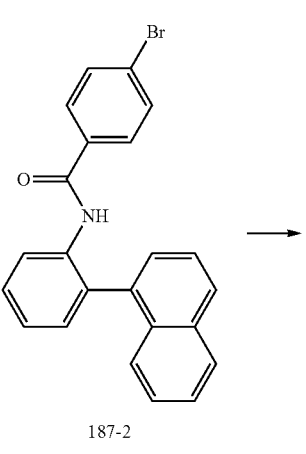
187-2

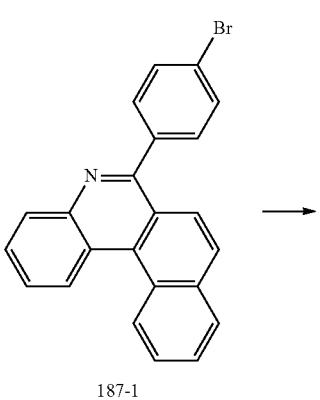
187-1

496
-continued

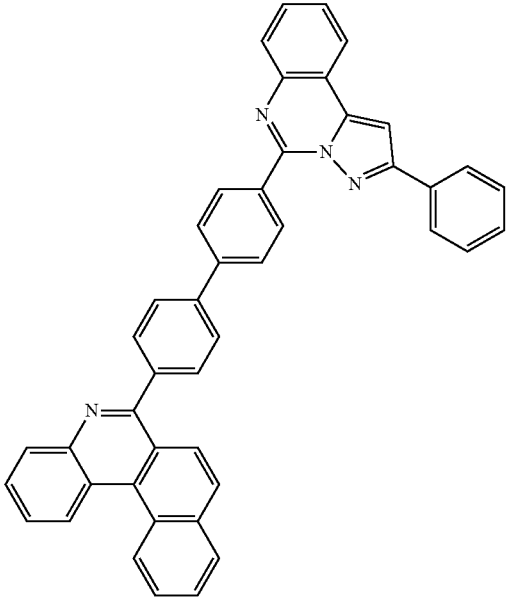
189

Preparation of Compound 189

Compound 187-1 (10.0 g, 26.0 mmol), (4-(2-phenylpyrazolo[1,5-c]quinazolin-5-yl)phenyl)boronic acid (14.2 g, 39.0 mmol), Pd(PPh$_3$)$_4$ (1.50 g, 1.30 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 189 (11.0 g, 68%) was obtained.

PREPARATION EXAMPLE 15

Preparation of Compound 227

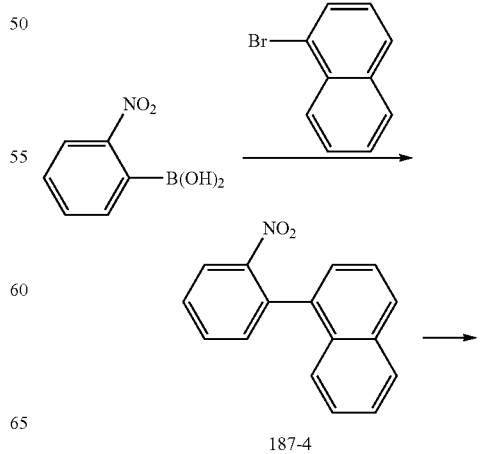
187-4

-continued

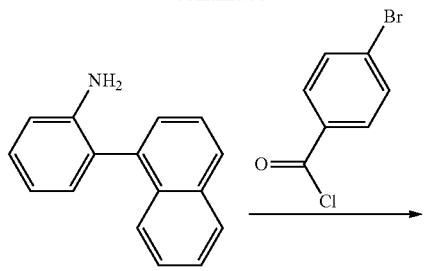
187-3

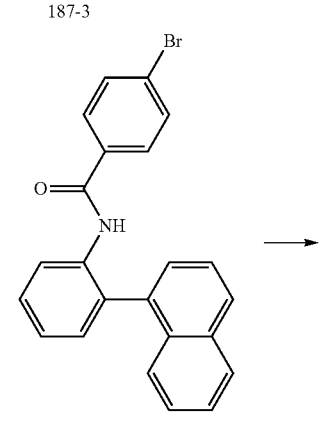
187-2

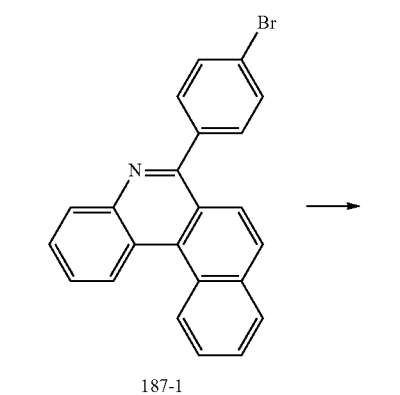
187-1

227-1

-continued

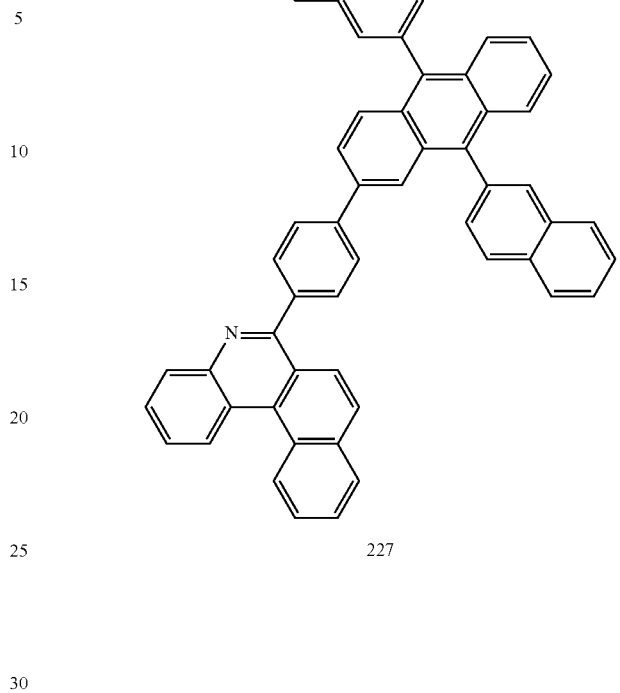
227

Preparation of Compound 227-1

Compound 187-1 (10.0 g, 26.0 mmol), bis(pinacolato)diborone (8.0 g, 31.2 mmol), Pd(dppf)$_2$Cl$_2$ (1.06 g, 1.3 mmol), potassium acetate (7.6 g, 78.0 mmol), and DMF (200 ml) were added and then, refluxed for 18 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 227-1 (10.0 g, 89%) was obtained.

Preparation of Compound 227

Compound 227-1 (10.0 g, 23.2 mmol), 2-bromo-9,10-di(naphthalene-2-yl)anthracene (17.7 g, 34.8 mmol), Pd(PPh$_3$)$_4$ (1.34 g, 1.16 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 227 (8.2 g, 48%) was obtained.

PREPARATION EXAMPLE 16

Preparation of Compound 238

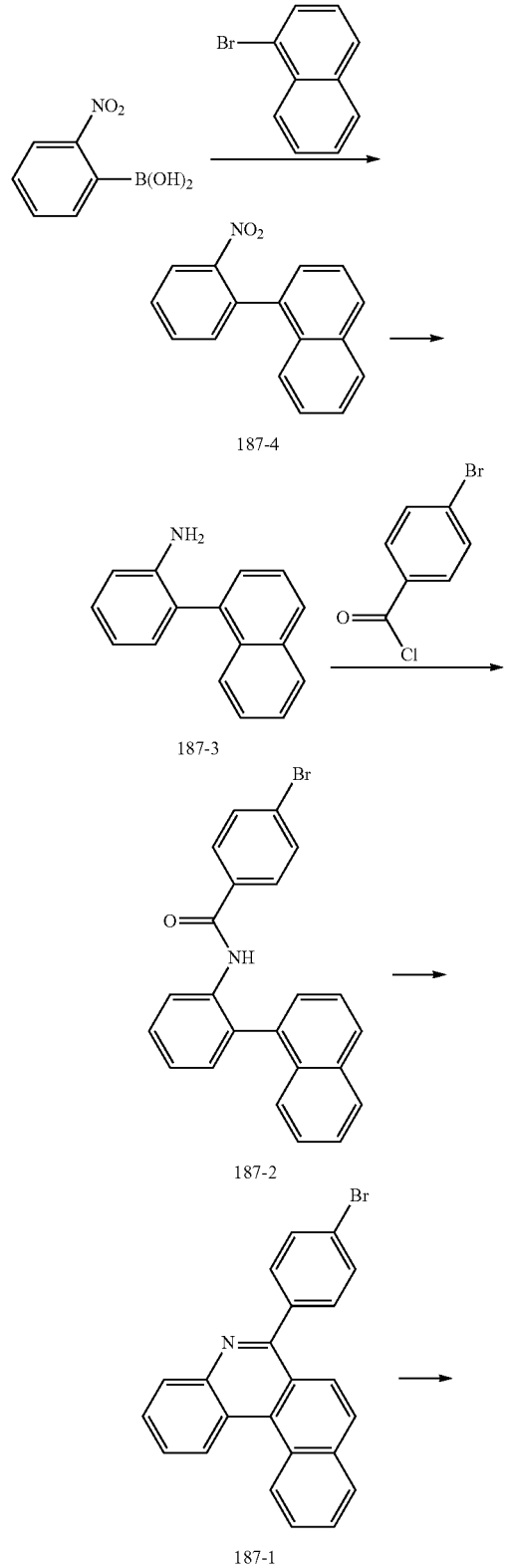

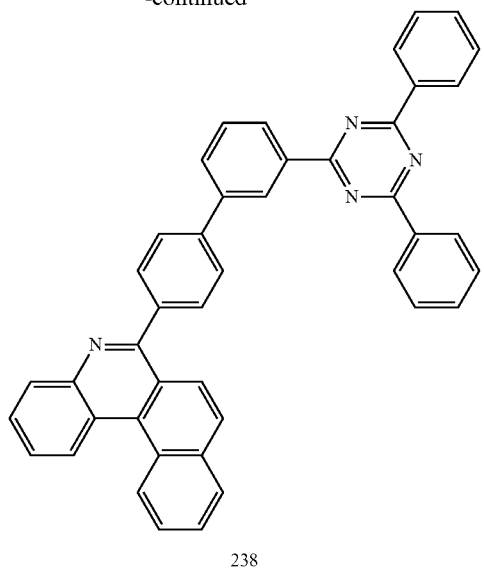

238

Preparation of Compound 238

Compound 187-1 (10.0 g, 26.0 mmol), 2,4-diphenyl-6-(3-(4,4,5,5-tetramethyl-1,3,2-dioxaborolan-2-yl)phenyl)-1,3,5-triazine (17.0 g, 39.0 mmol), Pd(PPh$_3$)$_4$ (1.50 g, 1.30 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 238 (6.0 g, 48%) was obtained.

PREPARATION EXAMPLE 17

Preparation of Compound 325

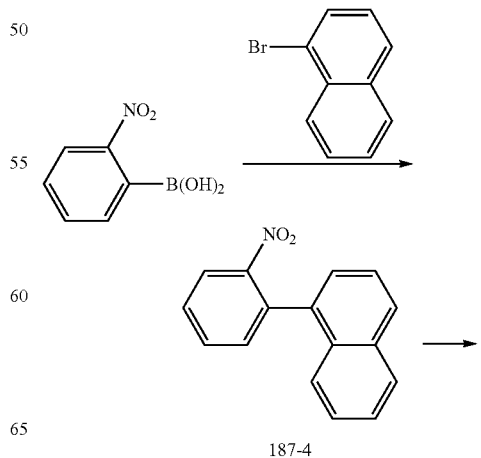

187-4

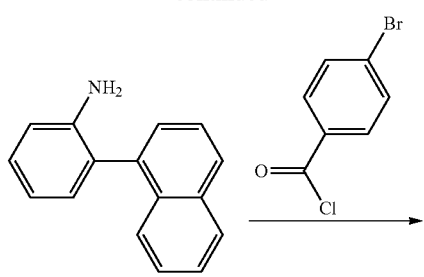
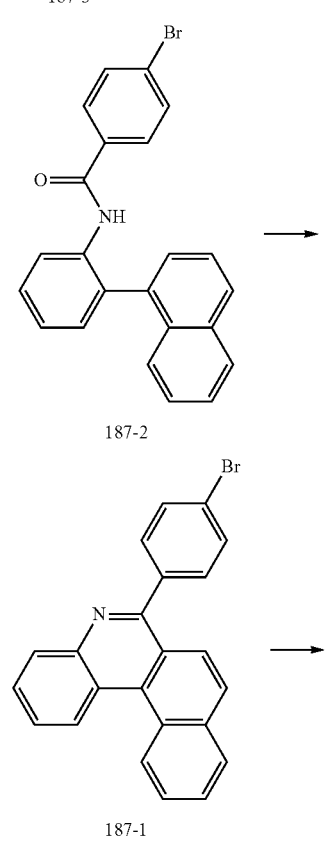
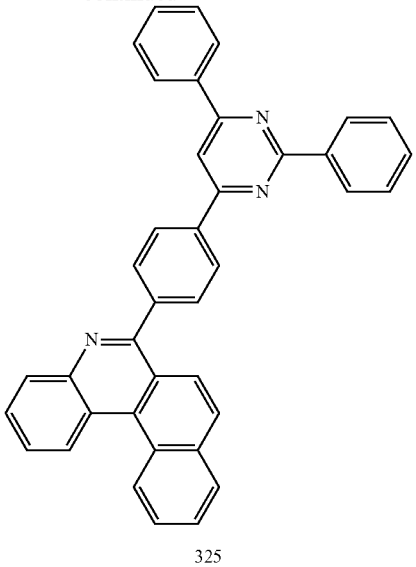

Preparation of Compound 325

Compound 227-1 (10.0 g, 23.2 mmol), 4-bromo-2,6-diphenylpyrimidine (10.7 g, 34.8 mmol), Pd(PPh$_3$)$_4$ (1.34 g, 1.16 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 325 (10.5 g, 85%) was obtained.

PREPARATION EXAMPLE 18

Preparation of Compound 365

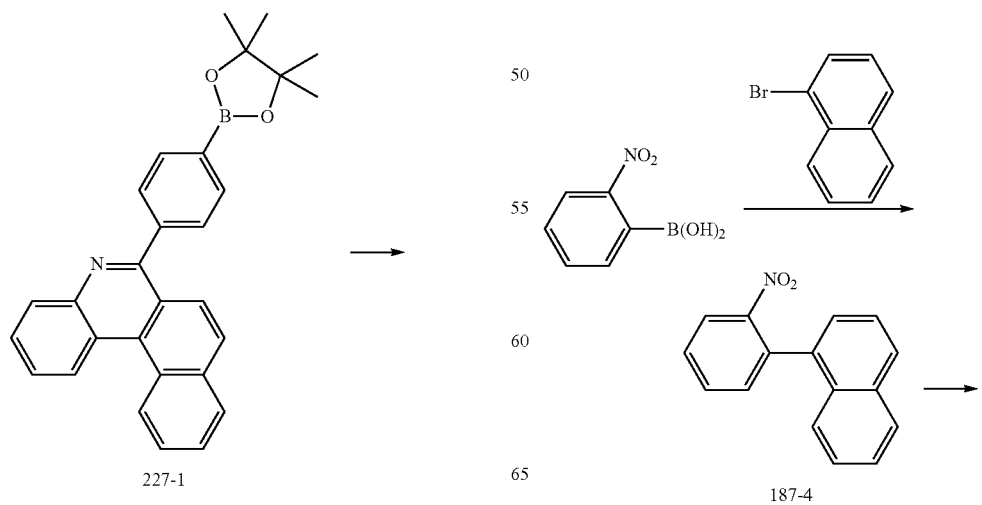

-continued

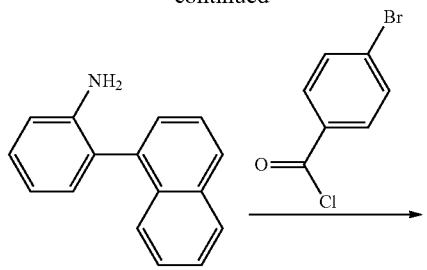

187-3

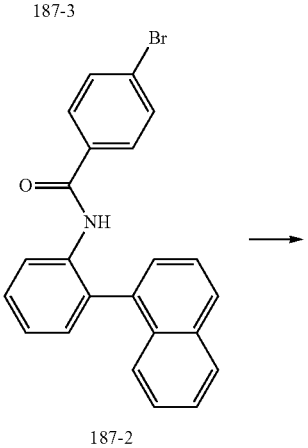

187-2

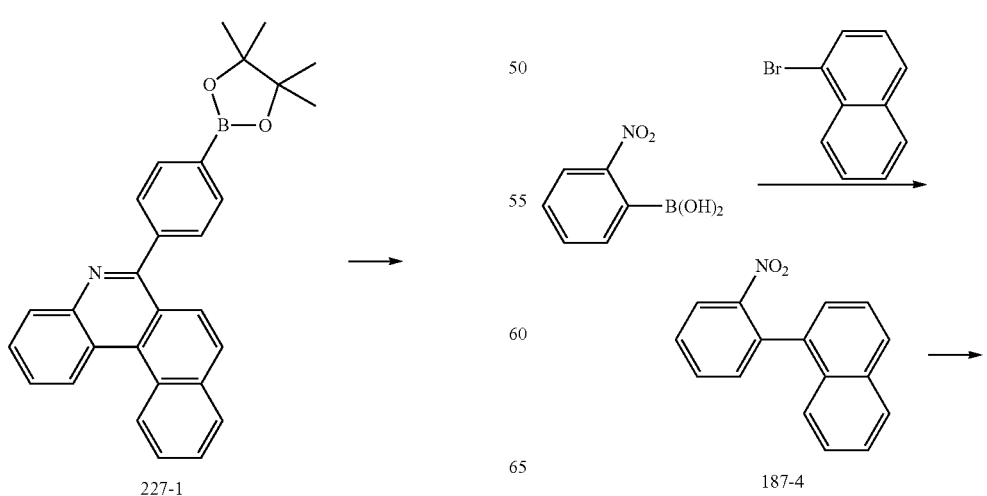

227-1                    187-1

-continued

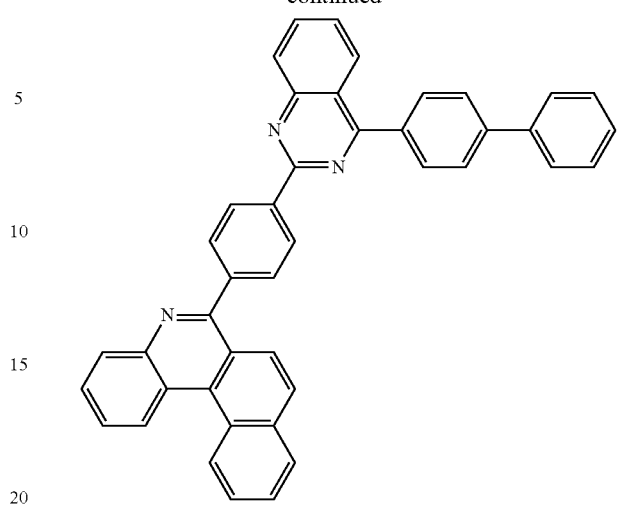

365

Preparation of Compound 365

Compound 227-1 (10.0 g, 23.2 mmol), 4-([1,1'-biphenyl]-4-yl)-2-bromoquinazoline (12.5 g, 34.8 mmol), Pd(PPh$_3$)$_4$ (1.34 g, 1.16 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 365 (7.2 g, 53%) was obtained.

PREPARATION EXAMPLE 19

Preparation of Compound 390

187-4

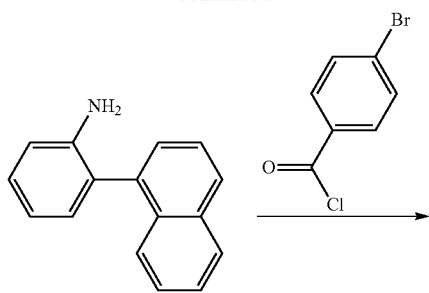

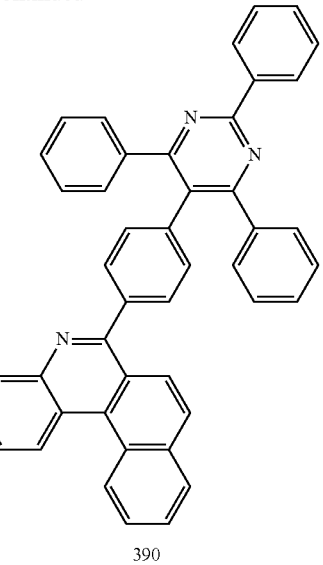

Preparation of Compound 390

Compound 227-1 (10.0 g, 23.2 mmol), 5-bromo-2,4,6-triphenylpyrimidine (13.5 g, 34.8 mmol), Pd(PPh$_3$)$_4$ (1.34 g, 1.16 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 390 (7.0 g, 49%) was obtained.

PREPARATION EXAMPLE 20

Preparation of Compound 457

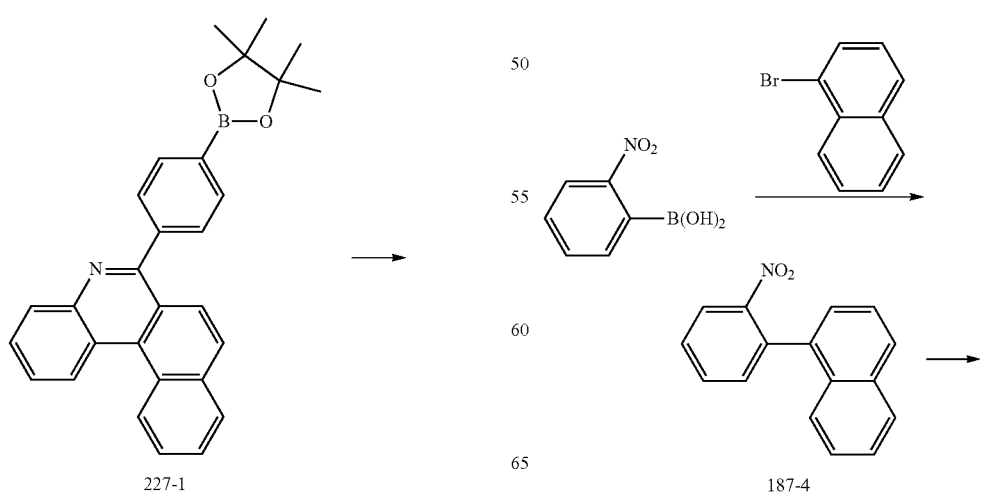

507
-continued

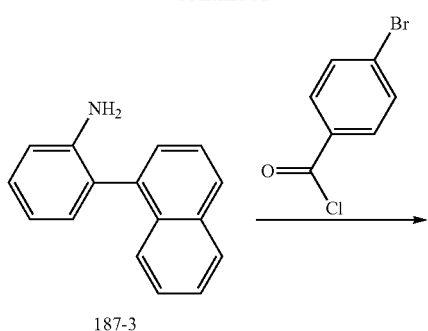
187-3

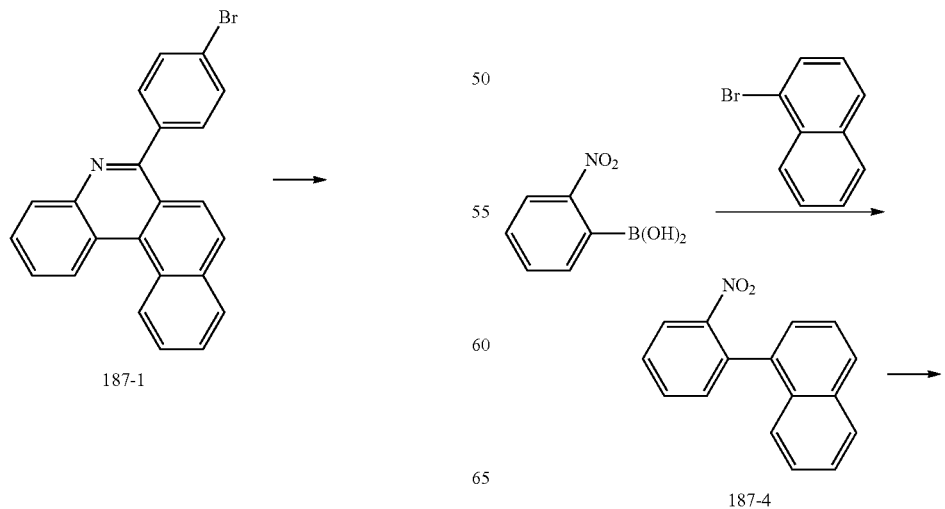

508
-continued

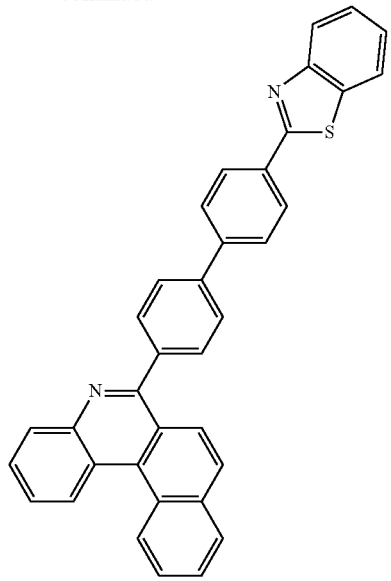
457

Preparation of Compound 457

Compound 187-1 (10.0 g, 26.0 mmol), 2-(4-(4,4,5,5-tetramethyl-1,3,2-dioxaborolan-2-yl)phenyl)benzo[d]thiazole (13.2 g, 39.0 mmol), Pd(PPh$_3$)$_4$ (1.50 g, 1.30 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 457 (8.6 g, 64%) was obtained.

PREPARATION EXAMPLE 21

Preparation of Compound 219

509
-continued

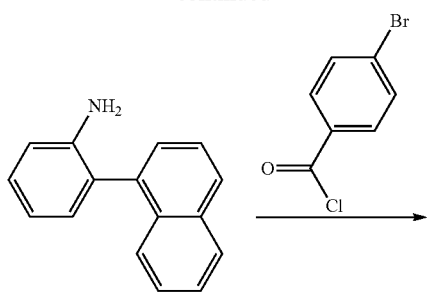
187-3

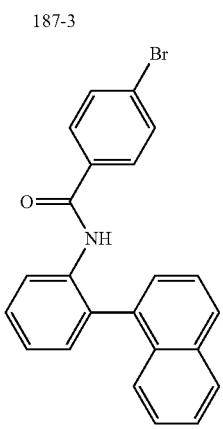
187-2

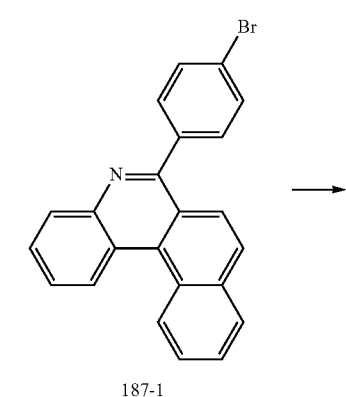
187-1

227-1

510
-continued

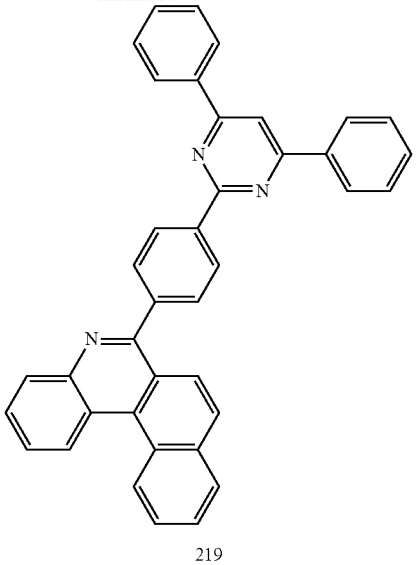
219

Preparation of Compound 219

Compound 227-1 (10.0 g, 23.2 mmol), 2-chloro-4,6-diphenylpyrimidine (9.3 g, 34.8 mmol), Pd(PPh$_3$)$_4$ (1.34 g, 1.16 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 219 (8.6 g, 69%) was obtained.

PREPARATION EXAMPLE 22

Preparation of Compound 802

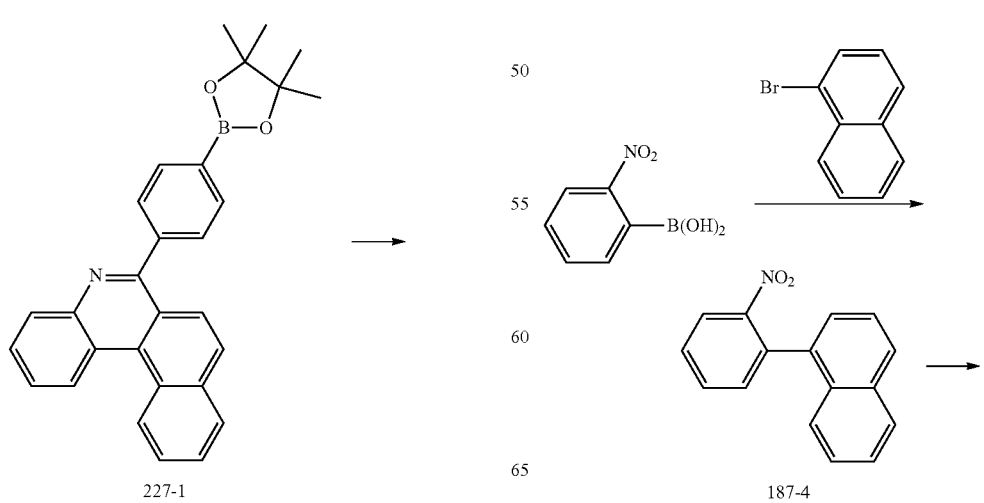
187-4

511
-continued

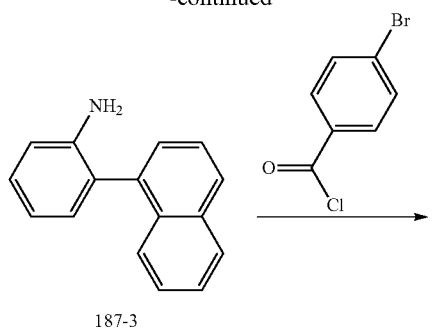
187-3

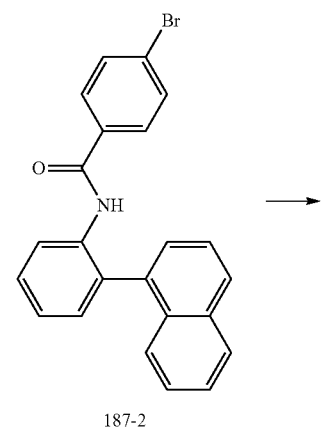
187-2

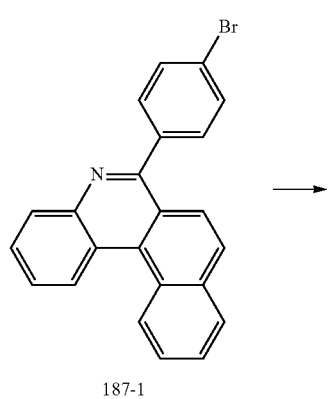
187-1

802

512

Preparation of Compound 802

Compound 187-1 (10.0 g, 26.0 mmol), phenanthren-9-ylboronic acid (8.6 g, 39.0 mmol), Pd(PPh$_3$)$_4$ (1.50 g, 1.30 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 802 (7.5 g, 60%) was obtained.

PREPARATION EXAMPLE 23

Preparation of Compound 812

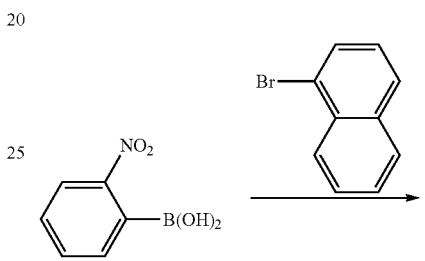

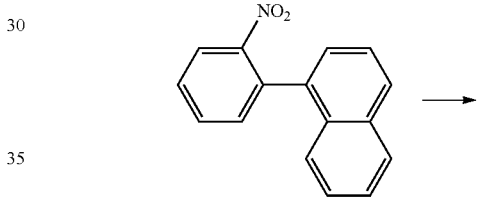
187-4

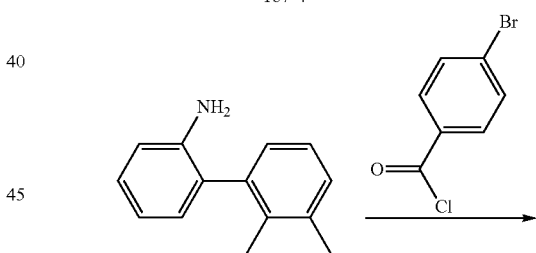
187-3

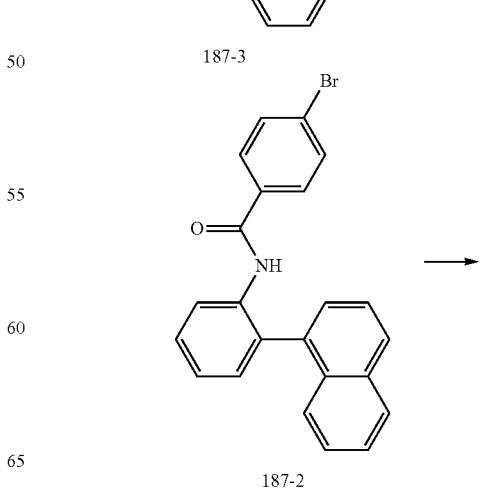
187-2

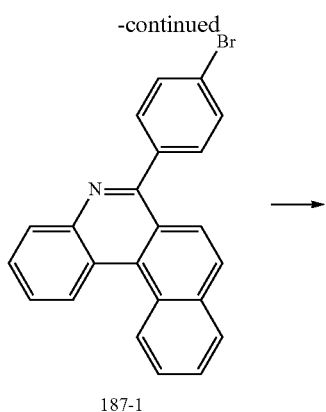

187-1

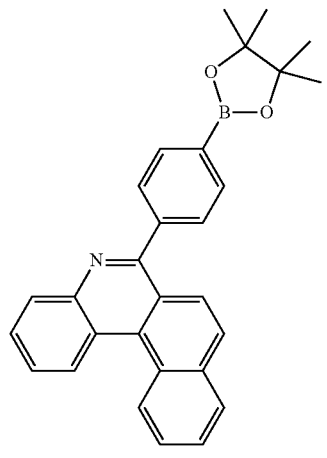

227-1

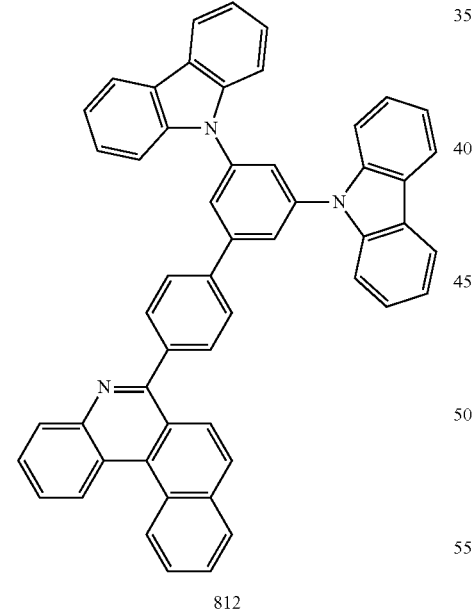

812

Preparation of Compound 812

Compound 227-1 (10.0 g, 23.2 mmol), 9,9'-(5-bromo-1,3-phenylene)bis(9H-carbazole) (17.0 g, 34.8 mmol), Pd(PPh$_3$)$_4$ (1.34 g, 1.16 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 812 (10.7 g, 65%) was obtained.

PREPARATION EXAMPLE 24

Preparation of Compound 815

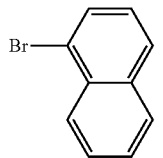

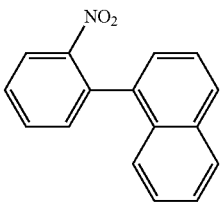

187-4

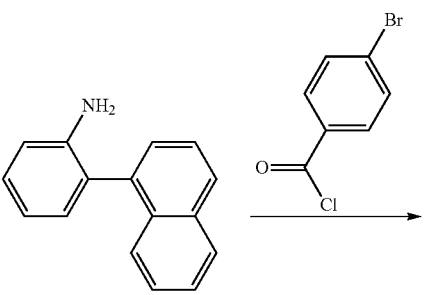

187-3

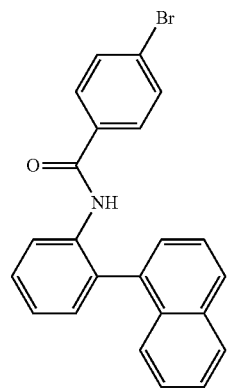

187-2

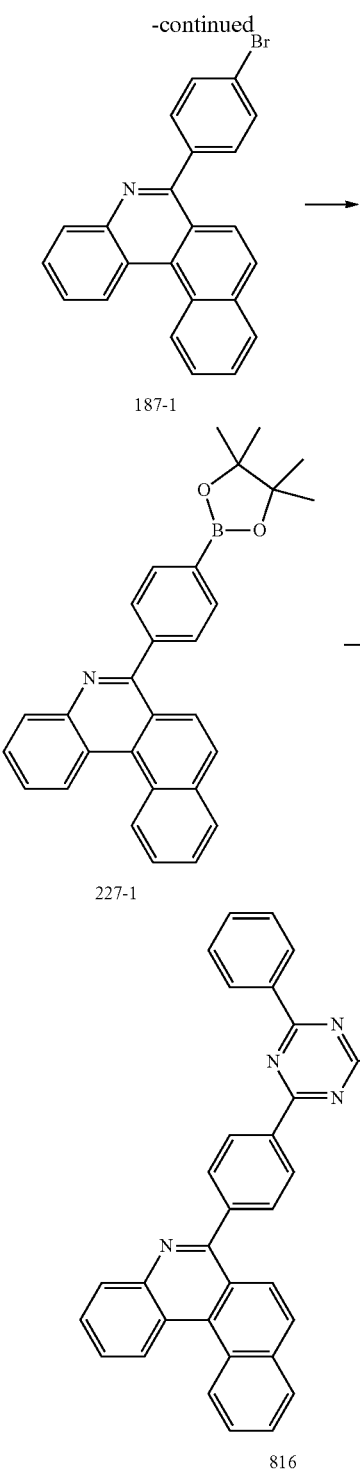

187-1

227-1

816

Preparation of Compound 815

Compound 227-1 (10.0 g, 23.2 mmol), 2-chloro-4,6-diphenyl-1,3,5-triazine (9.3 g, 34.8 mmol), Pd(PPh₃)₄ (1.34 g, 1.16 mmol), 2M K₂CO₃ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO₄, and after the solvent was removed with a rotary evaporator, the resultant reaction product was purified by column chromatography using dichloromethane and hexane as a developing solvent, and the target compound 815 (8.5 g, 68%) was obtained.

PREPARATION EXAMPLE 25

Preparation of Compound 1

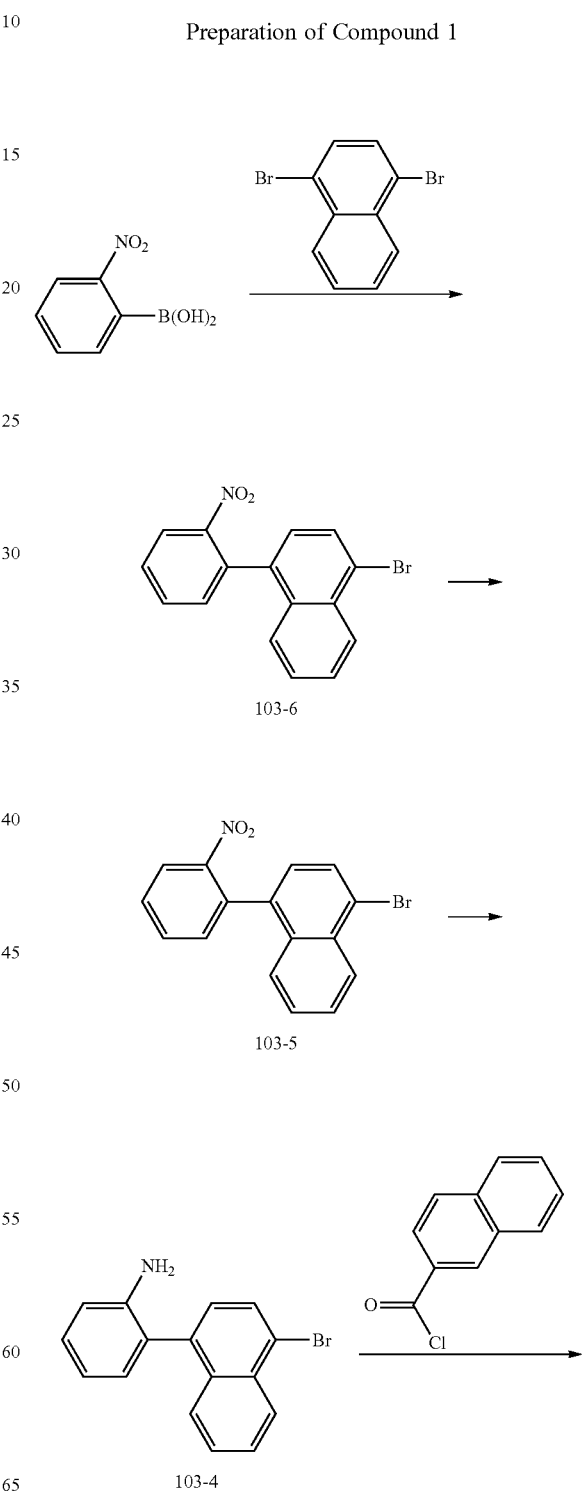

103-6

103-5

103-4

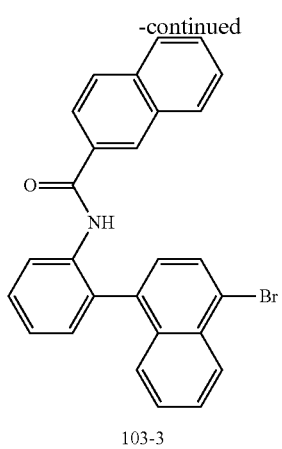

2M K₂CO₃ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO₄, and after the solvent was removed with a rotary evaporator, the resultant reaction product was purified by column chromatography using dichloromethane and hexane as a developing solvent, and the target compound 1 (8.5 g, 68%) was obtained.

PREPARATION EXAMPLE 26

Preparation of Compound 75

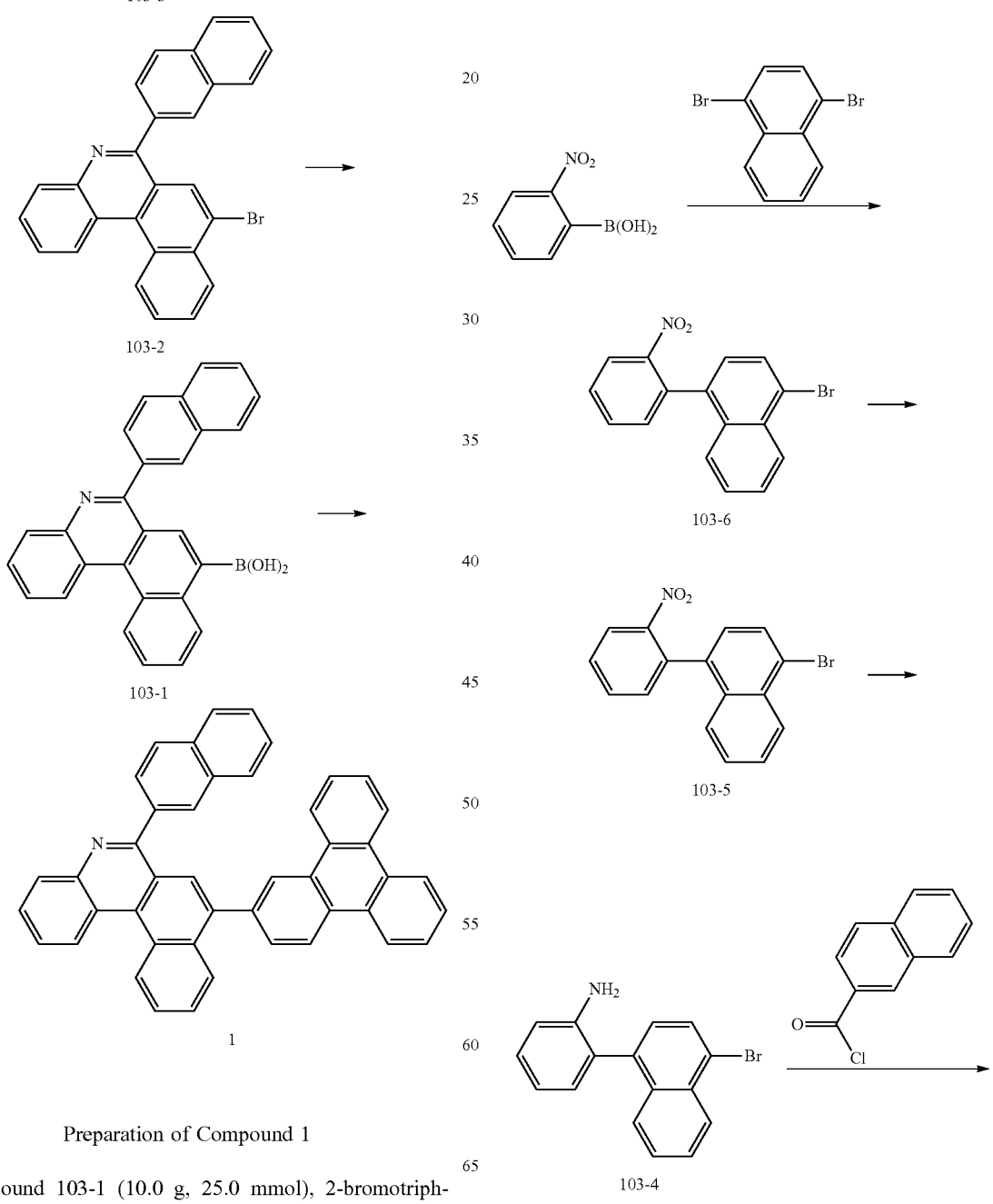

Preparation of Compound 1

Compound 103-1 (10.0 g, 25.0 mmol), 2-bromotriphenylene (11.5 g, 37.5 mmol), Pd(PPh₃)₄ (1.44 g, 1.25 mmol), -continued

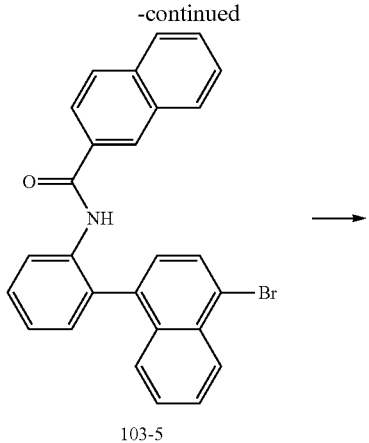

103-5

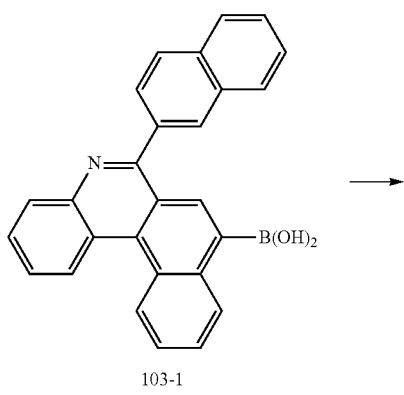

103-2

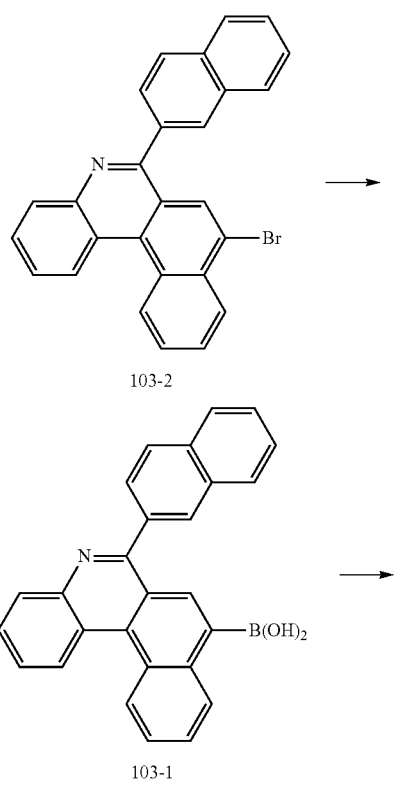

103-1

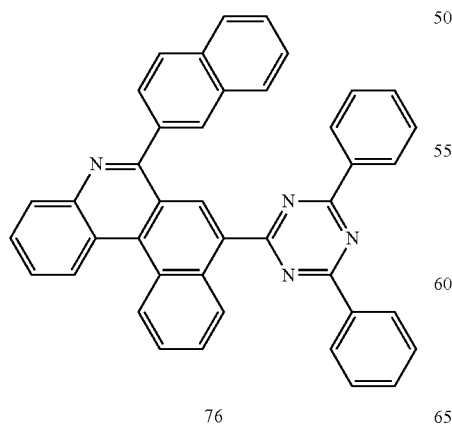

76

Preparation of Compound 75

Compound 103-1 (10.0 g, 25.0 mmol), 2-chloro-4,6-diphenyl-1,3,5-triazine (10.0 g, 37.5 mmol), Pd(PPh$_3$)$_4$ (1.44 g, 1.25 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 75 (8.5 g, 68%) was obtained.

PREPARATION EXAMPLE 27

Preparation of Compound 100

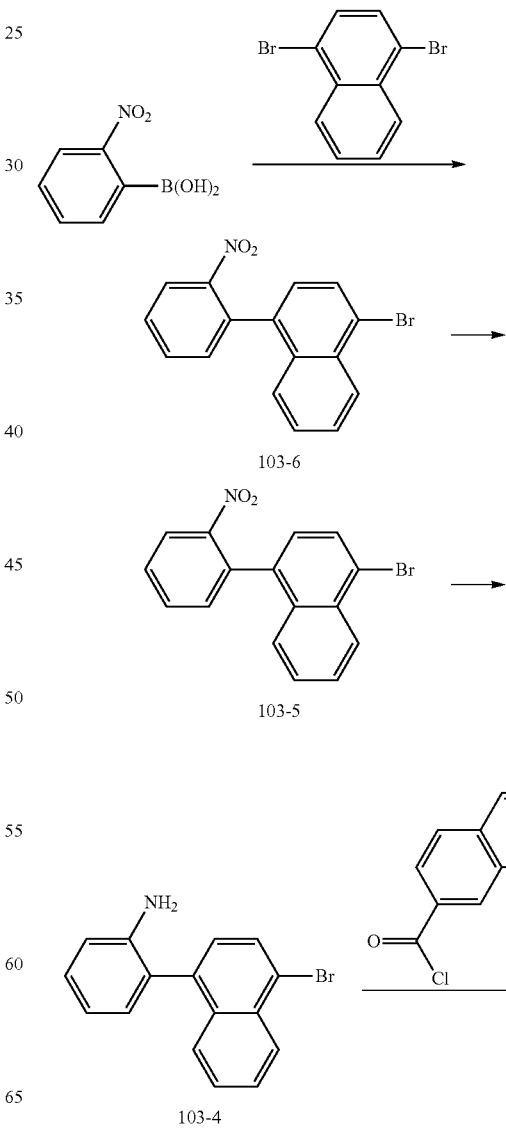

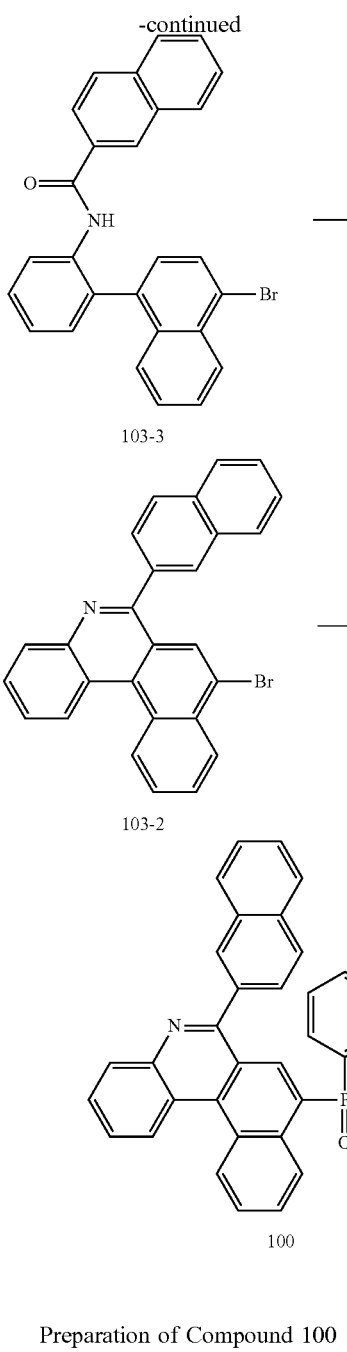

103-3

103-2

100

Preparation of Compound 100

After Compound 103-2 (8.85 g, 23.0 mmol) was dissolved in THF, 2.5 M n-BuLi (11.9 ml, 29.9 mmol) was slowly added dropwise thereto at −78° C. Then, the resultant reaction product was stirred for 30 minutes. After chlorodiphenylphosphine (14.2 ml, 29.9 mmol) was added thereto, the resultant reaction product was stirred for 1 hour. After the reaction was completed, methanol was added thereto with stirring for 1 hour and the resultant reaction product was extracted with distilled water and EA. After the organic layer was dried using anhydrous $MgSO_4$, the solvent was removed with a rotary evaporator. After dichloromethane (210 ml) was added to the concentrate and dissolved therein, hydrogen peroxide (7.0 ml) was added thereto with stirring at room temperature for 3 hours. After the reaction was completed, the resultant reaction product was extracted with distilled water and EA. The organic layer was dried using anhydrous $MgSO_4$, and after the solvent was removed with a rotary evaporator, toluene was added thereto and heated to be dissolved. Then, the resultant reaction product was recrystallized, and the target compound 100 (9.42 g, 81%) was obtained.

PREPARATION EXAMPLE 28

Preparation of Compound 504

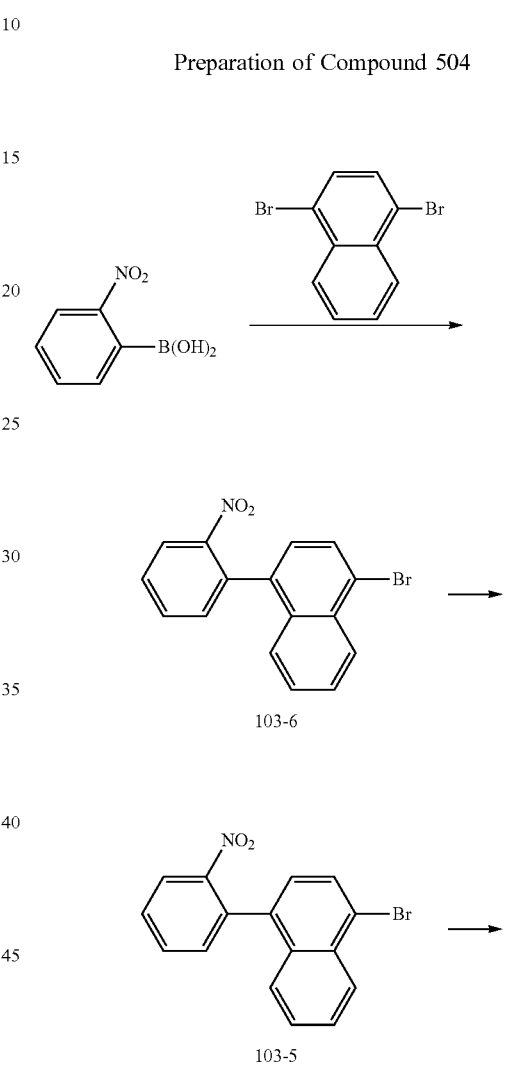

103-6

103-5

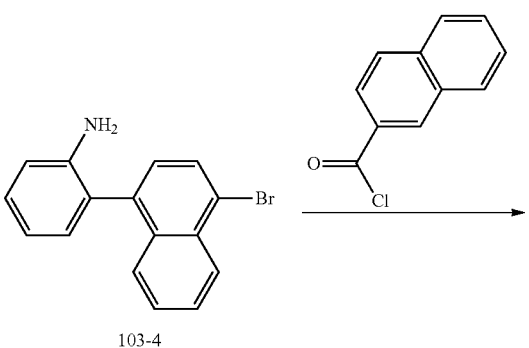

103-4

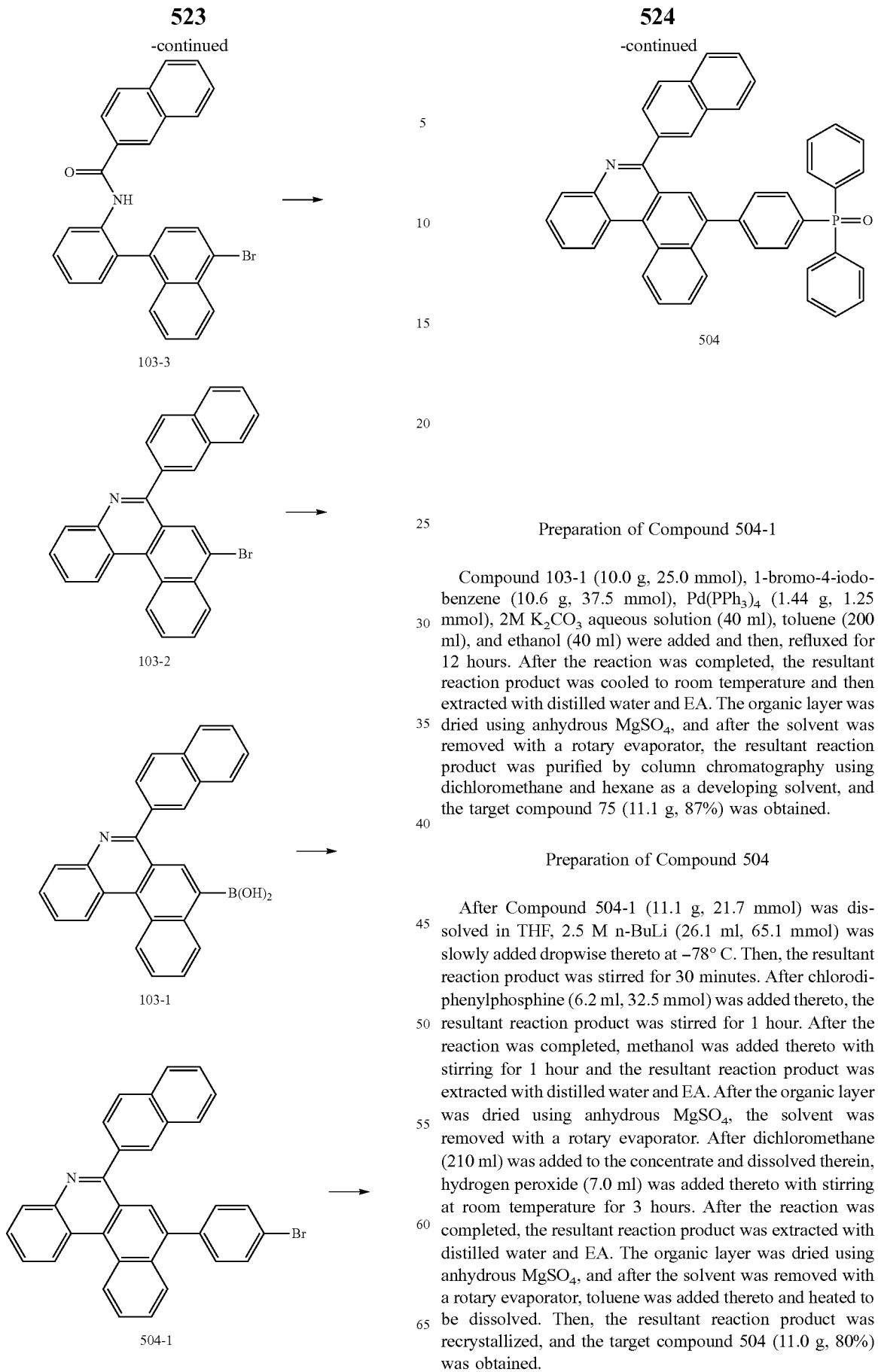

Preparation of Compound 504-1

Compound 103-1 (10.0 g, 25.0 mmol), 1-bromo-4-iodobenzene (10.6 g, 37.5 mmol), Pd(PPh$_3$)$_4$ (1.44 g, 1.25 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 75 (11.1 g, 87%) was obtained.

Preparation of Compound 504

After Compound 504-1 (11.1 g, 21.7 mmol) was dissolved in THF, 2.5 M n-BuLi (26.1 ml, 65.1 mmol) was slowly added dropwise thereto at −78° C. Then, the resultant reaction product was stirred for 30 minutes. After chlorodiphenylphosphine (6.2 ml, 32.5 mmol) was added thereto, the resultant reaction product was stirred for 1 hour. After the reaction was completed, methanol was added thereto with stirring for 1 hour and the resultant reaction product was extracted with distilled water and EA. After the organic layer was dried using anhydrous MgSO$_4$, the solvent was removed with a rotary evaporator. After dichloromethane (210 ml) was added to the concentrate and dissolved therein, hydrogen peroxide (7.0 ml) was added thereto with stirring at room temperature for 3 hours. After the reaction was completed, the resultant reaction product was extracted with distilled water and EA. The organic layer was dried using anhydrous MgSO$_4$, and after the solvent was removed with a rotary evaporator, toluene was added thereto and heated to be dissolved. Then, the resultant reaction product was recrystallized, and the target compound 504 (11.0 g, 80%) was obtained.

PREPARATION EXAMPLE 29
Preparation of Compound 509
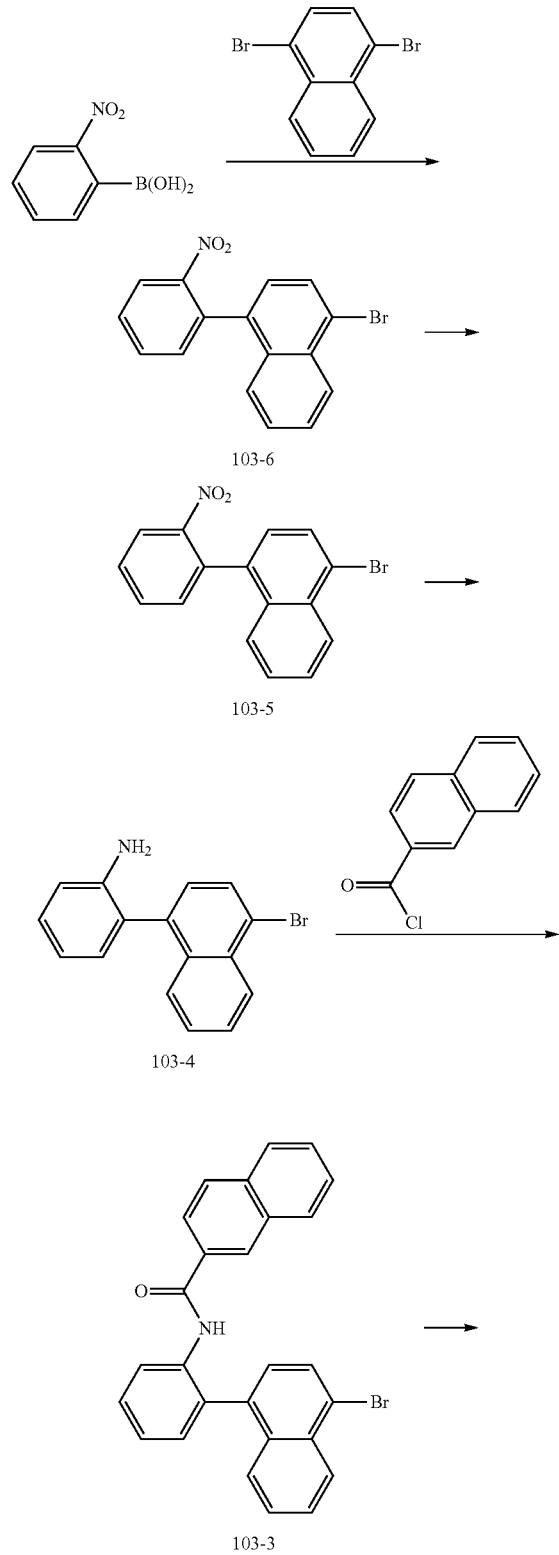
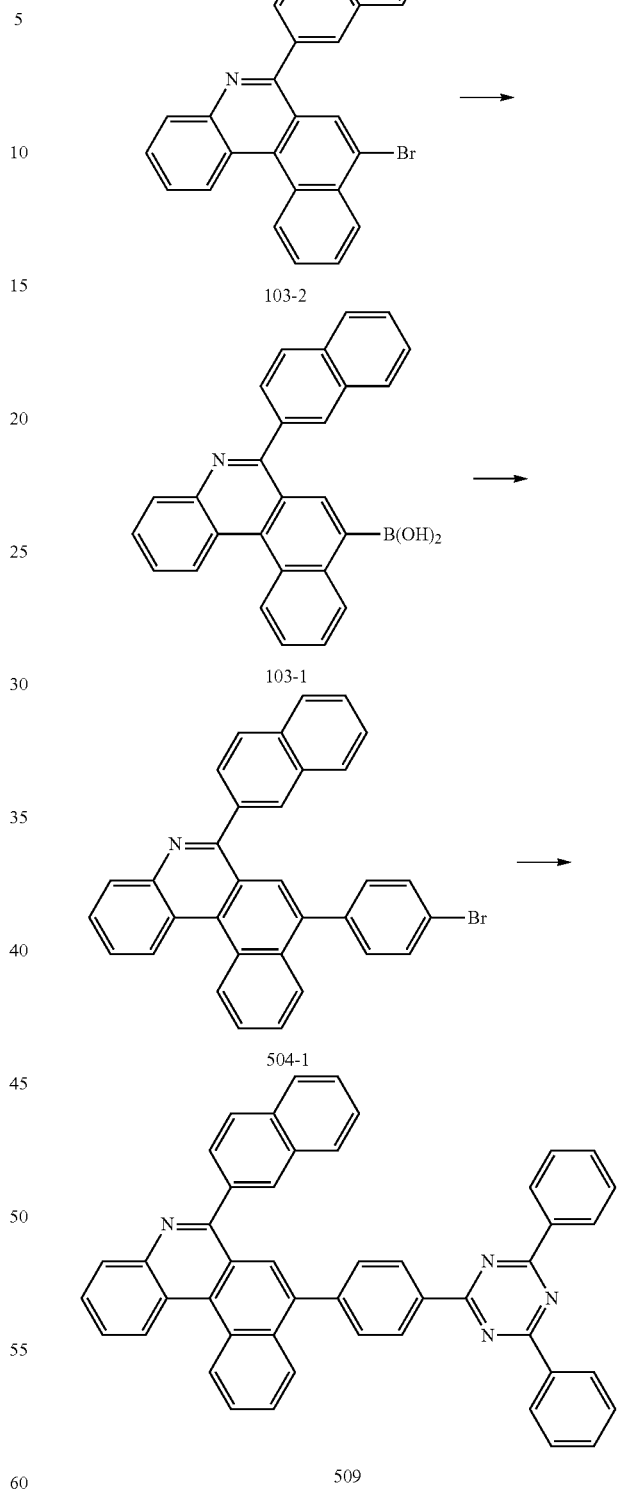
Preparation of Compound 509
Compound 504-1 (10.0 g, 19.6 mmol), (4,6-diphenyl-1,3,5-triazin-2-yl)boronic acid (8.1 g, 29.3 mmol), Pd(PPh$_3$)$_4$ (1.13 g, 0.98 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 509 (6.3 g, 49%) was obtained.

PREPARATION EXAMPLE 30

Preparation of Compound 530

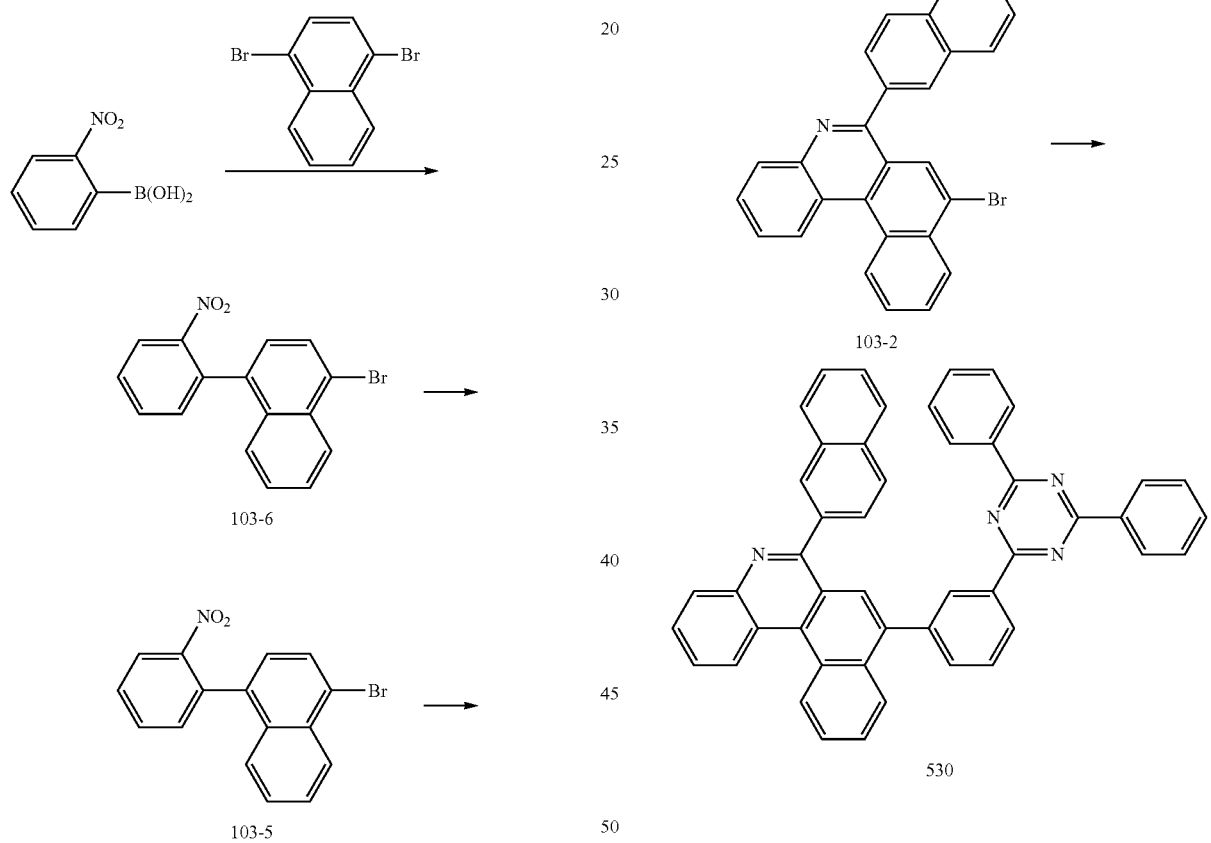

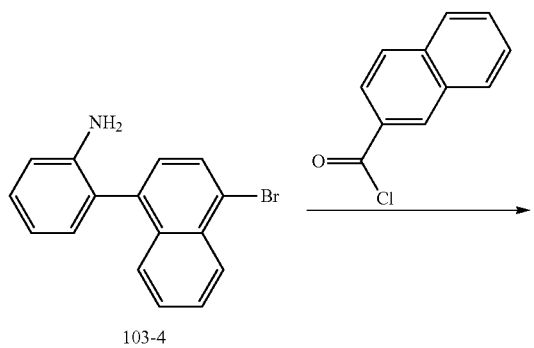

103-4

Preparation of Compound 530

Compound 103-2 (10.0 g, 23.0 mmol), 2,4-diphenyl-6-(3-(4,4,5,5-tetramethyl-1,3,2-dioxaborolan-2-yl)phenyl)-1,3,5-triazine (15.0 g, 34.5 mmol), Pd(PPh$_3$)$_4$ (1.32 g, 1.15 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 530 (10.2 g, 67%) was obtained.

PREPARATION EXAMPLE 31

Preparation of Compound 566

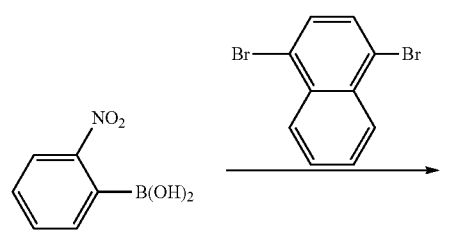

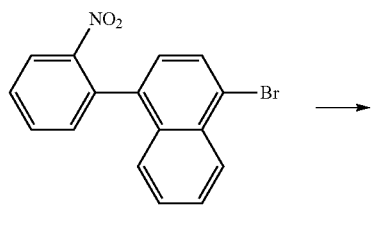

103-6

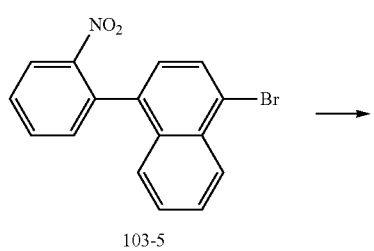

103-5

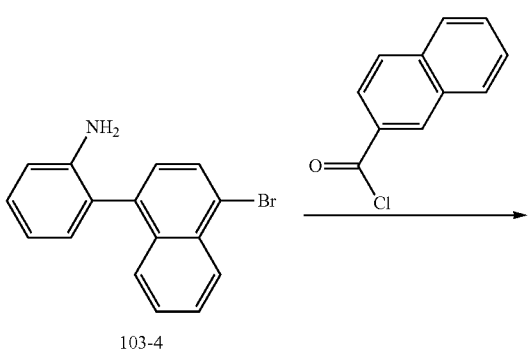

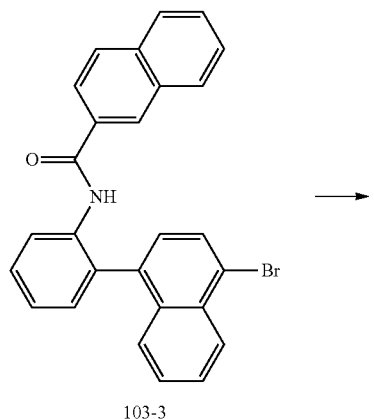

103-3

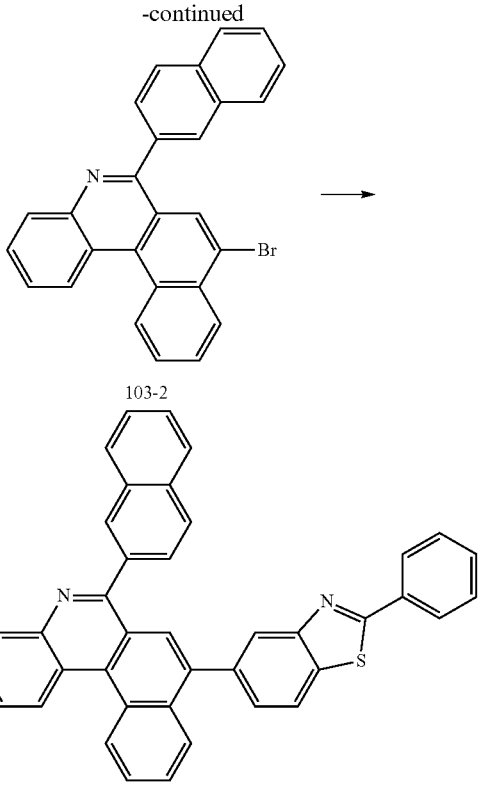

103-2

566

Preparation of Compound 566

Compound 103-2 (10.0 g, 23.0 mmol), 2-phenyl-5-(4,4,5,5-tetramethyl-1,3,2-dioxaborolan-2-yl)benzo[d]thiazole (11.6 g, 34.5 mmol), Pd(PPh$_3$)$_4$ (1.32 g, 1.15 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 566 (9.35 g, 72%) was obtained.

PREPARATION EXAMPLE 32

Preparation of Compound 655

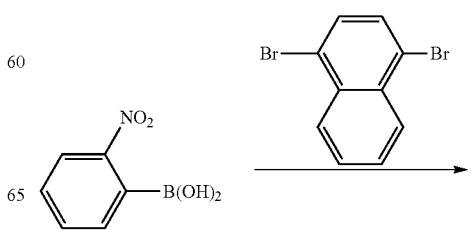

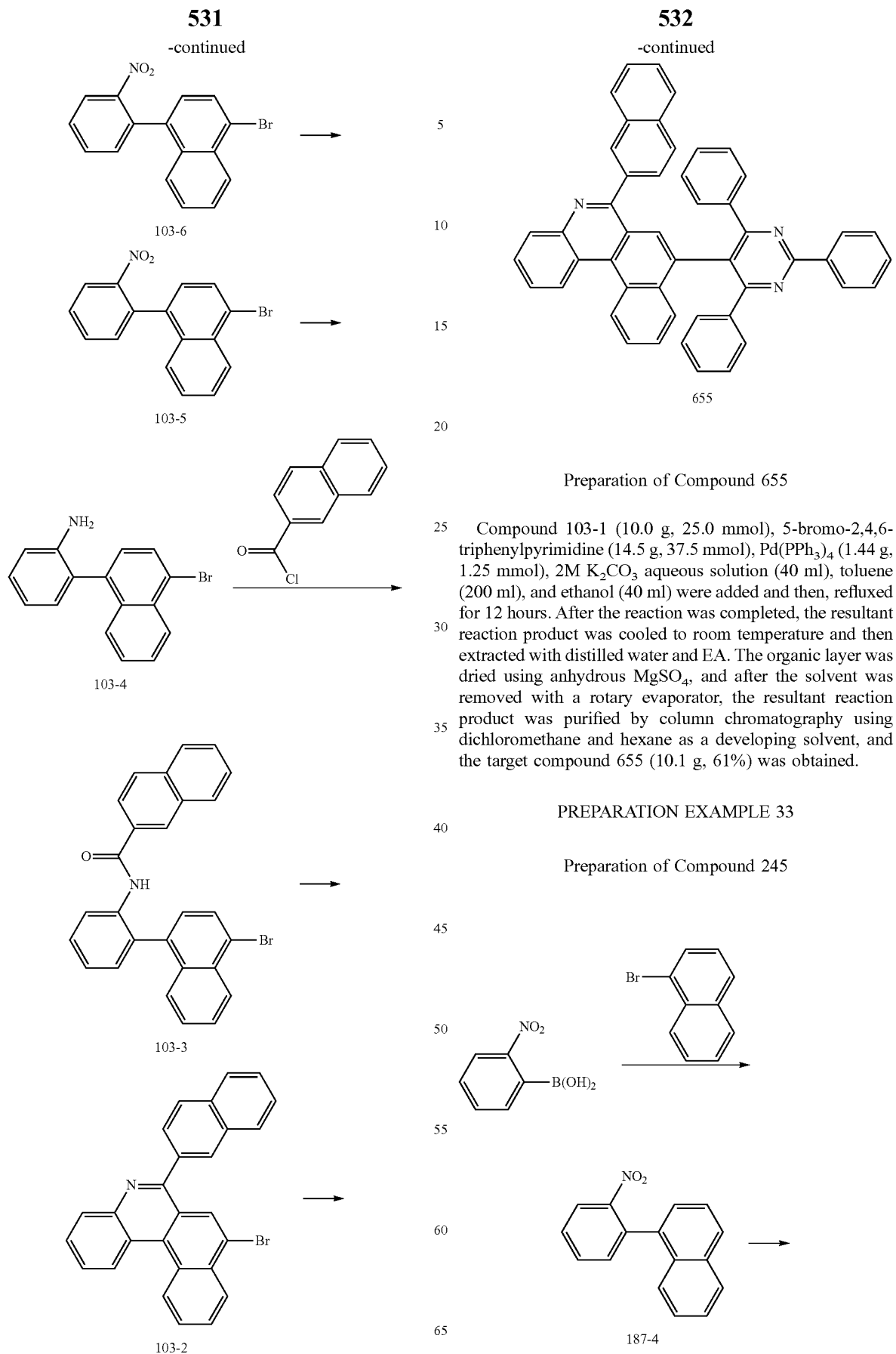

Preparation of Compound 655

Compound 103-1 (10.0 g, 25.0 mmol), 5-bromo-2,4,6-triphenylpyrimidine (14.5 g, 37.5 mmol), Pd(PPh$_3$)$_4$ (1.44 g, 1.25 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 655 (10.1 g, 61%) was obtained.

PREPARATION EXAMPLE 33

Preparation of Compound 245

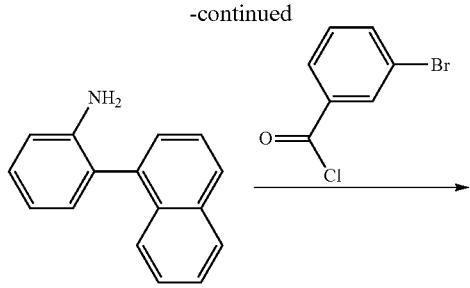

187-3

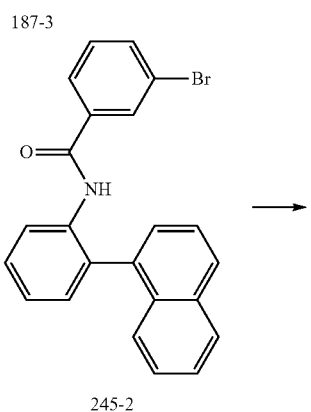

245-2

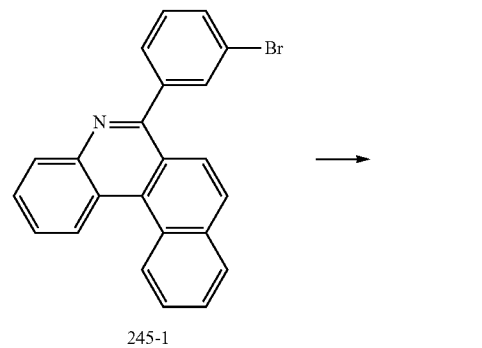

245-1

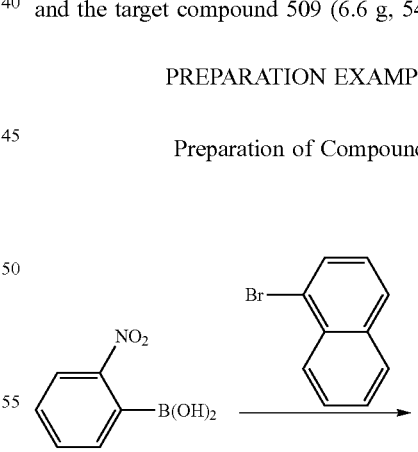

246

Preparation of Compound 245-2

After Compound 187-3 (7.92 g, 36.1 mmol) was dissolved in THF, TEA (15.0 ml, 108 mmol) and 3-bromobenzoyl chloride (11.8 g, 54.1 mmol) were added thereto at 0° C. Then, a temperature was increased to room temperature and the resultant reaction product was stirred for 2 hours. After the reaction was completed, the resultant reaction product was extracted with distilled water and EA. The organic layer was dried using anhydrous $MgSO_4$, and after the solvent was removed with a rotary evaporator, the resultant reaction product was purified by column chromatography using dichloromethane and hexane as a developing solvent, and the target compound 245-2 (13.6 g, 94%) was obtained.

Preparation of Compound 245-1

After Compound 245-2 (13.6 g, 33.9 mmol) was dissolved in nitrobenzene, $POCl_3$ (1.58 ml, 16.9 mmol) was added thereto at room temperature. Then, the resultant reaction product was stirred at 150° C. for 18 hours. After the reaction was completed, the resultant reaction product was neutralized with $NaHCO_3$ and extracted with EA. The organic layer was dried using anhydrous $MgSO_4$, and after the solvent was removed with a rotary evaporator, the resultant reaction product was purified by column chromatography using dichloromethane and methanol as a developing solvent, and the target compound 245-1 (8.85 g, 68%) was obtained.

Preparation of Compound 245

Compound 245-1 (8.85 g, 22.9 mmol), (4,6-diphenyl-1,3,5-triazin-2-yl)boronic acid (9.5 g, 34.3 mmol), $Pd(PPh_3)_4$ (1.32 g, 1.14 mmol), 2M $K_2CO_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous $MgSO_4$, and after the solvent was removed with a rotary evaporator, the resultant reaction product was purified by column chromatography using dichloromethane and hexane as a developing solvent, and the target compound 509 (6.6 g, 54%) was obtained.

PREPARATION EXAMPLE 34

Preparation of Compound 809

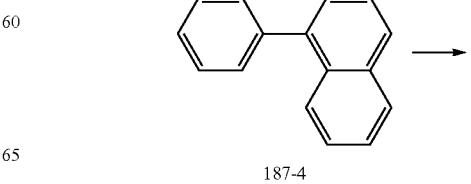

187-4

535

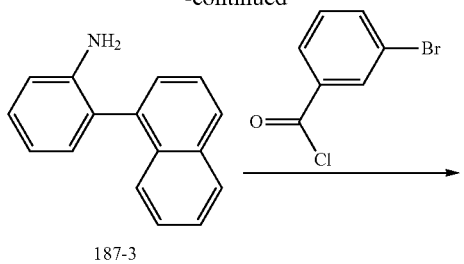

187-3

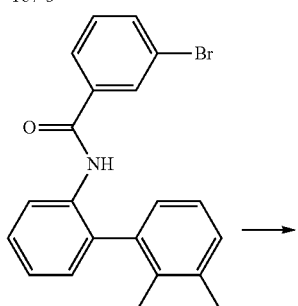

245-2

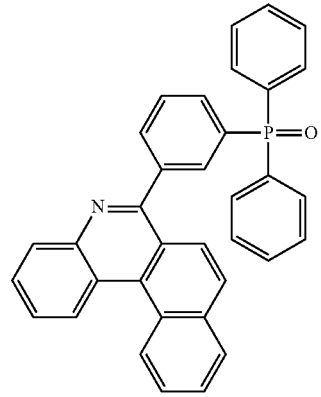

245-1

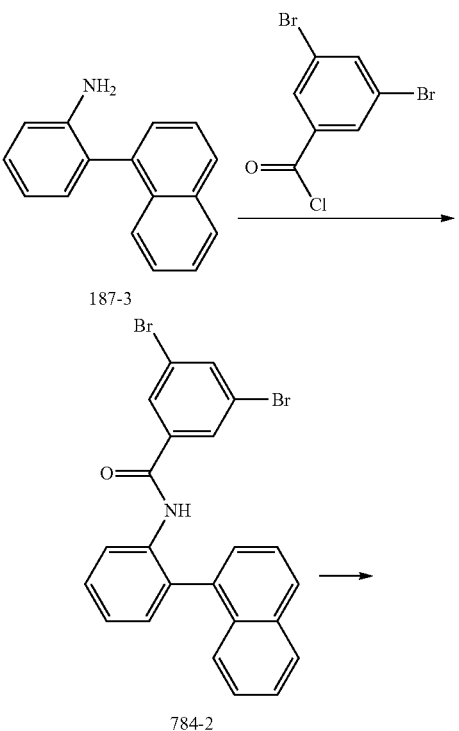

809

Preparation of Compound 809

After Compound 245-1 (10.0 g, 26.0 mmol) was dissolved in THF, 2.5 M n-BuLi (13.5 ml, 33.8 mmol) was slowly added dropwise thereto at −78° C. Then, the resultant reaction product was stirred for 30 minutes. After chlorodiphenylphosphine (6.2 ml, 33.8 mmol) was added thereto, the resultant reaction product was stirred for 1 hour. After the reaction was completed, methanol was added thereto with stirring for 1 hour and the resultant reaction product was

536 extracted with distilled water and EA. After the organic layer was dried using anhydrous MgSO₄, the solvent was removed with a rotary evaporator. After dichloromethane (210 ml) was added to the concentrate and dissolved therein, hydrogen peroxide (7.0 ml) was added thereto with stirring at room temperature for 3 hours. After the reaction was completed, the resultant reaction product was extracted with distilled water and EA. The organic layer was dried using anhydrous MgSO₄, and after the solvent was removed with a rotary evaporator, toluene was added thereto and heated to be dissolved. Then, the resultant reaction product was recrystallized, and the target compound 809 (10.6 g, 81%) was obtained,

PREPARATION EXAMPLE 35

Preparation of Compound 784

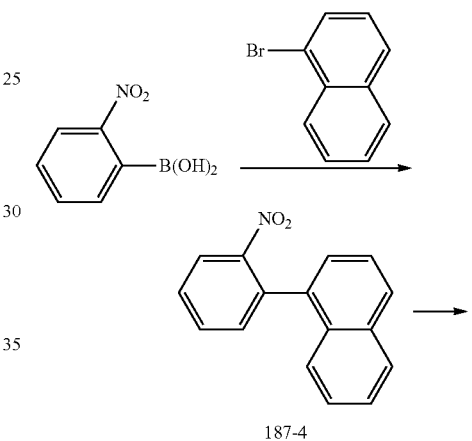

187-4

784-2

Preparation of Compound 784-2

After Compound 187-3 (10.0 g, 45.6 mmol) was dissolved in THF, TEA (19.0 ml, 136 mmol) and 3,5-dibromobenzoyl chloride (11.8 g, 68.4 mmol) were added thereto at 0° C. Then, a temperature was increased to room temperature and the resultant reaction product was stirred for 2 hours. After the reaction was completed, the resultant reaction product was extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 784-2 (21.5 g, 98%) was obtained.

Preparation of Compound 784-1

After Compound 784-2 (21.5 g, 44.7 mmol) was dissolved in nitrobenzene, POCl$_3$ (2.09 ml, 22.4 mmol) was added thereto at room temperature. Then, the resultant reaction product was stirred at 150° C. for 18 hours. After the reaction was completed, the resultant reaction product was neutralized with NaHCO$_3$ and extracted with EA. The organic layer was dried using anhydrous MgSO$_4$, and after the solvent was removed with a rotary evaporator, the resultant reaction product was purified by column chromatography using dichloromethane and methanol as a developing solvent, and the target compound 784-1 (13.5 g, 65%) was obtained.

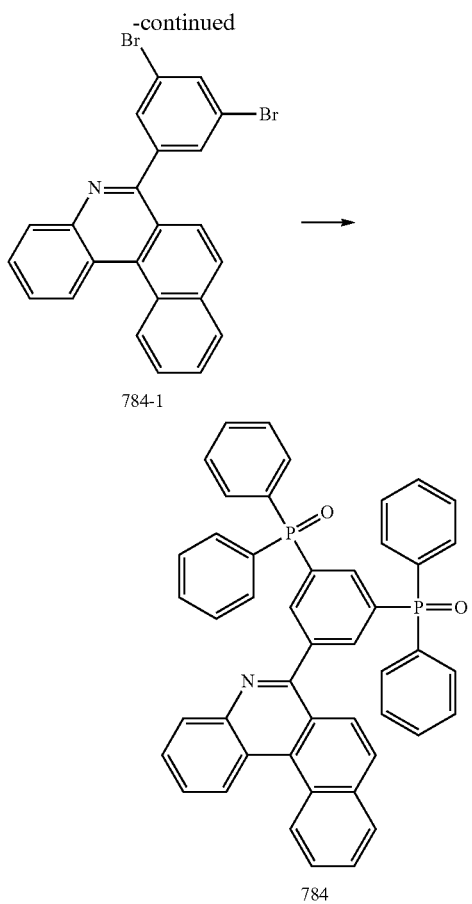

Preparation of Compound 784

After Compound 245-1 (13.5 g, 29.1 mmol) was dissolved in THF, 2.5 M n-BuLi (30.2 ml, 75.6 mmol) was slowly added dropwise thereto at −78° C. Then, the resultant reaction product was stirred for 30 minutes. After chlorodiphenylphosphine (13.9 ml, 75.6 mmol) was added thereto, the resultant reaction product was stirred for 1 hour. After the reaction was completed, methanol was added thereto with stirring for 1 hour and the resultant reaction product was extracted with distilled water and EA. After the organic layer was dried using anhydrous MgSO$_4$, the solvent was removed with a rotary evaporator. After dichloromethane (450 ml) was added to the concentrate and dissolved therein, hydrogen peroxide (15.0 ml) was added thereto with stirring at room temperature for 3 hours. After the reaction was completed, the resultant reaction product was extracted with distilled water and EA. The organic layer was dried using anhydrous MgSO$_4$, and after the solvent was removed with a rotary evaporator, toluene was added thereto and heated to be dissolved. Then, the resultant reaction product was recrystallized, and the target compound 784 (17.4 g, 85%) was obtained.

PREPARATION EXAMPLE 36

Preparation of Compound 758

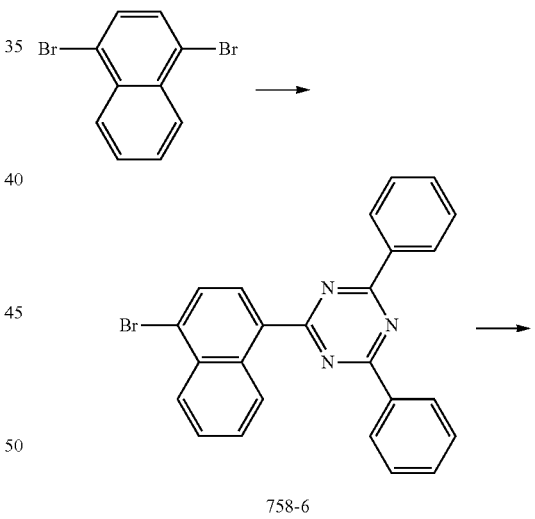

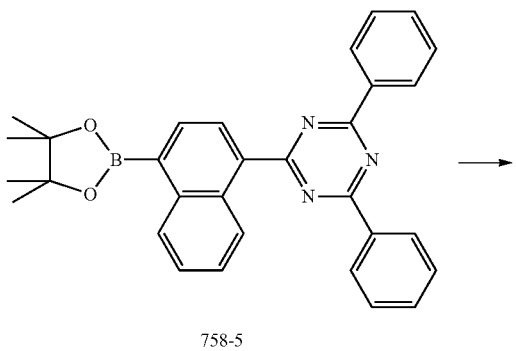

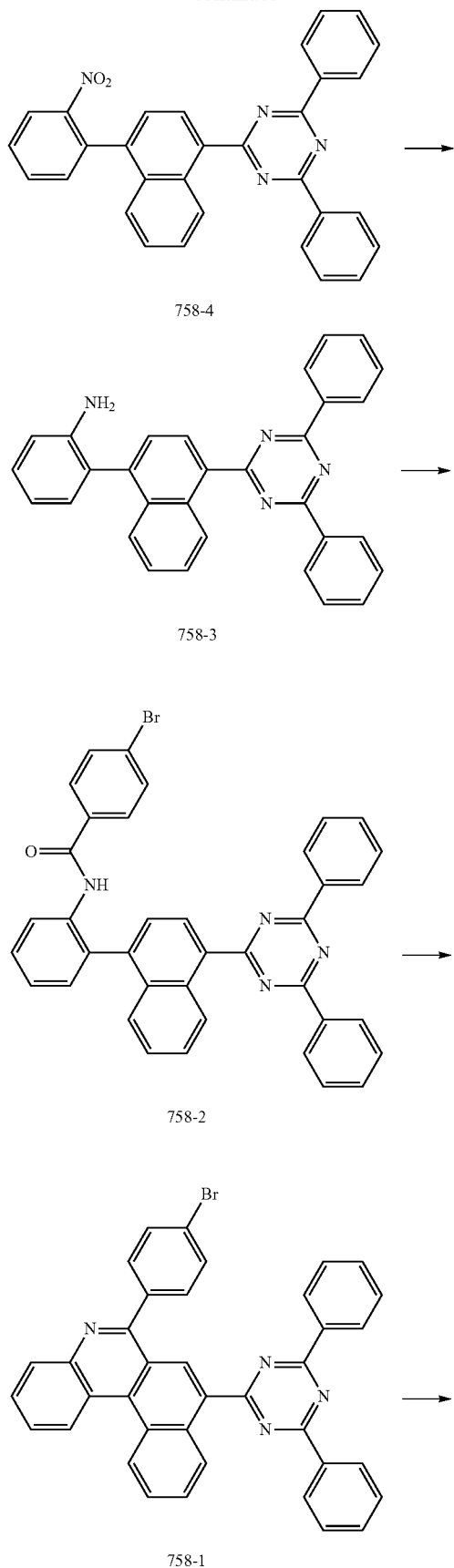

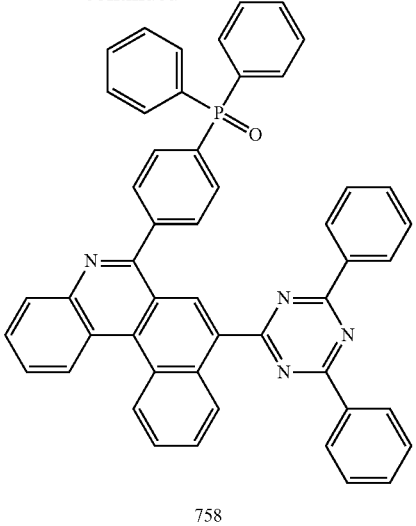

758

Preparation of Compound 758-6

A compound 1,4-dibromobenzene (10.0 g, 34.9 mmol), (4,6-diphenyl-1,3,5-triazin-2-yl)boronic acid (10.6 g, 38.4 mmol), Pd(PPh$_3$)$_4$ (2.01 g, 1.74 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 758-6 (13.3 g, 87%) was obtained.

Preparation of Compound 758-5

Compound 758-6 (13.3 g, 30.4 mmol), bis(pinacolato)diborone (9.25 g, 36.4 mmol), Pd(dppf)$_2$Cl$_2$ (1.24 g, 1.52 mmol), KOAc (8.95 g, 91.2 mmol), and DMF (250 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using EA as a developing solvent, and the target compound 758-5 (13.1 g, 89%) was obtained.

Preparation of Compound 758-4

Compound 758-5 (13.1 g, 27.0 mmol), 1-bromo-2-nitrobenzene (8.19 g, 40.6 mmol), Pd(PPh$_3$)$_4$ (1.56 g, 1.35 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 758-4 (11.0 g, 85%) was obtained.

Preparation of Compound 758-3

Compound 758-4 (11.0 g, 23.0 mmol) was dissolved in methanol and then substituted with nitrogen. After Pd/C (10 wt %) was added thereto, the resultant reaction product was substituted with hydrogen and stirred at room temperature for 1 hour. After the reaction was completed, the resultant reaction product was allowed to pass through a Cellite, and the target compound 758-3 (10.1 g, 98%) was obtained.

Preparation of Compound 758-2

The target compound 758-2 (14.1 g, 99%) was obtained by the same preparation method as Compound 187-2 in the preparation example 10 except that Compound 758-3 was used instead of Compound 187-3.

Preparation of Compound 758-1

The target compound 758-1 (8.9 g, 65%) was obtained by the same preparation method as Compound 187-1 in the preparation example 10 except that Compound 758-2 was used instead of Compound 187-2.

Preparation of Compound 758

The target compound 758 (8.5 g, 80%) was obtained by the same preparation method as Compound 201-1 in the preparation example 10 except that Compound 758-1 was used instead of Compound 201-1.

PREPARATION EXAMPLE 37

Preparation of Compound 760

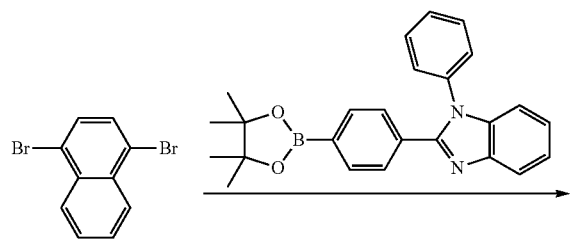

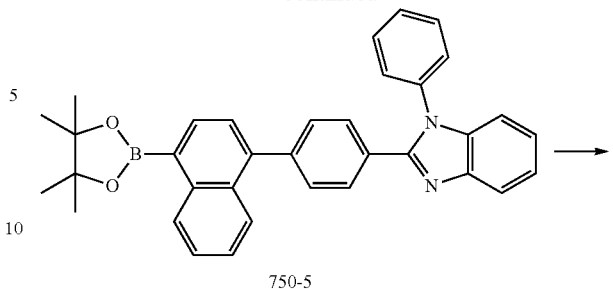

750-5

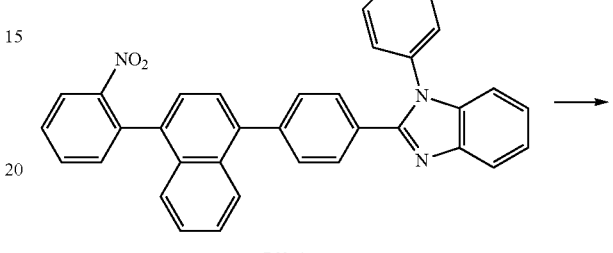

760-4

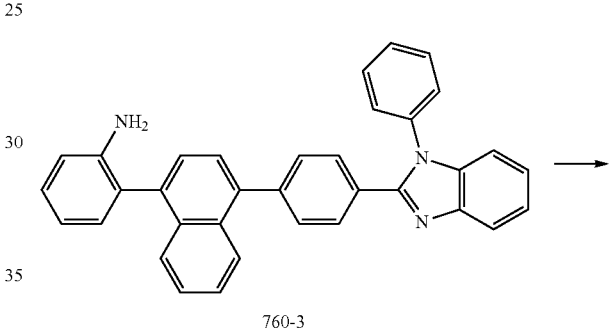

760-3

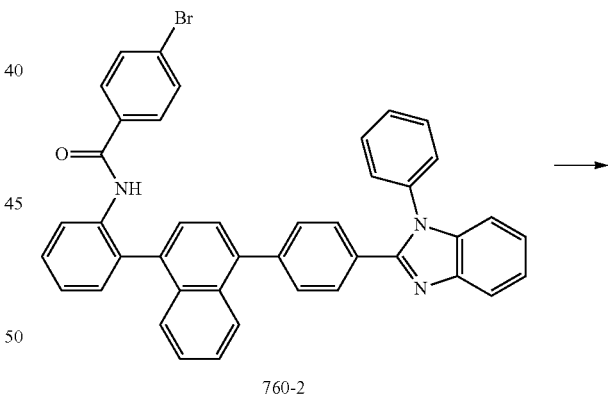

760-2

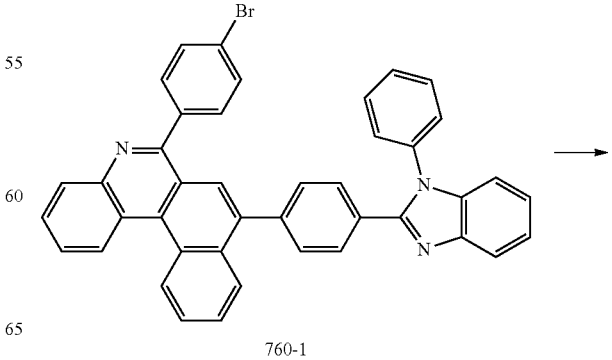

760-6

760-1

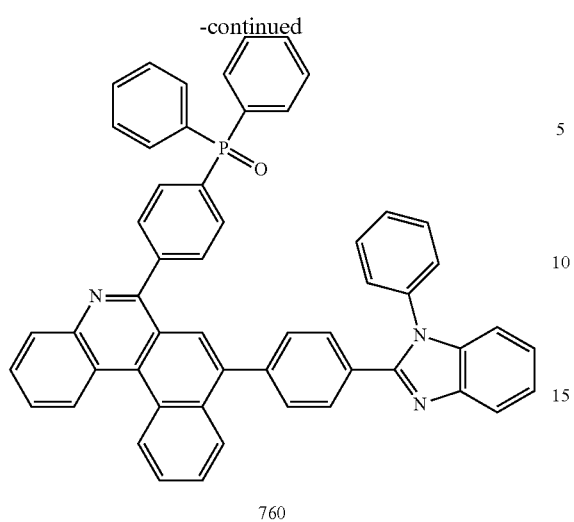

760

Preparation of Compound 760-6

The target compound 760-6 was obtained by the same preparation method as Compound 758-6 in the preparation example 36 except that 1-phenyl-2-(4-(4,4,5,5-tetramethyl-1,3,2-dioxaborolan-2-yl)phenyl)-1H-benzo[d]imidazole was used instead of (4,6-diphenyl-1,3,5-triazin-2-yl)boronic acid.

Preparation of Compound 760-5

The target compound 760-5 was obtained by the same preparation method as Compound 758-5 in the preparation example 36 except that Compound 760-6 was used instead of Compound 758-6.

Preparation of Compound 760-4

The target compound 760-4 was obtained by the same preparation method as Compound 758-4 in the preparation example 36 except that Compound 760-5 was used instead of Compound 758-5.

Preparation of Compound 760-3

The target compound 760-3 was obtained by the same preparation method as Compound 758-3 in the preparation example 36 except that Compound 760-4 was used instead of Compound 758-4.

Preparation of Compound 760-2

The target compound 760-2 was obtained by the same preparation method as Compound 187-2 in the preparation example 10 except that Compound 760-3 was used instead of Compound 187-3.

Preparation of Compound 760-1

The target compound 760-1 was obtained by the same preparation method as Compound 187-1 in the preparation example 10 except that Compound 760-2 was used instead of Compound 187-2.

Preparation of Compound 760

The target compound 760 was obtained by the same preparation method as Compound 201-1 in the preparation example 10 except that Compound 760-1 was used instead of Compound 201-1.

PREPARATION EXAMPLE 38

Preparation of Compound 762

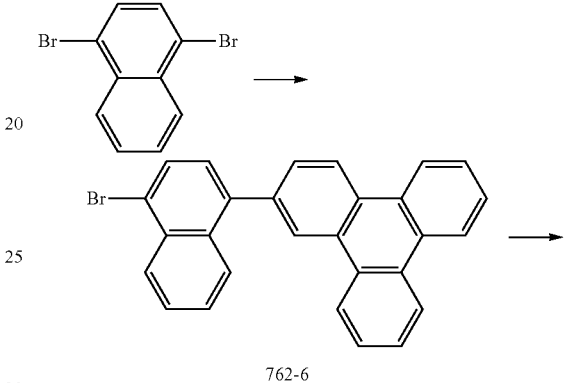

762-6

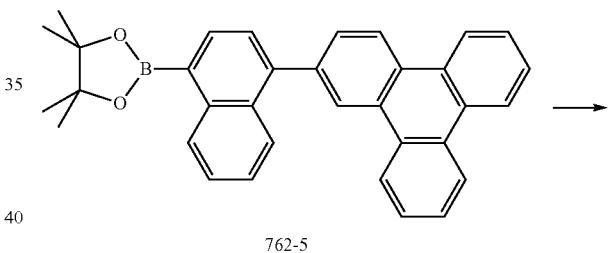

762-5

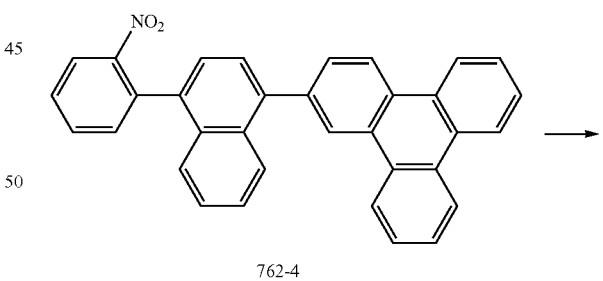

762-4

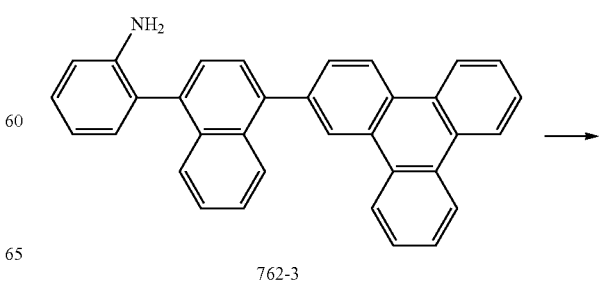

762-3

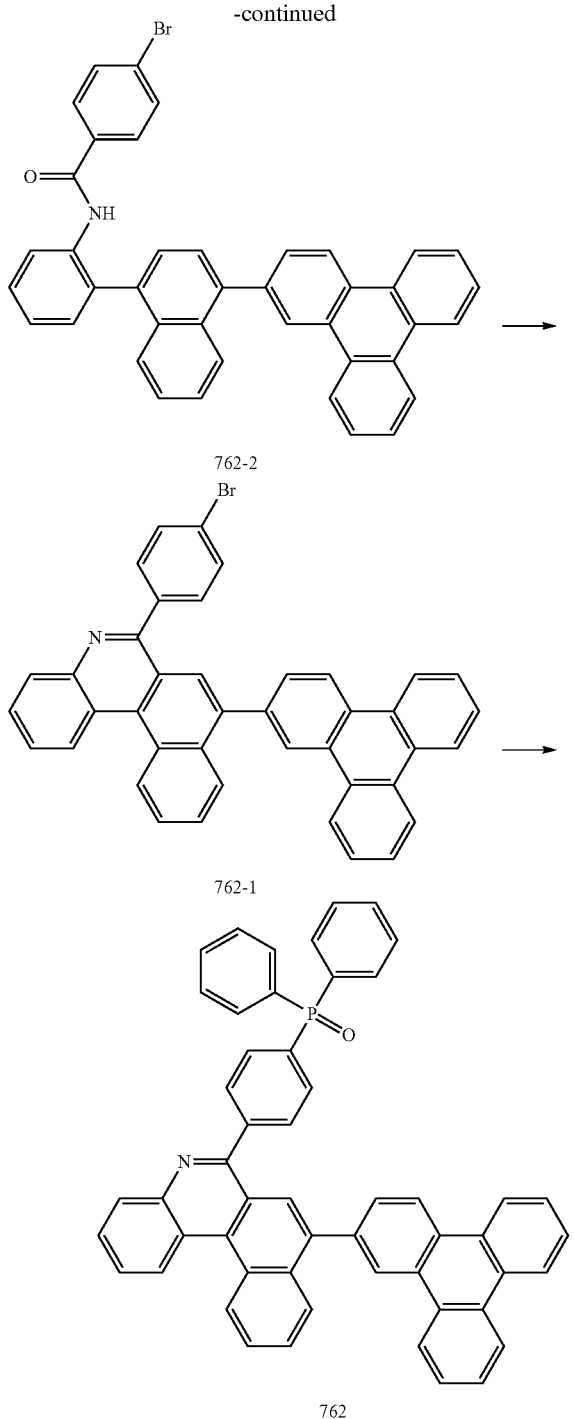

762-2

762-1

762

Preparation of Compound 762-6

The target compound 762-6 was obtained by the same preparation method as Compound 758-6 in the preparation example 36 except that 4,4,5,5-tetramethyl-2-(triphenylene-2-yl)-1,3,2-dioxaborolan was used instead of (4,6-diphenyl-1,3,5-triazin-2-yl)boronic acid.

Preparation of Compound 762-5

The target compound 762-5 was obtained by the same preparation method as Compound 758-5 in the preparation example 36 except that Compound 762-6 was used instead of Compound 758-6.

Preparation of Compound 762-4

The target compound 762-4 was obtained by the same preparation method as Compound 758-4 in the preparation example 36 except that Compound 762-5 was used instead of Compound 758-5.

Preparation of Compound 762-3

The target compound 762-3 was obtained by the same preparation method as Compound 758-3 in the preparation example 36 except that Compound 762-4 was used instead of Compound 758-4.

Preparation of Compound 762-2

The target compound 762-2 was obtained by the same preparation method as Compound 187-2 in the preparation example 10 except that Compound 762-3 was used instead of Compound 187-3.

Preparation of Compound 762-1

The target compound 762-1 was obtained by the same preparation method as Compound 187-1 in the preparation example 10 except that Compound 762-2 was used instead of Compound 187-2.

Preparation of Compound 762

The target compound 762 was obtained by the same preparation method as Compound 201-1 in the preparation example 10 except that Compound 762-1 was used instead of Compound 201-1.

PREPARATION EXAMPLE 39

Preparation of Compound 788

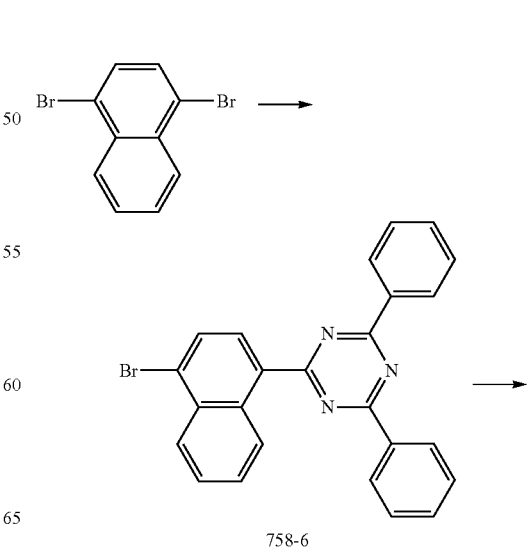

758-6

-continued

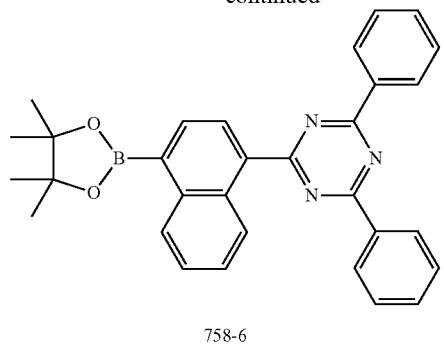

758-6

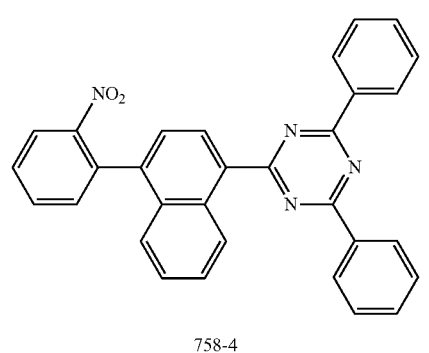

758-4

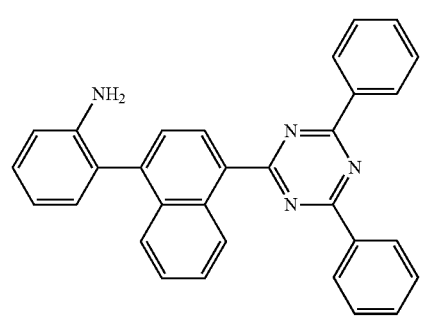

758-3

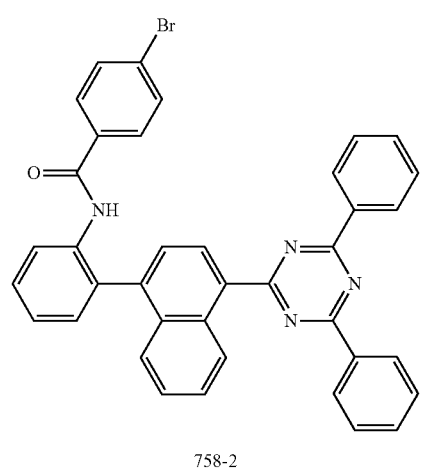

758-2

-continued

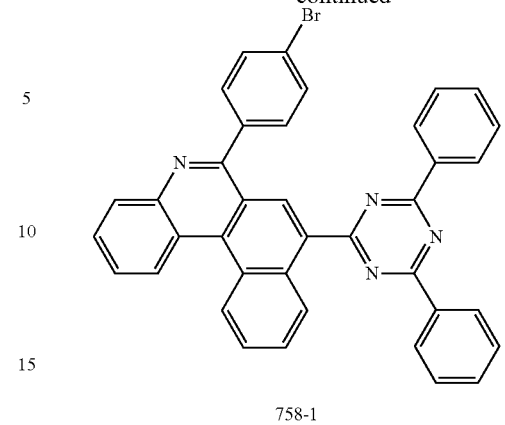

Preparation of Compound 788

Compound 758-1 (8.9 g, 22.9 mmol), (4,6-diphenyl-1,3,5-triazin-2-yl)boronic acid (9.5 g, 34.3 mmol), Pd(PPh$_3$)$_4$ (1.32 g, 1.14 mmol), 2M K$_2$CO$_3$ aqueous solution (40 ml), toluene (200 ml), and ethanol (40 ml) were added and then, refluxed for 12 hours. After the reaction was completed, the resultant reaction product was cooled to room temperature and then extracted with distilled water and EA. The organic layer was dried using anhydrous MgSO$_4$, and after the solvent was removed with a rotary evaporator, the resultant reaction product was purified by column chromatography using dichloromethane and hexane as a developing solvent, and the target compound 788 (8.9 g, 51%) was obtained.

PREPARATION EXAMPLE 40

Preparation of Compound 853

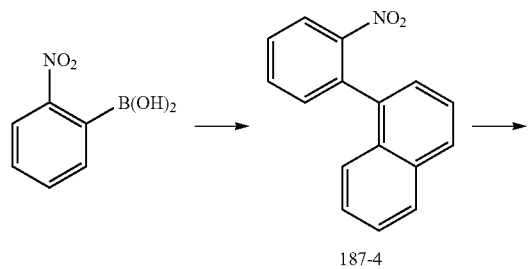

187-4

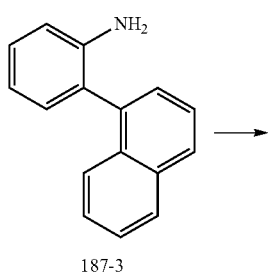

187-3

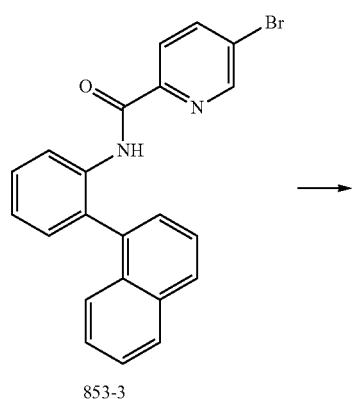

853-3

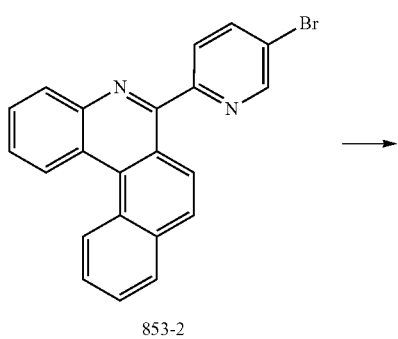

853-2

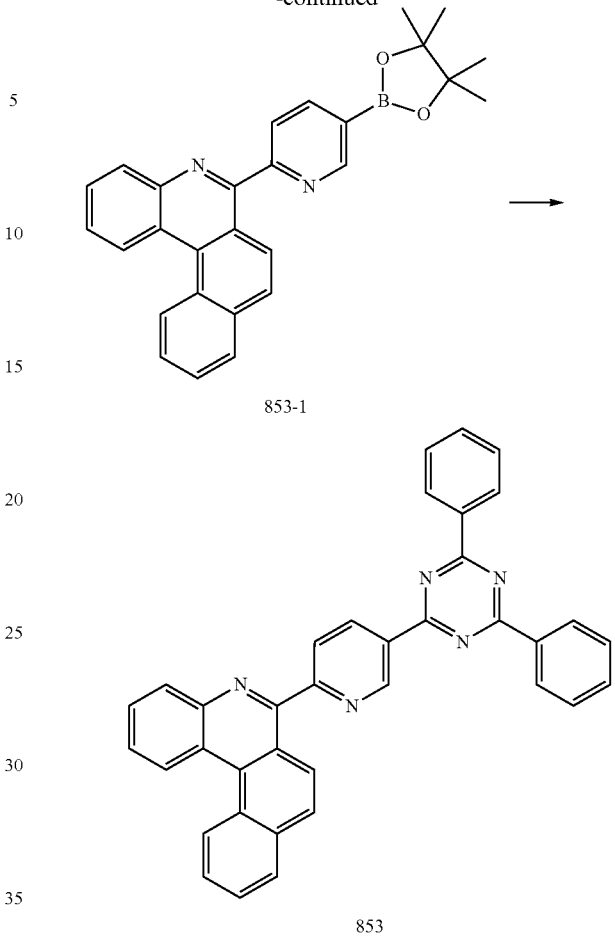

853-1

853

Preparation of Compound 853-3

Compound 187-3 (7.92 g, 36.1 mmol) was dissolved in THF, TEA (15.0 ml, 108 mmol) and 5-bromopicolinoyl chloride (11.9 g, 54.1 mmol) were added thereto at 0° C., and then the resulting mixture was warmed to room temperature and stirred for 3 hours. After the reaction was completed, extraction was performed with distilled water and MC. After the organic layer was dried over anhydrous MgSO$_4$, the solvent was removed by a rotary evaporator, the resulting product was filtered with silica gel, and then purification was performed by column chromatography using dichloromethane and hexane as a developing solvent to obtain Target Compound 853-3 (12.8 g, 87%).

Preparation of Compound 853-2

After Compound 853-3 (12.8 g, 31.7 mmol) was dissolved in nitrobenzene, POCl$_3$ (2.96 ml, 31.7 mmol) was added thereto at room temperature, and then the resulting mixture was stirred at 150° C. for 18 hours. After the reaction was completed, the resulting product was neutralized with NaHCO$_3$, and then extracted with MC. After the organic layer was dried over anhydrous MgSO$_4$, the solvent was removed by a rotary evaporator, and then purification was performed by column chromatography using dichloromethane and hexane as a developing solvent to obtain Target Compound 853-1 (7.9 g, 64%).

Preparation of Compound 853-1

Compound 853-2 (7.9 g, 20.5 mmol), bis(pinacolato)diborone (10.4 g, 41 mmol), Pd(dppf)$_2$Cl$_2$ (746 mg, 1.02 mmol), potassium acetate (6.0 g, 61.5 mmol), and DMF (70 ml) were mixed, and then the resulting mixture was refluxed for 18 hours. After the reaction was completed, the mixture was cooled to room temperature, and then extracted with distilled water and MC. After the organic layer was dried over anhydrous MgSO$_4$, the solvent was removed by a rotary evaporator, and then purification was performed by column chromatography using dichloromethane and EA as a developing solvent to obtain Target Compound 853-1 (8.1 g, 91%).

Preparation of Compound 853

Compound 853-1 (8.1 g, 18.7 mmol), 2-chloro-4,6-diphenyl-1,3,5-triazine (5.0 g, 18.7 mmol), Pd(PPh$_3$)$_4$ (2.1 g, 1.87 mmol), a 2 M K$_2$CO$_3$ aqueous solution (40 ml), toluene (200 ml), and ethanol (40 ml) were mixed, and then the resulting mixture was refluxed for 12 hours. After the reaction was completed, the mixture was cooled to room temperature, and then extracted with distilled water and MC. After the organic layer was dried over anhydrous MgSO$_4$, the solvent was removed by a rotary evaporator, and purification was performed by column chromatography using dichloromethane and EA as a developing solvent to obtain Target Compound 853 (8.5 g, 84%).

PREPARATION EXAMPLE 41

Preparation of Compound 855

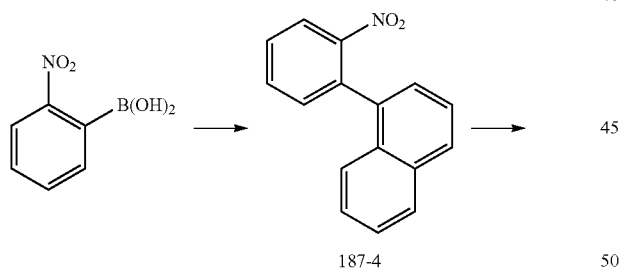

187-4

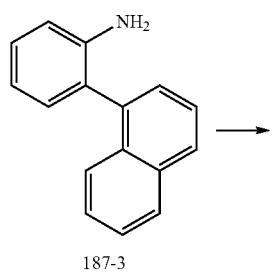

187-3

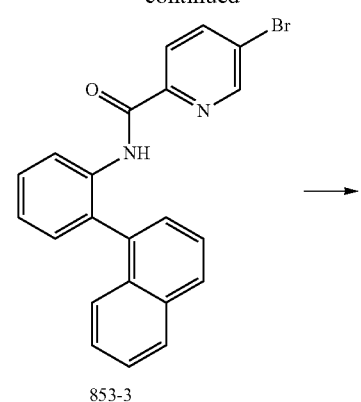

853-3

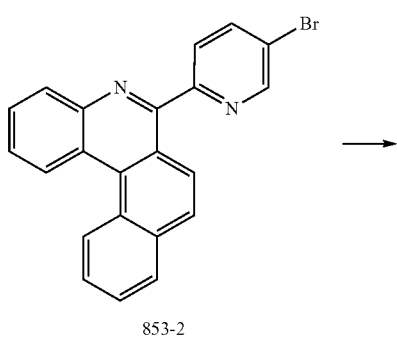

853-2

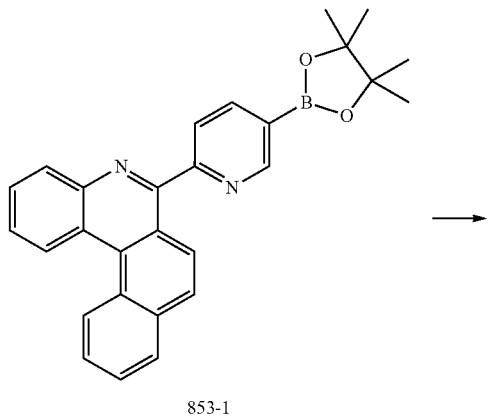

853-1

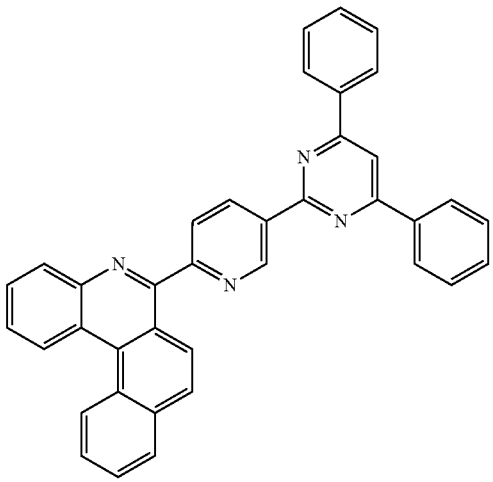

855

Preparation of Compound 855

Compound 853-1 (10 g, 23.13 mmol), 4-bromo-2,6-diphenylpyridine (6.16 g, 23.13 mmol), Pd(PPh$_3$)$_4$ (2.6 g, 2.3 mmol), a 2 M K$_2$CO$_3$ aqueous solution (40 ml), toluene (200 ml), and ethanol (40 ml) were mixed, and then the resulting mixture was refluxed for 8 hours. After the reaction was completed, the mixture was cooled to room temperature, and then extracted with distilled water and MC. After the organic layer was dried over anhydrous MgSO$_4$, the solvent was removed by a rotary evaporator, and purification was performed by column chromatography using dichloromethane and EA as a developing solvent to obtain Target Compound 855 (10.2 g, 82%).

PREPARATION EXAMPLE 42

Preparation of Compound 857

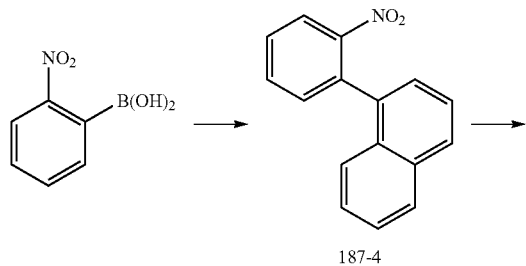

187-4

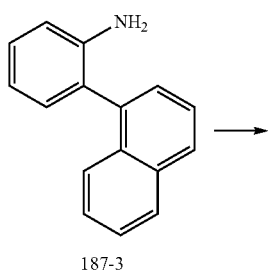

187-3

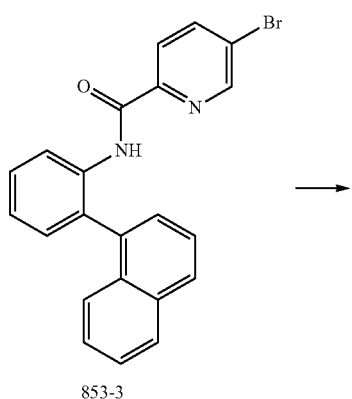

853-3

-continued

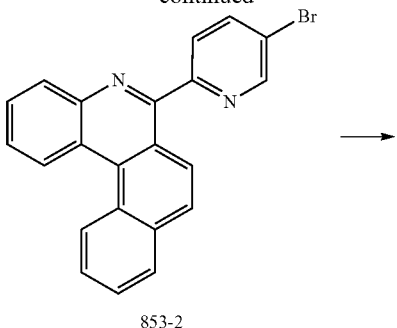

853-2

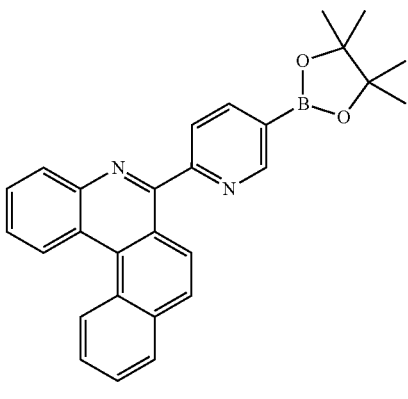

853-1

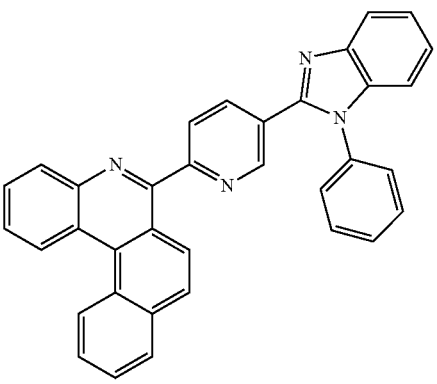

857

Compound 853-1 (10 g, 23.13 mmol), 4-bromo-2,6-diphenylpyridine (6.16 g, 23.13 mmol), Pd(PPh$_3$)$_4$ (2.6 g, 2.3 mmol), a 2 M K$_2$CO$_3$ aqueous solution (40 ml), toluene (200 ml), and ethanol (40 ml) were mixed, and then the resulting mixture was refluxed for 8 hours. After the reaction was completed, the mixture was cooled to room temperature, and then extracted with distilled water and MC. After the organic layer was dried over anhydrous MgSO$_4$, the solvent was removed by a rotary evaporator, and purification was performed by column chromatography using dichloromethane and EA as a developing solvent to obtain Target Compound 857 (8.7 g, 87%).

PREPARATION EXAMPLE 43

Preparation of Compound 877

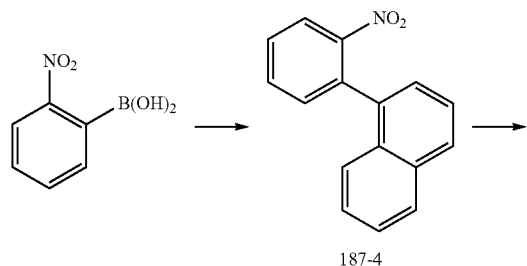

187-4

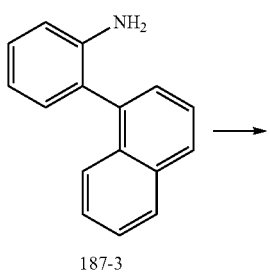

187-3

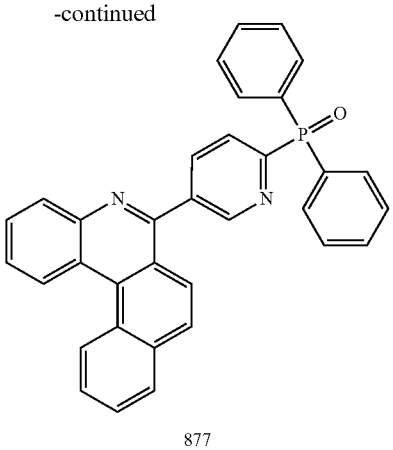

877

Preparation of Compound 877-2

Compound 187-3 (10 g, 45.6 mmol) was dissolved in THF, TEA (19.1 ml, 136.8 mmol) and 6-bromonicotinoyl chloride (12 g, 54.72 mmol) were added thereto at 0° C., and then the resulting mixture was warmed to room temperature and stirred for 3 hours. After the reaction was completed, extraction was performed with distilled water and MC. After the organic layer was dried over anhydrous MgSO$_4$, the solvent was removed by a rotary evaporator, the resulting product was filtered with silica gel, and then purification was performed by column chromatography using dichloromethane and hexane as a developing solvent to obtain Target Compound 877-2 (15 g, 81.9%).

Preparation of Compound 877-1

After Compound 877-2 (15 g, 37.2 mmol) was dissolved in nitrobenzene, POCl$_3$ (3.47 ml, 37.2 mmol) was added thereto at room temperature, and then the resulting mixture was stirred at 150° C. for 18 hours. After the reaction was completed, the resulting product was neutralized with NaHCO$_3$, and then extracted with MC. After the organic layer was dried over anhydrous MgSO$_4$, the solvent was removed by a rotary evaporator, and then purification was performed by column chromatography using dichloromethane and methanol as a developing solvent to obtain Target Compound 877-1 (12.2 g, 85%).

Preparation of Compound 877

Target Compound 877 (11.4 g, 71%) was obtained by performing the preparation in the same manner as the preparation of Compound 201-1 in Preparation Example 10, except that Compound 877-1 was used instead of Compound 201-1.

PREPARATION EXAMPLE 44

Preparation of Compound 885

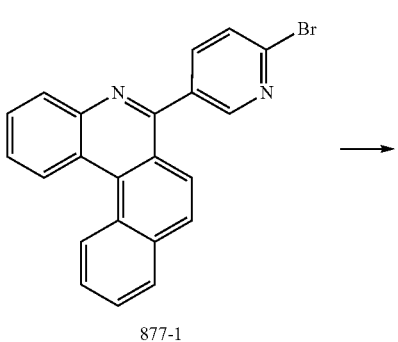

877-2

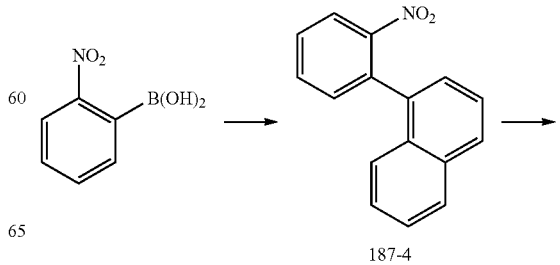

187-4

877-1

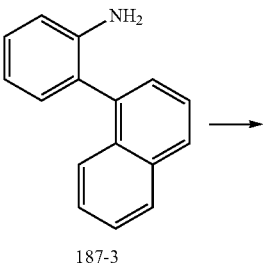

187-3

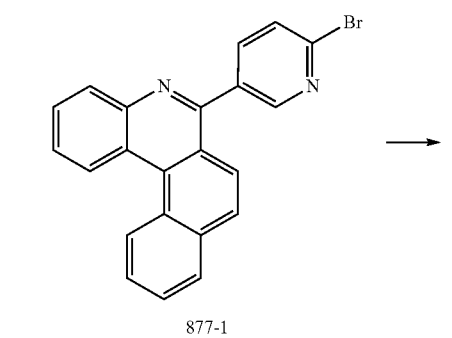

877-2

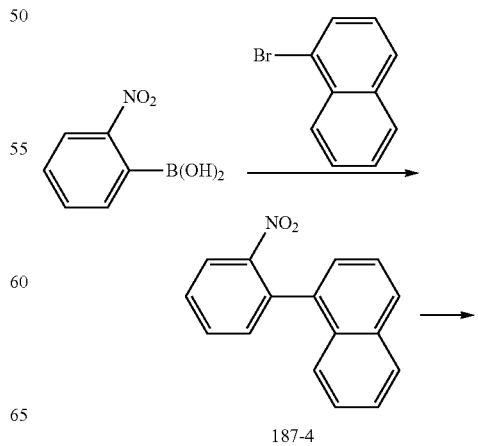

877-1

885-1

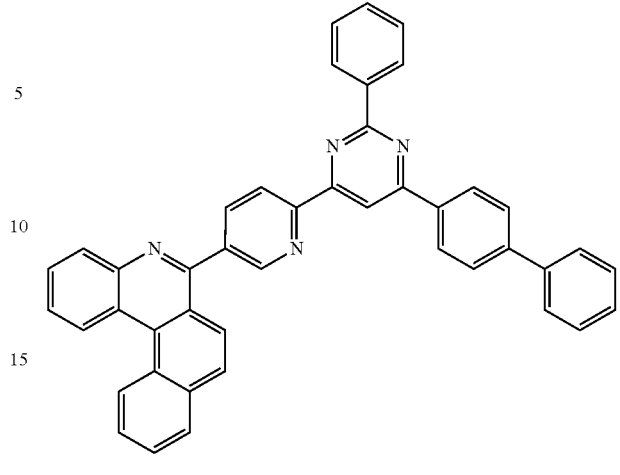

885

Preparation of Compound 885-1

Target Compound 885-1 (9.8 g, 87%) was obtained by performing the preparation in the same manner as the preparation of Compound 853-1 in Preparation Example 40, except that Compound 877-1 was used instead of Compound 853-2.

Preparation of Compound 885

Compound 885-1 (9 g, 20.8 mmol), 4-([1,1'-biphenyl]-4-yl)-6-bromo-2-phenylpyridine (8.05 g, 20.8 mmol), Pd(PPh$_3$)$_4$ (2.3 g, 2.0 mmol), a 2 M K$_2$CO$_3$ aqueous solution (40 ml), toluene (200 ml), and ethanol (40 ml) were mixed, and then the resulting mixture was refluxed for 8 hours. After the reaction was completed, the mixture was cooled to room temperature, and then extracted with distilled water and MC. After the organic layer was dried over anhydrous MgSO$_4$, the solvent was removed by a rotary evaporator, and purification was performed by column chromatography using dichloromethane and EA as a developing solvent to obtain Target Compound 885 (10.3 g, 81%).

PREPARATION EXAMPLE 45

Preparation of Compound 895

187-4

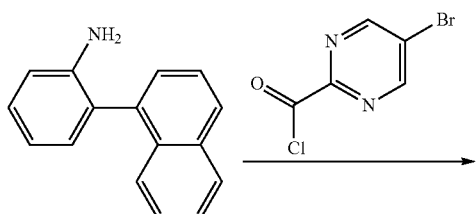

187-3

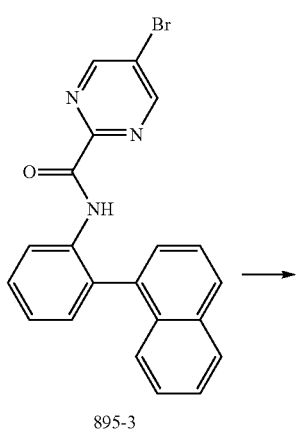

895-3

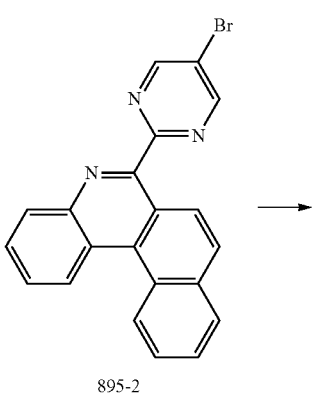

895-2

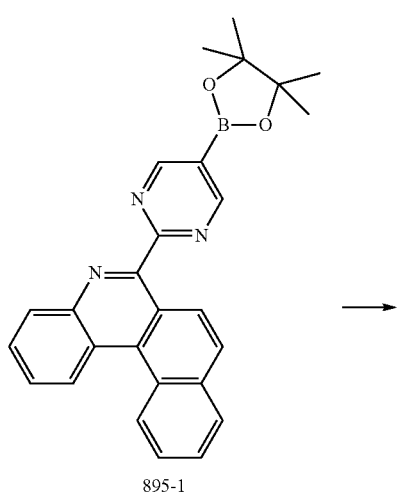

895-1

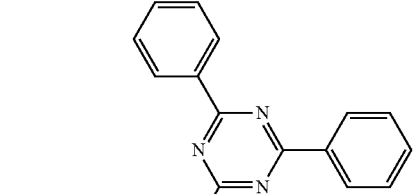

895

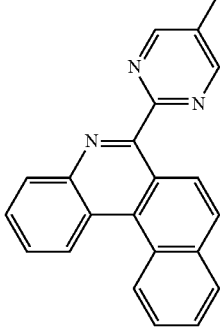

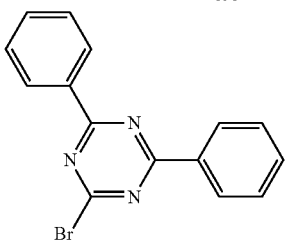

2-bromo-4,6-diphenyl-1,3,5-triazine

Preparation of Compound 895-3

Target Compound 895-3 was obtained by performing the preparation in the same manner as the preparation of Compound 187-2 in Preparation Example 10, except that 5-bromopyrimidine-2-carbonyl chloride was used instead of 4-bromobenzoyl chloride.

Preparation of Compound 895-2

Target Compound 895-2 was obtained by performing the preparation in the same manner as the preparation of Compound 187-1 in Preparation Example 10, except that Compound 895-3 was used instead of Compound 187-2.

Preparation of Compound 895-1

Target Compound 895-1 was obtained by performing the preparation in the same manner as the preparation of Compound 227-1 in Preparation Example 15, except that Compound 895-2 was used instead of Compound 187-1.

Preparation of Compound 895

Target Compound 895 was obtained by performing the preparation in the same manner as the preparation of Compound 815 in Preparation Example 24, except that Compound 895-1 was used instead of Compound 227-1.

PREPARATION EXAMPLE 46
Preparation of Compound 898
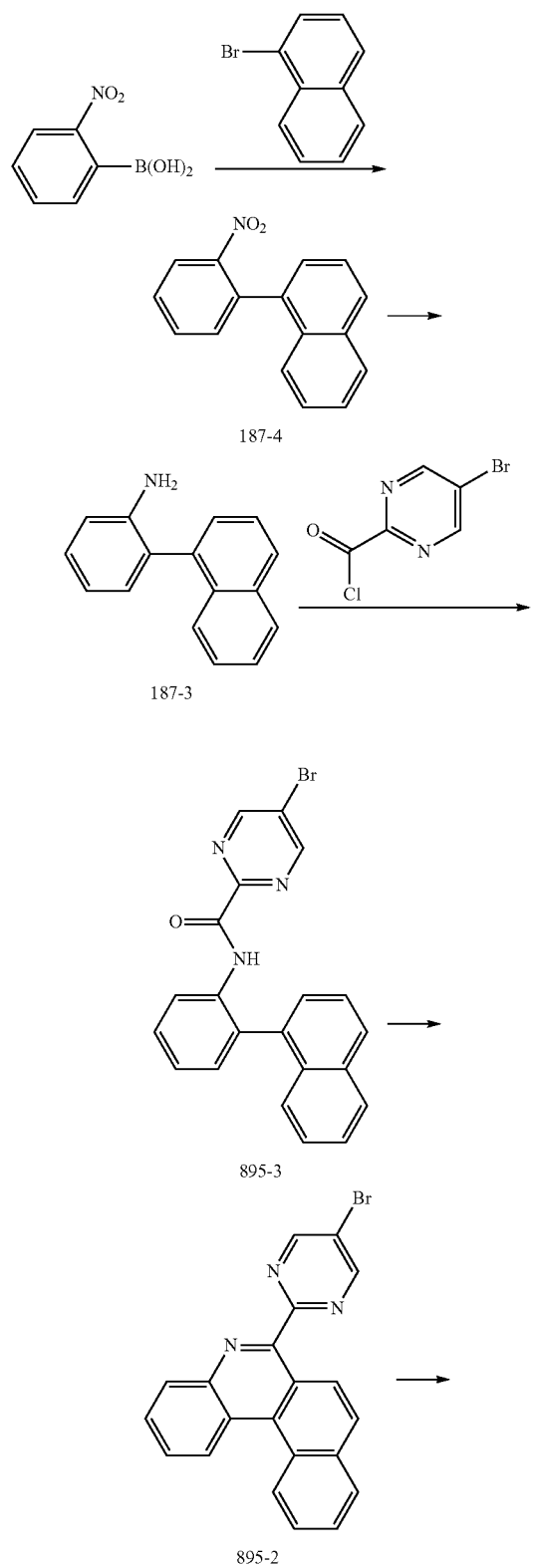
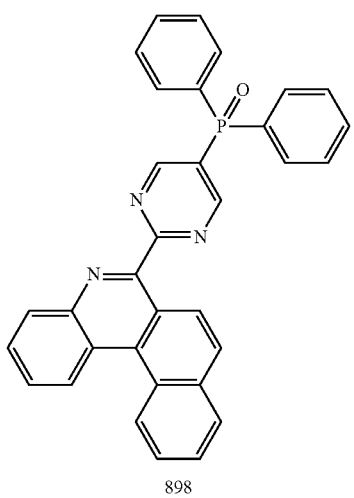 [SMILES: O=P(c1ccccc1)(c1ccccc1)c1cnc(-c2nc3ccccc3c3c2ccc2ccccc23)nc1]
Preparation of Compound 898
Target Compound 898 was obtained by performing the preparation in the same manner as the preparation of Compound 201 in Preparation Example 11, except that Compound 895-2 was used instead of Compound 201-1.
PREPARATION EXAMPLE 47
Preparation of Compound 905
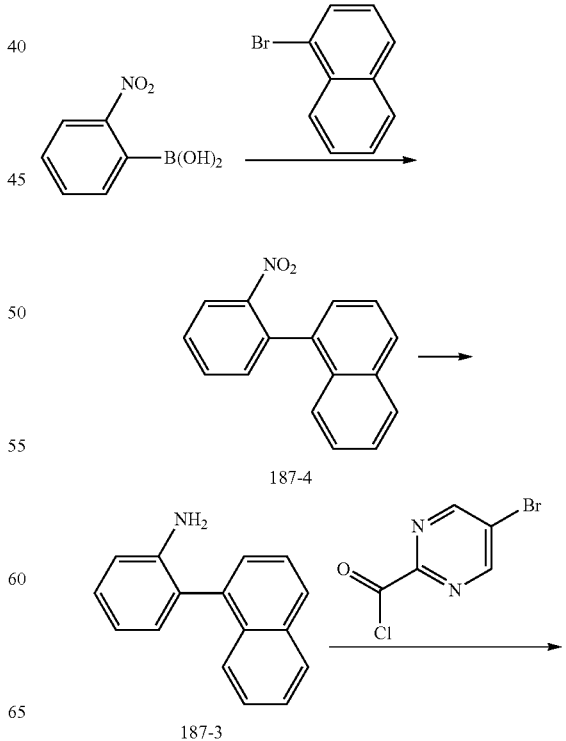

-continued

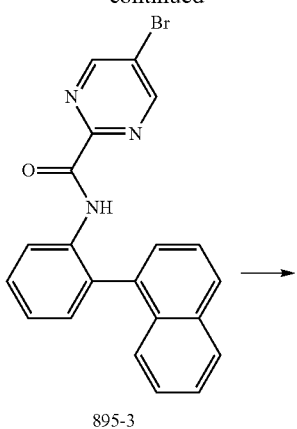

895-3

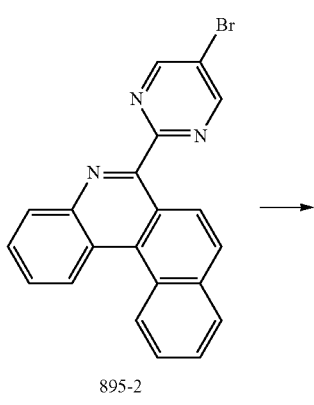

895-2

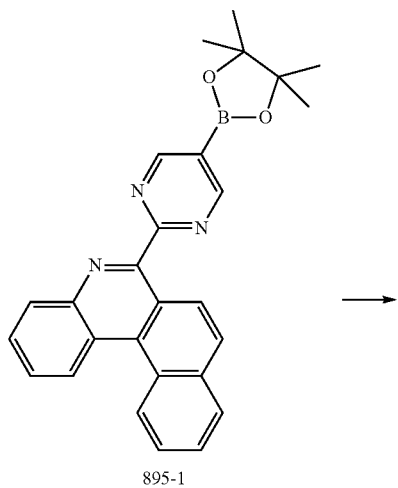

895-1

-continued

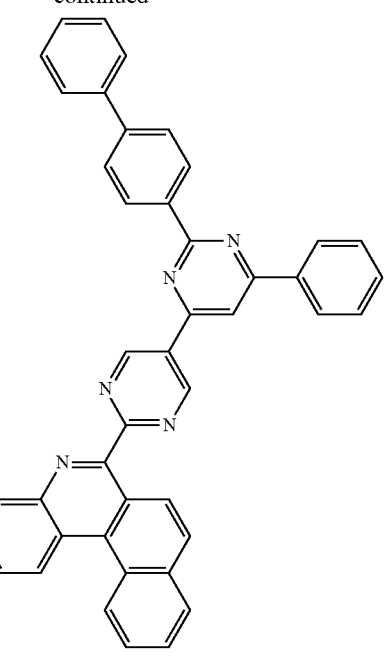

905

Preparation of Compound 905

Target Compound 905 was obtained by performing the preparation in the same manner as in the preparation of Compound 815 in Preparation Example 24, except that in Preparation Example 24, Compound 895-1 was used instead of Compound 227-1, and 2-([1,1'-biphenyl]-4-yl)-4-bromo-6-phenylpyrimidine was used instead of 2-bromo-4,6-diphenyl-1,3,5-triazine.

PREPARATION EXAMPLE 48

Preparation of Compound 920

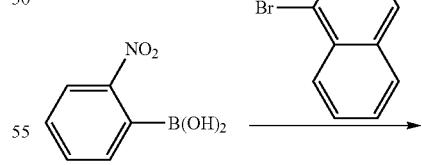

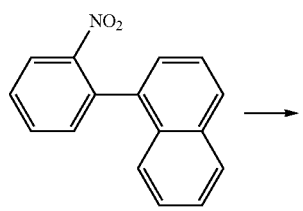

187-4

565
-continued

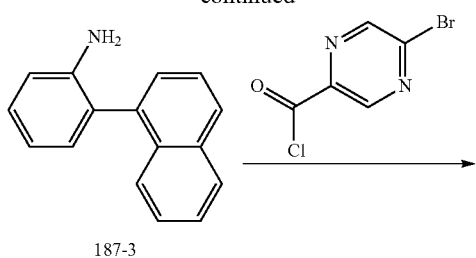

187-3

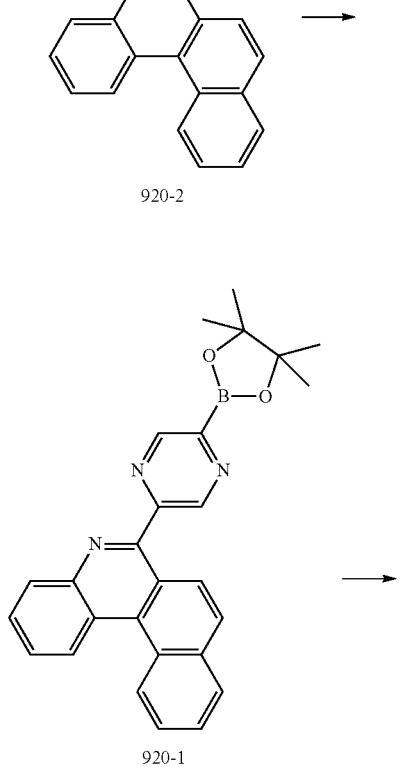

920-3

920-2

920-1

566
-continued

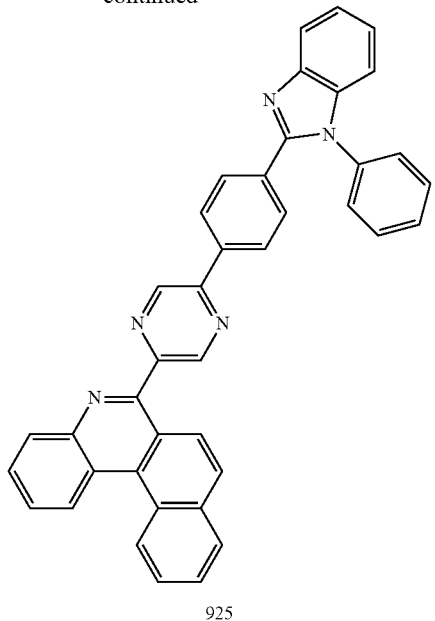

925

Preparation of Compound 920-3

Target Compound 920-3 was obtained by performing the preparation in the same manner as the preparation of Compound 187-2 in Preparation Example 10, except that 5-bromopyrazine-2-carbonyl chloride was used instead of 4-bromobenzoyl chloride.

Preparation of Compound 920-2

Target Compound 920-2 was obtained by performing the preparation in the same manner as the preparation of Compound 187-1 in Preparation Example 10, except that Compound 920-3 was used instead of Compound 187-2.

Preparation of Compound 920-1

Target Compound 920-1 was obtained by performing the preparation in the same manner as the preparation of Compound 227-1 in Preparation Example 15, except that Compound 920-2 was used instead of Compound 187-1.

Preparation of Compound 920

Target Compound 920 was obtained by performing the preparation in the same manner as the preparation of Compound 187 in Preparation Example 10, except that Compound 920-1 was used instead of Compound 227-1.

PREPARATION EXAMPLE 49

Preparation of Compound 925

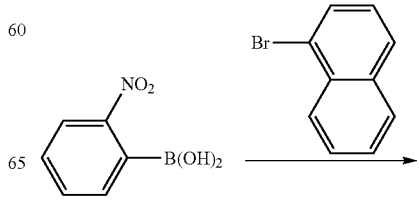

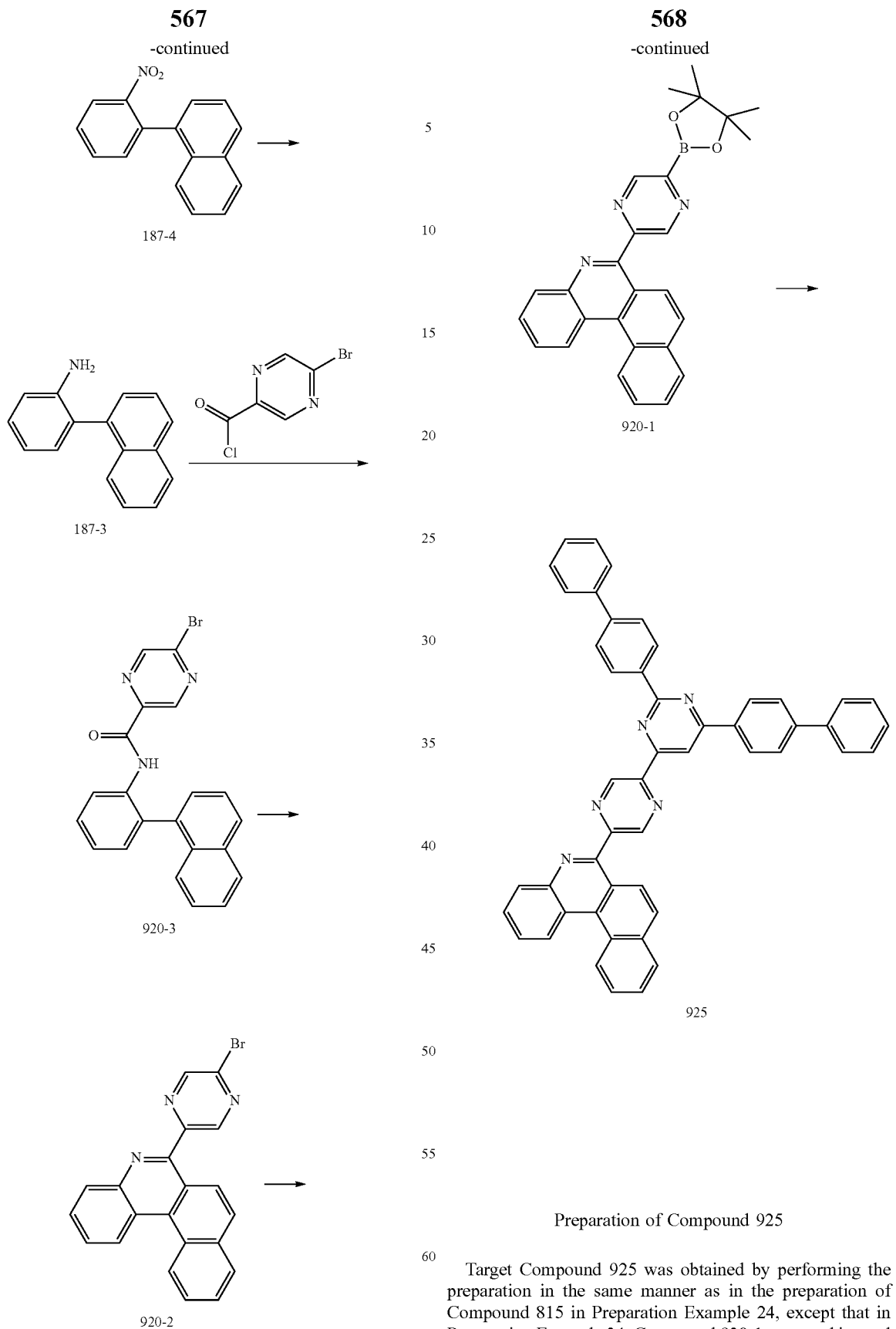
Preparation of Compound 925
Target Compound 925 was obtained by performing the preparation in the same manner as in the preparation of Compound 815 in Preparation Example 24, except that in Preparation Example 24, Compound 920-1 was used instead of Compound 227-1, and 2,4-di([1,1'-biphenyl]-4-yl)-6-bromopyridine was used instead of 2-bromo-4,6-diphenyl-1,3,5-triazine.

PREPARATION EXAMPLE 50

Preparation of Compound 947

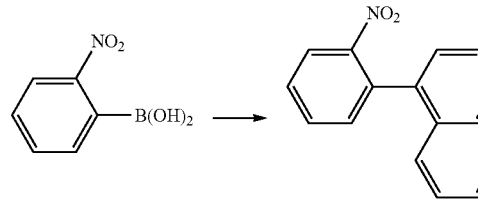

187-4

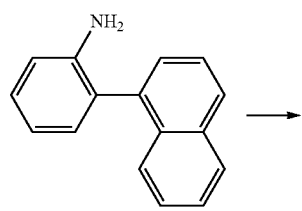

187-3

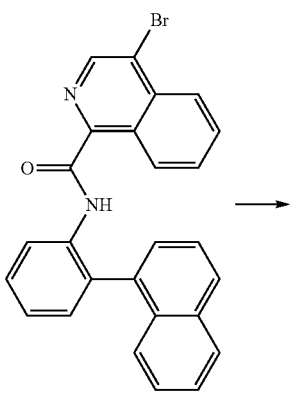

947-3

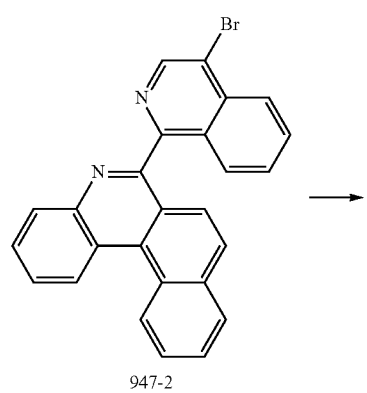

947-2

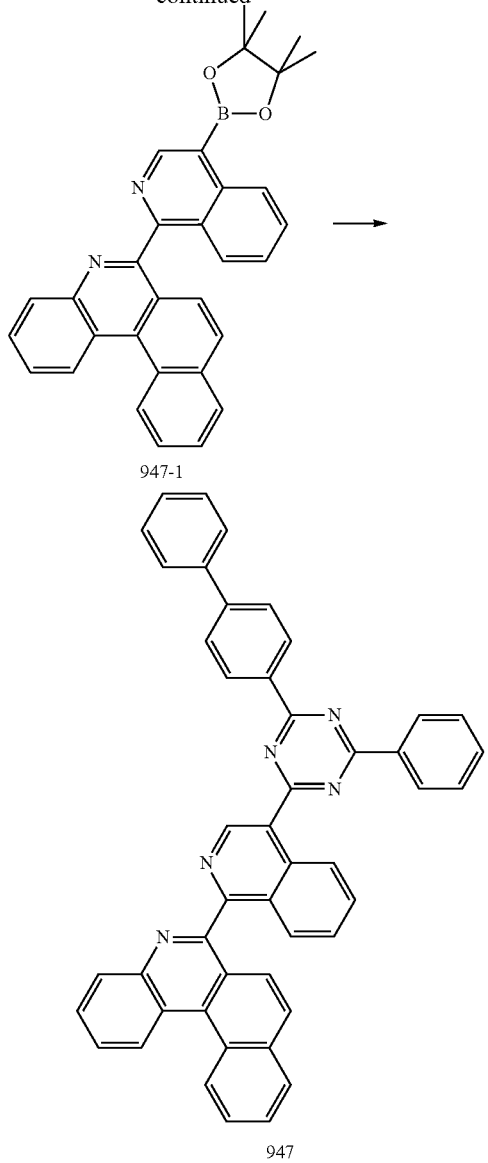

947-1

947

Preparation of Compound 947-3

Target Compound 947-3 was obtained by performing the preparation in the same manner as in the preparation of Compound 187-2 in Preparation Example 10, except that 4-bromoisoquinoline-1-carbonyl chloride was used instead of 4-bromobenzoyl chloride.

Preparation of Compound 947-2

Target Compound 947-2 was obtained by performing the preparation in the same manner as the preparation of Compound 187-1 in Preparation Example 10, except that Compound 947-3 was used instead of Compound 187-2.

Preparation of Compound 947-1

Target Compound 947-1 was obtained by performing the preparation in the same manner as the preparation of Compound 227-1 in Preparation Example 15, except that Compound 947-2 was used instead of Compound 187-1.

Preparation of Compound 947

Target Compound 947 was obtained by performing the preparation in the same manner as in the preparation of Compound 227 in Preparation Example 15, except that Compound 947-1 was used as a starting material, and a compound 2-([1,1'-biphenyl]-4-yl)-4-bromo-6-phenylpyridine was used instead of a compound 2-bromo-9,10-di(naphthalen-2-yl)anthracene.

PREPARATION EXAMPLE 51

Preparation of Compound 949

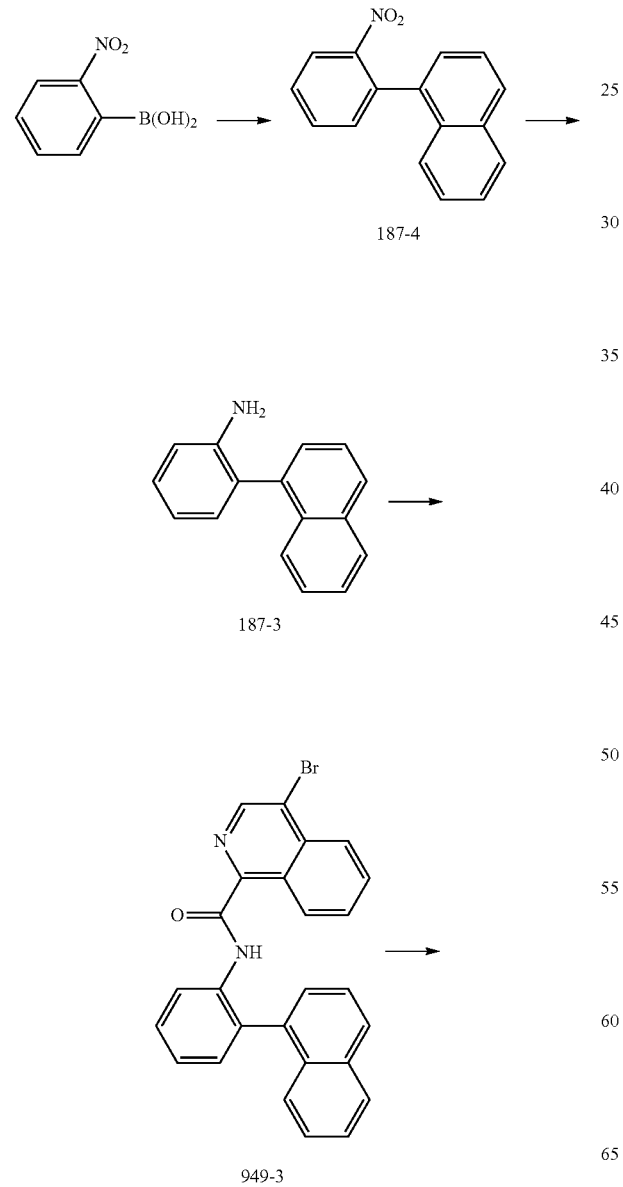

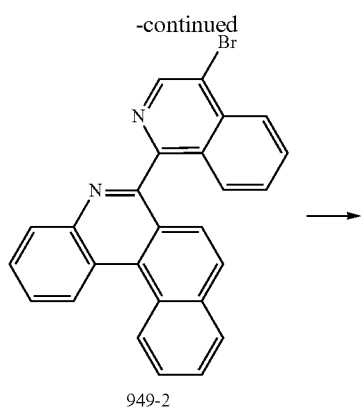

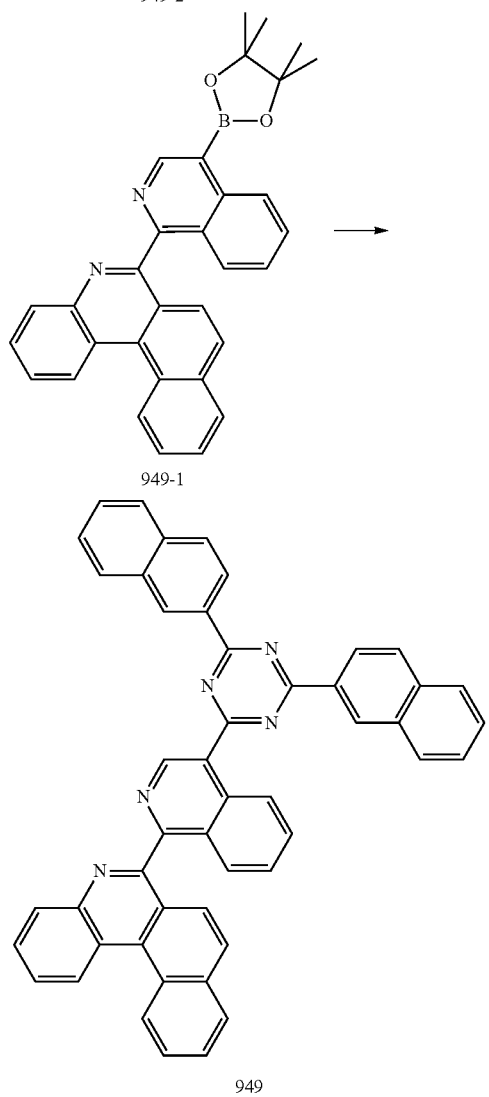

Preparation of Compound 949-3

Target Compound 949-3 was obtained by performing the preparation in the same manner as in the preparation of Compound 187-2 in Preparation Example 10, except that a compound 4-bromoisoquinoline-1-carbonyl chloride was used instead of 4-bromobenzoyl chloride.

573

Preparation of Compound 949-2

Target Compound 949-2 was obtained by performing the preparation in the same manner as the preparation of Compound 187-1 in Preparation Example 10, except that Compound 949-3 was used instead of Compound 187-2.

Preparation of Compound 949-1

Target Compound 949-1 was obtained by performing the preparation in the same manner as the preparation of Compound 227-1 in Preparation Example 15, except that Compound 949-2 was used instead of Compound 187-1.

Preparation of Compound 949

Target Compound 949 was obtained by performing the preparation in the same manner as in the preparation of Compound 227 in Preparation Example 15, except that Compound 949-1 was used as a starting material, and a compound 2-bromo-4,6-di(naphthalen-2-yl)-1,3,5-triazine was used instead of a compound 2-bromo-9,10-di(naphthalen-2-yl)anthracene.

PREPARATION EXAMPLE 52

Preparation of Compound 972

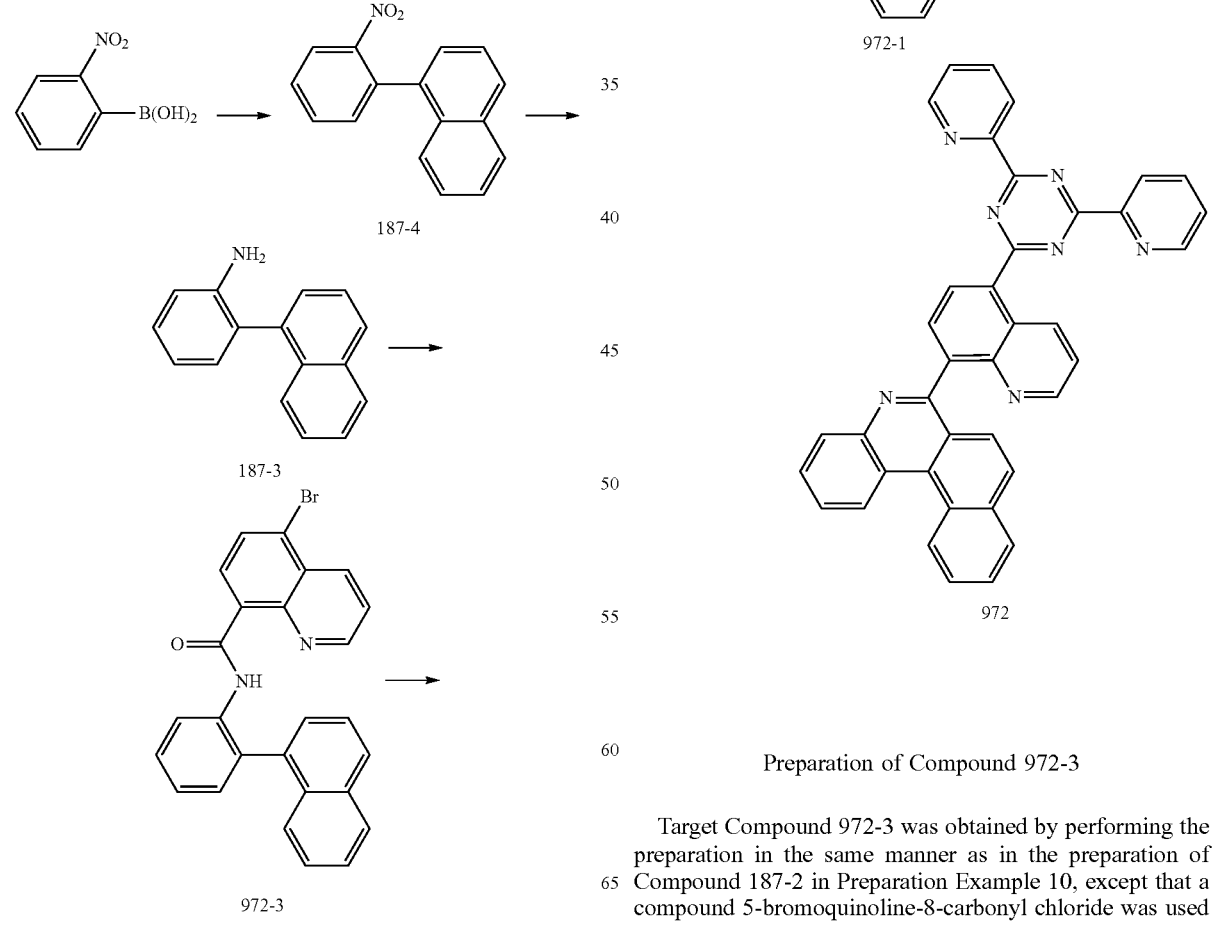

Preparation of Compound 972-3

Target Compound 972-3 was obtained by performing the preparation in the same manner as in the preparation of Compound 187-2 in Preparation Example 10, except that a compound 5-bromoquinoline-8-carbonyl chloride was used instead of 4-bromobenzoyl chloride.

Preparation of Compound 972-2

Target Compound 972-2 was obtained by performing the preparation in the same manner as the preparation of Compound 187-1 in Preparation Example 10, except that Compound 972-3 was used instead of Compound 187-2.

Preparation of Compound 972-1

Target Compound 972-1 was obtained by performing the preparation in the same manner as the preparation of Compound 227-1 in Preparation Example 15, except that Compound 972-2 was used instead of Compound 187-1.

Preparation of Compound 972

Target Compound 972 was obtained by performing the preparation in the same manner as in the preparation of Compound 227 in Preparation Example 15, except that Compound 972-1 was used as a starting material, and a compound 2-bromo-4,6-di(pyridin-2-yl)-1,3,5-triazine was used instead of a compound 2-bromo-9,10-di(naphthalen-2-yl)anthracene.

PREPARATION EXAMPLE 53

Preparation of Compound 974

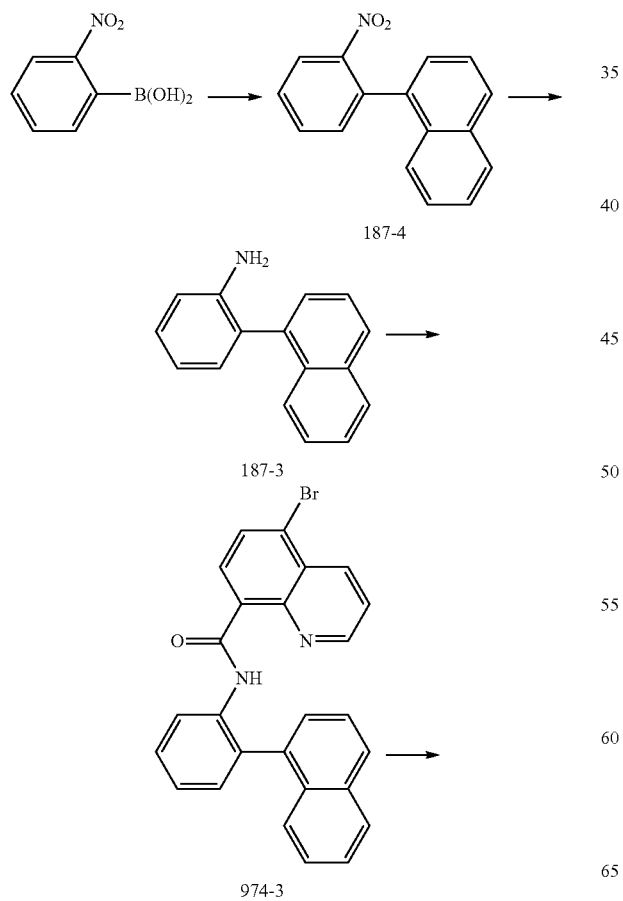

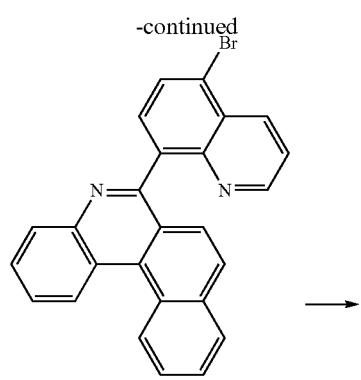

974-2

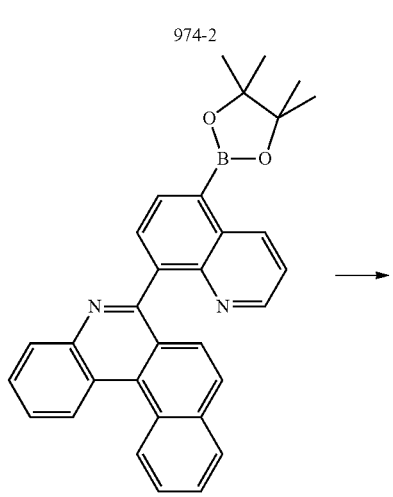

974-1

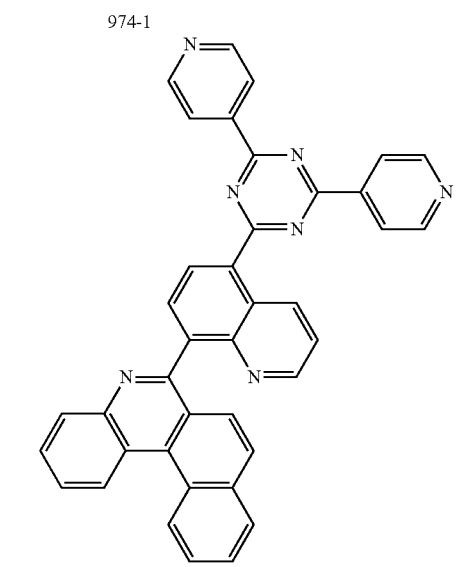

974

Preparation of Compound 974-3

Target Compound 974-3 was obtained by performing the preparation in the same manner as in the preparation of Compound 187-2 in Preparation Example 10, except that a compound 5-bromoquinoline-8-carbonyl chloride was used instead of 4-bromobenzoyl chloride.

577

Preparation of Compound 974-2

Target Compound 974-2 was obtained by performing the preparation in the same manner as the preparation of Compound 187-1 in Preparation Example 10, except that Compound 974-3 was used instead of Compound 187-2.

Preparation of Compound 974-1

Target Compound 974-1 was obtained by performing the preparation in the same manner as the preparation of Compound 227-1 in Preparation Example 15, except that Compound 974-2 was used instead of Compound 187-1.

Preparation of Compound 974

Target Compound 974 was obtained by performing the preparation in the same manner as in the preparation of Compound 227 in Preparation Example 15, except that Compound 974-1 was used as a starting material, and a compound 2-bromo-4,6-di(pyridin-4-yl)-1,3,5-triazine was used instead of a compound 2-bromo-9,10-di(naphthalen-2-yl)anthracene.

PREPARATION EXAMPLE 54

Preparation of Compound 977

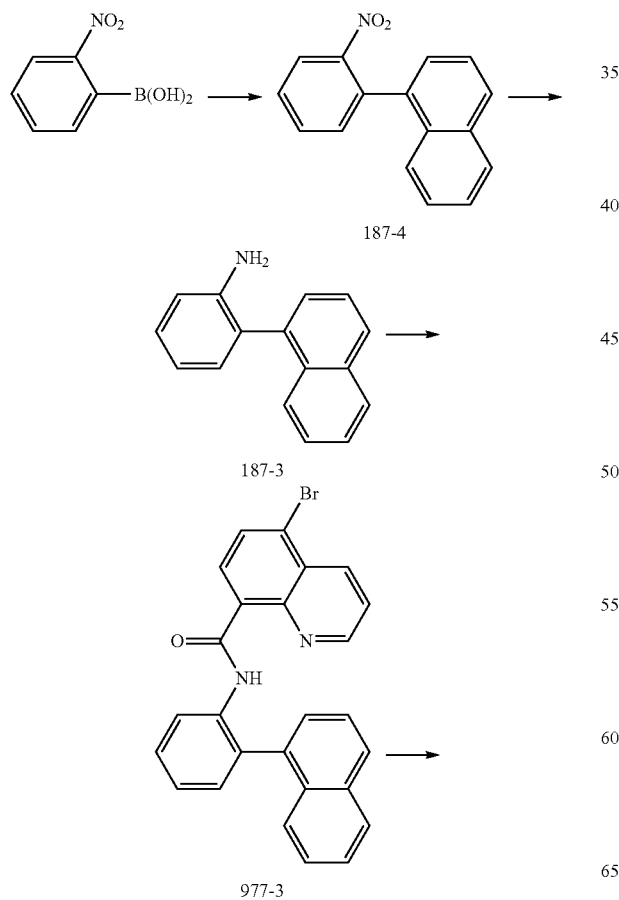

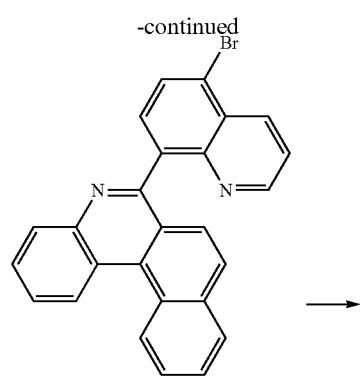

977-2

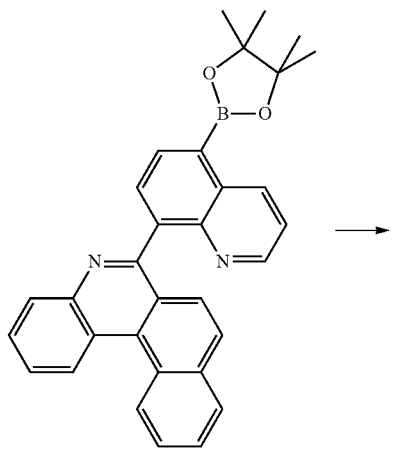

977-1

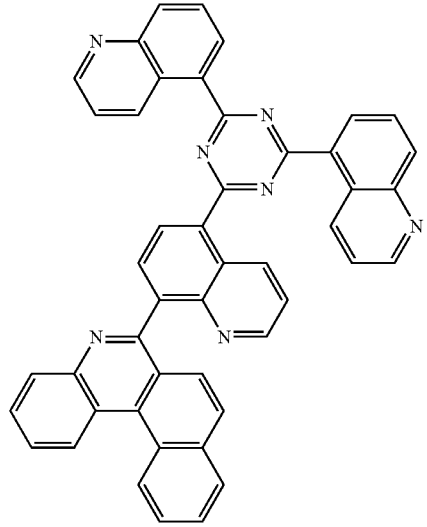

977

Preparation of Compound 977-3

Target Compound 977-3 was obtained by performing the preparation in the same manner as in the preparation of Compound 187-2 in Preparation Example 10, except that a compound 5-bromoquinoline-8-carbonyl chloride was used instead of 4-bromobenzoyl chloride.

Preparation of Compound 977-2

Target Compound 977-2 was obtained by performing the preparation in the same manner as the preparation of Compound 187-1 in Preparation Example 10, except that Compound 977-3 was used instead of Compound 187-2.

Preparation of Compound 977-1

Target Compound 977-1 was obtained by performing the preparation in the same manner as the preparation of Compound 227-1 in Preparation Example 15, except that Compound 977-2 was used instead of Compound 187-1.

Preparation of Compound 977

Target Compound 977 was obtained by performing the preparation in the same manner as in the preparation of Compound 227 in Preparation Example 15, except that Compound 977-1 was used as a starting material, and a compound 5,5'-(6-bromo-1,3,5-triazine-2,4-diyl)diquinoline was used instead of a compound 2-bromo-9,10-di(naphthalen-2-yl)anthracene.

PREPARATION EXAMPLE 55

Preparation of Compound 981

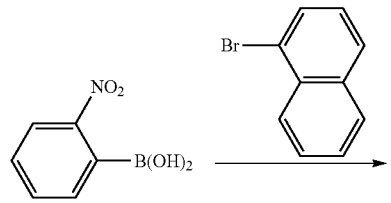

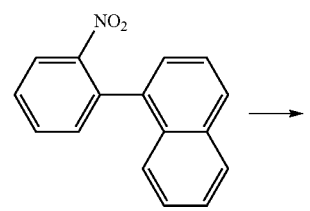

187-4

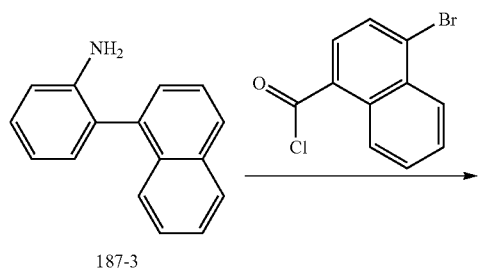

187-3

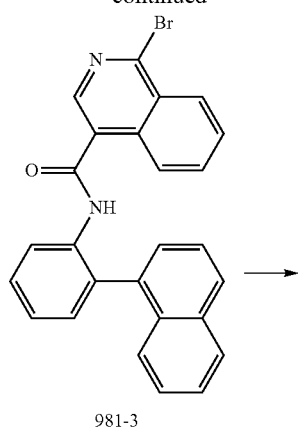

981-3

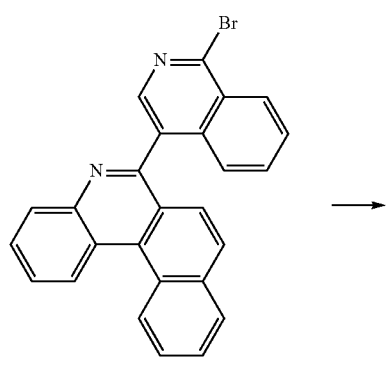

981-2

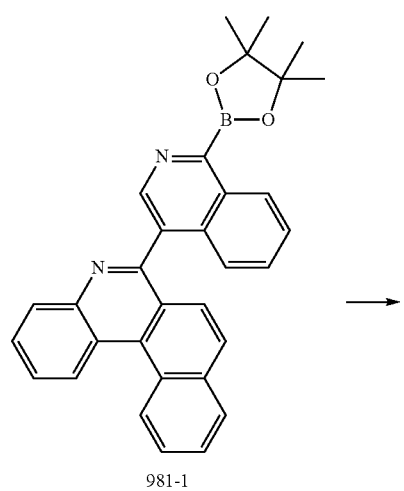

981-1

581

-continued

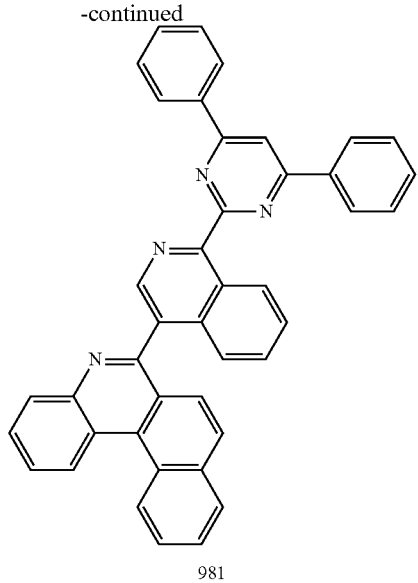

981

Preparation of Compound 981-3

Target Compound 981-3 was obtained by performing the preparation in the same manner as the preparation of Compound 187-2 in Preparation Example 10, except that 4-bromo-1-naphthoyl chloride was used instead of the compound 4-bromobenzoyl chloride.

Preparation of Compound 981-2

Target Compound 981-2 was obtained by performing the preparation in the same manner as the preparation of Compound 187-1 in Preparation Example 10, except that Compound 981-3 was used instead of Compound 187-2.

Preparation of Compound 981-1

Target Compound 981-1 was obtained by performing the preparation in the same manner as the preparation of Compound 758-5 in Preparation Example 36, except that Compound 981-2 was used instead of Compound 758-6.

Preparation of Compound 981

Target Compound 981 was obtained by performing the preparation in the same manner as the preparation of Compound 219 in Preparation Example 21, except that Compound 981-1 was used instead of Compound 227-1.

PREPARATION EXAMPLE 56

Preparation of Compound 982

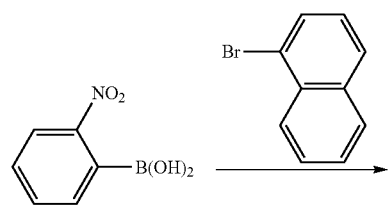

582

-continued

583
-continued
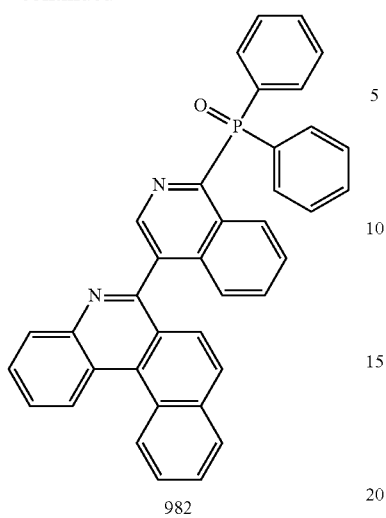
982
Preparation of Compound 982
Target Compound 982 was obtained by performing the preparation in the same manner as the preparation of Compound 201 in Preparation Example 11, except that Compound 981-2 was used instead of Compound 201-1.
PREPARATION EXAMPLE 57
Preparation of Compound 993
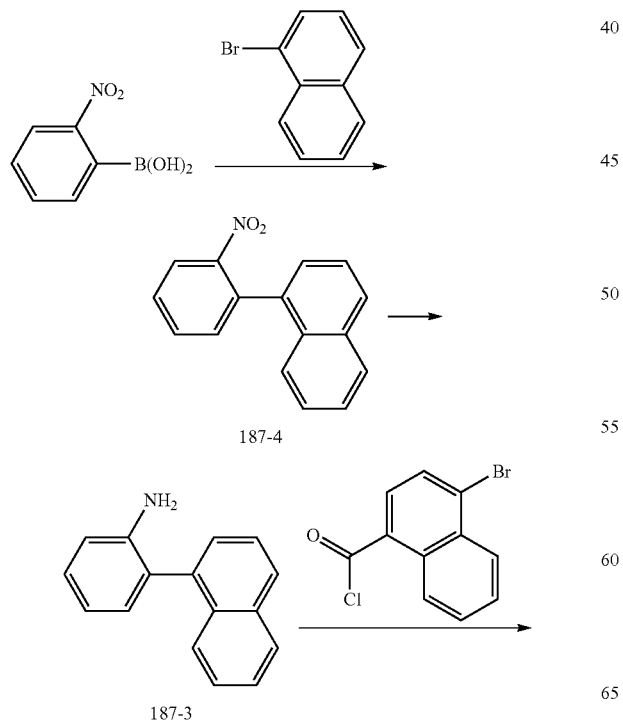
584
-continued
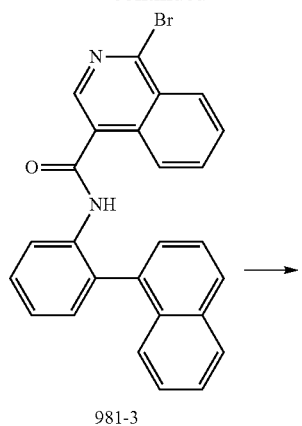
981-3
981-2
981-1

-continued
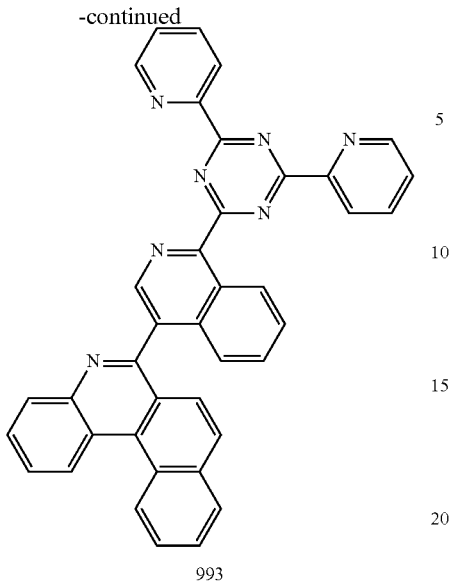
993
Preparation of Compound 993
Target Compound 993 was obtained by performing the preparation in the same manner as the preparation of Compound 981 in Preparation Example 55, except that 2-chloro-4,6-di(pyridin-2-yl)-1,3,5-triazine was used instead of the compound 2-chloro-4,6-diphenylpyrimidine.
PREPARATION EXAMPLE 58
Preparation of Compound 1009
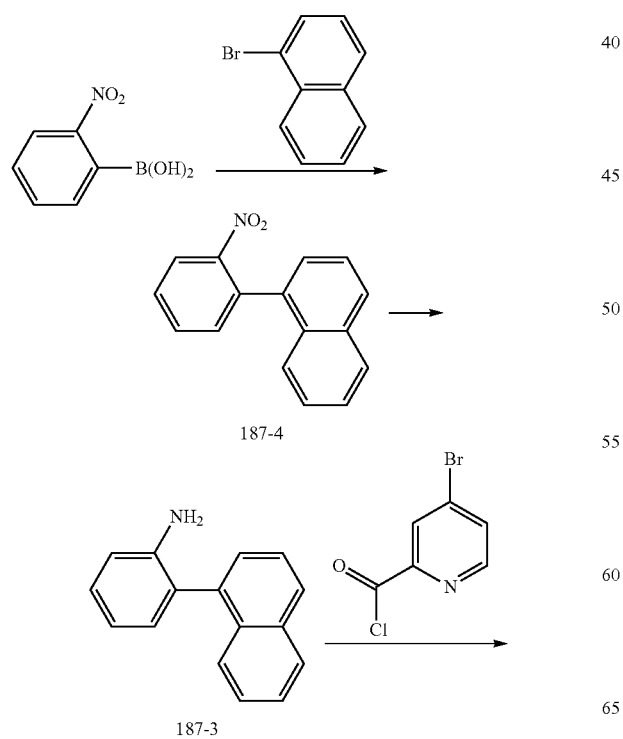
-continued
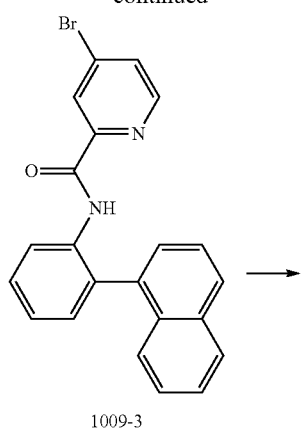
1009-3
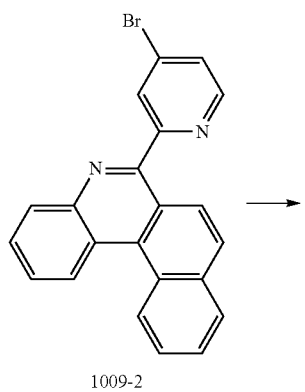
1009-2
1009-1

-continued

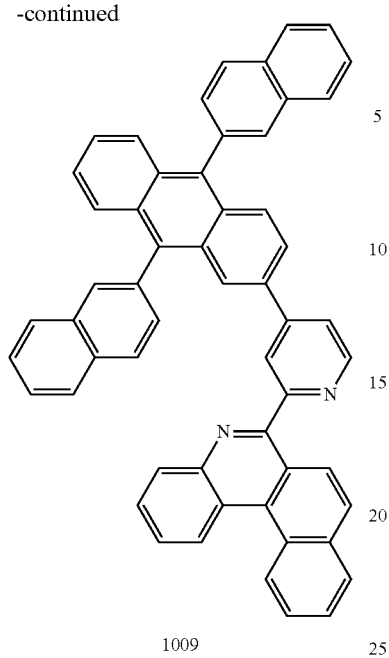

1009

Preparation of Compound 1009-3

Target Compound 1009-3 was obtained by performing the preparation in the same manner as the preparation of Compound 187-2 in Preparation Example 10, except that 4-bromopicolinoyl chloride was used instead of the compound 4-bromobenzoyl chloride.

Preparation of Compound 1009-2

Target Compound 1009-2 was obtained by performing the preparation in the same manner as the preparation of Compound 187-1 in Preparation Example 10, except that Compound 1009-3 was used instead of Compound 187-2.

Preparation of Compound 1009-1

Target Compound 1009-1 was obtained by performing the preparation in the same manner as the preparation of Compound 758-5 in Preparation Example 36, except that Compound 1009-2 was used instead of Compound 758-6.

Preparation of Compound 1009

Target Compound 1009 was obtained by performing the preparation in the same manner as the preparation of Compound 227 in Preparation Example 15, except that Compound 1009-1 was used instead of Compound 227-1.

PREPARATION EXAMPLE 59

Preparation of Compound 1017

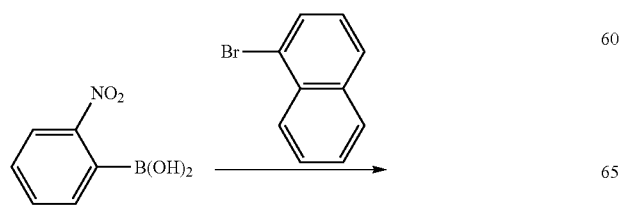

-continued

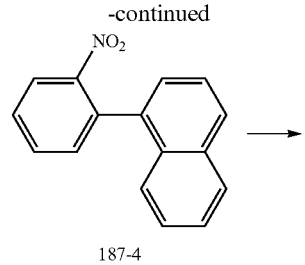

187-4

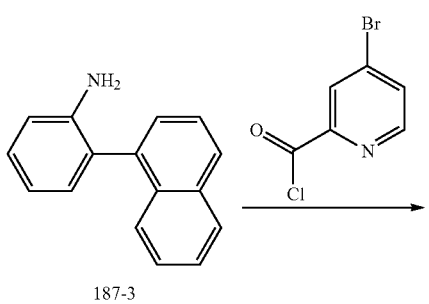

187-3

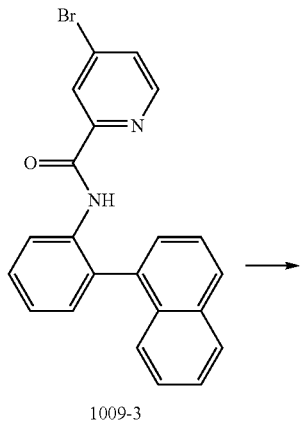

1009-3

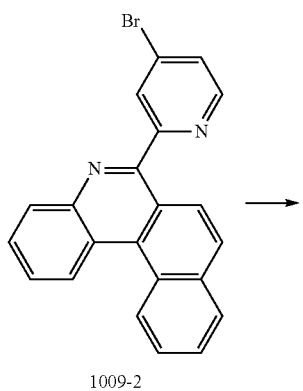

1009-2

1009-1

1017

Preparation of Compound 1017

Target Compound 1017 was obtained by performing the preparation in the same manner as in the preparation of Compound 1009 in Preparation Example 58, except that 2-chloro-4,6-di(pyridin-4-yl)-1,3,5-triazine was used instead of the compound 2-bromo-9,10-di(naphthalen-2-yl) anthracene.

PREPARATION EXAMPLE 60

Preparation of Compound 1025

187-4

187-3

1025-3

1025-2

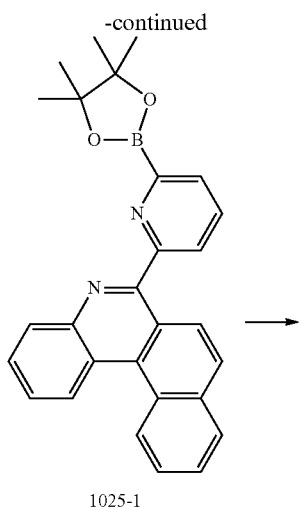

1025-1

1025

Preparation of Compound 1025-3

Target Compound 1025-3 was obtained by performing the preparation in the same manner as the preparation of Compound 187-2 in Preparation Example 10, except that 6-bromopicolinoyl chloride was used instead of the compound 4-bromobenzoyl chloride.

Preparation of Compound 1025-2

Target Compound 1025-2 was obtained by performing the preparation in the same manner as the preparation of Compound 187-1 in Preparation Example 10, except that Compound 1025-3 was used instead of Compound 187-2.

Preparation of Compound 1025-1

Target Compound 1025-1 was obtained by performing the preparation in the same manner as the preparation of Compound 758-5 in Preparation Example 36, except that Compound 1025-2 was used instead of Compound 758-6.

Preparation of Compound 1025

Target Compound 1025 was obtained by performing the preparation in the same manner as the preparation of Compound 187 in Preparation Example 10, except that Compound 1025-1 was used instead of Compound 187-1.

The compound of the chemical formula 1 was prepared according to the above-described preparation examples except that kinds or positions of the substituents are modified. Synthesis thereof was checked, and the check results were as listed in Table 1 and Table 2, and illustrated in FIG. 4 to FIG. 59.

The following Table 1 lists $^1$H NMR (CDCl$_3$, 200 Mz) measurement data, and the following Table 2 lists measurement data obtained by an FD-spectrometer (FD-MS: Field desorption mass spectrometry).

TABLE 1

| Compound | $^1$H NMR (CDCl$_3$, 200 Mz) |
|---|---|
| 1 | 7.52-7.55 (2H, m), 7.58-7.70 (4H, m), 7.72 (1H, t), 7.80-7.92 (5H, m), 7.97-8.04 (3H, m), 8.20-8.23 (2H, m), 8.35 (1H, s), 8.45 (1H, d), 8.58 (1H, d), 8.65-8.68 (3H, m), 8.74 (1H, d), 8.79 (1H, s), 9.15 (1H, d), 9.32 (1H, d) |
| 3 | 7.59-7.70 (8H, m), 7.85 (1H, t), 7.90 (1H, d), 7.92 (1H, d), 7.94-8.07 (5H, m), 8.20 (1H, d), 8.37 (1H, d), 8.43-8.46 (2H, m), 8.54 (2H, m), 8.79 (1H, d), 8.85 (1H, s), 9.11 (1H, d) |
| 5 | 7.59-7.70 (10H, m), 7.84 (1H, t), 7.90-7.94 (3H, m), 8.00 (1H, d), 8.06 (2H, d), 8.79 (1H, s), 8.20 (1H, s), 8.35 (2H, m), 8.54 (1H, d), 8.57 (1H, d), 8.85 (2H, s), 9.27 (1H, s) |
| 9 | 7.38-7.47 (5H, m), 7.55-7.63 (10H, m), 7.70 (1H, t), 7.85 (1H, t), 7.94-8.09 (11H, m), 8.20 (3H, m), 8.37-8.42 (2H, m), 8.54 (2H, m), 8.85 (1H, s), 8.99 (1H, s) |
| 10 | 7.38-7.47 (5H, m), 7.53-7.61 (11H, m), 7.94-8.06 (12H, m), 8.09 (1H, d), 8.20 (2H, m), 8.31 (1H, s), 8.37 (1H, d), 8.42 (1H, d), 8.54 (1H, s), 8.85 (1H, d), 8.99 (1H, s) |
| 11 | 7.37-7.38 (5H, m), 7.55-7.70 (8H, m), 7.85 (1H, t), 7.94-8.09 (7H, m), 8.20-8.21 (5H, m), 8.37 (1H, d), 8.54 (2H, d), 8.85 (1H, s) |
| 12 | 7.35-7.38 (5H, m), 7.55 (1H, s), 7.59-7.63 (5H, m), 7.70 (1H, t), 7.77 (1H, t), 7.85 (1H, t), 7.94 (1H, d), 7.99-8.01 (3H, m), 8.06-8.09 (4H, m), 8.20-8.21 (5H, m), 8.37 (1H, d), 8.50 (1H, d), 8.85 (1H, s), 8.91 (1H, d) |

TABLE 1-continued

| Compound | ¹H NMR (CDCl₃, 200 Mz) |
|---|---|
| 14 | 7.37-7.38 (5H, t), 7.41-7.46 (4H, m), 7.53-7.65 (7H, m), 7.79 (2H, d), 7.98-8.06 (6H, m), 8.14 (1H, d), 8.18 (1H, d), 8.21 (4H, d), 8.37 (1H, d), 8.54 (1H, d), 8.85 (1H, s), 9.01 (1H, d) |
| 16 | 7.37-7.41 (6H, m), 7.49 (4H, t), 7.53 (1H, t), 7.59-7.65 (5H, m), 7.75 (4H, d), 7.98-8.00 (4H, m), 8.04 (3H, s), 8.06 (2H, d), 8.14 (1H, d), 8.21 (4H, d), 8.37 (1H, d), 8.54 (1H, d), 8.85 (1H, s) |
| 17 | 7.25 (4H, m), 7.37-7.46 (7H, m), 7.59-7.61 (8H, m), 7.70 (1H, t), 7.79 (2H, d), 7.85 (1H, t), 7.94-8.00 (6H, m), 8.06-8.07 (3H, m), 8.20-8.22 (4H, m), 8.37 (1H, d), 8.54 (2H, m), 8.85 (1H, s) |
| 20 | 7.38 (1H, d), 7.55-7.62 (6H, m), 7.70-7.71 (3H, m), 7.85-7.87 (3H, m), 7.94-8.00 (3H, m), 8.04 (1H, d), 8.06 (2H, d), 8.20-8.23 (2H, m), 8.37 (1H, d), 8.69 (2H, d), 8.85 (1H, s), 9.57 (1H, s) |
| 26 | 7.23 (1H, t), 7.32 (1H, d), 7.38-7.40 (2H, m), 7.59-7.62 (3H, m), 7.70 (1H, t), 7.74 (1H, t), 7.85 (4H, m), 7.94-8.00 (4H, m), 8.06 (2H, d), 8.20 (1H, d), 8.32 (1H, s), 8.37 (1H, d), 8.55-8.59 (3H, m), 8.69 (2H, d), 8.85 (1H, s), 9.18 (1H, d), 9.39 (1H, s) |
| 29 | 7.16-7.20 (2H, m), 7.35 (1H, t), 7.50 (1H, t), 7.59-7.61 (5H, m), 7.70 (1H, t), 7.85 (1H, t), 7.94-8.06 (6H, m), 8.12 (1H, d), 8.19-8.21 (2H, m), 8.37 (1H, d), 8.55 (1H, d), 8.85 (1H, s), 8.97 (1H, m) |
| 30 | 7.16-7.20 (2H, m), 7.35 (1H, t), 7.50 (1H, t), 7.58-7.62 (5H, m), 7.70 (1H, t), 7.79 (1H, t), 7.85 (1H, t), 7.94-8.00 (4H, m), 8.06-8.08 (2H, m), 8.11 (1H, d), 8.19-8.20 (2H, m), 8.37 (1H, d), 8.55 (1H, d), 8.85 (1H, s) |
| 34 | 7.41-7.49 (7H, m), 7.53-7.62 (6H, m), 7.65-7.68 (2H, m), 7.75-7.77 (5H, m), 7.89 (2H, s), 7.98-8.00 (5H, m), 8.06 (2H, d), 8.13-8.14 (2H, m), 8.21 (1H, s), 8.30 (1H, d), 8.37 (1H, d), 8.54 (1H, d), 8.85 (1H, s) |
| 36 | 7.16-7.20 (2H, m), 7.35 (1H, t), 7.47-7.68 (10H, m), 7.84-8.00 (5H, m), 8.06 (2H, d), 8.09 (1H, d), 8.19-8.21 (2H, m), 8.31 (1H, d), 8.37 (1H, d), 8.54-8.56 (2H, m), 8.85 (1H, s) |
| 39 | 1.69 (6H, s), 7.28, 1H, t), 7.38 (1H, t), 7.55-7.61 (5H, m), 7.70 (1H, t), 7.78 (1H, d), 7.85-7.94 (4H, m), 8.00-8.09 (5H, m), 8.20 (1H, d), 8.37 (1H, d), 8.54 (2H, m), 8.85 (1H, s) |
| 40 | 1.69 (6H, s), 7.28 (1H, t), 7.38 (1H, t), 7.53-7.55 (2H, m), 7.59-7.62 (4H, m), 7.78-7.79 (2H, m), 7.87-7.90 (4H, m), 7.99-8.00 (3H, m), 8.06-8.09 (3H, m), 8.37 (1H, d), 8.54 (1H, d), 8.85 (1H, s) |
| 42 | 7.0-7.18 (6H, m), 7.26-7.28 (5H, m), 7.38 (1H, t), 7.55-7.61 (3H, m), 7.78 (1H, d), 7.89-7.90 (2H, m), 7.94-8.09 (8H, m), 8.31 (1H, d), 8.37 (1H, d), 8.54 (1H, d), 8.85 (1H, s) |
| 44 | 7.35-7.38 (7H, m), 7.46-7.47 (5H, m), 7.53-7.65 (8H, m), 7.87 (1H, d), 7.98-8.00 (4H, m), 8.06-8.08 (4H, m), 8.14 (1H, d), 8.37 (1H, d), 8.54 (1H, d), 8.85 (1H, s) |
| 48 | 7.38 (1H, d), 7.47 (1H, d), 7.55-7.72 (12H, m), 7.85 (1H, t), 7.88 (1H, d), 7.94-8.06 (5H, m), 8.11-8.13 (3H, m), 8.20-8.23 (3H, m), 8.37 (1H, d), 8.43 (1H, d), 8.51 (2H, d), 8.85 (1H, s) |
| 57 | 7.53-7.61 (6H, m), 7.70 (1H, t), 7.83-7.85 (3H, m), 7.94 (1H, d), 7.96 (2H, d), 8.00-8.06 (5H, m), 8.20-8.22 (2H, m), 8.37-8.41 (5H, m), 8.85 (1H, s), 8.97 (2H, m), 9.14 (2H, s) |
| 63 | 7.59-7.62 (5H, m), 7.70 (1H, t), 7.85-7.87 (3H, m), 7.94-8.00 (4H, m), 8.06 (2H, d), 8.20-8.22 (5H, m), 8.37-8.41 (2H, m), 8.49-8.50 (3H, m), 8.85 (1H, s), 8.94 (2H, d), 9.02-9.07 (2H, m) |
| 65 | 7.53-7.63 (6H, m), 7.70 (1H, t), 7.83-7.85 (3H, m), 7.94-8.06 (9H, m), 8.17-8.20 (2H, m), 8.37-8.41 (4H, m), 8.57 (1H, s), 8.65 (1H, d), 8.85 (2H, s), 9.39 (1H, s) |
| 68 | 7.59-7.62 (7H, m), 7.70 (1H, t), 7.85 (1H, t), 7.93-8.06 (14H, m), 8.20-8.23 (2H, m), 8.37 (1H, d), 8.46-8.49 (4H, m), 8.85 (1H, s) |
| 75 | 7.48 (t, 4H), 7.59 (2H, t), 7.64-7.66 (2H, m), 7.80 (1H, t), 7.85-7.92 (3H, m), 8.04 (1H, m), 8.10 (1H, m), 8.17 (2H, m), 8.46 (2H, d), 8.66 (4H, d), 9.11 (1H, d), 9.27 (1H, d), 9.41 (2H, m) |
| 77 | 7.59-7.70 (13H, m), 7.85-8.06 (9H, m), 8.17-8.21 (4H, m), 8.37 (1H, d), 8.84-8.85 (3H, m), 8.97 (2H, m), 9.08 (2H, d) |
| 78 | 6.90 (2H, t), 7.14 (2H, d), 7.38 (2H, t), 7.59-7.70 (4H, m), 7.85 (1H, t), 7.94-8.06 (11H, m), 8.20 (1, d), 8.37 (3H, d), 8.69 (4H, d), 8.85 (1H, s), 9.07 (1H, d) |
| 81 | 7.53-7.70 (9H, m), 7.83-7.85 (3H, m), 7.94-.06 (8H, m), 8.20-8.21 (2H, m), 8.37 (1H, d), 8.65 (2H, d), 8.85 (1H, s), 8.97 (2H, m) |
| 82 | 7.29 (2H, d), 7.54-7.70 (7H, m), 7.85 (3H, t), 7.94-8.00 (12H, m), 8.20-8.21 (2H, m), 8.37 (1H, d), 8.69-8.71 (6H, m), 8.85 (1H, s), 8.97 (2H, m) |
| 83 | 7.49-7.70 (13H, m), 7.73 (1H, t), 7.85 (1H, t), 7.94 (2H, m), 8.00 (1H, d), 8.06-8.08 (3H, m), 8.20 (3H, m), 8.29 (4H, d), 8.37 (1H, d), 8.54 (2H, m), 8.85 (1H, s) |
| 89 | 7.53 (2H, t), 7.59-7.70 (5H, m), 7.72 (1H, d), 7.83-7.85 (3H, m), 7.96-8.06 (9H, m), 8.17-8.20 (2H, m), 8.37-8.41 (5H, m), 8.85 (1H, s), 9.14 (2H, s) |
| 91 | 7.49-7.62 (11H, m), 7.94-8.00 (7H, m), 8.06 (2H, d), 8.23-8.25 (2H, m), 8.37-8.39 (3H, m), 8.54 (1H, d), 8.85 (1H, s) |
| 93 | 7.53-7.70 (13H, m), 7.88-7.90 (3H, m), 7.99 (2H, d), 8.00-8.06 (5H, m), 8.17 (2H, d), 8.23 (1H, s), 8.30 (1H, d), 8.37 (1H, d), 8.43 (1H, d), 8.54 (1H, d), 8.84-8.85 (3H, m), 9.08 (2H, d) |
| 95 | 7.52-7.62 (7H, m), 7.87 (2H, t), 7.99-8.10 (7H, m), 8.23-8.24 (2H, m), 8.37 (1H, d), 8.50-8.54 (3H, m), 8.63 (2H, d), 8.85 (1H, s), 8.94 (2H, d) |
| 99 | 7.50-7.61 (10H, d), 7.70 (1H, t), 7.85 (1H, t), 7.94 (1H, d), 8.00 (1H, d), 8.06 (2H, d), 8.20-8.21 (2H, m), 8.36-8.37 (5H, m), 8.85 (1H, s), 8.97 (2H, m) |

TABLE 1-continued

| Compound | ¹H NMR (CDCl₃, 200 Mz) |
| --- | --- |
| 100 | 7.14-7.16 (6H, m), 7.51-7.58 (7H, m), 7.66 (1H, s), 7.67 (1H, t), 7.76-7.80 (4H, m), 7.84 (1H, s), 7.90 (2H, t), 8.41 (1H, d), 8.88 (1H, d), 9.05 (1H, d), 9.20 (1H, d) |
| 103 | 7.22-7.31 (1H, m), 7.32-7.36 (3H, m), 7.41-7.50 (5H, m), 7.53-7.58 (2H, m), 7.65-7.69 (3H, m), 7.72-7.91 (9H, m), 8.02 (2H, d), 8.26 (1H, s), 8.40 (1H, d), 9.06 (1H, d), 9.23 (1H, d) |
| 105 | 7.28 (1H, t), 7.38 (2H, d), 7.48-7.53 (3H, m), 7.59-7.62 (6H, m), 7.70-7.73 (2H, m), 7.81 (1H, d), 7.85 (1H, t), 7.94-7.95 (2H, d), 8.00 (1H, d), 8.05-8.07 (3H, m), 8.20 (1H, d), 8.37-8.38 (2H, m), 8.54-8.56 (3H, m), 8.85 (1H, s) |
| 106 | 7.27-735 (3H, m), 7.37-7.41 (3H, m), 7.50-7.58 (3H, m), 7.64-7.66 (2H, m), 7.70-7.84 (10H, m), 7.88-7.93 (2H, m), 8.02-8.06 (2H, m), 8.38 (1H, d), 9.08 (1H, d), 9.20 (1H, d) |
| 107 | 7.25-7.28 (3H, m), 7.38 (2H, d), 7.48 (2H, t), 7.53 (2H, t), 7.59-7.62 (5H, m), 7.65 (1H, t), 7.81 (1H, d), 7.96-8.00 (6H, m), 8.06 (2H, d), 8.14 (1H, d), 8.37 (1H, d), 8.54-8.56 (2H, m), 8.85 (1H, s) |
| 109 | 7.41-7.53 (4H, m), 7.61-7.62 (2H, m), 7.70 (1H, d), 7.75 (2H, d), 7.85-7.94 (4H, m), 7.99 (2H, d), 8.20 (1H, d), 8.54 (1H, d), 8.69 (2H, d) |
| 112 | 7.38-7.40 (3H, m), 7.53-7.66 (8H, m), 7.70 (1H, t), 7.85 (3H, m), 7.94-7.99 (6H, m), 8.06-8.09 (2H, m), 8.20 (1H, d), 8.54 (1H, d), 8.69 (2H, d) |
| 113 | 7.38 (1H, d), 7.53-7.70 (7H, m), 7.83-7.85 (3H, m), 7.94 (1H, d), 7.99 (2H, d), 8.06-8.09 (2H, m), 8.20 (1H, d), 8.54 (1H, d), 8.69 (2H, d) |
| 116 | 7.25 (2H, d), 7.39 (1H, t), 7.52 (2H, t), 7.61-7.62 (2H, m), 7.70 (1H, t), 7.77 (1H, t), 7.85 (1H, t), 7.94-7.99 (2H, m), 8.09 (1H, d), 8.20 (2H, d), 8.50-8.54 (2H, m), 8.69 (2H, d), 8.95 (1H, d) |
| 117 | 7.25 (4H, s), 7.38 (1H, d), 7.53-7.70 (7H, m), 7.83-7.86 (3H, m), 7.94-7.99 (4H, m), 8.06-8.09 (2H, m), 8.20 (1H, d), 8.54 (1H, d), 8.69 (2H, d) |
| 121 | 6.90 (1H, t), 7.14 (1H, d), 7.38 (1H, t), 7.53 (1H, t), 7.61-7.62 (2H, m), 7.70 (1H, t), 7.85 (1H, t), 7.94 (1H, d), 7.99 (2H, d), 8.20 (1H, d), 8.37 (1H, d), 8.54 (1H, d), 8.69 (4H, m) |
| 124 | 7.62 (1H, t), 7.73-7.85 (5H, m), 7.91-7.95 (6H, m), 8.08 (2H, d), 8.22 (1H, d), 8.43 (2H, d), 9.09 (1H, d), 9.21 (1H, d), 9.31 (1H, s) |
| 127 | 7.25-7.31 (3H, m), 7.53 (1H, t), 7.60-7.63 (3H, m), 7.70 (1H, t), 7.81-7.85 (2H, m), 7.94-7.99 (3H, m), 8.16-8.20 (2H, m), 8.51-8.54 (2H, m), 8.69 (2H, d), 9.19 (1H, s) |
| 129 | 7.53-7.75 (7H, m), 7.85-7.99 (8H, m), 8.20 (1H, d), 8.43-8.46 (2H, m), 8.54 (1H, d), 8.69-8.71 (3H, m), 9.11 (1H, d) |
| 132 | 7.23-7.28 (7H, m), 7.36-7.38 (2H, m), 7.48-7.53 (4H, m), 7.60-7.63 (3H, m), 7.70 (1H, t), 7.81-7.85 (4H, m), 7.94-7.96 (5H, m), 8.20 (1H, d), 8.54-8.56 (2H, m), 8.69 (2H, m) |
| 134 | 6.53 (1H, s), 7.22-7.25 (6H, m), 7,49-7.62 (7H, m), 7.70 (1H, t), 7.83-7.85 (5H, m), 7.94-7.99 (5H, m), 8.06 (2H, d), 8.13 (1H, d), 8.20 (1H, d), 8.54 (1H, d), 8.69 (2H, d) |
| 140 | 7.23-7.25 (6H, m), 7.45-7.53 (7H, m), 7.61-7.62 (2H, m), 7.70 (1H, t), 7.83-7.85 (3H, m), 7.94-7.99 (5H, m), 8.21 (1H, d), 8.32-8.36 (4H, m), 8.54 (1H, d), 8.69 (2H, d) |
| 146 | 7.50-7.53 (7H, m), 7.61-7.62 (2H, m), 7.70-7.77 (5H, m), 7.83-7.85 (3H, m), 7.94-7.99 (7H, m), 8.20 (1H, d), 8.54 (1H, d), 8.69 (2H, d) |
| 148 | 7.16-7.20 (2H, m), 7.35 (1H, t), 7.50-7.62 (5H, m), 7.70 (1H, t), 7.83-7.85 (3H, m), 7.91-7.94 (6H, m), 7.99 (2H, d), 8.19-8.20 (2H, m), 8.54-8.55 (2H, m), 8.69 (2H, d) |
| 153 | 7.16 (2H, t), 7.35 (2H, t), 7.47-7.53 (4H, m), 7.58-7.70 (8H, m), 7.77-7.89 (7H, m), 7.94-7.99 (7H, m), 8.20-8.21 (2H, m), 8.54-8.56 (3H, m), 8.69 (2H, d) |
| 158 | 7.41-7.53 (7H, m), 7.61-7.77 (8H, m), 7.85-7.94 (10H, m), 7.98-8.00 (3H, m), 8.13 (1H, d), 8.20 (1H, d), 8.30 (1H, d), 8.54 (1H, d), 8.69 (2H, d) |
| 162 | 7.25 (4H, s), 7.35-7.38 (9H, m), 7.46-7.53 (7H, m), 7.61-7.65 (4H, m), 7.70 (1H, t), 7.85-7.87 (5H, m), 7.94-7.99 (3H, m), 8.20 (1H, d), 8.54 (1H, d), 8.69 (2H, d) |
| 187 | 7.25-7.28 (3H, m), 7.38-7.53 (6H, m), 7.61-7.62 (3H, m), 7.70 (1H, t), 7.81-7.85 (4H, m), 7.94-7.99 (5H, m), 8.20 (1H, d), 8.54-8.56 (2H, m), 8.69 (2H, d) |
| 189 | 7.36 (1H, s), 7.42 (1H, t), 7.50 (2H, t), 7.61 (1H, t), 7.69 (1H, t), 7.72-7.80 (4H, m), 7.88-7.94 (7H, m), 8.03-8.10 (6H, m), 8.40 (1H, d), 8.71 (2H, d), 9.08 (1H, d), 9.20 (1H, d) |
| 201 | 7.50-7.54 (4H, m), 7.61 (2H, t), 7.76-7.89 (14H, m), 8.07 (1H, d), 8.36 (1H, d), 9.08 (1H, d), 9.19 (1H, d) |
| 219 | 7.49-7.55 (7H, m), 7.61-7.62 (2H, m), 7.70 (1H, t), 7.85 (1H, t), 7.94-7.99 (9H, m), 8.20-8.23 (2H, m), 8.54 (1H, d), 8.69 (2H, d) |
| 220 | 7.49-7.51 (6H, m), 7.59-7.61 (4H, m), 7.70 (1H, t), 7.75-7.77 (4H, m), 7.85 (3H, t), 7.94-7.97 (5H, m), 8.00 (1H, d), 8.05-8.07 (3H, m), 8.20 (1H, d), 8.37 (1H, d), 8.52-8.54 (2H, m), 8.85 (1H, s) |
| 226 | 7.25 (4H, s), 7.53 (1H, t), 7.61-7.62 (2H, m), 7.65-7.67 (2H, m), 7.70-7.72 (3H, m), 7.83-7.85 (5H, m), 7.94 (1H, d), 7.97-7.99 (2H, m), 8.11-8.13 (4H, m), 8.20 (1H, d), 8.51-8.54 (3H, m), 8.67-8.69 (2H, m) |
| 227 | 7.31-7.34 (2H, m), 7.60-7.65 (4H, m), 7.68-7.80 (13H, m), 7.84-7.90 (2H, m), 7.96-8.03 (4H, m), 8.06-8.08 (5H, m), 8.15 (2H, t), 8.33 (1H, d), 9.05 (1H, d), 9.18 (1H, d) |
| 238 | 7.59-7.66 (7H, m), 7.70-7.83 (4H, m), 7.87 (1H, t), 7.93-7.98 (7H, m), 8.08-8.10 (1H, m), 8.16 (1H, d), 8.48 (1H, m), 8.84 (5H, d), 9.09-9.12 (2H, m), 9.23 (1H, d) |
| 245 | 7.50 (6H, m), 7.53 (1H, t), 7.61-7.62 (m, 2H), 7.70 (1H, t), 7.73 (1H, t), 7.85 (1H, t), 7.94-7.99 (3H, m), 8.20 (1H, d), 8.33-8.38 (7H, m), 8.54 (1H, d) |

TABLE 1-continued

| Compound | ¹H NMR (CDCl₃, 200 Mz) |
|---|---|
| 325 | 7.44-7.54 (6H, m), 7.67-7.73 (3H, m), 7.77 (1H, t), 7.83 (1H, d), 7.90 (2H, d), 7.97 (1H, d), 8.01 (1H, d), 8.05 (1H, s)8.27 (2H, d), 8.36 (1H, d), 8.46 (2H, d), 8.72 (2H, d), 9.02 (1H, d), 9.14 (1H, d) |
| 365 | 7.43 (1H, t), 7.54 (2H, t), 7.60 (1H, t), 7.71-7.79 (4H, m), 7.84-7.96 (8H, m), 8.05 (4H, t), 8.25 (2H, t), 8.43 (1H, d), 8.97 (2H, d), 9.09 (1H, d), 9.19 (1H, d) |
| 390 | 7.21-7.24 (3H, m), 7.37-7.35 (6H, m), 7.50-7.54 (9H, m), 7.74-7.90 (6H, m), 8.06 (1H, m), 8.67 (2H, d), 9.05 (1H, d), 9.16 (1H, d) |
| 457 | 7.39 (1H, t), 7.52 (1H, t), 7.71-7.77 (3H, m), 7.79-7.87 (7H, m), 7.92 (2H, t), 8.04-8.06 (2H, m), 8.10 (1H, d), 8.21 (2H, d), 8.41 (1H, d), 9.06 (1H, d), 9.19 (1H, d) |
| 492 | 7.54-7.61 (6H, m), 7.73-7.85 (4H, m), 7.89-7.95 (3H, m), 8.04-8.07 (3H, m), 8.33-8.35 (4H, m), 8.42 (1H, d), 8.96 (2H, d), 9.10 (1H, d), 9.22 (1H, d) |
| 504 | 7.50-7.51 (6H, m), 7.59-7.61 (4H, m), 7.70 (1H, t), 7.75-7.77 (4H, m), 7.85 (1H, t), 7.94-7.97 (5H, m), 8.00 (1H, d), 8.06-8.07 (3H, m), 8.20 (1H, d), 8.37 (1H, d), 8.54 (2H, m), 8.85 (1H, s) |
| 509 | 7.50 (6H, m), 7.59-7.61 (4H, m), 7.70 (1H, t), 7.85 (1H, t), 7.94 (1H, d), 8.00 (1H, d), 8.06 (2H, d), 8.21 (2H, d), 8.36-8.37 (5H, m), 8.85 (1H, s), 8.97 (2H, d) |
| 530 | 7.39 (1H, t), 7.48 (1H, t), 7.53-7.60 (6H, m), 7.67-7.75 (3H, m), 7.79-7.86 (4H, m), 7.91-8.02 (3H, m), 8.14 (2H, d), 8.33 (1H, s), 8.44 (1H, d), 8.76 (4H, d), 8.83 (1H, d), 8.91 (1H, s), 9.15 (1H, d), 9.31 (1H, d) |
| 566 | 7.49-7.55 (6H, m), 7.71 (1H, t), 7.78-7.97 (7H, m), 8.04 (1H, d), 8.06-8.10 (3H, m), 8.15 (1H, d), 8.21 (1H, s), 8.28 (1H, s), 8.43 (1H, d), 9.13 (1H, d), 9.29 (1H, d) |
| 655 | 6.94 (1H, d), 7.11 (4H, t), 7.21 (2H, t), 7.34 (4H, d), 7.50-7.57 (6H, m), 7.70 (1H, t), 7.73-7.78 (3H, m), 7.81-7.90 (4H, m), 7.97 (1H, s), 8.40 (1H, d), 8.64-8.67 (2H, m), 9.02 (1H, d), 9.15 (1H, d) |
| 758 | 7.42-7.45 (4H, m), 7.51-7.55 (8H, m), 7.70-7.89 (8H, m), 7.96-8.00 (2H, m), 8.07-8.09 (2H, m), 8.13 (1H, s), 8.20-8.23 (4H, m), 8.41 (2H, m), 8.98 (1H, s), 9.05-9.11 (2H, m), 9.21 (1H, d) |
| 760 | 7.26-7.31 (3H, m), 7.36 (1H, t), 7.43-7.46 (4H, m), 7.49-7.59 (9H, m), 7.69 (1H, t), 7.74-7.80 (8H, m), 7.82-7.94 (6H, m), 8.05 (1H, d), 8.38 (1H, d), 9.07 (1H, d), 9.21 (1H, d) |
| 762 | 7.39-7.43 (4H, m), 7.48-7.52 (2H, m), 7.59 (1H, t), 7.65-7.70 (8H, m), 7.77-7.89 (6H, mm), 7.93-7.95 (2H, m), 8.04 (1H, s), 8.20 (1H, d), 8.39 (1H, d), 8.56 (1H, d), 8.67-8.74 (3H, m), 8.75 (1H, s), 8.80 (1H, d), 9.12 (1H, d), 9.27 (1H, d) |
| 784 | 7.43-7.46 (8H, m), 7.52-7.55 (4H, m), 7.66-7.83 (14H, m), 7.96-8.05 (2H, m), 8.28 (1H, d), 8.38 (2H, d), 9.04 (1H, d), 9.15 (1H, d) |
| 788 | 7.49-7.52 (12H, m), 7.59 (2H, m), 7.70 (1H, t), 7.85 (1H, t), 7.94-7.96 (3H, m), 8.20-8.21 (2H, m), 8.34-8.36 (3H, m), 8.69 (2H, d), 8.96-8.97 (2H, m) |
| 802 | 7.60-7.88 (11H, m), 7.93-7.98 (4H, m), 8.08-8.14 (2H, m), 8.18 (1H, d), 8.48 (1H, d), 8.77 (1H, d), 8.83 (1H, d), 9.11 (1H, d), 9.24 (1H, d) |
| 809 | 7.37-7.41 (4H, m), 7.44-7.48 (2H, m), 7.62-7.77 (10H, m), 7.82-7.87 (1H, m), 7.95-7.98 (3H, m), 8.98 (1H, d), 9.08 (1H, d) |
| 812 | 7.16-7.20 (4H, m), 7.35 (2H, t), 7.50-7.61 (8H, m), 7.70 (1H, t), 7.84-7.85 (3H, m), 7.94-7.99 (5H, m), 8.17-8.20 (5H, m), 8.54-8.55 (3H, m), 8.69 (2H, d) |
| 815 | 7.59-7.66 (8H, m), 7.81-7.83 (2H, m), 7.99-8.05 (4H, m), 8.11 (1H, d), 8.84 (5H, d), 9.03 (2H, d), 9.12 (1H, d), 9.23 (1H, d) |
| 853 | δ = 8.99 (1H, s), 8.81 (1H, s), 8.54 (1H, m), 8.28 (4H, d), 8.16 (1H, m), 8.06 (1H, d), 7.98~7.88 (3H, m), 7.78 (1H, t), 7.67~7.41 (10H, m) |
| 855 | δ = 8.99 (1H, d), 8.81 (1H, s), 8.59 (1H, s), 8.54 (1H, m), 8.16 (1H, m), 8.06 (1H, d), 7.98~7.78 (8H, m), 7.67~7.41 (10H, m) |
| 857 | δ = 8.99 (1H, d), 8.81 (1H, s), 8.56~8.54 (2H, m), 8.16 (1H, m), 8.06~7.92 (4H, m), 7.67~7.45 (10H, m), 7.22 (2H, m) |
| 877 | δ = 9.09 (1H, s), 8.54 (1H, m), 8.39 (1H, d), 8.16 (1H, m), 8.06 (1H, d), 7.98~7.92 (2H, dd), 7.78~7.60 (9H, m), 7.45~7.38 (7H, m) |
| 885 | δ = 9.38 (1H, s), 9.19 (1H, s), 8.54 (2H, m), 8.30~8.28 (4H, m), 8.16~8.06 (3H, m), 7.98~7.78 (5H, m), 7.67~7.41 (12H, m) |
| 895 | δ = 9.37 (2H, S), 8.54 (1H, d), 8.36 (4H, m), 8.14 (1H, t), 7.99~7.96 (3H, m), 7.83 (1H, t), 7.69~7.50 (10H, m) |
| 898 | δ = 9.26 (2H, s), 8.54 (1H, d), 8.14 (1H, d), 7.99~7.96 (3H, m), 7.83~7.69 (6H, m), 9.62~7.51 (9H, m) |
| 905 | δ = 9.37 (2H, s), 8.54 (1H, d), 8.41 (1H, s), 8.14 (1H, t), 7.99~7.94 (7H, m), 7.83 (1H, t), 7.69~7.51 (9H, m) |
| 920 | δ = 8.80 (2H, d), 8.79 (2H, s), 8.56~8.54 (2H, t), 8.14 (1H, d), 8.00~7.96 (3H, m), 7.83~7.81 (2H, m), 7.69~7.53 (8H, m), 7.38 (2H, d), 7.28 (1H, t) |
| 925 | δ = 8.97 (1H, s), 8.79 (2H, s), 8.54 (1H, d), 8.30 (2H, d), 8.14 (1H, d), 7.99~7.96 (5H, t), 7.83~7.75 (7H, m), 7.67~7.41 (10H, m), 7.25 (1H, d) |
| 947 | 7.25 (2H, d), 7.41-7.83 (16H, m), 7.94-7.99 (8H, m), 8.14 (1H, s), 8.41 (1H, s), 8.54 (1H, d), 8.96 (1H, s) |
| 949 | 7.53-7.69 (10H, m), 7.73-7.83 (2H, m), 7.96-8.16 (1H, m), 8.49-8.54 (3H, m), 8.96 (1H, s), 9.09 (2H, s) |
| 972 | 7.40 (2H, t), 7.53-7.70 (5H, m), 7.85-7.99 (6H, m), 8.20-8.24 (3H, m), 8.42-8.59 (5H, m), 8.94-8.99 (2H, m) |
| 974 | 7.53-7.69 (6H, m), 7.80-7.83 (2H, m), 7.96-7.99 (4H, m), 8.14 (1H, d), 8.25 (4H, d), 8.54 (1H, d), 8.81 (4H, d), 8.96 (1H, s) |
| 977 | 7.53-7.70 (1H, m), 7.85 (1H, t), 7.94-8.08 (7H, m), 8.20-8.23 (3H, m), 8.42-8.54 (5H, m), 8.94-8.99 (4H, m) |

TABLE 1-continued

| Compound | $^1$H NMR (CDCl$_3$, 200 Mz) |
|---|---|
| 981 | δ = 9.54 (1H, s), 8.54 (1H, d), 8.37 (1H, s), 8.14 (d, 1H), 7.99 (3H, m), 7.94-7.96 (5H, m), 7.83 (2H, m), 7.49-7.69 (12H, m) |
| 982 | 9.55 (1H, s), 8.54 (1H, d), 8.14 (1H, d), 7.69-7.99 (4H, m), 7.83 (2H, m), 7.75-7.77 (4H, m), 7.68-7.69 (2H, m), 7.61-7.62)3H, m), 7.53 (1H, t), 7.50-7.51 (6H, m) |
| 993 | 9.54 (1H, s), 8.59 (2H, d), 8.54 (1H, d), 8.24 (2H, d), 8.14 (1H, d), 7.66-7.99 (4H, m), 7.83 (1H, d), 7.83-7.85 (4H, m), 7.68-7.69 (2H, m), 7.61-7.62 (3H, m), 7.53 (1H, t), 7.40 (2H, t) |
| 1009 | 9.40 (1H, s), 9.13 (1H, s), 8.54-8.59 (2H, m), 8.36 (1H, d), 8.20 (2H, d), 8.14 (2H, m), 8.06-8.09 (4H, m), 7.96-7.99 (5H, m), 7.83 (1H, t), 7.76 (1H, d), 7.69 (1H, t), 7.60-7.63 (6H, m), 7.53-7.55 (3H, m), 7.47 (2H, t), 7.38 (2H, d) |
| 1017 | 9.40 (1H, s), 8.81 (4H, m), 8.54-8.59 (2H, m), 8.25-8.27 (4H, m), 8.14 (2H, m), 7.96-7.99 (3H, m), 7.83 (1H, t), 7.69 (1H, t), 7.61-7.62 (2H, m), 7.53 (1H, t) |
| 1025 | 8.78 (1H, d), 8.69 (2H, d), 8.54-8.56 (2H, m), 8.14 (1H, d), 7.96-7.99 (5H, m), 7.81-7.83 (2H, m), 7.69 (1H, t), 7.61-7.63 (3H, m), 7.52-7.53 (2H, m), 7.48 (2H, t), 7.37-7.38 (3H, m), 7.28 (1H, t), 6.88 (1H, d) |

TABLE 2

| Compound | FD-MS | Compound | FD-MS |
|---|---|---|---|
| 1 | m/z = 581.21<br>C45H27N = 581.72 | 2 | m/z = 581.21<br>C45H27N = 581.72 |
| 3 | m/z = 531.20<br>C41H25N = 531.66 | 4 | m/z = 531.20<br>C41H25N = 531.66 |
| 5 | m/z = 581.21<br>C45H27N = 581.72 | 6 | m/z = 581.21<br>C45H27N = 581.72 |
| 7 | m/z = 783.29<br>C61H37N = 783.97 | 8 | m/z = 783.29<br>C61H37N = 783.97 |
| 9 | m/z = 783.29<br>C61H37N = 783.97 | 10 | m/z = 783.29<br>C61H37N = 783.97 |
| 11 | m/z = 657.25<br>C51H31N = 657.82 | 12 | m/z = 657.25<br>C51H31N = 657.82 |
| 13 | m/z = 733.28<br>C57H35N = 733.91 | 14 | m/z = 733.28<br>C57H35N = 733.91 |
| 15 | m/z = 759.29<br>C59H37N = 759.95 | 16 | m/z = 759.29<br>C59H37N = 759.95 |
| 17 | m/z = 835.32<br>C65H41N = 836.05 | 18 | m/z = 835.32<br>C65H41N = 836.05 |
| 19 | m/z = 558.21<br>C42H26N2 = 558.68 | 20 | m/z = 558.21<br>C42H26N2 = 558.68 |
| 21 | m/z = 634.24<br>C48H30N2 = 634.78 | 22 | m/z = 634.24<br>C48H30N2 = 634.78 |
| 23 | m/z = 585.22<br>C43H27N3 = 585.71 | 24 | m/z = 585.22<br>C43H27N3 = 585.71 |
| 25 | m/z = 662.25<br>C48H30N4 = 662.80 | 26 | m/z = 662.25<br>C48H30N4 = 662.80 |
| 27 | m/z = 608.23<br>C46H28N2 = 608.74 | 28 | m/z = 608.23<br>C46H28N2 = 608.74 |
| 29 | m/z = 520.19<br>C39H24N2 = 520.63 | 30 | m/z = 520.19<br>C39H24N2 = 520.63 |
| 31 | m/z = 672.26<br>C51H32N2 = 672.83 | 32 | m/z = 672.26<br>C51H32N2 = 672.83 |
| 33 | m/z = 748.29<br>C57H36N2 = 748.93 | 34 | m/z = 748.29<br>C57H36N2 = 748.93 |
| 35 | m/z = 596.23<br>C45H28N2 = 596.73 | 36 | m/z = 596.23<br>C45H28N2 = 596.73 |
| 37 | m/z = 669.25<br>C52H31N = 669.83 | 38 | m/z = 669.25<br>C52H31N = 669.83 |
| 39 | m/z = 547.23<br>C42H29N = 547.70 | 40 | m/z = 547.23<br>C42H29N = 547.70 |
| 41 | m/z = 671.26<br>C52H33N = 671.84 | 42 | m/z = 671.26<br>C52H33N = 671.84 |
| 43 | m/z = 687.24<br>C51H33NSi = 687.92 | 44 | m/z = 687.24<br>C51H33NSi = 687.92 |
| 45 | m/z = 685.22<br>C51H31NSi = 685.90 | 46 | m/z = 685.22<br>C51H31NSi = 685.90 |
| 47 | m/z = 696.26<br>C53H32N2 = 696.85 | 48 | m/z = 696.26<br>C53H32N2 = 696.85 |
| 49 | m/z = 631.23<br>C49H29N = 631.78 | 50 | m/z = 631.23<br>C49H29N = 631.78 |
| 51 | m/z = 584.23<br>C44H28N2 = 584.72 | 52 | m/z = 684.26<br>C52H32N2 = 684.84 |
| 53 | m/z = 784.29<br>C60H36N2 = 784.96 | 54 | m/z = 738.28<br>C54H34N4 = 738.89 |

TABLE 2-continued

| Compound | FD-MS | Compound | FD-MS |
|---|---|---|---|
| 55 | m/z = 686.25<br>C50H30N4 = 686.82 | 56 | m/z = 838.31<br>C62H38N4 = 839.01 |
| 57 | m/z = 686.25<br>C50H30N4 = 686.82 | 58 | m/z = 838.31<br>C62H38N4 = 839.01 |
| 59 | m/z = 584.23<br>C44H28N2 = 584.72 | 60 | m/z = 684.26<br>C52H32N2 = 684.84 |
| 61 | m/z = 784.29<br>C60H36N2 = 784.96 | 62 | m/z = 738.28<br>C54H34N4 = 738.89 |
| 63 | m/z = 686.25<br>C50H30N4 = 686.82 | 64 | m/z = 838.31<br>C62H38N4 = 839.01 |
| 65 | m/z = 686.25<br>C50H30N4 = 686.82 | 66 | m/z = 838.31<br>C62H38N4 = 839.01 |
| 67 | m/z = 585.22<br>C43H27N3 = 585.71 | 68 | m/z = 685.25<br>C51H31N3 = 685.83 |
| 69 | m/z = 785.28<br>C59H35N3 = 785.95 | 70 | m/z = 739.27<br>C53H33N5 = 739.88 |
| 71 | m/z = 687.24<br>C49H29N5 = 687.81 | 72 | m/z = 839.30<br>C61H37N5 = 840.00 |
| 73 | m/z = 687.24<br>C49H29N5 = 687.81 | 74 | m/z = 839.30<br>C61H37N5 = 840.00 |
| 75 | m/z = 586.22<br>C42H26N4 = 586.70 | 76 | m/z = 686.25<br>C50H30N4 = 686.82 |
| 77 | m/z = 786.28<br>C58H34N4 = 786.94 | 78 | m/z = 740.27<br>C52H32N6 = 740.87 |
| 79 | m/z = 688.24<br>C48H28N6 = 688.79 | 80 | m/z = 840.30<br>C60H36N6 = 840.99 |
| 81 | m/z = 688.24<br>C48H28N6 = 688.79 | 82 | m/z = 840.30<br>C60H36N6 = 840.99 |
| 83 | m/z = 660.26<br>C50H32N2 = 660.82 | 84 | m/z = 760.29<br>C58H36N2 = 760.94 |
| 85 | m/z = 784.29<br>C60H36N2 = 784.96 | 86 | m/z = 738.28<br>C54H34N4 = 738.89 |
| 87 | m/z = 686.25<br>C50H30N4 = 686.82 | 88 | m/z = 838.31<br>C62H38N4 = 839.01 |
| 89 | m/z = 686.25<br>C50H30N4 = 686.82 | 90 | m/z = 838.31<br>C62H38N4 = 839.01 |
| 91 | m/z = 585.22<br>C43H27N3 = 585.71 | 92 | m/z = 685.25<br>C51H31N3 = 685.83 |
| 93 | m/z = 785.28<br>C59H35N3 = 785.95 | 94 | m/z = 739.27<br>C53H33N5 = 739.88 |
| 95 | m/z = 687.24<br>C49H29N5 = 687.81 | 96 | m/z = 839.30<br>C61H37N5 = 840.00 |
| 97 | m/z = 687.24<br>C49H29N5 = 687.81 | 98 | m/z = 839.30<br>C61H37N5 = 840.00 |
| 99 | m/z = 586.22<br>C42H26N4 = 586.70 | 100 | m/z = 555.18<br>C39H26NOP = 555.62 |
| 101 | m/z = 555.18<br>C39H26NOP = 555.62 | 102 | m/z = 623.24<br>C46H29N3 = 623.76 |
| 103 | m/z = 623.24<br>C46H29N3 = 623.76 | 104 | m/z = 623.24<br>C46H29N3 = 623.76 |
| 105 | m/z = 623.24<br>C46H29N3 = 623.76 | 106 | m/z = 623.24<br>C46H29N3 = 623.76 |
| 107 | m/z = 623.24<br>C46H29N3 = 623.76 | 108 | m/z = 674.25<br>C49H30N4 = 674.81 |
| 109 | m/z = 381.15<br>C29H19N = 381.48 | 110 | m/z = 457.18<br>C35H23N457.58 |
| 111 | m/z = 457.18<br>C35H23N = 457.58 | 112 | m/z = 557.21<br>C43H27N = 557.70 |
| 113 | m/z = 431.17<br>C33H21N = 431.54 | 114 | m/z = 507.20<br>C39H25N = 507.64 |
| 115 | m/z = 507.20<br>C39H25N = 507.64 | 116 | m/z = 431.17<br>C33H21N = 431.54 |
| 117 | m/z = 507.20<br>C39H25N = 507.64 | 118 | m/z = 481.18<br>C37H23N = 481.60 |
| 119 | m/z = 557.21<br>C43H27N = 557.70 | 120 | m/z = 557.21<br>C43H27N = 557.70 |
| 121 | m/z = 382.15<br>C28H18N2 = 382.47 | 122 | m/z = 459.17<br>C33H21N3 = 459.55 |
| 123 | m/z = 459.17<br>C33H21N3 = 459.55 | 124 | m/z = 432.16<br>C32H20N2 = 432.53 |
| 125 | m/z = 508.19<br>C38H24N2 = 508.62 | 126 | m/z = 508.19<br>C38H24N2 = 508.62 |
| 127 | m/z = 432.16<br>C32H20N2 = 432.53 | 128 | m/z = 508.19<br>C38H24N2 = 508.62 |
| 129 | m/z = 481.18<br>C37H23N = 481.60 | 130 | m/z = 558.21<br>C42H26N2 = 558.68 |
| 131 | m/z = 558.21<br>C42H26N2 = 558.68 | 132 | m/z = 649.25<br>C48H31N3 = 649.80 |

TABLE 2-continued

| Compound | FD-MS | Compound | FD-MS |
|---|---|---|---|
| 133 | m/z = 649.25<br>C48H31N3 = 649.80 | 134 | m/z = 700.26<br>C51H32N4 = 700.84 |
| 135 | m/z = 624.23<br>C45H28N4 = 624.75 | 136 | m/z = 649.25<br>C48H31N3 = 649.80 |
| 137 | m/z = 649.25<br>C48H31N3 = 649.80 | 138 | m/z = 700.26<br>C51H32N4 = 700.84 |
| 139 | m/z = 700.26<br>C51H32N4 = 700.84 | 140 | m/z = 688.26<br>C50H32N4 = 688.83 |
| 141 | m/z = 687.27<br>C51H33N3 = 687.85 | 142 | m/z = 687.27<br>C51H33N3 = 687.85 |
| 143 | m/z = 688.26<br>C50H32N4 = 688.83 | 144 | m/z = 687.27<br>C51H33N3 = 687.85 |
| 145 | m/z = 687.27<br>C51H33N3 = 687.85 | 146 | m/z = 581.19<br>C41H28NOP = 581.65 |
| 147 | m/z = 657.22<br>C47H32NOP = 657.75 | 148 | m/z = 546.21<br>C41H26N2 = 546.67 |
| 149 | m/z = 546.21<br>C41H26N2 = 546.67 | 150 | m/z = 622.24<br>C47H30N2 = 622.77 |
| 151 | m/z = 622.24<br>C47H30N2 = 622.77 | 152 | m/z = 787.30<br>C59H37N3 = 787.97 |
| 153 | m/z = 787.30<br>C59H37N3 = 787.97 | 154 | m/z = 863.33<br>C65H41N3 = 864.06 |
| 155 | m/z = 863.33<br>C65H41N3 = 864.06 | 156 | m/z = 622.24<br>C47H30N2 = 622.77 |
| 157 | m/z = 622.24<br>C47H30N2 = 622.77 | 158 | m/z = 698.27<br>C53H34N2 = 698.87 |
| 159 | m/z = 698.27<br>C53H34N2 = 698.87 | 160 | m/z = 863.33<br>C65H41N3 = 864.06 |
| 161 | m/z = 787.30<br>C59H37N3 = 787.97 | 162 | m/z = 715.27<br>C53H37NSi = 715.97 |
| 163 | m/z = 715.27<br>C53H37NSi = 715.97 | 164 | m/z = 305.12<br>C23H15N = 305.38 |
| 165 | m/z = 381.15<br>C29H19N = 381.48 | 166 | m/z = 381.15<br>C29H19N = 381.48 |
| 167 | m/z = 481.18<br>C37H23N = 481.60 | 168 | m/z = 355.14<br>C27H17N = 355.44 |
| 169 | m/z = 431.17<br>C33H21N = 431.54 | 170 | m/z = 431.17<br>C33H21N = 431.54 |
| 171 | m/z = 355.14<br>C27H17N = 355.44 | 172 | m/z = 431.17<br>C33H21N = 431.54 |
| 173 | m/z = 405.15<br>C31H19N = 405.50 | 174 | m/z = 481.18<br>C37H23N = 481.60 |
| 175 | m/z = 481.18<br>C37H23N = 481.60 | 176 | m/z = 306.12<br>C22H14N2 = 306.37 |
| 177 | m/z = 383.14<br>C27H17N3 = 383.45 | 178 | m/z = 383.14<br>C27H17N3 = 383.45 |
| 179 | m/z = 356.13<br>C26H16N2 = 356.43 | 180 | m/z = 432.16<br>C32H20N2 = 432.53 |
| 181 | m/z = 432.16<br>C32H20N2 = 432.53 | 182 | m/z = 356.13<br>C26H16N2 = 356.43 |
| 183 | m/z = 432.16<br>C32H20N2 = 432.53 | 184 | m/z = 405.15<br>C31H19N = 405.50 |
| 185 | m/z = 482.18<br>C36H22N2 = 482.59 | 186 | m/z = 482.18<br>C36H22N2 = 482.59 |
| 187 | m/z = 573.22<br>C42H27N3 = 573.70 | 188 | m/z = 573.22<br>C42H27N3 = 573.70 |
| 189 | m/z = 624.23<br>C45H28N4 = 624.75 | 190 | m/z = 548.20<br>C39H24N4 = 548.65 |
| 191 | m/z = 573.22<br>C42H27N3 = 573.70 | 192 | m/z = 573.22<br>C42H27N3 = 573.70 |
| 193 | m/z = 624.23<br>C45H28N4 = 624.75 | 194 | m/z = 624.23<br>C45H28N4 = 624.75 |
| 195 | m/z = 612.23<br>C44H28N4 = 612.74 | 196 | m/z = 611.24<br>C45H29N3 = 611.75 |
| 197 | m/z = 611.24<br>C45H29N3 = 611.75 | 198 | m/z = 612.23<br>C44H28N4 = 612.74 |
| 199 | m/z = 611.24<br>C45H29N3 = 611.75 | 200 | m/z = 611.24<br>C45H29N3 = 611.75 |
| 201 | m/z = 505.16<br>C35H24NOP = 505.56 | 202 | m/z = 581.19<br>C41H28NOP = 581.65 |
| 203 | m/z = 470.18<br>C35H22N2 = 470.57 | 204 | m/z = 470.18<br>C35H22N2 = 470.57 |
| 205 | m/z = 546.21<br>C41H26N2 = 546.67 | 206 | m/z = 546.21<br>C41H26N2 = 546.67 |
| 207 | m/z = 711.27<br>C53H33N3 = 711.87 | 208 | m/z = 711.27<br>C53H33N3 = 711.87 |
| 209 | m/z = 787.30<br>C59H37N3 = 787.97 | 210 | m/z = 787.30<br>C59H37N3 = 787.97 |

TABLE 2-continued

| Compound | FD-MS | Compound | FD-MS |
|---|---|---|---|
| 211 | m/z = 546.21<br>C41H26N2 = 546.67 | 212 | m/z = 546.21<br>C41H26N2 = 546.67 |
| 213 | m/z = 622.24<br>C47H30N2 = 622.77 | 214 | m/z = 622.24<br>C47H30N2 = 622.77 |
| 215 | m/z = 787.30<br>C59H37N3 = 787.97 | 216 | m/z = 711.27<br>C53H33N3 = 711.87 |
| 217 | m/z = 639.24<br>C47H33NSi = 639.87 | 218 | m/z = 639.24<br>C47H33NSi = 639.87 |
| 219 | m/z = 535.20<br>C39H25N3 = 535.65 | 220 | m/z = 631.21<br>C45H30NOP = 631.71 |
| 221 | m/z = 555.18<br>C39H26NOP = 555.62 | 222 | m/z = 631.21<br>C45H30NOP = 631.71 |
| 223 | m/z = 555.18<br>C39H26NOP = 555.62 | 224 | m/z = 631.21<br>C45H30NOP = 631.71 |
| 225 | m/z = 658.24<br>C50H30N2 = 658.80 | 226 | m/z = 658.24<br>C50H30N2 = 658.80 |
| 227 | m/z = 733.28<br>C57H35N = 733.91 | 228 | m/z = 733.28<br>C57H35N = 733.91 |
| 229 | m/z = 607.23<br>C47H29N = 607.76 | 230 | m/z = 636.23<br>C46H28N4 = 636.76 |
| 231 | m/z = 736.26<br>C54H32N4 = 736.88 | 232 | m/z = 614.22<br>C42H26N6 = 614.71 |
| 233 | m/z = 614.22<br>C42H26N6 = 614.71 | 234 | m/z = 614.22<br>C42H26N6 = 614.71 |
| 235 | m/z = 712.26<br>C52H32N4 = 712.86 | 236 | m/z = 712.26<br>C52H32N4 = 712.86 |
| 237 | m/z = 812.29<br>C60H36N4 = 812.98 | 238 | m/z = 612.23<br>C44H28N4 = 612.74 |
| 239 | m/z = 614.22<br>C42H26N6 = 614.71 | 240 | m/z = 614.22<br>C42H26N6 = 614.71 |
| 241 | m/z = 614.22<br>C42H26N6 = 614.71 | 242 | m/z = 712.26<br>C52H32N4 = 712.86 |
| 243 | m/z = 712.26<br>C52H32N4 = 712.86 | 244 | m/z = 812.29<br>C60H36N4 = 812.98 |
| 245 | m/z = 812.29<br>C60H36N4 = 812.98 | 246 | m/z = 538.19<br>C36H22N6 = 538.61 |
| 247 | m/z = 538.19<br>C36H22N6 = 538.61 | 248 | m/z = 538.19<br>C36H22N6 = 538.61 |
| 249 | m/z = 636.23<br>C46H28N4 = 636.76 | 250 | m/z = 636.23<br>C46H28N4 = 636.76 |
| 251 | m/z = 736.26<br>C54H32N4 = 736.88 | 252 | m/z = 614.22<br>C42H26N6 = 614.71 |
| 253 | m/z = 614.22<br>C42H26N6 = 614.71 | 254 | m/z = 614.22<br>C42H26N6 = 614.71 |
| 255 | m/z = 712.26<br>C52H32N4 = 712.86 | 256 | m/z = 712.26<br>C52H32N4 = 712.86 |
| 257 | m/z = 812.29<br>C60H36N4 = 812.98 | 258 | m/z = 812.29<br>C60H36N4 = 812.98 |
| 259 | m/z = 612.23<br>C44H28N4 = 612.74 | 260 | m/z = 614.22<br>C42H26N6 = 614.71 |
| 261 | m/z = 614.22<br>C42H26N6 = 614.71 | 262 | m/z = 614.22<br>C42H26N6 = 614.71 |
| 263 | m/z = 712.26<br>C52H32N4 = 712.86 | 264 | m/z = 712.26<br>C52H32N4 = 712.86 |
| 265 | m/z = 635.24<br>C47H29N3 = 635.77 | 266 | m/z = 635.24<br>C47H29N3 = 635.77 |
| 267 | m/z = 735.27<br>C55H33N3 = 735.89 | 268 | m/z = 735.27<br>C55H33N3 = 735.89 |
| 269 | m/z = 611.24<br>C45H29N3 = 611.75 | 270 | m/z = 611.24<br>C45H29N3 = 611.75 |
| 271 | m/z = 687.27<br>C51H33N3 = 687.85 | 272 | m/z = 687.27<br>C51H33N3 = 687.85 |
| 273 | m/z = 611.24<br>C45H29N3 = 611.75 | 274 | m/z = 611.24<br>C45H29N3 = 611.75 |
| 275 | m/z = 711.27<br>C53H33N3 = 711.87 | 276 | m/z = 811.30<br>C61H37N3 = 811.99 |
| 277 | m/z = 763.30<br>C57H37N3 = 763.94 | 278 | m/z = 687.27<br>C51H33N3 = 687.85 |
| 279 | m/z = 687.27<br>C51H33N3 = 687.85 | 280 | m/z = 763.30<br>C57H37N3 = 763.94 |
| 281 | m/z = 687.27<br>C51H33N3 = 687.85 | 282 | m/z = 687.27<br>C51H33N3 = 687.85 |
| 283 | m/z = 763.30<br>C57H37N3 = 763.94 | 284 | m/z = 687.27<br>C51H33N3 = 687.85 |
| 285 | m/z = 687.27<br>C51H33N3 = 687.85 | 286 | m/z = 611.24<br>C45H29N3 = 611.75 |
| 287 | m/z = 711.27<br>C53H33N3 = 711.87 | 288 | m/z = 711.27<br>C53H33N3 = 711.87 |

TABLE 2-continued

| Compound | FD-MS | Compound | FD-MS |
|---|---|---|---|
| 289 | m/z = 811.30<br>C61H37N3 = 811.99 | 290 | m/z = 763.30<br>C57H37N3 = 763.94 |
| 291 | m/z = 687.27<br>C51H33N3 = 687.85 | 292 | m/z = 687.27<br>C51H33N3 = 687.85 |
| 293 | m/z = 635.24<br>C47H29N3 = 635.77 | 294 | m/z = 635.24<br>C47H29N3 = 635.77 |
| 295 | m/z = 735.27<br>C55H33N3 = 735.89 | 296 | m/z = 687.27<br>C51H33N3 = 687.85 |
| 297 | m/z = 611.24<br>C45H29N3 = 611.75 | 298 | m/z = 611.24<br>C45H29N3 = 611.75 |
| 299 | m/z = 687.27<br>C51H33N3 = 687.85 | 300 | m/z = 611.24<br>C45H29N3 = 611.75 |
| 301 | m/z = 611.24<br>C45H29N3 = 611.75 | 302 | m/z = 711.27<br>C53H33N3 = 711.87 |
| 303 | m/z = 711.27<br>C53H33N3 = 711.87 | 304 | m/z = 811.30<br>C61H37N3 = 811.99 |
| 305 | m/z = 763.30<br>C57H37N3 = 763.94 | 306 | m/z = 687.27<br>C51H33N3 = 687.85 |
| 307 | m/z = 687.27<br>C51H33N3 = 687.85 | 308 | m/z = 763.30<br>C57H37N3 = 763.94 |
| 309 | m/z = 687.27<br>C51H33N3 = 687.85 | 310 | m/z = 687.27<br>C51H33N3 = 687.85 |
| 311 | m/z = 611.24<br>C45H29N3 = 611.75 | 312 | m/z = 611.24<br>C45H29N3 = 611.75 |
| 313 | m/z = 711.27<br>C53H33N3 = 711.87 | 314 | m/z = 811.30<br>C61H37N3 = 811.99 |
| 315 | m/z = 763.30<br>C57H37N3 = 763.94 | 316 | m/z = 687.27<br>C51H33N3 = 687.85 |
| 317 | m/z = 687.27<br>C51H33N3 = 687.85 | 318 | m/z = 763.30<br>C57H37N3 = 763.94 |
| 319 | m/z = 687.27<br>C51H33N3 = 687.85 | 320 | m/z = 687.27<br>C51H33N3 = 687.85 |
| 321 | m/z = 763.30<br>C57H37N3 = 763.94 | 322 | m/z = 687.27<br>C51H33N3 = 687.85 |
| 323 | m/z = 687.27<br>C51H33N3 = 687.85 | 324 | m/z = 763.30<br>C57H37N3 = 763.94 |
| 325 | m/z = 535.20<br>C39H25N3 = 535.65 | 326 | m/z = 635.24<br>C47H29N3 = 635.77 |
| 327 | m/z = 635.24<br>C47H29N3 = 635.77 | 328 | m/z = 735.27<br>C55H33N3 = 735.89 |
| 329 | m/z = 687.27<br>C51H33N3 = 687.85 | 330 | m/z = 610.24<br>C46H30N2 = 610.76 |
| 331 | m/z = 610.24<br>C46H30N2 = 610.76 | 332 | m/z = 611.24<br>C45H29N3 = 611.75 |
| 333 | m/z = 611.24<br>C45H29N3 = 611.75 | 334 | m/z = 611.24<br>C45H29N3 = 611.75 |
| 335 | m/z = 536.20<br>C38H24N4 = 536.64 | 336 | m/z = 612.23<br>C44H28N4 = 612.74 |
| 337 | m/z = 612.23<br>C44H28N4 = 612.74 | 338 | m/z = 711.27<br>C53H33N3 = 711.87 |
| 339 | m/z = 711.27<br>C53H33N3 = 711.87 | 340 | m/z = 612.23<br>C44H28N4 = 612.74 |
| 341 | m/z = 711.27<br>C53H33N3 = 711.87 | 342 | m/z = 711.27<br>C53H33N3 = 711.87 |
| 343 | m/z = 811.30<br>C61H37N3 = 811.99 | 344 | m/z = 763.30<br>C57H37N3 = 763.94 |
| 345 | m/z = 687.27<br>C51H33N3 = 687.85 | 346 | m/z = 687.27<br>C51H33N3 = 687.85 |
| 347 | m/z = 763.30<br>C57H37N3 = 763.94 | 348 | m/z = 687.27<br>C51H33N3 = 687.85 |
| 349 | m/z = 687.27<br>C51H33N3 = 687.85 | 350 | m/z = 612.23<br>C44H28N4 = 612.74 |
| 351 | m/z = 688.26<br>C50H32N4 = 688.83 | 352 | m/z = 688.26<br>C50H32N4 = 688.83 |
| 353 | m/z = 711.27<br>C53H33N3 = 711.87 | 354 | m/z = 711.27<br>C53H33N3 = 711.87 |
| 355 | m/z = 811.30<br>C61H37N3 = 811.99 | 356 | m/z = 763.30<br>C57H37N3 = 763.94 |
| 357 | m/z = 687.27<br>C51H33N3 = 687.85 | 358 | m/z = 687.27<br>C51H33N3 = 687.85 |
| 359 | m/z = 763.30<br>C57H37N3 = 763.94 | 360 | m/z = 687.27<br>C51H33N3 = 687.85 |
| 361 | m/z = 687.27<br>C51H33N3 = 687.85 | 362 | m/z = 612.23<br>C44H28N4 = 612.74 |
| 363 | m/z = 688.26<br>C50H32N4 = 688.83 | 364 | m/z = 688.26<br>C50H32N4 = 688.83 |
| 365 | m/z = 585.22<br>C43H27N3 = 585.71 | 366 | m/z = 509.19<br>C37H23N3 = 509.61 |

TABLE 2-continued

| Compound | FD-MS | Compound | FD-MS |
|---|---|---|---|
| 367 | m/z = 585.22<br>C43H27N3 = 585.71 | 368 | m/z = 559.20<br>C41H25N3 = 559.67 |
| 369 | m/z = 559.20<br>C41H25N3 = 559.67 | 370 | m/z = 585.22<br>C43H27N3 = 585.71 |
| 371 | m/z = 661.25<br>C49H31N3 = 661.81 | 372 | m/z = 635.24<br>C47H29N3 = 635.77 |
| 373 | m/z = 635.24<br>C47H29N3 = 635.77 | 374 | m/z = 585.22<br>C43H27N3 = 585.71 |
| 375 | m/z = 661.25<br>C49H31N3 = 661.81 | 376 | m/z = 635.24<br>C47H29N3 = 635.77 |
| 377 | m/z = 635.24<br>C47H29N3 = 635.77 | 378 | m/z = 509.19<br>C37H23N3 = 509.61 |
| 379 | m/z = 585.22<br>C43H27N3 = 585.71 | 380 | m/z = 559.20<br>C41H25N3 = 559.67 |
| 381 | m/z = 559.20<br>C41H25N3 = 559.67 | 382 | m/z = 585.22<br>C43H27N3 = 585.71 |
| 383 | m/z = 661.25<br>C49H31N3 = 661.81 | 384 | m/z = 635.24<br>C47H29N3 = 635.77 |
| 385 | m/z = 635.24<br>C47H29N3 = 635.77 | 386 | m/z = 585.22<br>C43H27N3 = 585.71 |
| 387 | m/z = 661.25<br>C49H31N3 = 661.81 | 388 | m/z = 635.24<br>C47H29N3 = 635.77 |
| 389 | m/z = 635.24<br>C47H29N3 = 635.77 | 390 | m/z = 611.24<br>C45H29N3 = 611.75 |
| 391 | m/z = 763.30<br>C57H37N3 = 763.94 | 392 | m/z = 763.30<br>C57H37N3 = 763.94 |
| 393 | m/z = 711.27<br>C53H33N3 = 711.87 | 394 | m/z = 711.27<br>C53H33N3 = 711.87 |
| 395 | m/z = 687.27<br>C51H33N3 = 687.85 | 396 | m/z = 687.27<br>C51H33N3 = 687.85 |
| 397 | m/z = 661.25<br>C49H31N3 = 661.81 | 398 | m/z = 661.25<br>C49H31N3 = 661.81 |
| 399 | m/z = 711.27<br>C53H33N3 = 711.87 | 400 | m/z = 661.25<br>C49H31N3 = 661.81 |
| 401 | m/z = 711.27<br>C53H33N3 = 711.87 | 402 | m/z = 611.24<br>C45H29N3 = 611.75 |
| 403 | m/z = 763.30<br>C57H37N3 = 763.94 | 404 | m/z = 763.30<br>C57H37N3 = 763.94 |
| 405 | m/z = 711.27<br>C53H33N3 = 711.87 | 406 | m/z = 711.27<br>C53H33N3 = 711.87 |
| 407 | m/z = 687.27<br>C51H33N3 = 687.85 | 408 | m/z = 687.27<br>C51H33N3 = 687.85 |
| 409 | m/z = 687.27<br>C51H33N3 = 687.85 | 410 | m/z = 509.19<br>C37H23N3 = 509.61 |
| 411 | m/z = 585.22<br>C43H27N3 = 585.71 | 412 | m/z = 585.22<br>C43H27N3 = 585.71 |
| 413 | m/z = 585.22<br>C43H27N3 = 585.71 | 414 | m/z = 661.25<br>C49H31N3 = 661.81 |
| 415 | m/z = 661.25<br>C49H31N3 = 661.81 | 416 | m/z = 585.22<br>C43H27N3 = 585.71 |
| 417 | m/z = 661.25<br>C49H31N3 = 661.81 | 418 | m/z = 661.25<br>C49H31N3 = 661.81 |
| 419 | m/z = 661.25<br>C49H31N3 = 661.81 | 420 | m/z = 559.20<br>C41H25N3 = 559.67 |
| 421 | m/z = 559.20<br>C41H25N3 = 559.67 | 422 | m/z = 509.19<br>C37H23N3 = 509.61 |
| 423 | m/z = 585.22<br>C43H27N3 = 585.71 | 424 | m/z = 585.22<br>C43H27N3 = 585.71 |
| 425 | m/z = 585.22<br>C43H27N3 = 585.71 | 426 | m/z = 661.25<br>C49H31N3 = 661.81 |
| 427 | m/z = 661.25<br>C49H31N3 = 661.81 | 428 | m/z = 585.22<br>C43H27N3 = 585.71 |
| 429 | m/z = 661.25<br>C49H31N3 = 661.81 | 430 | m/z = 483.17<br>C35H21N3 = 483.57 |
| 431 | m/z = 559.20<br>C41H25N3559.67 | 432 | m/z = 559.20<br>C41H25N3 = 559.67 |
| 433 | m/z = 483.17<br>C35H21N3 = 483.57 | 434 | m/z = 497.19<br>C36H23N3 = 497.60 |
| 435 | m/z = 497.19<br>C36H23N3 = 497.60 | 436 | m/z = 497.19<br>C36H23N3 = 497.60 |
| 437 | m/z = 497.19<br>C36H23N3 = 497.60 | 438 | m/z = 497.19<br>C36H23N3 = 497.60 |
| 439 | m/z = 497.19<br>C36H23N3 = 497.60 | 440 | m/z = 497.19<br>C36H23N3 = 497.60 |
| 441 | m/z = 497.19<br>C36H23N3 = 497.60 | 442 | m/z = 449.19<br>C32H23N3 = 449.56 |
| 443 | m/z = 449.19<br>C32H23N3 = 449.56 | 444 | m/z = 525.22<br>C38H27N3 = 525.65 |

TABLE 2-continued

| Compound | FD-MS | Compound | FD-MS |
| --- | --- | --- | --- |
| 445 | m/z = 525.22<br>C38H27N3 = 525.65 | 446 | m/z = 525.22<br>C38H27N3 = 525.65 |
| 447 | m/z = 449.19<br>C32H23N3 = 449.56 | 448 | m/z = 573.22<br>C42H27N3 = 573.70 |
| 449 | m/z = 449.19<br>C32H23N3 = 449.56 | 450 | m/z = 525.22<br>C38H27N3 = 525.65 |
| 451 | m/z = 525.22<br>C38H27N3 = 525.65 | 452 | m/z = 573.22<br>C42H27N3 = 573.70 |
| 453 | m/z = 525.22<br>C38H27N3 = 525.65 | 454 | m/z = 525.22<br>C38H27N3 = 525.65 |
| 455 | m/z = 449.19<br>C32H23N3 = 449.56 | 456 | m/z = 573.22<br>C42H27N3 = 573.70 |
| 457 | m/z = 514.15<br>C36H22N2S514.65 | 458 | m/z = 514.15<br>C36H22N2S = 514.65 |
| 459 | m/z = 514.15<br>C36H22N2S = 514.65 | 460 | m/z = 514.15<br>C36H22N2S = 514.65 |
| 461 | m/z = 514.15<br>C36H22N2S = 514.65 | 462 | m/z = 514.15<br>C36H22N2S = 514.65 |
| 463 | m/z = 514.15<br>C36H22N2S514.65 | 464 | m/z = 514.15<br>C36H22N2S = 514.65 |
| 465 | m/z = 534.21<br>C40H26N2 = 534.66 | 466 | m/z = 610.24<br>C46H30N2 = 610.76 |
| 467 | m/z = 536.20<br>C38H24N4 = 536.64 | 468 | m/z = 536.20<br>C38H24N4 = 536.64 |
| 469 | m/z = 536.20<br>C38H24N4 = 536.64 | 470 | m/z = 612.23<br>C44H28N4 = 612.74 |
| 471 | m/z = 612.23<br>C44H28N4 = 612.74 | 472 | m/z = 612.23<br>C44H28N4 = 612.74 |
| 473 | m/z = 459.17<br>C33H21N3 = 459.55 | 474 | m/z = 459.17<br>C33H21N3 = 459.55 |
| 475 | m/z = 535.20<br>C39H25N3 = 535.65 | 476 | m/z = 535.20<br>C39H25N3 = 535.65 |
| 477 | m/z = 535.20<br>C39H25N3 = 535.65 | 478 | m/z = 534.21<br>C40H26N2 = 534.66 |
| 479 | m/z = 610.24<br>C46H30N2 = 610.76 | 480 | m/z = 536.20<br>C38H24N4 = 536.64 |
| 481 | m/z = 536.20<br>C38H24N4 = 536.64 | 482 | m/z = 536.20<br>C38H24N4 = 536.64 |
| 483 | m/z = 612.23<br>C44H28N4 = 612.74 | 484 | m/z = 612.23<br>C44H28N4 = 612.74 |
| 485 | m/z = 612.23<br>C44H28N4 = 612.74 | 486 | m/z = 459.17<br>C33H21N3 = 459.55 |
| 487 | m/z = 459.17<br>C33H21N3 = 459.55 | 488 | m/z = 459.17<br>C33H21N3 = 459.55 |
| 489 | m/z = 535.20<br>C39H25N3 = 535.65 | 490 | m/z = 535.20<br>C39H25N3 = 535.65 |
| 491 | m/z = 535.20<br>C39H25N3 = 535.65 | 492 | m/z = 611.24<br>C45H29N3 = 611.75 |
| 493 | m/z = 859.32<br>C67H41N = 860.07 | 494 | m/z = 859.32<br>C67H41N = 860.07 |
| 495 | m/z = 733.28<br>C57H35N = 733.91 | 496 | m/z = 733.28<br>C57H35N = 733.91 |
| 497 | m/z = 683.26<br>C53H33N = 683.85 | 498 | m/z = 607.23<br>C47H29N = 607.76 |
| 499 | m/z = 859.32<br>C67H41N = 860.07 | 500 | m/z = 859.32<br>C67H41N = 860.07 |
| 501 | m/z = 683.26<br>C53H33N = 683.85 | 502 | m/z = 607.23<br>C47H29N = 607.76 |
| 503 | m/z = 707.24<br>C51H34NOP = 707.81 | 504 | m/z = 631.21<br>C45H30NOP = 631.71 |
| 505 | m/z = 707.24<br>C51H34NOP = 707.81 | 506 | m/z = 707.24<br>C51H34NOP = 707.81 |
| 507 | m/z = 837.31<br>C63H39N3 = 838.03 | 508 | m/z = 837.31<br>C63H39N3 = 838.03 |
| 509 | m/z = 662.25<br>C48H30N4 = 662.80 | 510 | m/z = 664.24<br>C46H28N6 = 664.77 |
| 511 | m/z = 664.24<br>C46H28N6 = 664.77 | 512 | m/z = 664.24<br>C46H28N6 = 664.77 |
| 513 | m/z = 762.28<br>C56H34N4 = 762.92 | 514 | m/z = 762.28<br>C56H34N4 = 762.92 |
| 515 | m/z = 862.31<br>C64H38N4 = 863.04 | 516 | m/z = 738.28<br>C54H34N4 = 738.89 |
| 517 | m/z = 740.27<br>C52H32N6 = 740.87 | 518 | m/z = 740.27<br>C52H32N6 = 740.87 |
| 519 | m/z = 740.27<br>C52H32N6 = 740.87 | 520 | m/z = 838.31<br>C62H38N4 = 839.01 |
| 521 | m/z = 838.31<br>C62H38N4 = 839.01 | 522 | m/z = 938.34<br>C70H42N4 = 939.13 |

TABLE 2-continued

| Compound | FD-MS | Compound | FD-MS |
|---|---|---|---|
| 523 | m/z = 738.28<br>C54H34N4738.89 | 524 | m/z = 740.27<br>C52H32N6 = 740.87 |
| 525 | m/z = 740.27<br>C52H32N6 = 740.87 | 526 | m/z = 740.27<br>C52H32N6740.87 |
| 527 | m/z = 838.31<br>C62H38N4 = 839.01 | 528 | m/z = 838.31<br>C62H38N4 = 839.01 |
| 529 | m/z = 938.34<br>C70H42N4939.13 | 530 | m/z = 662.25<br>C48H30N4 = 662.80 |
| 531 | m/z = 664.24<br>C46H28N6 = 664.77 | 532 | m/z = 664.24<br>C46H28N6 = 664.77 |
| 533 | m/z = 664.24<br>C46H28N6 = 664.77 | 534 | m/z = 762.28<br>C56H34N4 = 762.92 |
| 535 | m/z = 762.28<br>C56H34N4 = 762.92 | 536 | m/z = 862.31<br>C64H38N4 = 863.04 |
| 537 | m/z = 738.28<br>C54H34N4 = 738.89 | 538 | m/z = 740.27<br>C52H32N6 = 740.87 |
| 539 | m/z = 740.27<br>C52H32N6 = 740.87 | 540 | m/z = 740.27<br>C52H32N6 = 740.87 |
| 541 | m/z = 838.31<br>C62H38N4 = 839.01 | 542 | m/z = 838.31<br>C62H38N4 = 839.01 |
| 543 | m/z = 938.34<br>C70H42N4 = 939.13 | 544 | m/z = 738.28<br>C54H34N4 = 738.89 |
| 545 | m/z = 740.27<br>C52H32N6 = 740.87 | 546 | m/z = 740.27<br>C52H32N6 = 740.87 |
| 547 | m/z = 740.27<br>C52H32N6740.87 | 548 | m/z = 838.31<br>C62H38N4 = 839.01 |
| 549 | m/z = 838.31<br>C62H38N4 = 839.01 | 550 | m/z = 938.34<br>C70H42N4 = 939.13 |
| 551 | m/z = 761.28<br>C57H35N3 = 761.93 | 552 | m/z = 761.28<br>C57H35N3 = 761.93 |
| 553 | m/z = 861.31<br>C65H39N3 = 862.05 | 554 | m/z = 813.31<br>C61H39N3 = 814.00 |
| 555 | m/z = 737.28<br>C55H35N3 = 737.91 | 556 | m/z = 813.31<br>C61H39N3 = 814.00 |
| 557 | m/z = 737.28<br>C55H35N3 = 737.91 | 558 | m/z = 737.28<br>C55H35N3 = 737.91 |
| 559 | m/z = 837.31<br>C63H39N3 = 838.03 | 560 | m/z = 837.31<br>C63H39N3 = 838.03 |
| 561 | m/z = 937.35<br>C71H43N3938.15 | 562 | m/z = 889.35<br>C67H43N3 = 890.10 |
| 563 | m/z = 813.31<br>C61H39N3 = 814.00 | 564 | 889.35<br>C67H43N3 = 890.10 |
| 565 | m/z = 813.31<br>C61H39N3 = 814.00 | 566 | m/z = 564.17<br>C40H24N2S = 564.71 |
| 567 | m/z = 661.25<br>C49H31N3 = 661.81 | 568 | m/z = 761.28<br>C57H35N3 = 761.93 |
| 569 | m/z = 761.28<br>C57H35N3761.93 | 570 | m/z = 861.31<br>C65H39N3 = 862.05 |
| 571 | m/z = 813.31<br>C61H39N3 = 814.00 | 572 | m/z = 737.28<br>C55H35N3 = 737.91 |
| 573 | m/z = 813.31<br>C61H39N3 = 814.00 | 574 | m/z = 737.28<br>C55H35N3 = 737.91 |
| 575 | m/z = 662.25<br>C48H30N4 = 662.80 | 576 | m/z = 738.28<br>C54H34N4 = 738.89 |
| 577 | m/z = 738.28<br>C54H34N4 = 738.89 | 578 | m/z = 737.28<br>C55H35N3 = 737.91 |
| 579 | m/z = 837.31<br>C63H39N3 = 838.03 | 580 | m/z = 837.31<br>C63H39N3 = 838.03 |
| 581 | m/z = 937.35<br>C71H43N3 = 938.15 | 582 | m/z = 889.35<br>C67H43N3 = 890.10 |
| 583 | m/z = 813.31<br>C61H39N3 = 814.00 | 584 | m/z = 889.35<br>C67H43N3 = 890.10 |
| 585 | m/z = 813.31<br>C61H39N3 = 814.00 | 586 | m/z = 738.28<br>C54H34N4 = 738.89 |
| 587 | m/z = 814.31<br>C60H38N4 = 814.99 | 588 | m/z = 814.31<br>C60H38N4 = 814.99 |
| 589 | m/z = 737.28<br>C55H35N3 = 737.91 | 590 | m/z = 837.31<br>C63H39N3 = 838.03 |
| 591 | m/z = 837.31<br>C63H39N3 = 838.03 | 592 | m/z = 937.35<br>C71H43N3 = 938.15 |
| 593 | m/z = 889.35<br>C67H43N3 = 890.10 | 594 | m/z = 813.31<br>C61H39N3 = 814.00 |
| 595 | m/z = 889.35<br>C67H43N3 = 890.10 | 596 | m/z = 813.31<br>C61H39N3 = 814.00 |
| 597 | m/z = 738.28<br>C54H34N4 = 738.89 | 598 | m/z = 814.31<br>C60H38N4 = 814.99 |
| 599 | m/z = 814.31<br>C60H38N4 = 814.99 | 600 | m/z = 661.25<br>C49H31N3 = 661.81 |

TABLE 2-continued

| Compound | FD-MS | Compound | FD-MS |
|---|---|---|---|
| 601 | m/z = 761.28<br>C57H35N3 = 761.93 | 602 | m/z = 761.28<br>C57H35N3 = 761.93 |
| 603 | m/z = 861.31<br>C65H39N3 = 862.05 | 604 | m/z = 813.31<br>C61H39N3 = 814.00 |
| 605 | m/z = 737.28<br>C55H35N3 = 737.91 | 606 | m/z = 813.31<br>C61H39N3 = 814.00 |
| 607 | m/z = 737.28<br>C55H35N3 = 737.91 | 608 | m/z = 662.25<br>C48H30N4 = 662.80 |
| 609 | m/z = 738.28<br>C54H34N4 = 738.89 | 610 | m/z = 738.28<br>C54H34N4 = 738.89 |
| 611 | m/z = 837.31<br>C63H39N3 = 838.03 | 612 | m/z = 837.31<br>C63H39N3 = 838.03 |
| 613 | m/z = 937.35<br>C71H43N3 = 938.15 | 614 | m/z = 889.35<br>C67H43N3 = 890.10 |
| 615 | m/z = 813.31<br>C61H39N3 = 814.00 | 616 | m/z = 889.35<br>C67H43N3 = 890.10 |
| 617 | m/z = 813.31<br>C61H39N3 = 814.00 | 618 | m/z = 737.28<br>C55H35N3 = 737.91 |
| 619 | m/z = 837.31<br>C63H39N3 = 838.03 | 620 | m/z = 837.31<br>C63H39N3 = 838.03 |
| 621 | m/z = 37.35<br>C71H43N3 = 938.15 | 622 | m/z = 889.35<br>C67H43N3 = 890.10 |
| 623 | m/z = 813.31<br>C61H39N3 = 814.00 | 624 | m/z = 889.35<br>C67H43N3 = 890.10 |
| 625 | m/z = 813.31<br>C61H39N3 = 814.00 | 626 | m/z = 738.28<br>C54H34N4 = 738.89 |
| 627 | m/z = 814.31<br>C60H38N4 = 814.99 | 628 | m/z = 814.31<br>C60H38N4 = 814.99 |
| 629 | m/z = 711.27<br>C53H33N3 = 711.87 | 630 | m/z = 635.24<br>C47H29N3 = 635.77 |
| 631 | m/z = 711.27<br>C53H33N3 = 711.87 | 632 | m/z = 685.25<br>C51H31N3 = 685.83 |
| 633 | m/z = 685.25<br>C51H31N3 = 685.83 | 634 | m/z = 685.25<br>C51H31N3 = 685.83 |
| 635 | m/z = 787.30<br>C59H37N3 = 787.97 | 636 | m/z = 761.28<br>C57H35N3 = 761.93 |
| 637 | m/z = 761.28<br>C57H35N3 = 761.93 | 638 | m/z = 761.28<br>C57H35N3 = 761.93 |
| 639 | m/z = 787.30<br>C59H37N3 = 787.97 | 640 | m/z = 761.28<br>C57H35N3 = 761.93 |
| 641 | m/z = 711.27<br>C53H33N3 = 711.87 | 642 | m/z = 711.27<br>C53H33N3 = 711.87 |
| 643 | m/z = 635.24<br>C47H29N3 = 635.77 | 644 | m/z = 711.27<br>C53H33N3 = 711.87 |
| 645 | m/z = 685.25<br>C51H31N3 = 685.83 | 646 | m/z = 685.25<br>C51H31N3 = 685.83 |
| 647 | m/z = 711.27<br>C53H33N3 = 711.87 | 648 | m/z = 787.30<br>C59H37N3 = 787.97 |
| 649 | m/z = 761.28<br>C57H35N3 = 761.93 | 650 | m/z = 761.28<br>C57H35N3 = 761.93 |
| 651 | m/z = 711.27<br>C53H33N3 = 711.87 | 652 | m/z = 787.30<br>C59H37N3 = 787.97 |
| 653 | m/z = 761.28<br>C57H35N3 = 761.93 | 654 | m/z = 761.28<br>C57H35N3 = 761.93 |
| 655 | m/z = 737.28<br>C55H35N3 = 737.91 | 656 | m/z = 889.35<br>C67H43N3 = 890.10 |
| 657 | m/z = 889.35<br>C67H43N3 = 890.10 | 658 | m/z = 837.31<br>C63H39N3 = 838.03 |
| 659 | m/z = 837.31<br>C63H39N3 = 838.03 | 660 | m/z = 813.31<br>C61H39N3 = 814.00 |
| 661 | m/z = 813.31<br>C61H39N3 = 814.00 | 662 | m/z = 787.30<br>C59H37N3 = 787.97 |
| 663 | m/z = 787.30<br>C59H37N3 = 787.97 | 664 | m/z = 837.31<br>C63H39N3 = 838.03 |
| 665 | m/z = 737.28<br>C55H35N3 = 737.91 | 666 | m/z = 889.35<br>C67H43N3 = 890.10 |
| 667 | m/z = 889.35<br>C67H43N3 = 890.10 | 668 | m/z = 837.31<br>C63H39N3 = 838.03 |
| 669 | m/z = 837.31<br>C63H39N3 = 838.03 | 670 | m/z = 813.31<br>C61H39N3 = 814.00 |
| 671 | m/z = 813.31<br>C61H39N3 = 814.00 | 672 | m/z = 787.30<br>C59H37N3 = 787.97 |
| 673 | m/z = 787.30<br>C59H37N3 = 787.97 | 674 | m/z = 837.31<br>C63H39N3 = 838.03 |
| 675 | m/z = 635.24<br>C47H29N3 = 635.77 | 676 | m/z = 711.27<br>C53H33N3 = 711.87 |
| 677 | m/z = 711.27<br>C53H33N3 = 711.87 | 678 | m/z = 711.27<br>C53H33N3 = 711.87 |

TABLE 2-continued

| Compound | FD-MS | Compound | FD-MS |
|---|---|---|---|
| 679 | m/z = 787.30<br>C59H37N3 = 787.97 | 680 | m/z = 787.30<br>C59H37N3 = 787.97 |
| 681 | m/z = 711.27<br>C53H33N3 = 711.87 | 682 | m/z = 787.30<br>C59H37N3 = 787.97 |
| 683 | m/z = 787.30<br>C59H37N3 = 787.97 | 684 | m/z = 635.24<br>C47H29N3 = 635.77 |
| 685 | m/z = 711.27<br>C53H33N3 = 711.87 | 686 | m/z = 711.27<br>C53H33N3 = 711.87 |
| 687 | m/z = 711.27<br>C53H33N3 = 711.87 | 688 | m/z = 787.30<br>C59H37N3 = 787.97 |
| 689 | m/z = 787.30<br>C59H37N3 = 787.97 | 690 | m/z = 711.27<br>C53H33N3 = 711.87 |
| 691 | m/z = 787.30<br>C59H37N3 = 787.97 | 692 | m/z = 609.22<br>C45H27N3 = 609.73 |
| 693 | m/z = 685.25<br>C51H31N3 = 685.83 | 694 | m/z = 685.25<br>C51H31N3 = 685.83 |
| 695 | m/z = 787.30<br>C59H37N3 = 787.97 | 696 | m/z = 609.22<br>C45H27N3 = 609.73 |
| 697 | m/z = 685.25<br>C51H31N3 = 685.83 | 698 | m/z = 685.25<br>C51H31N3 = 685.83 |
| 699 | m/z = 623.24<br>C46H29N3 = 623.76 | 700 | m/z = 623.24<br>C46H29N3 = 623.76 |
| 701 | m/z = 623.24<br>C46H29N3 = 623.76 | 702 | m/z = 623.24<br>C46H29N3 = 623.76 |
| 703 | m/z = 623.24<br>C46H29N3 = 623.76 | 704 | m/z = 623.24<br>C46H29N3 = 623.76 |
| 705 | m/z = 623.24<br>C46H29N3 = 623.76 | 706 | m/z = 623.24<br>C46H29N3 = 623.76 |
| 707 | m/z = 575.24<br>C42H29N3 = 575.71 | 708 | m/z = 651.27<br>C48H33N3 = 651.81 |
| 709 | m/z = 651.27<br>C48H33N3 = 651.81 | 710 | m/z = 699.27<br>C52H33N3 = 699.86 |
| 711 | m/z = 651.27<br>C48H33N3 = 651.81 | 712 | m/z = 651.27<br>C48H33N3 = 651.81 |
| 713 | m/z = 575.24<br>C42H29N3 = 575.71 | 714 | m/z = 699.27<br>C52H33N3 = 699.86 |
| 715 | m/z = 575.24<br>C42H29N3 = 575.71 | 716 | m/z = 651.27<br>C48H33N3 = 651.81 |
| 717 | m/z = 651.27<br>C48H33N3 = 651.81 | 718 | m/z = 699.27<br>C52H33N3 = 699.86 |
| 719 | m/z = 651.27<br>C48H33N3 = 651.81 | 720 | m/z = 651.27<br>C48H33N3 = 651.81 |
| 721 | m/z = 575.24<br>C42H29N3 = 575.71 | 722 | m/z = 699.27<br>C52H33N3 = 699.86 |
| 723 | m/z = 640.20<br>C46H28N2S = 640.80 | 724 | m/z = 640.20<br>C46H28N2S = 640.80 |
| 725 | m/z = 640.20<br>C46H28N2S = 640.80 | 726 | m/z = 640.20<br>C46H28N2S = 640.80 |
| 727 | m/z = 640.20<br>C46H28N2S = 640.80 | 728 | m/z = 640.20<br>C46H28N2S = 640.80 |
| 729 | m/z = 640.20<br>C46H28N2S = 640.80 | 730 | m/z = 640.20<br>C46H28N2S = 640.80 |
| 731 | m/z = 660.26<br>C50H32N2 = 660.82 | 732 | m/z = 736.29<br>C56H36N2 = 736.92 |
| 733 | m/z = 662.25<br>C48H30N4 = 662.80 | 734 | m/z = 662.25<br>C48H30N4 = 662.80 |
| 735 | m/z = 662.25<br>C48H30N4 = 662.80 | 736 | m/z = 738.28<br>C54H34N4 = 738.89 |
| 737 | m/z = 738.28<br>C54H34N4 = 738.89 | 738 | m/z = 738.28<br>C54H34N4 = 738.89 |
| 739 | m/z = 585.22<br>C43H27N3 = 585.71 | 740 | m/z = 585.22<br>C43H27N3 = 585.71 |
| 741 | m/z = 585.22<br>C43H27N3 = 585.71 | 742 | m/z = 661.25<br>C49H31N3 = 661.81 |
| 743 | m/z = 661.25<br>C49H31N3 = 661.81 | 744 | m/z = 661.25<br>C49H31N3 = 661.81 |
| 745 | m/z = 736.29<br>C56H36N2 = 736.92 | 746 | m/z = 662.25<br>C48H30N4 = 662.80 |
| 747 | m/z = 738.28<br>C54H34N4 = 738.89 | 748 | m/z = 662.25<br>C48H30N4 = 662.80 |
| 749 | m/z = 662.25<br>C48H30N4 = 662.80 | 750 | m/z = 738.28<br>C54H34N4 = 738.89 |
| 751 | m/z = 585.22<br>C43H27N3 = 585.71 | 752 | m/z = 585.22<br>C43H27N3 = 585.71 |
| 753 | m/z = 585.22<br>C43H27N3 = 585.71 | 754 | m/z = 661.25<br>C49H31N3 = 661.81 |
| 755 | m/z = 661.25<br>C49H31N3 = 661.81 | 756 | m/z = 661.25<br>C49H31N3 = 661.81 |

TABLE 2-continued

| Compound | FD-MS | Compound | FD-MS |
|---|---|---|---|
| 757 | m/z = 738.28<br>C54H34N4 = 738.89 | 758 | m/z = 735.24<br>C51H34N3OP = 735.83 |
| 759 | m/z = 735.24<br>C51H34N3OP = 735.83 | 760 | m/z = 773.26<br>C54H36N3OP = 773.88 |
| 761 | m/z = 632.20<br>C44H29N2OP = 632.70 | 762 | m/z = 731.24<br>C53H34NOP = 731.83 |
| 763 | m/z = 811.28<br>C57H38N3OP = 811.92 | 764 | m/z = 697.23<br>C48H32N3OP = 697.78 |
| 765 | m/z = 887.31<br>C63H42N3OP = 888.02 | 766 | m/z = 683.21<br>C47H30N3OP = 683.75 |
| 767 | m/z = 709.23<br>C49H32N3OP = 709.79 | 768 | m/z = 759.24<br>C53H34N3OP = 759.85 |
| 769 | m/z = 773.26<br>C54H36N3OP = 773.88 | 770 | m/z = 659.21<br>C45H30N3OP = 659.73 |
| 771 | m/z = 736.24<br>C50H33N4OP = 736.81 | 772 | m/z = 735.24<br>C51H34N3OP735.83 |
| 773 | m/z = 773.26<br>C54H36N3OP = 773.88 | 774 | m/z = 735.24<br>C51H34N3OP = 735.83 |
| 775 | m/z = 731.24<br>C53H34NOP = 731.83 | 776 | m/z = 632.20<br>C44H29N2OP = 632.70 |
| 777 | m/z = 811.28<br>C57H38N3OP = 811.92 | 778 | m/z = 697.23<br>C48H32N3OP = 697.78 |
| 779 | m/z = 887.31<br>C63H42N3OP = 888.02 | 780 | m/z = 683.21<br>C47H30N3OP = 683.75 |
| 781 | m/z = 709.23<br>C49H32N3OP = 709.79 | 782 | m/z = 759.24<br>C53H34N3OP = 759.85 |
| 783 | m/z = 773.26<br>C54H36N3OP = 773.88 | 784 | m/z = 705.20<br>C47H33NO2P2 = 705.73 |
| 785 | m/z = 659.21<br>C45H30N3OP = 659.73 | 786 | m/z = 736.24<br>C50H33N4OP = 736.81 |
| 787 | m/z = 762.28<br>C56H34N4 = 762.92 | 788 | m/z = 767.28<br>C53H33N7 = 767.90 |
| 789 | m/z = 662.25<br>C48H30N4 = 662.80 | 790 | m/z = 662.25<br>C48H30N4 = 662.80 |
| 791 | m/z = 843.31<br>C59H37N7 = 843.99 | 792 | m/z = 843.31<br>C59H37N7 = 843.99 |
| 793 | m/z = 762.28<br>C56H34N4 = 762.92 | 794 | m/z = 767.28<br>C53H33N7 = 767.90 |
| 795 | m/z = 612.23<br>C44H28N4 = 612.74 | 796 | m/z = 612.23<br>C44H28N4 = 612.74 |
| 797 | m/z = 662.25<br>C48H30N4 = 662.80 | 798 | m/z = 662.25<br>C48H30N4 = 662.80 |
| 799 | m/z = 843.31<br>C59H37N7 = 843.99 | 800 | m/z = 843.31<br>C59H37N7 = 843.99 |
| 801 | m/z = 557.21<br>C43H27N = 557.70 | 802 | m/z = 481.18<br>C37H23N = 481.60 |
| 803 | m/z = 733.28<br>C57H35N = 733.91 | 804 | m/z = 607.23<br>C47H29N = 607.76 |
| 805 | m/z = 607.23<br>C47H29N = 607.76 | 806 | m/z = 557.21<br>C43H27N = 557.70 |
| 807 | m/z = 607.23<br>C47H29N = 607.76 | 808 | m/z = 581.19<br>C41H28NOP = 581.65 |
| 809 | m/z = 505.16<br>C35H24NOP = 505.56 | 810 | m/z = 581.19<br>C41H28NOP = 581.65 |
| 811 | m/z = 733.28<br>C57H35N = 733.91 | 812 | m/z = 711.27<br>C53H33N3 = 711.87 |
| 813 | m/z = 711.27<br>C53H33N3 = 711.87 | 814 | m/z = 581.19<br>C41H28NOP = 581.65 |
| 815 | m/z = 536.20<br>C38H24N4 = 536.64 | 816 | m/z = 538.19<br>C36H22N6 = 538.61 |
| 817 | m/z = 481.18<br>C37H23N = 481.60 | 818 | m/z = 538.19<br>C36H22N6 = 538.61 |
| 819 | m/z = 538.19<br>C36H22N6 = 538.61 | 820 | m/z = 636.23<br>C46H28N4 = 636.76 |
| 821 | m/z = 564.17<br>C40H24N2S = 564.71 | 822 | m/z = 767.28<br>C53H33N7 = 767.90 |
| 823 | m/z = 811.30<br>C61H37N3 = 811.99 | 824 | m/z = 687.27<br>C51H33N3 = 687.85 |
| 825 | m/z = 687.27<br>C51H33N3 = 687.85 | 826 | m/z = 612.23<br>C44H28N4 = 612.74 |
| 827 | m/z = 688.26<br>C50H32N4 = 688.83 | 828 | m/z = 688.26<br>C50H32N4 = 688.83 |
| 829 | m/z = 711.27<br>C53H33N3711.87 | 830 | m/z = 711.27<br>C53H33N3 = 711.87 |
| 831 | m/z = 811.30<br>C61H37N3 = 811.99 | 832 | m/z = 763.30<br>C57H37N3 = 763.94 |
| 833 | m/z = 687.27<br>C51H33N3 = 687.85 | 834 | m/z = 687.27<br>C51H33N3 = 687.85 |

TABLE 2-continued

| Compound | FD-MS | Compound | FD-MS |
|---|---|---|---|
| 835 | m/z = 763.30<br>C57H37N3 = 763.94 | 836 | m/z = 687.27<br>C51H33N3 = 687.85 |
| 837 | m/z = 687.27<br>C51H33N3 = 687.85 | 838 | m/z = 612.23<br>C44H28N4 = 612.74 |
| 839 | m/z = 688.26<br>C50H32N4 = 688.83 | 840 | m/z = 688.26<br>C50H32N4 = 688.83 |
| 841 | m/z = 535.20<br>C39H25N3535.65 | 842 | m/z = 635.24<br>C47H29N3 = 635.77 |
| 843 | m/z = 635.24<br>C47H29N3 = 635.77 | 844 | m/z = 735.27<br>C55H33N3 = 735.89 |
| 845 | m/z = 687.27<br>C51H33N3 = 687.85 | 846 | m/z = 611.24<br>C45H29N3 = 611.75 |
| 847 | m/z = 611.24<br>C45H29N3 = 611.75 | 848 | m/z = 687.27<br>C51H33N3 = 687.85 |
| 849 | m/z = 611.24<br>C45H29N3 = 611.75 | 850 | m/z = 611.24<br>C45H29N3 = 611.75 |
| 851 | m/z = 536.20<br>C38H24N4 = 536.64 | 852 | m/z = 612.23<br>C44H28N4 = 612.74 |
| 853 | m/z = 537.61<br>(C37H23N5 = 537.20) | 854 | m/z = 536.62<br>(C38H24N4 = 536.20) |
| 855 | m/z = 536.62<br>(C38H24N4 = 536.20) | 856 | m/z = 506.53<br>(C34H23N2OP = 506.15) |
| 857 | m/z = 498.58<br>(C35H22N4 = 498.18) | 858 | m/z = 382.46<br>(C28H18N2 = 382.15) |
| 859 | m/z = 432.51<br>(C32H20N2 = 432.16) | 860 | m/z = 432.51<br>(C32H20N2 = 432.16) |
| 861 | m/z = 734.88<br>(C56H34N2 = 734.27) | 862 | m/z = 688.82<br>(C50H32N4 = 688.26) |
| 863 | m/z = 612.72<br>(C44H28N4 = 612.23) | 864 | m/z = 612.72<br>(C44H28N4 = 612.23) |
| 865 | m/z = 637.73<br>(C45H27N5 = 637.23) | 866 | m/z = 637.73<br>(C45H27N5 = 637.23) |
| 867 | m/z = 539.59<br>(C35H21N7 = 539.19) | 868 | m/z = 539.59<br>(C35H21N7 = 539.19) |
| 869 | m/z = 539.59<br>(C35H21N7 = 539.19) | 870 | m/z = 565.67<br>(C39H27N5 = 565.23) |
| 871 | m/z = 433.50<br>(C31H19N3 = 433.16) | 872 | m/z = 433.50<br>(C31H19N3 = 433.16) |
| 873 | m/z = 433.50<br>(C31H19N3 = 433.16) | 874 | m/z = 537.61<br>(C37H23N5 = 537.20) |
| 875 | m/z = 536.62<br>(C38H24N4 = 536.20) | 876 | m/z = 536.62<br>(C38H24N4 = 536.20) |
| 877 | m/z = 506.53<br>(C34H23N2OP = 506.15) | 878 | m/z = 498.58<br>(C35H22N4 = 498.18) |
| 879 | m/z = 382.46<br>(C28H18N2 = 382.15) | 880 | m/z = 432.51<br>(C32H20N2 = 432.16) |
| 881 | m/z = 432.51<br>(C32H20N2 = 432.16) | 882 | m/z = 734.88<br>(C56H34N2 = 734.27) |
| 883 | m/z = 688.82<br>(C50H32N4 = 688.26) | 884 | m/z = 612.72<br>(C44H28N4 = 612.23) |
| 885 | m/z = 612.72<br>(C44H28N4 = 612.23) | 886 | m/z = 637.73<br>(C45H27N5 = 637.23) |
| 887 | m/z = 637.73<br>(C45H27N5 = 637.23) | 888 | m/z = 539.59<br>(C35H21N7 = 539.19) |
| 889 | m/z = 539.59<br>(C35H21N7 = 539.19) | 890 | m/z = 539.59<br>(C35H21N7 = 539.19) |
| 891 | m/z = 565.67<br>(C39H27N5 = 565.23) | 892 | m/z = 433.50<br>(C31H19N3 = 433.16) |
| 893 | m/z = 433.50<br>(C31H19N3 = 433.16) | 894 | m/z = 433.50<br>(C31H19N3 = 433.16) |
| 895 | m/z = 538.19<br>(C36H22N6 = 538.61) | 896 | m/z = 537.20<br>(C37H23N5 = 537.63) |
| 897 | m/z = 537.20<br>(C37H23N5 = 537.63) | 898 | m/z = 507.15<br>(C33H22N3OP = 507.53) |
| 899 | m/z = 575.21<br>(C40H25N5 = 575.67) | 900 | m/z = 383.14<br>(C27H17N3 = 383.45) |
| 901 | m/z = 433.16<br>(C31H19N3 = 433.51) | 902 | m/z = 433.16<br>(C31H19N3 = 433.51) |
| 903 | m/z = 735.27<br>(C55H33N3 = 735.89) | 904 | m/z = 689.26<br>(C49H31N5 = 689.82) |
| 905 | m/z = 613.23<br>(C43H27N5 = 613.72) | 906 | m/z = 613.23<br>(C43H27N5 = 613.72) |
| 907 | m/z = 638.22<br>(C44H26N6 = 638.73) | 908 | m/z = 638.22<br>(C44H26N6 = 638.73) |
| 909 | m/z = 540.18<br>(C34H20N8 = 540.59) | 910 | m/z = 540.18<br>(C34H20N8 = 540.59) |
| 911 | m/z = 540.18<br>(C34H20N8 = 540.59) | 912 | m/z = 566.22<br>(C38H26N6 = 566.67) |

TABLE 2-continued

| Compound | FD-MS | Compound | FD-MS |
|---|---|---|---|
| 913 | m/z = 434.15 (C30H18N4 = 434.50) | 914 | m/z = 434.15 (C30H18N4 = 434.50) |
| 915 | m/z = 434.15 (C30H18N4 = 434.50) | 916 | m/z = 538.19 (C36H22N6 = 538.61) |
| 917 | m/z = 537.20 (C37H23N5 = 537.63) | 918 | m/z = 537.20 (C37H23N5 = 537.63) |
| 919 | m/z = 507.15 (C33H22N3OP = 507.53) | 920 | m/z = 575.21 (C40H25N5 = 575.67) |
| 921 | m/z = 383.14 (C27H17N3 = 383.45) | 922 | m/z = 433.16 (C31H19N3 = 433.51) |
| 923 | m/z = 433.16 (C31H19N3 = 433.51) | 924 | m/z = 735.27 (C55H33N3 = 735.89) |
| 925 | m/z = 689.26 (C49H31N5 = 689.82) | 926 | m/z = 613.23 (C43H27N5 = 613.72) |
| 927 | m/z = 613.23 (C43H27N5 = 613.72) | 928 | m/z = 638.22 (C44H26N6 = 638.73) |
| 929 | m/z = 638.22 (C44H26N6 = 638.73) | 930 | m/z = 540.18 (C34H20N8 = 540.59) |
| 931 | m/z = 540.18 (C34H20N8 = 540.59) | 932 | m/z = 540.18 (C34H20N8 = 540.59) |
| 933 | m/z = 566.22 (C38H26N6 = 566.67) | 934 | m/z = 434.15 (C30H18N4 = 434.50) |
| 935 | m/z = 434.15 (C30H18N4 = 434.50) | 936 | m/z = 434.15 (C30H18N4 = 434.50) |
| 937 | m/z = 587.69 (C41H25N5 = 587.21) | 938 | m/z = 586.70 (C42H26N4 = 586.22) |
| 939 | m/z = 586.70 (C42H26N4 = 586.22) | 940 | m/z = 556.60 (C38H25N2OP = 556.17) |
| 941 | m/z = 548.65 (C39H24N4 = 548.20) | 942 | m/z = 432.53 (C32H20N2 = 432.16) |
| 943 | m/z = 482.59 (C36H22N2 = 482.18) | 944 | m/z = 482.59 (C36H22N2 = 482.18) |
| 945 | m/z = 784.96 (C60H36N2 = 784.29) | 946 | m/z = 738.89 (C54H34N4 = 738.28) |
| 947 | m/z = 662.80 (C48H30N4 = 662.25) | 948 | m/z = 662.80 (C48H30N4 = 662.25) |
| 949 | m/z = 687.81 (C49H29N5 = 687.24) | 950 | m/z = 687.81 (C49H29N5 = 687.24) |
| 951 | m/z = 589.66 (C39H23N7 = 589.20) | 952 | m/z = 589.66 (C39H23N7 = 589.20) |
| 953 | m/z = 589.66 (C39H23N7 = 589.20) | 954 | m/z = 615.74 (C43H29N5 = 615.24) |
| 955 | m/z = 689.78 (C47H27N7 = 689.23) | 956 | m/z = 689.78 (C47H27N7 = 689.23) |
| 957 | m/z = 689.78 (C47H27N7 = 689.23) | 958 | m/z = 587.69 (C41H25N5 = 587.21) |
| 959 | m/z = 586.70 (C42H26N4 = 586.22) | 960 | m/z = 586.70 (C42H26N4 = 586.22) |
| 961 | m/z = 556.60 (C38H25N2OP = 556.17) | 962 | m/z = 548.65 (C39H24N4 = 548.20) |
| 963 | m/z = 432.53 (C32H20N2 = 432.16) | 964 | m/z = 482.59 (C36H22N2 = 482.18) |
| 965 | m/z = 482.59 (C36H22N2 = 482.18) | 966 | m/z = 784.96 (C60H36N2 = 784.29) |
| 967 | m/z = 738.89 (C54H34N4 = 738.28) | 968 | m/z = 662.80 (C48H30N4 = 662.25) |
| 969 | m/z = 662.80 (C48H30N4 = 662.25) | 970 | m/z = 687.81 (C49H29N5 = 687.24) |
| 971 | m/z = 687.81 (C49H29N5 = 687.24) | 972 | m/z = 589.66 (C39H23N7 = 589.20) |
| 973 | m/z = 589.66 (C39H23N7 = 589.20) | 974 | m/z = 589.66 (C39H23N7 = 589.20) |
| 975 | m/z = 615.74 (C43H29N5 = 615.24) | 976 | m/z = 689.78 (C47H27N7 = 689.23) |
| 977 | m/z = 689.78 (C47H27N7 = 689.23) | 978 | m/z = 689.78 (C47H27N7 = 689.23) |
| 979 | m/z = 587.21 (C41H25N5 = 587.69) | 980 | m/z = 586.22 (C42H26N4 = 586.70) |
| 981 | m/z = 586.22 (C42H26N4 = 586.70) | 982 | m/z = 556.17 (C38H25N2OP = 556.60) |
| 983 | m/z = 624.23 (C45H28N4 = 624.75) | 984 | m/z = 432.16 (C32H20N2 = 432.53) |
| 985 | m/z = 482.18 (C36H22N2 = 482.59) | 986 | m/z = 482.18 (C36H22N2 = 482.59) |
| 987 | m/z = 784.29 (C60H36N2 = 784.96) | 988 | m/z = 738.28 (C54H34N4 = 738.89) |
| 989 | m/z = 662.25 (C48H30N4 = 662.80) | 990 | m/z = 662.25 (C48H30N4 = 662.80) |

TABLE 2-continued

| Compound | FD-MS | Compound | FD-MS |
|---|---|---|---|
| 991 | m/z = 687.24 (C49H29N5 = 687.81) | 992 | m/z = 687.24 (C49H29N5 = 687.81) |
| 993 | m/z = 589.20 (C39H23N7 = 589.66) | 994 | m/z = 589.20 (C39H23N7 = 589.66) |
| 995 | m/z = 589.20 (C39H23N7 = 589.66) | 996 | m/z = 615.24 (C43H29N5 = 615.74) |
| 997 | m/z = 483.17 (C35H21N3 = 483.57) | 998 | m/z = 483.17 (C35H21N3 = 483.57) |
| 999 | m/z = 483.17 (C35H21N3 = 483.57) | 1000 | m/z = 433.16 (C31H19N3 = 433.51) |
| 1001 | m/z = 537.20 (C37H23N5 = 537.63) | 1002 | m/z = 536.20 (C38H24N4 = 536.64) |
| 1003 | m/z = 536.20 (C38H24N4 = 536.64) | 1004 | m/z = 506.15 (C34H23N2OP = 506.54) |
| 1005 | m/z = 574.22 (C41H26N4 = 574.69) | 1006 | m/z = 382.15 (C28H18N2 = 382.47) |
| 1007 | m/z = 432.16 (C32H20N2 = 432.53) | 1008 | m/z = 432.16 (C32H20N2 = 432.53) |
| 1009 | m/z = 734.27 (C56H34N2 = 734.90) | 1010 | m/z = 688.26 (C50H32N4 = 688.83) |
| 1011 | m/z = 612.23 (C44H28N4 = 612.74) | 1012 | m/z = 612.23 (C44H28N4 = 612.74) |
| 1013 | m/z = 637.23 (C45H27N5 = 637.75) | 1014 | m/z = 637.23 (C45H27N5 = 637.75) |
| 1015 | m/z = 539.19 (C35H21N7 = 539.60) | 1016 | m/z = 539.19 (C35H21N7 = 539.60) |
| 1017 | m/z = 539.19 (C35H21N7 = 539.60) | 1018 | m/z = 565.23 (C39H27N5 = 565.68) |
| 1019 | m/z = 433.16 (C31H19N3 = 433.51) | 1020 | m/z = 433.16 (C31H19N3 = 433.51) |
| 1021 | m/z = 537.20 (C37H23N5 = 537.63) | 1022 | m/z = 536.20 (C38H24N4 = 536.64) |
| 1023 | m/z = 536.20 (C38H24N4 = 536.64) | 1024 | m/z = 506.15 (C34H23N2OP = 506.54) |
| 1025 | m/z = 574.22 (C41H26N4 = 574.69) | 1026 | m/z = 382.15 (C28H18N2 = 382.47) |
| 1027 | m/z = 432.16 (C32H20N2 = 432.53) | 1028 | m/z = 432.16 (C32H20N2 = 432.53) |
| 1029 | m/z = 734.27 (C56H34N2 = 734.90) | 1030 | m/z = 688.26 (C50H32N4 = 688.83) |
| 1031 | m/z = 612.23 (C44H28N4 = 612.74) | 1032 | m/z = 612.23 (C44H28N4 = 612.74) |
| 1033 | m/z =: 637.23 (C45H27N5 = 637.75) | 1034 | m/z = 637.23 (C45H27N5 = 637.75) |
| 1035 | m/z = 539.19 (C35H21N7 = 539.60) | 1036 | m/z = 539.19 (C35H21N7 = 539.60) |
| 1037 | m/z = 539.19 (C35H21N7 = 539.60) | 1038 | m/z = 565.23 (C39H27N5 = 565.68) |
| 1039 | m/z = 433.16 (C31H19N3 = 433.51) | 1040 | m/z = 433.16 (C31H19N3 = 433.51) |
| 1041 | m/z = 433.16 (C31H19N3 = 433.51) | | |

Further, FIG. 4 to FIG. 25 are graphs each illustrating a PL (Photoluminescence) or LTPL (Low Temperature Photoluminescence) emission/absorption spectrum of a compound in a specific UV wavelength region.

PL was measured at room temperature using an LS55 luminescent spectrometer manufactured by Perkin Elmer, and LTPL was measured using an F7000 luminescent spectrometer manufactured by HITACHI, and analyzed using liquid nitrogen under low-temperature conditions of −196° C. (77K).

FIG. 4 is a graph illustrating a PL spectrum of a compound 1 at a wavelength of 259 nm.

FIG. 5 is a graph illustrating an LTPL spectrum of the compound 1 at a wavelength of 388 nm.

FIG. 6 is a graph illustrating a PL spectrum of a compound 75 at a wavelength of 271 nm.

FIG. 7 is a graph illustrating an LTPL spectrum of the compound 75 at a wavelength of 356 nm.

FIG. 8 is a graph illustrating a PL spectrum of a compound 100 at a wavelength of 281 nm.

FIG. 9 is a graph illustrating an LTPL spectrum of the compound 100 at a wavelength of 381 nm.

FIG. 10 is a graph illustrating a PL spectrum of a compound 106 at a wavelength of 317 nm.

FIG. 11 is a graph illustrating an LTPL spectrum of the compound 106 at a wavelength of 381 nm.

FIG. 12 is a graph illustrating a PL spectrum of a compound 112 at a wavelength of 267 nm.

FIG. 13 is a graph illustrating an LTPL spectrum of the compound 112 at a wavelength of 323 nm.

FIG. 14 is a graph illustrating a PL spectrum of a compound 124 at a wavelength of 284 nm.

FIG. 15 is a graph illustrating an LTPL spectrum of the compound 124 at a wavelength of 382 nm.

FIG. 16 is a graph illustrating a PL spectrum of a compound 168 at a wavelength of 305 nm.

FIG. 17 is a graph illustrating an LTPL spectrum of the compound 168 at a wavelength of 387 nm.

FIG. 18 is a graph illustrating a PL spectrum of a compound 189 at a wavelength of 284 nm.

FIG. 19 is a graph illustrating an LTPL spectrum of the compound 189 at a wavelength of 284 nm.

FIG. 20 is a graph illustrating a AL spectrum of a compound 201 at a wavelength of 282 nm.

FIG. 21 is a graph illustrating an LTPL spectrum of the compound 201 at a wavelength of 282 nm.

FIG. 22 is a graph illustrating a PL spectrum of a compound 227 at a wavelength of 229 nm.

FIG. 23 is a graph illustrating an LTPL spectrum of the compound 227 at a wavelength of 323 nm.

FIG. 24 is a graph illustrating a PL spectrum of a compound 238 at a wavelength of 277 nm.

FIG. 25 is a graph illustrating an LTPL spectrum of the compound 238 at a wavelength of 382 nm.

FIG. 26 is a graph illustrating a PL spectrum of a compound 325 at a wavelength of 270 nm.

FIG. 27 is a graph illustrating an LTPL spectrum of the compound 325 at a wavelength of 381 nm.

FIG. 28 is a graph illustrating a PL spectrum of a compound 365 at a wavelength of 285 nm.

FIG. 29 is a graph illustrating an LTPL spectrum of the compound 365 at a wavelength of 381 nm.

FIG. 30 is a graph illustrating a PL spectrum of a compound 390 at a wavelength of 283 nm.

FIG. 31 is a graph illustrating an LTPL spectrum of the compound 390 at a wavelength of 381 nm.

FIG. 32 is a graph illustrating a PL spectrum of a compound 457 at a wavelength of 321 nm.

FIG. 33 is a graph illustrating an LTPL spectrum of the compound 457 at a wavelength of 321 nm.

FIG. 34 is a graph illustrating a PL spectrum of a compound 492 at a wavelength of 285 nm.

FIG. 35 is a graph illustrating an LTPL spectrum of the compound 492 at a wavelength of 381 nm.

FIG. 36 is a graph illustrating a PL spectrum of a compound 504 at a wavelength of 223 nm.

FIG. 37 is a graph illustrating an LTPL spectrum of the compound 504 at a wavelength of 387 nm.

FIG. 38 is a graph illustrating a PL spectrum of a compound 530 at a wavelength of 227 nm.

FIG. 39 is a graph illustrating an LTPL spectrum of the compound 530 at a wavelength of 387 nm.

FIG. 40 is a graph illustrating a PL spectrum of a compound 566 at a wavelength of 294 nm.

FIG. 41 is a graph illustrating an LTPL spectrum of the compound 566 at a wavelength of 387 nm.

FIG. 42 is a graph illustrating a PL spectrum of a compound 655 at a wavelength of 254 nm.

FIG. 43 is a graph illustrating an LTPL spectrum of the compound 655 at a wavelength of 370 nm.

FIG. 44 is a graph illustrating a PL spectrum of a compound 758 at a wavelength of 311 nm.

FIG. 45 is a graph illustrating an LTPL spectrum of the compound 758 at a wavelength of 282 nm.

FIG. 46 is a graph illustrating a PL spectrum of a compound 760 at a wavelength of 301 nm.

FIG. 47 is a graph illustrating an LTPL spectrum of the compound 760 at a wavelength of 388 nm.

FIG. 48 is a graph illustrating a PL spectrum of a compound 762 at a wavelength of 260 nm.

FIG. 49 is a graph illustrating an LTPL spectrum of the compound 762 at a wavelength of 290 nm.

FIG. 50 is a graph illustrating a PL spectrum of a compound 784 at a wavelength of 282 nm.

FIG. 51 is a graph illustrating an LTPL spectrum of the compound 784 at a wavelength of 382 nm.

FIG. 52 is a graph illustrating a PL spectrum of a compound 802 at a wavelength of 257 nm.

FIG. 53 is a graph illustrating an LTPL spectrum of the compound 802 at a wavelength of 381 nm.

FIG. 54 is a graph illustrating a PL spectrum of a compound 809 at a wavelength of 280 nm.

FIG. 55 is a graph illustrating an LTPL spectrum of the compound 809 at a wavelength of 381 nm.

FIG. 56 is a graph illustrating a PL spectrum of a compound 812 at a wavelength of 239 nm.

FIG. 57 is a graph illustrating an LTPL spectrum of the compound 812 at a wavelength of 382 nm.

FIG. 58 is a graph illustrating a PL spectrum of a compound 815 at a wavelength of 275 nm.

FIG. 59 is a graph illustrating an LTPL spectrum of the compound 815 at a wavelength of 362 nm.

In the PL/LTPL graphs as illustrated in FIG. 4 to FIG. 59, the y-axis represents intensity and the x-axis represents a wavelength (unit: nm).

Manufacturing of Organic Electroluminescent Device

COMPARATIVE EXAMPLE 1

First, a transparent electrode ITO thin film obtained from an OLED glass (manufactured by Samsung Corning Co., Ltd.) was ultrasonic cleaned using trichloroethylene, acetone, ethanol, and distilled water in sequence for each 5 minutes, and was used after being put into isopropanol.

Then, an ITO substrate was installed in a vacuum deposition apparatus. Thereafter, within a vacuum chamber, 4,4',4"-tris(N,N-(2-naphthyl)-phenylamino)triphenyl amine (2-TNATA) was vacuum-deposited to a thickness of 600 Å on the ITO so as to form a hole injection layer.

Then, N,N'-bis(α-naphthyl)-N,N'-diphenyl-4,4'-diamine (NPB) was vacuum-deposited to a thickness of 300 Å on the hole injection layer so as to form a hole transport layer.

Thereafter, a light emitting layer was vacuum-deposited to a thickness of 200 Å on the hole transport layer with a blue emission host material H1 and a blue emission dopant material D1 at a mixing ratio of 95:5.

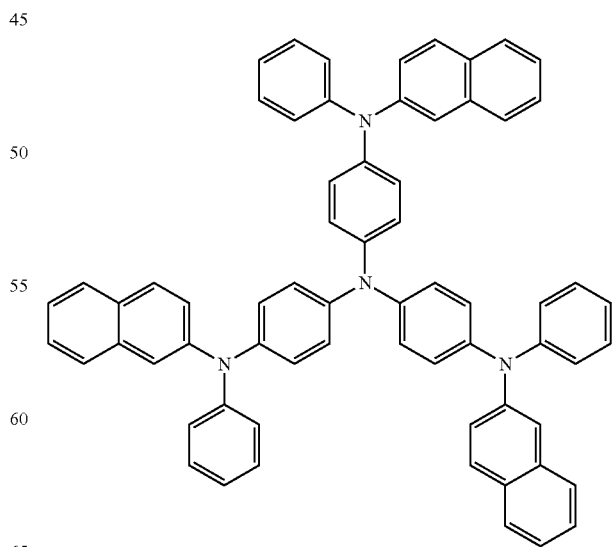

2-TNATA

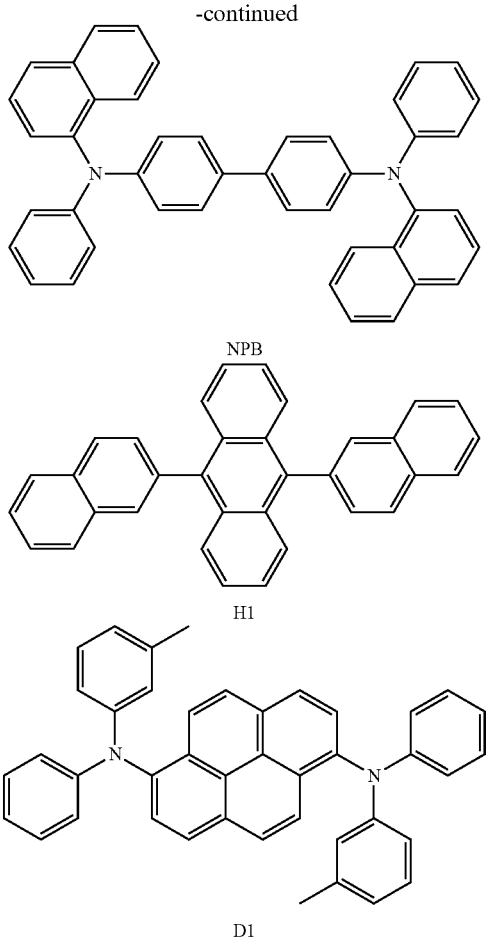

NPB

H1

D1

Then, a compound of the following structural formula E1 was deposited to a thickness of 300 Å on the light emitting layer so as to form an electron transport layer.

E1

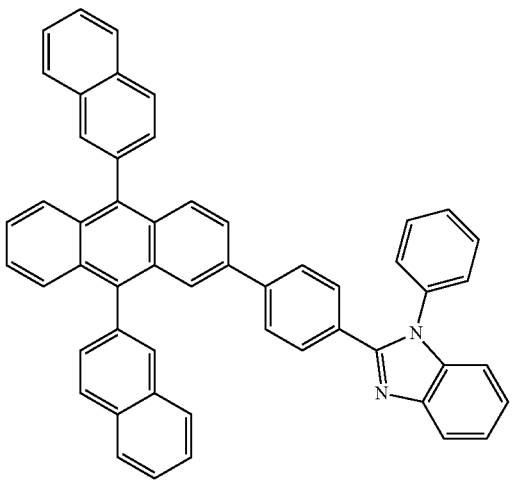

Thereafter, lithium fluoride (LiF) was deposited as an electron injection layer to a thickness of 10 Å on the electron transport layer, and Al was deposited as a cathode to a thickness of 1000 Å on the electron injection layer, thereby manufacturing an OLED device.

Meanwhile, each of all the organic compounds necessary for manufacturing of an OLED device was vacuumed, sublimed, and purified under $10^{-6}$ to $10^{-8}$ torr, and used for manufacturing OLED.

EXAMPLE 1 TO EXAMPLE 52

Organic electroluminescent devices of the example 1 to the example 52 were manufactured in the same manner as the comparative example 1 except that the compounds as prepared in the above-described preparation examples and listed in the following Table 3 were used instead of E1 used for forming the electron transport layer in the comparative example 1.

EXPERIMENTAL EXAMPLE

Evaluation of Organic Electroluminescent Device

Driving voltage, efficiency, color coordinate, and life span of the organic electroluminescent devices respectively manufactured in the above-described comparative example 1 and examples 1 to 39 were measured at a luminescent brightness 700 $cd/m^2$, and the results thereof were as listed in the following Table 3.

Herein, the life span was measured using an M6000PMX manufactured by McScience Co., Ltd.

TABLE 3

| | Electron transport layer material | Luminescent brightness (cd/m²) | Driving voltage (V) | Efficiency (cd/A) | Color coordinate (x, y) | | Life span (T₅₀) |
|---|---|---|---|---|---|---|---|
| | | | | | x | y | |
| Comparative Example 1 | E1 | 700 | 4.70 | 4.50 | 0.150 | 0.180 | 330 |
| Example 1 | Compound 1 | 700 | 4.73 | 6.07 | 0.148 | 0.186 | 25 |
| Example 2 | Compound 75 | 700 | 4.61 | 4.48 | 0.149 | 0.167 | 566 |
| Example 3 | Compound 100 | 700 | 5.14 | 3.21 | 0.148 | 0.177 | 442 |
| Example 4 | Compound 103 | 700 | 4.65 | 5.10 | 0.148 | 0.17 | 132 |
| Example 5 | Compound 106 | 700 | 4.84 | 5.00 | 0.148 | 0.182 | 145 |
| Example 6 | Compound 112 | 700 | 4.13 | 5.47 | 0.153 | 0.182 | 144 |
| Example 7 | Compound 124 | 700 | 4.18 | 5.80 | 0.15 | 0.167 | 68 |
| Example 8 | Compound 189 | 700 | 4.94 | 4.77 | 0.149 | 0.171 | 187 |
| Example 9 | Compound 201 | 700 | 5.72 | 4.04 | 0.153 | 0.169 | 590 |
| Example 10 | Compound 227 | 700 | 4.32 | 5.27 | 0.153 | 0.166 | 146 |
| Example 11 | Compound 238 | 700 | 4.61 | 4.56 | 0.153 | 0.175 | 672 |
| Example 12 | Compound 245 | 700 | 4.37 | 4.94 | 0.153 | 0.177 | 595 |
| Example 13 | Compound 325 | 700 | 4.33 | 5.64 | 0.153 | 0.18 | 84 |
| Example 14 | Compound 365 | 700 | 4.86 | 4.41 | 0.153 | 0.172 | 288 |
| Example 15 | Compound 390 | 700 | 4.01 | 5.70 | 0.15 | 0.167 | 96 |
| Example 16 | Compound 457 | 700 | 4.63 | 5.31 | 0.148 | 0.167 | 150 |
| Example 17 | Compound 219 | 700 | 4.20 | 5.94 | 0.149 | 0.169 | 32 |

TABLE 3-continued

| Electron transport layer material | Luminescent brightness (cd/m²) | Driving voltage (V) | Efficiency (cd/A) | Color coordinate (x, y) x | y | Life span (T₅₀) |
|---|---|---|---|---|---|---|
| Example 18 | Compound 504 | 700 | 4.58 | 4.48 | 0.149 | 0.167 | 547 |
| Example 19 | Compound 509 | 700 | 4.60 | 4.53 | 0.153 | 0.167 | 557 |
| Example 20 | Compound 530 | 700 | 4.96 | 4.18 | 0.15 | 0.167 | 557 |
| Example 21 | Compound 566 | 700 | 4.57 | 4.94 | 0.148 | 0.169 | 384 |
| Example 22 | Compound 655 | 700 | 4.25 | 4.33 | 0.149 | 0.167 | 240 |
| Example 23 | Compound 758 | 700 | 4.72 | 4.47 | 0.149 | 0.168 | 576 |
| Example 24 | Compound 760 | 700 | 4.84 | 4.33 | 0.153 | 0.167 | 595 |
| Example 25 | Compound 762 | 700 | 4.98 | 4.37 | 0.15 | 0.165 | 624 |
| Example 26 | Compound 784 | 700 | 5.31 | 4.55 | 0.148 | 0.17 | 518 |
| Example 27 | Compound 788 | 700 | 4.96 | 4.71 | 0.149 | 0.168 | 672 |
| Example 28 | Compound 802 | 700 | 5.46 | 5.02 | 0.153 | 0.167 | 240 |
| Example 29 | Compound 809 | 700 | 5.55 | 4.07 | 0.15 | 0.169 | 169 |
| Example 30 | Compound 812 | 700 | 6.09 | 4.20 | 0.148 | 0.167 | 115 |
| Example 31 | Compound 815 | 700 | 4.84 | 4.49 | 0.149 | 0.165 | 660 |
| Example 32 | Compound 853 | 700 | 4.84 | 5.00 | 0.148 | 0.182 | 25 |
| Example 33 | Compound 855 | 700 | 4.84 | 5.00 | 0.148 | 0.182 | 366 |
| Example 34 | Compound 857 | 700 | 4.13 | 5.47 | 0.153 | 0.182 | 442 |
| Example 35 | Compound 877 | 700 | 4.32 | 5.27 | 0.153 | 0.166 | 132 |
| Example 36 | Compound 885 | 700 | 4.61 | 4.56 | 0.153 | 0.175 | 145 |
| Example 37 | Compound 895 | 700 | 4.37 | 4.94 | 0.153 | 0.177 | 144 |
| Example 38 | Compound 898 | 700 | 4.33 | 5.64 | 0.153 | 0.180 | 68 |
| Example 39 | Compound 905 | 700 | 4.84 | 5.00 | 0.148 | 0.182 | 187 |
| Example 40 | Compound 920 | 700 | 4.13 | 5.47 | 0.153 | 0.182 | 490 |
| Example 41 | Compound 925 | 700 | 4.32 | 5.27 | 0.153 | 0.166 | 146 |
| Example 42 | Compound 947 | 700 | 4.61 | 4.56 | 0.153 | 0.175 | 372 |
| Example 43 | Compound 949 | 700 | 4.84 | 5.00 | 0.148 | 0.182 | 395 |
| Example 44 | Compound 972 | 700 | 4.13 | 5.47 | 0.153 | 0.182 | 84 |
| Example 45 | Compound 974 | 700 | 4.32 | 5.27 | 0.153 | 0.166 | 288 |
| Example 46 | Compound 977 | 700 | 4.61 | 4.56 | 0.153 | 0.175 | 96 |
| Example 47 | Compound 981 | 700 | 4.37 | 4.94 | 0.153 | 0.177 | 150 |
| Example 48 | Compound 982 | 700 | 4.33 | 5.64 | 0.153 | 0.180 | 32 |
| Example 49 | Compound 993 | 700 | 4.32 | 5.27 | 0.153 | 0.166 | 347 |
| Example 50 | Compound 1009 | 700 | 4.61 | 4.56 | 0.153 | 0.175 | 357 |
| Example 51 | Compound 1017 | 700 | 4.37 | 4.94 | 0.153 | 0.177 | 457 |
| Example 52 | Compound 1025 | 700 | 4.33 | 5.64 | 0.153 | 0.180 | 384 |

As can be seen from the results listed in Table 3, each organic electroluminescent device using a compound according to the exemplary embodiment of the present application as an electron transport layer material has a low driving voltage, an improved luminescent efficiency, and a remarkably improved life span, as compared with the comparative example 1.

That is, the compounds according to the present application are excellent in electron transport, and if they are used in a cell, driving characteristics can be improved. Due to a hole blocking function caused by a low HOMO value of the compound, the number of holes shifted from a light emitting layer to a layer comprising the compound according to the present application is reduced, and, thus, it is possible to improve a luminescent efficiency and a life span.

What is claimed is:
1. A compound of the following chemical formula 1:

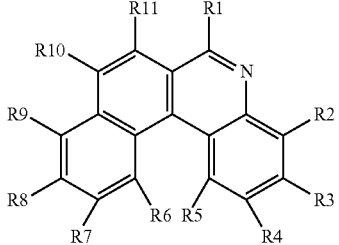

[Chemical Formula 1]

wherein in the chemical formula 1,

R1 is -(A)m-(B)n,

A is selected from the group consisting of substituted or unsubstituted $C_6$ to $C_{60}$ monocyclic or polycyclic arylene; and substituted or unsubstituted $C_2$ to $C_{60}$ monocyclic or polycyclic heteroarylene, B is selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R"; and —P(=O)RR', m is an integer of 1 to 5, n is an integer of 1 to 3, and when m and n are independently integers of 2 or more, multiple A and B are the same as or different from each other, R2 to R11 are the same as or different from each other, and are each independently one selected from the group consisting of hydrogen; deuterium; halogen; linear or branched substituted or unsubstituted $C_1$ to $C_{60}$ alkyl; linear or branched substituted or unsubstituted $C_2$ to $C_{60}$ alkenyl; linear or branched substituted or unsubstituted $C_2$ to $C_{60}$ alkynyl; linear or branched substituted or unsubstituted $C_1$ to $C_{60}$ alkoxy; linear or branched substituted or unsubstituted $C_6$ to $C_{60}$ aryloxy; substituted or unsubstituted $C_3$ to $C_{60}$ monocyclic or polycyclic cycloalkyl; substituted or unsubstituted $C_2$ to $C_{60}$ monocyclic or polycyclic heterocycloalkyl; substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R"; —P(=O)RR'; substituted or unsubstituted $C_1$ to $C_{20}$ alkylamine; substituted or unsubstituted $C_6$ to $C_{60}$ monocyclic or polycyclic arylamine; and substituted or unsubstituted $C_2$ to $C_{60}$ monocyclic or polycyclic heteroarylamine; and R, R', and R" R11 are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

2. The compound of claim 1, wherein the term "substituted or unsubstituted" refers to a group that is substituted or is not further substituted with one or more substituents selected from the group consisting of linear or branched $C_1$ to $C_{60}$ alkyl; linear or branched $C_2$ to $C_{60}$ alkenyl; linear or branched $C_2$ to $C_{60}$ alkynyl; $C_3$ to $C_{60}$ monocyclic or polycyclic cycloalkyl; $C_2$ to $C_{60}$ monocyclic or polycyclic heterocycloalkyl; $C_6$ to $C_{60}$ monocyclic or polycyclic aryl; $C_2$ to $C_{60}$ monocyclic or polycyclic heteroaryl; —SiRR'R"; —P(=O)RR'; $C_1$ to $C_{20}$ alkylamine; $C_6$ to $C_{60}$ monocyclic or polycyclic arylamine; and $C_2$ to $C_{60}$ monocyclic or polycyclic heteroarylamine; or a substituent bonded to two or more selected from the substituents, and R, R', and R" are the same as or different from each other, and are each independently one selected from the group consisting of hydrogen; deuterium; linear or branched $C_1$ to $C_{60}$ alkyl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; $C_6$ to $C_{60}$ monocyclic or polycyclic aryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; and $C_2$ to $C_{60}$ monocyclic or polycyclic heteroaryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl.

3. The compound of claim 1, wherein
A is selected from the group consisting of $C_6$ to $C_{60}$ monocyclic or polycyclic arylene unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; and $C_2$ to $C_{60}$ monocyclic or polycyclic heteroarylene unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl, B is selected from the group consisting of hydrogen; deuterium; linear or branched $C_1$ to $C_{60}$ alkyl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; $C_6$ to $C_{60}$ monocyclic or polycyclic aryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; $C_2$ to $C_{60}$ monocyclic or polycyclic heteroaryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; —SiRR'R"; and —P(=O)RR', and the R, R', and R" are the same as or different from each other, and are each independently one selected from the group consisting of hydrogen; deuterium; linear or branched $C_1$ to $C_{60}$ alkyl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; $C_6$ to $C_{60}$ monocyclic or polycyclic aryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl; and $C_2$ to $C_{60}$ monocyclic or polycyclic heteroaryl unsubstituted or substituted with linear or branched $C_1$ to $C_{60}$ alkyl, $C_6$ to $C_{60}$ monocyclic or polycyclic aryl, or $C_2$ to $C_{60}$ monocyclic or polycyclic heteroaryl, m is an integer of 1 to 5, n is an integer of 1 to 3, and when m and n are independently integers of 2 or more, multiple A and B are the same as or different from each other.

4. The compound of claim 1, wherein the R1 is substituted or unsubstituted $C_6$ to $C_{20}$ monocyclic or polycyclic aryl; or substituted or unsubstituted $C_2$ to $C_{20}$ monocyclic or polycyclic heteroaryl.

5. The compound of claim 1, wherein the R2 to R11 are hydrogen or deuterium.

6. The compound of claim 1, wherein at least one of the R2 to R11 is selected from the group consisting of substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R"; —P(=O)RR'; substituted or unsubstituted $C_1$ to $C_{20}$ alkylamine; substituted or unsubstituted $C_6$ to $C_{60}$ monocyclic or polycyclic arylamine; and substituted or unsubstituted $C_2$ to $C_{60}$ monocyclic or polycyclic heteroarylamine, and the R, R', and R" are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

7. The compound of claim 1, wherein one of the R2 to R11 is substituted or unsubstituted $C_6$ to $C_{60}$ monocyclic or polycyclic aryl; substituted or unsubstituted $C_2$ to $C_{60}$ monocyclic or polycyclic heteroaryl; —SiRR'R"; or —P(=O)RR', and the R, R', and R" are the same as or different from each other, and are each independently one selected from the group consisting of hydrogen; deuterium; linear or branched substituted or unsubstituted $C_1$ to $C_{60}$ alkyl; substituted or unsubstituted $C_6$ to $C_{60}$ monocyclic or polycyclic aryl; and substituted or unsubstituted $C_2$ to $C_{60}$ monocyclic or polycyclic heteroaryl.

8. The compound of claim 1, wherein the chemical formula 1 is selected from the following chemical formulas:

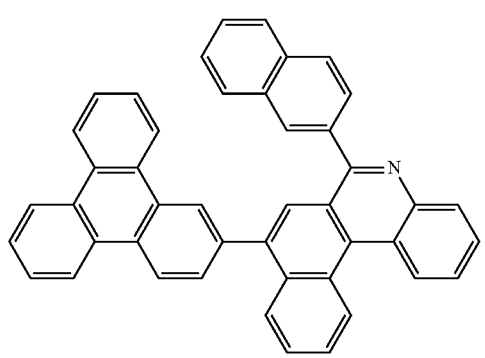

-continued
2
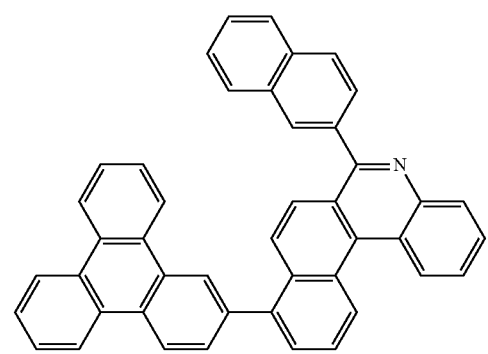
3
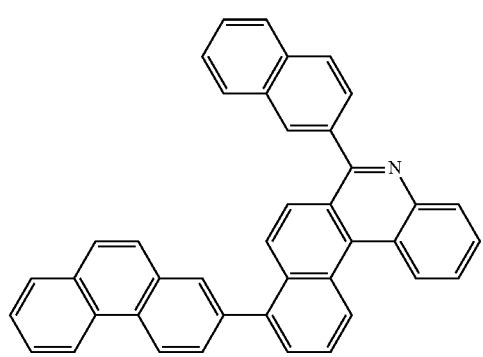
4
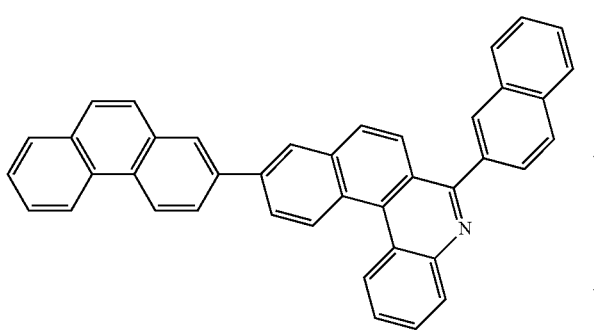
5
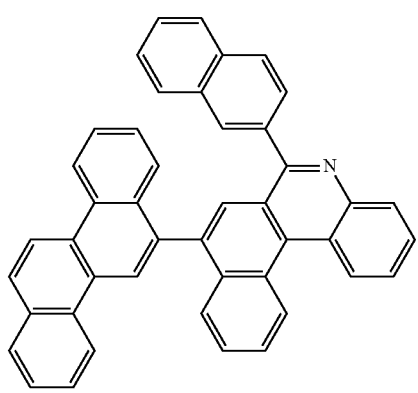
-continued
6
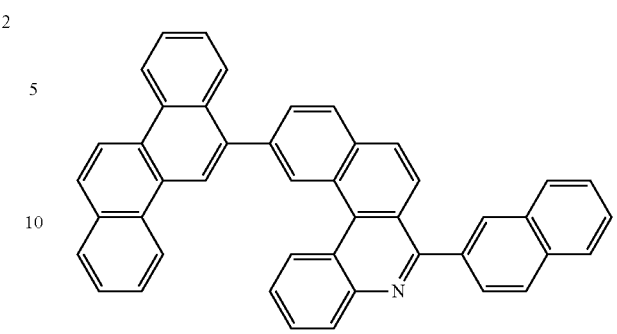
7
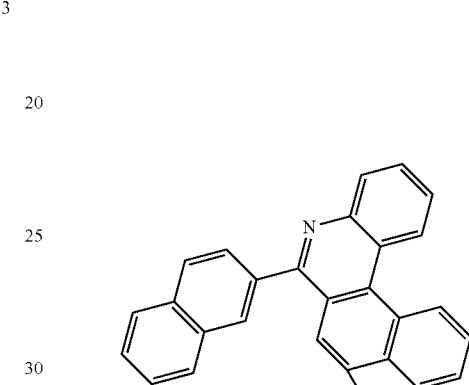
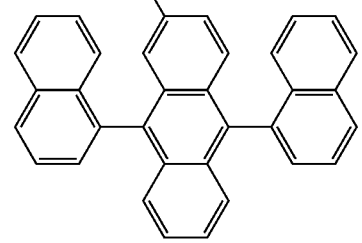
8
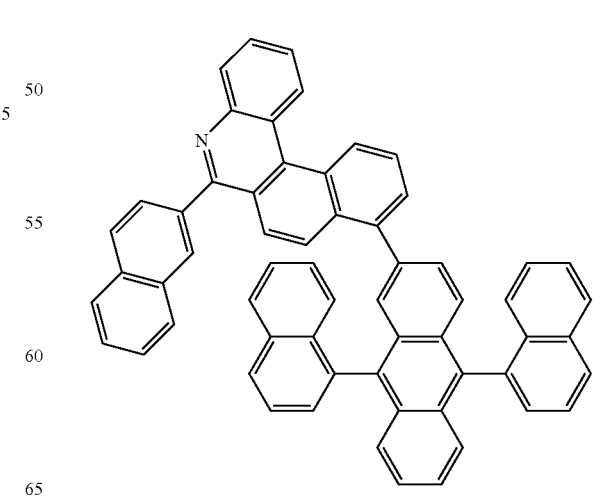

637
-continued
9
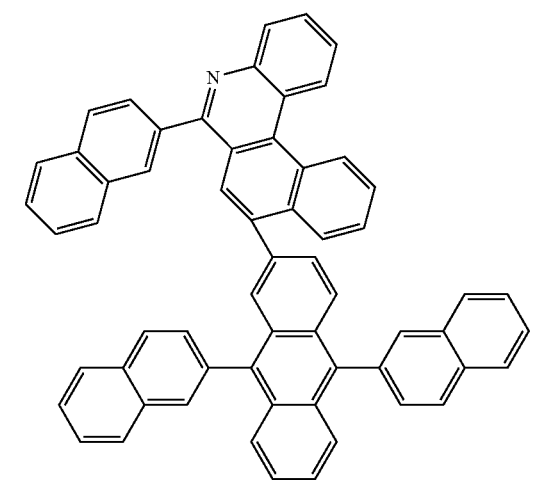
10
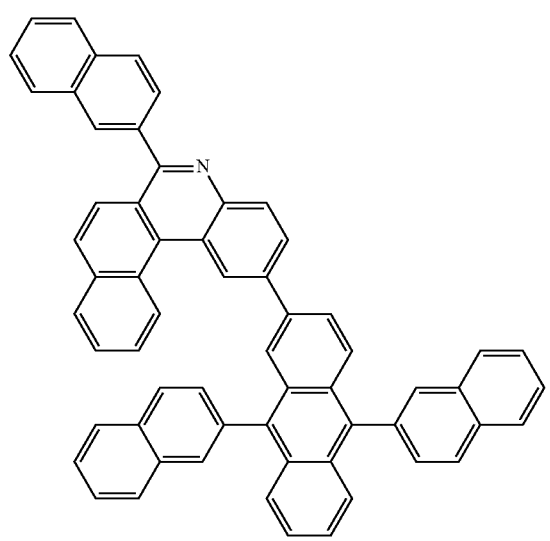
11
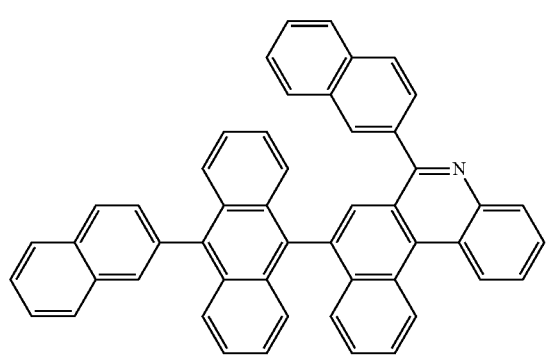
638
-continued
12
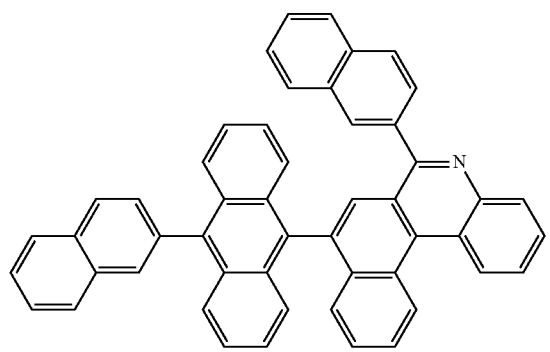
13
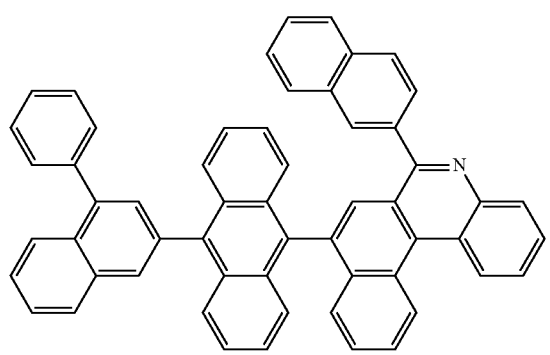
14
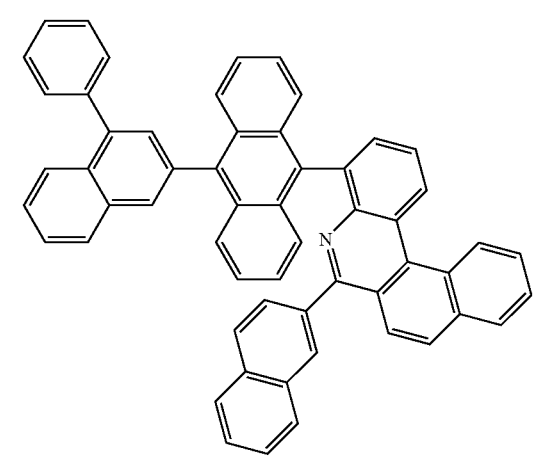
15
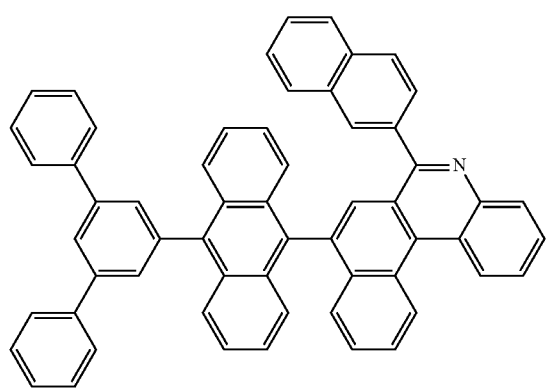

16
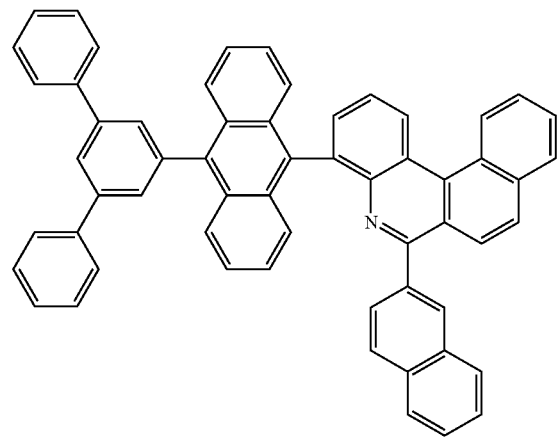
17
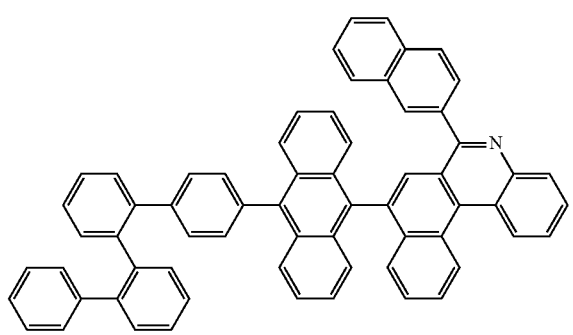
18
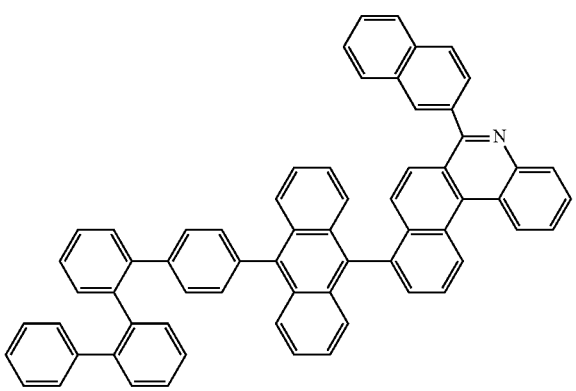
19
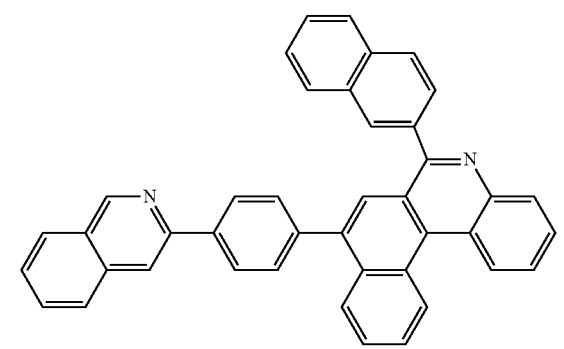
20
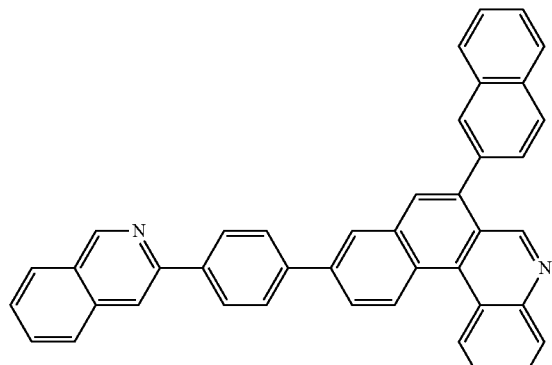
21
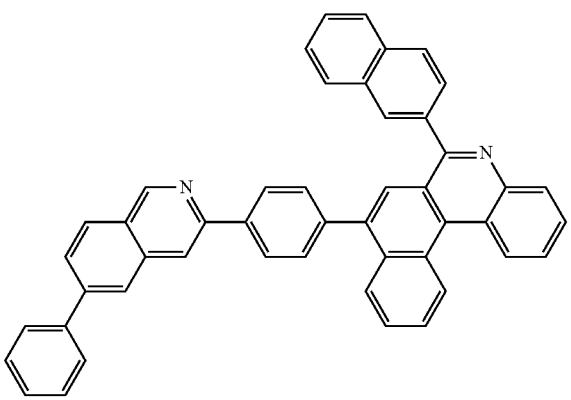
22
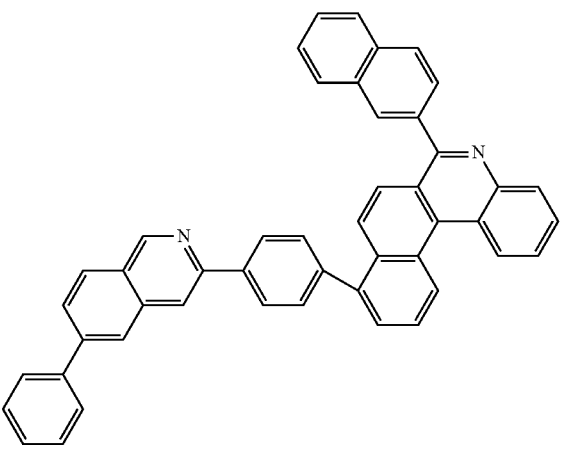
23
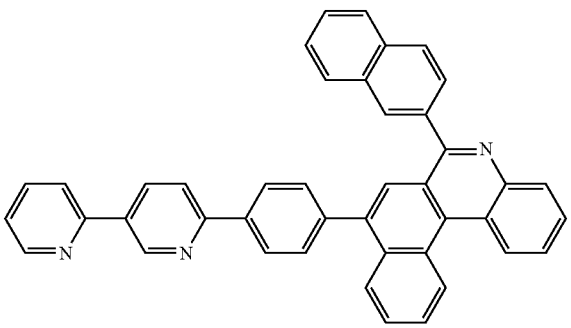

24
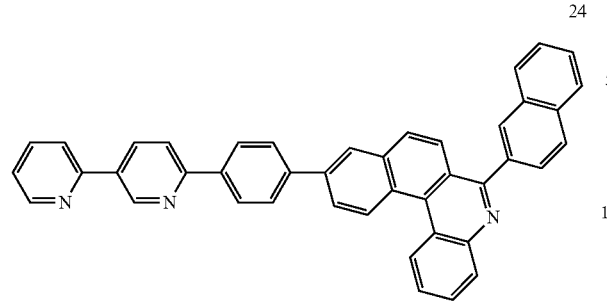
25
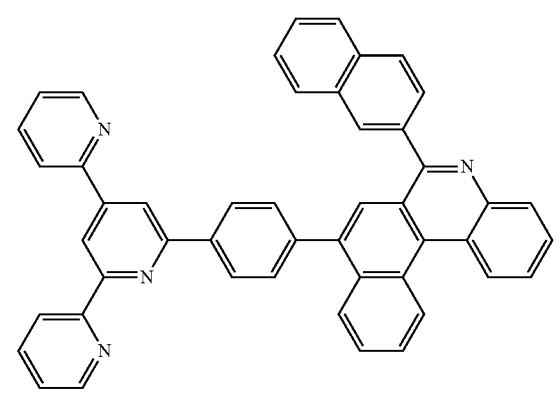
26
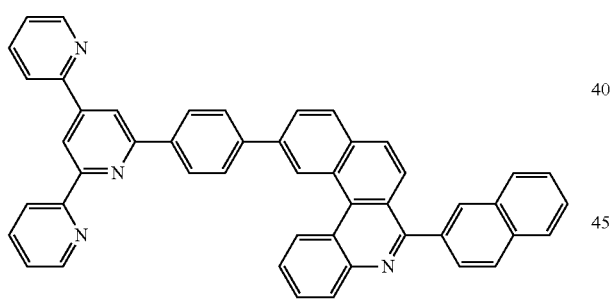
27
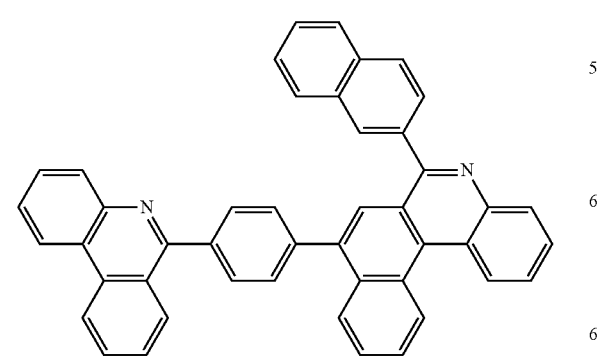
28
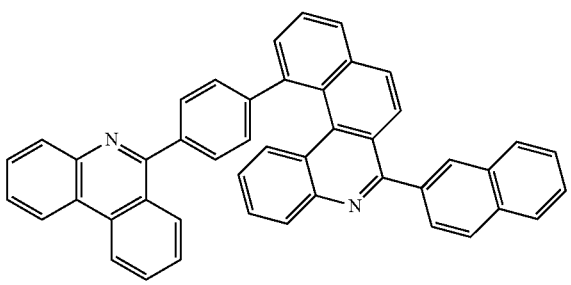
29
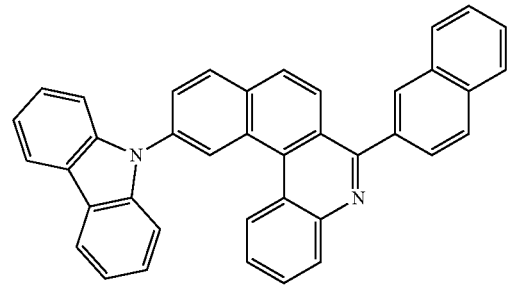
30
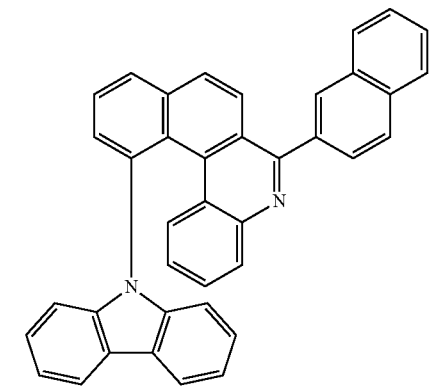
31
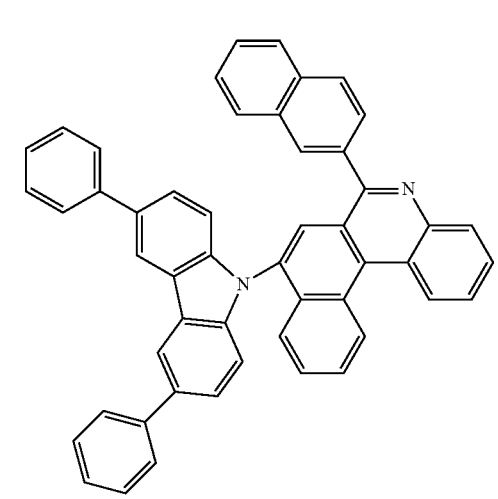

32
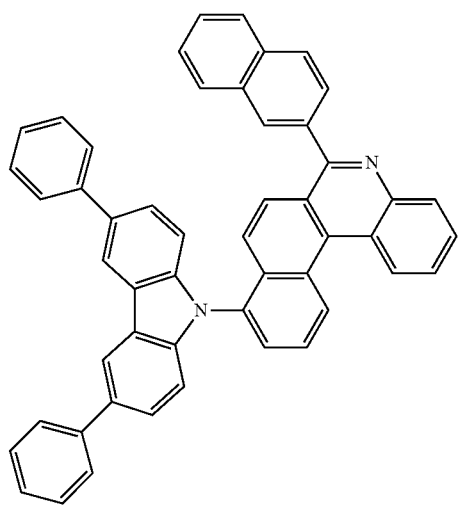
33
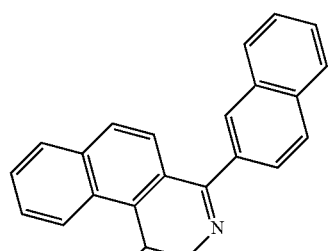
34
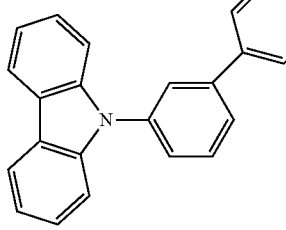
35
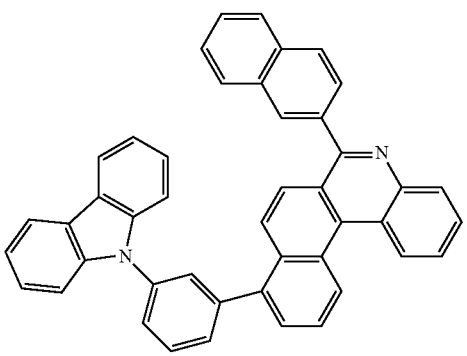
36
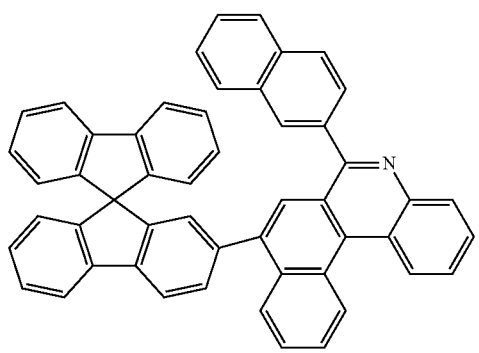
37
38
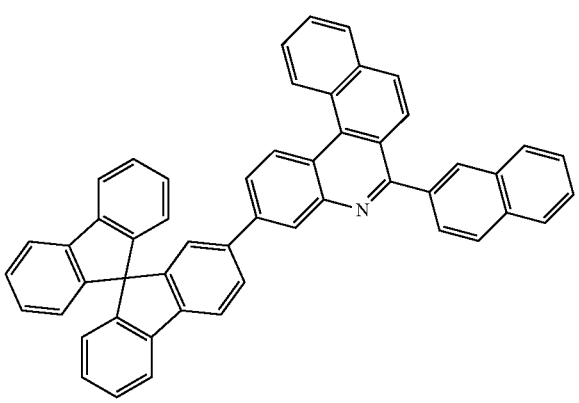

39
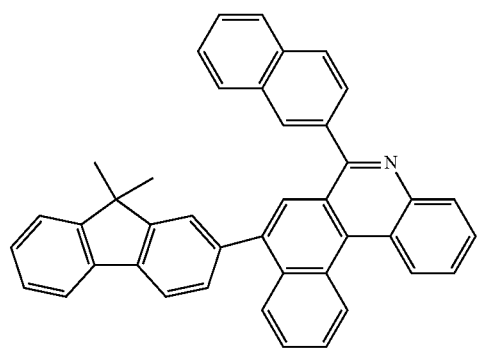
40
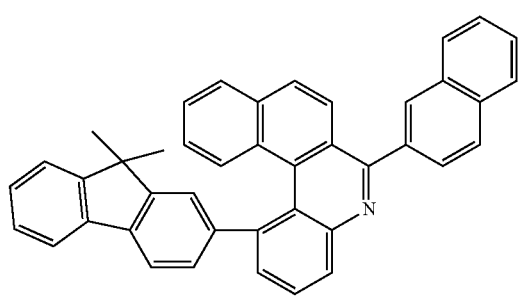
41
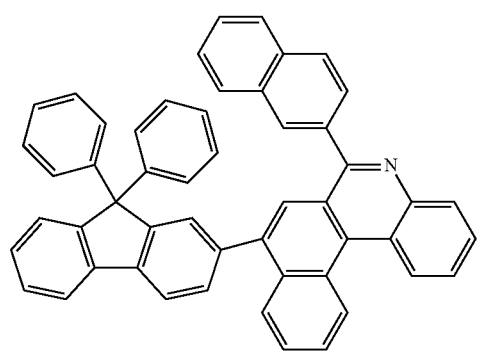
42
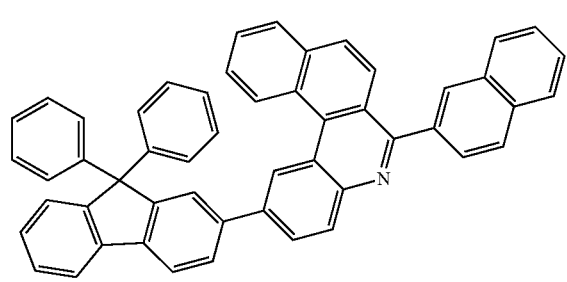
43
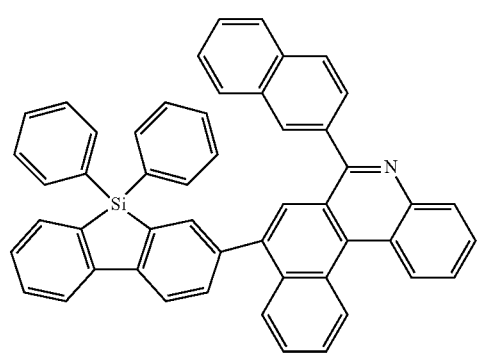
44
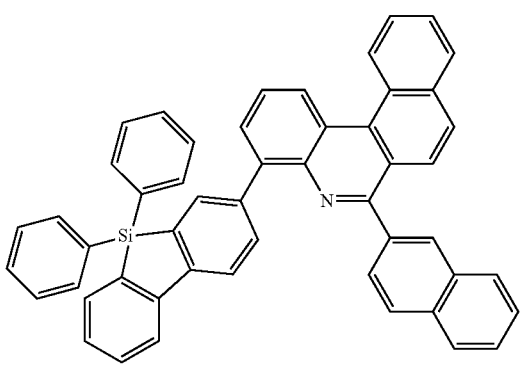
45
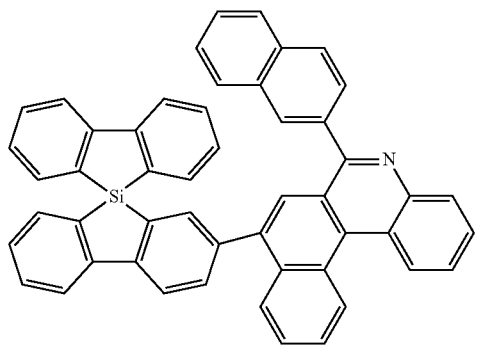
46
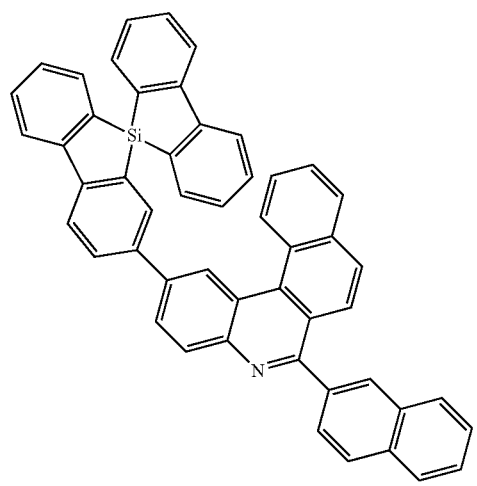
47
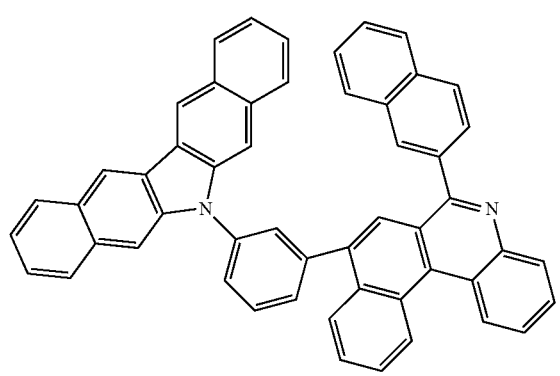

-continued
48
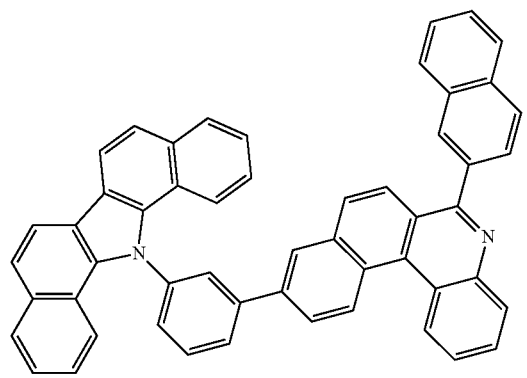
49
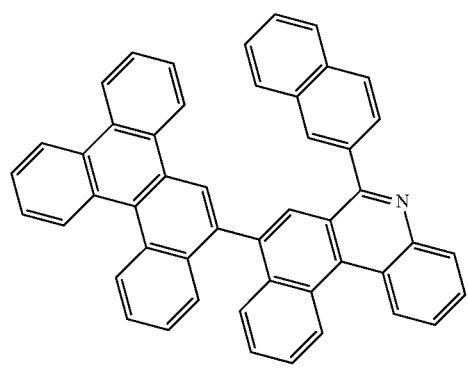
50
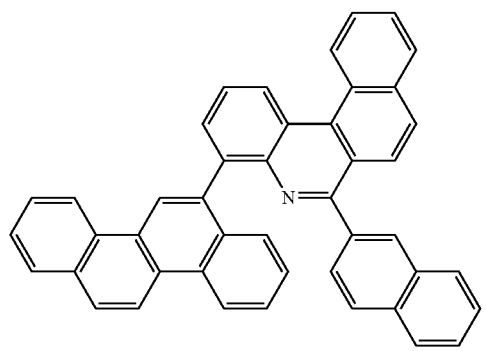
51
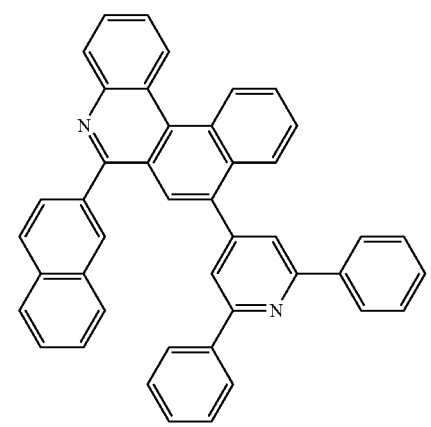
-continued
52

53

54
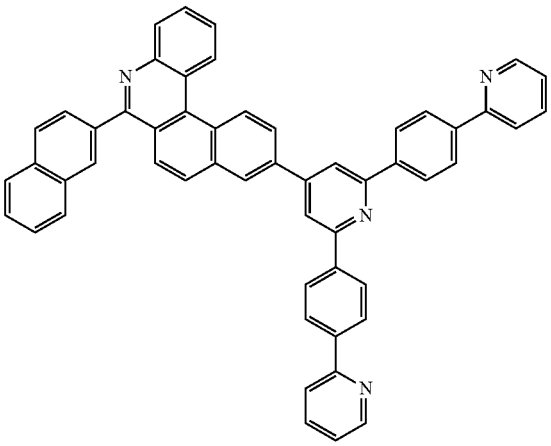
55
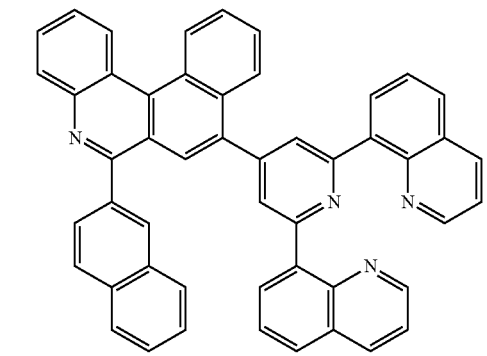

-continued
56
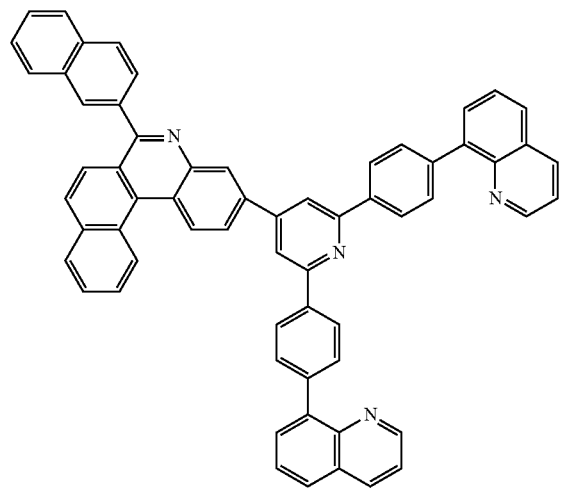
57
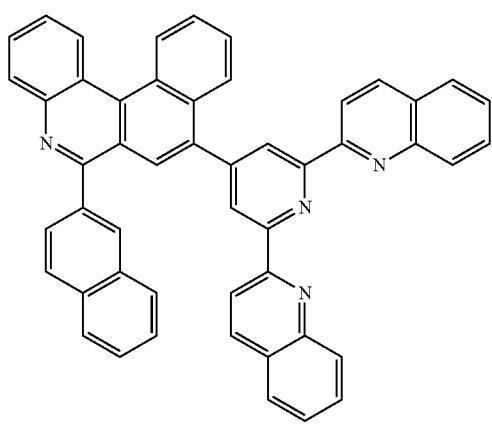
58
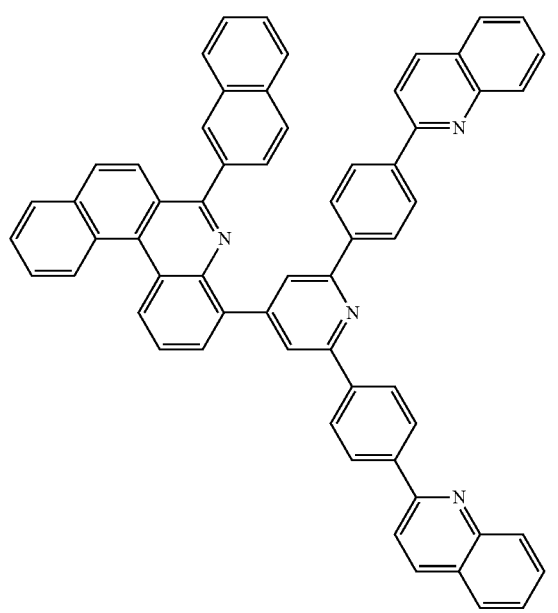
-continued
59
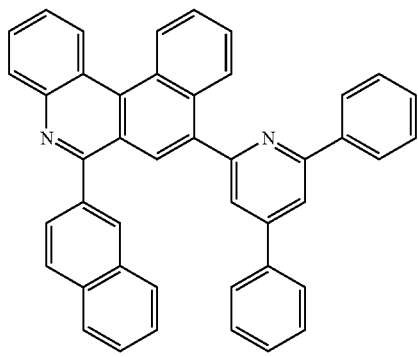
60
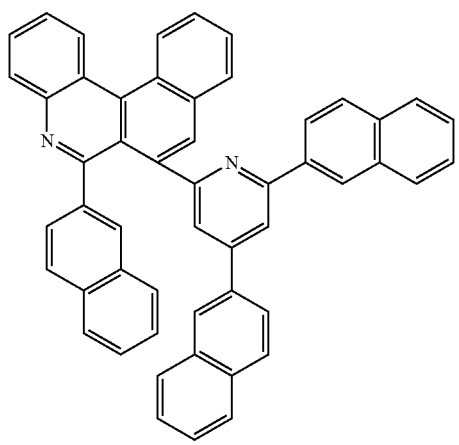
61
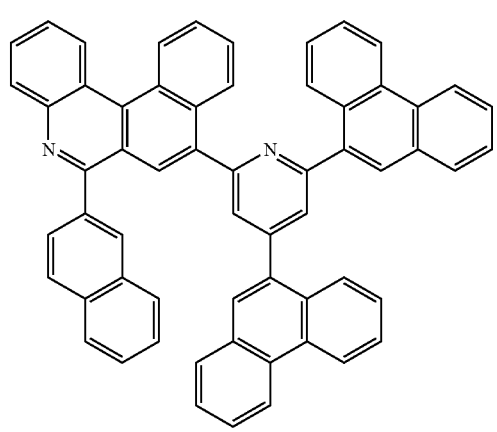

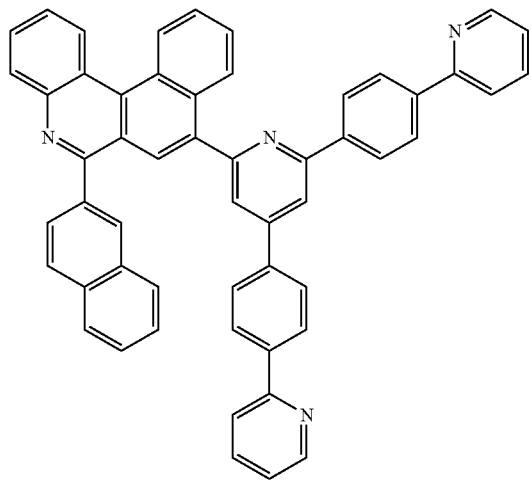
62
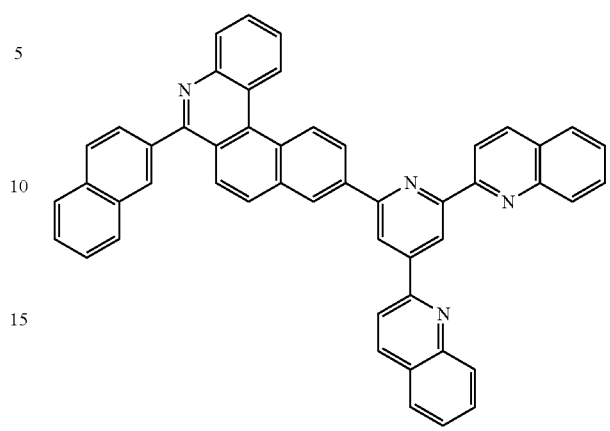
65
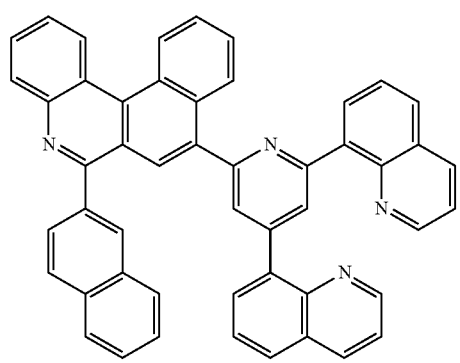
63
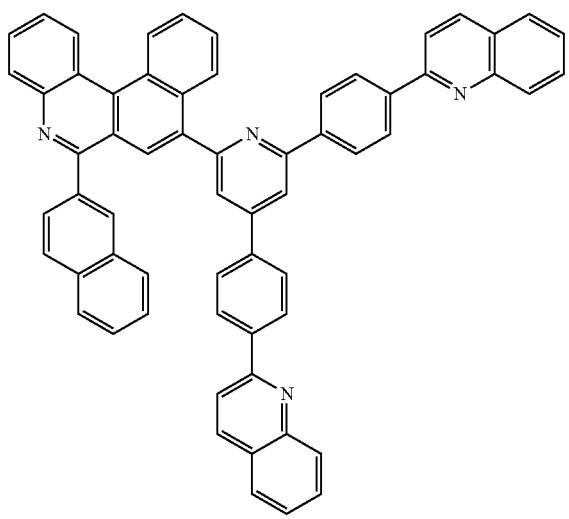
66
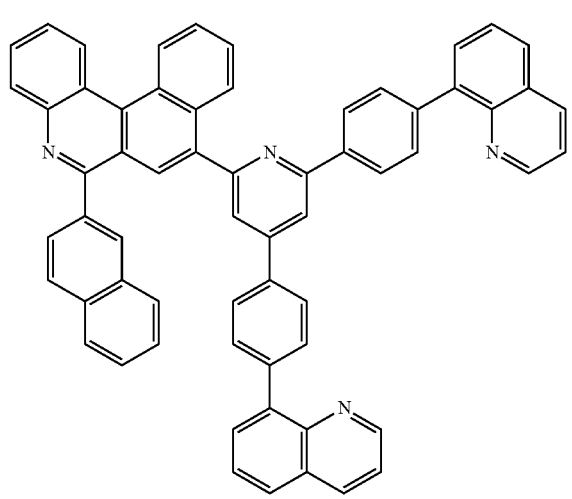
64
67

-continued
68
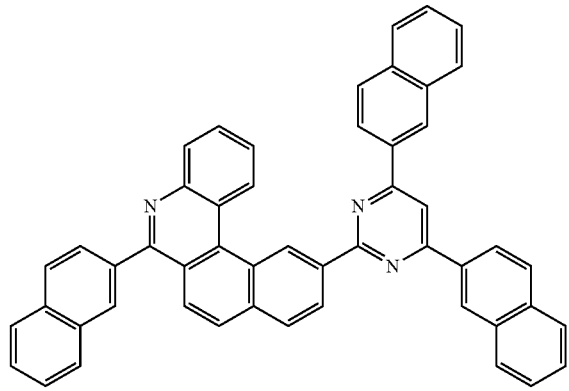
69
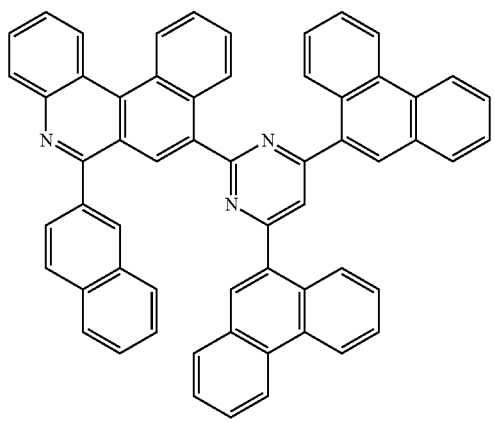
70
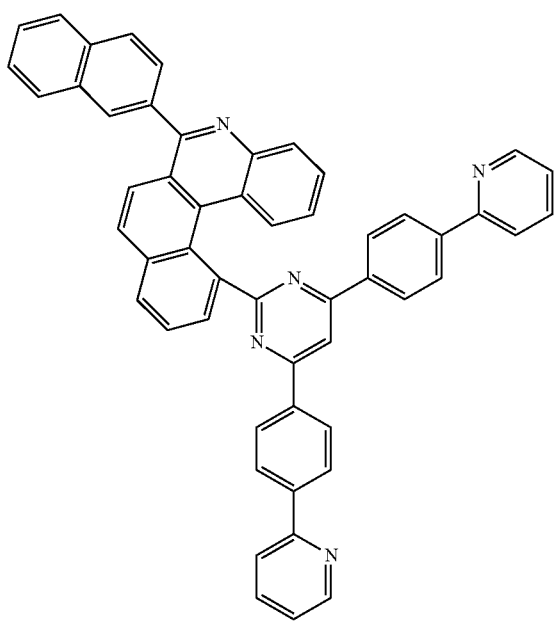
-continued
71
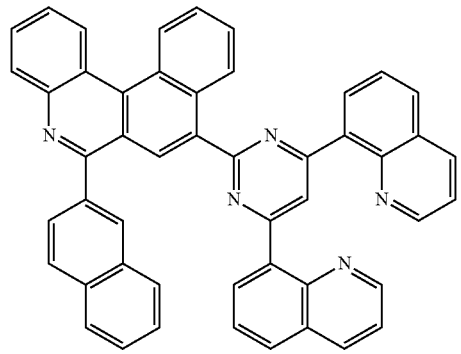
72
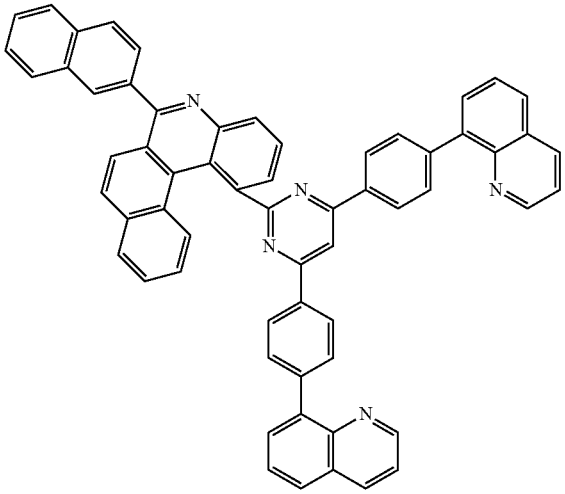
73
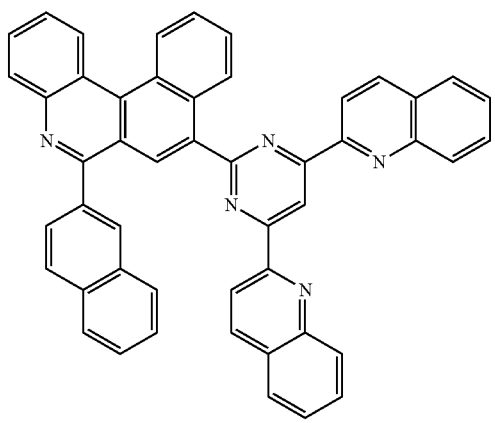

74
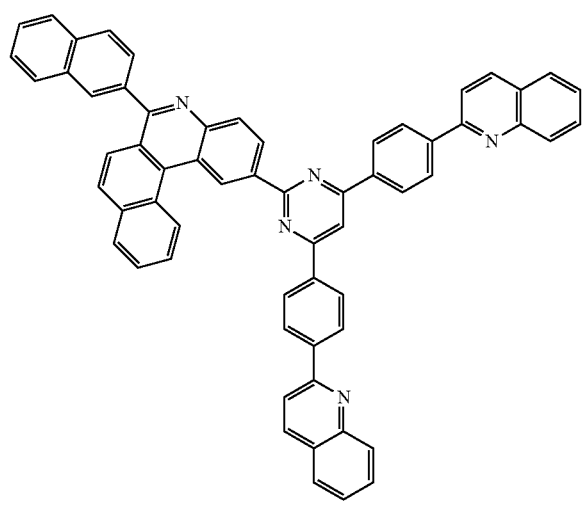
77
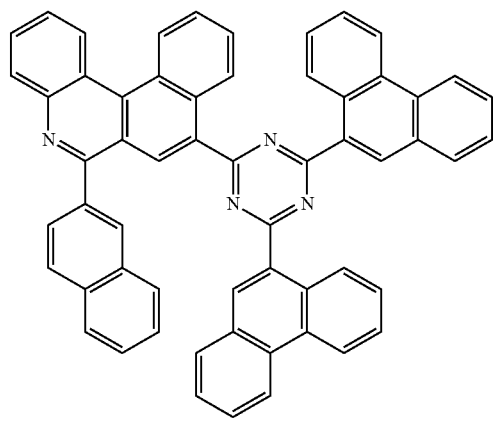
75
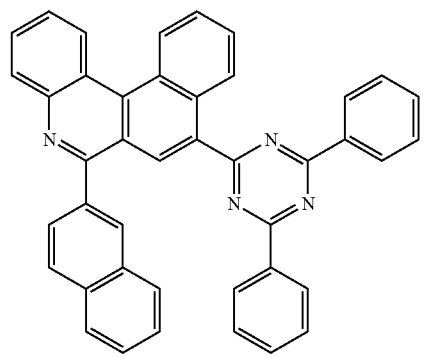
78
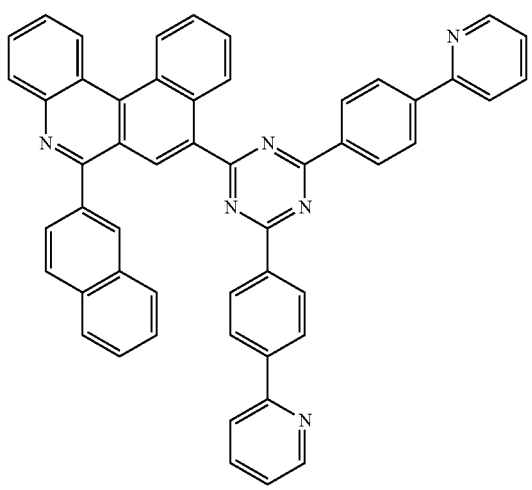
76
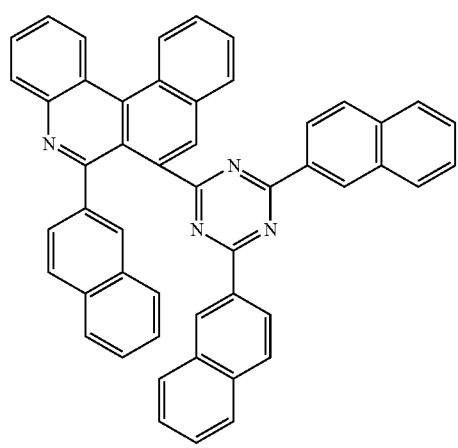
79
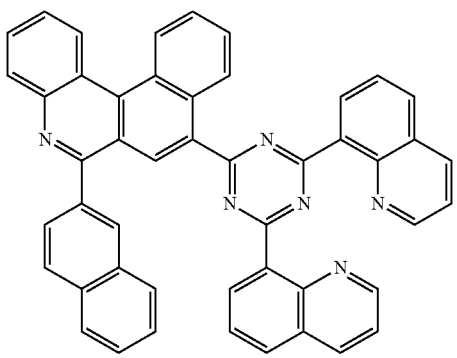

80
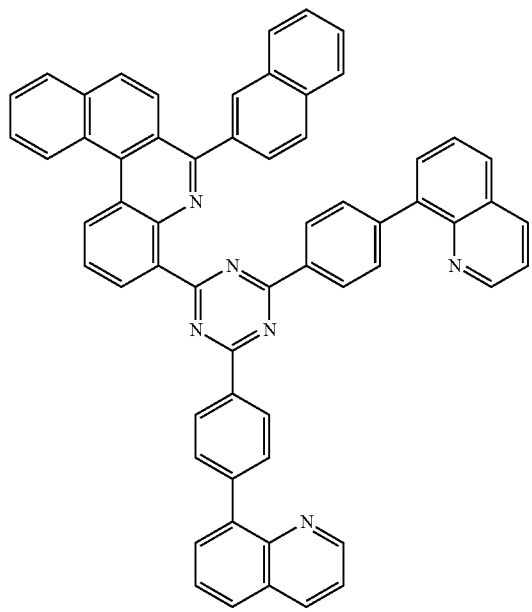
81
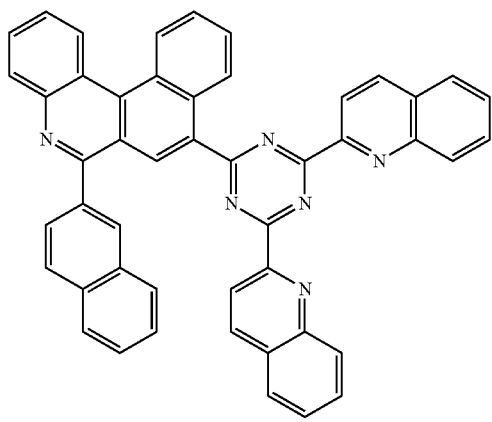
82
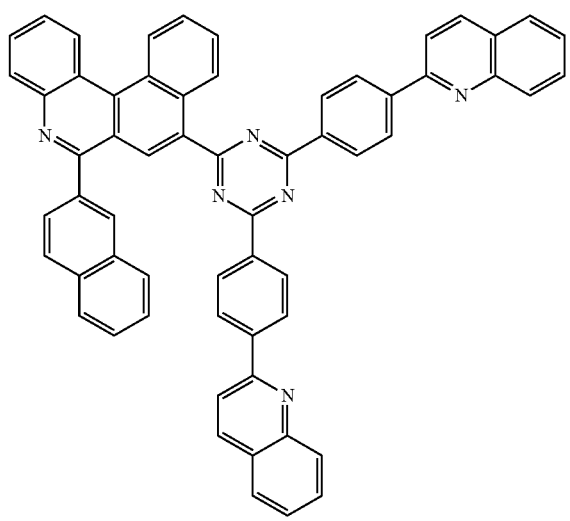
83
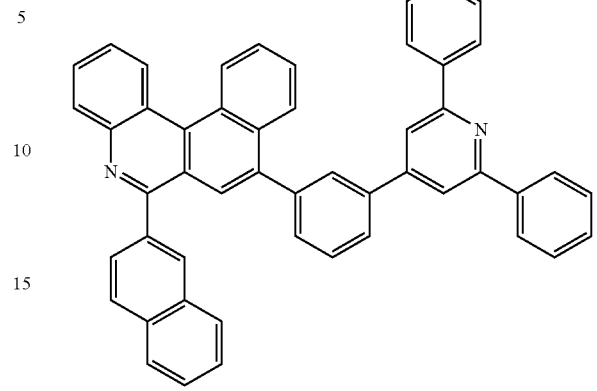
84
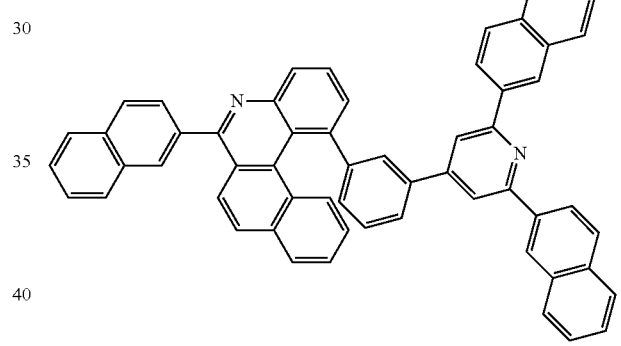
85
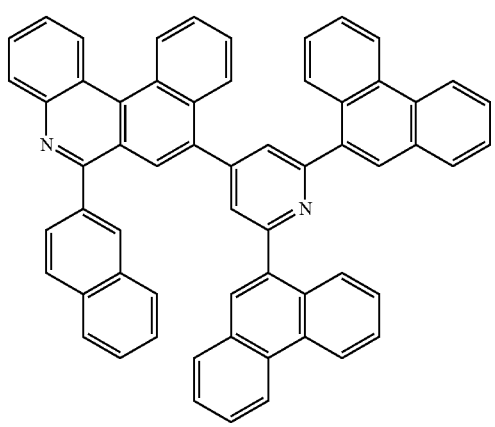

86
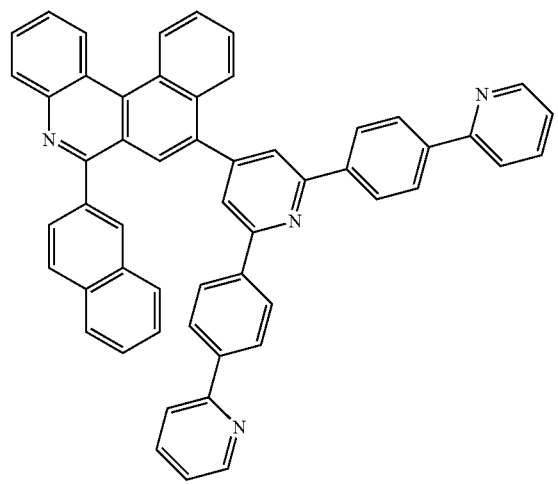
87
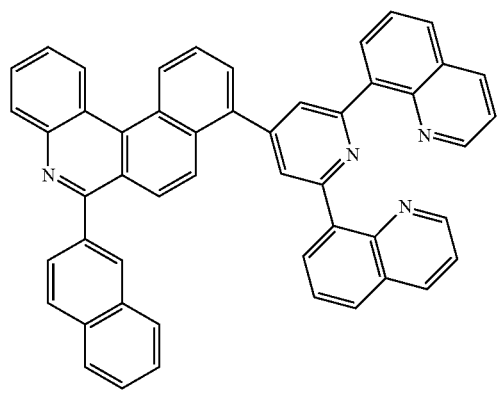
88
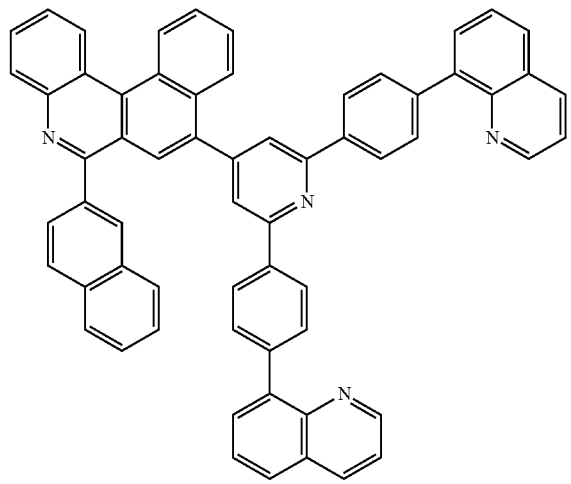
89
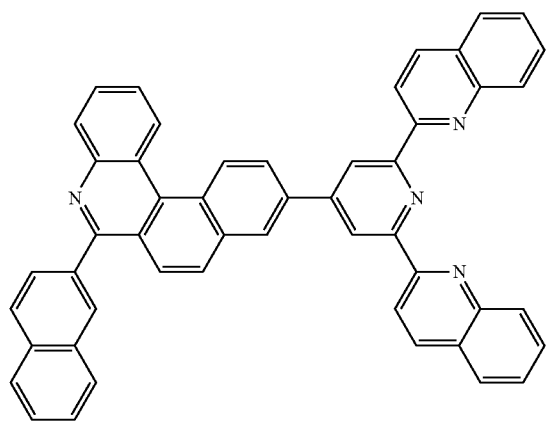
90
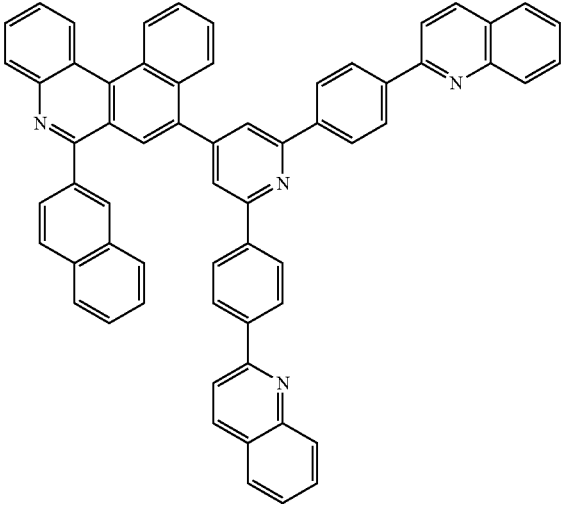
91
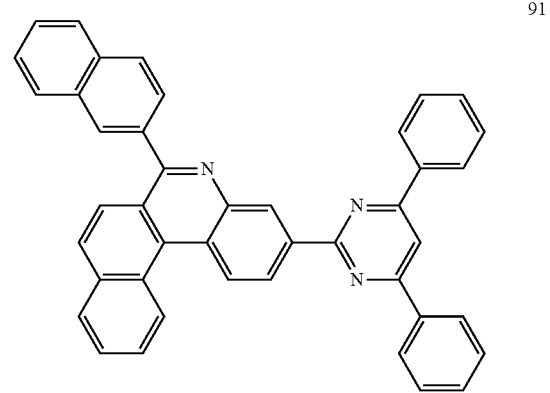

661
-continued
92
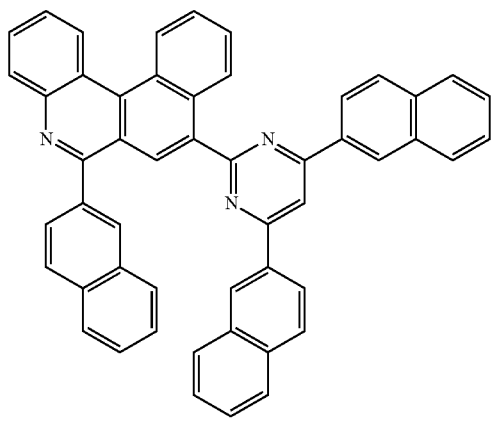
93
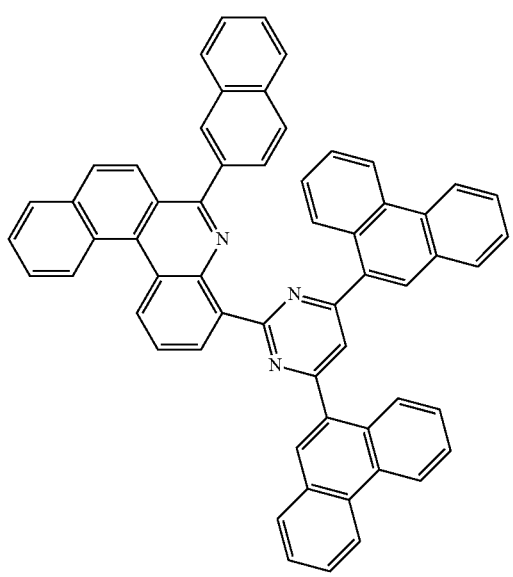
94
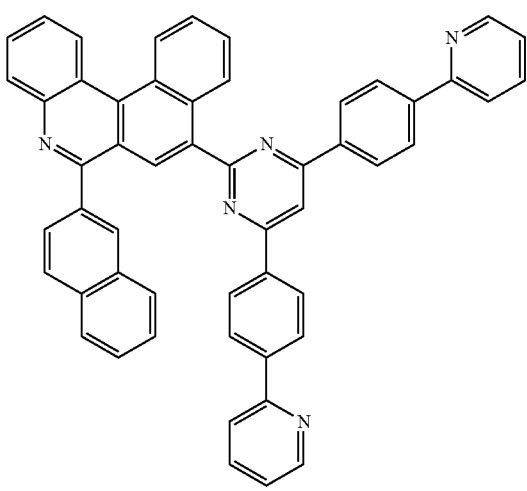
662
-continued
95
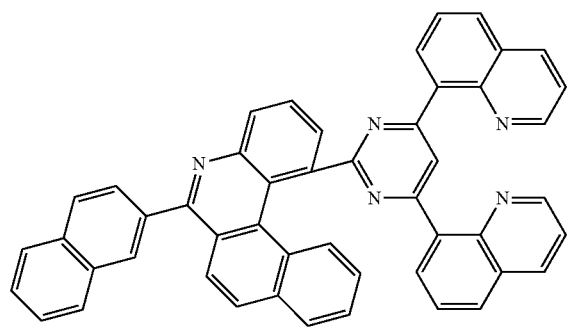
96
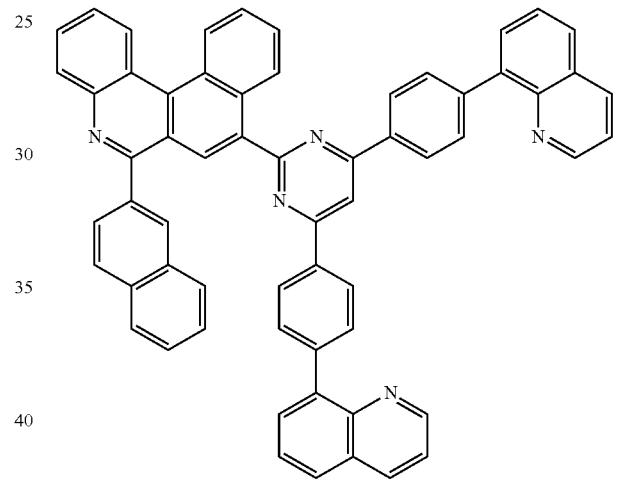
97
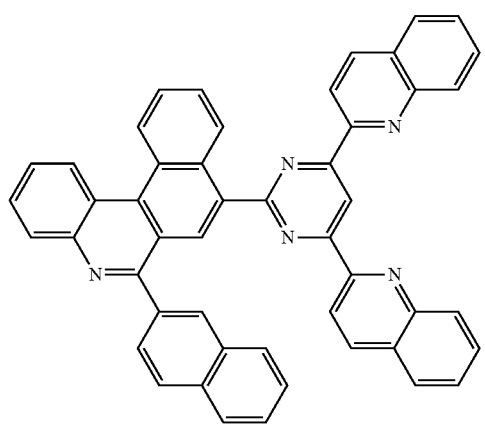

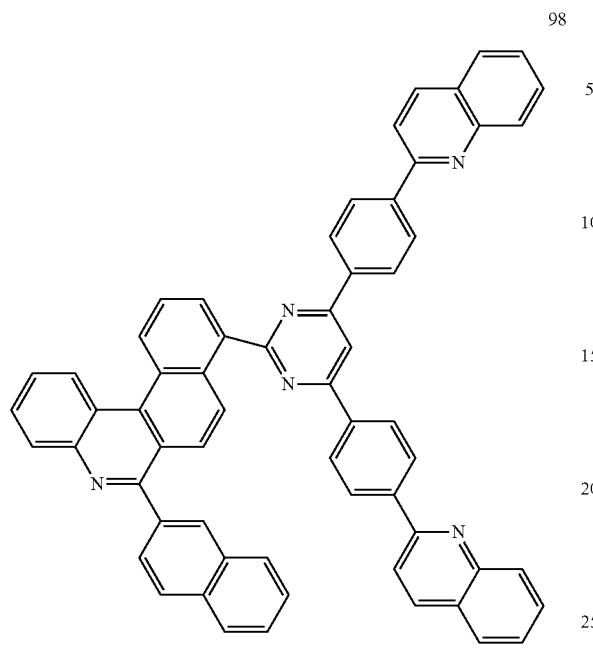
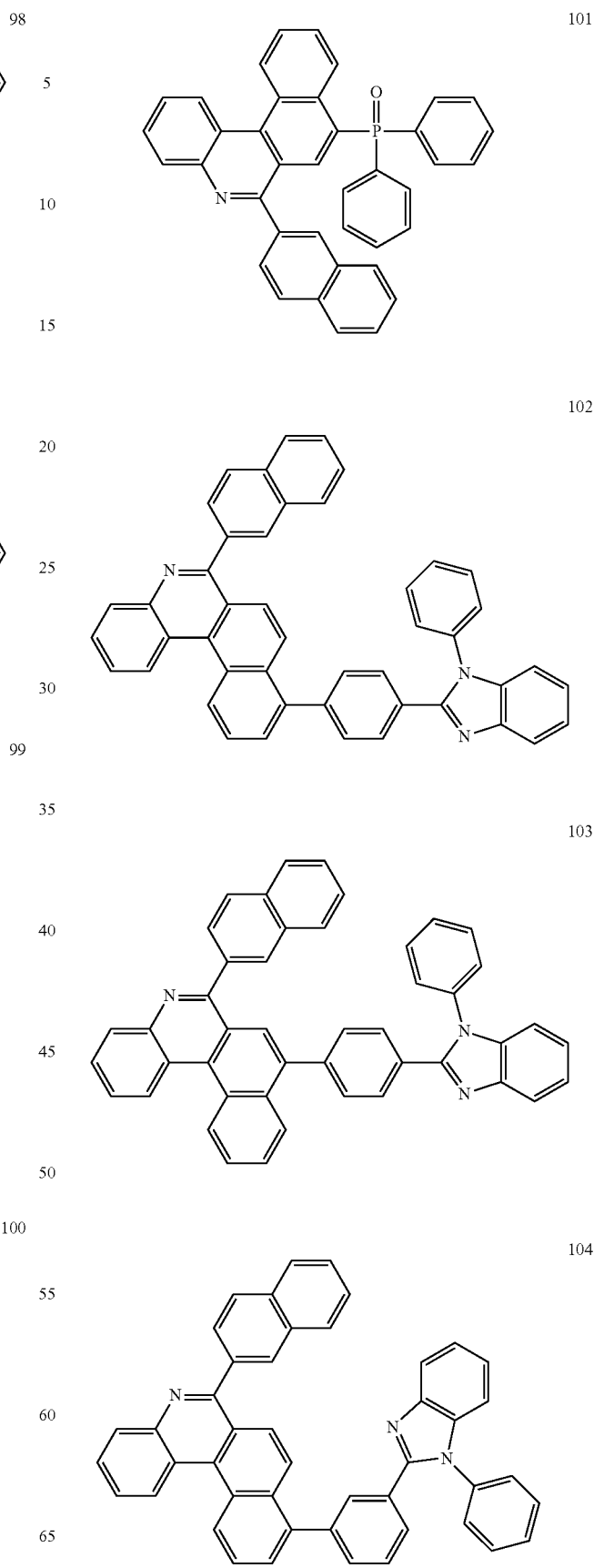

665
-continued
105
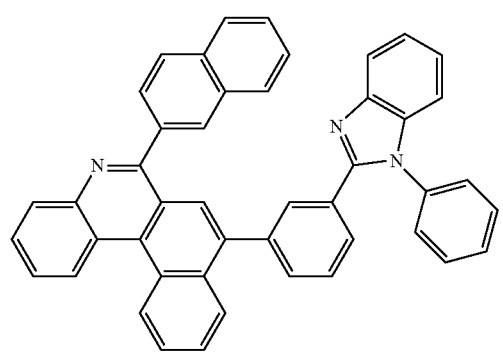
106
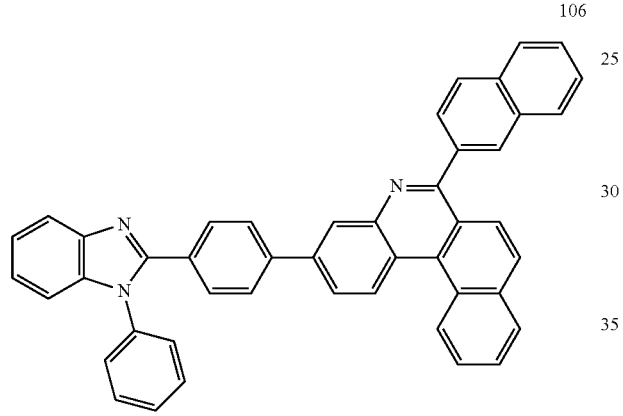
107
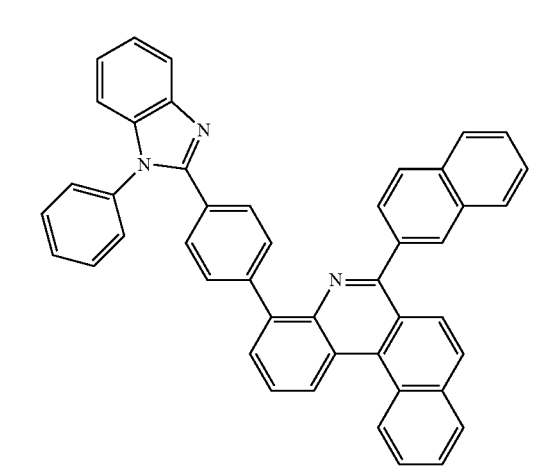
666
-continued
108
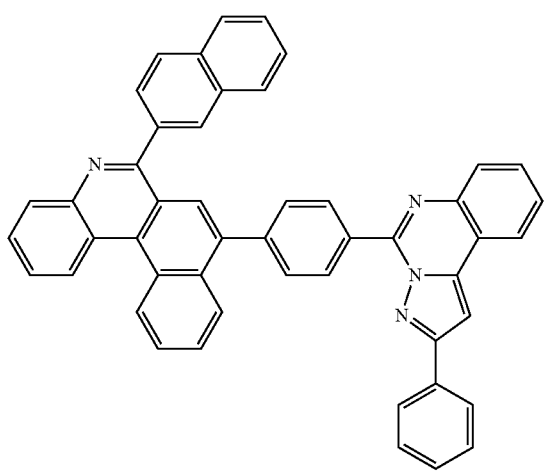
109
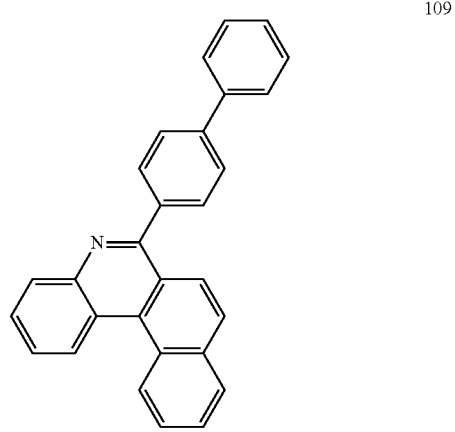
110
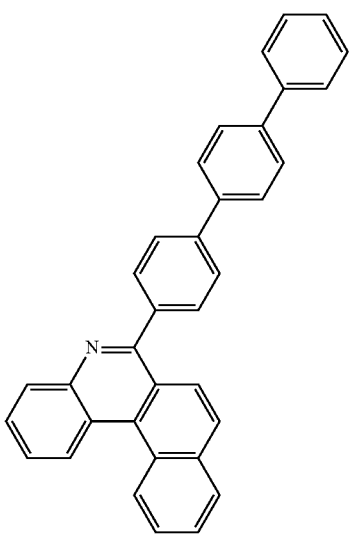

111
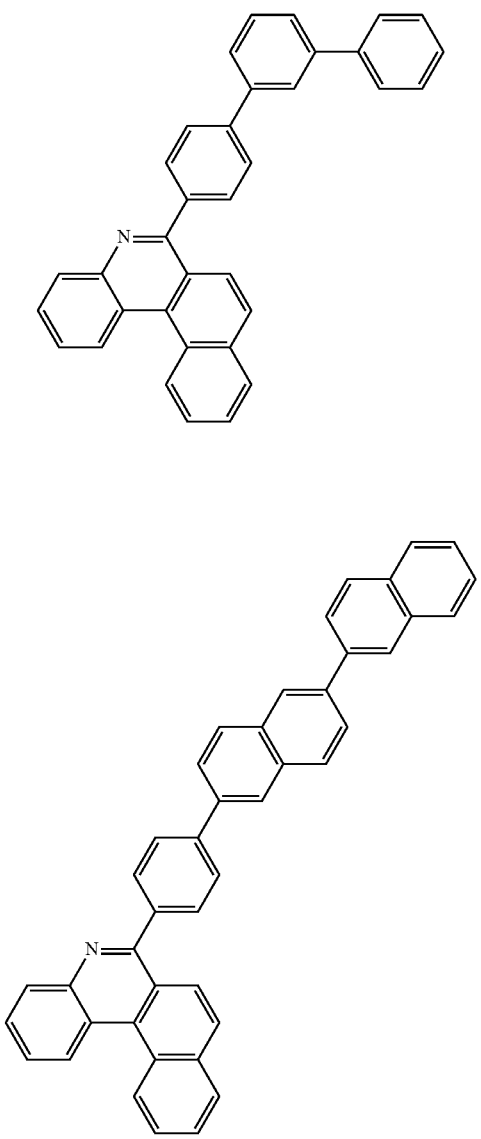
112
113
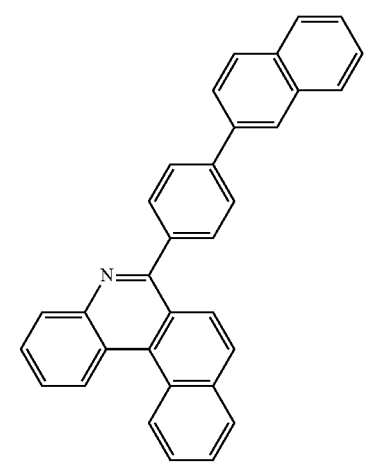
114
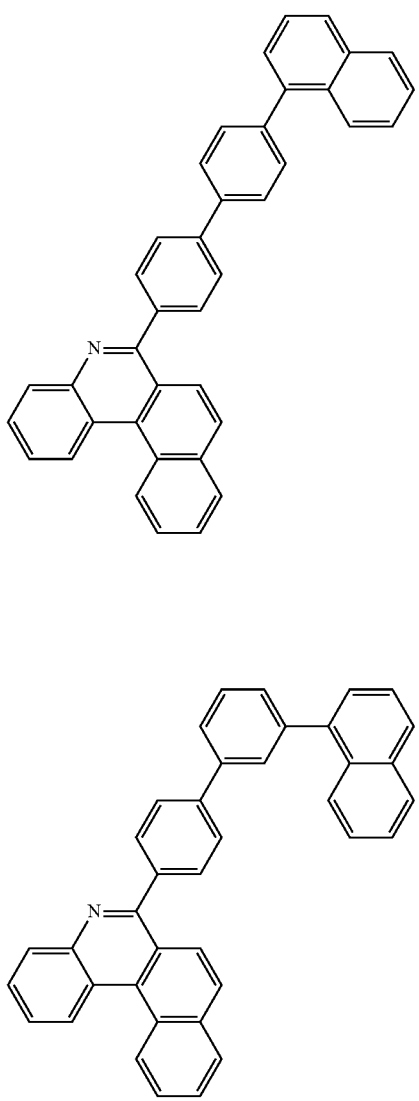
115
116
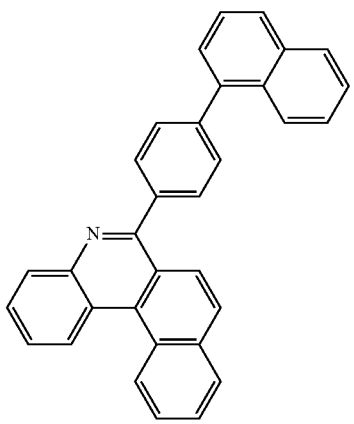

117
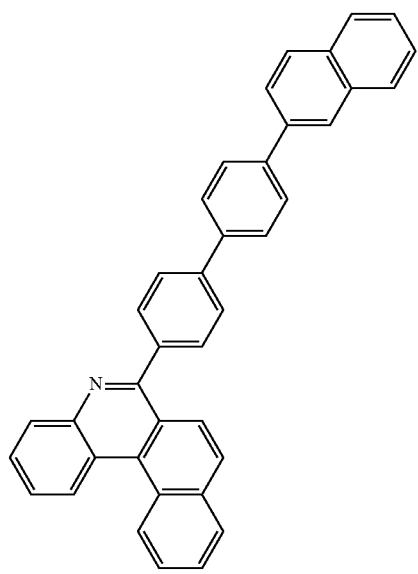
118
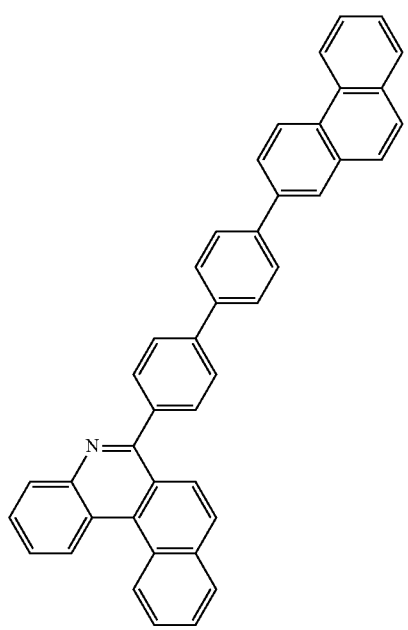
119
120
121
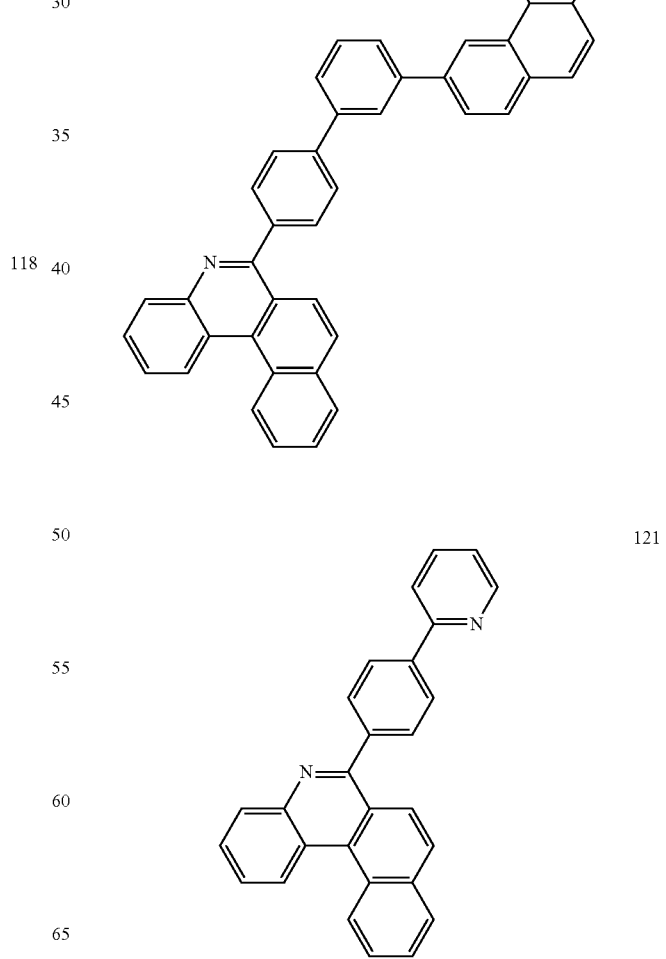

-continued
122
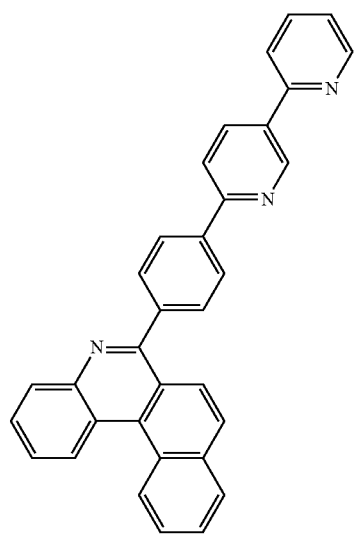
123
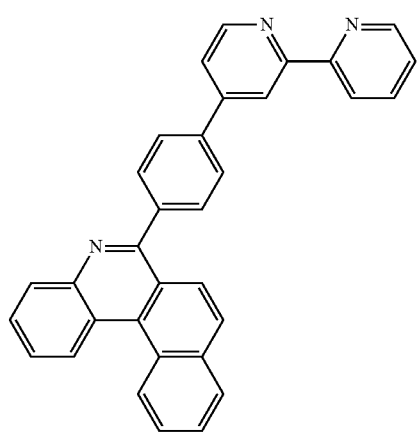
124
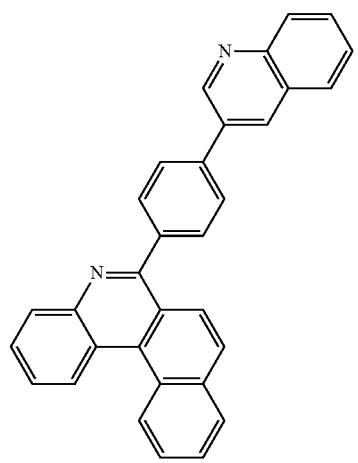
-continued
125
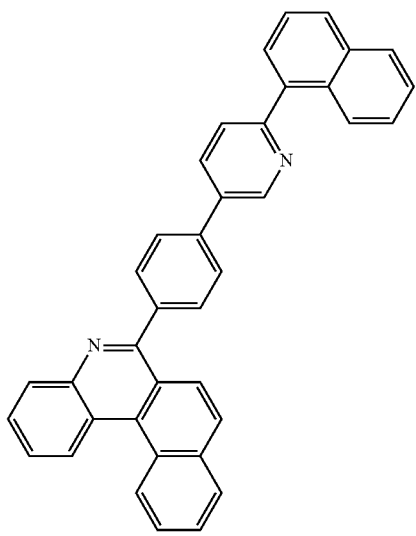
126
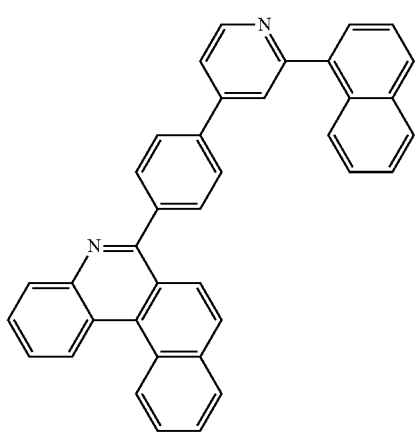
127
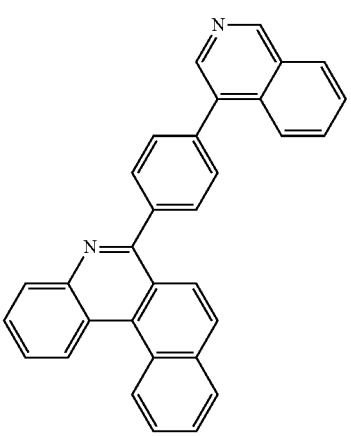

128
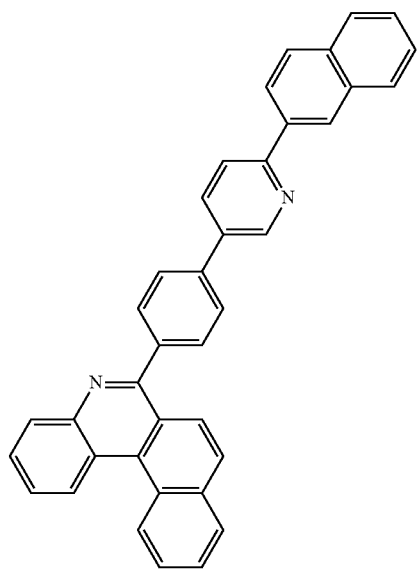
129
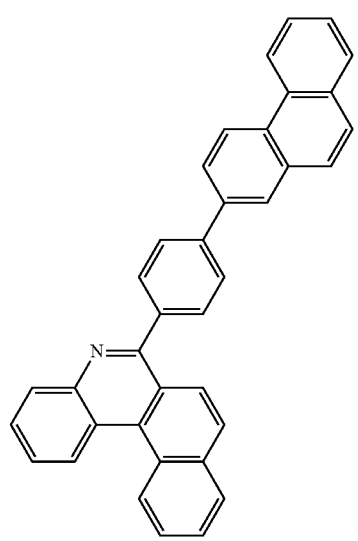
130
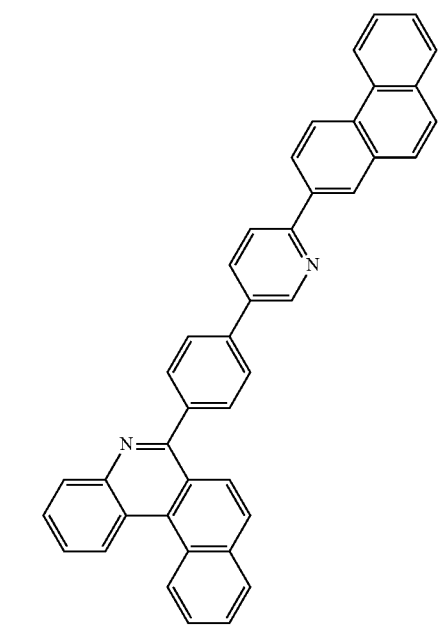
131

132
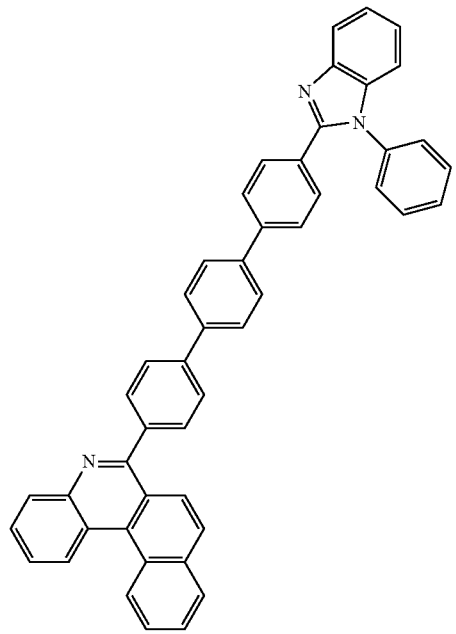
133
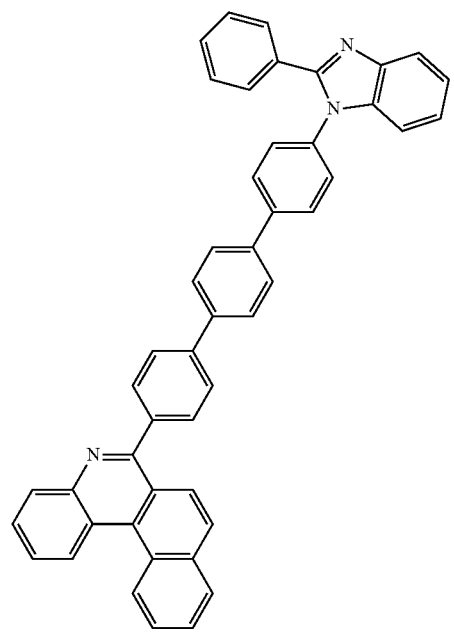
134
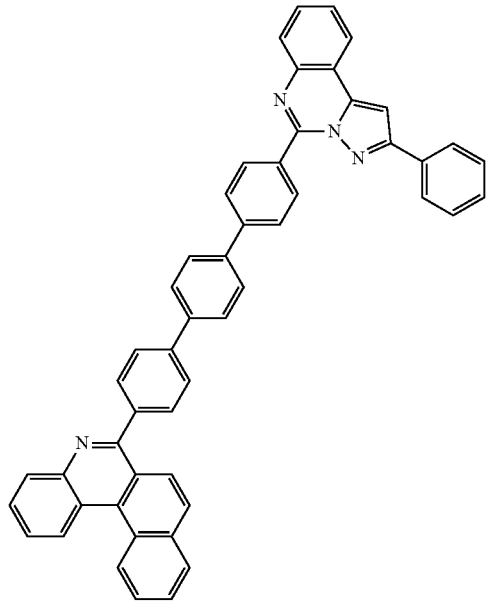
135
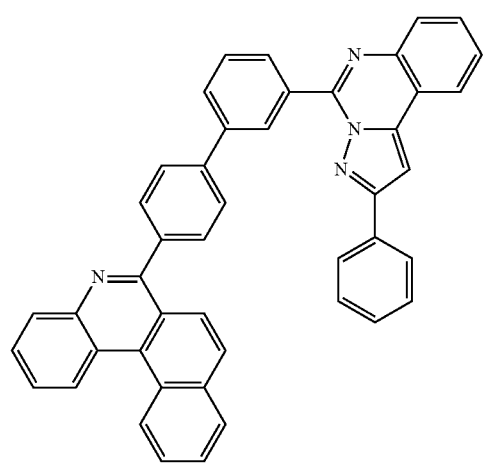
136
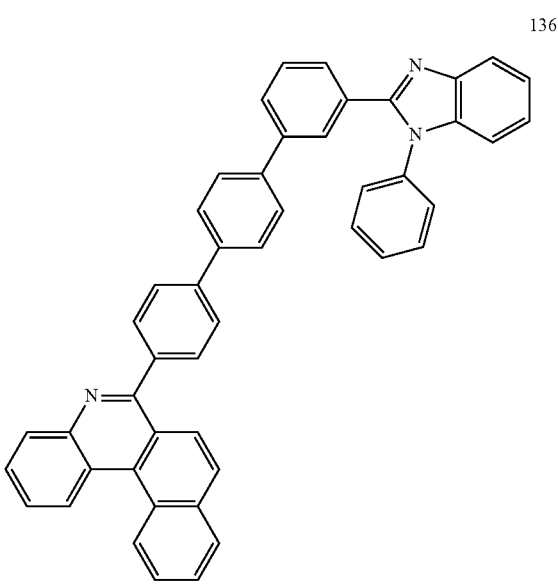

677
-continued
138
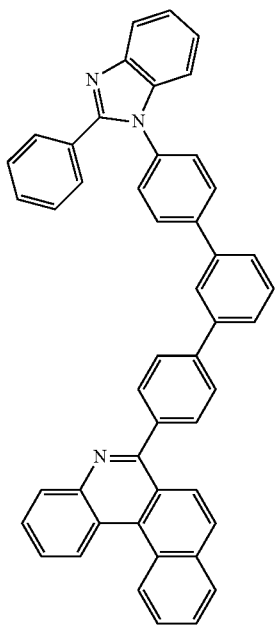
678
-continued
140
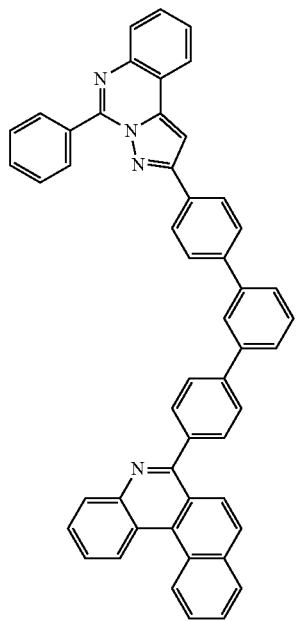
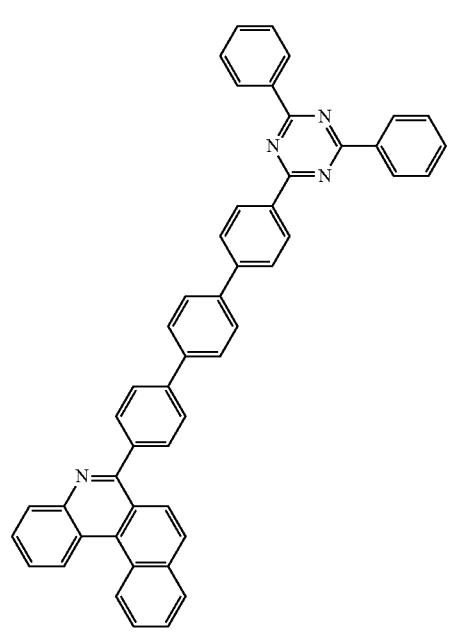

679
-continued
141
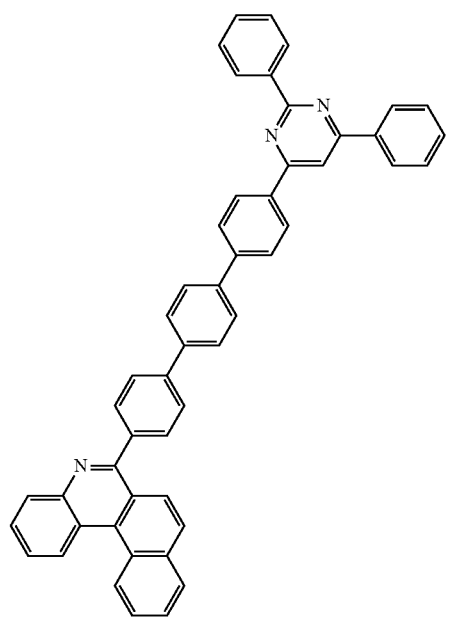
142
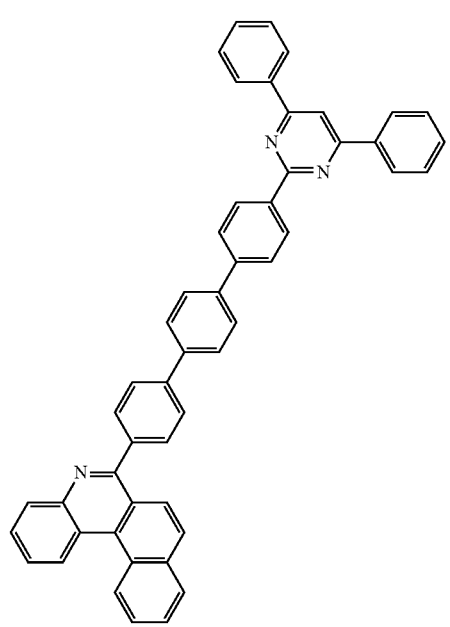
680
-continued
143
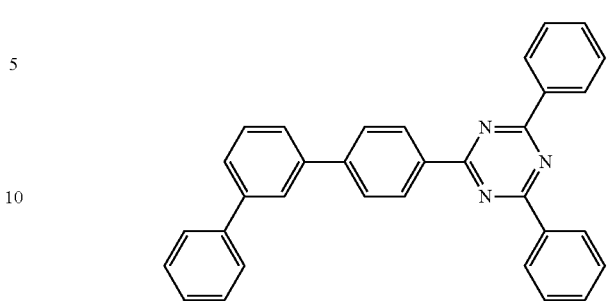
144
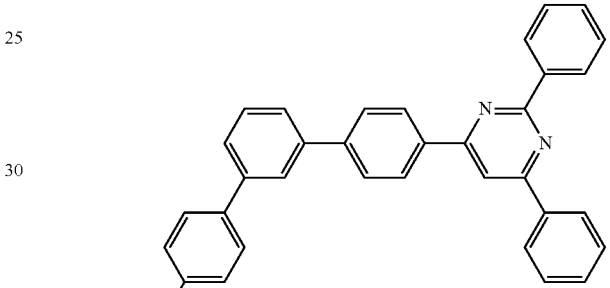
145
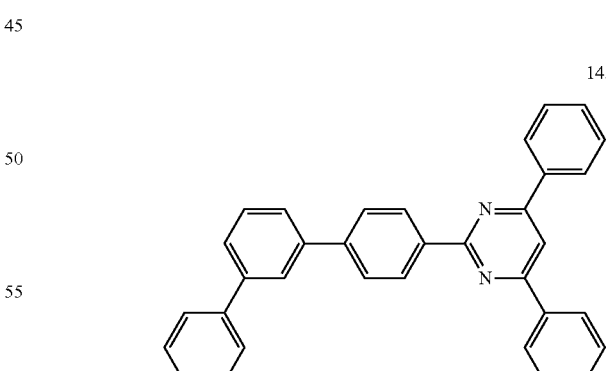

681
-continued
682
-continued
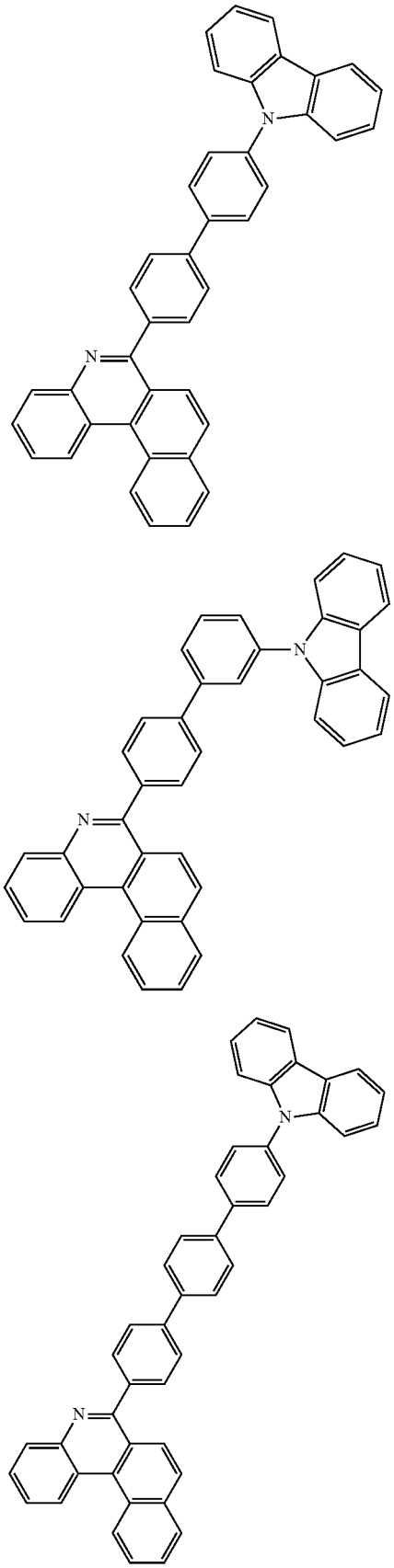

683
-continued
151
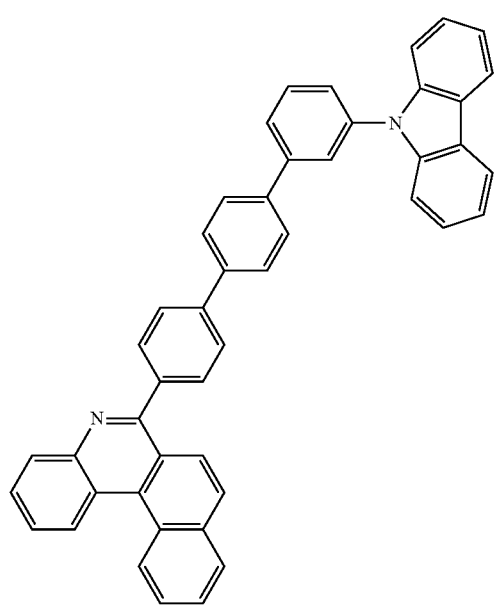
152
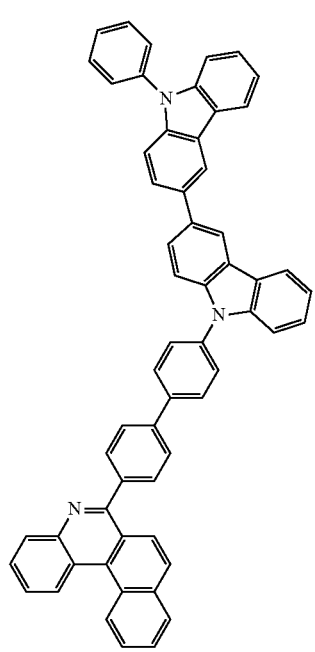
684
-continued
153
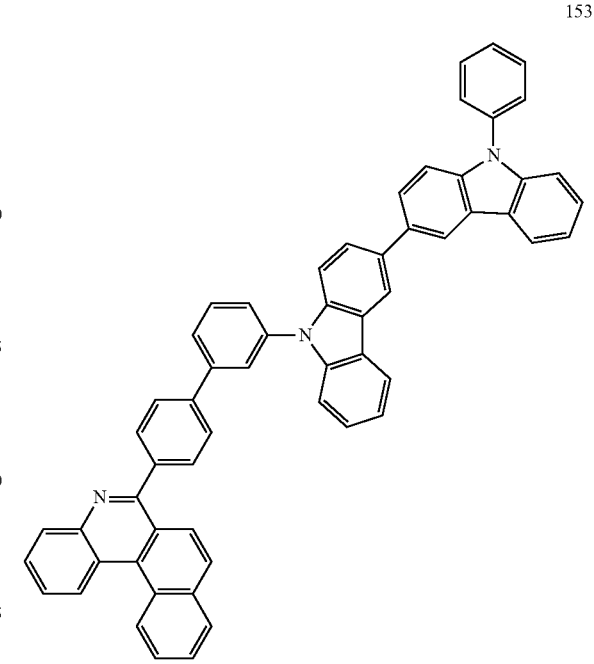
154

155
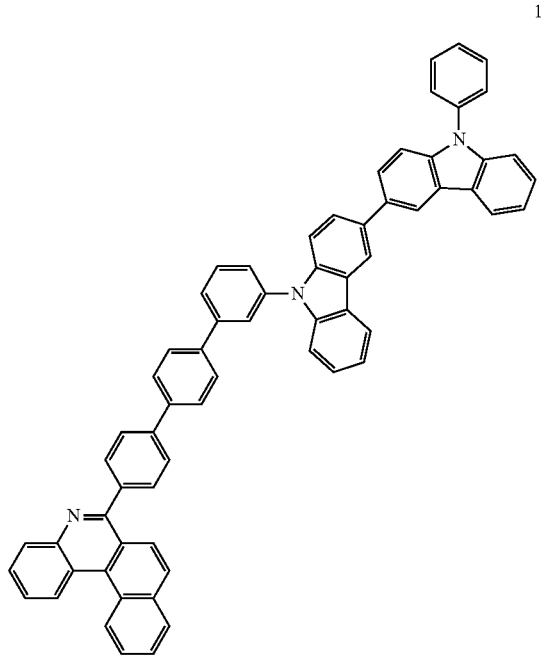
156
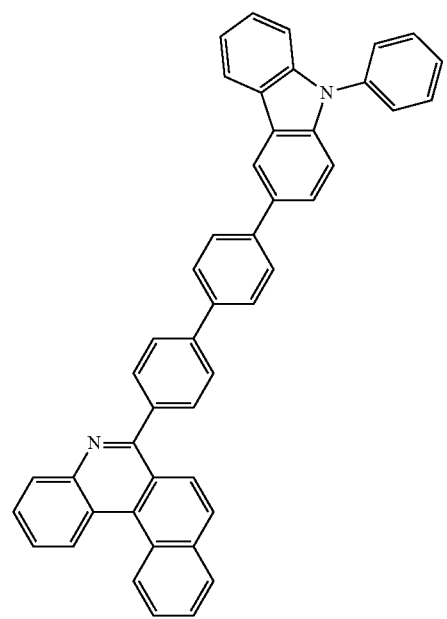
157
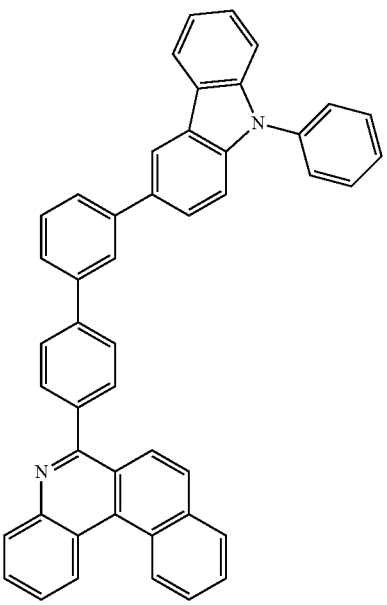
158
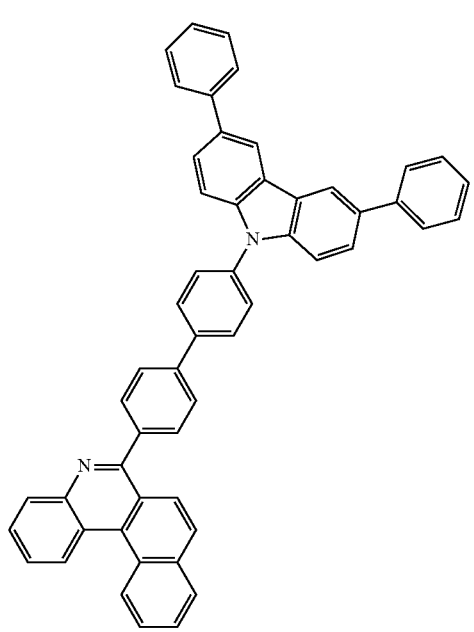

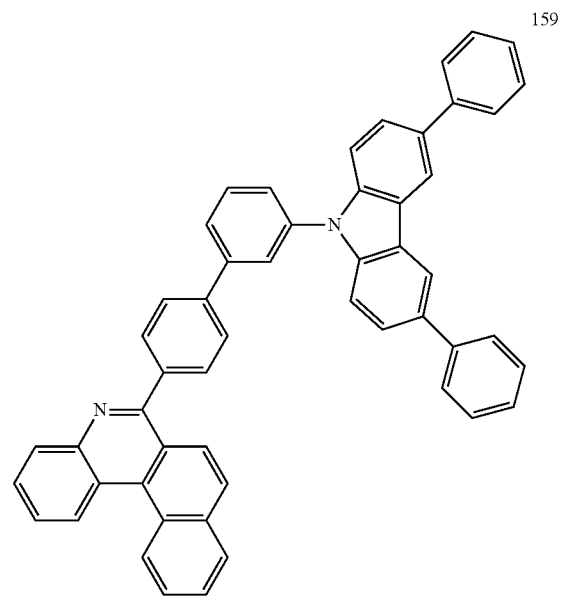
159
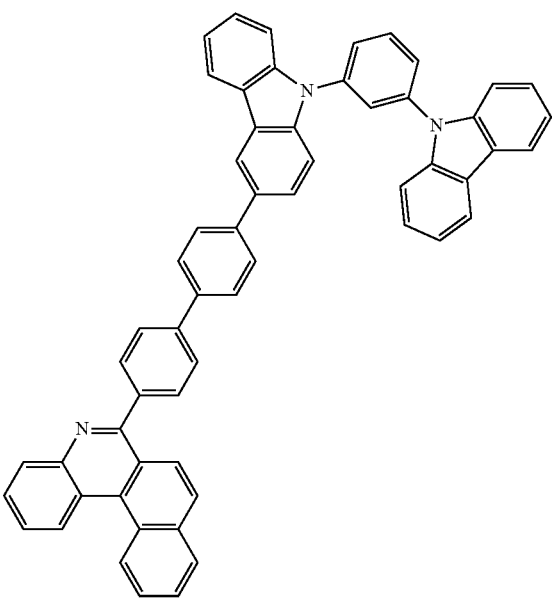
161
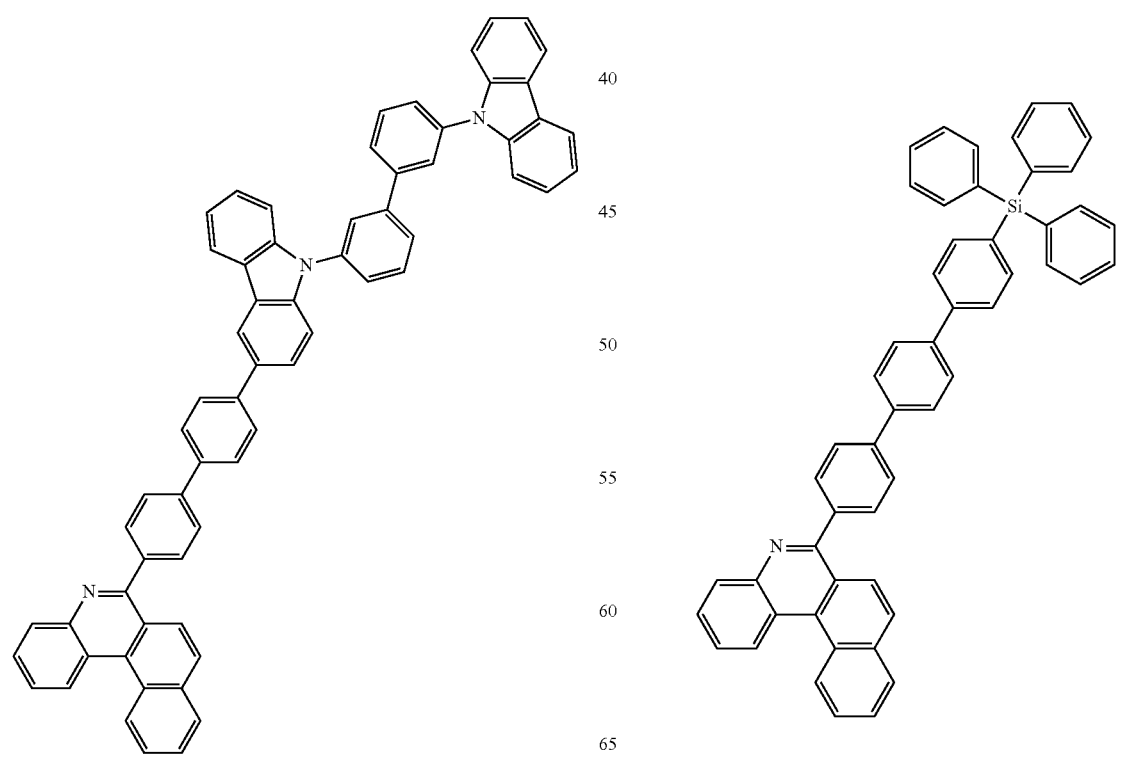
160
162

163
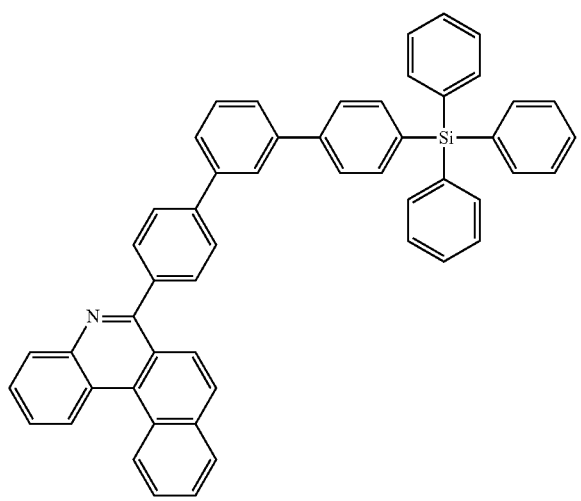
164
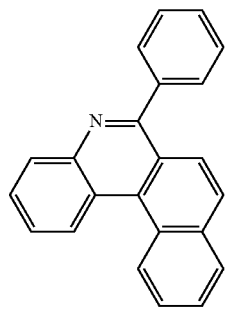
165
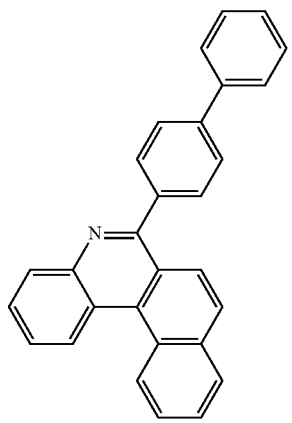
166
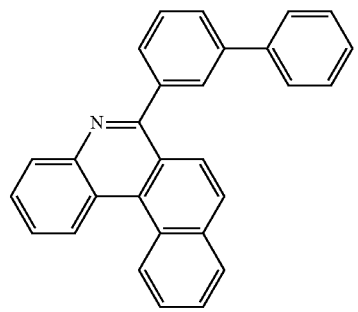
167
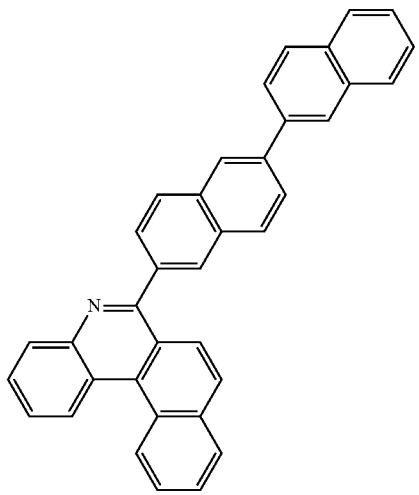
168
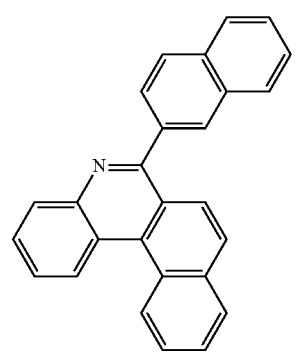
169
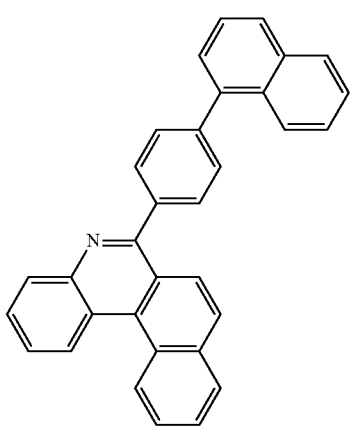
170
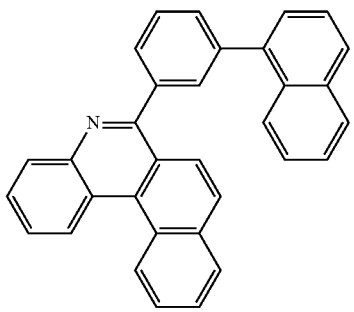

691
-continued
171
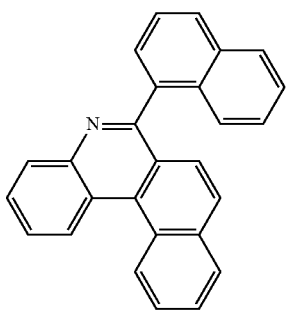
172
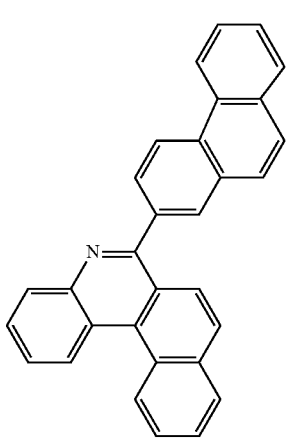
173
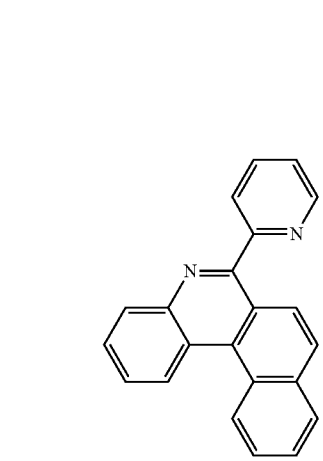
692
-continued
174
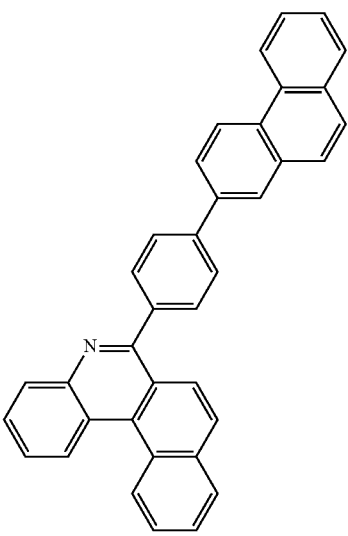
175
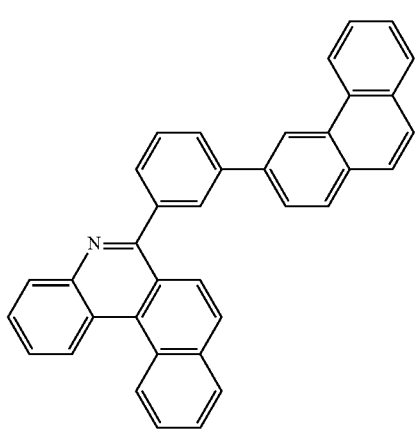
176

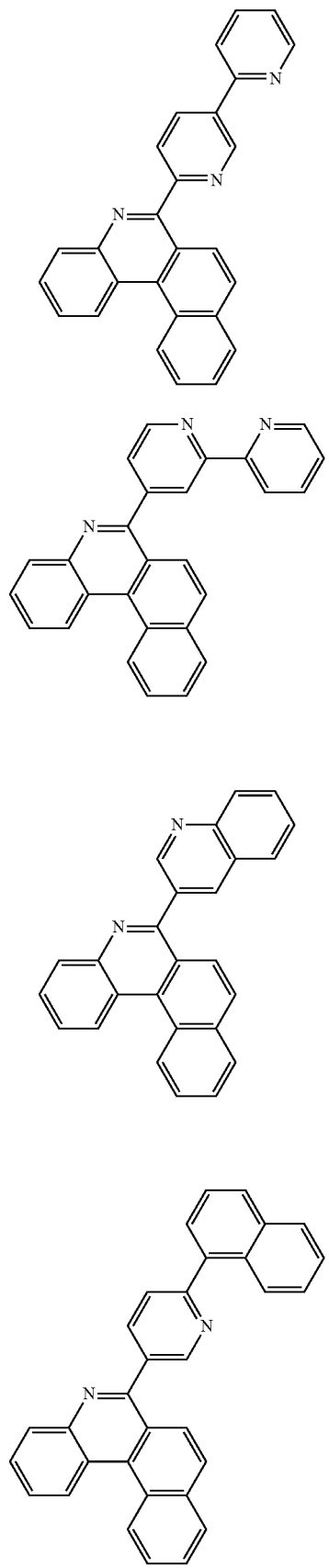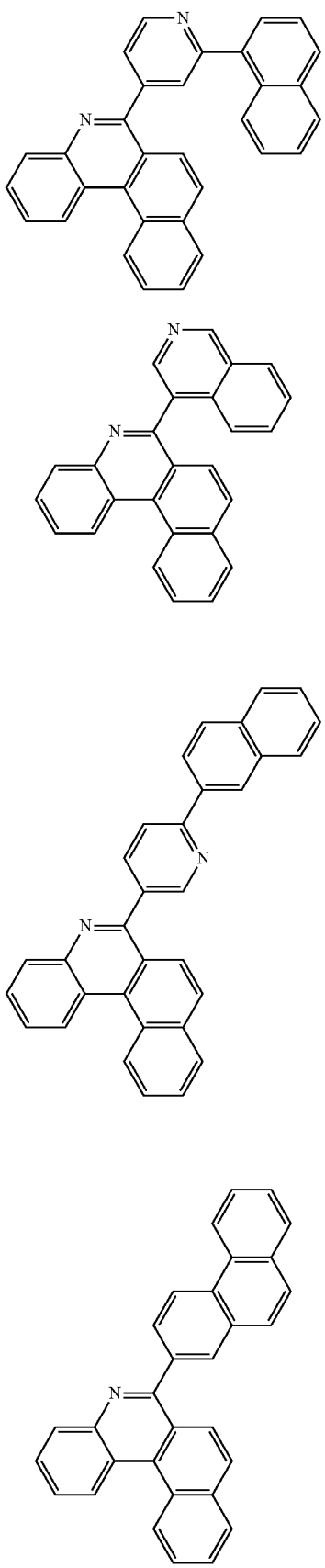

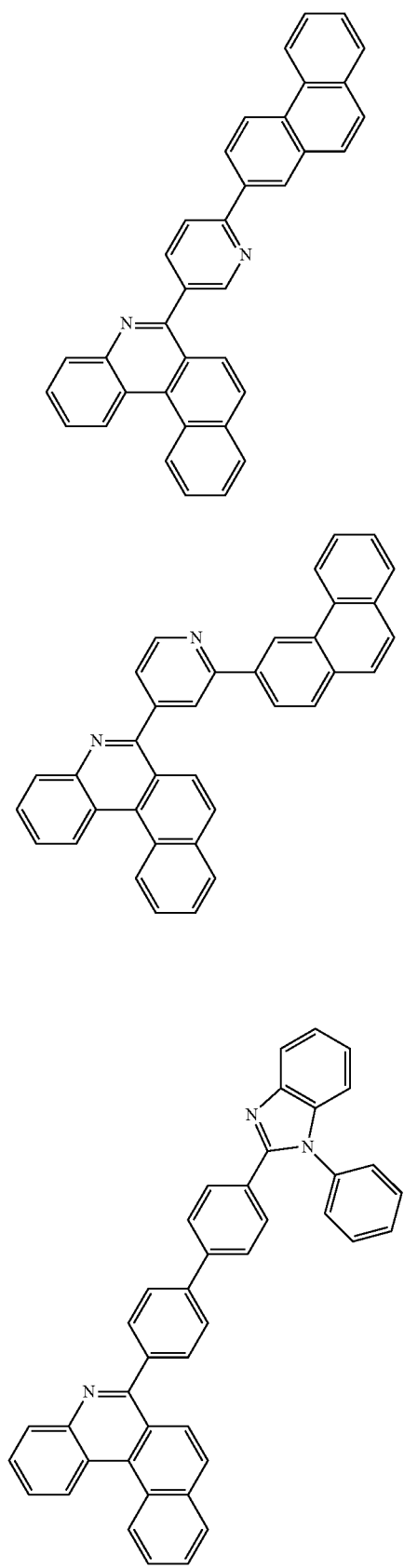

697
-continued
698
-continued
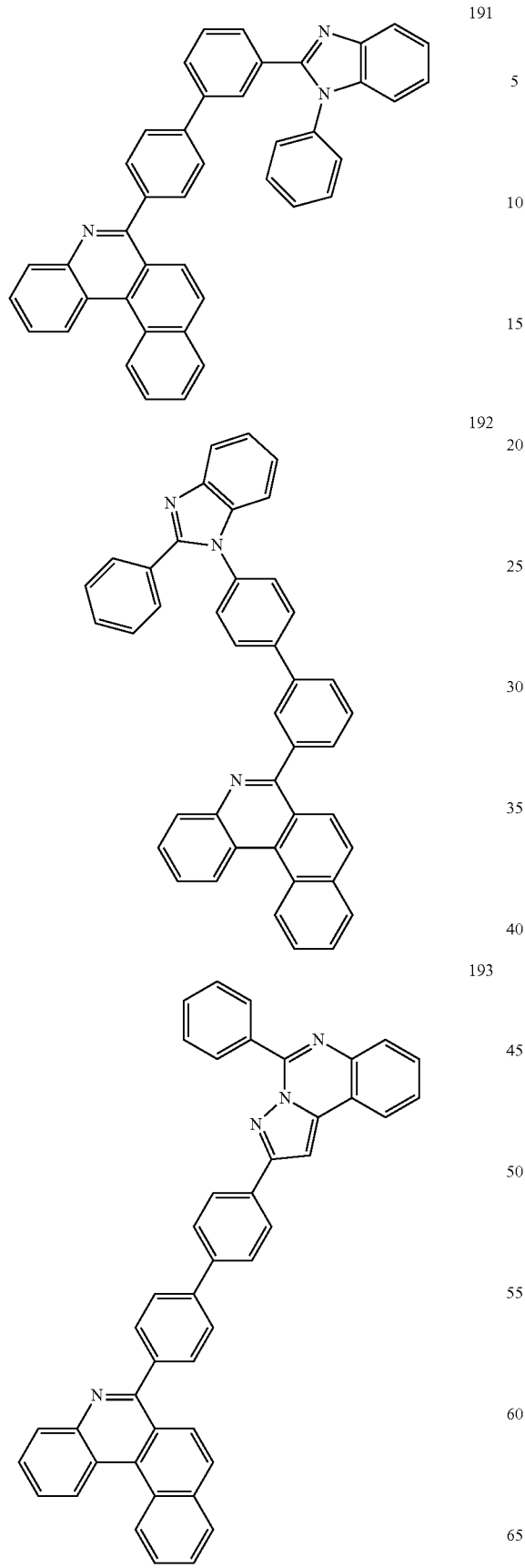
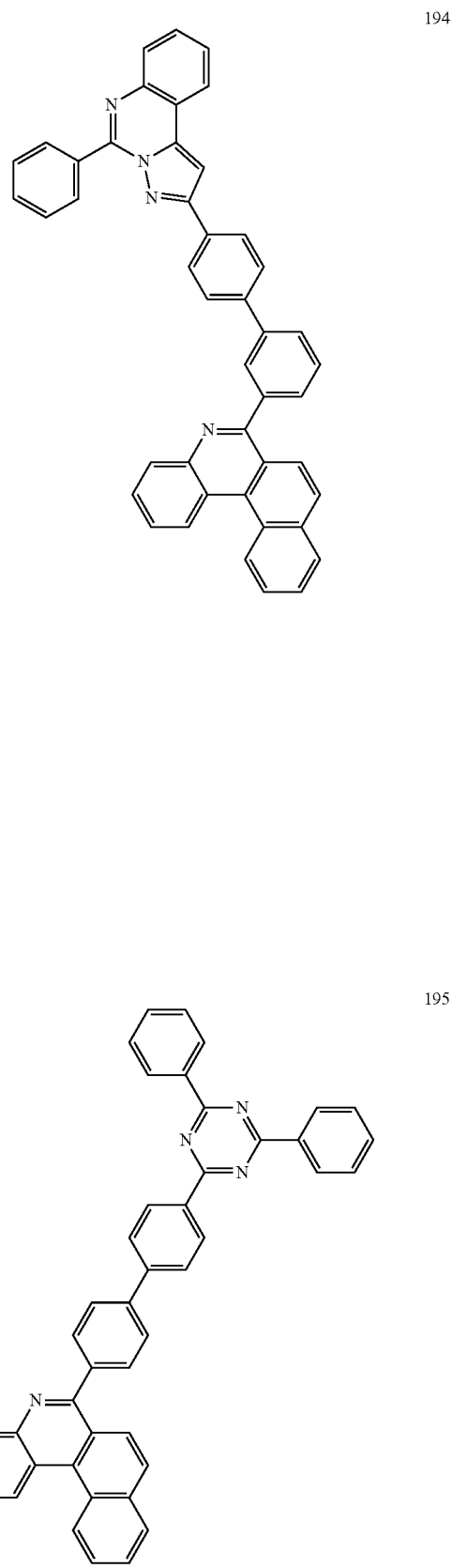

-continued
196
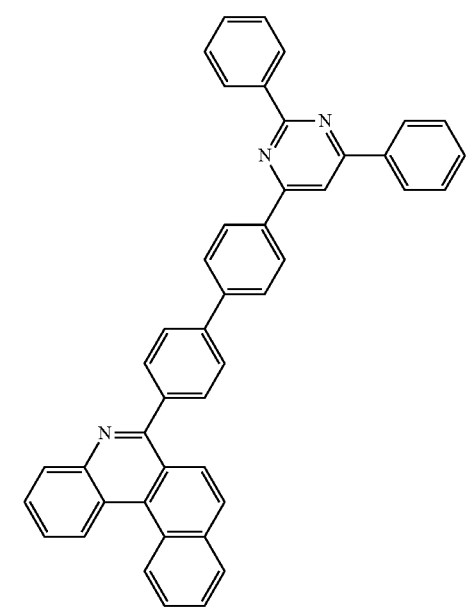
197
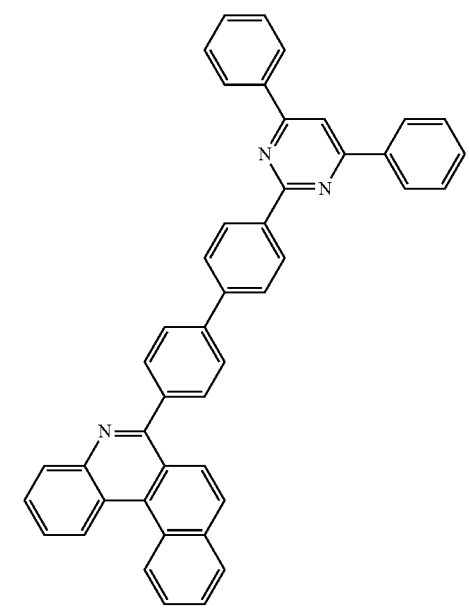
198
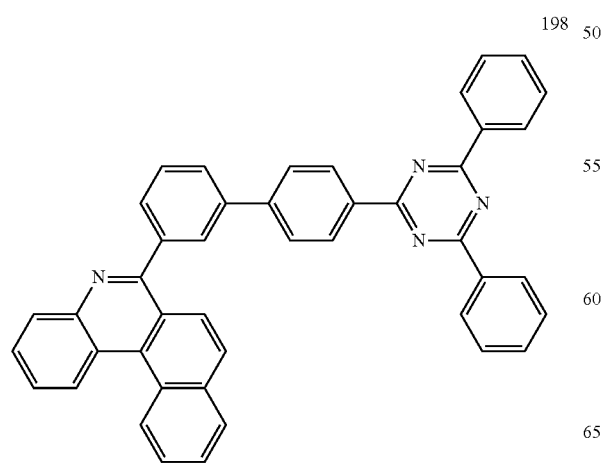
-continued
199
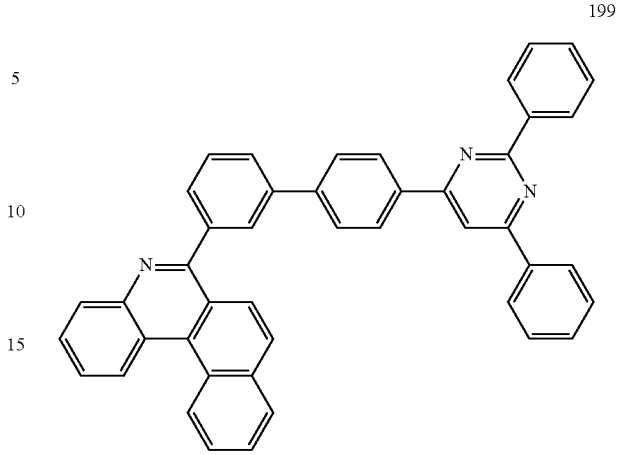
200
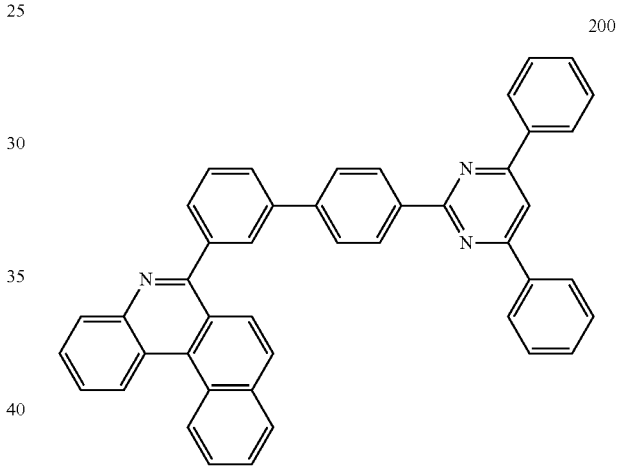
201
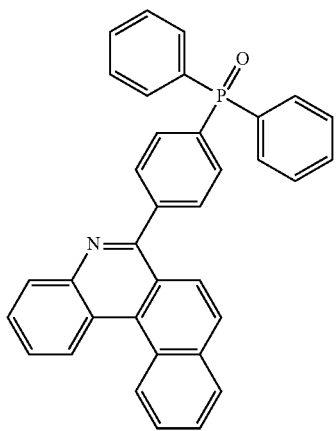

701
-continued
702
-continued
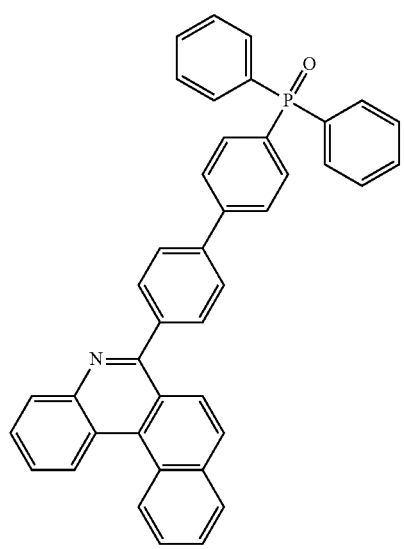
202
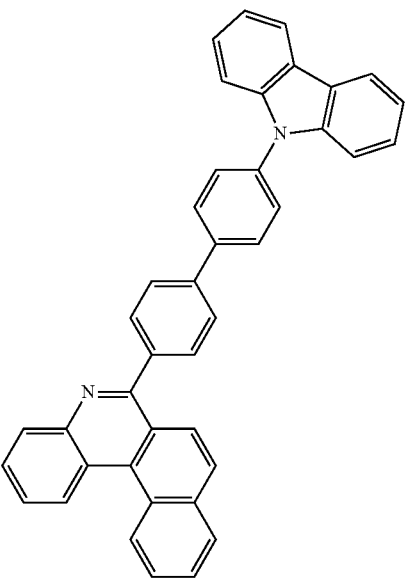
205
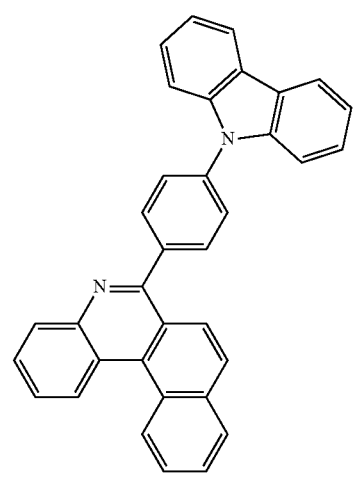
203
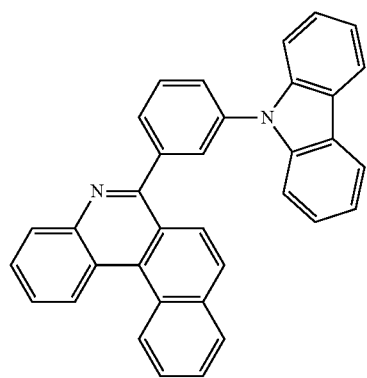
204
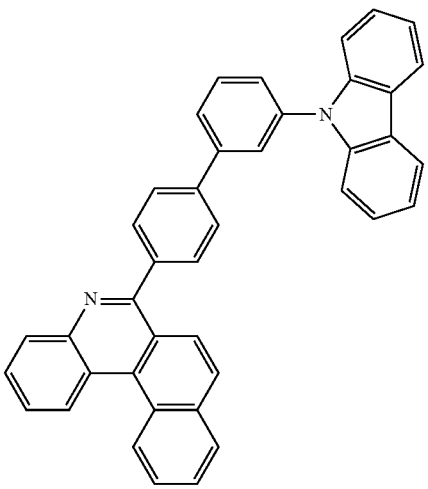
206

703
-continued
704
-continued
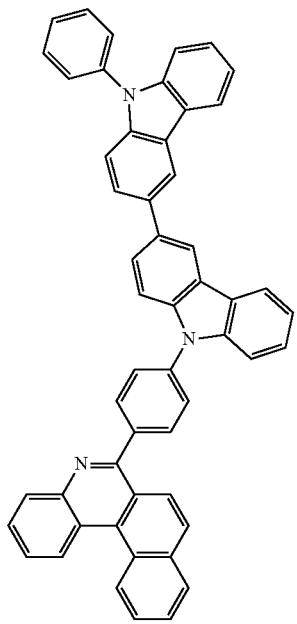
207
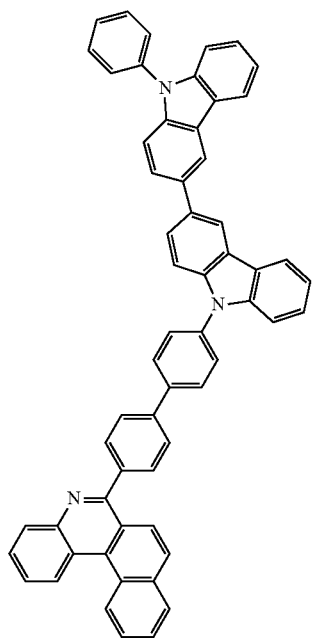
209
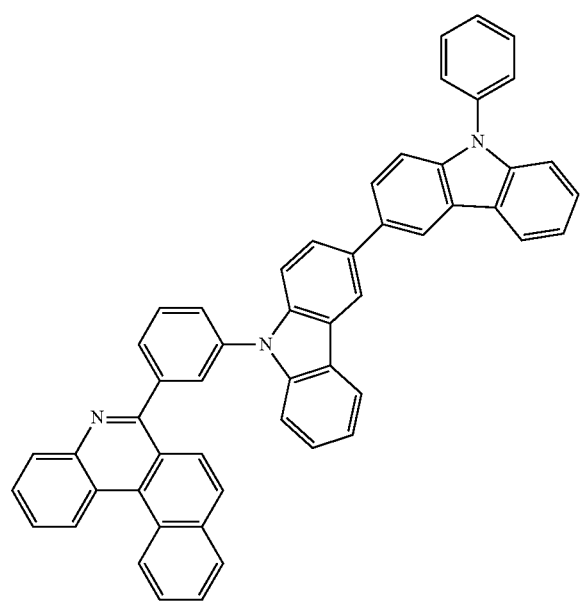
208
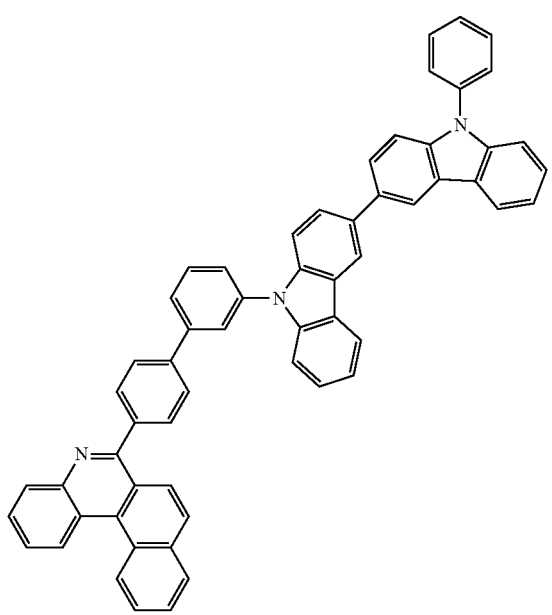
210

705
-continued
211
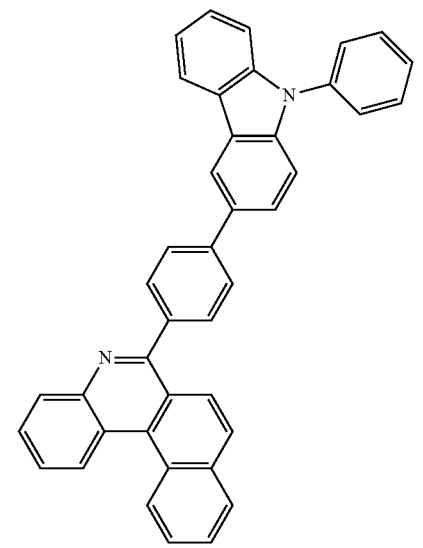
212
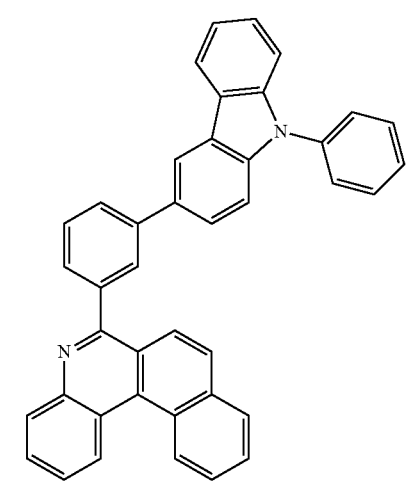
213
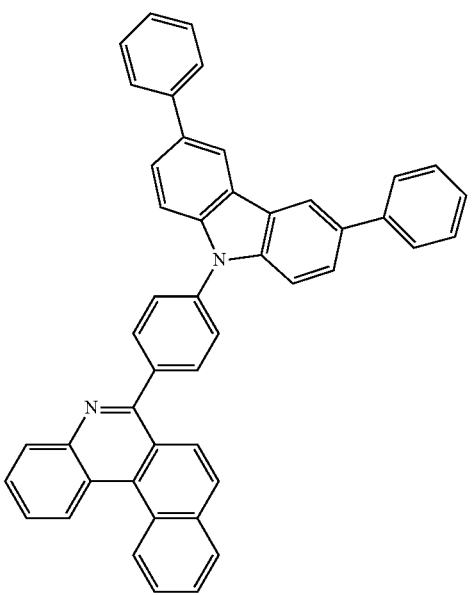
706
-continued
214
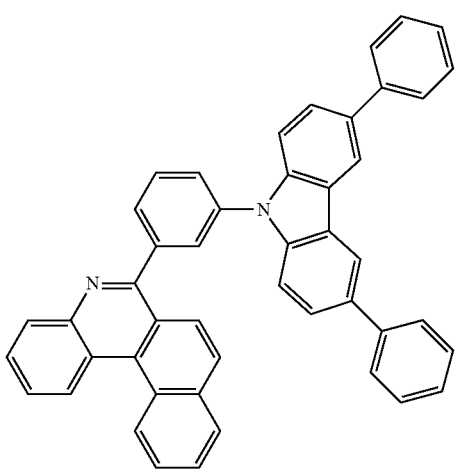
215
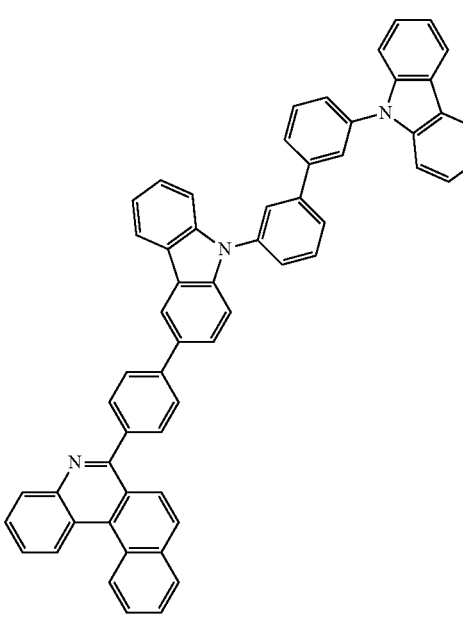
216
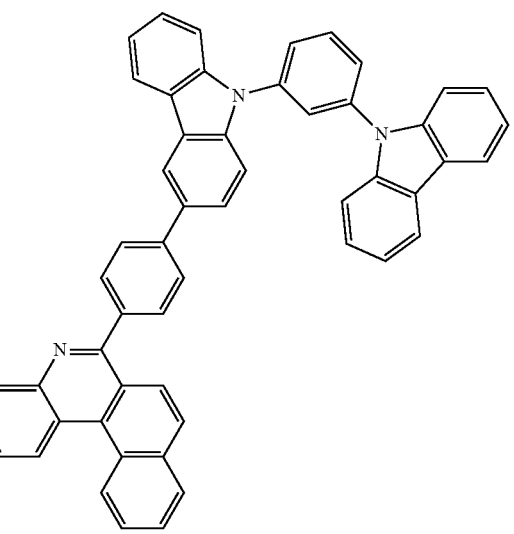

707
-continued
217
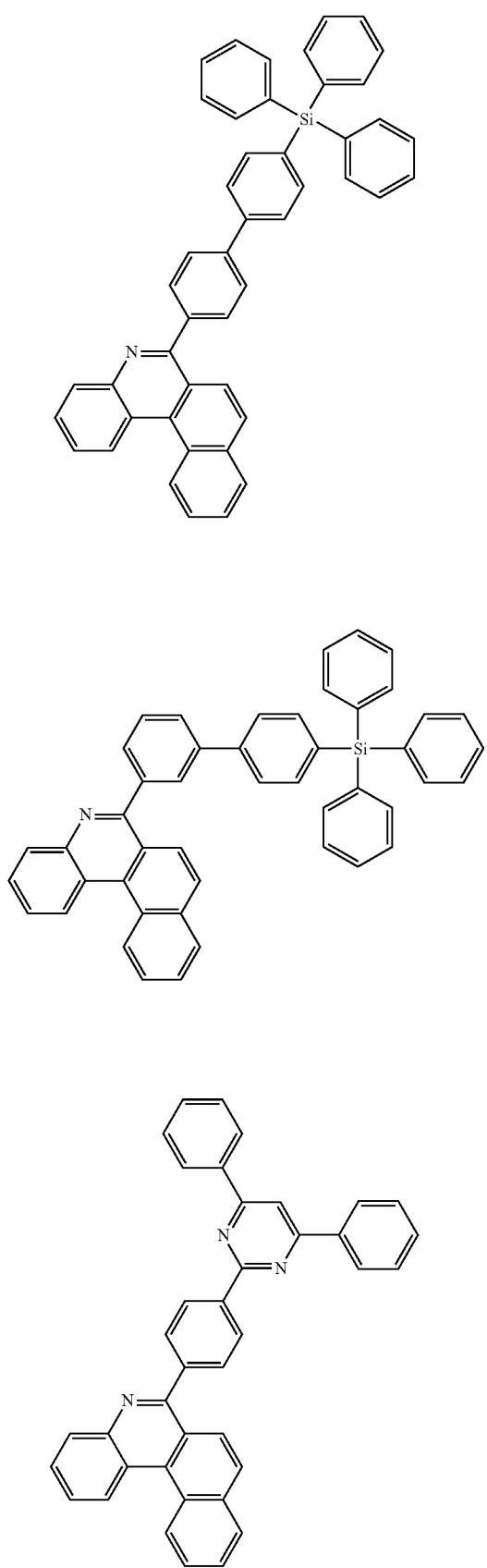
218
219
708
-continued
220
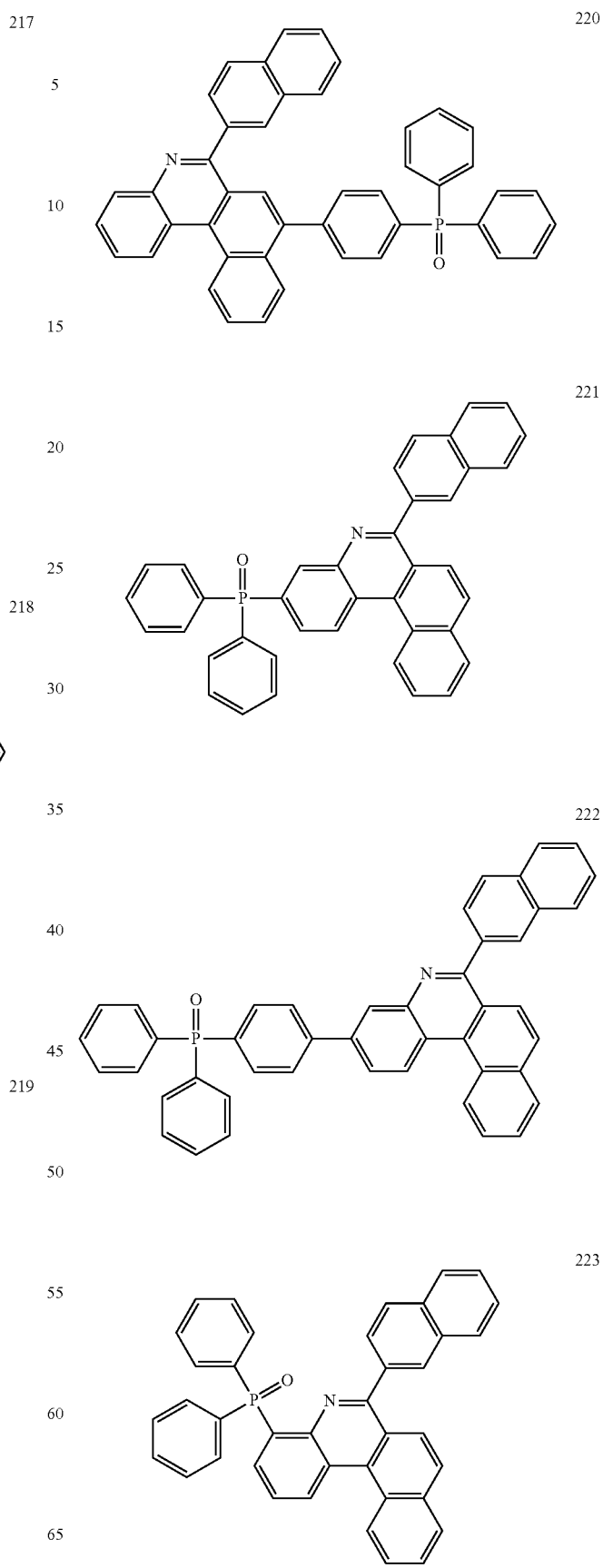
221
222
223

709
-continued
224
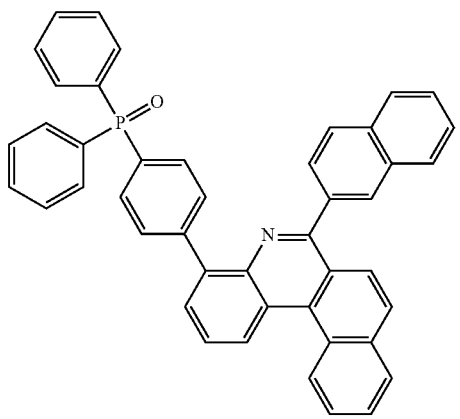
225
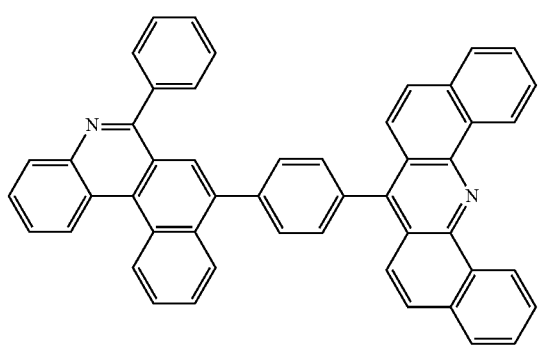
226
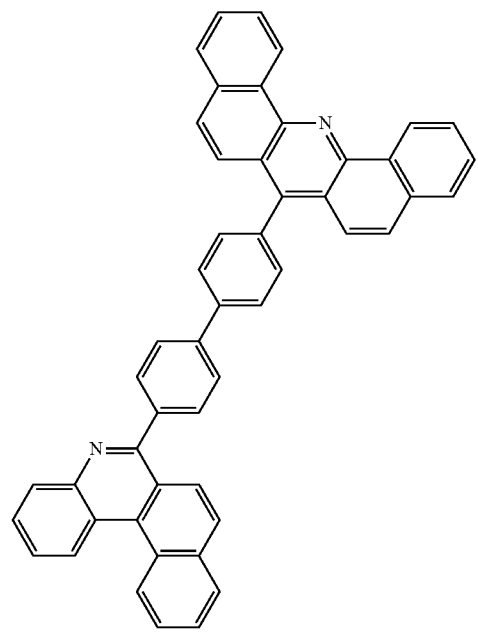
710
-continued
227
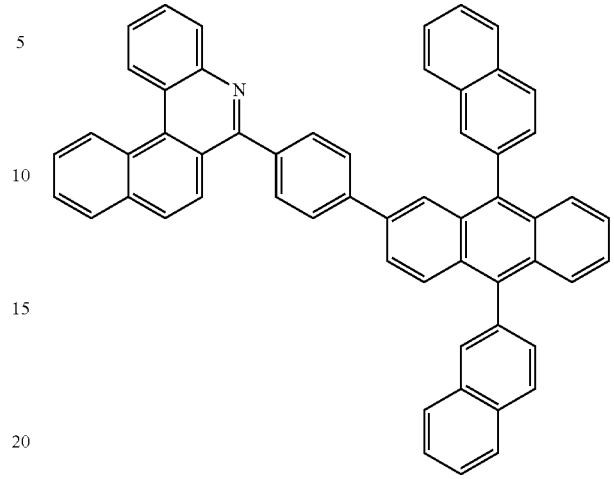
228
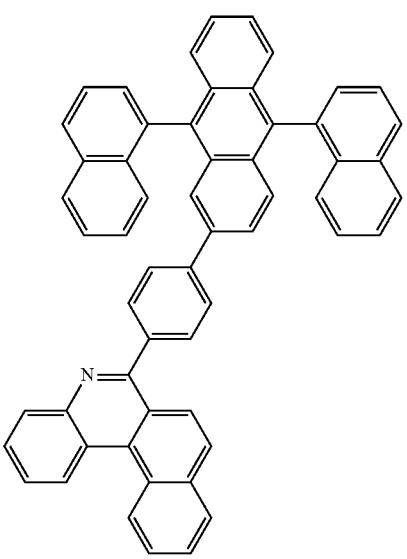
229

711
-continued
230
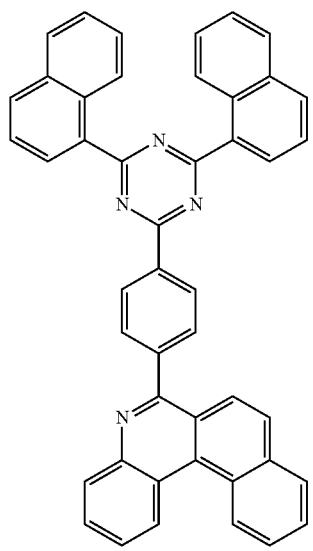
231
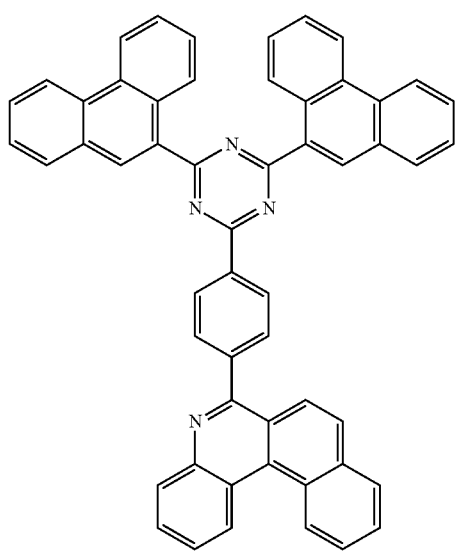
712
-continued
232
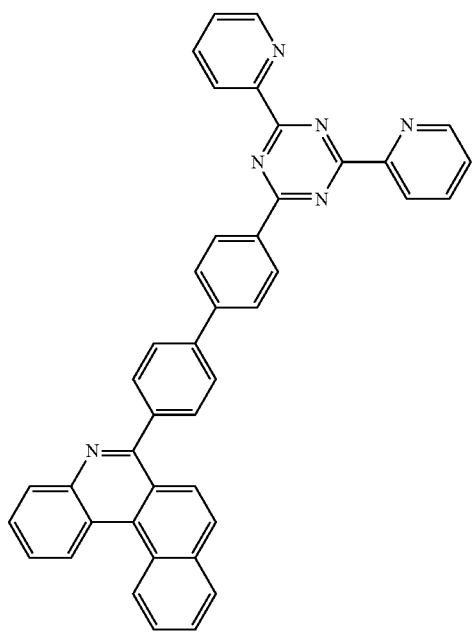
233
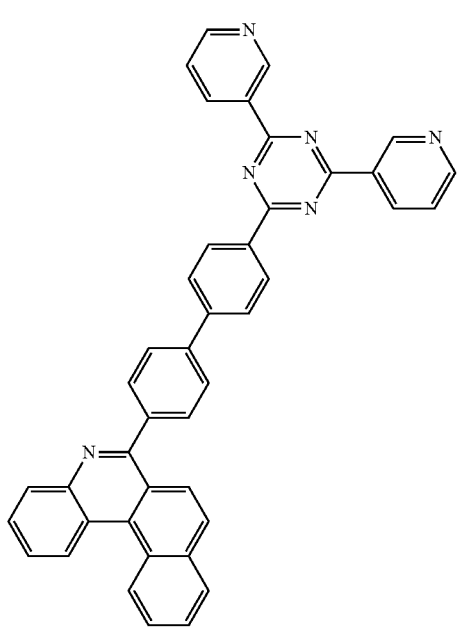

713
-continued
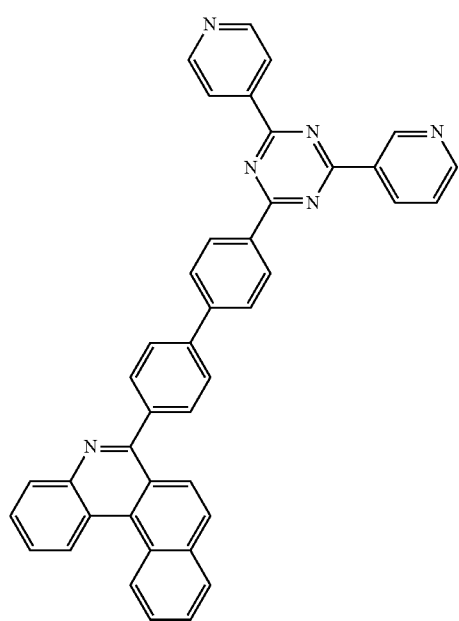
234
714
-continued
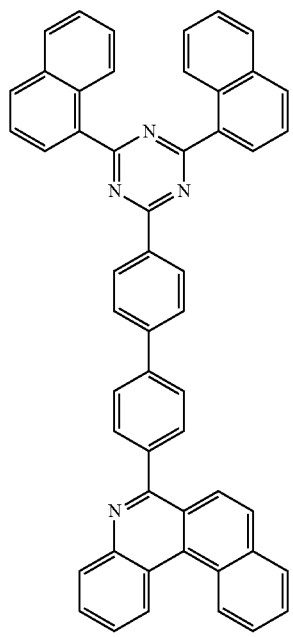
236
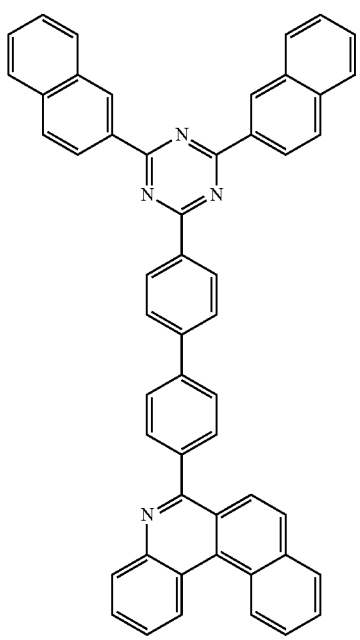
235
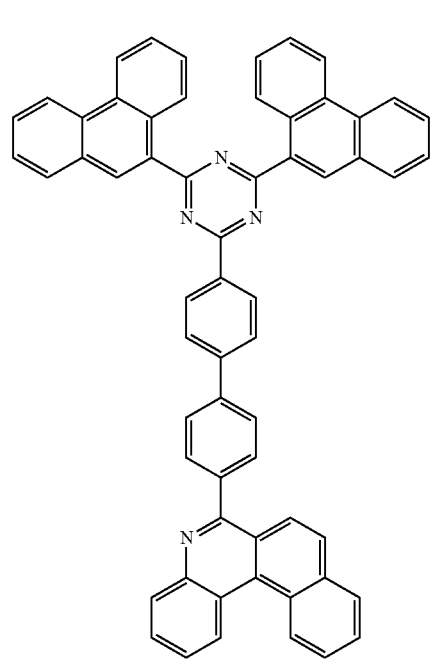
237

238
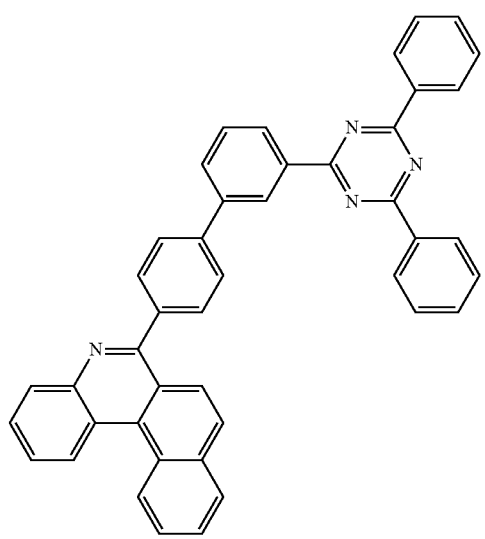
239
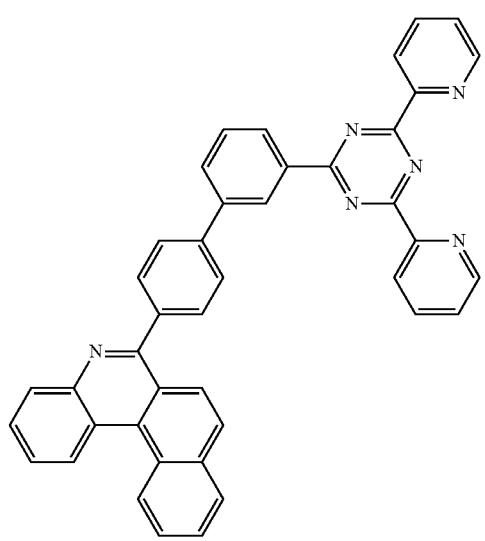
240
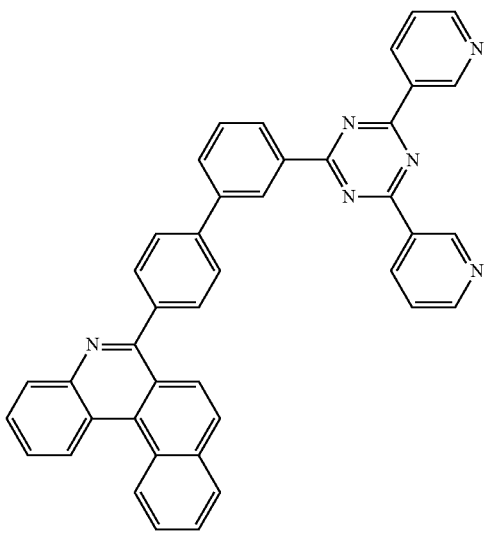
241
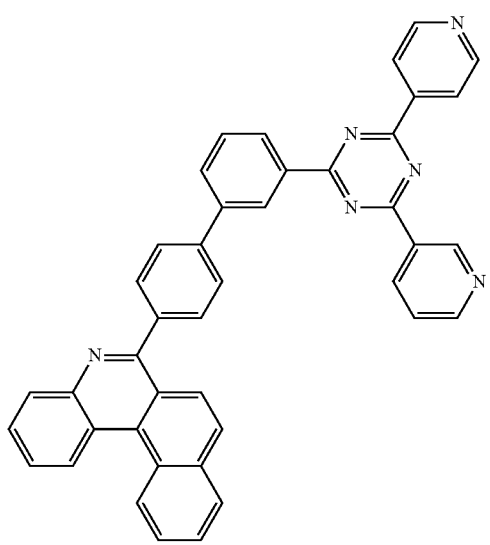
242
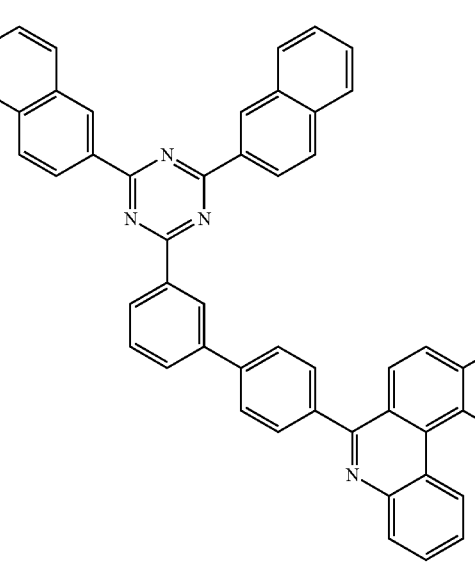
243

717
-continued
244
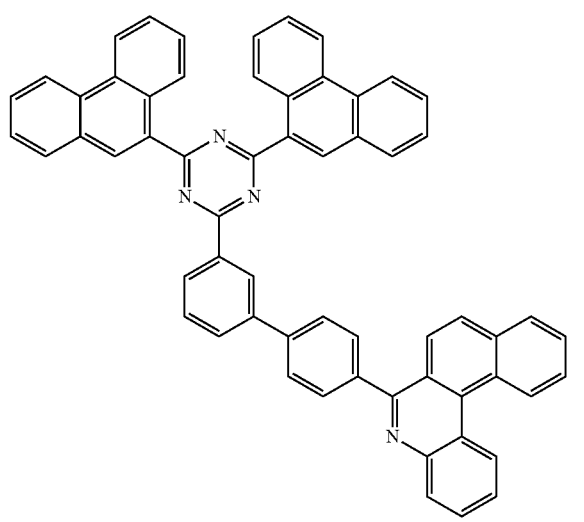
245
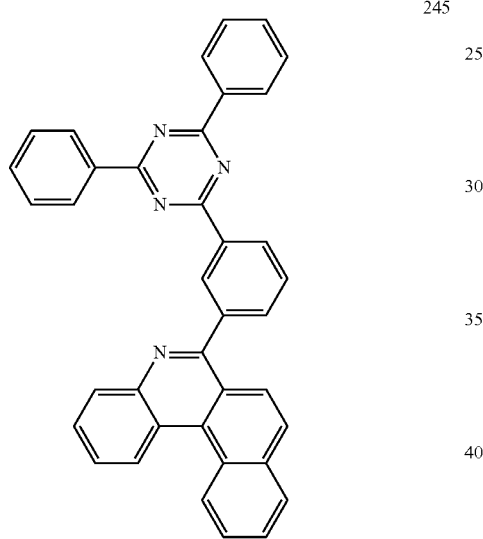
246
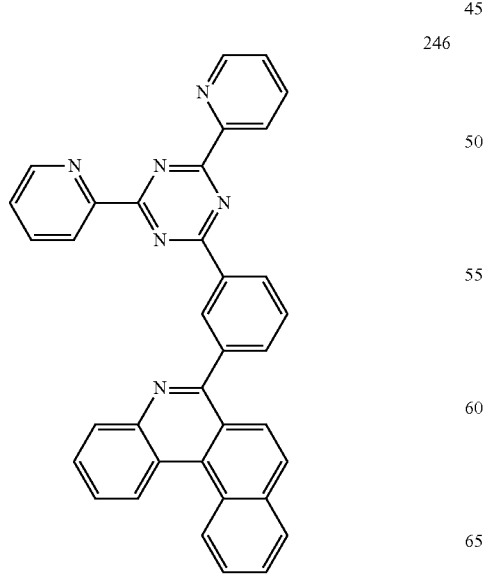
718
-continued
247
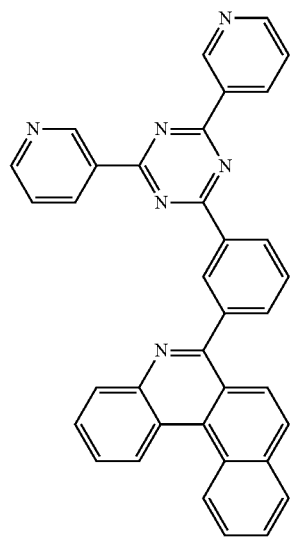
248
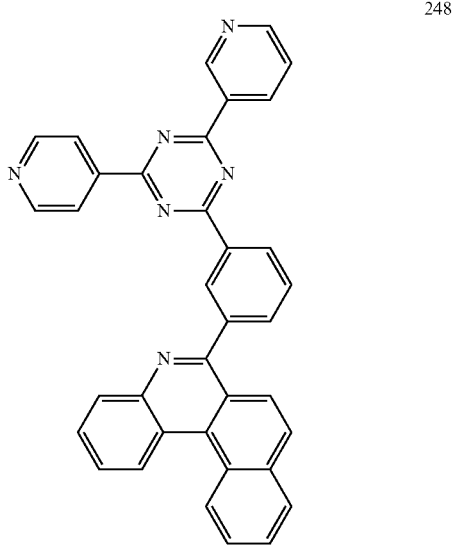
249
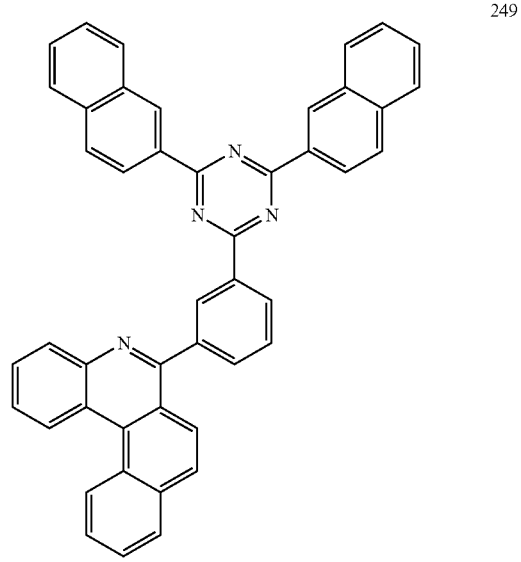

719
-continued
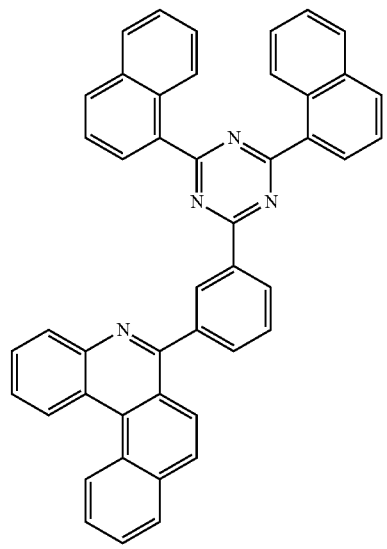
250
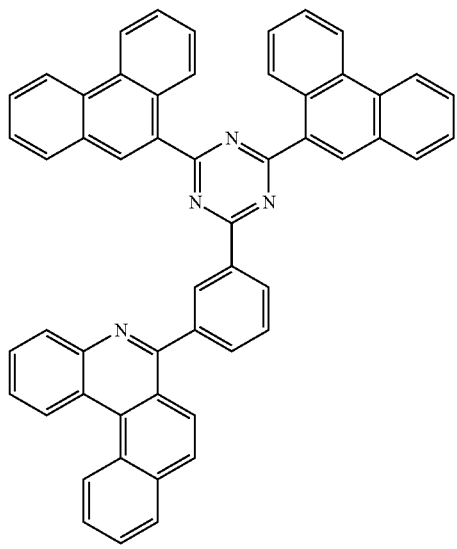
251
720
-continued
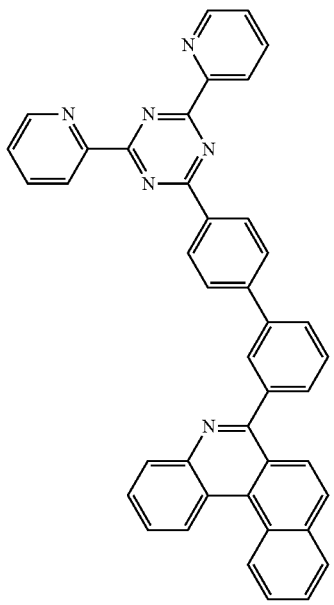
252
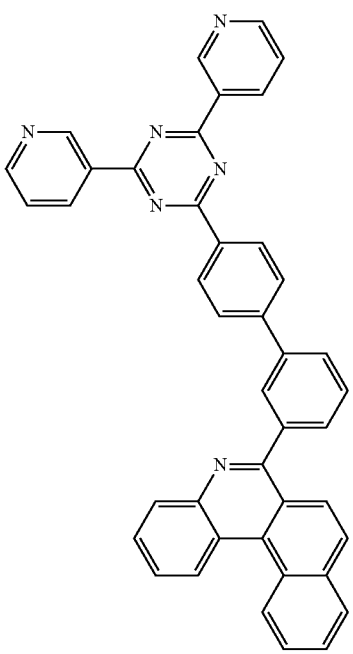
253

721
254
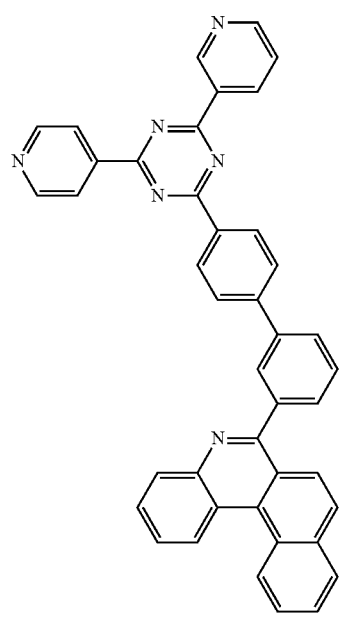
255
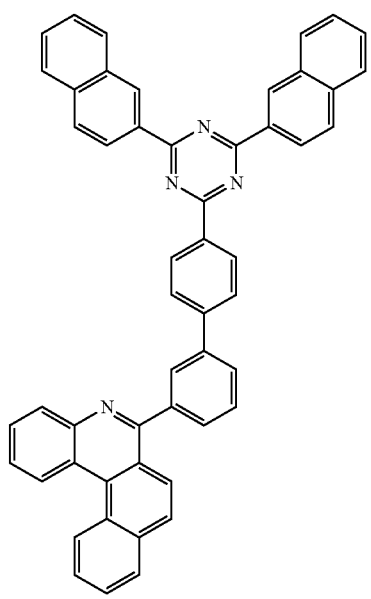
722
256
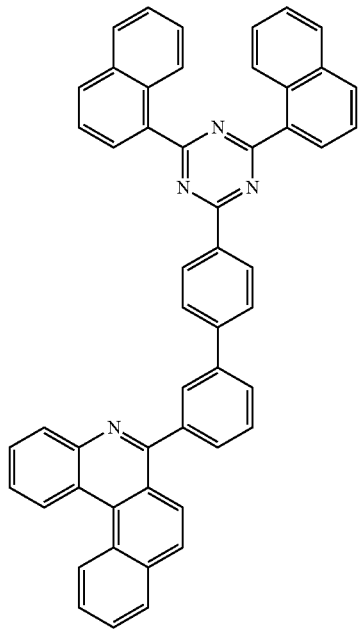
257
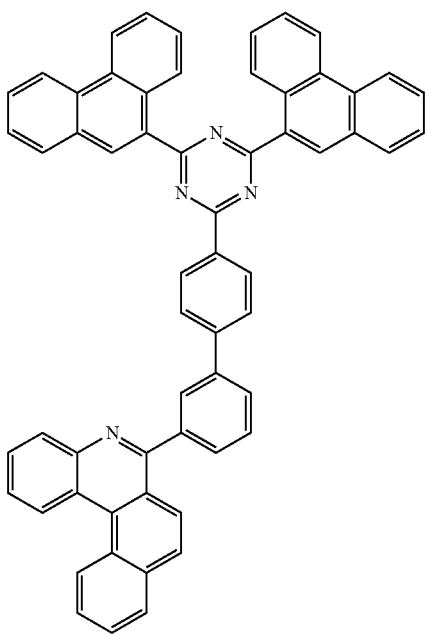

258
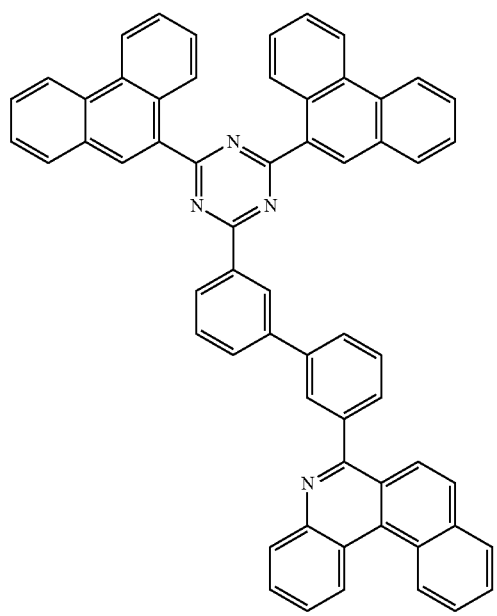
259
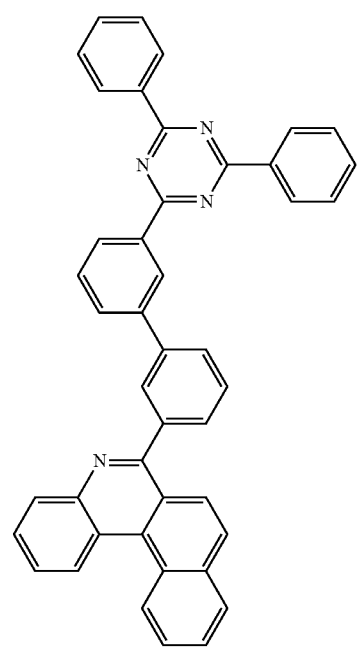
260
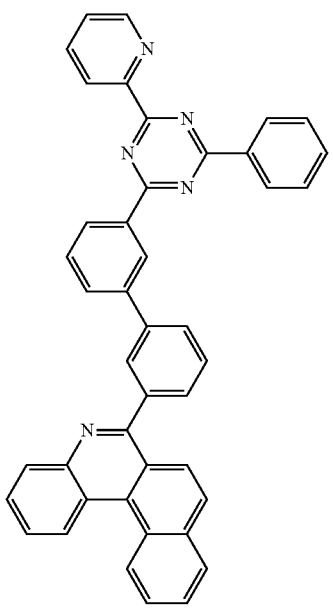
261
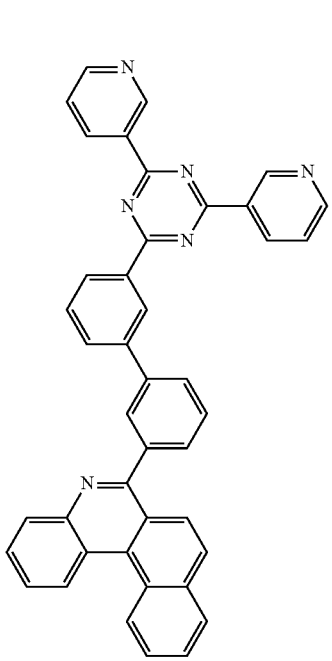

262
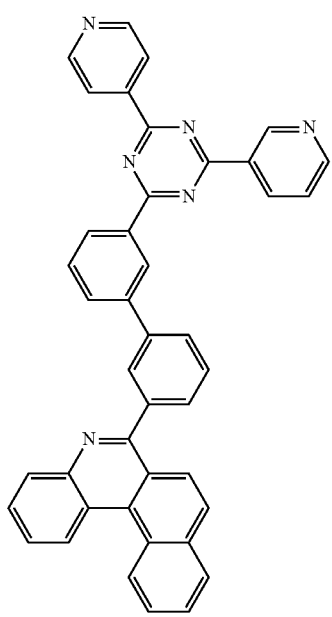
263
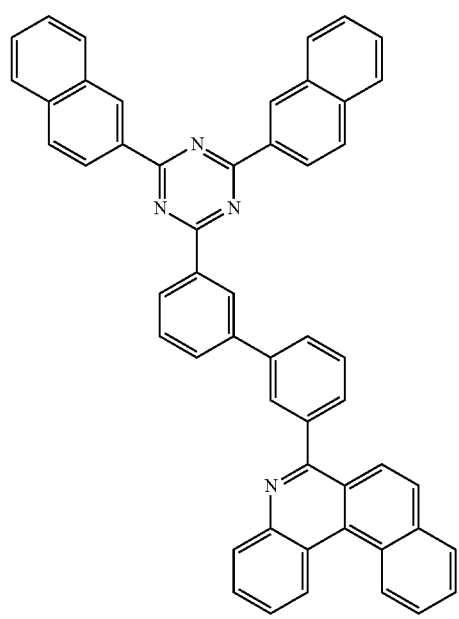
264
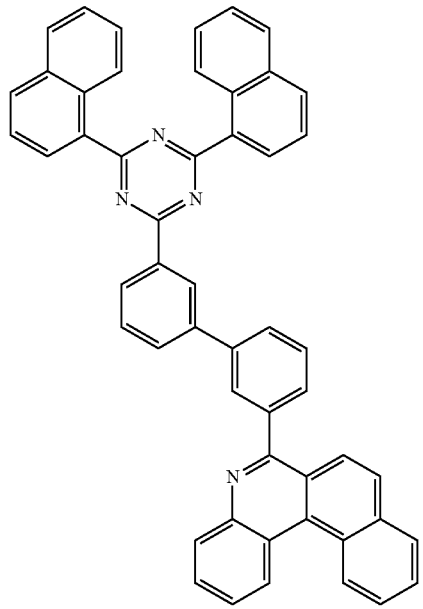
265
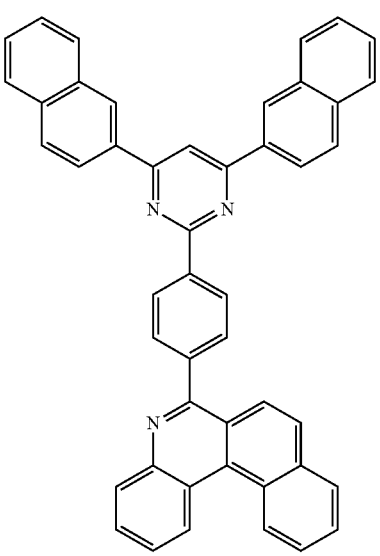

727
-continued
728
-continued
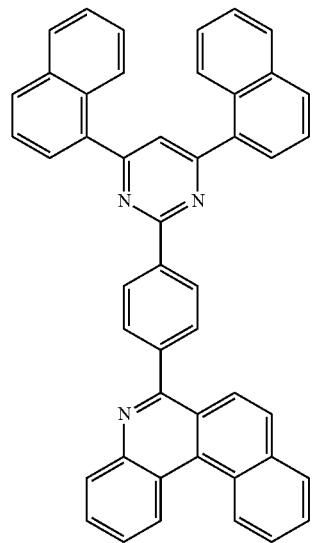
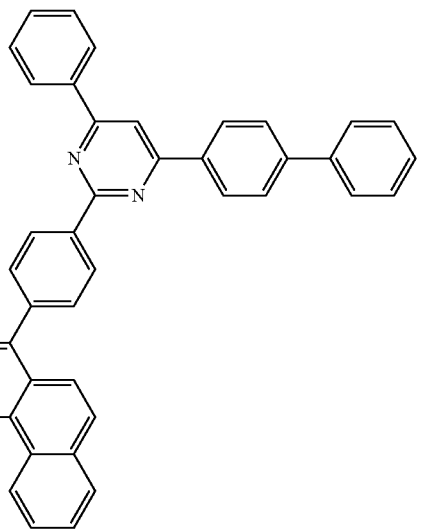
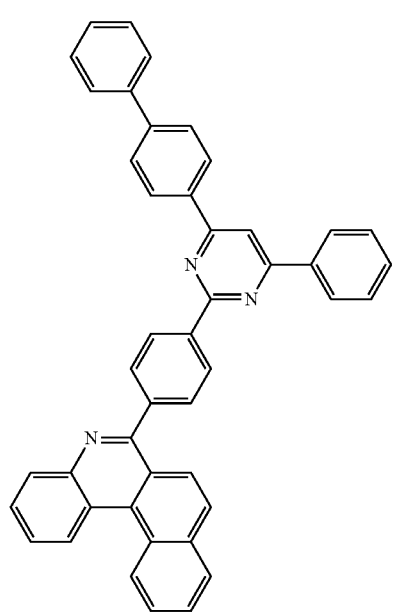

729
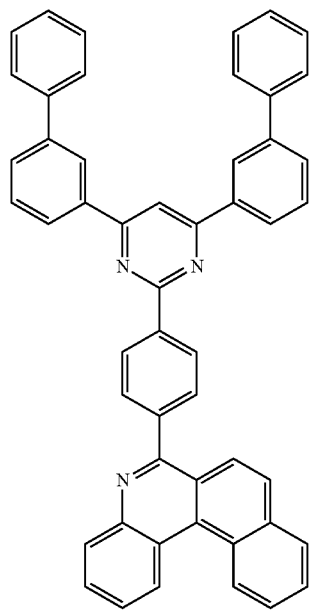
730
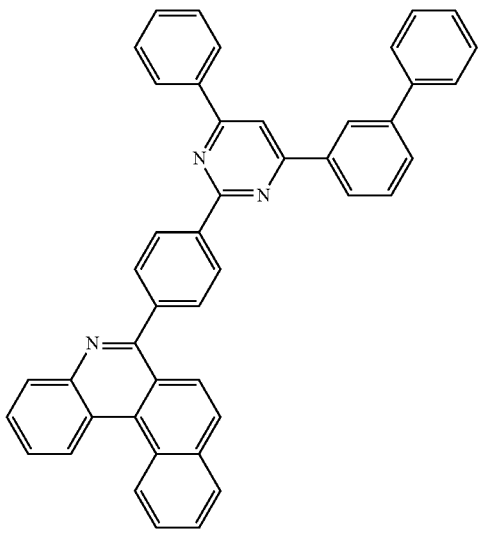
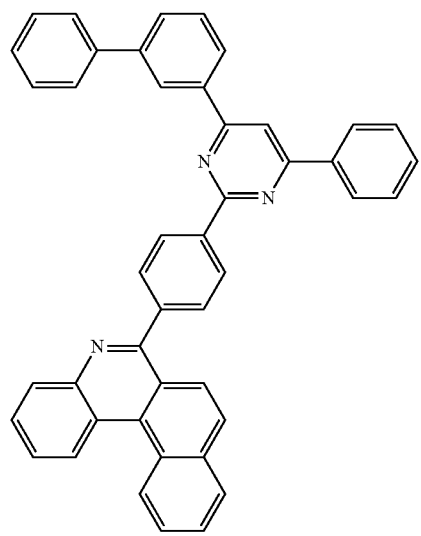
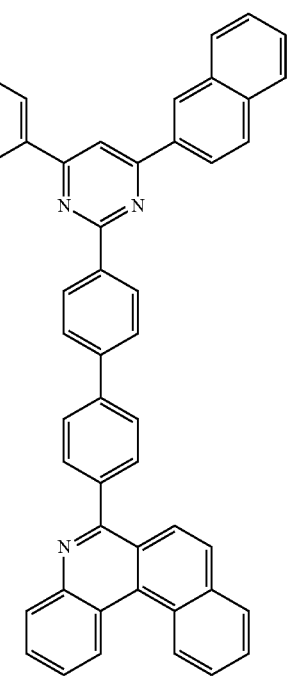

731
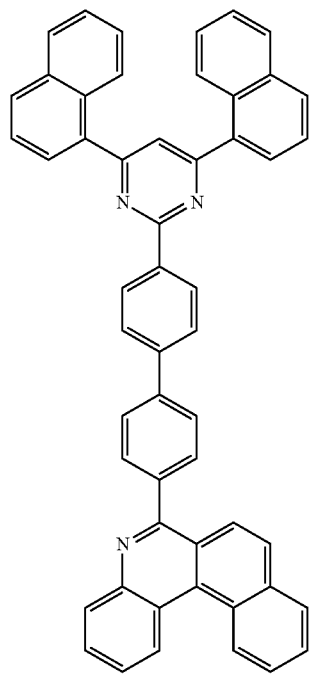
732
-continued
275
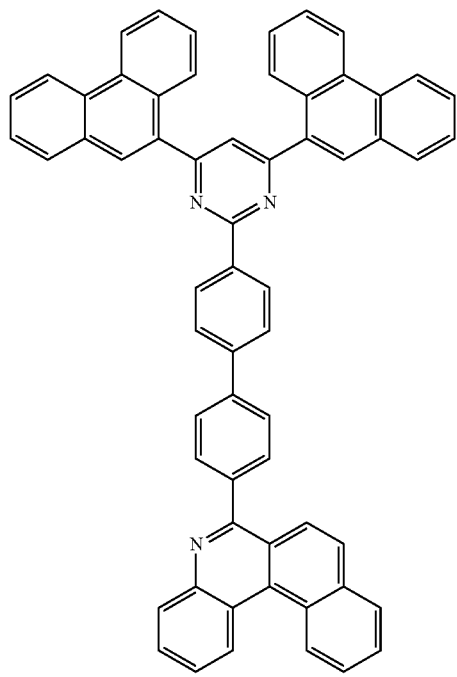
176
277
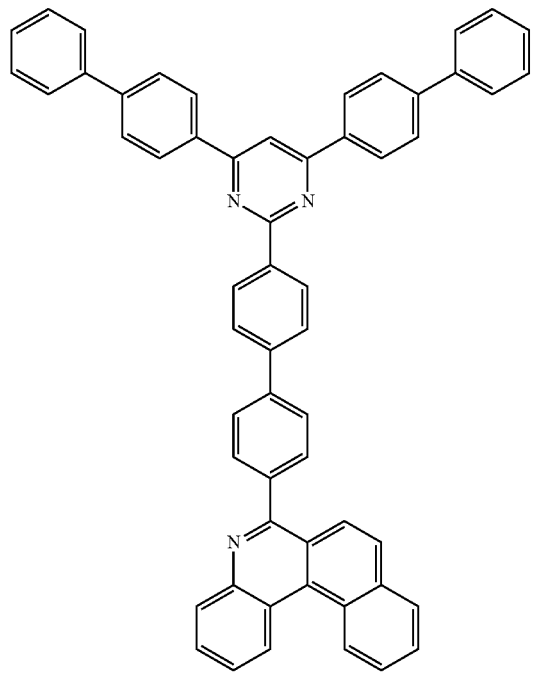
278
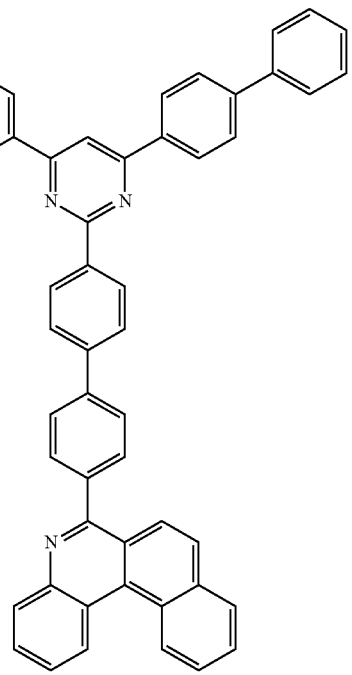

-continued
279
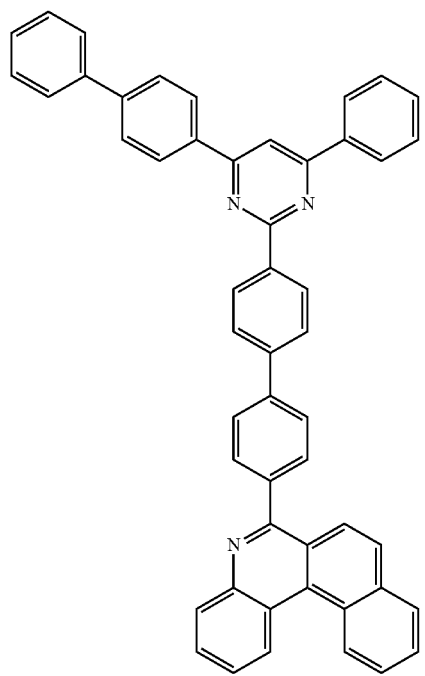
280
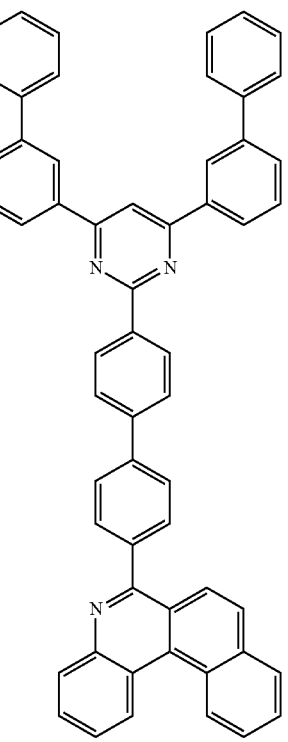
281
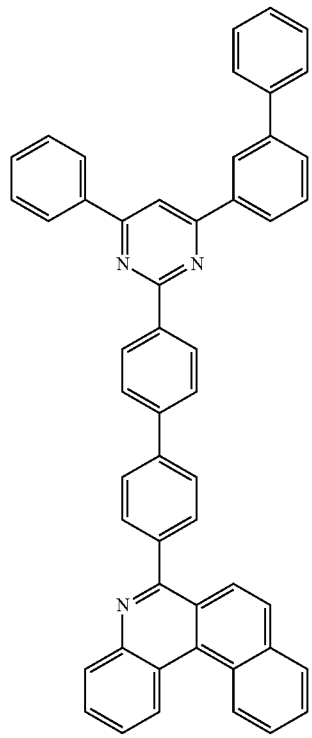
282
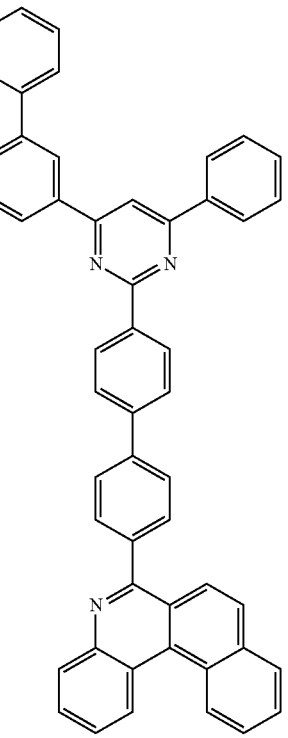

-continued
283
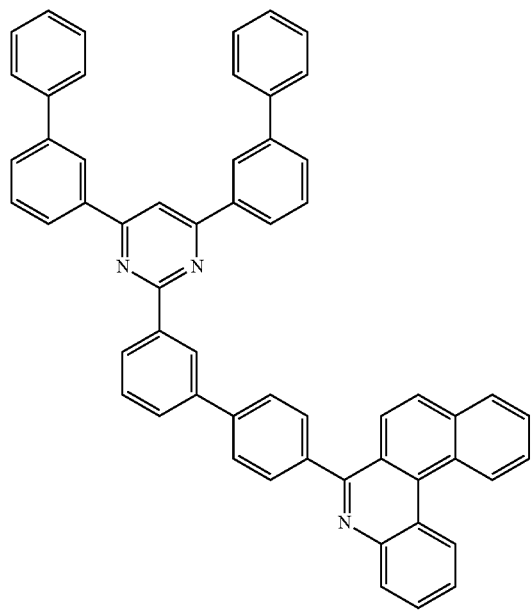
284
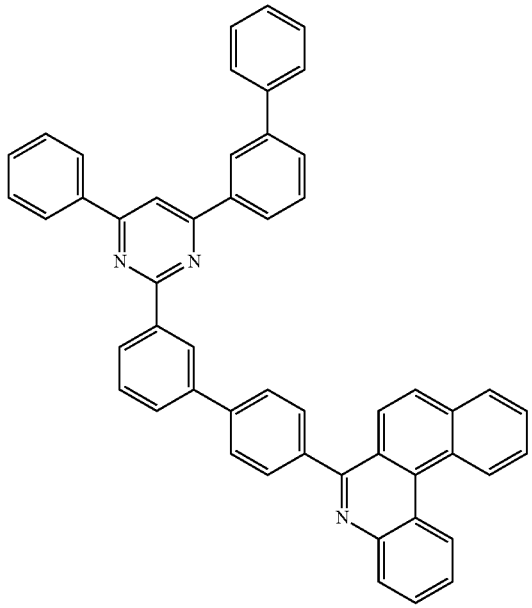
285
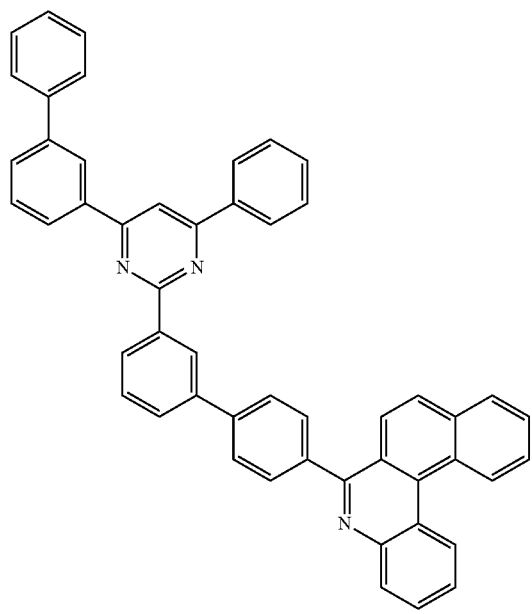
286
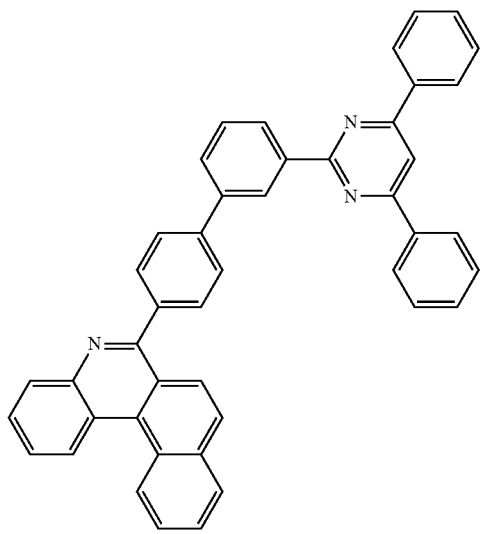

287
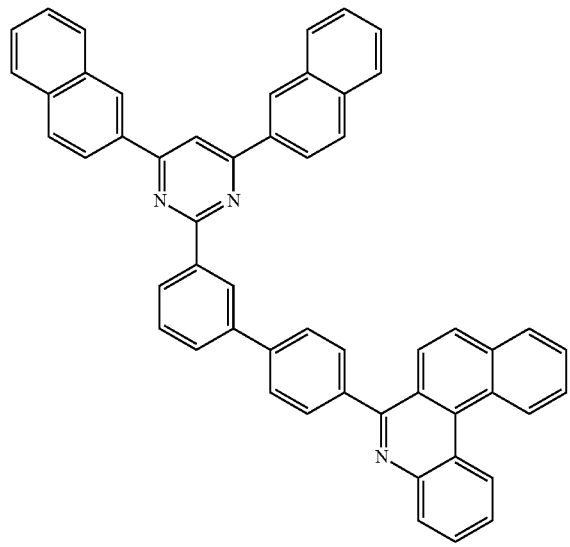
288
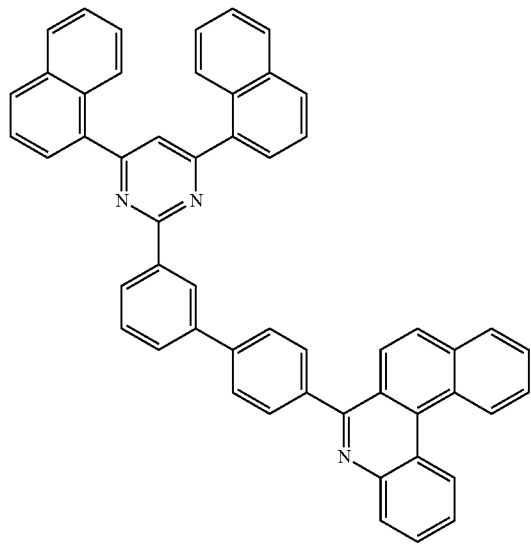
289
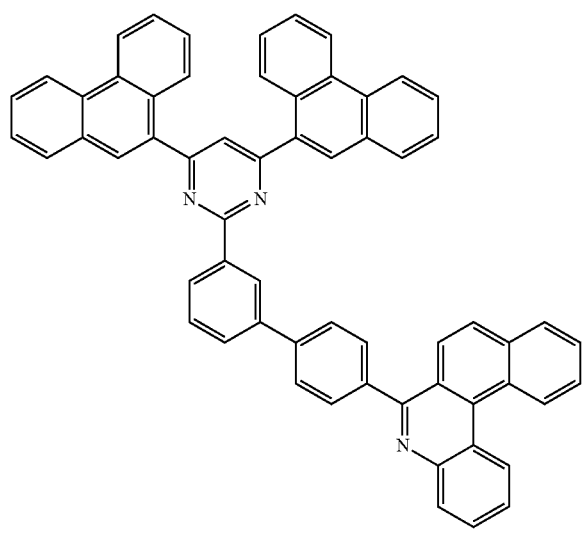
290
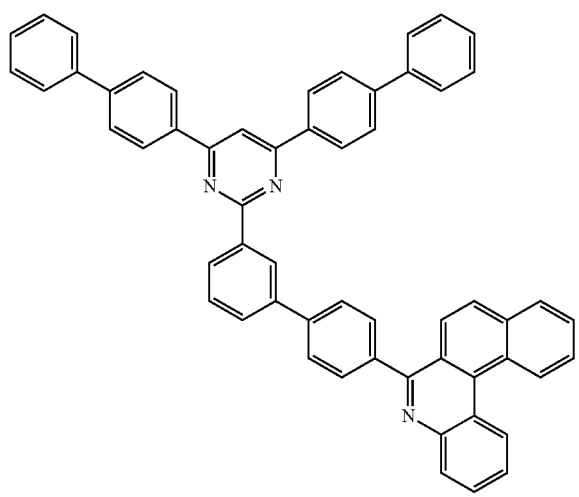

-continued
291 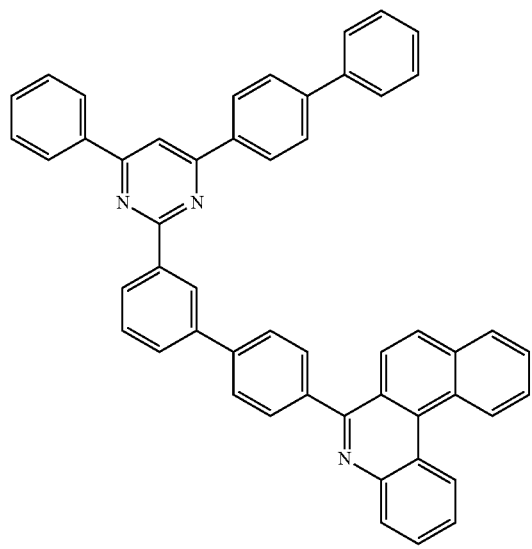
292 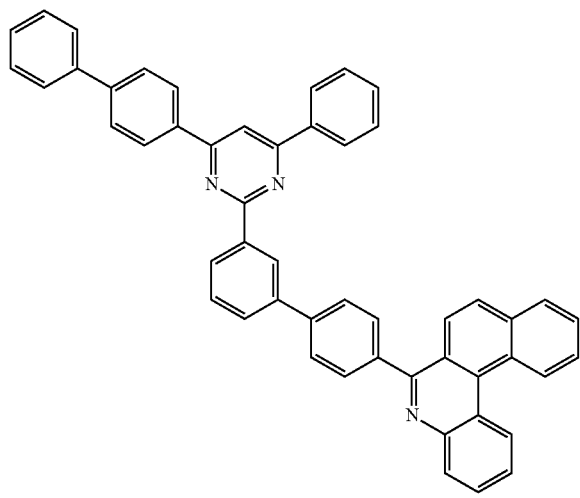
293 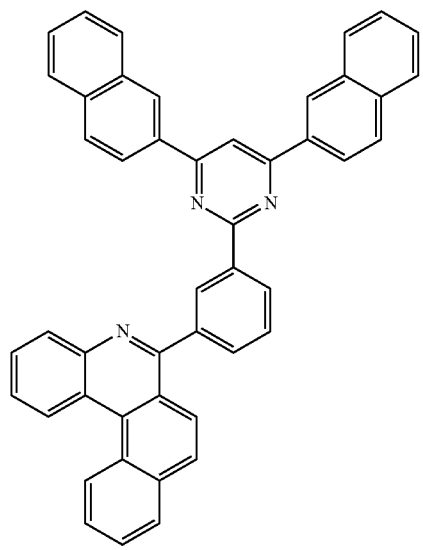
294 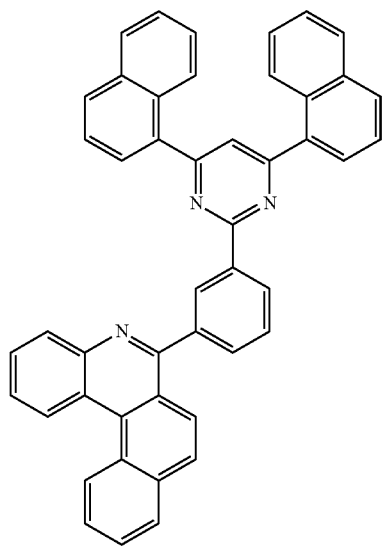

741 742
295
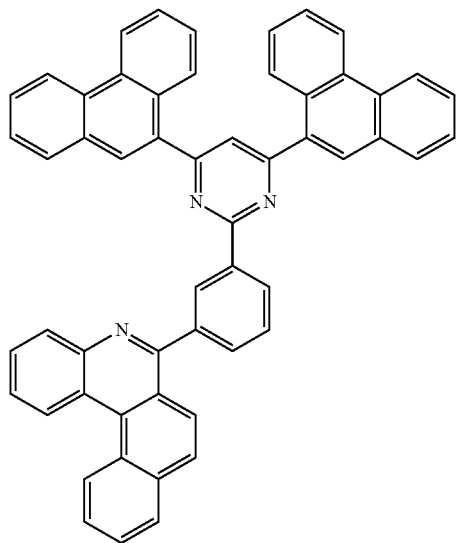
296
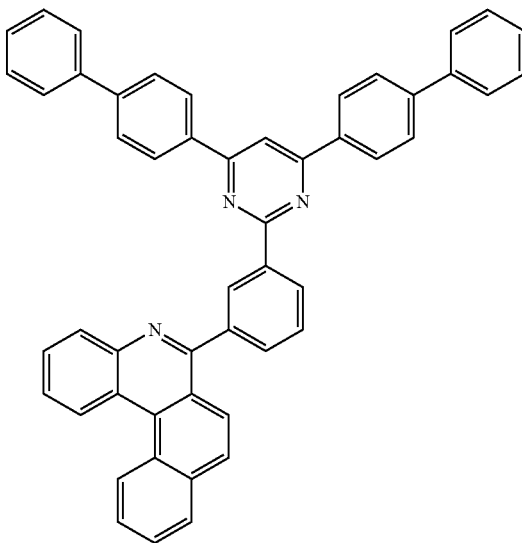
297
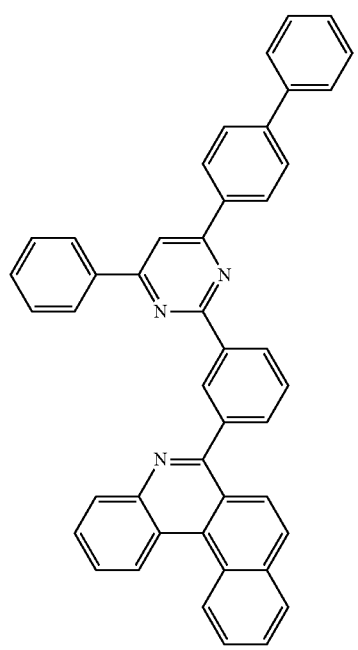
298
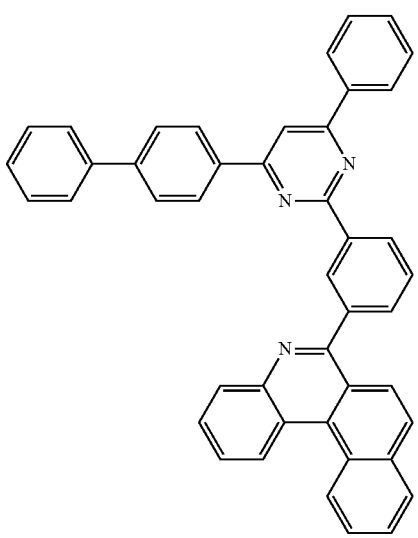

743
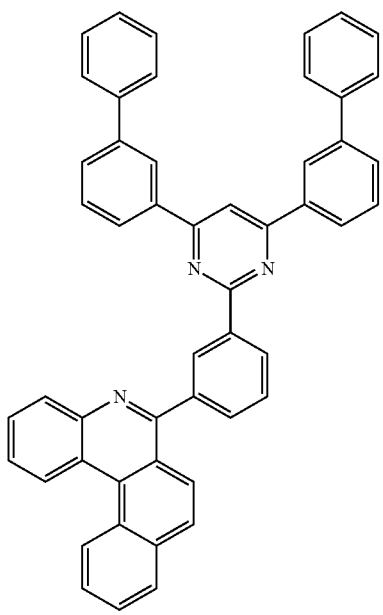
299
744
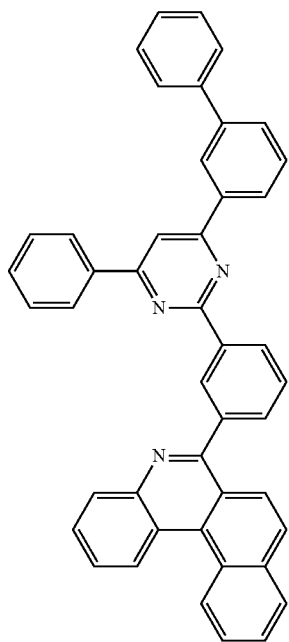
300
-continued
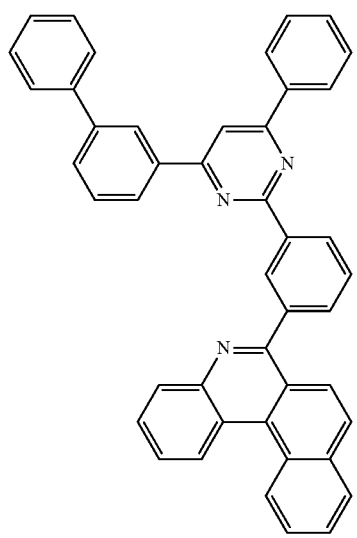
301
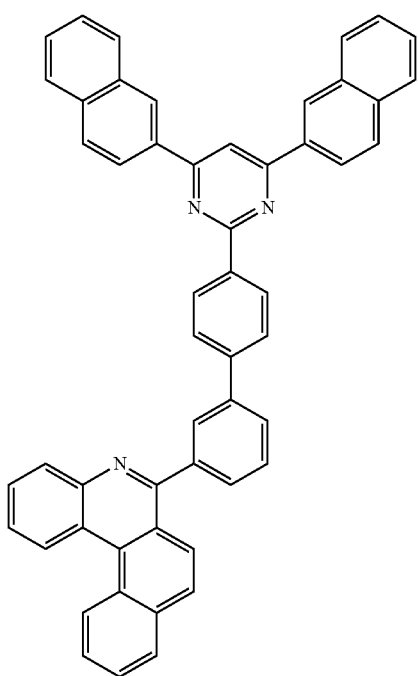
302

745
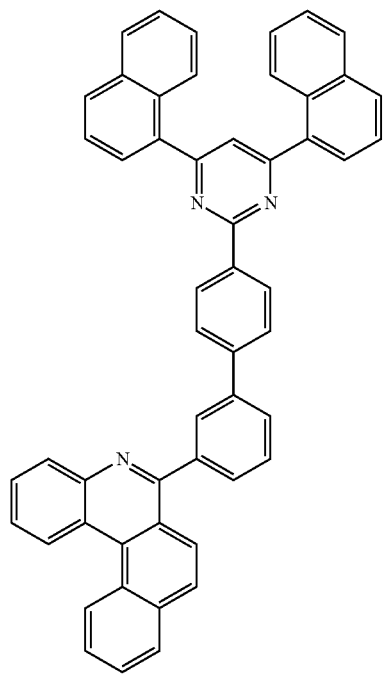
746
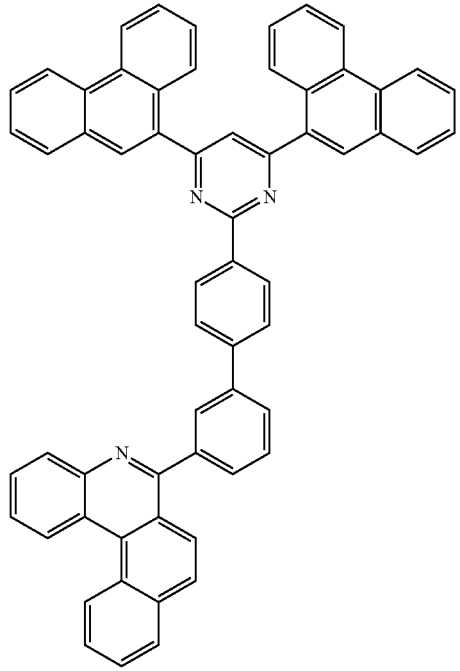
-continued
305
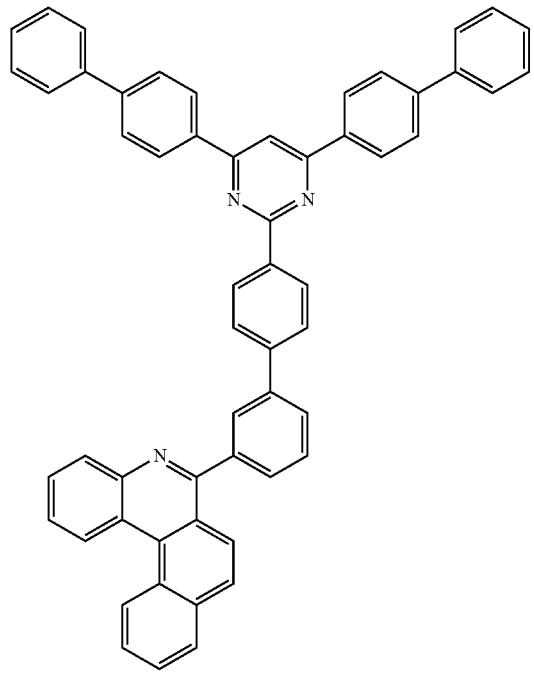
306
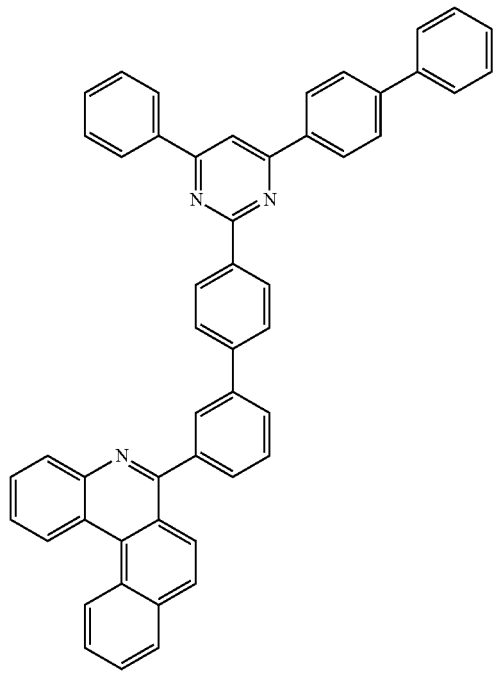

-continued
747
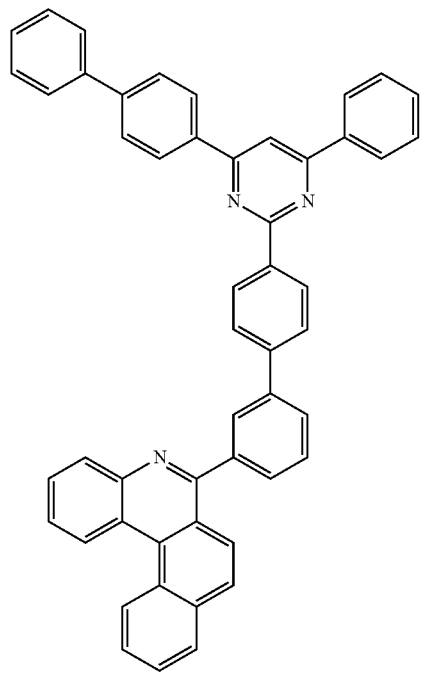
307
748
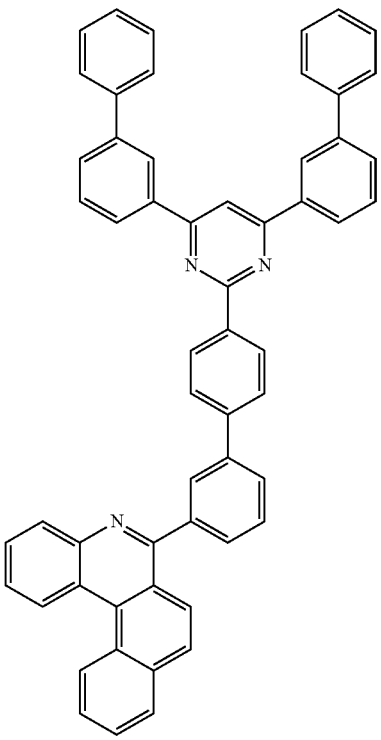
308
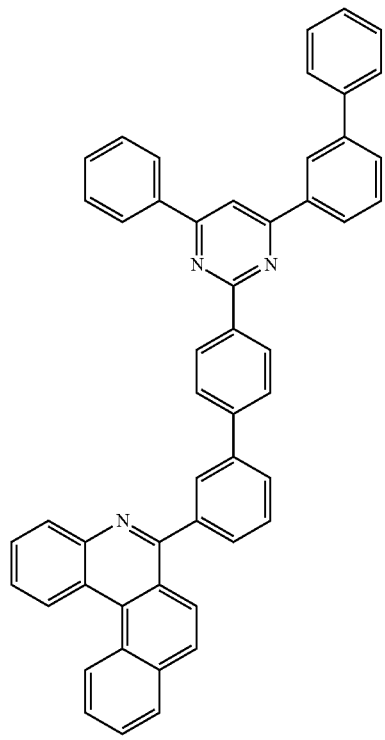
309
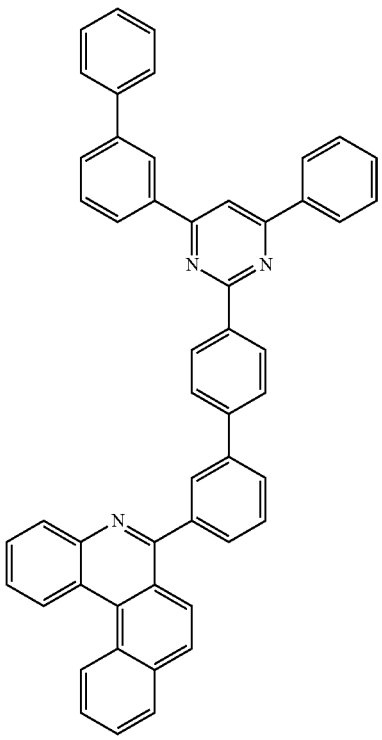
310

749
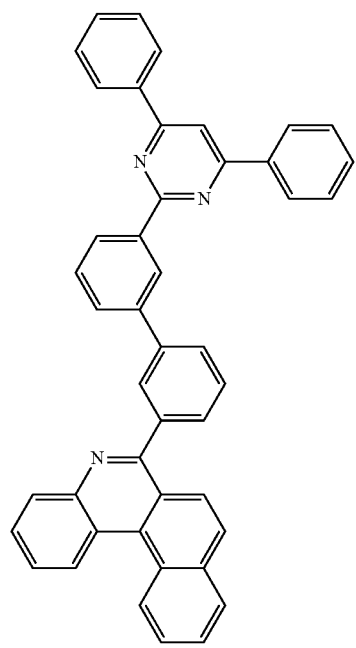
750
-continued
311
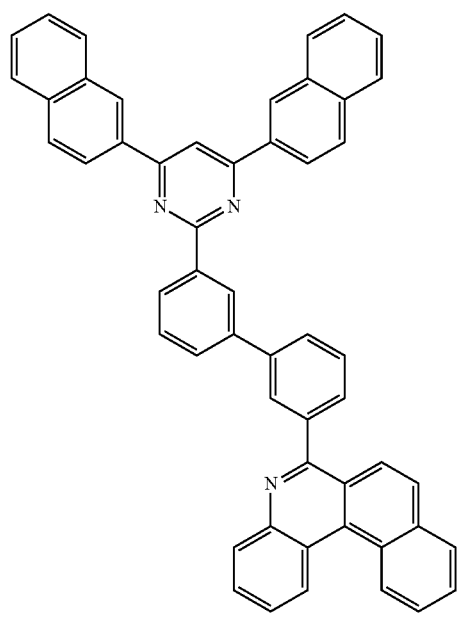
312
313
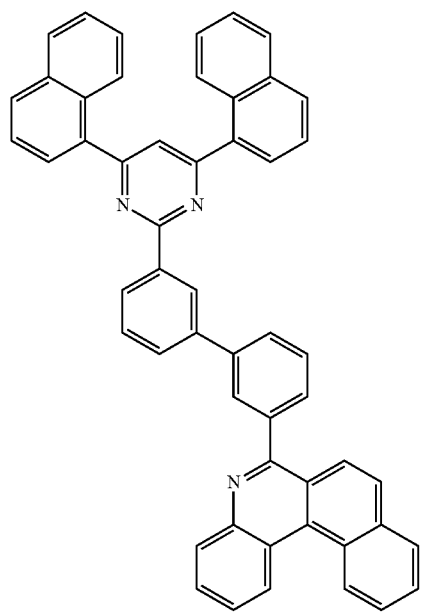
314
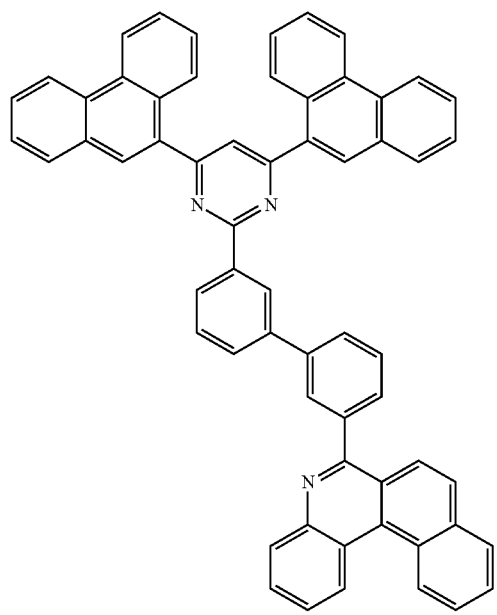

-continued
751
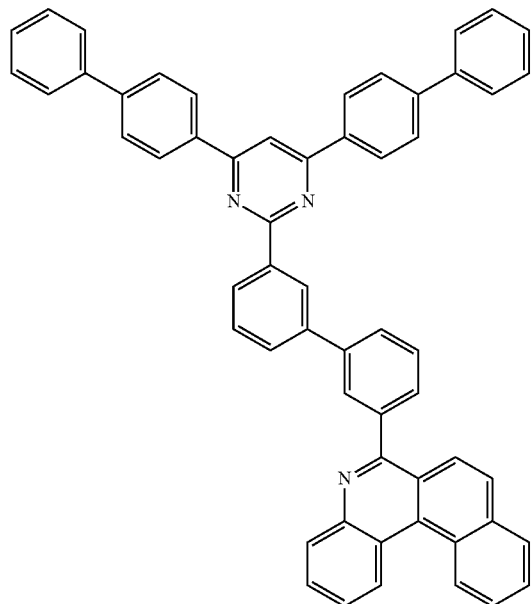
315
752
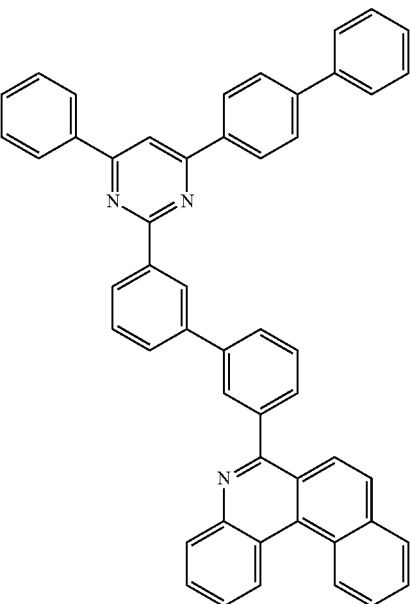
316
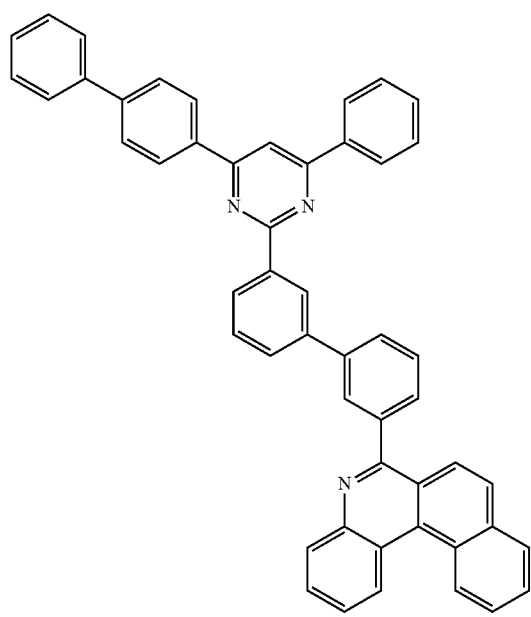
317
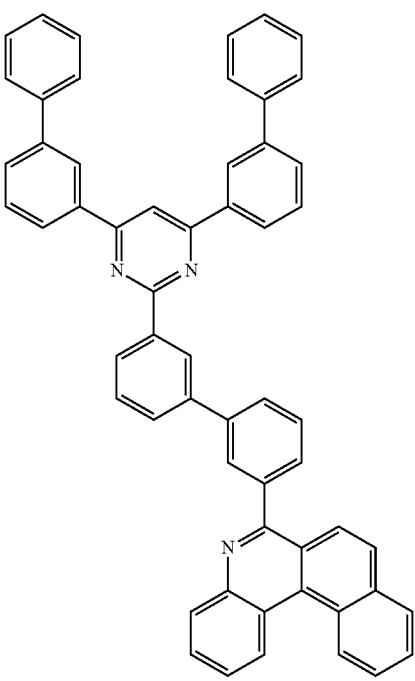
318

753
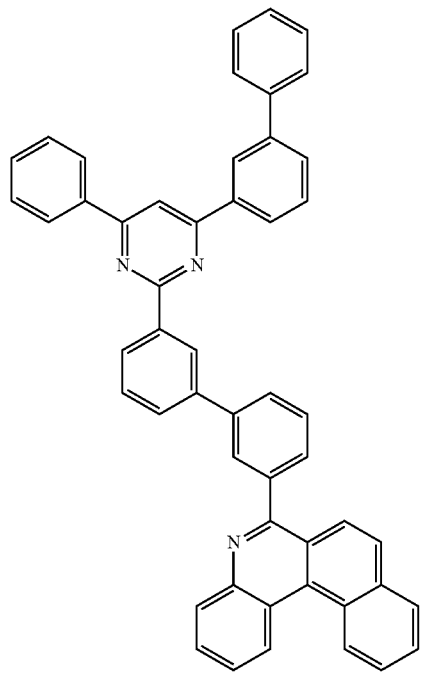
754
-continued
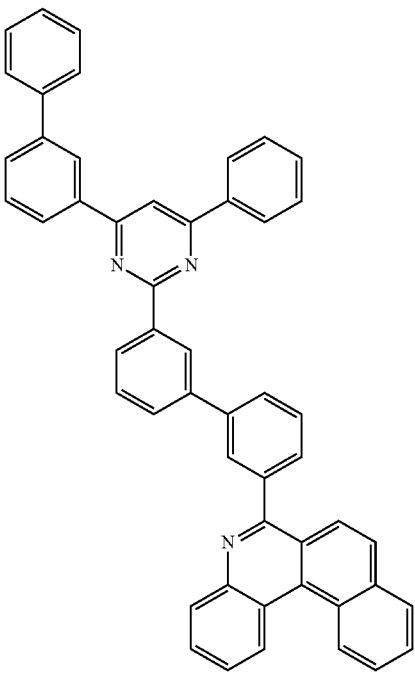
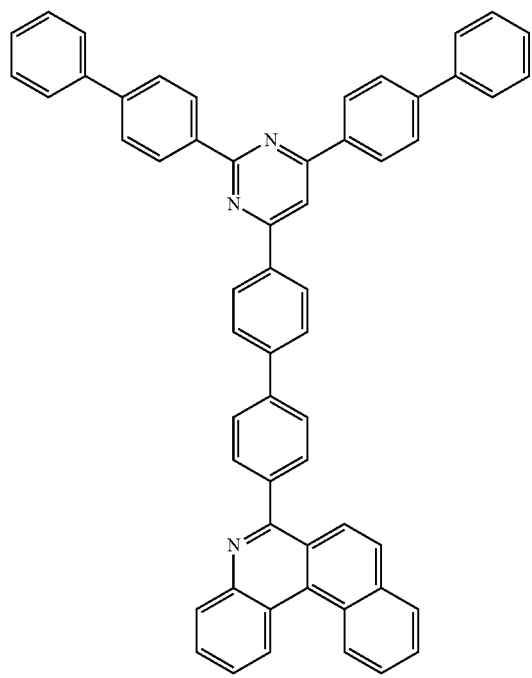
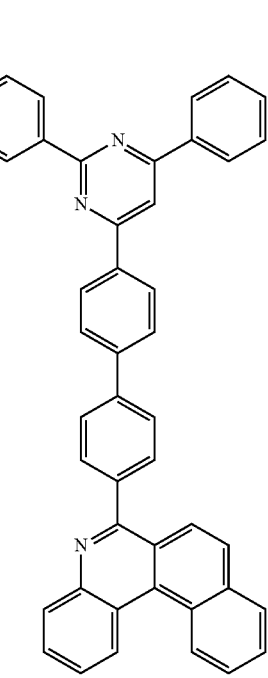

-continued
323
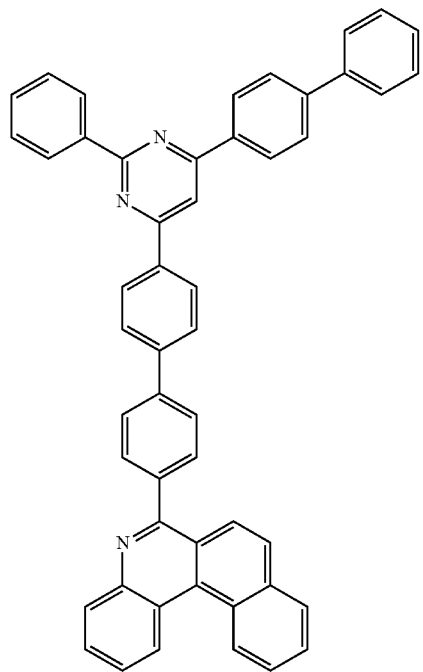
324
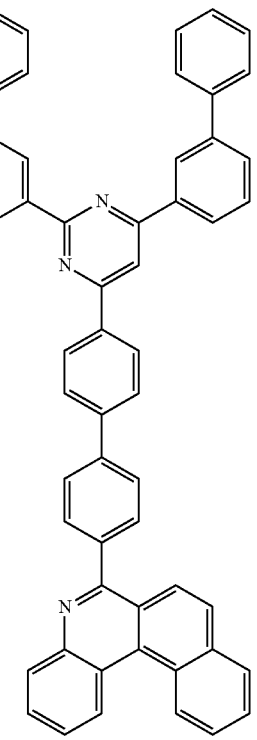
325
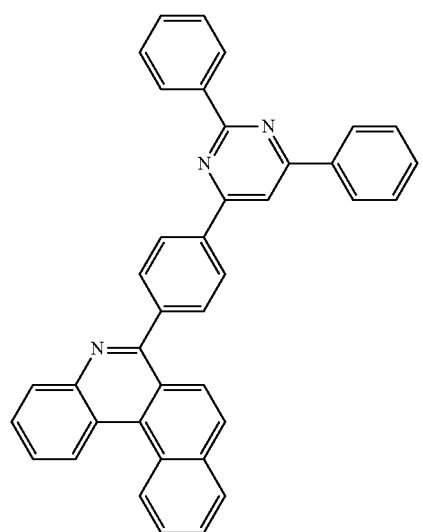
326
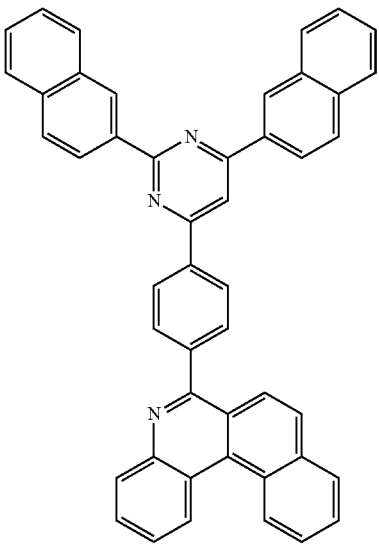

-continued
757      758
327
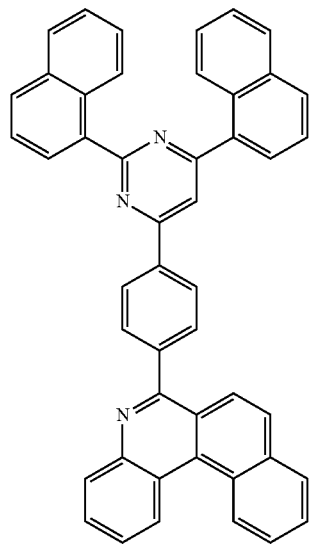
328
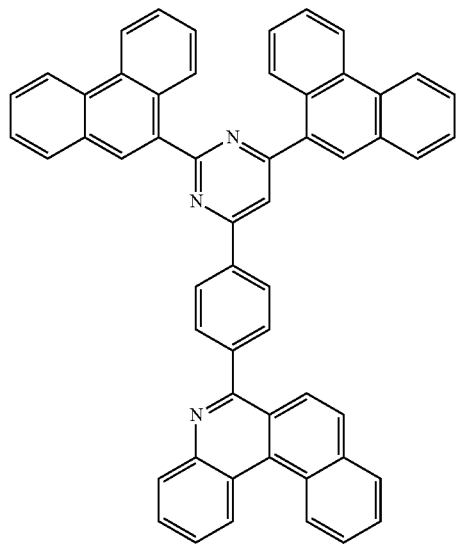
329
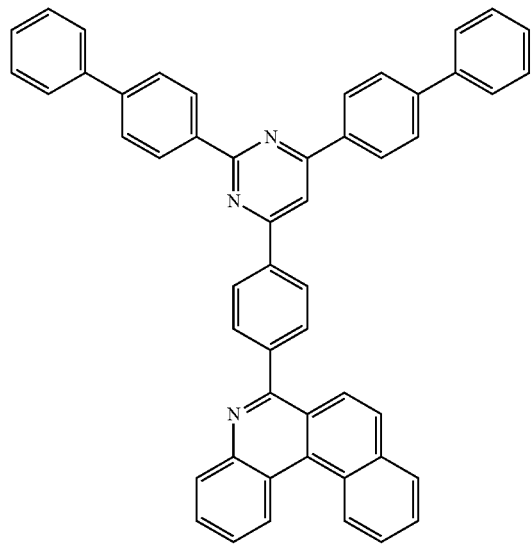
330
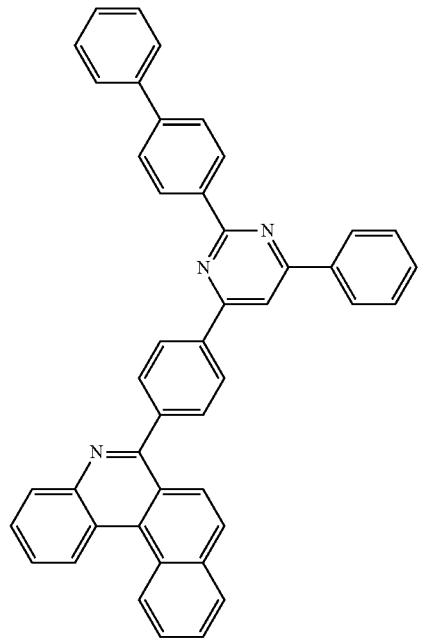

-continued
331 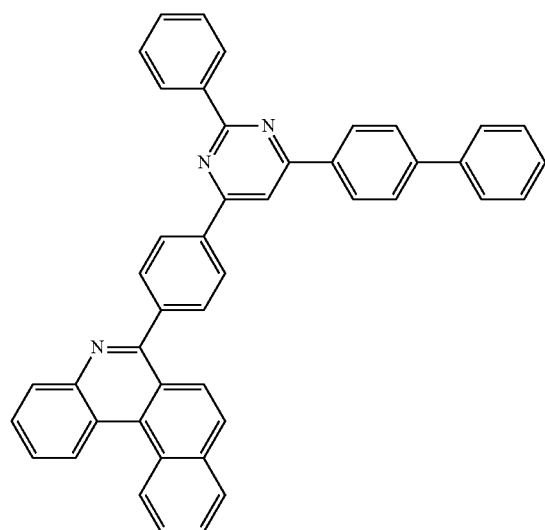
332 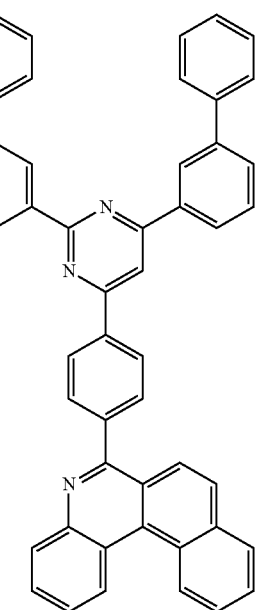
333 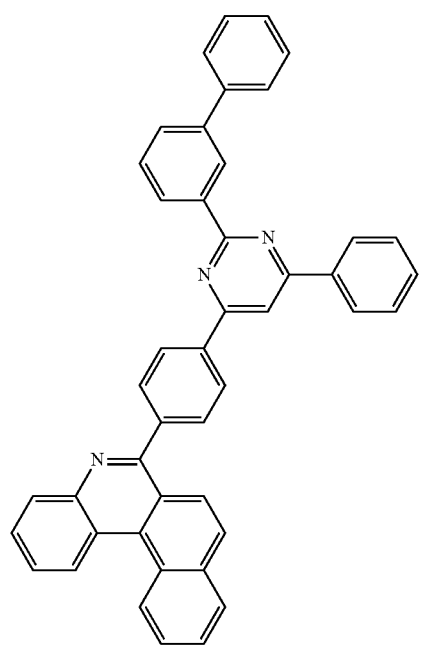
334 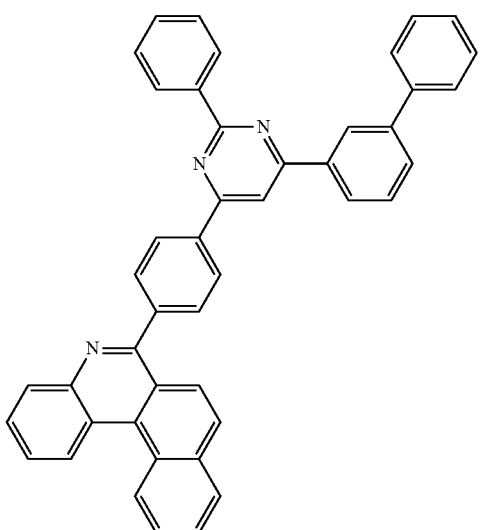

335
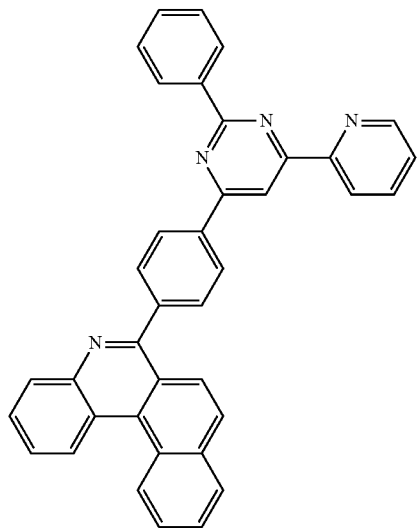
336
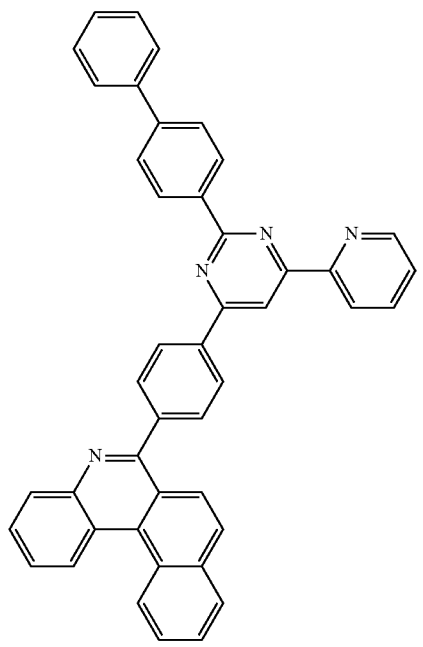
337
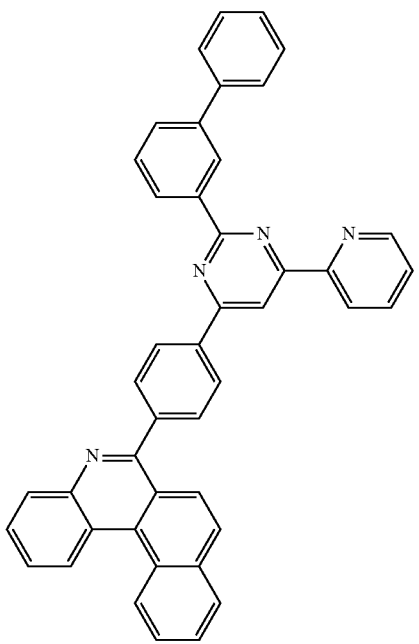

-continued
763
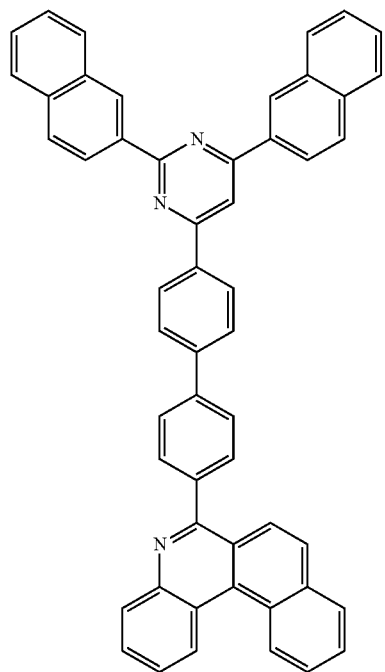
764
338
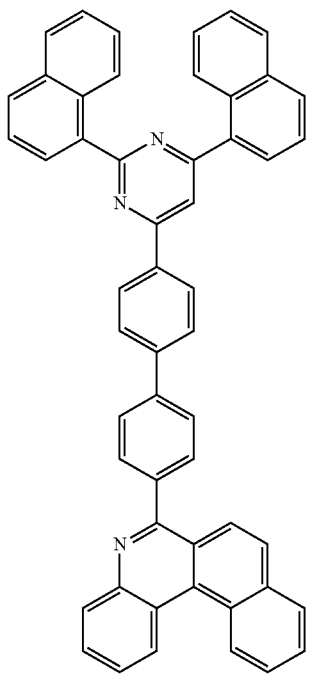
339
340
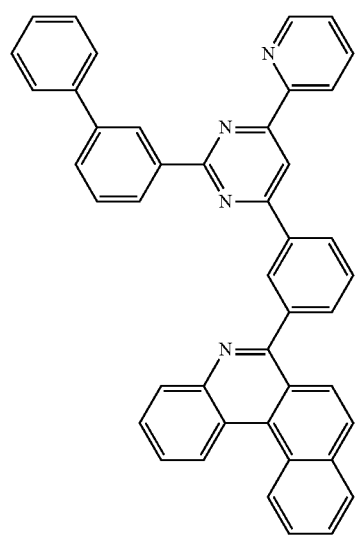
341
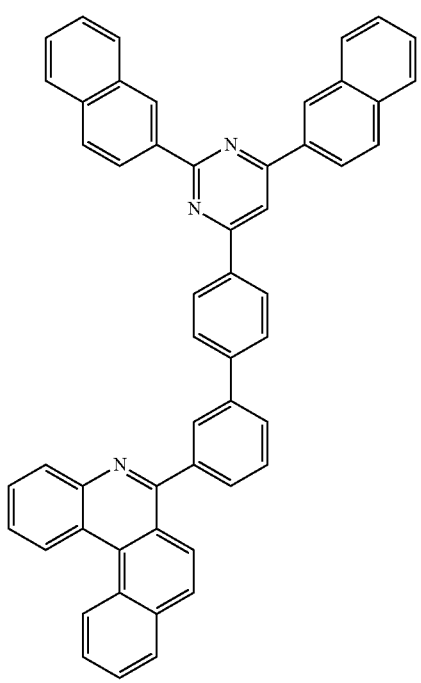

-continued
765
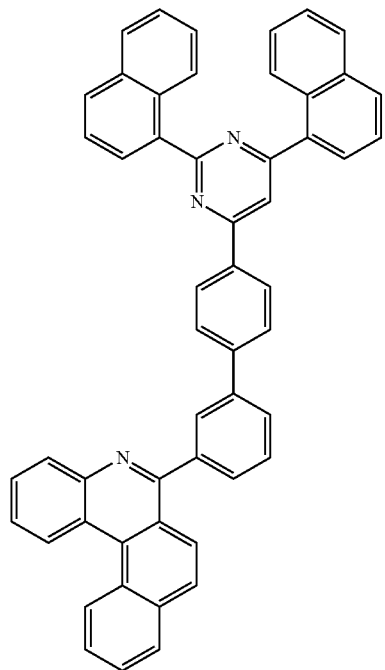
766
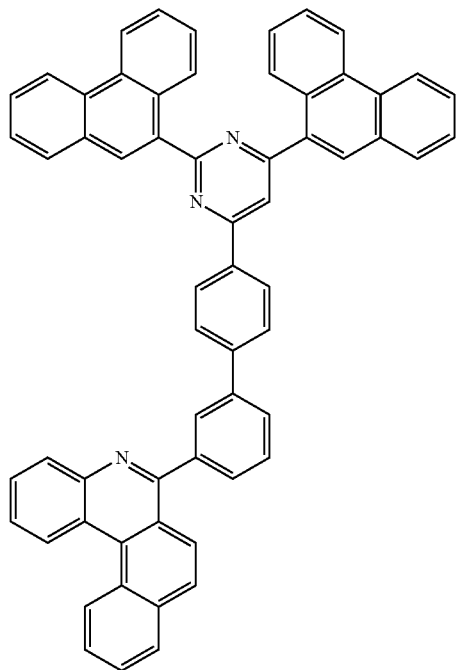
344
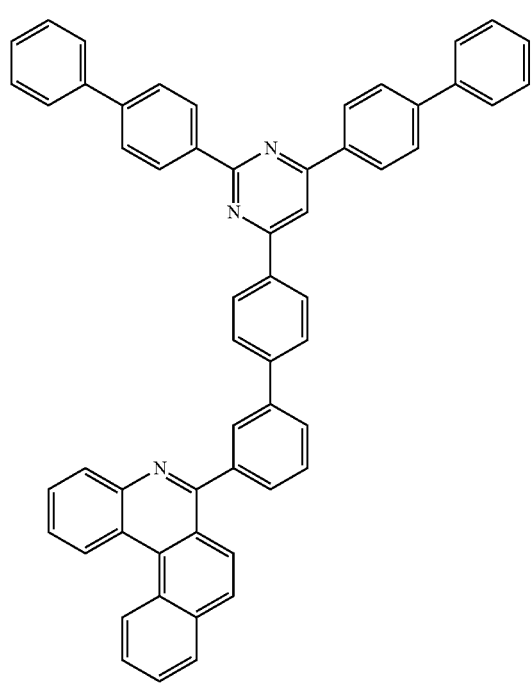
345
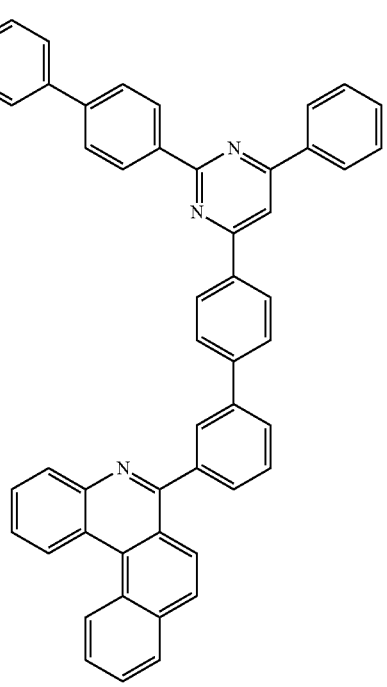

-continued
346
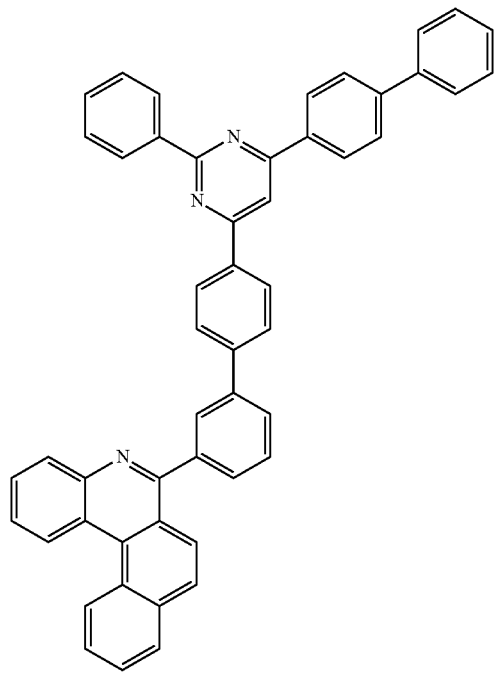
347
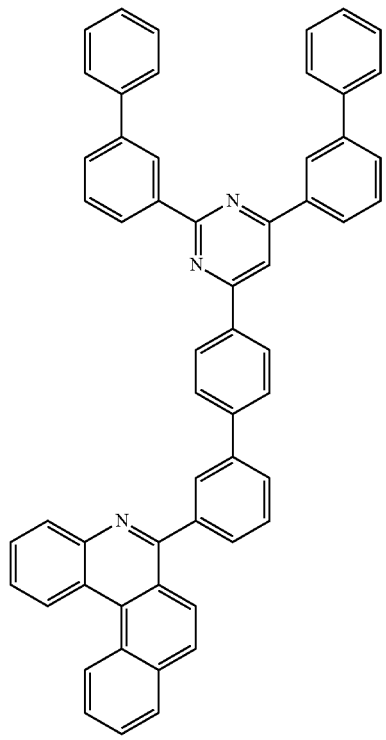
348
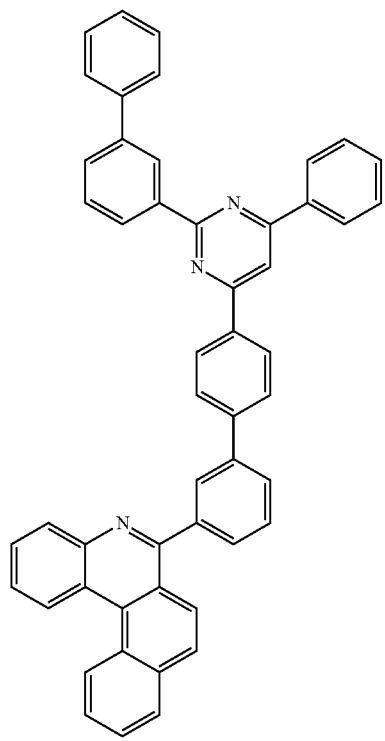
349
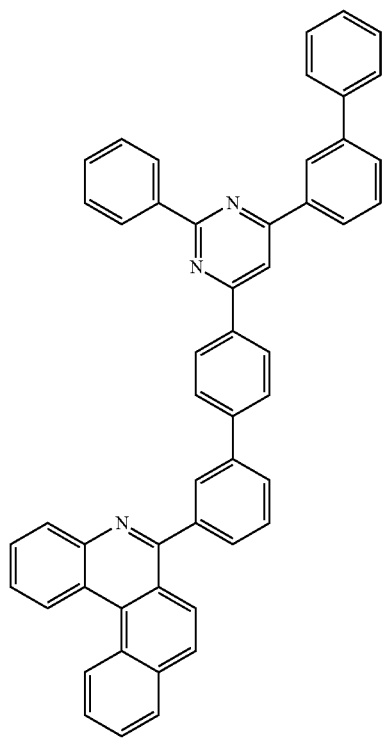

-continued
350 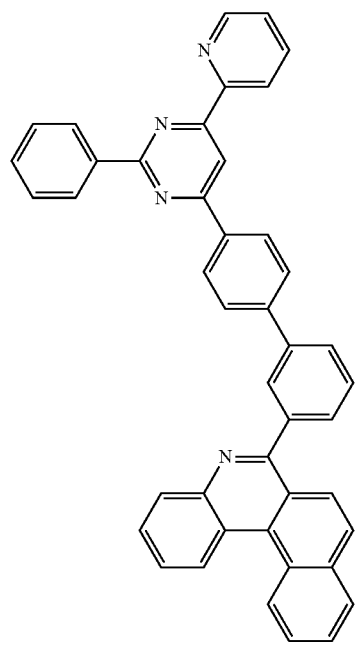
351 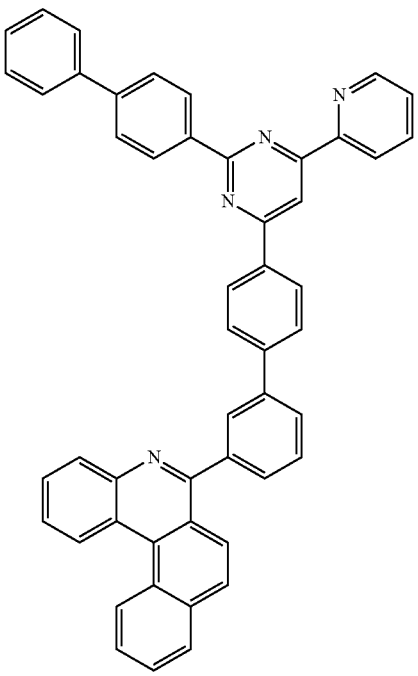
352 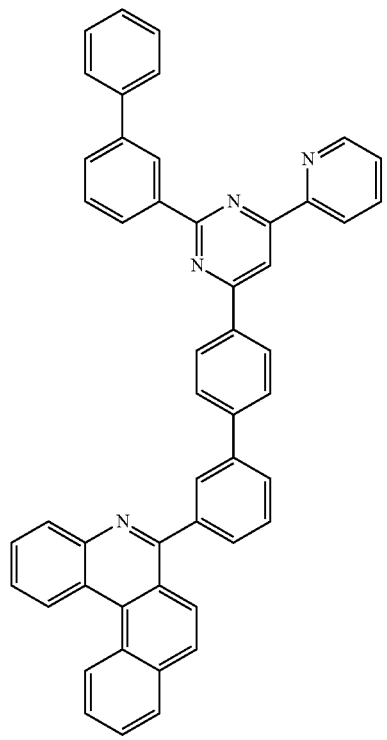
353 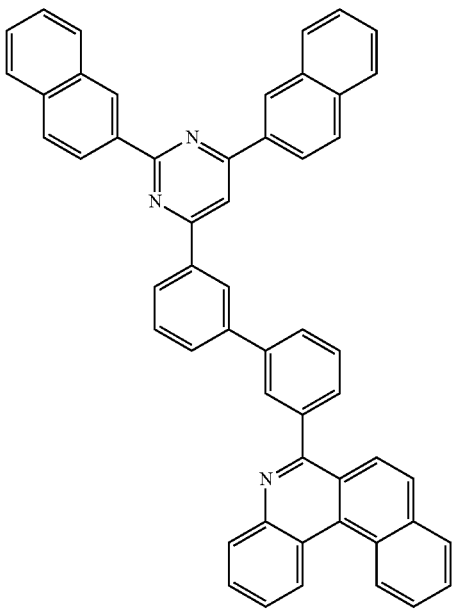

-continued
354
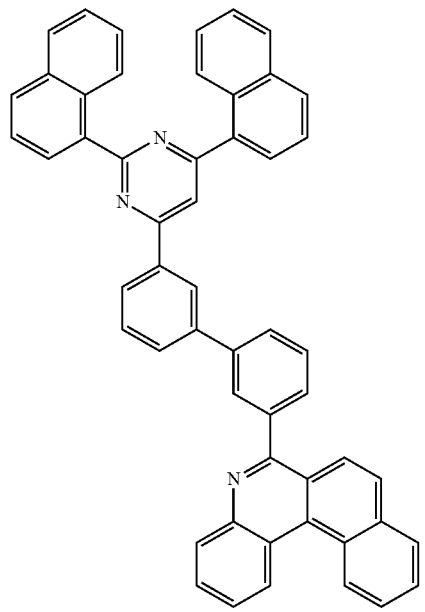
355
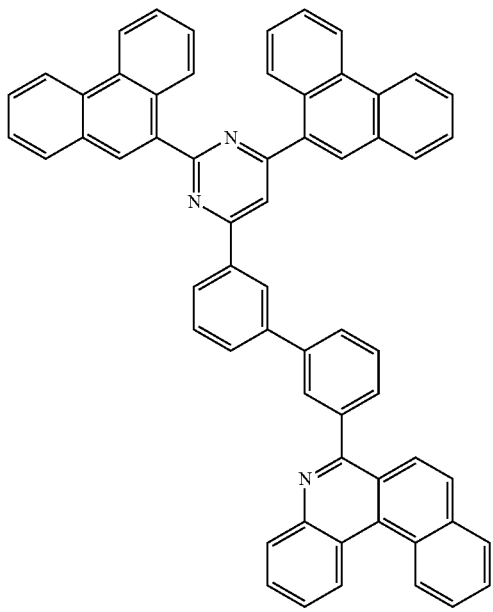
356
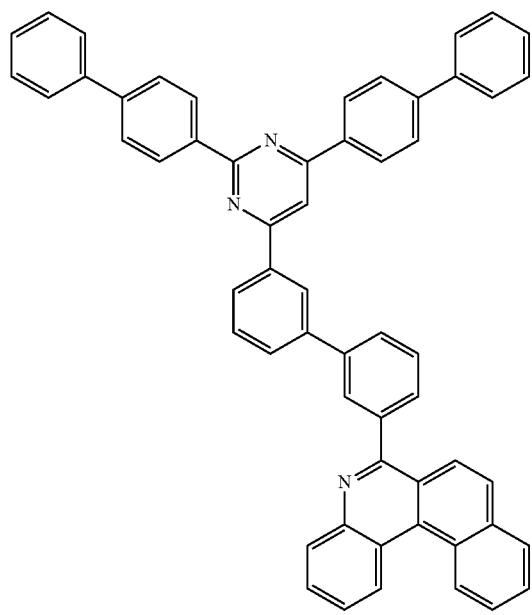
357
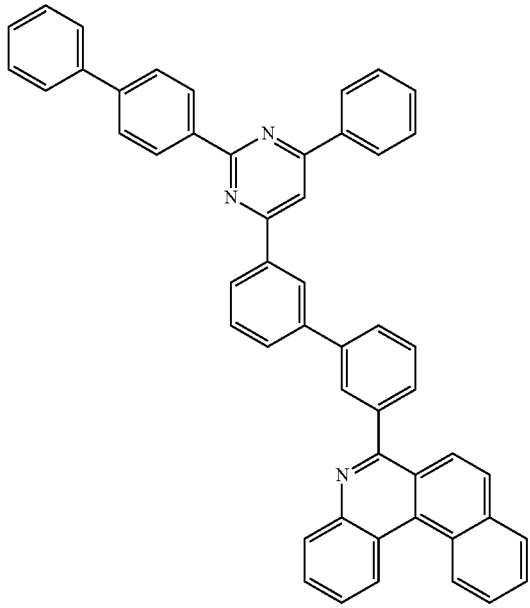

773
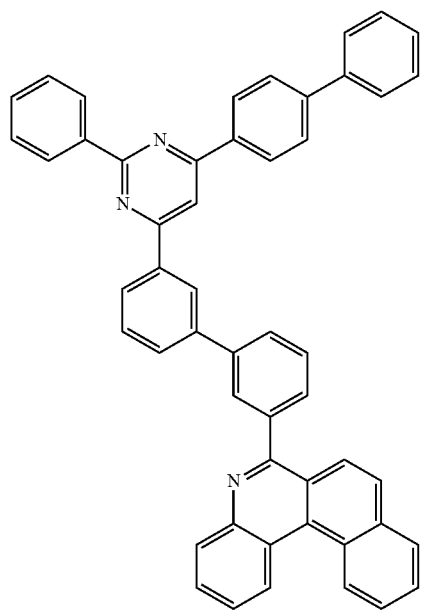
774
-continued
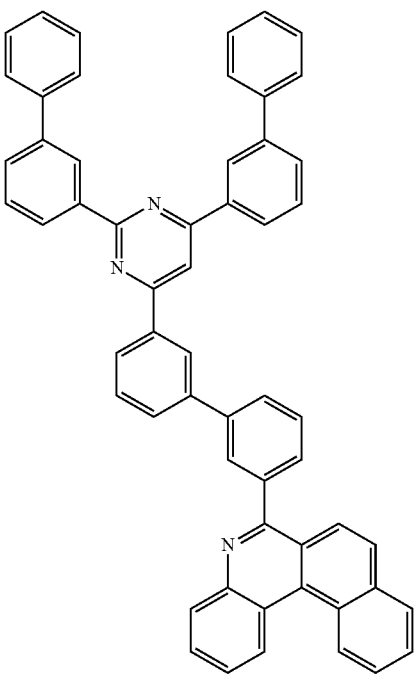
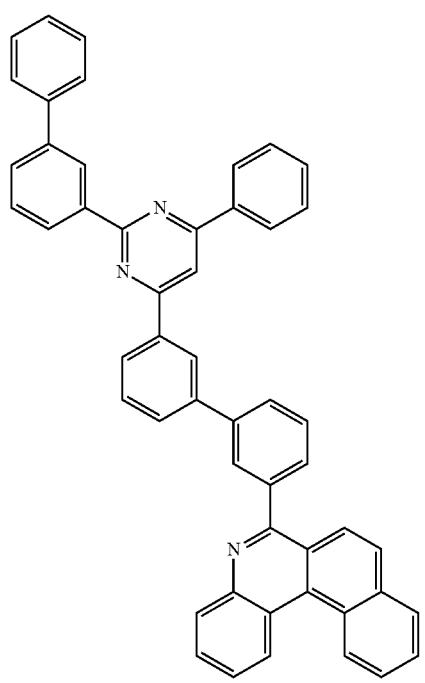
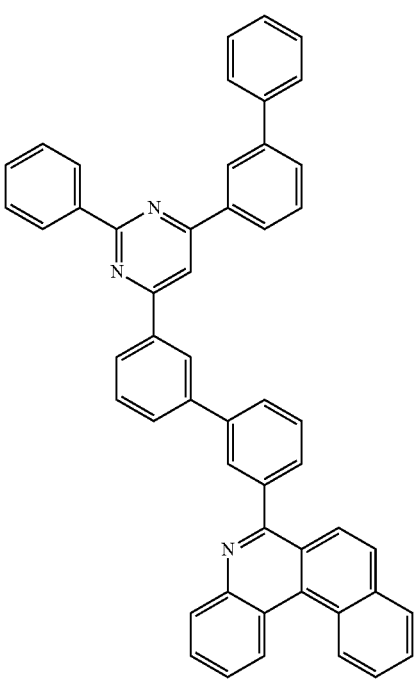

-continued
362 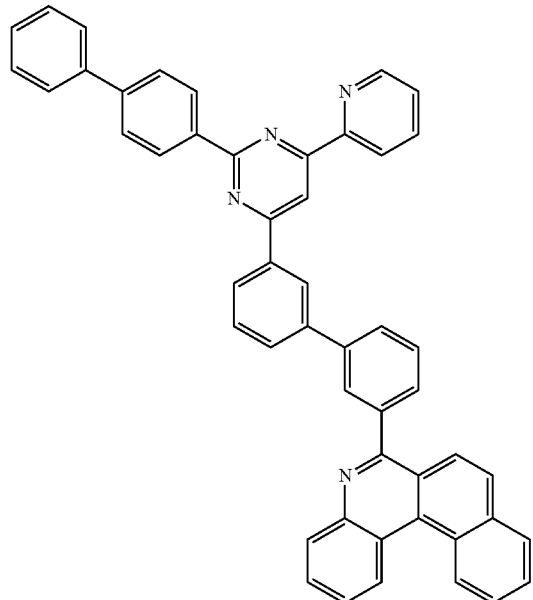
363
364 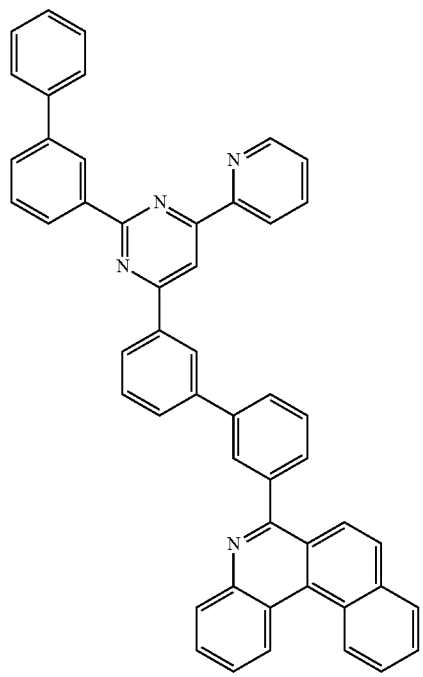
365 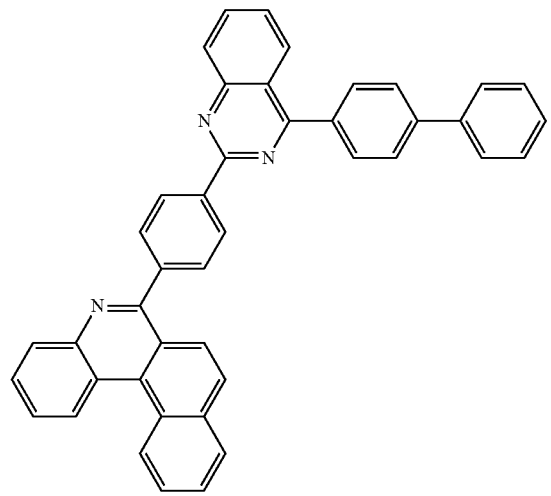
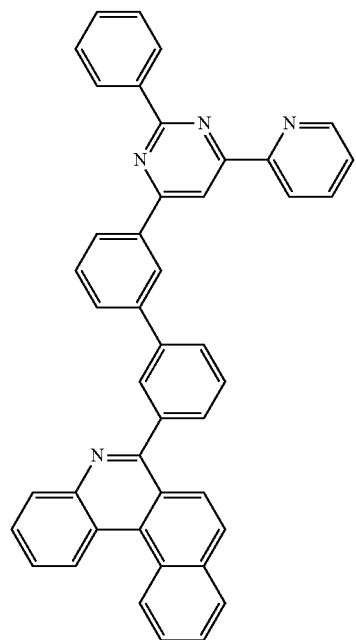

-continued
366
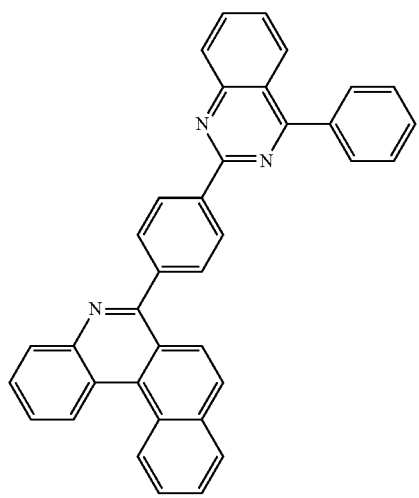
367
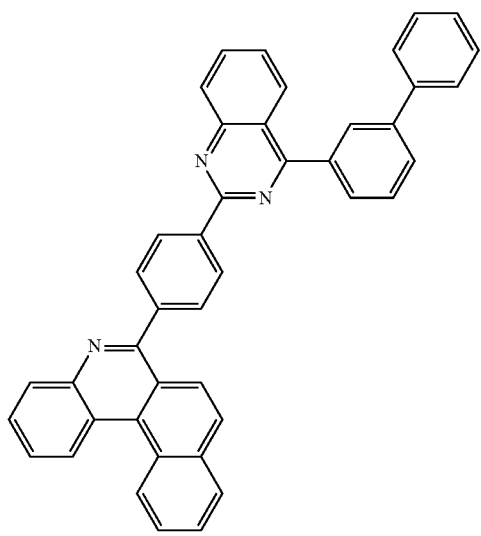
368
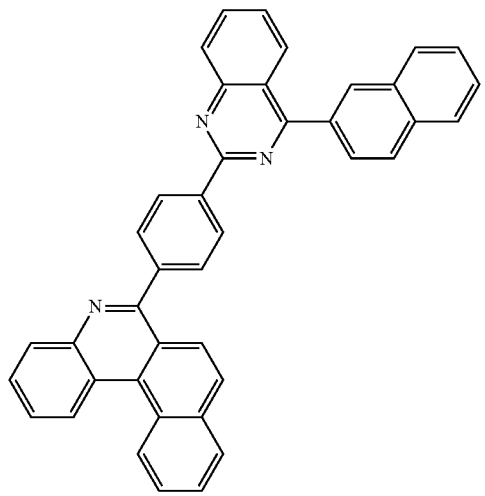
369
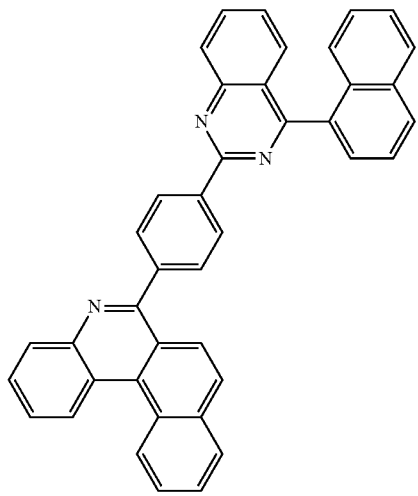

-continued
370
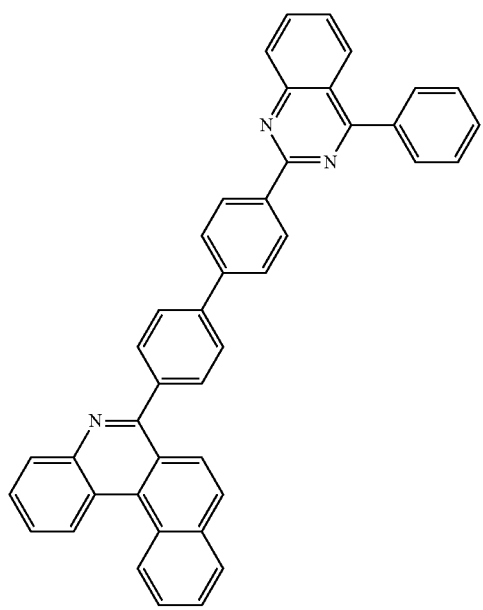
371
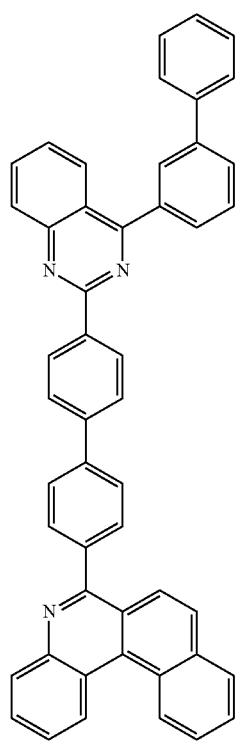
372
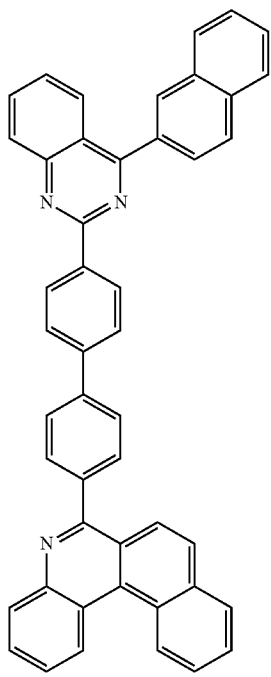
373
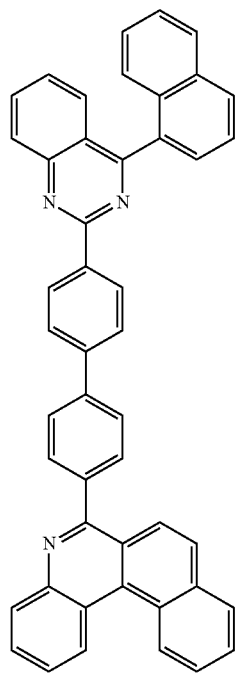

-continued
374
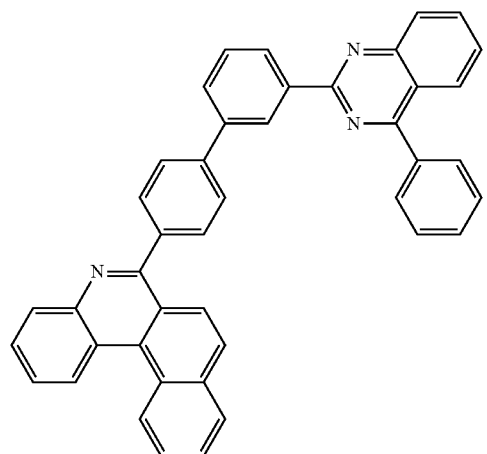
375
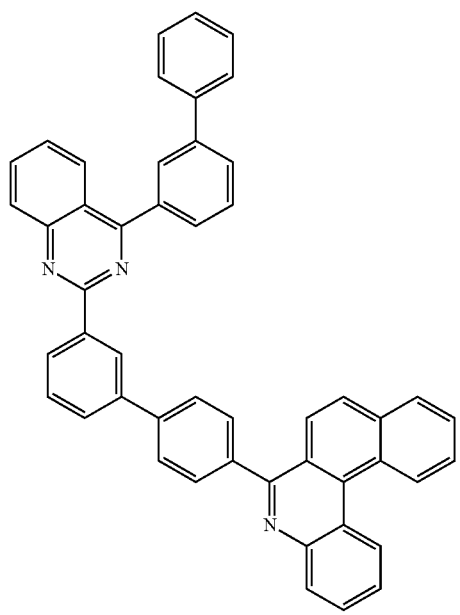
376
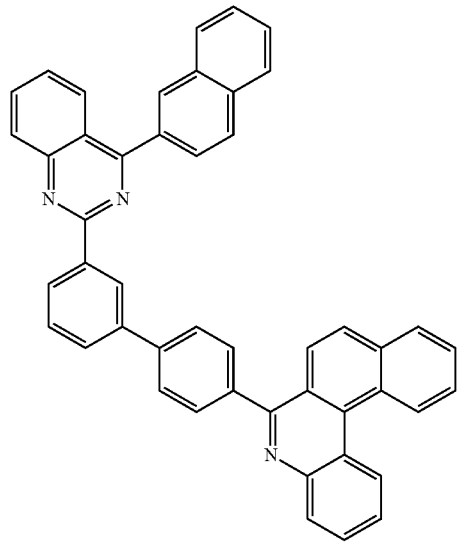
377
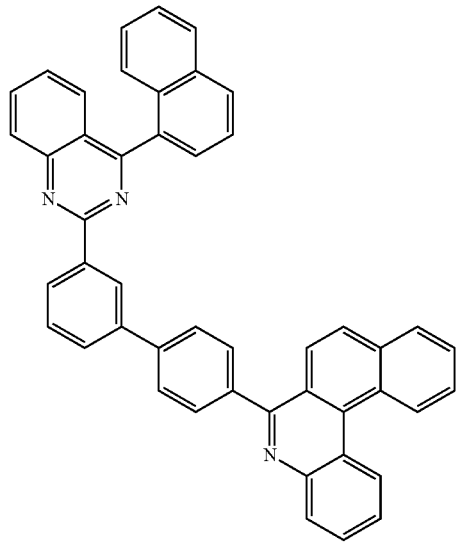

-continued
378 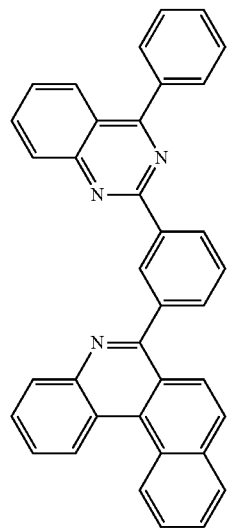
379 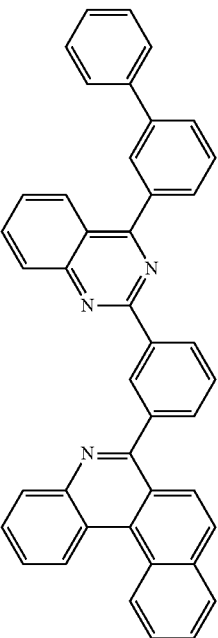
380 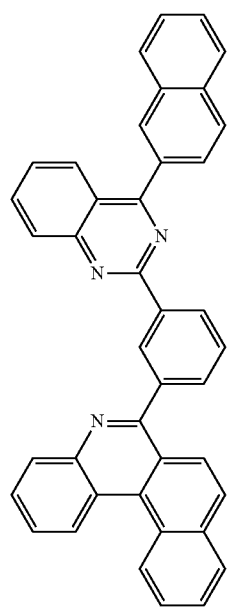
381 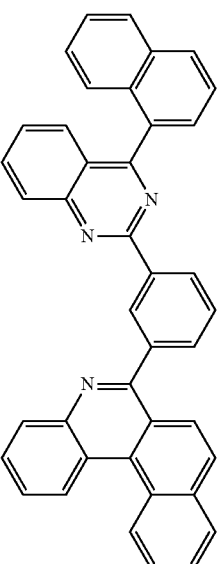

-continued
382
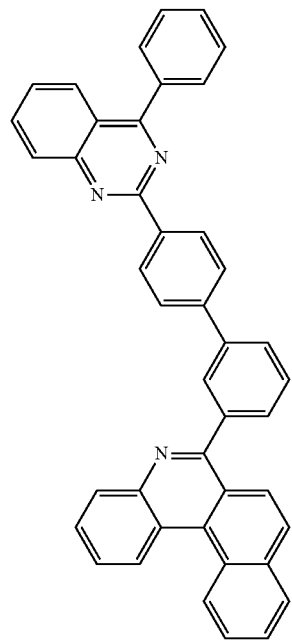
383
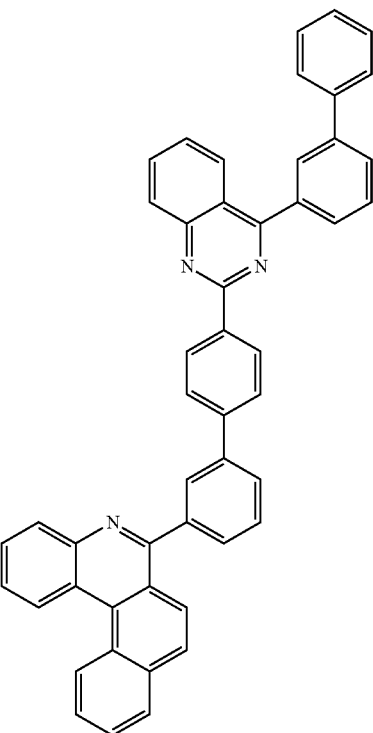
384
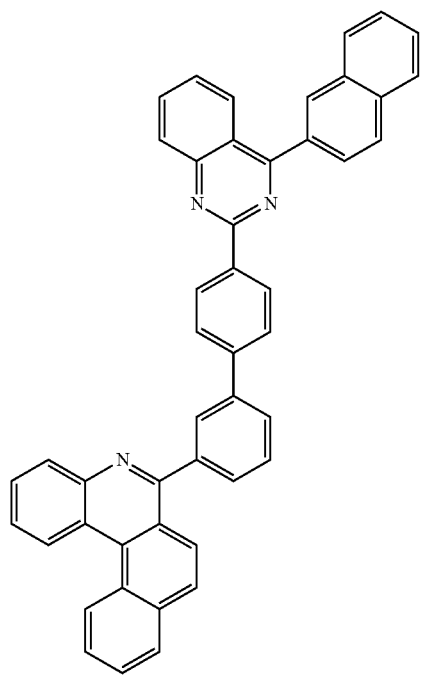
385
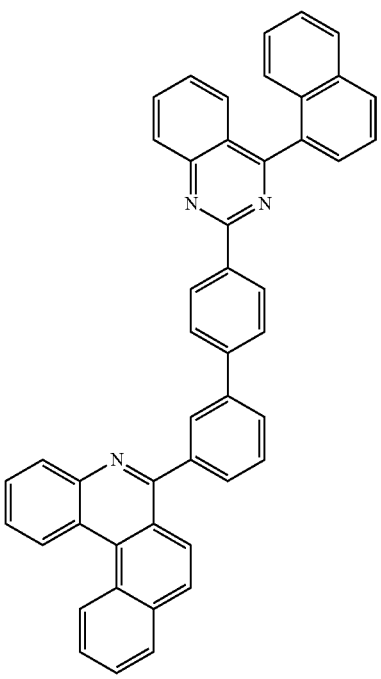

-continued
386
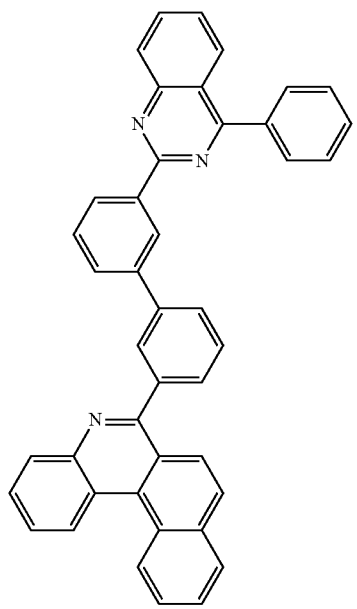
387
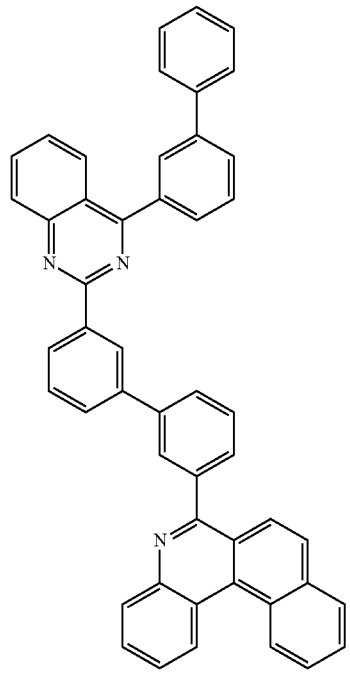
388
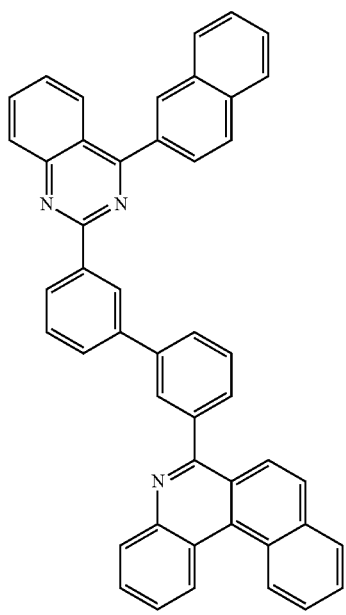
389
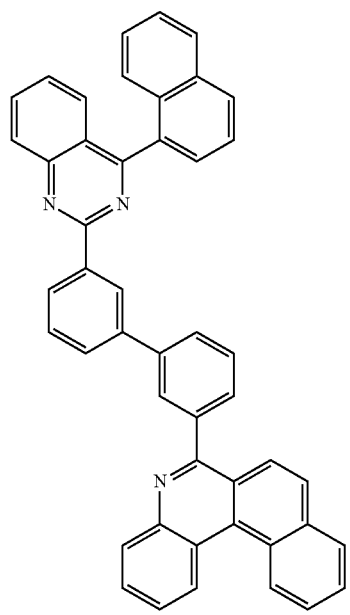

-continued
389
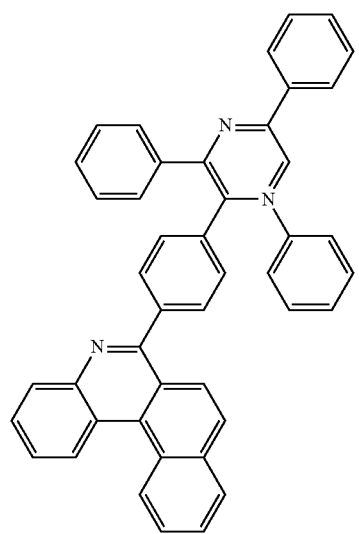
390
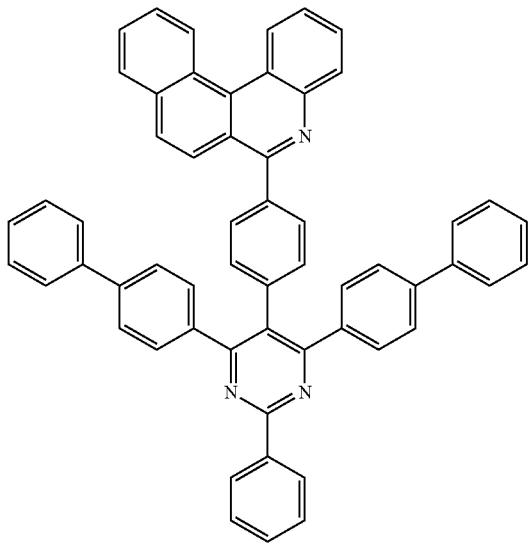
391
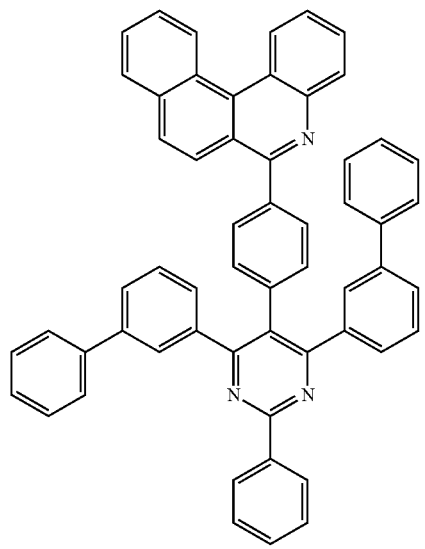
392
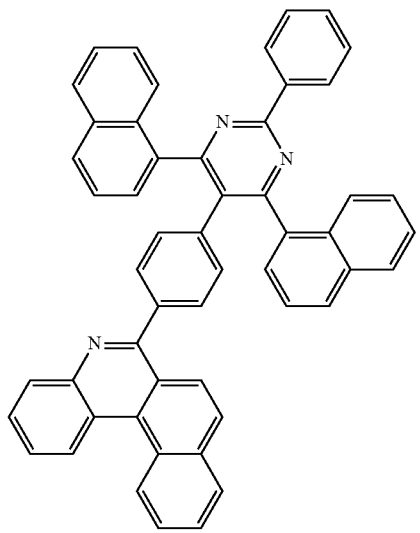
393

791 792
-continued
394 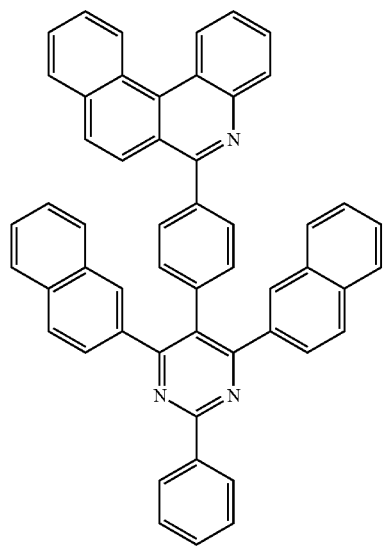 395 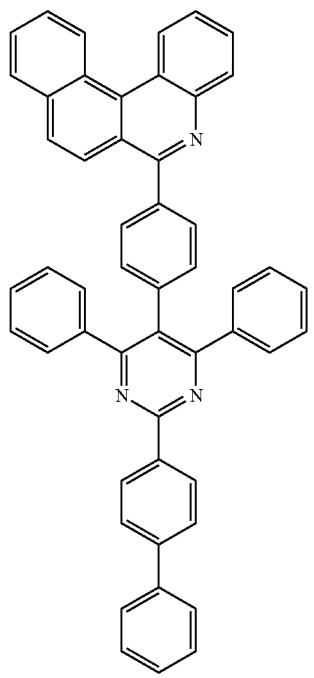
396 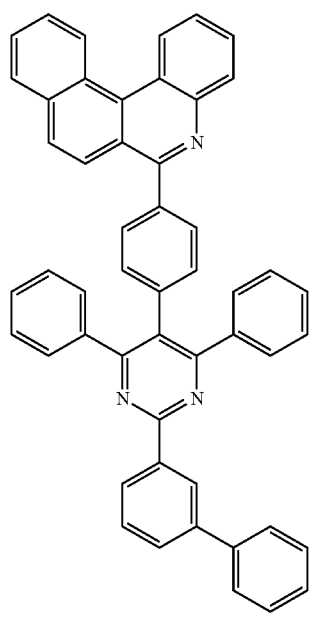 397 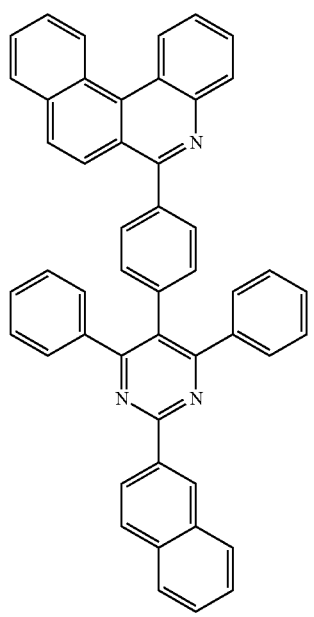

793
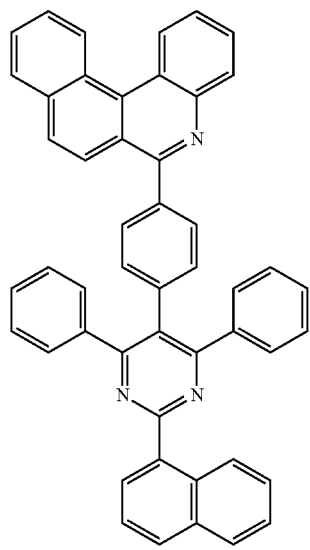
794
-continued
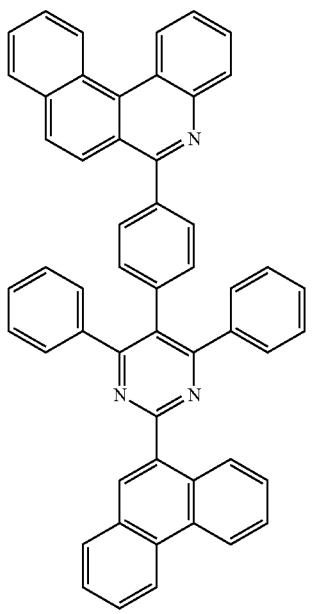
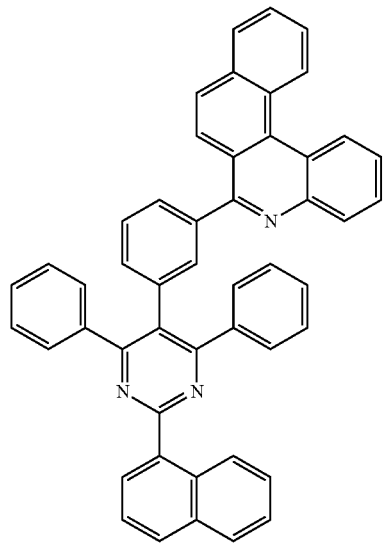
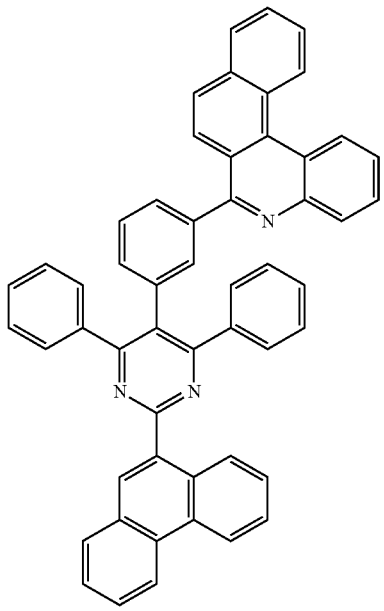

-continued
795
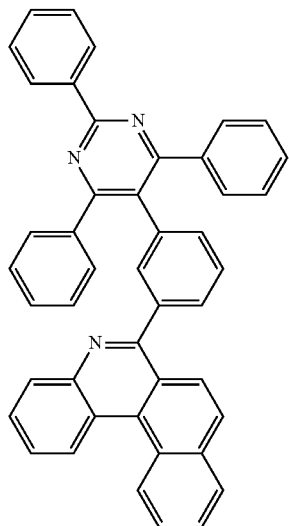
402
796
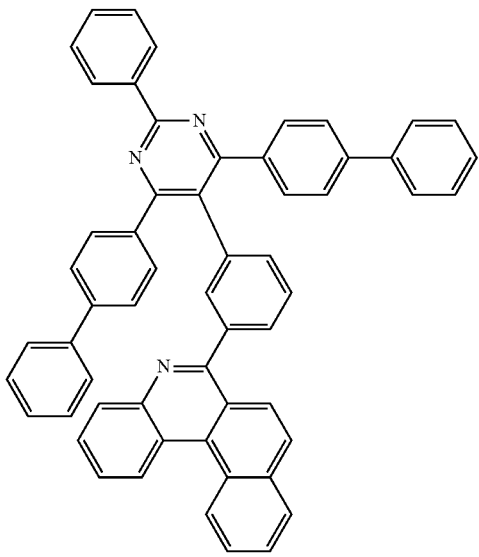
403
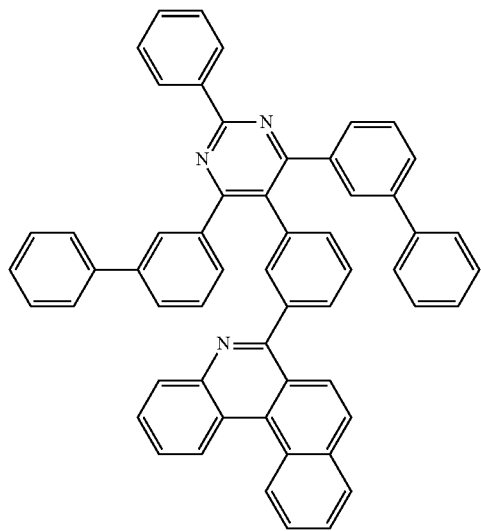
404
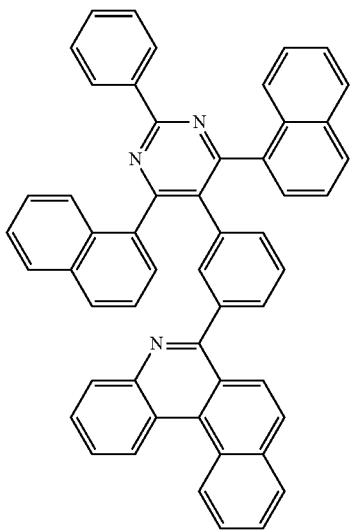
405

406
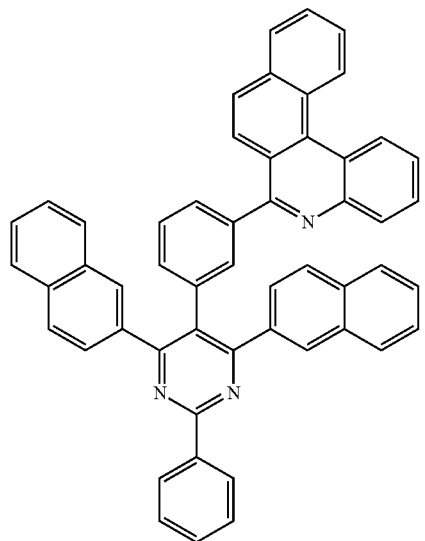
407
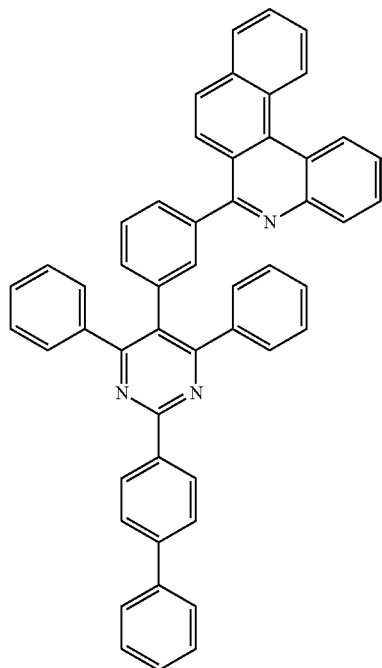
408
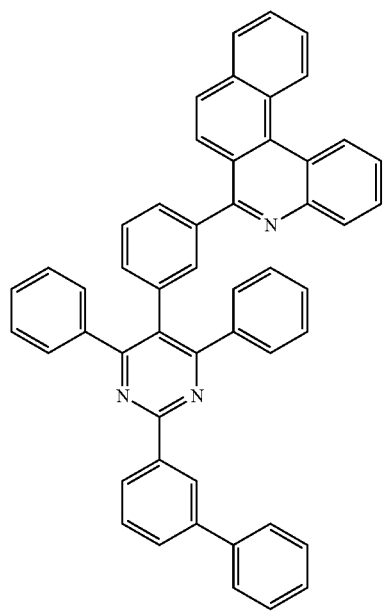
409
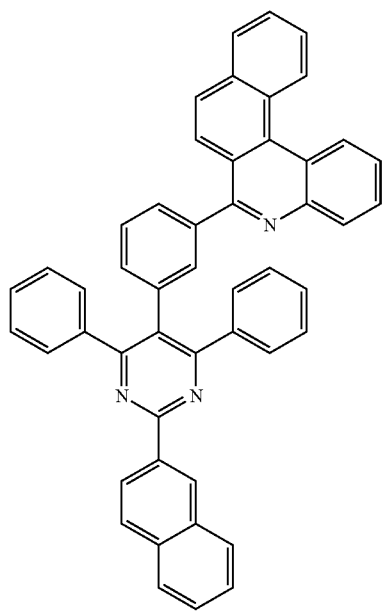

-continued
410
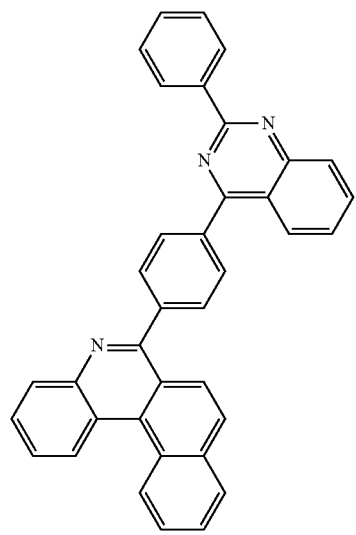
411
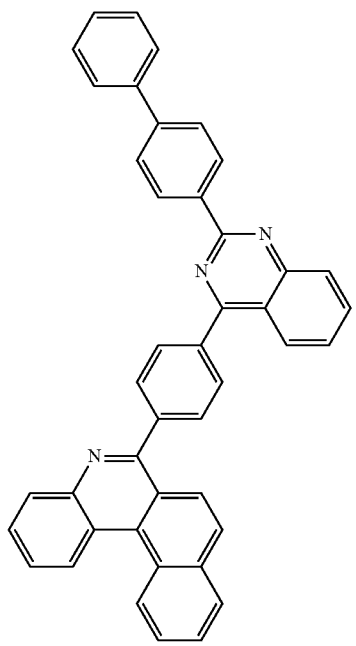
412
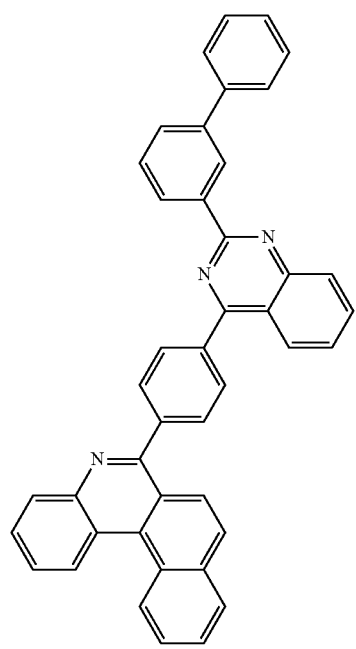
413
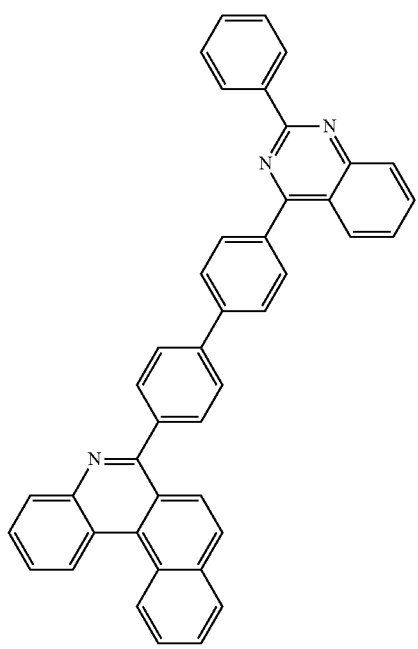

801
-continued
414
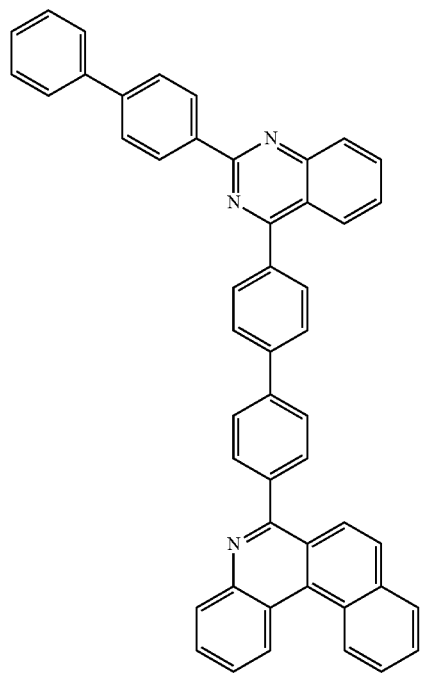
802
415
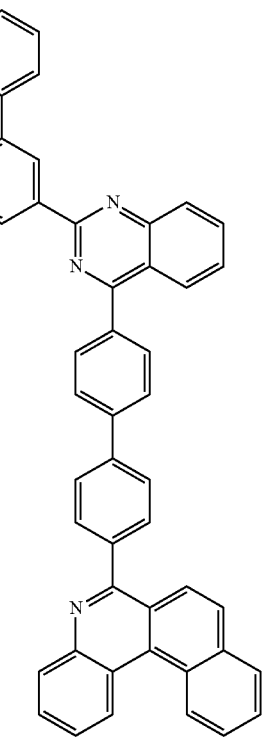
416
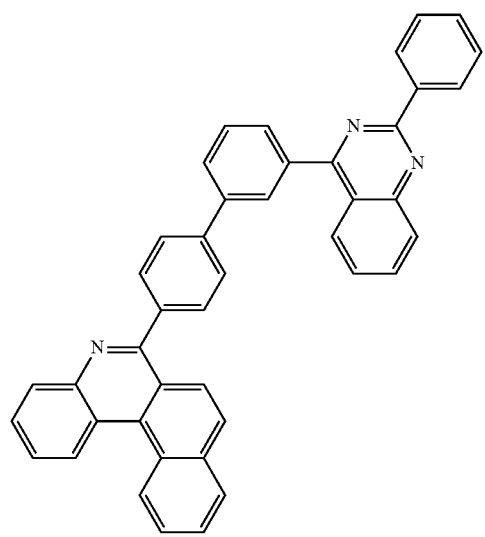
417
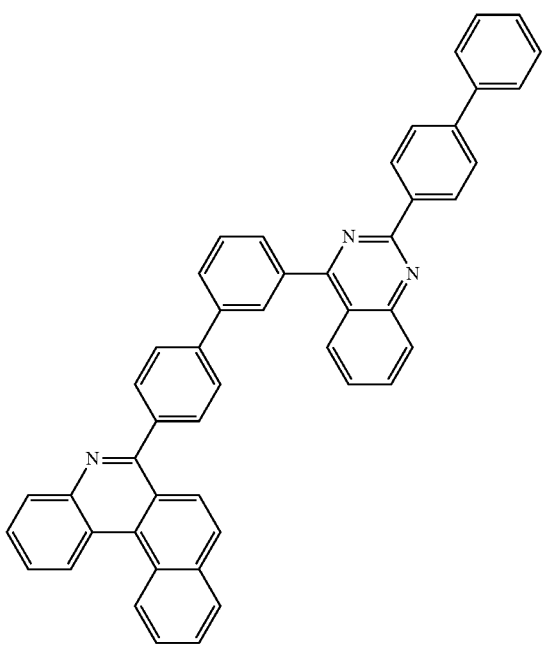

418
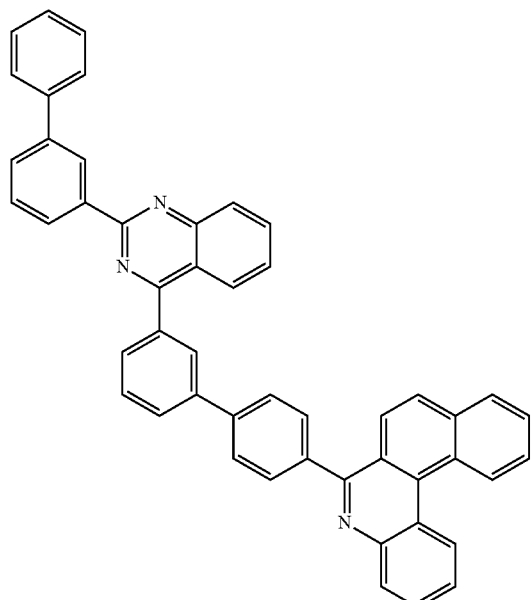
419
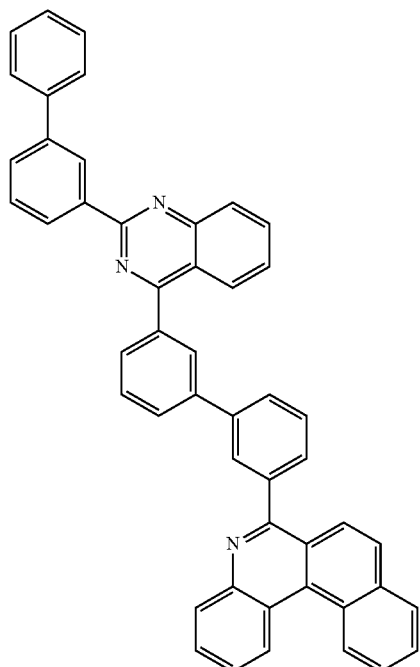
420
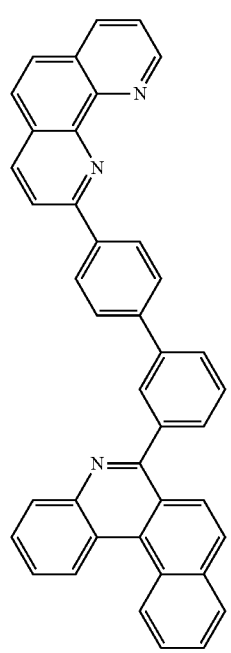
421
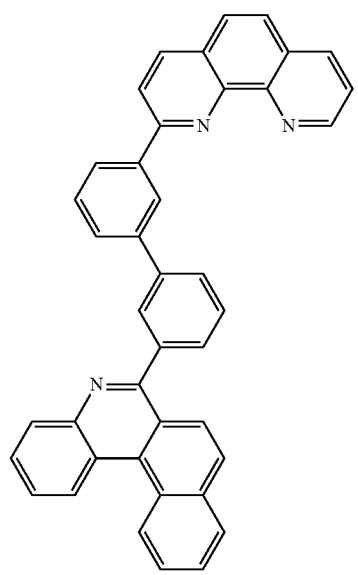

-continued
805
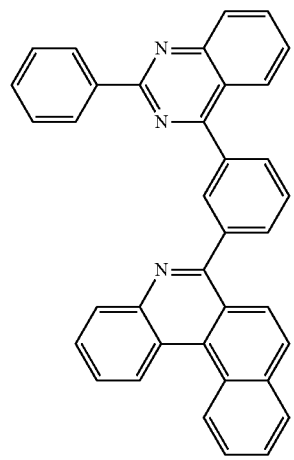
806
422
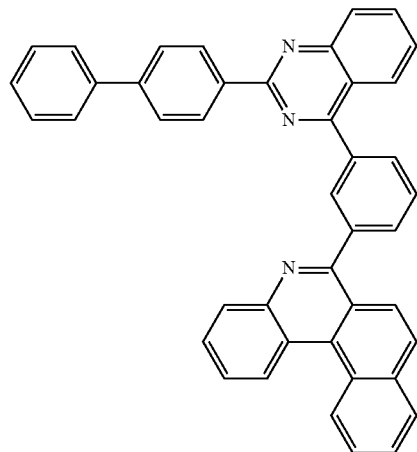
423
424
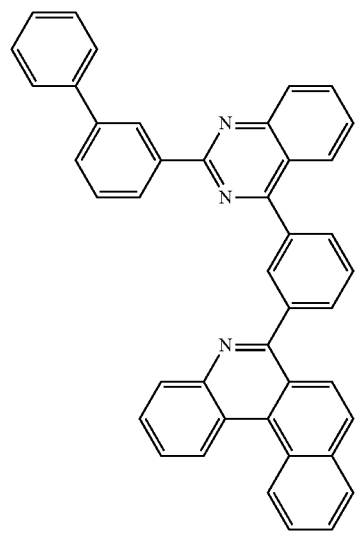
425
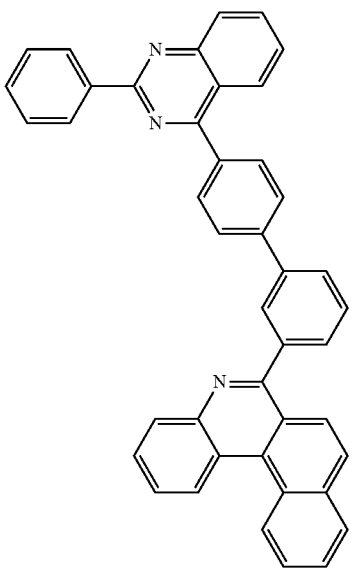

-continued
807
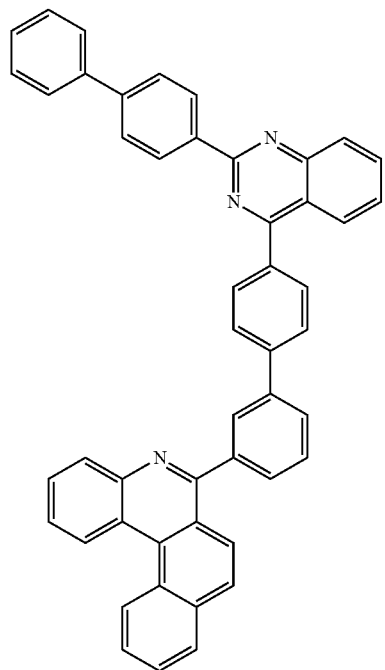
426
808
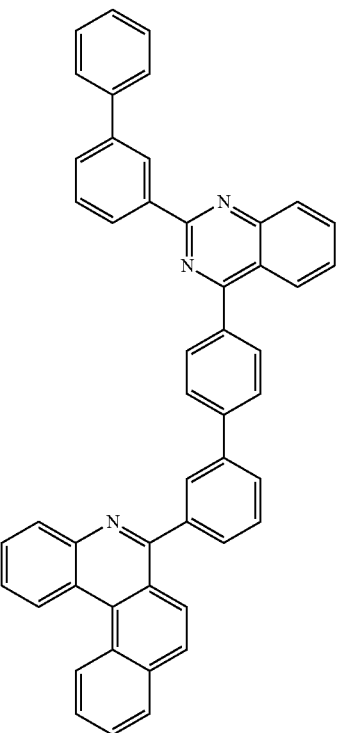
427
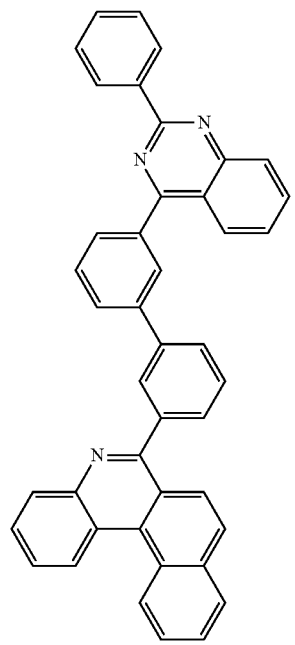
428
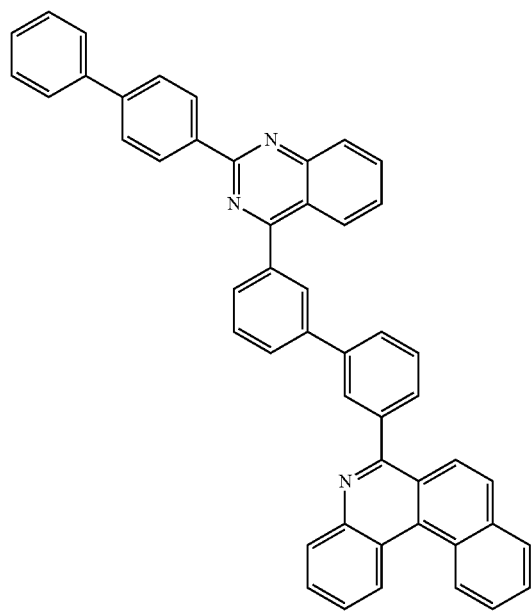
429

-continued
809
430
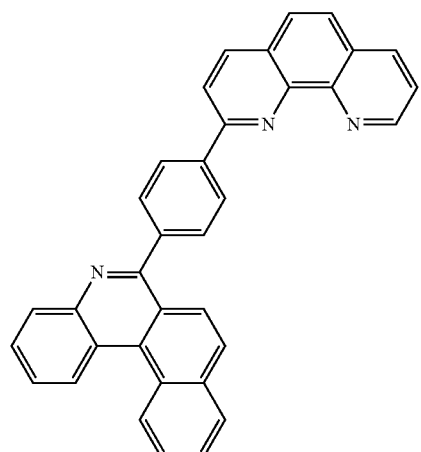
810
431
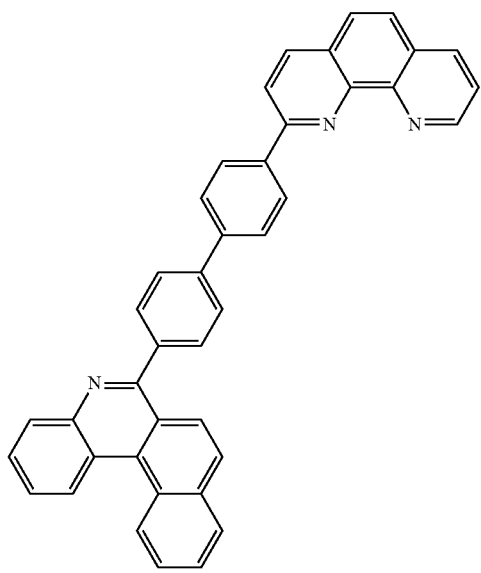
432
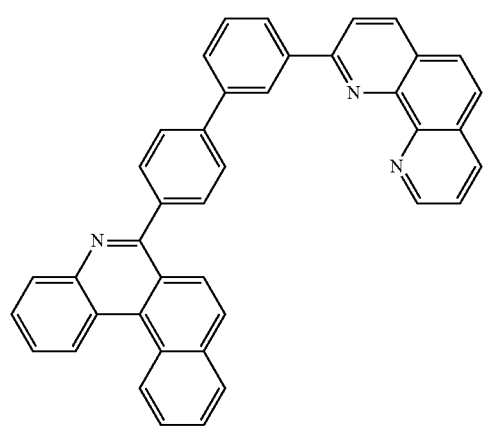
433
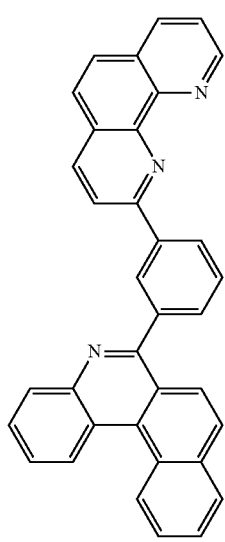

-continued
811     812
434     435
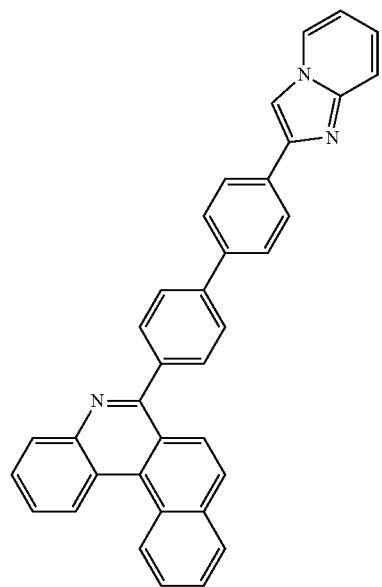 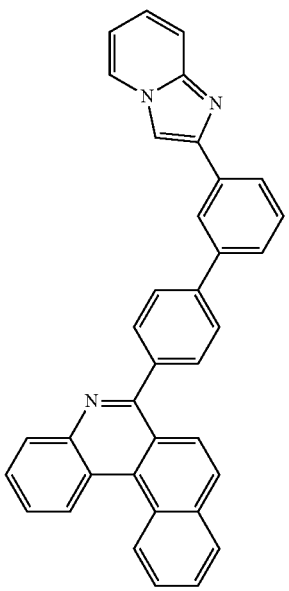
436     437
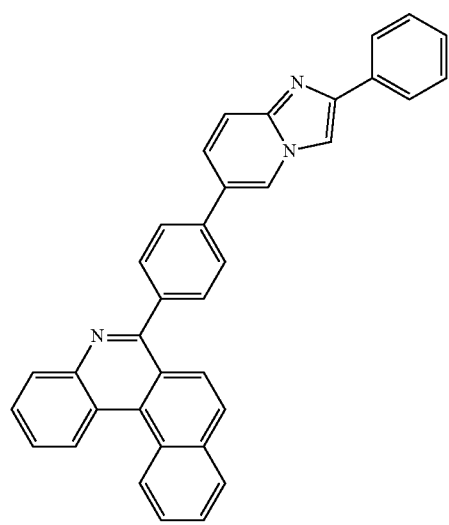 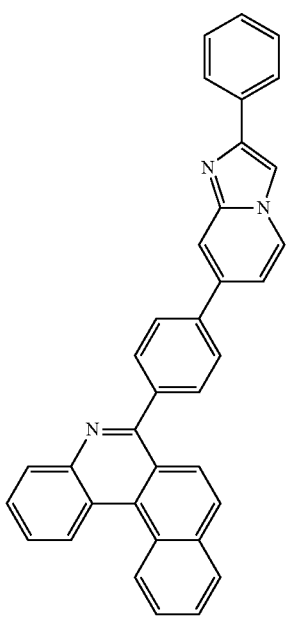

-continued
438
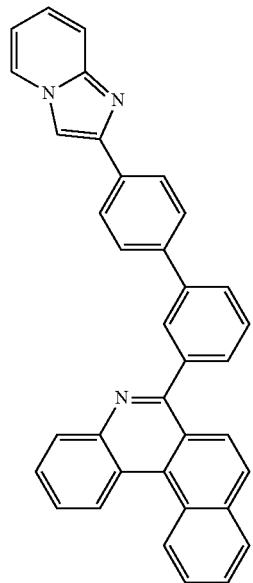
439
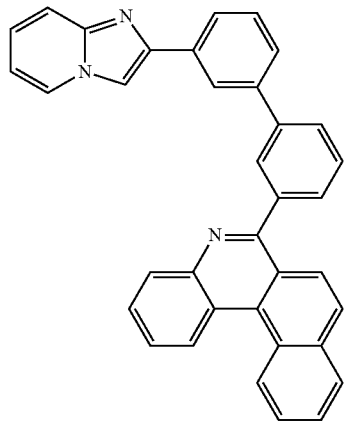
440
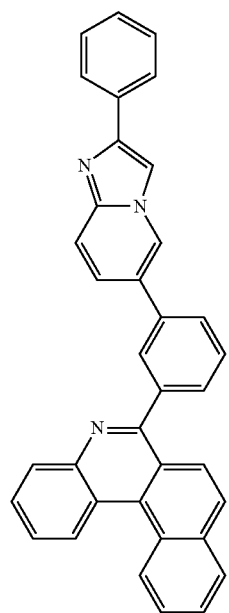
441
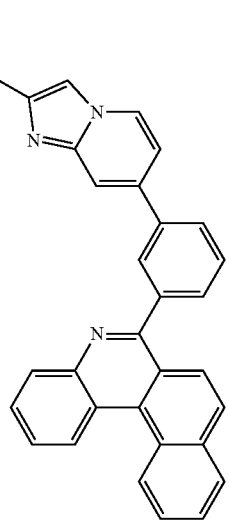

-continued
442
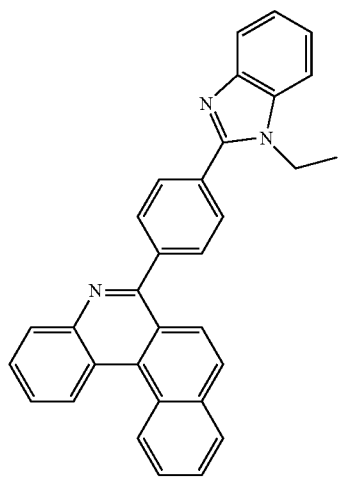
443
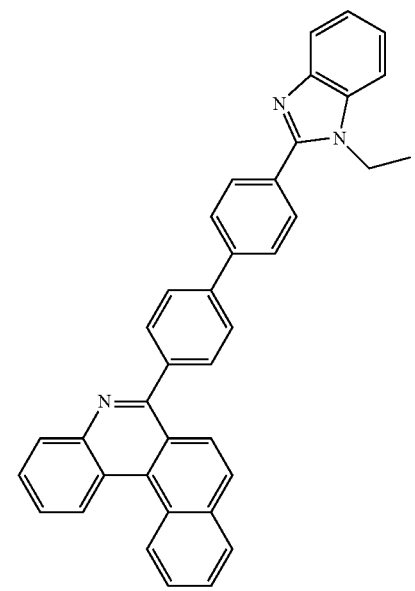
444
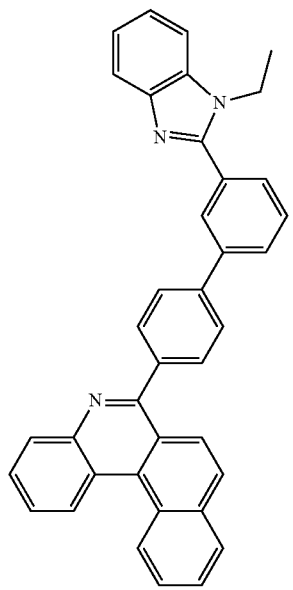
445
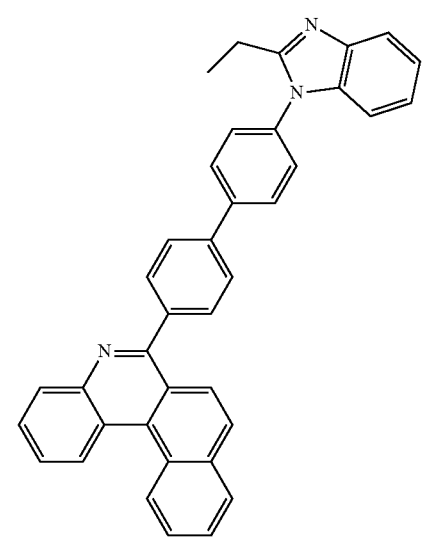
446
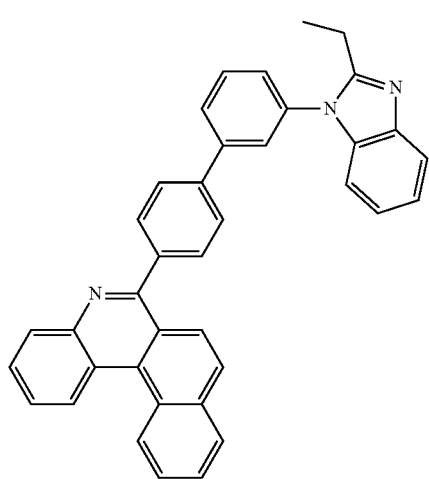
447
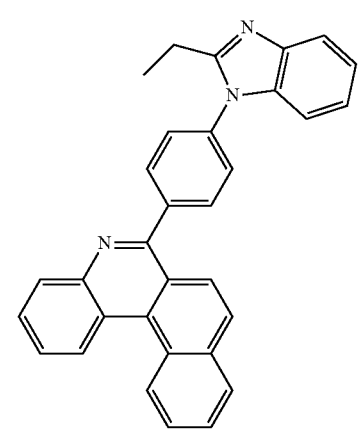

-continued
448 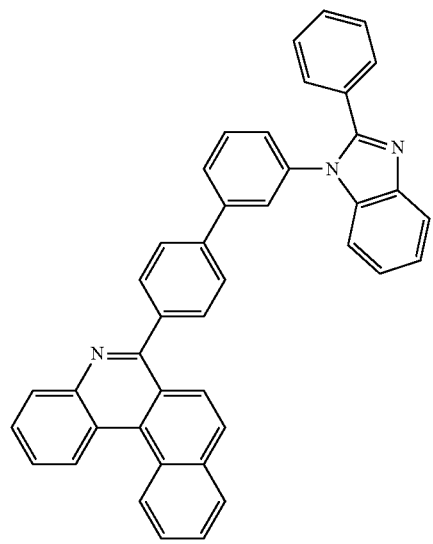 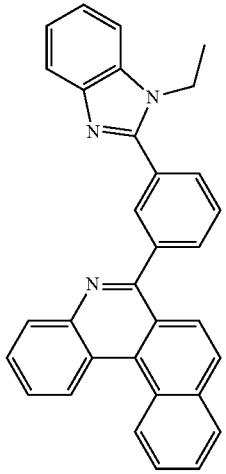 449
450 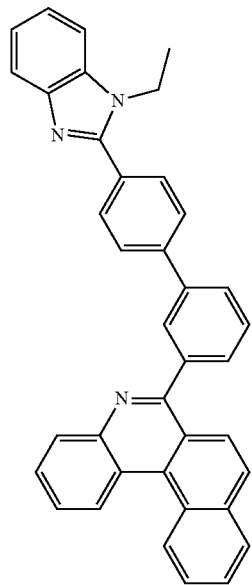 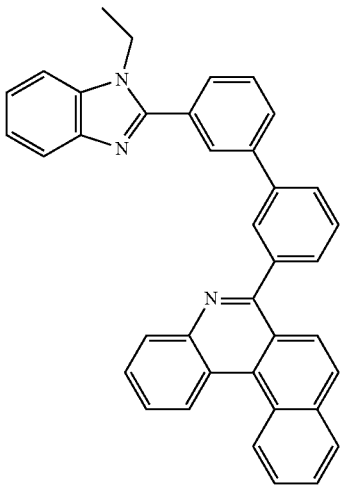 451

-continued
452 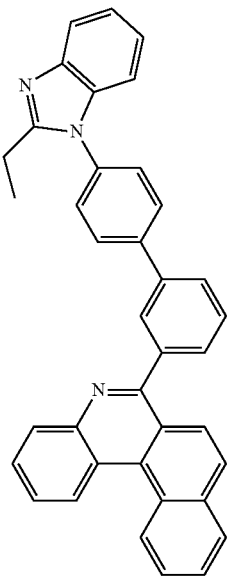
453 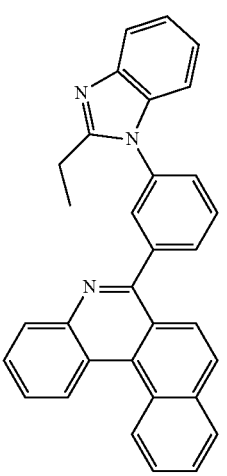
454 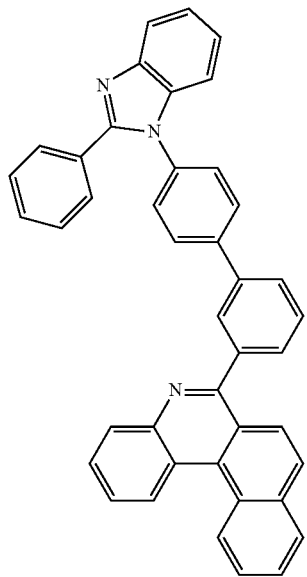
455 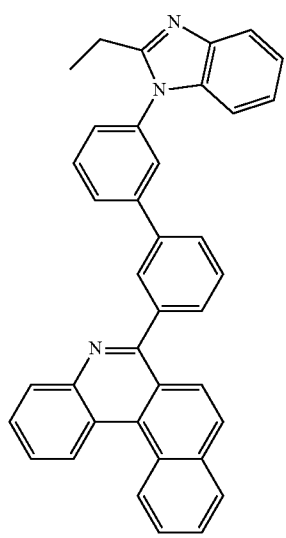

821
822
-continued
456
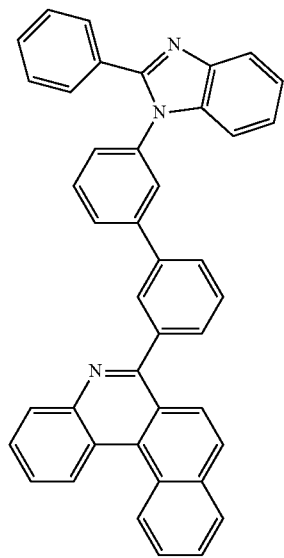
457
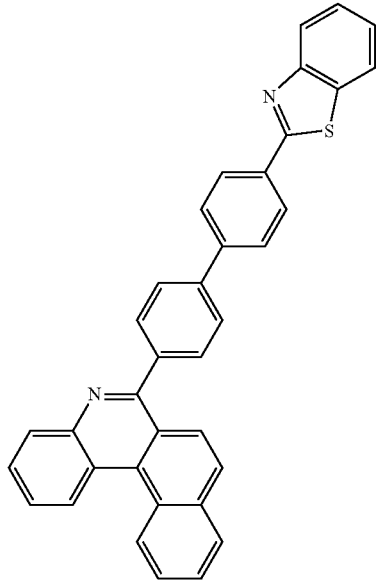
458
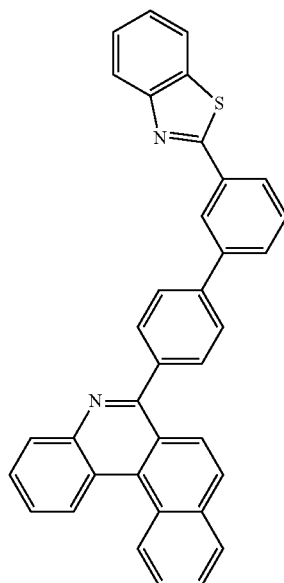
459
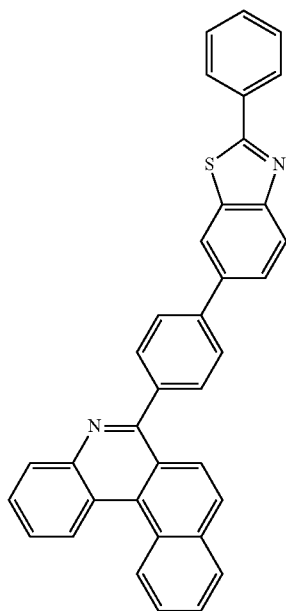

-continued
460
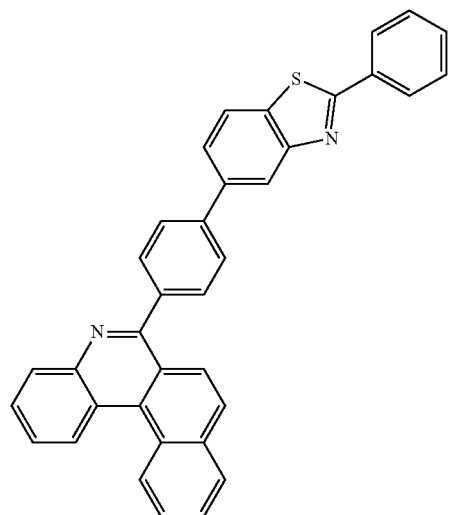
461
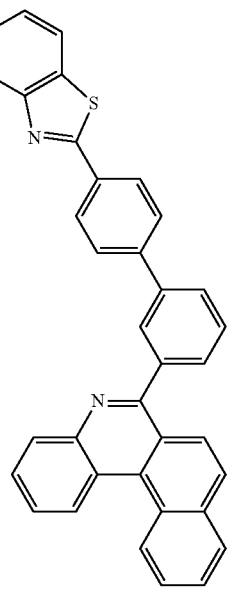
462
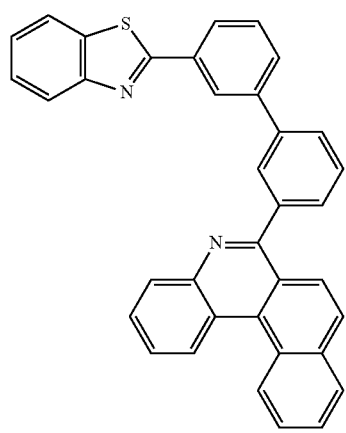
463
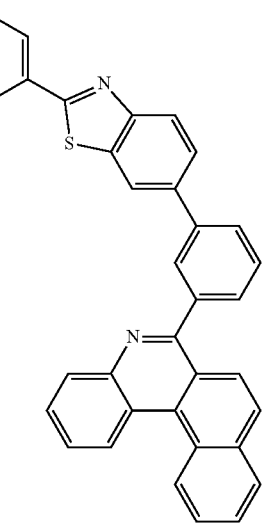

-continued
464
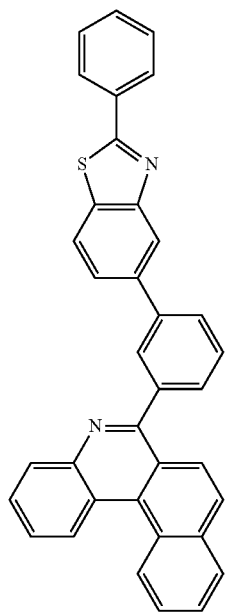
465
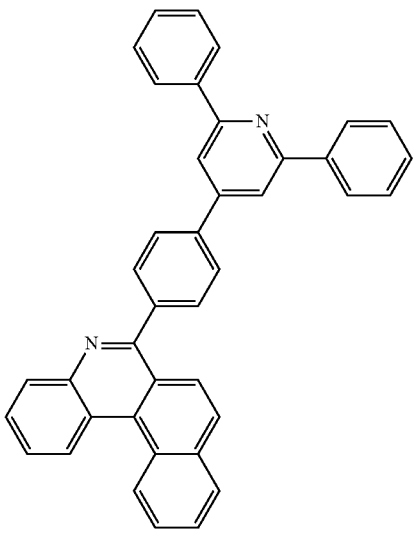
466
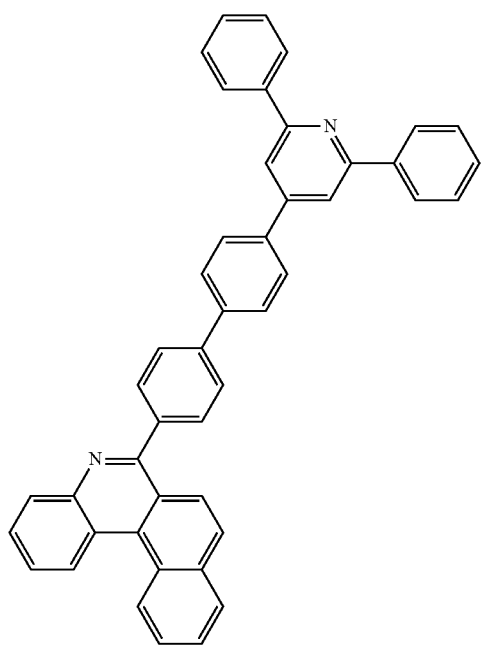
467
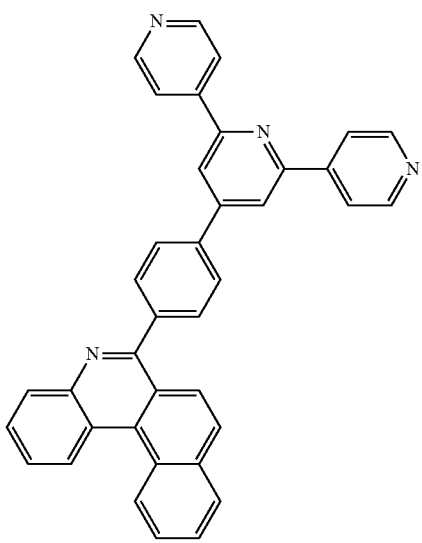

-continued
468
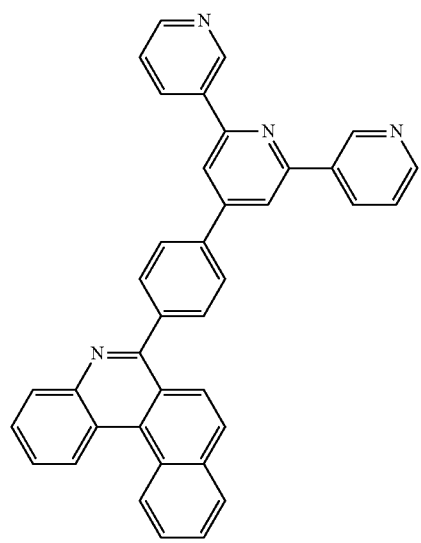
469
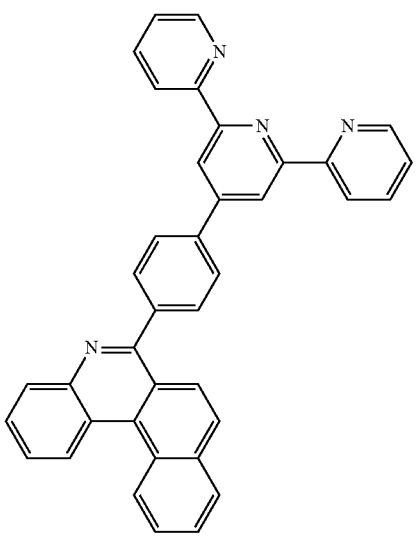
470
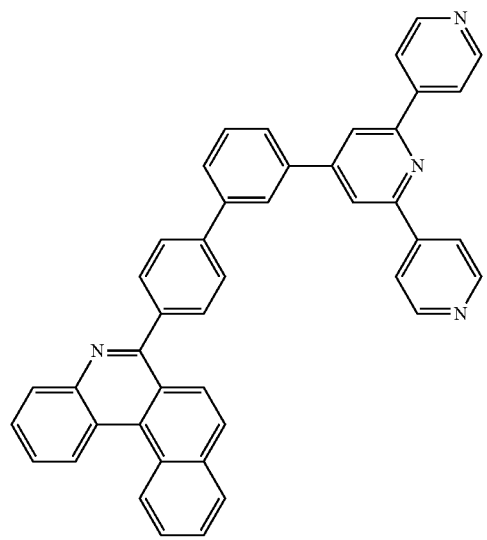
471
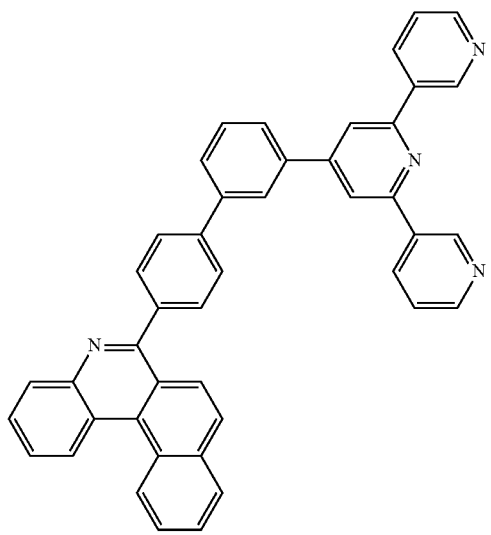
472
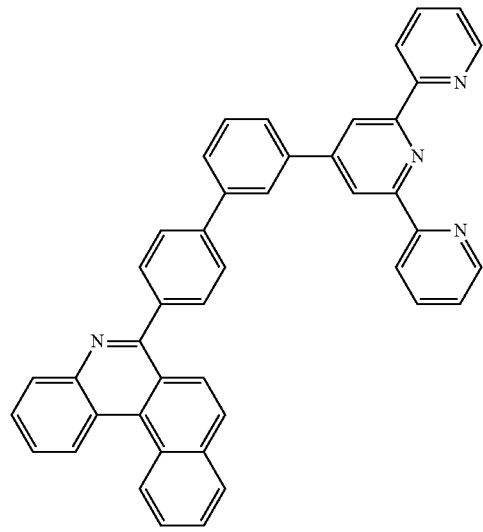
473
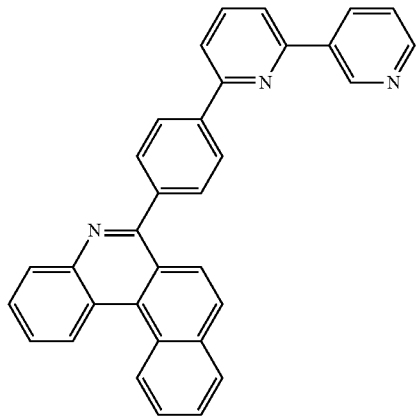

-continued
474
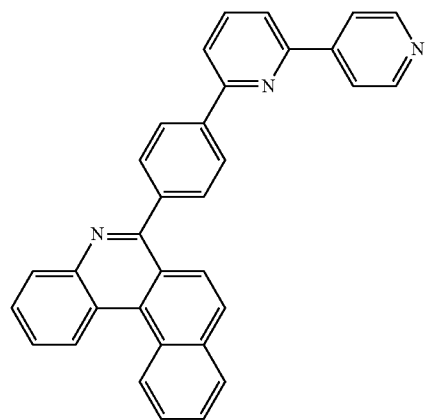
475
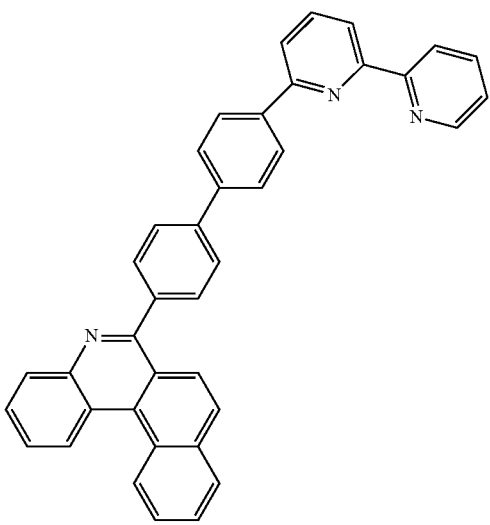
476
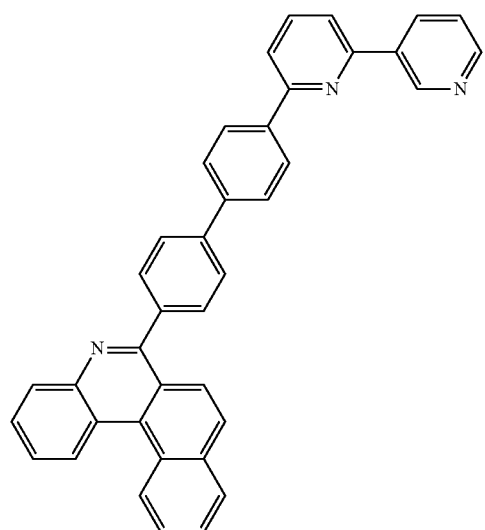
477
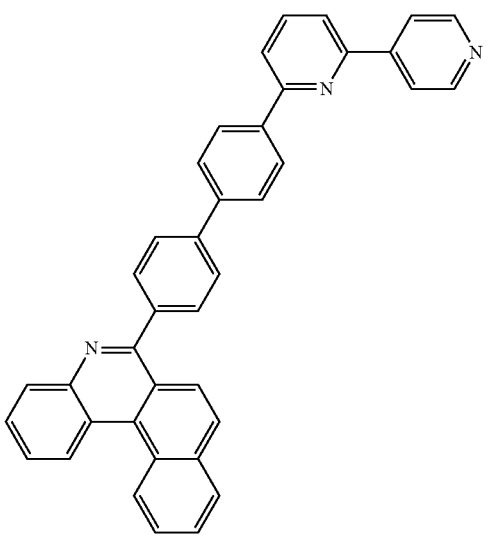

831 832
-continued
478 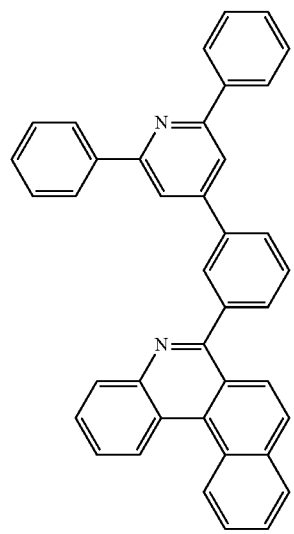 479 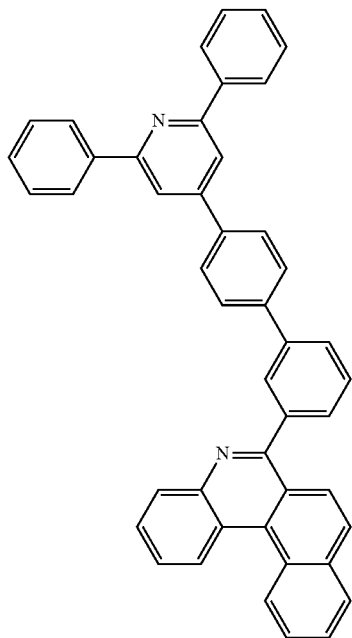
480 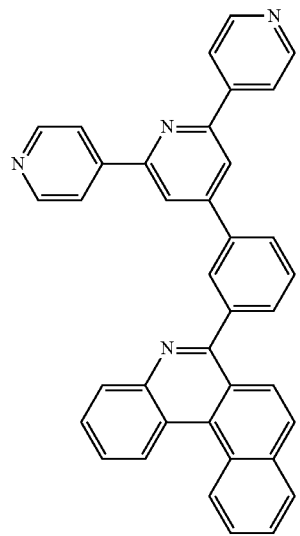 481 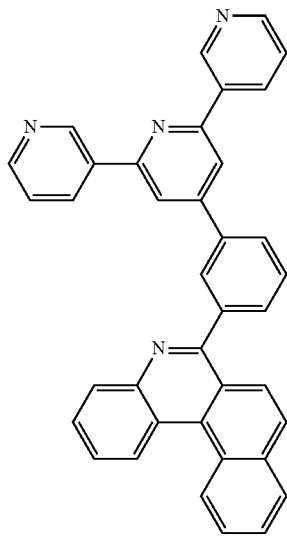

-continued
833
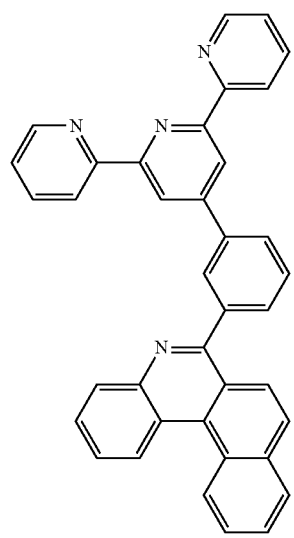
482
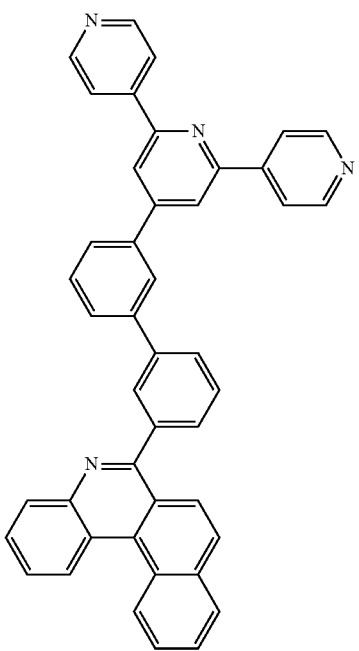
484
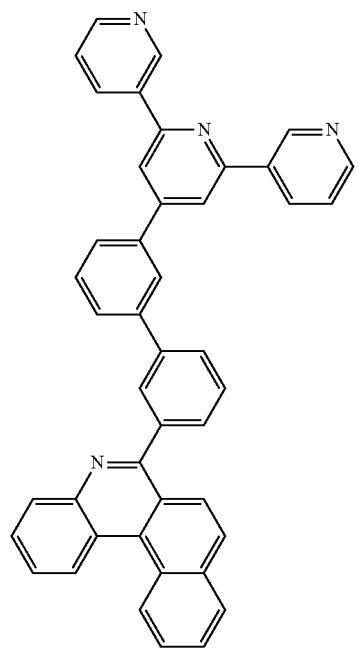
483
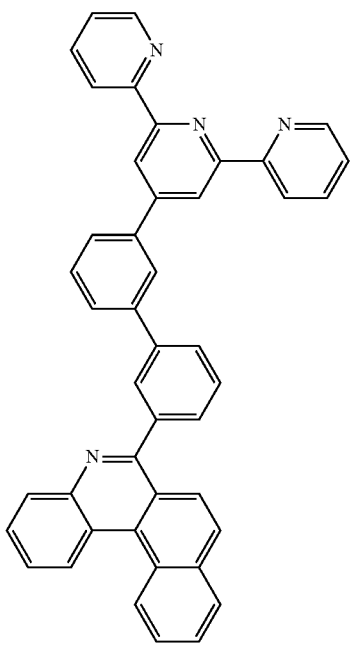

-continued
486 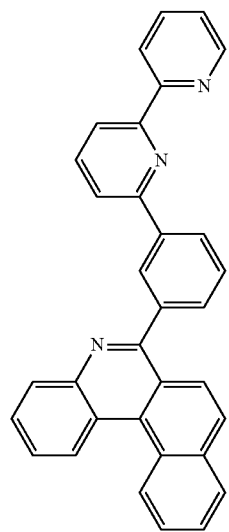 487 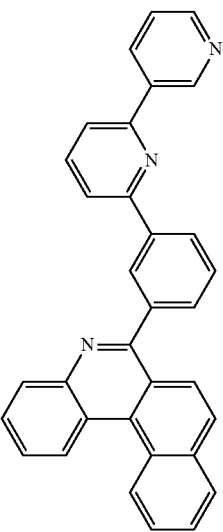
488 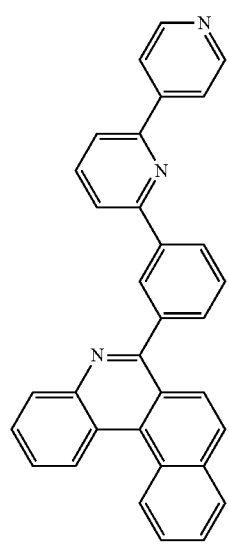 489 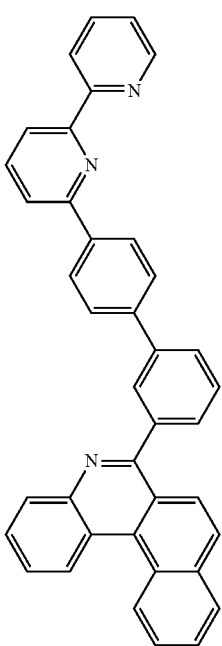

-continued
490
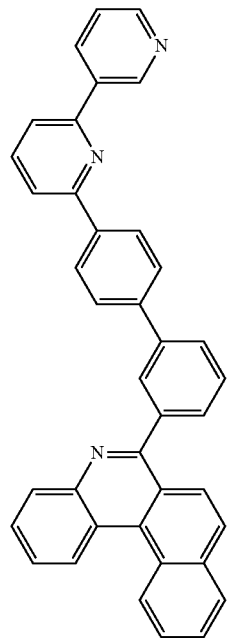
491
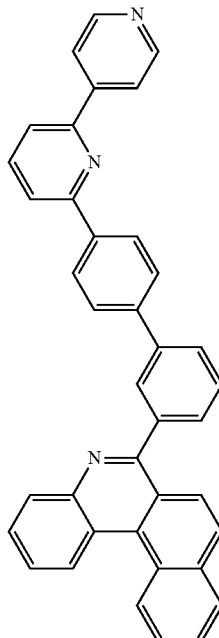
492
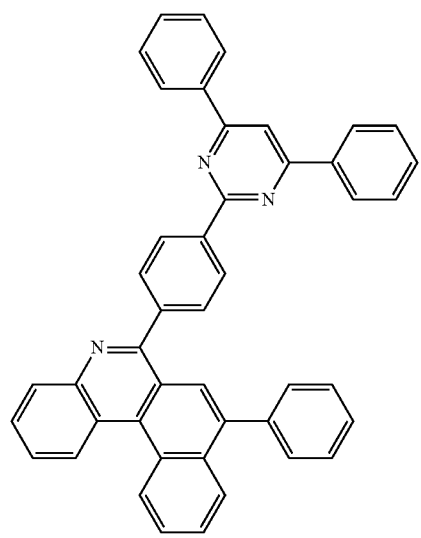
493
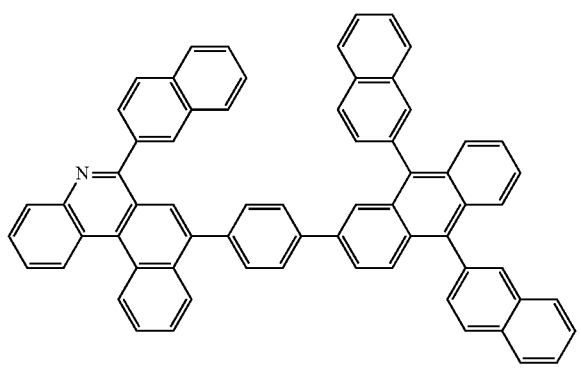
494
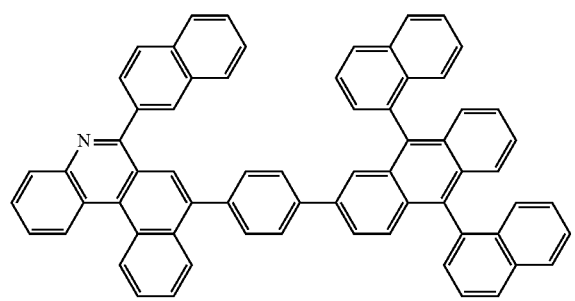
495
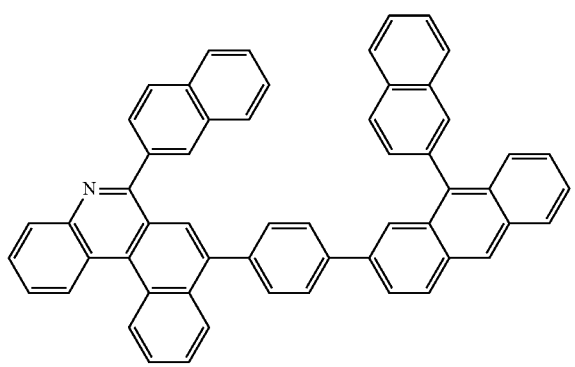

496
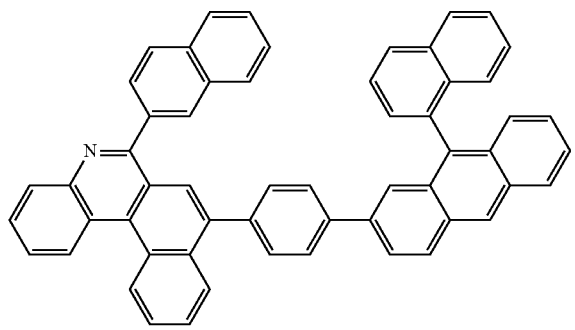
497
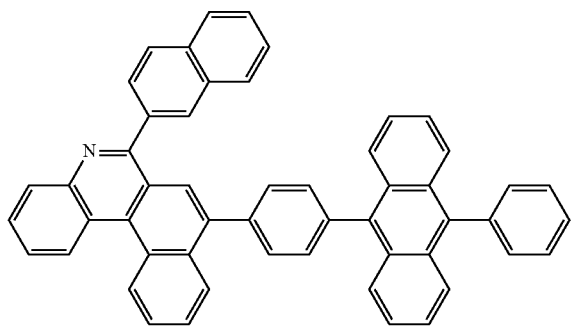
498
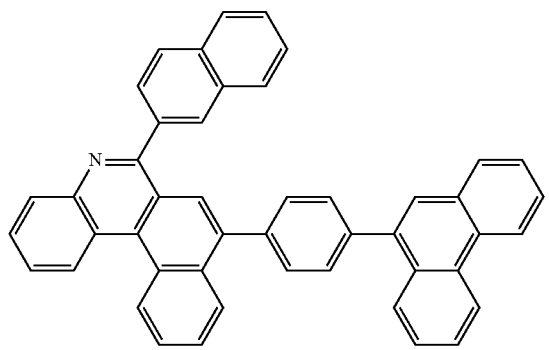
499
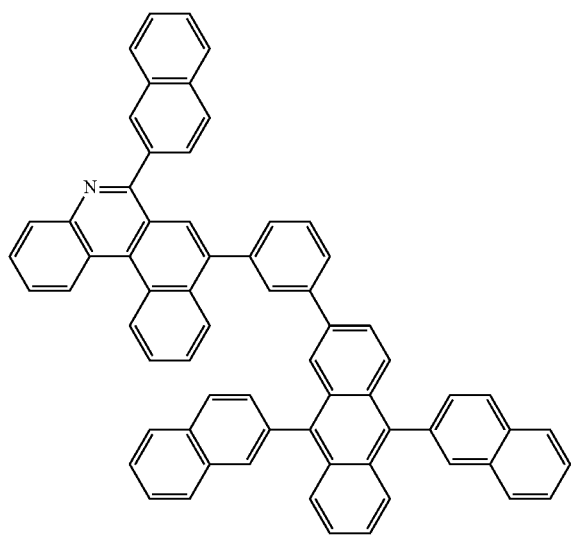
500
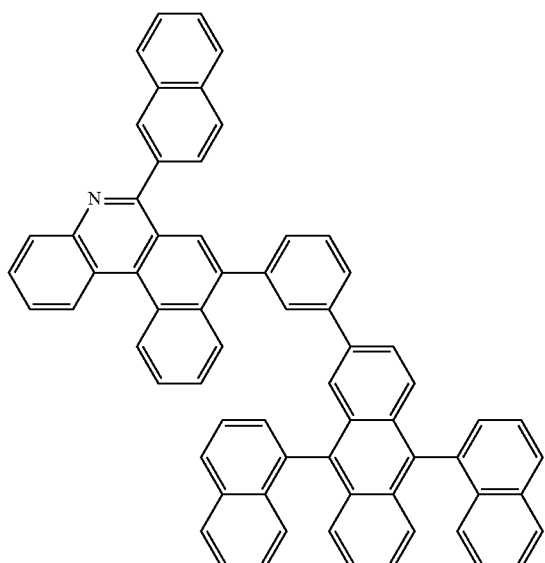

-continued
501
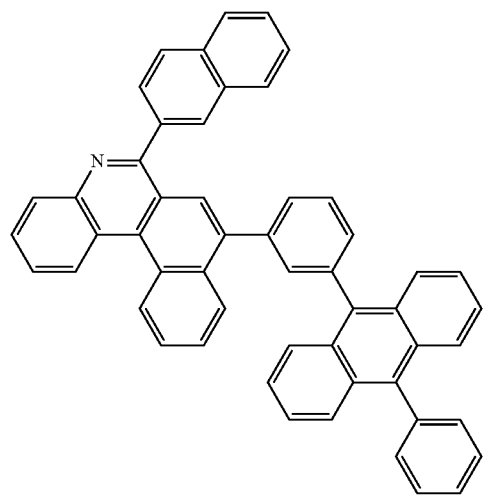
502
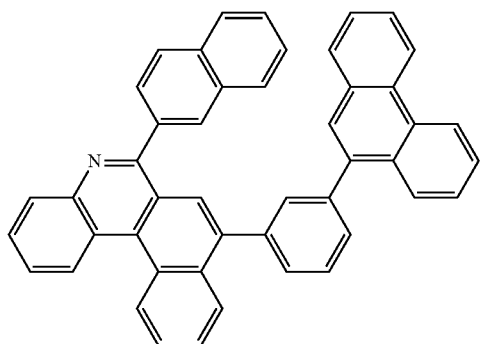
503
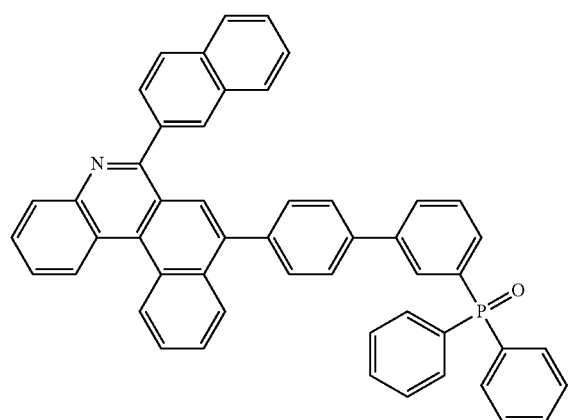
504
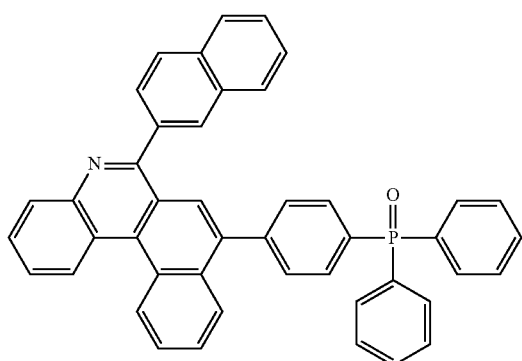
505
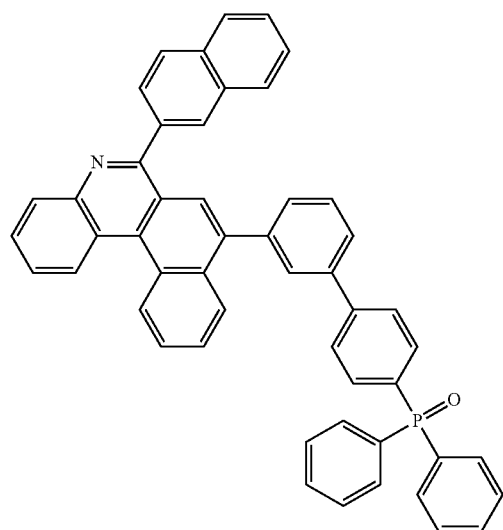
506
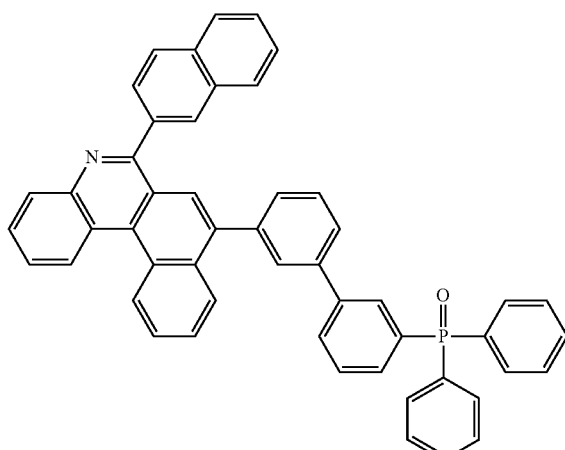

-continued
507
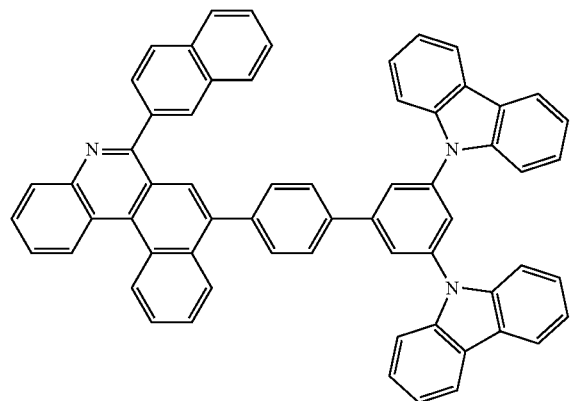
508
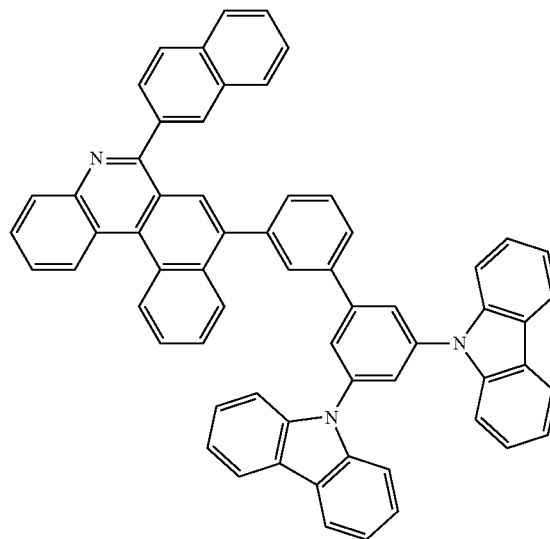
509
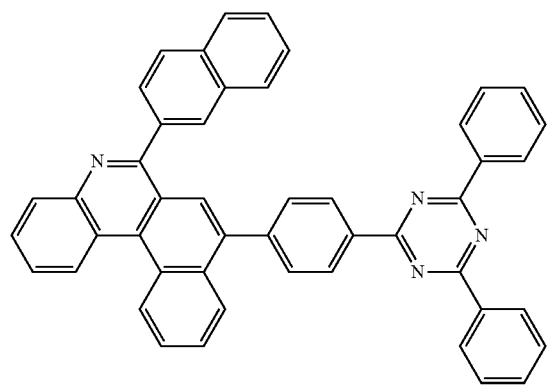
510
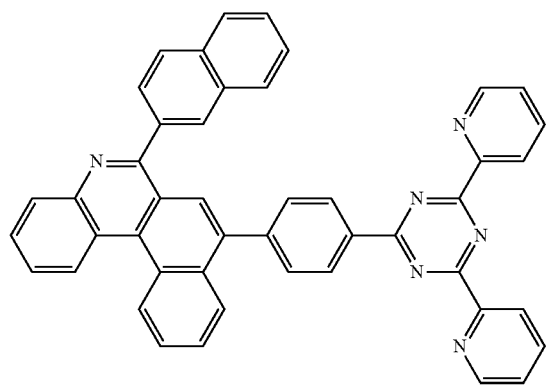
511
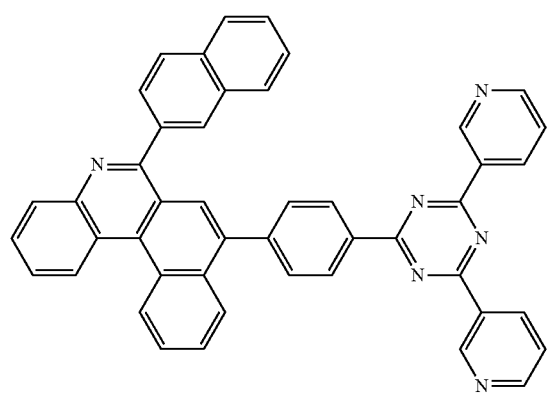
512
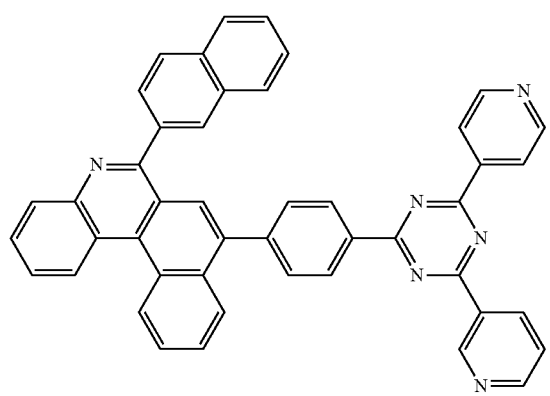

-continued
513
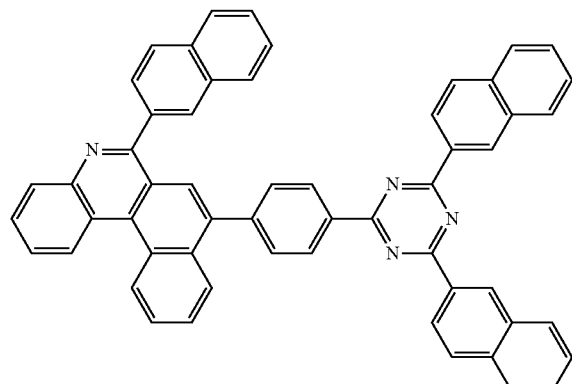
514
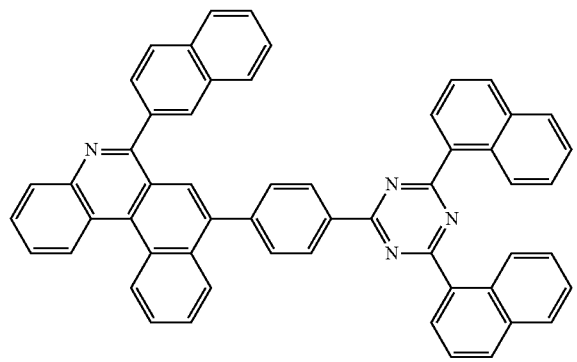
515
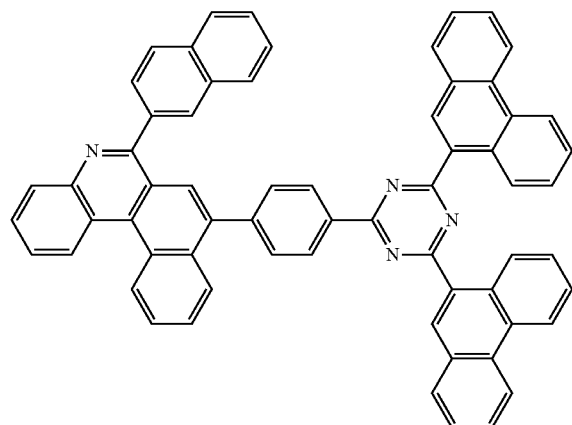
516
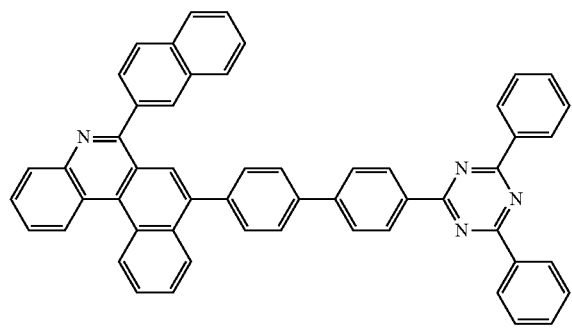
517
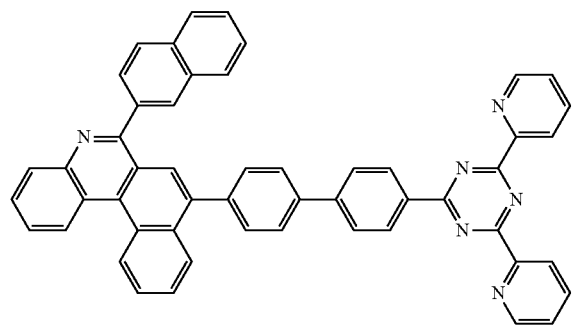
518
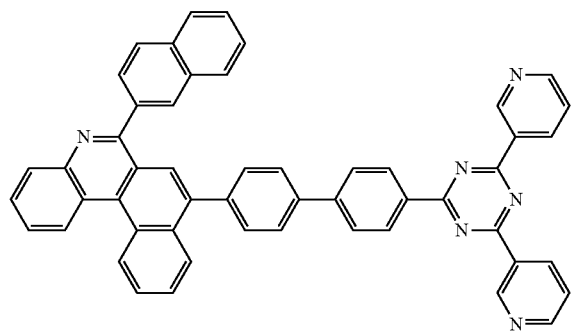
519
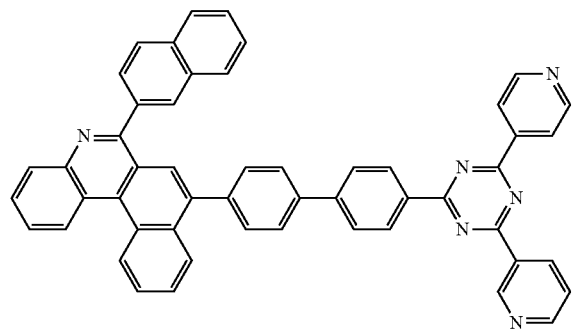
520
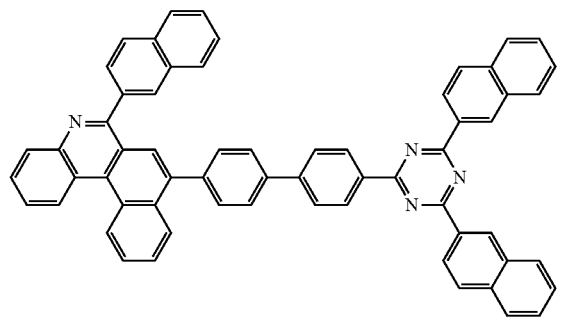

-continued
521
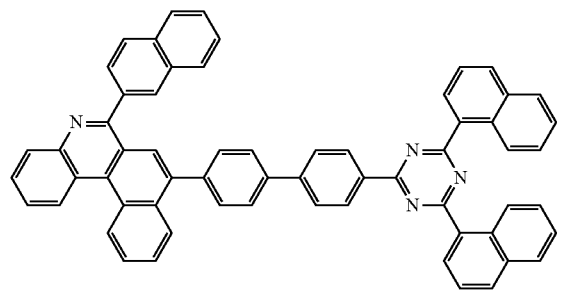
522
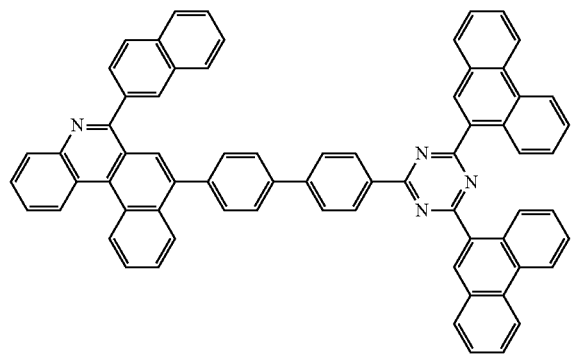
523
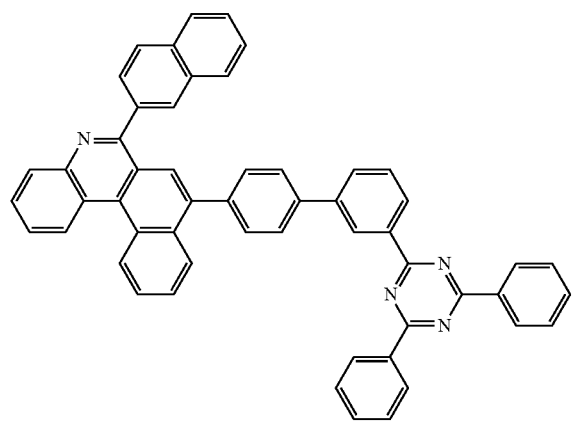
524
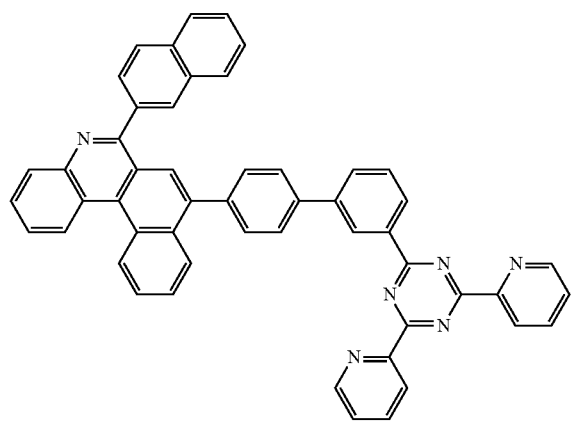
525
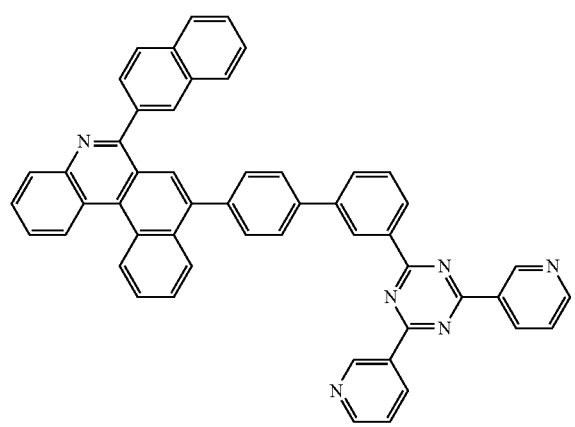
526
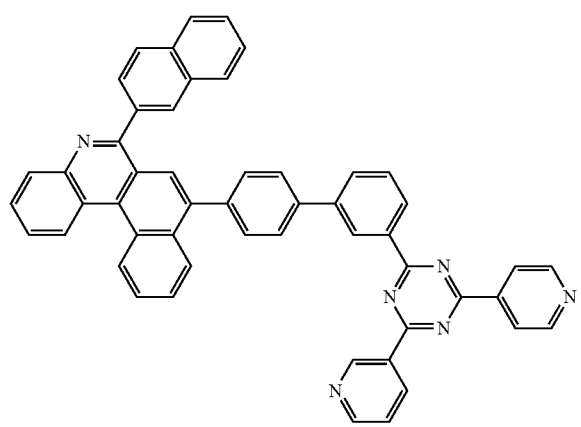

-continued
527
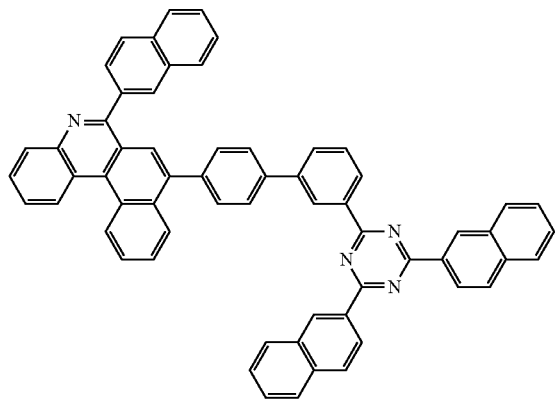
528
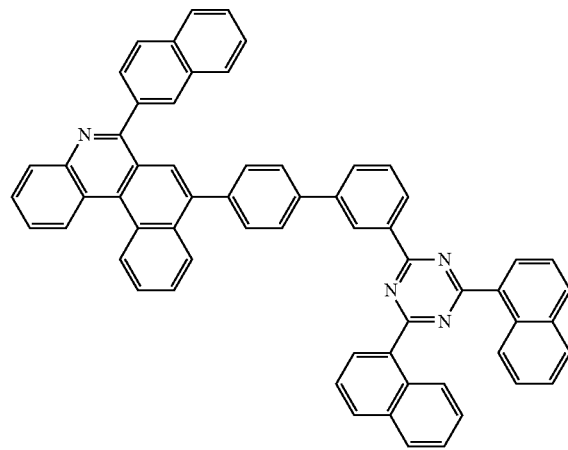
529
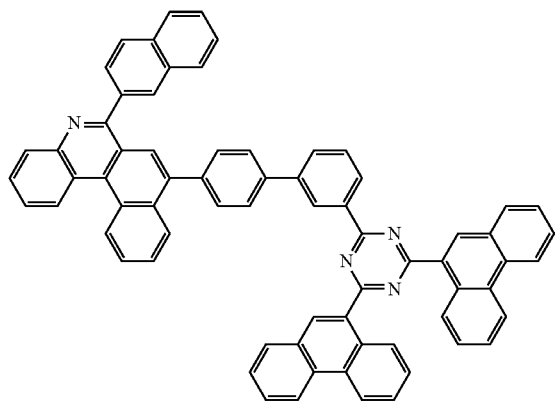
530
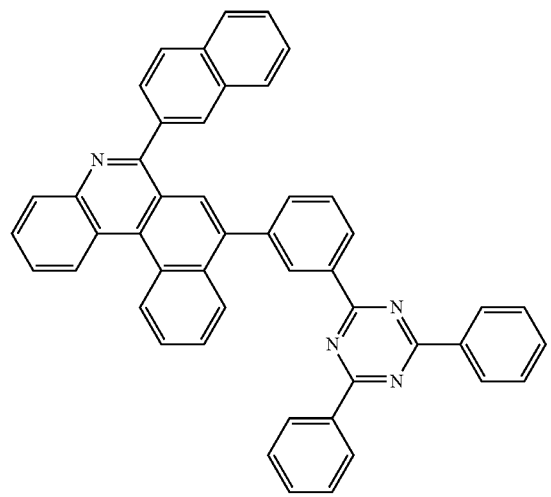
531
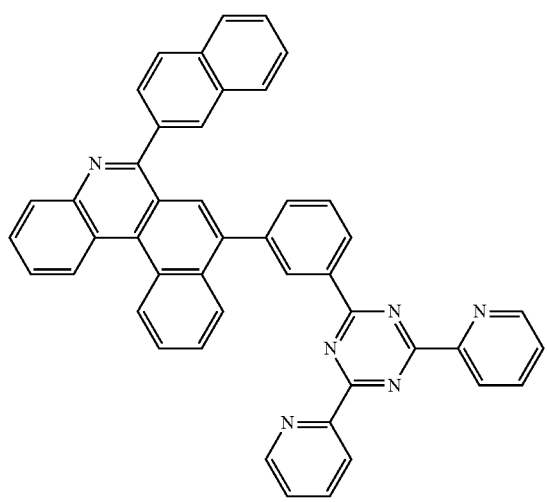
532
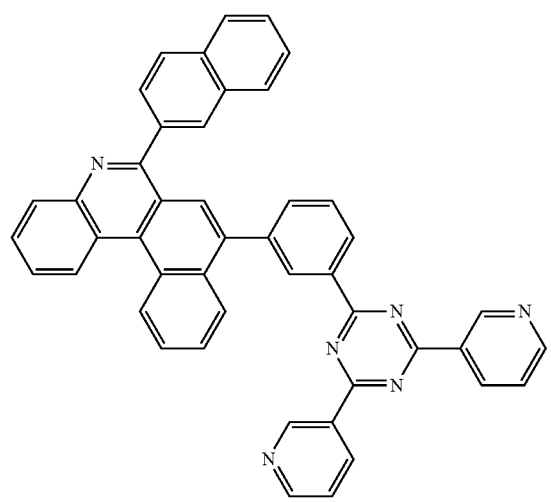

-continued
533
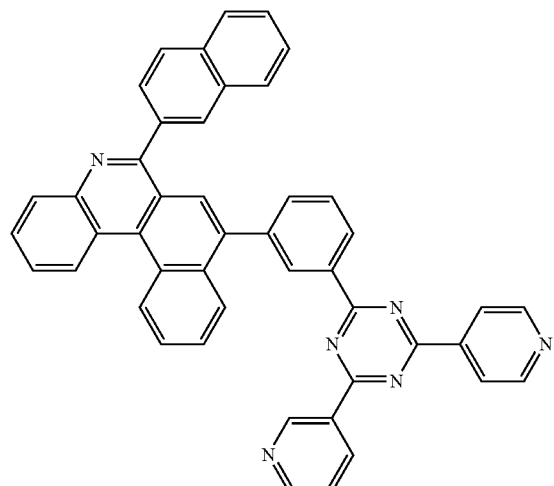
534
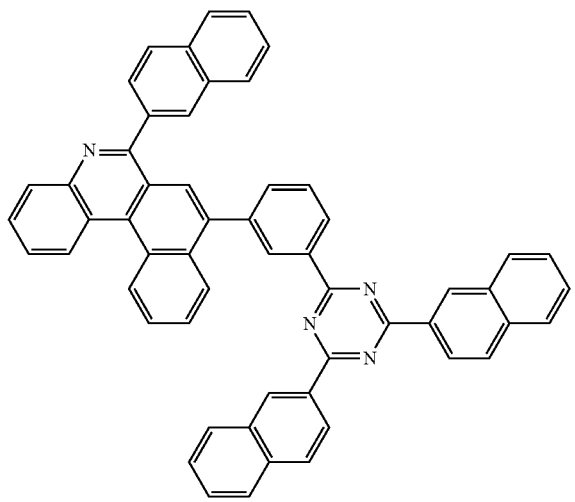
535
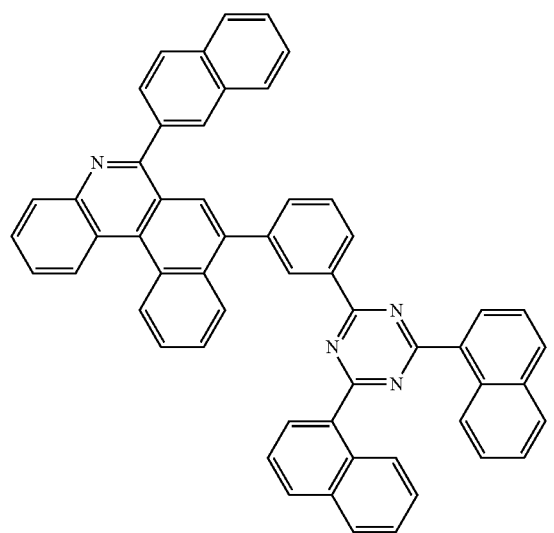
536
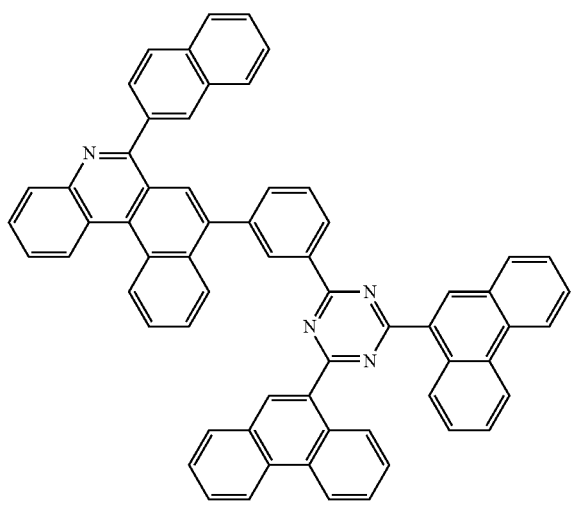
537
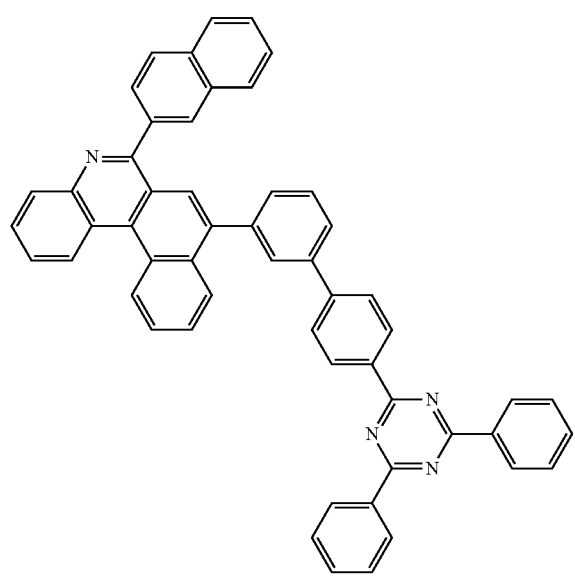
538
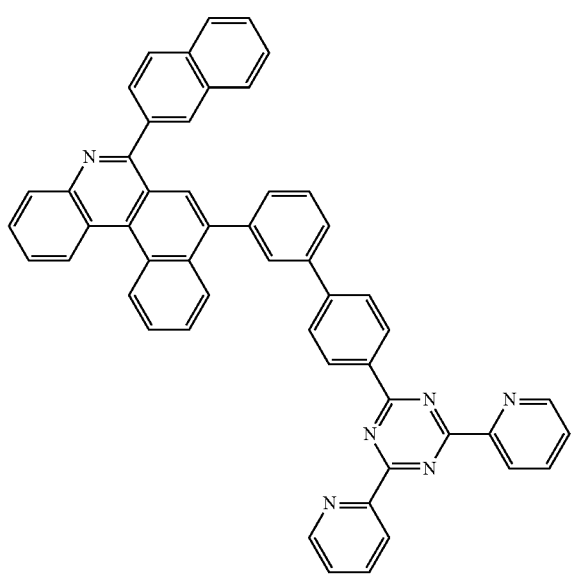

853
854
-continued
539
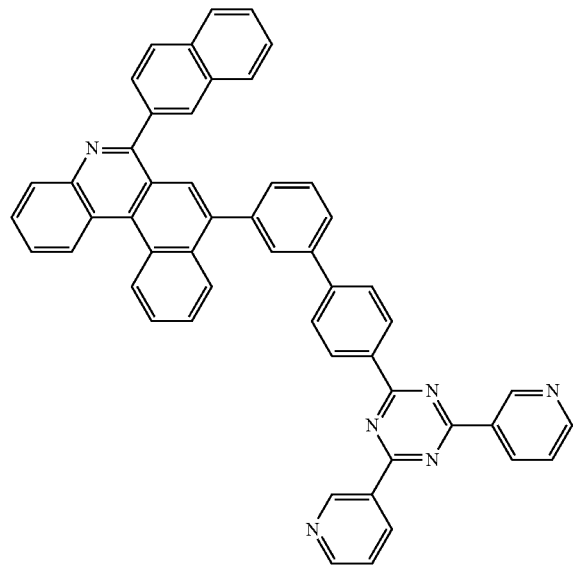
540
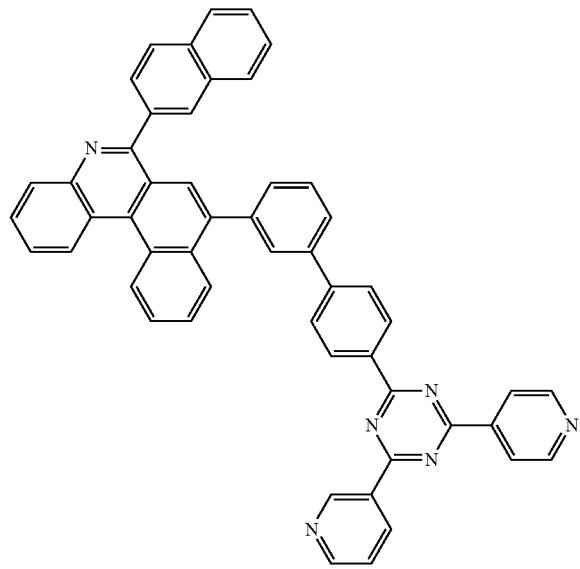
541
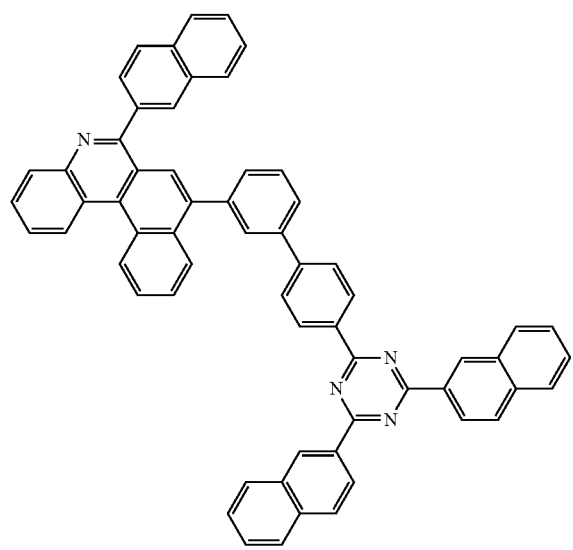
542
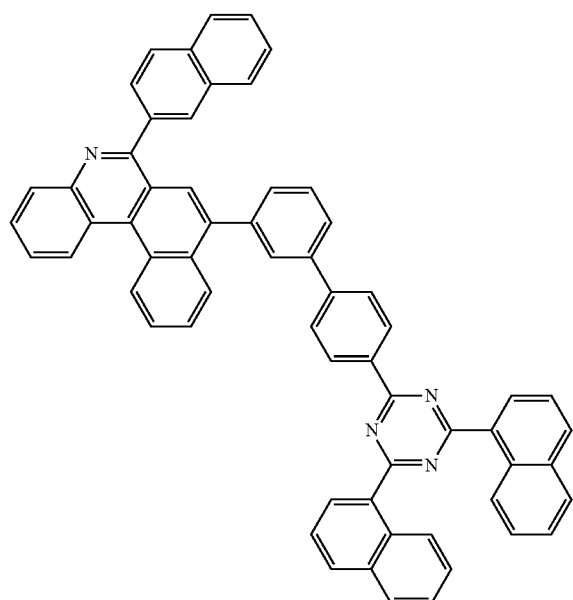

-continued
543
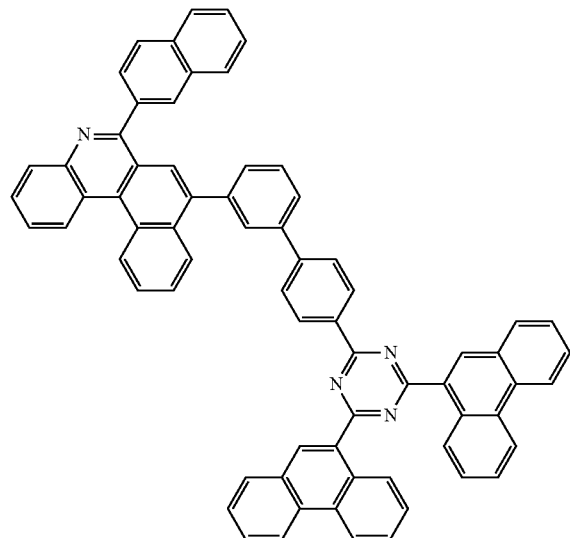
544
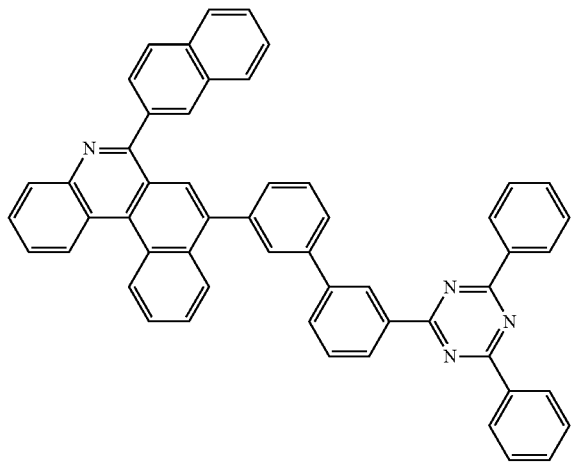
545
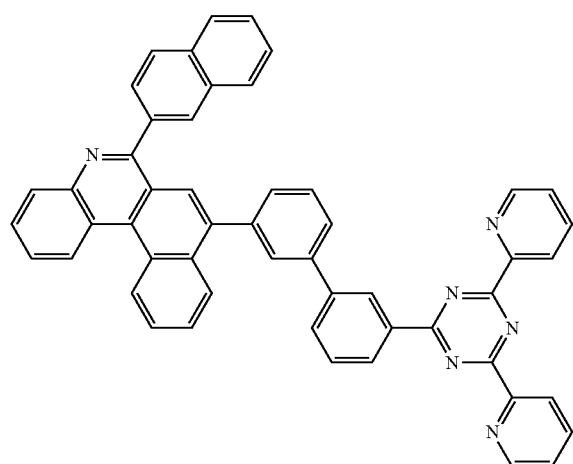
546
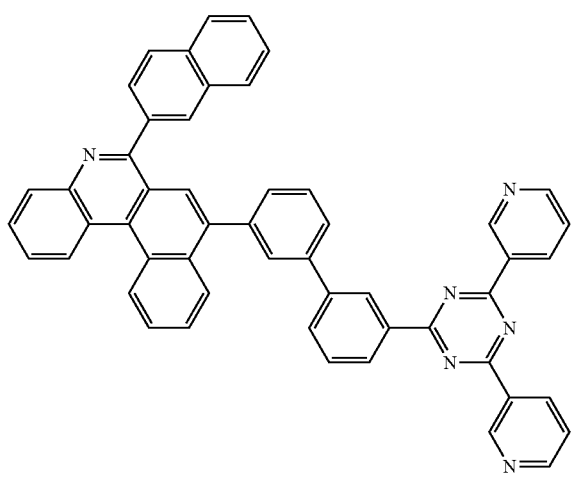
547
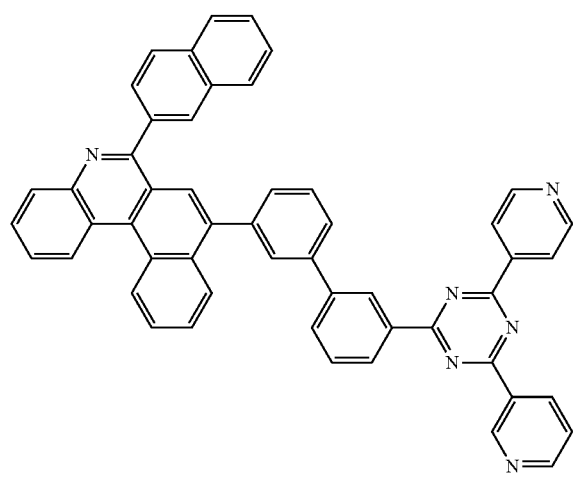
548
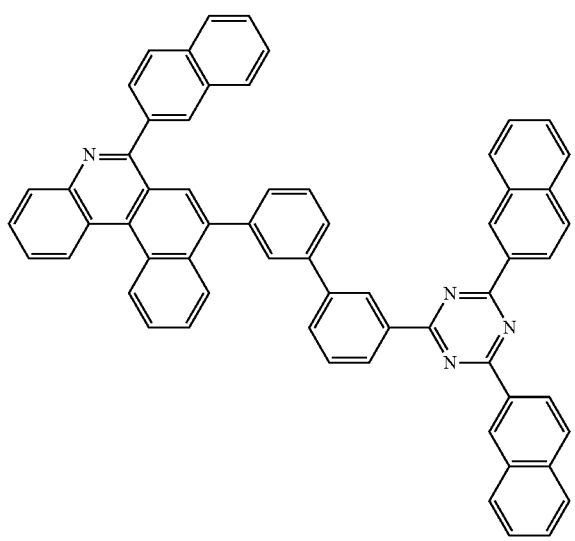

549
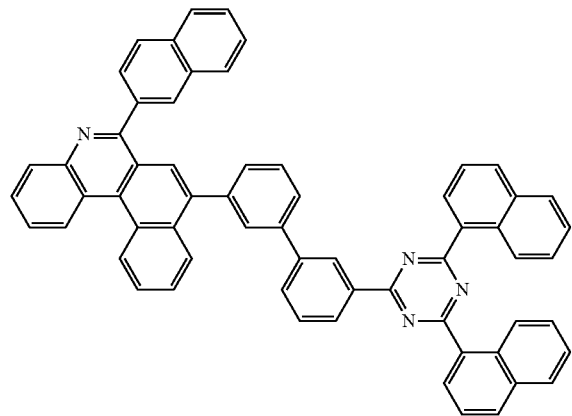
550
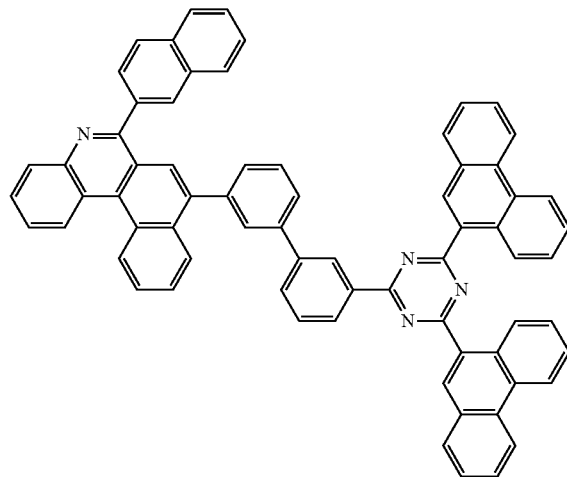
551
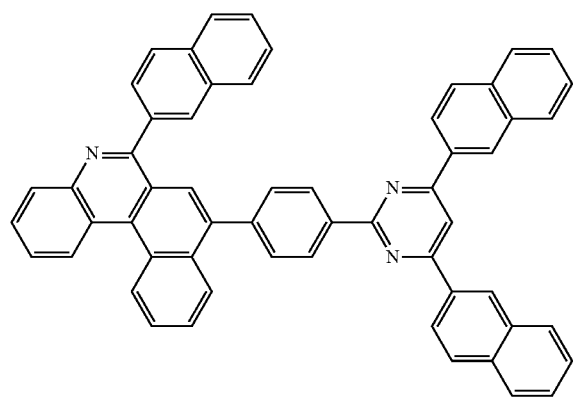
552
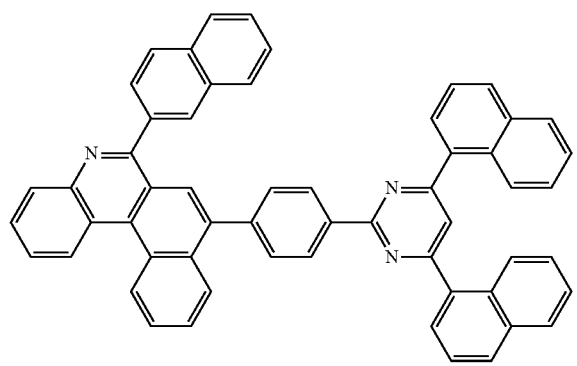
553
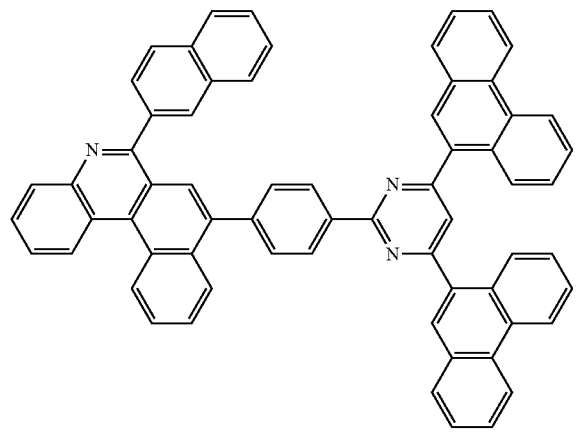
554
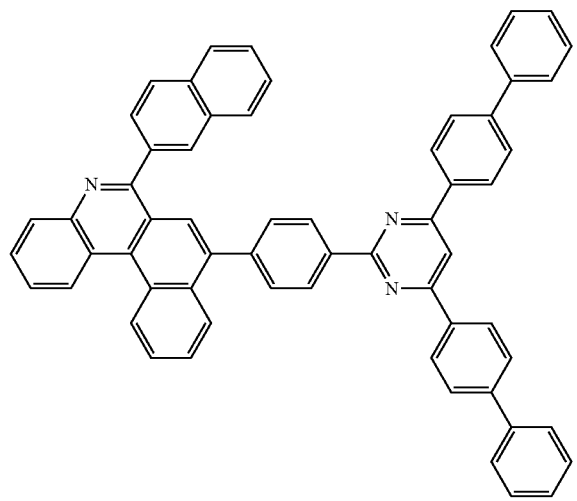

-continued
555
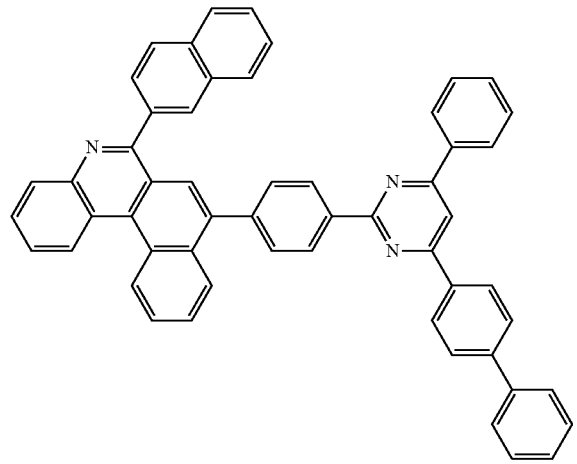
556
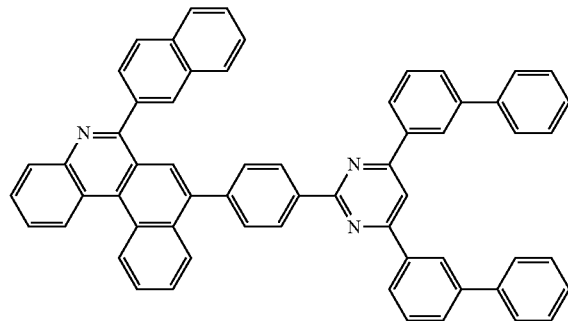
557
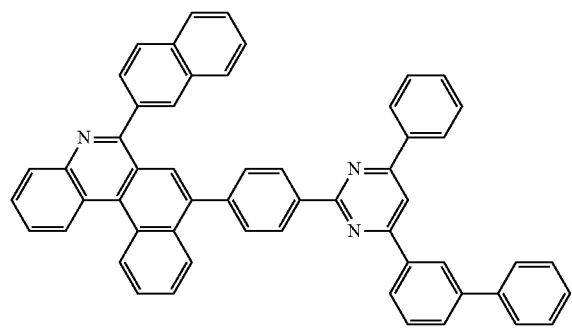
558
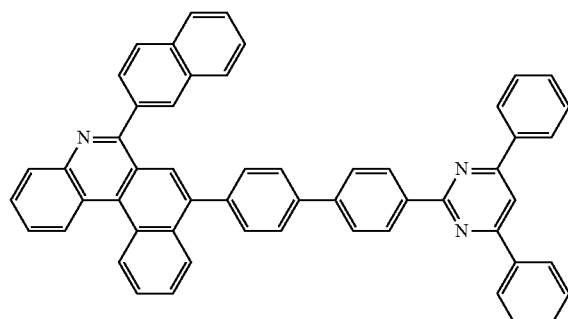
559
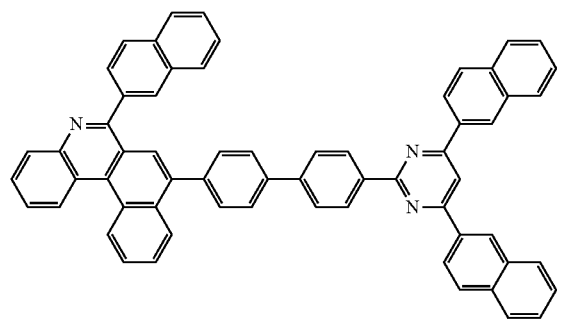
560
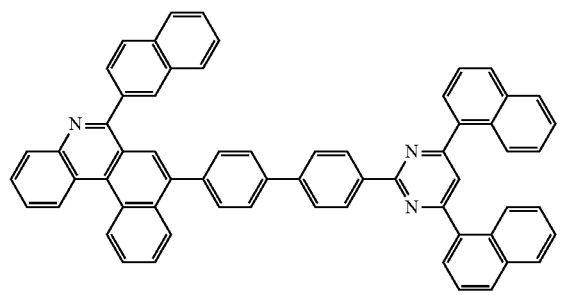
561
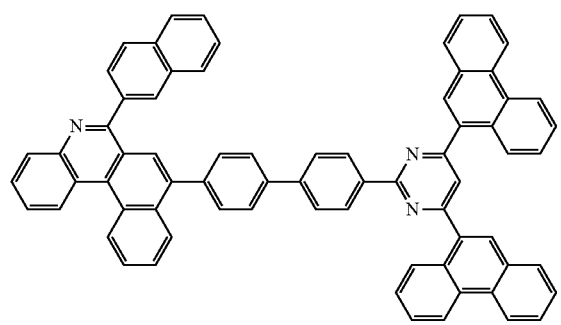
562
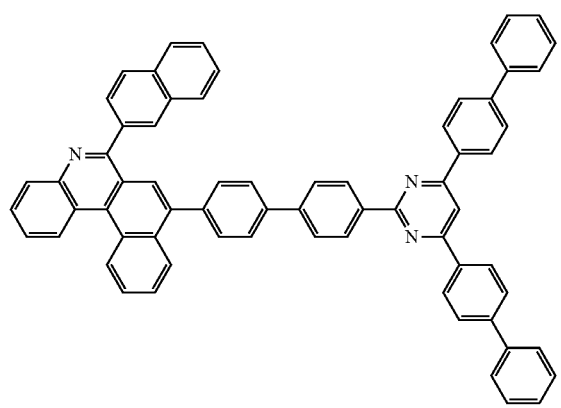

563
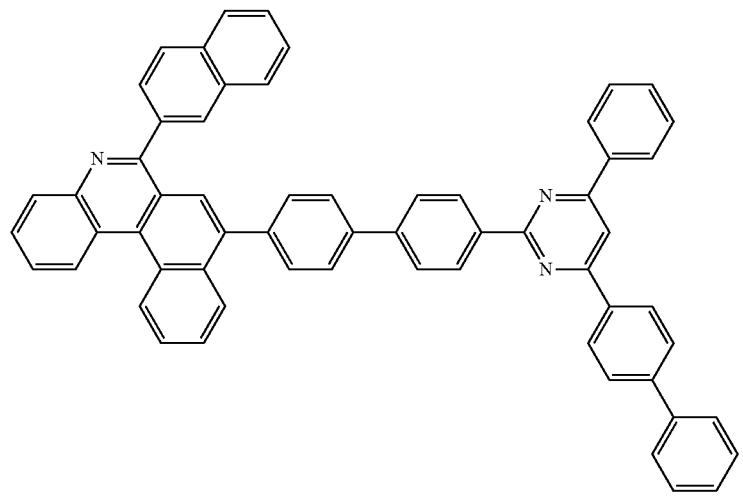
564
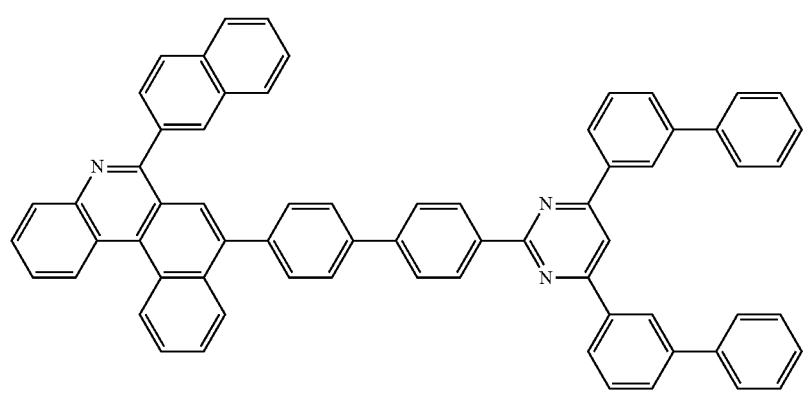
565
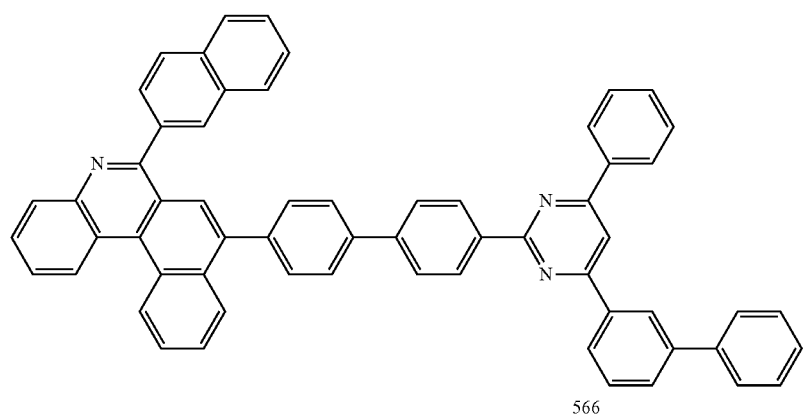
566
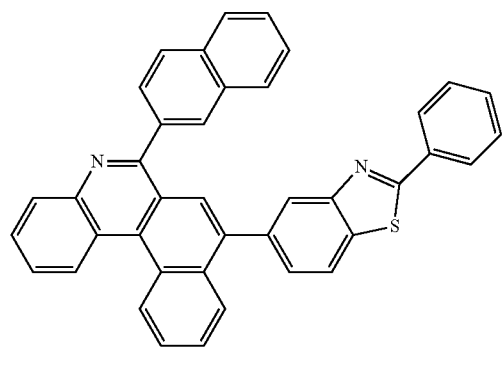
567
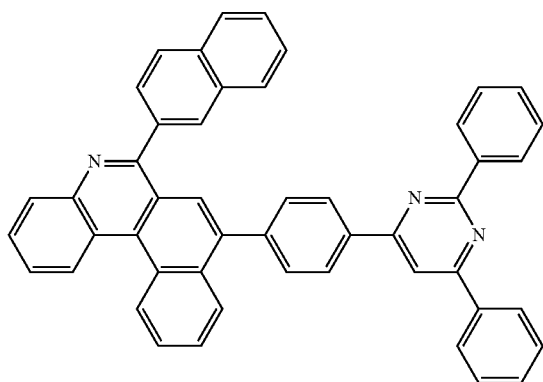

568
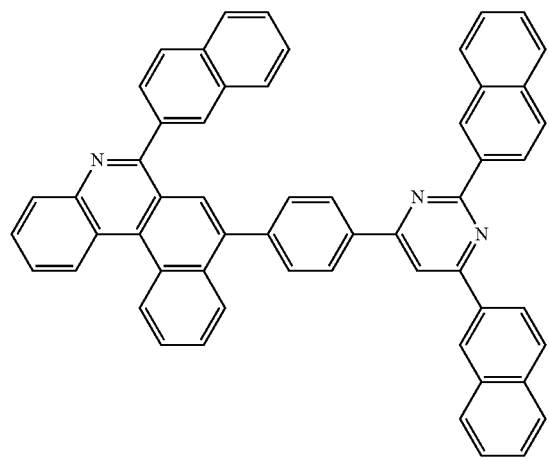
569
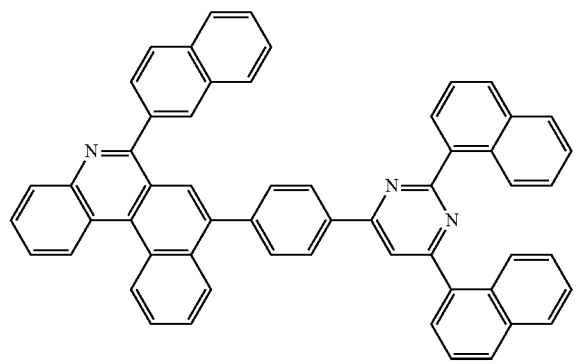
570
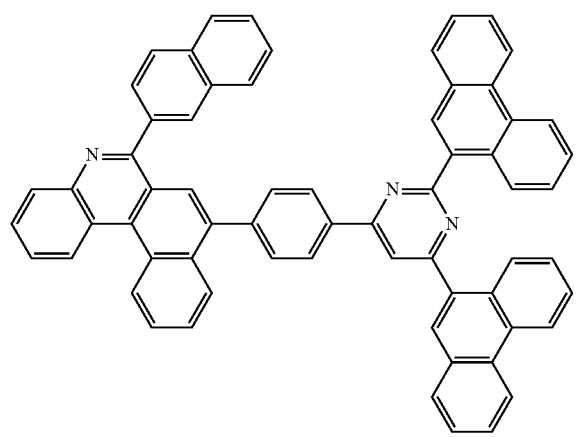
571
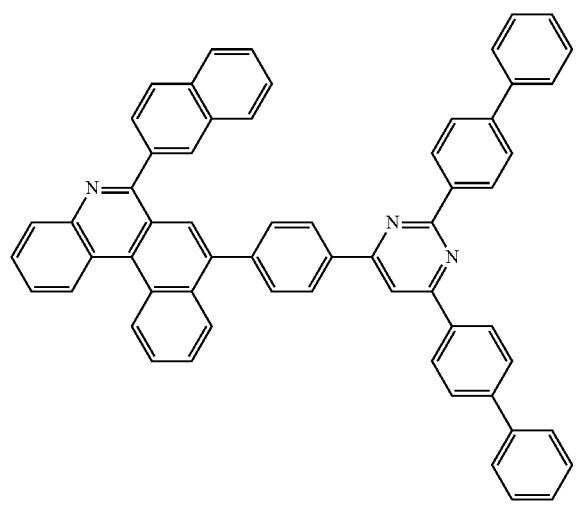
572
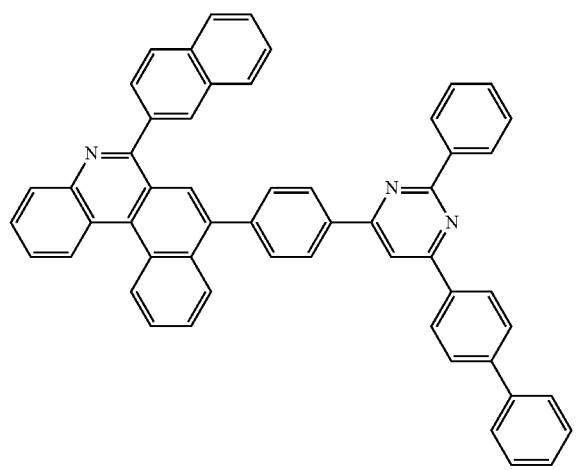

-continued
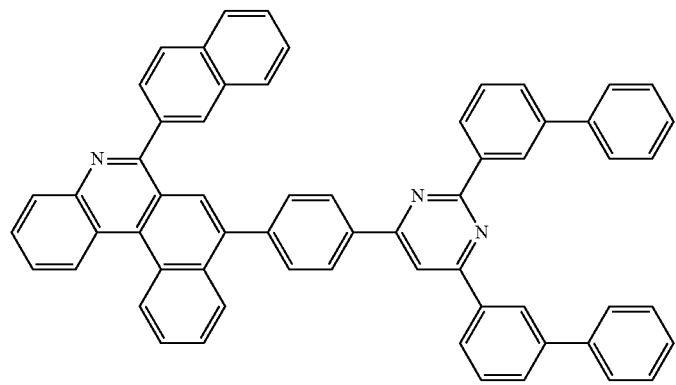
573
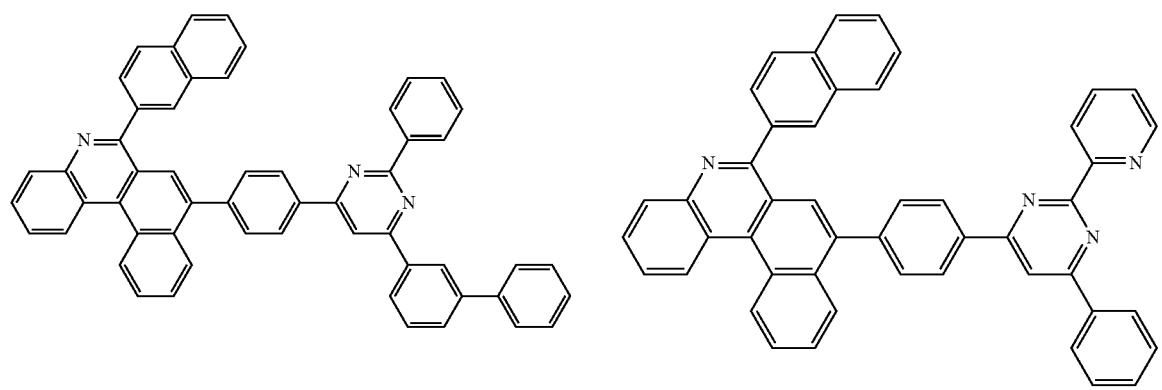
574  575
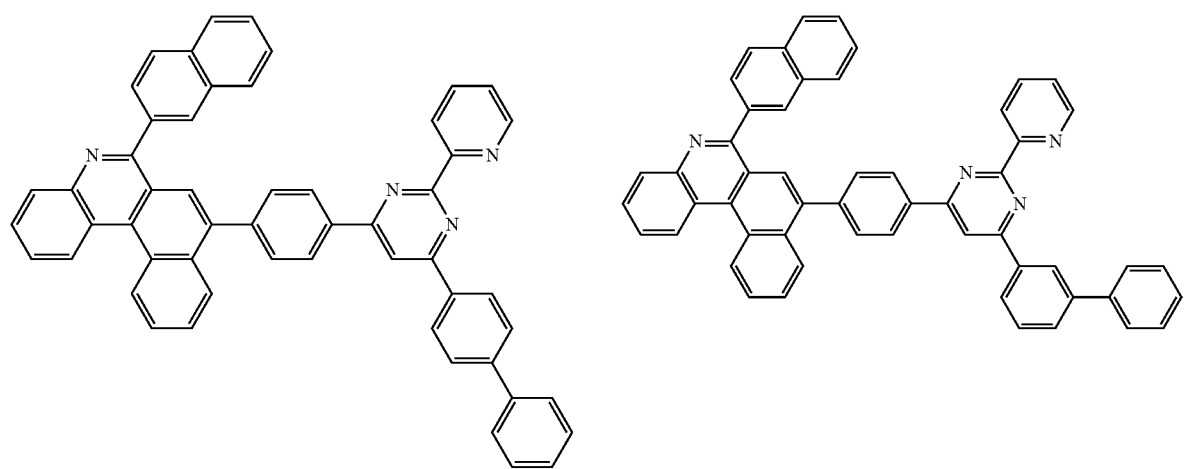
576  577

578
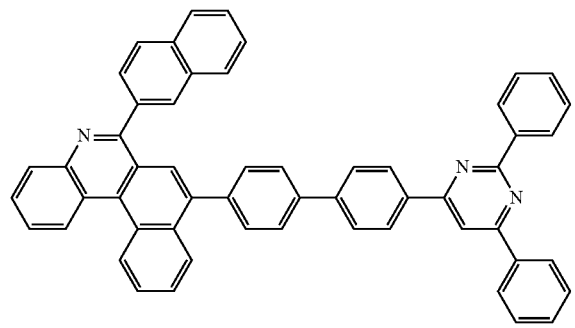
579
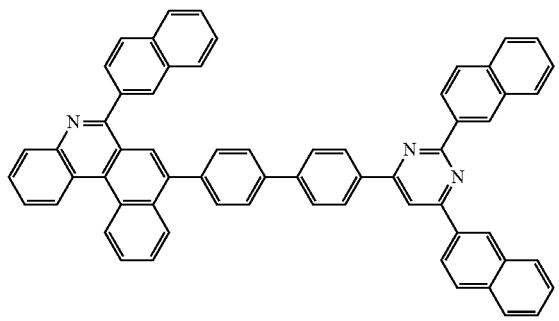
580
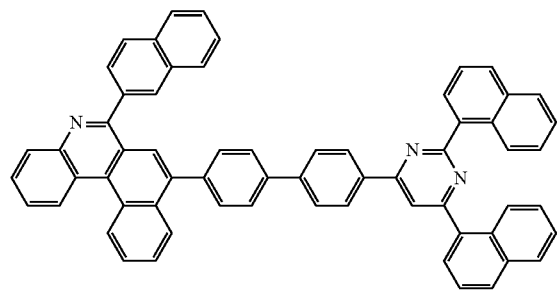
581
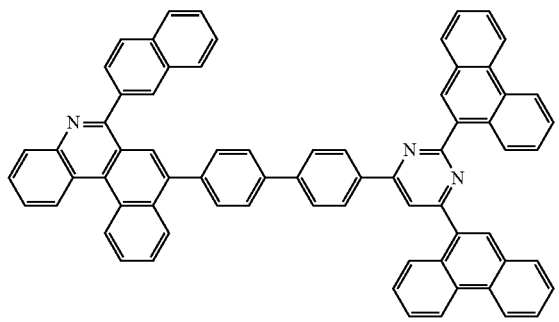
582
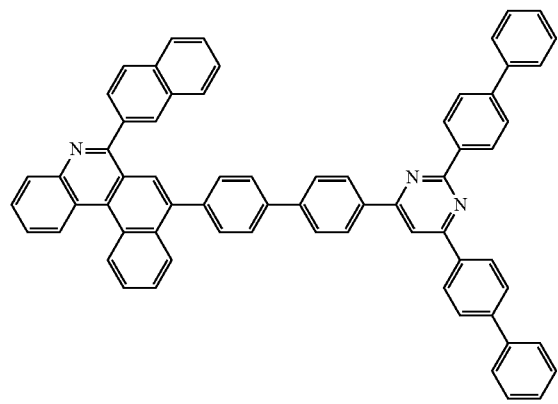
583
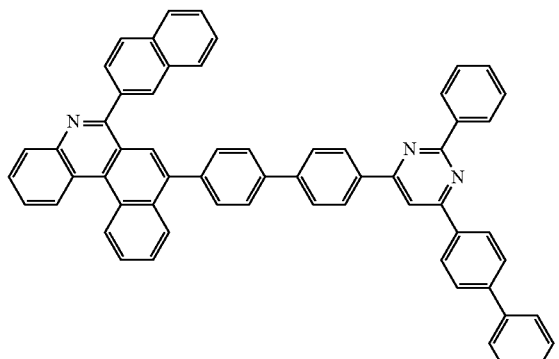
584
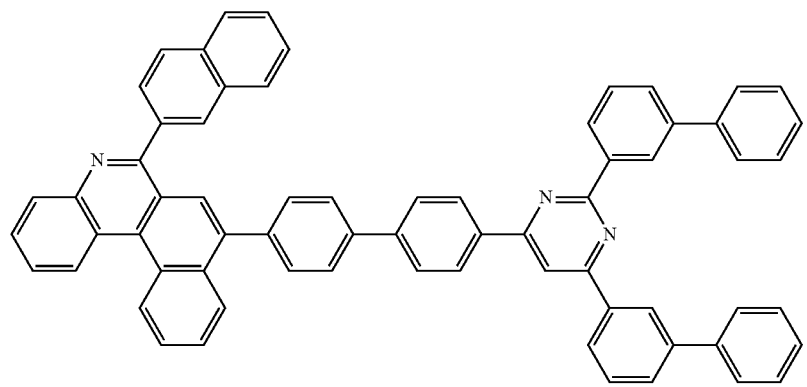

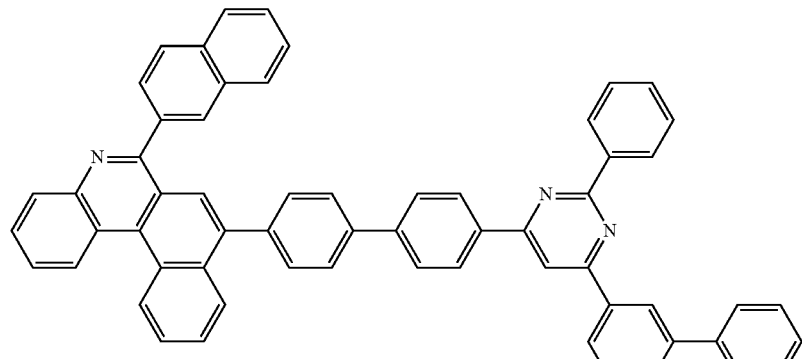
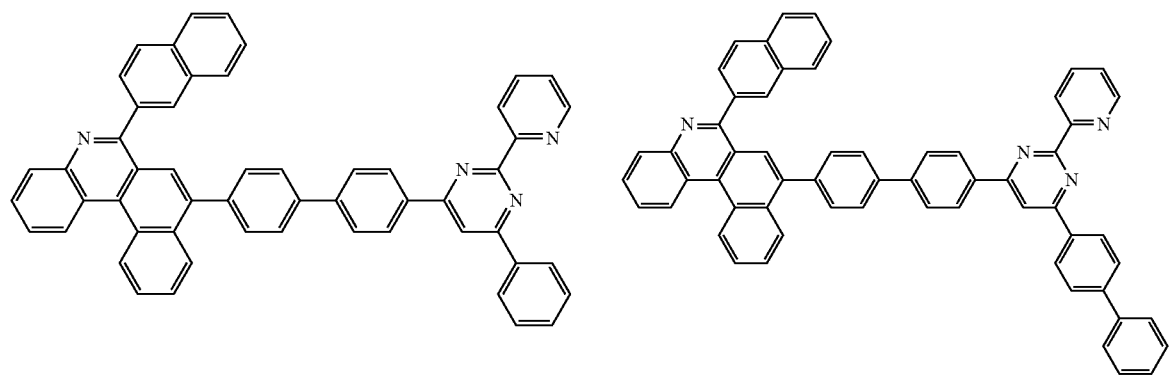
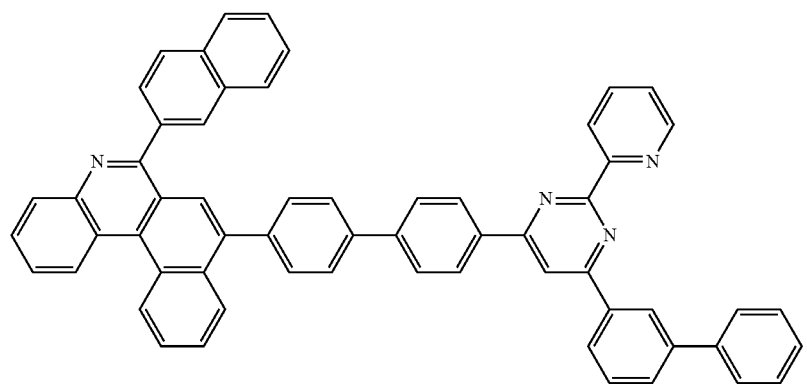
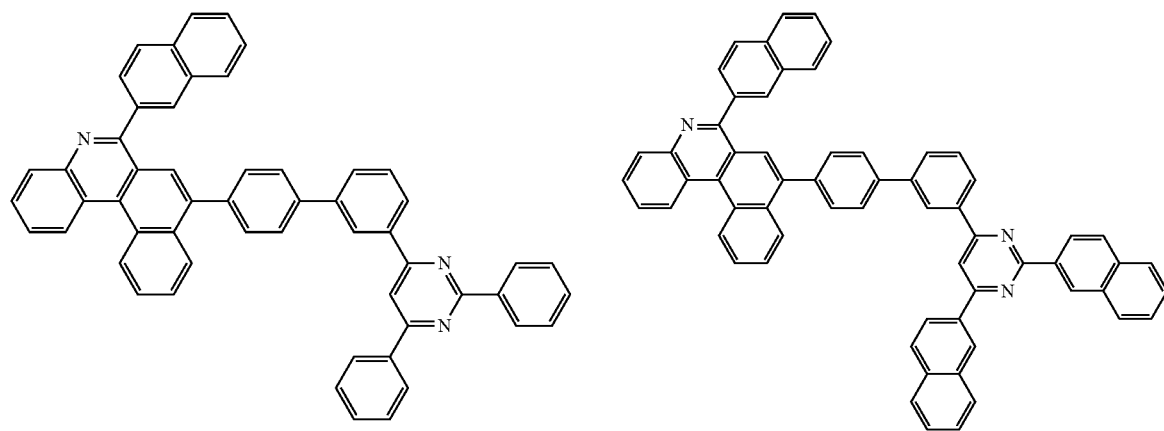

591
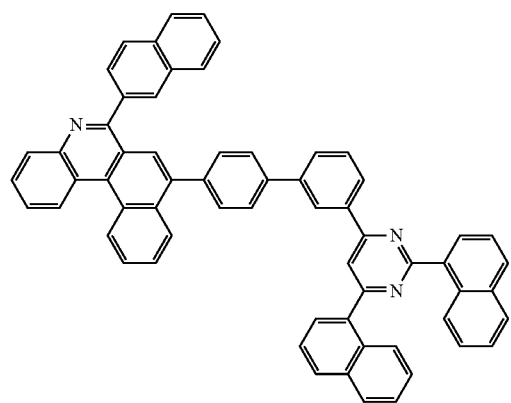
592
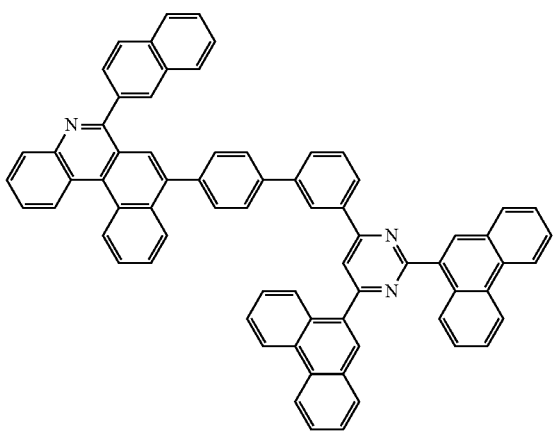
593
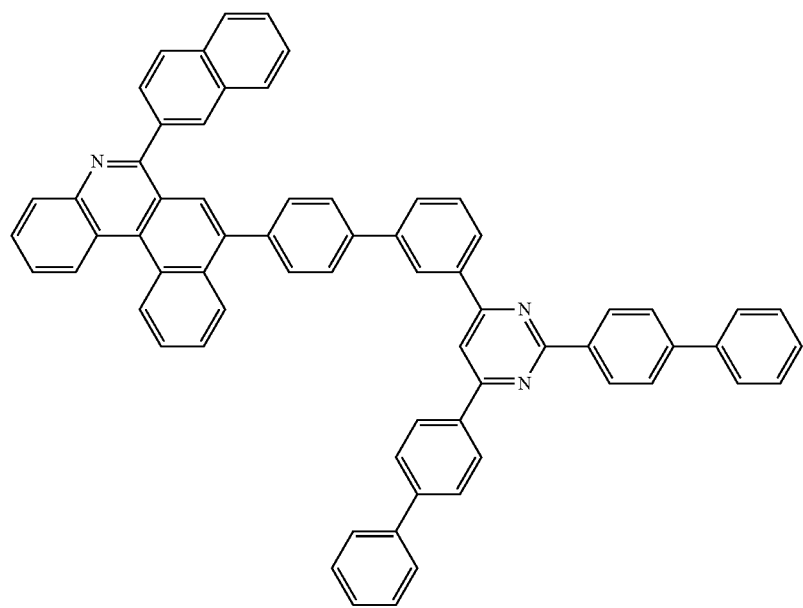
594
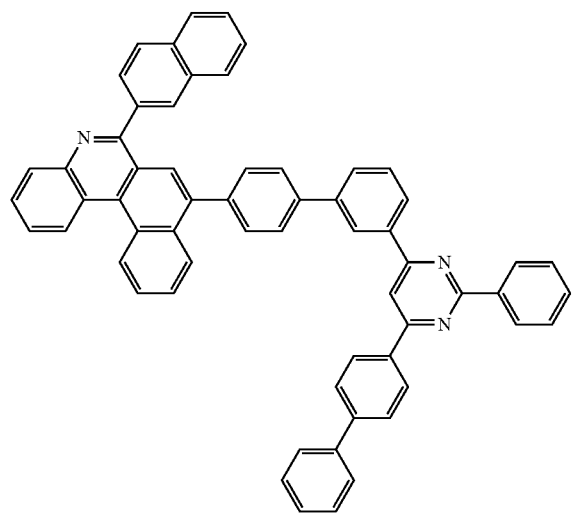
595
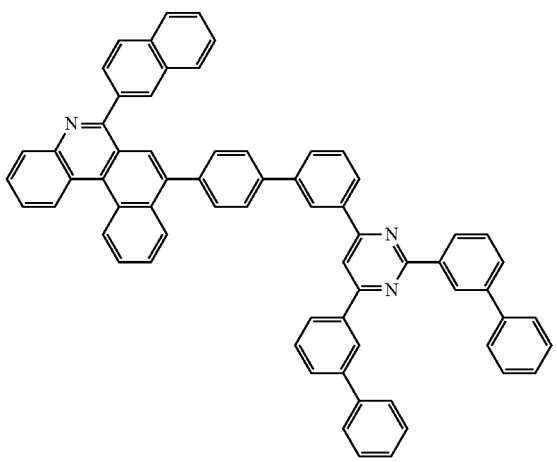

-continued
596
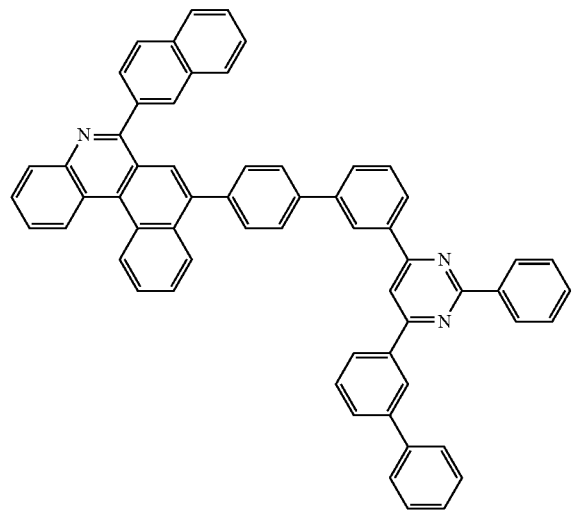
597
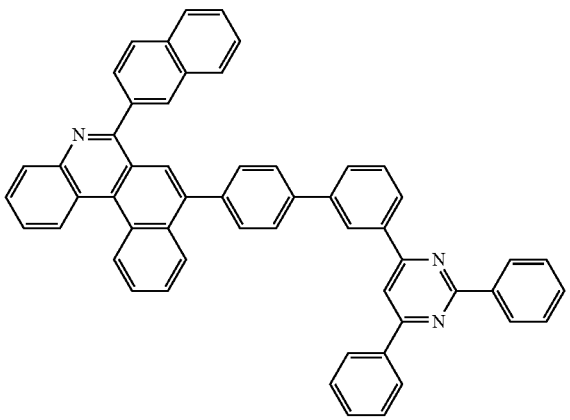
598
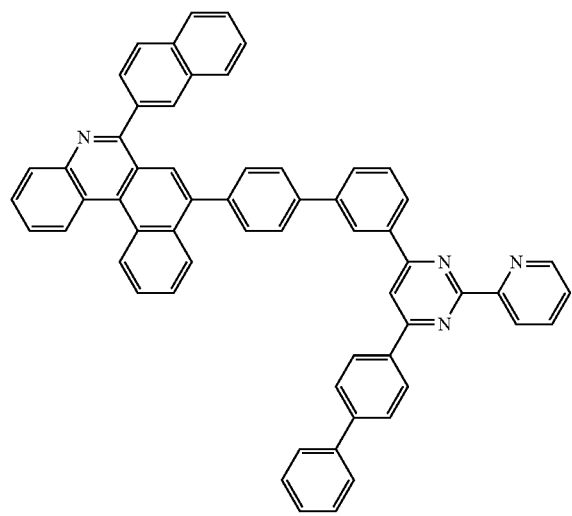
599
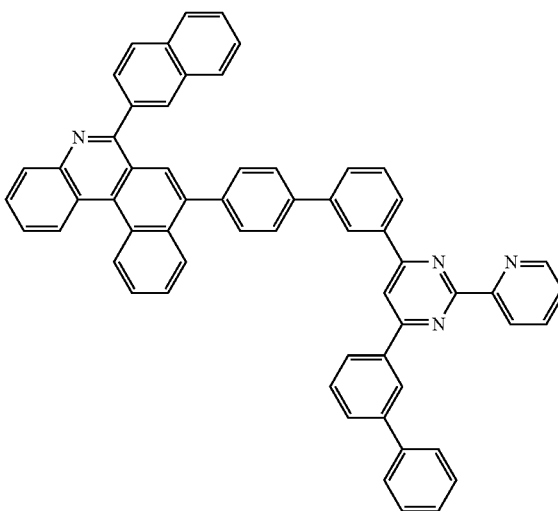
600
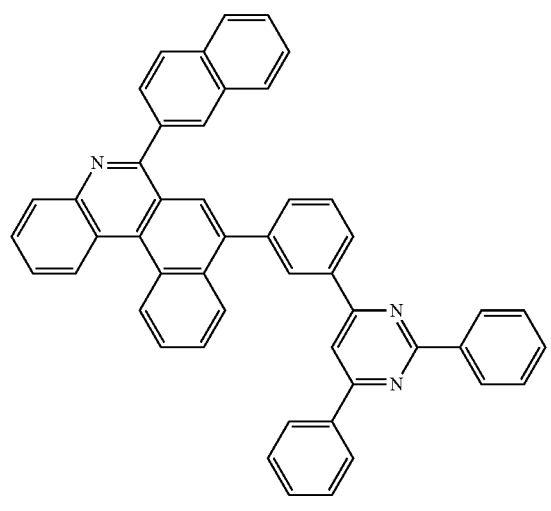
601
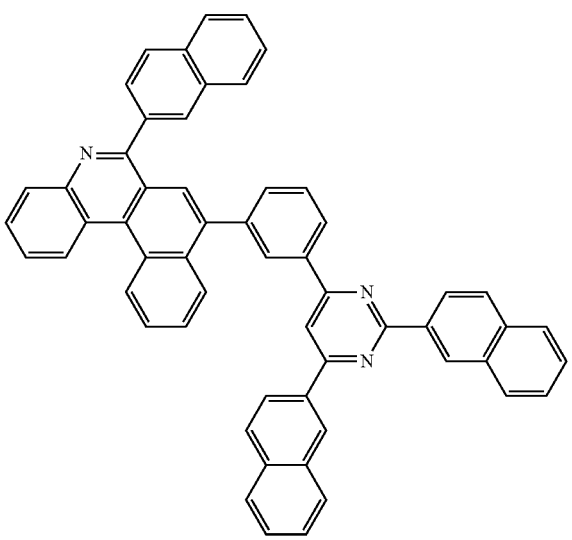

-continued
602
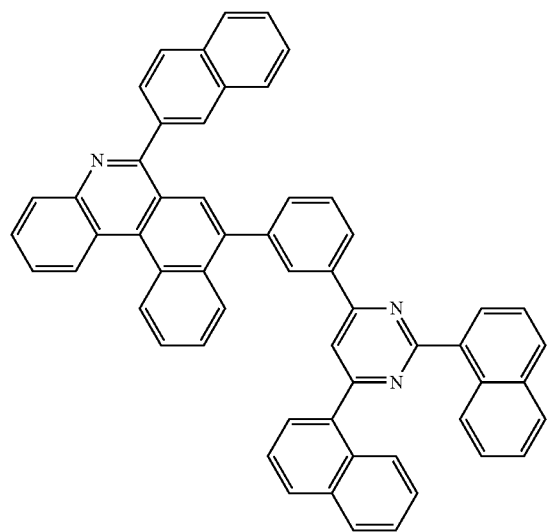
603
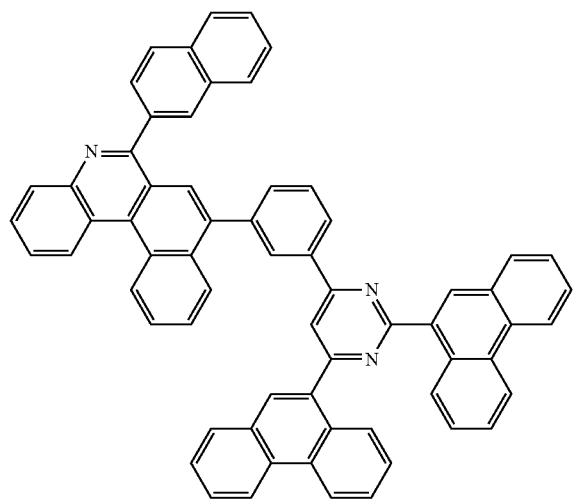
604
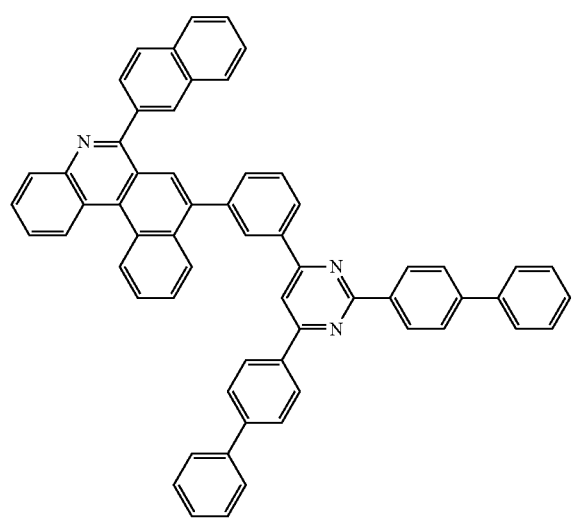
605
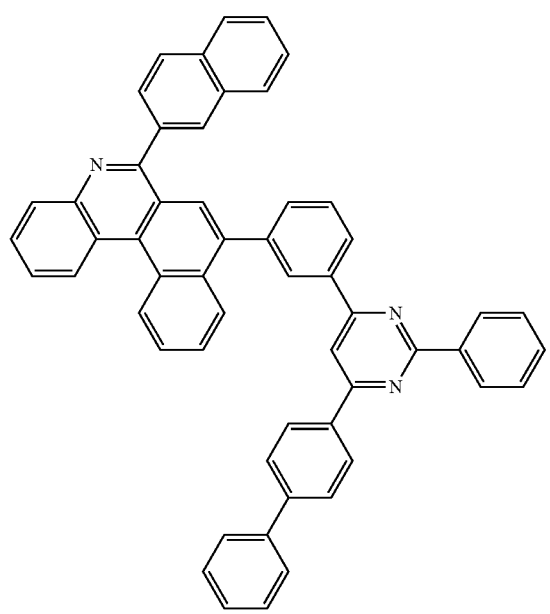

-continued
877
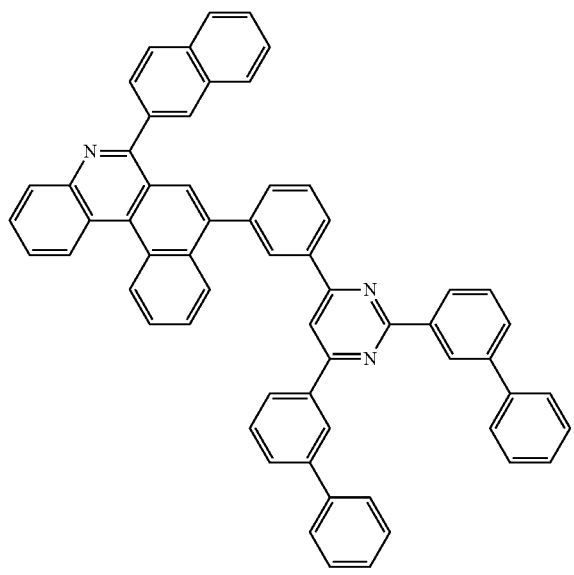
606
878
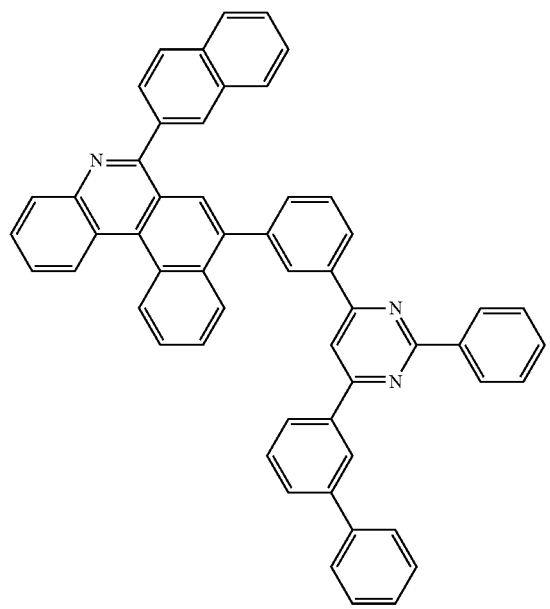
607
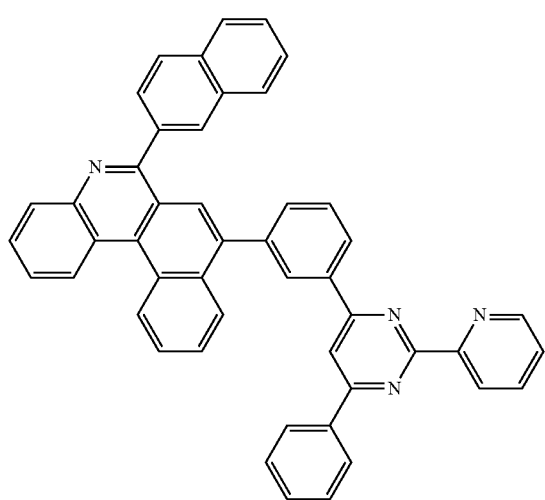
608

-continued
609
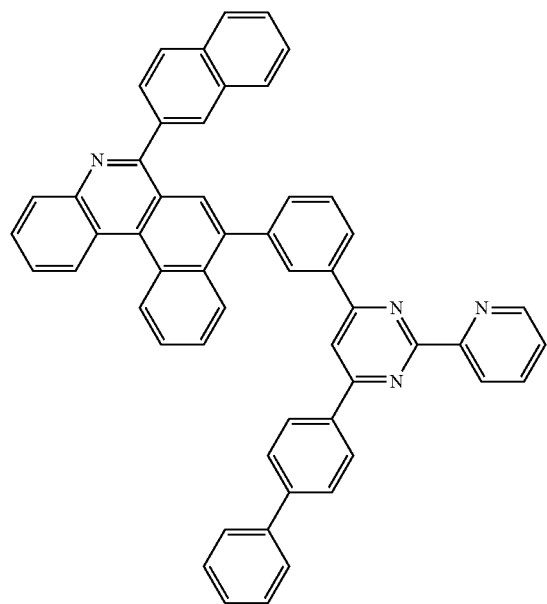
610
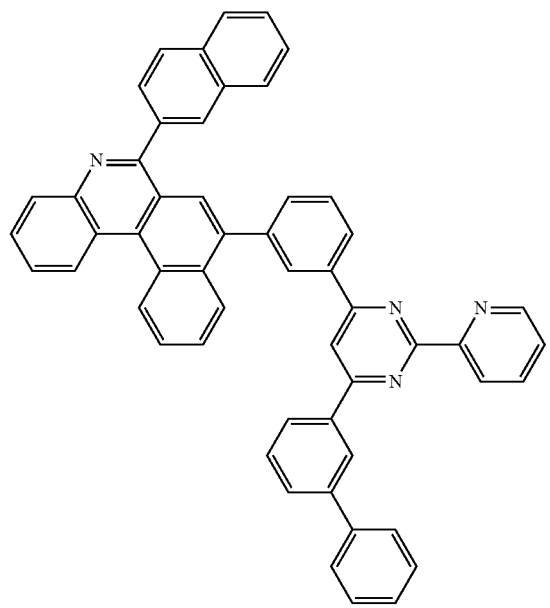
611
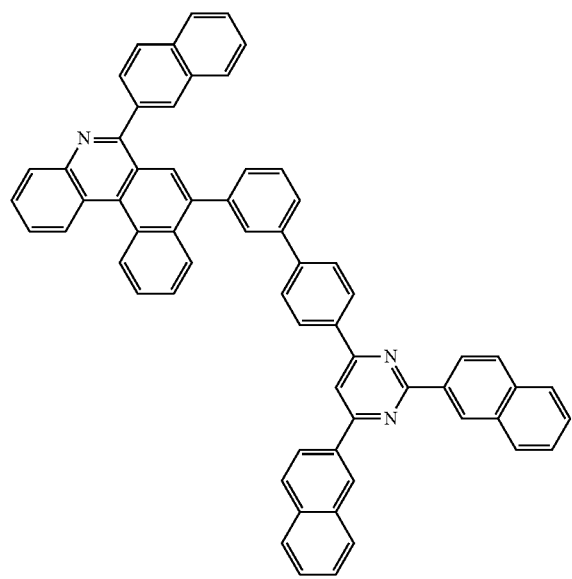
612
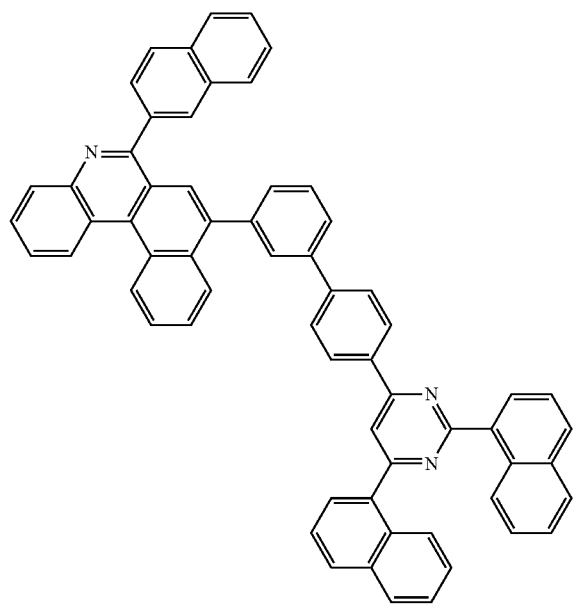

-continued
613
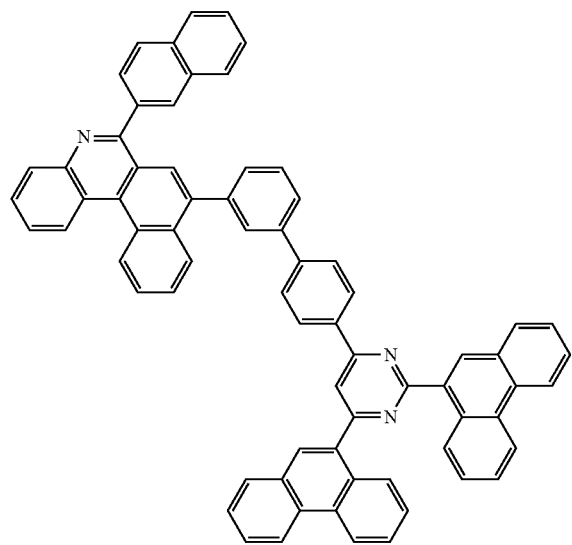
614
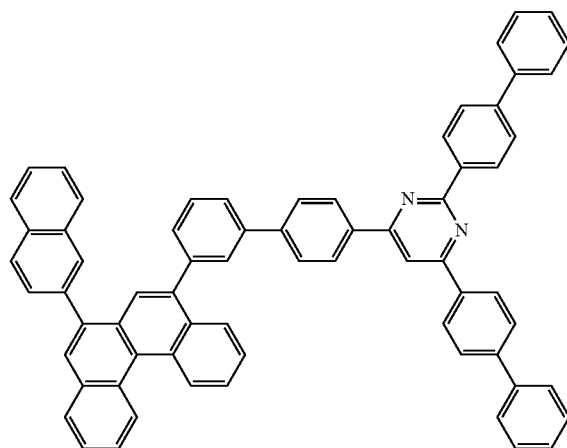
615
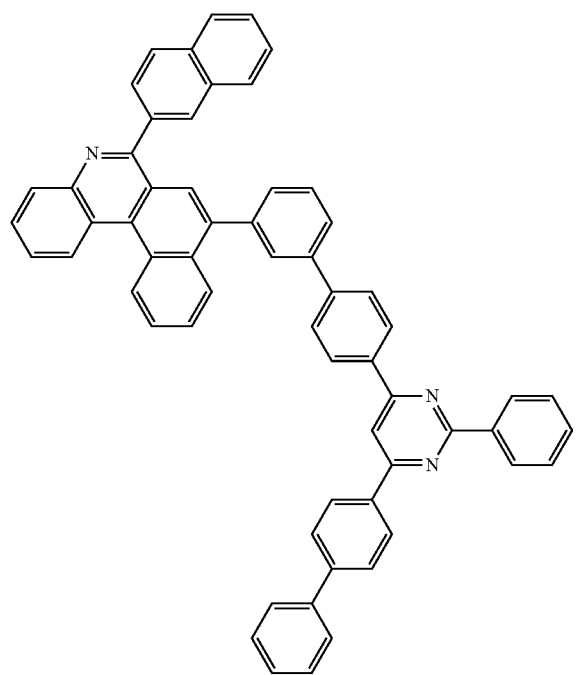
616
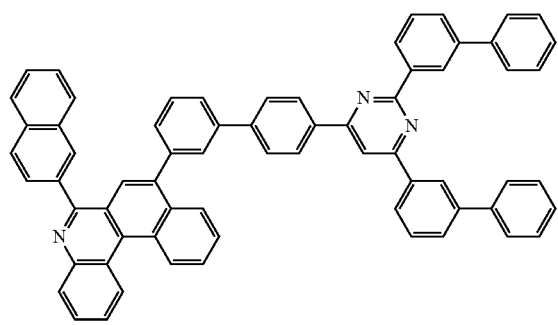

883 884
-continued
617
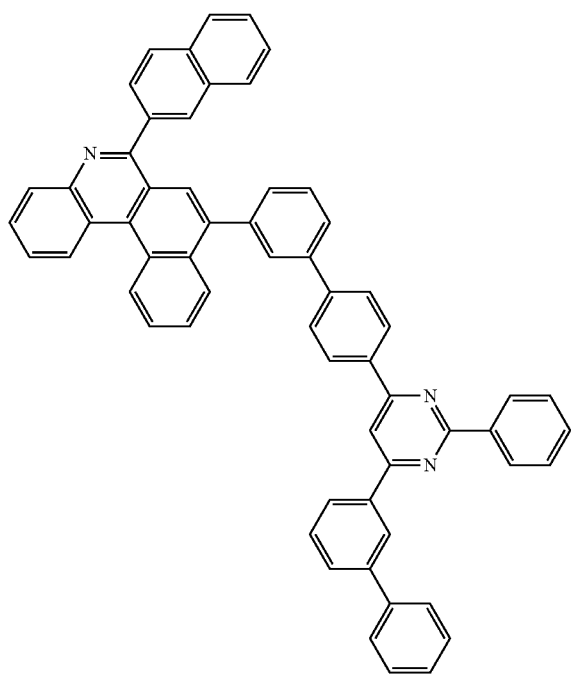
618
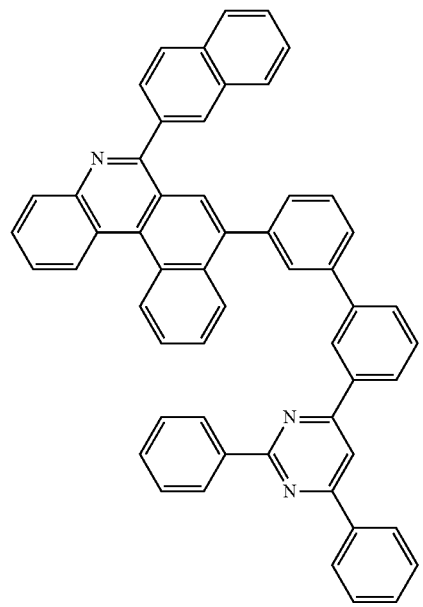
619
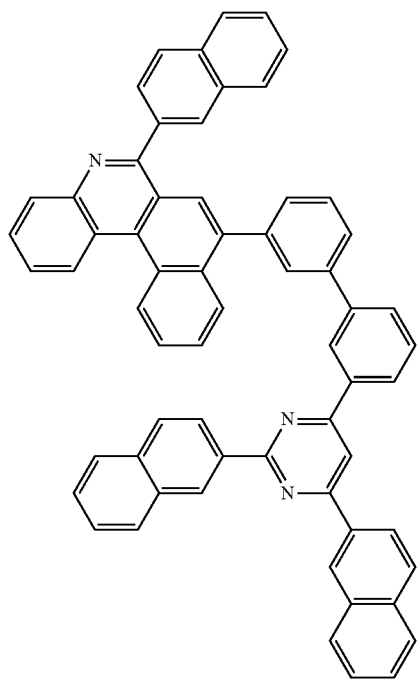
620
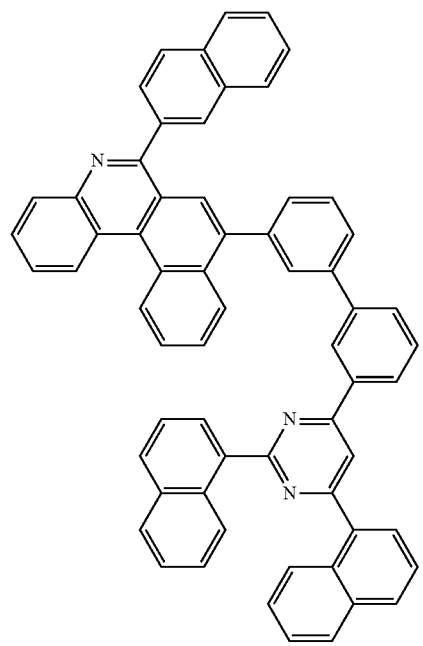

885 886
-continued
621
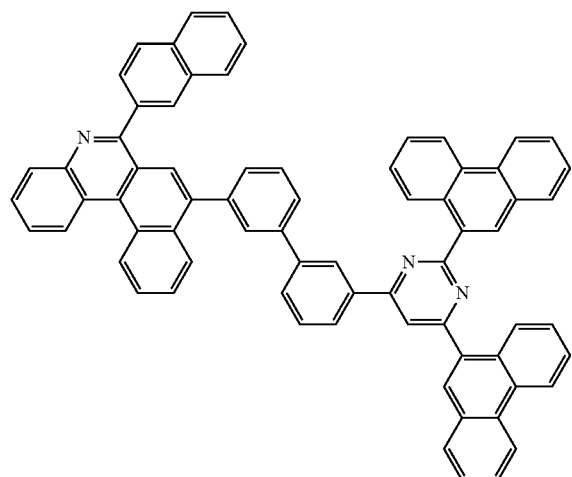
622
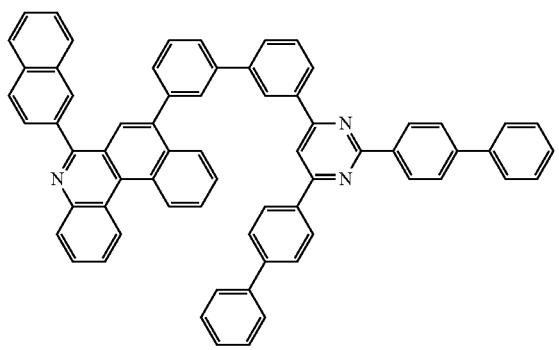
623
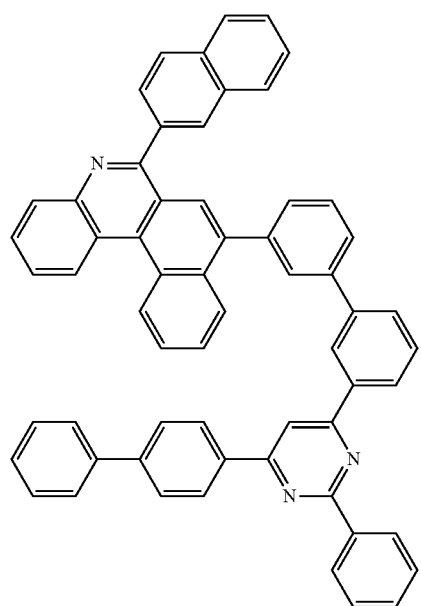
624
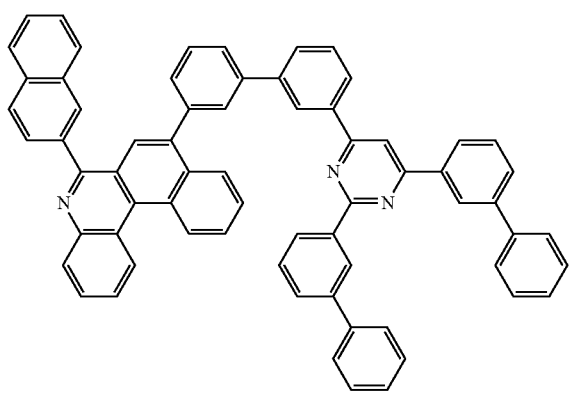

-continued
625
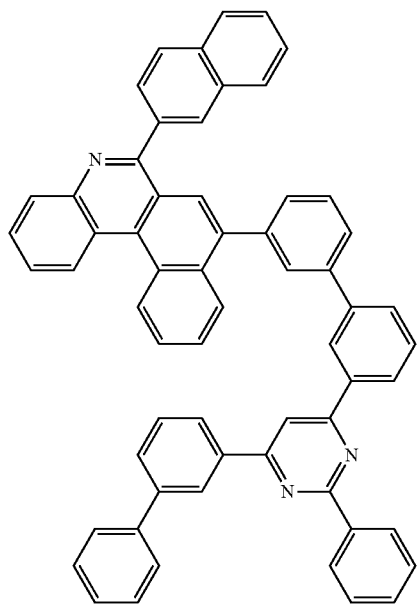
626
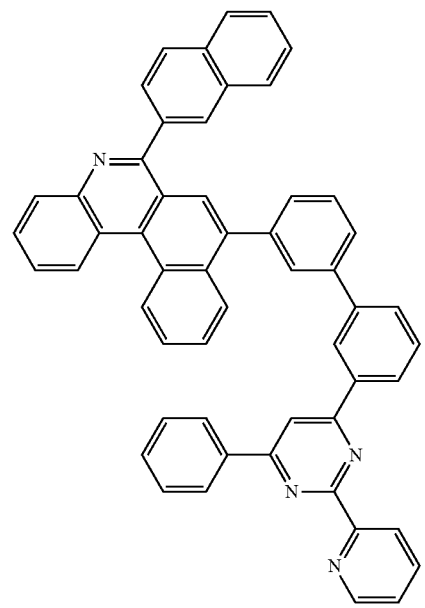
627
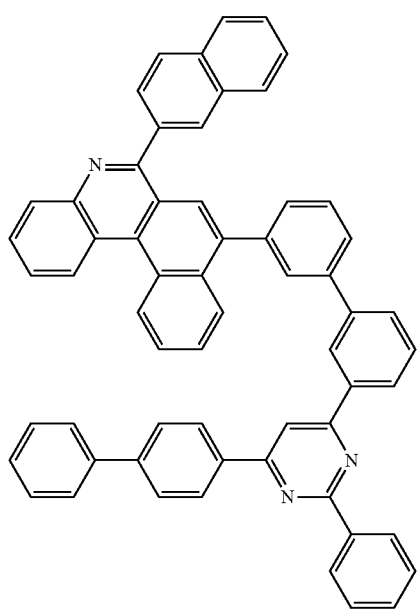
628
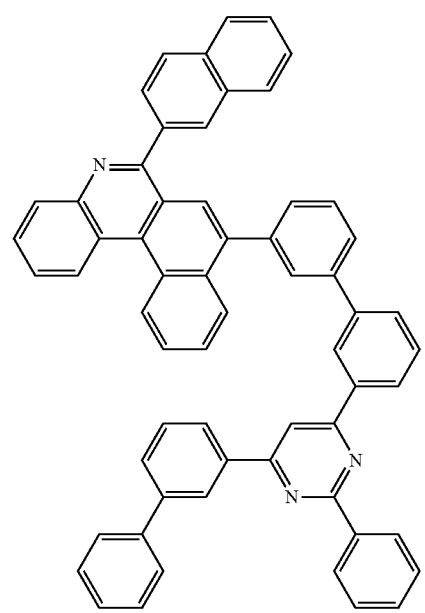
629
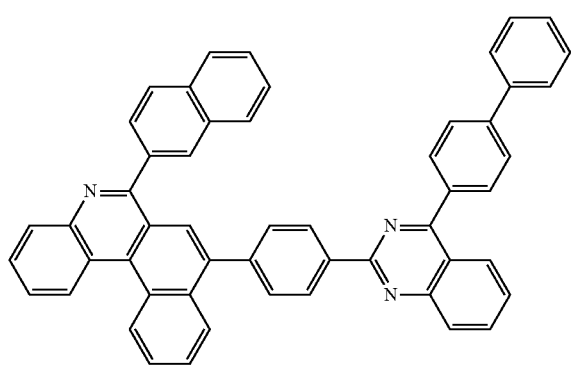
630
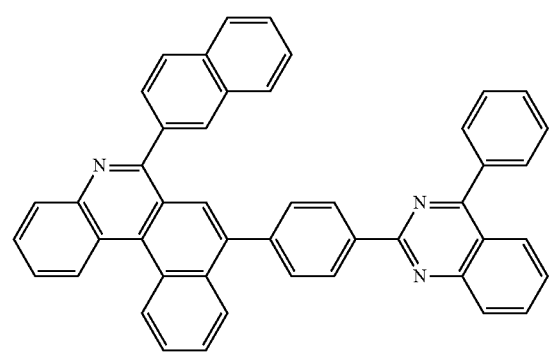

631
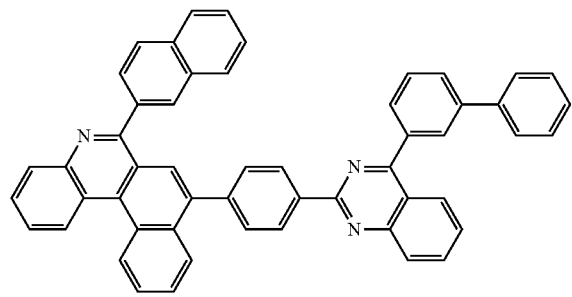
632
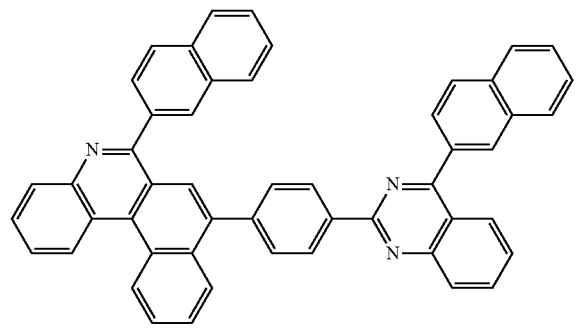
633
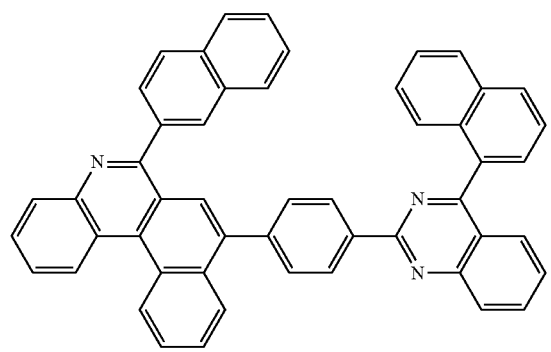
634
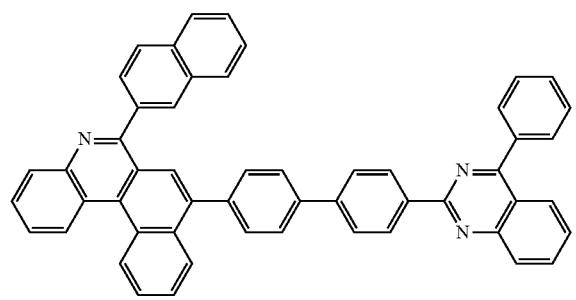
635
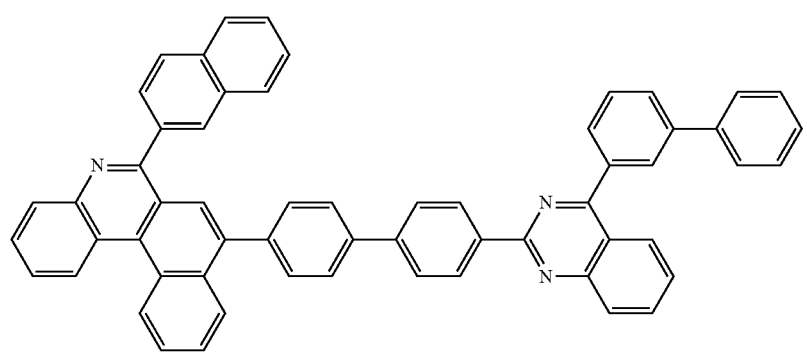
636
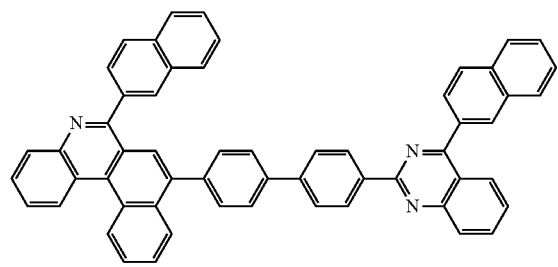
637
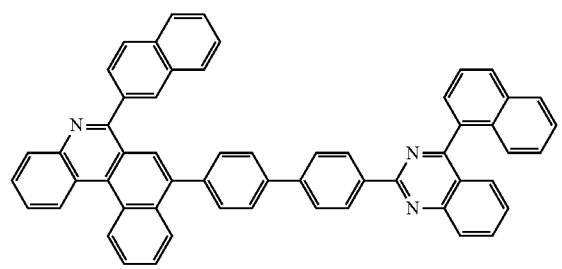

-continued
638
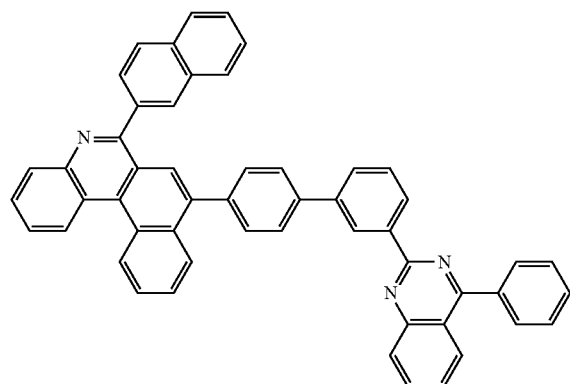
639
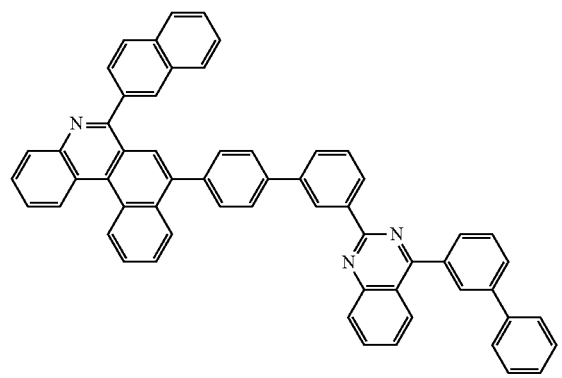
640
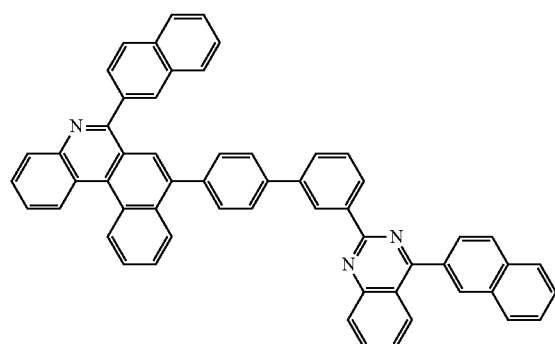
641
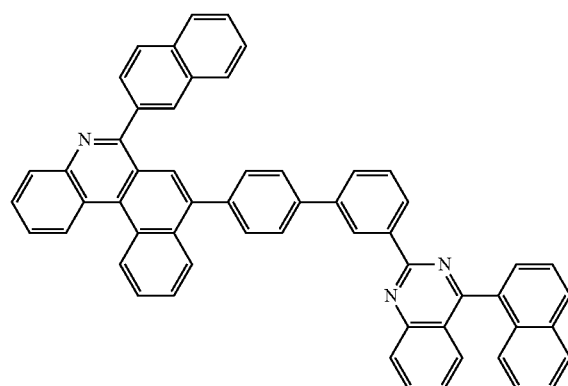
642
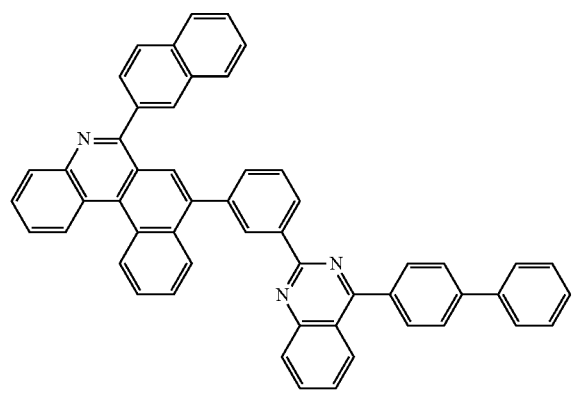
643
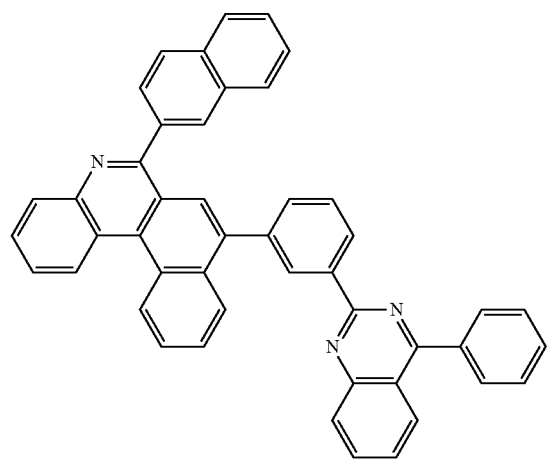

-continued
644
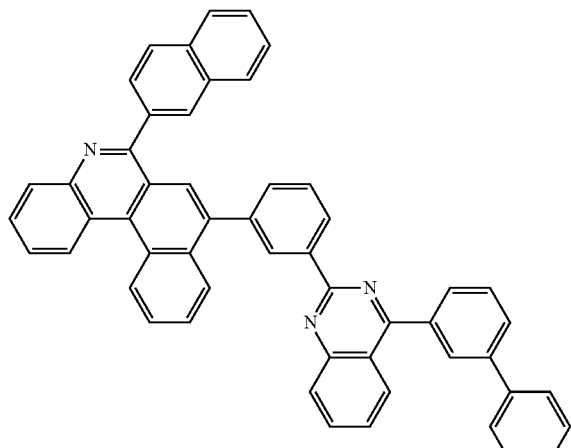
645
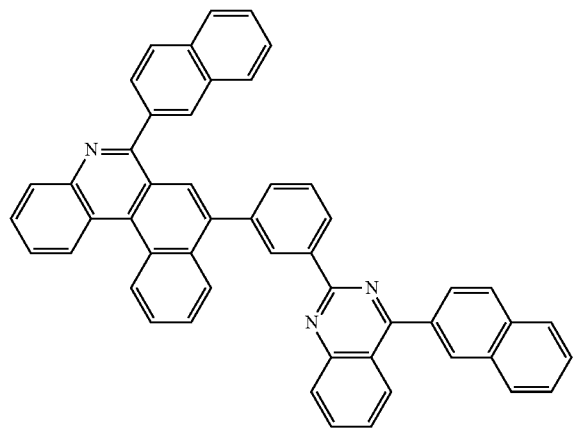
646
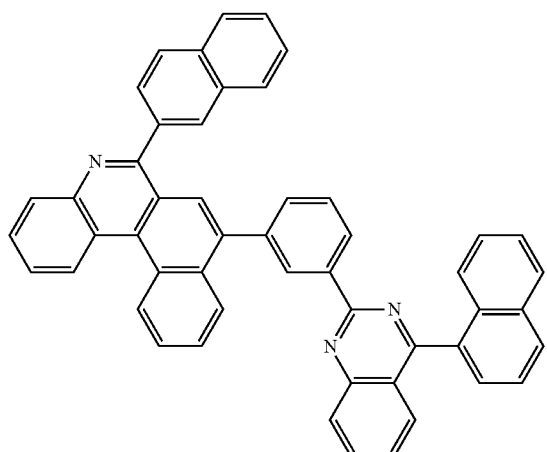
647
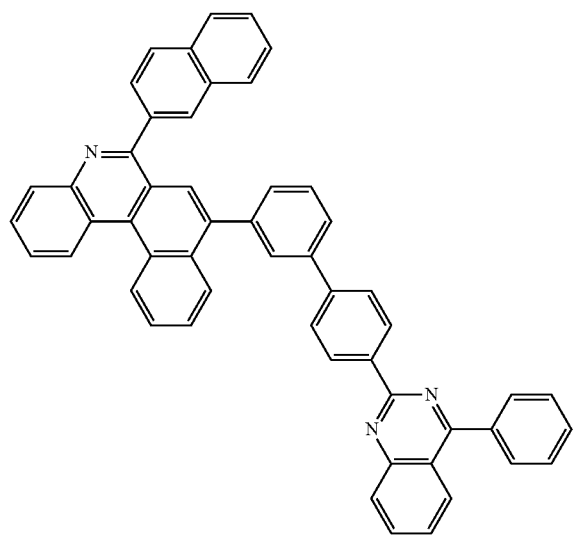
648
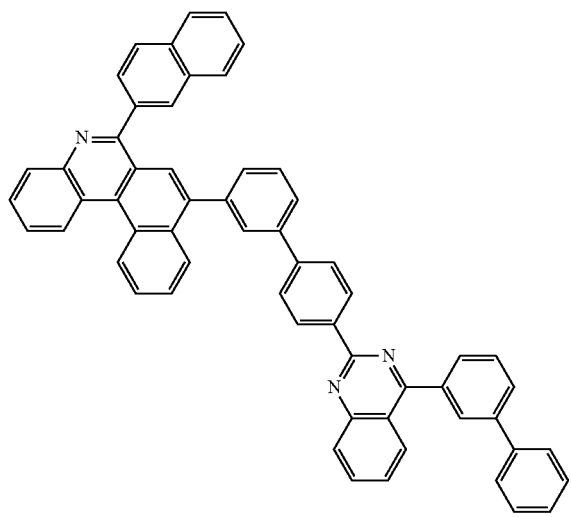
649
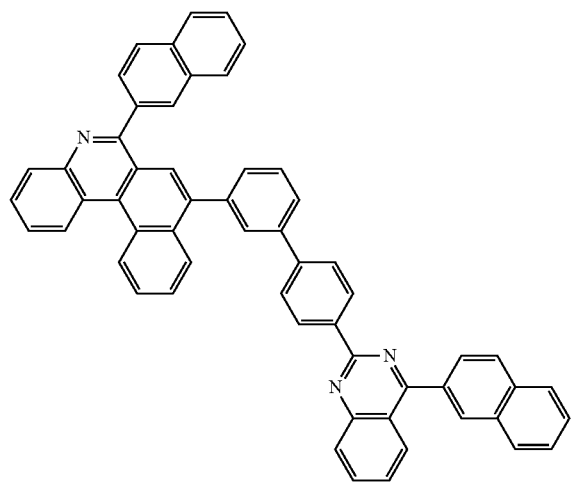

-continued
650
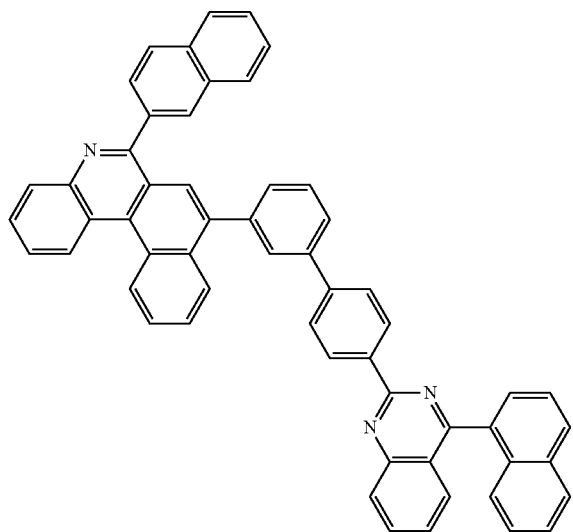
651
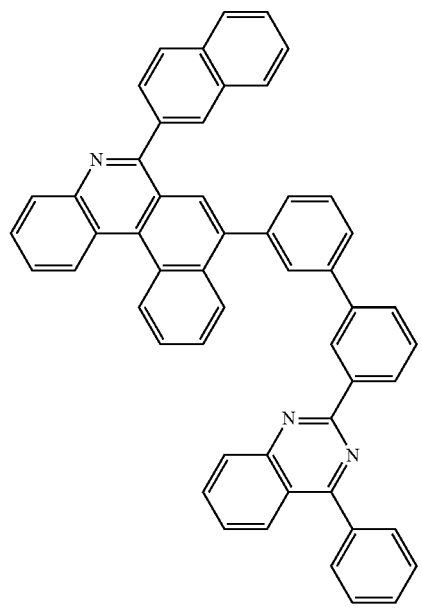
652
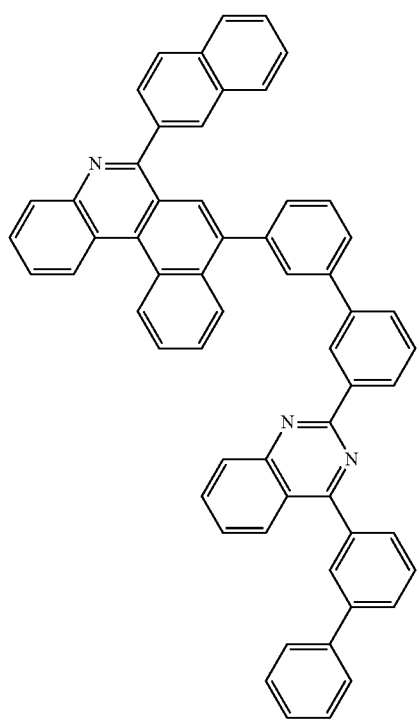
653
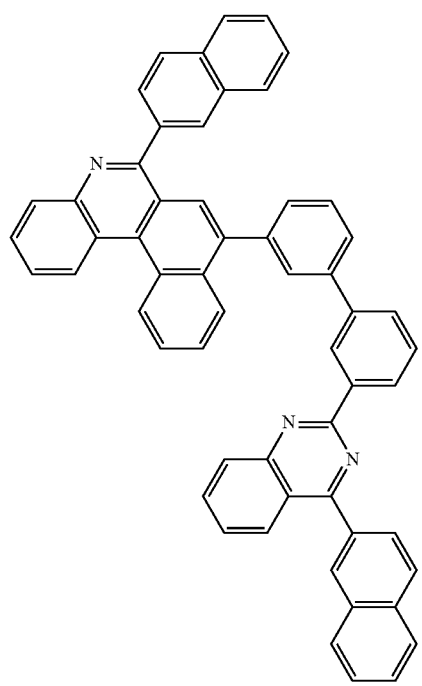

-continued
897
654
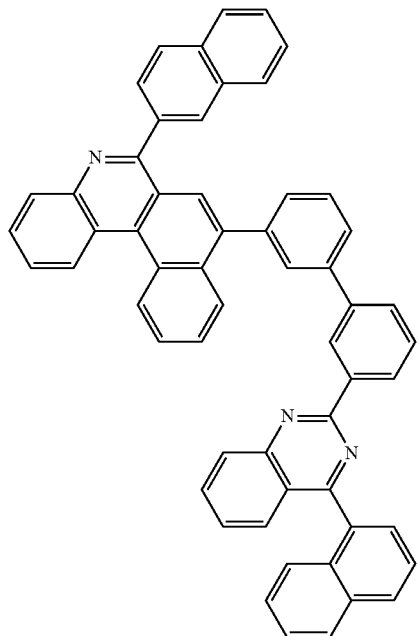
898
655
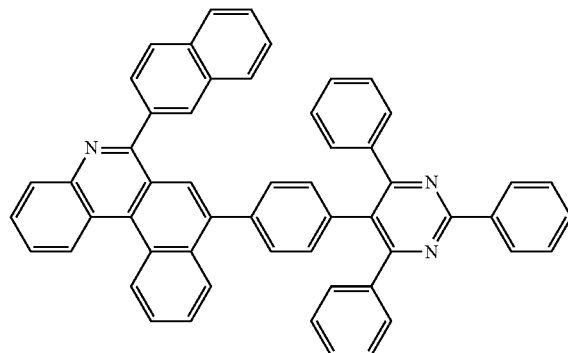
656
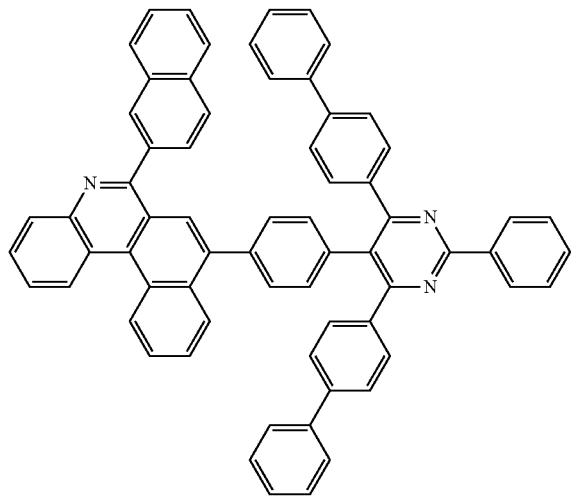
657
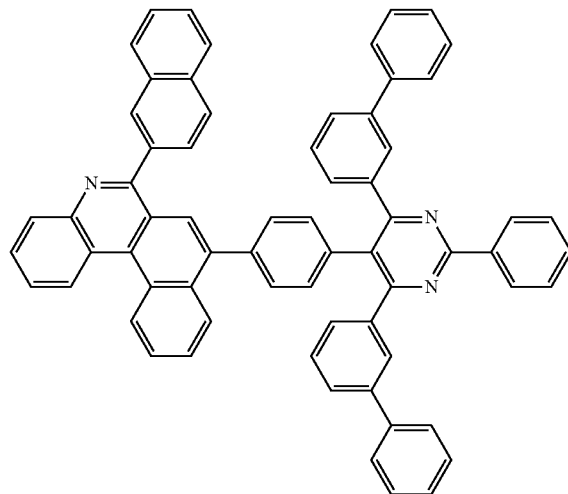
658
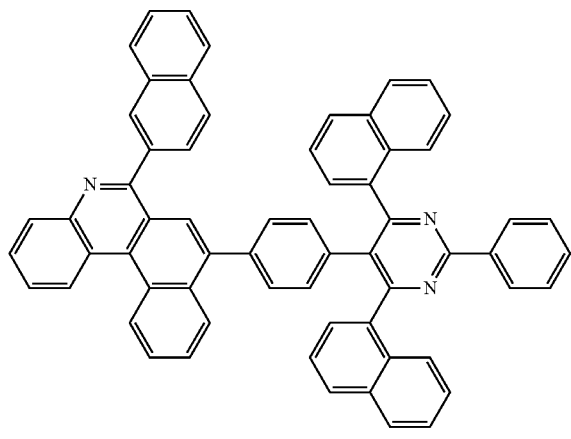
659
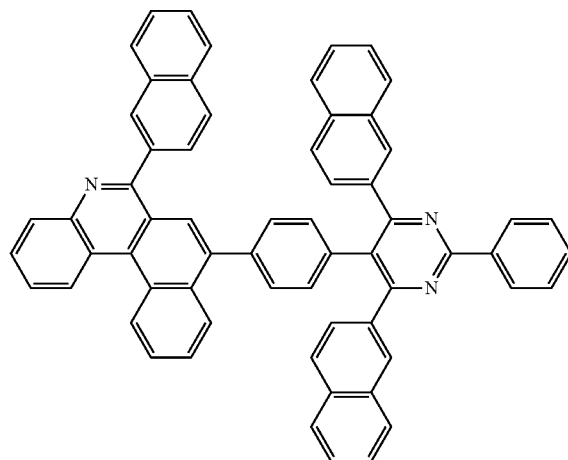

-continued
660
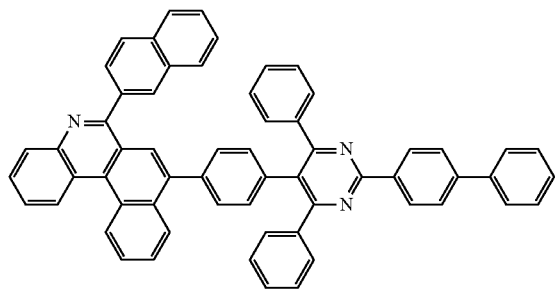
661
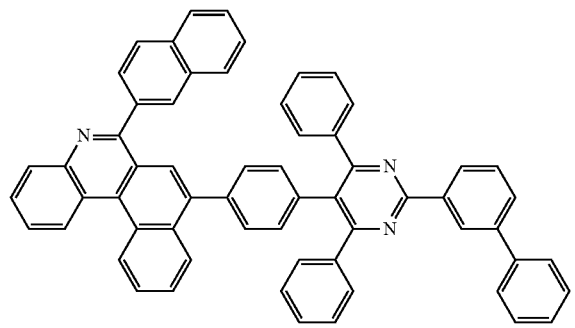
662
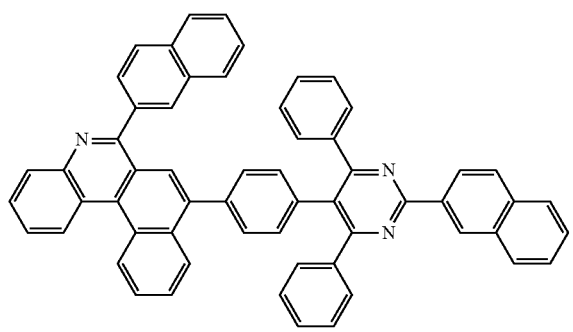
663
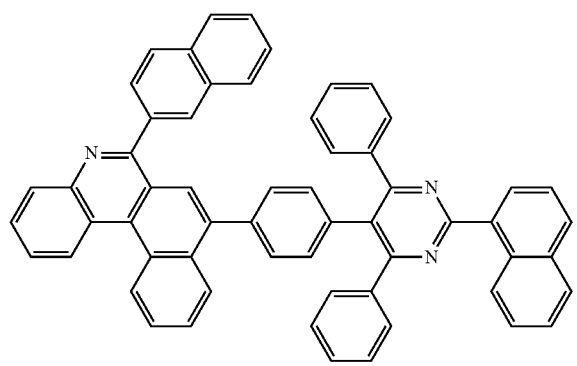
664
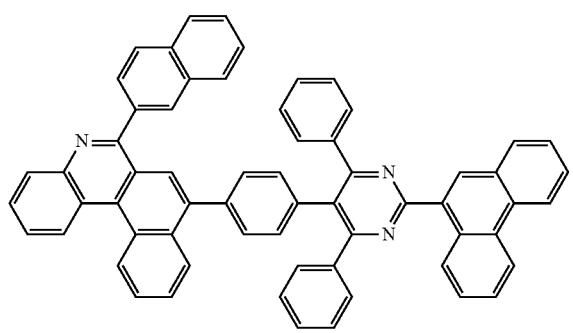
665
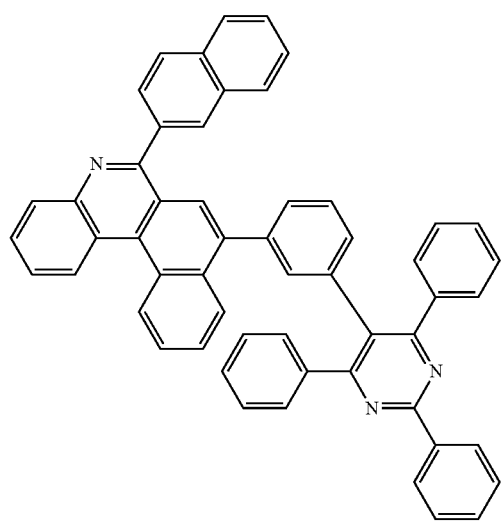

-continued

| 901 | 902 |
|---|---|
| 666 | 667 |
| 668 | 669 |

-continued
903
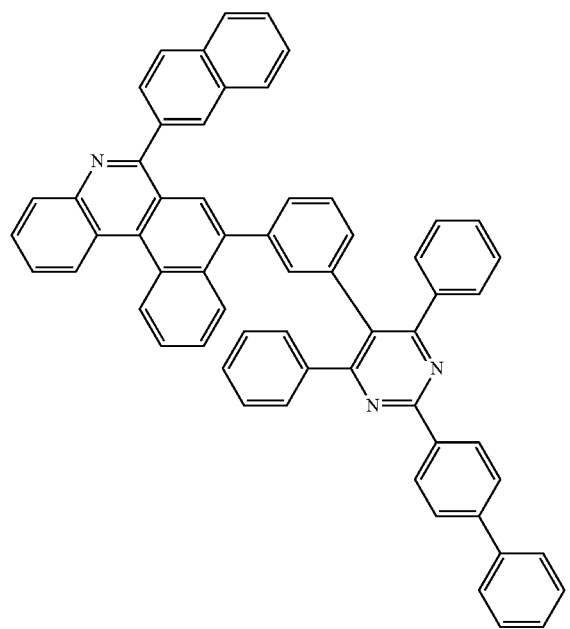
670
904
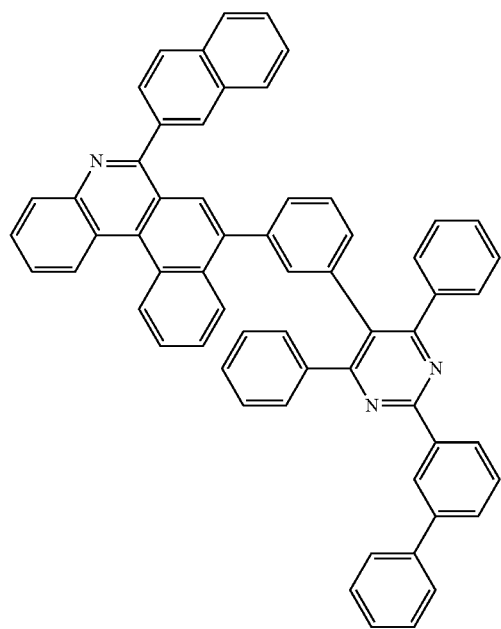
671
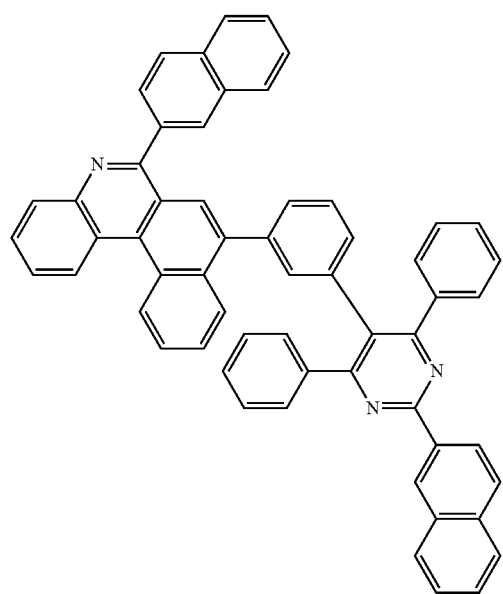
672
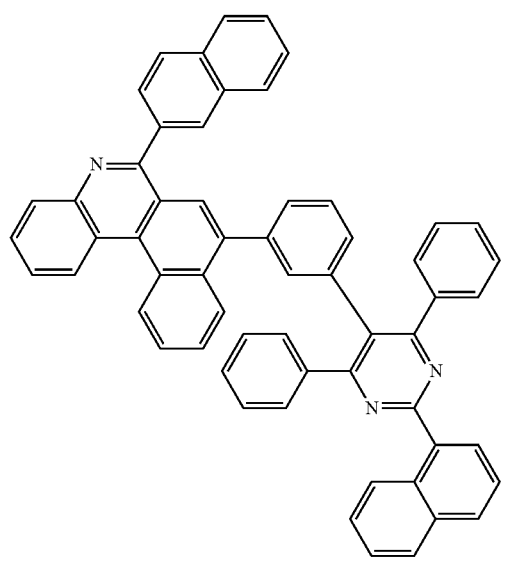
673

-continued
674
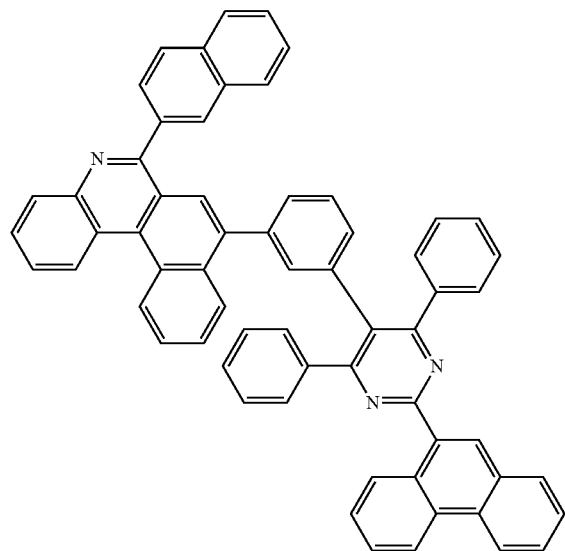
675
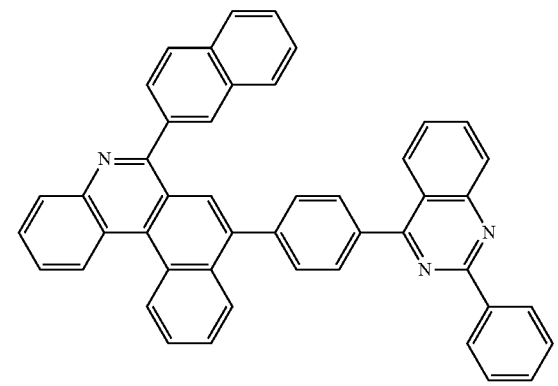
676
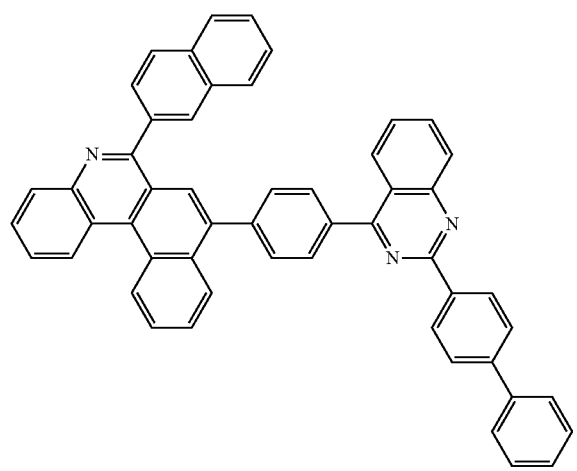
677
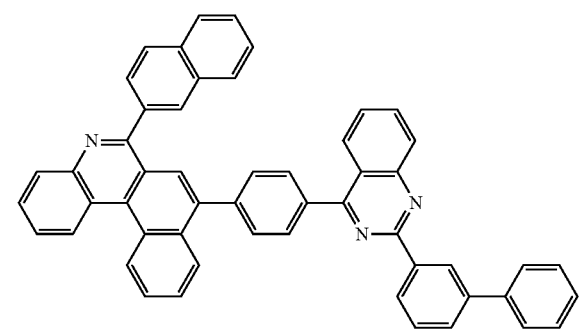
678
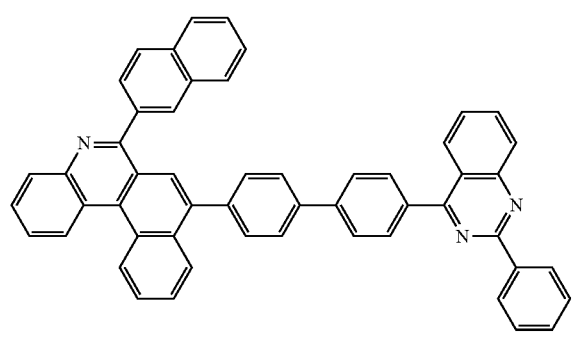
679
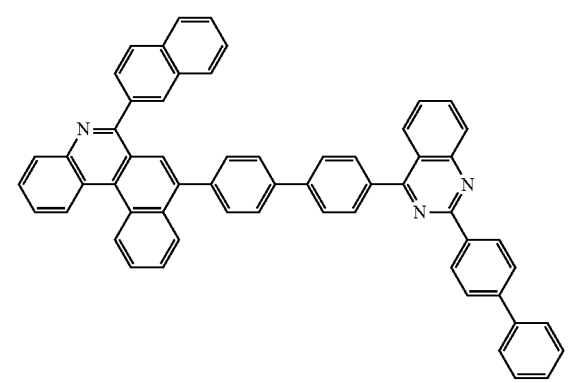

-continued
680
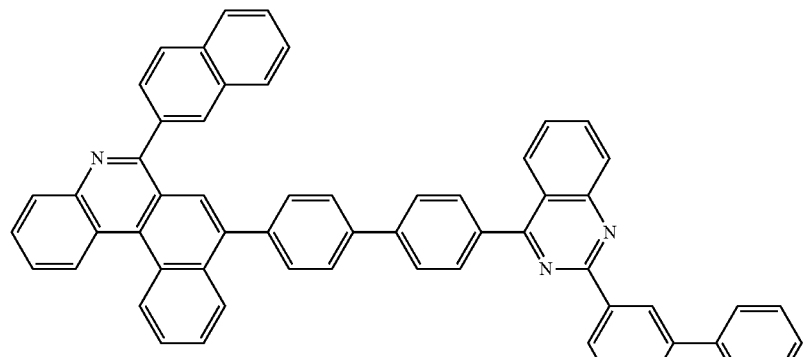
681
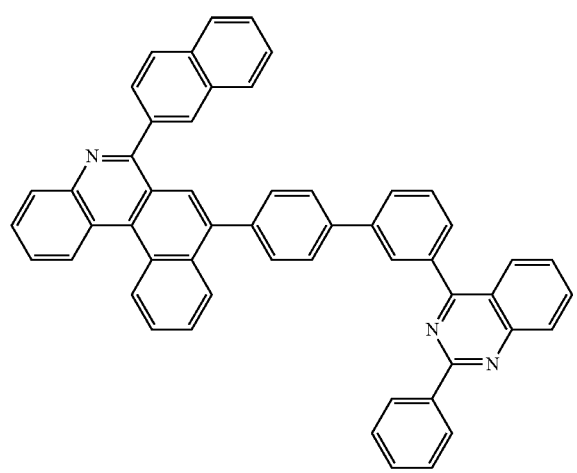
682
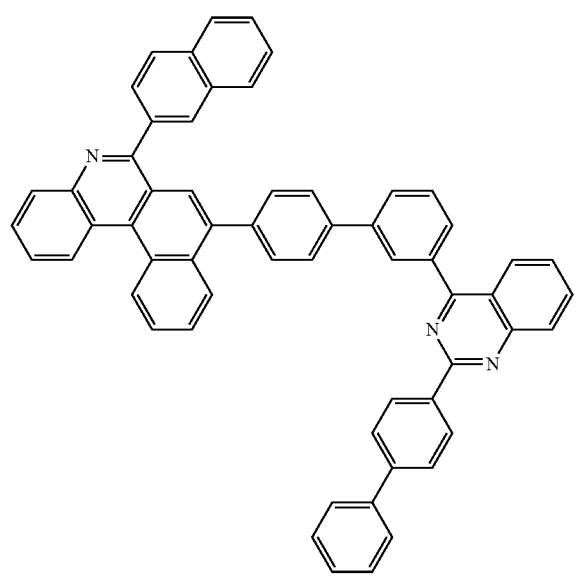
683
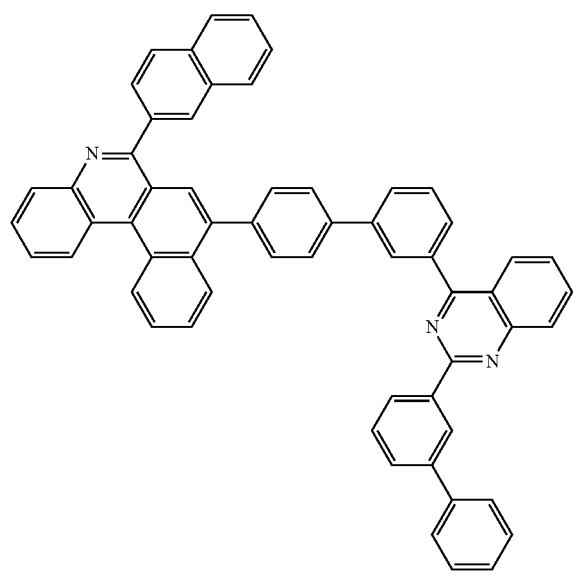
684
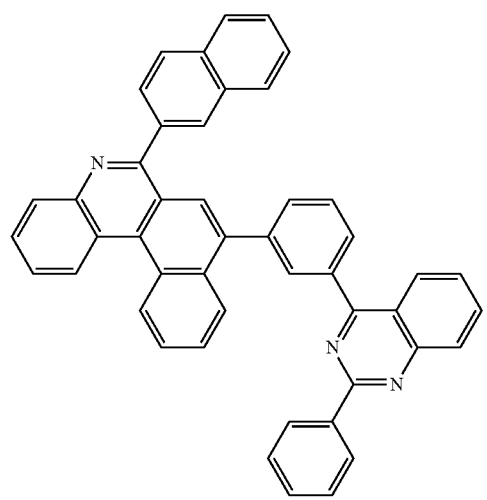

-continued
909
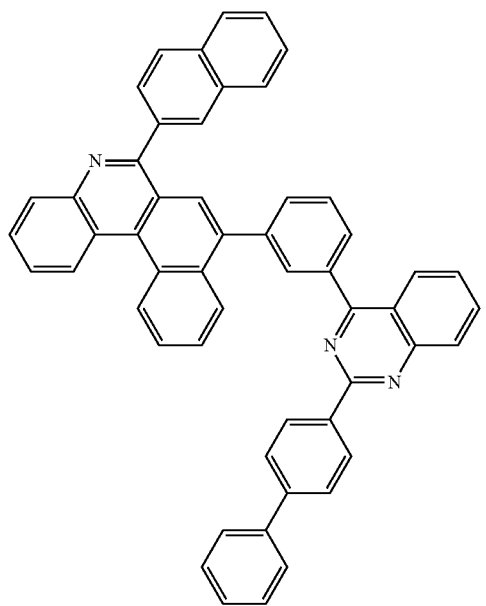
910
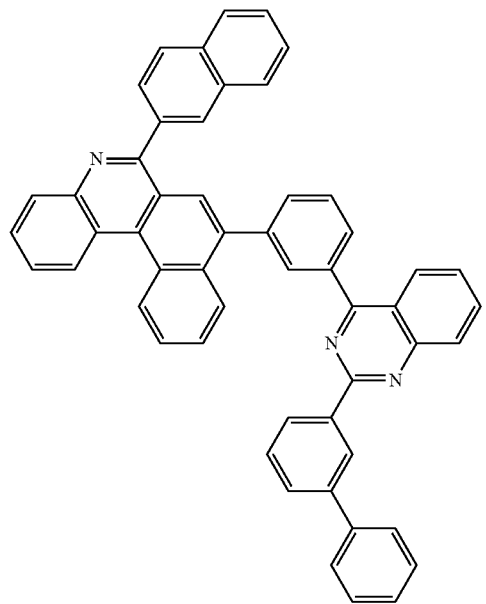
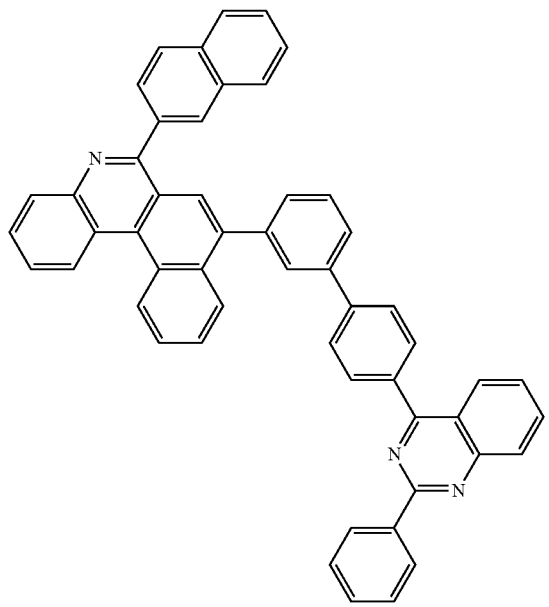
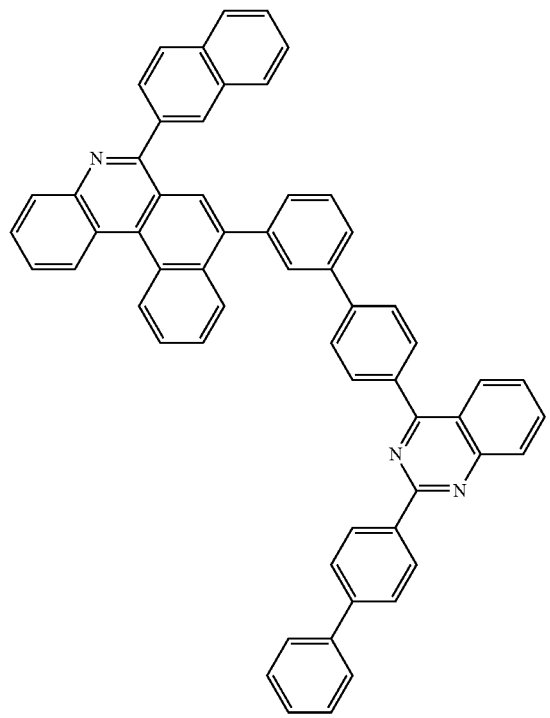

-continued
911
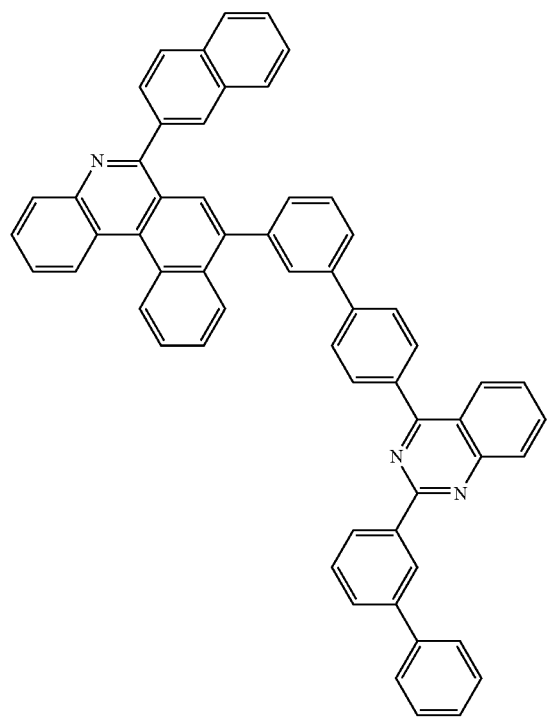
689
912
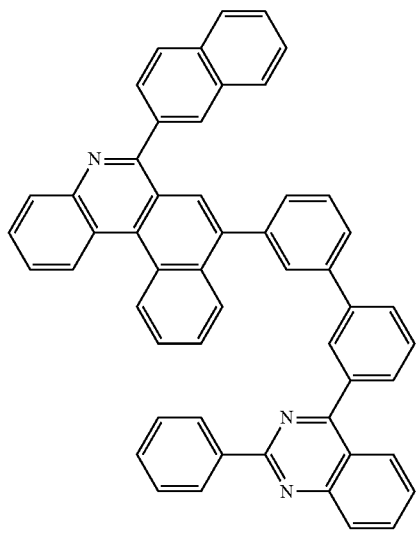
690
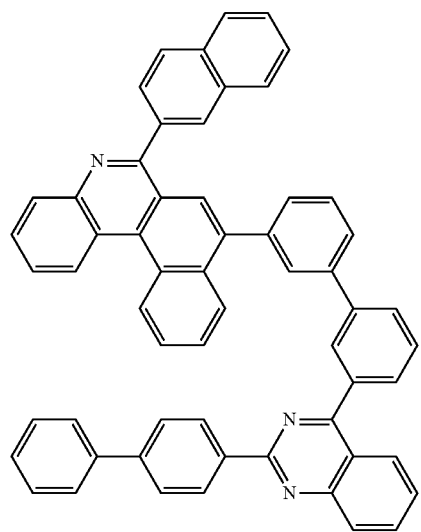
691
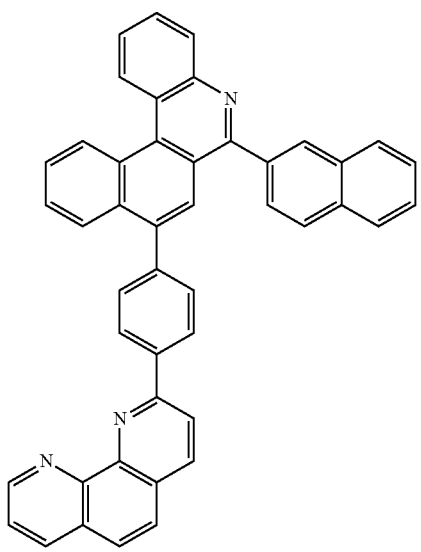
692

913 914
-continued
| 693 | 694 |
|---|---|
| 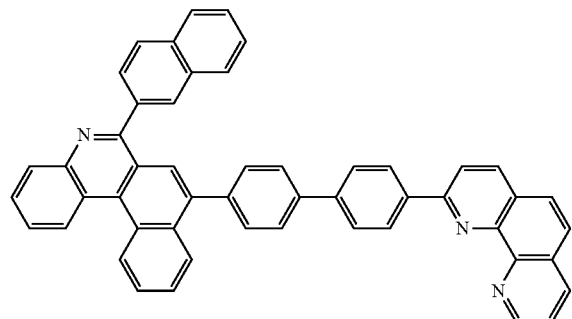 | 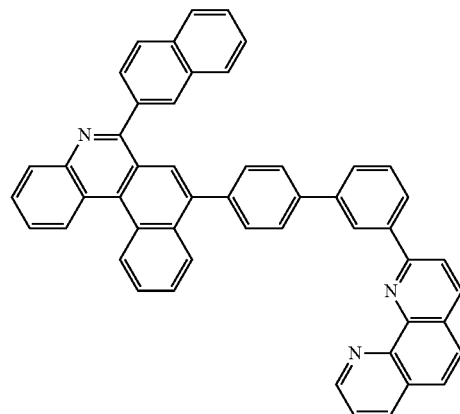 |
| 695 | 696 |
| 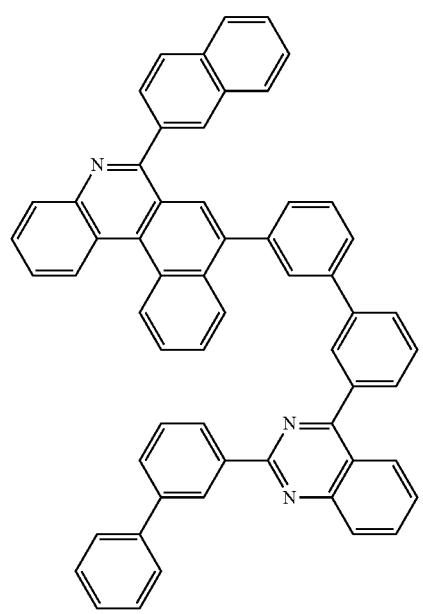 | 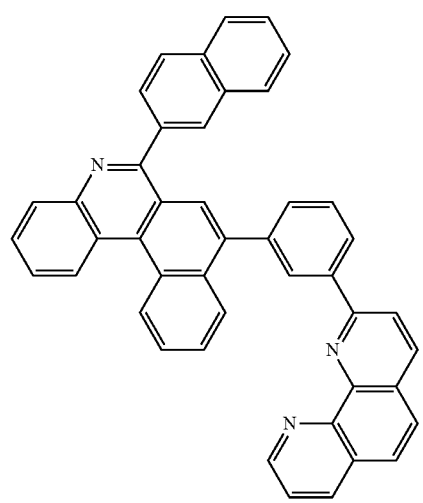 |
| 697 | 698 |
| 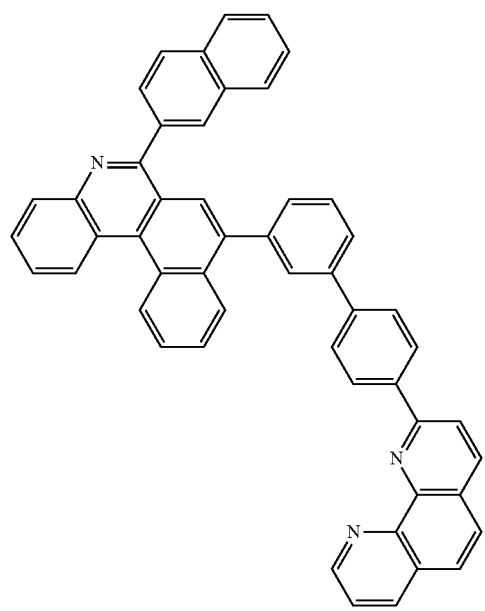 | 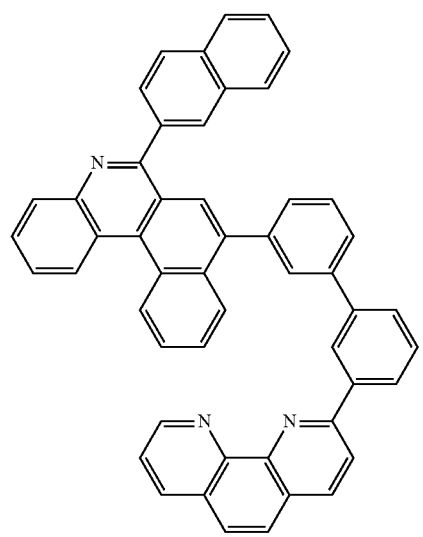 |

915
916
-continued
699 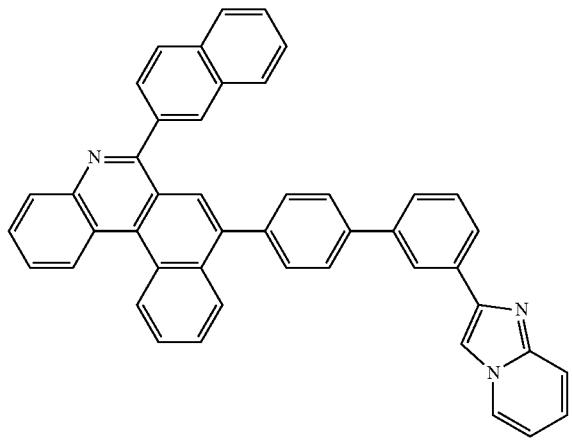 700
701 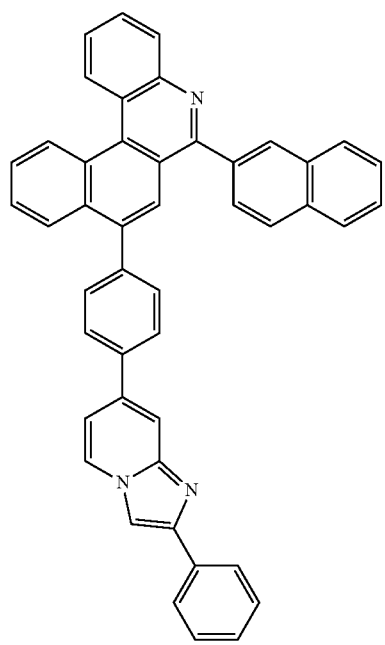 702
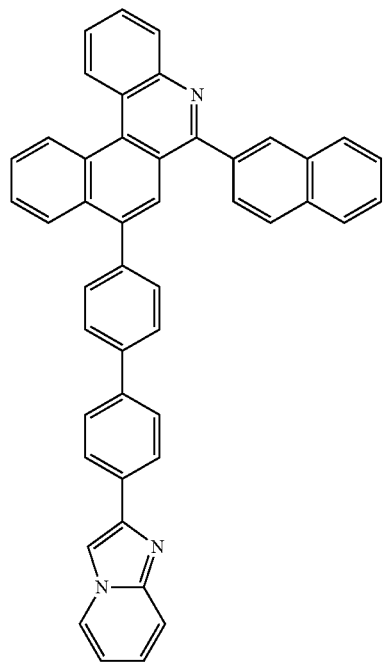

917 918
-continued
703 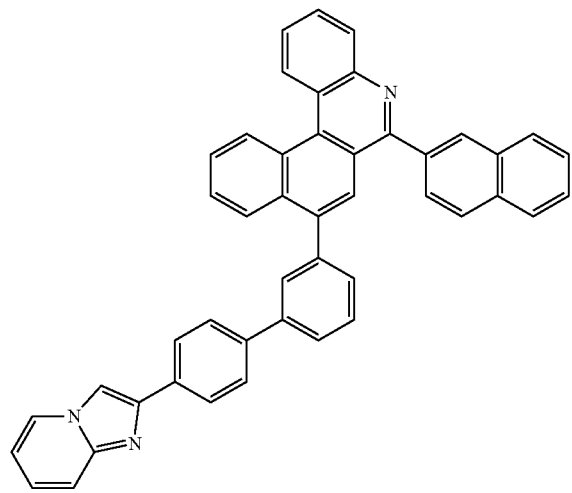
704 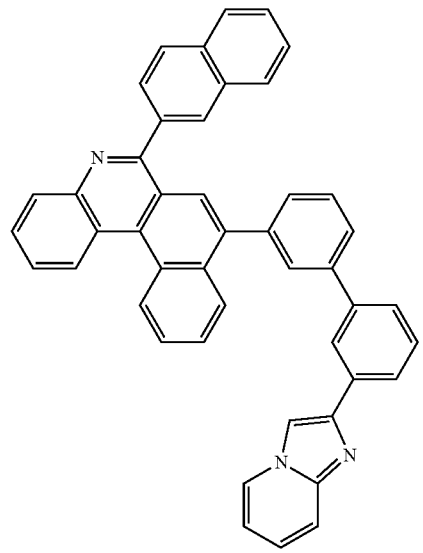
705 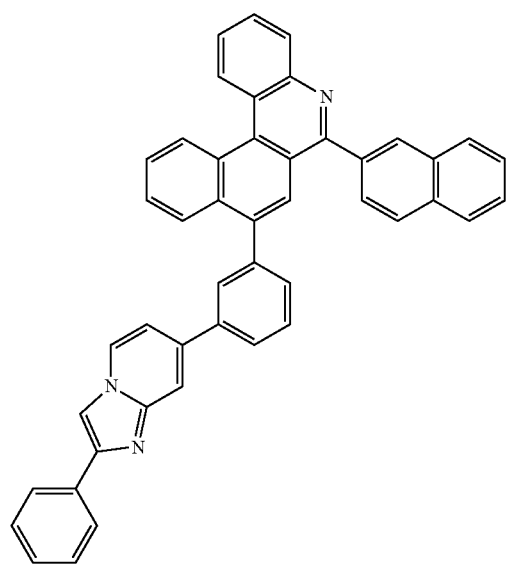
706 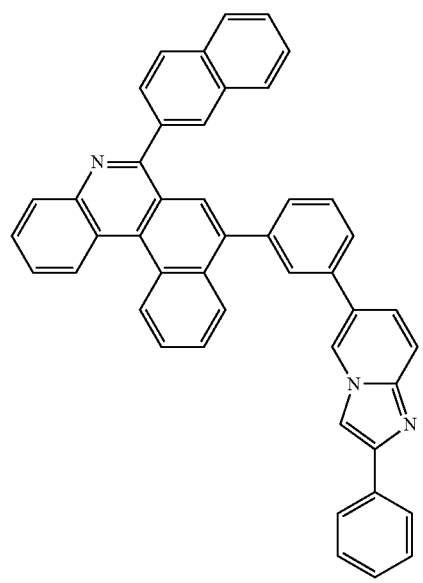
707 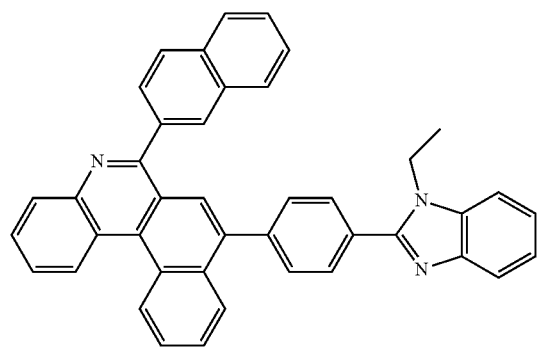
708 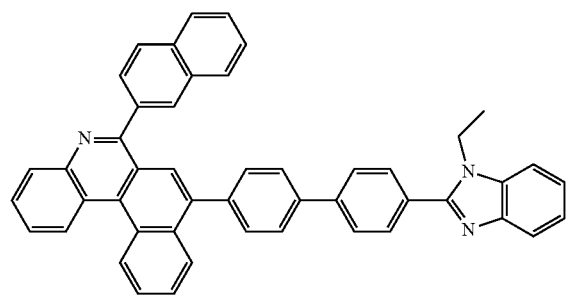

-continued
709
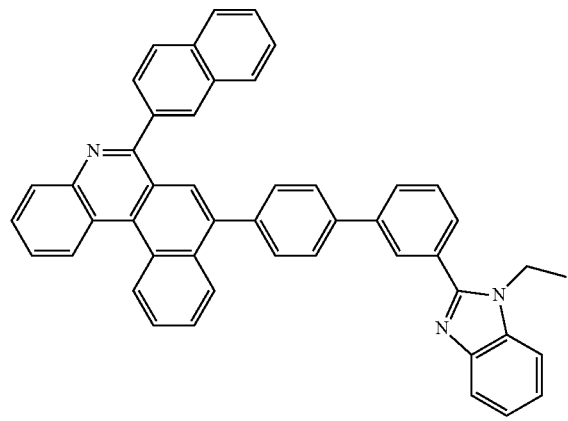
710
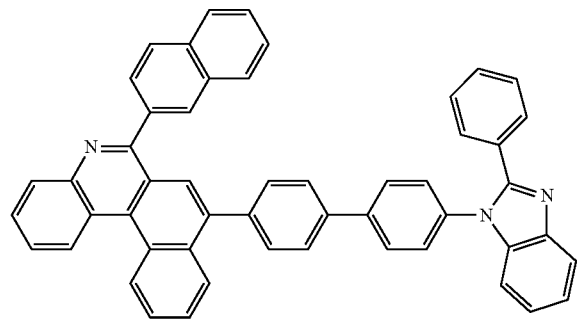
711
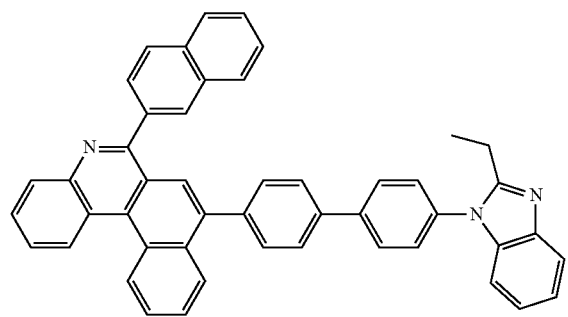
712
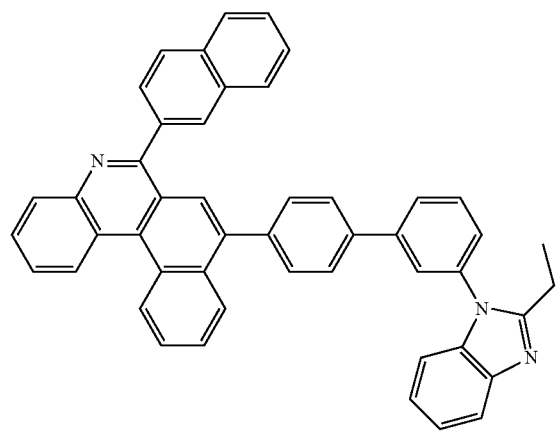
713
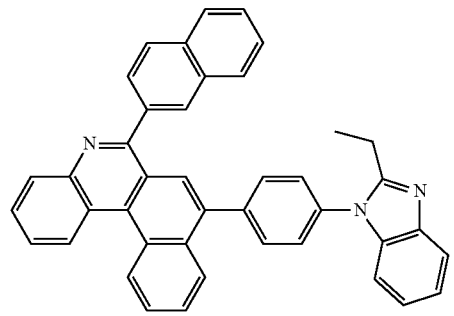
714
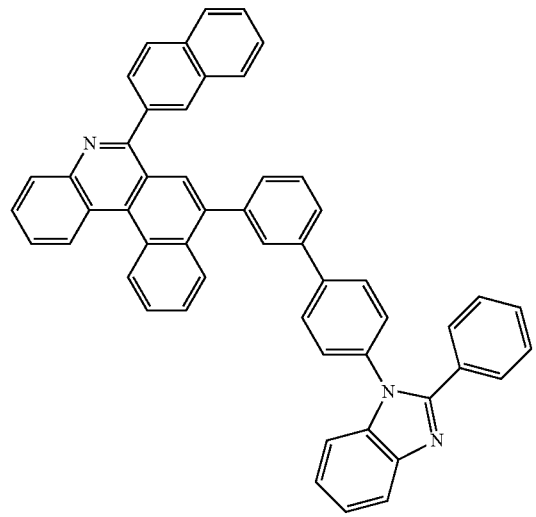

-continued
921
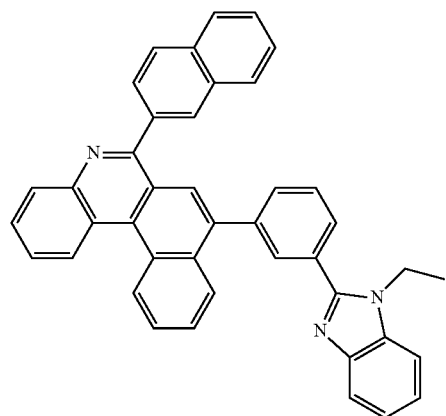
715
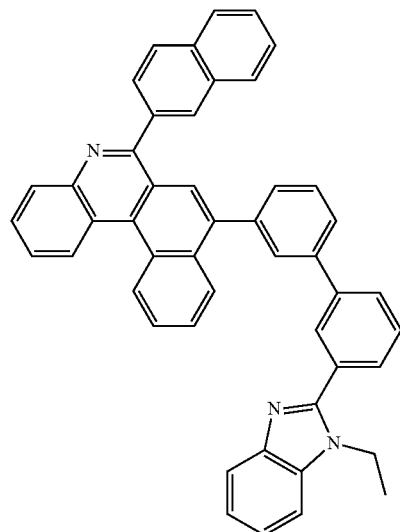
717
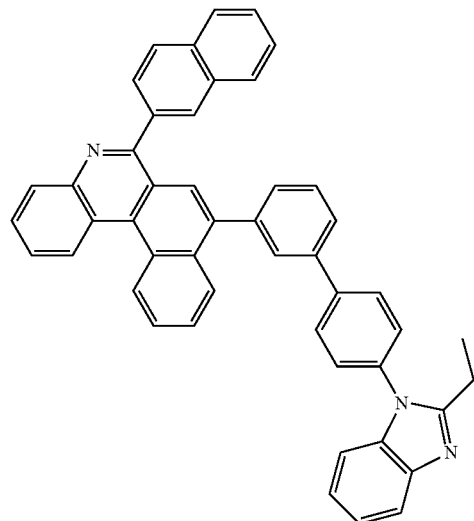
719
922
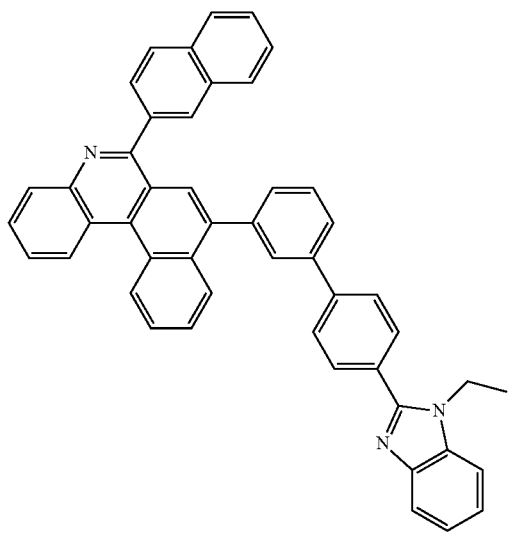
716
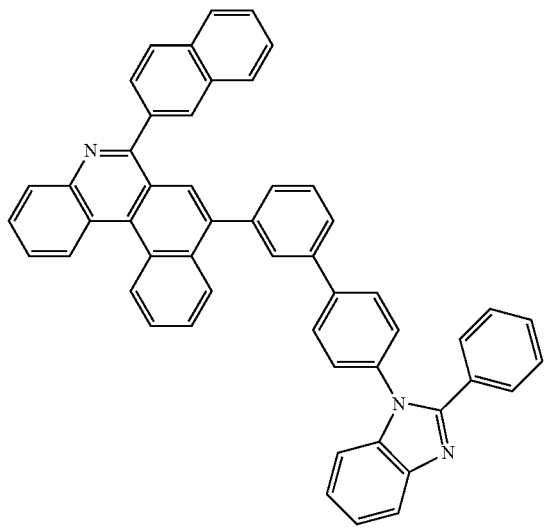
718
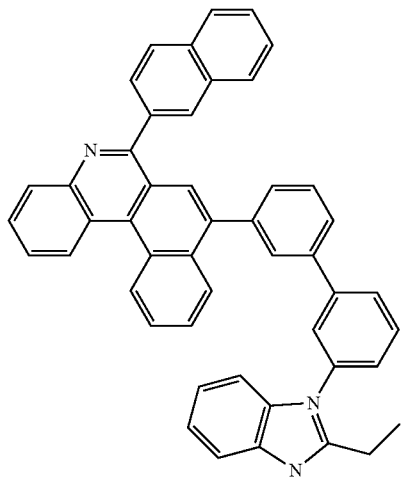
720

-continued
721
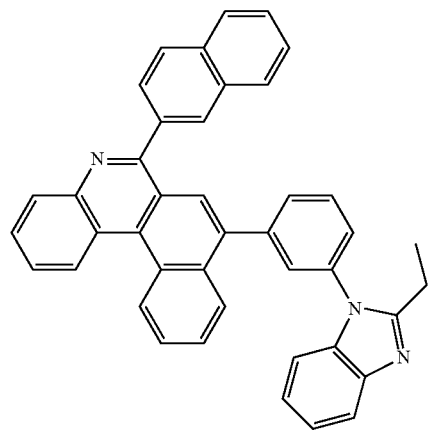
722
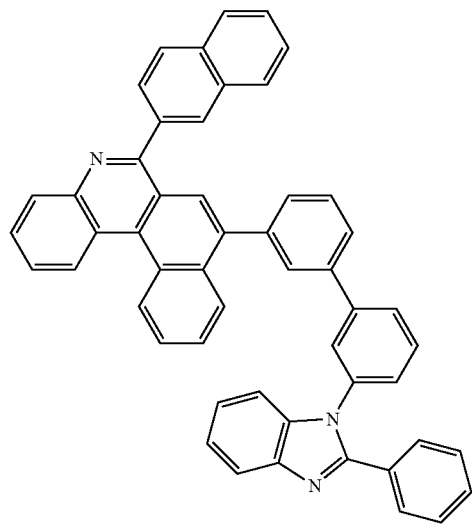
723
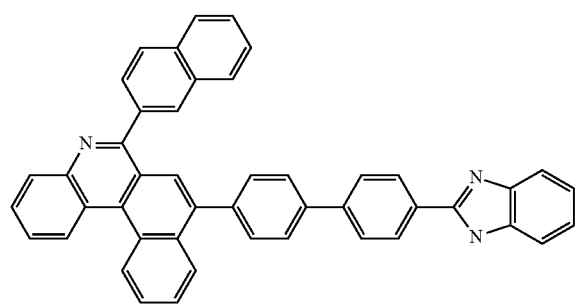
724
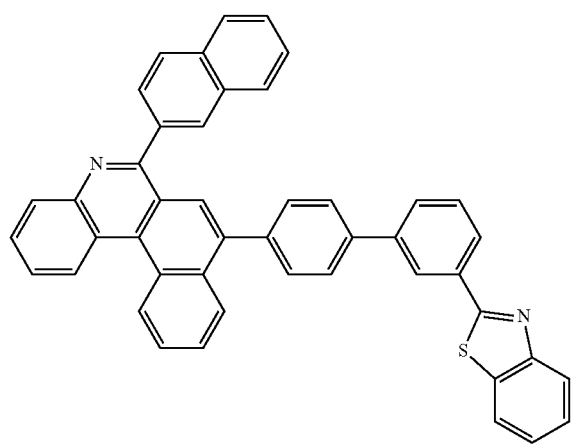
725
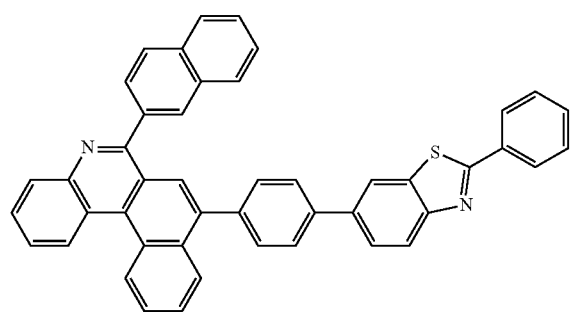
726
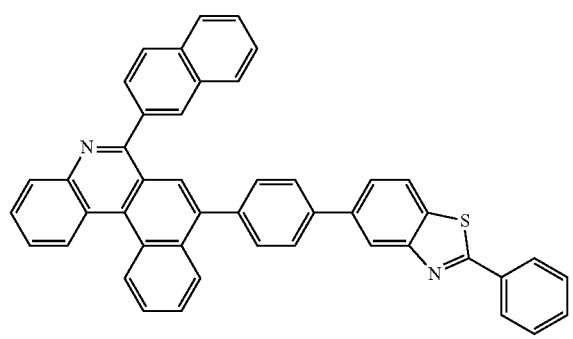

-continued
727
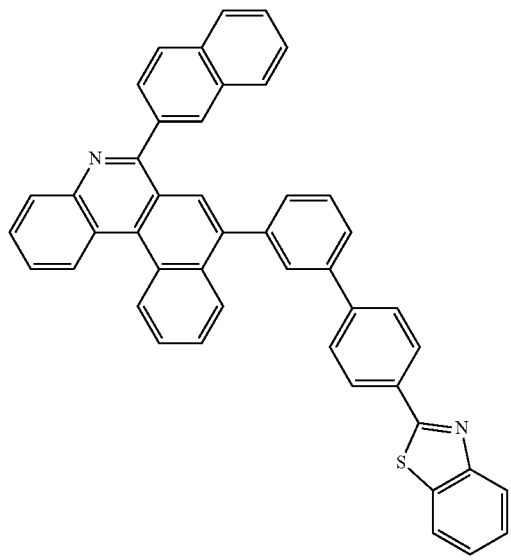
728
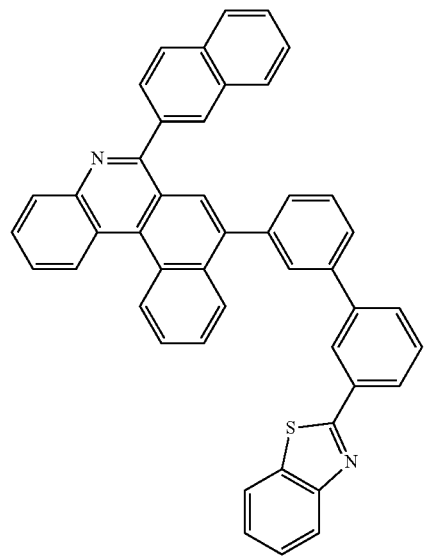
729
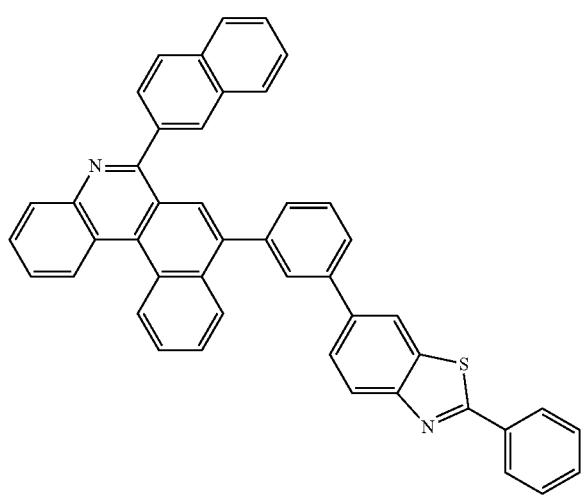
730
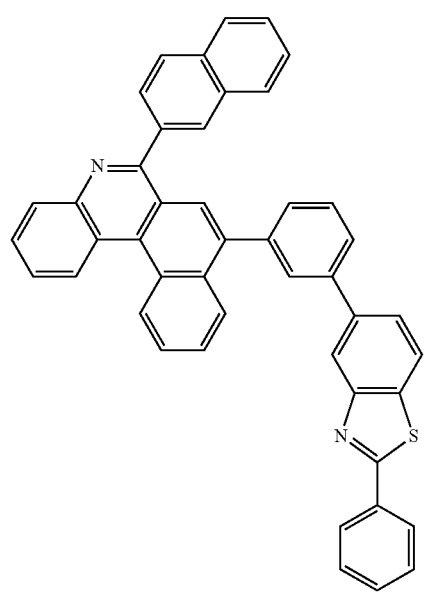
731
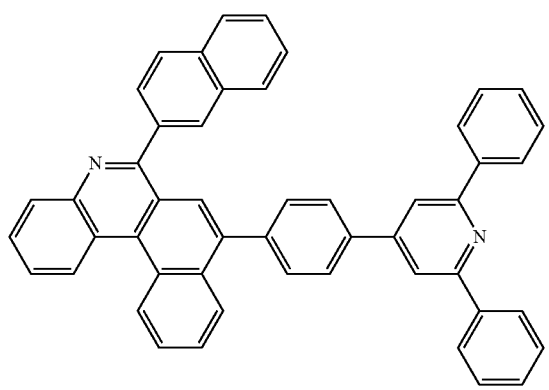
732
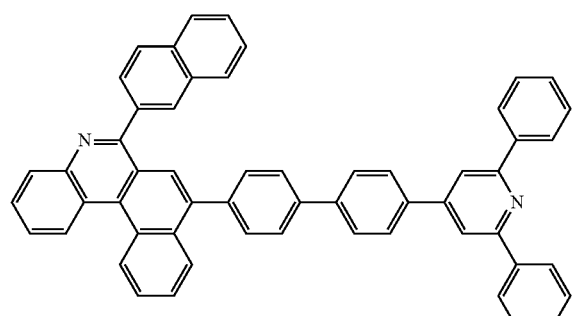

927 928
-continued
733
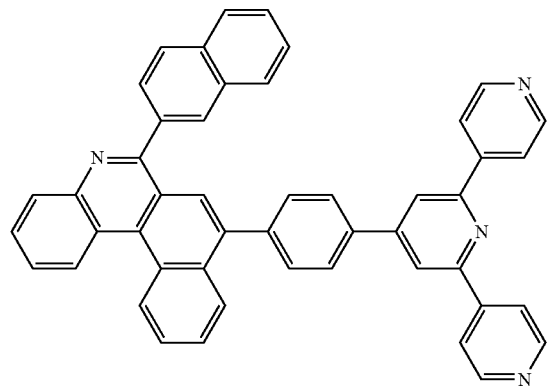
734
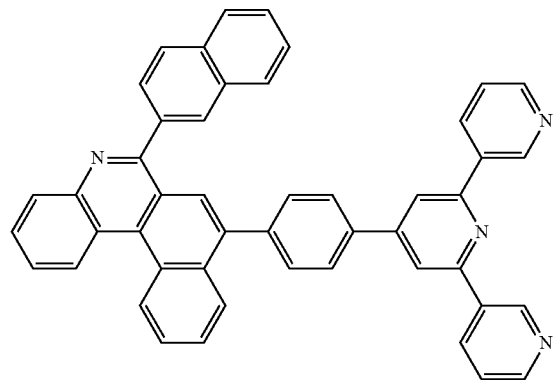
735
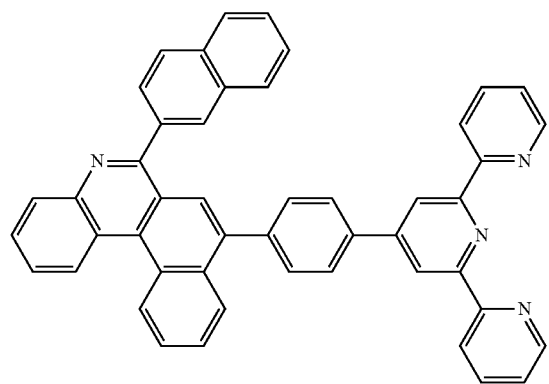
736
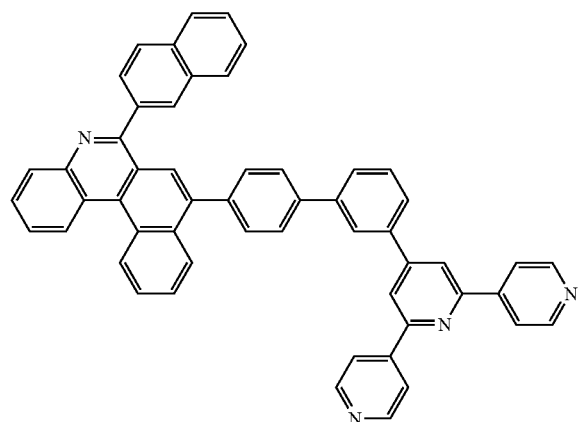
737
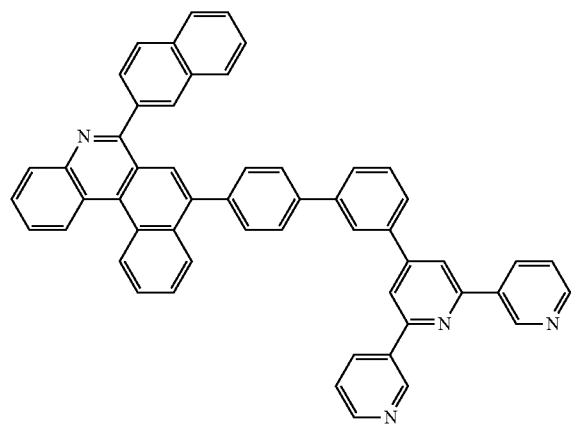
738
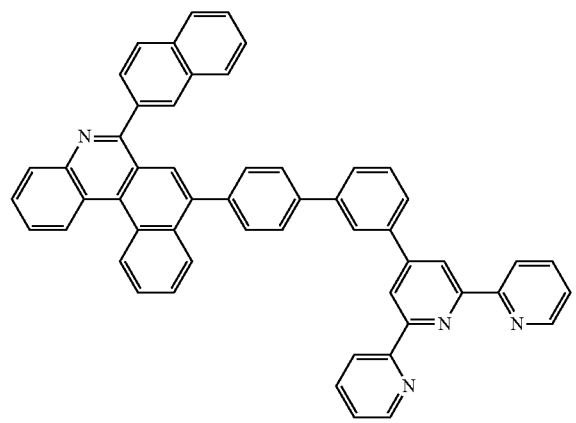

929 930
-continued
739
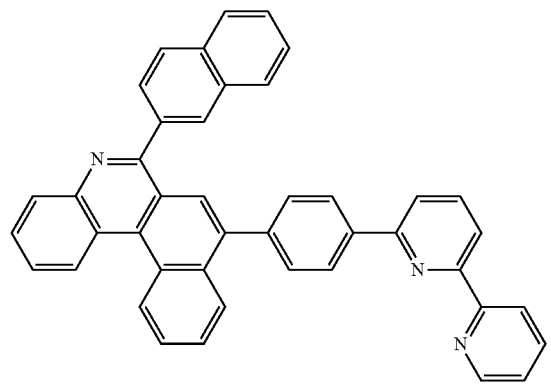
740
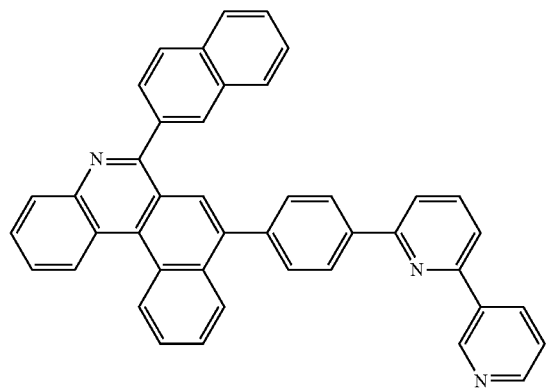
741
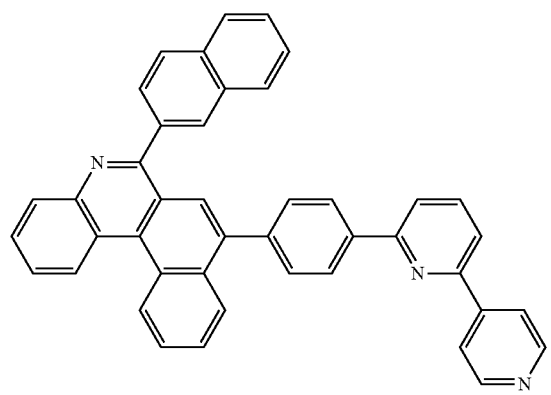
742
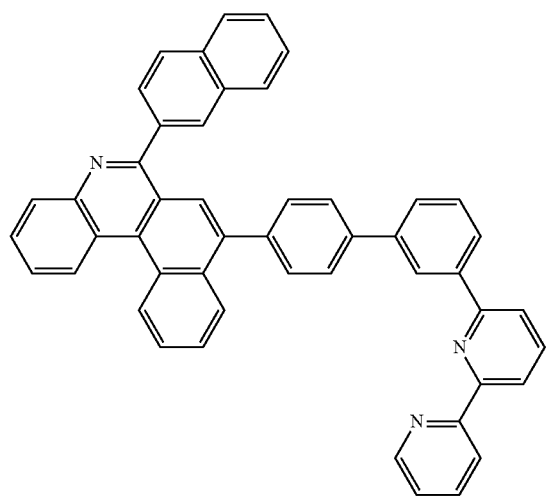
743
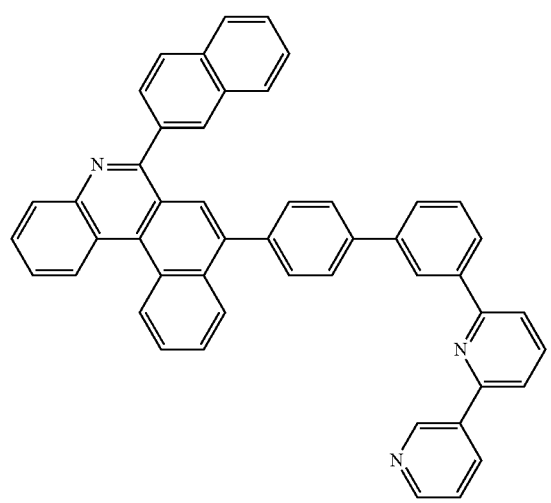
744
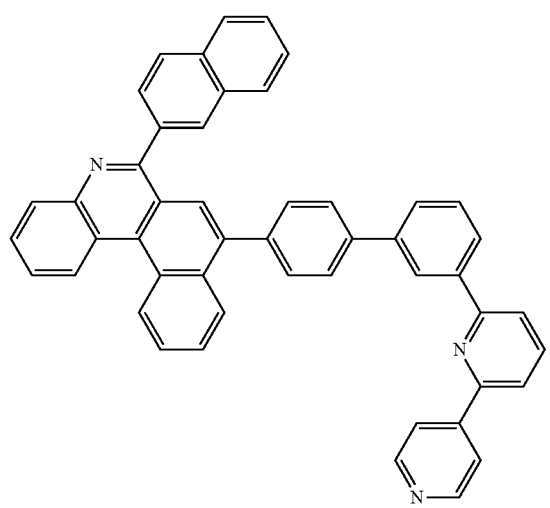

-continued
931
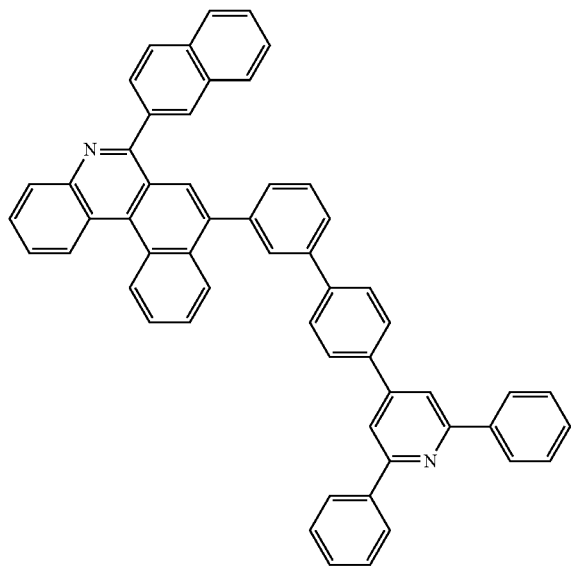
932
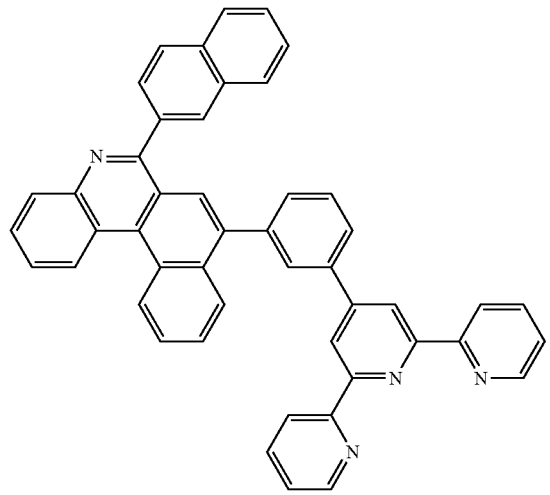
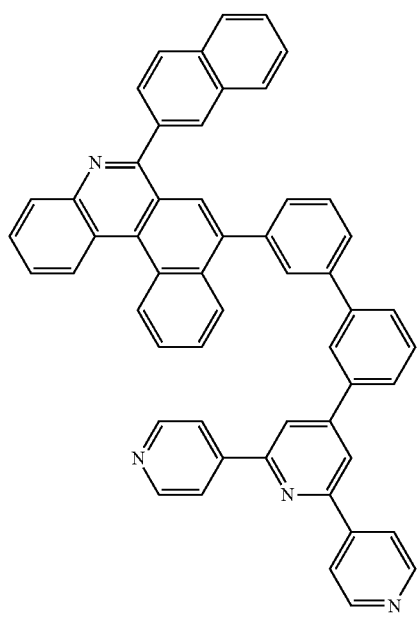
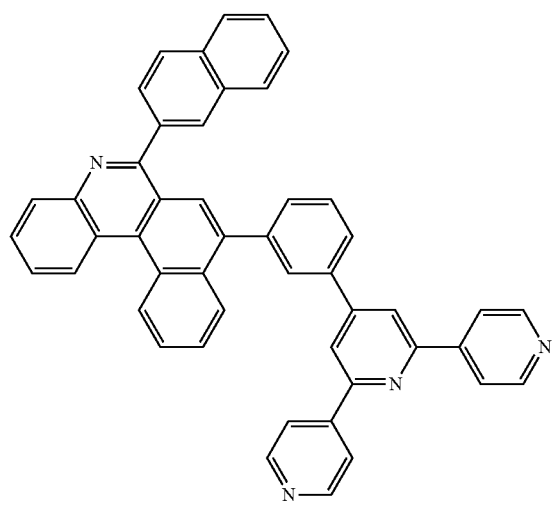

-continued
933
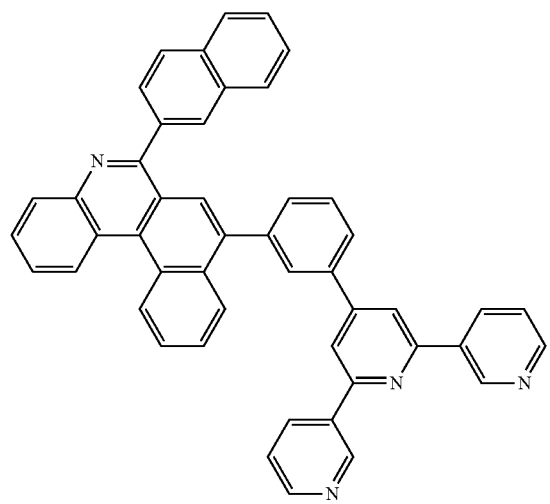
749
934
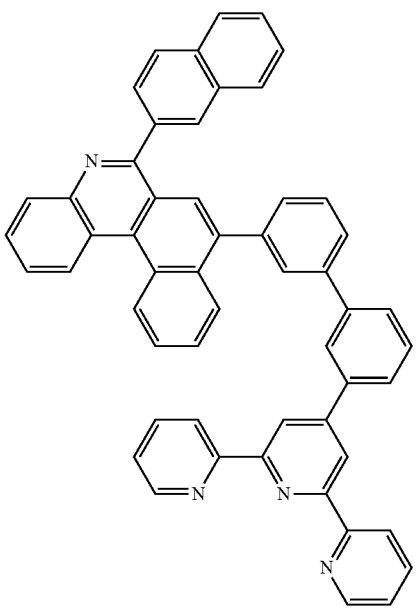
750
751
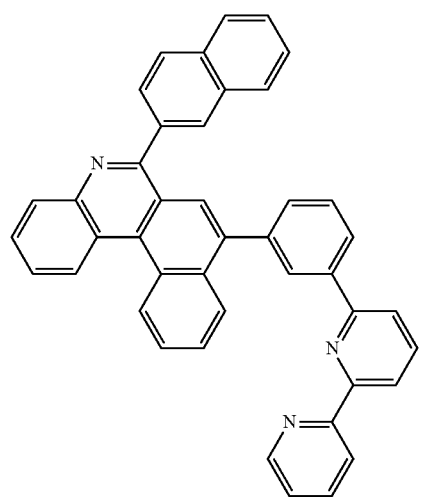
752
753
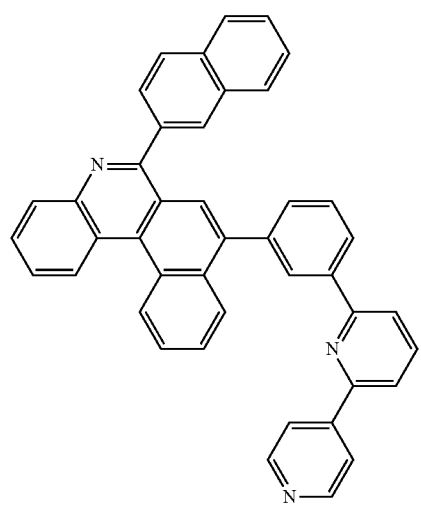
754
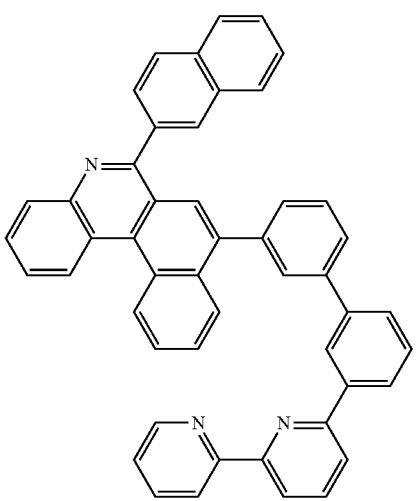

755
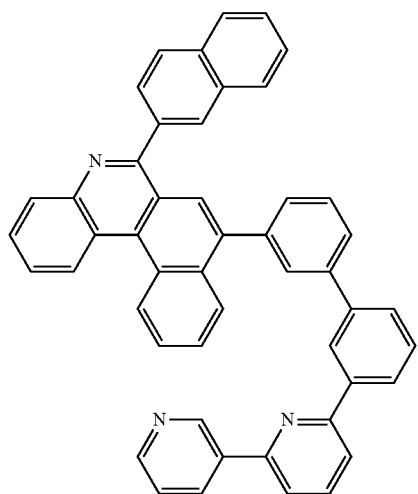
756
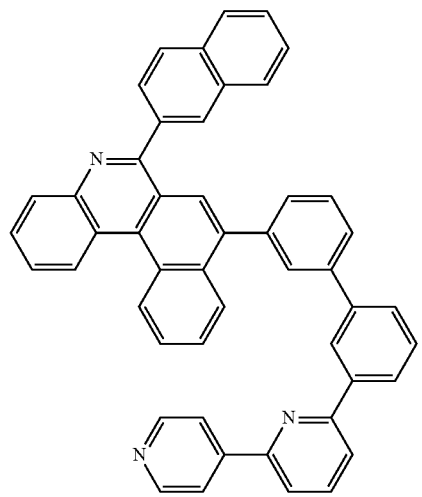
757
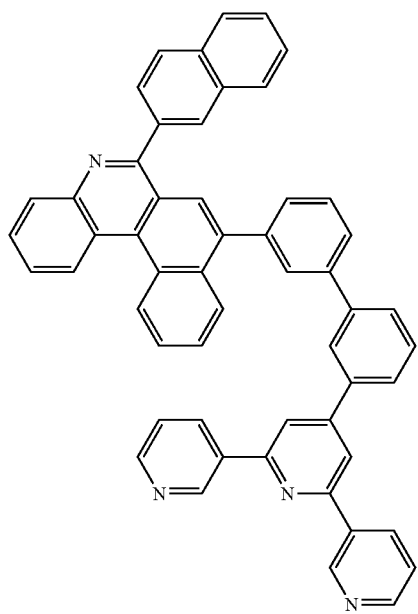
758
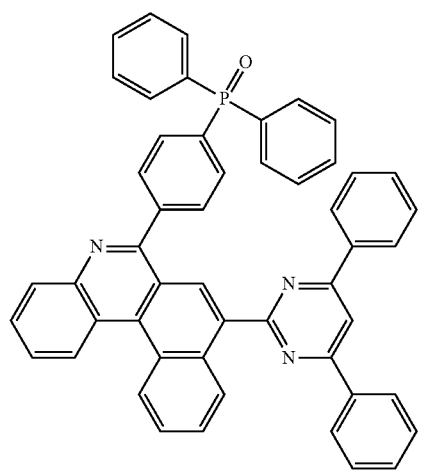
759
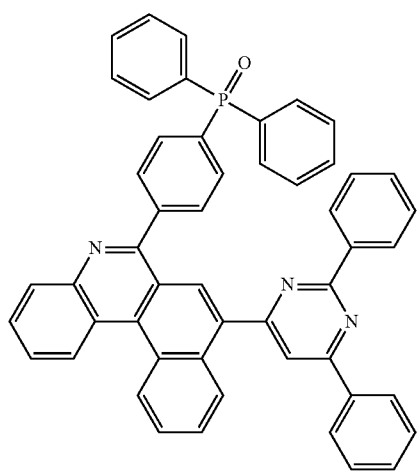
760
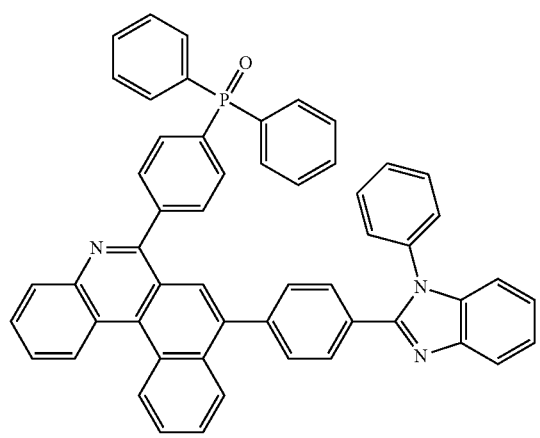

-continued
761
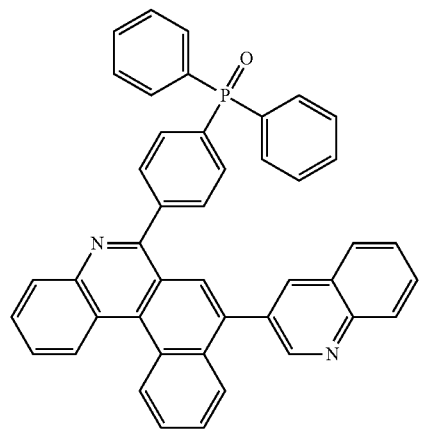
762
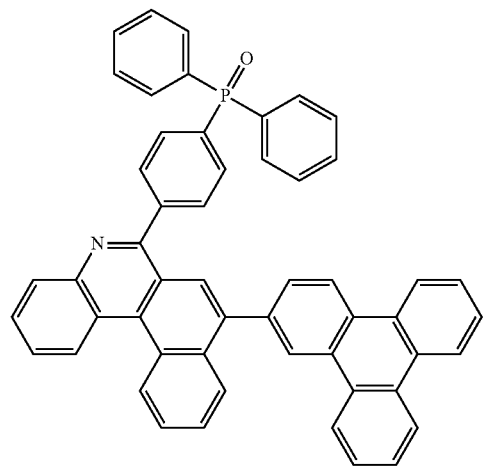
763
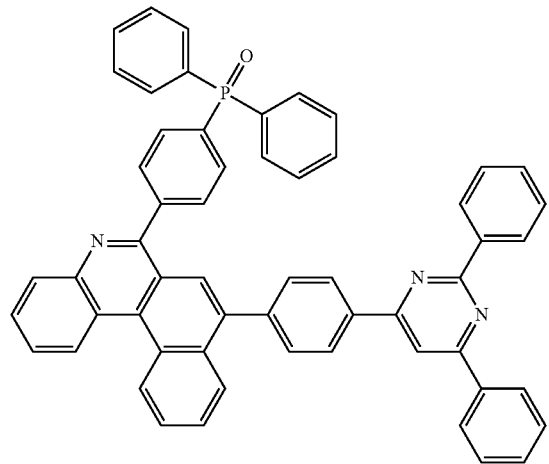
764
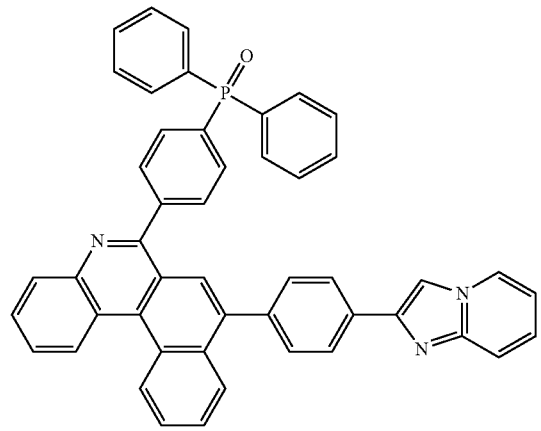
765
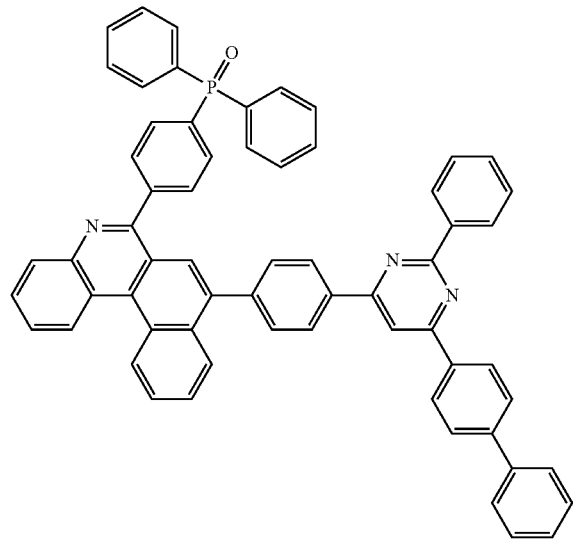
766
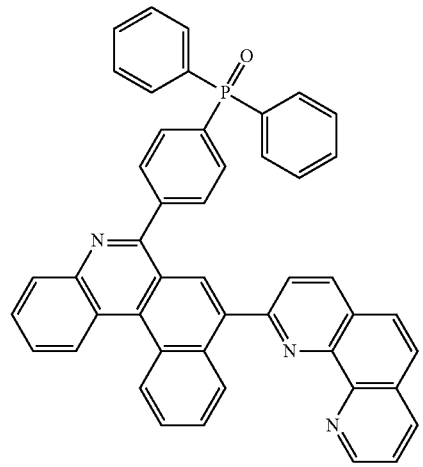

-continued
767
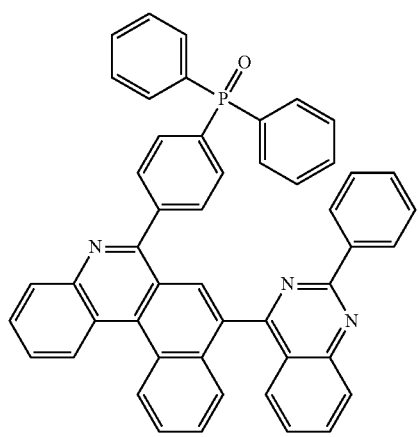
768
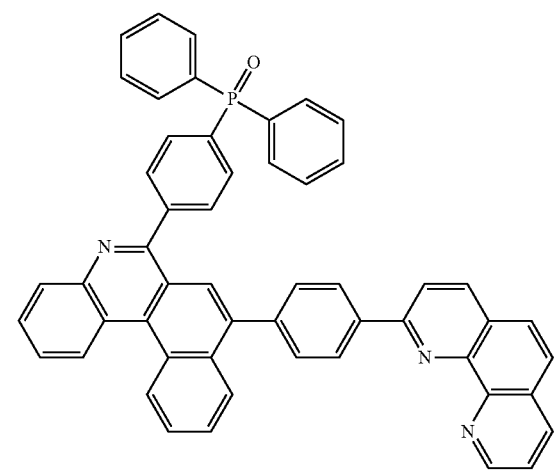
769
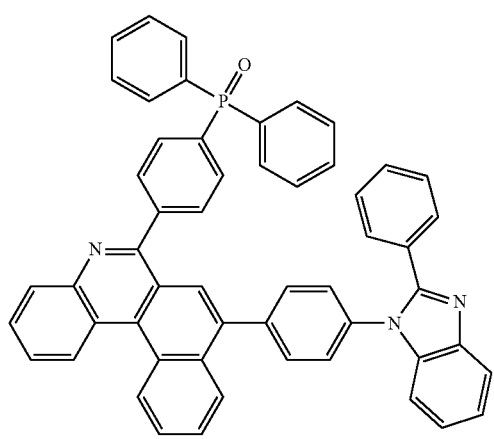
770
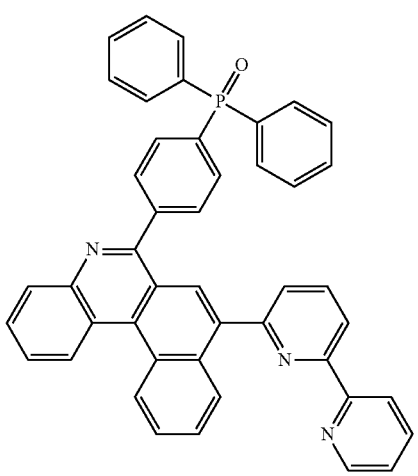
771
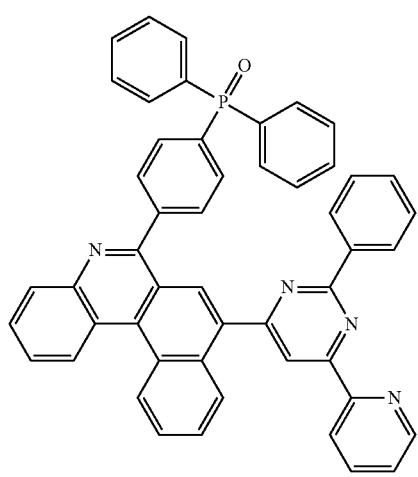
772
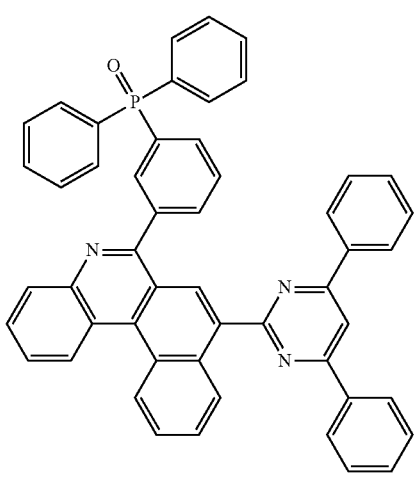

-continued
773
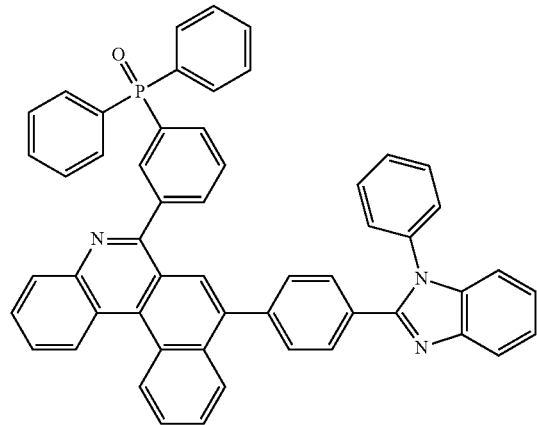
774
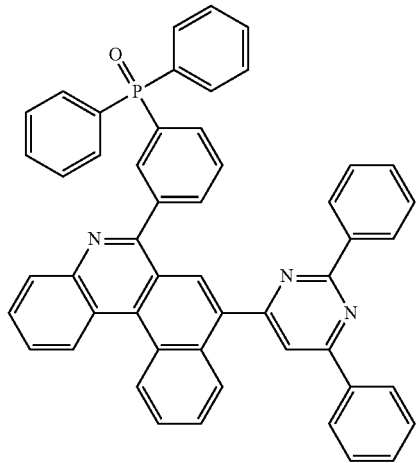
775
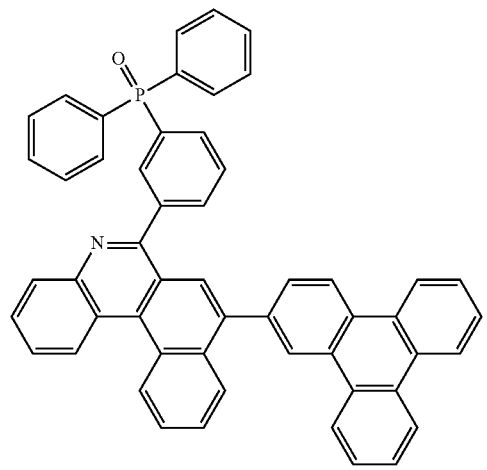
776
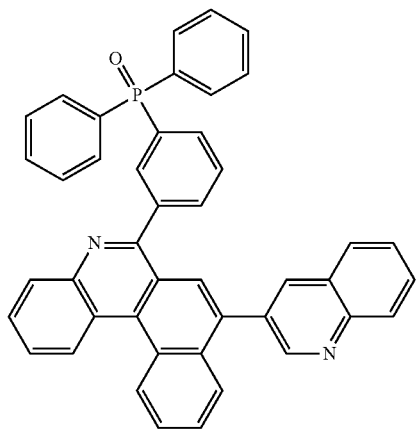
777
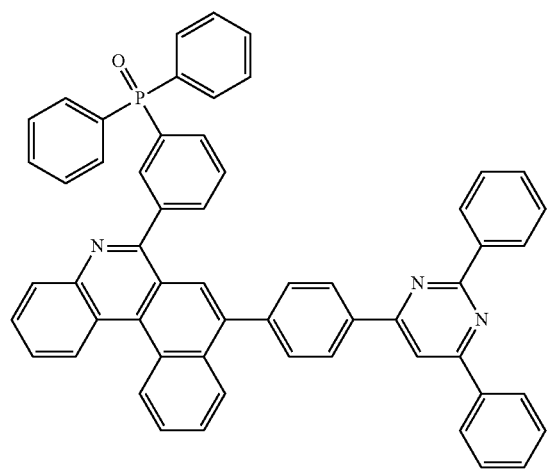
778
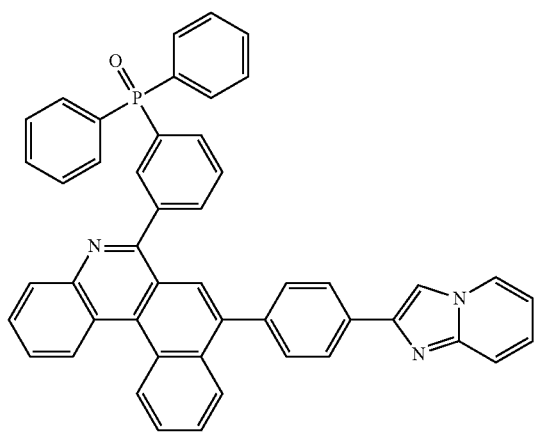

-continued
779
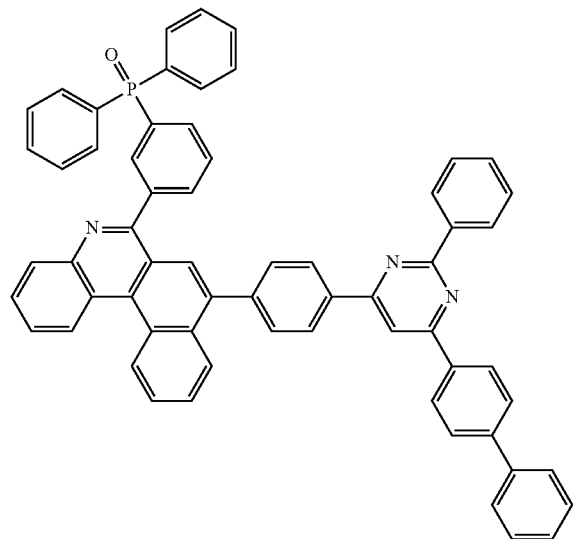
780
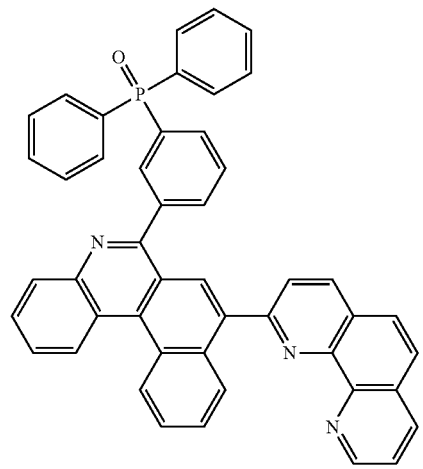
781
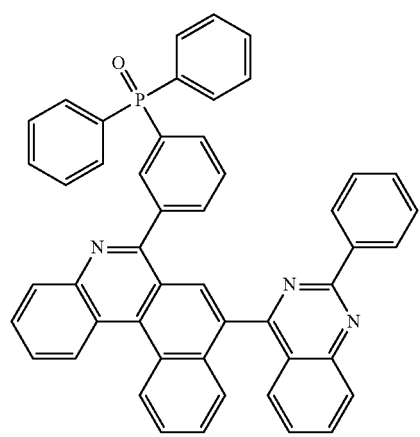
782
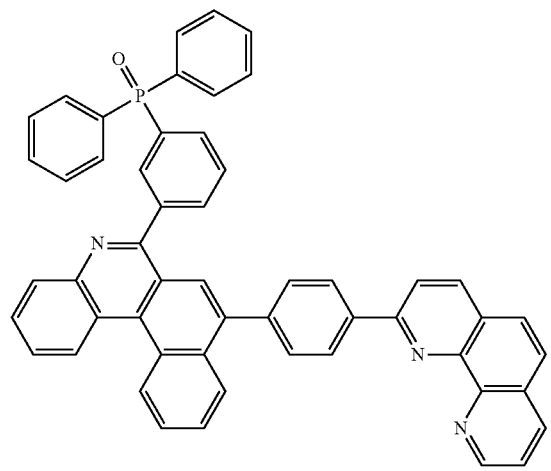
783
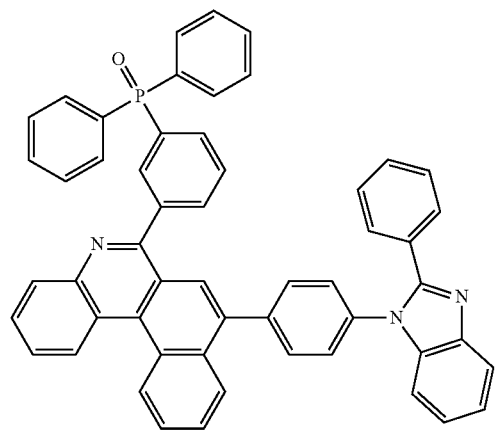
784
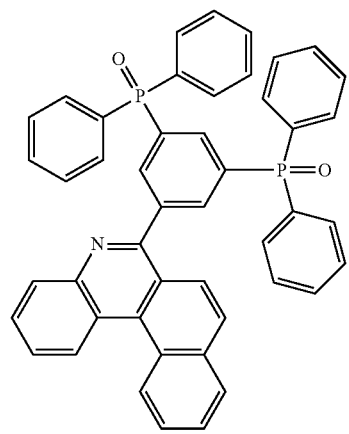

-continued
785
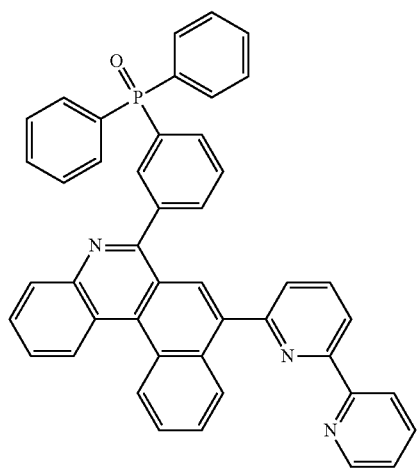
786
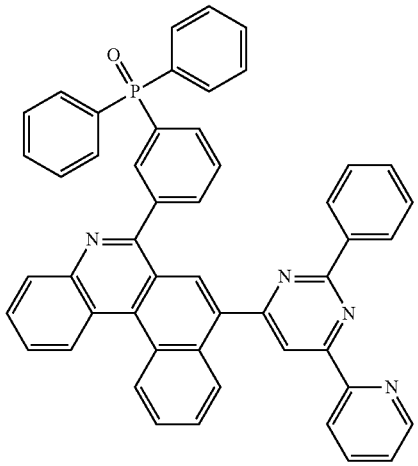
787
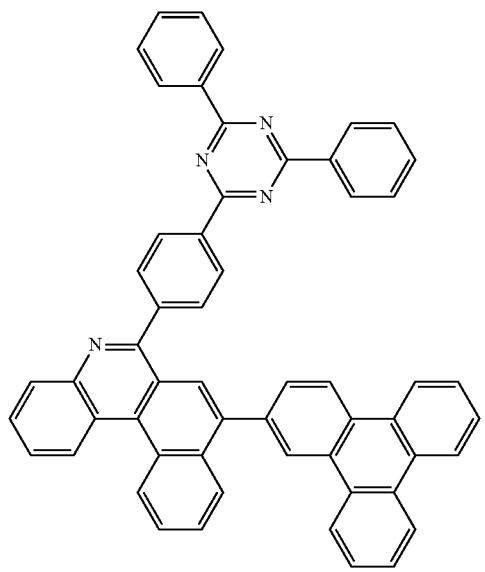
788
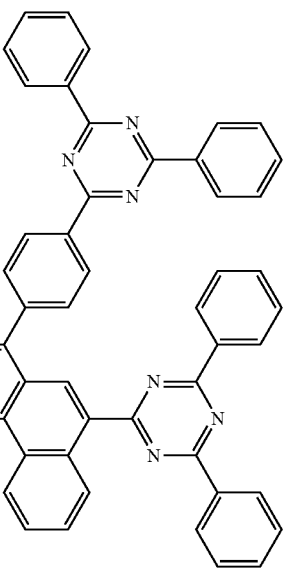
789
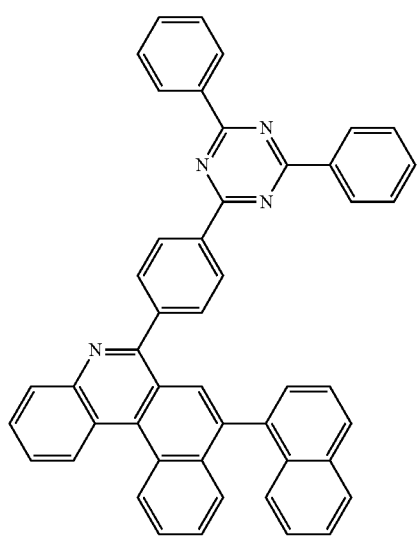
790
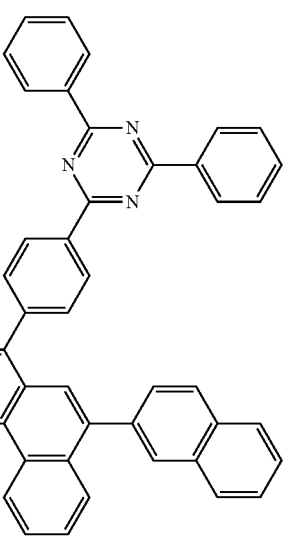

-continued
791
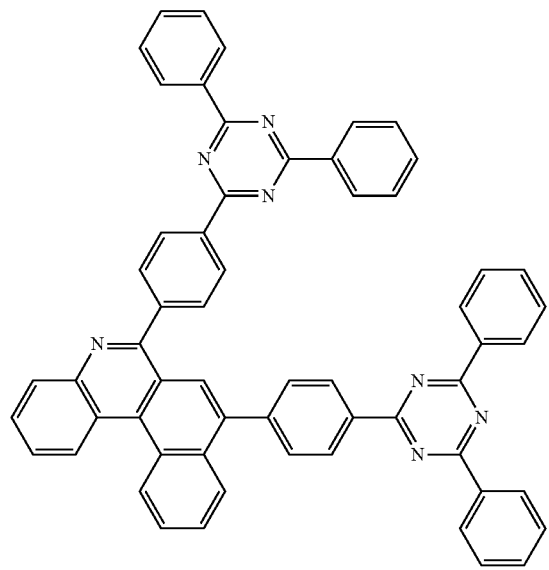
792
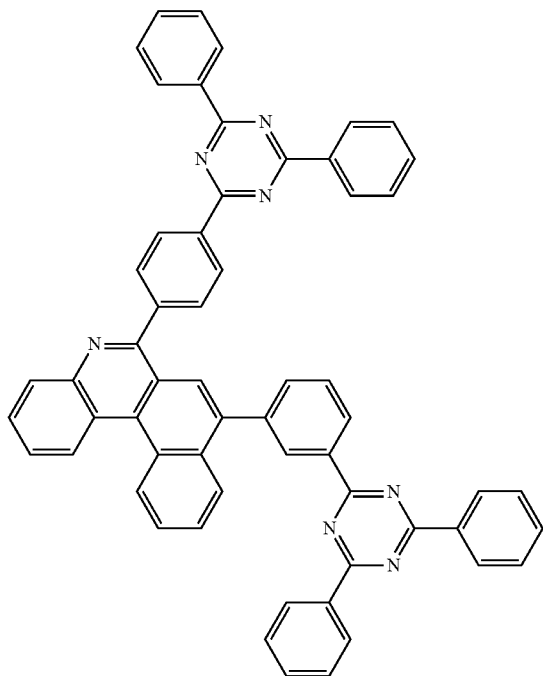
793
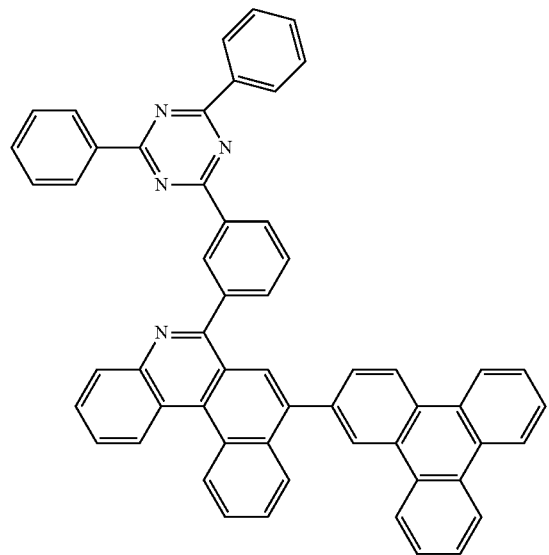
794
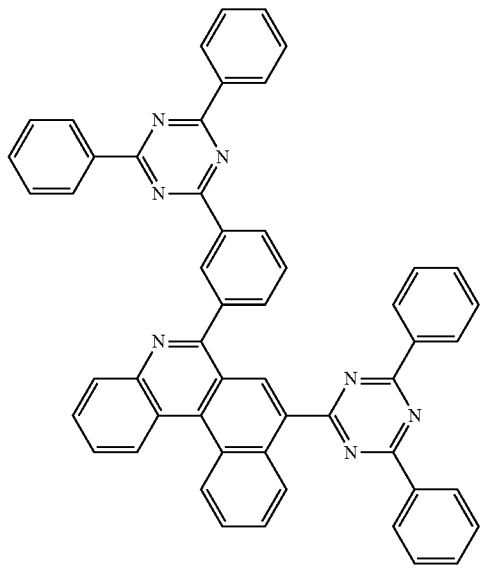

-continued
795
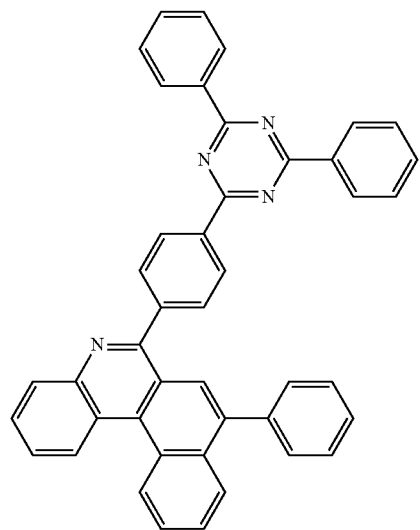
796
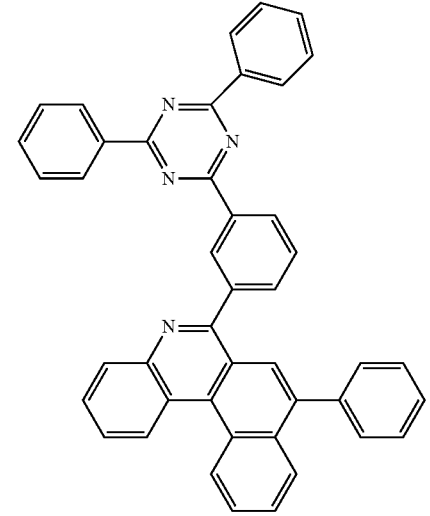
797
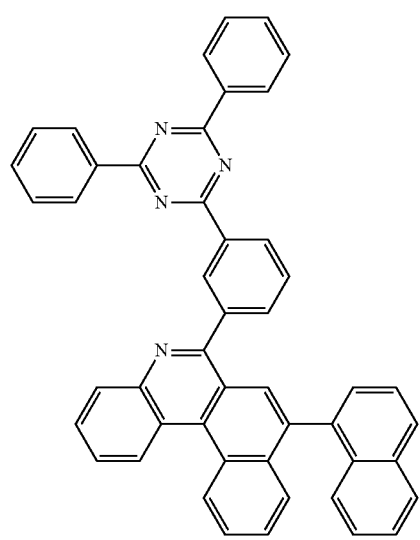
798
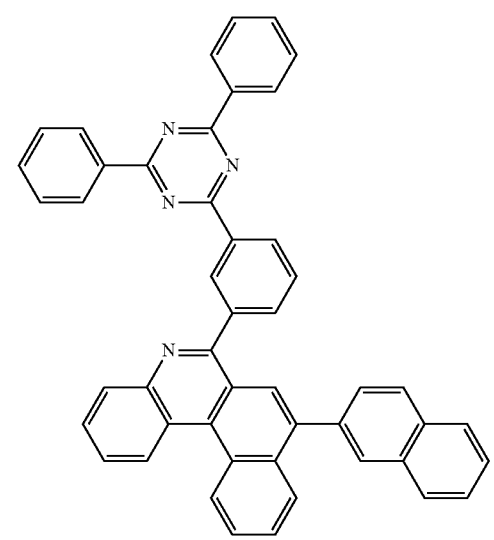
799
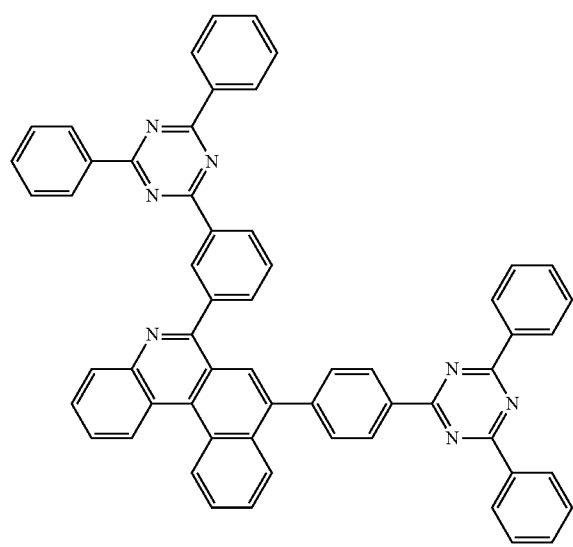
800
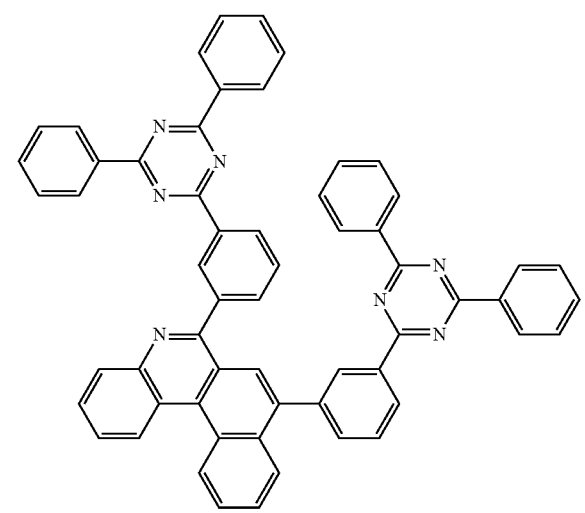

-continued
951 952
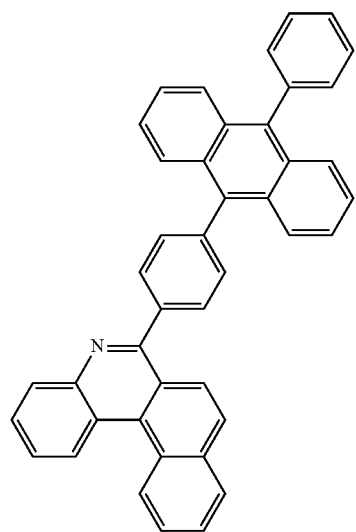
801
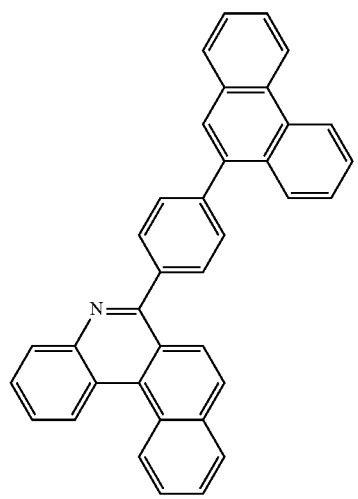
802
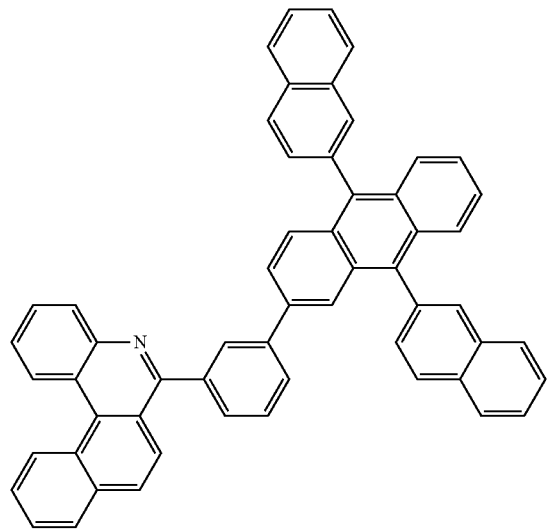
803
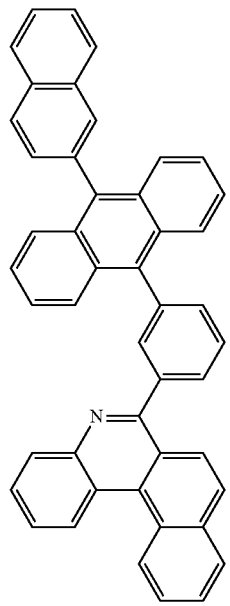
804

-continued
805
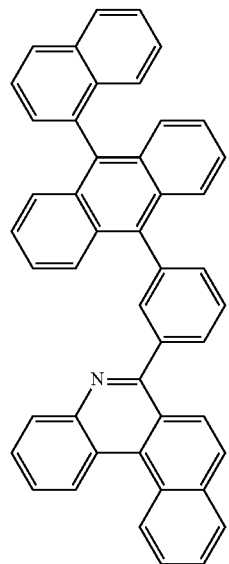
806
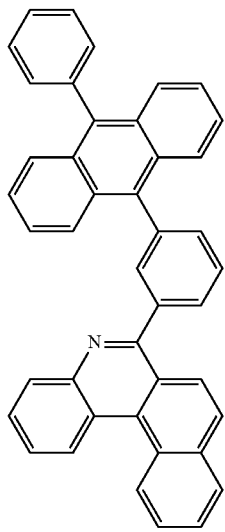
807
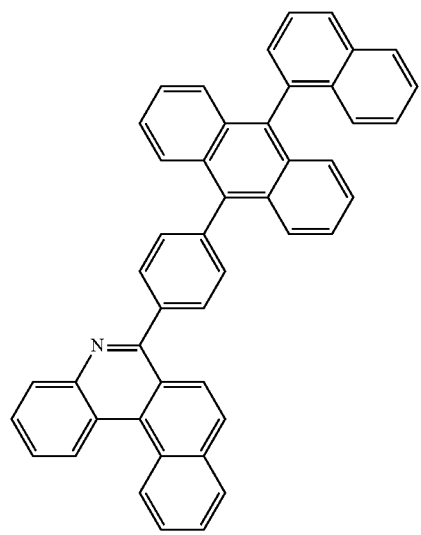
808
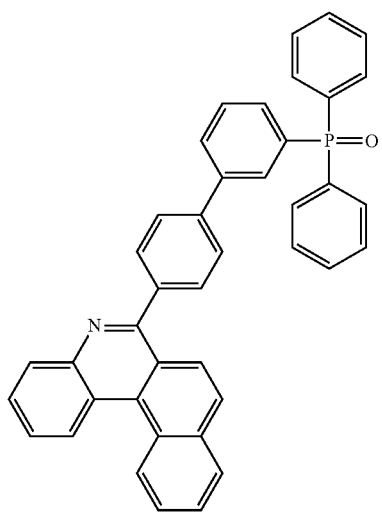
809
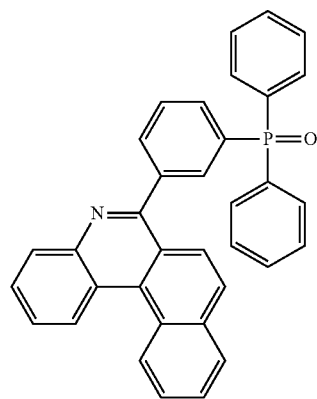
810
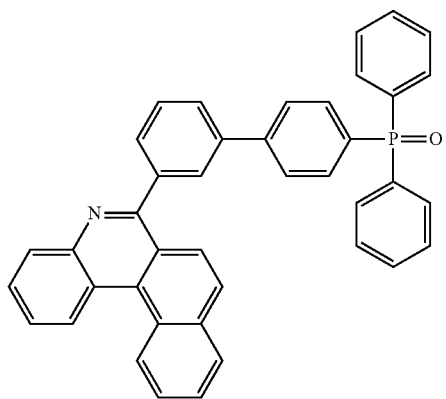

-continued
811
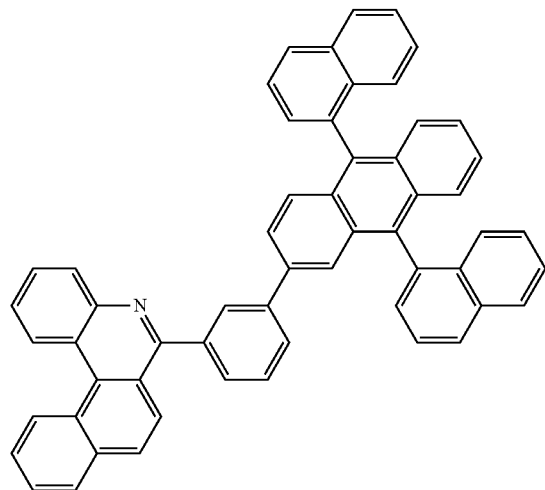
812
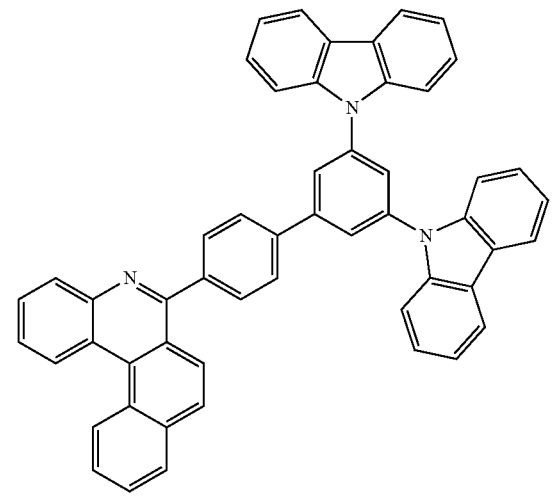
813
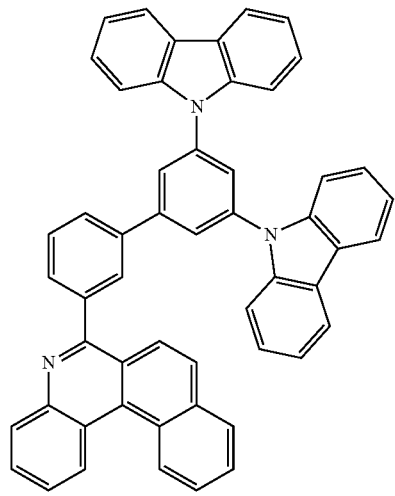
814
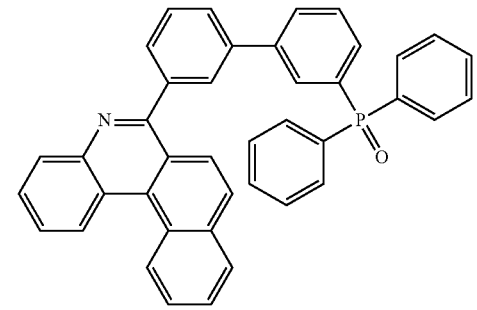
815
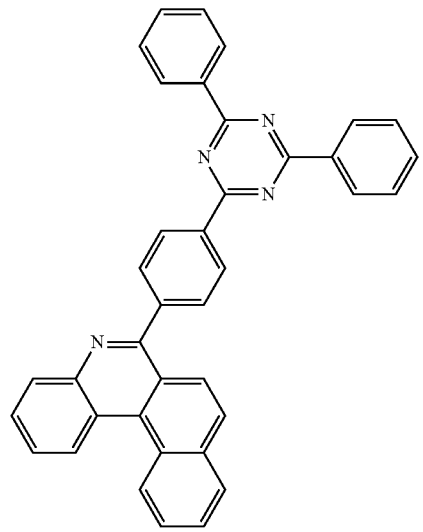
816
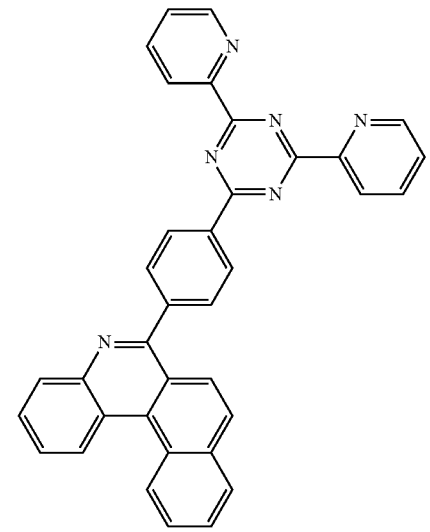

-continued
817
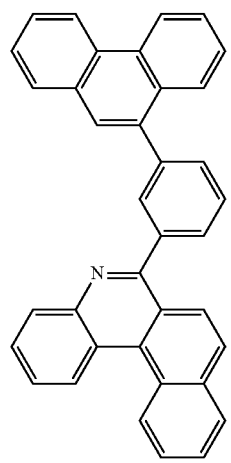
818
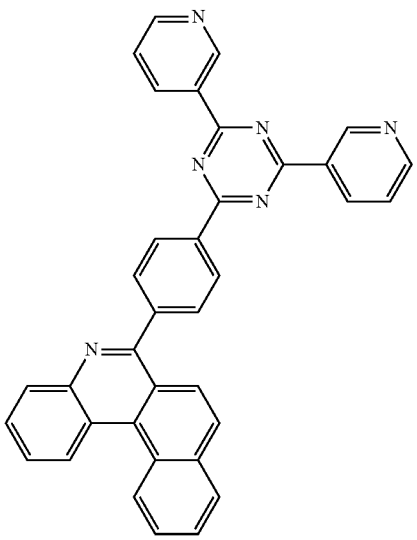
819
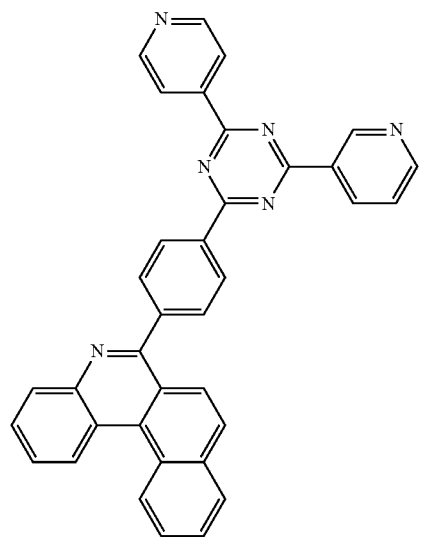
820
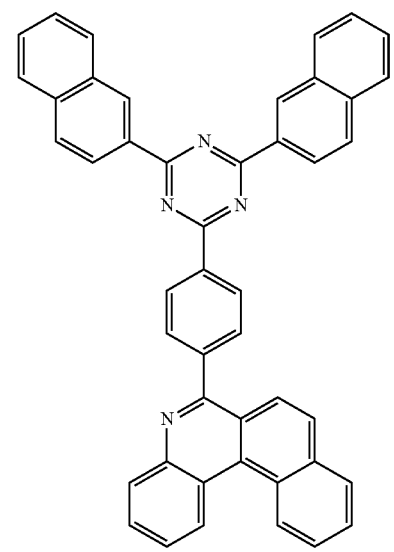
821
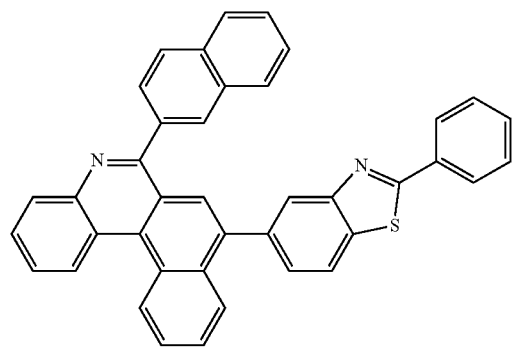
822
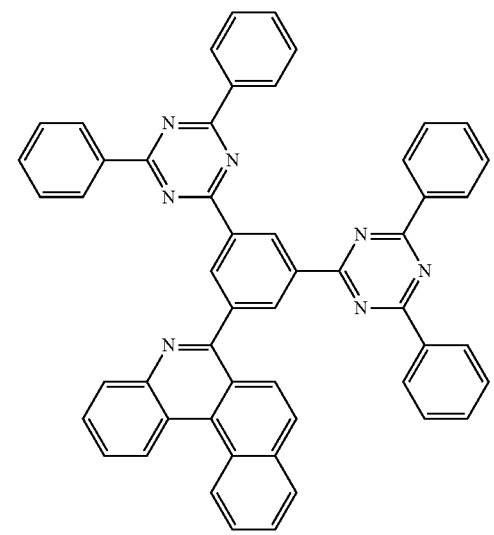

-continued
959
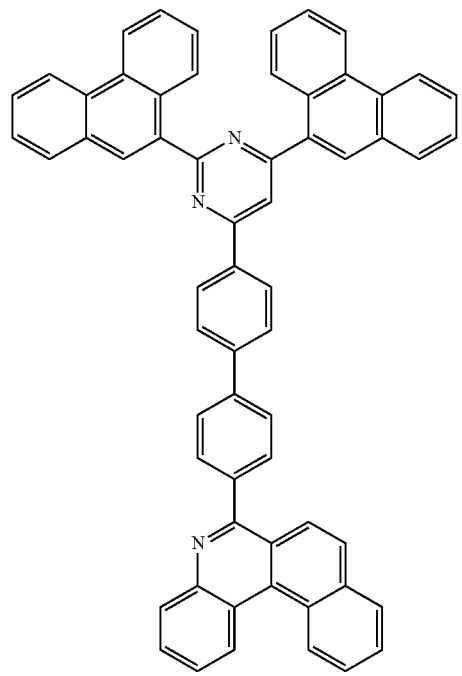
823
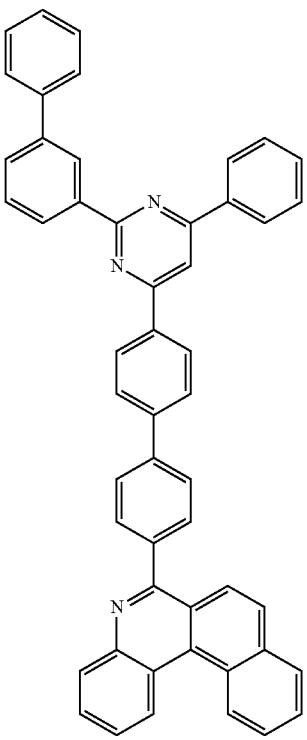
960
824
825
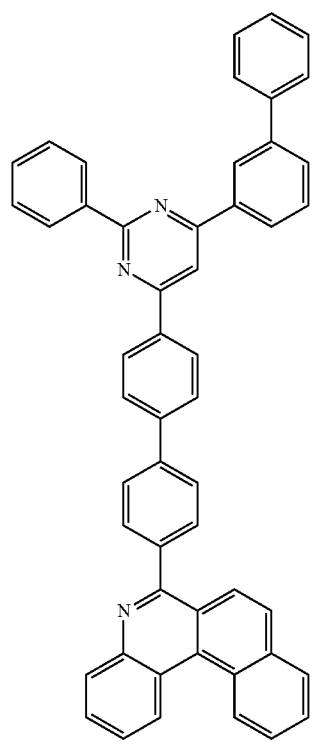
826
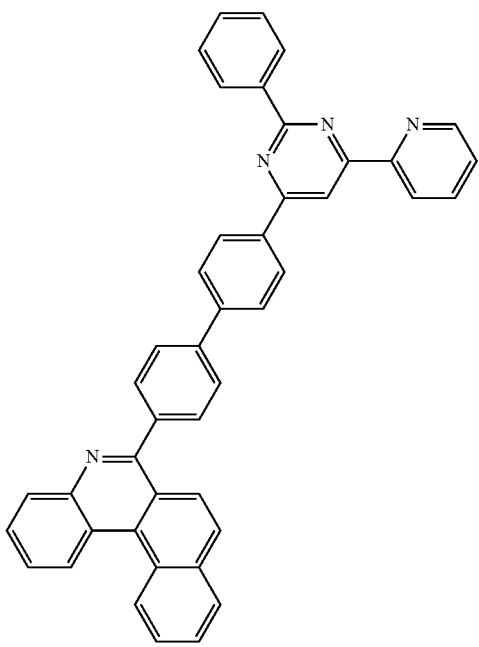

961 962
-continued
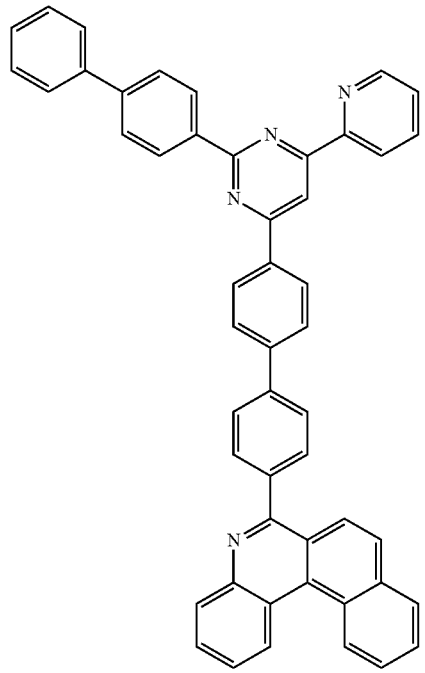
827
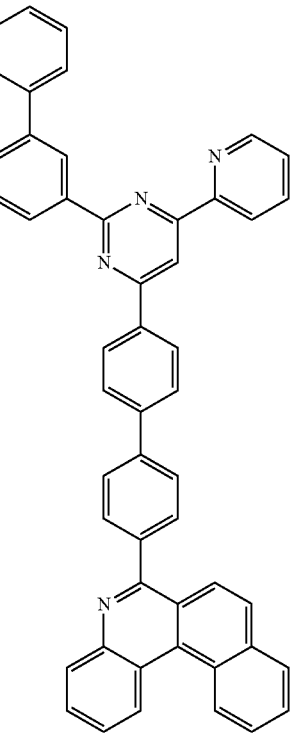
828
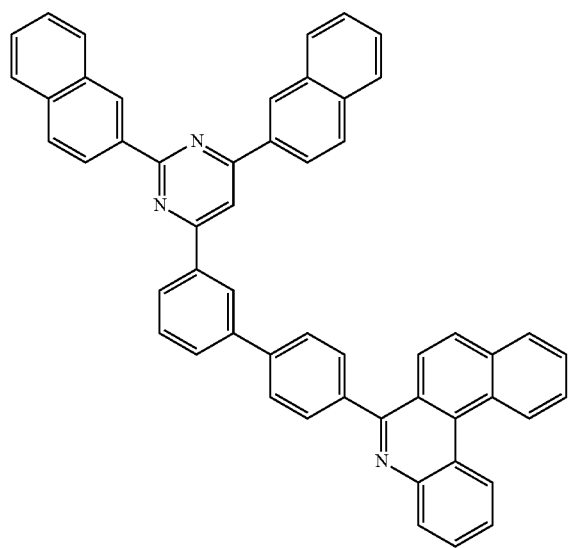
829
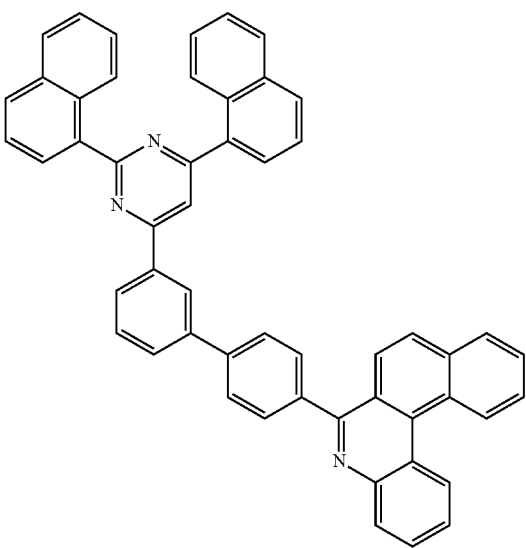
830

-continued
963
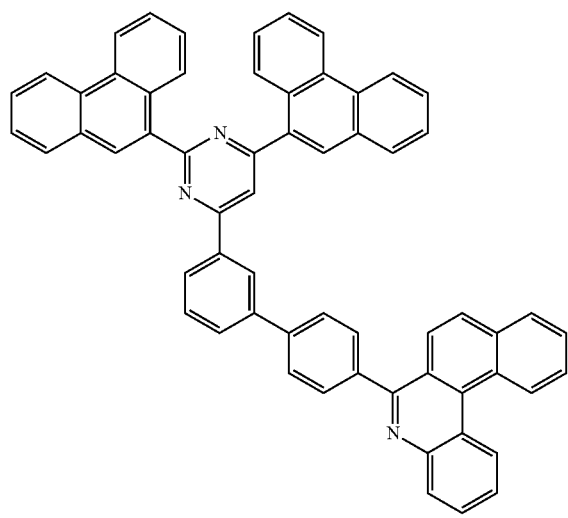
831
964
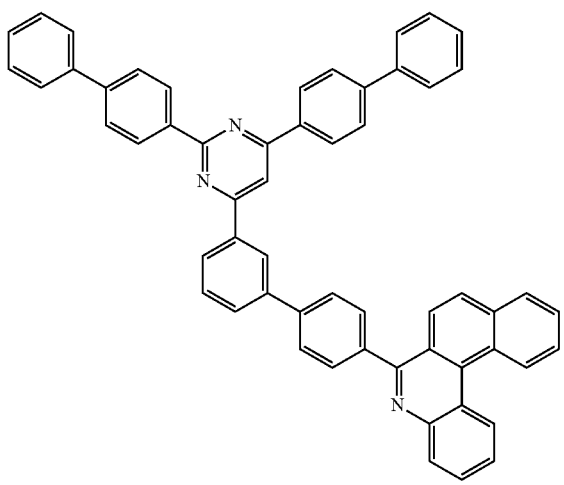
832
833
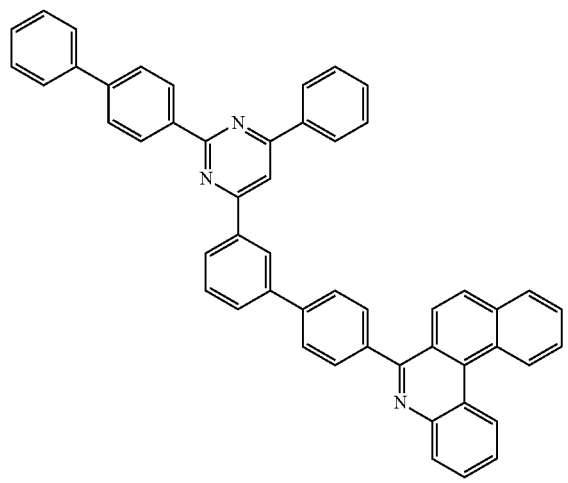
834
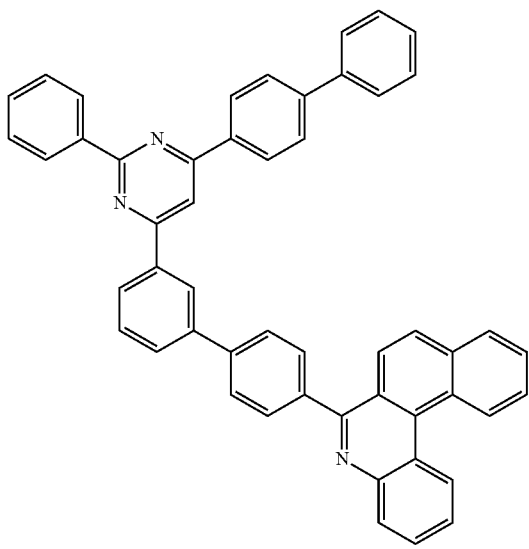

-continued
965
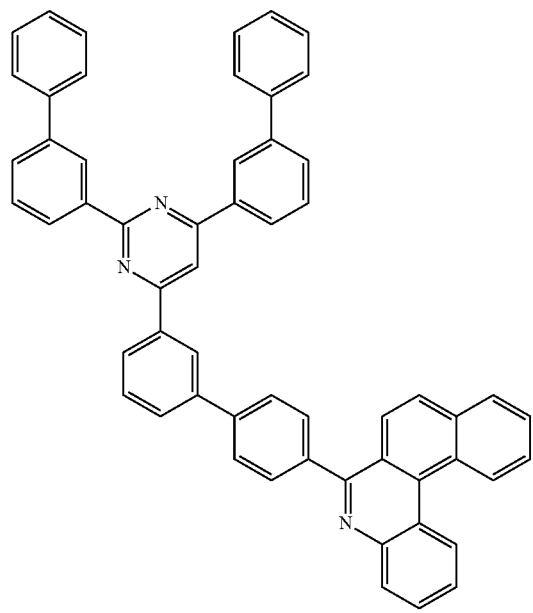
835
966
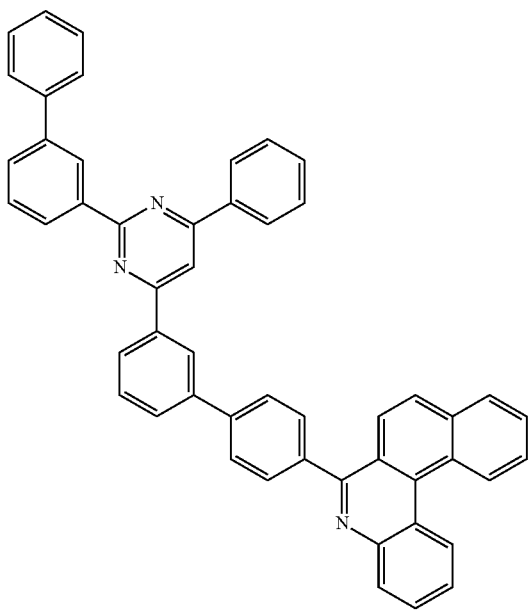
837
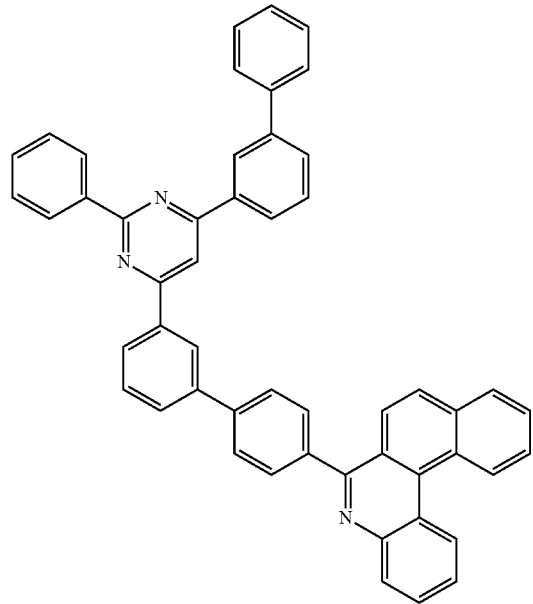
836
838
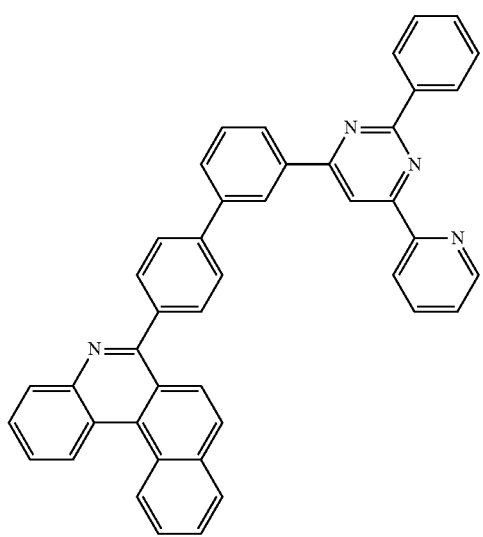

-continued
839
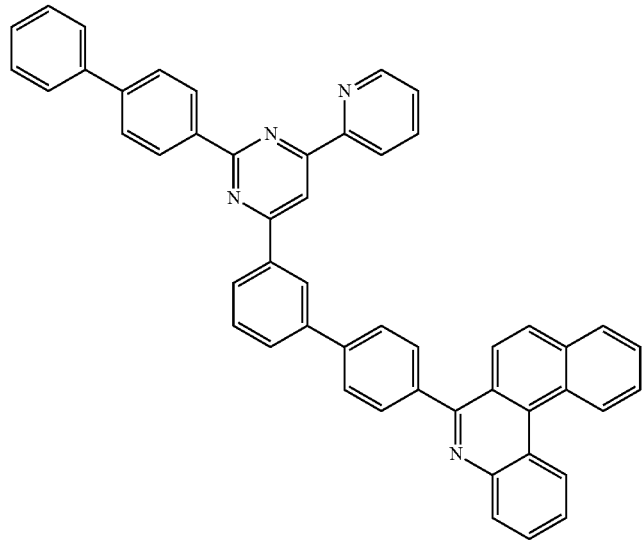
840
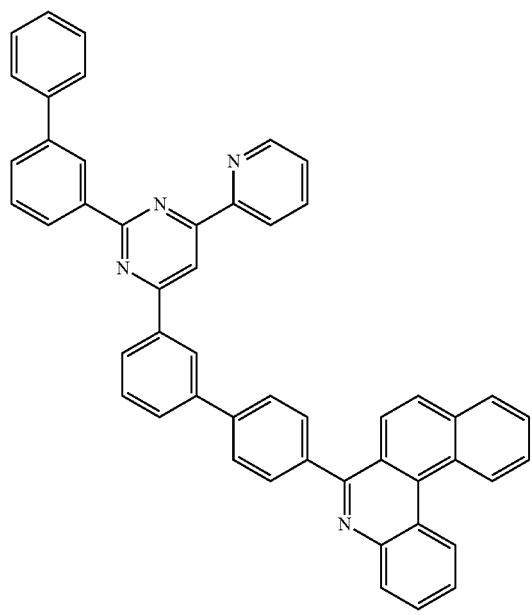
841
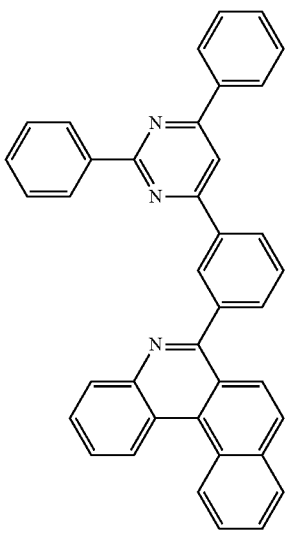

969
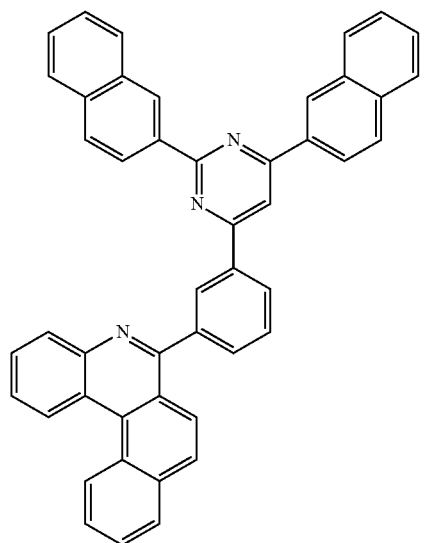
970
-continued
842
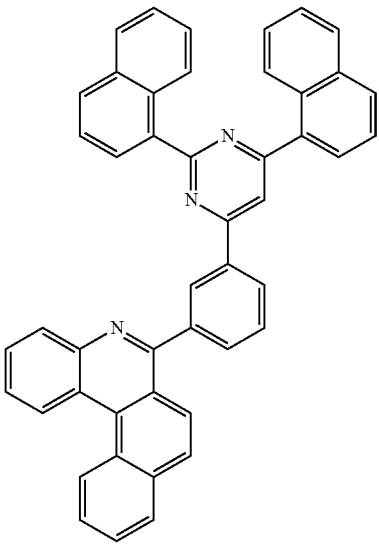
843
844
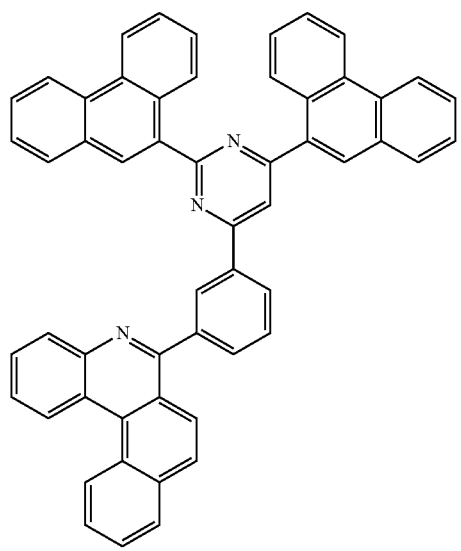
845
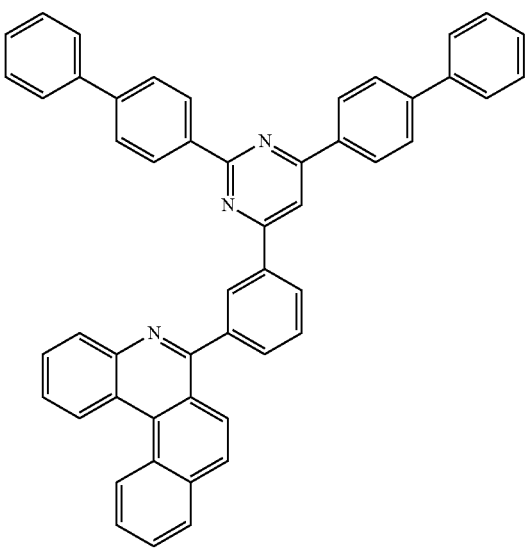

-continued
971
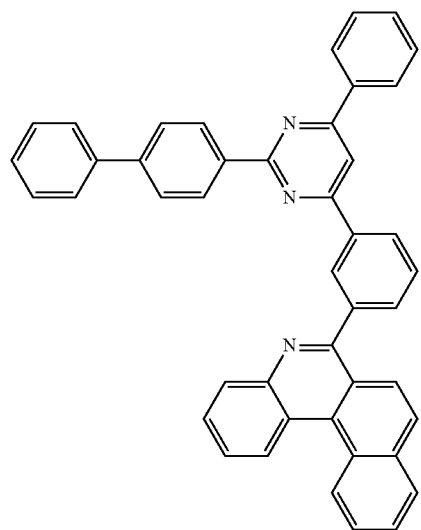
846
972
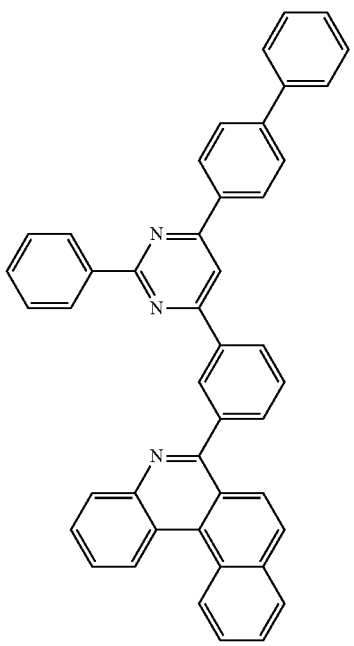
847
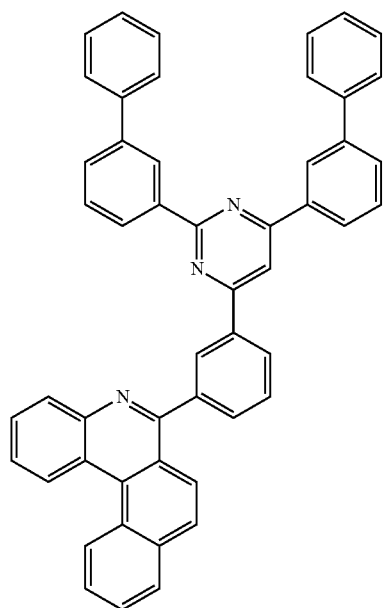
848
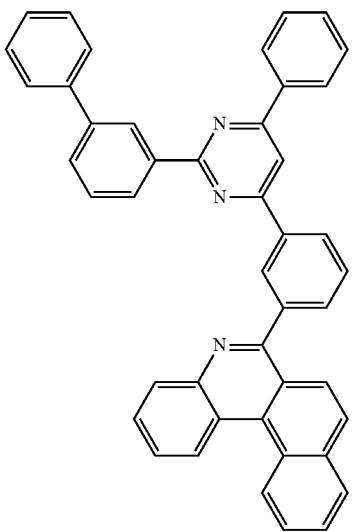
849

-continued
973 850 974
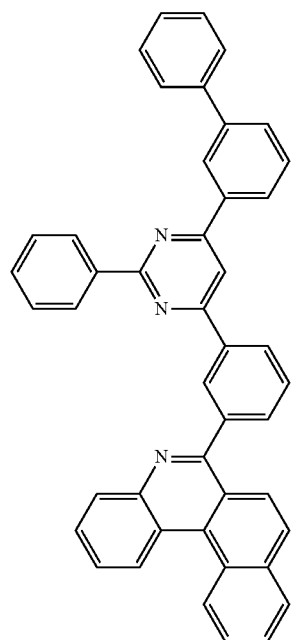 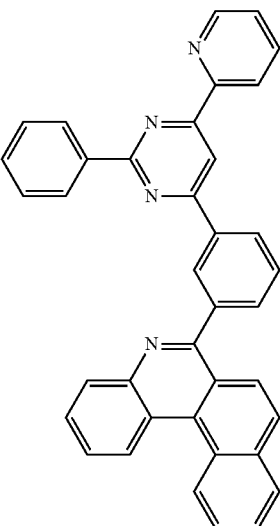
852
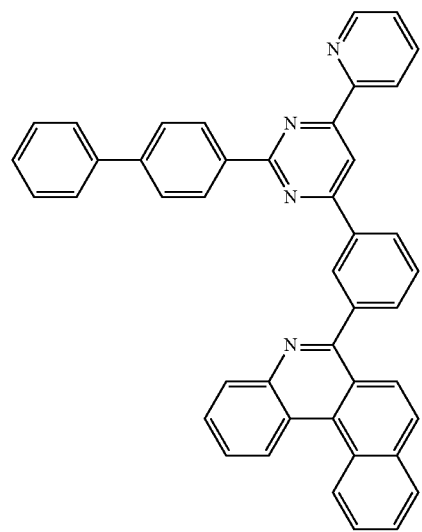

975
853
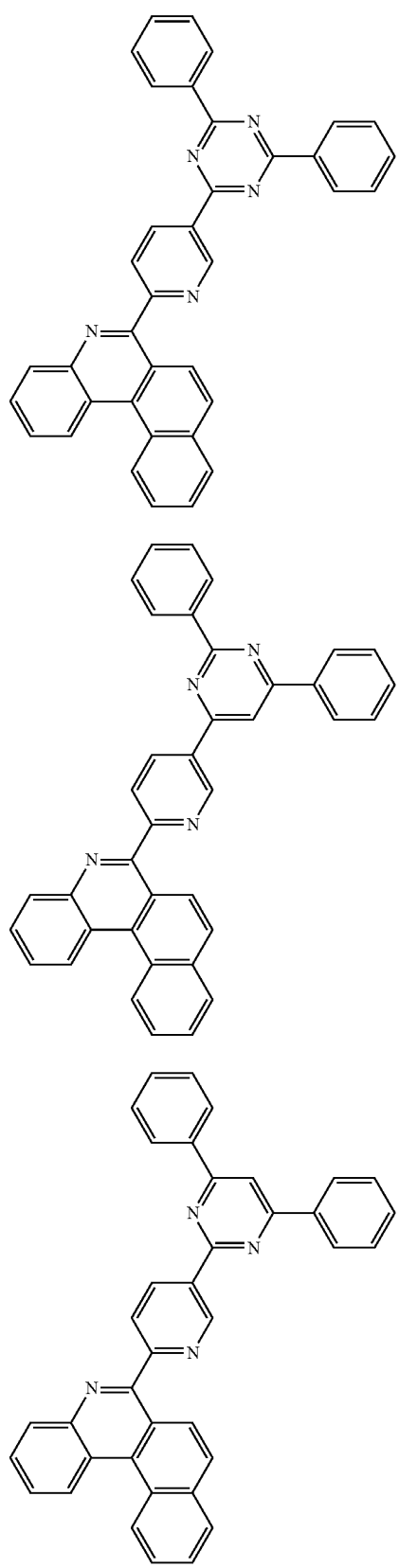
854
855
-continued
856
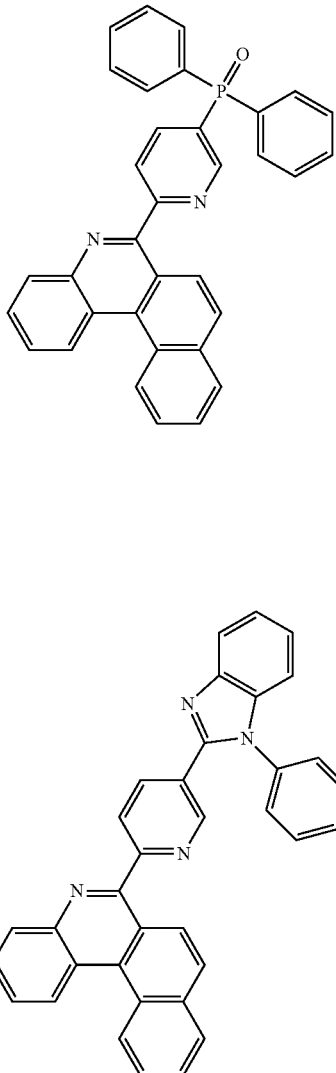
857
858
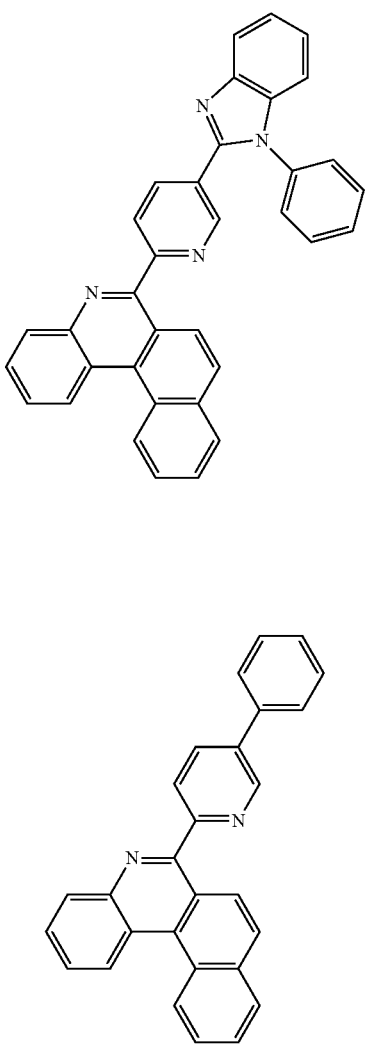

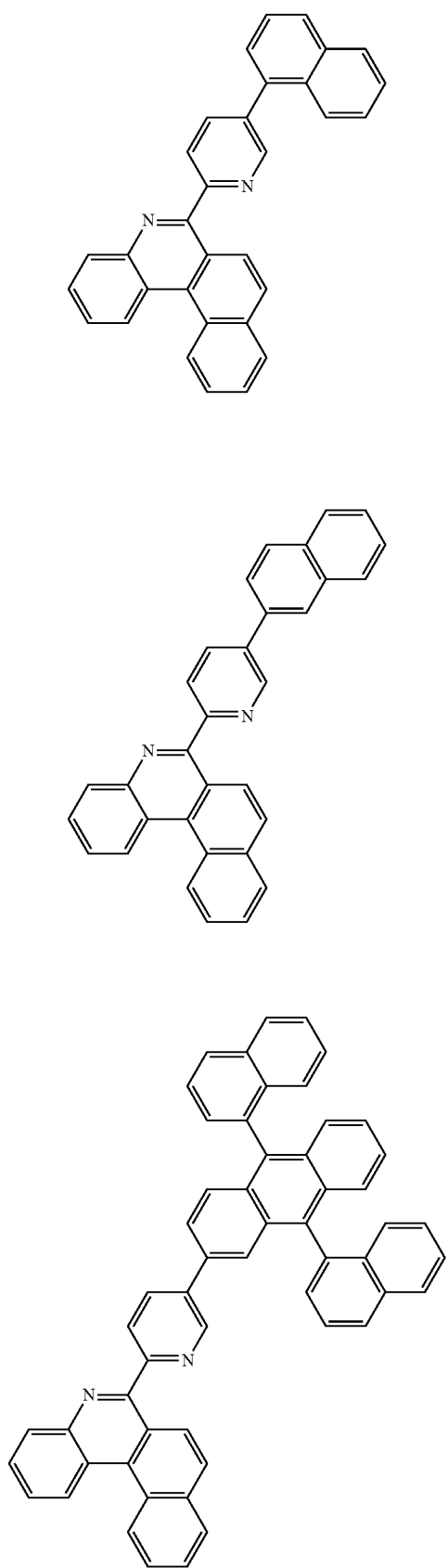
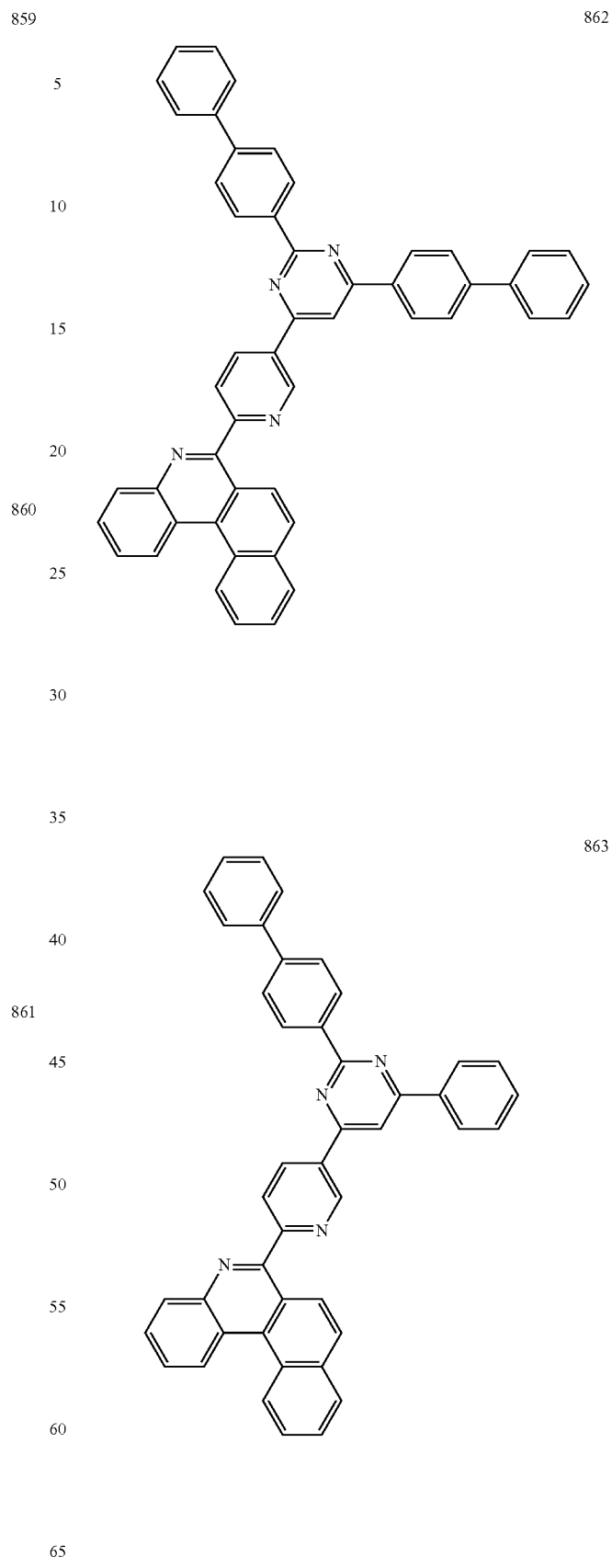

979
-continued
864
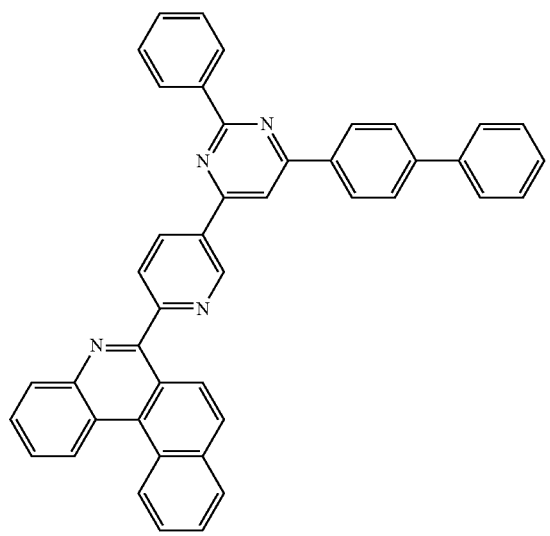
865
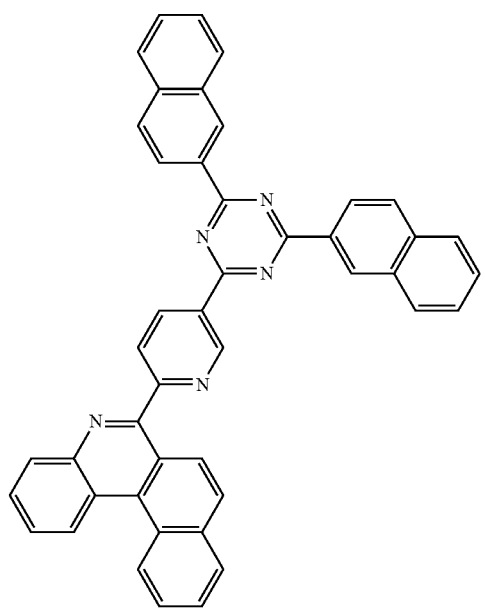
980
-continued
866
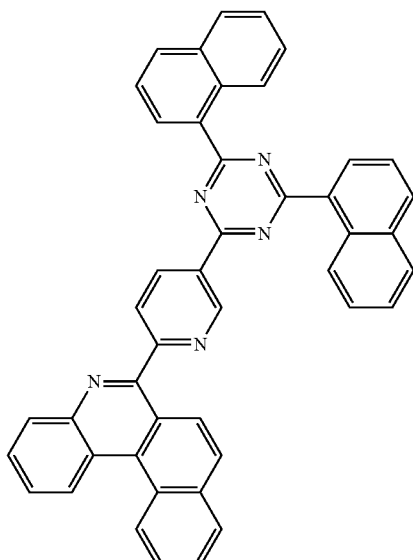
867
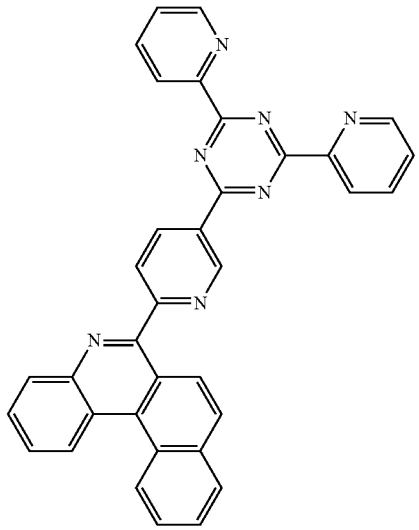
868
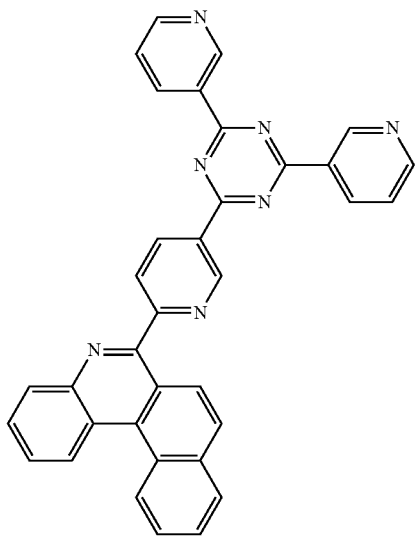

981
-continued
869
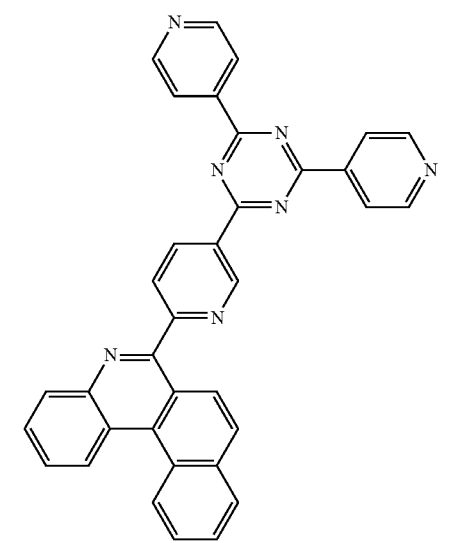
870
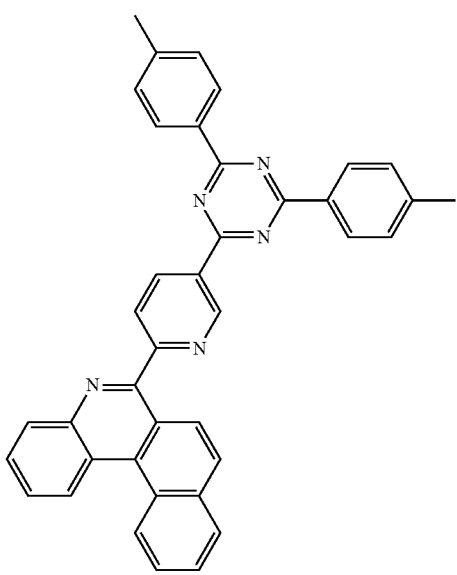
871
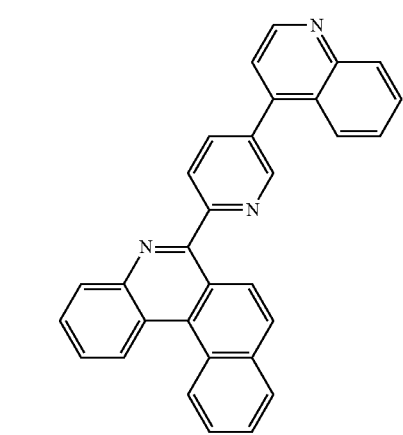
982
-continued
872
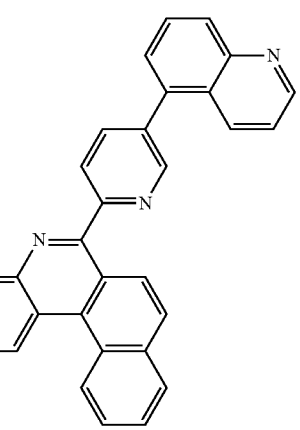
873
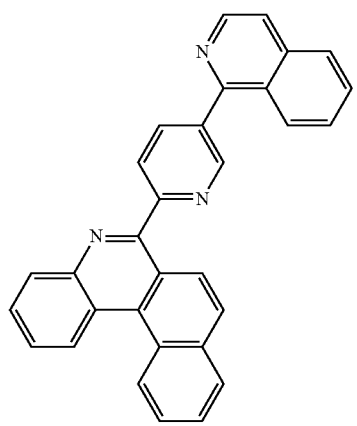
874
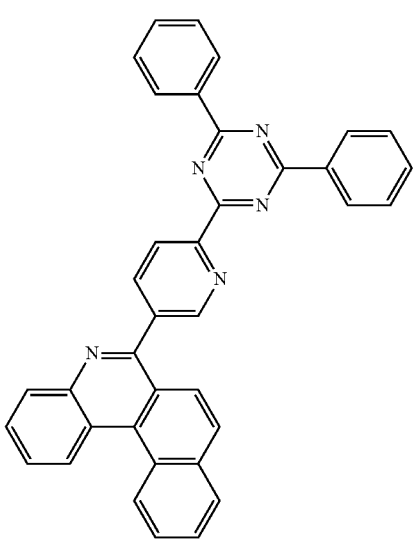

-continued
875
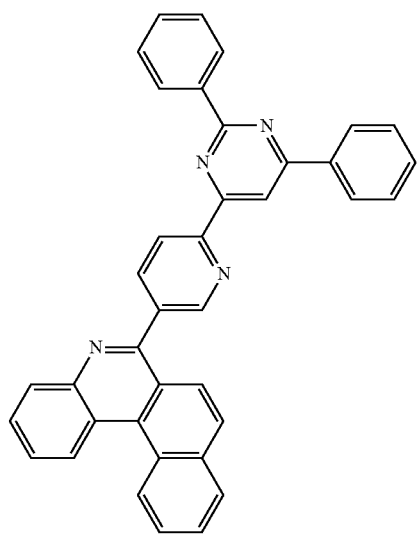
876
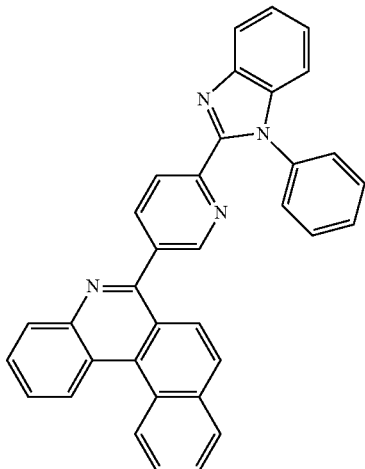
877
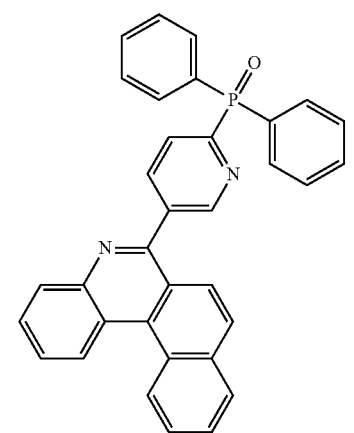
-continued
878
879
880
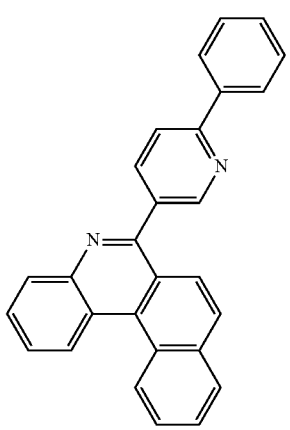

985
-continued
881
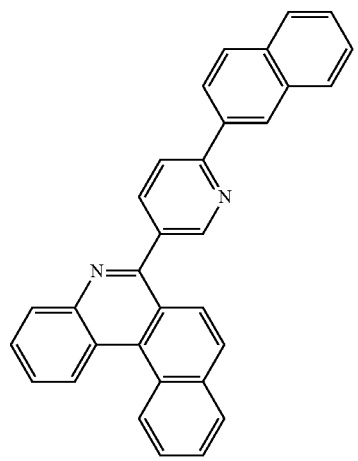
882
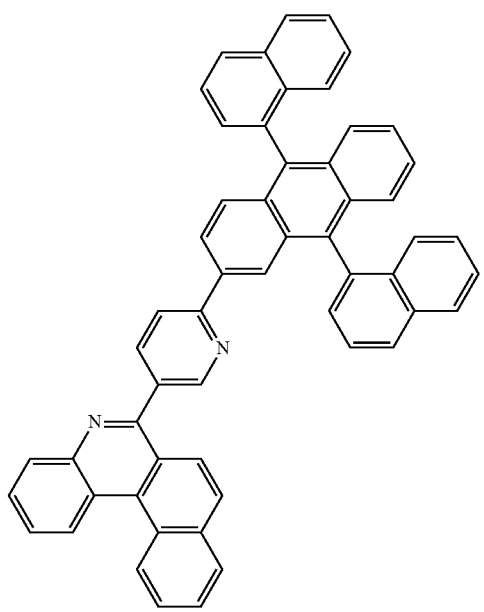
986
-continued
883
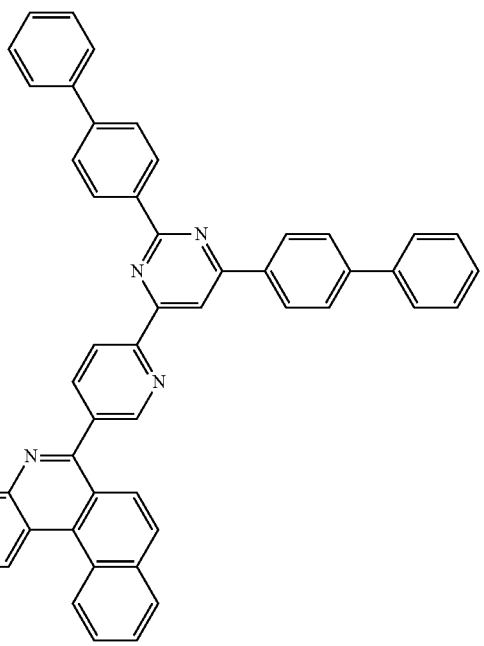
884
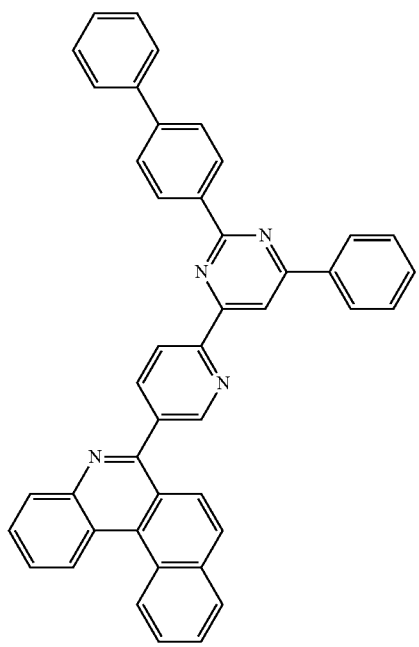

987
-continued
885
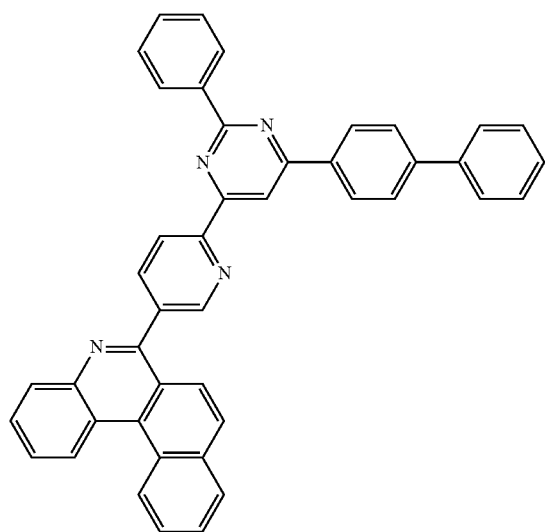
886
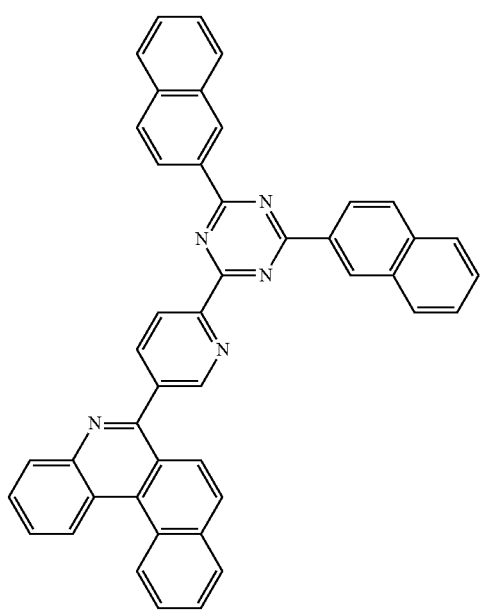
988
-continued
887
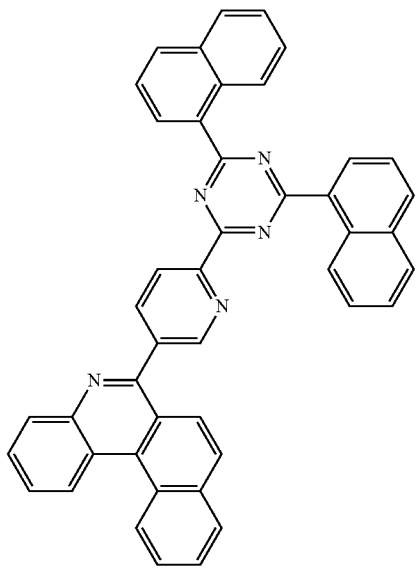
888
889

| 890 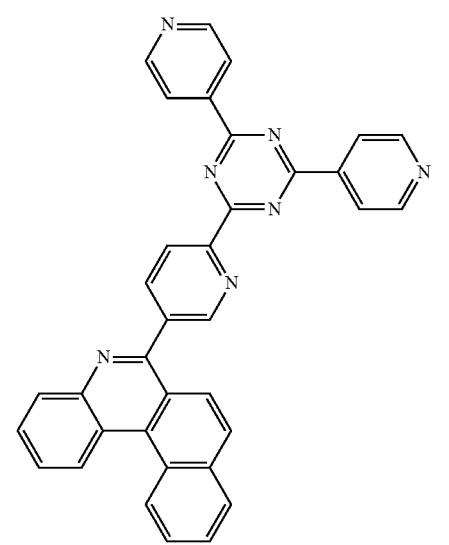 | 893 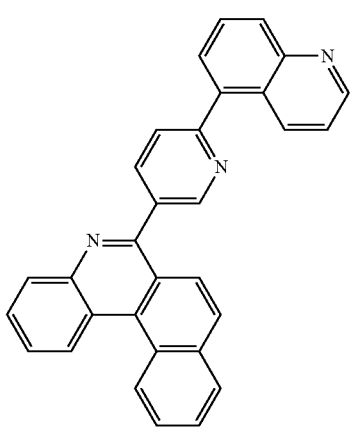 |
| --- | --- |
| 891 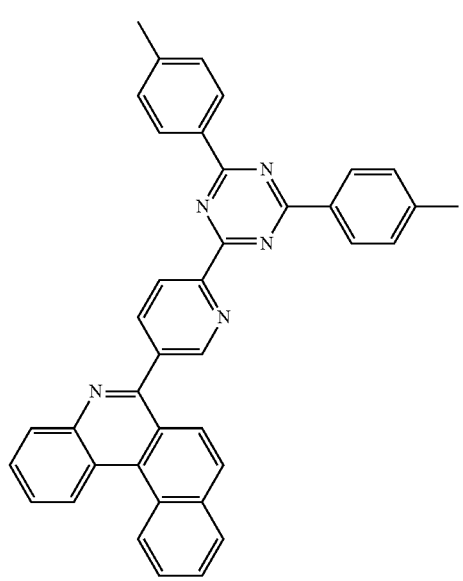 | 894 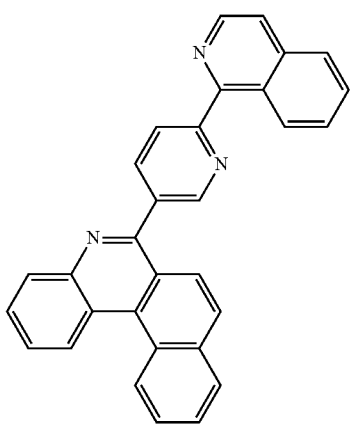 |
| 892 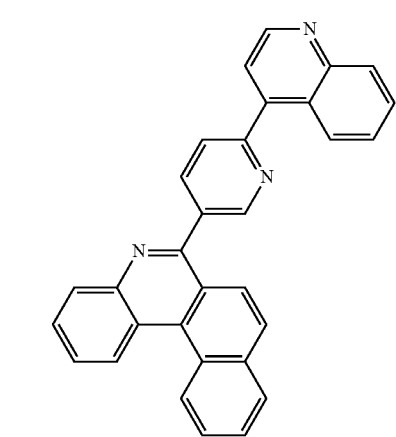 | 895 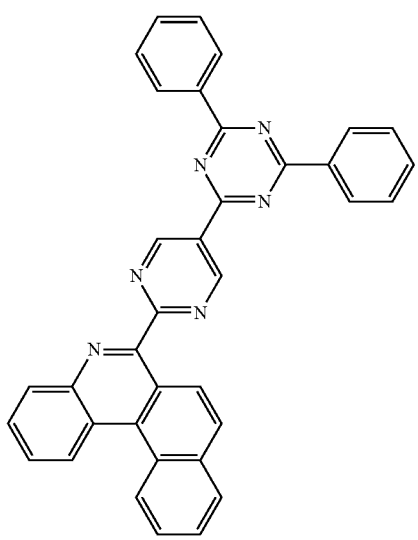 |

896 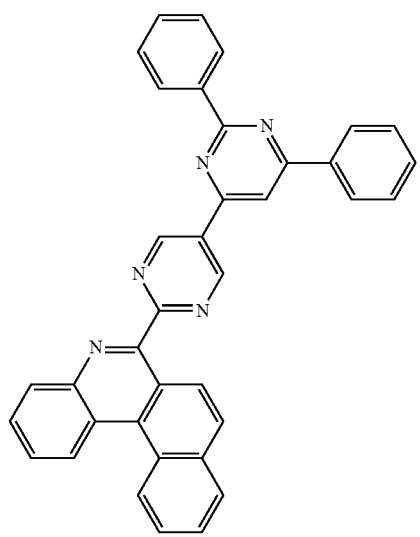
897 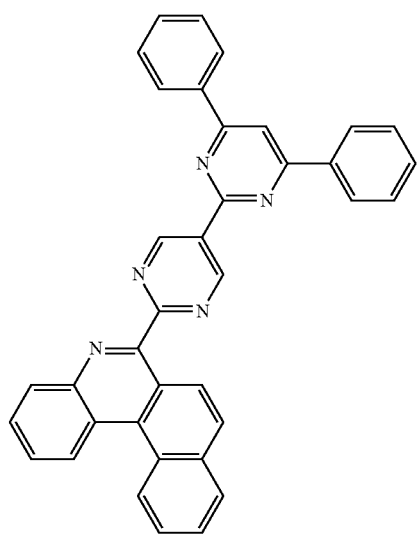
898 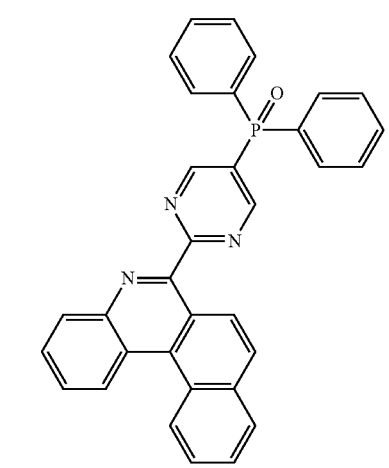
899 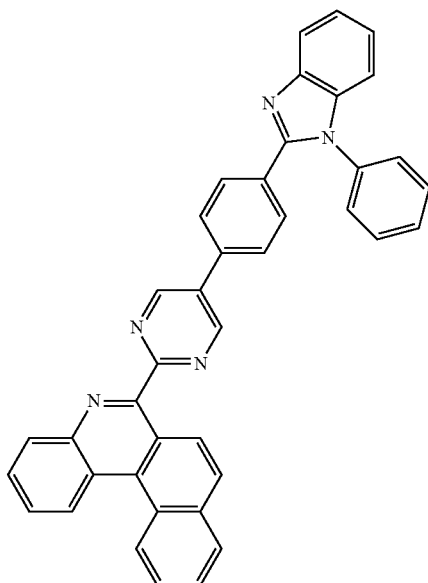
900 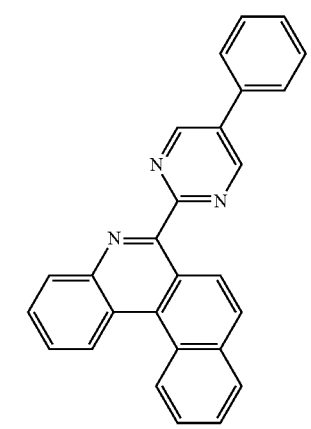
901 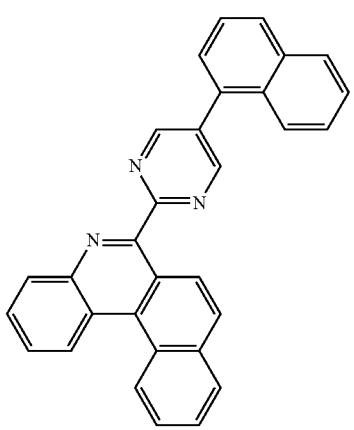

993
-continued
994
-continued
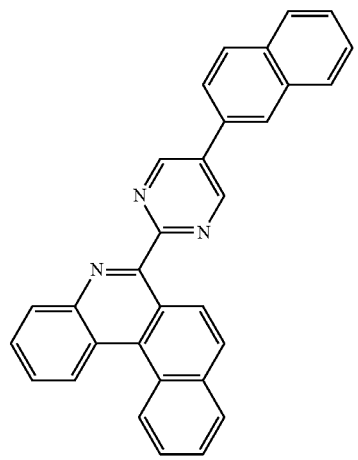
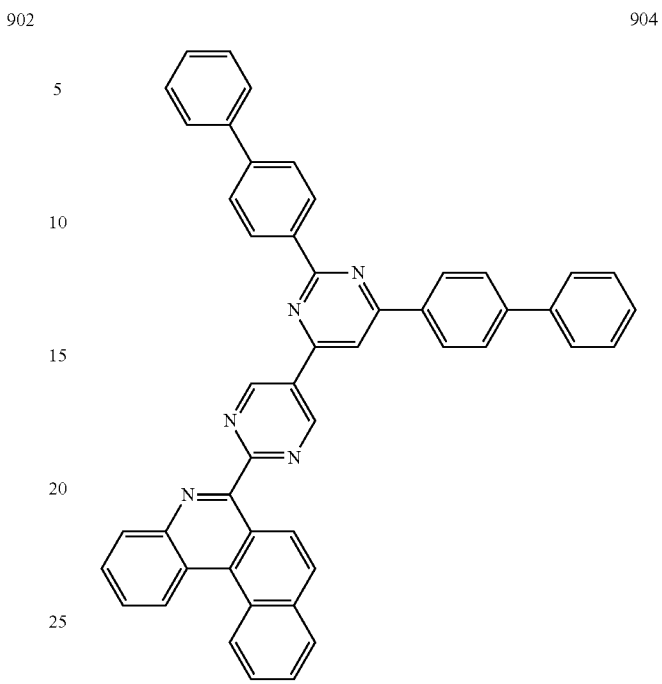

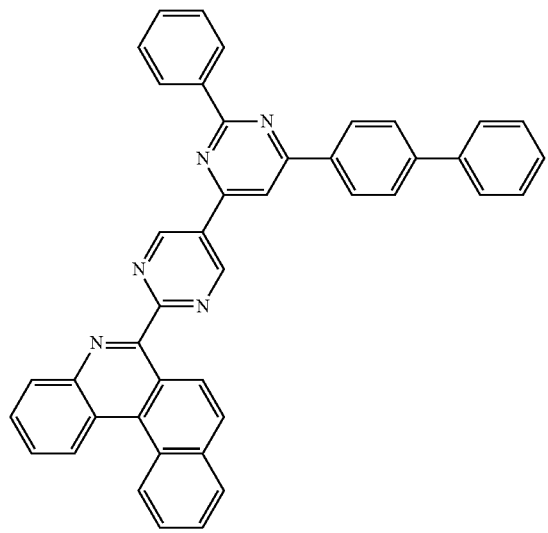
906
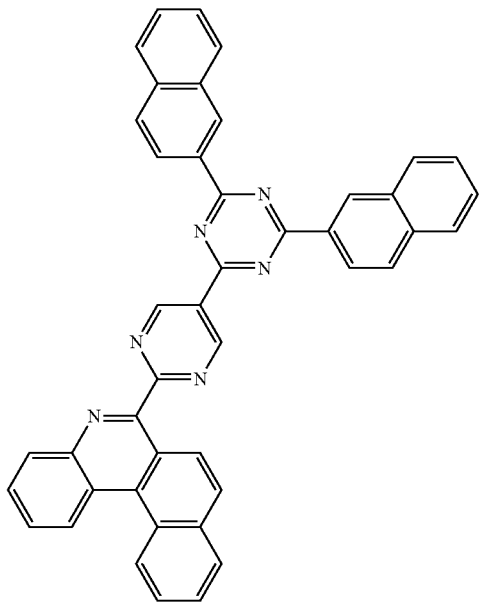
908
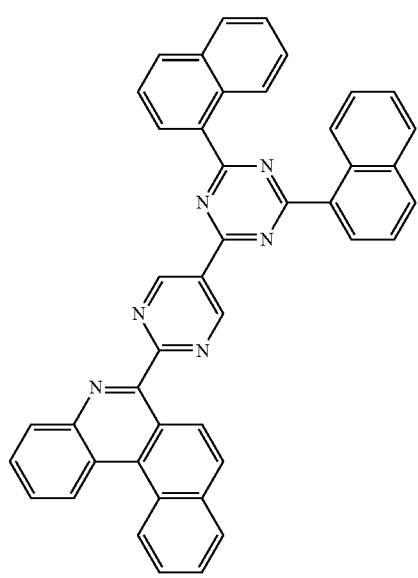
907
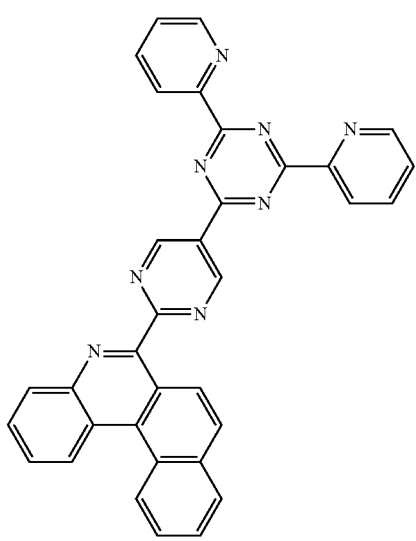
909

-continued
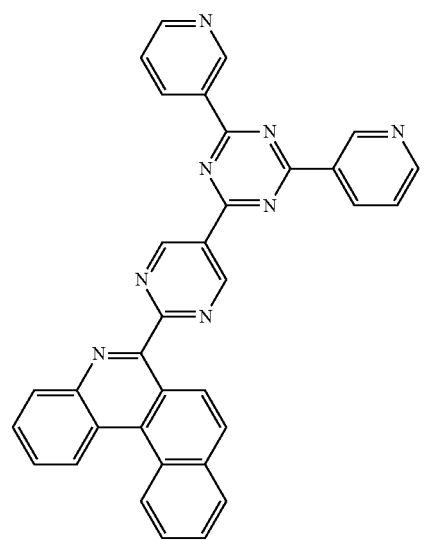
910
911
912
-continued
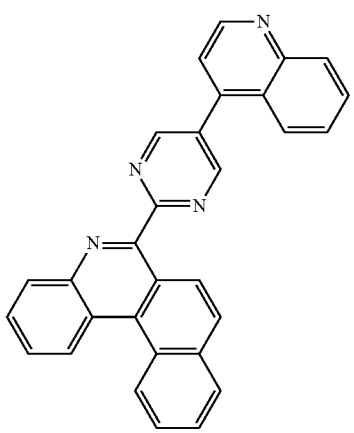
913
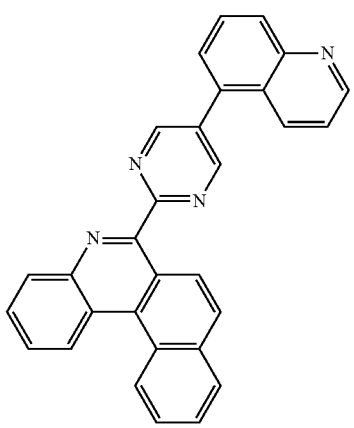
914
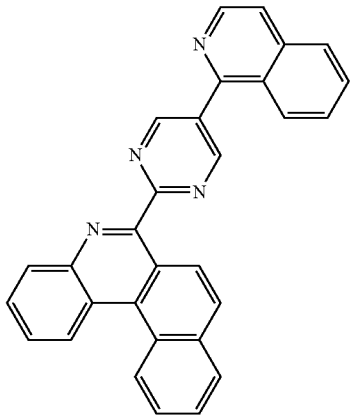
915

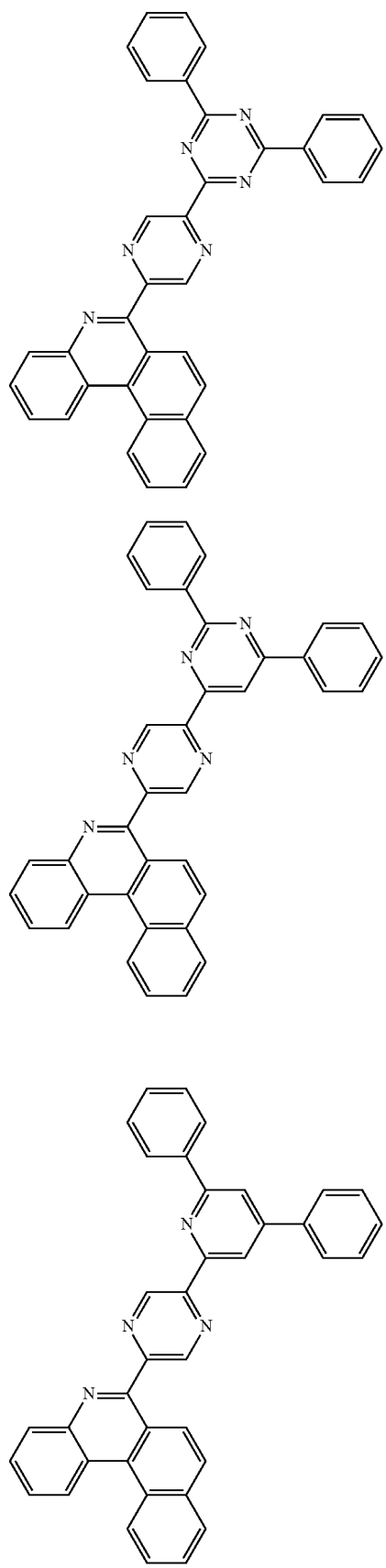
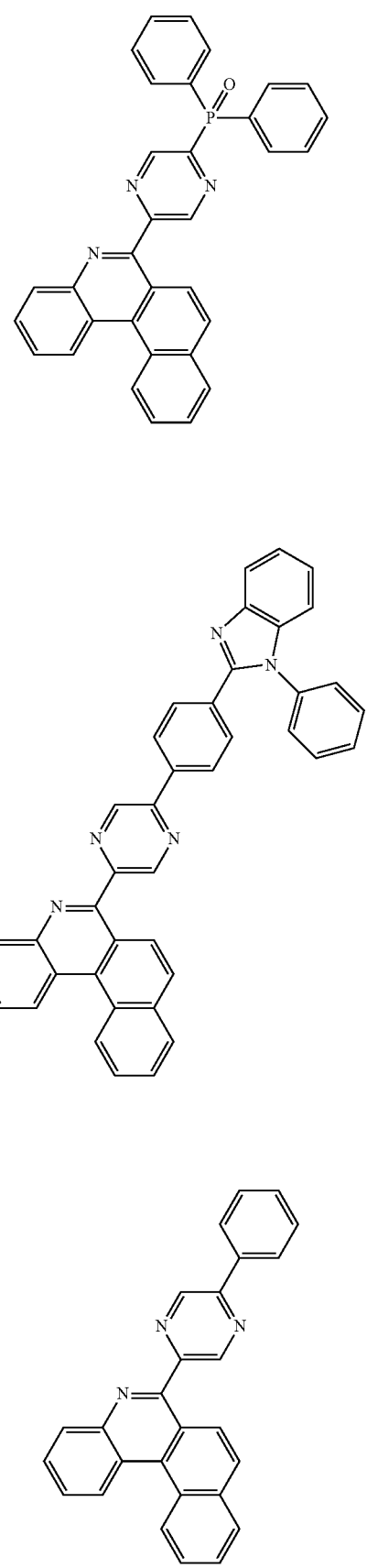

-continued
922
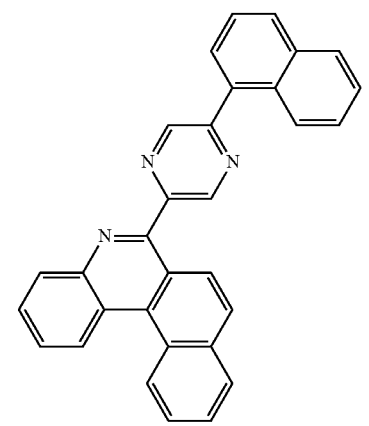
923
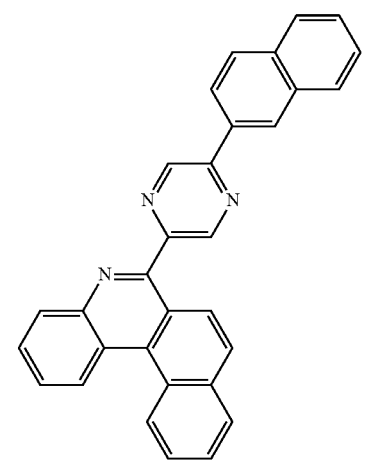
924
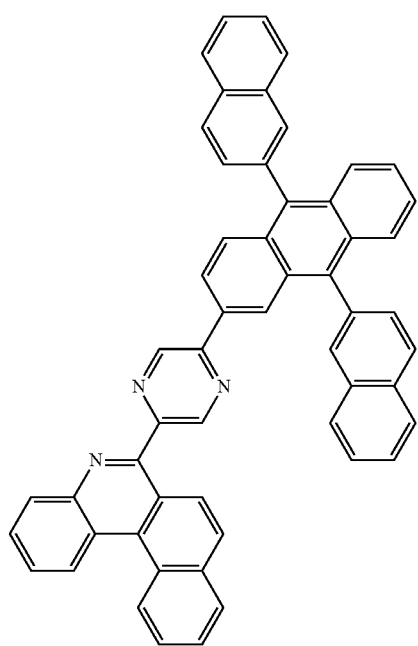
-continued
925
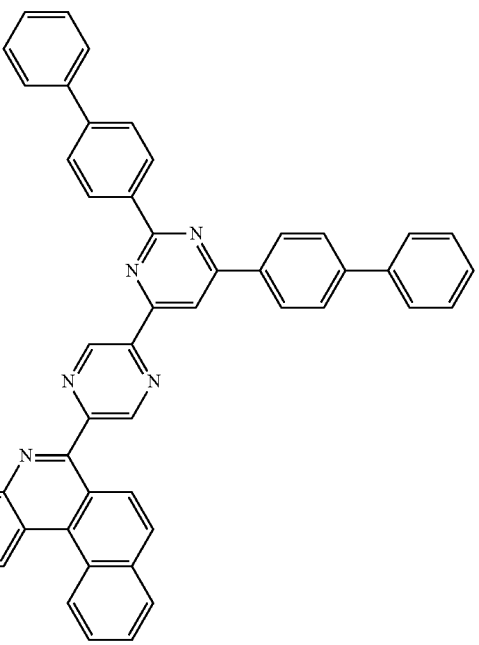
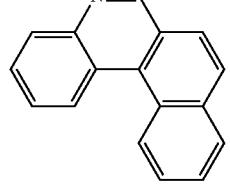
926
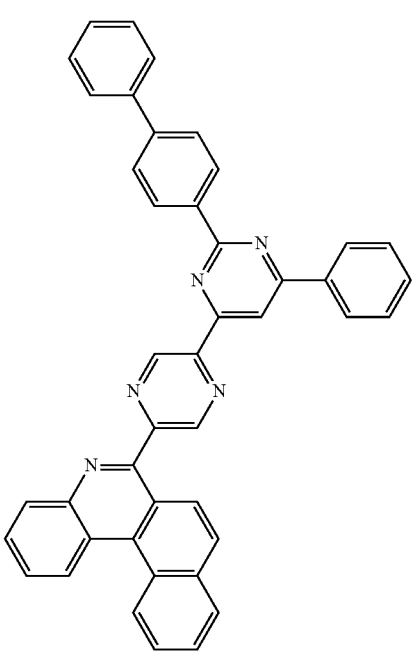

927
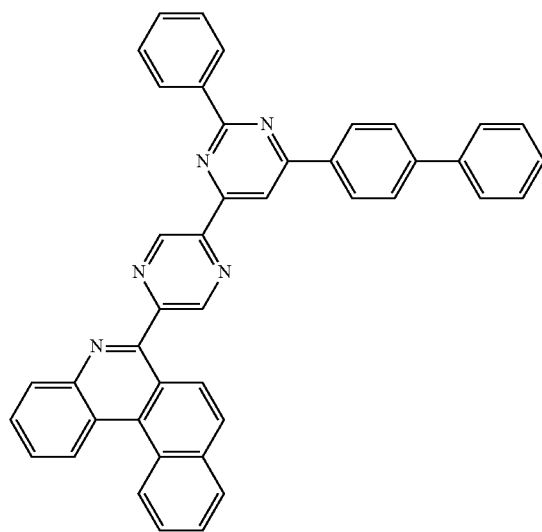
928
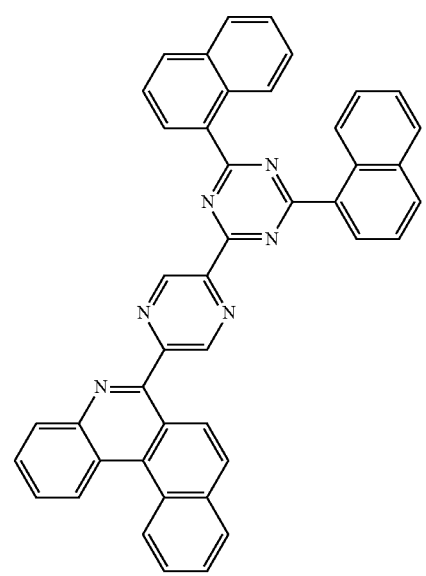
929
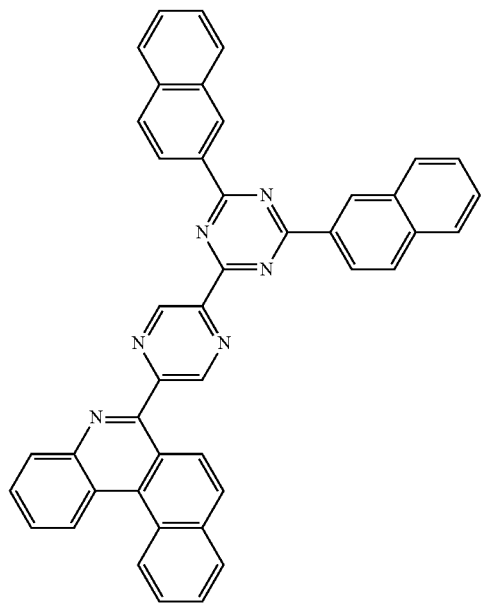
930
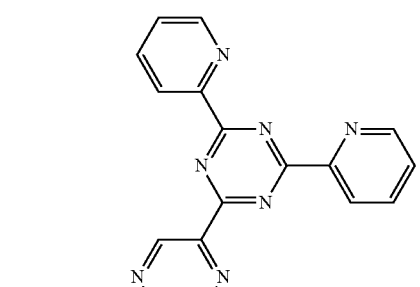
931
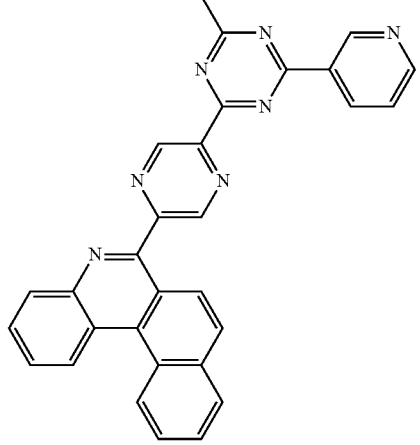

1005
-continued
932
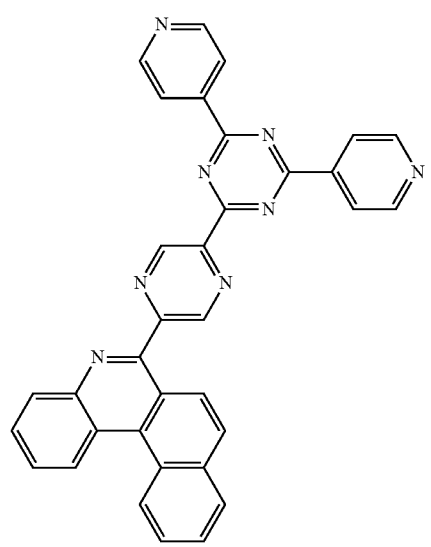
933
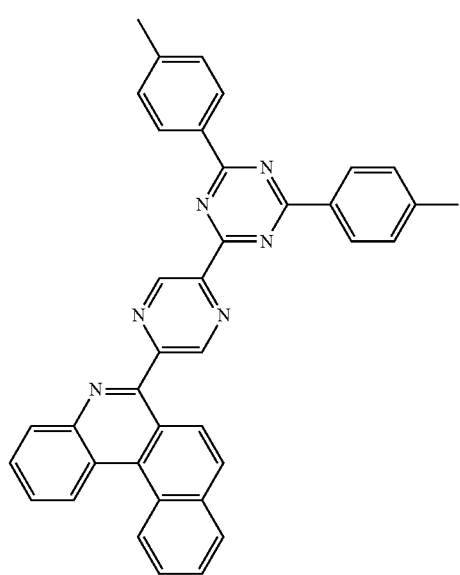
934
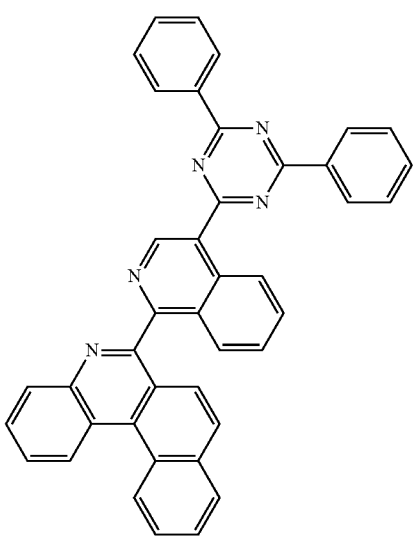
1006
-continued
935
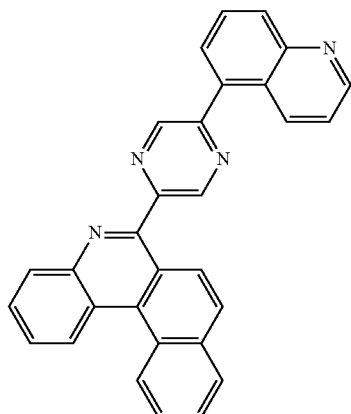
936
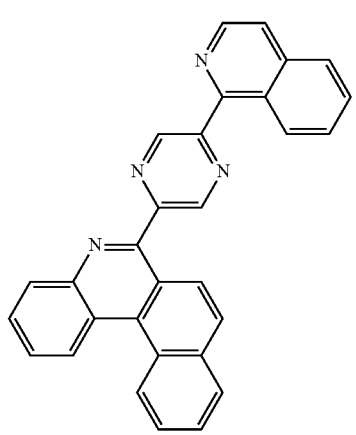
937

-continued
938
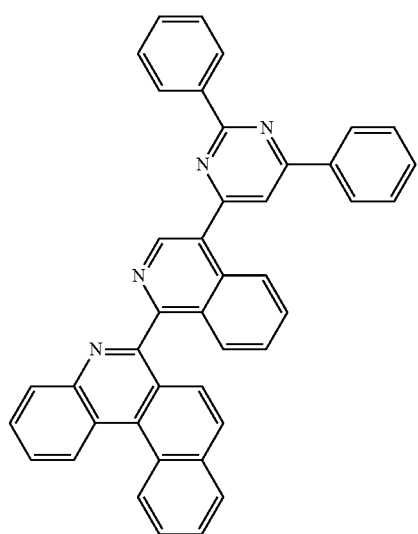
939
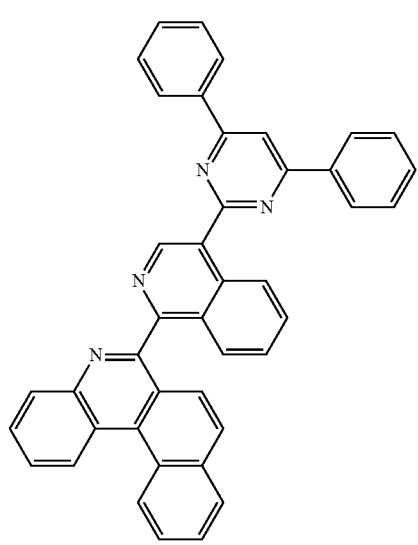
940
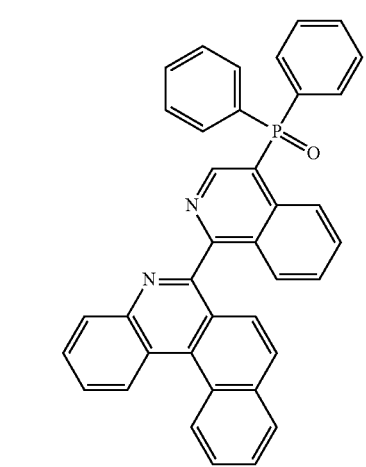
-continued
941
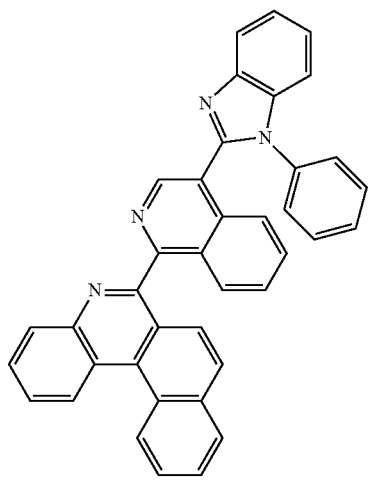
942
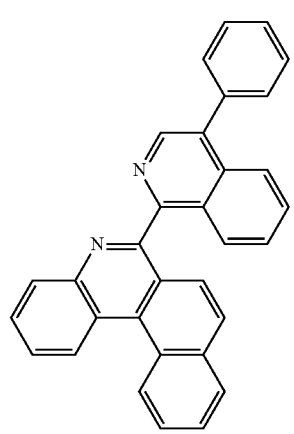
943
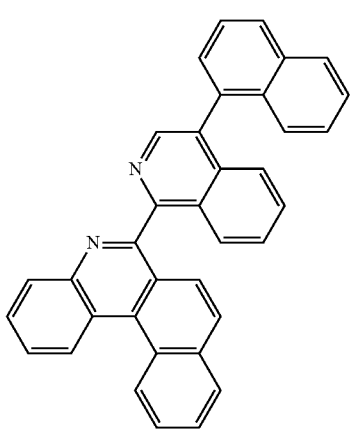

1009
-continued
944
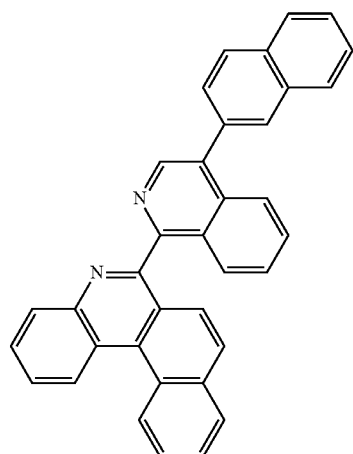
945
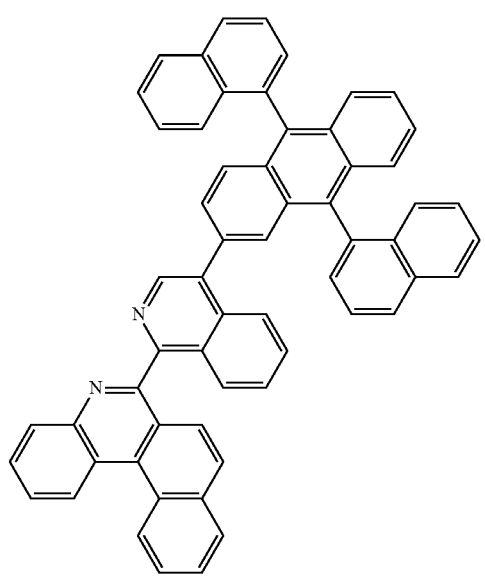
1010
-continued
946
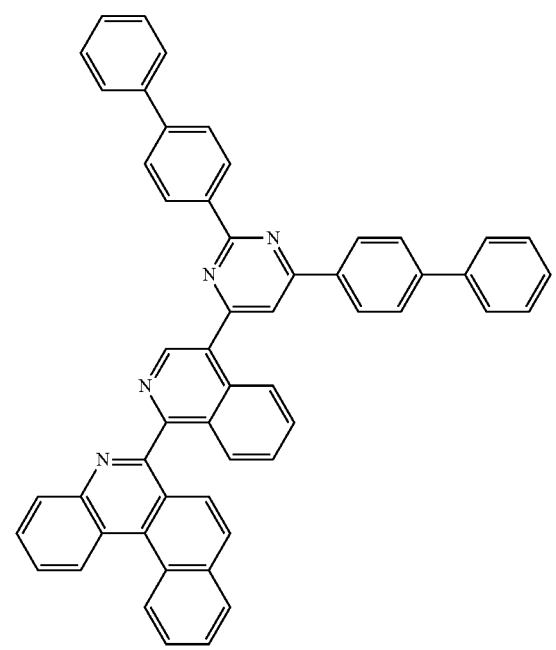
947
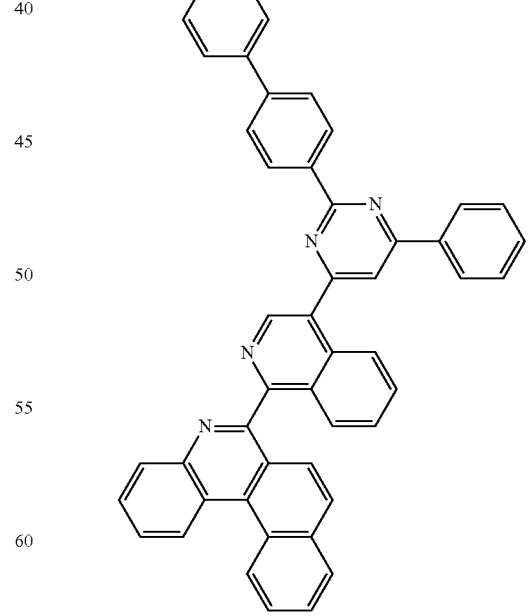

1011
-continued
948
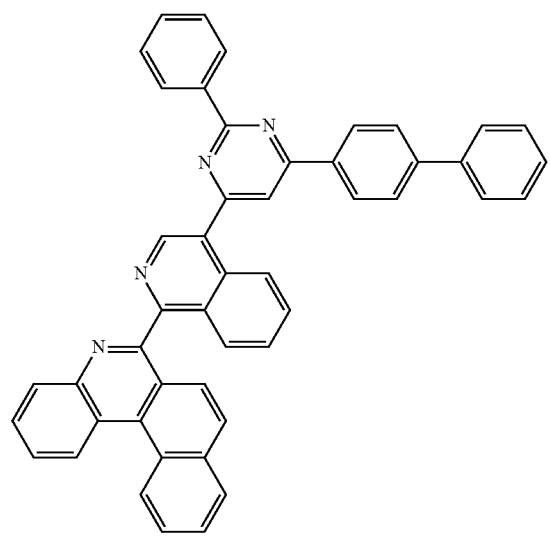
949
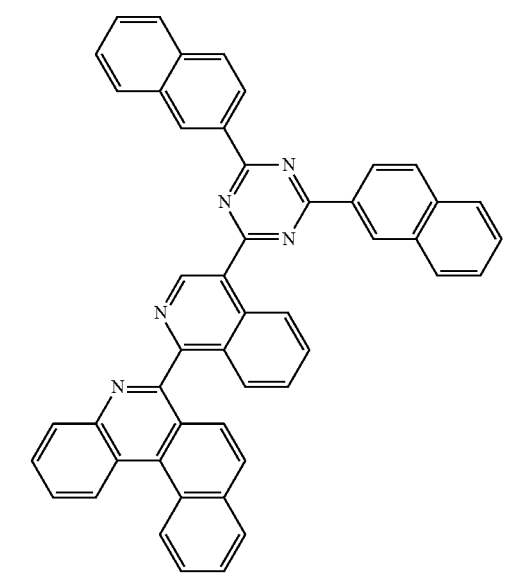
1012
-continued
950
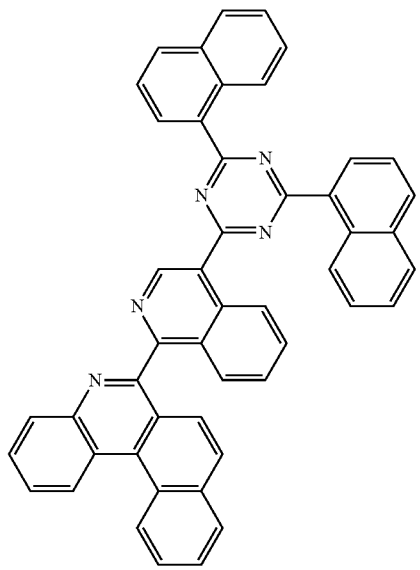
951
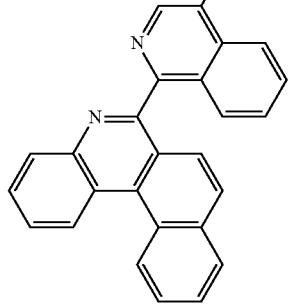
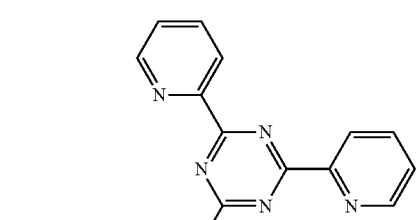
952
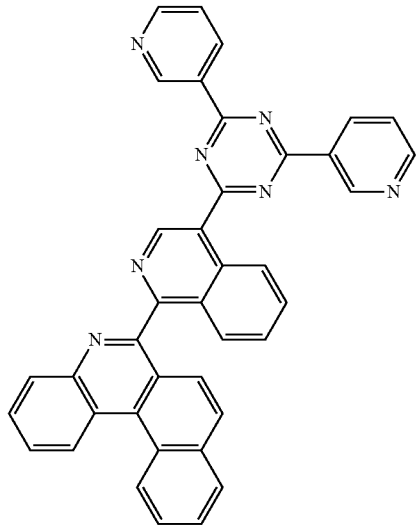

1013
-continued
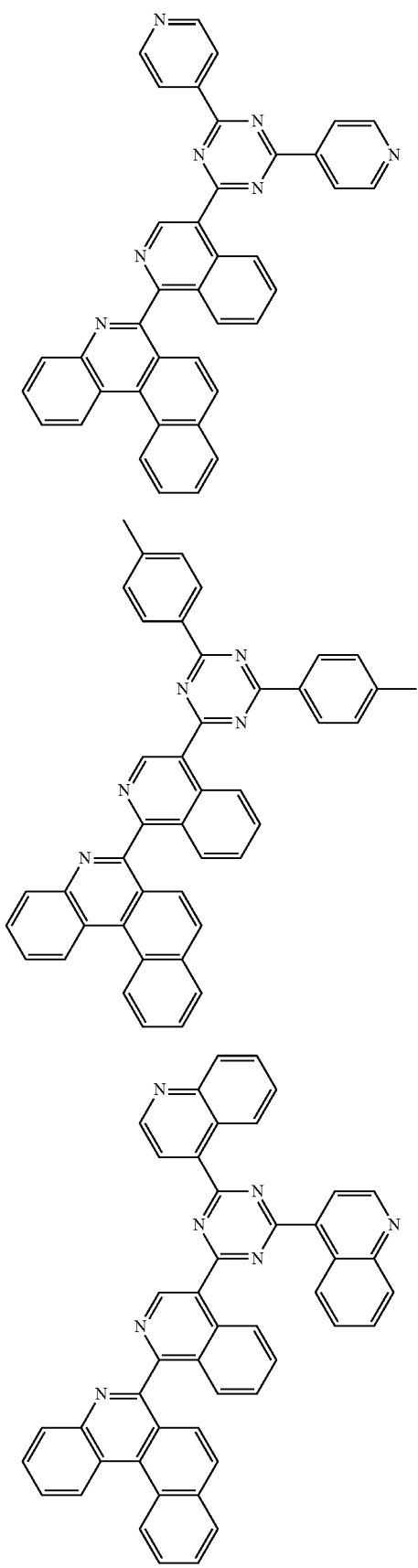
1014
-continued
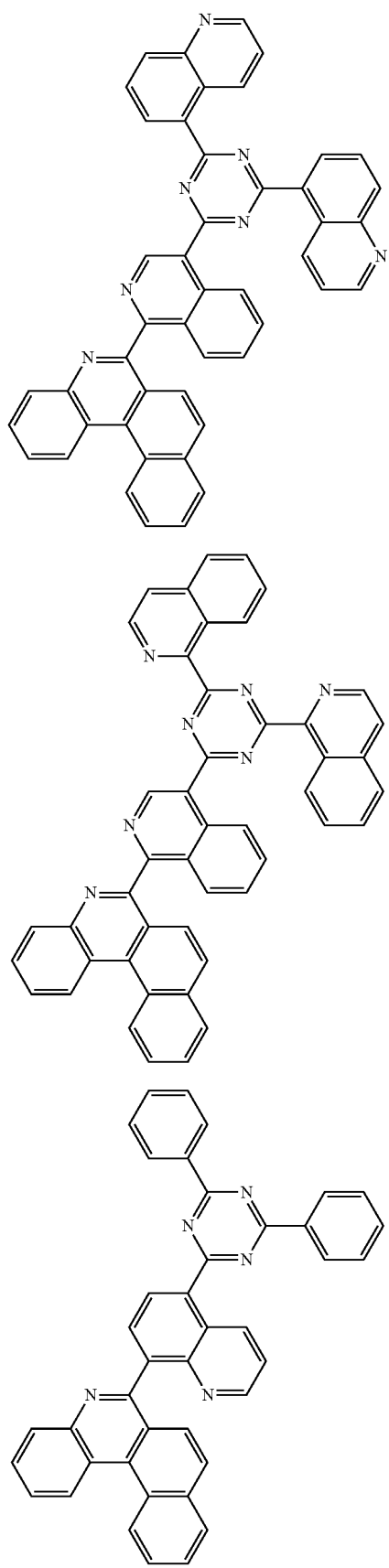

959
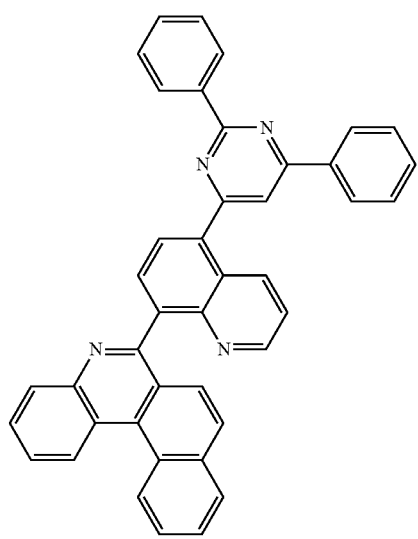
960
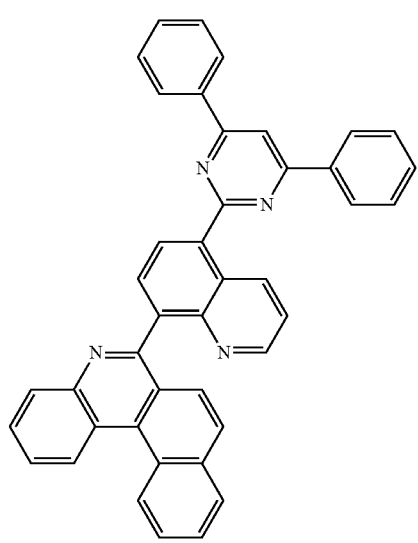
961
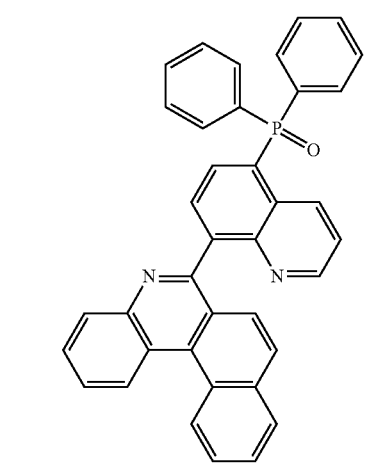
962
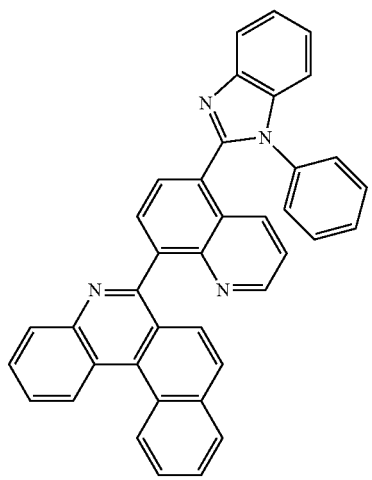
963
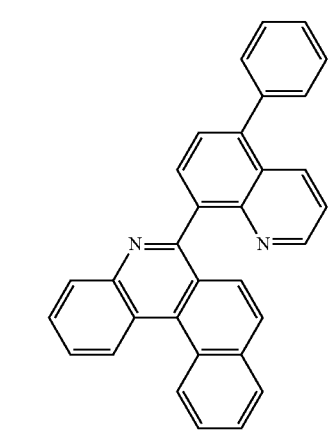
964
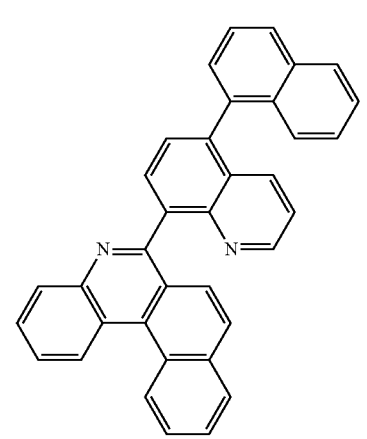

1017
-continued
965
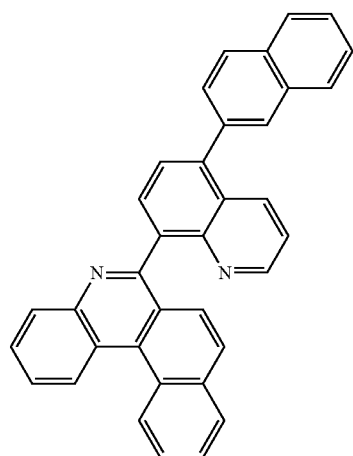
966
1018
-continued
967
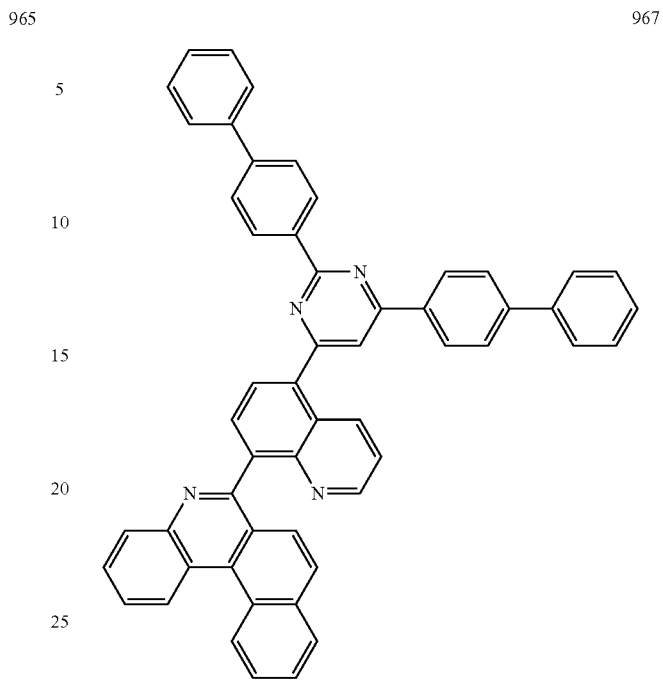
968
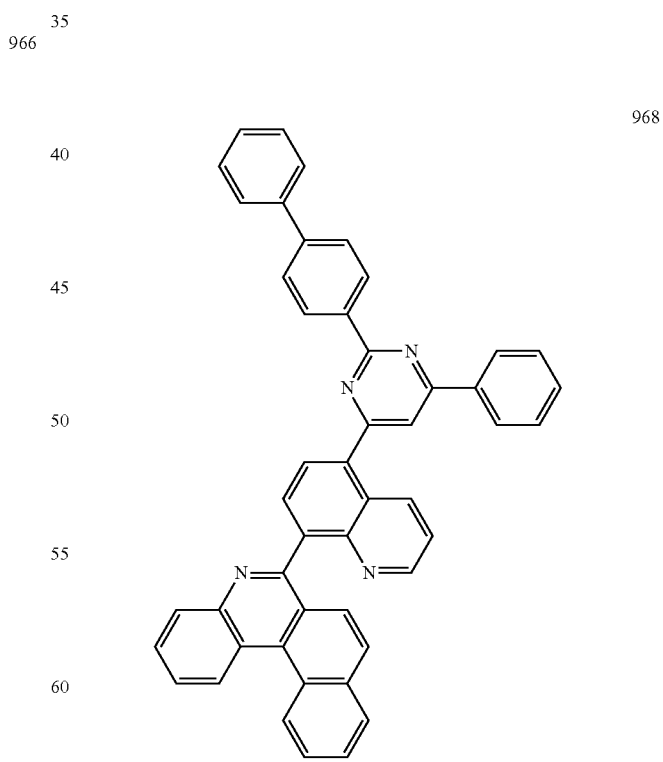

1019
-continued
969
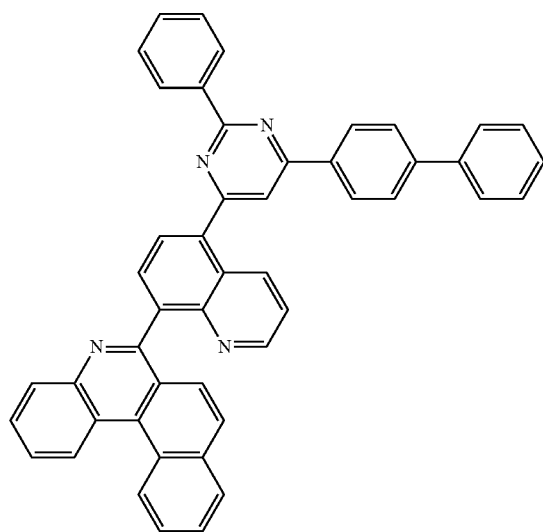
970
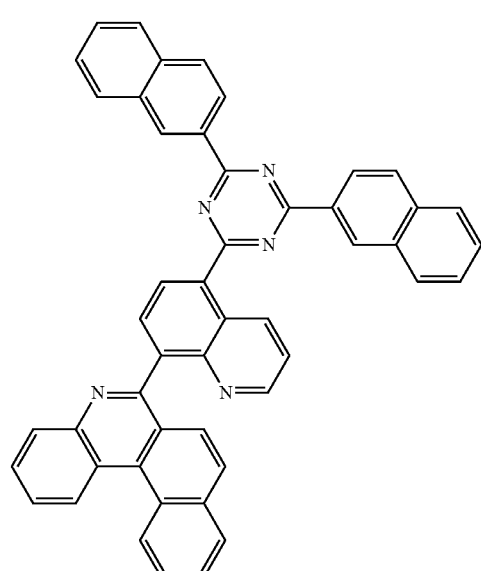
1020
-continued
971
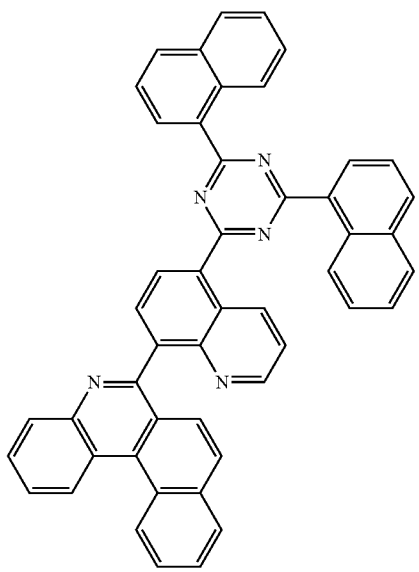
972
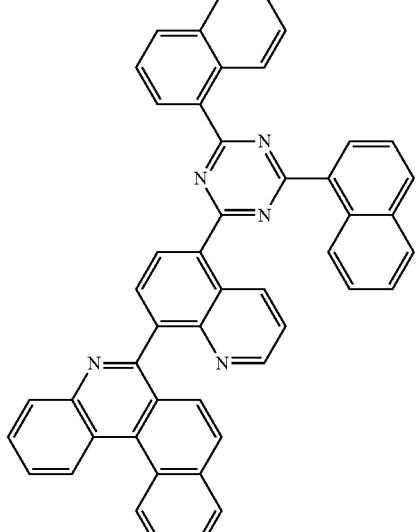
973
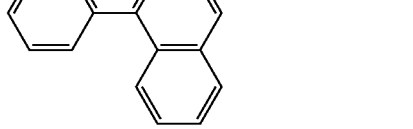

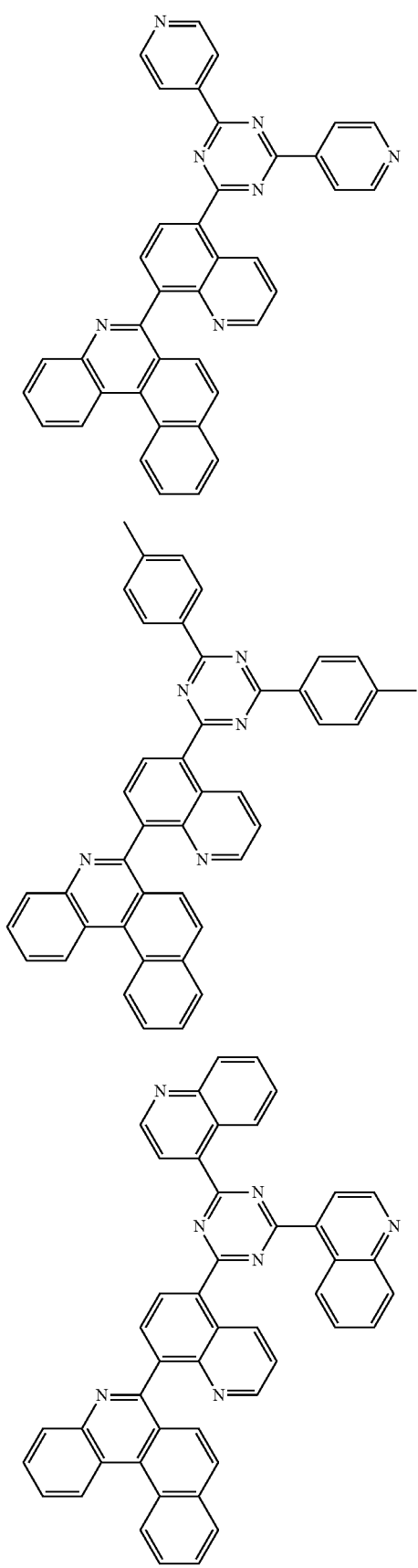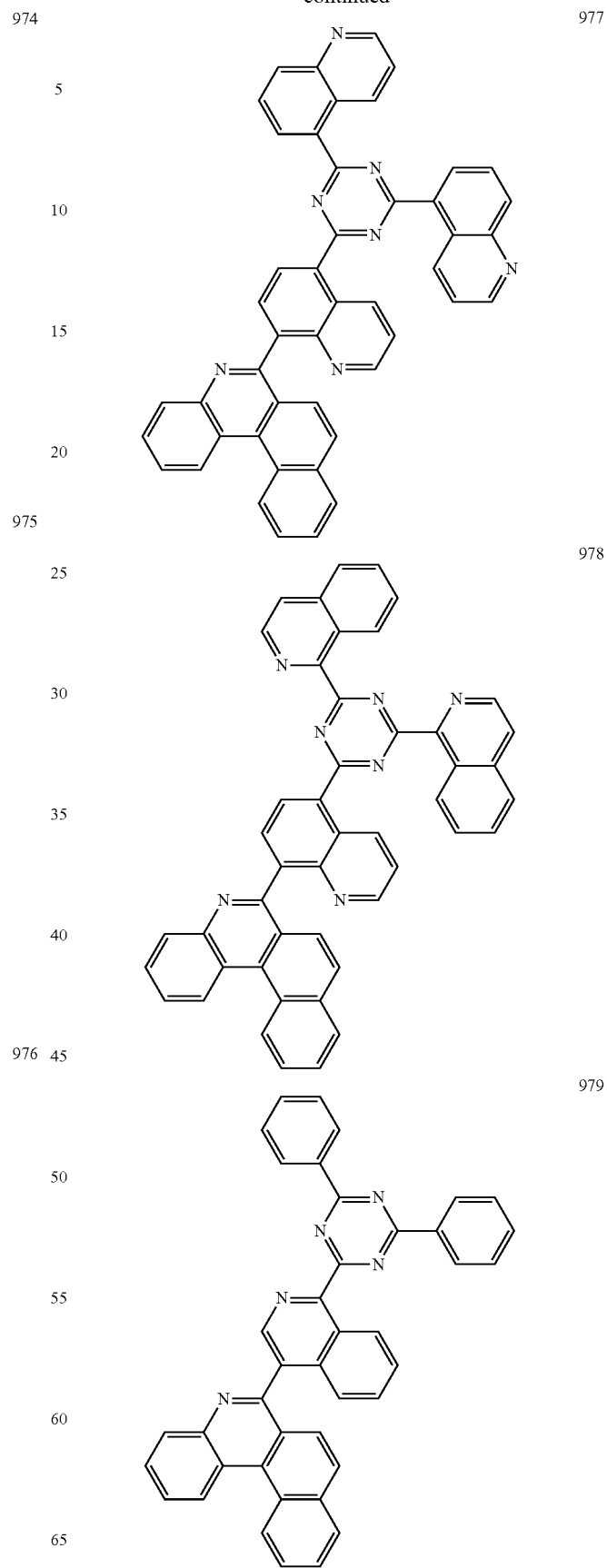

1023
-continued
980
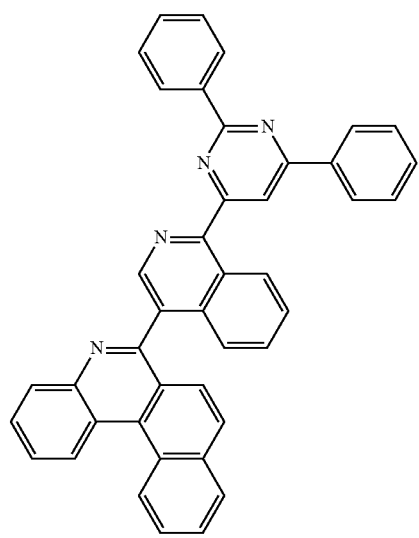
981
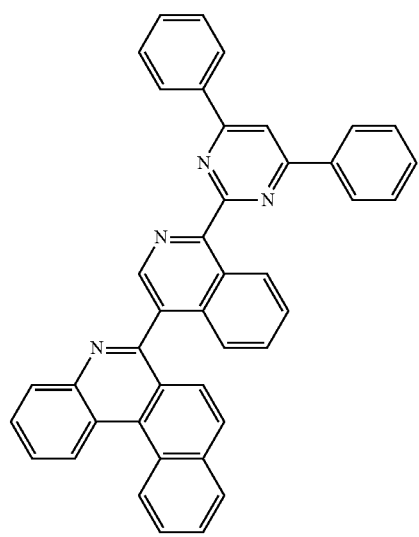
982
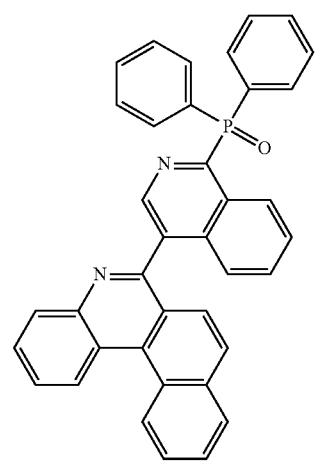
1024
-continued
983
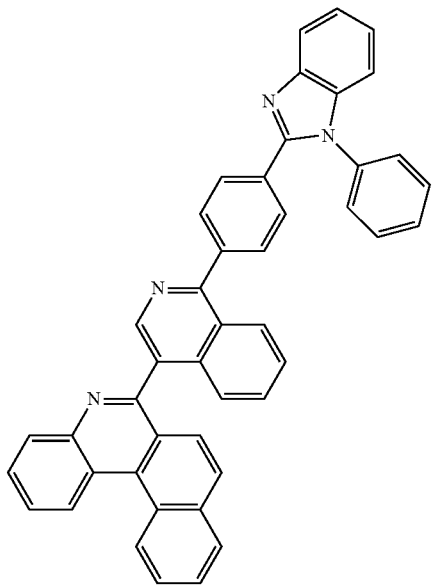
984
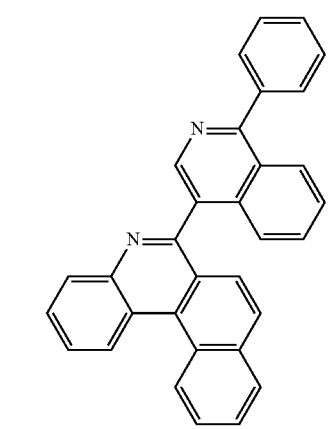
985
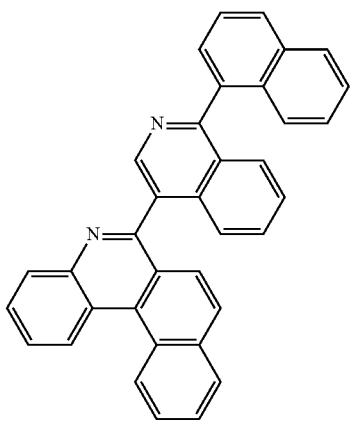

1025
-continued
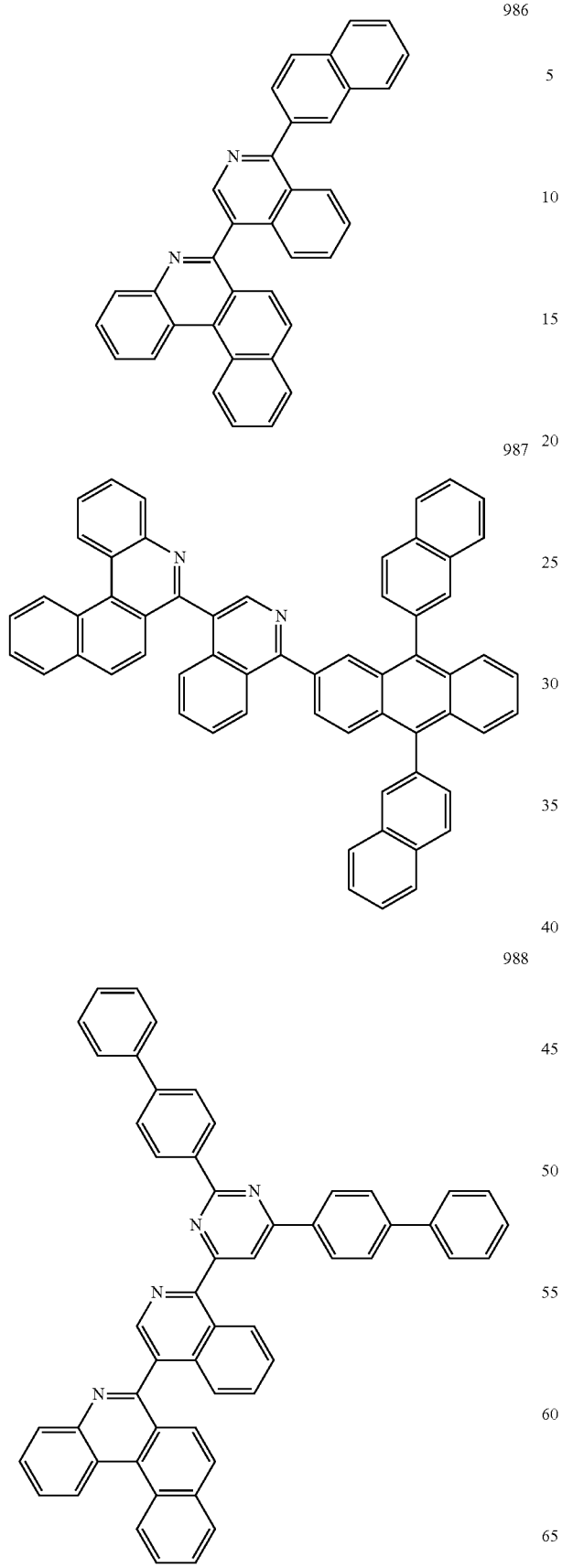
1026
-continued
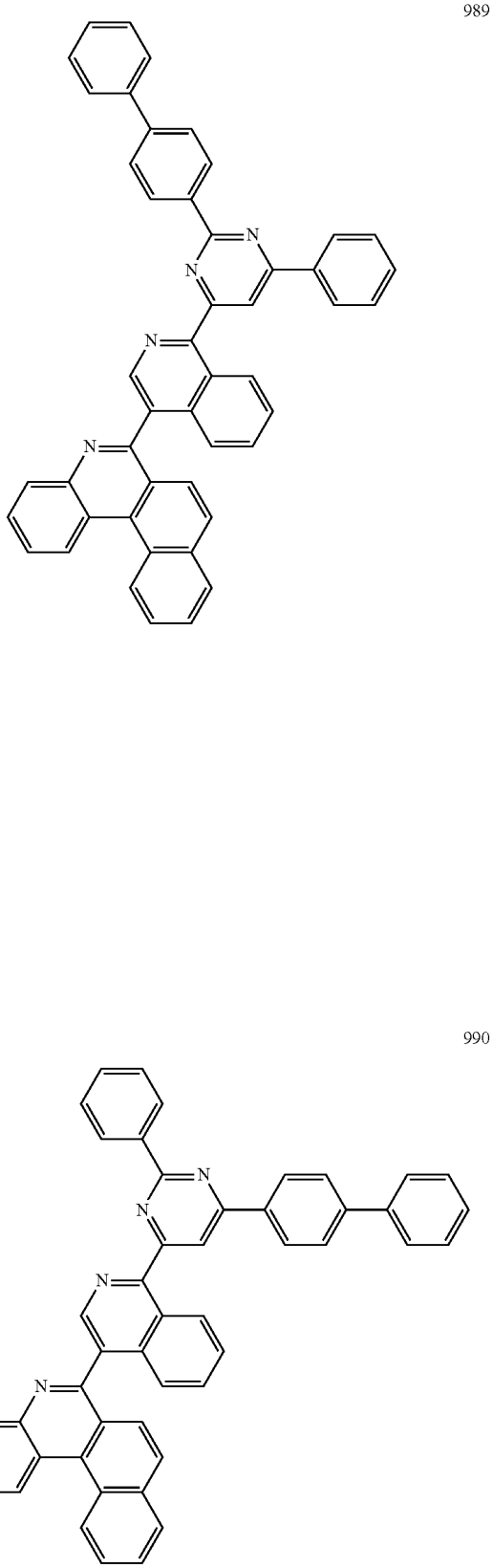

1027
-continued
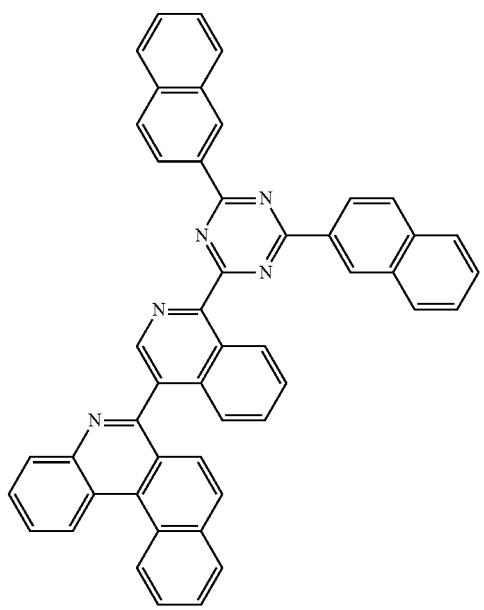
991
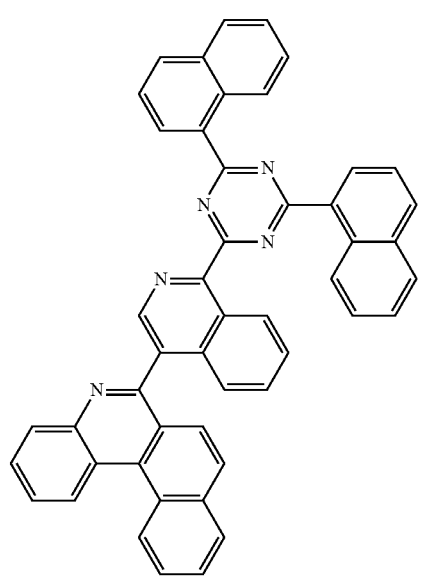
992
1028
-continued
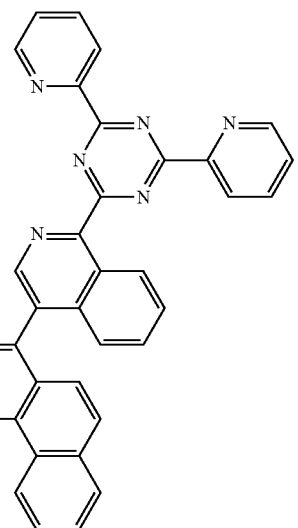
993
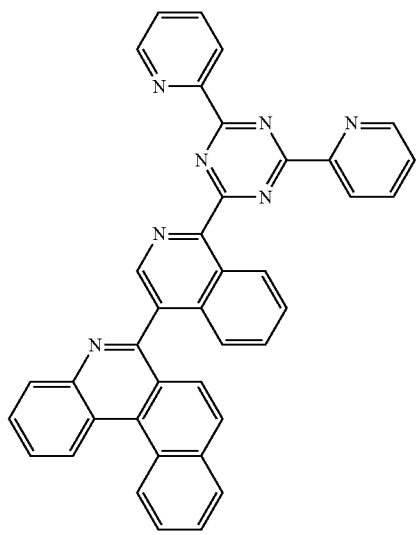
994
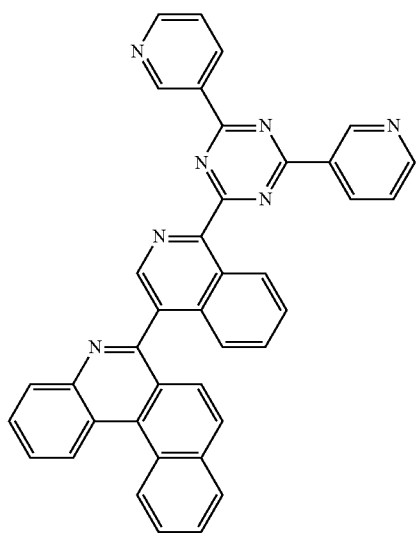
995

996
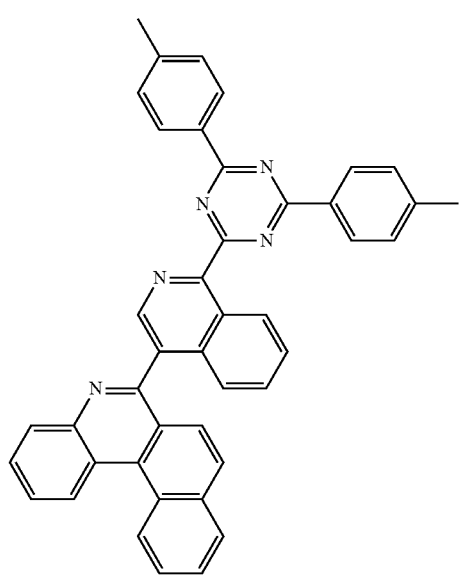
997
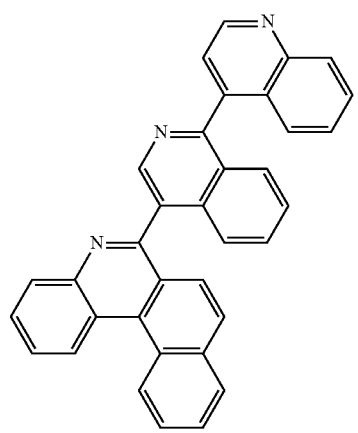
998
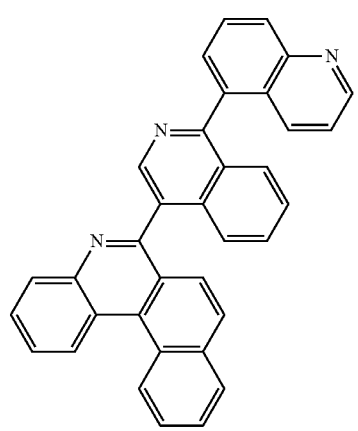
999
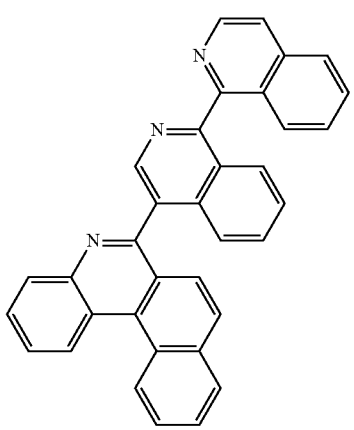
1000
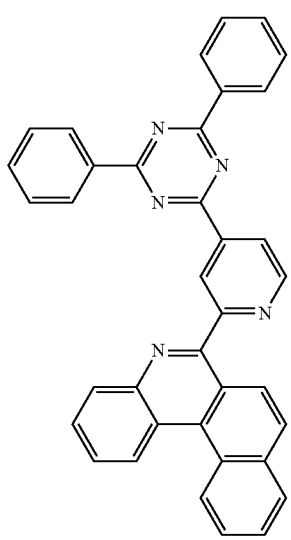
1001

-continued
1002
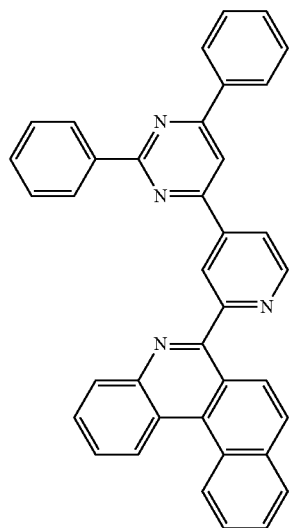
1003
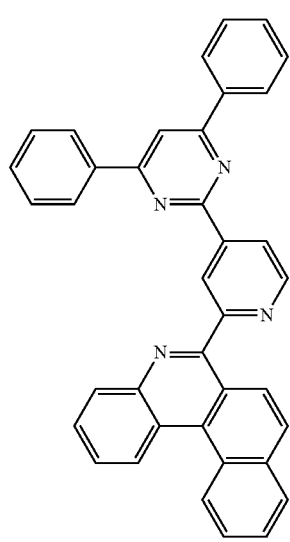
1004
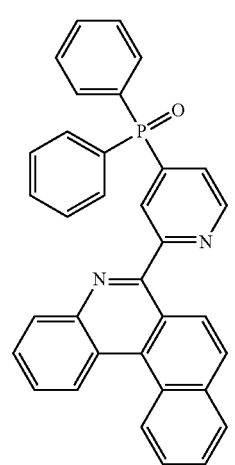
-continued
1005
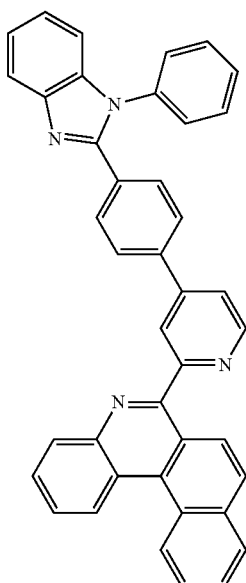
1006
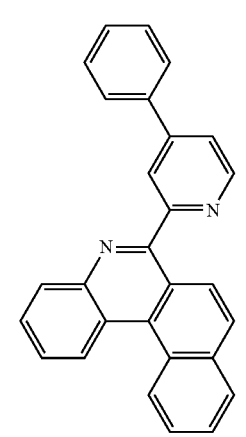
1007
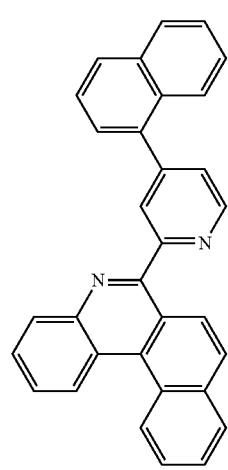

1033
-continued
1034
-continued
1008
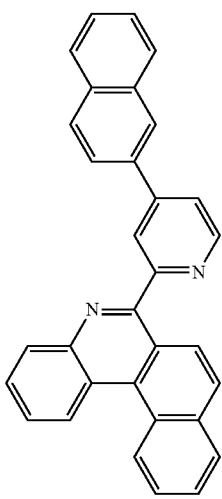
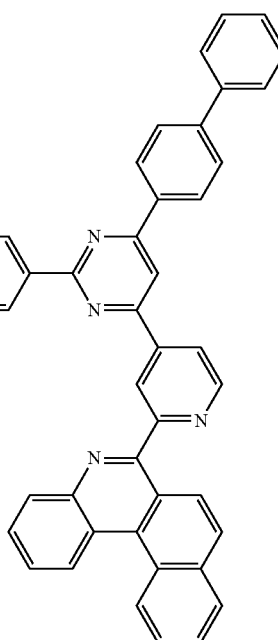
1010
1009
1011
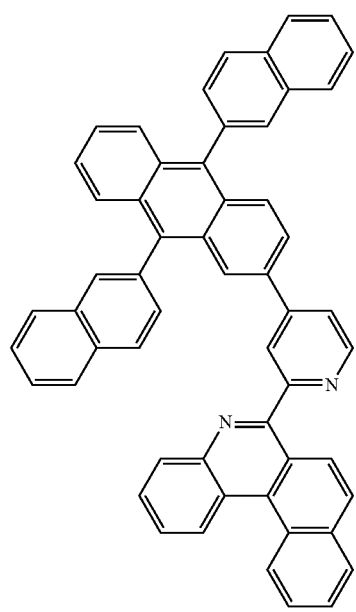

1035
-continued
1012
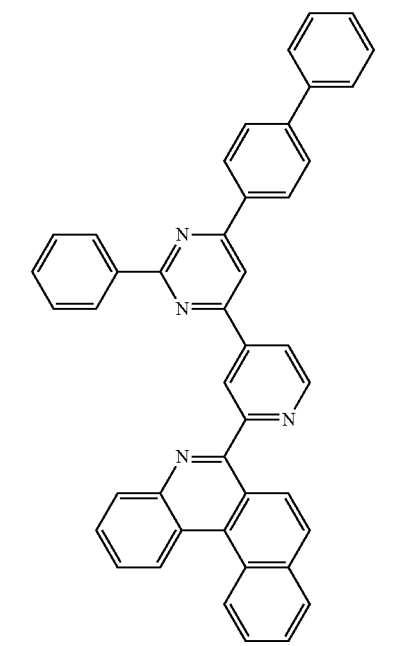
1036
-continued
1014
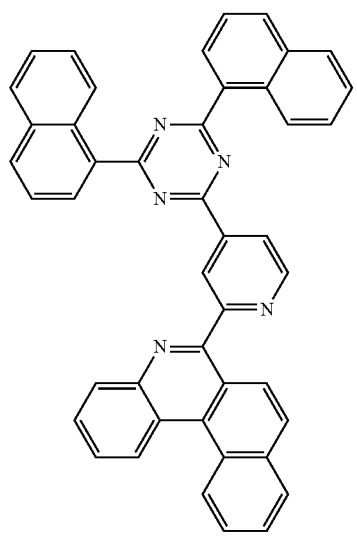
1015
1013
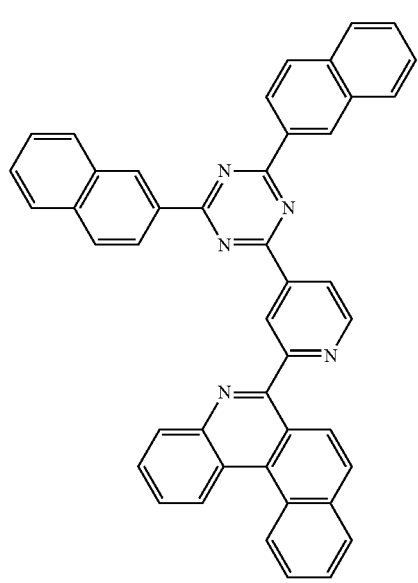
1016

-continued
1017
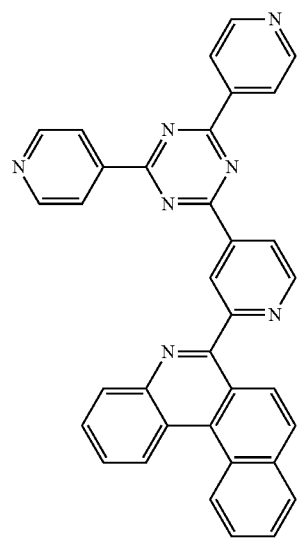
1018
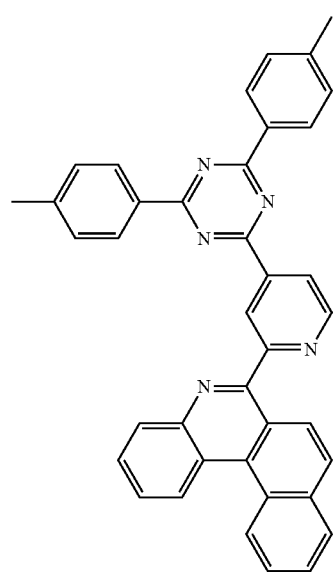
1019
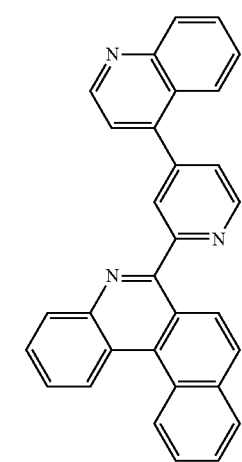
-continued
1020
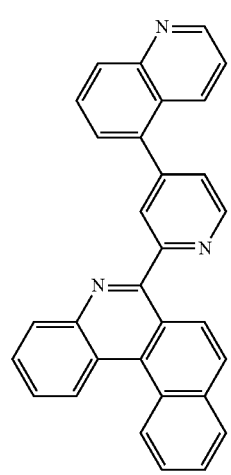
1021
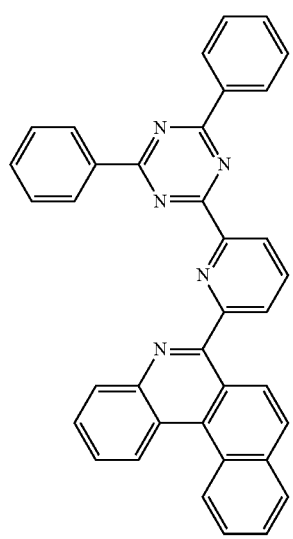
1022
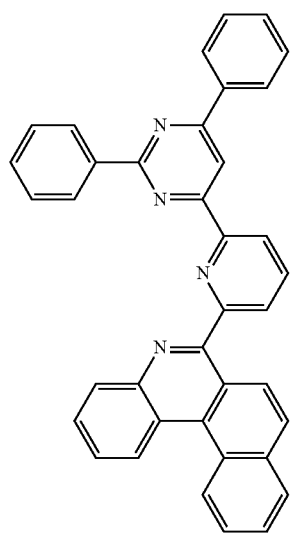

1039
-continued
1023
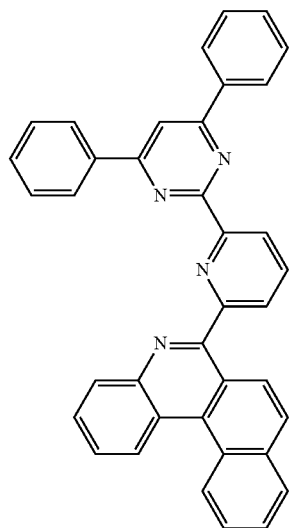
1024
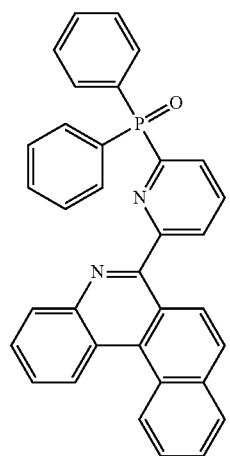
1025
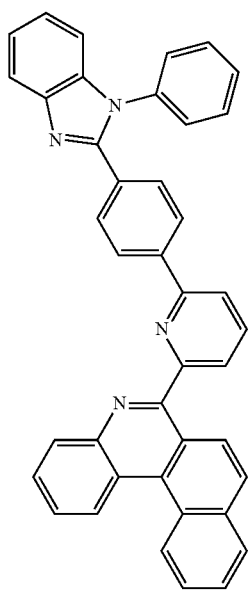
1040
-continued
1026
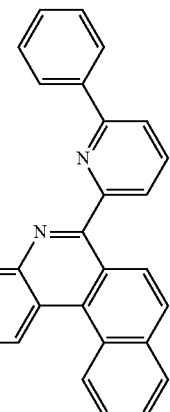
1027
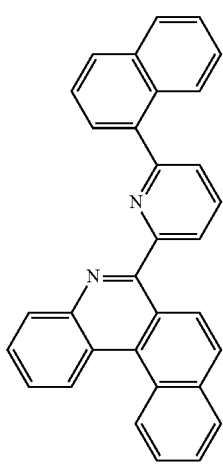
1028
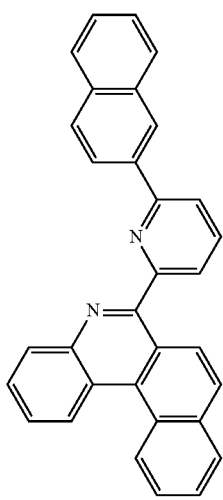

1041
-continued
1029
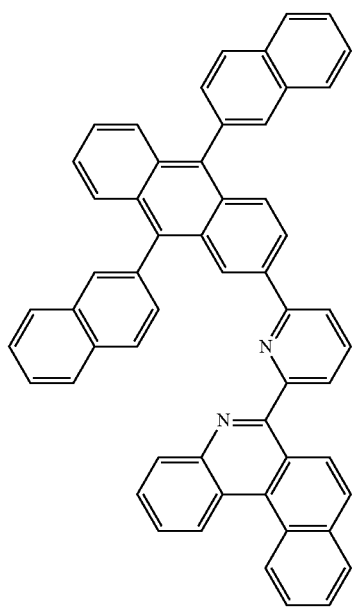
1030
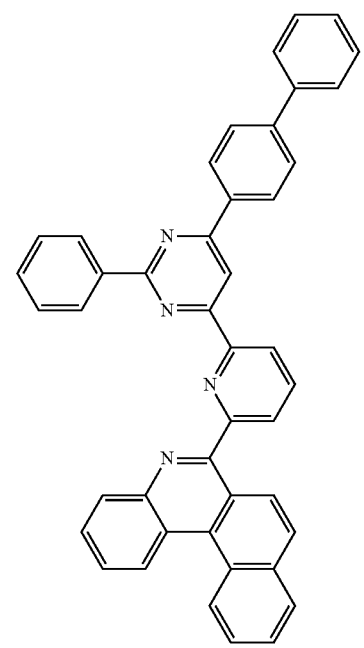
1042
-continued
1031
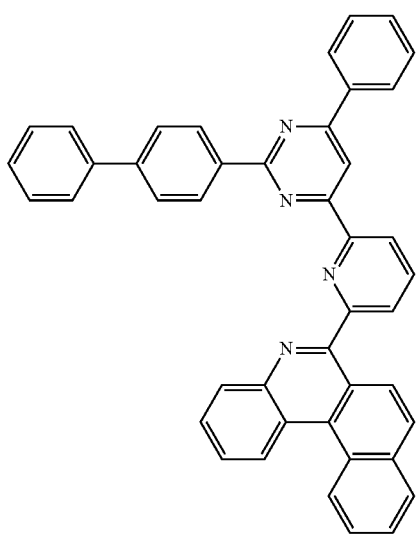
1032

1043
-continued
1033
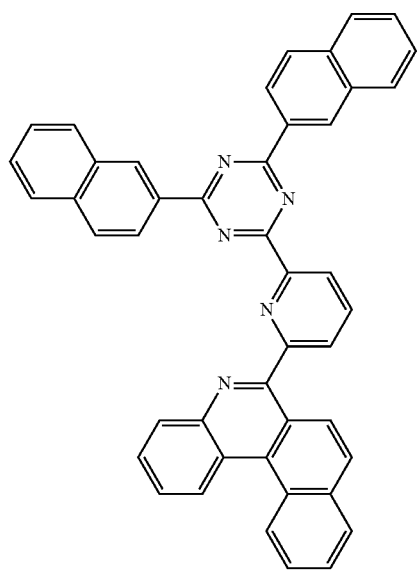
1034
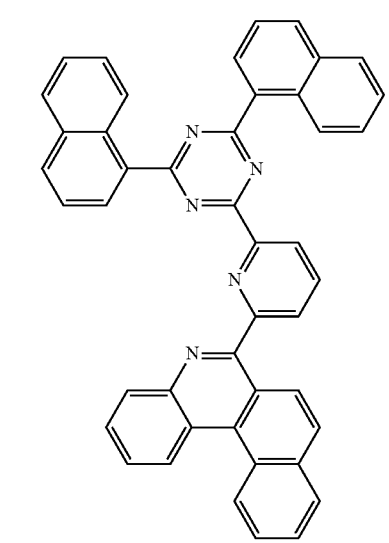
1035
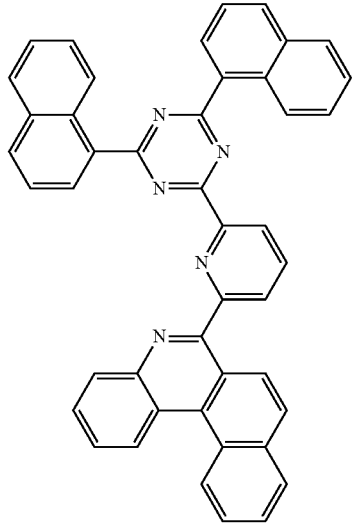
1044
-continued
1036
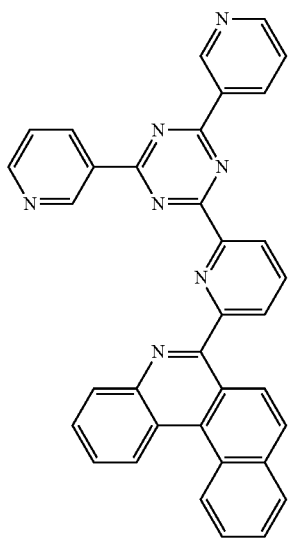
1037
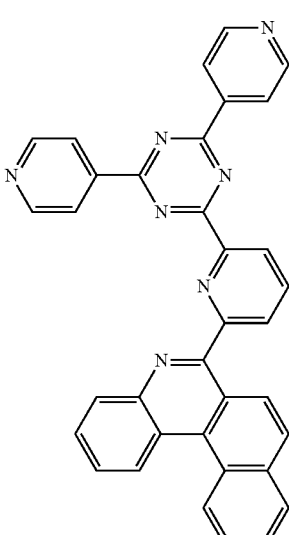
1038
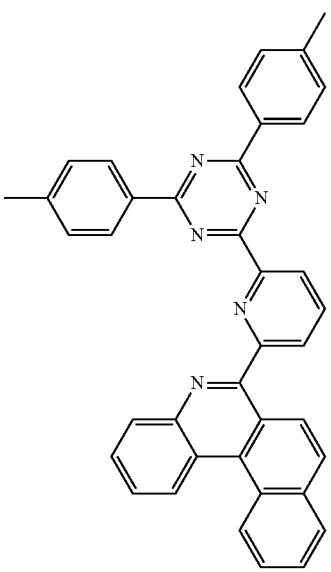

-continued
1039
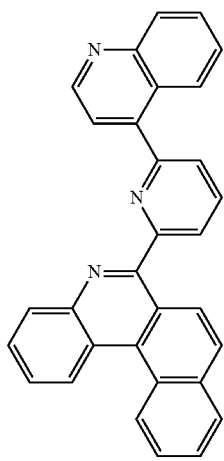
1040
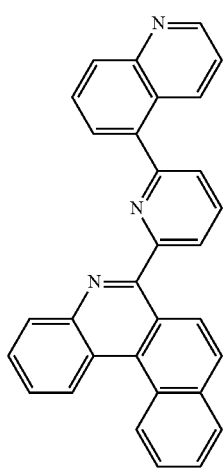
1041
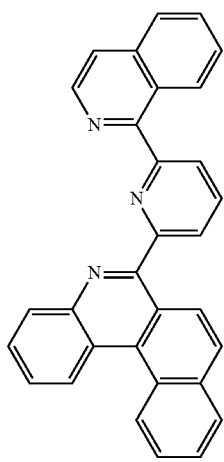
1029
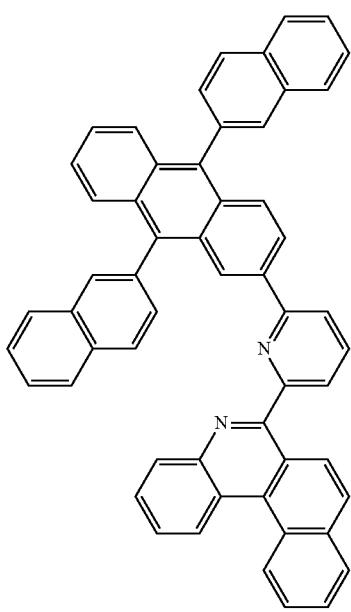
1030
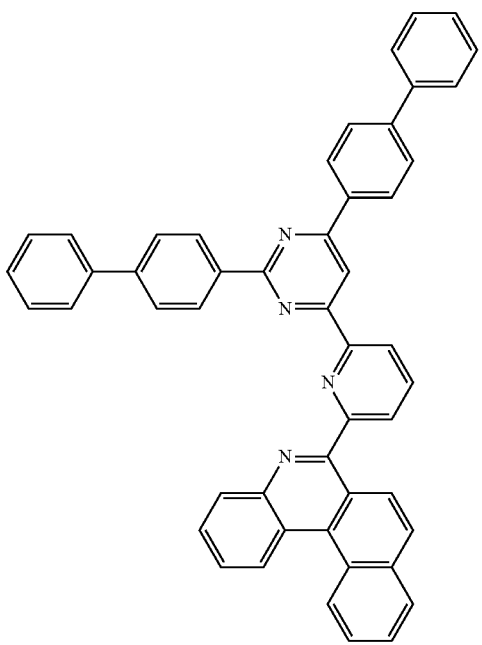

1047
-continued
1031
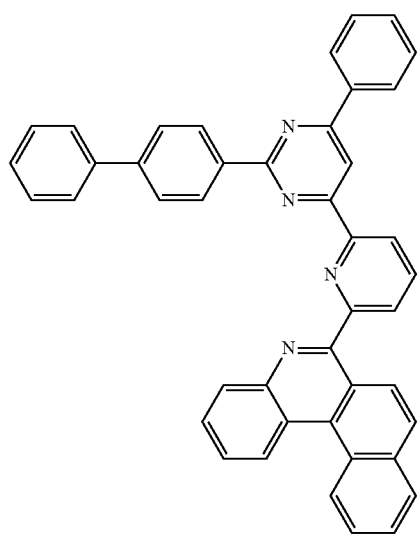
1032
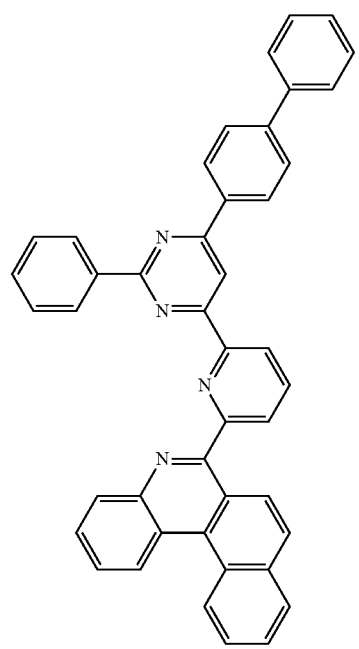
1048
-continued
1033
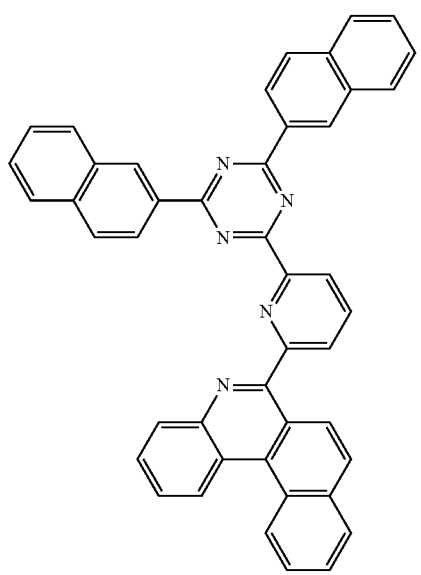
1034
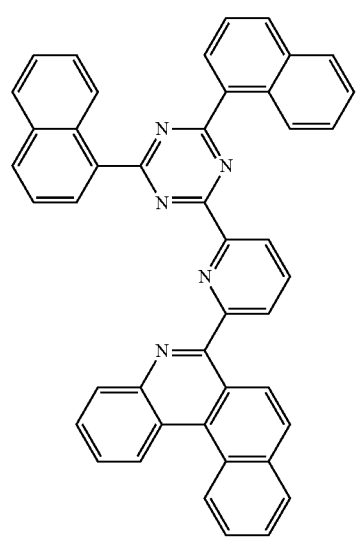
1035
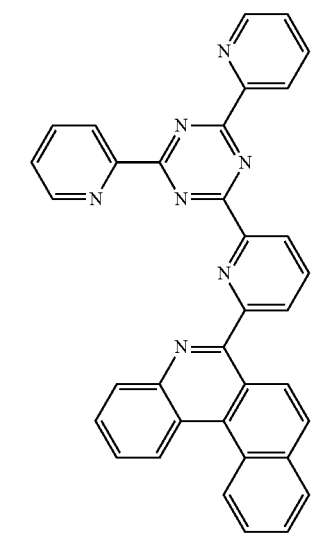

-continued

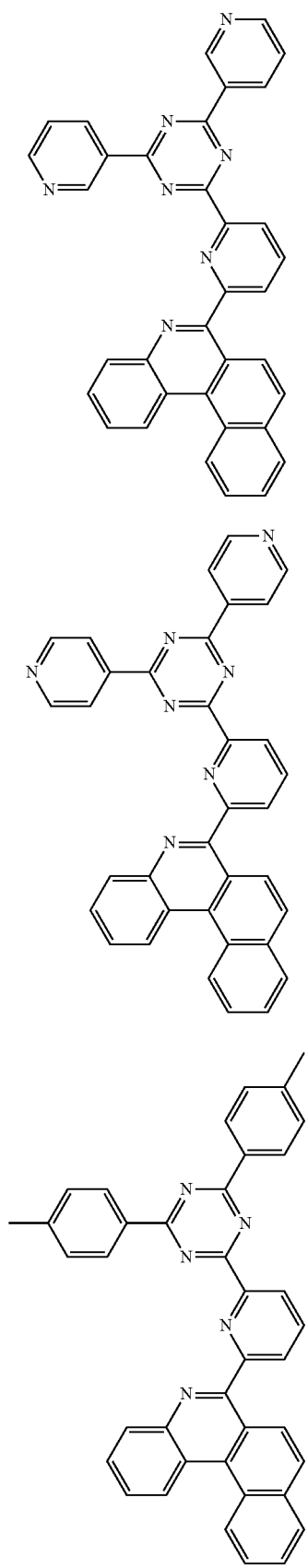

-continued

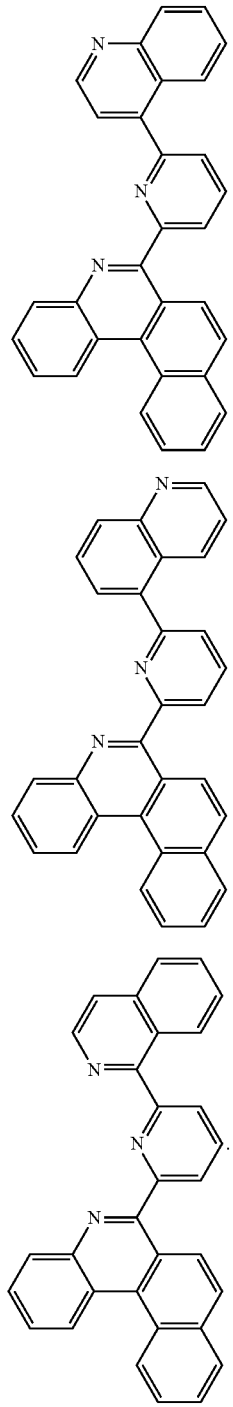

9. An organic light emitting device comprising:
an anode;
a cathode; and
one or more organic material layers provided between the anode and the cathode,
wherein one or more layers of the organic material layers include the compound of claim 1.

10. The organic light emitting device of claim 9, wherein an organic material layer including the compound of the chemical formula 1 is at least one selected from a hole injection layer, a hole transport layer, a light emitting layer, a hole blocking layer, an electron transport layer, and an electron injection layer.

11. The organic light emitting device of claim 9, wherein an organic material layer including the compound of the chemical formula 1 is a light emitting layer.

12. The organic light emitting device of claim 9, wherein an organic material layer including the compound of the chemical formula 1 is an electron injection layer or an electron transport layer.

* * * * *